United States Patent
Song et al.

(10) Patent No.: US 10,435,388 B2
(45) Date of Patent: Oct. 8, 2019

(54) SELECTIVE INHIBITORS OF CLINICALLY IMPORTANT MUTANTS OF THE EGFR TYROSINE KINASE

(71) Applicant: CS PHARMATECH LIMITED, Grand Cayman (KY)

(72) Inventors: Yuntao Song, Palo Alto, CA (US); Alexander James Bridges, Saline, MI (US)

(73) Assignee: CS Pharmatech Limited, Grand Cayman (KY)

(*) Notice: Subject to any disclaimer, the term of this patent is extended or adjusted under 35 U.S.C. 154(b) by 0 days.

(21) Appl. No.: 16/068,559

(22) PCT Filed: Jan. 6, 2017

(86) PCT No.: PCT/US2017/012466
§ 371 (c)(1),
(2) Date: Jul. 6, 2018

(87) PCT Pub. No.: WO2017/120429
PCT Pub. Date: Jul. 13, 2017

(65) Prior Publication Data
US 2019/0023689 A1 Jan. 24, 2019

Related U.S. Application Data

(60) Provisional application No. 62/399,730, filed on Sep. 26, 2016, provisional application No. 62/276,221, filed on Jan. 7, 2016.

(51) Int. Cl.
| | |
|---|---|
| *C07D 403/04* | (2006.01) |
| *C07D 471/04* | (2006.01) |
| *C08F 20/58* | (2006.01) |
| *C08F 20/60* | (2006.01) |
| *C07D 401/14* | (2006.01) |
| *C07D 405/14* | (2006.01) |
| *C07D 401/04* | (2006.01) |
| *C07D 403/14* | (2006.01) |
| *A61P 35/00* | (2006.01) |

(52) U.S. Cl.
CPC ............ *C07D 403/04* (2013.01); *A61P 35/00* (2018.01); *C07D 401/04* (2013.01); *C07D 401/14* (2013.01); *C07D 403/14* (2013.01); *C07D 405/14* (2013.01); *C07D 471/04* (2013.01); *C08F 20/58* (2013.01); *C08F 20/60* (2013.01)

(58) Field of Classification Search
CPC .. C07D 403/04; C07D 401/04; C07D 401/14; C07D 403/14; C07D 405/14; C07D 471/04
See application file for complete search history.

(56) References Cited

U.S. PATENT DOCUMENTS

| | | | |
|---|---|---|---|
| 10,179,784 B2* | 1/2019 | Jiang | A61K 31/437 |
| 2004/0048868 A1 | 3/2004 | Edwards et al. | |
| 2014/0243336 A1 | 8/2014 | Altman et al. | |
| 2016/0303121 A1 | 10/2016 | Singh et al. | |
| 2017/0008889 A1* | 1/2017 | Lan | A61K 31/506 |
| 2017/0313714 A1* | 11/2017 | Wei | C07D 403/12 |
| 2017/0355696 A1* | 12/2017 | Jiang | A61K 31/437 |

FOREIGN PATENT DOCUMENTS

| | | |
|---|---|---|
| CN | 104761544 A | 7/2015 |
| CN | 104761585 A | 7/2015 |
| CN | 104788427 A | 7/2015 |
| CN | 104844580 A | 8/2015 |
| CN | 104860941 A | 8/2015 |
| CN | 105001208 A | 10/2015 |
| CN | 105085489 A | 11/2015 |
| CN | 105315259 A | 2/2016 |
| CN | 105461695 A | 4/2016 |
| CN | 106117185 A | 11/2016 |
| CN | 106279160 A | 1/2017 |
| CN | 106749193 A | 5/2017 |

(Continued)

OTHER PUBLICATIONS

International Search Report and Written Opinion issued by the International Searching Authority for Application No. PCT/US2017/012466, dated May 4, 2017, 9 pages.

International Search Report and Written Opinion issued by the International Searching Authority for Application No. PCT/US2018/040904, dated Oct. 29, 2018, 10 pages.

Lehr et al., "Production, purification and characterization of non-myristylated human T-cell protein tyrosine kinase in a baculovirus expression system," Gene 169(2):275-279 (1996).

Gish et al., "Bacterial expression, purification and preliminary kinetic description of the kinase domain of v-fps," Protein Eng. 8(6):609-614 (1995).

(Continued)

*Primary Examiner* — Alexander R Pagano
(74) *Attorney, Agent, or Firm* — Cooley LLP

(57) ABSTRACT

The present invention provides compounds of Formula (I) or a subgeneric structure or species thereof or a pharmaceutically acceptable salt, ester, solvate, and/or prodrug thereof and methods and compositions for treating or ameliorating abnormal cell proliferative disorders, such as cancer, wherein A, $R^2$, $R^3$, $R^{10}$, $E^1$, $E^2$, $E^3$, Y, and Z are as defined herein.

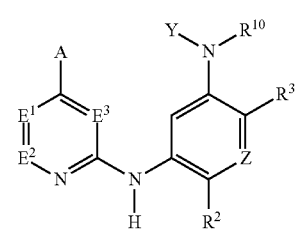

24 Claims, No Drawings

(56) References Cited

FOREIGN PATENT DOCUMENTS

| | | | |
|---|---|---|---|
| CN | 106749193 A * | 5/2017 | |
| CN | 106928150 A | 7/2017 | |
| WO | WO 2013/13014448 A1 | 1/2013 | |
| WO | WO 2015/050989 A2 | 4/2015 | |
| WO | WO 2015/127872 A1 | 9/2015 | |
| WO | WO 2015/175632 A1 | 11/2015 | |
| WO | WO 2015/188777 A1 | 12/2015 | |
| WO | WO 2015/195228 A1 | 12/2015 | |
| WO | WO-2015188777 A1 * | 12/2015 | ........... A61K 31/506 |
| WO | WO 2016/015453 A1 | 2/2016 | |
| WO | WO 2016/029839 A1 | 3/2016 | |
| WO | WO 2016/054987 A1 | 4/2016 | |
| WO | WO 2016/060443 A2 | 4/2016 | |
| WO | WO 2016/070816 A1 | 5/2016 | |
| WO | WO 2016/0102076 A1 | 6/2016 | |
| WO | WO 2016/105525 A2 | 6/2016 | |
| WO | WO 2016/173438 A1 | 11/2016 | |
| WO | WO 2016/183278 A1 | 11/2016 | |
| WO | WO 2017/008761 A1 | 1/2017 | |
| WO | WO 2017/114500 A1 | 7/2017 | |
| WO | WO 2017/120429 A1 | 7/2017 | |
| WO | WO 2017/190637 A1 | 11/2017 | |
| WO | WO 2017/197062 A1 | 11/2017 | |
| WO | WO 2018/019204 A1 | 2/2018 | |
| WO | WO 2019/010295 A1 | 1/2019 | |

OTHER PUBLICATIONS

Braunwalder et al., "A solid-phase assay for the determination of protein tyrosine kinase activity of c-src using scintillating microtitration plates," Anal. Biochem. 234(1):23-26 (1996).

Wu et al., "Measurement of Cdk4 Kinase Activity Using an Affinity Peptide-Tagging Technology," Comb Chem High Throughput Screen. 3(1):27-36 (2000).

Cleaveland et al., "A microtiter-based assay for the detection of protein tyrosine kinase activity," Anal Biochem. 190(2):249-253 (1990).

Seethala et al., "A fluorescence polarization competition immunoassay for tyrosine kinases,"Anal Biochem. 255(2):257-262 (1998).

Kolb et al., "Tyrosine Kinase assays adapted to homogeneous time-resolved fluorescence," Drug Discov. Today 3:333-342 (1998).

Handbook of Pharmaceutical Salts: Properties, Selection, and Use by Stahl and Wermuth (Wiley-VCH, Weinheim, Germany, 2002), 333 pages.

Pro-drugs as Novel Delivery Systems, vol. 14, ACS Symposium Series (T Higuchi and W Stella), 249 pages.

Remington's Pharmaceutical Sciences, 19th Edition (Mack Publishing Company, 1995), 783 pages.

Extended European Search Report issued by the European Patent Office for Application No. 17736401.5, dated Jun. 25, 2019, 9 pages.

* cited by examiner

SELECTIVE INHIBITORS OF CLINICALLY IMPORTANT MUTANTS OF THE EGFR TYROSINE KINASE

CROSS-REFERENCE TO RELATED APPLICATIONS

The present application is a U.S. National Stage Application under 35 U.S.C. § 371 of International Application No. PCT/US2017/12466, filed Jan. 6, 2017, which claims priority to U.S. Provisional Application No. 62/276,221, filed Jan. 7, 2016, and U.S. Provisional Application No. 62/399,730, filed Sep. 26, 2016, each of which is incorporated herein by reference in its entirety for all purposes.

FIELD OF THE INVENTION

The present invention relates to compounds of formula (I) or subgeneric structures or species thereof or their pharmaceutically acceptable salts ester, solvate, and/or prodrug thereof, and pharmaceutical compositions comprising such compounds or a pharmaceutically acceptable salt ester, solvate, and/or prodrug thereof. The compounds and salts of the present invention inhibit kinases, especially the epidermal growth factor receptor EGFR, and particular mutants of it, important in developing resistance to treatment by EGFR inhibitory therapy, and are useful for treating or ameliorating abnormal cell proliferative disorders, such as cancer.

BACKGROUND OF THE INVENTION

The current invention pertains to biarylamino compounds which are useful as highly selective inhibitors of certain protein tyrosine kinases, PTKs, which are one of the subclasses of the protein kinases, PKs. PKs are very important signaling entities in intracellular communication, where they modify many proteins by catalyzing the transfer of a phosphate group from ATP acting as a phosphodonor to a phenolic hydroxyl on a tyrosine side chain of the protein. Frequently, the tyrosine kinases are incorporated into the intracellular domain of a very large transmembrane protein, which has a cognate ligand binding domain in the extracellular domain, whereby ligand binding activates the tyrosine kinase intracellularly. Such molecules are receptor tyrosine kinases (RTKs).

Structurally, the kinases are quite well understood. There is a kinase domain, which may be the whole protein, or only one domain of a much larger modular protein, and this domain has a basic conserved structure of about 35 kD, consisting of two lobes, the N-terminal one being mainly made up of β-sheets, and the larger C-terminal domain mainly of α-helices. There is a deep cleft between the two lobes which binds both ATP and the substrate. The substrate binding domain is quite large, and rather variable, and is used to discriminate between different protein substrates, and maintain specificity of phosphorylation. This specificity can be very variable, with some enzymes such as MEK having only one known substrate, and others being able to phosphorylate hundreds of distinct hydroxyls in proteins.

Phosphorylation frequently changes the conformation of the modified protein, often converting enzymes from an inactive form to an active form, or vice versa, or causing the protein to associate closely with specific binding partners, or perhaps dissociate from them, leading to changes in cellular localization, or assembly, or disassembly, of functioning multi-protein complexes. Many of the transducers of signals into cells, and from the cell surface into the nucleus are either PKs, or controlled by PKs, especially RTKs. Because of this, inhibitors of the kinase activity of PKs can have very drastic effects on cellular signaling, damping down both normal responses to external signals, and inappropriate overresponses, usually caused by mutations in the signaling molecules themselves. Although such pathways are very widespread in the body, and are involved in one way or another in most bodily functions, and the diseases that can arise from their malfunction, inhibitors of PKs are particularly useful in treating cancer and immunological disorders, both disease classes where overactivity of PKs, especially RTKs, has been widely documented, and where they often play crucial roles in driving the disease process itself.

Kinases have been shown to be very important effectors of many disease processes, especially in cancer. Cellular proliferation is controlled at many different levels by kinases, and, under normal circumstances for cells to proliferate, signals have to be sent from outside the cell, where they bind to receptors and activate the receptors. Many of the important receptors in cell signaling are kinases, especially RTKs, or are directly coupled to kinases which themselves are activated by the activated receptor. Once these kinases have been activated, they in turn activate signaling cascades, which usually involve several further kinases in an amplifying wave of phosphorylation, which lead eventually to the translocation into, and activation of, transcription factors in the nucleus. Activation of the transcription factors engenders proteins being produced which carry out various programs within the cell, including those which start the cell into the proliferative cycle. Usually, once this process has gone on for a number of hours, the newly synthesized proteins will continue the process, without need for further extracellular input. If the proliferative cell cycle is initiated, the first set of proteins synthesized includes both further transcription factors, and their activators to drive later stages of the cell cycle, and effectors, which start the process of duplicating and dividing the cell. Kinases are major controllers of every step in this process. When this process is not controlled properly, and cells can execute the cell cycle without appropriate external control, they become transformed, and can form a tumor, if the immune system fails to eradicate them.

When transformed cells are examined, one of their invariant characteristics is hyperphosphorylation, showing that these cells have an overall surfeit of kinase activity, especially in the absence of any growth factors. Hyperphosphorylation can be caused by a very wide variety of mutations in the cell. For example by the cell inappropriately producing its own ligand for one of the receptor-linked kinases. Or one of these kinases may be heavily overexpressed, due either to a failure to control its expression properly, or to multiple extra copies of the gene being present in the cell. Another very common genetic defect is a mutation in the coding region of the kinase, which leads to a kinase which is constitutively active, and has no need for the appropriate signal to active it. Sometimes the kinase may not be inappropriately active, but a phosphatase, which is supposed to limit its signaling by removing the phosphate from target molecules, is inactivated by mutation or deletion. Examination of both cell culture tumors and isolates from clinical tumors will almost always find defects of this sort in the phosphorylation system of the tumor cells.

In the late 1980s, several small molecule kinase inhibitors were discovered. These molecules almost invariably bind in the catalytic cleft of the kinase, and compete with ATP for its binding site. Thus they are ATP-competitive, and most inhibitors discovered since then fall into this class. However, kinase inhibitors have been occasionally discovered which compete with the protein substrate, substrate-competitive, or more commonly with both ATP and substrate, dual inhibitors, or are neither competitive with receptor nor substrate, non-competitive inhibitors. After allowing for differences in cellular penetration, one finds that there is a very good correlation between the potency of these compounds in isolated kinase enzyme inhibitory assays, and inhibition of the kinase in cells. For many kinases, there is also an excellent correlation between loss of phosphorylation of downstream targets, and inhibition of cellular proliferation. As this correlation has been shown thousands of times, with dozens of different kinases, it is a clear demonstration that aberrant kinase signaling can cause uncontrolled proliferation in transformed cells, and that in many cases, blockade of the over-activated kinase can stop the proliferation. In many cases the kinase inhibitor alone can actually induce apoptosis in the transformed cells, leading to shrinkage of the tumor. This can occur because various genetic lesions in the cell have been detected by the cellular proof-reading system, and as a result several pro-apoptotic mechanisms are usually activated in these cells, but aberrant phosphorylation may well be involved in suppressing the ongoing apoptotic process. Some kinase inhibitors, especially those which target kinases involved late in the cell cycle are intrinsically cytotoxic, as cells interrupted during mitosis tend to apoptose very readily. Although, good proof that these abilities in cells could prevent tumors grown as xenografts in nude mice was initially slow in coming, as the agents improved, it became routine to demonstrate that kinase inhibitors could slow the growth of tumors which express the kinase oncogenes being targeted, and the better agents cause the tumors to regress in size often to the point of immeasurability, and on rare occasions the tumors do not regrow after dosing is stopped, suggesting the animals may have been cured of the tumor. Furthermore, the in vivo efficacy correlates with the cellular and enzymatic activity, after one has correlated for tumor exposure.

Clinical proof was slower in coming, probably partly because clinical tumors are often much more complex than tumors grown under carefully controlled conditions, partly because mice are a lot more biochemically robust than humans, and can tolerate larger relative doses of the drugs, and mainly because it is usually very difficult to know which are the appropriate kinases to inhibit in any given randomly presenting human tumor. However imatinib, a reasonably potent inhibitor of the fusion oncogenic TK BCR-ABL, with truly outstanding pharmacokinetic properties, was approved for chronic myelogenous leukemia (CML) in 2000. This kinase inhibitor provides a very convincing clinical proof of concept for the theory, as about two thirds of CML patients (whose tumors almost by definition contain one of two forms of BCR-ABL) respond very well to treatment, and usually the leukemia cells almost completely disappear from circulation. Surprisingly, mutation around this blockade appears to be very slow, and even after 10 years of treatment the drug is still effective in 80% of patients. This has not proved to be the general case, probably partly because most tumors are found much later in their biological history than are CMLs, and have had much longer to become genetically heterogeneous, and partly because very few tumors are as dependent on one oncogene as CML is on BCR-ABL.

Epidermal Growth Factor Receptor Tyrosine Kinase Inhibitors

Two 4-anilinoquinazoline inhibitors of the epidermal growth factor RTK (EGFR, erbB-1), gefitinib and erlotinib, were approved for use in lung cancer around 10 years ago. EGFR is one of the most commonly disregulated kinases seen in solid tumors, with overexpression or mutation being seen often in 50% or more of a tumor type, including non-small cell lung cancer (NSCLC). Despite excellent activity of these inhibitors against a wide variety of xenografts overexpressing EGFR, very limited activity was seen in NSCLC, with only about 10% of patients responding to the drug, and the average response only lasting a year or so, although occasionally a much more durable responder is found. Surprisingly, in other tumor types known to overexpress EGFR, especially colorectal cancer (CRC) no meaningful activity was demonstrated, although the anti-EGFR monoclonal antibody Erbitux has shown quite good clinical activity in CRC, for which it has been approved for use.

When close examination of NSCLC responders was made, it was found that the majority of good responders had one of a few single mutations in EGFR (sm-EGFR), with those containing wild-type receptor (wt-EGFR) usually not responding appreciably, regardless of expression level. Such mutations are very rare in CRC, which tends towards overexpressed wt-EGFR, or overexpressed autocrine ligand expression. When these mutants, especially EGFR L858R, and EGFR del746-750, were analyzed it was found that they have the properties of being both intrinsically activated, which means that they were driving proliferation without an external signal, and also binding ATP more weakly than wt EGFR, (higher $K_m$) whilst having similar affinity to wt EGFR for the inhibitors. This meant that, as these inhibitors are ATP-competitive, that it was easier to compete ATP off the enzyme and shut down kinase activity in susceptible mutants than in the wt, giving a de facto boost to inhibitor potency in the mutants. At the same time these tumors had become more dependent on EGFR signaling for proliferation and survival than most tumors, because the signals had been reliably overactive ever since the original mutation event.

As stated earlier, solid tumors such as lung cancers are usually quite old by the time they are discovered, probably on average being 6-12 years beyond the arising of the original transformed founder cell. One of the properties of transformed cells is that they lose control over their DNA replication quality control, so their spontaneous mutation rate is much higher than that of untransformed cells. As mutations occur most easily during DNA replication, and these cells are replicating very quickly, this adds further to the mutation rate. The result is that as a tumor ages it will pick up an ever-increasing number of mutations, and it does so in a stochastic fashion, so that sub-clones of the tumor arise over time with somewhat different genetics from the original tumor, and one another. These sub-clones are not only involved in a survival struggle with the body itself, but with one another as they compete amongst themselves for the limited resources available to them. If one changes the environment for the dominant tumor clone, such that it becomes relatively less well adapted to its new environment, for example by adding an effective inhibitor to it, a previously much less successful minor clone may be able to take over the niche being vacated, if it is not as affected by said inhibitor. Alternatively, unless one either kills the clone outright, or completely shuts down proliferation, it will continue to spawn mutations, and if a mutation gets around the inhibition, this sub-clone will now be free to proliferate, without hindrance from either the inhibitor or the inhibited parental clone. Thus natural selection predicts that cancers, just like infectious diseases, should be able to develop drug resistance, and as the selection process is largely driven by competition between tumor sub-clones within a single host, the overall effect is to favor more aggressive sub-clones, and tumors generally become more deadly as they evolve.

When responders to gefitinib and erlotinib were followed, it was found that the onset of resistance could be correlated with several different genetic changes. In rare cases the tumors seem to pick up a totally different signaling system to drive the tumor, but usually the resistance involves tweaking of the original system. EGFR is a member of the erbB (Type I) subfamily of RTKs, along with erbB-2, erbB-3 and erbB-4. These receptors are activated by ligands which induce them to dimerize, and although EGFR-EGFR homodimers are quite commonly used in signaling, the more usual course in this family is for the ligands to induce heterodimerization, such that the signaling entity will be for example EGFR:erbB-2 or erb-B2:erbB-3 and an appropriate ligand. The simplest way to reactivate the system is to increase the expression of one of the other erbBs, and this is frequently seen, even before treatment, and may help to explain why a lot of wt EGFR overexpressing tumors do not respond to EGFR inhibition. A somewhat related mechanism involves the RTK HGFR, which although not a erbB family member has been shown to form oncogenic heterodimers with erbB family members, especially erbB-3, when overexpressed, and overexpression of HGFR is a common resistance mechanism to EGFR inhibitors. At least in laboratory settings, addition of an HGFR inhibitor to these cells restores sensitivity to EGFR inhibitors. The third, and commonest, mode of resistance is a further mutation in EGFR, giving doubly mutant receptor (dm-EGFR) which reduces its sensitivity to the EGFR inhibitor. The commonest of these is the so-called "gatekeeper" mutation T790M, and NSCLCs with double mutants such as L858R/T790M are commonly seen in initial responders, who have subsequently developed resistance to EGFR inhibitors. Whether such sub-clones were present all along, or whether they only arise after treatment is not known, but it seems most probable that the mutation is already present in short term responders, and may arise as a de novo mutation in long term responders who develop resistance late.

Initially, it was believed that these mutations block the inhibitors sterically from binding to the mutant enzyme, hence reducing their affinity, and efficacy. However, more recent studies suggest that the commonest mutations have very little effect on inhibitor affinity, but lead to restoration of ATP-binding affinity to that of wt EGFR, or possibly up to 10-fold greater, with the result that the achievable concentrations of the inhibitors are no longer high enough to shut down signaling to a therapeutically useful extent. In principle, one simply needs to improve the affinity of the inhibitors enough to overcome the increased ATP affinity, but in practice this is very difficult to do, because gefitinib and erlotinib are already very potent, subnanomolar, EGFR inhibitors with good PK properties, and yet have mediocre activity against tumors driven by wt EGFR. Furthermore, although the T790M mutant does not reduce the affinity of EGFR for erlotinib and gefitinib, it does limit the ways that one could increase affinity in the anilinoquinazoline chemotype of these two inhibitors. Therefore, to find greater affinity for the T790M-type mutants, new chemical templates have been examined, and some, especially U-shaped inhibitors of the type discussed later, appear to have considerable promise in this area.

EGFR receptors play an important role throughout the body, especially in the entire gastrointestinal epithelium and skin, which are both proliferatively very active tissues. As two of the major, dose-limiting toxicities of EGFR inhibitors are skin rashes and serious GI disturbances, these are almost certainly largely mechanism-based toxicities. As long as the tumor is driven by wt EGFR this is very difficult to avoid by rational design, especially for an oral agent, where GI tract exposure is obligate, but if the tumor is driven by mutant EGFR, one may be able to mitigate the toxicity seen with the approved drugs. For NSCLCs which respond to EGFR inhibitors, the initial target is not wt-EGFR, but one of a limited number of sm-EGFRs, and the later target is a dm-EGFR, both of which should at least in principle have different SARs to wt-EGFR, giving one at least the theoretical possibility of reducing side effects by finding inhibitors which have considerably better affinity for sm- and/or dm-EGFR over wt-EGFR. Due to the similarity between EGFR and the mutant-EGFRs, and the fact that the original inhibitors only worked because they already were better inhibitors of sm-EGFR than wt-EGFR, not due to intrinsic affinity, but ATP-competition, this might be expected to be a difficult feat to accomplish. Unfortunately, clinical observation suggests that the aberrant EGFR systems driving tumors need to be very heavily suppressed to produce meaningful efficacy, whereas the suppression of wt-EGFR signaling in normal tissues at high enough levels to induce limiting toxicities is relatively easy to accomplish. However EGFR inhibitors with enhanced affinity for EGFR mutants, especially T790M dm-EGFRs have been found and examples of many of these are in the literature, with several now in clinical trials. This patent application describes compounds which fit one of these criteria.

Inhibitors of EGFR which have considerably greater affinity for a mutant EGFR than the wt EGFR should at an optimal dose be able to inhibit proliferation in tumors driven by that mutant, whilst having relatively little, if any effect on EGFR signaling in untransformed tissues, where wt EGFR is responsible for the EGFR signaling. This should allow considerably larger doses of mutant-selective EGFR inhibitors to be given, increasing both the efficacy against the mutant-driven tumor and the therapeutic index. It should be noted that because of mutant effects on ATP-binding, that is essentially what is already happening with responders to erlotinib and gefitinib, where the responding mutants are actually more sensitive to the inhibitors than wt EGFR, due mainly to their diminished affinity for the competing ligand ATP. Several third generation EGFR inhibitors have now been revealed, with some in the clinic. These compounds are generally irreversible inhibitors, initially based off of a U-shaped dianilinopyrimidine scaffold, but this been extended to several related scaffolds, but all bind in a similar mode to the dianilinopyrimidines. In general these compounds are very potent inhibitors of the mutant EGFRs, containing the T790M mutation, and are somewhat less potent against wt EGFR, and some of the other mutations. Because of this profile, it is believed that the mechanism-based toxicities of wt EGFR inhibition should be considerably reduced, while retaining very strong inhibitory potency against tumors driven by the appropriate EGFR mutations. Thus compounds of this type may be especially useful as second line therapy, after a patient previously sensitive to first line erlotinib or gefitinib therapy becomes resistant. Not only will these inhibitors allow the appropriate mutant receptors to be inhibited as strongly as previously, but they should do this whilst themselves not inducing appreciable mechanism-induced toxicity through EGFR inhibition. The macrocyclic amine inhibitors of the present invention are irreversible inhibitors of EFGR, with a similar selective profile for mutant over wt EGFR inhibition to these agents, and excellent pharmacokinetic properties, and will therefore prove to be excellent agents for second line treatment of NSCLC, and any other tumors driven by this sub-family of mutated EGFR kinases.

Another method of increasing the potency of especially EGFR inhibitors was developed in the mid-1990s. Many sites on proteins are quite strongly nucleophilic, either because they are intrinsically nucleophilic, with cysteine thiols being the principle example, with lysine amines, histidine imidazoles, and serine, threonine and tyrosine hydroxyls also being less potent possibilities, or because they have been deliberately activated, as in the catalytic hydroxyls in many amidases. Such residues can often be targeted by electrophiles, which modify the protein under rather mild conditions. Depending on the function of the modified residue, and its position on the protein, this may or may not lead to a loss of enzyme function. It was realized that a subset of TKs use a cysteine residue on the edge of the ATP binding cleft to form a hydrogen bond to the ribose of ATP, whereas the majority use a threonine for this purpose. The EGFR family all contains this cysteine ($C^{797}$ in EGFR). It was hypothesized that this cysteine could be alkylated by an alkylating moiety attached to an inhibitor, which bound in the ATP-binding site, and presented the electrophile in the vicinity of the cysteine sulfur. Indeed many of the first generation of EGFR inhibitors were potent electrophiles, which may well have targeted $Cys^{797}$ or other nucleophiles on EGFR. Unfortunately, this inhibition did not lead to very potent inhibitors, nor did it lead to very selective inhibitors, suggesting that the electrophiles were reactive enough, and non-discriminating enough to react with a wide variety of proteins, especially kinases, and that in many of these cases the alkylation was occurring in either the catalytic domain, or a controlling "switch region" of the enzyme. To make this concept useful, the alkylating moiety would have to be of low intrinsic reactivity, because one does not want it to indiscriminately react with the vast array of nucleophiles in the body, both for potential PK and toxicity reasons. To get an alkylating agent to react with this necessarily rather weak electrophile with high selectivity, it was shown that the compound itself had to have both high (non-covalent) affinity for the binding site, and would have to bind preferentially in a conformation which placed the weak electrophile in close proximity to the electrophile. Lastly, it was also found that the reaction needed to be fast relative to the plasma half-life of the inhibitor, or most of it would wash out of the body without ever reacting with the crucial cysteine. Such irreversibly inhibitory compounds were discovered, and it was found that they not only were much more potent inhibitors of EGFR in vivo than the theoretically equipotent reversible inhibitors, but as a bonus they made (at least in the case of the anilinoquinazolines and the related 3-cyanoquinolines) a rather poor erbB-2 and erbB-4 inhibitory template into very potent inhibitors of all of the erbBs, demonstrating that if the binding mode were really good in its placement of the alkylating moiety, very high non-covalent affinity for the target might be less vital. Most of the second generation EGFR inhibitors which went into the clinic are irreversible inhibitors of EGFR, using acrylamide derivatives as electrophiles, and they appear to be more active in general in the clinic than reversible inhibitors, but they also tend to have higher toxicity, so only one, afatinib, has shown a good enough profile to gain approval.

Many different classes of kinase inhibitors have been developed, and several have been successfully approved and marketed. One of the molecular scaffolds which appears to produce potent inhibition of a large number of kinases, is a series of three concatenated rings, of which two, and frequently all three, are aromatic, which can form a U-shaped structure when binding to a kinase. The two distal rings can be directly linked to the central ring by bonds, or via various linkers consisting of 1-3 atom chains. The central ring, which is almost invariably a nitrogen-containing heteroaromatic system with an NH group adjacent to a ring nitrogen, forms 1-3 hydrogen bonds to the backbone of residues in the hinge domain of kinases, between the N- and C-terminal lobes, just prior to the so called DFG loop, an invariant structure in kinases, which has to be placed correctly for an active conformation of the enzyme to be achieved. This end of the inhibitor also occupies a part of the adenine-binding region of the kinase, which tends to be very hydrophobic, whereas the two rings, which make the "stems" of the U, occupy a broad channel frequently filling part of the space normally occupied by the rest of the ATP molecule. Although quite a lot of affinity for specific kinases comes from decorating these core rings with selected substituents which produce favorable interactions with hopefully unique structural determinants in the target kinases, and/or unfavorable interactions with kinases, which one does not wish to inhibit, a lot of the affinity and selectivity for various kinases comes from the various torsions and bend angles between the three rings, and some substituents which optimize affinity for the target kinase may not themselves interacting directly with the protein, but may control the most stable conformations of the three rings with respect to one another. Thus the purpose of some substituents can be to affect the overall internal energy of the inhibitory molecule, in order to stabilize a favorable conformation for binding, rather than directly interact with the kinase.

None of the first and second generation EGFR/erbB-2 inhibitors which entered the clinic show the U-shaped binding mode. They have the 4-anilino (or extended 4-anilino) group binding into a cleft between the β4 sheet and the αC-helix, which is behind the vital $L^{745}$-$D^{855}$ salt bridge, and the DFG loop of which $D^{855}$ is a part.

SUMMARY OF THE INVENTION

The present invention provides, in part, novel compounds and pharmaceutically acceptable salts, solvates, esters, and/or prodrugs thereof that can selectively modulate the activity of protein kinases especially of the Type I receptor tyrosine kinase (RTK) family, or erbB family, and most particularly of certain mutated forms of the EGFR receptor, which provide resistance to current EGFR-based inhibitory therapies. This inhibitory activity affects biological functions, including but not limited to, cell proliferation and cell invasiveness, inhibiting metastasis, inducing apoptosis or inhibiting angiogenesis. Also provided are pharmaceutical compositions and medicaments, comprising the compounds or salts of the invention, alone or in combination with other therapeutic agents or palliative agents.

In one embodiment, the present invention relates to a compound of the formula (I):

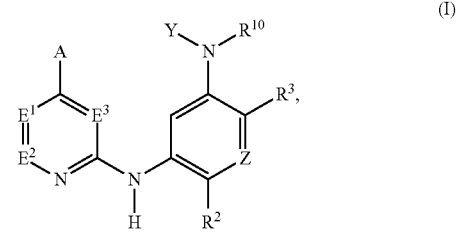

or a stereoisomer or a pharmaceutically acceptable salt, solvate, ester, or prodrug thereof;

wherein,

A is

A¹ 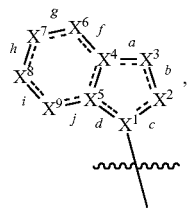

A² 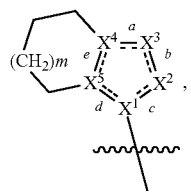

A³ 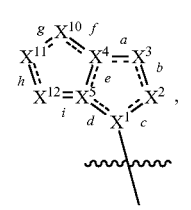

A⁴ᵃ 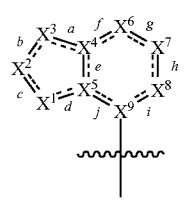

A⁴ᵇ 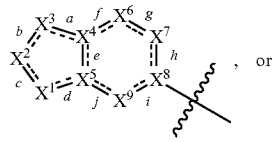, or

A⁵ 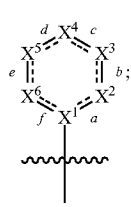

each of a, b, c, d, e, f, g, h, i and j are independently either (formal) double bonds or (formal) single bonds, and none of $X^1, X^2, X^3, X^4, X^5, X^6, X^7, X^8, X^9, X^{10}, X^{11}$, and $X^{12}$ has two (formal) double bonds attached thereto:

each of $X^1, X^2, X^3, X^6, X^7, X^8, X^9, X^{10}, X^{11}$, and $X^{12}$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$; or alternatively each of $X^1, X^2, X^3, X^6, X^7, X^8, X^9, X^{10}, X^{11}$, and $X^{12}$ is selected from the group consisting of: C, CH, CR$^4$, C(R$^4$)$_2$, CR$^{13}$, CH$_2$, C=O, C=S, C=NR$^{13}$, N, NR$^4$, NR$^{13}$, N(O), S, S(O), S(O)$_2$, S(=O)(=NR$^{13}$), S(=NR$^{13}$)$_2$, and O;

in A$^1$, A$^2$, A$^3$, A$^{4a}$, and A$^{4b}$, each of X$^4$ and X$^5$ is independently C or N, and at least one of X$^4$ and X$^5$ must be involved in a formal double bond;

at least four of $X^1, X^2, X^3, X^4, X^5, X^6, X^7, X^8, X^9, X^{10}, X^{11}$, and $X^{12}$ are C, CR$^4$, or C(R$^4$)$_2$;

in A$^1$, A$^2$, A$^3$ and A$^5$, X$^1$ is C, CH or N;

in A$^{4a}$, X$^9$ is C, CH or N;

in A$^{4b}$, X$^8$ is C, CH or N;

in A$^{4a}$ and A$^{4b}$, X$^1$ is N, NR$^{13}$, C(R$^4$)$_2$, C(O), S(O)$_x$, S(=O)(=NR$^{13}$), S(=NR$^{13}$)$_2$, or CR$^4$;

in A$^1$, A$^2$, A$^3$, A$^{4a}$, and A$^{4b}$, X$^2$ is N, NR$^{13}$, C(R$^4$), S(O)$_x$, S(=O)(=NR$^{13}$), S(=NR$^{13}$)$_2$, C(O), or CR$^4$;

in A$^1$, A$^2$, A$^3$, A$^{4a}$, and A$^{4b}$, X$^3$ is N, NR$^{13}$, C(R$^4$)$_2$, C(O), S(O)$_x$, S(=O)(=NR$^{13}$), S(=NR$^{13}$)$_2$, or CR$^4$;

in A$^5$, at least three of X$^2$, X$^3$, X$^4$, X$^5$ and X$^6$ are C, C(R$^4$)$_2$, C=O or CR$^4$;

E$^1$ and E$^2$ are independently C—R$^1$ or N with the proviso that E$^1$ and E$^2$ are not both N;

E$^3$ and Z are independently CH or N;

Y is

Y¹ 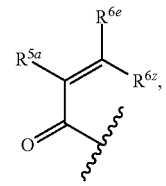

Y² 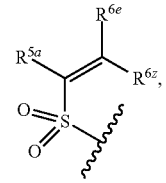

Y³ 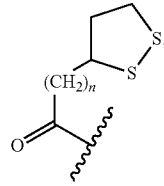

Y⁴ 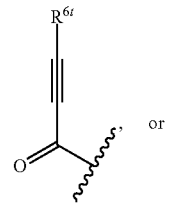, or

-continued

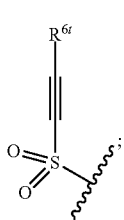

R$^1$ is independently selected from hydrogen, fluoro, chloro, bromo, methyl, ethyl, hydroxyl, methoxy, ethoxy, isopropoxy, —OCF$_3$, —OCH$_2$CF$_3$, —OCH$_2$CHF$_2$, ethenyl, ethynyl, CF$_3$, CHF$_2$, CHO, CH$_2$OH, CONH$_2$, CO$_2$Me, CONHMe, CONMe$_2$, and cyano;

R$^2$ is R$^{10}$, —OCF$_3$, —OCHF$_2$, —OCF$_2$CF$_3$, —OCH$_2$CHF$_2$, —OCH$_2$CF$_3$, cyclopropyl, cyclopropoxy, methoxy, ethoxy, or isopropoxy:

R$^3$ is C$_{2-6}$ alkenyl-R$^7$, C$_{2-6}$ alkynyl-R$^7$, N(R$^{10}$)C$_{2-6}$ alkyl-NR$^{10}$R$^{10}$, N(R$^{10}$)C$_{2-6}$ alkyl-R$^7$, O(CH$_2$)$_p$R$^7$, N(R$^{10}$)C(=O)(CH$_2$)$_p$R$^7$, C(R$^5$)=C(R$^5$)(CH$_2$)$_p$R$^7$, or R$^7$;

each R$^4$ is independently H, cyano, nitro, halo, —C$_{1-6}$ alkyl, —C$_{1-6}$haloalkyl, C$_{1-6}$ acyl-C$_{1-6}$ alkyl-, R$^7$—(CH$_2$)$_p$C(=O)—C$_{1-6}$ alkyl-, carboxy-C$_{1-6}$ alkyl-, C$_{1-6}$ alkyloxycarbonyl-C$_{1-6}$ alkyl-, R$^7$—(CH$_2$)$_p$O—C(=O)—C$_{1-6}$ alkyl-, R$^8$R$^9$N—C(=O)C$_{1-6}$ alkyl-, R$^7$—C$_{2-6}$alkyl-N(R$^{10}$)—C(=O)C$_{1-6}$ alkyl-, —C$_{1-6}$ hydroxyalkyl, C$_{1-6}$ alkoxy-C$_{1-6}$ alkyl-, R$^7$(CH$_2$)$_p$OC$_{1-6}$ alkyl-, C$_{1-6}$ acyloxy-C$_{1-6}$ alkyl-, R$^7$—(CH$_2$)$_p$C(=O)O—C$_{1-6}$ alkyl-, C$_{1-6}$ alkoxy-C(=O)O—C$_{1-6}$ alkyl-, R$^7$(CH$_2$)$_p$O—C(=O)—OC$_{1-6}$ alkyl-, R$^8$R$^9$N—C(=O)OC$_{1-6}$ alkyl-, C$_{1-6}$ alkyl-N(R$^{10}$)C(=O)O—C$_{1-6}$ alkyl-, R$^7$(CH$_2$)$_p$N(R$^{10}$)—C(=O)O—C$_{1-6}$ alkyl-, R$^8$R$^9$N—C$_{1-6}$ alkyl-, R$^{13}$R$^{13}$N—C$_{1-6}$ alkyl-, R$^7$—C$_{1-6}$ alkyl-, C$_{1-6}$ acylN(R$^{13}$)—C$_{1-6}$ alkyl-, R$^7$—C$_{1-6}$ acylN(R$^{10}$)—C$_{1-6}$ alkyl-, R$^7$—(CH$_2$)$_p$C(=O)(N(R$^{10}$)—C$_{1-6}$ alkyl-, R$^7$—C$_{0-6}$ alkylC(=O)N(R$^{10}$)—C$_{1-6}$ alkyl-, C$_{1-6}$ alkoxy-C(=O)N(R$^{10}$)—C$_{1-6}$ alkyl-, R$^7$—(CH$_2$)$_p$OC(=O)N(R$^{10}$)C$_{1-6}$ alkyl-, R$^8$R$^9$NC(=O)N(R$^{10}$)C$_{1-6}$ alkyl-, R$^{10}$SO$_2$—N(R$^{10}$)—C$_{1-6}$ alkyl-, R$^7$—SO$_2$—N(R$^{10}$)—C$_{1-6}$ alkyl-, C$_{1-6}$ alkylS(O)$_x$—C$_{1-6}$ alkyl-, R$^7$—(CH$_2$)$_p$S(O)$_x$C$_{1-6}$ alkyl-, R$^7$SO$_2$C$_{1-6}$ alkyl-, C$_{1-6}$ alkylS(=O)(=NR13)-C$_{1-6}$ alkyl-, C$_{1-6}$ haloalkyl S(=O)(=NR$^{13}$)—C$_{1-6}$ alkyl-, C$_{1-6}$ alkylS(=NR$^{13}$)(=NR$^{13}$)—C$_{1-6}$ alkyl-, C$_{1-6}$ haloalkyl S(=NR$^{13}$)(=NR$^{13}$)—C$_{1-6}$ alkyl-, R$^7$S(=O)(=NR$^{13}$)C$_{1-6}$ alkyl-, R$^7$S(=NR$^{13}$)(=NR$^{13}$)—C$_{1-6}$ alkyl-, —C$_{2-6}$ alkenyl, —C$_{2-6}$ haloalkenyl, R$^7$—C$_{3-6}$ alkenyl-, C$_{1-6}$ alkoxy-C$_{3-6}$ alkenyl-, —C$_{2-6}$ alkynyl, —C$_{2-6}$haloalkynyl, R$^7$—C$_{2-6}$ alkynyl-, C$_{2-6}$ alkynyl-, C$_{1-6}$ acyl-, R$^7$—(CH$_2$)$_p$C(=O)—, R$^7$—C$_{1-6}$ alkyl-C(=O)—, C$_{1-6}$ hydroxyalkyl-C(=O)—, C$_{1-6}$ alkoxy-C$_{1-6}$ alkyl-C(=O)—, C$_{1-6}$ alkylS(O)$_x$—C$_{1-6}$ alkyl-C(=O)—, carboxy, —C$_{1-6}$ alkoxycarbonyl, R$^7$—(CH$_2$)$_p$oxycarbonyl-, —C(=O)NR$^8$R$^9$, R$^7$—(CH$_2$)$_p$—N(R$^{10}$)—C(=O)—, hydroxyl, —C$_{1-6}$ alkoxy, —C$_{1-6}$haloalkoxy, C$_{1-6}$ alkyl-N(R$^{10}$)$_p$C(=O)—C$_{1-6}$ alkoxy-, R$^7$(CH$_2$)$_p$O—, R$^7$(CH$_2$)$_p$OC(=O))OC$_{2-6}$ alkoxy-, R$^7$(CH$_2$)$_p$N(R$^{10}$)—C(=O)O—C$_{2-6}$ alkoxy-, R$^8$R$^9$N—C(=O)OC$_{2-6}$ alkoxy-, C$_{1-6}$ alkoxy-C(=O)N(R$^{10}$)—C$_{2-6}$ alkoxy-, R$^7$—(CH$_2$)$_p$OC(=O)N(R$^{10}$)C$_{2-6}$ alkoxy-, R$^8$R$^9$NC(=O)N(R$^{10}$)C$_{2-6}$ alkoxy-, C$_{1-6}$ alkoxycarbonylC$_{1-6}$ alkoxy-, R$^7$(CH$_2$)$_p$ OC(=O)C$_{1-6}$ alkoxy-, C$_{1-6}$ acyloxy, R$^7$—(CH$_2$)$_p$C(=O)O—, —NR$^8$R$^9$, —NR$^{13}$R$^{13}$, R$^8$R$^9$N—C$_{2-6}$alkyl-N(R$^{10}$)—, R$^7$—C$_{2-6}$alkyl-N(R$^{10}$)—, C$_{1-6}$ acyl-N(R$^{10}$)—, C$_{1-6}$ alkoxycarbonyl-N(R$^{10}$)—, R$^8$R$^9$ N—C(=O)—N(R$^{10}$)—, R$^7$—C$_{1-6}$acyl-N(R$^{10}$)—, C$_{1-6}$ alkylS(O)$_2$—N(R$^{10}$)—, R$^{10}$S(O)$_2$—N(R$^{10}$)—, C$_{1-6}$ haloalkylS(O)$_2$—N(R$^{10}$)—, R$^7$SO$_2$—N(R$^{10}$)—, thio, C$_{1-6}$ alkylS(O)$_x$—, C$_{1-6}$haloalkylS(O)$_x$—, R$^7$—(CH$_2$)$_p$S(O)$_2$—, R$^7$SO$_2$—, C$_{1-6}$ alkyl-S(=O)(=NR$^{13}$)—, C$_{1-6}$ haloalkyl-S(=O)(=NR$^{13}$)—, C$_{1-6}$ alkylS(=O)(=NR$^{13}$)(=NR$^{13}$)—, C$_{1-6}$ haloalkyl-S(=NR$^{13}$)(=NR$^{13}$)—, R$^7$S(=O)(=NR$^{13}$)—, R$^7$S(=NR$^{13}$)(=NR$^{13}$)—, C$_{6-12}$ aryl, C$_6$-C$_{12}$ aryl-C$_1$-C$_6$ alkyl-, 5-12 membered heteroaryl, 5-12 membered heteroaryl-C$_1$-C$_6$ alkyl-, C$_{3-8}$ cycloalkyl-, C$_{3-8}$ cycloalkyl-C$_1$-C$_6$ alkyl-, C$_{3-8}$ cycloalkenyl-, C$_{3-8}$ cycloalkenyl-C$_1$-C$_6$alkyl-, 4-12 membered monocyclic or bicyclic heterocyclyl-, or 4-12 membered monocyclic or bicyclic heterocyclyl-C$_1$-C$_6$ alkyl-;

in R$^3$, R$^5$ is H, F, CF$_3$, CHF$_2$, or C$_1$-C$_6$ alkyl;

in Y$^1$ and Y$^2$, R$^{5a}$ is H, F, Cl, CF$_3$, CHF$_2$, CF$_2$C$_{1-6}$ alkyl, CF$_2$CH$_2$NR$^8$R$^9$, CH$_2$NR$^8$R$^9$, CN, or C$_{1-6}$ alkyl;

in Y$^1$ and Y$^2$, R$^{6e}$ is R$^{10}$, H, F, aryl, heteroaryl, cycloalkyl, heterocycloalkyl, (CH$_2$)$_m$CHR$^{10}$R$^7$, CF$_2$(CH$_2$)$_m$CHR$^{10}$R$^7$, or C(R$^{10}$)$_2$R$^7$;

in Y$^4$ and Y$^5$, R$^{6t}$ is C$_{1-6}$ alkyl, C$_{3-6}$ cycloalkyl, aryl, heteroaryl, heterocycloalkyl, (CH$_2$)$_m$CHR$^{10}$R$^7$, C(R$^{10}$)$_2$R$^7$;

in Y$^1$ and Y$^2$, R$^{6z}$ is H, F, Cl, CF$_3$, CHF$_2$, CF$_2$C$_{1-6}$ alkyl or C$_{1-6}$ alkyl; or alternatively, in Y$^1$ and Y, R$^{6e}$ and R$^{6z}$, taken together, form R$^{6e}$R$^{6z}$C=; or alternatively, in Y$^1$ and Y$^2$, R$^{6e}$ and R$^{6z}$, taken together with the sp$^2$ carbon atom to which both are attached, form an alicyclic ring of 4 to 7 members wherein one of the ring atoms are optionally replaced by NR$^8$, O, S(O)$_x$, S(=O)(=NR$^8$), P=O, P(=O)(OR$^8$), OP(=O)(OR$^8$)O, and the alicyclic ring is optionally substituted with one or more substituents selected from the group consisting of halogen, oxo, OH, OR$^8$, and NR$^8$R$^9$;

R$^7$ is OH, NR$^8$R$^9$, O(CH$_2$)$_q$NR$^8$R$^9$, C$_{1-6}$ alkoxy, C$_{1-6}$ alkoxy-C$_{1-6}$ alkoxy, C$_{2-6}$ hydroxyalkoxy, oxetanyl, oxetanyloxy, oxetanylamino, oxolanyl, oxolanyloxy, oxolanylamino, oxanyl oxanyloxy, oxanylamino, oxepanyl, oxepanyloxy, oxepanylamino, azetidinyl, azetidinyloxy, azetidylamino, pyrrolidinyl, pyrolidinyloxy, pyrrolidinylamino, piperidinyl, piperidinyloxy, piperidinylamino, azepanyl, azepanyloxy, azepanylamino, dioxolanyl, dioxanyl, morpholino, thiomorpholino, thiomorpholino-S,S-dioxide, piperazino, dioxepanyl, dioxcpanyloxy, dioxcpanylamino, oxazepanyl, oxazepanyloxy, oxazepanylamino, diazepanyl, diazepanyloxy, diazepanylamino, (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5diazaspiro[3.4]oct-2-yl, (3aR,6aR)-5-methylhexa-hydro-pyrrolo[3,4-b]pyrrol-(2H)-yl, I-methyl-1,2,3,6-tetrahydropyridin-4-yl, 4-methylpiperizin-1-yl, 4-[2(dimethylamino)-2-oxoethyl]piperazin-1-yl, methyl[2-(4-methylpiperazin-1yl)ethyl]amino, methyl[2-(morpholin-4-yl)ethyl]amino, 1-amino-1,2,3,6tetrahydropyridin-4-yl, 4-[(2S)-2-aminopropanoyl]piperazin-1-yl, all of which may be optionally substituted with OH, OR$^{10}$, oxo, halogen, R$^{10}$, CH$_2$OR$^{10}$, or CH$_2$NR$^8$R$^9$;

R$^8$ and R$^9$ are independently H, —CD$_3$, C$_{1-6}$ alkyl, C$_{1-6}$ haloalkyl, C$_{3-6}$ alkenyl, C$_{3-6}$ haloalkenyl, C$_{3-6}$ alkynyl, C$_3$-C$_6$ haloalkynyl, C$_{3-8}$ cycloalkyl, C$_{3-8}$ cycloalkyl-C$_1$-C$_6$ alkyl-, C$_{3-8}$ halocycloalkyl, C$_{3-8}$ halocycloalkyl-C$_1$-C$_6$ alkyl-, C$_{3-6}$ cycloalkenyl, C$_{3-8}$ cycloalkenyl-C$_1$-C$_6$ alkyl-, C$_{3-8}$ halocycloalkenyl, C$_{3-8}$ halocycloalkenyl-C$_1$-C$_6$ alkyl-, C$_1$-C$_6$ acyl. C$_1$-C$_6$ acyl-C$_1$-C$_6$ alkyl-, 4-12 membered monocyclic or bicyclic heterocyclyl, 4-12 membered monocyclic or bicyclic heterocyclyl-C$_1$-C$_6$ alkyl-, C$_6$-C$_{12}$ aryl, C$_6$-C$_{12}$ aryl-C$_1$-C$_6$ alkyl-, 5-12 membered heteroaryl, or 5-12 membered heteroaryl-C$_1$-C$_6$ alkyl-; and R$^8$ and R$^9$ may be further independently substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, and the heterocyclic ring is optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, $-CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$;

each $R^{11}$ is independently hydrogen, $C_1$-$C_6$ alkyl, $C_3$-$C_6$ alkenyl, $C_3$-$C_6$ alkynyl, $C_3$-$C_6$ cycloalkyl, $C_6$-$C_{12}$ aryl, 4-12 membered heterocyclyl, or 5-12 membered heteroaryl; or alternatively, two $R^{11}$, taken together with the heteroatom(s) attached thereto, form a 5-8 membered heterocyclyl ring, which is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl $C_{1-6}$ alkoxy-$C_{1-6}$ alkoxy, $C_{2-6}$ hydroxyalkoxy, oxo, thiono, cyano and halo;

each $R^{12}$ is independently selected from $C_1$-$C_6$ alkyl, $C_2$-$C_6$ alkenyl, $C_2$-$C_6$ alkynyl, $C_3$-$C_6$ cycloalkyl, $C_6$-$C_{12}$ aryl, 4-12 membered heterocyclyl, and 5-12 membered heteroaryl;

each $R^{13}$ is independently H, $-CD_3$, cyano, $-C_{1-6}$ alkyl, $-C_{1-6}$ haloalkyl, $C_{1-6}$ acyl-$C_{1-6}$ alkyl-, $R^7-(CH_2)_pC(=O)-C_{1-6}$ alkyl-, carboxy-$C_{1-6}$ alkyl-, $C_{1-6}$ alkyloxycarbonyl-$C_{1-6}$ alkyl-, $R^7-(CH_2)_pO-C(=O)-C_{1-6}$ alkyl-, $R^8R^9N-C(=O)C_{1-6}$ alkyl-, $R^7-C_{2-6}$ alkyl-$N(R^{10})-C(=O)C_{1-6}$ alkyl-, $-C_{2-6}$ hydroxyalkyl, $C_{1-6}$ alkoxy-$C_{2-6}$ alkyl-, $R^7(CH_2)_pOC_{2-6}$ alkyl-, $C_{1-6}$ acyloxy-$C_{2-6}$ alkyl-, $R^7-(CH_2)C(=O)O-C_{2-6}$ alkyl-, $C_{1-6}$ alkoxy-$C(=O)O-C_{2-6}$ alkyl-, $R^7(CH_2)_pO-C(=O)-OC_{2-6}$ alkyl-, $R^8R^9N-C(=O)OC_{2-6}$ alkyl-, $C_{1-6}$ alkyl-$N(R^{10})C(=O)O-C_{2-6}$ alkyl-, $R^7(CH_2)_pN(R^{10})-C(=O)O-C_{2-6}$ alkyl-, $R^8R^9N-C_{2-6}$ alkyl-, $R^7-C_{2-6}$ alkyl-, $C_{1-6}$ acyl$N(R^{10})-C_{2-6}$ alkyl-, $R^7-C_{1-6}$ acyl$N(R^{10})-C_{2-6}$ alkyl-, $R^7-(CH_2)_pC(=O)N(R^{10})-C_{2-6}$ alkyl-, $R^7-C_6$ alkylC(=O)N(R^{10})-C_{2-6}$ alkyl-, $C_{1-6}$ alkoxy-$C(=O)N(R^{10})-C_{2-4}$ alkyl-, $R^7-(CH_2)_pOC(=O)N(R^{10})C_{2-6}$ alkyl-, $R^8R^9NC(=O)N(R^{10})C_{2-6}$ alkyl-, $R^{10}SO_2-N(R^{10})-C_{2-6}$ alkyl-, $R^7-SO_2-N(R^{10})-C_{2-6}$ alkyl-, $C_{1-6}$ alkylS(O)-$C_{2-6}$ alkyl-, $R^7-(CH_2)_pS(O)_xC_{2-6}$ alkyl-, $R^7SO_2C_{2-6}$ alkyl-, $C_{1-6}$ alkylS(=O)(=N R^{10})-C_{2-6}$ alkyl-, $C_{1-6}$ haloalkyl $S(=O)(=N R^{10})-C_{2-6}$ alkyl-, $C_{1-6}$ alkylS(=N R^{10})(=N R^{10})-C_{2-6}$ alkyl-, $C_{1-6}$ haloalkyl $S(=N R^{10})(=N R^{10})-C_{2-6}$ alkyl-, $R^7S(=O)(=N R^{10})C_{2-6}$ alkyl-, $R^7S(=NR^{13})(=NR^{13})-C_{2-6}$ alkyl-, $-C_{3-6}$ alkenyl, $-C_{3-6}$ haloalkenyl. $R^7-C_{4-6}$ alkenyl-, $C_{1-6}$ alkoxy-$C_{4-6}$ alkenyl-, $-C_{2-6}$ alkynyl, $-C_{2-6}$ haloalkynyl, $R^7-C_{2-6}$ alkynyl-, $C_{2-6}$ alkynyl-, $C_{1-6}$ acyl-, $R^7-(CH_2)_pC(=O)-$, $R^7-C_{1-6}$ alkyl-$C(=O)-$, $C_{1-6}$ hydroxyalkyl-$C(=O)-$, $C_{1-6}$ alkoxy-$C_{1-6}$ alkyl-$C(=O)-$, $C_{1-6}$ alkylS(O)$_x-C_{1-6}$ alkyl-$C(=O)-$, $-C_{1-6}$ alkoxycarbonyl, $R^7-(CH_2)_p$oxycarbonyl-, $-C(=O)NR^8R^9$, $R^7-(CH_2)_p-N(R^{10})-C(=O)-$, hydroxyl, $-C_{1-6}$ alkoxy, $-C_{1-6}$ haloalkoxy, $C_{1-6}$ alkyl-$N(R^{10})_pC(=O)-C_{1-6}$ alkoxy-, $R^7(CH_2)_pO-$, $R^7(CH_2)_pOC(=O)OC_{2-6}$ alkoxy-, $R^7(CH_2)_pN(R^{10})-C(=O)O-C_{2-6}$ alkoxy-, $R^8R^9N-C(=O)OC_{2-6}$ alkoxy-, $C_{1-6}$ alkoxy-$C(=O)N(R^{10})-C_{2-6}$ alkoxy-, $R^7-(CH_2)_pOC(=O)N(R^{10})C_{2-6}$ alkoxy-, $R^8R^9NC(=O)N(R^{10})C_{2-6}$ alkoxy-, $C_{1-6}$ alkoxycarbonyl$C_{1-6}$ alkoxy-, $R^7(CH_2)_pOC(=O)C_{1-6}$ alkoxy-, $C_{1-6}$ acyloxy, $R^7-(CH_2)_pC(=O)O-$, $-NR^8R^9$, $R^8R^9N-C_{2-6}$alkyl-$N(R^{10})-$, $R^7-C_{2-6}$alkyl-$N(R^{10})-$, $C_{1-6}$ acyl-$N(R^{10})-$, $C_{1-6}$ alkoxycarbonyl-$N(R^{10})-$, $R^8R^9 N-C(=O)-N(R^{10})-$, $R^7-C_{1-6}$acyl-$N(R^{10})-$, $C_{1-6}$ alkylS(O)$_2-N(R^7-$, $R^{10}S(O)_2-N(R^{10})-$, $C_{1-6}$ haloalkylS(O)$_2-N(R^{10})-$, $R^7SO_2-N(R^{10})-$, $C_{1-6}$ alkylS(O)$_x-$, $C_{1-6}$ haloalkylS(O)$_x-$, $R^7-(CH_2)_pS(O)_2$, $R^7SO_2-$, $C_{1-6}$ alkyl-$S(=O)(=N R^{10})-$, $C_{1-6}$ haloalkyl-$S(=O)(=N R^{10})-$, $C_{6-12}$ aryl, $C_6$-$C_{12}$ aryl-$C_1$-$C_6$ alkyl-, 5-12 membered heteroaryl, 5-12 membered heteroaryl-$C_1$-$C_6$ alkyl-, $C_{3-8}$ cycloalkyl-, $C_{3-8}$ cycloalkyl-$C_1$-$C_6$ alkyl-, $C_{3-8}$ cycloalkenyl-, $C_{3-8}$ cycloalkenyl-$C_1$-$C_6$ alkyl-, 4-12 membered monocyclic or bicyclic heterocyclyl-, or 4-12 membered monocyclic or bicyclic heterocyclyl-$C_1$-$C_6$alkyl-; or alternatively, two $R^4$, two $R^{13}$, or $R^{13}$ and $R^4$, taken together with atoms attached thereto, form a ring of 5-7 members, which may be aromatic or partially saturated, and which may contain up to two heteroatoms chosen from N, O and S; and the 5-7 member ring is optionally further substituted by is selected from the group consisting of $=O$ (oxo), $=S$, $=NR^{13}$, $(=O)_2$, $(O)(NR^{13})$, $R^4$, and $R^{13}$;

m is 0, 1, 2, or 3;

n=1, 2, or 3;

p=0, 1, 2, 3, or 4;

q=2, 3, or 4; and x=0, 1, or 2.

In one embodiment, the compounds of Formula (I) exclude the compounds exemplified in CN 105085489 A, WO 2015/127872, WO2013/014448, CN 105001208 A, CN 104844580 A, WO 2015/175632, WO 2015/188777, WO 2016/105525, WO02016060443, WO 2016/029839, WO 2016/054987, WO 2016/015453, WO 2016/070816, and/or WO 2015/195228.

In one embodiment, the compounds of Formula (I) exclude the compounds exemplified in CN 104761585 A and/or CN 104761544 A.

In one embodiment, the compound of the present disclosure relates to compound of formula (IB):

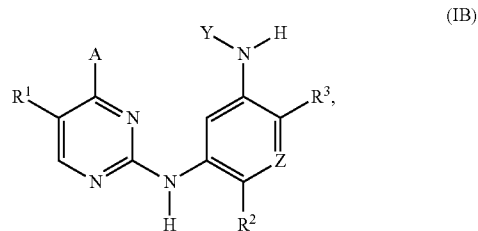

(IB)

or a stereoisomer or a pharmaceutically acceptable salt, solvate, ester, tautomer, or prodrug thereof;

wherein,

A is

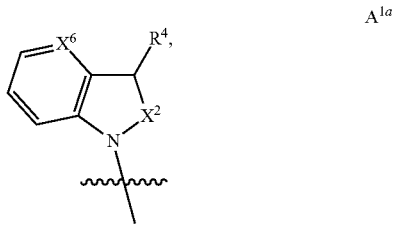

$A^{1a}$

-continued

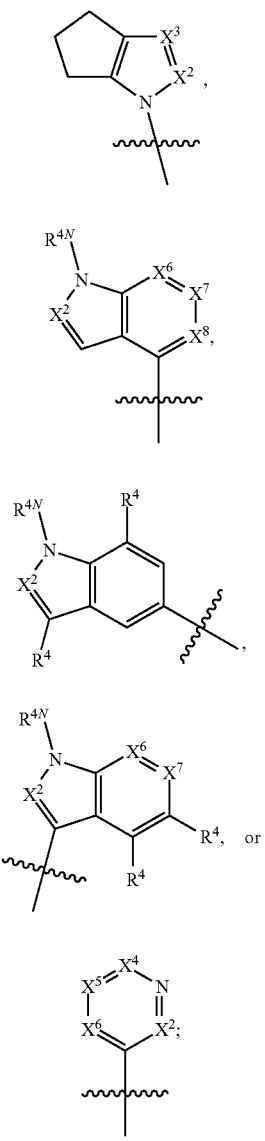

$A^{2a}$, $A^{4a'}$, $A^{4b'}$, $A^{1b}$, $A^{5a}$ each of $X^2$, $X^3$, $X^4$, $X^5$, $X^6$, $X^7$, and $X^8$ is independently $CR^4$ or N; wherein not more than two of $X^2$, $X^3$, $X^4$, $X^5$, $X^6$, $X^7$, and $X^8$ are N:

each of $X^{10}$ and $X^{12}$ is independently S, N, or $CR^4$; wherein at least one of $X^{10}$ and $X^{12}$ is S;

Z is CH or N;

Y is

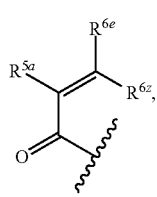

$Y^1$

-continued

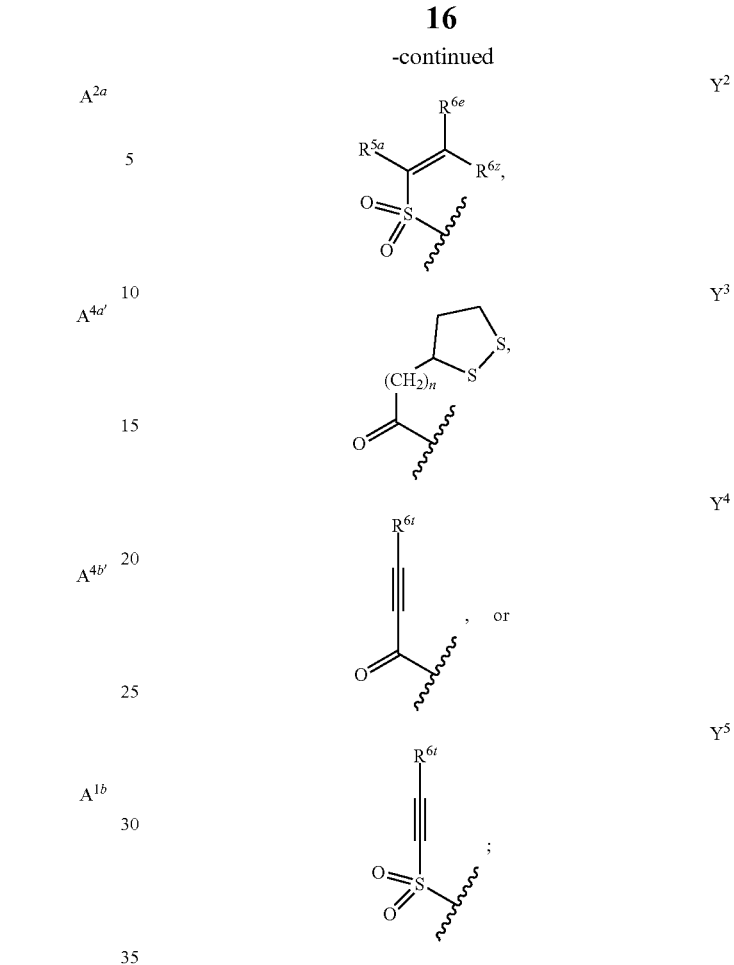

$Y^2$, $Y^3$, $Y^4$, or $Y^5$;

$R^1$ is independently selected from hydrogen, fluoro, chloro, bromo, methyl, ethyl, hydroxyl, methoxy, ethoxy, isopropoxy, cyclopropoxy, —$OCF_3$, —$OCH_2CF_3$, —$OCH_2CHF_2$, ethenyl, ethynyl, —$CF_3$, —$CHF_2$, —CHO, —$CH_2OH$, —$CONH_2$, —$CO_2Me$, —CONHMe, —$CONMe_2$, and cyano;

$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropox;

$R^3$ is —$N(R^{10})C_{2-6}$ alkyl-$NR^{10}R^{10}$, —$N(R^{10})C_{2-6}$ alkyl-$R^7$, —$O(CH_2)_pR^7$, —$N(R^{10})C(=O)(CH_2)R^7$, or $R^7$;

each $R^4$ is independently H, cyano, nitro, halo, —$C_{1-6}$ alkyl, —$C_{1-6}$ haloalkyl, -carboxy-$C_{1-6}$ alkyl, —$C_{1-6}$ hydroxyalkyl, $R^8R^9N$—$C_{1-6}$ alkyl-, —$C_{2-6}$ alkenyl, —$C_{2-6}$ alkynyl, $C_{1-6}$ acyl-, $R^7$—$(CH_2)_pC(=O)$—, $C_{1-6}$ hydroxyalkyl-C(=O)—, carboxy, —$C_{1-6}$ alkoxycarbonyl, —$C(=O)NR^8R^9$, hydroxyl, —$C_{1-6}$ alkoxy, —$C_{1-6}$ acyloxy, —$NR^8R^9$, $C_{1-6}$ acyl-$N(R^{10})$—, pyrazole, 123-triazole, tetrazole, ($C_{1-6}$ alkyl)$SO_2$—, or $R^7SO_2$—;

$R^{4N}$ is H, —$CD_3$, —$C_{1-6}$ alkyl, —$C_{1-6}$ haloalkyl, or —$CH_2C(=O)NR^8R^9$;

in $Y^1$ and $Y^2$, $R^{5a}$ is H, F, Cl, $CF_3$, $CHF_2$, $CF_2C_{1-6}$ alkyl, $CF_2CH_2NR^8R^9$, $CH_2NR^8R^9$, CN, or $C_{1-6}$ alkyl;

in $Y^1$ and $Y^2$, $R^{6e}$ is $R^{10}$, H, F, aryl, heteroaryl, cycloalkyl, heterocycloalkyl, $(CH_2)_mCHR^{10}R^7$, $CF_2(CH_2)_mCHR^{10}R^7$, or $C(R^{10})_2R^7$;

in $Y^4$ and $Y^5$, $R^{6t}$ is $C_{1-6}$ alkyl, $C_{3-6}$ cycloalkyl, aryl, heteroaryl, heterocycloalkyl, $(CH_2)_mCHR^{10}R^7$, $C(R^{10})_2R^7$;

in $Y^1$ and $Y^2$, $R^{6z}$ is H, F, Cl, $CF_3$, $CHF_2$, $CF_2C_{1-6}$ alkyl or $C_{1-6}$ alkyl; or alternatively in Y¹ and Y², R⁶ᵉ and R⁶ᶻ, taken together, form =CR⁶ᵉ'R⁶ᶻ' (allene), wherein R⁶ᵉ' is R¹⁰, H, F, aryl, heteroaryl, cycloalkyl, heterocycloalkyl, (CH₂)ₘCHR¹⁰R⁷, CF₂(CH₂)ₘCHR¹⁰R⁷, or C(R¹⁰)₂R⁷ and wherein, R⁶ᶻ' is H, F, Cl, CF₃, CHF₂, CF₂C₁₋₆ alkyl or C₁₋₆ alkyl; or alternatively in Y¹ and Y², R⁶ᵉ and R⁶ᶻ, taken together with the sp² carbon atom to which both are attached, form an alicyclic ring of 4 to 7 members wherein one of the ring atoms are optionally replaced by NR⁸, O, S(O)ₓ, S(=O)(=NR⁸), P=O, P(=O)(OR⁸), OP(=O)OR⁸)O, and the alicyclic ring is optionally substituted with one or more substituents selected from the group consisting of halogen, oxo, OH, OR⁸, and NR⁸R⁹;

R⁷ is OH, NR⁸R⁹, O(CH₂)qNR⁸R⁹, C₁₋₆ alkoxy, C₁₋₆ alkoxy-C₁₋₆ alkoxy, C₂₋₆ hydroxyalkoxy, oxetanyl, oxetanyloxy, oxetanylamino, oxolanyl, oxolanyloxy, oxolanylamino, oxanyl oxanyloxy, oxanylamino, oxepanyl, oxepanyloxy, oxepanylamino, azetidinyl, azetidinyloxy, azetidylamino, pyrrolidinyl, pyrolidinyloxy, pyrrolidinylamino, piperidinyl, piperidinyloxy, piperidinylamino, azepanyl, azepanyloxy, azepanylamino, dioxolanyl, dioxanyl, morpholino, thiomorpholino, thiomorpholino-S,S-dioxide, piperazino, dioxepanyl, dioxcpanyloxy, dioxcpanylamino, oxazepanyl, oxazepanyloxy, oxazepanylamino, diazepanyl, diazepanyloxy, diazepanylamino, (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5diazaspiro[3.4]oct-2-yl, (3aR, 6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2(dimethylamino)-2-oxoethyl]piperazin-1-yl, methyl[2-(4-methylpiperazin-1yl)ethyl]amino, methyl[2-(morpholin-4-yl)ethyl]amino, 1-amino-1,2,3,6tetrahydropyridin-4-yl, 4-[(2S)-2-aminopropanoyl]piperazin-1-yl, all of which may be optionally substituted with OH, OR¹⁰, oxo, halogen, R¹⁰, CH₂OR¹⁰, or CH₂NR⁸R⁹;

R⁸ and R⁹ are each independently H, —CD₃, C₁₋₆ alkyl, C₃₋₆ alkenyl, C₃₋₆ alkynyl, C₃₋₈ cycloalkyl, —(C₁₋₃ alkyl)-(C₃₋₈ cycloalkyl), C₃₋₈ cycloalkenyl, C₁-C₆ acyl, 4-12 membered monocyclic or bicyclic heterocyclyl, 4-12 membered monocyclic or bicyclic heterocyclyl-C₁-C₆ alkyl-, C₆-C₁₂ aryl, 5-12 membered heteroaryl; wherein R⁸ and R⁹ may be further independently substituted with up to three substituents chosen from hydroxyl, C₁₋₆ alkoxy, C₁₋₆ hydroxyalkyl, C₁₋₆ alkoxy-C₁₋₆ alkyl, C₁₋₆ alkoxy-C₁₋₆ alkoxy, C₂₋₆ hydroxyalkoxy, oxo, thiono, cyano or halo; or alternatively, R⁸ and R⁹, taken together with the N atom to which they are both attached, form a heterocyclic ring of 4-7 members, containing up to one other heteroatom selected from O, S, or NR¹¹, or a heterobicyclic ring of 7-12 members which may be fused, bridged or spiro, and contain up to two other heteroatoms chosen from O, S(O)ₓ, or NR¹¹, and these heterocyclic rings are optionally substituted with up to three substituents chosen from hydroxyl, C₁₋₆ alkoxy, C₁₋₆ hydroxyalkyl, C₁₋₆ alkoxy-C₁₋₆ alkyl, C₁₋₆ alkoxy-C₁₋₆ alkoxy, C₂₋₆ hydroxyalkoxy, oxo, thiono, cyano or halo;

each R¹⁰ is independently H, —CD₃, C₁₋₆ alkyl, C₃₋₆ cycloalkyl, C₂₋₆ hydroxyalkyl, C₁₋₆ alkoxy-C₁₋₆ alkyl or C₂₋₆ alkyl-NR⁸R⁹;

alternatively, two R¹⁰ on the same N atom to which they are both attached, form a heterocyclic ring of 5-6 members, containing up to one other heteroatom selected from O, S, or NR¹¹;

each R¹¹ is independently hydrogen or C₁-C₆ alkyl, which is optionally substituted with up to three substituents selected from hydroxyl, oxo, thiono, cyano or halo;

m is 0, 1, 2, or 3;
p=0, 1, 2, 3, or 4;
q=2, 3, or 4; and
x=0, 1, or 2.

In one embodiment, the compound of the present disclosure relates to compounds of formula (IIIB):

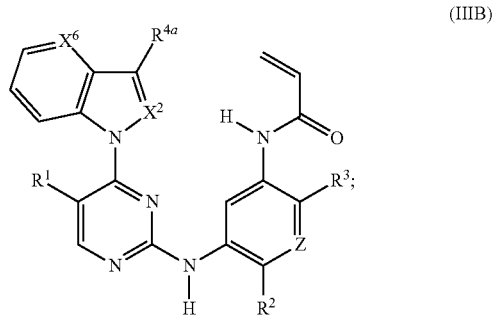

(IIIB)

or a stereoisomer or a pharmaceutically acceptable salt, solvate, ester, tautomer, or prodrug thereof;
wherein:
X² is CH, C(C₁₋₆ alkyl) or N;
X⁶ is CR⁴ or N;
Z is CH or N;
R¹ is independently selected from hydrogen, fluoro, chloro, bromo, methyl, ethyl, ethynyl, CF₃, CHF₂ or cyano;
R² is —OCF₃, —OCHF₂, —OCF₂CF₃, —OCH₂CHF₂, —OCH₂CF₃, cyclopropoxy, methoxy, —OCD₃, ethoxy, or isopropoxy;
R³ is N(R¹⁰)C₂₋₆ alkyl-NR¹⁰R¹⁰ or N(R¹⁰)C₂₋₆ alkyl-R⁷;
R⁴ is H, cyano, halo, —C₁₋₆ alkyl, or —C₁₋₆ haloalkyl;
R⁴ᵃ is, cyano, —C₁₋₆ haloalkyl, —C₁₋₆ hydroxyalkyl, —C(=O)OH, —C(=O)CH₂OH, C₁₋₆ acyl-, pyrazole, 123-triazole, tetrazole, —C(=O)NR⁸R⁹, —CH₂NR⁸R⁹, —NR⁸R⁹, C₁₋₆ acyl-N(R¹⁰)—, (C₁₋₃ alkyl)SO₂NH—, (C₁₋₆ alkyl)SO₂— or R⁷SO₂—;
R⁷ is OH, NR⁸R⁹ or —O(CH₂)qNR⁸R⁹;
R⁸ and R⁹ are independently H, —CD₃, C₁₋₆ alkyl, cyclopropyl, monocyclic or bicyclic C₄₋₈ cycloalkyl, (C₃₋₆ cycloalkyl)-(C₁₋₃ alkyl)-, C₁-C₆acyl, phenyl, monocyclic heteroaryl, or monocyclic heterocyclyl; and R⁸ and R⁹ may be further independently substituted with up to three substituents chosen from hydroxyl, C₁₋₆ alkoxy, oxo, thiono, cyano or halo; or alternatively, R⁸ and R⁹, taken together with the N atom to which they are both attached, form a heterocyclic ring of 4-7 members, containing up to one other heteroatom chosen from O, S, or NR¹¹,
each R¹⁰ is independently H, —CD₃, C₁₋₆ alkyl, C₃₋₆ cycloalkyl, C₂₋₆ hydroxyalkyl, C₂₋₆ alkyl-NR⁸R⁹;
alternatively, two R¹⁰ on the same N atom to which they are both attached, form a heterocyclic ring of 5-6 members, containing up to one other heteroatom selected from O, S, or NR¹¹;
each R¹¹ is independently hydrogen or C₁-C₆alkyl, which is optionally substituted with up to three substituents selected from hydroxyl, oxo, thiono, cyano and halo;
p=0, 1, 2, 3, or 4; and
q=2, 3, or 4.

In one embodiment of the compounds of formula (IIIB), Z is N; and
R² is —OCF₃, —OCHF₂, —OCF₂CF₃, —OCH₂CHF₂, —OCH₂CF₃, or cyclopropoxy, methoxy, —OCD₃, ethoxy, or isopropoxy.

In one embodiment, the compound of the present disclosure relates to compounds of formula (IVB):

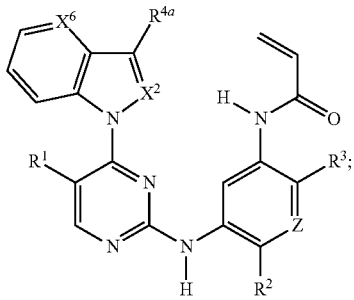

(IVB)

or a stereoisomer or a pharmaceutically acceptable salt, solvate, ester, tautomer, or prodrug thereof;
wherein
$X^2$ is CH, CCH$_3$, or N;
$X^6$ is CR$^4$ or N;
Z is CH or N;
$R^1$ is selected from hydrogen, methyl, fluoro, chloro, bromo, —CF$_3$, or cyano;
$R^2$ is —OCF$_3$, —OCHF$_2$, —OCF$_2$CF$_3$, —OCH$_2$CHF$_2$, —OCH$_2$CF$_3$, cyclopropoxy, methoxy, —OCD$_3$, ethoxy, or isopropoxy;
$R^3$ is N(R$^{10}$)C$_{2-6}$ alkyl-NR$^{10}$R$^{10}$;
$R^4$ is H, cyano, halo, —C$_{1-6}$ alkyl, —C$_{1-6}$ haloalkyl;
$R^{4a}$ is independently cyano, —C$_{1-6}$ hydroxyalkyl, C$_{1-6}$ acyl-, pyrazole, 123-triazole, tetrazole, —C(=O)NR$^8$R$^9$, —NR$^8$R$^9$, C$_{1-6}$ acyl-N(R$^{10}$)—, (C$_{1-3}$ alkyl)SO$_2$NH—, (C$_{1-6}$ alkyl)SO$_2$—, or R$^7$SO$_2$—;
$R^7$ is —OH or —NR$^8$R$^9$;
$R^8$ and $R^9$ are independently H, —CD$_3$, C$_{1-6}$ alkyl, C$_{3-8}$ cycloalkyl, C$_{3-8}$ cycloalkyl-(C$_{1-3}$ alkyl)-, C$_1$-C$_6$acyl, phenyl, monocyclic heteroaryl, or monocyclic heterocyclyl; and R$^8$ and R$^9$ may be further independently substituted with up to three substituents chosen from hydroxyl, C$_{1-6}$ alkoxy, oxo, thiono, cyano or halo; or
alternatively, R$^8$ and R$^9$, taken together with the N atom to which they are both attached, form a heterocyclic ring of 4-7 members, containing up to one other heteroatom chosen from O, S, or NR$^{11}$,
each R$^{10}$ is independently H, —CD$_3$, C$_{1-6}$ alkyl, C$_{3-6}$ cycloalkyl, C$_{2-6}$ hydroxyalkyl, C$_{2-6}$ alkyl-NR$^8$R$^9$;
alternatively, two R$^{10}$ on the same N atom to which they are both attached, form a heterocyclic ring of 5-6 members, containing up to one other heteroatom selected from O, S, or NR$^{11}$;
each R$^{11}$ is independently hydrogen or C$_1$-C$_6$ alkyl, which is optionally substituted with up to three substituents selected from hydroxyl, oxo, thiono, cyano and halo; and
q=2, 3, or 4.
In one embodiment of compounds of formula (IVB),
$X^2$ is CH, CCH$_3$, or N;
$X^6$ is CH, CCH$_3$, or N;
Z is CH or N;
$R^1$ is hydrogen, methyl, or chloro;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is —NR$^8$R$^9$;
$R^8$ and $R^9$ are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

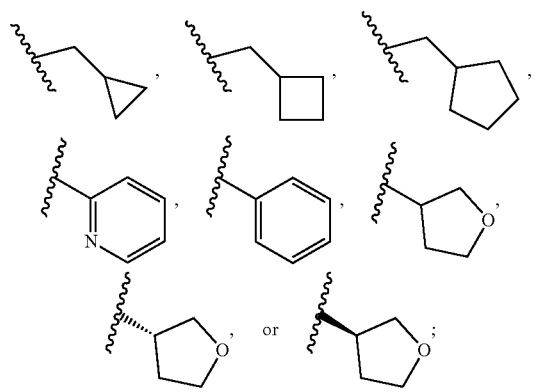

alternatively, R$^8$ and R$^9$, taken together with the N atom to which they are both attached, form a heterocyclic ring of 5-6 members, containing up to one other heteroatom chosen from O, S, or NR$^{11}$;
each R$^{10}$ is independently H, —CD$_3$, methyl, ethyl, or isopropyl; or
alternatively, two R$^{10}$ on the same N atom to which they are both attached, form a heterocyclic ring of 5-6 members, containing up to one other heteroatom selected from O, S, or NR$^{11}$.
In one embodiment of compounds of formula (IVB),
$X^2$ is CH or N;
$X^6$ is CH or N;
Z is CH or N;
$R^1$ is hydrogen;
$R^2$ is —OCH$_2$CHF$_2$, methoxy, ethoxy, or isopropoxy;
$R^3$ is —N(CH$_3$)CH$_2$CH$_2$NR$^{10}$R$^{10}$;
$R^{4a}$ is —NR$^8$R$^9$;
$R^8$ and $R^9$ are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

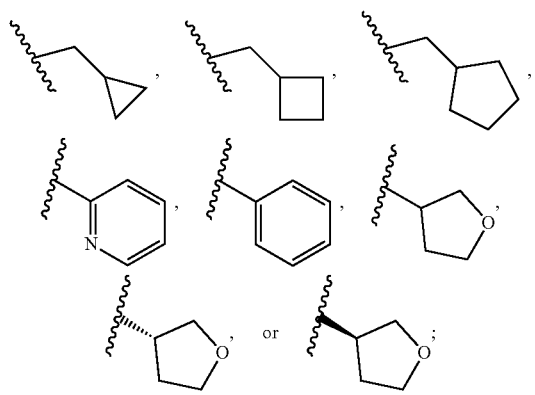

alternatively, R$^8$ and R$^9$, taken together with the N atom to which they are both attached, form a heterocyclic ring of 5-6 members, containing up to one other heteroatom chosen from O, S, or NR$^{11}$; and
each R$^{10}$ is independently H, —CD$_3$, methyl, ethyl, or isopropyl.
In one embodiment of compounds of formula (IVB),
$X^2$ is N;
$X^6$ is CH, CCH$_3$, or N;
Z is CH or N;
$R^1$ is hydrogen, methyl, or chloro;

$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is —NR$^8$R$^9$;
$R^8$ and $R^9$ are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

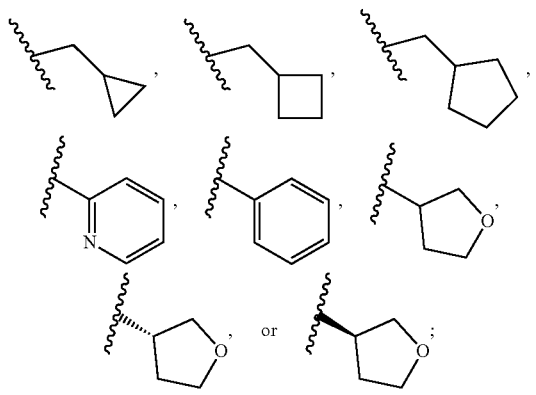

or
alternatively, $R^8$ and $R^9$, taken together with the N atom to which they are both attached, form a heterocyclic ring of 5-6 members, containing up to one other heteroatom chosen from O, S, or NR$^{11}$; and
each $R^{10}$ is independently H, —CD$_3$, methyl, ethyl, or isopropyl; or
alternatively, two $R^{10}$ on the same N atom to which they are both attached, form a heterocyclic ring of 5-6 members, containing up to one other heteroatom selected from O, S, or NR$^{13}$.

In one embodiment of compounds of formula (IVB),
$X^2$ is N;
$X^6$ is CH or N;
Z is CH or N;
$R^1$ is hydrogen;
$R^2$ is —OCH$_2$CHF$_2$, methoxy, ethoxy, or isopropoxy;
$R^3$ is —N(CH$_3$)CH$_2$CH$_2$NR$^{10}$R$^{10}$;
$R^{4a}$ is —NR$^8$R$^9$;
$R^8$ and $R^9$ are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

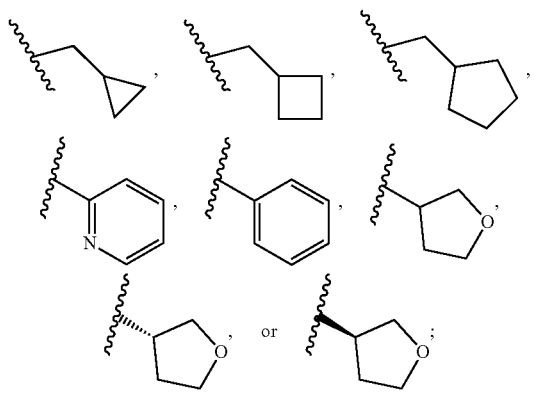

alternatively, $R^8$ and $R^9$, taken together with the N atom to which they are both attached, form a heterocyclic ring of 5-6 members, containing up to one other heteroatom chosen from O, S, or NR$^{11}$; and
each $R^{10}$ is independently H, —CD$_3$, methyl, ethyl, or isopropyl.

In one embodiment of compounds of formula (IVB),
$X^2$ is N or CH;
$X^6$ is CH;
Z is CH;
$R^1$ is hydrogen;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is N(CH$_3$)CH$_2$CH$_2$NR$^{10}$R$^{10}$;
$R^{4a}$ is —CH$_2$OH, —CH(OH)CH$_3$), —C(OH)(CH$_3$)$_2$, —CH(OH)(CH$_2$CH$_3$), —C(OH)(CH$_2$CH$_3$)$_2$, or —C(OH)(CH$_3$)(CH$_2$CH$_3$); and
each $R^{11}$ is independently H, —CD$_3$, methyl, ethyl, or isopropyl.

In one embodiment of compounds of formula (IVB),
$X^2$ is N or CH;
$X^6$ is CH;
Z is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ is —CH$_2$OH, —CH(OH)(CH$_3$), or —C(OH)(CH$_3$)$_2$; and
each $R^{10}$ is independently H, —CD$_3$, methyl, ethyl, or isopropyl.

In one embodiment of compounds of formula (IVB),
$X^2$ is N or CH;
$X^6$ is CH, CCH$_3$, or N;
Z is CH;
$R^1$ is hydrogen;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is —C(=O)NR$^8$R$^9$;
$R^8$ and $R^9$ are independently H, —CD$_3$, methyl, ethyl, or isopropyl; and
each $R^{10}$ is independently H, —CD$_3$, methyl, ethyl, or isopropyl; or
alternatively, two $R^{10}$ on the same N atom to which they are both attached, form a heterocyclic ring of 5-6 members, containing up to one other heteroatom selected from O, S, or NR$^{11}$.

In one embodiment of compounds of formula (IVB),
$X^2$ is N or CH;
$X^6$ is N or CH;
Z is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ is —C(=O)NR$^8$R$^9$;
$R^8$ and $R^9$ are independently H, —CD$_3$, methyl, ethyl, or isopropyl; and
each $R^{10}$ is independently H, —CD$_3$, methyl, ethyl, or isopropyl.

In one embodiment of compounds of formula (IVB), $R^2$ is —OCH$_2$CHF$_2$, —OCH$_2$CF$_3$, cyclopropoxy, methoxy, —OCD$_3$, ethoxy, or isopropoxy.

In one embodiment, the compound of the present disclosure relates to compounds of formula (VB):

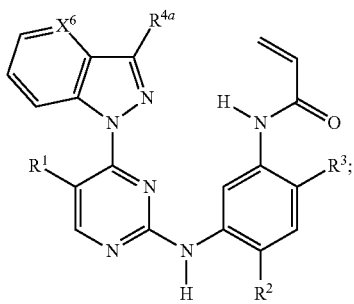

(VB)

or a stereoisomer or a pharmaceutically acceptable salt, solvate, ester, tautomer, or prodrug thereof;
wherein
$X^6$ is $CR^4$ or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^4$ is H, cyano, halo, —$C_{1-6}$ alkyl, or —$C_{1-6}$ haloalkyl;
$R^{4a}$ is cyano, —$C_{1-6}$ haloalkyl, —$C_{1-6}$ hydroxyalkyl, —C(=O)$NR^8R^9$, —$CH_2NR^8R^9$, —$NR^8R^9$, $C_{1-6}$ acyl-N($R^{10}$)—, ($C_{1-3}$ alkyl)$SO_2NH$—, ($C_{1-6}$ alkyl)$SO_2$— or $R^7SO_2$—;
$R^7$ is —$NR^8R^9$;
$R^8$ and $R^9$ are independently H, —$CD_3$, $C_{1-6}$ alkyl, cyclopropyl, monocyclic or bicyclic $C_{4-8}$ cycloalkyl, —($C_{1-3}$ alkyl)-($C_{3-8}$ cycloalkyl), $C_1$-$C_6$ acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or
alternatively, $R^8$ and $R^9$, taken together with the N atom to which they are both attached, form a heterocyclic ring of 4-7 members, containing up to one other heteroatom chosen from O, S, or $NR^{11}$; and
each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (VB),
$X^6$ is CH, $CCH_3$, or N;
$R^1$ is hydrogen, methyl, or chloro;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, cyclopropyl, —C(=O)$CH_3$, —C(=O)$CH_2CH_3$, —C(=O)CH($CH_3$)$_2$,

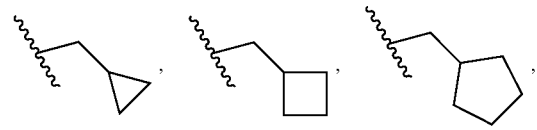

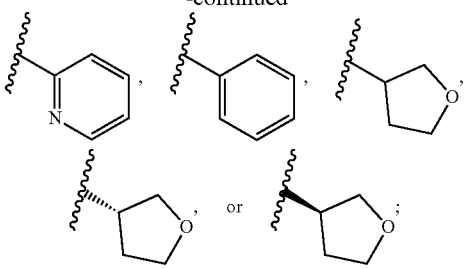

alternatively, $R^8$ and $R^9$, taken together with the N atom to which they are both attached, form a heterocyclic ring of 5-6 members, containing up to one other heteroatom chosen from O, S, or $NR^{11}$,
each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VB),
$X^6$ is CH or N;
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, cyclopropyl, —C(=O)$CH_3$, —C(=O)$CH_2CH_3$, —C(=O)CH($CH_3$)$_2$,

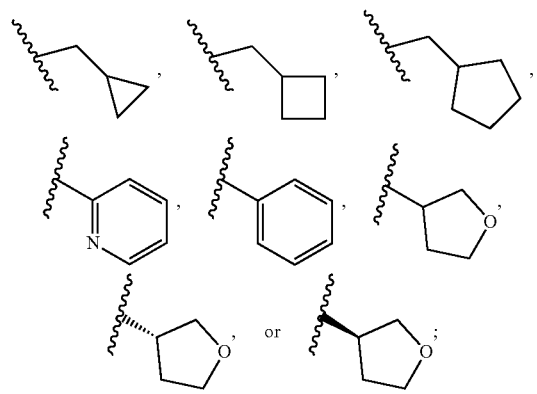

alternatively, $R^8$ and $R^9$, taken together with the N atom to which they are both attached, form a heterocyclic ring of 5-6 members, containing up to one other heteroatom chosen from O, S, or $NR^{11}$; and
each $R^{10}$ is independently H, —$CD_3$, methyl, ethyl, or isopropyl.

In one embodiment of compounds of formula (VB),
$X^6$ is CH;
$R^1$ is hydrogen, methyl, or chloro;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, cyclopropyl, —C(=O)$CH_3$, —C(=O)$CH_2CH_3$, —C(=O)CH($CH_3$)$_2$,

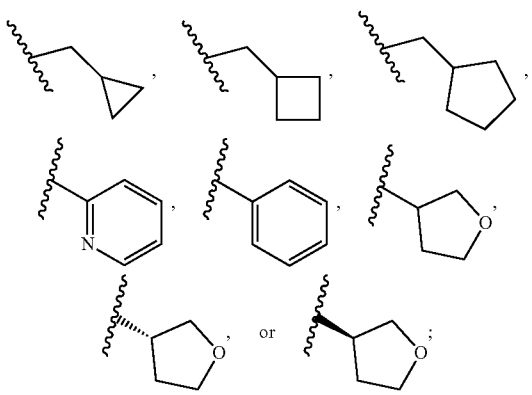

alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, $-CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VB),
$X^6$ is CH;
$R^1$ is hydrogen;
$R^2$ is methoxy, ethoxy, or isopropoxy;
$R^3$ is $-N(CH_3)CH_2CH_2NR^{10}R^{10}$;
$R^{4a}$ is $-NR^8R^9$;
$R^8$ and $R^9$ are independently H, $-CD_3$, methyl, ethyl, isopropyl, cyclopropyl, $-C(=O)CH_3$, $-C(=O)CH_2CH_3$, $-C(=O)CH(CH_3)_2$,

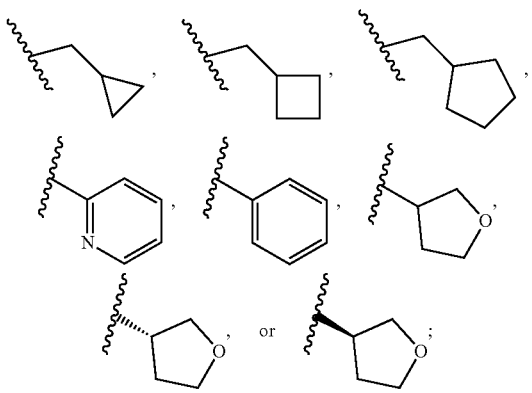

alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, $-CD_3$, methyl, ethyl, or isopropyl.

In one embodiment of compounds of formula (VB),
$X^6$ is N;
$R^1$ is hydrogen;
$R^2$ is $-OCF_3$, $-OCHF_2$, $-OCH_2CHF_2$, $-OCH_2CF_3$, cyclopropoxy, methoxy, ethoxy, or isopropoxy;
$R^3$ is $-N(CH_3)CH_2CH_2NR^{10}R^{10}$;
$R^{4a}$ is $-NR^8R^9$;
$R^8$ and $R^9$ are independently H, $-CD_3$, methyl, ethyl, or isopropyl; or alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, $-CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VB),
$X^6$ is N;
$R^1$ is hydrogen;
$R^2$ is methoxy, ethoxy, or isopropoxy;
$R^3$ is $-N(CH_3)CH_2CH_2NR^{10}R^{10}$;
$R^{4a}$ is $-NR^8R^9$;
$R^8$ and $R^9$ are independently H, $-CD_3$, methyl, ethyl, or isopropyl; and
each $R^{10}$ is independently H, $-CD_3$, methyl, ethyl, or isopropyl.

In one embodiment of compounds of formula (VB).
$X^6$ is CH;
$R^1$ is hydrogen;
$R^2$ is $-OCF_3$, $-OCHF_2$, $-OCH_2CHF_2$, $-OCH_2CF_3$, cyclopropoxy, methoxy, ethoxy, or isopropoxy;
$R^3$ is $-N(CH_3)CH_2CH_2NR^{10}R^{10}$;
$R^{4a}$ is $-CH_2OH$, $-CH(OH)(CH_3)$, $-C(OH)(CH_3)_2$, $-CH(OH)(CH_2CH_3)$, $-C(OH)(CH_2CH_3)_2$, or $-C(OH)(CH_3)(CH_2CH_3)$; and
each $R^{10}$ is independently H, $-CD_3$, methyl, ethyl, or isopropyl.

In one embodiment of compounds of formula (VB),
$X^6$ is CH;
$R^1$ is hydrogen;
$R^2$ is methoxy, ethoxy, or isopropoxy;
$R^3$ is $-N(CH_3)CH_2CH_2NR^{10}R^{10}$;
$R^{4a}$ is $-CH_2OH$, $-CH(OH)(CH_3)$, or $-C(OH)(CH_3)_2$; and
each $R^{10}$ is independently H, $-CD_3$, methyl, ethyl, or isopropyl.

In one embodiment of compounds of formula (IVB) or formula (VB), $R^2$ is $-OCH_2CHF_2$, $-OCH_2CF_3$, methoxy, $-OCD_3$, or ethoxy.

In one embodiment of compounds of formula (IVB) or formula (VB), $R^3$ is $-N(CH_3)CH_2CH_2N(R^{10})_2$. In another embodiment, $R^3$ is $-N(CH_3)CH_2CH_2N(CH_3)_2$.

In one embodiment of compounds of formula (NB) or formula (VB), $R^{10}$ is H, $-CH_3$, $-CD_3$, $-CH_2CH_3$, or isopropyl.

In one embodiment of compounds of formula (NB) or formula (VB), $R^{4a}$ is $-NR^8R^9$ or $-C(=O)NR^8R^9$. In another embodiment, $R^{4a}$ is $-C_{1-6}$ hydroxyalkyl.

In one embodiment of compounds of formula (IVB) or formula (VB), $R^8$ and $R^9$ are independently H, $-CH_3$, $-CD_3$, $-CH_2CH_3$, isopropyl, cyclopropyl, $-C(=O)CH_3$, $-C(=O)CH_2CH_3$, $-C(=O)CH(CH_3)_2$,

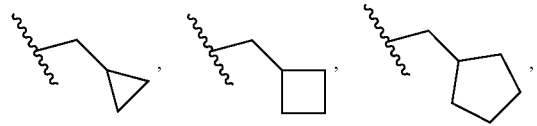

-continued
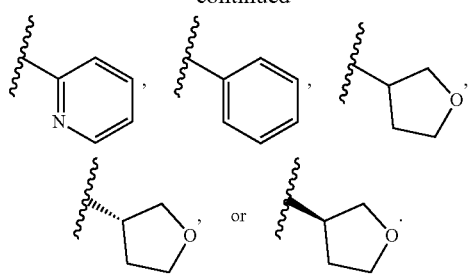
In another embodiment, $R^8$ and $R^9$ are independently H, —CH$_3$, —CD$_3$, —CH$_2$CH$_3$, or isopropyl.
In one embodiment of compounds of formula (IVB) or formula (VB), $X^6$ is N, CH, or C(CH$_3$).
In one embodiment of compounds of f formula (VB), a compound is selected from:
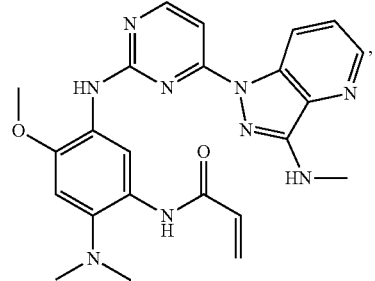
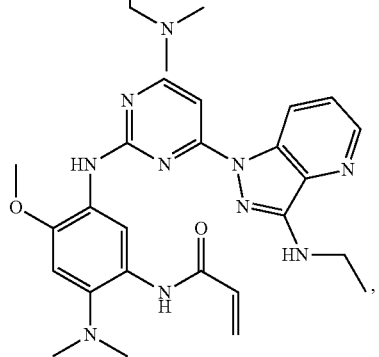
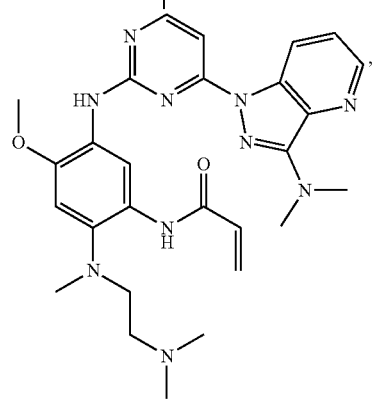
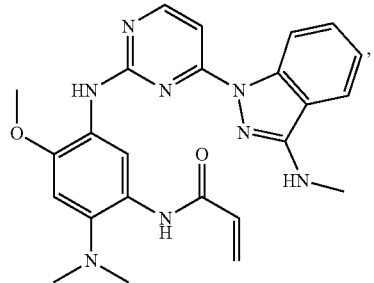
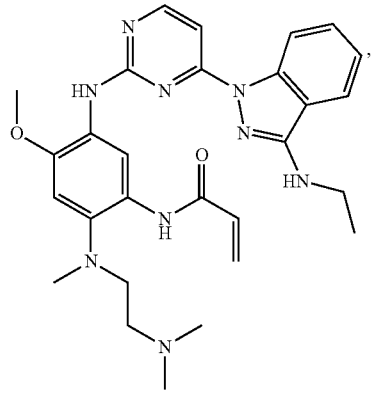
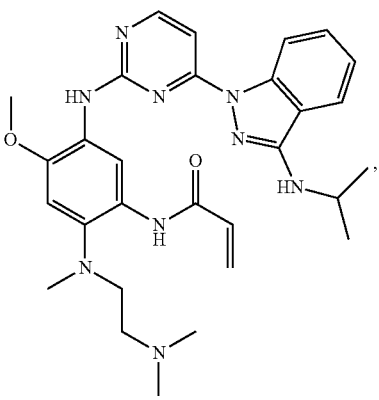
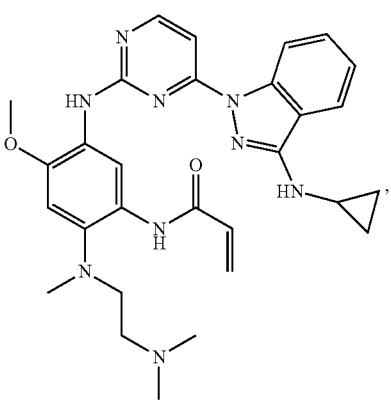

-continued
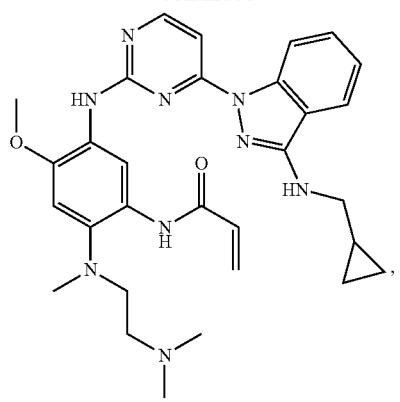
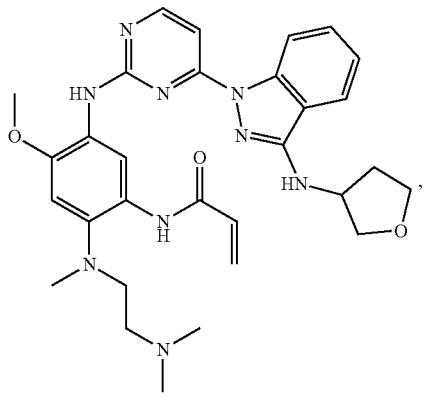
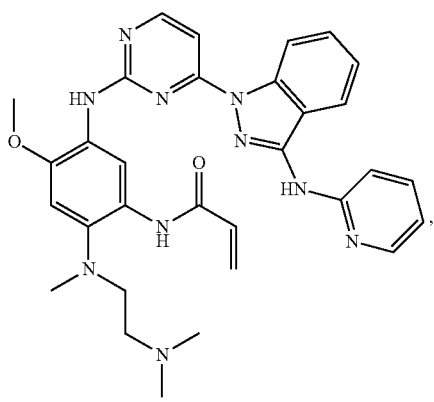
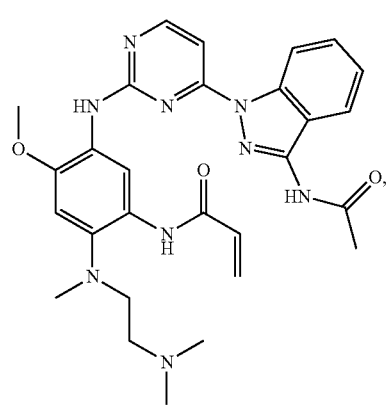
-continued
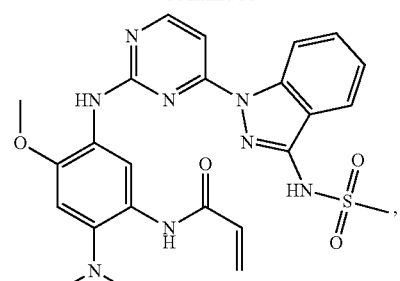
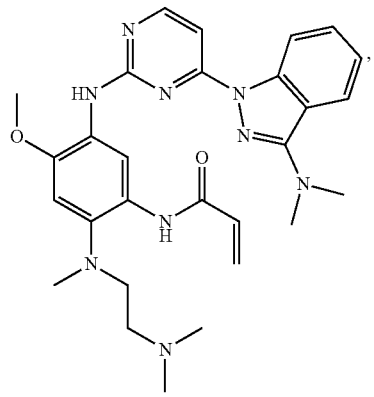
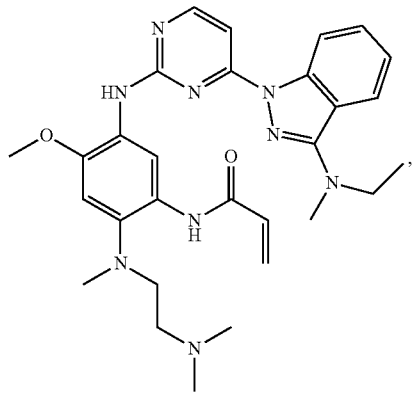
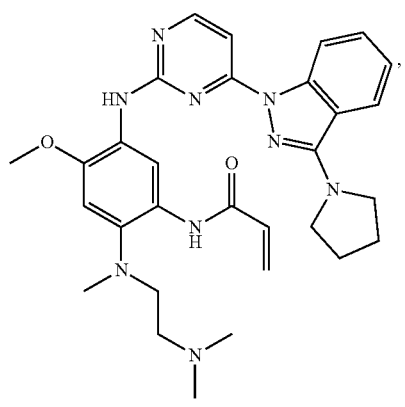

31
-continued
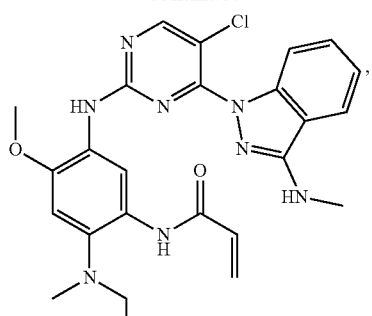
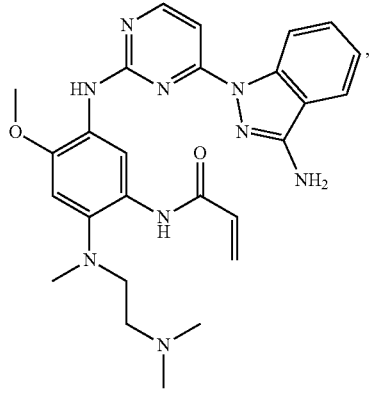
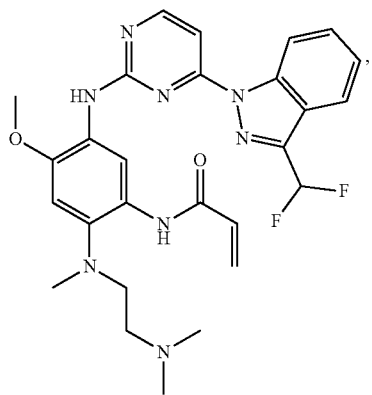
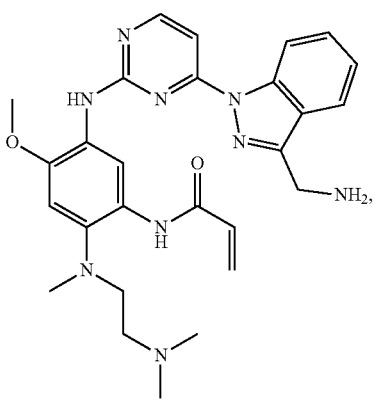
32
-continued
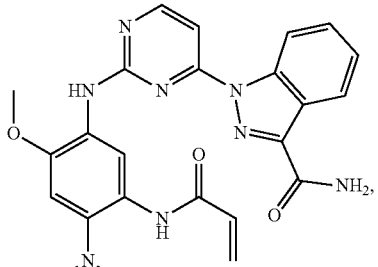
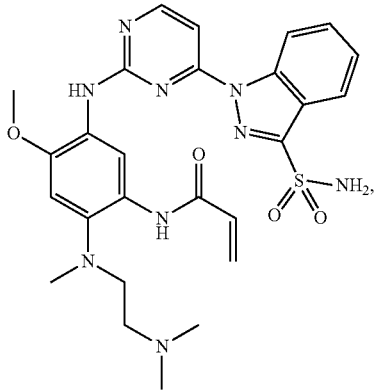
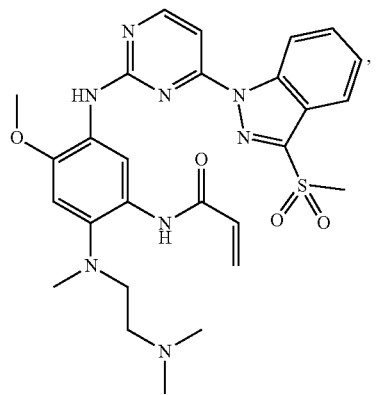
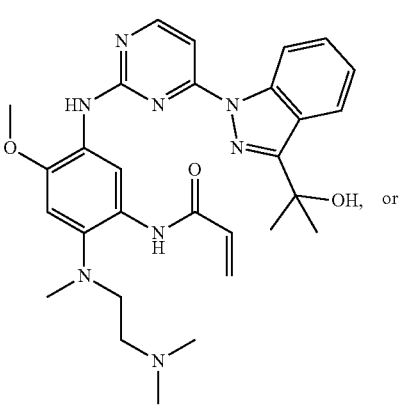

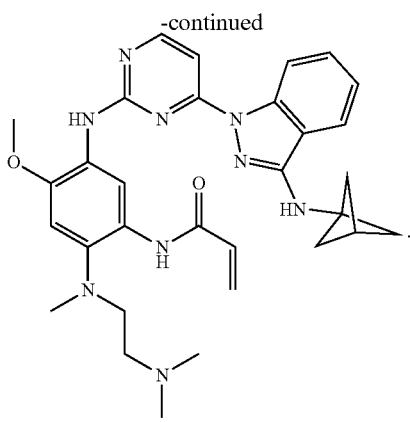

One embodiment of the present disclosure relates to compounds of formula (VIB):

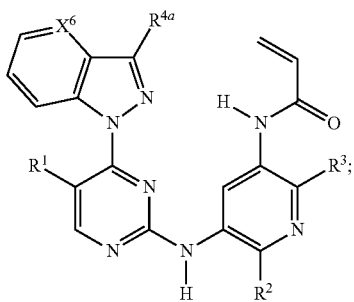

(VIB)

or a stereoisomer or a pharmaceutically acceptable salt, solvate, ester, tautomer, or prodrug thereof;
wherein
$X^6$ is $CR^4$ or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^4$ is H, $CH_3$, $CH_2CH_3$, or isopropyl;
$R^{4a}$ is cyano, —$C_{1-6}$ haloalkyl, $C_{1-6}$ hydroxyalkyl-C(=O)—, —C(=O)$NR^8R^9$, —$NR^8R^9$, $C_{1-6}$ acyl-N($R^{10}$)—, ($C_{1-3}$alkyl)$SO_2NH$— or $R^7SO_2$—;
$R^7$ is —$NR^8R^9$;
$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or
alternatively, $R^8$ and $R^9$, taken together with the N atom to which they are both attached, form a heterocyclic ring of 4-7 members, containing up to one other heteroatom chosen from O, S, or $NR^{11}$; and
each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (VIB),
$X^6$ is CH, $CCH_3$, or N;
$R^1$ is hydrogen, methyl, or chloro;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, cyclopropyl, —C(=O)$CH_3$, —C(=O)$CH_2CH_3$, C(=O)CH$(CH_3)_2$,

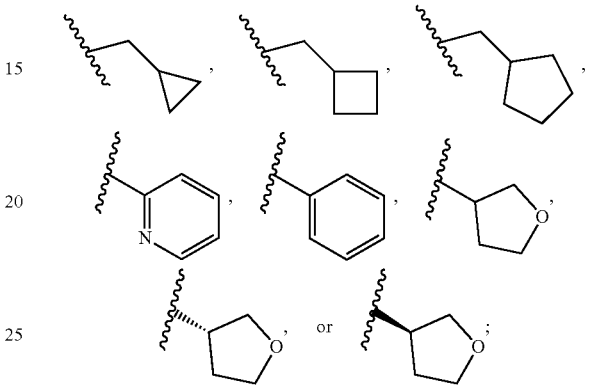

alternatively, $R^8$ and $R^9$, taken together with the N atom to which they are both attached, form a heterocyclic ring of 5-6 members, containing up to one other heteroatom chosen from O, S, or $NR^{11}$; and
each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VIB).
$X^6$ is CH or N;
$R^1$ is hydrogen;
$R^2$ is —$OCH_2CHF_2$, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, or isopropyl; and each $R^{10}$ is independently H, —$CD_3$, methyl, ethyl, or isopropyl.

In one embodiment of compounds of formula (VIB),
$X^6$ is CH;
$R^1$ is hydrogen;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, —C(=O)$CH_3$, —C(=O)$CH_2CH_3$, or —C(=O)CH$(CH_3)_2$; or
alternatively, $R^8$ and $R^9$, taken together with the N atom to which they are both attached, form a heterocyclic ring of 5-6 members, containing up to one other heteroatom chosen from O, S, or $NR^{11}$; and
each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VIB),
X⁶ is CH;
R¹ is hydrogen;
R¹ is —OCH₂CHF₂, methoxy, ethoxy, or isopropoxy;
R³ is —N(CH₃)CH₂CH₂NR¹⁰R¹⁰;
R⁴ᵃ is —NR⁸R⁹;
R⁸ and R⁹ are independently H, —CD₃, methyl, ethyl, or isopropyl; and
each R¹⁰ is independently H, —CD₃, methyl, ethyl, or isopropyl.

In one embodiment of compounds of formula (VIB), R² is —OCH₂CHF₂, —OCH₂CF₃, cyclopropoxy, methoxy, —OCD₃, or ethoxy.

In one embodiment of compounds of formula (VIB), R³ is —N(CH)CH₂CH₂N(CH₃)₂.

In one embodiment of compounds of formula (VIB), R¹⁰ is H, —CH₃, —CD₃, —CH₂CH₃, or isopropyl.

In one embodiment of compounds of formula (VIB), R⁴ᵃ is —NR⁸R⁹.

In one embodiment of compounds of formula (VIB), R⁸ and R⁹ are independently H, —CH₃, —CD₃, —CH₂CH₃, isopropyl, or cyclopropyl.

In one embodiment of compounds of formula (VIB), a compound is selected from:

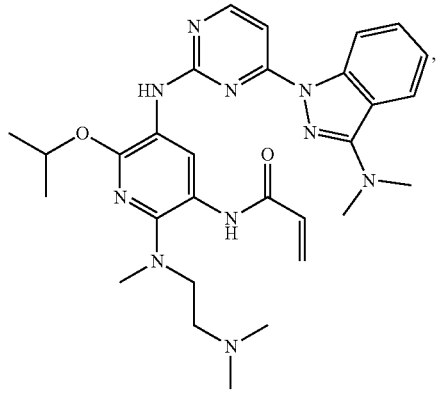
,

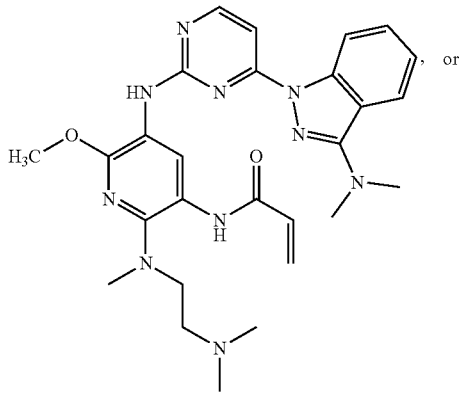
, or

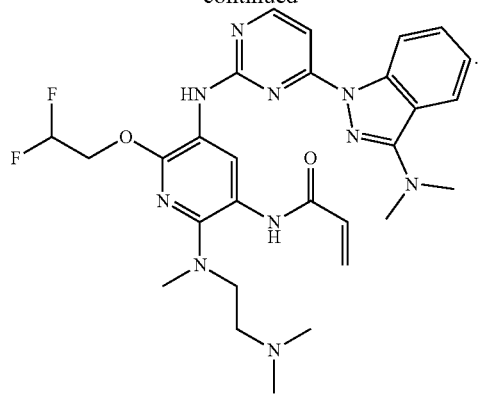

.

One embodiment of the present disclosure relates to compounds of formula (VIIB):

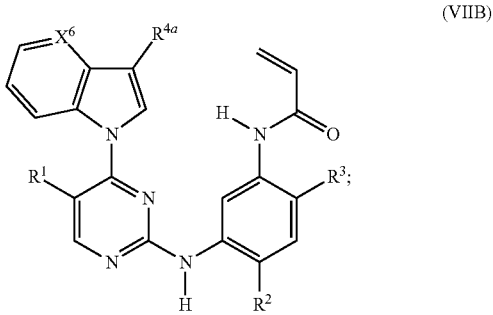

(VIIB)

or a stereoisomer or a pharmaceutically acceptable salt, solvate, ester, tautomer, or prodrug thereof;
wherein
X⁶ is CR⁴ or N;
R¹ is selected from hydrogen, methyl, fluoro, chloro, bromo, CF₃, or cyano;
R² is —OCF₃, —OCHF₂, —OCF₂CF₃, —OCH₂CHF₂, —OCH₂CF₃, cyclopropoxy, methoxy, —OCD₃, ethoxy, or isopropoxy;
R³ is N(R¹⁰)C₂₋₆ alkyl-NR¹⁰R¹⁰;
R⁴ is H, cyano, halo, —C₁₋₆ alkyl, or —C₁₋₆ haloalkyl;
R⁴ᵃ is cyano, halo, C₁₋ₛ acyl-, —C₁₋₆ hydroxyalkyl, pyrazole, 123-triazole, tetrazole, —C(=O)OH, —C(=O)CH₂OH, —C(=O)NR⁸R⁹, —CH₂NR⁸R⁹, —NR⁸R⁹, C₁₋₆ acyl-N(R¹⁰)—, (C₁₋₃ alkyl)SO₂NH—, R¹⁰SO₂— or R⁷SO₂—;
R⁷ is —NR⁸R⁹;
R⁸ and R⁹ are independently H, —CD₃, C₁₋₆ alkyl, C₃₋₆ cycloalkyl, C₃₋ cycloalkyl-(C₁₋₃ alkyl)-, C₁-C₆acyl, phenyl, monocyclic heteroaryl, or monocyclic heterocyclyl; and R⁸ and R⁹ may be further independently substituted with up to three substituents chosen from hydroxyl, C₁₋₆ alkoxy, oxo, thiono, cyano or halo; and
each R¹⁰ is independently H, —CD₃, or C₁₋₆ alkyl; or alternatively, two R¹⁰ on the same N atom to which they are both attached, form a heterocyclic ring of 5-6 members, containing up to one other heteroatom selected from O, S, or NR¹¹; and
each R¹¹ is independently hydrogen or C₁-C₆ alkyl, which is optionally substituted with up to three substituents selected from hydroxyl, oxo, thiono, cyano and halo.

In one embodiment of compounds of formula (VIIB),
$X^6$ is CH;
$R^1$ is hydrogen, methyl, or chloro;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is —C(=O)CH$_3$, —C(=O) CH$_2$CH$_3$, or —C(=O)CH(CH$_3$)$_2$; and
each $R^{10}$ is independently H, —CD$_3$, methyl, ethyl, or isopropyl.

In one embodiment of compounds of formula (VIIB),
$X^6$ is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ is —C(=O)CH$_3$, —C(=O) CH$_2$CH$_3$, or —C(=O)CH(CH$_3$)$_2$; and
each $R^{10}$ is independently H, —CD$_3$, methyl, ethyl, or isopropyl.

In one embodiment of compounds of formula (VIIB),
$X^6$ is CH;
$R^1$ is hydrogen;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is $R^7SO_2$—;
$R^7$ is —NR$^8$R$^9$;
$R^8$ and $R^9$ are independently H, —CD$_3$, methyl, ethyl, or isopropyl; and
each $R^{10}$ is independently H, —CD$_3$, methyl, ethyl, or isopropyl; or
alternatively, two $R^{10}$ on the same N atom to which they are both attached, form a heterocyclic ring of 5-6 members, containing up to one other heteroatom selected from O, S, or NR$^{11}$.

In one embodiment of compounds of formula (VIIB),
$X^6$ is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ is $R^7SO_2$—;
$R^7$ is —NR$^8$R$^9$;
$R^8$ and $R^9$ are independently H, —CD$_3$, methyl, ethyl, or isopropyl; and
each $R^{10}$ is independently H, —CD$_3$, methyl, ethyl, or isopropyl.

In one embodiment of compounds of formula (VIIB),
$X^6$ is N, CH, or CCH$_3$;
$R^1$ is hydrogen;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is

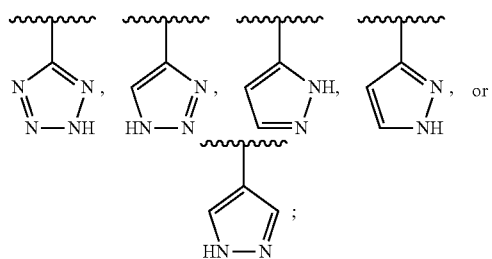

and
each $R^{10}$ is independently H, —CD$_3$, methyl, ethyl, or isopropy.

In one embodiment of compounds of formula (VIIB),
$X^6$ is N or CH;
$R^1$ is hydrogen;
$R^2$ is methoxy, ethoxy, or isopropoxy;
$R^3$ is N(CH$_3$)CH$_2$CH$_2$NR$^{10}$R$^{10}$;
$R^3$ is N(CH$_3$)CH$_2$CH$_2$NR$^{10}$R$^{10}$;
$R^{4a}$ is

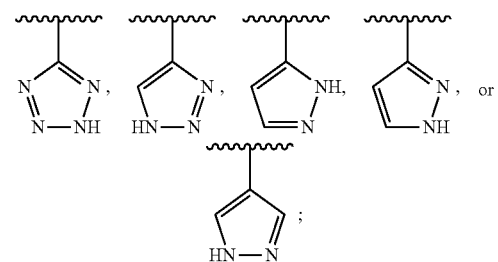

and
each $R^{10}$ is independently H, —CD$_3$, methyl, ethyl, or isopropyl.

In one embodiment of compounds of formula (VIIB), $R^2$ is methoxy, —OCD$_3$, ethoxy, or isopropoxy.

In one embodiment of compounds of formula (VIIB), $R^3$ is —N(CH$_3$)CH$_2$CH$_2$N(CH$_3$)$_2$.

In one embodiment of compounds of formula (VIIB), $R^{10}$ is H, —CH$_3$, —CD$_3$, —CH$_2$CH$_3$, or isopropyl.

In one embodiment of compounds of formula (VIIB), $R^4$ is —C(=O)NR$^8$R$^9$, —NR$^8$R$^9$ or $R^7SO_2$—. In another embodiment, $R^{4a}$ is cyano, halo, C$_1$—, acyl-, —C$_{1-6}$ hydroxyalkyl, C$_{1-6}$ alkyl or —C$_{1-6}$ haloalkyl. In some embodiments, $R^{4a}$ is —C(=O)CH$_3$, —C(=O)CH$_2$CH$_3$, or —C(=O)CH(CH$_3$)$_2$.

In one embodiment of compounds of formula (VIIB), $R^8$ and $R^9$ are independently H, —CH$_3$, —CD$_3$, —CH$_2$CH$_3$, isopropyl, or cyclopropyl.

In one embodiment of compounds of formula (VIIB), a compound is selected from:

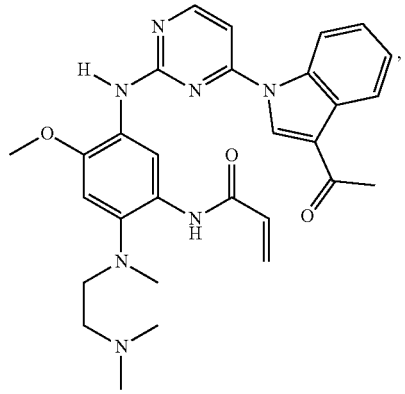

39
-continued
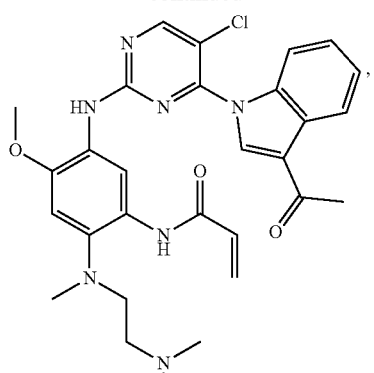
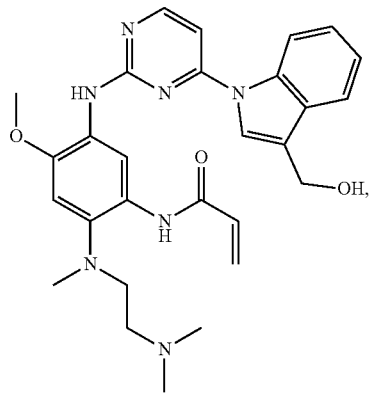
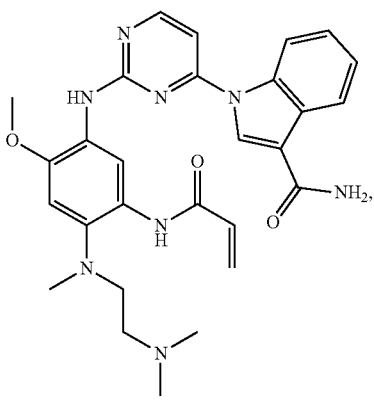
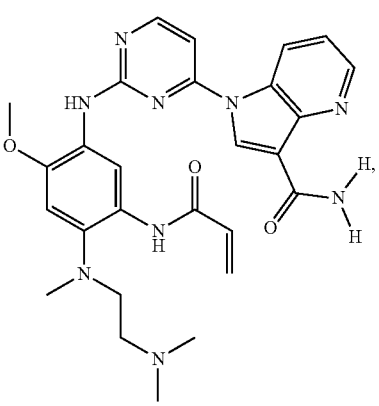
40
-continued
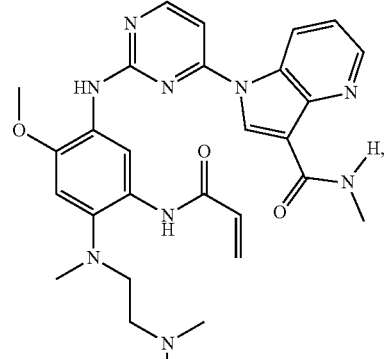
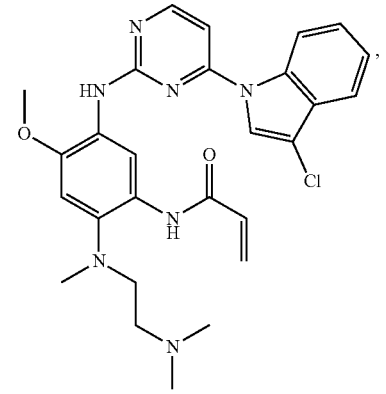
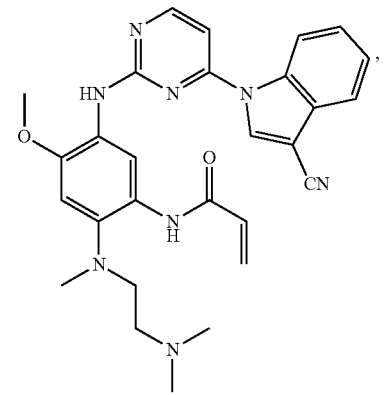
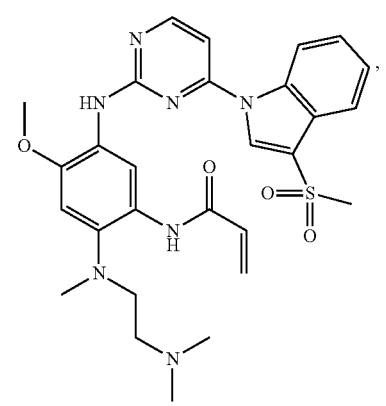

41
-continued
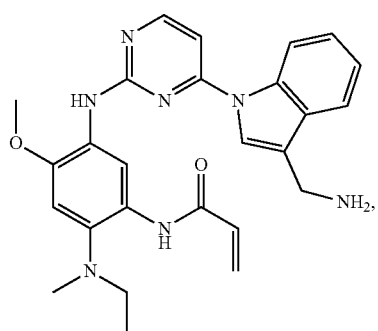
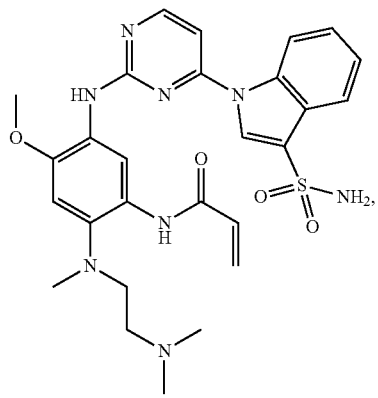
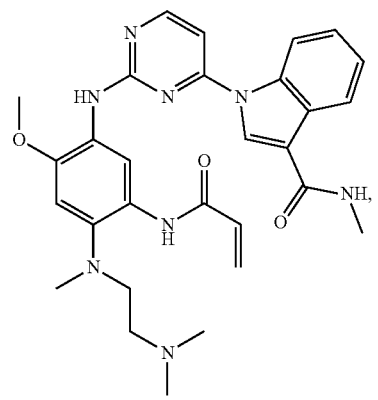
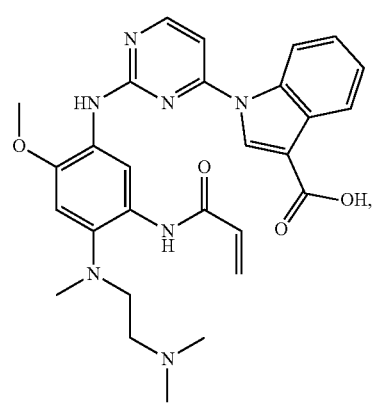
42
-continued
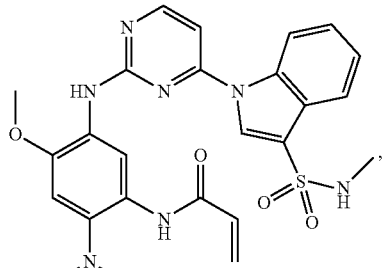
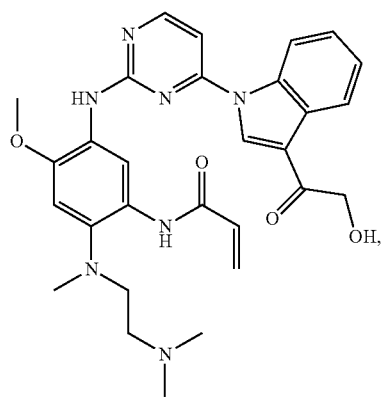
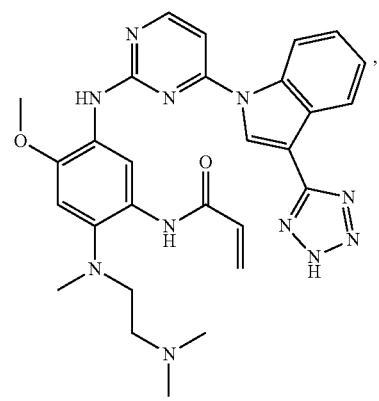
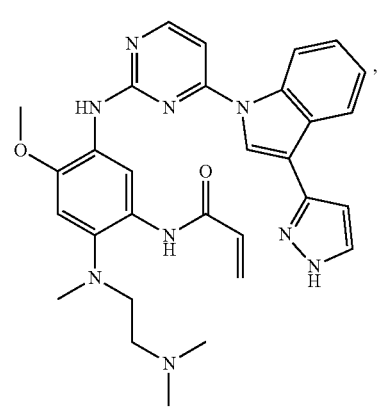

-continued

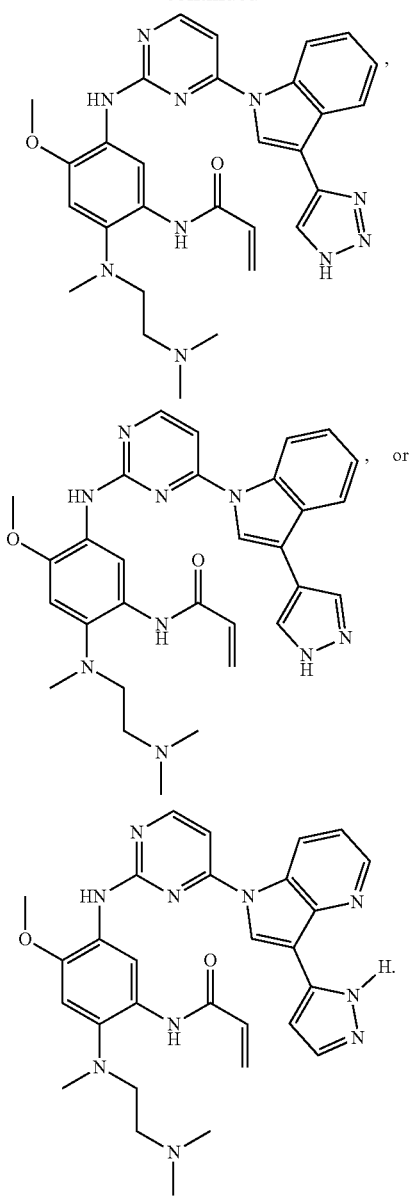

One embodiment of the present disclosure relates to compounds of formula (VIIIB):

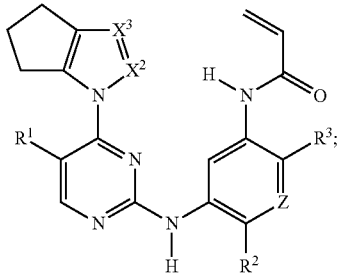

(VIIIB)

or a stereoisomer or a pharmaceutically acceptable salt, solvate, ester, tautomer, or prodrug thereof;

wherein:

each of $X^2$ and $X^3$ is independently $CR^4$ or N; wherein one of $X^2$ and $X^3$ is N and the other is $CR^4$;

Z is CH or N;

$R^1$ is independently selected from hydrogen, fluoro, chloro, bromo, methyl, ethyl, hydroxyl, methoxy, ethoxy, isopropxy, cyclopropoxy, —$OCF_3$, —$OCH_2CF_3$, —$OCH_2CHF_2$, ethenyl, ethynyl, $CF_3$, $CHF_2$, CHO, $CH_2OH$, $CONH_2$, $CO_2Me$, CONHMe, $CONMe_2$, and cyano;

$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropoxy;

$R^3$ is $N(R^{10})C_{2-6}$ alkyl-$NR^{10}R^{10}$, $N(R^{10})C_{2-6}$ alkyl-$R^7$, $O(CH_2)_pR^7$, $N(R^{10})C(=O)(CH_2)_pR^7$ or $R^7$;

each $R^4$ is independently H, cyano, nitro, halo, —$C_{1-6}$ alkyl, —$C_{1-6}$ haloalkyl, carboxy-$C_{14}$, alkyl, —$C_{1-6}$ hydroxyalkyl, $R^8R^9N$—$C_{1-6}$, alkyl-, —$C_{2-6}$ alkenyl, —$C_{2-6}$ alkynyl, $C_{1-6}$ acyl-, $R^7$—$(CH_2)_pC(=O)$—, $C_{1-6}$ hydroxyalkyl-C(=O)—, carboxy, —$C_{1-6}$ alkoxycarbonyl, —C(=O)$NR^8R^9$, hydroxyl, alkoxy, $C_{1-6}$ acyloxy, —$NR^8R^9$, $C_{1-6}$ acyl-$N(R^{10})$—, $R^7SO_2$—, $R^7$ is OH, $NR^8R^9$, $O(CH_2)_qNR^8R^9$, $C_{1-6}$ alkoxy, or $C_{2-6}$ hydroxyalkoxy;

$R^8$ and $R^9$ are independently H, —$CD_3$, $C_{1-6}$ alkyl, $C_{3-6}$ alkenyl, $C_{3-6}$ alkynyl, $C_{3-8}$ cycloalkyl, $C_{3-8}$ cycloalkenyl, $C_1$-$C_6$acyl, 4-12 membered monocyclic or bicyclic heterocyclyl, 4-12 membered monocyclic or bicyclic heterocyclyl-$C_1$-$C_6$ alkyl-, $C_6$-$C_{12}$ aryl, 5-12 membered heteroaryl; and $R^8$ and $R^9$ may be further independently substituted with up to three substituents chosen from hydroxyl, $C_{1-6}$ alkoxy, $C_{1-6}$ hydroxyalkyl$C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, or a heterobicyclic ring of 7-12 members which may be fused, bridged or spiro, and contain up to two other heteroatoms chosen from O, $S(O)_x$, or $NR^{11}$, and these heterocyclic rings are optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo:

each $R^{10}$ is independently H, —$CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$; or alternatively, two $R^{10}$ on the same N atom to which they are both attached, form a heterocyclic ring of 5-6 members, containing up to one other heteroatom selected from O, S, or $NR^{11}$;

each $R^{11}$ is independently hydrogen or $C_1$-$C_6$ alkyl, which is optionally substituted with up to three substituents selected from hydroxyl, oxo, thiono, cyano and halo;

p=0, 1, 2, 3, or 4:

q=2, 3, or 4; and x=0, 1, or 2.

One embodiment of the present disclosure relates to compounds of formula (IXB):

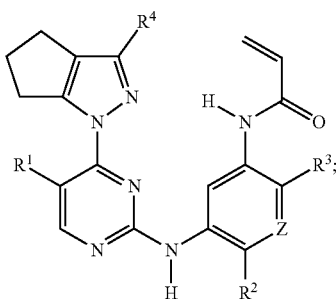

(IXB)

or a stereoisomer or a pharmaceutically acceptable salt, solvate, ester, tautomer, or prodrug thereof;
wherein
Z is CH or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^4$ is H, cyano, halo, —$C_{1-6}$ alkyl, —$C_{1-6}$ haloalkyl, $C_{1-6}$ hydroxyalkyl-C(=O)—, —C(=O)$NR^8R^9$, —$NR^8R^9$, $C_{1-6}$ acyl-N($R^{10}$)—, ($C_{1-3}$alkyl)$SO_2$NH— or $R^7SO_2$—;
$R^7$ is —$NR^8R^9$;
$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or
alternatively, $R^8$ and $R^9$, taken together with the N atom to which they are both attached, form a heterocyclic ring of 4-7 members, containing up to one other heteroatom chosen from O, S, or $NR^{11}$; and
each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (IXB), Z is CH.

In one embodiment of compounds of formula (IXB), $R^2$ is —$OCH_2CHF_2$, —$OCH_2CF_3$, methoxy, —$OCD_3$, or ethoxy.

In one embodiment of compounds of formula (IXB), $R^3$ is —$N(CH_3)CH_2CH_2N(CH_3)_2$.

In one embodiment of compounds of formula (IXB), $R^{10}$ is H, —$CH_3$, —$CD_3$, —$CH_2CH_3$, or isopropyl.

In one embodiment of compounds of formula (IXB), $R^4$ is —C(=O)$NR^8R^9$, —$NR^8R^9$ or $R^7SO_2$—.

In one embodiment of compounds of formula (IXB), $R^8$ and $R^9$ are independently H, —$CH_3$, —$CD_3$, —$CH_2CH_3$, isopropyl, or cyclopropyl.

In one embodiment of compounds of formula (IXB), the compound is:

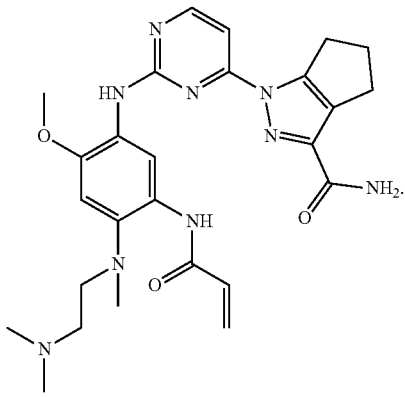 [SMILES: C=CC(=O)Nc1cc(Nc2nccc(-n3nc(C(N)=O)c4c3CCC4)n2)c(OC)cc1N(C)CCN(C)C]

One embodiment of the present disclosure relates to compounds of formula (XIIIB):

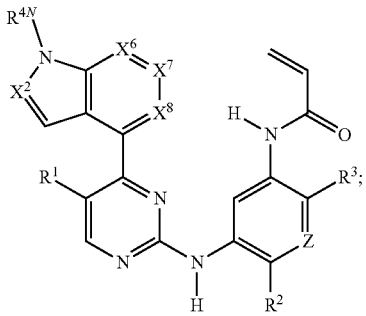

(XIIIB)

or a stereoisomer or a pharmaceutically acceptable salt, solvate, ester, tautomer, or prodrug thereof;
wherein:
each of $X^2$, $X^6$, $X^7$, and $X^8$ is independently $CR^4$ or N; wherein not more than two of $X^2$, $X^6$, $X^7$, and $X^8$ are N;
Z is CH or N;
$R^1$ is independently selected from hydrogen, fluoro, chloro, bromo, methyl, ethyl, hydroxyl, methoxy, ethoxy, isopropxy, cyclopropoxy, —$OCF_3$, —$OCH_2CF_3$, —$OCH_2CHF_2$, ethenyl, ethynyl, $CF_3$, $CHF_2$, CHO, $CH_2OH$, $CONH_2$, $CO_2Me$, CONHMe, $CONMe_2$, and cyano;
$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropoxy;
$R^3$ is $N(R^{10})C_{1-6}$ alkyl-$NR^{10}R^{10}$, $N(R^{10})C_{2-6}$ alkyl-$R^7$, $O(CH_2)_pR^7$, $N(R^{10})C(=O)(CH_2)_pR^7$ or $R^7$;
each $R^4$ is independently H, cyano, nitro, halo, —$C_{1-6}$ alkyl, —$C_{1-6}$ haloalkyl, carboxy-$C_{1-6}$ alkyl, —$C_{1-6}$ hydroxyalkyl, $R^8R^9N$—$C_{1-6}$ alkyl-, —$C_{2-6}$ alkenyl, —$C_{2-6}$ alkynyl, $C_{1-6}$ acyl-, $R^7$—$(CH_2)_pC(=O)$—, $C_{1-6}$ hydroxyalkyl-C(=O)—, carboxy, —$C_{1-6}$ alkoxycarbonyl, —C(=O)$NR^8R^9$, hydroxyl, alkoxy, —$OCD_3$, $C_{1-6}$ acyloxy, —$NR^8R^9$, $C_{1-6}$ acyl-N($R^{10}$)—, $R^7SO_2$—;
$R^{4N}$ is H, —$CD_3$, —$C_{1-6}$ alkyl, or —$C_{1-6}$ haloalkyl;
wherein when $X^6$ is C—OH, $X^7$ is N, and $X^8$ is $CR^4$, then the bicyclic ring containing $X^2$ can be tautomerized between

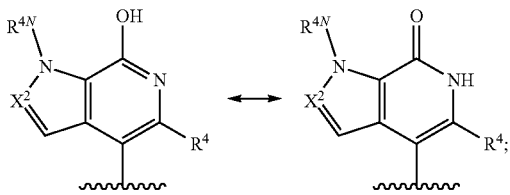

$R^7$ is OH $NR^8R^9$, $O(CH_2)_qNR^8R^9$, $C_{1-6}$ alkoxy, or $C_{2-6}$ hydroxyalkoxy;

$R^8$ and $R^9$ are independently H, —$CD_3$, $C_{1-6}$ alkyl, $C_{3-6}$ alkenyl, $C_{3-6}$ alkynyl, $C_{3-8}$ cycloalkyl, $C_{3-8}$ cycloalkenyl, $C_1$-$C_6$ acyl, 4-12 membered monocyclic or bicyclic heterocyclyl, 4-12 membered monocyclic or bicyclic heterocyclyl-$C_1$-$C_6$alkyl-, $C_6$-$C_{12}$ aryl, 5-12 membered heteroaryl; and $R^8$ and $R^9$ may be further independently substituted with up to three substituents chosen from hydroxyl, $C_{1-6}$ alkoxy, $C_{1-6}$ hydroxyalkyl$C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, or a heterobicyclic ring of 7-12 members which may be fused, bridged or spiro, and contain up to two other heteroatoms chosen from O, $S(O)_x$, or $NR^{11}$, and these heterocyclic rings are optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, —$CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$; or alternatively, two $R^{10}$ on the same N atom to which they are both attached, form a heterocyclic ring of 5-6 members, containing up to one other heteroatom selected from O, S, or $NR^{11}$;

each $R^{11}$ is independently hydrogen or $C_1$-$C_6$ alkyl, which is optionally substituted with up to three substituents selected from hydroxyl, oxo, thiono, cyano and halo;

p=0, 1, 2, 3, or 4;

q=2, 3, or 4; and x=0, 1, or 2.

One embodiment of the present disclosure relates to compounds of formula (XIVB):

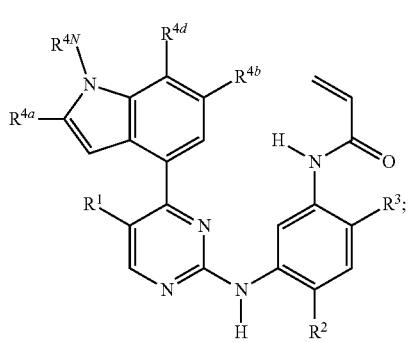

(XIVB)

or a stereoisomer or a pharmaceutically acceptable salt, solvate, ester, tautomer, or prodrug thereof;

wherein;

Z is CH or N;

$R^1$ is selected from hydrogen, methyl, fluoro, chloro, bromo, $CF_3$, or cyano;

$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;

$R^3$ is $N(R^{10})C_{2-6}$ alkyl-$NR^{10}R^{10}$;

$R^{4a}$ is H, cyano, halo, —$C_{1-6}$ alkyl, or —$C_{1-6}$ haloalkyl;

one of $R^{4b}$ and $R^{4d}$ is —C(=O)$NR^8R^9$ or —$NR^8R^9$ and the other is H;

$R^{4N}$ is H, —$C_{1-6}$ alkyl, or —$CD_3$;

$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, —$CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (XIVB),

Z is CH;

$R^1$ is hydrogen, methyl, or chloro;

$R^2$ is -$OCH_2CHF_2$, cyclopropoxy, methoxy, ethoxy, or isopropoxy;

$R^3$ is $N(CH_3)CH_2CH_2NR^{10}R^{10}$;

$R^{4a}$ is H, chloro, methyl, or —$CF_3$;

$R^{4b}$ is —C(=O)$NR^8R^9$;

$R^{4d}$ is H;

$R^{4N}$ is H, —$CD_3$, methyl, ethyl, or isopropyl;

$R^8$ and $R^9$ are independently H, methyl, ethyl, or isopropyl; and each $R^{10}$ is independently H, —$CD_3$, methyl, ethyl, or isopropyl; or alternatively, two $R^D$ on the same N atom to which they are both attached, form a heterocyclic ring of 5-6 members, containing up to one other heteroatom selected from O, S, or $NR^{11}$.

In one embodiment of compounds of formula (XIVB),

Z is CH;

$R^1$ is hydrogen or chloro;

$R^2$ is methoxy, ethoxy, or isopropoxy;

$R^3$ is $N(CH_3)CH_2CH_2NR^{10}R^{10}$;

$R^{4a}$ is H, chloro, methyl, or —$CF_3$;

$R^{4b}$ is —C(=O)$NR^8R^9$;

$R^{4d}$ is H;

$R^{4N}$ is H, —$CD_3$, methyl, ethyl, or isopropyl;

$R^8$ and $R^9$ are independently H, methyl, ethyl, or isopropyl; and each $R^{10}$ is independently H, —$CD_3$, methyl, ethyl, or isopropyl.

In one embodiment of compounds of formula (XIVB),

Z is CH;

$R^1$ is hydrogen;

$R^2$ is —$OCF_3$, —$OCHF_2$, —$OCF_2CF_3$, —$OCH_2CHF_2$, —$OCH_2CF_3$, cyclopropoxy, methoxy, ethoxy, or isopropoxy;

$R^3$ is —$N(CH_3)CH_2CH_2NR^{10}R^{10}$;

$R^{4a}$ is H, chloro, methyl, or —$CF_3$;

$R^{4d}$ is —C(=O)$NR^8R^9$;

$R^{4b}$ is H;

$R^{4N}$ is H, —CD$_3$, methyl, ethyl, or isopropyl;
$R^8$ and $R^9$ are independently H or methyl; and
each $R^{10}$ is independently H, —CD$_3$, methyl, ethyl, or isopropyl.

In one embodiment of compounds of formula (XIVB),
Z is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ is H, chloro, methyl, or —CF$_3$;
$R^{4d}$ is —C(=O)NR$^8$R$^9$;
$R^{4b}$ is H;
$R^{4N}$ is H, —CD$_3$, methyl, ethyl, or isopropyl;
$R^8$ and $R^9$ are independently H or methyl; and
each $R^{10}$ is independently H, —CD$_3$, methyl, ethyl, or isopropyl.

In one embodiment of compounds of formula (XIVB), $R^2$ is methoxy, —OCD$_3$, or ethoxy.

In one embodiment of compounds of formula (XIVB), $R^3$ is —N(CH$_3$)CH$_2$CH$_2$N(CH$_3$)$_2$.

In one embodiment of compounds of formula (XIVB), $R^{10}$ is H, —CH$_3$, —CD$_3$, —CH$_2$CH$_3$, or isopropyl.

In one embodiment of compounds of formula (XIVB), $R^{4N}$ is H, or —CH$_3$, —CD$_3$, —CH$_2$CH$_3$.

In one embodiment of compounds of formula (XIVB), $R^{4a}$ is H, —CH$_3$, or halo.

In one embodiment of compounds of formula (XIVB), $R^{4b}$ is —C(=O)NR$^8$R$^9$ or —NR$^8$R$^9$, and $R^{4d}$ is H.

In one embodiment of compounds of formula (XIVB), $R^{4d}$ is —C(=O)NR$^8$R$^9$ or —NR$^8$R$^9$, and $R^{4b}$ is H.

In one embodiment of compounds of formula (XIVB), $R^8$ and $R^9$ are independently H, —CH$_3$, —CD$_3$, —CH$_2$CH$_3$, isopropyl, or cyclopropyl.

In one embodiment of compounds of formula (XIVB), a compound is selected from

One embodiment of the present disclosure relates to compounds of formula (XVB):

(XVB)

or a stereoisomer or a pharmaceutically acceptable salt, solvate, ester, tautomer, or prodrug thereof,
wherein;
Z is CH or N;
$R^1$ is selected from hydrogen, fluoro, chloro, bromo, CF$_3$, or cyano;
$R^2$ is —OCF$_3$, —OCHF$_2$, —OCF$_2$CF$_3$, —OCH$_2$CHF$_2$, —OCH$_2$CF$_3$, cyclopropoxy, methoxy, —OCD$_3$, ethoxy, or isopropoxy;
$R^3$ is N(R$^{10}$)C$_{2-6}$ alkyl-NR$^{10}$R$^{10}$;
$R^{4a}$ is H, cyano, halo, —C$_{1-6}$ alkyl, or —C$_{1-6}$ haloalkyl;
$R^{4b}$ is hydrogen; hydroxyl, —OCD$_3$, methoxy, ethoxy, isopropoxy, cyclopropoxy, —C(=O)NR$^8$R$^9$ or —NR$^8$R$^9$;
R is H;
$R^{4N}$ is H, —C$_{1-6}$ alkyl, or —CD$_3$;
wherein when $R^{4b}$ is —OH, then the bicyclic ring containing can be tautomerized between

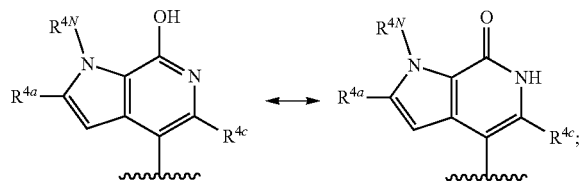

R⁷ is —NR⁸R⁹;

R⁸ and R⁹ are independently H, —CD₃, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and R⁸ and R⁹ may be further independently substituted with up to three substituents chosen from hydroxyl, $C_{1-6}$ alkoxy, oxo, thiono, cyano or halo; and each R¹⁰ is independently H, —CD₃, or $C_{1-6}$ alkyl; or alternatively, two R¹⁰ on the same N atom to which they are both attached, form a heterocyclic ring of 5-6 members, containing up to one other heteroatom selected from O, S, or NR¹¹; and each R¹¹ is independently hydrogen or $C_1$-$C_6$ alkyl, which is optionally substituted with up to three substituents selected from hydroxyl, oxo, thiono, cyano and halo.

In one embodiment of compounds of formula (XVB),
Z is CH;
R¹ is hydrogen;
R² is —OCH₂CHF₂, cyclopropoxy, methoxy, ethoxy, or isopropoxy;
R³ is —N(CH₃)CH₂CH₂NR¹⁰R¹⁰;
R⁴ is H, chloro, methyl, or —CF₃;
R⁴ᵇ is —OCD₃, methoxy, ethoxy, isopropoxy, or —NR⁸R⁹;
R⁴ᶜ is H;
R⁴ᴺ is H, —CD₃, methyl, ethyl, or isopropyl;
R⁸ and R⁹ are independently H, methyl, or ethyl; and
each R¹⁰ is independently H, —CD₃, methyl, ethyl, or isopropyl.

In one embodiment of compounds of formula (XVB),
Z is CH;
R¹ is hydrogen;
R² is —OCD₃, methoxy, ethoxy, or isopropoxy;
R³ is —N(CH₃)CH₂CH₂NR¹⁰R¹⁰;
R⁴ᵃ is H, chloro, methyl, or —CF₃;
R⁴ᵇ is —OCD₃, methoxy, ethoxy, isopropoxy;
R⁴ᶜ is H; and
R⁴ᴺ is H, —CD₃, methyl, ethyl, or isopropyl;
each R¹⁰ is independently H, —CD₃, methyl, ethyl, or isopropyl.

In one embodiment of compounds of formula (XVB), R² is —OCH₂CHF₂, methoxy, —OCD₃, or ethoxy.

In one embodiment of compounds of formula (XVB), R³ is —N(CH₂)CH₂CH₂N(CH₃)₂.

In one embodiment of compounds of formula (XVB), R¹⁰ is H, —CH₃, —CD₃, —CH₂CH₃, or isopropyl.

In one embodiment of compounds of formula (XVB), R⁴ᴺ is H, or —CH₃, —CD₃, —CH₂CH₃.

In one embodiment of compounds of formula (XVB), R⁴ᵃ is H, —CH₃, or halo.

In one embodiment of compounds of formula (XVB), R⁴ᵇ is H, methoxy, —OCD₃, ethoxy, —C(=O)NR⁸R⁹ or —NR⁸R⁹, and R⁴ᶜ is H.

In one embodiment of compounds of formula (XVB), R⁸ and R⁹ are independently H, —CH₃, —CD₃, —CH₂CH₃, isopropyl, or cyclopropyl.

In one embodiment of compounds of formula (XVB), a compound is selected from:

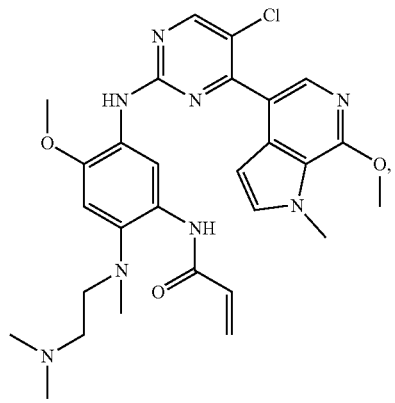

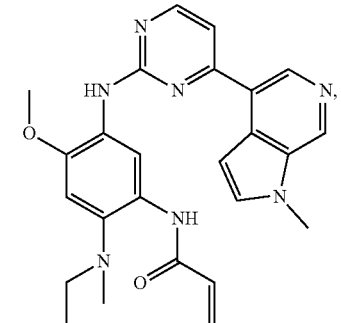

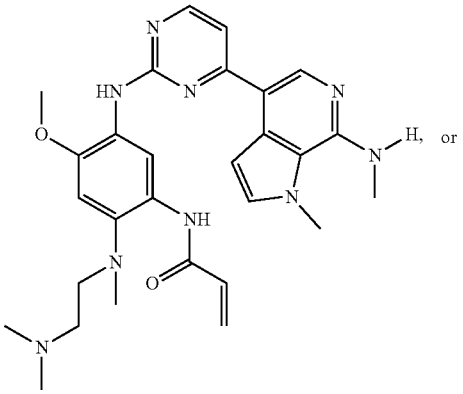

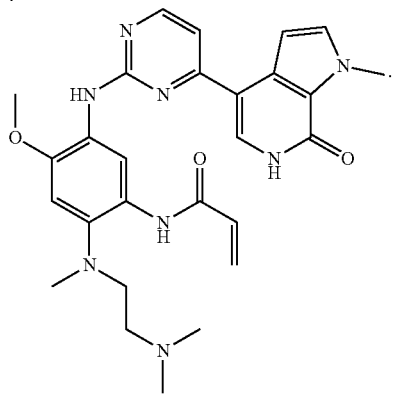

One embodiment of the present disclosure relates to compounds of formula (XVIB):

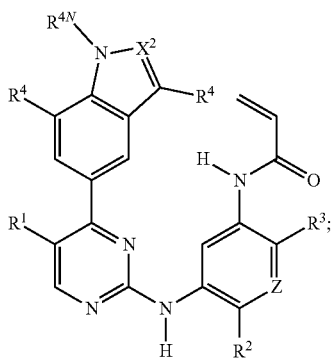

(XVIB)

or a stereoisomer or a pharmaceutically acceptable salt, solvate, ester, tautomer, or prodrug thereof;
wherein:
X$^2$ is CR$^4$ or N;
Z is CH or N;
R$^1$ is independently selected from hydrogen, fluoro, chloro, bromo, methyl, ethyl, hydroxyl, methoxy, ethoxy, isopropxy, cyclopropoxy, —OCF$_3$, —OCH$_2$CF, —OCH$_2$CHF$_2$, ethenyl, ethynyl, CF$_3$, CHF$_2$, CHO, CH$_2$OH, CONH$_2$, CO$_2$Me, CONHMe, CONMe$_2$, and cyano;
R$^2$ is —OCF$_3$, —OCHF$_2$, —OCF$_2$CF$_3$, —OCH$_2$CHF$_2$, —OCH$_2$CF$_3$, cyclopropyl, cyclopropoxy, methoxy, —OCD$_3$, ethoxy, or isopropoxy;
R$^3$ is N(R$^{10}$)C$_{2-6}$ alkyl-NR$^{10}$R$^{10}$, N(R$^{10}$)C$_{2-6}$ alkyl-R$^7$, O(CH$_2$)$_p$R$^7$, N(R$^{10}$)C(=O)(CH$_2$)$_p$R$^7$ or R$^7$;
each R$^4$ is independently H, cyano, halo, —C$_{1-6}$ alkyl, —C$_{1-6}$haloalkyl, carboxy-C$_{1-6}$ alkyl, —C$_{1-6}$ hydroxyalkyl, R$^8$R$^9$N—C$_{1-6}$ alkyl-, —C$_{2-6}$alkenyl, —C$_{2-6}$alkenyl, C$_{1-6}$ acyl-, R$^7$—(CH$_2$)$_p$C(=O)—, C$_{1-6}$ hydroxyalkyl-C(=O)—, carboxy, —C$_{1-6}$ alkoxycarbonyl, —C(=O)NR$^8$R$^9$, hydroxyl, alkoxy, C$_{1-6}$ acyloxy, —NR$^8$R$^9$, C$_{1-6}$ acyl-N(R$^{10}$)—, R$^7$SO$_2$—;
R$^{4N}$ is H, —CD$_3$, —C$_{1-6}$ alkyl, or —C$_{1-6}$ haloalkyl;
R$^7$ is OH, NR$^8$R$^9$, O(CH$_2$)$_q$NR$^8$R$^9$, C$_{1-6}$ alkoxy, or C$_{2-6}$ hydroxyalkoxy;
R$^8$ and R$^9$ are independently H, —CD$_3$, C$_{1-6}$ alkyl, C$_{3-6}$ alkenyl, C$_{3-6}$ alkynyl, C$_{3-8}$ cycloalkyl, C$_{3-8}$ cycloalkenyl, C$_1$-C$_6$ acyl, 4-12 membered monocyclic or bicyclic heterocyclyl, 4-12 membered monocyclic or bicyclic heterocyclyl-C$_1$-C$_6$alkyl-, C$_6$-C$_{12}$ aryl, 5-12 membered heteroaryl; and R$^8$ and R$^9$ may be further independently substituted with up to three substituents chosen from hydroxyl, C$_{1-6}$ alkoxy, C$_{1-6}$ hydroxyalkylC$_{2-6}$ hydroxyalkoxy, oxo, thiono, cyano or halo; or
alternatively, R$^8$ and R$^9$, taken together with the N atom to which they are both attached, form a heterocyclic ring of 4-7 members, containing up to one other heteroatom chosen from O, S, or NR$^{11}$, or a heterobicyclic ring of 7-12 members which may be fused, bridged or spiro, and contain up to two other heteroatoms chosen from O, S(O)$_x$, or NR$^{11}$, and these heterocyclic rings are optionally substituted with up to three substituents chosen from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano or halo;
each R$^{10}$ is independently H, —CD$_3$, C$_{1-6}$ alkyl, C$_{3-6}$ cycloalkyl, C$_{2-6}$ hydroxyalkyl, C$_{1-6}$ alkoxy-C$_{1-6}$ alkyl or C$_{2-6}$ alkyl-NR$^8$R$^9$; or alternatively, two R$^{10}$ on the same N atom to which they are both attached, form a heterocyclic ring of 5-6 members, containing up to one other heteroatom selected from O, S, or NR$^{11}$;
each R$^{11}$ is independently hydrogen or C$_1$-C$_6$ alkyl, which is optionally substituted with up to three substituents selected from hydroxyl, oxo, thiono, cyano and halo;
p=0, 1, 2, 3, or 4:
q=2, 3, or 4; and
x=0, 1, or 2.

One embodiment of the present disclosure relates to compounds of formula (XVIIB):

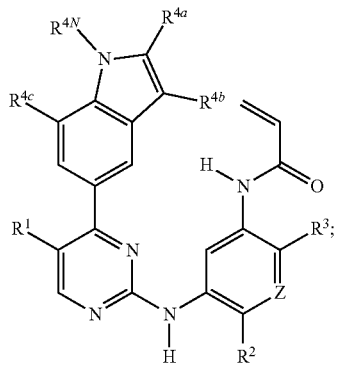

(XVIIB)

or a stereoisomer or a pharmaceutically acceptable salt, solvate, ester, tautomer, or prodrug thereof;
wherein;
Z is CH or N;
R$^1$ is selected from hydrogen, methyl, fluoro, chloro, bromo, CF$_3$, or cyano;
R$^2$ is —OCF$_3$, —OCHF$_2$, —OCF$_2$CF$_3$, —OCH$_2$CHF$_2$, —OCH$_2$CF$_3$, cyclopropoxy, methoxy, —OCD$_3$, ethoxy, or isopropoxy;
R$^3$ is N(R$^{10}$)C$_{2-6}$ alkyl-NR$^{10}$R$^{10}$;
R$^{4a}$ and R$^{4b}$ are each independently H, halo, —C$_{1-6}$ alkyl, or —C$_{1-6}$ haloalkyl;
R$^{4c}$ is cyano, —C(=O)NR$^8$R$^9$ or —NR$^8$R$^9$;
R$^{4N}$ is H, —C$_{1-6}$ alkyl, or —CD$_3$;
R$^8$ and R$^9$ are independently H, —CD$_3$, C$_{1-6}$ alkyl, C$_{3-8}$ cycloalkyl, C$_{3-8}$ cycloalkyl-(C$_{1-3}$ alkyl)-, C$_1$-C$_6$acyl, phenyl, monocyclic heteroaryl, or monocyclic heterocyclyl; and R$^8$ and R$^9$ may be further independently substituted with up to three substituents chosen from hydroxyl.
C$_{1-6}$ alkoxy, oxo, thiono, cyano or halo; and
each R$^{10}$ is independently H, —CD$_3$, or C$_{1-6}$ alkyl; or alternatively, two R$^{10}$ on the same N atom to which they are both attached, form a heterocyclic ring of 5-6 members, containing up to one other heteroatom selected from O, S, or NR$^{11}$; and
each R$^{11}$ is independently hydrogen or C$_1$-C$_6$ alkyl, which is optionally substituted with up to three substituents selected from hydroxyl, oxo, thiono, cyano and halo.

In one embodiment of compounds of formula (XVIIB),
Z is CH;
R$^1$ is hydrogen;
R$^2$ is —OCH$_2$CHF$_2$, cyclopropoxy, methoxy, ethoxy, or isopropoxy;
R$^3$ is —N(CH$_3$)CH$_2$CH$_2$NR$^{10}$R$^{10}$;
R$^{4a}$ and R$_{4b}$ are each independently H, chloro, methyl, or —CF$_3$;
R$^{4c}$ is cyano or —C(=O)NR$^8$R$^9$;

$R^{4N}$ is H, —CD$_3$, methyl, or ethyl;
$R^8$ and $R^9$ are independently H or methyl; and
each $R^{10}$ is independently H, —CD$_3$, methyl, ethyl, or isopropyl; or alternatively, two $R^{10}$ on the same N atom to which they are both attached, form a heterocyclic ring of 5-6 members, containing up to one other heteroatom selected from O, S, or NR$^{11}$.

In one embodiment of compounds of formula (XVIIB),
Z is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ and $R^{4b}$ are each independently H, chloro, methyl, or —CF$_3$;
$R^{4c}$ is cyano or —C(=O)NR$^8$R$^9$;
$R^{4N}$ is H, —CD$_3$, methyl, or ethyl;
$R^8$ and $R^9$ are independently H or methyl; and
each $R^{10}$ is independently H, —CD$_3$, methyl, ethyl, or isopropyl.

In one embodiment of compounds of formula (XVIIB), $R^2$ is methoxy, —OCD$_3$, or ethoxy.

In one embodiment of compounds of formula (XVIIB), $R^3$ is —N(CH$_3$)CH$_2$CH$_2$N(CH$_3$)$_2$.

In one embodiment of compounds of formula (XVIIB), $R^{10}$ is H, —CH$_3$, —CD$_3$, —CH$_2$CH$_3$, or isopropyl.

In one embodiment of compounds of formula (XVIIB), $R^{4N}$ is H, or —CH$_3$, —CD$_3$, —CH$_2$CH$_3$.

In one embodiment of compounds of formula (XVIIB), $R^{4a}$ and $R^{4b}$ is each H, —CH$_3$, or halo.

In one embodiment of compounds of formula (XVIIB), $R^{4c}$ is cyano, —C(=O)NR$^8$R$^9$ or —NR$^8$R$^9$.

In one embodiment of compounds of formula (XVIIB), $R^8$ and $R^9$ are independently H, —CH$_3$, —CD$_3$, —CH$_2$CH$_3$, isopropyl, or cyclopropyl.

In one embodiment of compounds of formula (XVIIB), a compound is selected from:

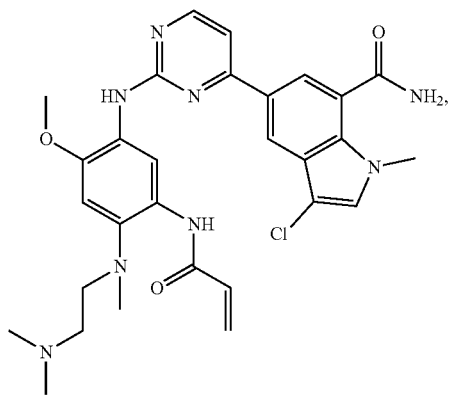

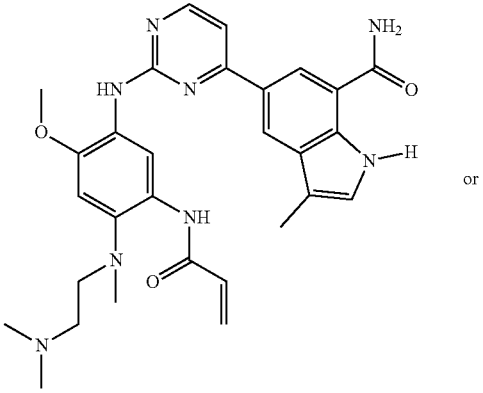

or

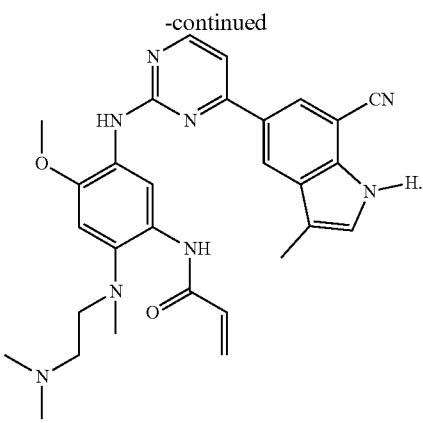

One embodiment of the present disclosure relates to compounds of formula (XVIIIB):

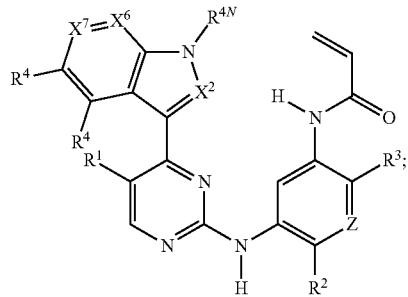

(XVIIIB)

or a stereoisomer or a pharmaceutically acceptable salt, solvate, ester, tautomer, or prodrug thereof;
wherein:

$X^2$, $X^6$, and $X^7$ is each independently CR$^4$ or N; wherein not more than two of $X^2$, $X^6$, and $X^7$ are N;

Z is CH or N;

$R^1$ is independently selected from hydrogen, fluoro, chloro, bromo, methyl, ethyl, hydroxyl, methoxy, ethoxy, isopropxy, cyclopropoxy, —OCF$_3$, —OCH$_2$CF$_3$, —OCH$_2$CHF$_2$, ethenyl, ethynyl, CF$_3$, CHF$_2$, CHO, CH$_2$OH, CONH$_2$, CO$_2$Me, CONHMe, CONMe$_2$, and cyano;

$R^2$ is —OCF$_3$, —OCHF$_2$, —OCF$_2$CF$_3$, —OCH$_2$CHF$_2$, —OCH$_2$CF$_3$, cyclopropyl, cyclopropoxy, methoxy, —OCD$_3$, ethoxy, or isopropoxy;

$R^3$ is N(R$^{10}$)C$_{2-6}$ alkyl-NR$^{10}$R$^{10}$, N(R$^{10}$)C$_{2-6}$ alkyl-R$^7$, O(CH$_2$)$_p$R$^7$, N(R$^{10}$)C(=O)(CH$_2$)$_p$R$^7$ or R$^7$;

each $R^4$ is independently H, cyano, nitro, halo, —C$_{1-6}$ alkyl, —C$_{1-6}$ haloalkyl, carboxy-C$_{1-6}$ alkyl, —C$_{1-6}$ hydroxyalkyl, R$^8$R$^9$N—C$_{1-6}$ alkyl-, —C$_{2-6}$ alkenyl, —C$_{2-6}$ alkynyl, C$_{1-6}$ acyl-, R$^7$—(CH$_2$)$_p$C(=O)—, C$_{1-6}$ hydroxyalkyl-C(=O)—, carboxy, —C$_{1-6}$ alkoxycarbonyl, —C(=O)NR$^8$R$^9$, hydroxyl, alkoxy, C$_{1-6}$ acyloxy, —NR$^8$R$^9$, C$_{1-6}$ acyl-N(R$^{10}$)—, R$^7$SO$_2$—;

$R^{4N}$ is H, —CD$_3$, —C$_{1-6}$ alkyl, —C$_{1-6}$ haloalkyl, or —CH$_2$C(=O)NR$^8$R$^9$;

wherein when $X^6$ is C—OH and $X^7$ is N, then the bicyclic ring containing $X^2$ can be tautomerized between

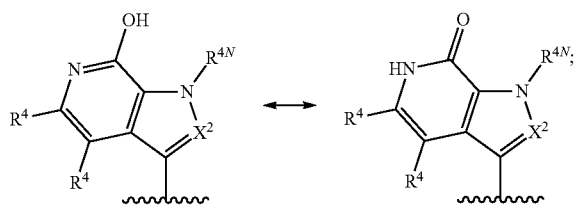

$R^7$ is OH, $NR^8R^9$, $O(CH_2)_qNR^8R^9$, $C_{1-6}$ alkoxy, or $C_{2-6}$ hydroxyalkoxy;

$R^8$ and $R^9$ are independently H, —$CD_3$, $C_{1-6}$ alkyl, $C_{3-6}$ alkenyl, $C_{3-6}$ alkynyl, $C_{3-8}$ cycloalkyl, $C_{3-8}$ cycloalkenyl, $C_1$-$C_6$ acyl, 4-12 membered monocyclic or bicyclic heterocyclyl, 4-12 membered monocyclic or bicyclic heterocyclyl-$C_1$-$C_6$alkyl-, $C_6$-$C_{12}$ aryl, 5-12 membered heteroaryl; and $R^8$ and $R^9$ may be further independently substituted with up to three substituents chosen from hydroxyl, $C_{1-6}$ alkoxy, $C_{1-6}$ hydroxyalkyl $C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, or a heterobicyclic ring of 7-12 members which may be fused, bridged or spiro, and contain up to two other heteroatoms chosen from O, $S(O)_x$, or $NR^{11}$, and these heterocyclic rings are optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, —$CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$alkyl, which is optionally substituted with up to three substituents selected from hydroxyl, oxo, thiono, cyano and halo, p=0, 1, 2, 3, or 4:
q=2, 3, or 4; and
x=0, 1, or 2.

One embodiment of the present disclosure relates to compounds of formula (XIXB):

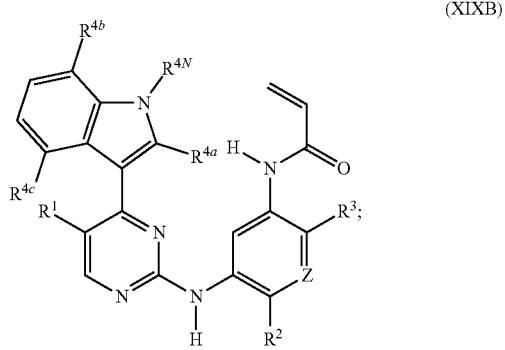

(XIXB)

or a stereoisomer or a pharmaceutically acceptable salt, solvate, ester, tautomer, or prodrug thereof;

wherein;

Z is CH or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^{4a}$ is H, halo, or —$C_{1-6}$ alkyl;
$R^{4b}$ is H, halo, cyano, —C(=O)$NR^8R^9$, —$NR^8R^9$, or $R^7SO_2$—;
$R^{4c}$ is H, halo, methyl, ethyl, or cyano;
$R^{4N}$ is H, —$C_{1-6}$ alkyl, —$CH_2C(=O)NR^8R^9$, or —$CD_3$;
wherein, at least one of $R^{4a}$, $R^{4b}$, or $R^{4c}$ is not H;
$R^7$ is —$NR^8R^9$;
$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (XIXB), $R^2$ is —$OCH_2CHF_2$, methoxy, —$OCD_3$, or ethoxy.

In one embodiment of compounds of formula (XIXB), $R^3$ is —$N(CH_3)CH_2CH_2N(CH_3)_2$.

In one embodiment of compounds of formula (XIXB), $R^{10}$ is H, —$CH_3$, —$CD_3$, —$CH_2CH_3$, or isopropyl.

In one embodiment of compounds of formula (XIXB), $R^{4N}$ is H, or —$CH_3$, —$CD_3$, —$CH_2CH_3$.

In one embodiment of compounds of formula (XIXB), $R^{4a}$ is H, —$CH_3$, or halo.

In one embodiment of compounds of formula (XIXB), $R^{4b}$ is —C(=O)$NR^8R^9$, —$NR^8R^9$, $R^7SO_2$—, —$C_{1-6}$ alkyl or cyano, and $R^{4c}$ is H. In another embodiment, $R^{4c}$ is methyl, ethyl, or halo, and $R^{4b}$ is H.

In one embodiment of compounds of formula (XIXB), $R^8$ and $R^9$ are independently H, —$CH_3$, —$CD_3$, —$CH_2CH_3$, isopropyl, or cyclopropyl.

In one embodiment of compounds of formula (XIXB), a compound is selected from:

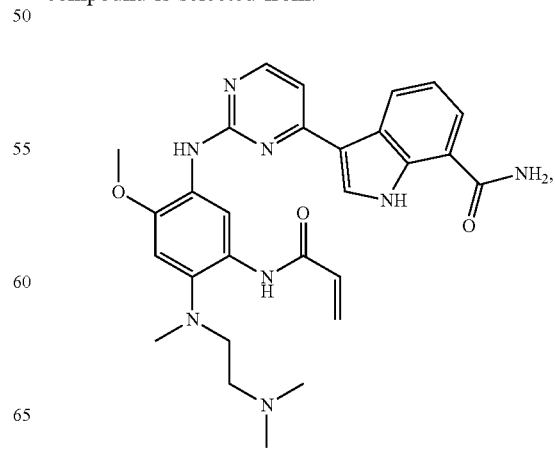

-continued
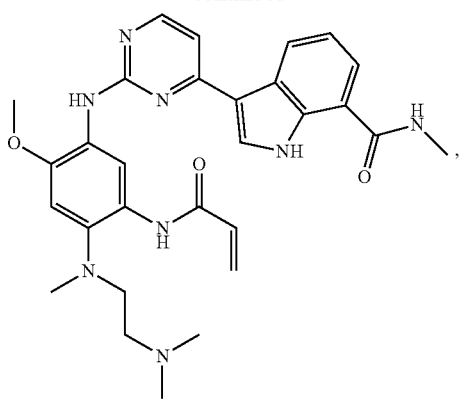
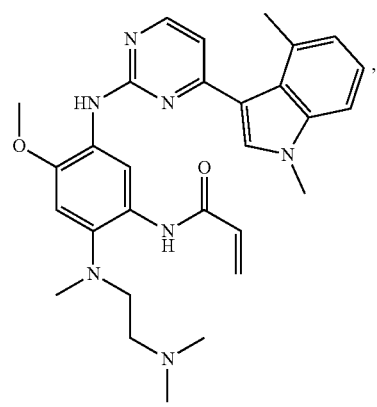
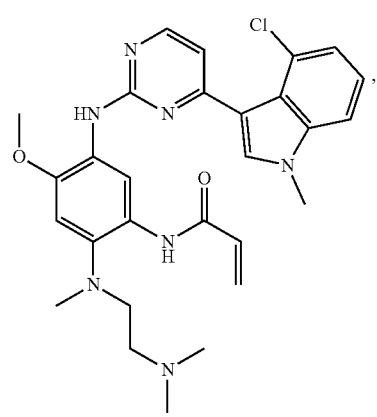
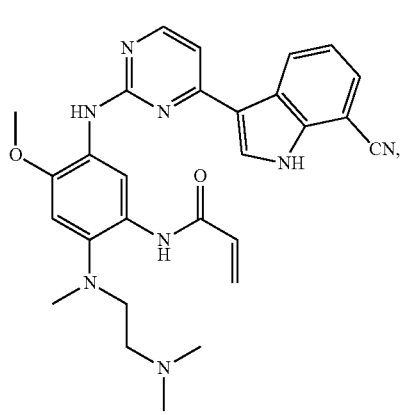
-continued
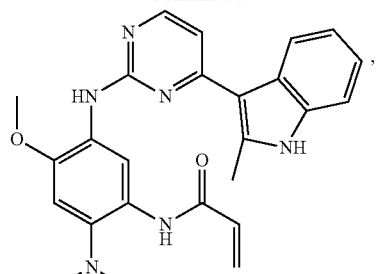
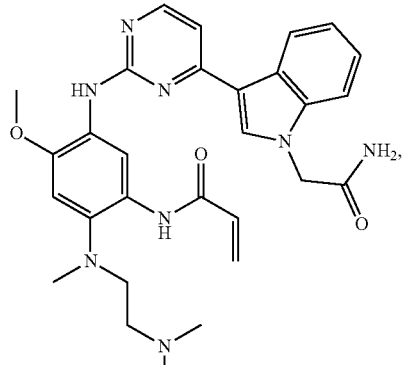
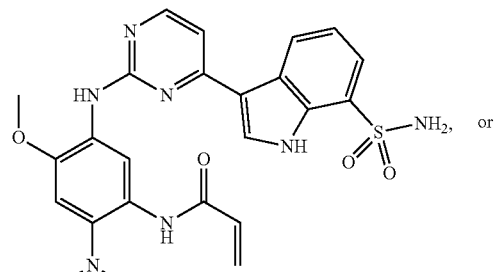
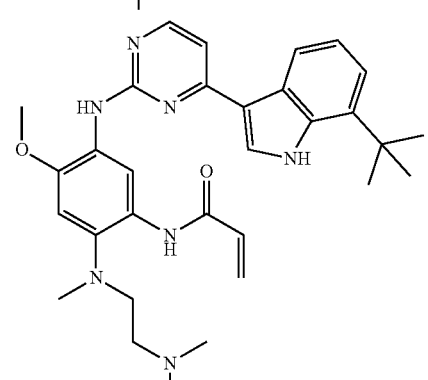
One embodiment of the present disclosure relates to compounds of formula (XXB):

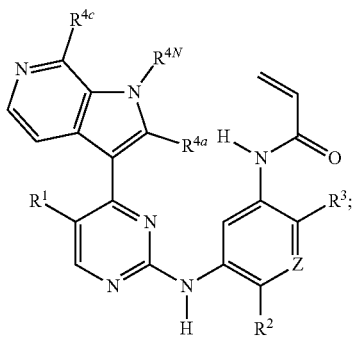

(XXB)

or a stereoisomer or a pharmaceutically acceptable salt, solvate, ester, tautomer, or prodrug thereof;
wherein:

Z is CH or N;

$R^1$ is selected from hydrogen, methyl, fluoro, chloro, bromo, $CF_3$, or cyano;

$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;

$R^3$ is $N(R^{10})C_{2-6}$ alkyl-$NR^{10}R^{10}$;

$R^{4a}$ is H, halo, or —$C_{1-6}$ alkyl;

$R^{4c}$ is H, halo, hydroxyl, —$C_{1-6}$ alkyl, —$C_{1-6}$ alkoxy, cyano, —C(=O)$NR^8R^9$, or —$NR^8R^9$;

$R^{4N}$ is H, —$C_{1-6}$ alkyl, or —$CD_3$;

wherein when $R^{4c}$ is —OH, then the bicyclic ring can be tautomerized between

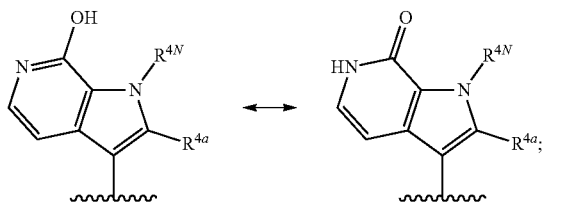

$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, —$CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^1$ is independently hydrogen or $C_1$-$C_6$ alkyl, which is optionally substituted with up to three substituents selected from hydroxyl, oxo, thiono, cyano and halo.

In one embodiment of compounds of formula (XXB),
Z is CH;
$R^1$ is hydrogen;
$R^2$ is cyclopropoxy, methoxy, ethoxy, or isopropoxy;
$R^3$ is —$N(CH_3)CH_2CH_2NR^{10}R^{10}$;
$R^{4a}$ is H;
$R^{4c}$ is —$OCD_3$, methoxy, ethoxy, or —$NR^8R^9$;
$R^{4N}$ is H, —$CD_3$, methyl, ethyl, or isopropyl;
$R^8$ and $R^9$ are independently H or methyl; and each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^1$.

In one embodiment of compounds of formula (XXB),
Z is CH,
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is H;
$R^{4c}$ is —$OCD_3$·, methoxy, ethoxy, or —$NR^8R^9$;
$R^{4N}$ is H, —$CD_3$, methyl, ethyl, or isopropyl;
$R^8$ and $R^9$ are independently H or methyl; and
each $R^{10}$ is independently H, —$CD_3$, methyl, ethyl, or isopropyl.

In one embodiment of compounds of formula (XXB), $R^2$ is methoxy, —$OCD_3$, or ethoxy.

In one embodiment of compounds of formula (XXB), $R^3$ is —$N(CH_3)CH_2CH_2N(CH_3)_2$.

In one embodiment of compounds of formula (XXB), $R^{10}$ is H, —$CH_3$, —$CD_3$, —$CH_2CH_3$, or isopropyl.

In one embodiment of compounds of formula (XXB), $R^{4N}$ is H, or —$CH_3$, —$CD_3$, —$CH_2CH_3$.

In one embodiment of compounds of formula (XXB), $R^{4a}$ is H, —$CH_3$, or halo.

In one embodiment of compounds of formula (XXB), $R^4$ is methoxy, —$OCD_3$, ethoxy, isopropoxy, cyclopropoxy, or —$NR^8R^9$.

In one embodiment of compounds of formula (XXB), $R^8$ and $R^9$ are independently H, —$CH_3$, —$CD_3$, —$CH_2CH_3$, isopropyl, or cyclopropyl.

In one embodiment of compounds of formula (XXB), a compound is selected from:

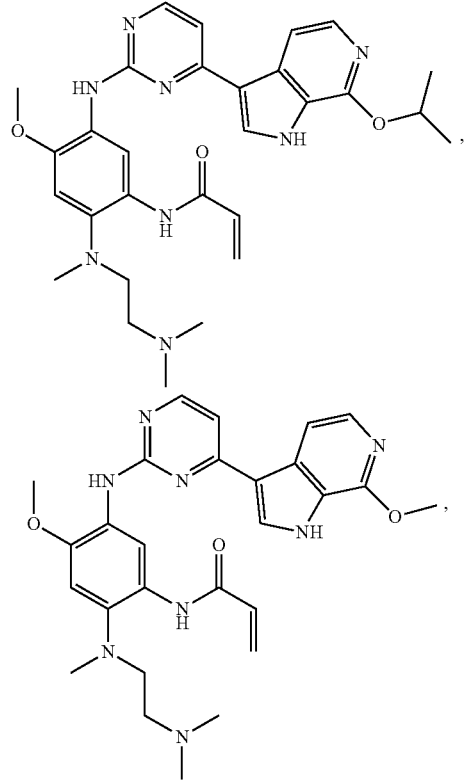

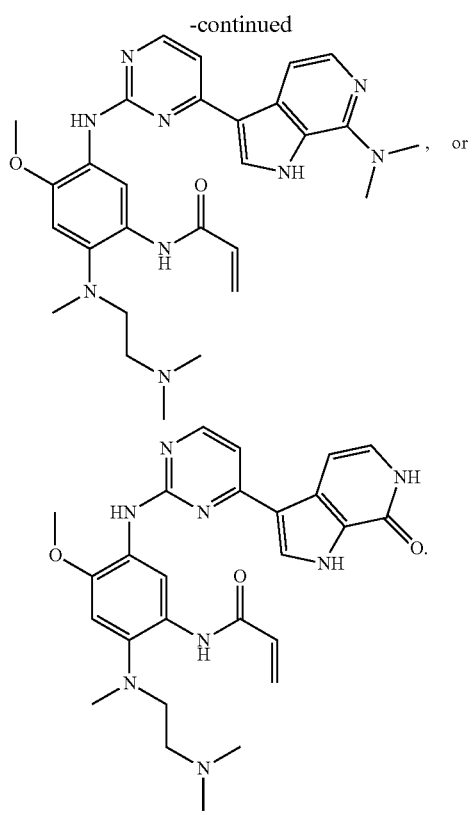

One embodiment of the present disclosure relates to compounds of formula (XXIB):

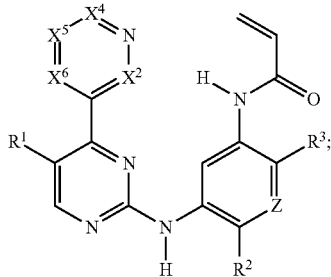

(XXIB)

or a stereoisomer or a pharmaceutically acceptable salt, solvate, ester, tautomer, or prodrug thereof;
wherein:
each of $X^2$, $X^4$, $X^5$, and $X^6$ is independently $CR^4$ or N;
wherein not more than two of $X^2$, $X^4$, $X^5$, and $X^6$ are N;
Z is CH or N;
$R^1$ is independently selected from hydrogen, fluoro, chloro, bromo, methyl, ethyl, hydroxyl, methoxy, ethoxy, isopropxy, cyclopropoxy, —OCF$_3$, —OCH$_2$CF$_3$, —OCH$_2$CHF$_2$, ethenyl, ethynyl, CF$_3$, CHF$_2$, CHO, CH$_2$OH, CONH$_2$, CO$_2$Me, CONHMe, CONMe$_2$, and cyano;
$R^2$ is —OCF$_3$, —OCHF$_2$, —OCF$_2$CF$_3$, —OCH$_2$CHF$_2$, —OCH$_2$CF$_3$, cyclopropyl, cyclopropoxy, methoxy, —OCD$_3$, ethoxy, or isopropoxy;
$R^3$ is N(R$^{10}$)C$_{2-6}$ alkyl-NR$^{10}$R$^{10}$, N(R$^{10}$)C$_{2-6}$ alkyl-R$^7$, O(CH$_2$)$_p$R$^7$, N(R$^{10}$)C(=O)(CH$_2$)$_p$R$^7$ or R$^7$;
each $R^4$ is independently H, cyano, nitro, halo, —C$_{1-6}$ alkyl, —C$_{1-6}$ haloalkyl, carboxy-C$_{1-6}$ alkyl, —C$_{1-6}$ hydroxy-alkyl, R$^8$R$^9$N—C$_{1-6}$ alkyl-, —C$_{2-6}$ alkenyl, —C$_{2-6}$ alkynyl, C$_{1-6}$ acyl-, R$^7$—(CH$_2$)$_p$C(=O)—, C$_{1-6}$ hydroxyalkyl-C(=O)—, carboxy, —C$_{1-6}$ alkoxycarbonyl, —C(=O)NR$^8$R$^9$, hydroxyl, alkoxy, C$_{1-6}$ acyloxy, —NR$^8$R$^9$, C$_{1-6}$ acyl-N(R$^{10}$)—, R$^7$SO$_2$—,
wherein when $X^5$ is $CR^4$ and $X^4$ is C—OH, then the ring containing $X^2$ can be tautomerized between

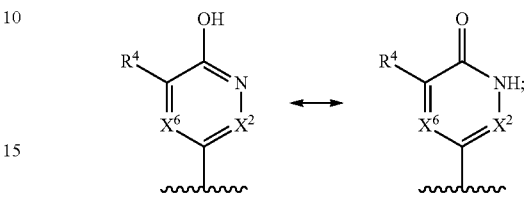

wherein when $X^4$ is $CR^4$ and $X^2$ is C—OH, then the ring containing $X^2$ can be tautomerized between

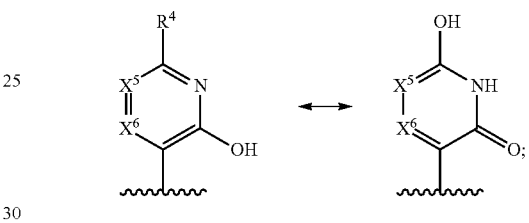

$R^7$ is OH, NR$^8$R$^9$, O(CH$_2$)$_q$NR$^8$R$^9$, C$_{1-6}$ alkoxy, or C$_{2-6}$ hydroxyalkoxy;
$R^8$ and $R^9$ are independently H, —CD$_3$, C$_{1-6}$ alkyl, C$_{3-6}$ alkenyl, C$_{3-6}$ alkynyl, C$_{3-8}$ cycloalkyl, C$_{3-8}$ cycloalkenyl, C$_1$-C$_6$ acyl, 4-12 membered monocyclic or bicyclic heterocyclyl, 4-12 membered monocyclic or bicyclic heterocyclyl-C$_1$-C$_6$ alkyl-, C$_6$-C$_{12}$ aryl, 5-12 membered heteroaryl; and R$^8$ and R$^9$ may be further independently substituted with up to three substituents chosen from hydroxyl, C$_{1-6}$ alkoxy, C$_{1-6}$ hydroxyalkylC$_{2-6}$ hydroxyalkoxy, oxo, thiono, cyano or halo; or
alternatively, R$^8$ and R$^9$, taken together with the N atom to which they are both attached, form a heterocyclic ring of 4-7 members, containing up to one other heteroatom chosen from O, S, or NR$^{11}$, or a heterobicyclic ring of 7-12 members which may be fused, bridged or spiro, and contain up to two other heteroatoms chosen from O, S(O)$_x$, or NR$^{11}$, and these heterocyclic rings are optionally substituted with up to three substituents chosen from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano or halo;
each R$^{10}$ is independently H, —CD$_3$, C$_{1-6}$ alkyl, C$_{3-6}$ cycloalkyl, C$_{2-6}$ hydroxyalkyl, C$_{1-6}$ alkoxy-C$_{1-6}$ alkyl or C$_{2-6}$ alkyl-NR$^8$R$^9$; or
alternatively, two R$^{10}$ on the same N atom to which they are both attached, form a heterocyclic ring of 5-6 members, containing up to one other heteroatom selected from O, S, or NR$^{11}$:
each R$^{11}$ is independently hydrogen or C$_1$-C$_6$ alkyl, which is optionally substituted with up to three substituents selected from hydroxyl, oxo, thiono, cyano and halo;
p=0, 1, 2, 3, or 4;
q=2, 3, or 4; and
x=0, 1, or 2.
One embodiment of the present disclosure relates to compounds of formula (XXIIB):

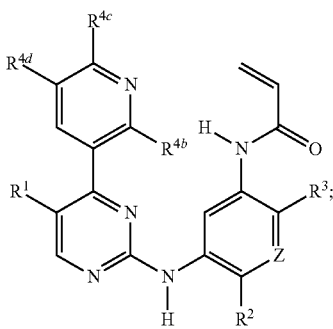

(XXIIB)

or a stereoisomer or a pharmaceutically acceptable salt, solvate, ester, tautomer, or prodrug thereof;
wherein;
Z is CH or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^{4b}$, $R^{4c}$ and $R^{4d}$ is each H, halo, hydroxyl, —$C_{1-6}$ alkyl, cyano, $C_{1-6}$ acyl-, —C(=O)$NR^8R^9$, or —$NR^8R^9$;
wherein when $R^{4b}$ is hydroxyl, then the pyridine ring with $R^{4b}$ substituent can be tautomerized between

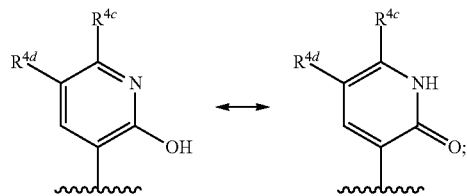

wherein when $R^{4c}$ is hydroxyl, then the pyridine ring with $R^{4c}$ substituent be tautomerized between

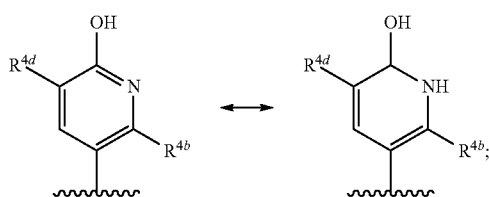

$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and
each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$alkyl, which is optionally substituted with up to three substituents selected from hydroxyl, oxo, thiono, cyano and halo.

In one embodiment of compounds of formula (XXIIB),
Z is CH;
$R^1$ is hydrogen, methyl, or chloro;
$R^2$ is —$OCF_3$, —$OCHF_2$, —$OCF_2CF_3$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4b}$ is H;
$R^{4c}$ is —$NHR^8$; wherein $R^8$ is H, —$CD_3$, methyl, ethyl, or isopropyl;
$R^{4d}$ is —C(=O)$CH_3$, —C(=O)$CH_2CH_3$, —C(=O)CH($CH_3$)$_2$, —C(=O)$NH_2$, —C(=O)$NHCH_3$, or —C(=O)N($CH_3$)$_2$; and
each $R^{10}$ is independently H, —$CD_3$, methyl, ethyl, or isopropyl.

In one embodiment of compounds of formula (XXIIB),
Z is CH;
$R^1$ is hydrogen or chloro;
$R^2$ is methoxy, ethoxy, or isopropoxy;
$R^3$ is —$N(CH_3)CH_2CH_2NR^{10}R^{10}$;
$R^{4b}$ is H:
$R^{4c}$ is —$NHR^8$; wherein $R^8$ is H, —$CD_3$, methyl, ethyl, or isopropyl;
$R^{4d}$ is —C(=O)$CH_3$, —C(=O)$CH_2CH_3$, —C(=O)CH($CH_3$)$_2$, —C(=O)$NH_2$, —C(=O)$NHCH_3$, or —C(=O)N($CH_3$)$_2$; and
each $R^{10}$ is independently H, —$CD_3$, methyl, ethyl, or isopropyl.

In one embodiment of compounds of formula (XXIIB), $R^2$ is —$OCH_2CHF_2$, methoxy, —$OCD_3$, or ethoxy.

In one embodiment of compounds of formula (XXIIB), $R^3$ is —$N(CH_3)CH_2CH_2N(CH_3)_2$.

In one embodiment of compounds of formula (XXIIB), $R^{10}$ is H, —$CH_3$, —$CD_3$, —$CH_2CH_3$, or isopropyl.

In one embodiment of compounds of formula (XXIIB), $R^{4b}$ is H, or —$CH_3$, —$CD_3$, —$CH_2CH_3$. In another embodiment $R^{4b}$ is H.

In one embodiment of compounds of formula (XXIIB), $R^{4c}$ is H or —$NR^8R^9$.

In one embodiment of compounds of formula (XXIIB), $R^{4d}$ is H, $C_{1-6}$ acyl-, or —C(=O)$NR^8R^9$.

In one embodiment of compounds of formula (XXIIB), $R^8$ and $R^9$ are independently H, —$CH_3$, —$CD_3$, —$CH_2CH_3$, isopropyl, or cyclopropyl.

In one embodiment of compounds of formula (XXIIB), a compound is selected from:

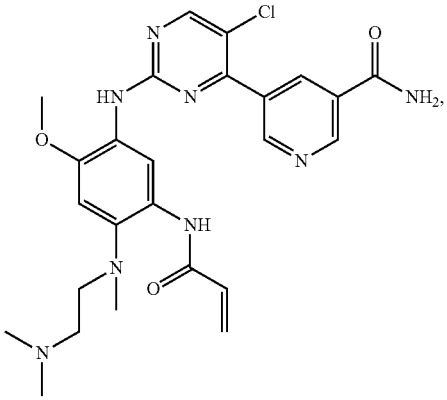

67
-continued
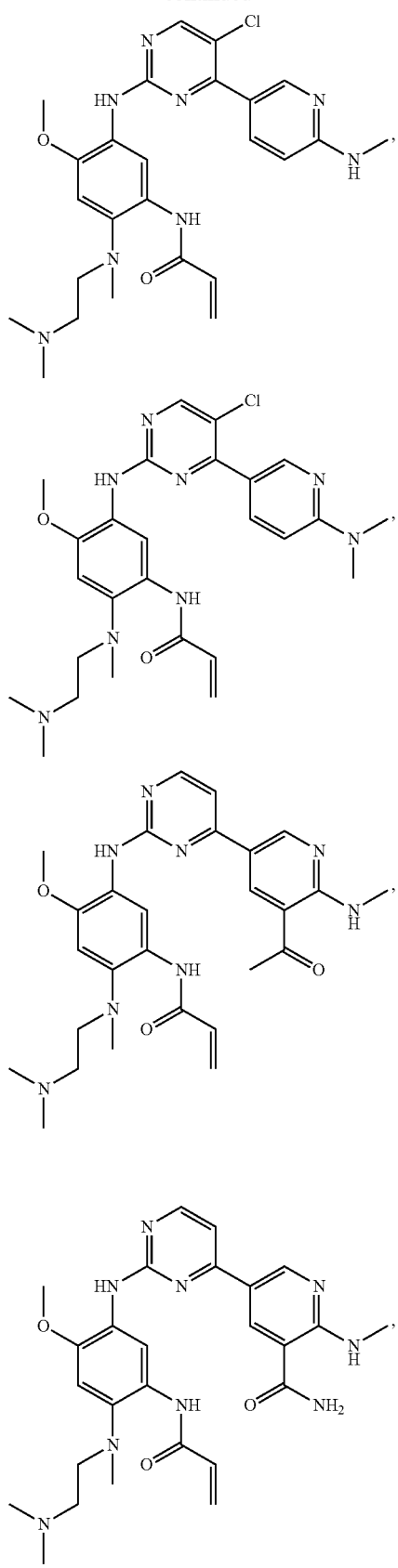
68
-continued
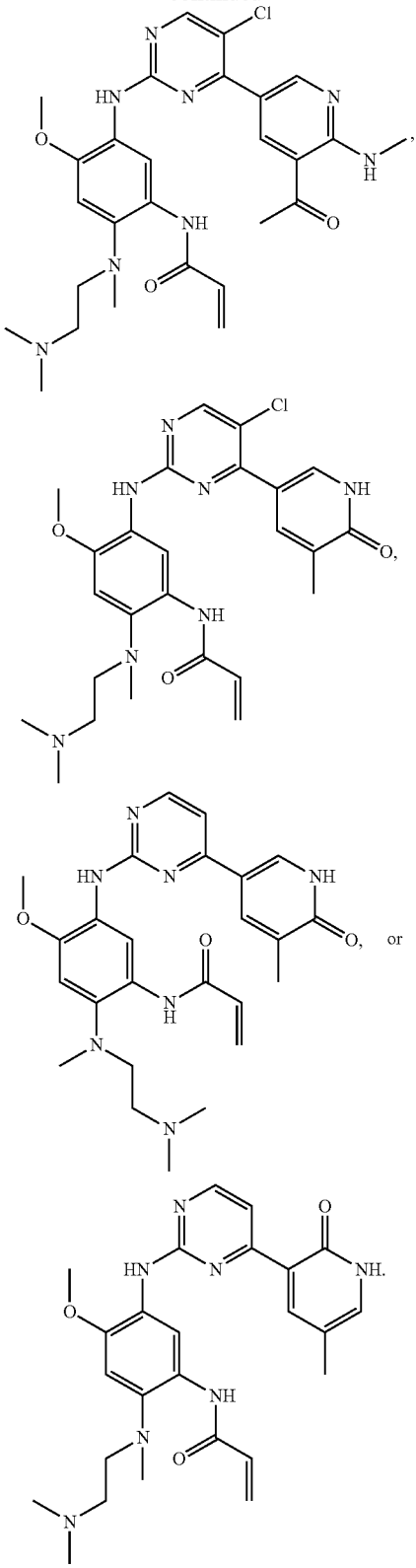
In one embodiment, the present disclosure relates to one or more of the following compounds:

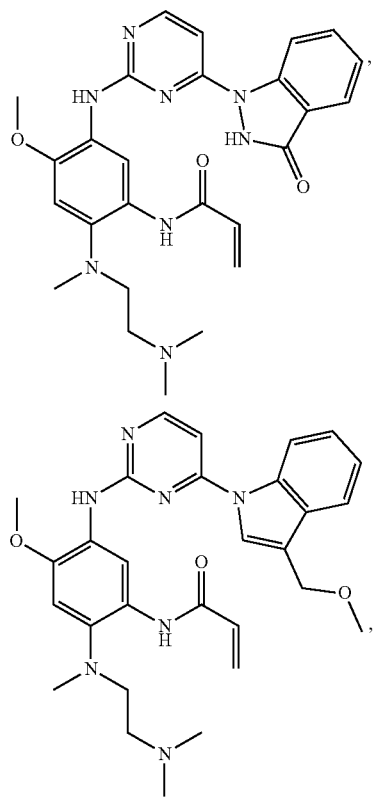
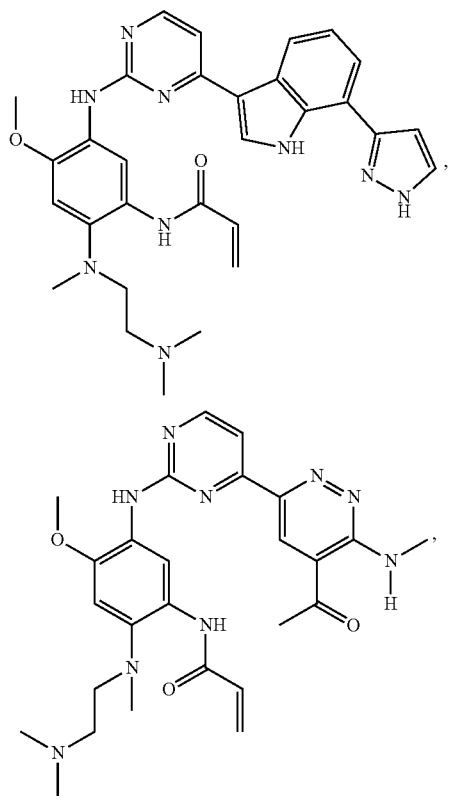
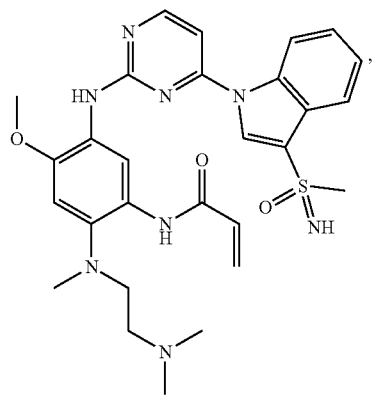
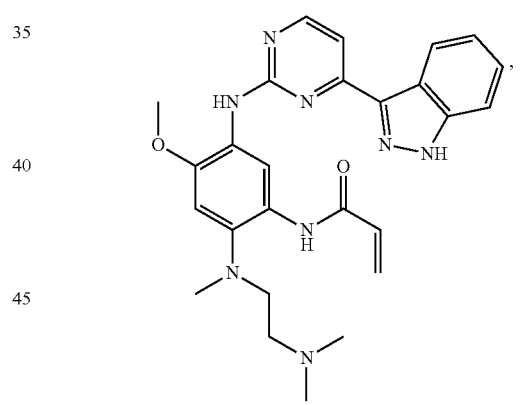
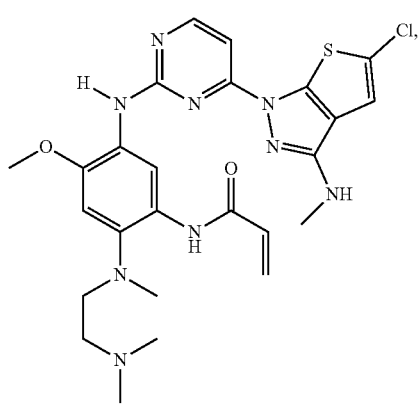
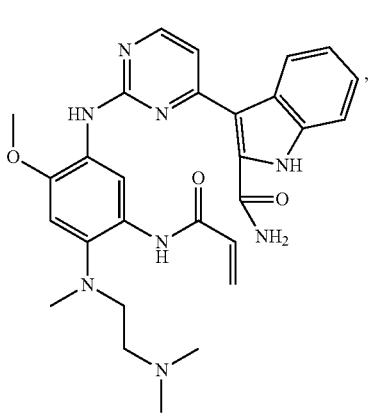

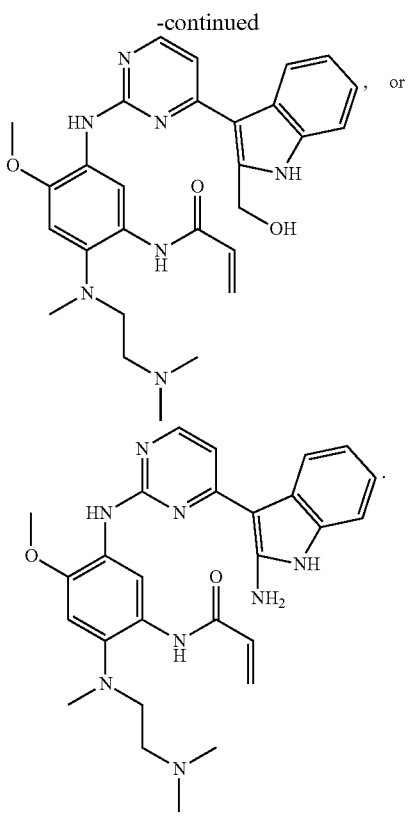

, or

In one embodiment, the present disclosure relates to a pharmaceutical composition comprising a compound of the invention or a pharmaceutically acceptable salt, solvate, ester, or prodrug thereof, and a pharmaceutically acceptable carrier.

In one embodiment, the present disclosure relates to a method for treating cancer in a patient in need thereof, comprising administering to the patient a therapeutically effective amount of a compound of the invention or a pharmaceutically acceptable salt, solvate, ester, or prodrug thereof.

In one embodiment, the method disclosed herein is useful for treating cancer selected from lung cancer, colorectal cancer, pancreatic cancer, head and neck cancers, breast cancer, ovarian cancer, uterine cancer, liver cancer, and stomach cancer. In another embodiment, the cancer is non-small cell lung cancer (NSCLC).

In one embodiment, the method disclosed herein relates to treatment of cancer, wherein the cancer results from a mutation in the exon 20 domain of EGFR. In some embodiments, the mutation in the exon 20 domain of EGFR is selected from NPG, ASV, or T790M. In one embodiment, the mutation in the exon 20 domain of EGFR is T790M concurrent with an exon 19 insertion mutation or an exon 21 point mutation.

In one embodiment, the method disclosed herein relates to treatment of cancer, wherein the patient is resistant to a kinase inhibitor other that a compound of the invention or a pharmaceutically acceptable salt, solvate, ester, or prodrug thereof. In another embodiment, the kinase inhibitor is an EGFR inhibitor.

The present disclosure also relates to a method for inhibiting EGFR, or a mutation thereof, in a patient in need thereof, comprising administering to the patient a therapeutically effective amount of a compound of the invention or a pharmaceutically acceptable salt, solvate, ester, or prodrug thereof. In one embodiment, the mutation is in the exon 20 domain of EGFR.

DETAILED DESCRIPTION

Definitions

The term "alkyl" refers to a saturated, monovalent aliphatic hydrocarbon radical including straight chain and branched chain groups having the specified number of carbon atoms. The term "$C_{1-6}$ alkyl" or "$C_1$-$C_6$ alkyl" refers to a branched or straight chained alkyl radical containing from 1 to 6 carbon atoms, such as methyl, ethyl, n-propyl, isopropyl, n-butyl, isobutyl, sec butyl, t-butyl, pentyl, hexyl, and the like. Similarly, the term "$C_{1-4}$ alkyl" or "$C_1$-$C_4$ alkyl" refers to a branched or straight chained alkyl radical containing from 1 to 4 carbon atoms, such as methyl, ethyl, n-propyl, isopropyl, n-butyl, isobutyl, sec-butyl, t-butyl, and the like.

As used herein, the term "halogen" or "halo" refers to fluoro, chloro, bromo, or iodo (F, Cl, Br, I), and in some instances, substituted alkyl groups may be specifically named with reference to the substituent group. For example, "haloalkyl" refers to an alkyl group having the specified number of carbon atoms that is substituted by one or more halo substituents, and typically contain 1-6 carbon atoms and 1, 2 or 3 halo atoms (i.e., "$C_1$-$C_6$ haloalkyl"). Thus, a $C_1$-$C_6$ haloalkyl group includes trifluoromethyl (—$CF_3$) and difluoromethyl (—$CF_2H$).

Similarly, "hydroxyalkyl" refers to an alkyl group having the specified number of carbon atoms that is substituted by one or more hydroxy substituents, and typically contain 1-6 carbon atoms and 1, 2 or 3 hydroxy (i.e., "$C_1$-$C_6$ hydroxyalkyl"). Thus, $C_1$-$C_6$ hydroxyalkyl includes hydroxymethyl (—$CH_2OH$) and 2-hydroxyethyl (—$CH_2CH_2OH$).

The term "$C_{1-6}$ alkoxy", "$C_1$-$C_6$ alkoxy" or "$OC_{1-6}$ alkyl" refers to a straight or branched alkoxy group containing from 1 to 6 carbon atoms, such as methoxy, ethoxy, n-propoxy, isopropoxy, n-butoxy, isobutoxy, sec-butoxy, t-butoxy, pentoxy, hexoxy, and the like. The term "$C_{1-4}$ alkoxy", "$C_1$-$C_4$ alkoxy", "$OC_{1-4}$ alkyl" refers to a straight or branched alkoxy group containing from 1 to 4 carbon atoms, such as methoxy, ethoxy, n-propoxy, isopropoxy, n-butoxy, isobutoxy, sec-butoxy, t-butoxy, and the like.

The term "$C_{3-6}$ cycloalkoxy", "$C_3$-$C_6$ cycloalkoxy", or "$OC_{3-6}$ cycloalkyl" refers to a cyclic alkoxy radical containing from 3 to 6 carbon atoms such as cyclopropoxy, cyclobutoxy, cyclopentoxy, and the like.

"Alkoxyalkyl" refers to an alkyl group having the specified number of carbon atoms that is substituted by one or more alkoxy substituents. Alkoxyalkyl groups typically contain 1-6 carbon atoms in the alkyl portion and are substituted by 1, 2 or 3 $C_1$-$C_4$ alkyoxy substituents. Such groups are sometimes described herein as $C_1$-$C_4$ alkyoxy-$C_1$-$C_6$ alkyl. "Aminoalkyl" refers to alkyl group having the specified number of carbon atoms that is substituted by one or more substituted or unsubstituted amino groups, as such groups are further defined herein.

Aminoalkyl groups typically contain 1-6 carbon atoms in the alkyl portion and are substituted by 1, 2 or 3 amino substituents. Thus, a $C_1$-$C_6$ aminoalkyl group includes, for example, aminomethyl (—$CH_2NH_2$), N,N-dimethylaminoethyl (—$CH_2CH_2N(CH_3)_2$), 3-(N-cyclopropylamino)propyl (—$CH_2CH_2CH_2NH$-$^c$Pr) and N-pyrrolidinylethyl (—$CH_2CH_2N$-pyrrolidinyl).

"Alkenyl" refers to an alkyl group, as defined herein, consisting of at least two carbon atoms and at least one carbon-carbon double bond. Typically, alkenyl groups have 2 to 20 carbon atoms ("$C_2$-$C_{20}$ alkenyl"), preferably 2 to 12 carbon atoms ("$C_2$-$C_{12}$ alkenyl"), more preferably 2 to 8 carbon atoms ("$C_2$-$C_8$ alkenyl"), or 2 to 6 carbon atoms ("$C_2$-$C_6$ alkenyl"), or 2 to 4 carbon atoms ("$C_2$-4 alkenyl"). Representative examples include ethenyl, 1-propenyl, 2-propenyl, 1-, 2-, or 3-butenyl, and the like. A "$C_2$-$C_6$ alkenyl" denotes a straight-chain or branched group containing 2 to 6 carbon atoms and at least one double bond between two $sp^2$ hybridized carbon atoms. This also applies if they carry substituents or occur as substituents of other radicals, for example in O—($C_2$-$C_6$) alkenyl radicals. Examples of suitable $C_2$-$C_6$ alkenyl radicals are n-propenyl, isopropenyl, n-butenyl, iso-butenyl, n-pentenyl, sec-pentenyl, n-hexenyl, sec-hexenyl, and the like. Alkenyl groups may be unsubstituted or substituted by the same groups that are described herein as suitable for alkyl.

"Alkynyl" refers to an alkyl group, as defined herein, consisting of at least two carbon atoms and at least one carbon-carbon triple bond. Alkynyl groups have 2 to 20 carbon atoms ("$C_2$-$C_{20}$ alkynyl"), preferably 2 to 12 carbon atoms ("$C_2$-$C_{12}$ alkynyl"), more preferably 2 to 8 carbon atoms ("$C_2$-$C_8$ alkynyl"), or 2 to 6 carbon atoms ("$C_2$-$C_6$ alkynyl"), or 2 to 4 carbon atoms ("$C_2$-$C_4$ alkynyl"). Representative examples include, but are not limited to, ethynyl, 1-propynyl, 2-propynyl, 1-, 2-, or 3-butynyl, and the like. Alknyl groups may be unsubstituted or substituted by the same groups that are described herein as suitable for alkyl. A "$C_2$-$C_6$ alkynyl" denotes a straight-chain or branched group containing 2 to 6 carbon atoms and at least one triple bond between two sp hybridized carbon atoms. This also applies if they carry substituents or occur as substituents of other radicals, for example in O—($C_2$-$C_6$)alkynyl radicals. Examples of suitable $C_2$-$C_6$ alkynyl radicals are propynyl, butynyl, pentynyl, hexynyl, and the like.

"Alkylene" as used herein refers to a divalent hydrocarbyl group having the specified number of carbon atoms which can link two other groups together. Sometimes it refers to —($CH_2$)n- where n is 1-8, and preferably n is 1-4. Where specified, an alkylene can also be substituted by other groups and may include one or more degrees of unsaturation (i.e., an alkenylene or alkynylene moiety) or rings. The open valences of an alkylene need not be at opposite ends of the chain. Thus —CH(Me)- and —C(Me)$_2$- are also included within the scope of the term 'alkylenes', as are cyclic groups such as cyclopropan-1,1-diyl and unsaturated groups such as ethylene (—CH=CH—) or propylene (—$CH_2$CH=CH—). Where an alkylene group is described as optionally substituted, the substituents include those typically present on alkyl groups as described herein.

"Heteroalkylene" refers to an alkylene group as described above, wherein one or more non-contiguous carbon atoms of the alkylene chain are replaced by —N—, —O—, —P— or —S—, in manifestations such as —N(R)—, —P(=O)(R)—, —S(O)$_x$— or —S(=O)(=N$R^{10}$)—, where R is H or $C_1$-$C_4$ alkyl and x is 0-2. For example, the group —O—($CH_2$)$_{1-4}$— is a '$C_2$-$C_5$'-heteroalkylene group, where one of the carbon atoms of the corresponding alkylene is replaced by O.

"Aryl" or "aromatic" refers to an all-carbon monocyclic or fused-ring polycyclic having a completely conjugated pi-electron system and possessing aromaticity. The terms "$C_6$-$C_{12}$ aryl" and "$C_{6-12}$ aryl" are included within this term and encompass aromatic ring systems of 6 to 12 carbons and containing no heteroatoms within the ring system. Examples of aryl groups are phenyl and naphthalenyl. The aryl group may be substituted or unsubstituted.

Substituents on adjacent ring carbon atoms of a $C_6$-$C_{12}$ aryl may combine to form a 5- or 6-membered carbocyclic ring optionally substituted by one or more substituents, such as oxo, $C_1$-$C_6$ alkyl, hydroxyl, amino and halogen, or a 5- or 6-membered heterocyclic ring containing one, two or three ring heteroatoms selected from N, O and S(O), (where x is 0, 1 or 2) optionally substituted by one or more substituents, such as oxo, $C_1$-$C_6$ alkyl, hydroxyl, amino and halogen. Examples of aryl groups include phenyl, biphenyl, naphthyl, anthracenyl, phenanthrenyl, indanyl, indenyl, and tetrahydronaphthyl. The aryl group may be unsubstituted or substituted as further described herein.

"Heteroaryl" or "heteroaromatic" refers to monocyclic or fused bicyclic or polycyclic ring systems having the well-known characteristics of aromaticity that contain the specified number of ring atoms and include at least one heteroatom selected from N, O, and S as a ring member in an aromatic ring. The inclusion of a heteroatom permits aromaticity in 5-membered rings as well as 6-membered rings. Typically, heteroaryl groups contain 5 to 20 ring atoms ("5-20 membered heteroaryl"), preferably 5 to 14 ring atoms ("5-14 membered heteroaryl"), and more preferably 5 to 12 ring atoms ("5-12 membered heteroaryl") or 5 to 6 ring atoms ("5-6 membered heteroaryl"). Heteroaryl rings are attached to the base molecule via a ring atom of the heteroaromatic ring, such that aromaticity is maintained. Thus, 6-membered heteroaryl rings may be attached to the base molecule via a ring C atom, while 5-membered heteroaryl rings may be attached to the base molecule via a ring C or N atom. The heteroaryl group may be unsubstituted or substituted as further described herein. As used herein, "5-6 membered heteroaryl" refers to a monocyclic group of 5 or 6 ring atoms containing one, two or three ring heteroatoms selected from N, O, and S, but including tetrazolyl with 4 nitrogens, the remaining ring atoms being C, and, in addition, having a completely conjugated pi-electron system. Substituents on adjacent ring atoms of a 5- or 6-membered heteroaryl may combine to form a fused 5- or 6-membered carbocyclic ring optionally substituted by one or more substituents, such as oxo, C1-C6 alkyl, hydroxyl, amino and halogen, or a fused 5- or 6-membered heterocyclic ring containing one, two or three ring heteroatoms selected from N, O, and S(O)$_x$ (where x is 0, 1 or 2) optionally substituted by one or more substituents, such as oxo, C1-C6 alkyl, hydroxyl, amino and halogen. If said fused ring is itself aromatic, it is referred to as a fused (bicyclic) heteroaromatic species, regardless of whether the second ring contains heteroatoms. A pharmaceutically acceptable heteroaryl is one that is sufficiently stable to be attached to a compound of the invention, formulated into a pharmaceutical composition and subsequently administered to a patient in need thereof.

Examples of 5-membered heteroaryl rings containing 1, 2 or 3 heteroatoms independently selected from O, N, and S, include pyrrolyl, thienyl, furanyl, pyrazolyl, imidazolyl, oxazolyl, isoxazolyl, thiazolyl, isothiazolyl, triazolyl, tetrazolyl, oxadiazolyl and thiadiazolyl. Preferred 6-membered heteroaryl rings contain 1 or 2 nitrogen atoms. Examples of 6-membered heteroaryl are pyridyl, pyridazinyl, pyrimidinyl and pyrazinyl. Examples of fused heteroaryl rings include benzofuran, benzothiophene, indole, benzimidazole, indazole, quinolone, isoquinoline, purine, pyrrolopyrimidine, napthyridine and carbazole.

An "arylene" as used herein refers to a bivalent radical derived from an aromatic hydrocarbon by removal of a hydrogen atom from each of two carbon atoms of the nucleus. In frequent embodiments, the arylene ring is a 1,2-disubstituted or a 1,3-disubstituted arylene. The aryl ring of the arylene moiety may be optionally substituted on open valence positions with groups suitable for an aryl ring, to the extent such substitution is indicated. Preferably, the arylene ring is a $C_6$-$C_{12}$ arylene ring, for example a 1,2-phenylene or 1,3-phenylene moiety.

Similarly, a "heteroarylene" as used herein refers to a bivalent radical derived from a heteroaromatic ring by removal of a hydrogen atom from each of two carbon or a carbon atom and a nitrogen atom of the nucleus. In frequent embodiments, the heteroarylene ring is a 1,2-disubstituted or a 1,3-disubstituted heteroarylene. The heteroaryl ring of the heteroarylene moiety is optionally substituted with groups suitable for an heteroaryl ring, to the extent such substitution is indicated. Preferably, the heteroarylene ring is a 5-12 membered, possibly fused, heteroarylene ring, more preferably a 5-6 membered heteroarylene ring, each of which may be optionally substituted.

The terms "heteroalicyclic", "heterocyclyl", or "heterocyclic" may be used interchangeably herein to refer to a non-aromatic, saturated or partially unsaturated ring system containing the specified number of ring atoms, including at least one heteroatom selected from N, O, and S as a ring member, wherein the heterocyclic ring is connected to the base molecule via a ring atom, which may be C or N. Heteroalicyclic rings may be fused to one or more other heteroalicyclic or carbocyclic rings, which fused rings may be saturated, partially unsaturated or aromatic. Preferably, heteroalicyclic rings contain 1 to 4 heteroatoms selected from N, O, and S as ring members, and more preferably 1 to 2 ring heteroatoms, provided that such heteroalicyclic rings do not contain two contiguous oxygen atoms. Heteroalicyclic groups may be unsubstituted or substituted by the same groups that are described herein as suitable for alkyl, aryl or heteroaryl.

Preferred heteroalicyclic groups include 3-12 membered heteroalicyclic groups, 5-8 membered heterocyclyl (or heteroalicyclic) groups, 4-12 membered heteroalicyclic monocycles, and 6-12 membered heteroalicyclic bicycles in accordance with the definition herein. As used herein, "3-12 membered heteroalicyclic" refers to a monocyclic or bicyclic group having 3 to 12 ring atoms, in which one, two, three or four ring atoms are heteroatoms selected from N, O, P(O), S(O)$_x$ (where x is 0, 1, 2) and S(=O)(=N R$^{10}$) the remaining ring atoms being C. The ring may also have one or more double bonds. However, the ring does not have a completely conjugated pi-electron system. Substituents on two ring carbon atoms may combine to form a 5- or 6-membered bridged ring that is either carbocyclic or heteroalicyclic containing one, two or three ring heteroatoms selected from N, O and S(O)$_x$ (where x is 0, 1 or 2). The heteroalicyclic group is optionally substituted by oxo, hydroxyl, amino. $C_1$-$C_6$-alkyl and the like.

In frequent embodiments, heteroalicyclic groups contain 3-12 ring members, including both carbon and non-carbon heteroatoms, and preferably 4-6 ring members. In certain preferred embodiments, substituent groups comprising 3-12 membered heteroalicyclic groups are selected from azetidinyl, pyrrolidinyl, piperidinyl, piperazinyl, morpholinyl and thiomorpholinyl rings, each of which may be optionally substituted to the extent such substitution makes chemical sense.

It is understood that no more than two N, O or S atoms are ordinarily connected sequentially, except where an oxo or aza group is attached to N, P or S in a higher formal oxidation state than its basal state (eg $N^{5+}$, $P^{5+}$, $S^{6+}$) to form groups such as, but not limited to, nitro, phosphinyl, phosphinamido, sulfoximino and sulfonyl group, or in the case of certain heteroaromatic rings, such as triazine, triazole, tetrazole, oxadiazole, thiadiazole, and the like.

"Cycloalkyl" refers to a non-aromatic, saturated or partially unsaturated carbocyclic ring system containing the specified number of carbon atoms, which may be a monocyclic, bridged, fused, or spiral bicyclic or polycyclic ring system that is connected to the base molecule through a carbon atom of the cycloalkyl ring. Typically, the cycloalkyl groups of the invention contain 3 to 12 carbon atoms ("C3-C12 cycloalkyl"), preferably 3 to 8 carbon atoms ("C3-C8 cycloalkyl"). Other cycloalkyl groups include partially unsaturated moieties from 4 to 7 carbons ("C4-C7 cycloalkenyl"). Representative examples include, e.g., cyclopropane, cyclobutane, cyclopentane, cyclopentene, cyclohexane, cyclohexene, cyclohexadiene, cycloheptane, cycloheptatriene, adamantane, and the like. Cycloalkyl groups may be unsubstituted or substituted by the same groups that are described herein as suitable for alkyl.

As used herein, "$C_3$-$C_6$ cycloalkyl" refers to an all-carbon, monocyclic or fused-ring polycyclic group of 3 to 6 carbon atoms.

"Cycloalkylalkyl" may be used to describe a cycloalkyl ring, typically a C3-C8 cycloalkyl, which is connected to the base molecule through an alkylene linker, typically a C1-C4 alkylene. Cycloalkylalkyl groups are described by the total number of carbon atoms in the carbocyclic ring and linker, and typically contain from 4-12 carbon atoms ("C4-C12 cycloalkylalkyl"). Thus a cyclopropylmethyl group is a C4-cycloalkylalkyl group and a cyclohexylethyl is a C8-cycloalkylalkyl, Cycloalkylalkyl groups may be unsubstituted or substituted on the cycloalkyl and/or alkylene portions by the same groups that are described herein as suitable for alkyl groups.

An "arylalkyl" group refers to an aryl group as described herein which is linked to the base molecule through an alkylene or similar linker. Arylalkyl groups are described by the total number of carbon atoms in the ring and linker. Thus a benzyl group is a C7-arylalkyl group and a phenylethyl is a C8-arylalkyl. Typically, arylalkyl groups contain 7-16 carbon atoms ("C7-C16 arylalkyl"), wherein the aryl portion contains 6-12 carbon atoms and the alkylene portion contains 1-4 carbon atoms. Such groups may also be represented as —C1-C4 alkylene-C6-C12 aryl.

"Heteroarylalkyl" refers to a heteroaryl group as described above that is attached to the base molecule through an alkylene linker, and differs from "arylalkyl" in that at least one ring atom of the aromatic moiety is a heteroatom selected from N, O and S. Heteroarylalkyl groups are sometimes described herein according to the total number of non-hydrogen atoms (i.e., C, N, S and O atoms) in the ring and linker combined, excluding substituent groups. Thus, for example, pyridinylmethyl may be referred to as a "C7"-heteroarylalkyl. Typically, unsubstituted heteroarylalkyl groups contain 6-20 non hydrogen atoms (including C, N. S and O atoms), wherein the heteroaryl portion typically contains 5-12 atoms and the alkylene portion typically contains 1-4 carbon atoms. Such groups may also be represented as —C1-C4 alkylene-5-12 membered heteroaryl.

Similarly, "arylalkoxy" and "heteroarylalkoxy" refer to aryl and heteroaryl groups, attached to the base molecule through a heteroalkylene linker (i.e., —O-alkylene-), wherein the groups are described according to the total number of non-hydrogen atoms (i.e., C, N, S and O atoms)

in the ring and linker combined. Thus, —O—CH₂-phenyl and —O—CH₂-pyridinyl groups would be referred to as C8-arylalkoxy and C8-heteroarylalkoxy groups, respectively.

Where an arylalkyl, arylalkoxy, heteroarylalkyl or heteroarylalkoxy group is described as optionally substituted, the substituents may be on either the divalent linker portion or on the aryl or heteroaryl portion of the group. The substituents optionally present on the alkylene or heteroalkylene portion are the same as those described above for alkyl or alkoxy groups generally, while the substituents optionally present on the aryl or heteroaryl portion are the same as those described above for aryl or heteroaryl groups generally.

"Hydroxy" refers to an —OH group.

"Acyl" refers to a monovalent group —C(O)alkyl wherein the alkyl portion has the specified number of carbon atoms (typically C1-C8, preferably C1-C6 or C1-C4) and may be substituted by groups suitable for alkyl. Thus, C1-C4 acyl includes a —C(O)C1-C4 alkyl substituent, e.g., —C(O)CH3. Similarly, "acyloxy" refers to a monovalent group —OC(O)alkyl wherein the alkyl portion has the specified number of carbon atoms (typically C1-C8, preferably C1-C6 or C1-C4) and may be substituted by groups suitable for alkyl. Thus, C1-C4 acyloxy includes a —OC(O)C1-C4 alkyl substituent, e.g., —OC(O)CH₃.

The term "monocyclic or bicyclic ring system" refers to a an aromatic, saturated or partially unsaturated ring system containing the specified number of ring atoms, and may optionally include one or more heteroatoms selected from N, O, and S as a ring member, wherein the heterocyclic ring is connected to the base molecule via a ring atom, which may be C or N. Included within this term are the terms "cycloalkyl", "aryl", "heterocyclyl", and "heteroaryl". Typically, the monocyclic or bicyclic ring system of the invention contain 4 to 12 members atoms ("4-12 membered monocyclic or bicyclic ring system"). Bicyclic systems may be connected via a 1,1-fusion (spiro), a 1,2-fusion (fused) or a 1,>2-fusion (bridgehead). Representative examples include cyclopentane, cyclopentene, cyclohexane, norbornyl, spiro[2.3]hexane, phenyl, biphenyl, naphthyl, anthracenyl, phenanthrenyl, pyrrolyl, thienyl, furanyl, pyrazolyl, imidazolyl, oxazolyl, isoxazolyl, thiazolyl, azetidinyl, pyrrolidinyl, piperidinyl, piperazinyl, benzothiophenyl, indolyl, and the like.

Representative examples of the central azine system are illustrated below, but the invention is not limited to these examples:

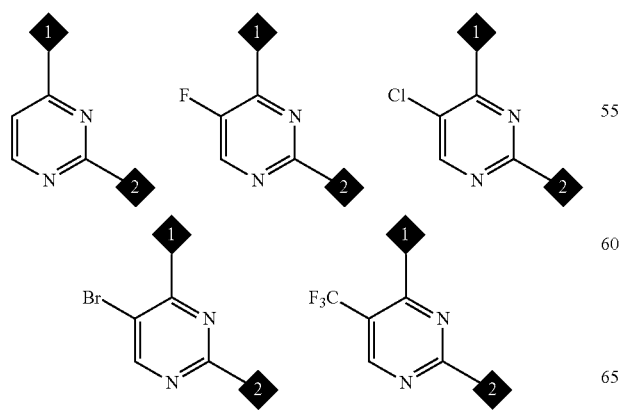

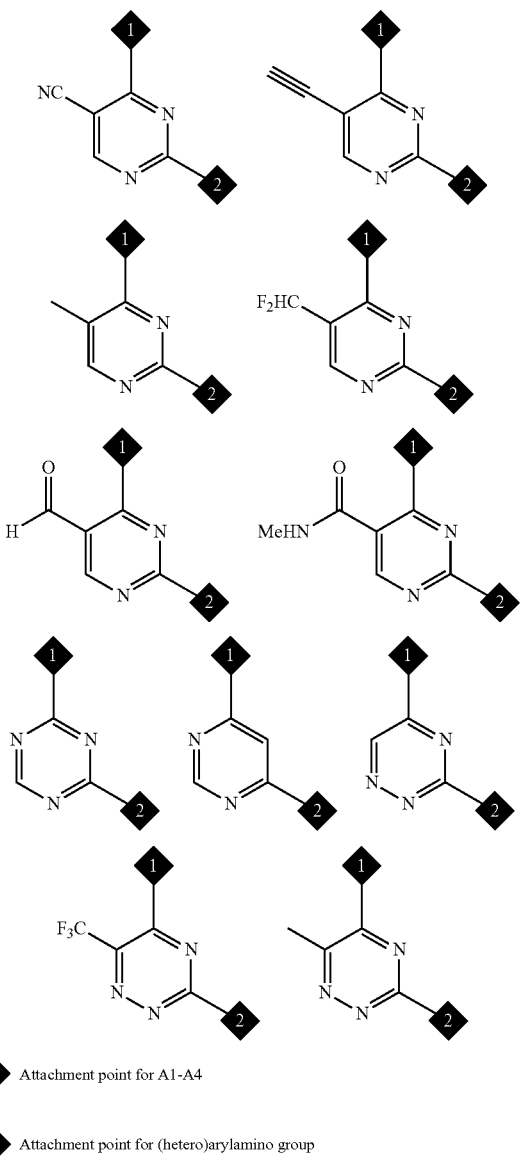

Representative examples of the 5,6-bicyclic azaaromatics which can be A¹ are illustrated below, but the invention is not limited to these examples:

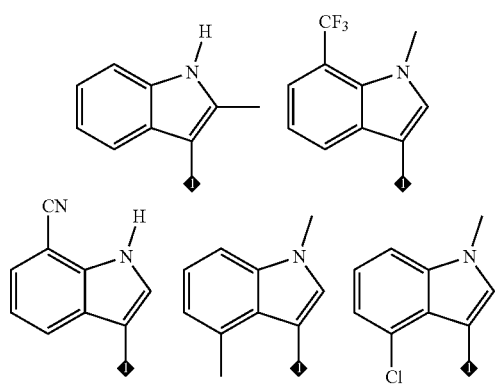

79
-continued
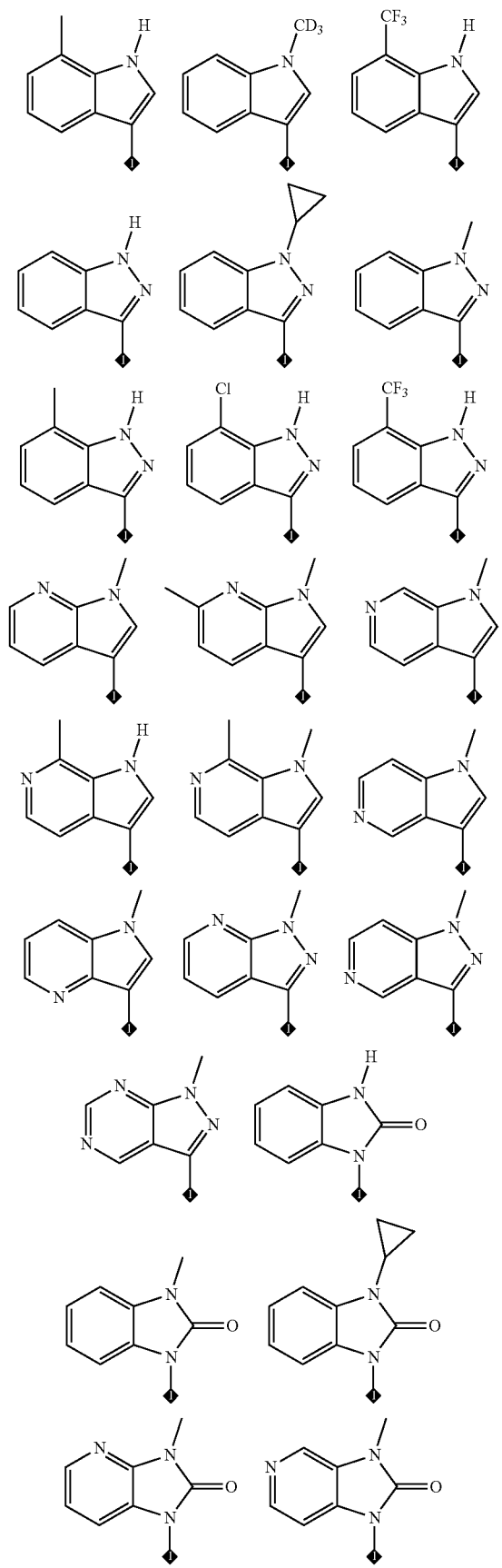
80
-continued
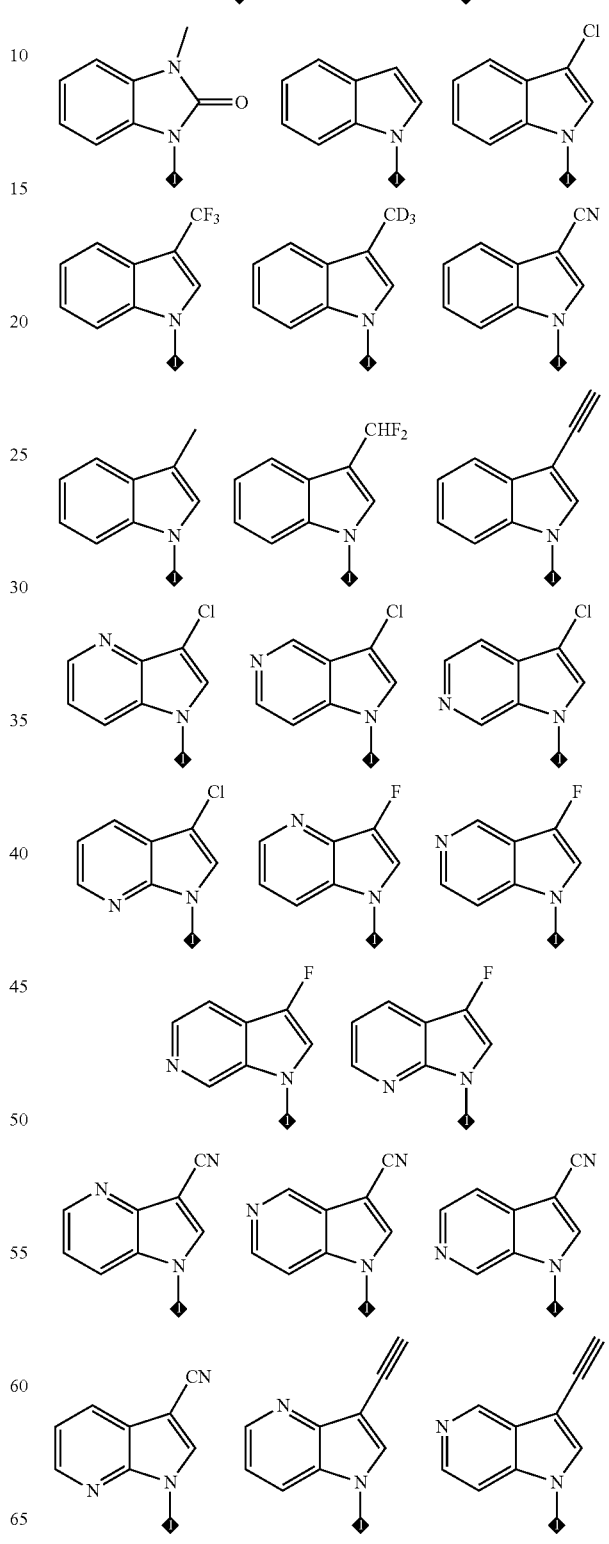

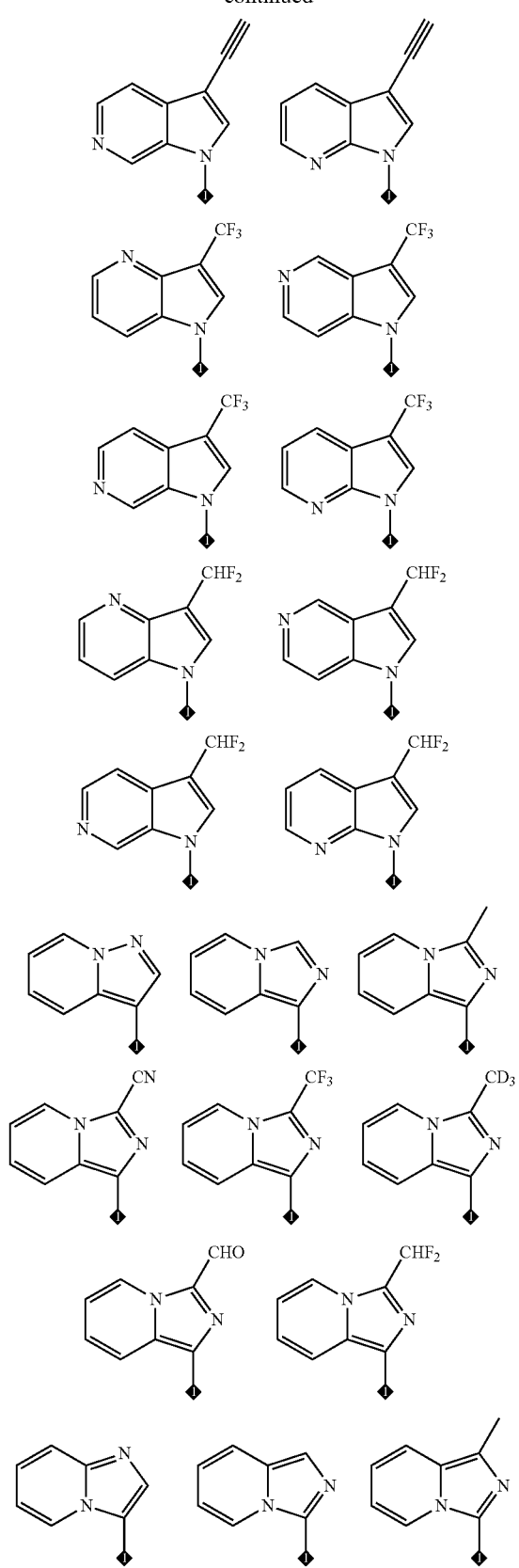
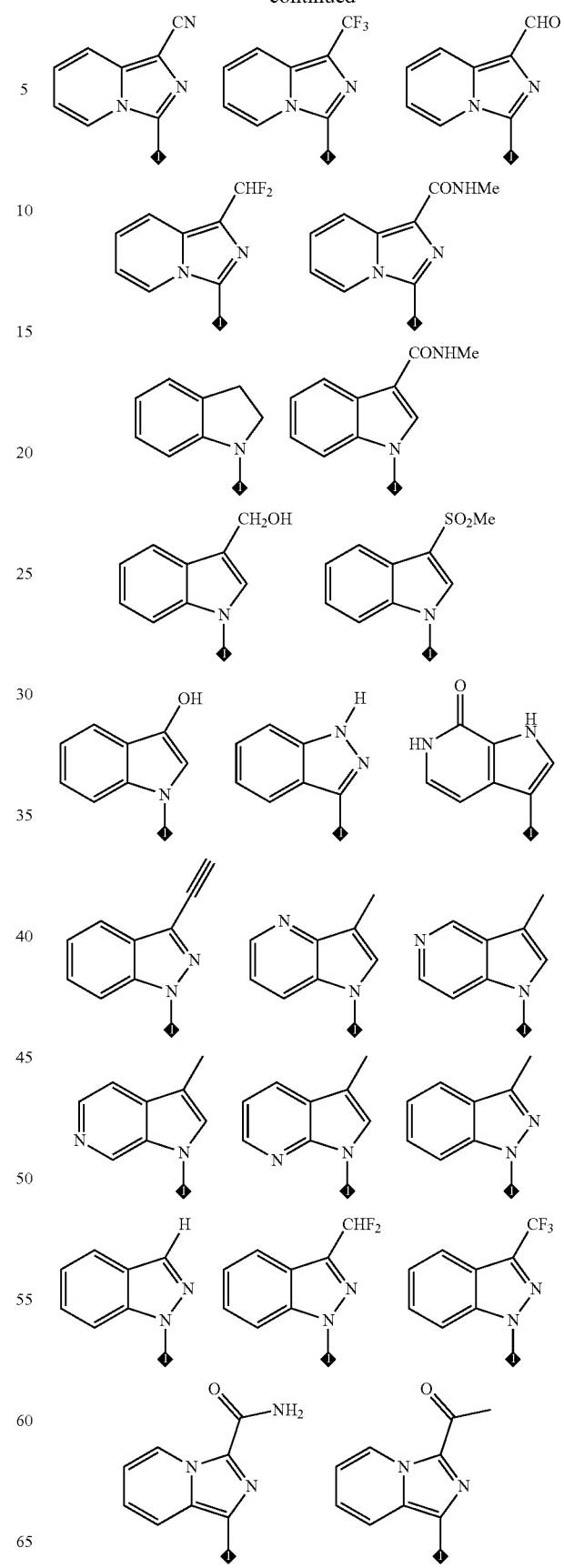

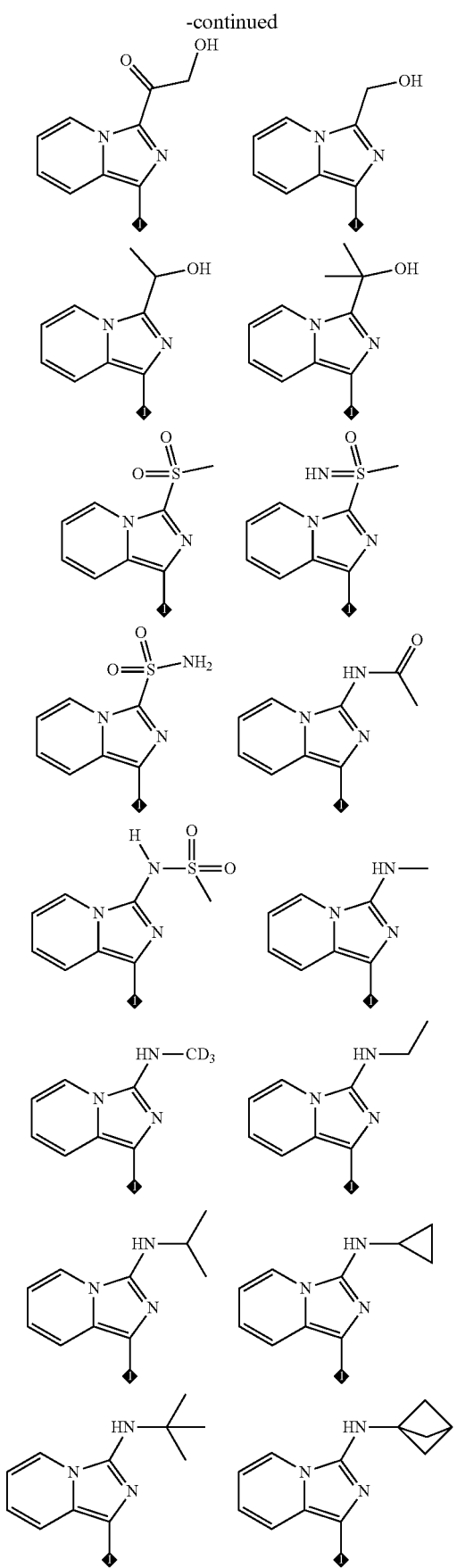
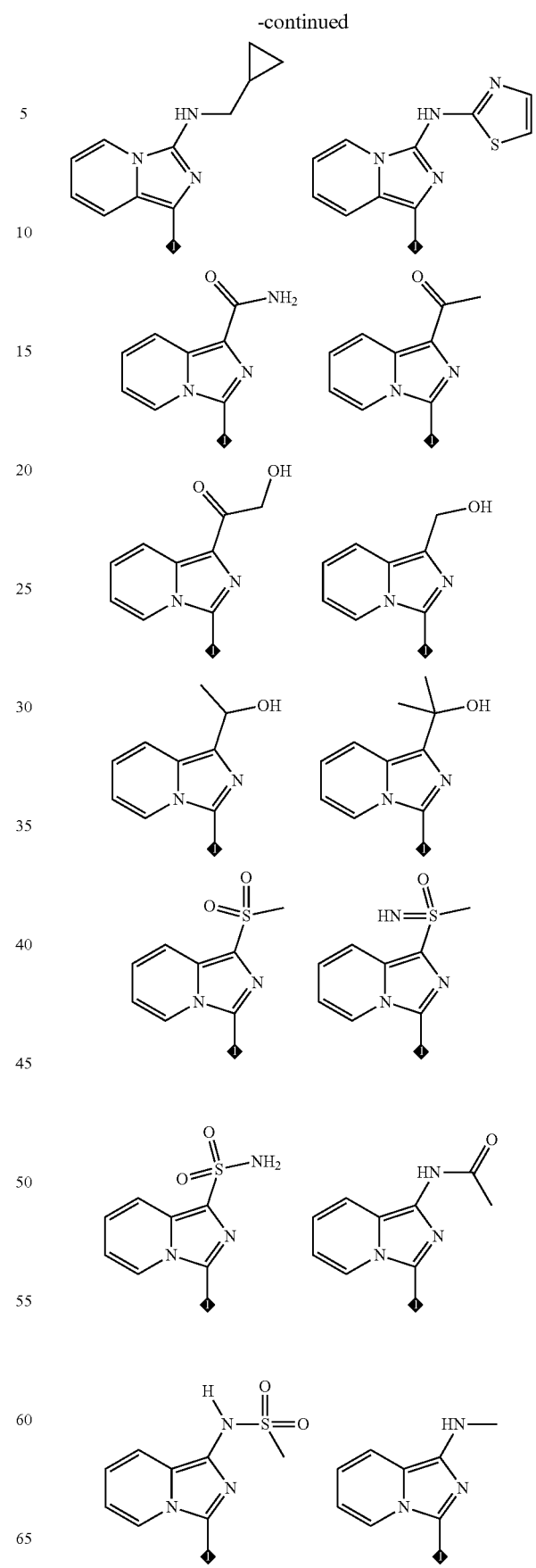

-continued
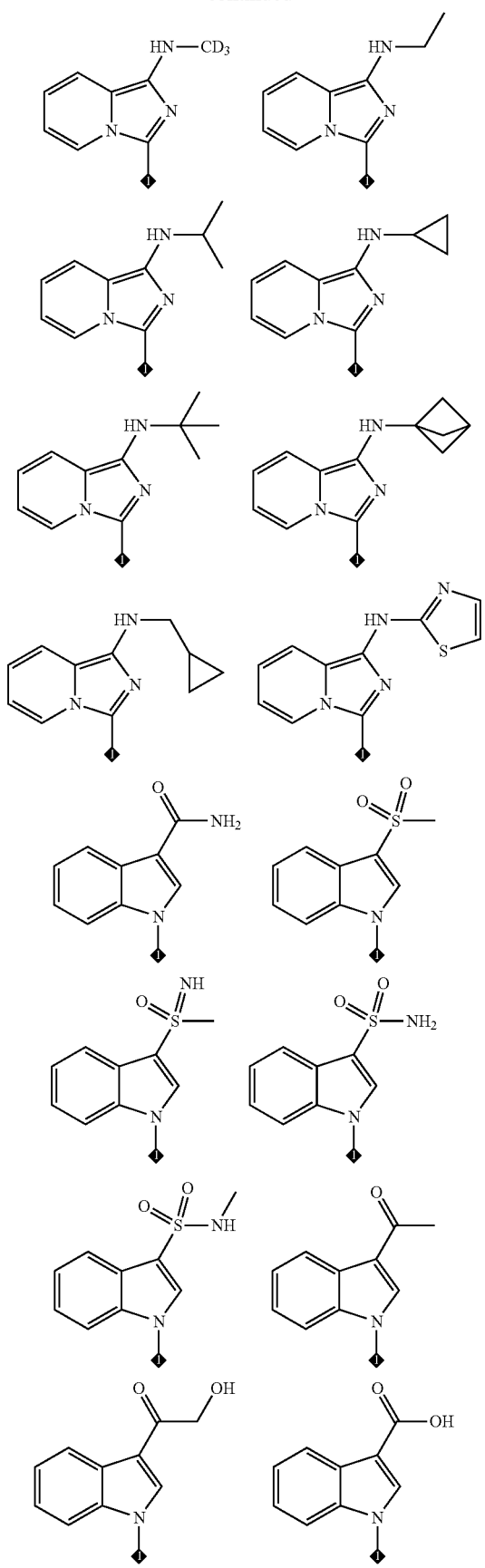
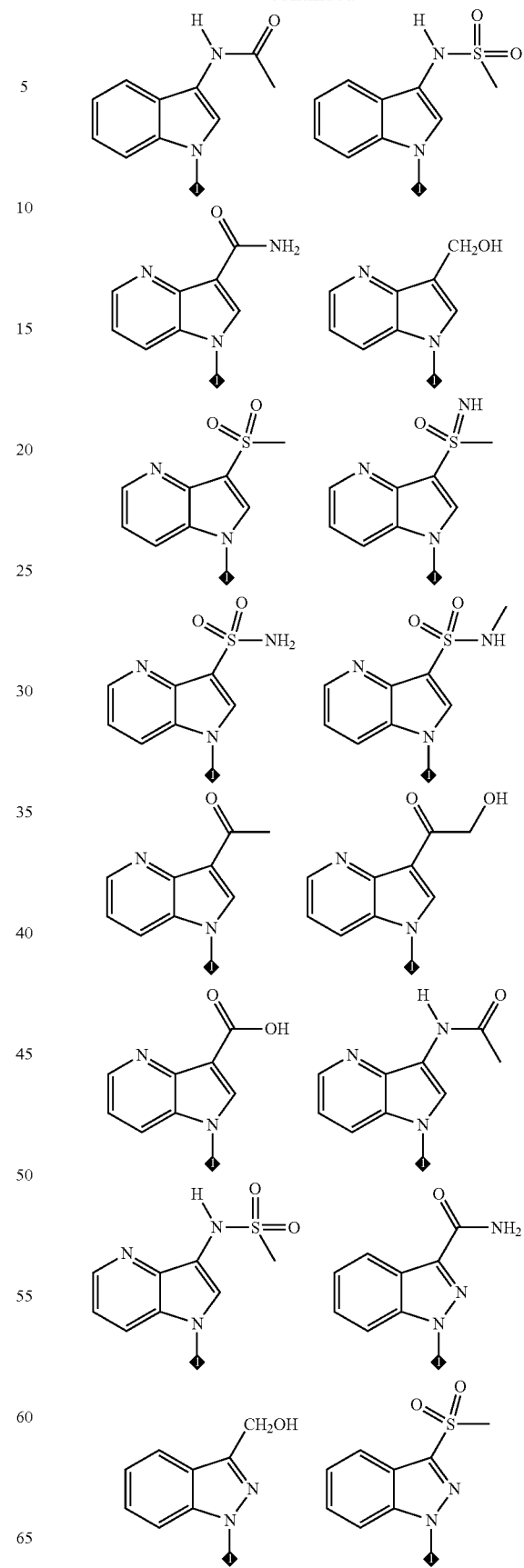

87
-continued
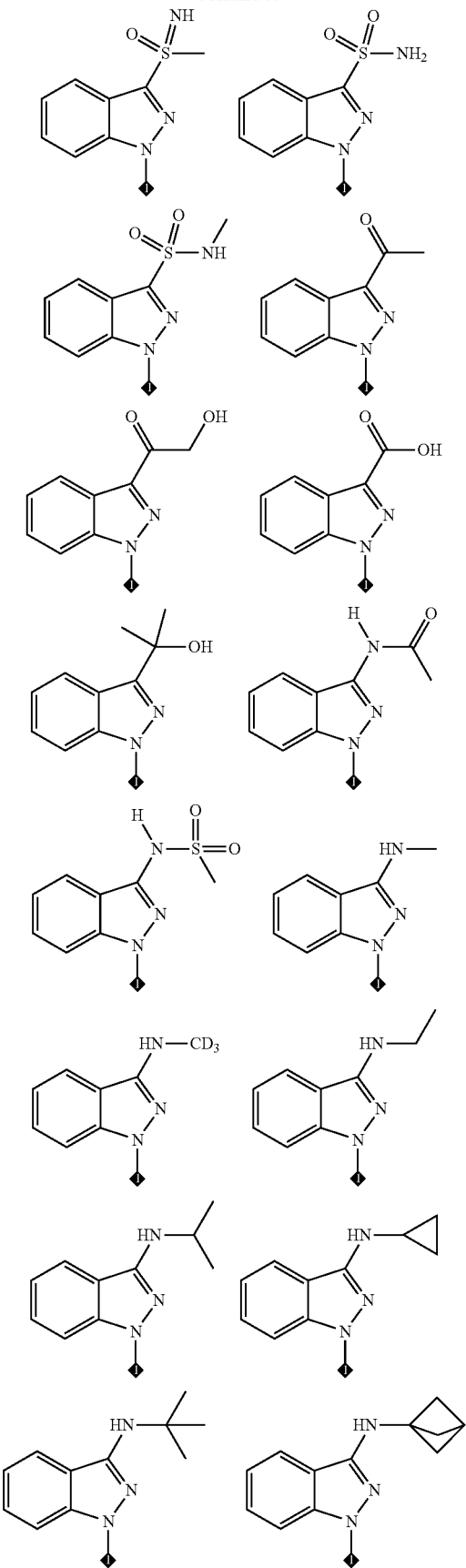
88
-continued
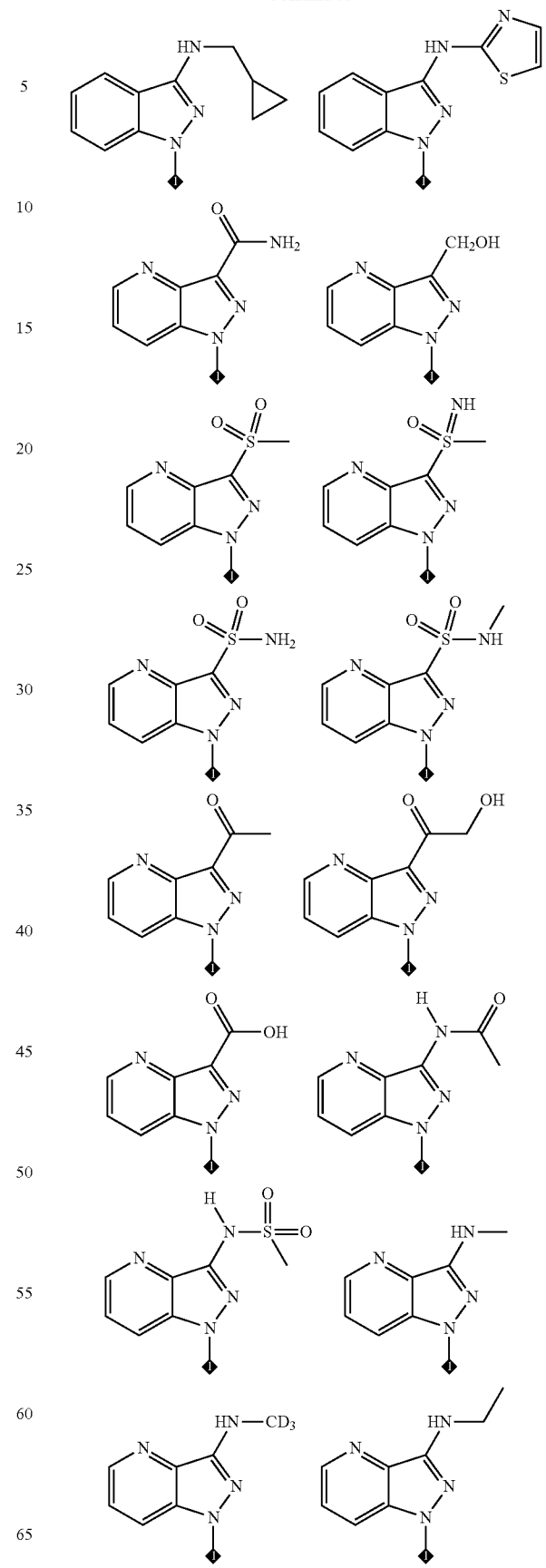

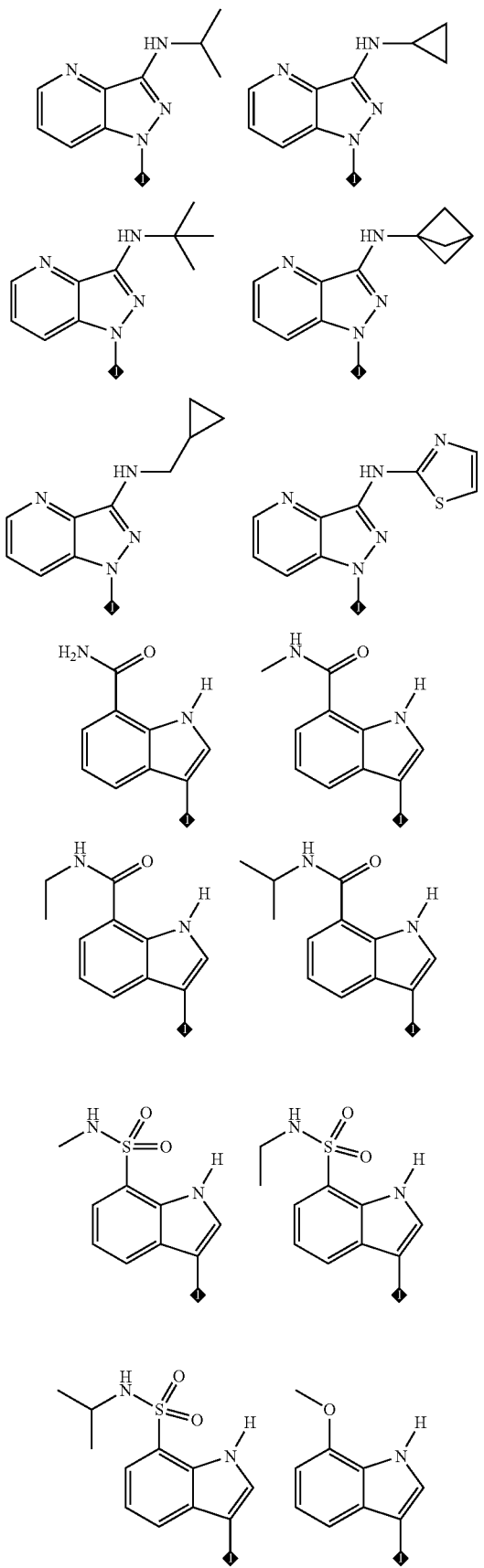
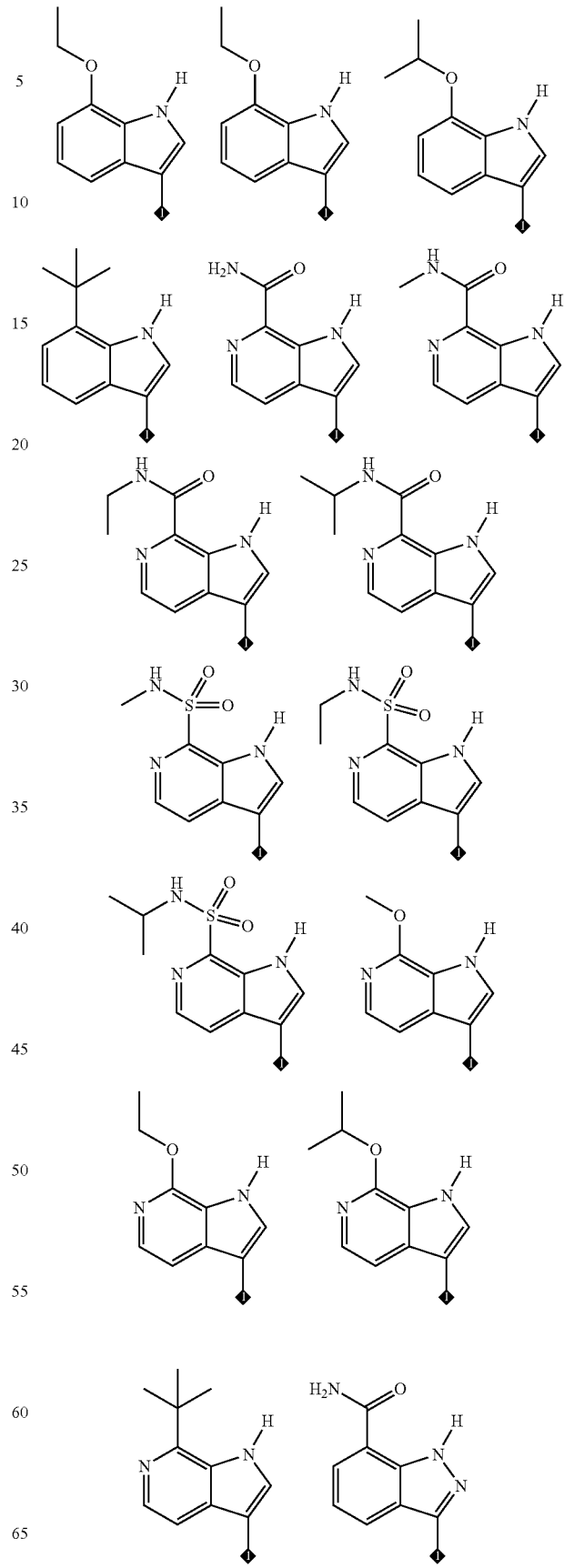

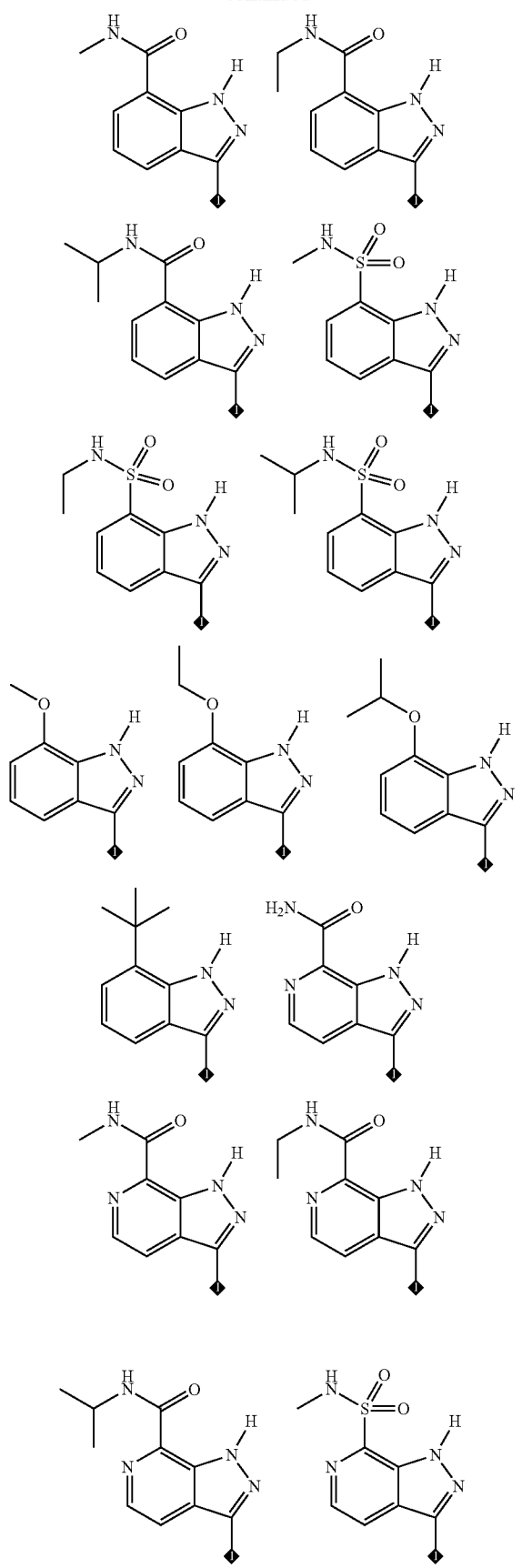
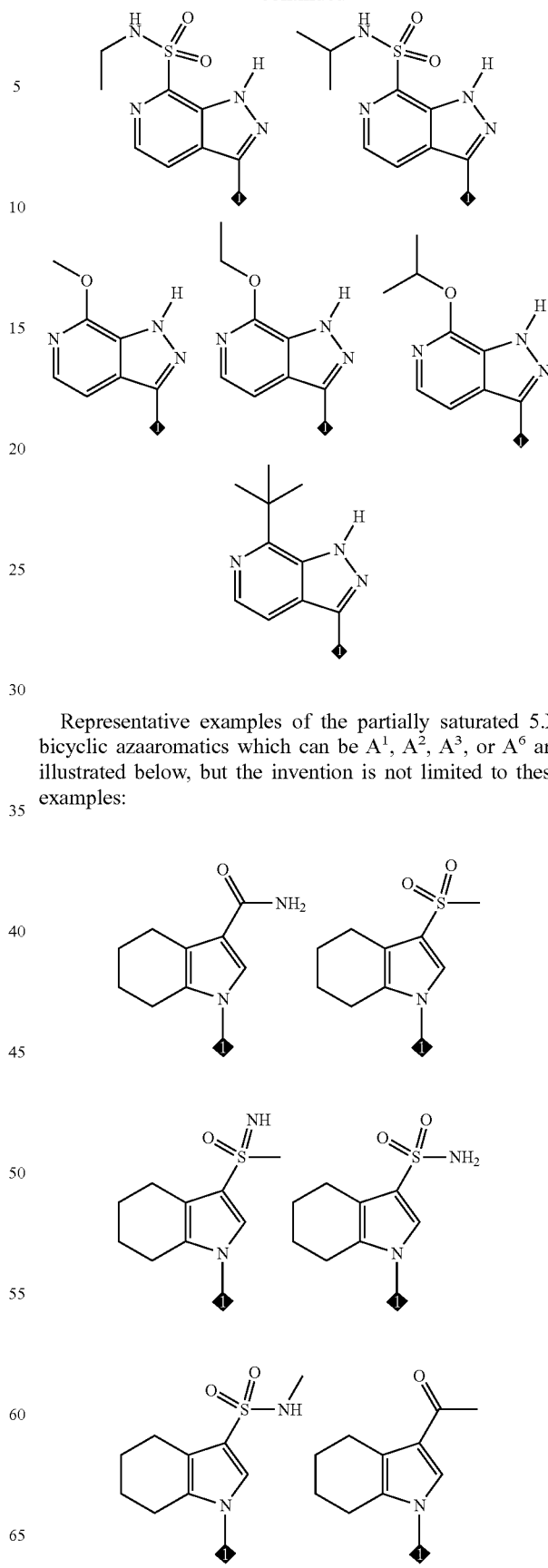
Representative examples of the partially saturated 5.X bicyclic azaaromatics which can be $A^1$, $A^2$, $A^3$, or $A^6$ are illustrated below, but the invention is not limited to these examples:

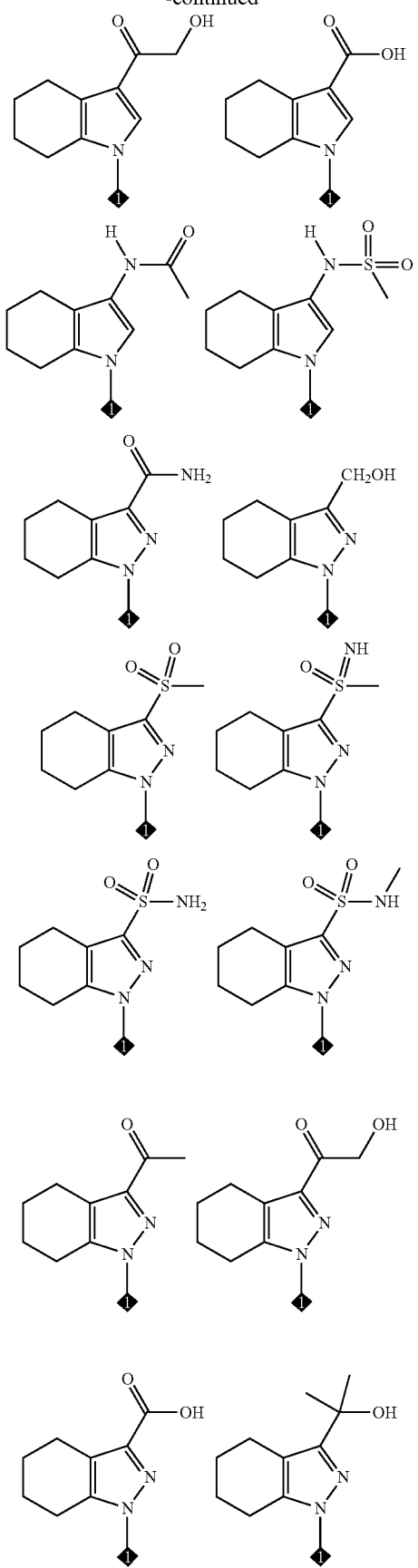
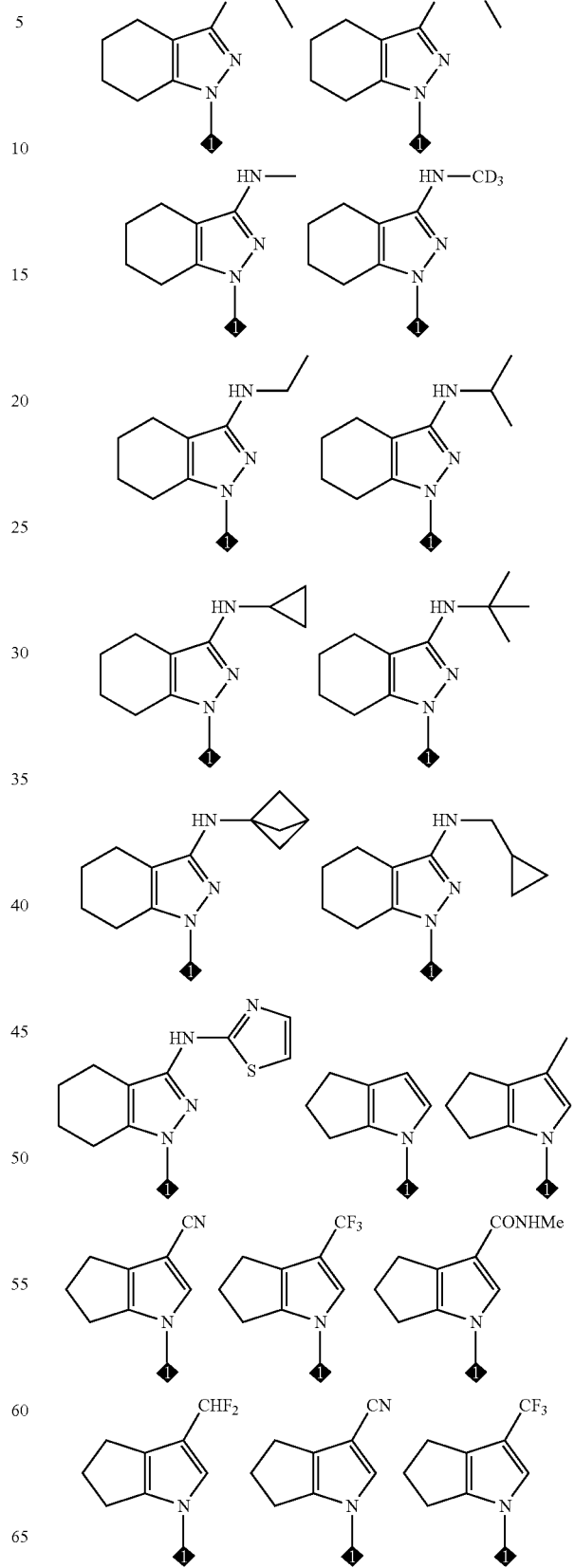

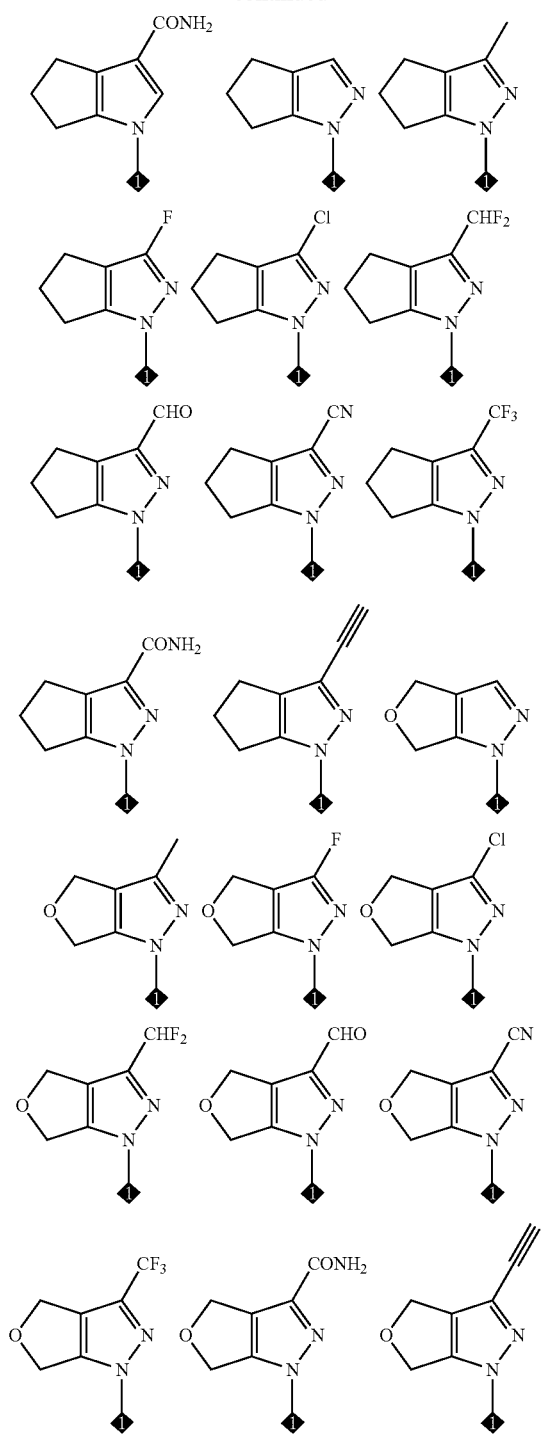
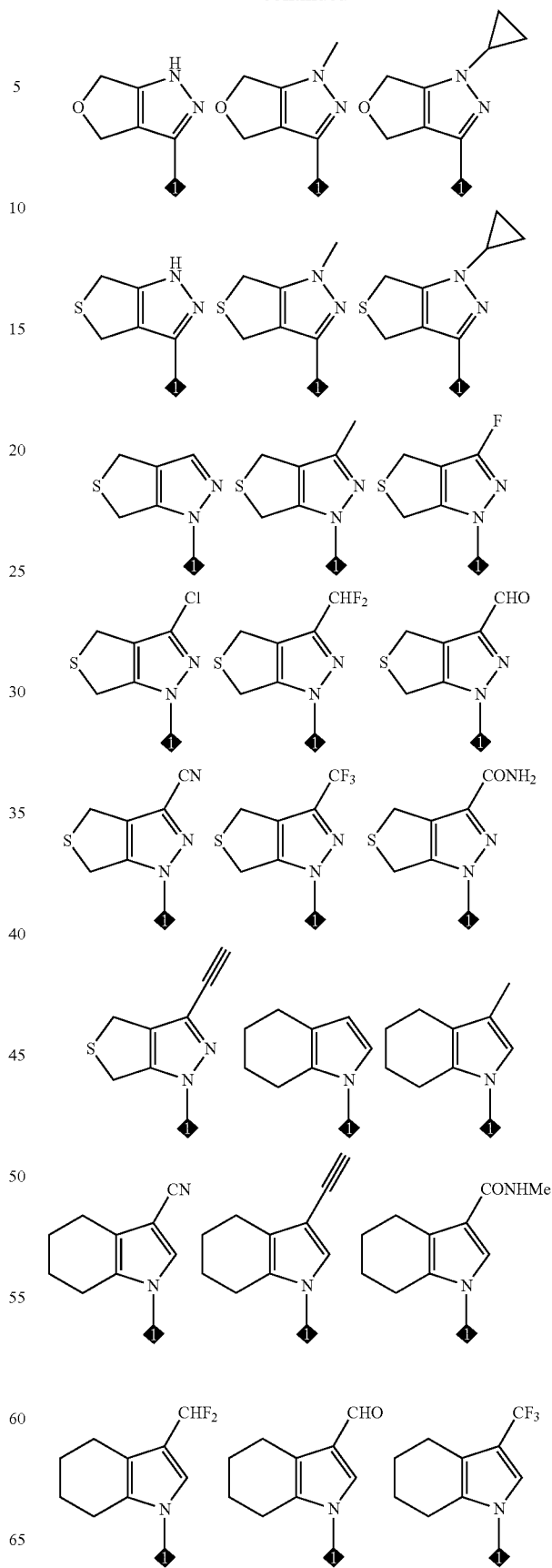

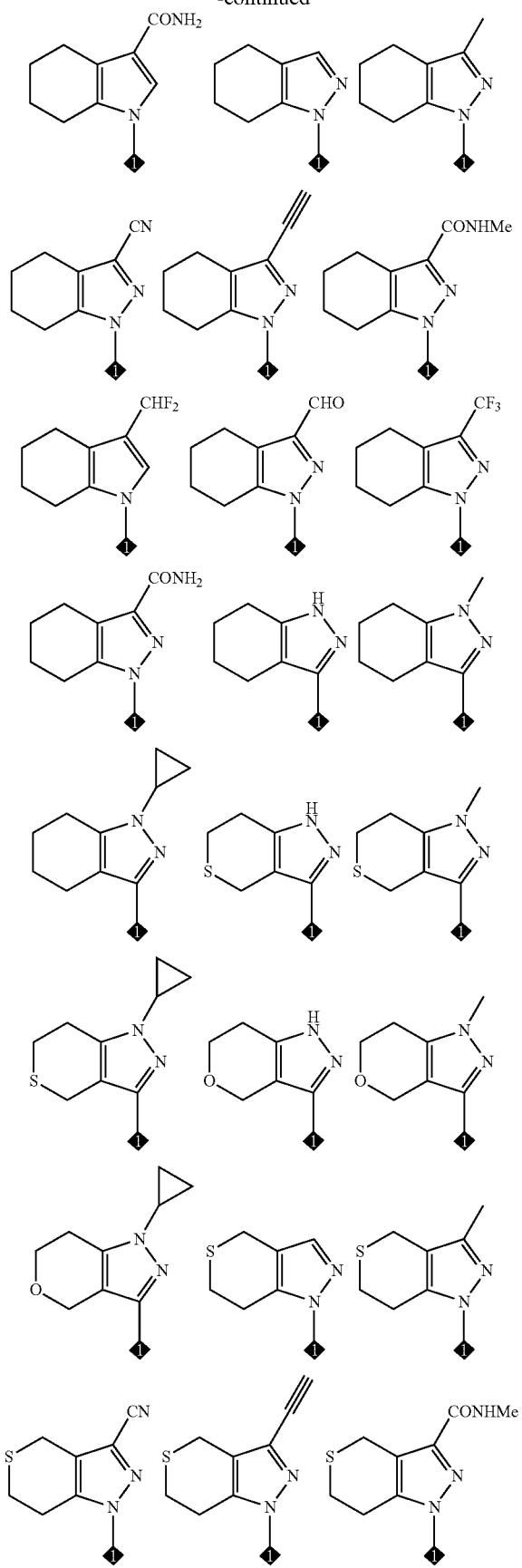
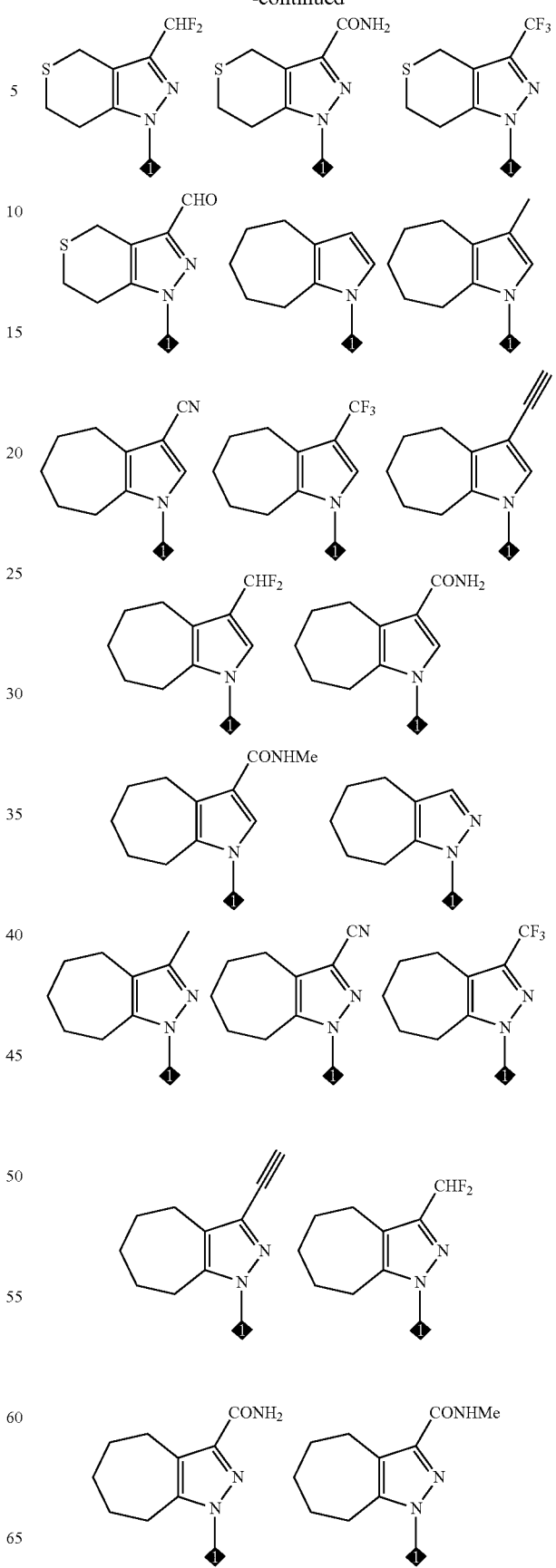

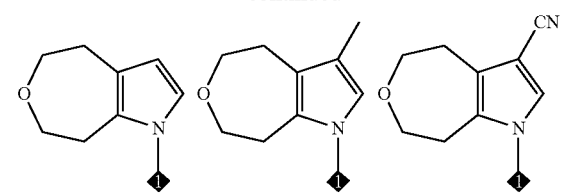
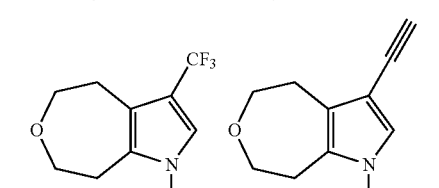
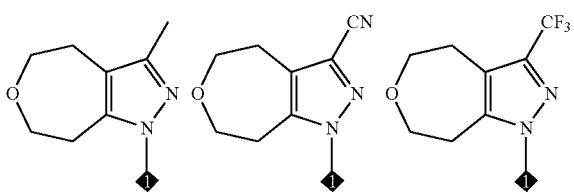
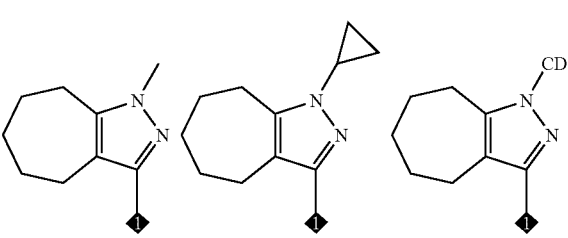
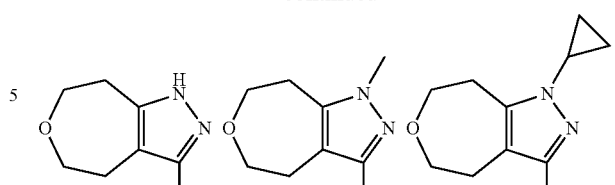
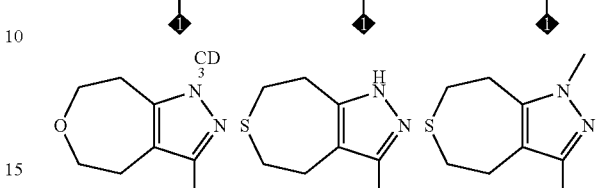
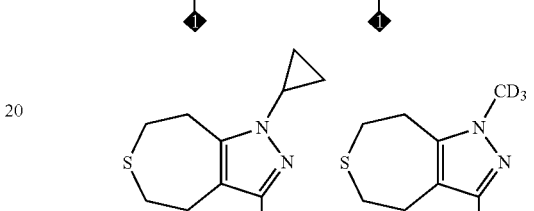
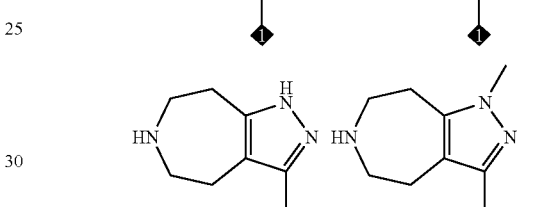
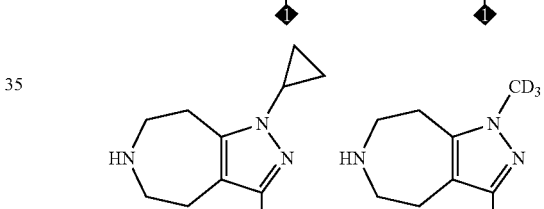

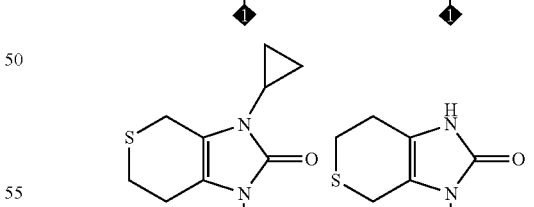
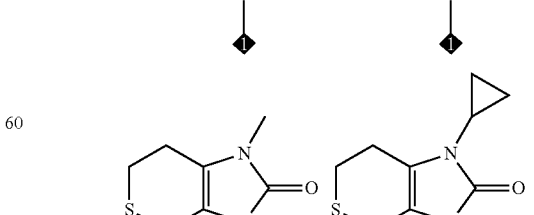

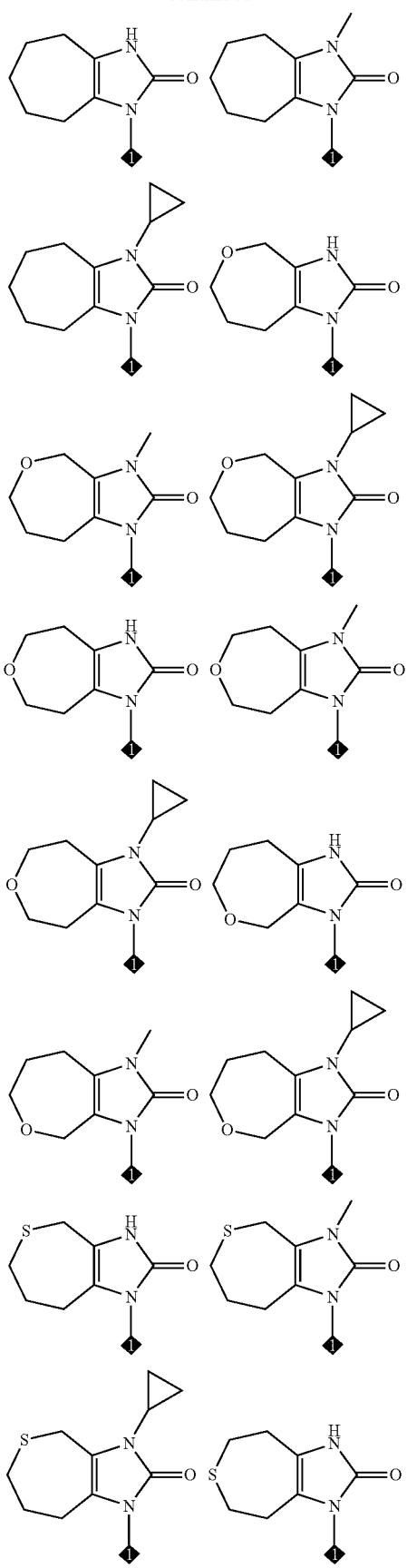
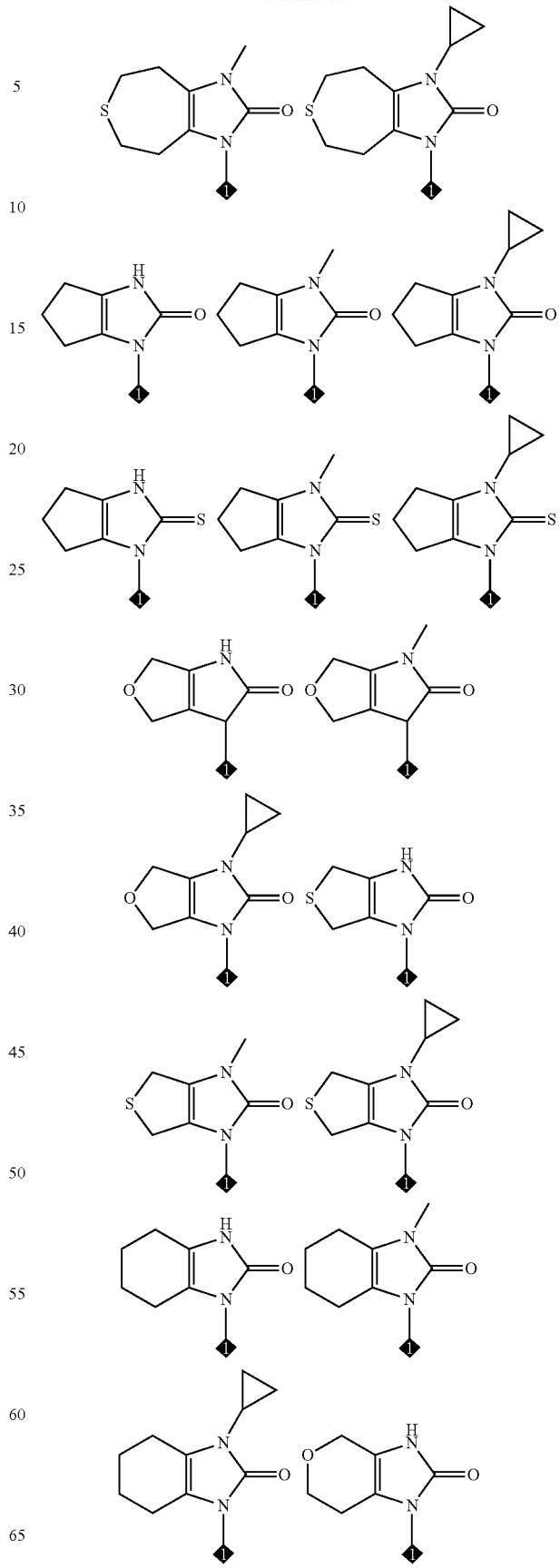

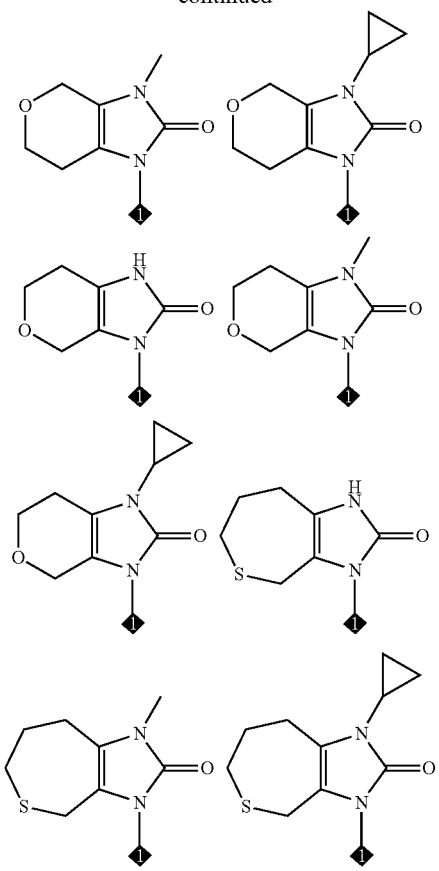
Point of attachment
Representative examples of the 5.5 bicyclic azaaromatics which can be $A^3$ are illustrated below, but the invention is not limited to these examples:
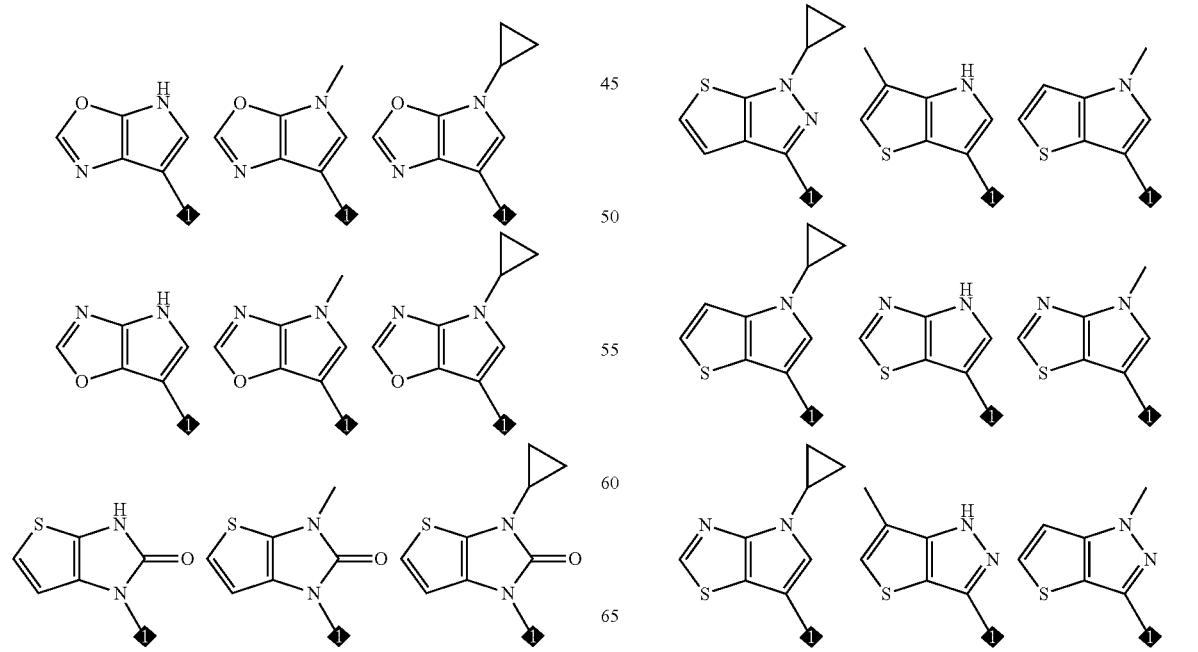

105
-continued
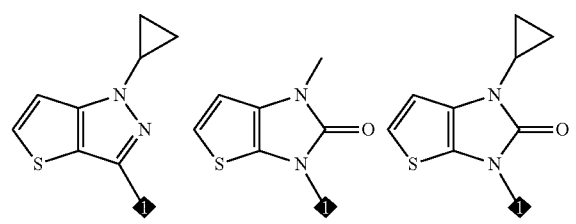
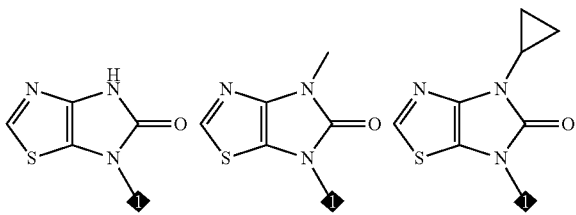
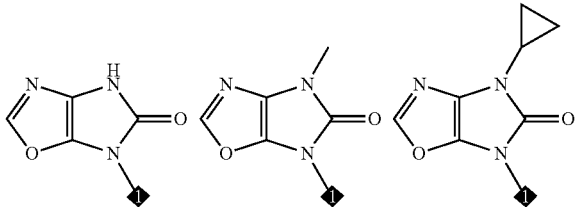
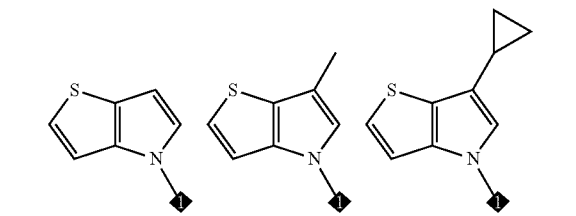
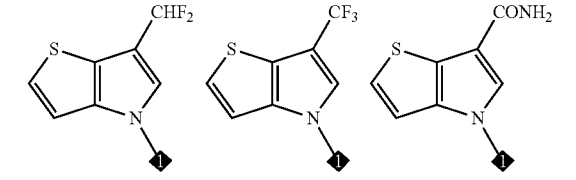
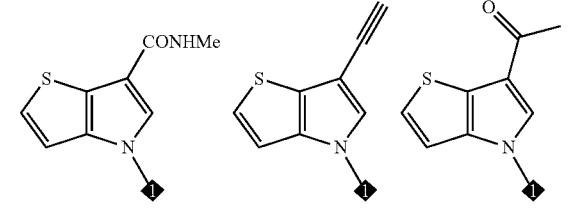
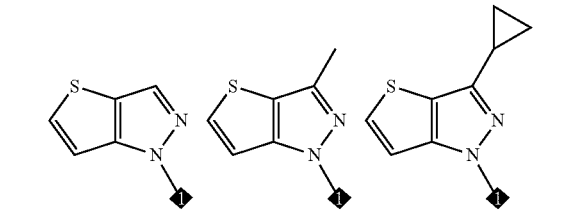
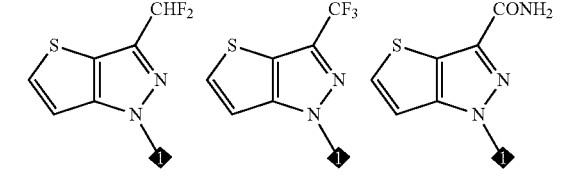
106
-continued
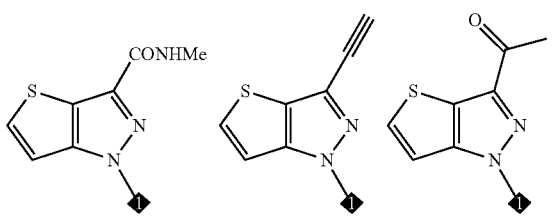
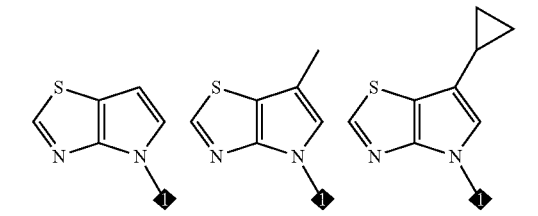
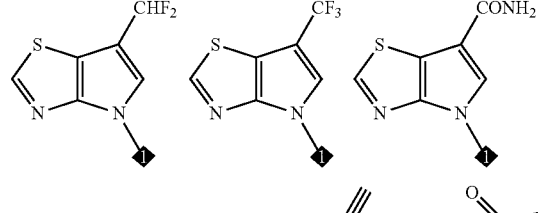
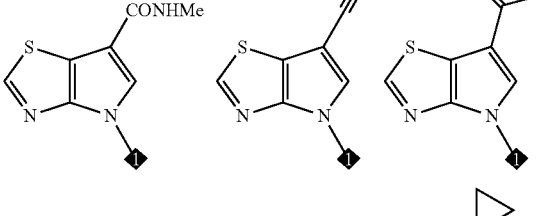
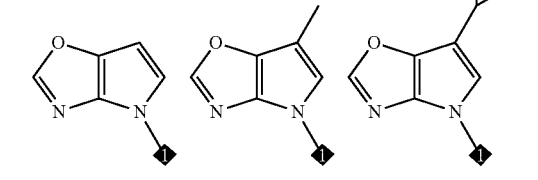
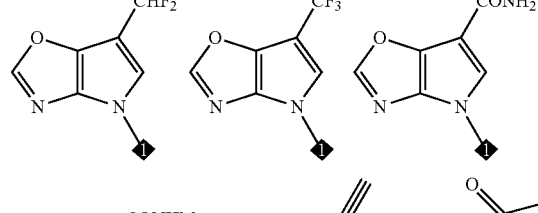
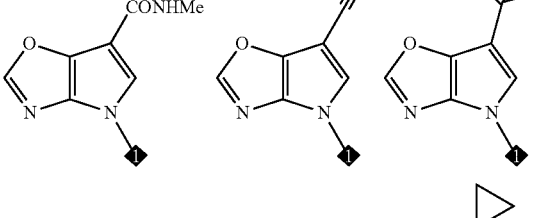
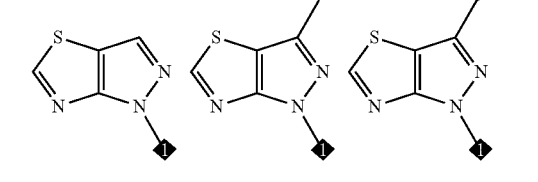

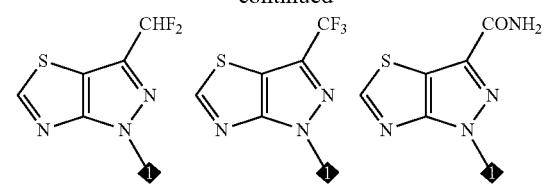
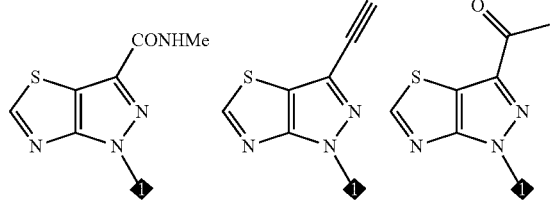
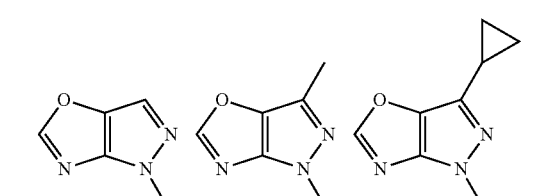
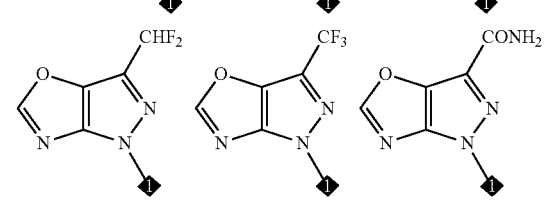
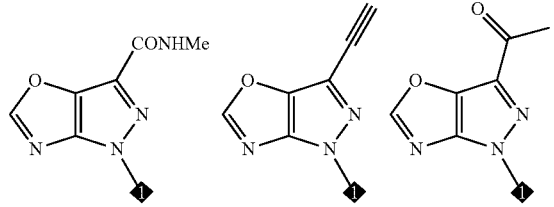
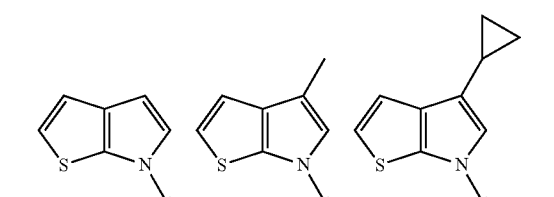
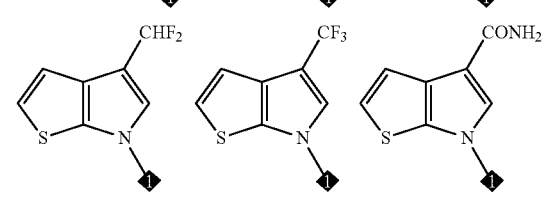
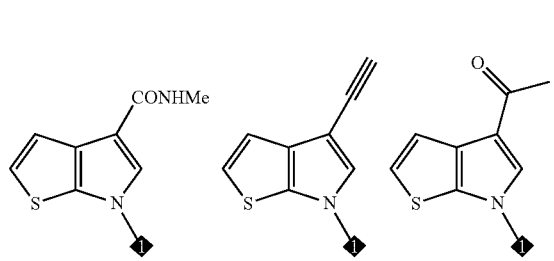
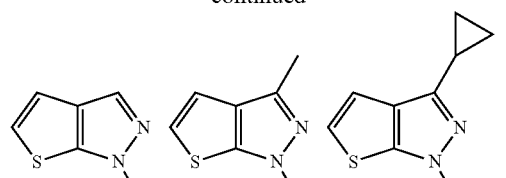
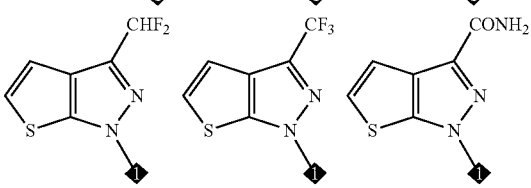
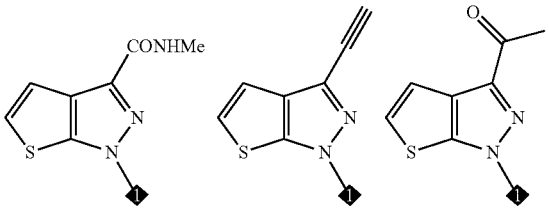
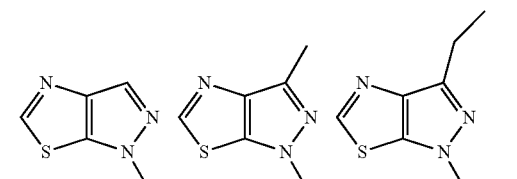
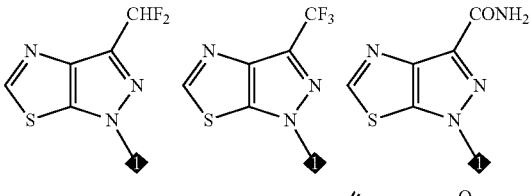
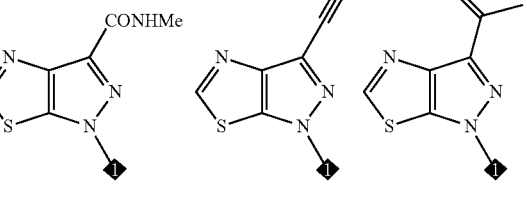
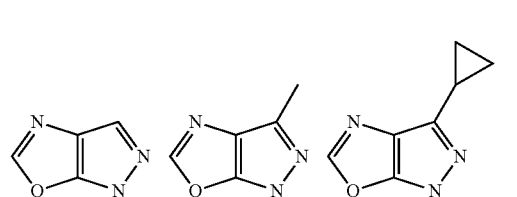
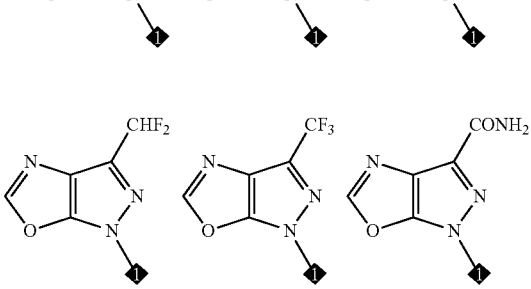

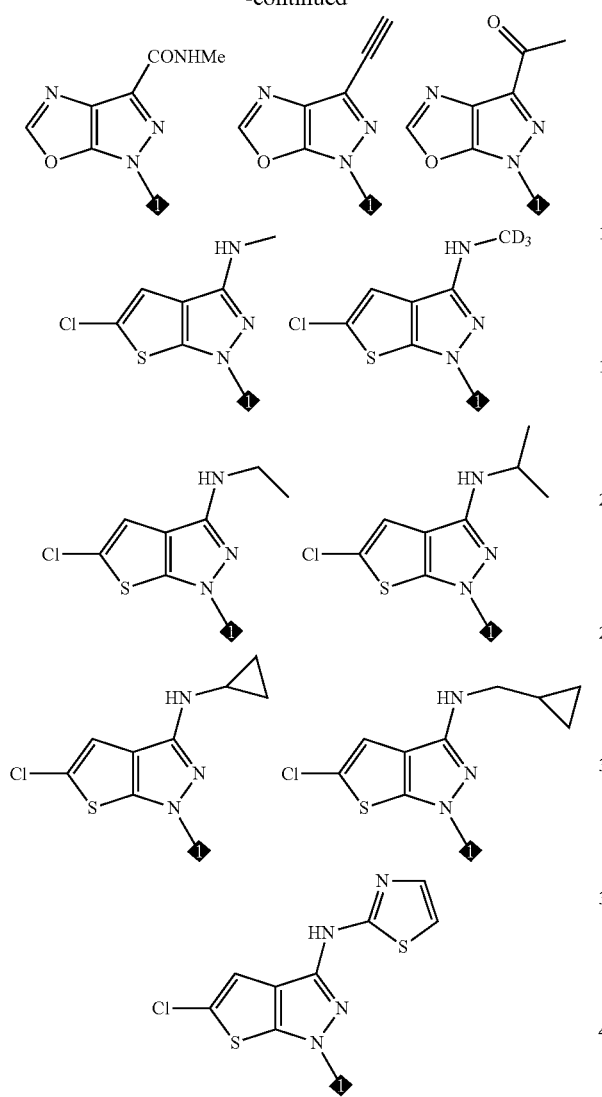
Point of attachment
Representative examples of the 6.5 bicyclic azaaromatics which can be $A^{4a}$ or $A^{4b}$ are illustrated below, but the invention is not limited to these examples:
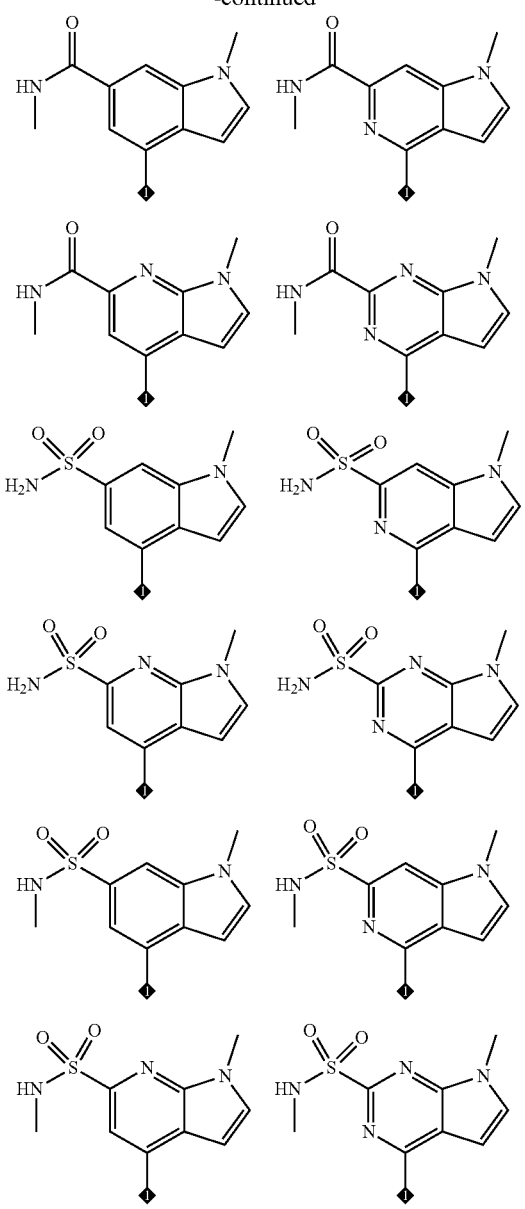
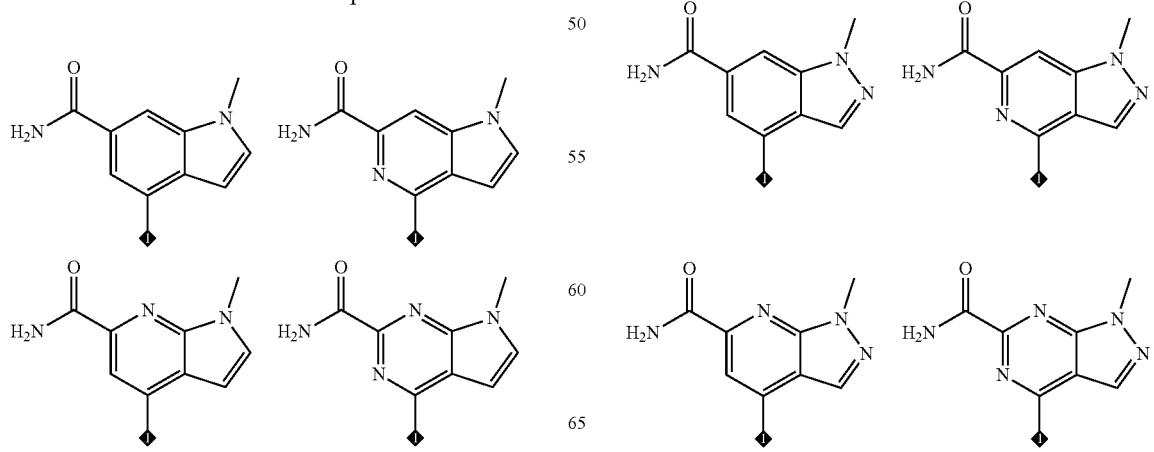

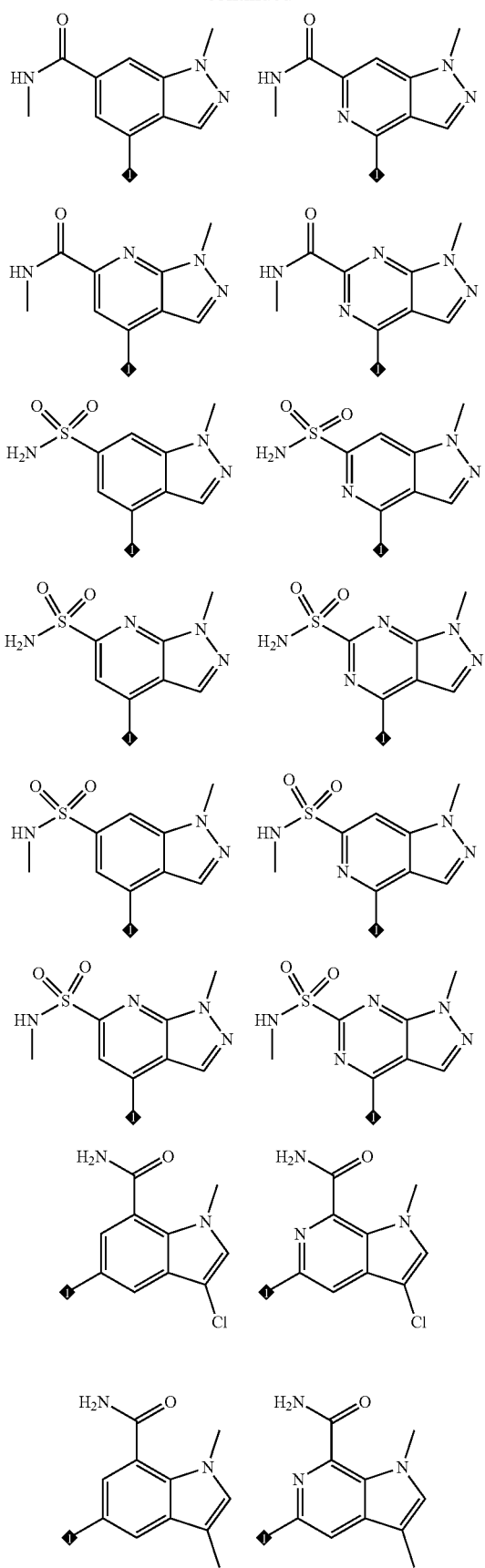
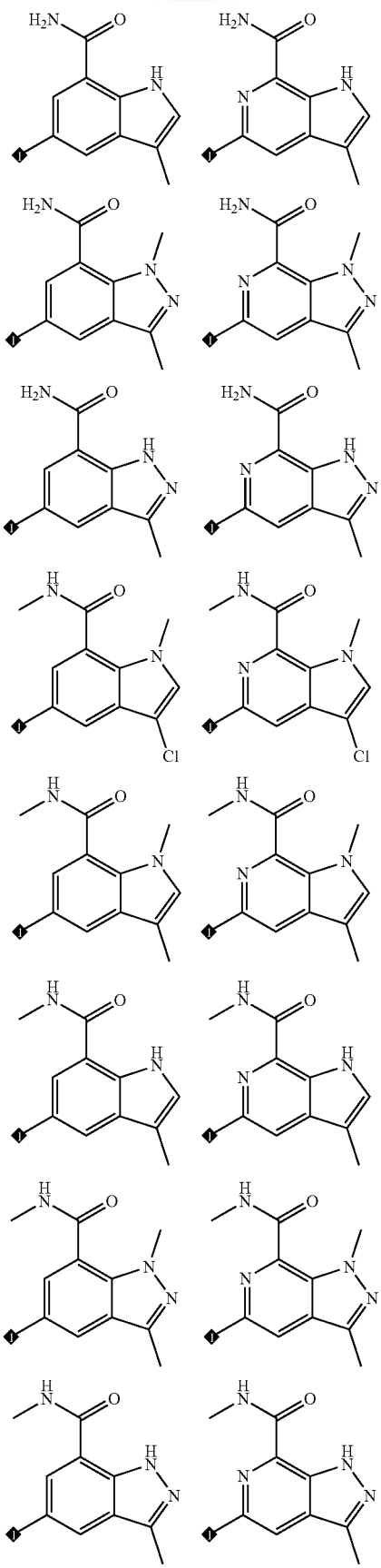

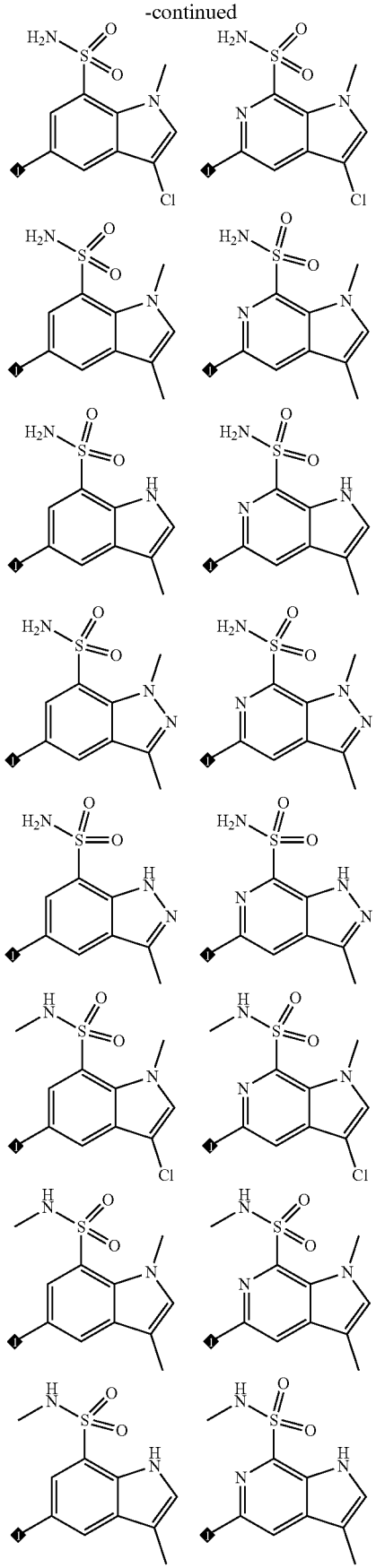
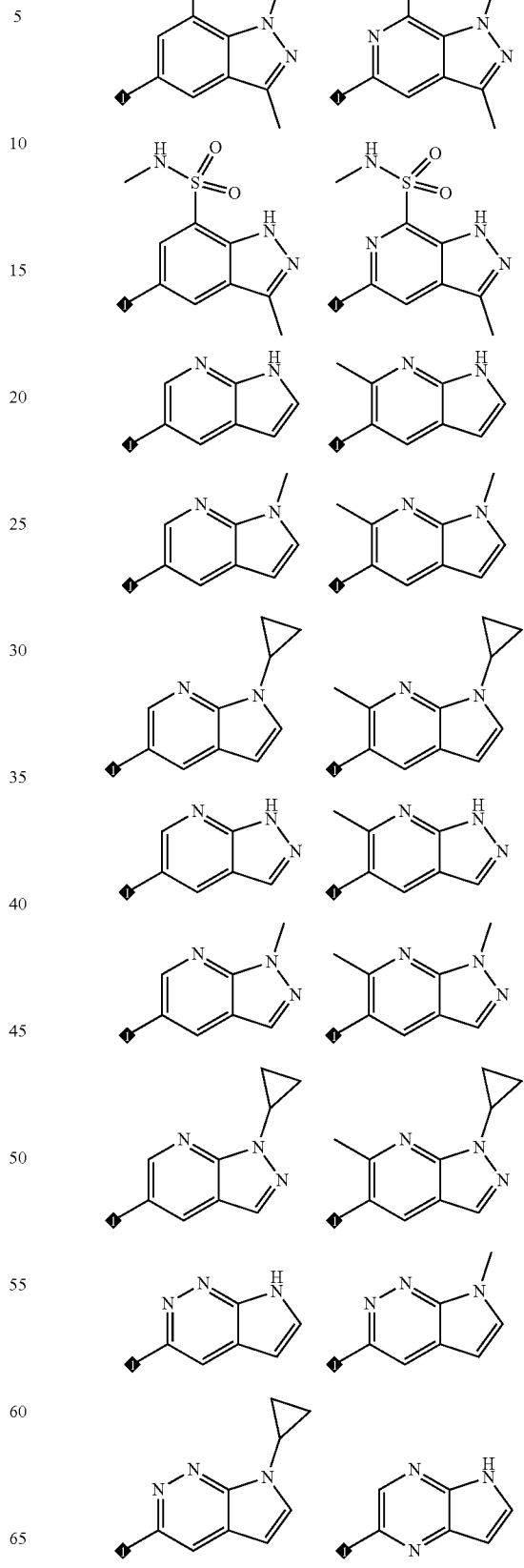

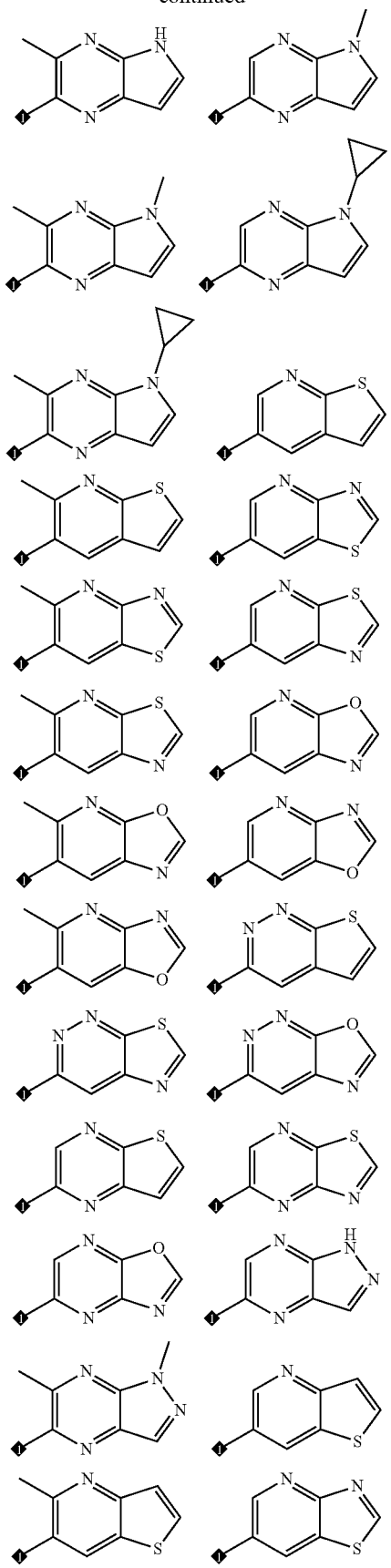
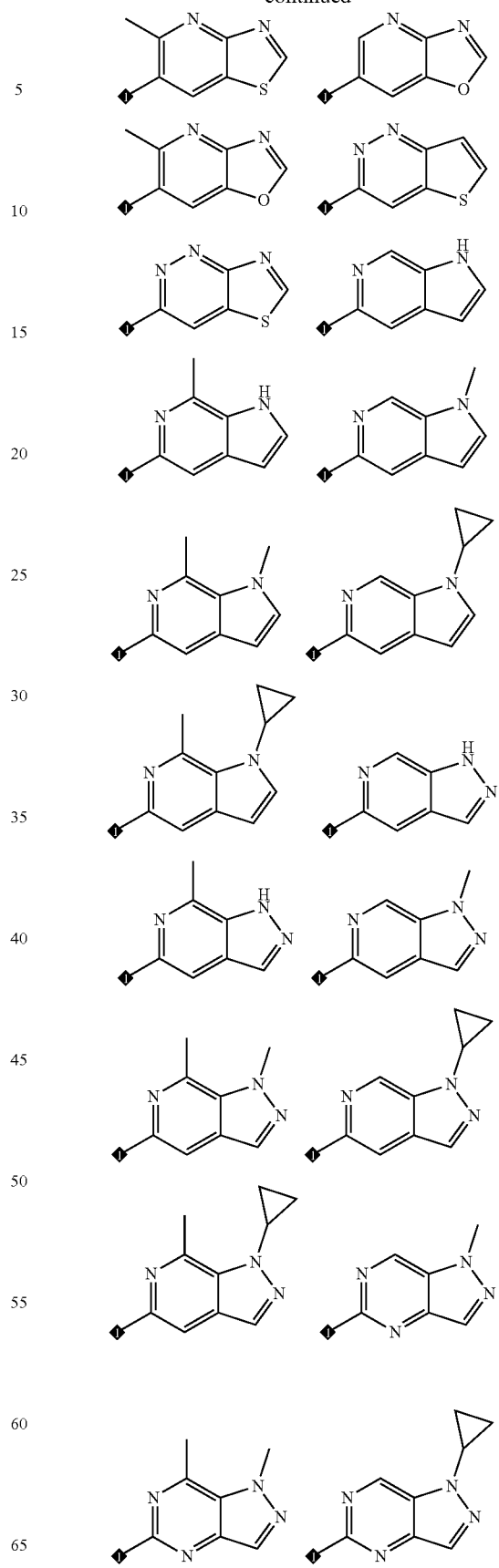

-continued
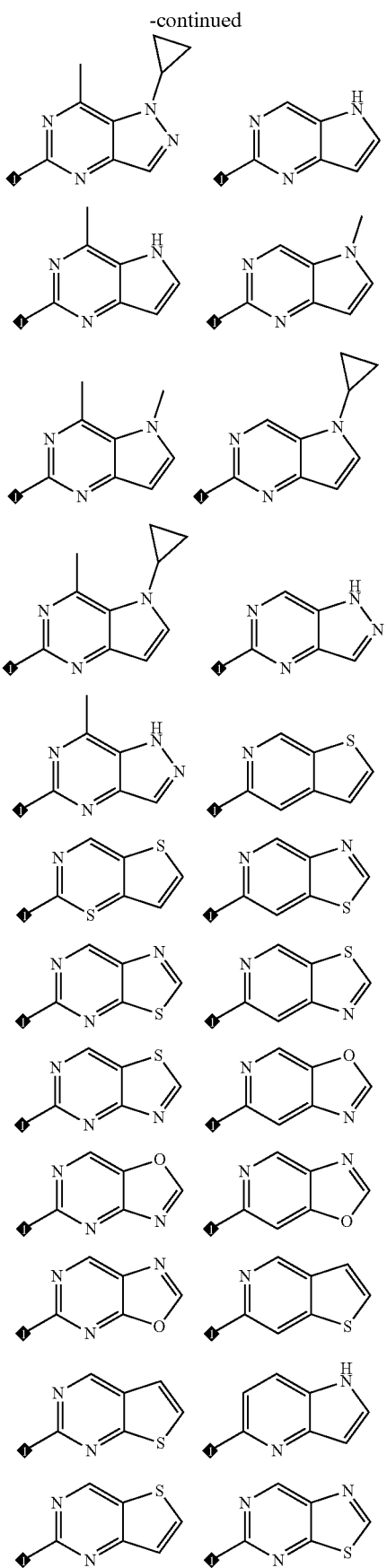
-continued
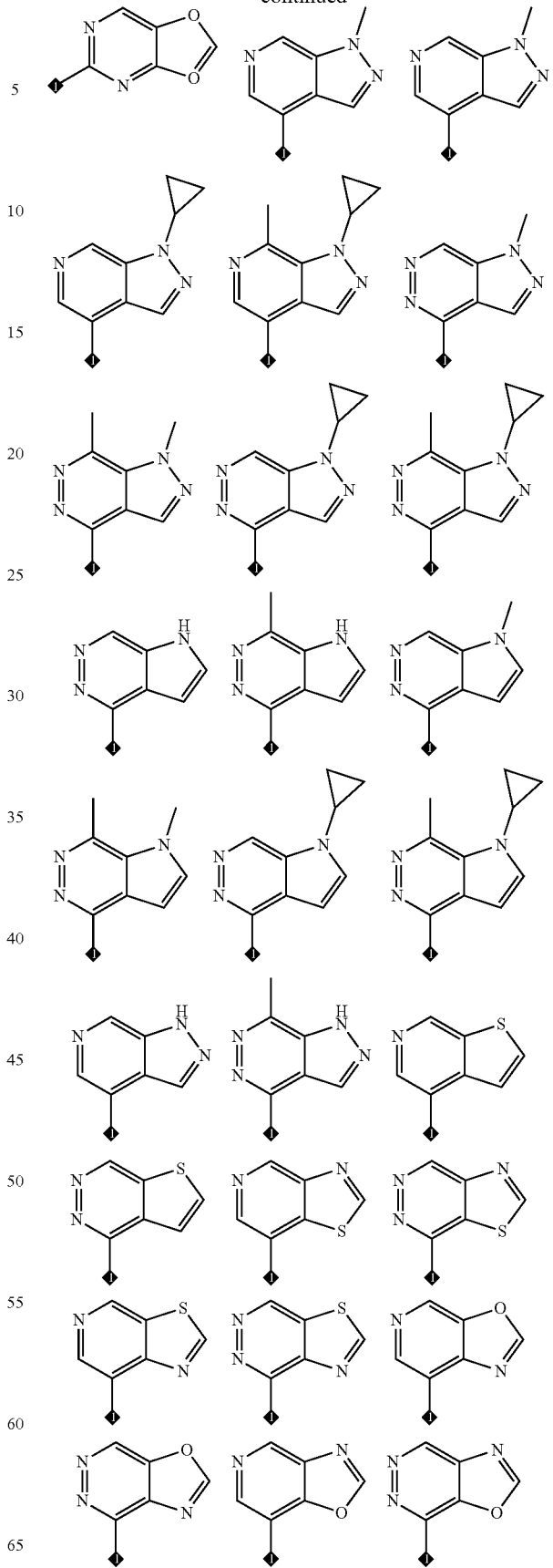

119
-continued
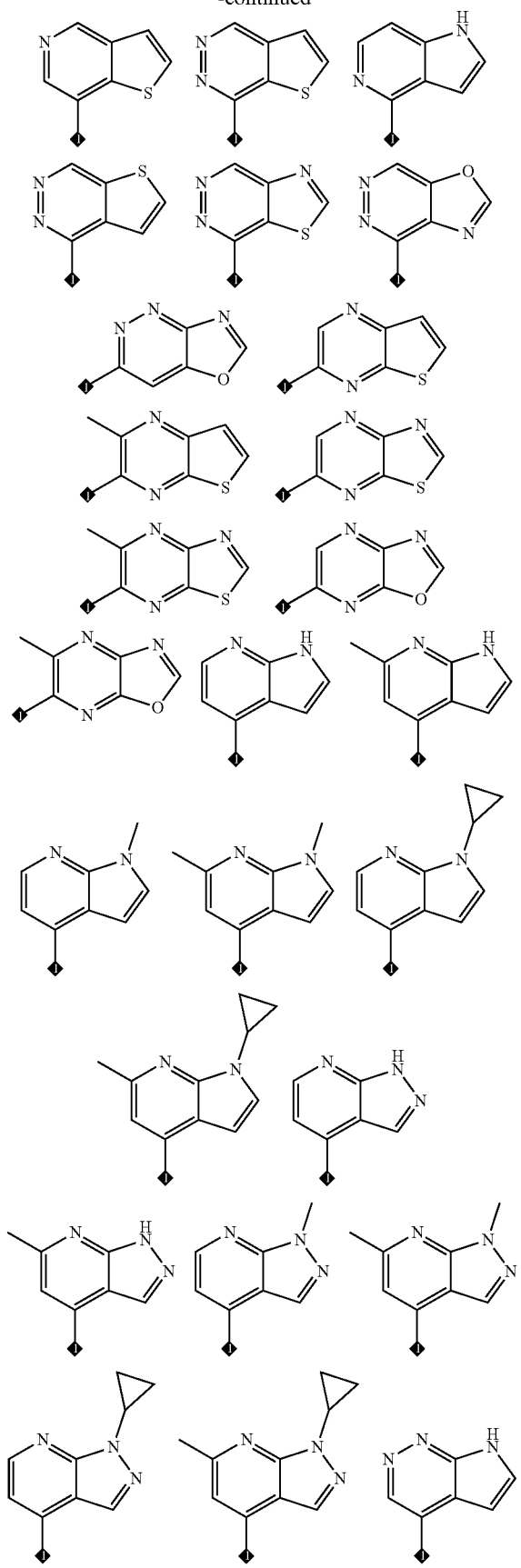
120
-continued
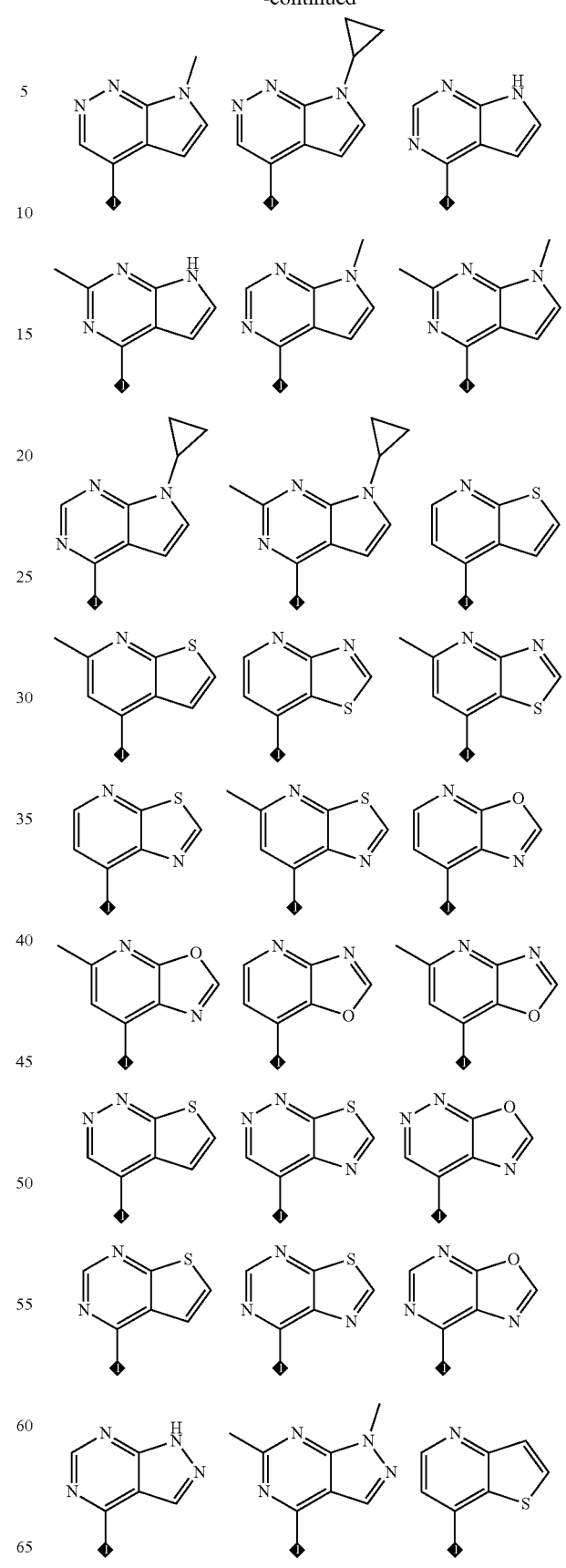

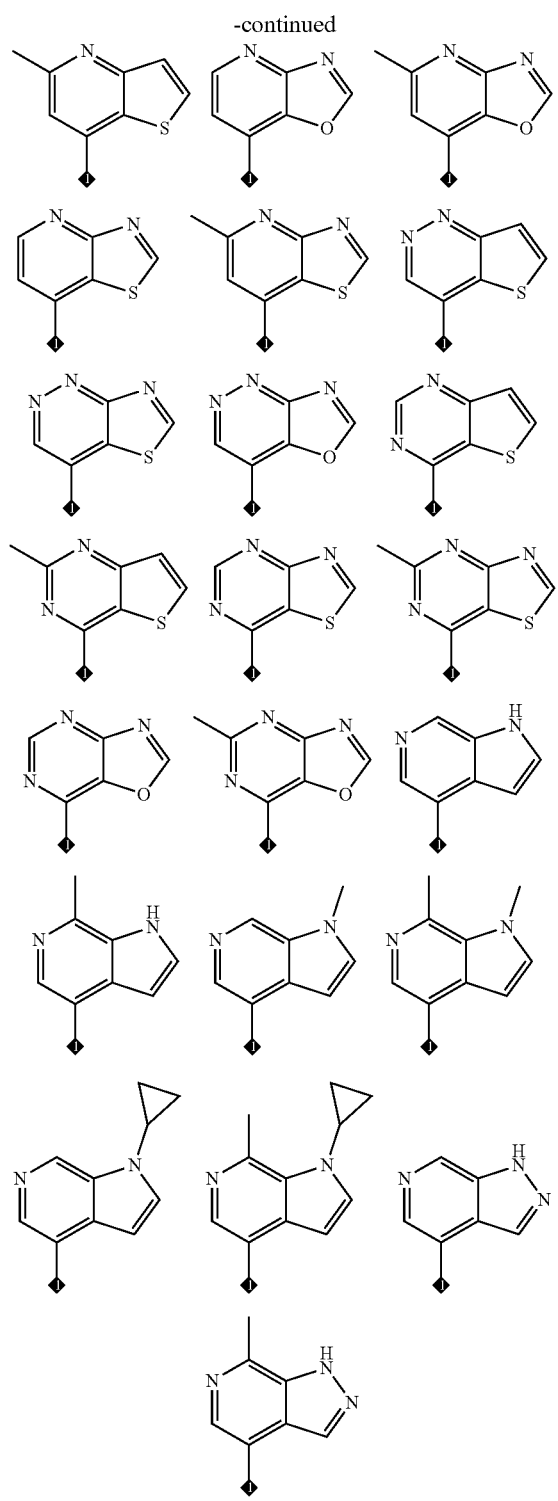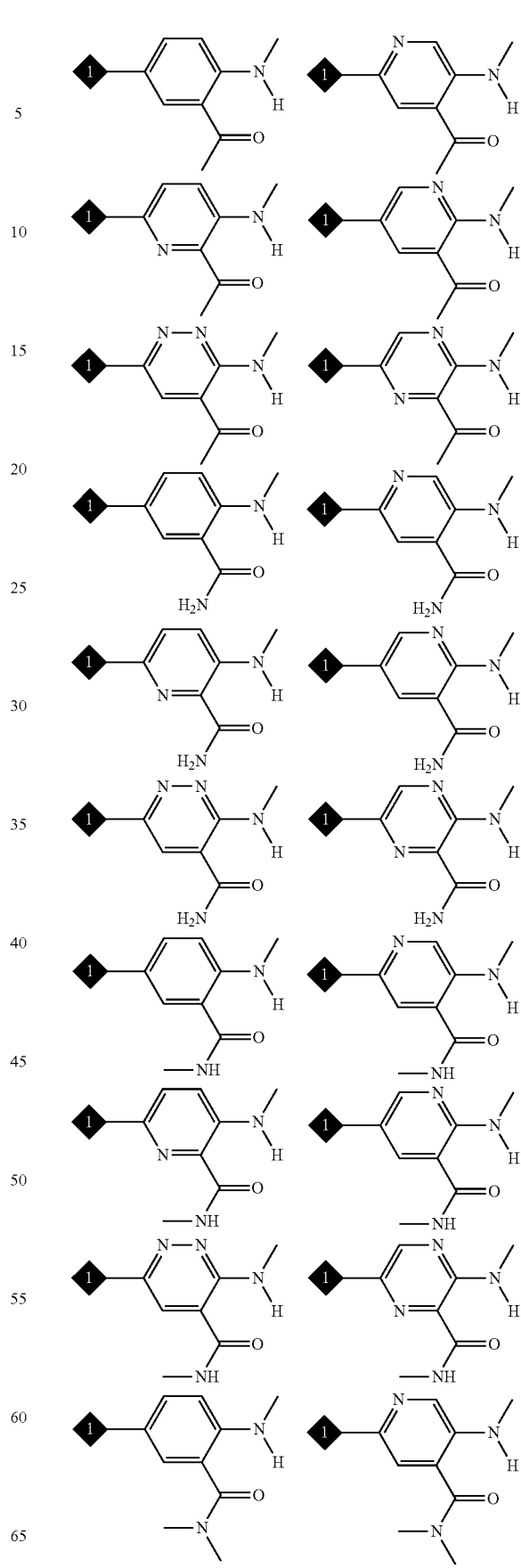
Representative examples of the $A^5$ are illustrated below, but the invention is not limited to these examples:

-continued

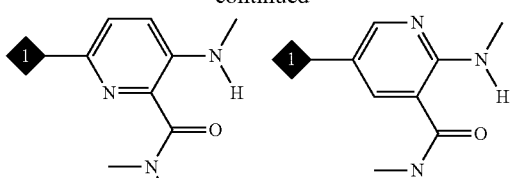

As used herein the term "replaced" in the context such as "a methylene unit is replaced by C=O" refers to exchange of functional group, for example, —CH₂— (methylene unit) is exchanged with —C(O)— (carbonyl group).

All alkyl, alkenyl, alkynyl, cycloalkyl, cycloalkenyl, monocyclic and bicyclic heterocycles, aryl (monocyclic and bicyclic), heteroaryl (monocyclic and bicyclic), cycloalkylalkyl, arylalkyl, arylalkoxy, heteroarylalkyl or heteroarylalkoxy groups (which include any C1-6 alkyl, C2-6 alkenyl, C2-6 alkynyl, C3-6 cycloalkyl, C4-6 cycloalkenyl, C6-12 bicycloalkyl, saturated monocyclic heterocycles of 4-12 atoms or saturated bicyclic heterocycles of 6-12 atoms, all C6-12 aryl monocycles or bicycles and heteroaryl monocycles or bicycles of 6-12 atoms) can be optionally substituted with multiple substituents independently chosen from halogen, hydroxy, oxo, hydroxylamino, oximino, hydrazino, hydrazono, cyano, nitro, azido, NR$^8$R$^9$, OC1-6 alkyl, OC3-6 alkenyl, OC3-6 alkynyl, C1-6 alkyl, OC3-8 cycloalkyl, OC3-8 cycloalkenyl, C1-6 acyl, C1-6 acyloxy, N(R$^8$)COR$^4$, CO$_2$R$^4$, CONR$^8$R$^9$, NR$^8$CONR$^8$R$^9$, NR$^8$CO2R$^4$, OCO2R$^4$, OCONR$^8$R$^9$, S(O)$_x$R$^4$, S(R$^4$)(=O)=NR$^8$, S(=O)(=NR$^8$)NR$^8$R$^9$, SO2NR$^8$R$^9$, NR$^8$SO2R$^4$, NR$^8$SO2NR$^8$R$^9$, —NR$^8$S(=O)=NR$^8$)R$^4$, —N=S(=O)(R$^4$)R$^4$, —N=S(=O)(NR$^8$R$^9$)R$^4$, ONR$^8$R$^9$, ON(R$^8$)COR$^4$, ONR$^8$CONR$^8$R$^9$, ONR$^8$CO2R$^4$, ONR$^8$SO2R$^4$, ONR$^8$SO2NR$^8$R$^9$.

Compounds

In one embodiment, the present invention relates to a compound of the formula (I):

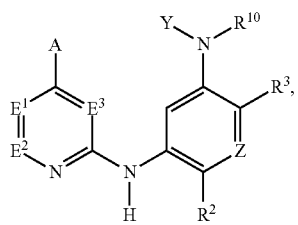 (I)

or a stereoisomer or a pharmaceutically acceptable salt, solvate, ester, tautomer, or prodrug thereof;

wherein,
A is

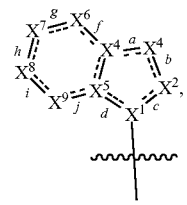 A$^1$

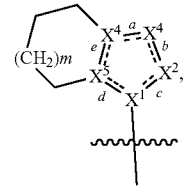 A$^2$

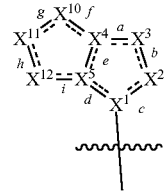 A$^3$

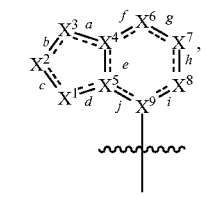 A$^{4a}$

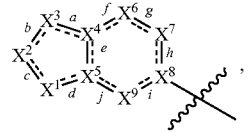 A$^{4b}$

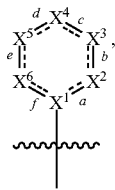 A$^5$ or A$^6$;

each of a, b, c, d, e, f, g, h, i and j are independently either (formal) double bonds or (formal) single bonds, and none of X$^1$, X$^2$, X$^3$, X$^4$, X$^5$, X$^6$, X$^7$, X$^8$, X$^9$, X$^{10}$, X$^{11}$, and X$^{12}$ has two (formal) double bonds attached thereto;

each of X$^1$, X$^2$, X$^5$, X$^6$, X$^7$, X$^8$, X$^9$, X$^{10}$, X$^{11}$, and X$^{12}$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$, or alternatively, each of X$^1$, X$^2$, X$^3$, X$^6$, X$^7$, X$^8$, X$^9$, X$^{10}$, X$^{11}$, and X$^{12}$ is selected from the group consisting of: C, CH, CR⁴, C(R⁴)₂, CR¹³, CH₂, C=O, C=S, C=NR¹³, N, NR⁴, NR¹³, N(O), S, S(O), S(O)₂, S(=O)(=NR¹³), S(=NR¹³)₂, and O;

in A¹, A², A³, A⁴ᵃ, and A⁴ᵇ, each of X⁴ and X⁵ is independently C or N;

at least four of X¹, X², X³, X⁴, X⁵, X⁶, X⁷, X⁸, X⁹, X¹⁰, X¹¹, and X¹² are C, CR⁴, or C(R⁴)₂;

in A¹, A², A³ and A⁵, X¹ is C, CH or N;

in A⁴ᵃ, X⁹ is C, CH or N;

in A⁴ᵇ, X⁸ is C, CH or N;

in A⁴ᵃ and A⁴ᵇ, X¹ is N, NR³, C(R⁴)₂, C(O), S(O)ₓ, S(=O)(=NR¹³), S(=NR¹³)₂, or CR⁴;

in A¹, A², A³, A⁴, and A⁴ᵇ, X² is N, NR¹³, C(R⁴)₂, S(O)ₓ, S(=O)(=NR¹³), S(=NR¹³)₂, C(O), or CR⁴;

in A¹, A², A³, A⁴ᵃ, and A⁴ᵇ, X³ is N, NR¹³, C(R⁴)₂, C(O), S(O)ₓ, S(=O)(=NR¹³), S(=NR¹³)₂, or CR⁴;

in A⁵, at least three of X², X³, X⁴, X⁵ and X⁶ are C, C=O, CR⁴, or C(R⁴)₂;

E¹ and E² are independently C—R¹ or N with the proviso that E¹ and E² are not both N;

E³ and Z are independently CH or N;

Y is

Y¹

Y²

Y³

Y⁴

Y⁵

R¹ is independently selected from hydrogen, fluoro, chloro, bromo, methyl, ethyl, hydroxyl, methoxy, ethoxy, isopropxy, —OCF₃, —OCH₂CF₃, —OCH₂CHF₂, ethenyl, ethynyl, CF₃, CHF₂, CHO, CH₂OH, CONH₂, CO₂Me, CONHMe, CONMe₂, and cyano;

R² is R¹⁰, —OCF₃, —OCHF₂, —OCF₂CF₃, —OCH₂CHF₂, —OCH₂CF₃, cyclopropyl, cyclopropoxy, methoxy, ethoxy, or isopropoxy;

R³ is C₂₋₆ alkenyl-R⁷, C₂₋₆ alkynyl-R⁷, N(R¹⁰)C₂₋₆ alkyl-NR¹⁰R¹⁰, N(R¹⁰)C₂₋₆ alkyl-R⁷, O(CH₂)ₚR⁷, N(R¹⁰)C(=O)(CH₂)ₚR⁷, C(R¹⁰)=C(R¹⁰)(CH₂)ₚR⁷, or R⁷;

each R⁴ is independently H, cyano, nitro, halo, —C₁₋₆ alkyl, —C₁₋₆ haloalkyl, C₁₋₆ acyl-C₁₋₆ alkyl-, R⁷—(CH₂)ₚC(=O)—C₁₋₆ alkyl-, carboxy-C-s alkyl-, C₂₋₆ alkyloxycarbonyl-C₁₋₆ alkyl-, R⁷—(CH₂)ₚO—C(=O)—C₁₋₆ alkyl-, R⁸R⁹N—C(=O)C₁₋₆ alkyl-, R⁷—C₂₋₆ alkyl-N(R¹⁰)—C(=O)C₁₋₆ alkyl-, —C₁₋₆ hydroxyalkyl, C₁₋₆ alkoxy-C₁₋₆ alkyl-, R⁷(CH₂)ₚOC₁₋₆ alkyl-, C₁₋₆ acyloxy-C₁₋₆ alkyl-, R⁷—(CH₂)ₚC(=O)O—C₁₋₆ alkyl-, C₁₋₆ alkoxy-C(=O)O—C₁₋₆ alkyl-, R⁷(CH₂)ₚ O—C(=O)—OC₁₋₆ alkyl-, R⁸R⁹N—C(=O)OC₁₋₆ alkyl-, C₁₋₆ alkyl-N(R¹⁰)C(=O)O—C₁₋₆ alkyl-, R⁷(CH₂)ₚN(R¹⁰)—C(=O)O—C₁₋₆ alkyl-, R⁸R⁹N—C₁₋₆ alkyl-, R¹³R¹³N—C₁₋₆ alkyl-, R⁷—C₁₋₆ alkyl-, C₁₋₆ acylN(R¹⁰)—C₁₋₆ alkyl-, R⁷—C₁₋₆ alkyl-, C₁₋₆ alkoxy-C(=O)N(R¹⁰))—C₁₋₆ alkyl-, R⁷—(CH₂)ₚOC(=O)N(R¹⁰)C₁₋₆ alkyl-, R⁸R⁹NC(=O)N(R¹⁰)C₁₋₆ alkyl-, R¹⁰SO₂—N(R¹⁰)—C₁₋₆ alkyl-, R⁷—SO₂—N(R¹⁰)—C₁₋₆ alkyl-, C₁₋₆ alkylS(O)ₓ—C₁₋₆ alkyl-, R⁷—(CH₂)ₚS(O)ₓC₁₋₆ alkyl-, R⁷SO₂C₁₋₆ alkyl-, C₁₋₆ alkylS(=O)(=NR¹³)—C₁₋₆ alkyl-, C₁₋₆ haloalkyl S(=O)(=NR¹³)—C₁₋₆ alkyl-, C₁₋₆ alkylS(=NR¹³)(=NR¹³)—C₁₋₆ alkyl-, C₁₋₆haloalkyl S(=NR¹³)(=NR¹³)—C₁₋₆ alkyl-, R⁷S(=O)(=NR¹³)C₁₋₆ alkyl-, R⁷S(=NR¹³)(=NR¹³)—C₁₋₆ alkyl-, —C₂₋₆ alkenyl, —C₂₋₆ haloalkenyl, R⁷—C₃₋₆ alkenyl-, C₁₋₆ alkoxy-C₁₋₆ alkenyl-, —C₂₋₆ alkynyl, —C₂₋₆ haloalkynyl, R⁷—C₂₋₆ alkynyl-, C₂₋₆ alkynyl-, C₁₋₆ acyl-, R⁷—(CH₂)ₚC(=O)—, R⁷—C₁₋₆ alkyl-C(=O)—, C₁₋₆ hydroxyalkyl-C(=O)—, C₁₋₆ alkoxy-C₁₋₆ alkyl-C(=O)—, C₁₋₆ alkylS(O)ₓ, —C₁₋₆ alkyl-C(=O)—, carboxy, —C₁₋₆ alkoxycarbonyl, R⁷—(CH₂)ₚoxycarbonyl-, —C(=O)NR⁸R⁹, R⁷—(CH₂)ₚ—N(R¹⁰)—C(=O)—, hydroxyl, —C₁₋₆ alkoxy, —C₁₋₆ haloalkoxy, C₁₋₆ alkyl-N(R¹⁰)ₚC(=O)—C₁₋₆ alkoxy-, R⁷(CH₂)ₚO—, R⁷(CH₂)ₚOC(=O)OC₂₋₆ alkoxy-, R⁷(CH₂)ₚN(R¹⁰)—C(=O)O—C₂₋₆ alkoxy-, R⁸R⁹N—C(=O)OC₂₋₆ alkoxy-, C₁₋₆ alkoxy-C(=O)N(R¹⁰)—C₂₋₆ alkoxy-, R⁷—(CH₂)ₚOC(=O)N(R¹³)C₂₋₆ alkoxy-, R⁸R⁹NC(=O)N(R¹⁰)C₂₋₆ alkoxy-, C₁₋₆ alkoxycarbonylC₁₋₆ alkoxy-, R⁷(CH₂)ₚ OC(=O)C₁₋₆ alkoxy-, C₁₋₆ acyloxy, R⁷—(CH₂)ₚC(=O)O—, —NR⁸R⁹, —NR¹³R¹³, R⁸R⁹N—C₂₋₆alkyl-N(R¹⁰)—, R⁷—C₂₋₆alkyl-N(R¹⁰)—, C₁₋₆acyl-N(R¹⁰)—, C₁₋₆ alkoxycarbonyl-N(R¹⁰)—, R⁸R⁹ N—C(=O)—N(R¹⁰)—, R⁷—C₁₋₆acyl-N(R¹⁰)—, C₁₋₆ alkylS(O)₂—N(R¹⁰)—, R¹⁰ S(O)₂—N(R¹⁰)—, C₁₋₆haloalkylS(O)₂—N(R¹⁰)—, R⁷SO₂—N(R¹⁰)—, thio, C₁₋₆ alkylS(O)ₓ—, C₁₋₆haloalkylS(O)ₓ—, R⁷—(CH₂)ₚS(O)₂—, R⁷SO₂—, C₁₋₆ alkyl-S(=O)(=NR¹³)—, C₁₋₆haloalkyl-S(=O)(=NR¹³)—, C₁₋₆alkylS(=NR¹³)(=NR¹³)—, C₁₋₆ haloalkyl-S(=NR¹³)(=NR¹³)—, R⁷S(=NR¹³)(NR¹³)—, R⁷S(=NR¹³)=NR¹³—, C₆₋₁₂ aryl, C₆-C₁₂ aryl-C₁-C₆ alkyl-, 5-12 membered heteroaryl, 5-12 membered heteroaryl-C₁-C₆ alkyl-, C₃₋₈ cycloalkyl-, C₃₋₈ cycloalkyl-C₁-C₆ alkyl-, C₃₋₈ cycloalkenyl-, C₃₋₈ cycloalkenyl-C₁-C₆alkyl-4-12 membered monocyclic or bicyclic heterocyclyl-, or 4-12 membered monocyclic or bicyclic heterocyclyl-C₁-C₆ alkyl-;

in R³, R⁵ is H, F, CF₃, CHF₂, or C₁-C₆ alkyl;

in Y¹ and Y², R⁵ᵃ is H, F, Cl, CF₃, CHF₂, CF₂C₁₋₆ alkyl, CF₂CH₂NR⁸R⁹, CH₂NR⁸R⁹, CN, or C₁₋₆ alkyl;

in $Y^1$ and $Y^2$, $R^{6e}$ is $R^{10}$, H, F, aryl, heteroaryl, cycloalkyl, heterocycloalkyl, $(CH_2)_mCHR^{10}R^7$, $CF_2(CH_2)_mCHR^{10}R^7$, or $C(R^{10})_2R^7$;

in $Y^4$ and $Y^5$, $R^{6t}$ is $C_{1-6}$ alkyl, $C_{3-6}$ cycloalkyl, aryl, heteroaryl, heterocycloalkyl, $(CH_2)_mCHR^{10}R^7$, $C(R^{10})_2R^7$;

in $Y^1$ and $Y^2$, $R^{6z}$ is H, F, Cl, $CF_3$, $CHF_2$, $CF_2C_{1-6}$ alkyl or $C_{1-6}$ alkyl; or alternatively in $Y^1$ and $Y^2$, $R^{6e}$ and $R^{6z}$, taken together, form $R^{6e}R^{6z}=$; or alternatively in $Y^1$ and $Y^2$, $R^{6e}$ and $R^{6z}$, taken together with the sp$^2$ carbon atom to which both are attached, form an alicyclic ring of 4 to 7 members wherein one of the ring atoms are optionally replaced by $NR^8$, O, $S(O)_x$, $S(=O)(=N R^{10})$, P=O, $P(=O)(OR^8)$, $OP(=O)(OR^8)O$, and the alicyclic ring is optionally substituted with one or more substituents selected from the group consisting of halogen, oxo, OH, $OR^8$, and $NR^8R^9$;

$R^7$ is OH, $NR^8R^9$, $O(CH_2)_qNR^8R^9$, $C_{1-6}$ alkoxy, $C_{2-6}$ alkoxy-$C_{1-6}$ alkoxy, $C_{2-6}$ hydroxyalkoxy, oxetanyl, oxetanyloxy, oxetanylamino, oxolanyl, oxolanyloxy, oxolanylamino, oxanyl oxanyloxy, oxanylamino, oxepanyl, oxepanyloxy, oxepanylamino, azetidinyl, azetidinyloxy, azetidylamino, pyrrolidinyl, pyrolidinyloxy, pyrrolidinylamino, piperidinyl, piperidinyloxy, piperidinylamino, azepanyl, azepanyloxy, azepanylamino, dioxolanyl, dioxanyl, morpholino, thiomorpholino, thiomorpholino-S,S-dioxide, piperazino, dioxepanyl, dioxepanyloxy, dioxepanylamino, oxazepanyl, oxazepanyloxy, oxazepanylamino, diazepanyl, diazepanyloxy, diazepanylamino, (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2(dimethylamino)-2-oxoethyl]piperazin-1-yl, methyl[2-(4-methylpiperazin-1yl)ethyl]amino, methyl[2-(morpholin-4-yl)ethyl]amino, 1-amino-1,2,3,6tetrahydropyridin-4-yl, 4-[(2S)-2-aminopropanoyl]piperazin-1-yl, all of which may be optionally substituted with OH, $OR^{10}$, oxo, halogen, $R^{10}$, $CH_2OR^{10}$, or $CH_2NR^8R^9$;

$R^8$ and $R^9$ are independently H, —$CD_3$, $C_{1-6}$ alkyl, $C_{1-6}$ haloalkyl, $C_{3-6}$ alkenyl, $C_{3-6}$ haloalkenyl, $C_{3-6}$ alkynyl, $C_3$-$C_6$ haloalkynyl, $C_{3-8}$ cycloalkyl, $C_{3-6}$ cycloalkyl-$C_{1-6}$ alkyl-, $C_{3-8}$ halocycloalkyl, $C_{3-8}$ halocycloalkyl-$C_1$-$C_6$ alkyl-, $C_{3-8}$ cycloalkenyl, $C_{3-8}$ cycloalkenyl-$C_1$-$C_6$ alkyl-, $C_{3-8}$ halocycloalkenyl, $C_{3-8}$ halocycloalkenyl-$C_1$-$C_6$ alkyl-, $C_1$-$C_6$ acyl, $C_1$-$C_6$acyl-$C_1$-$C_6$ alkyl-, 4-12 membered monocyclic or bicyclic heterocyclyl, 4-12 membered monocyclic or bicyclic heterocyclyl-$C_1$-$C_6$ alkyl-, $C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-; and $R^8$ and $R^9$ may be further independently substituted with up to three substituents chosen from hydroxyl, $C_{1-6}$ alkoxy, $C_{1-6}$ hydroxyalkl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, and the heterocyclic ring is optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, —$CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$;

each $R^{11}$ is independently hydrogen, $C_1$-$C_6$ alkyl, $C_3$-$C_6$ alkenyl, $C_3$-$C_6$ alkynyl, $C_3$-$C_6$ cycloalkyl, $C_6$-$C_{12}$ aryl, 4-12 membered heterocyclyl, or 5-12 membered heteroaryl; or alternatively, two $R^{11}$, taken together with the heteroatom(s) attached thereto, form a 5-8 membered heterocyclyl ring, which is optionally substituted with up to three substituents selected from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano and halo;

each $R^{13}$ is independently H, —$CD_3$, cyano, —$C_{1-6}$ alkyl, —$C_{1-6}$ haloalkyl, $C_{1-6}$ acyl-$C_{1-6}$ alkyl-, $R^7$—$(CH_2)_pC(=O)$—$C_{1-6}$ alkyl-, carboxy-$C_{1-6}$ alkyl-, $C_{1-6}$ alkyloxycarbonyl-$C_{1-6}$ alkyl-, $R^7$—$(CH_2)_pO$—$C(=O)$—$C_{1-6}$ alkyl-, $R^8R^9N$—$C(=O)C_{1-6}$ alkyl-, $R^7$—$C_{2-6}$alkyl-$N(R^{10})$—$C(=O)C_{1-6}$ alkyl-, —$C_{2-6}$ hydroxyalkyl, $C_{1-6}$ alkoxy-$C_{2-6}$ alkyl-, $R^7(CH_2)_pOC_{2-6}$ alkyl-, $C_{1-6}$ acyloxy-$C_{2-6}$ alkyl-, $R^7$—$(CH_2)_pC(=O)O$—$C_{2-6}$ alkyl-, $C_{1-6}$ alkoxy-$C(=O)O$—$C_{2-6}$ alkyl-, $R^7(CH_2)_pO$—$C(=O)$—$OC_{2-6}$ alkyl-, $R^8R^9N$—$C(=O)OC_{2-6}$ alkyl-, $C_{1-6}$ alkyl-$N(R^{10})C(=O)O$—$C_{2-6}$ alkyl-, $R^7(CH_2)_pN(R^{10})$—$C(=O)O$—$C_{2-6}$ alkyl-, $R^8R^9N$—$C_{2-6}$alkyl-, $R^7$—$C_{2-6}$alkyl-, $C_{1-6}$ acylN($R^{10})$—$C_{2-6}$alkyl-, $R^7$—$C_{4-6}$acylN($R^{10})$—$C_{2-6}$ alkyl-, $R^7$—$(CH_2)_pC(=O)N(R^{10})$—$C_{2-6}$ alkyl-, $R^7$—$C_{1-6}$ alkylC(=O)N($R^{10})$—$C_{2-6}$ alkyl-, $C_{1-6}$ alkoxy-$C(=O)N(R^{10})$—$C_{2-6}$ alkyl-, $R^7$—$(CH_2)_pOC(=O)N(R^{10})C_{2-6}$ alkyl-, $R^8R^9NC(=O)N(R^{10})C_{2-6}$ alkyl-, $R^{10}SO_2$—$N(R^{10})$—$C_{2-6}$ alkyl-, $R^7$—$SO_2$—$N(R^{10})$—$C_{2-6}$ alkyl-, $C_{1-6}$ alkylS(O)—$C_{2-6}$ alkyl-, $R^7$—$(CH_2)_pS(O)_xC_{2-6}$ alkyl-, $R^7SO_2C_{2-6}$ alkyl-, $C_{1-6}$ alkylS(=O)(=NR$^1$)—$C_{2-6}$ alkyl-, $C_{1-6}$ haloalkyl S(=O)(=N R$^{10}$)—$C_{2-6}$ alkyl-, $C_{1-6}$ alkylS(=NR$^{13}$)(=NR$^{13}$)—$C_{2-6}$ alkyl-, $C_{1-6}$ haloalkyl S(=N R$^{10}$)(=N R$^{10}$)—$C_{2-6}$ alkyl-, $R^7S(=O)(=N R^{10})C_{2-6}$ alkyl-, $R^7S(=NR^{13})(=NR^{13})$—$C_{2-6}$ alkyl-, —$C_{3-6}$ alkenyl, —$C_{3-6}$ haloalkenyl, R—$C_{4-6}$ alkenyl-, $C_{1-6}$ alkoxy-$C_{4-6}$ alkenyl-, —$C_{2-6}$ alkynyl, —$C_{2-6}$ haloalkynyl, $R^7$—$C_{2-6}$ alkynyl-, $C_{2-6}$ alkynyl-, $C_{1-6}$ acyl-, $R^7$—$(CH_2)_pC(=O)$—, $R^7$—$C_{1-6}$ alkyl-$C(=O)$—, $C_{1-6}$ hydroxyalkyl-$C(=O)$—, $C_{1-6}$ alkoxy-$C_{1-6}$ alkyl-$C(=O)$—, $C_{1-6}$ alkylS(O)$_x$—$C_{1-6}$ alkyl-$C(=O)$—, —$C_{1-6}$ alkoxycarbonyl, $R^7$—$(CH_2)_p$oxycarbonyl-, —$C(=O)NR^8R^9$, $R^7$—$(CH_2)_p$—$N(R^{10})$—$C(=O)$—, hydroxyl, —$C_{1-6}$ alkoxy, —$C_{1-6}$ haloalkoxy, $C_{1-6}$ alkyl-$N(R^{10})_pC(=O)$—$C_{1-6}$ alkoxy-, $R^7(CH_2)_pO$—, $R^7(CH_2)_pOC(=O)OC_{2-6}$ alkoxy-, $R^7(CH_2)N(R^{10})$—$C(=O)O$—$C_{2-6}$ alkoxy-, $R^8R^9N$—$C(=O)OC_{2-6}$ alkoxy-, $C_{1-6}$ alkoxy-$C(=O)N(R^{10})$—$C_{2-6}$ alkoxy-, $R^7$—$(CH_2)_pOC(=O)N(R^{10})C_{2-6}$ alkoxy-, $R^8R^9NC(=O)N(R^{10})C_{2-6}$ alkoxy-, $C_{1-6}$ alkoxycarbonylC$_{1-6}$ alkoxy-, $R^7(CH_2)_pOC(=O)C_{1-6}$ alkoxy-, —$C_{1-6}$ acyloxy, $R^7$—$(CH_2)_pC(=O)O$—, —$NR^8R^9$, $R^8R^9N$—$C_{2-6}$alkyl-$N(R^{10})$—, $R^7$—$C_{2-6}$alkyl-$N(R^{10})$—, $C_{1-6}$ acyl-$N(R^{10})$—, $C_{1-6}$ alkoxycarbonyl-$N(R^{10})$—, $R^8R^9$ N—C(=O)—$N(R^{10})$—, $R^7$—$C_{1-6}$ acyl-$N(R^{10})$—, $C_{1-6}$ alkyl S(O)$_2$—$N(R^{10})$—, $R^{10}S(O)_2$—$N(R^{10})$—, $C_{1-6}$ haloalkylS(O)$_2$—$N(R^{10})$—, $R^7SO_2$—$N(R^{10})$—, $C_{1-6}$ alkylS(O)$_x$—, $C_{1-6}$ haloalkylS(O)$_x$—, $R^7$—$(CH_2)_pS(O)_2$, $R^7SO_2$—, $C_{1-6}$ alkyl-S(=O)(=N R$^{10}$)—, $C_{1-6}$ haloalkyl-S(=O)(=N R$^{10}$)—, $C_{6-12}$ aryl, $C_{6-12}$ aryl-$C_1$-$C_6$alkyl-, 5-12 membered heteroaryl, 5-12 membered heteroaryl-$C_1$-$C_6$ alkyl-, $C_{3-8}$ cycloalkyl-, $C_{3-6}$ cycloalkyl-$C_1$-$C_6$ alkyl-, $C_{3-8}$ cycloalkenyl-, $C_{3-8}$ cycloalkenyl-$C_1$-$C_6$alkyl-, 4-12 membered monocyclic or bicyclic heterocyclyl-, or 4-12 membered monocyclic or bicyclic heterocyclyl-$C_1$-$C_6$ alkyl-; or alternatively, two $R^4$, tow $R^{13}$, or $R^{13}$ and $R^4$, taken together with atoms attached thereto, form a ring of 5-7 members, which may be aromatic or partially saturated, and which may contain up to two heteroatoms chosen from N, O and S; and the 5-7 member ring is optionally further substituted by is selected from the group consisting of =O (oxo), =S, =NR[13], (=O)$_2$, (O)(NR[13]), R[4], and R[13];
A[6] is selected from:
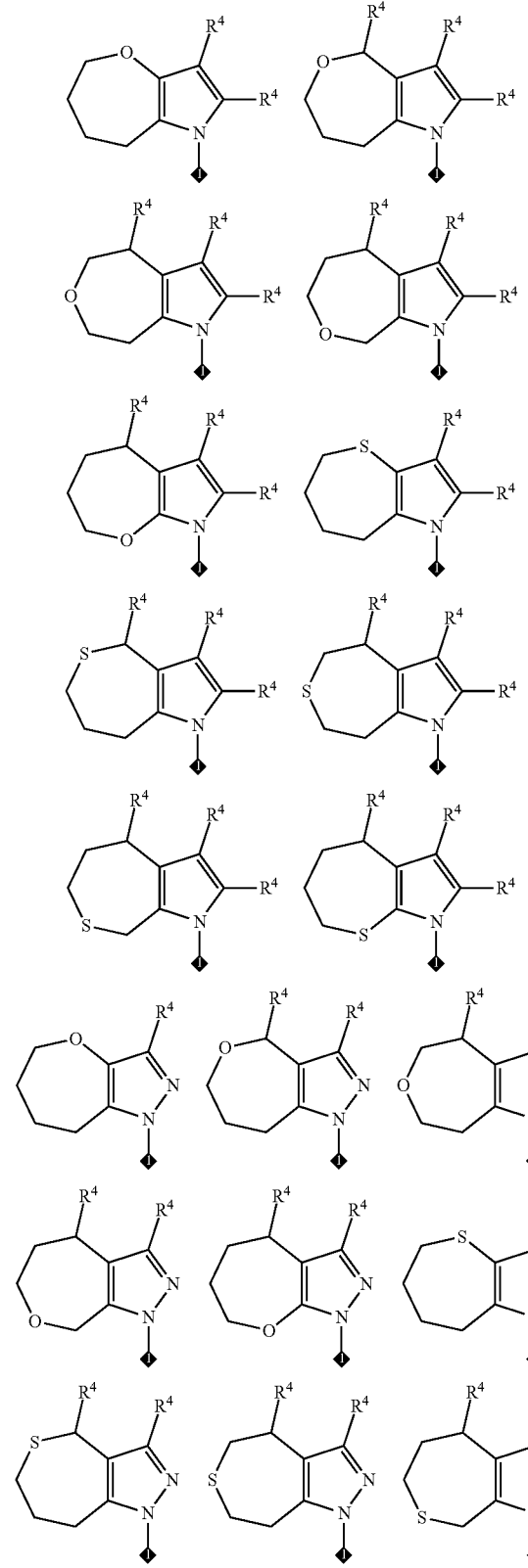
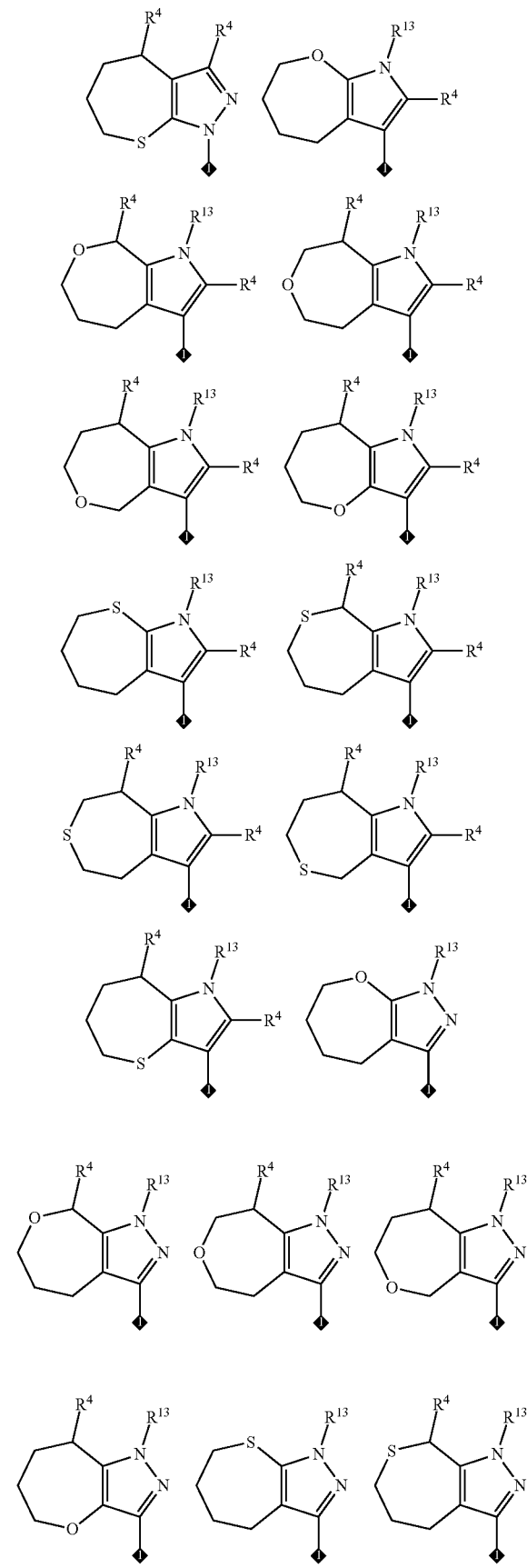

-continued
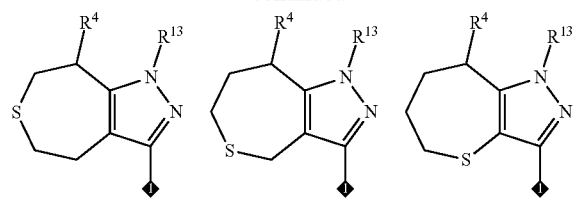
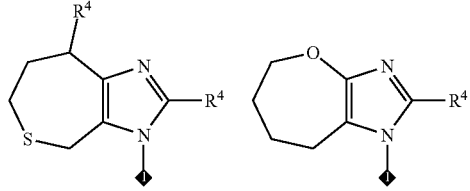
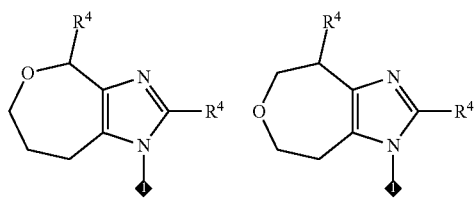
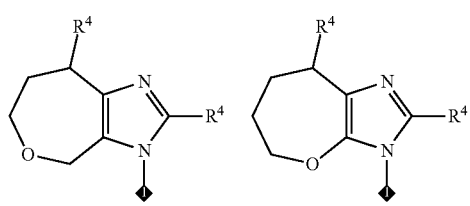
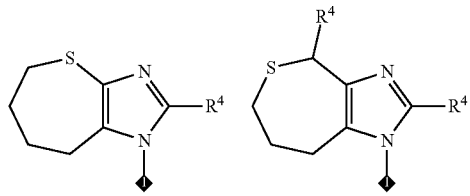
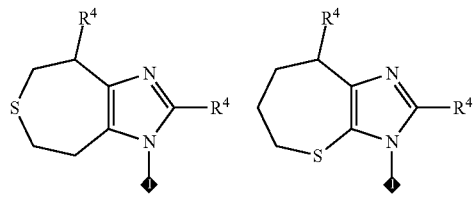
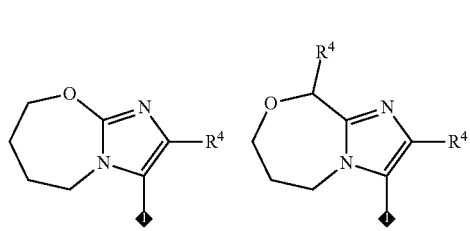
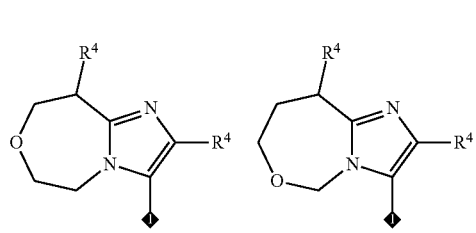
-continued
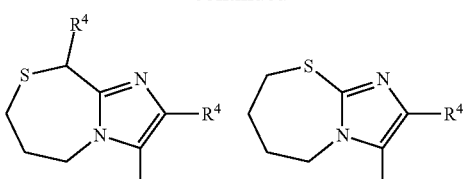
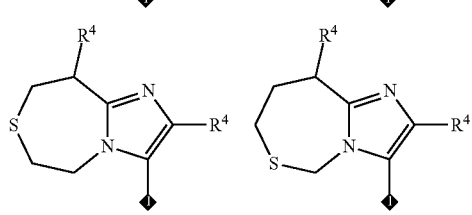
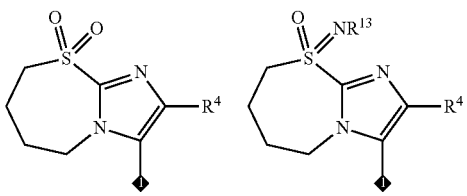
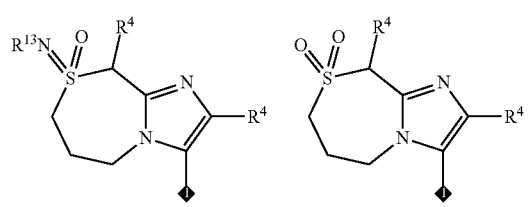
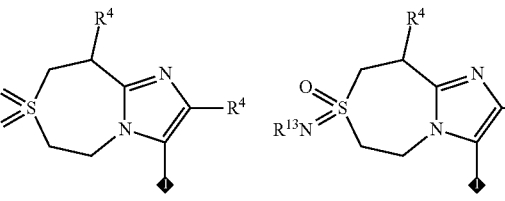
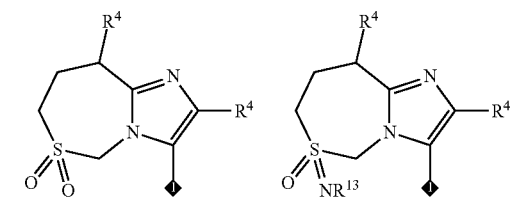
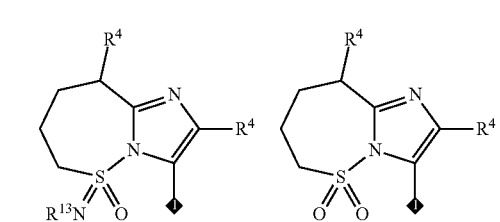
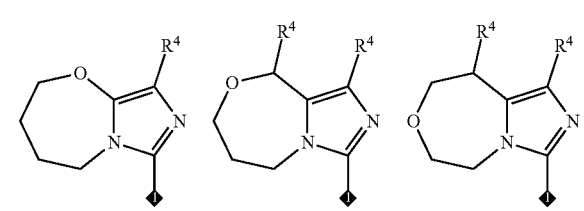

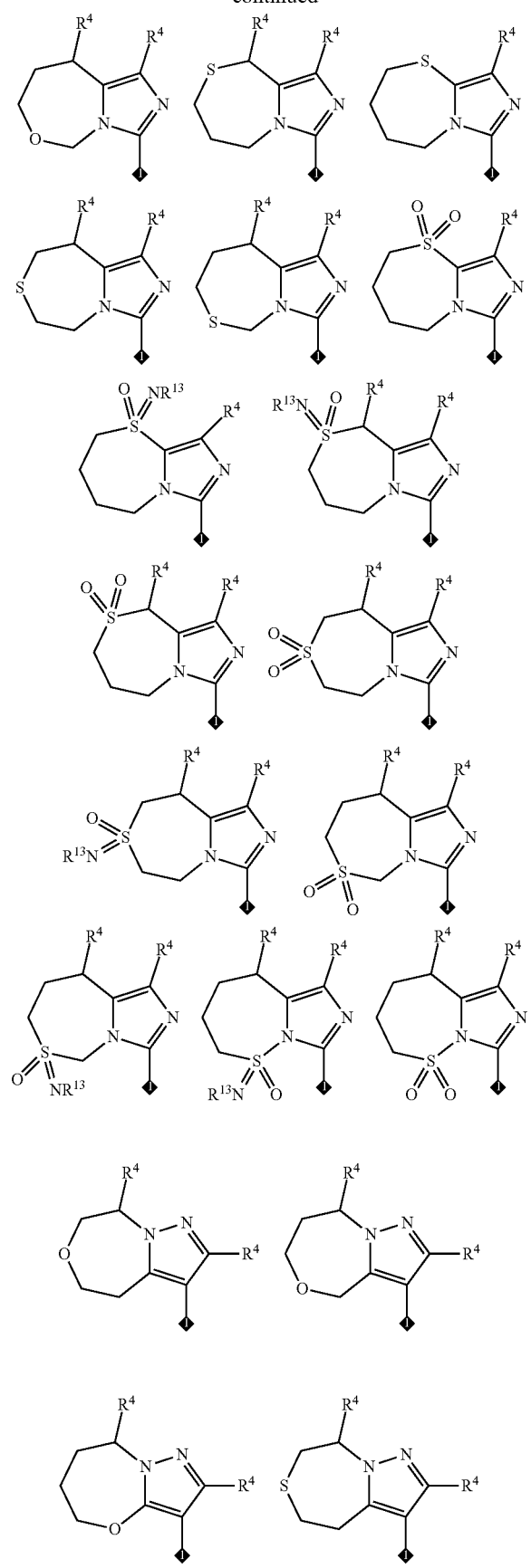
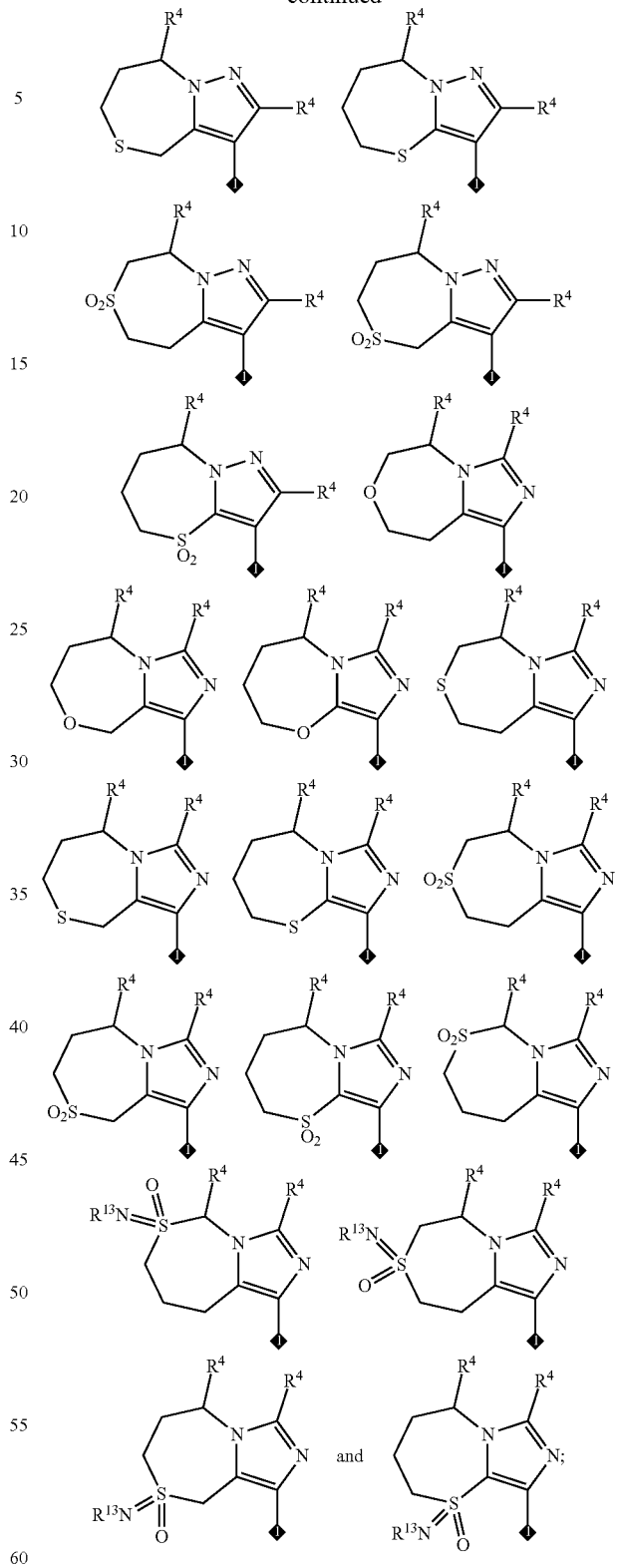
A² is optionally substituted with R⁴;
m is 0, 1, 2, or 3;
n=1, 2, or 3;
p=0, 1, 2, 3, or 4;
q=2, 3, or 4; and
x=0, 1, or 2.

In one embodiment of formula (I), each of $X^1$, $X^2$, $X^3$, $X^6$, $X^7$, $X^8$, $X^9$, $X^{10}$, $X^{11}$, and $X^{12}$ is selected from the group consisting of: C, CH, $CR^4$, $C(R^4)_2$, $CR^{13}$, $CH_2$, C=O, C=S, C=$NR^{13}$, N, $NR^4$, $NR^{13}$, N(O), S, S(O), S(O)$_2$, S(=O)(=$NR^{13}$), S(=$NR^{13}$)$_2$, and O.

In one embodiment of formula (I), if any of $X^2$, $X^3$, $X^6$, $X^7$, $X^8$, $X^9$, $X^{10}$, $X^{11}$, and $X^{12}$ is $NR^{13}$, O, S, C=O, C=$NR^{13}$, S=O or $SO_2$, none of the abovementioned bonds to said atom is a (formal) double bond; and at least four of $X^1$, $X^2$, $X^3$, $X^4$, $X^5$, $X^6$, $X^7$, $X^8$, $X^9$, $X^{10}$, $X^{11}$, and $X^{12}$ are C, $CR^4$, or $C(R^4)_2$.

In one embodiment of formula (I), each $X^1$, $X^2$, $X^3$, $X^6$, $X^7$, $X^8$, $X^9$, $X^{10}$, $X^{11}$, and $X^{12}$ is optionally substituted and is independently C or a heteroatom selected from the group consisting of N, S, O, and the functional groups of C=O, C=$NR^{13}$, $SO_2$ or S(O)($NR^{13}$);

In one embodiment of formula (I), in $A^1$ $A^2$, $A^3$, $A^{4a}$, and $A^{4b}$, no more than four, and no less than two of $X^1$, $X^2$, $X^3$, $X^4$, and $X^5$ can be C, $CR^4$, or $C(R^4)_2$.

In one embodiment of formula (I), in $A^1$, $A^2$ and $A^3$, if $X^1$, $X^4$ and $X^5$ are all C, then one of $X^2$ and $X^3$ is O, C=O, $SO_2$, N, $NR^{13}$ or S.

In one embodiment of formula (I), in $A^1$, $A^2$ and $A^3$, if $X^1$ is N, $X^2$ is C=O, $SO_2$, C=$NR^{13}$, $NR^{13}$ or C=S, and $X^4$ and $X^5$ are both C, then $X^3$ is $C(R^4)_2$, O, $NR^3$, C=O or S.

In one embodiment of formula (I), in $A^1$, $A^2$ and $A^3$, if $X^1$ is C, and $X^2$ and $X^3$ are $CR^4$ or N, one of $X^4$ and $X^5$ may be N, but if $X^1$ is N, or if one of $X^2$ or $X^3$ is not N or $CR^4$, both $X^4$ and $X^5$ are C.

In one embodiment of formula (I), in $A^{4a}$, and $A^{4b}$ at least one of $X^1$, $X^2$ and $X^3$ is $CR^4$ or N, and one of $X^4$ and $X^5$ is C or N, and the other is C.

In one embodiment of formula (I), in $A^2$, the methylene units in the non-aromatic ring are optionally substituted with up to three independent $R^4$; and optionally up to two of the methylene units are independently replaced by C=O, $C(R^4)_2$, $NR^{10}$, O or $S(O)_x$.

In one embodiment of formula (I), in $A^1$ $X^6$, $X^7$, $X^8$, and $X^9$ may be $CR^4$ N, $NR^{13}$, $C(R^1)_2$, C(O), or $S(O)_x$ with the proviso that at least two of them are $CR^4$, C(=O), C(=$NR^{13}$) or N.

In one embodiment of formula (I), in $A^3$, if $X^4$ or $X^5$ is N, then $X^{10}$, $X^{11}$, and $X^{12}$ are independently N or $CR^4$, with the proviso that at most two of $X^{10}$, $X^{11}$, and $X^{12}$ are N.

In one embodiment of formula (I), in $A^3$, if $X^4$ and $X^5$ are C, one of $X^{10}$, $X^{11}$, and $X^{12}$ is $NR^{10}$, O or S, then the remaining two are independently $CR^4$ or N.

In one embodiment of formula (I), in $A^{4a}$ and $A^{4b}$ $X^6$ and $X^7$ may be $CR^4$ N, $NR^{13}$, $C(R^1)_2$, C(O), or $S(O)_x$ with the proviso that at least two of them are $CR^4$, C(=O), C(=$NR^{13}$) or N.

In one embodiment of formula (I), in $A^{4a}$, $X^9$ is C, CH or N.

In one embodiment of formula (I), in $A^{4b}$, $X^8$ is C, CH or N.

In one embodiment of formula (I), in $A^5$, at least three of $X^2$, $X^3$, $X^4$, $X^5$ and $X^6$ are C, C=O, $CR^4$, or $C(R^4)_2$. In one embodiment of formula (I), in $A^5$, $X^1$ is C, CH or N.

In one embodiment of formula (I), when Z is CH, then A is not 4,5,6,7-tetrahydropyrazolo[1,5-a]pyridin-3-yl, 1H-indol-3-yl, 1-methyl-1H-indol-3-yl, or pyrazolo[1,5-a]pyridin-3-yl.

In one embodiment of formula (I), Z is N. In another embodiment, Z is CH.

In another embodiment of formula (I), $R^3$ is selected from the group consisting of (3R)-3-(dimethylamino)pyrrolidin-1-yl, (3S)-3-(dimethyl-amino)pyrrolidin-1-yl, 3-(dimethyl-amino)azetidin-1-yl, [2-(dimethylamino)ethyl]-(methyl)amino, [2-(methylamino)ethyl](methyl)amino, 5-methyl-2,5-diazaspiro[3.4]oct-2-yl, (3aR,6aR)-5-methylhexa-hydropyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl.

In another embodiment of formula (I), $R^3$ is —$N(R^{10})C_{2-6}$alkyl-$NR^{10}R^{10}$.

In another embodiment of formula (I), $R^1$ is selected from H, F, Cl, Br, $CF_3$, —CN, methyl, —$CHF_2$, ethynyl, methoxy, ethoxy, isopropxy, —$OCF_3$, —$OCH_2CF_3$, —$OCH_2CHF_2$, —CHO, —$CONH_2$, —CONHMe, or —$CONMe_2$.

In another embodiment of formula (I), $E^3$ is N.

In another embodiment of formula (I), $E^1$ and $E^2$ are each CH.

In one embodiment of formula (I), $E^1$, $E^2$ and $E^3$, together with the nitrogen and carbon atoms of the six-member ring, form a heteroaromatic ring selected from the group consisting of

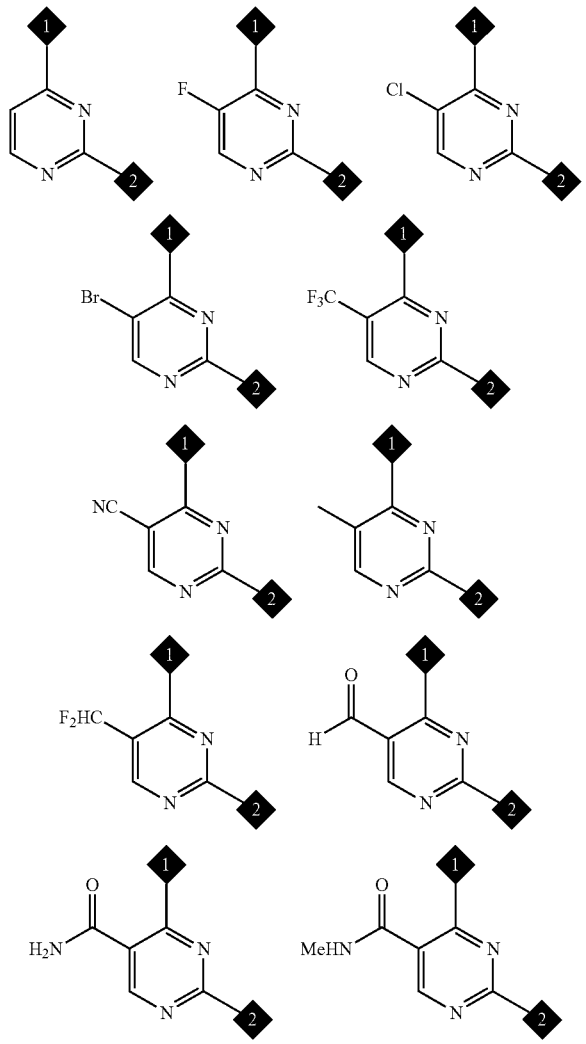

-continued

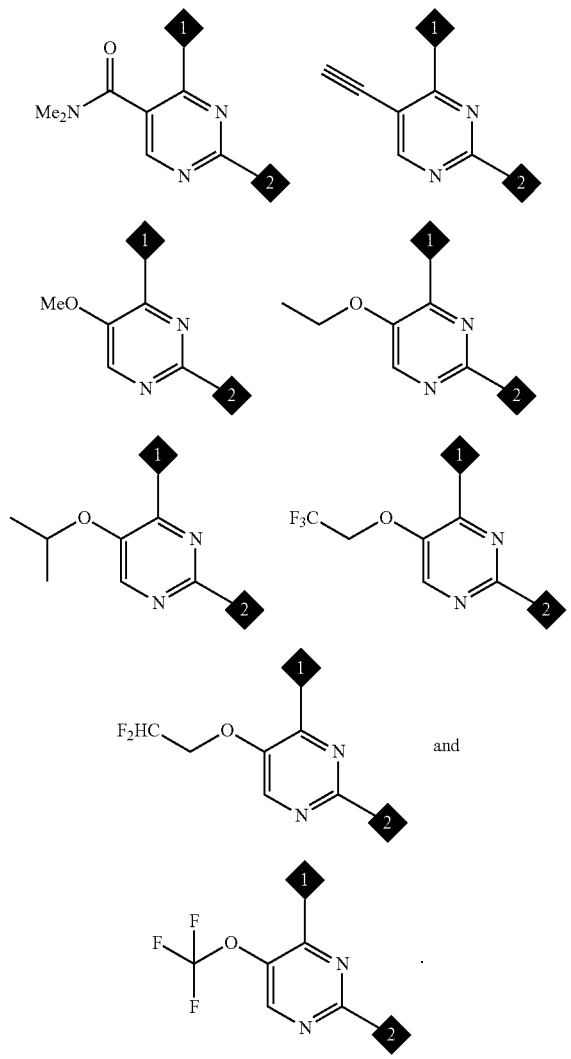

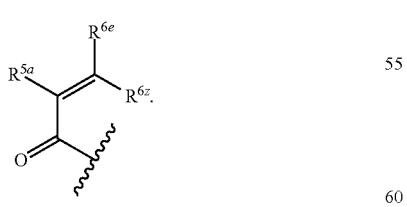

1 Attachment point for A1-A5

2 Attachment point for (hetero)arylamino group

In another embodiment of formula (I), Y is

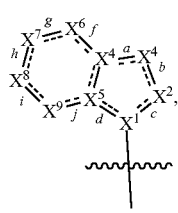

Various embodiments disclosed herein for formula (I) can also be applied to formulae IA), (IIA$^1$), (IIA$^2$), (IIA$^3$), (IIA$^{4a}$), (IIA$^{4b}$), and/or (IIA$^5$) below.

In one embodiment, the present invention relates to a compound of the formula (IA):

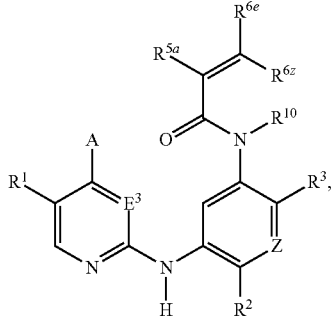
(IA)

or a stereoisomer or a pharmaceutically acceptable salt, solvate, ester, or prodrug thereof;

wherein,

A is

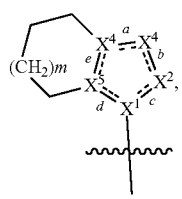 A$^1$

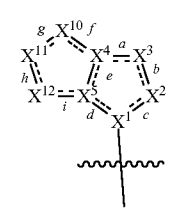 A$^2$

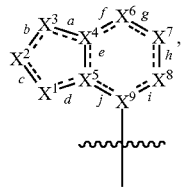 A$^3$

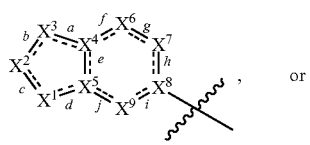 A$^{4a}$

A$^{4b}$

A⁵

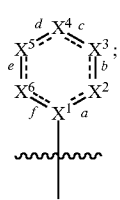

each of a, b, c, d, e, f, g, h, i and j are independently either (formal) double bonds or (formal) single bonds, and none of $X^1$, $X^2$, $X^3$, $X^4$, $X^5$, $X^6$, $X^7$, $X^8$, $X^9$, $X^{10}$, $X^{11}$, and $X^{12}$ has two (formal) double bonds attached thereto:

each of $X^1$, $X^2$, $X^3$, $X^6$, $X^7$, $X^8$, $X^9$, $X^{10}$, $X^{11}$, and $X^{12}$ is optionally substituted and is independently C or a heteroatom selected from the group consisting of N, S, and O; and the optional substituent is selected from the group consisting of =O (oxo), =S, =$NR^{13}$, (=O)$_2$, (O)($NR^{13}$), $R^4$, and $R^{13}$; or alternatively, each of $X^1$, $X^2$, $X^3$, $X^6$, $X^7$, $X^8$, $X^9$, $X^{10}$, $X^{11}$, and $X^{12}$ is selected from the group consisting of: C, CH, $CR^4$, $C(R^4)_2$, $CR^{13}$, $CH_2$, C=O, C=S, C=$NR^{13}$, N, $NR^4$, $NR^{13}$, N(O), S, S(O), $S(O)_2$, S(=O)(=$NR^{13}$), S(=$NR^{13})_2$, and O;

each of $X^4$ and $X^5$ is independently C or N;

at least four of $X^1$, $X^2$, $X^3$, $X^4$, $X^5$, $X^6$, $X^7$, $X^8$, $X^9$, $X^{10}$, $X^{11}$, and $X^{12}$ are C, $CR^4$, or $C(R^4)_2$;

in $A^1$, $A^2$, $A^3$ and $A^5$, $X^1$ is C, CH or N;

in $A^{4a}$, $X^9$ is C, CH or N;

in $A^{4b}$, $X^8$ is C, CH or N;

in $A^{4a}$ and $A^{4b}$, $X^1$ is N, $NR^{13}$, $C(R^4)_2$, C(O), $S(O)_x$, S(=O)(=$NR^{13}$), S(=$NR^{13})_2$, or $CR^4$;

in $A^1$, $A^2$, $A^3$, $A^{4a}$, and $A^{4b}$, $X^2$ is N, $NR^{13}$, $C(R^4)_2$, $S(O)_x$, S(=O)(=$NR^{13}$), S(=$NR^{13})_2$, C(O), or $CR^4$;

in $A^1$, $A^2$, $A^3$, $A^{4a}$ and $A^{4b}$, $X^3$ is N, $NR^{13}$, $C(R^4)_2$, C(O), $S(O)_x$, S(=O)(=$NR^{13}$), S(=$NR^{13})_2$, or $CR^4$;

in $A^5$, at least three of $X^2$, $X^3$, $X^4$, $X^5$ and $X^6$ are C, C=O, $CR^4$, or $C(R^4)_2$;

$E^3$ and Z are independently CH or N;

$R^1$ is independently selected from hydrogen, fluoro, chloro, bromo, methyl, ethyl, hydroxyl, methoxy, ethoxy, isopropxy, —$OCF_3$, —$OCH_2CF_3$, —$OCH_2CHF_2$, ethenyl, ethynyl, $CF_3$, $CHF_2$, CHO, $CH_2OH$, $CONH_2$, $CO_2Me$, $CONHMe$, $CONMe_2$, and cyano;

$R^2$ is $R^{10}$, —$OCF_3$, —$OCHF_2$, —$OCF_2CF_3$, —$OCH_2CHF_2$, —$OCH_2CF_3$, cyclopropyl, cyclopropoxy, methoxy, ethoxy, or isopropoxy;

$R^3$ is $C_{2-6}$ alkenyl-$R^7$, $C_{2-6}$ alkynyl-$R^7$, $N(R^{10})C_{2-6}$ alkyl-$NR^{10}R^{10}$, $N(R^{10})C_{2-6}$ alkyl-$R^7$, $O(CH_2)_pR^7$, $N(R^{10})C$(=O)$(CH_2)_pR$, $C(R^5)$=$C(R^{10})(CH_2)_pR^7$, or $R^7$;

each $R^4$ is independently H, cyano, nitro, halo, —$C_{1-6}$ alkyl, —$C_{1-6}$ haloalkyl, $C_{1-6}$ acyl-$C_{1-6}$ alkyl-, $R^7$—$(CH_2)_pC$(=O)—$C_{1-6}$ alkyl-, carboxy-$C_{1-6}$ alkyl-, $C_{1-6}$ alkyloxycarbonyl-$C_{1-6}$ alkyl-, $R^7$—$(CH_2)_pO$—C(=O)—$C_{1-6}$ alkyl-, $R^8R^9N$—C(=O)$C_{1-6}$ alkyl-, $R^7$—$C_{2-6}$ alkyl-$N(R^{10})$—C(=O)$C_{1-6}$ alkyl-, —$C_{1-6}$ hydroxyalkyl, $C_{1-6}$ alkoxy-$C_{1-6}$ alkyl-, $R^7(CH_2)_pOC_{2-6}$ alkyl-, $C_{1-6}$ acyloxy-$C_{1-6}$ alkyl-, $R^7$—$(CH_2)_pC$(=O)O—$C_{1-6}$ alkyl-, $C_{1-6}$ alkoxy-C(=O)O—$C_{1-6}$ alkyl-, $R^7(CH_2)_pO$—C(=O)—O$C_{1-6}$ alkyl-, $R^8R^9N$—C(=O)O$C_{1-6}$ alkyl-, $C_{1-6}$ alkyl-$N(R^{10})$C(=O)O—$C_{1-6}$ alkyl-, $R^7(CH_2)_pN(R^{10})$—C(=O)O—$C_{1-6}$ alkyl-, $R^8R^9N$—$C_{1-6}$ alkyl-, $R^{13}R^{13}N$—$C_{1-6}$ alkyl-, $R^7$—$C_{1-6}$ alkyl-, $C_{1-6}$ acyl$N(R^{10})$—$C_{1-6}$ alkyl-, $R^7$—$C_{1-6}$ alkyl-, $C_{1-6}$ alkoxy-C(=O)$N(R^{10})$)—$C_{1-6}$ alkyl-, $R^7$—$(CH_2)_pOC$(=O)$N(R^{10})C_{1-6}$ alkyl-, $R^8R^9NC$(=O)$N(R^{10})C_{1-6}$ alkyl-, $R^{10}SO_2$—N($R^{10}$)—$C_{1-6}$ alkyl-, $R^7$—$SO_2$—$N(R^{10})$—$C_{1-6}$ alkyl-, $C_{1-6}$ alkylS(O)$_x$—$C_{1-6}$ alkyl-, $R^7$—$(CH_2)_pS(O)_xC_{1-6}$ alkyl-, $R^7SO_2C_{1-6}$ alkyl-, $C_{1-6}$ alkylS(=O)($NR^{13}$)—$C_{1-6}$ alkyl-, $C_{1-6}$ haloalkyl S(=O)(=$NR^{13}$)—$C_{1-6}$ alkyl-, $C_{1-6}$ alkylS(=$NR^{13}$)(=$NR^{13}$)—$C_{1-6}$ alkyl-, $C_{1-6}$haloalkyl S(=$NR^{13}$)(=$NR^{13}$)—$C_{1-6}$ alkyl-, $R^7S$(=O)(=$NR^{13}$)$C_{1-6}$ alkyl-, $R^7S$(=$NR^{13}$)(=$NR^{13}$)—$C_{1-6}$ alkyl-, —$C_{2-6}$ alkenyl, —$C_{2-6}$ haloalkenyl, $R^7$—$C_{3-6}$ alkenyl-, $C_{1-6}$ alkoxy-$C_{1-6}$ alkenyl-, —$C_{2-6}$ alkynyl, —$C_{2-6}$ haloalkynyl, $R^7$—$C_{2-6}$ alkynyl-, $C_{2-6}$ alkynyl-, $C_{1-6}$ acyl-, $R^7$—$(CH_2)_pC$(=O)—, $R^7$—$C_{1-6}$ alkyl-C(=O)—, $C_{1-6}$ hydroxyalkyl-C(=O)—, $C_{1-6}$ alkoxy-$C_{1-6}$ alkyl-C(=O)—, $C_{1-6}$ alkylS(O)$_x$—$C_{1-6}$ alkyl-C(=O)—, carboxy, —$C_{1-6}$ alkoxycarbonyl, $R^7$—$(CH_2)_p$oxycarbonyl-, —C(=O)$NR^8R^9$, $R^7$—$(CH_2)_p$—$N(R^{10})$—C(=O)—, hydroxyl, —$C_{1-6}$ alkoxy, —$C_{1-6}$haloalkoxy, $C_{1-6}$ alkyl-N($R^{10}$)$_p$C(=O)—$C_{1-6}$ alkoxy-, $R^7(CH_2)_pO$—, $R^7(CH_2)_pOC$(=O)O$C_{2-6}$ alkoxy-, $R^7(CH_2)_pN(R^{10})$—C(=O)O—$C_{2-6}$ alkoxy-, $R^8R^9N$—C(=O)O$C_{2-6}$ alkoxy-, $C_{1-6}$ alkoxy-C(=O)$N(R^{10})$—$C_{2-6}$ alkoxy-, $R^7$—$(CH_2)_pOC$(=O)$N(R^{13})C_{2-6}$ alkoxy-, $R^8R^9NC$(=O)$N(R^{10})C_{2-6}$ alkoxy-, $C_{1-6}$ alkoxycarbonyl$C_{1-6}$ alkoxy-, $R^7(CH_2)_p$ OC(=O)$C_{1-6}$ alkoxy-, $C_{1-6}$ acyloxy, $R^7$—$(CH_2)_pC$(=O)O—, —$NR^8R^9$, —$NR^{13}R^{13}$, $R^8R^9N$—$C_{2-6}$alkyl-$N(R^{10})$—, $R^7$—$C_{2-6}$alkyl-$N(R^{10})$—, $C_{1-6}$acyl-$N(R^{10})$—, $C_{1-6}$ alkoxycarbonyl-N($R^{10}$)—, $R^8R^9$ N—C(=O)—$N(R^{10})$—, $R^7$—$C_{1-6}$acyl-N($R^{10}$)—, $C_{1-6}$ alkylS(O)$_2$—$N(R^{10})$—, $R^{10}S(O)_2$—$N(R^{10})$—, $C_{1-6}$haloalkylS(O)$_2$—$N(R^{10})$—, $R^7SO_2$—$N(R^{10})$—, thio, $C_{1-6}$ alkylS(O)$_x$—, $C_{1-6}$haloalkylS(O)$_x$—, $R^7$—$(CH_2)_p$S(O)$_2$—, $R^7SO_2$—, $C_{1-6}$ alkyl-S(=O)(=$NR^{13}$)—, $C_{1-6}$ haloalkyl-S(=O)(=$NR^{13}$)—, $C_{1-6}$ alkylS(=$NR^{13}$)(=$NR^{13}$)—, $C_{1-6}$ haloalkyl-S(=$NR^{13}$)($NR^{13}$)—, $R^7S$(=$NR^{13}$)($NR^{13}$)—, $R^7S$(=$NR^{13}$)(=$NR^{13}$)—, $C_{6-12}$ aryl, $C_6$-$C_{12}$ aryl-$C_1$-$C_6$ alkyl-, 5-12 membered heteroaryl, 5-12 membered heteroaryl-$C_1$-$C_6$ alkyl-, $C_{3-8}$ cycloalkyl-, $C_{3-8}$ cycloalkyl-$C_1$-$C_6$ alkyl-, $C_{3-8}$ cycloalkenyl-, $C_{3-8}$ cycloalkenyl-$C_1$-$C_6$alkyl-4-12 membered monocyclic or bicyclic heterocyclyl-, or 4-12 membered monocyclic or bicyclic heterocyclyl-$C_1$-$C_6$ alkyl-;

in $R^3$, $R^5$ is H, F, $CF_3$, $CHF_2$, or $C_1$-$C_6$ alkyl;

$R^{5a}$ is H, F, or CN;

$R^{6e}$ is H or F;

$R^{6z}$ is H or F;

$R^7$ is OH, $NR^8R^9$, $O(CH_2)_qNR^8R^9$, $C_{1-6}$ alkoxy, $C_{1-6}$ alkoxy-$C_{1-6}$ alkoxy, $C_{2-6}$ hydroxyalkoxy, oxetanyl, oxetanyloxy, oxetanylamino, oxolanyl, oxolanyloxy, oxolanylamino, oxanyl, oxanyloxy, oxanylamino, oxepanyl, oxepanyloxy, oxepanylamino, azetidinyl, azetidinyloxy, azetidylamino, pyrrolidinyl, pyrolidinyloxy, pyrrolidinylamino, piperidinyl, piperidinyloxy, piperidinylamino, azepanyl, azepanyloxy, azepanylamino, dioxolanyl, dioxanyl, morpholino, thiomorpholino, thiomorpholino-S,S-dioxide, piperazino, dioxepanyl, dioxepanyloxy, dioxepanylamino, oxazepanyl, oxazepanyloxy, oxazepanylamino, diazepanyl, diazepanyloxy, diazepanylamino, (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5diazaspiro[3.4]oct-2-yl, (3aR, 6aR)-5-methylhexa-hydro-pyrrolo[3,4-b]pyrrol-1(2H)-yl, I-methyl-1,2,3,6-tetrahydropyridin-4-yl, 4-methylpiperizin-1-yl, 4-[2(dimethylamino)-2-oxoethyl]piperazin-1-yl, methyl[2-(4-methylpiperazin-1yl)ethyl]amino, methyl[2-(morpholin-4-yl)ethyl]amino, 1-amino-1,2,3,6tetrahydropyridin-4-yl, 4-[(2S)-2-aminopropanoyl]piperazin-1-yl, all of which may be optionally substituted with OH, $OR^{10}$, oxo, halogen, $R^{10}$, $CH_2OR^{10}$, or $CH_2NR^8R^9$;

$R^8$ and $R^9$ are independently H, —$CD_3$, $C_{1-6}$ alkyl, $C_{1-6}$ haloalkyl, $C_{3-6}$ alkenyl, $C_{3-6}$ haloalkenyl, $C_{3-6}$ alkynyl, $C_3$-$C_6$ haloalkynyl, $C_{3-8}$ cycloalkyl, $C_3$a cycloalkyl-$C_1$-$C_6$ alkyl-, $C_{3-8}$ halocycloalkyl, $C_{3-8}$ halocycloalkyl-$C_1$-$C_6$ alkyl-, $C_{3-8}$ cycloalkenyl, $C_{3-8}$ cycloalkenyl-$C_1$-$C_6$ alkyl-, $C_{3-8}$ halocycloalkenyl, $C_{3-8}$ halocycloalkenyl-$C_1$-$C_6$ alkyl-, $C_1$-$C_6$ acyl, $C_1$-$C_6$acyl-$C_1$-$C_6$ alkyl-, 4-12 membered monocyclic or bicyclic heterocyclyl, 4-12 membered monocyclic or bicyclic heterocyclyl-$C_1$-$C_6$ alkyl-, $C_6$-$C_{12}$ aryl, $C_6$-$C_{12}$ aryl-$C_1$-$C_6$ alkyl-, 5-12 membered heteroaryl, or 5-12 membered heteroaryl-$C_1$-$C_6$ alkyl-; and $R^8$ and $R^9$ may be further independently substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, and the heterocyclic ring is optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, —$CD_3$, $C_{1-6}$ alkyl, $C_{3-6}$ cycloalkyl, $C_{1-6}$ hydroxyalkyl, $C_{1-6}$ alkoxy-$C_{1-6}$ alkyl or $C_{2-6}$ alkyl-$NR^8R^9$;

each $R^{11}$ is independently hydrogen, $C_1$-$C_6$ alkyl, $C_3$-$C_6$ alkenyl, $C_3$-$C_6$ alkynyl, $C_3$-$C_6$ cycloalkyl, $C_6$-$C_{12}$ aryl, 4-12 membered heterocyclyl, or 5-12 membered heteroaryl; or alternatively, two $R^{11}$, taken together with the heteroatom(s) attached thereto, form a 5-8 membered heterocyclyl ring, which is optionally substituted with up to three substituents selected from hydroxyl, $C_{1-6}$ alkoxy, $C_6$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano and halo;

each $R^{13}$ is independently H, —$CD_3$, cyano, —$C_{1-6}$ alkyl, —$C_{1-6}$ haloalkyl, $C_{1-6}$ acyl-$C_{1-6}$ alkyl-, $R^7$—$(CH_2)_pC(=O)$—$C_{1-6}$-alkyl-, carboxy-$C_{1-6}$ alkyl-, $C_{1-6}$ alkyloxycarbonyl-$C_{1-6}$ alkyl-, $R_7$—$(CH_2)_pO$—$C(=O)$—$C_{1-6}$ alkyl-, $R^8R^9N$—$C(=O)C_{1-6}$ alkyl-, $R^7$—$C_{2-6}$ alkyl-$N(R^{10})$—$C(=O)C_{1-6}$ alkyl-, —$C_{2-6}$ hydroxyalkyl, $C_{1-6}$ alkoxy-$C_{2-6}$ alkyl-, $R^7(CH_2)_pOC_{2-6}$ alkyl-, $C_{1-6}$ acyloxy-$C_{2-6}$ alkyl-, $R^7$—$(CH_2)_pC(=O)O$—$C_{2-6}$alkyl-, $C_{1-6}$ alkoxy-$C(=O)O$—$C_{2-6}$ alkyl-, $R^7(CH_2)_pO$—$C(=O)$—$OC_{2-6}$ alkyl-, $R^8R^9N$—$C(=O)OC_{2-6}$ alkyl-, $C_{1-6}$ alkyl-$N(R^{10})C(=O)O$—$C_{1-6}$ alkyl-, $R^7(CH_2)_pN(R^{10})$—$C(=O)O$—$C_{2-6}$ alkyl-, $R^8R^9N$—$C_{2-6}$ alkyl-, $R^7$—$C_{2-6}$ alkyl-, $C_{1-6}$ acylN$(R^{10})$—$C_{2-6}$ alkyl-, $R^7$—$C_{1-6}$ acylN$(R^{10})$—$C_{2-6}$ alkyl-, $R^7$—$(CH_2)_pC(=O)N(R^{10})$—$C_{2-6}$ alkyl-, $R^7$—$C_{1-6}$ alkylC$(=O)N(R^{10})$—$C_{2-6}$ alkyl-, $C_{1-6}$ alkoxy-$C(=O)N(R^{10})$—$C_{2-6}$ alkyl-, $R^7$—$(CH_2)_pOC(=O)N(R^{10})C_{2-6}$ alkyl-, $R^8R^9NC(=O)N(R^{10})C_{2-6}$ alkyl-, $R^{10}SO_2$—$N(R^{10})$—$C_{2-6}$ alkyl-, $R^7$—$SO_2$—$N(R^{10})$—$C_{2-6}$ alkyl-, $C_{1-6}$ alkylS$(O)_x$—$C_{2-6}$ alkyl-, $R^7$—$(CH_2)_pS(O)_xC_{2-6}$ alkyl-, $R^7SO_2C_{2-6}$ alkyl-, $C_{1-6}$ alkylS$(=O)(=NR^{10})$—$C_{2-6}$ alkyl-, $C_{1-6}$ haloalkyl S$(=O)(=N R^{10})$—$C_{2-6}$ alkyl-, $C_{1-6}$ alkylS$(=N R^{10})(=N R^{10})$—$C_{2-6}$ alkyl-, $C_{1-6}$ haloalkyl S$(=N R^{10})(=N R^{10})$—$C_{2-6}$ alkyl-, $R^7S(=O)(=N R^{10})C_{2-6}$ alkyl-, $R^7S(=NR^{13})(=NR^{13})$—$C_{2-6}$ alkyl-, —$C_{3-6}$ alkenyl, —$C_{3-6}$ haloalkenyl, $R^7$—$C_{1-6}$ alkenyl-, $C_{1-6}$ alkoxy-$C_{1-6}$ alkenyl-, —$C_{2-6}$ alkynyl, —$C_{2-6}$ haloalkenyl, $R^7$—$C_{2-6}$ alkynyl-, $C_{2-6}$ alkynyl-, $C_{1-6}$ acyl-, $R^7$—$(CH_2)_pC(=O)$—, $R^7$—$C_{1-6}$ alkyl-C$(=O)$—, $C_{1-6}$ hydroxyalkyl-C$(=O)$—, $C_{1-6}$ alkoxy-$C_{1-6}$ alkyl-C$(=O)$—, $C_{1-6}$ alkylS$(O)_x$—$C_{1-6}$ alkyl-C$(=O)$—, —$C_{1-6}$ alkoxycarbonyl, $R^7$—$(CH_2)_p$oxycarbonyl-, —$C(=O)NR^8R^9$, $R^7$—$(CH_2)_p$—$N(R^{10})$—$C(=O)$—, hydroxyl, —$C_{1-6}$ alkoxy, —$C_{1-6}$ haloalkoxy, $C_{1-6}$ alkyl-N$(R^{10})_pC(=O)$—$C_{1-6}$ alkoxy-, $R^7(CH_2)_pO$—, $R^7(CH_2)_pOC(=O)OC_{2-6}$ alkoxy-, $R^7(CH_2)_pN(R^{10})$—$C(=O)O$—$C_{2-6}$ alkoxy-, $R^8R^9N$—$C(=O)OC_{2-6}$ alkoxy-, $C_{1-6}$ alkoxy-$C(=O)N(R^{10})$—$C_{2-6}$ alkoxy-, $R^7$—$(CH_2)_pOC(=O)N(R^{10})C_{2-6}$ alkoxy-, $R^8R^9NC(=O)N(R^{10})C_{2-6}$ alkoxy-, $C_{1-6}$ alkoxycarbonylC$_{1-6}$ alkoxy-, $R^7(CH_2)_pOC(=O)C_{1-6}$ alkoxy-, —$C_{1-6}$ acyloxy, $R^7$—$(CH_2)_pC(=O)O$—, —$NR^8R^9$, $R^8R^9N$—$C_{2-6}$alkyl-N$(R^{10})$—, $R^7$—$C_{2-6}$alkyl-N$(R^{1i})$—, $C_{1-6}$ acyl-N$(R^{10})$—, $C_{1-6}$ alkoxycarbonyl-N$(R^{10})$—, $R^8R^9$ N—$C(=O)$—$N(R^{10})$—, $R^7$—$C_{1-6}$acyl-N$(R^{10})$—, $C_{1-6}$ alkylS$(O)_2$—$N(R^{10})$—, $R^{10}S(O)_2$—$N(R^{10})$—, $C_{1-6}$ haloalkylS$(O)_2$—$N(R^{10})$—, $R^7SO_2$—$N(R^{10})$—, $C_{1-6}$ alkylS$(O)_x$—, $C_{1-6}$ haloalkylS$(O)_x$—, $R^7$—$(CH_2)_pS(O)_2$, $R^7SO_2$—, $C_{1-6}$ alkyl-S$(=O)(=N R^{10})$—, $C_{1-6}$haloalkyl-S$(=O)(=N R^{10})$—, $C_{6-12}$ aryl, $C_6$-$C_{12}$ aryl-$C_1$-$C_6$alkyl-, 5-12 membered heteroaryl, 5-12 membered heteroaryl-$C_1$-$C_6$alkyl-, $C_{3-8}$ cycloalkyl-, $C_{3-8}$ cycloalkyl-$C_1$-$C_6$ alkyl-, $C_{3-8}$ cycloalkenyl-, $C_{3-8}$ cycloalkenyl-$C_1$-$C_6$alkyl-, 4-12 membered monocyclic or bicyclic heterocyclyl-, or 4-12 membered monocyclic or bicyclic heterocyclyl-$C_1$-$C_6$ alkyl-; or alternatively, two $R^4$, tow $R^{13}$, or $R^{13}$ and $R^4$, taken together with atoms attached thereto, form a ring of 5-7 members, which may be aromatic or partially saturated, and which may contain up to two heteroatoms chosen from N, O and S, and the 5-7 member ring is optionally further substituted by is selected from the group consisting of =O (oxo), =S, =$NR^{13}$, $(=O)_2$, $(O)(NR^{13})$, $R^4$, and $R^{13}$;

m is 0, 1, 2, or 3;

p=0, 1, 2, 3, or 4:

q=2, 3, or 4; and x=0, 1, or 2.

In some embodiments of formulae (I) or (IA), $R^3$ is —$N(R^{10})C_{2-6}$ alkyl-$NR^{10}R^{10}$.

In one embodiment of formulae (I) or (IA), $R^3$ is —$N(CH_3)$—$CH_2$—$CH_2$—$N(CH_3)_2$.

In one embodiment of formulae (I) or (IA), each $R^{10}$ is independently H, —$CD_3$, or $C_{1-6}$ alkyl.

In one embodiment of formulae (I) or (IA), $R^2$ is —$OCF_3$, —$OCHF_2$, —$OCF_2CF_3$, —$OCH_2CHF_2$, —$OCH_2CF_3$, methoxy, ethoxy, or isopropoxy.

In one embodiment of formulae (I) or (IA), A is $A^1$ and $X^1$ is N.

In one embodiment of formulae (I) or (IA), A is $A^2$ and $X^1$ is N.

In one embodiment of formulae (I) or (IA), A is $A^3$ and $X^1$ is N.

In one embodiment of formulae (I) or (IA), A is $A^{4a}$ and $X^9$ is C.

In one embodiment of formulae (I) or (IA), A is $A^{4b}$ and $X^8$ is C.

In one embodiment of formulae (I) or (IA), A is $A^5$ and $X^1$ is C or CH.

In another embodiment of formula (I) or (IA) $R^{5a}$, $R^{6e}$ and $R^{6z}$ are each H.

In one embodiment, the present invention relates to a compound of the formula (IIA$^1$)

(IIA¹)

or a stereoisomer or a pharmaceutically acceptable salt, solvate, ester, or prodrug thereof;
wherein:
A is

A¹ each of a, b, c, d, e, f, g, h, i and j are independently either (formal) double bonds or (formal) single bonds, and none of $X^1$, $X^2$, $X^3$, $X^4$, $X^5$, $X^6$, $X^7$, $X^8$, and $X^9$ has two (formal) double bonds attached thereto:

each of $X^1$, $X^2$, $X^3$, $X^6$, $X^7$, $X^8$, and $X^9$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$;

$X^1$ is C, CH or N;
$X^2$ is N, NR$^{13}$, C(R$^{10}$)$_2$, S(O)$_x$, C(O), or CR$^4$;
$X^3$ is N, NR$^{13}$, C(R$^{10}$)$_2$, C(O), S(O)$_x$, or CR$^4$;
$X^4$ and $X^5$ are independently C or N, with the proviso that $X^4$ and $X^5$ are not both N; and if $X^1$, $X^4$ and $X^5$ are all C, then one of $X^2$ and $X^3$ is O, S or NR$^{10}$;
$X^6$, $X^7$, $X^8$, and $X^9$ are independently CR$^4$ or N, with the proviso that at most two of $X^6$, $X^7$, $X^8$, and $X^9$ are N; and
R$^1$, R$^2$, R$^3$, R$^4$, R$^{10}$, and R$^{13}$ are as defined above for formulae (I) or (IA).

In one embodiment of formula (IIA¹), X³ is C—NR⁸R⁹ or C—NR¹³R¹³. In another embodiment, X³ is C—NHR⁹ or C—NHR¹³.

In one embodiment of formula (IIA¹), A¹ is selected from

A¹ᵃ

In one embodiment of formula (IIA¹), A¹ is selected from

A¹ᵇ

A¹ᶜ or

A¹ᵈ

In one embodiment of formula (IIA¹), A¹ is selected from the group consisting of:

-continued
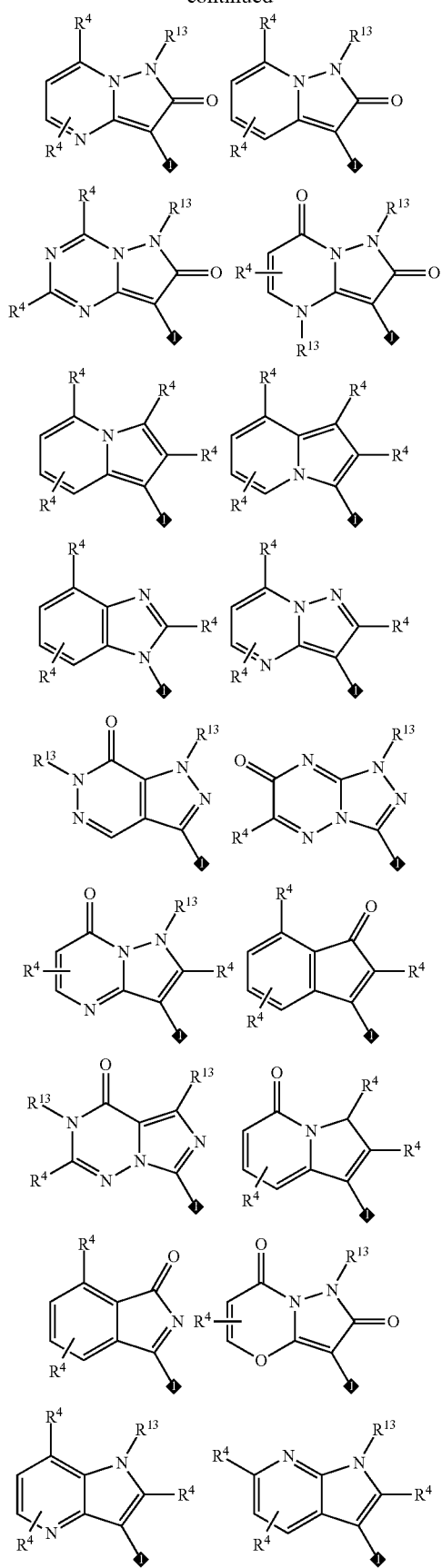
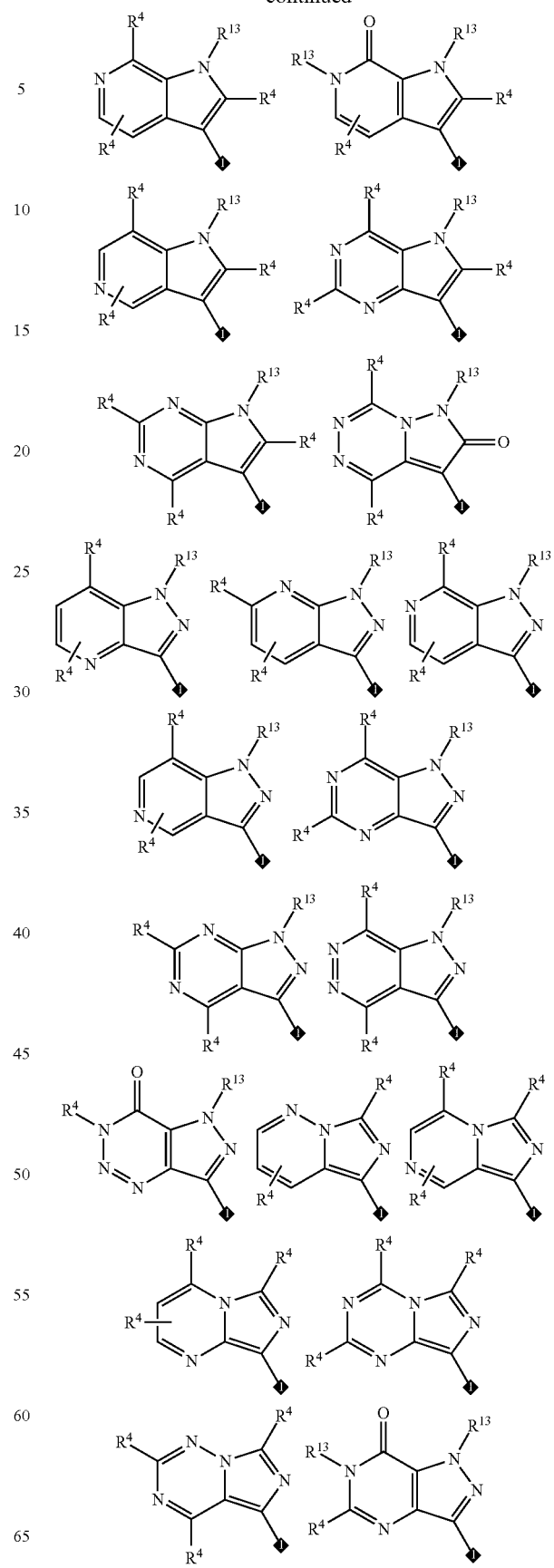

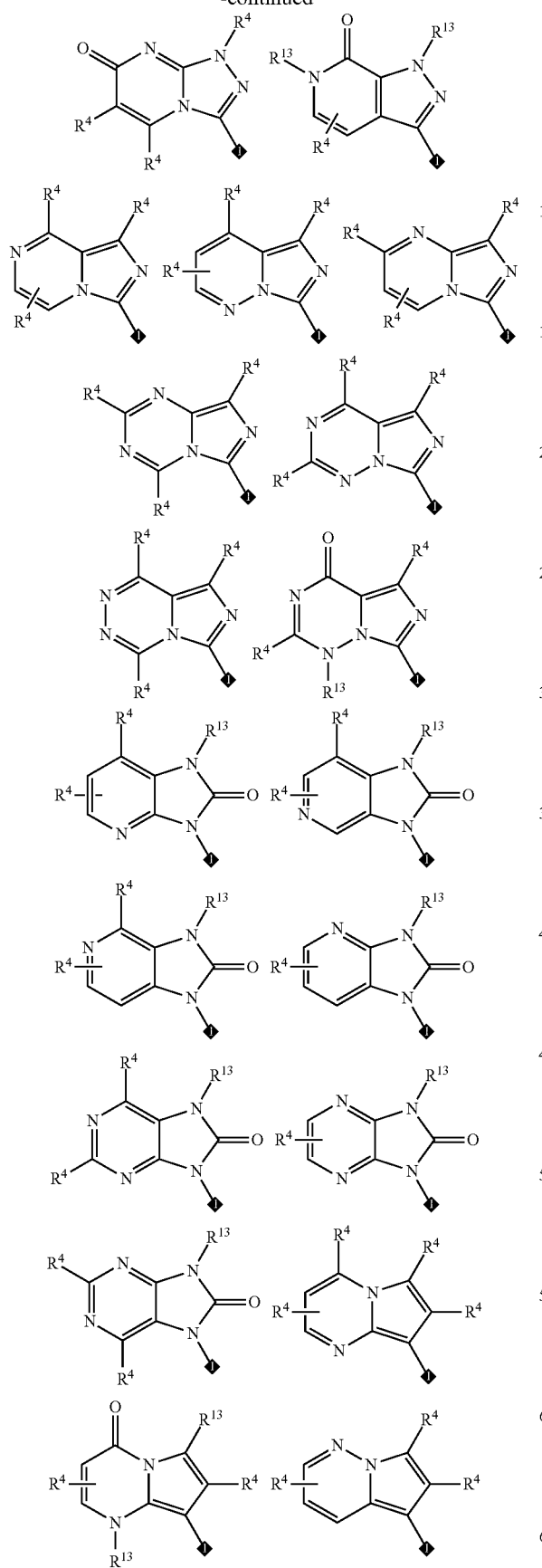
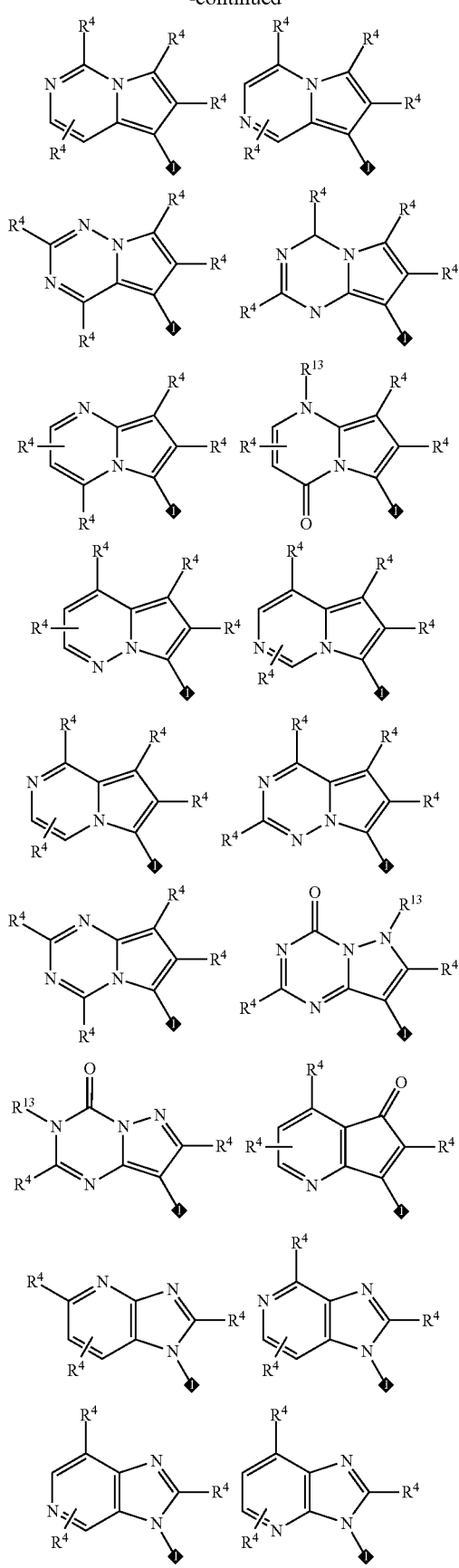

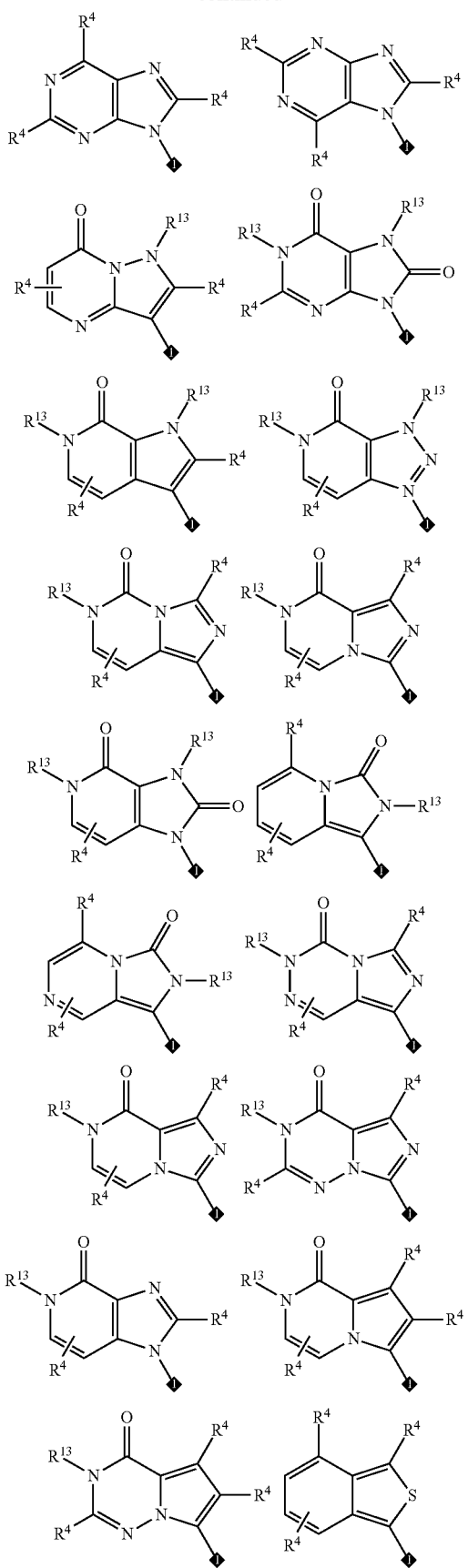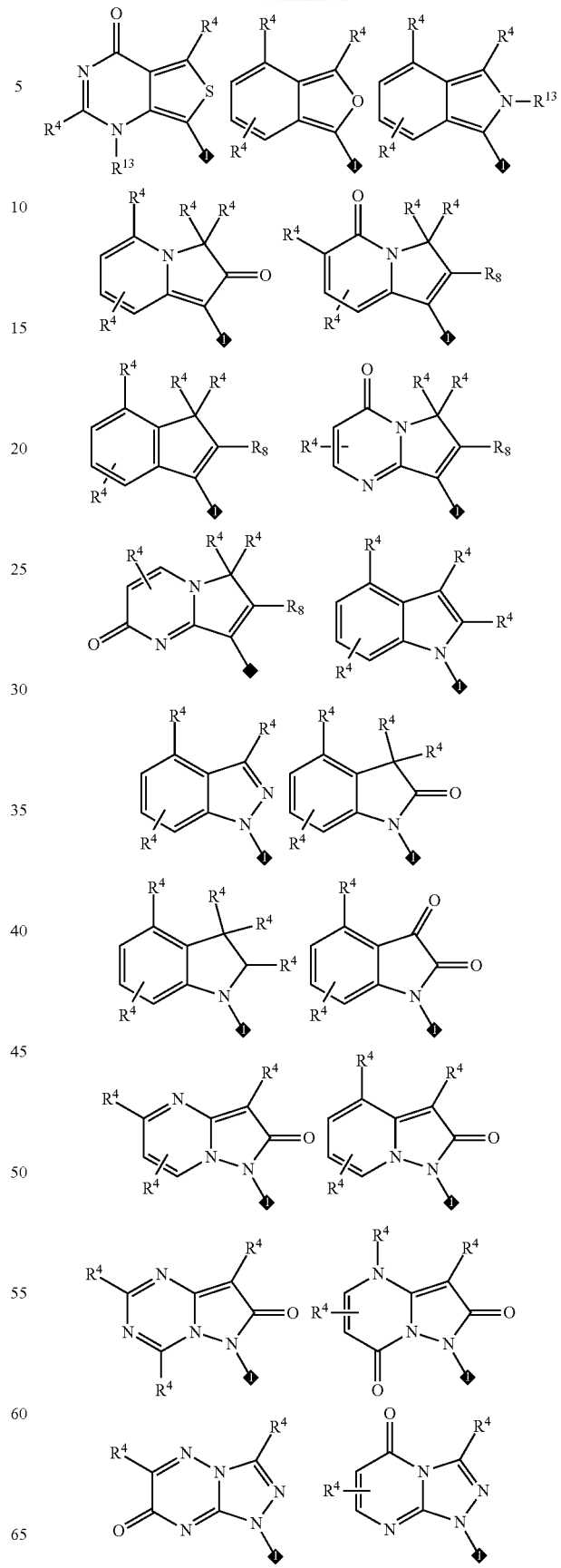

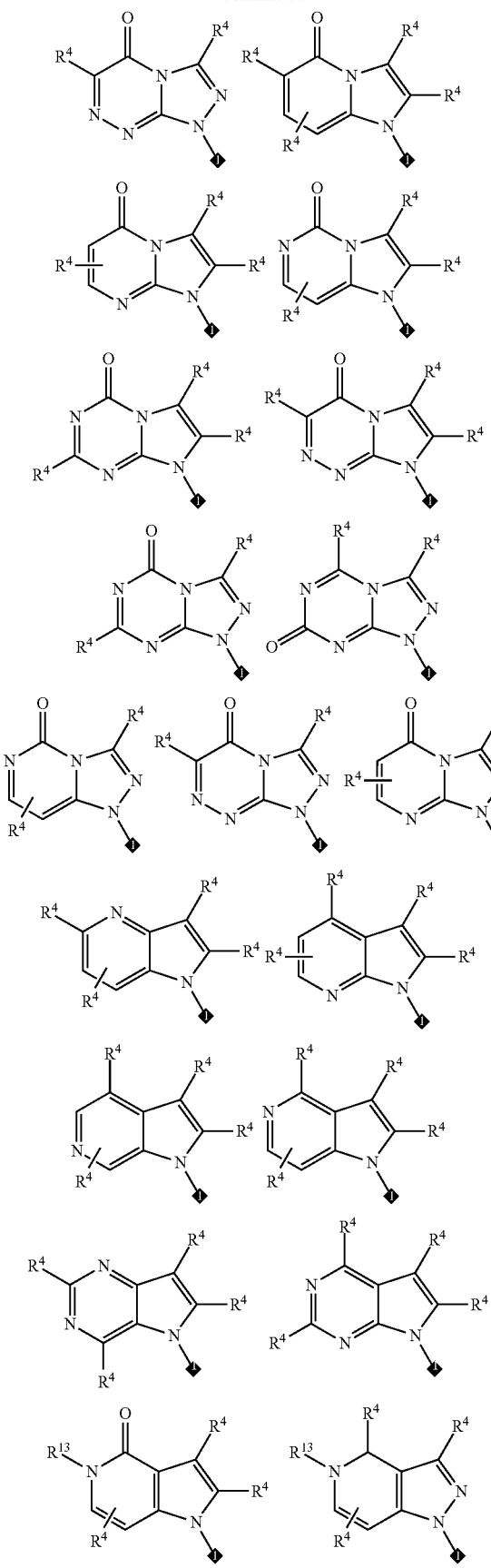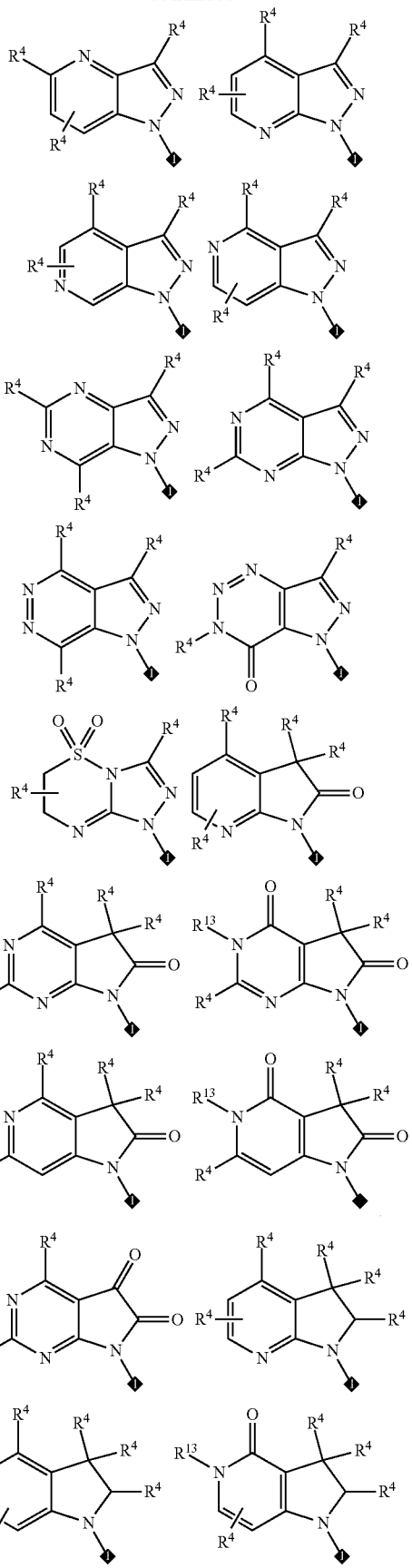

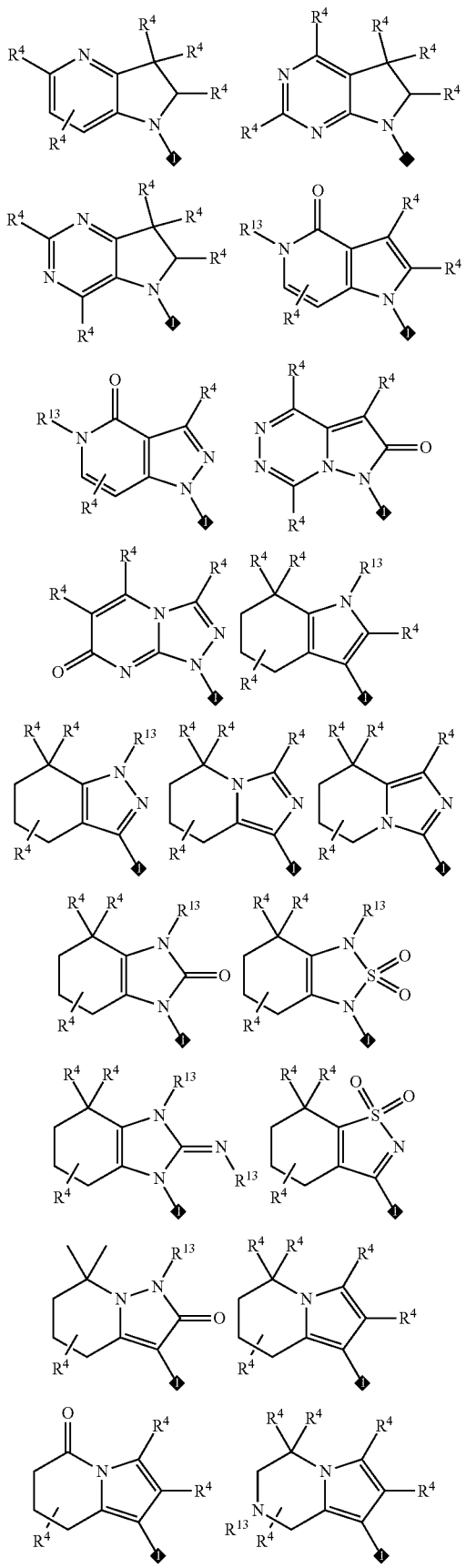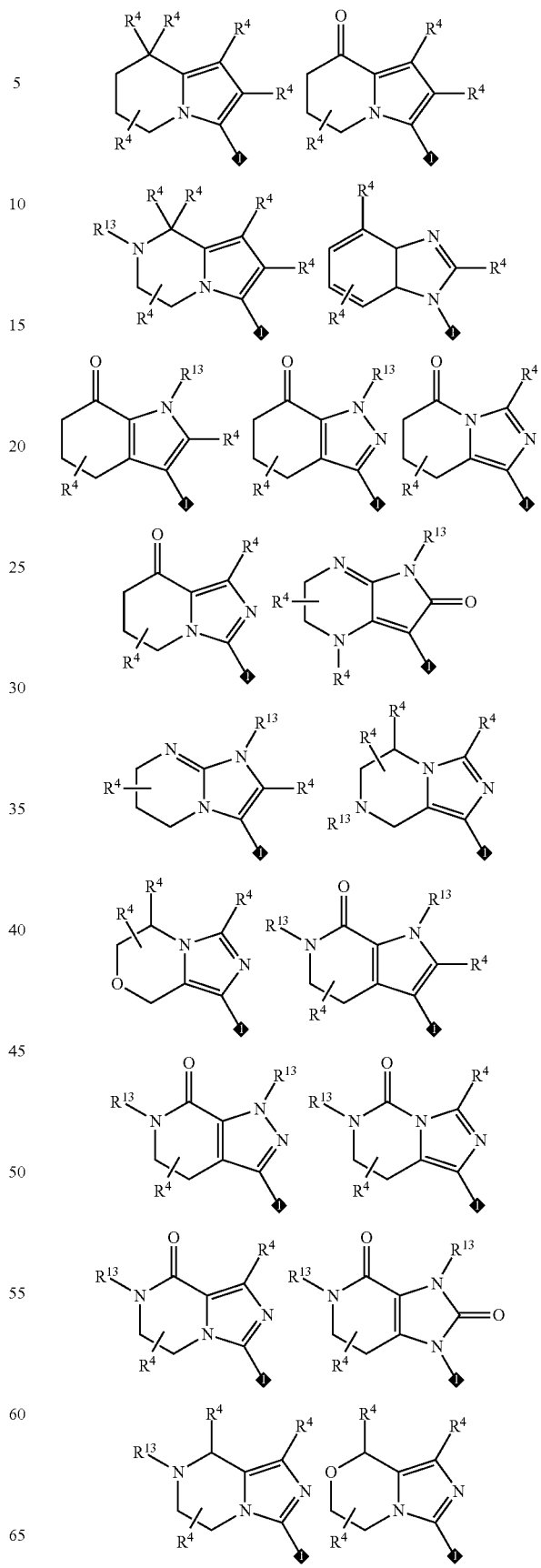

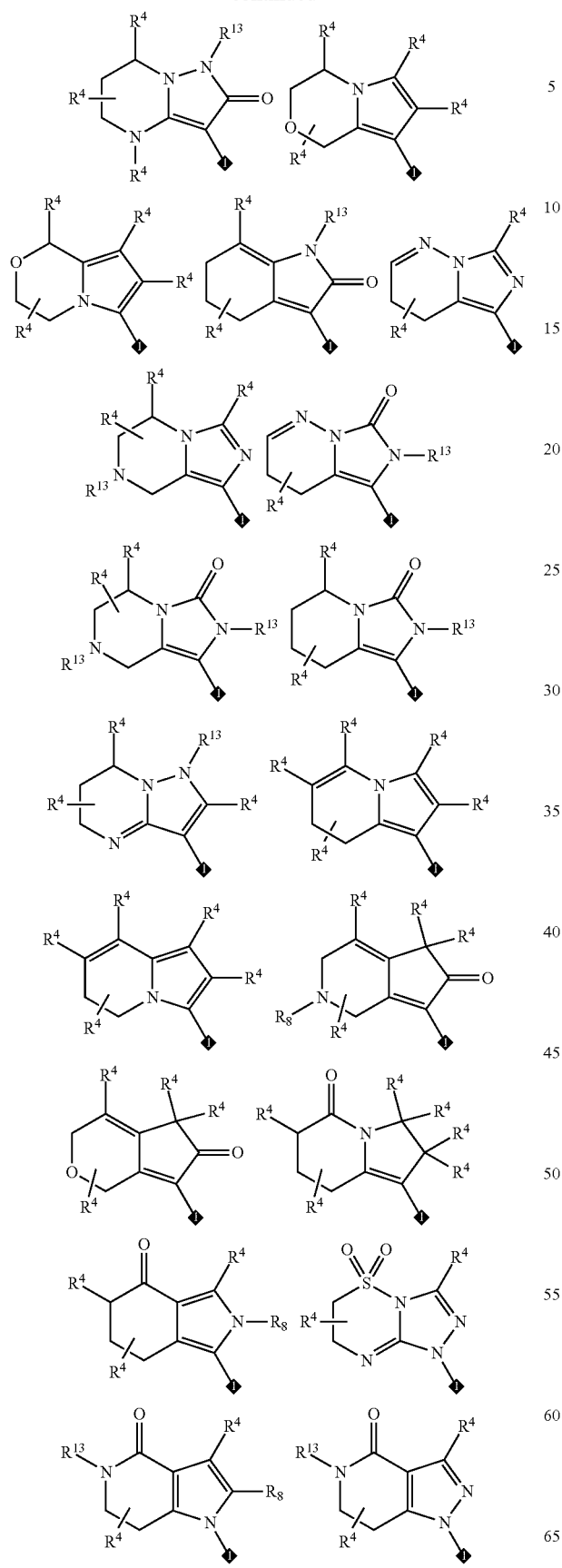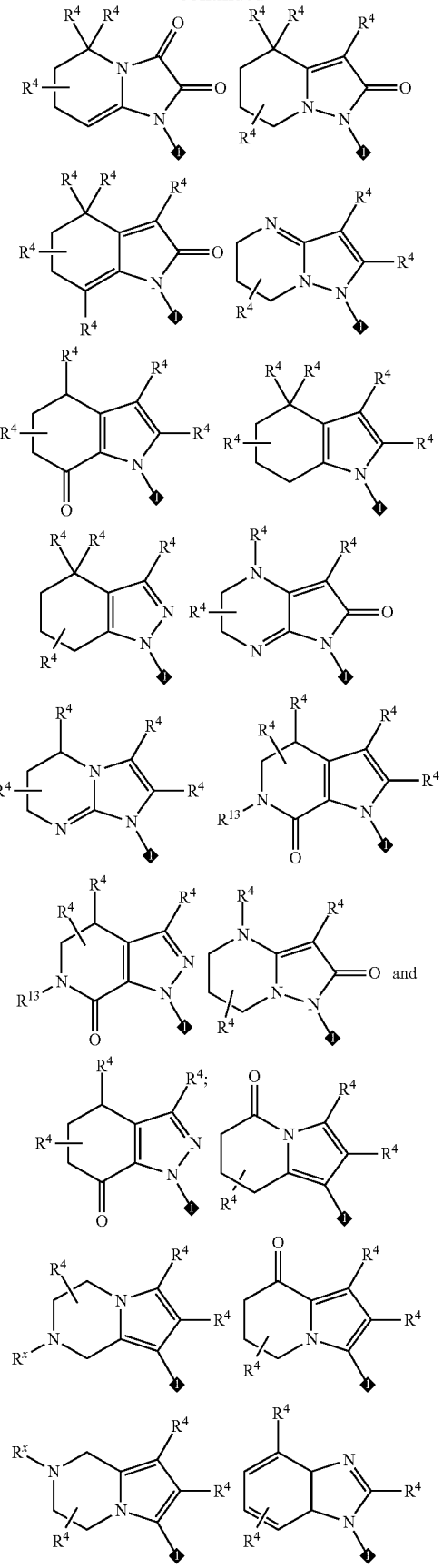

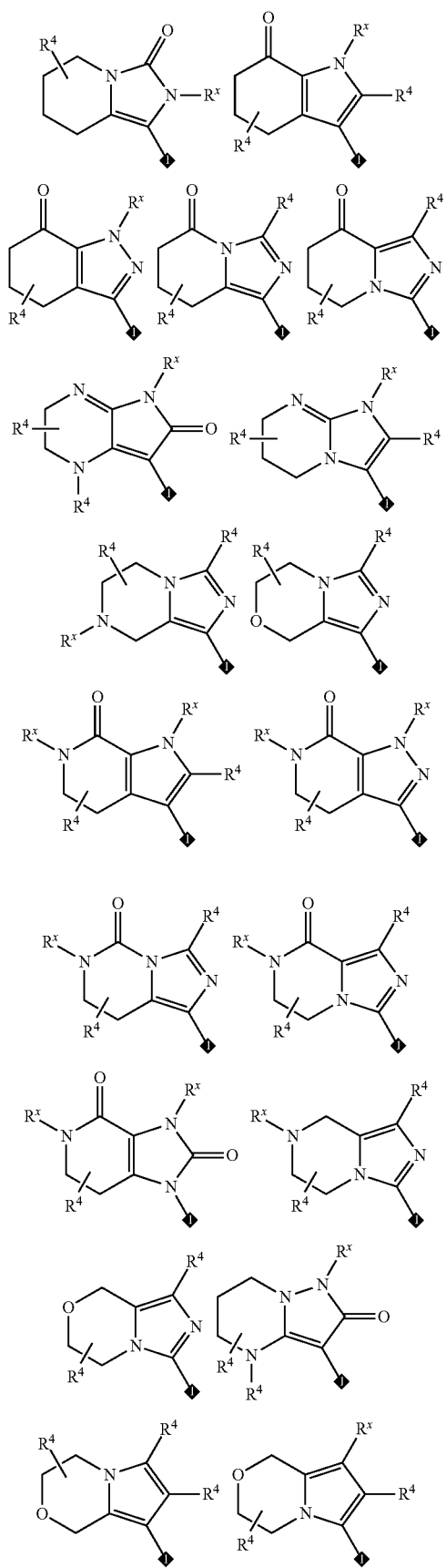
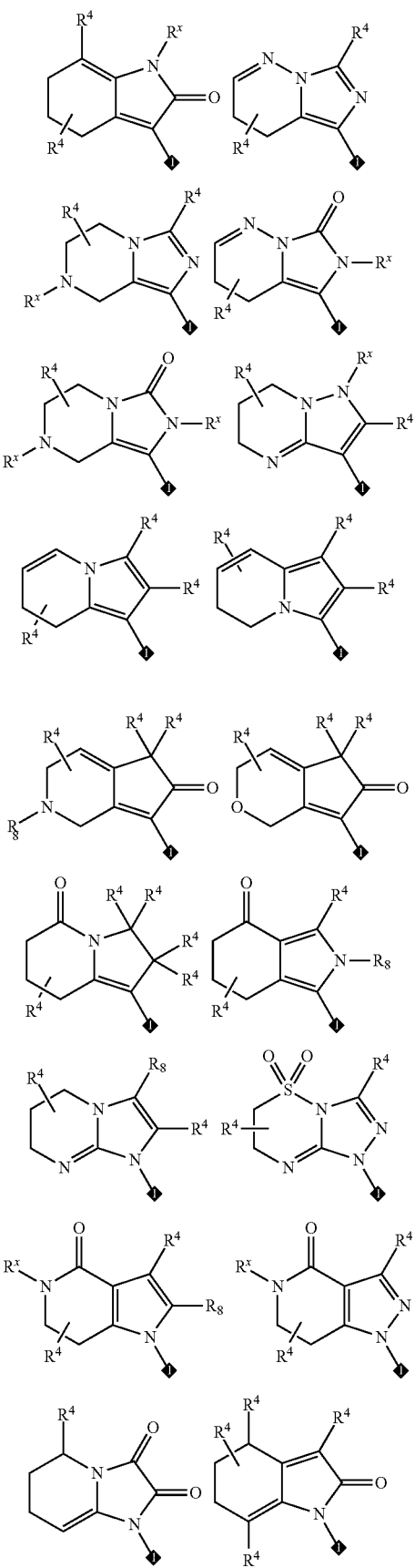

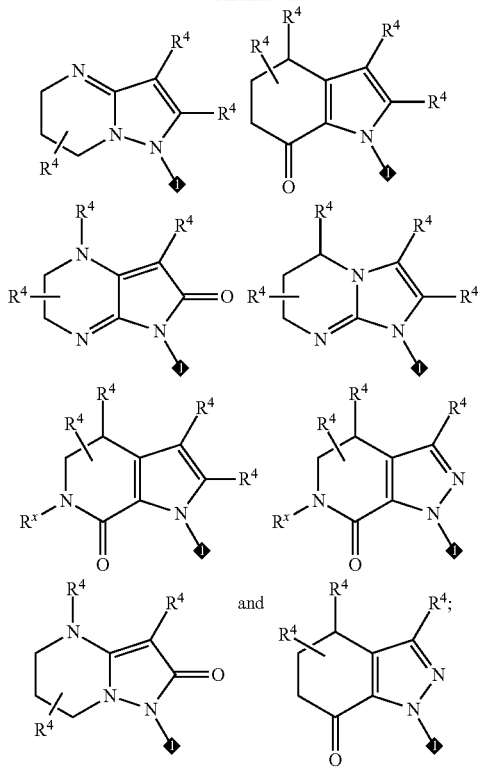
wherein $R^x$, $R^4$, and $R^{13}$ have the same definitions as described above for formula (I) or formula (IA).
In one embodiment of formula (IIA$^1$), A$^1$ is selected from the group consisting of:
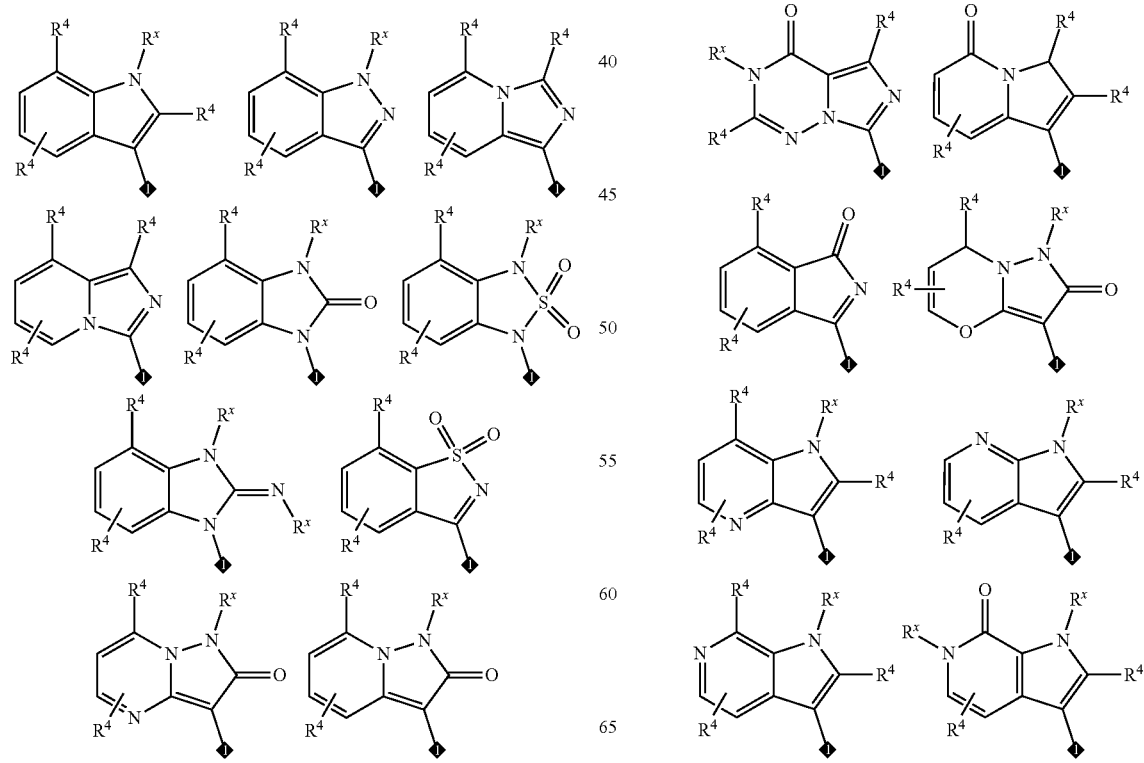

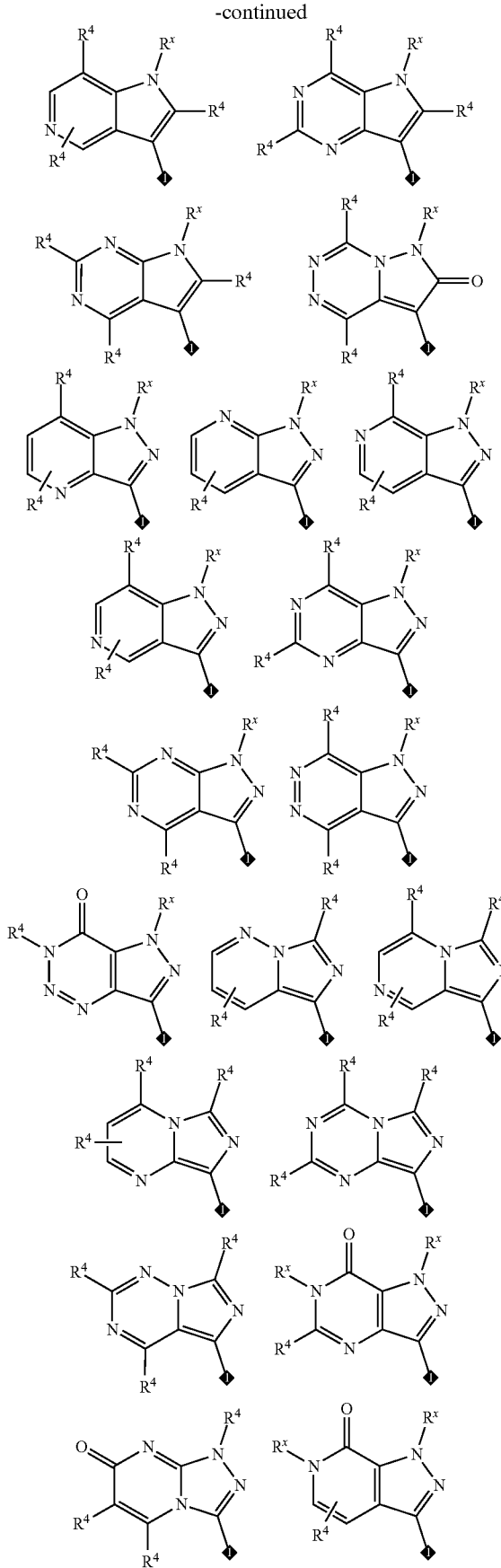
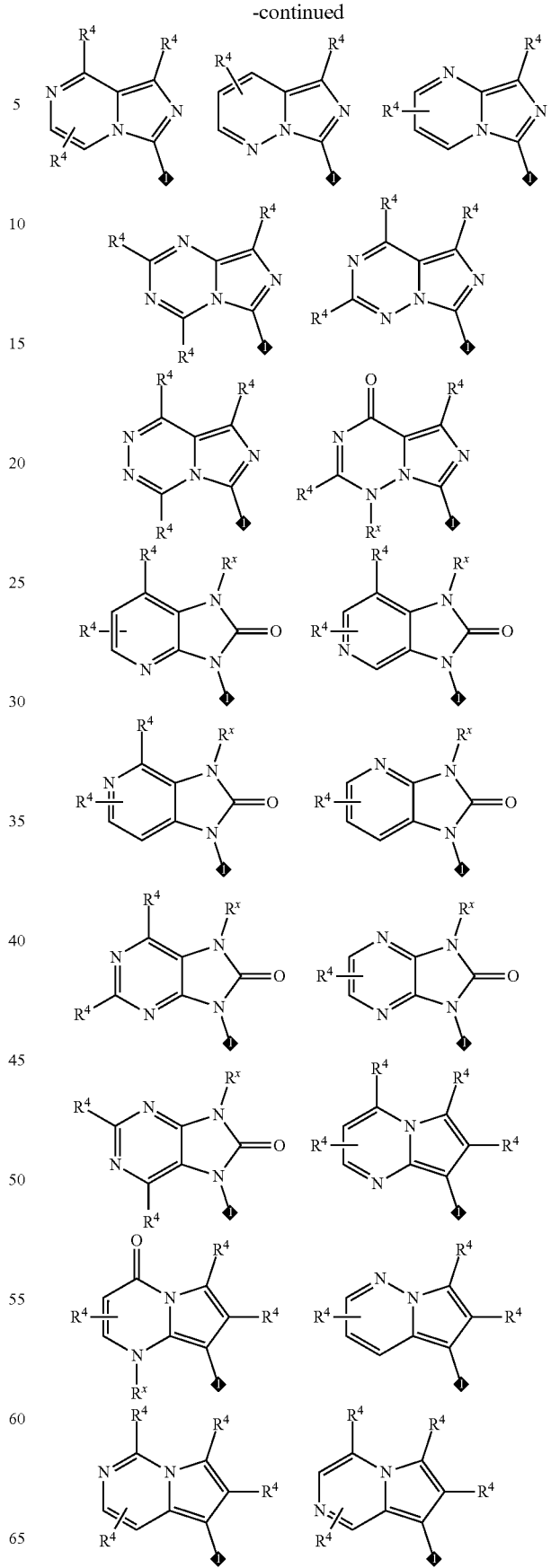

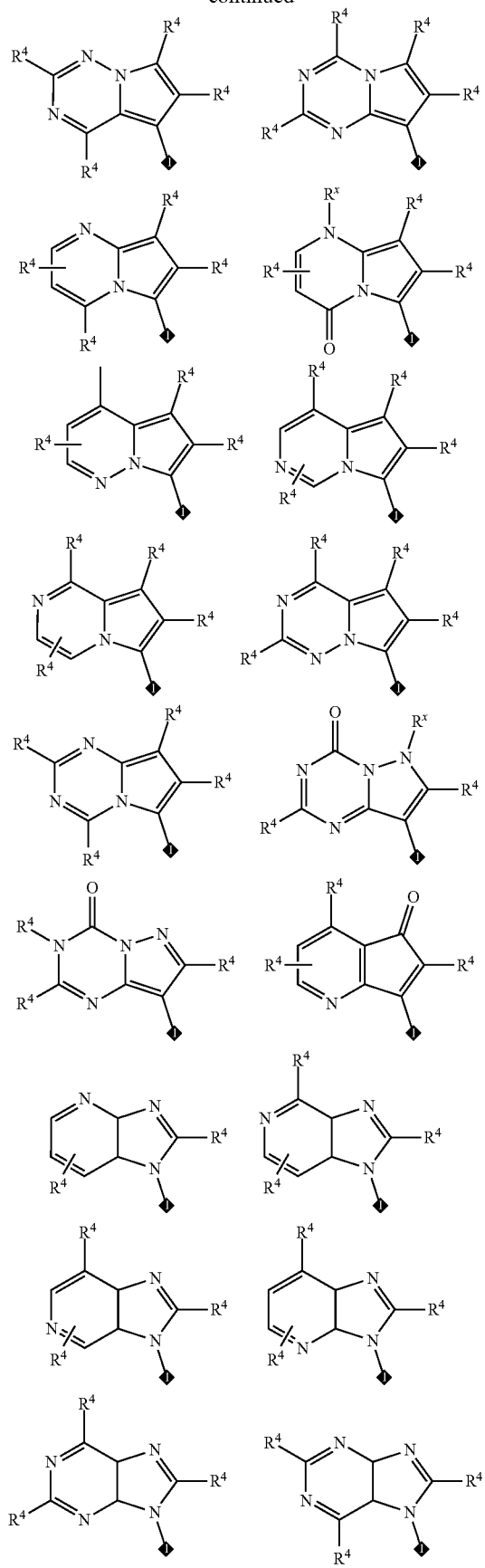
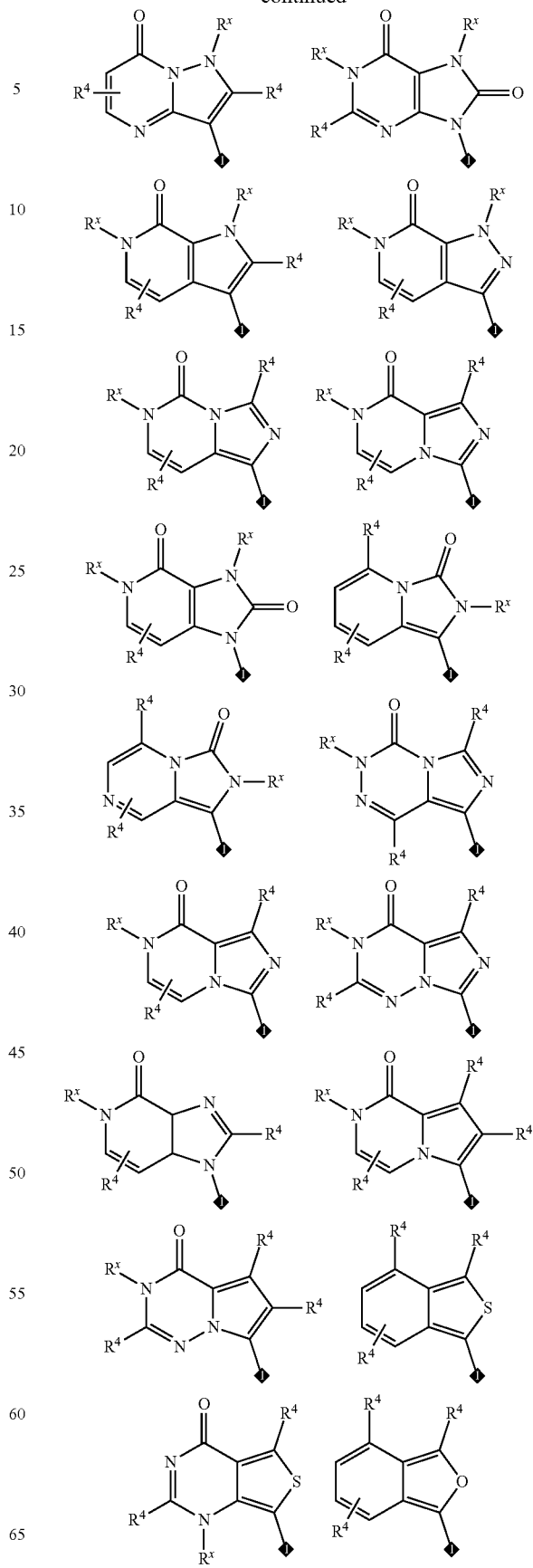

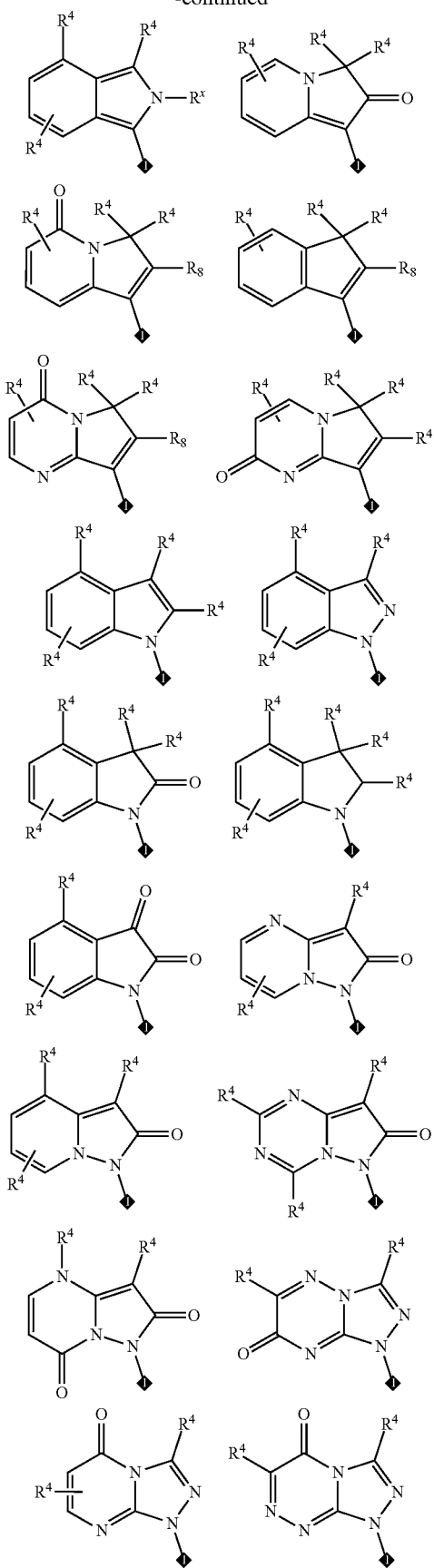
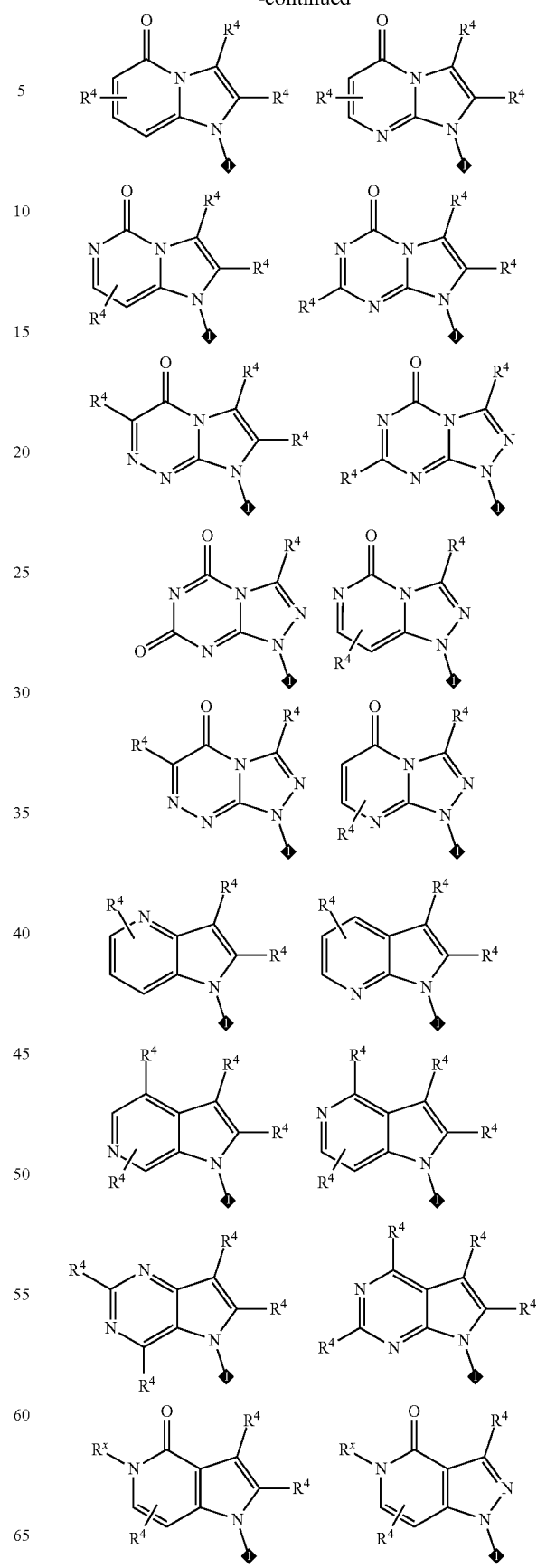

-continued
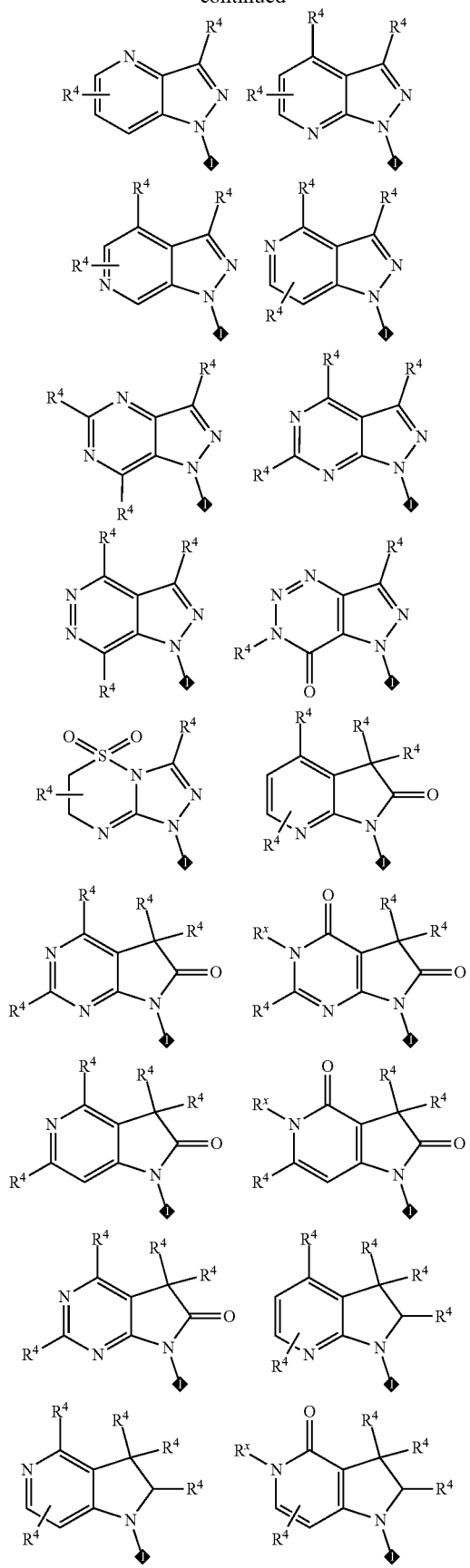
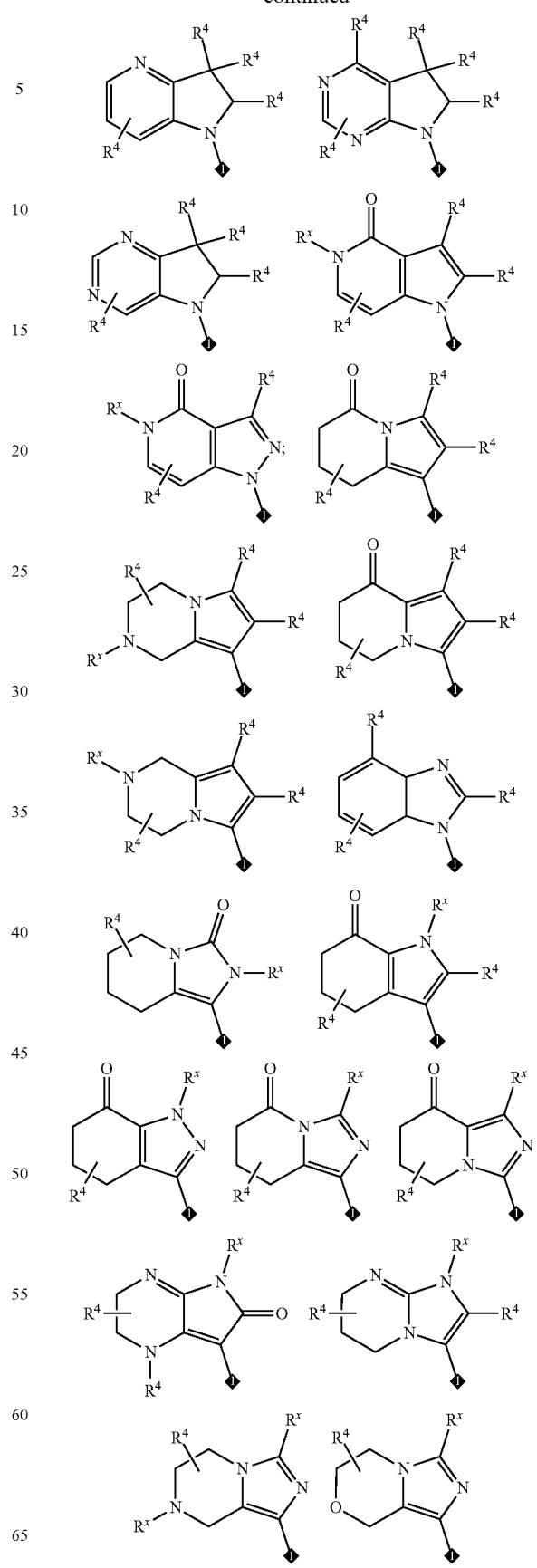

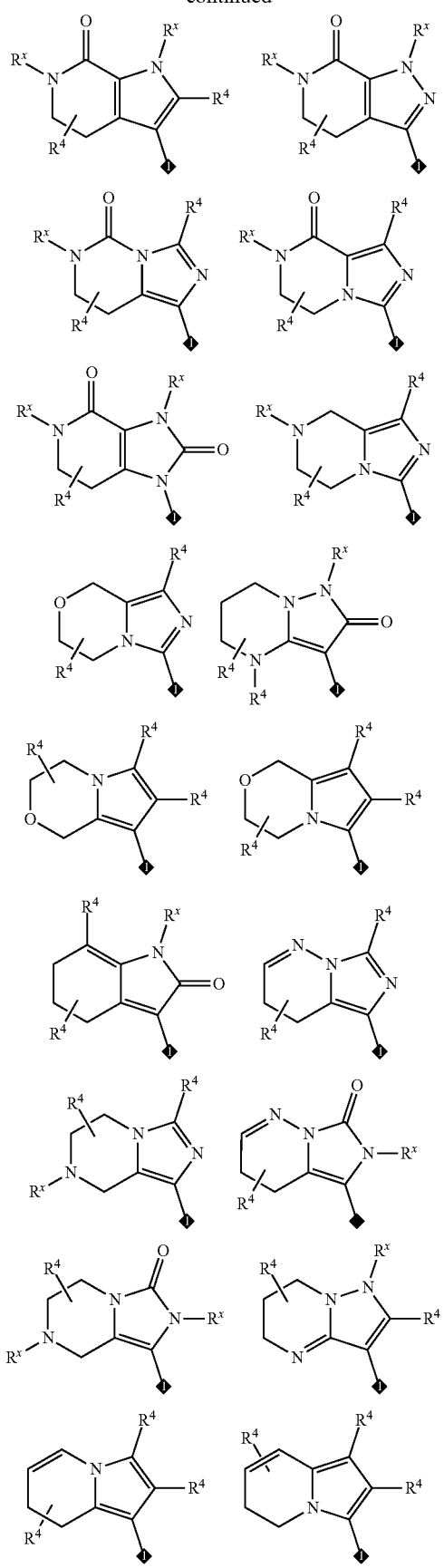
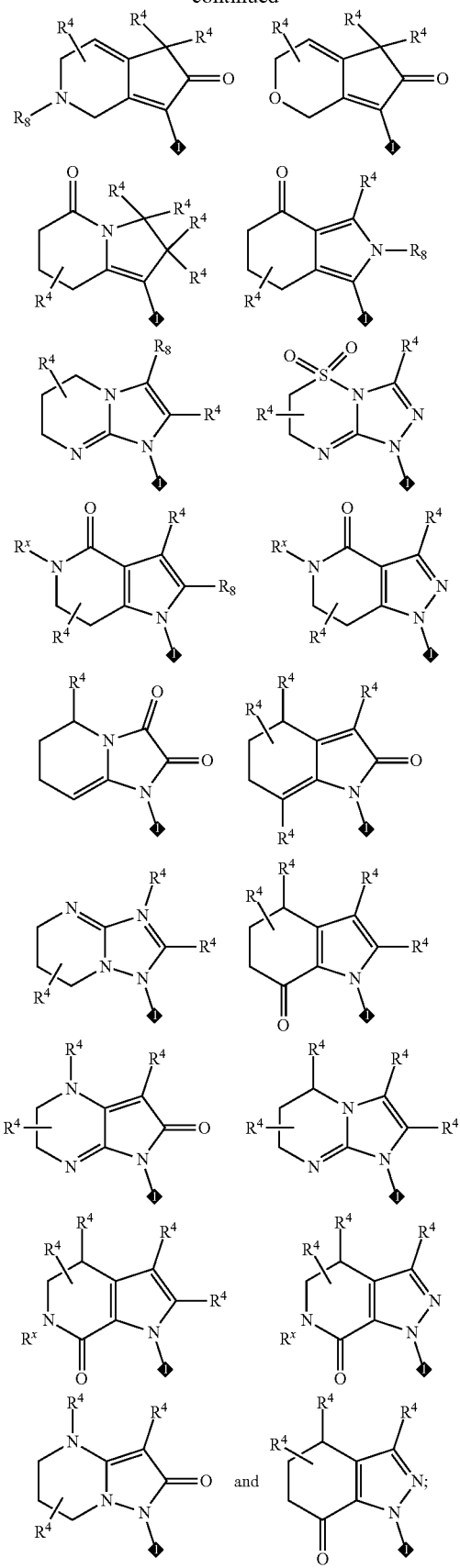

wherein $R^x$ is $R^{13}$; and $R^4$ and $R^{13}$ have the same definition as described for formula (I) or formula (IA).
In one embodiment of formula (IIA$^1$), A$^1$ is selected from the group consisting of:
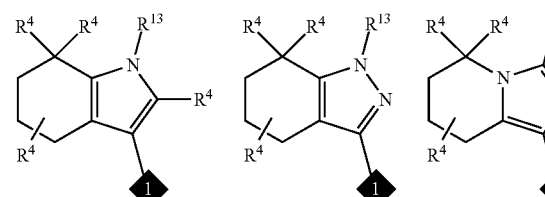
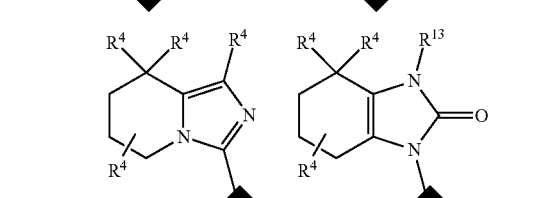
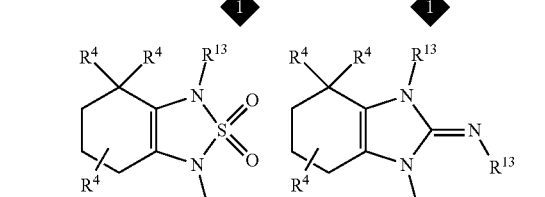
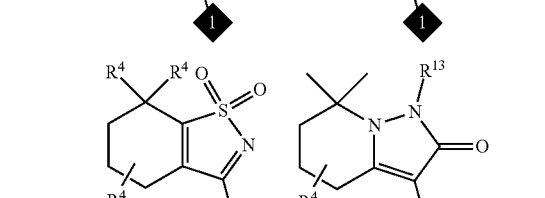
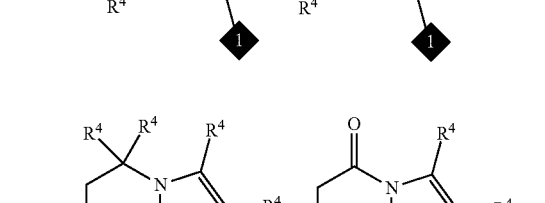
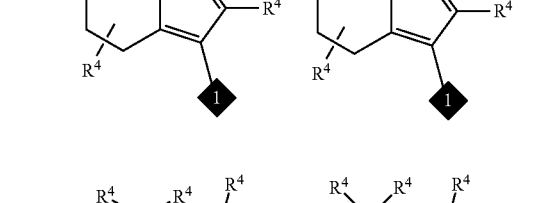
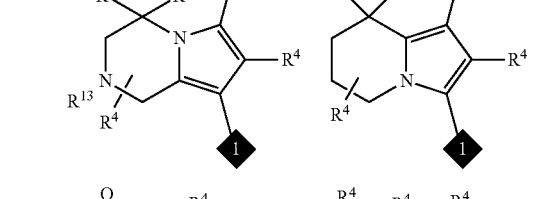
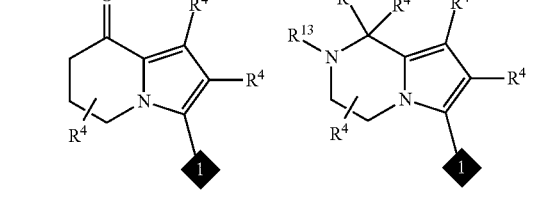
-continued
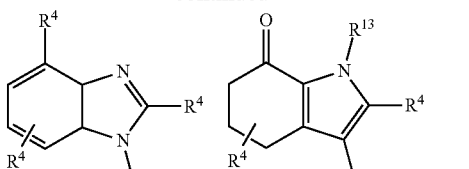
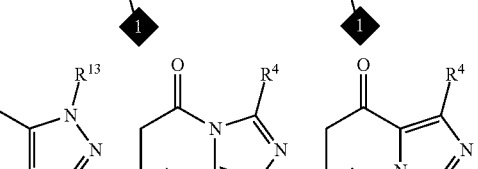
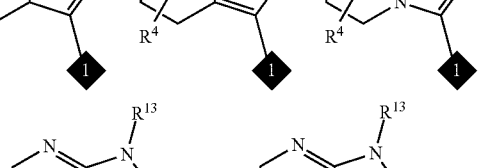
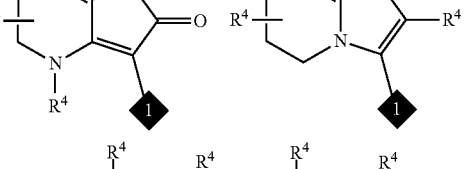
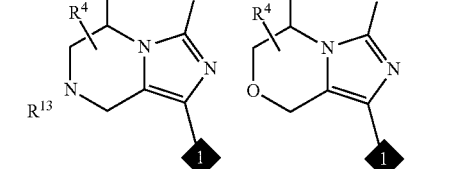
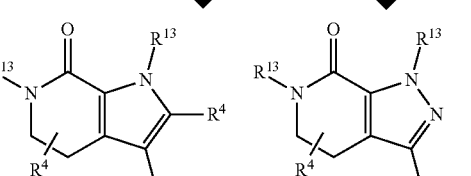
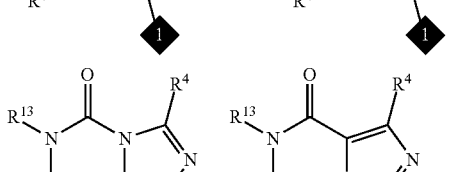
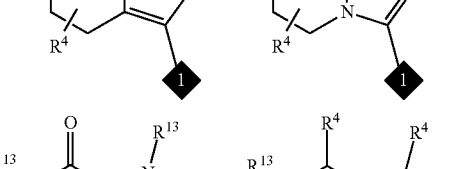
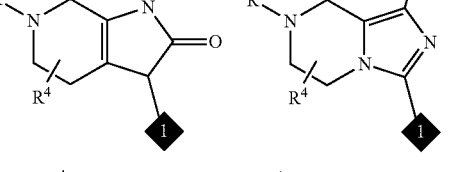
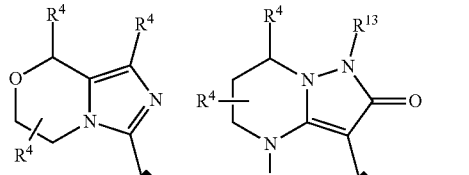

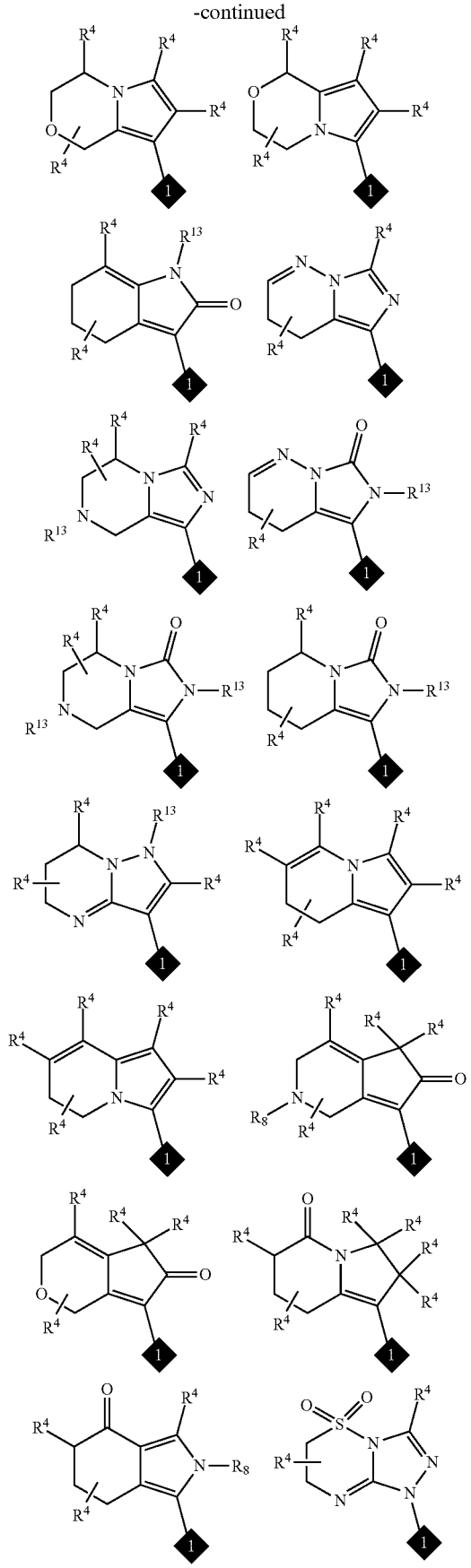
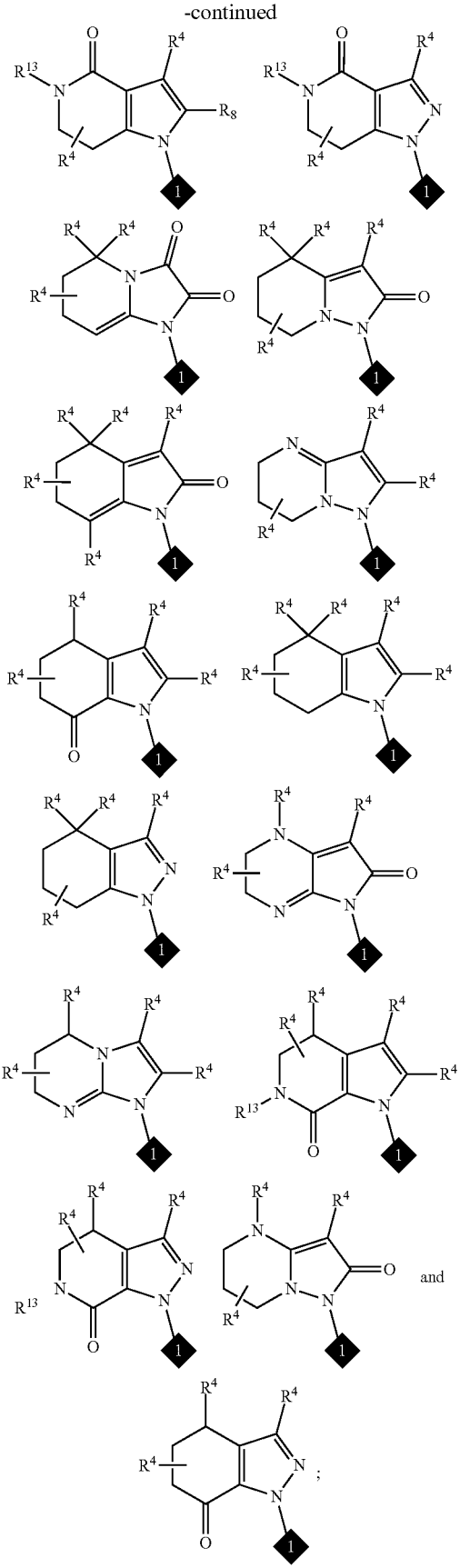

wherein $R^x$, $R^4$, and $R^{13}$ have the same definitions as described above for formula (I) or formula (IA).
In one embodiment of formula (IIA$^1$), $A^1$ is selected from the group consisting of:
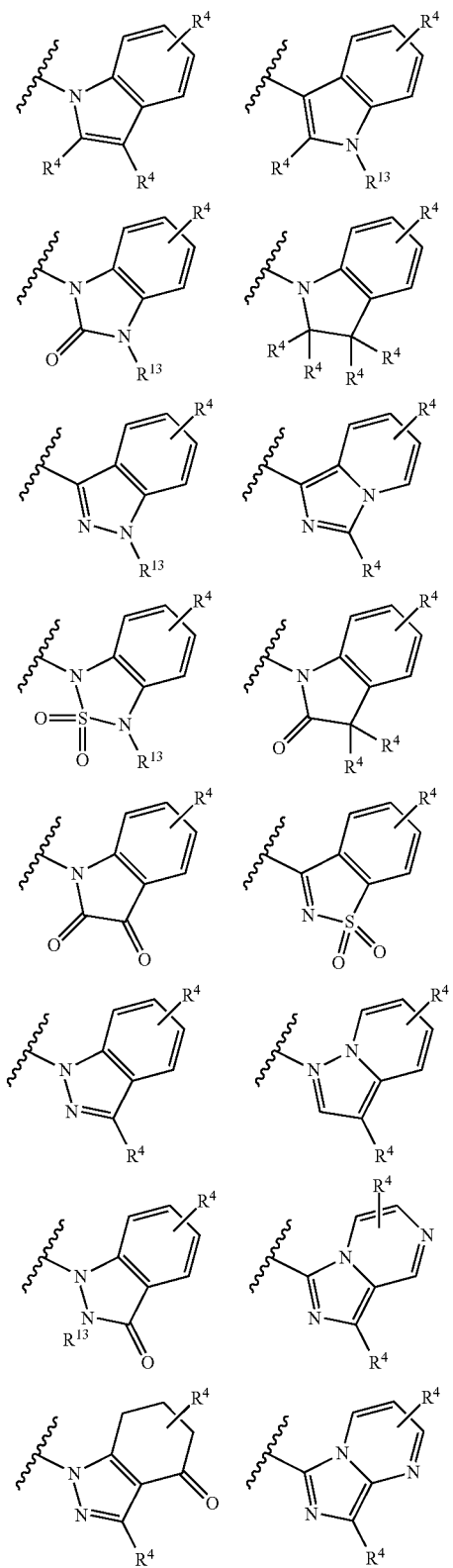
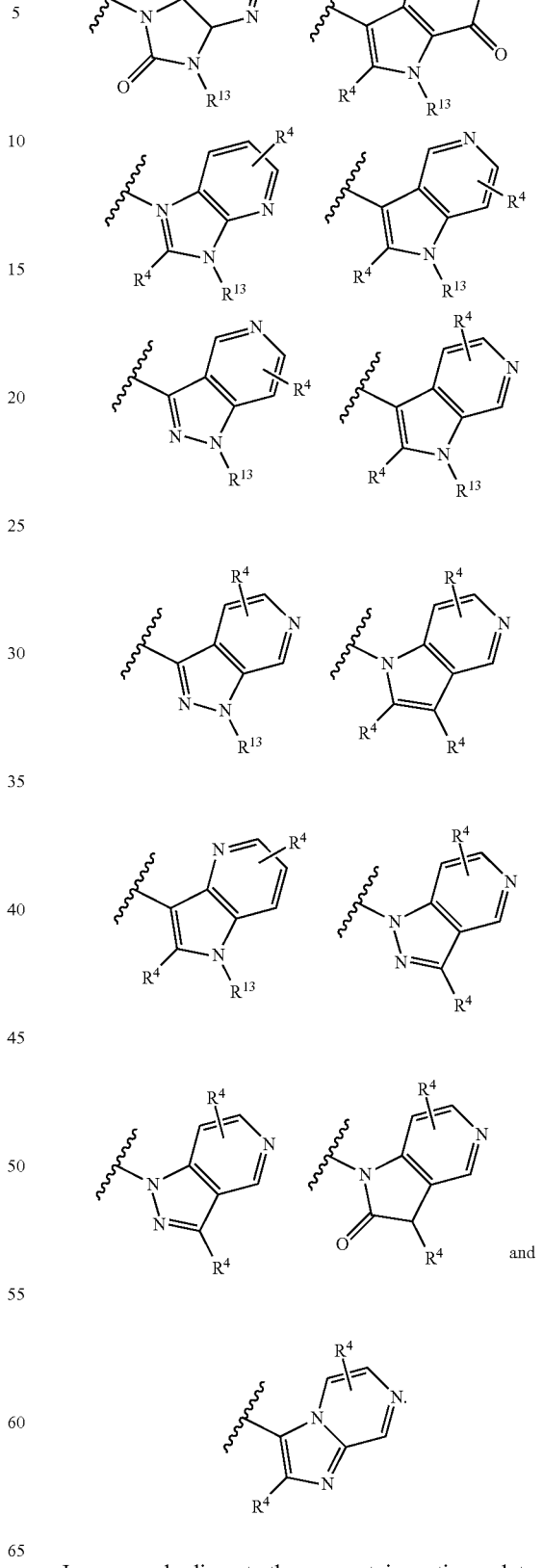
and
In one embodiment, the present invention relates to a compound of the formula (IIA$^2$)

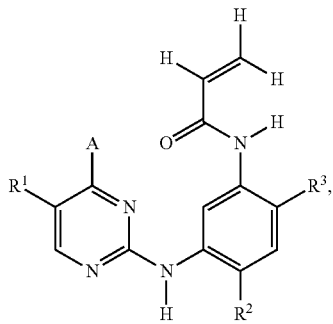

(IIA²)

or a stereoisomer or a pharmaceutically acceptable salt, solvate, ester, or prodrug thereof;
wherein:
A is

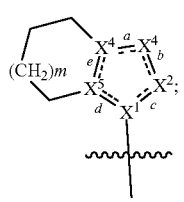

A² each of a, b, c, d, and e are independently either (formal) double bonds or (formal) single bonds, and none of $X^1$, $X^2$, $X^3$, $X^4$, and $X^1$ has two (formal) double bonds attached thereto;

each of $X^1$, $X^2$, $X^3$, $X^4$, and $X^5$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$;

$X^1$ is C, CH or N;
$X^2$ is N, NR$^{13}$, C(R$^4$)$_2$, S(O), C(O), or CR$^4$;
$X^1$ is N, NR$^{13}$, C(R$^4$)$_2$, C(O), S(O)$_x$, or CR$^4$;
wherein if $X^1$ is C, then one of $X^2$ or $X^3$ is O, S or NR$^{1i}$;
$X^4$ and $X^5$ are each independently C or N;

the carbocyclyl moiety containing $X^4$ and $X^5$ is optionally substituted with one, two, or three groups independently selected from C$_{1-6}$ alkyl, hydroxyl, halo and cyano; and up to two of the ring carbons of the carbocyclyl moiety are optionally replaced by C=O, C(NR$^4$)$_2$, NR$^{1i}$, O or S(O)$_x$; and R$^1$, R$^2$, R$^3$, R$^4$, R$^{10}$, and R$^{13}$ are the same as defined for formula (I) or (IA).

In one embodiment of formula (IIA), A² is selected from the group consisting of:

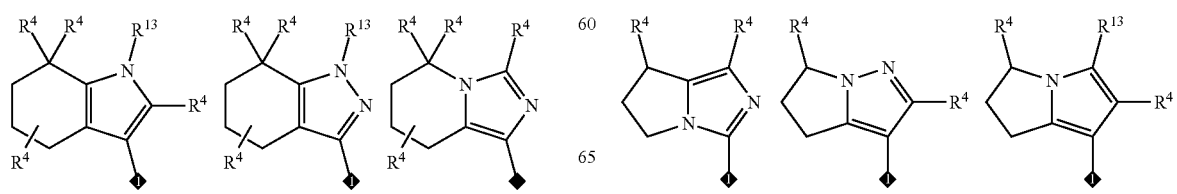

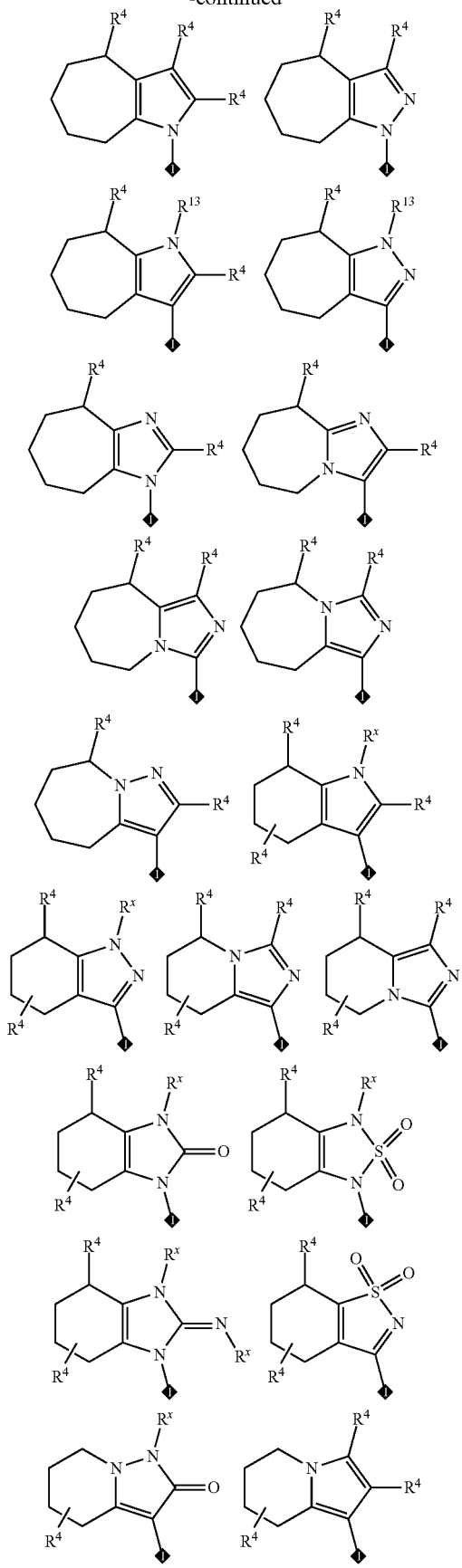
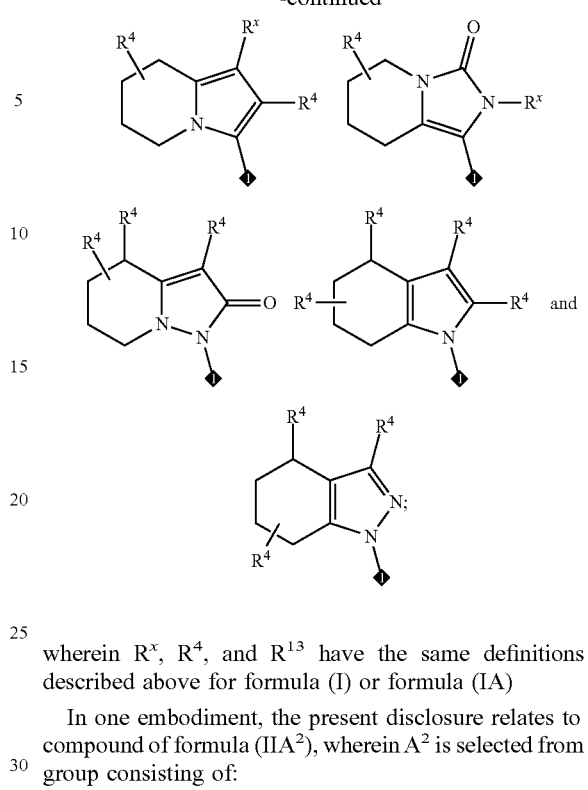
wherein $R^x$, $R^4$, and $R^{13}$ have the same definitions as described above for formula (I) or formula (IA)
In one embodiment, the present disclosure relates to the compound of formula (IIA²), wherein A² is selected from the group consisting of:
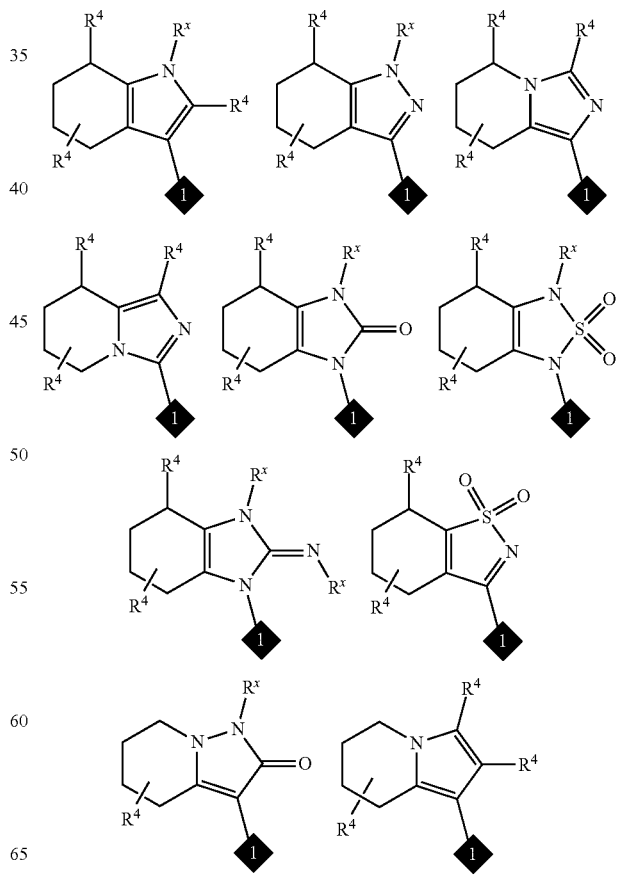

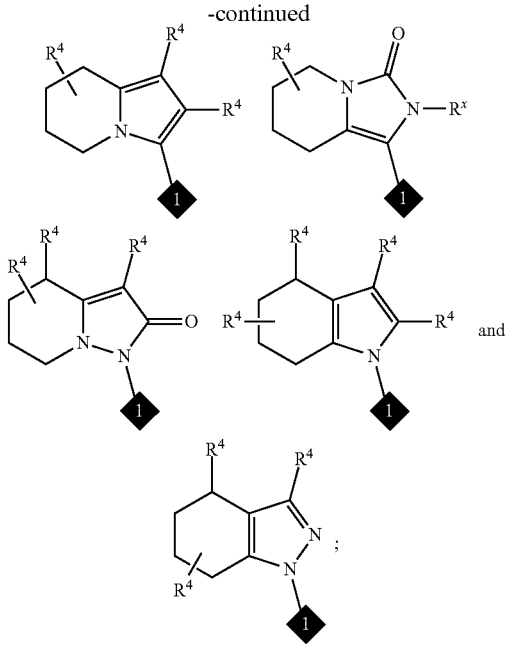

wherein $R^x$ is $R^{13}$; and $R^4$ and $R^{13}$ have the same definition as described for formula (I) or formula (IA).

In one embodiment of formula (IIA$^2$), A$^2$ is selected from the group consisting of:

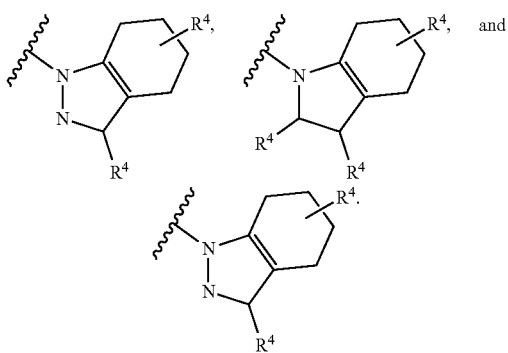

In one embodiment, the present invention relates to a compound of the formula (IIA$^3$)

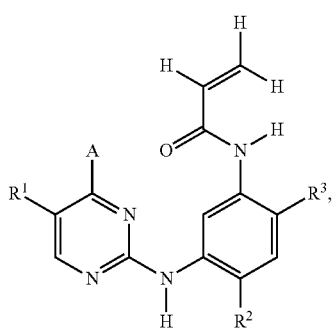

(IIA$^3$)

or a stereoisomer or a pharmaceutically acceptable salt, solvate, ester, or prodrug thereof;

wherein:
A is

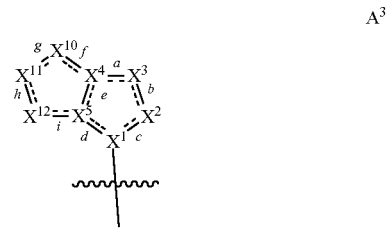

A$^3$ each of a, b, c, d, e, f, g, h, and i are independently either (formal) double bonds or (formal) single bonds, and none of $X^1$, $X^2$, $X^3$, $X^4$, $X^5$, $X^{10}$, $X^{11}$, and $X^{12}$ has two (formal) double bonds attached thereto;

each of $X^1$, $X^2$, $X^3$, $X^{10}$, $X^{11}$, and $X^{12}$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$;

wherein no more than four, and no less than two, of $X^1$, $X^2$, $X^3$, $X^4$, and $X^5$ can be C or CR$^4$;

$X^1$ is C, CH or N;
$X^2$ is N, NR$^{13}$, C(R$^4$)$_2$, S(O)$_x$, C(O), or CR$^4$;
$X^3$ is N, NR$^{13}$, C(R$^{10}$)$_2$, C(O), S(O)$_x$, or CR$^4$;

wherein if $X^1$, $X^4$ and $X^5$ are all C, then one of $X^2$ and $X^3$ is O, NR$^{10}$ or S;

wherein if $X^1$ is N, $X^2$ is C=O, C=NR$^{10}$ or C=S, and $X^4$ and $X^5$ are both C, then $X^3$ is C(R$^4$)$_2$, O, NR$^{10}$ or S;

$X^4$ and $X^5$ are independently C or N, with the proviso that $X^4$ and $X^5$ are not both N;

wherein if $X^4$ or $X^5$ is N, then $X^{10}$, $X^{11}$, and $X^{12}$ are independently N or CR$^4$, with the proviso that at most two of $X^{10}$, $X^{11}$, and $X^{12}$ are N;

wherein if $X^4$ and $X^5$ are C, one of $X^{10}$, $X^{11}$, and $X^{12}$ is NR$^{10}$, O or S, then the remaining two are independently CR$^4$ or N; and $R^1$, $R^2$, $R^3$, $R^4$, $R^{10}$, and $R^{13}$ are as defined in formula (I) or (IA).

In one embodiment of formula (IIA$^3$), A$^3$ is selected from the group consisting of:

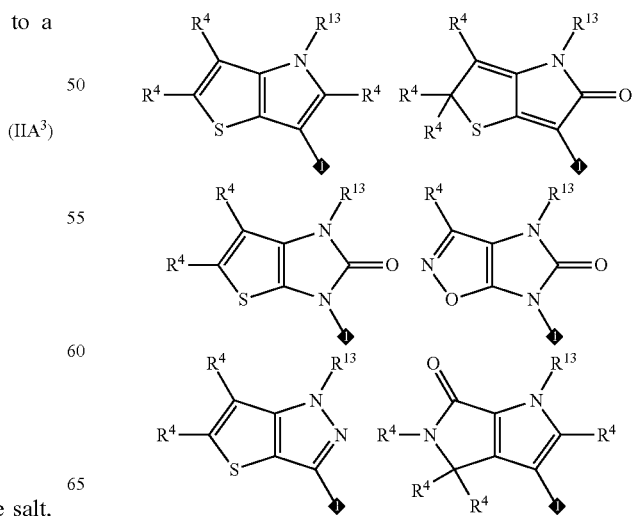

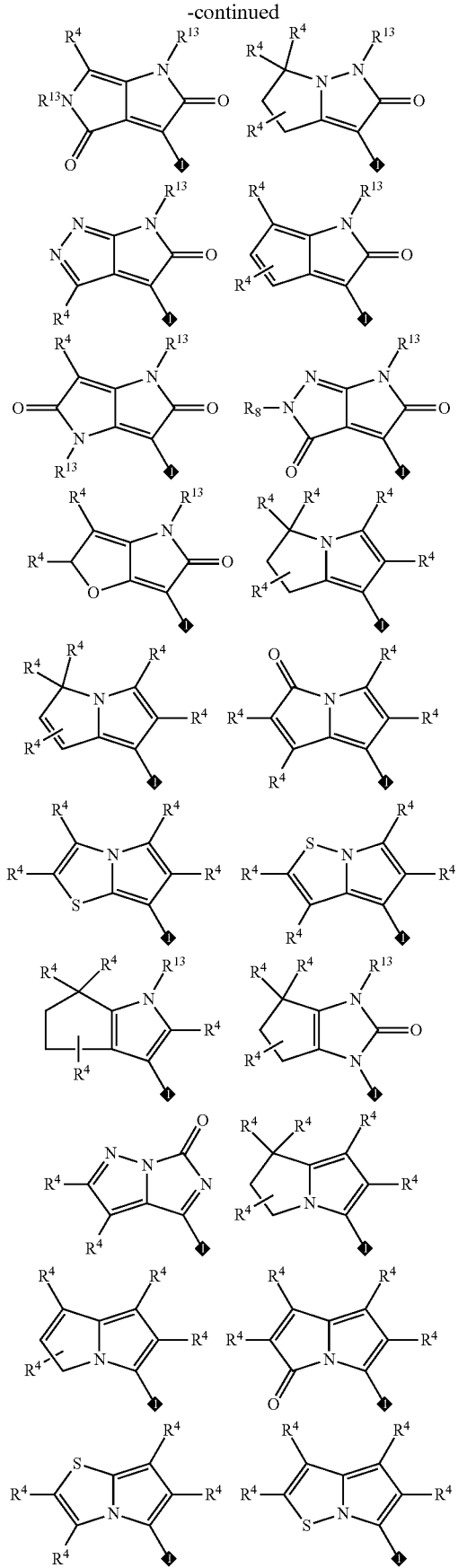
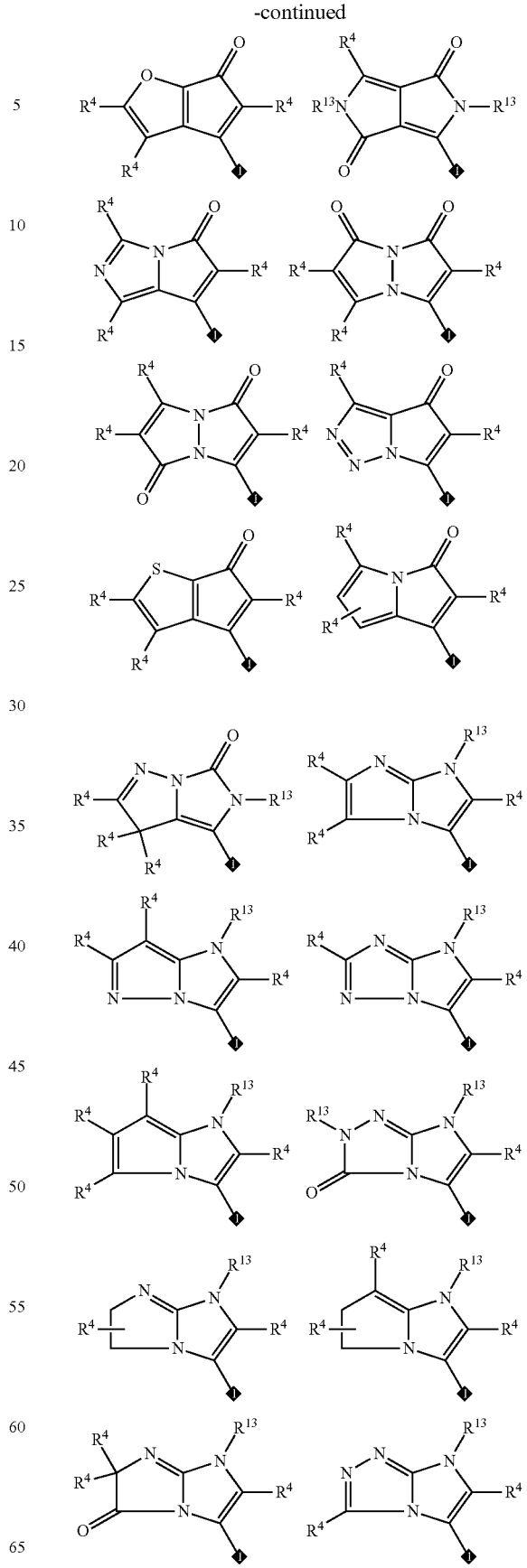

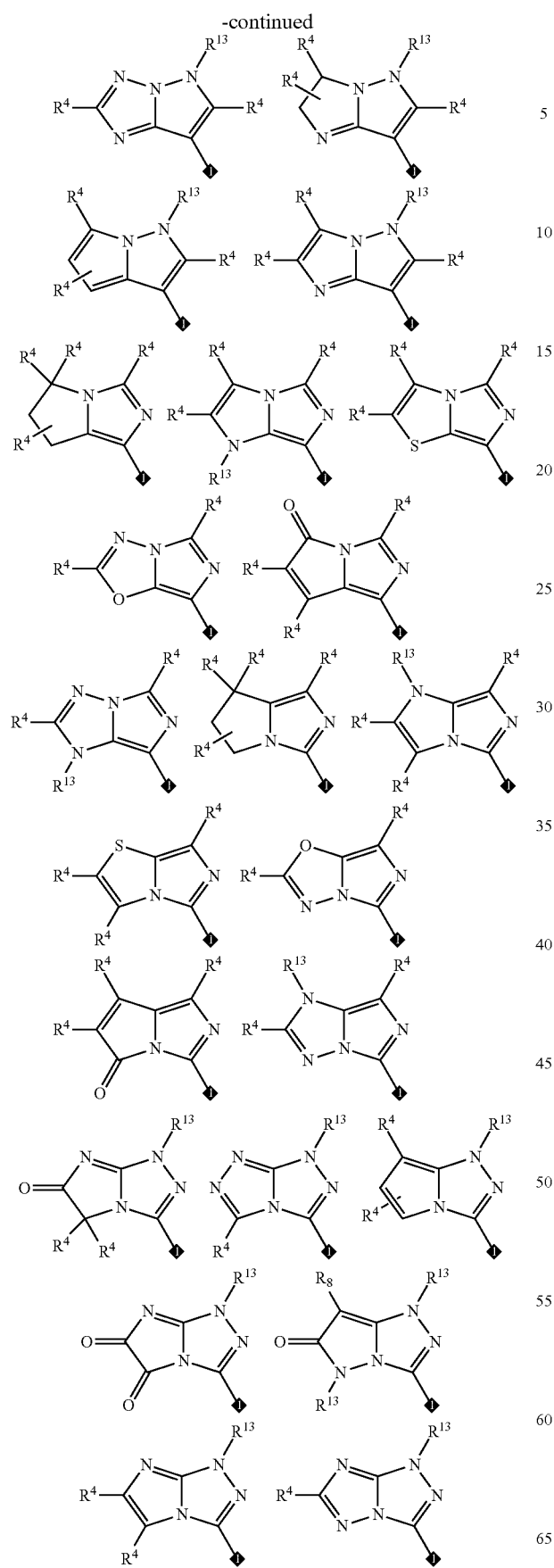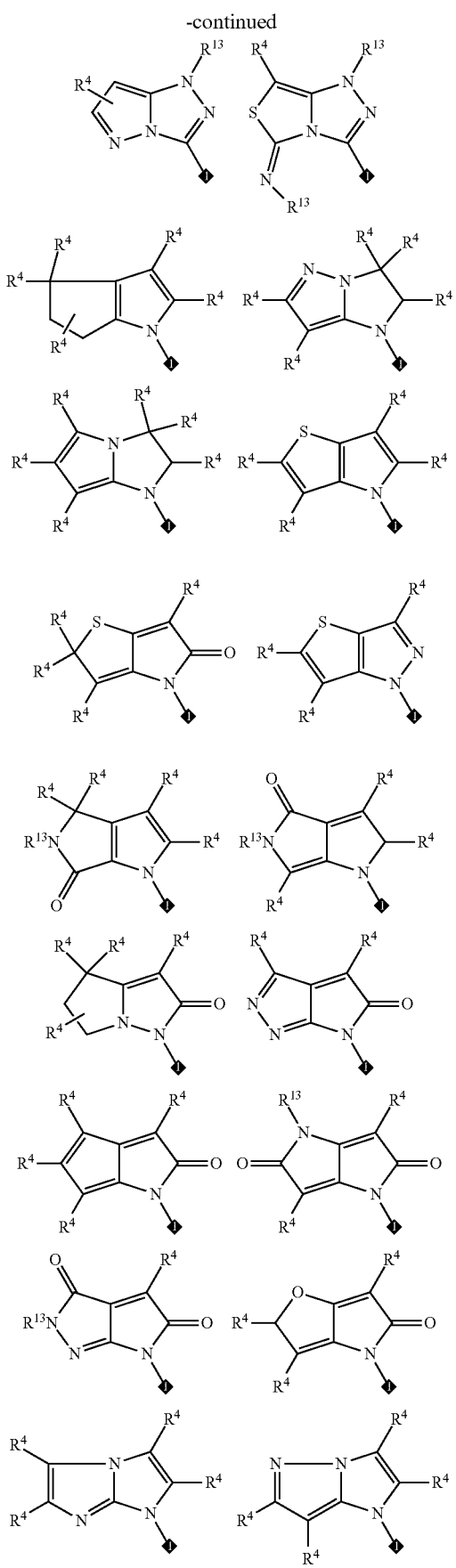

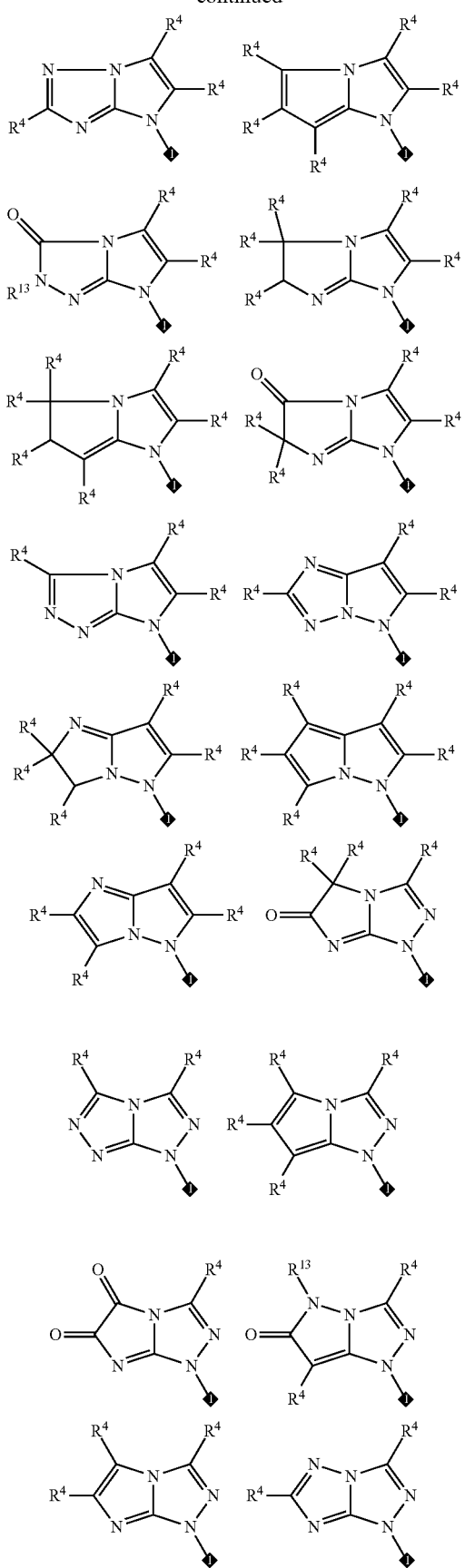
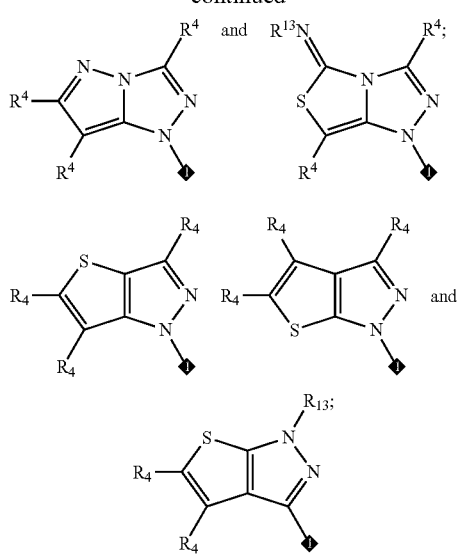
wherein $R^x$, $R^4$, and $R^{13}$ have the same definitions as described for formula (I) or formula (IA).
In one embodiment, the present disclosure relates to the compound of formula (IIA$^3$), wherein A$^3$ is selected from the group consisting of:
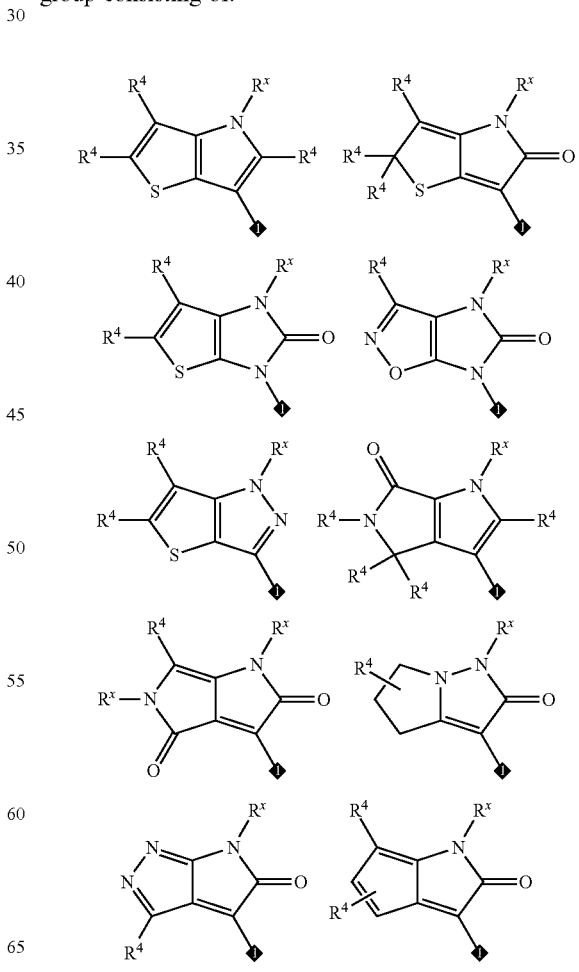

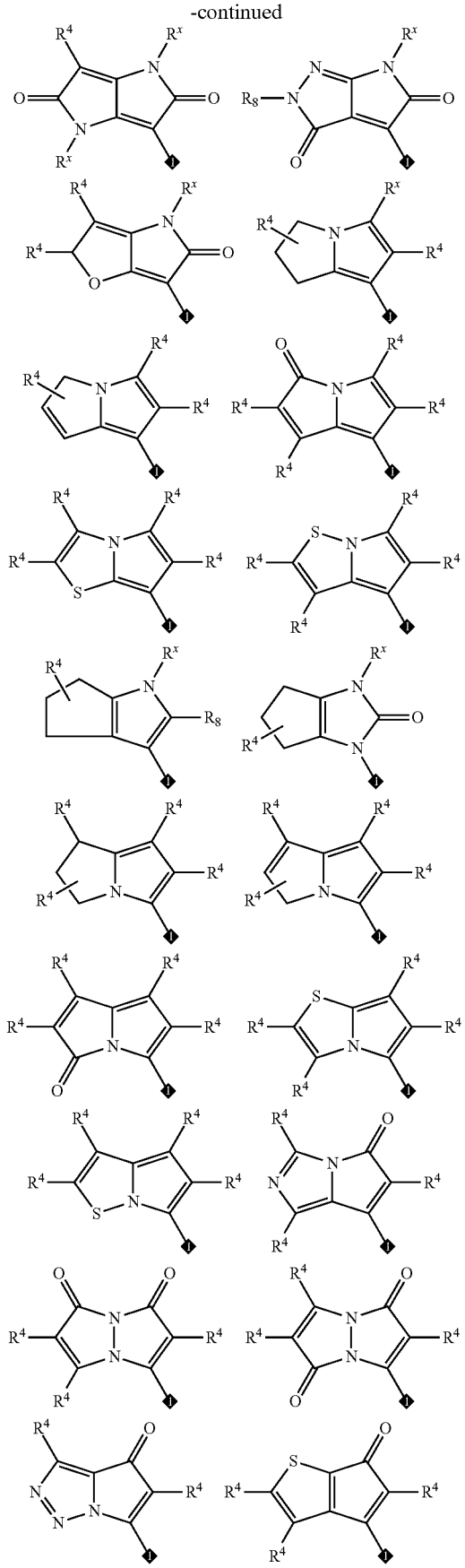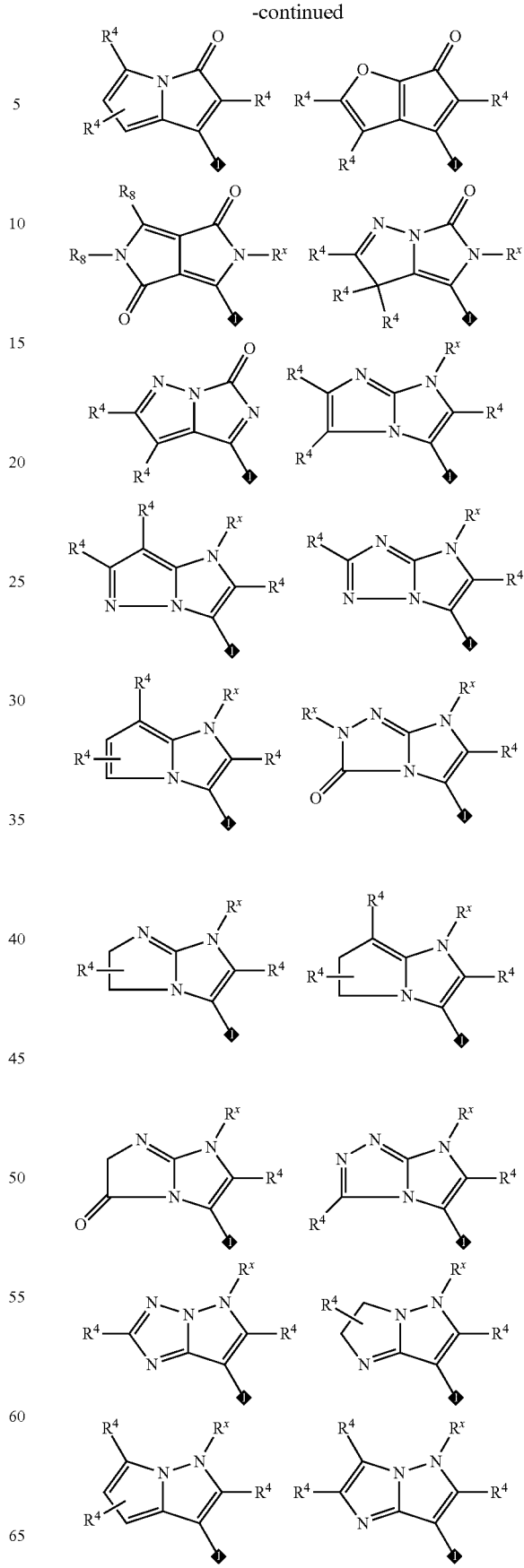

-continued
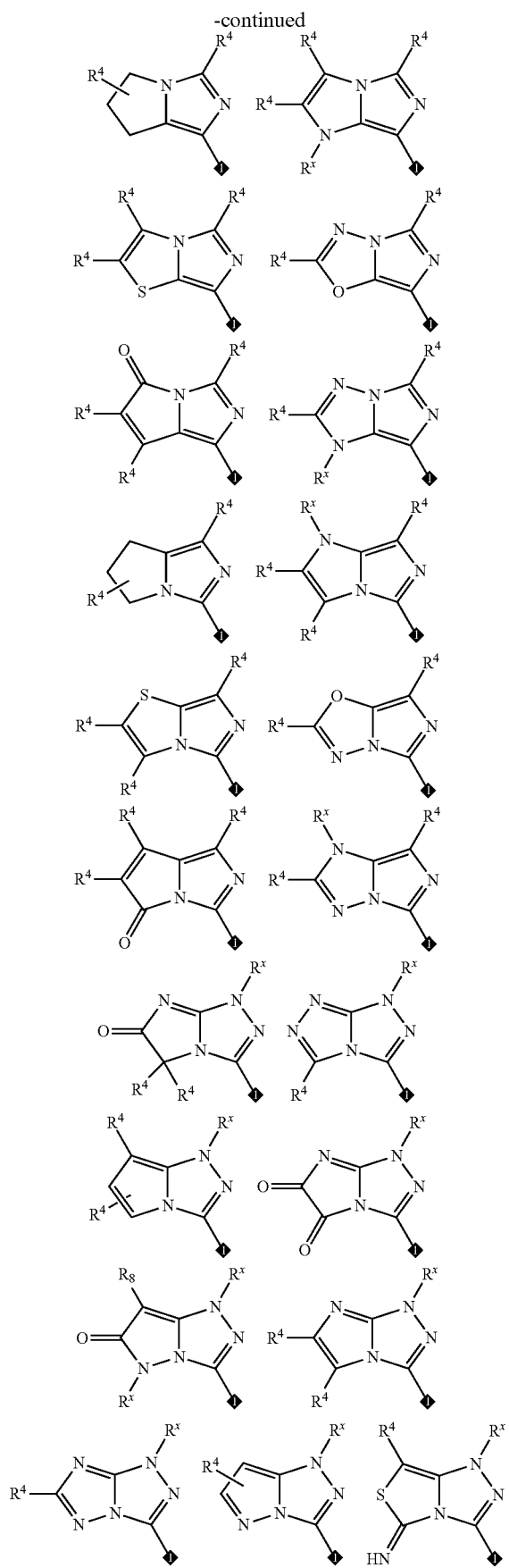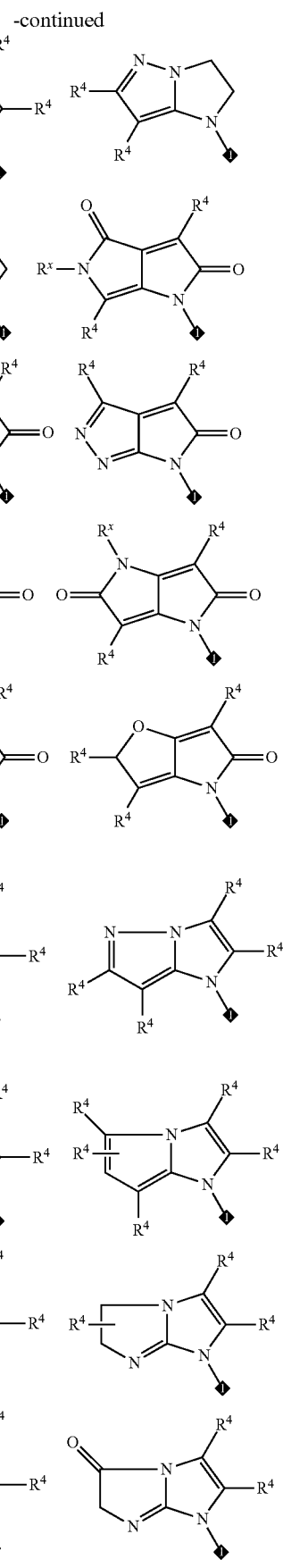

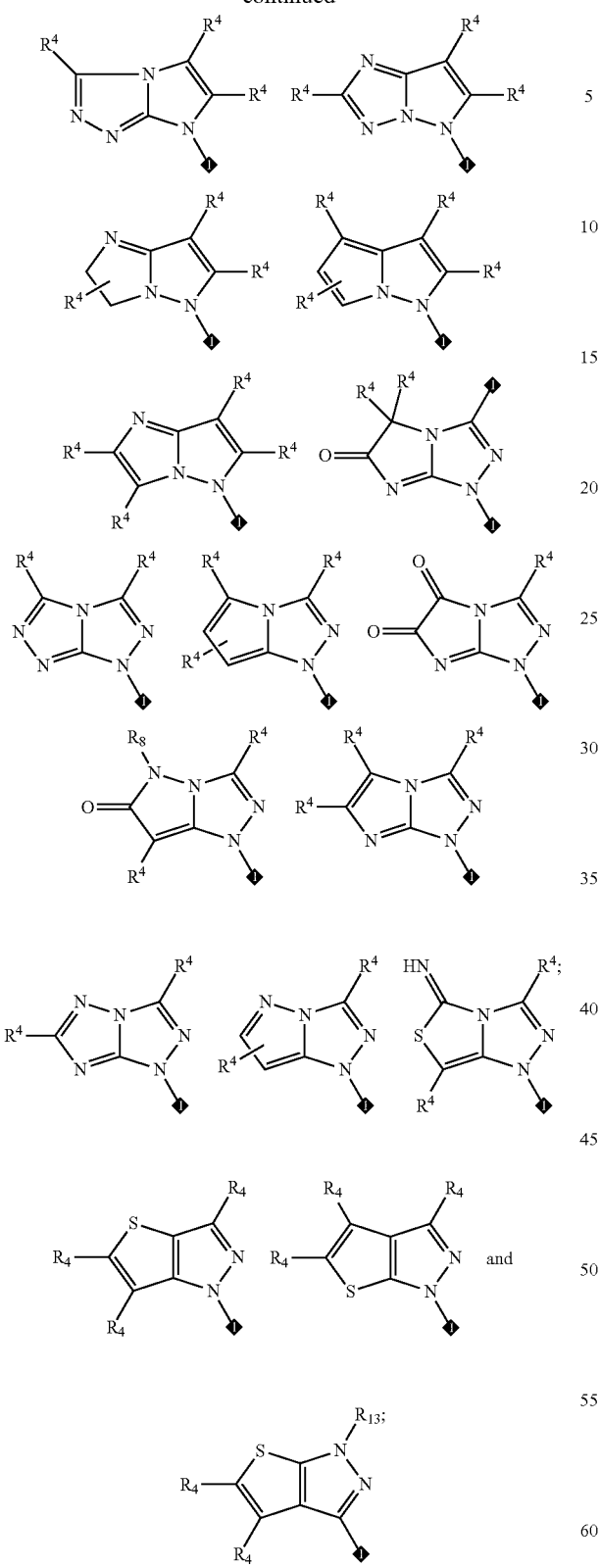
wherein $R^x$ is $R^{13}$; and $R^4$ and $R^{13}$ have the same definition as described for formula (I) or formula (IA). In one embodiment of formula (IIA³), A³ is selected from the group consisting of:

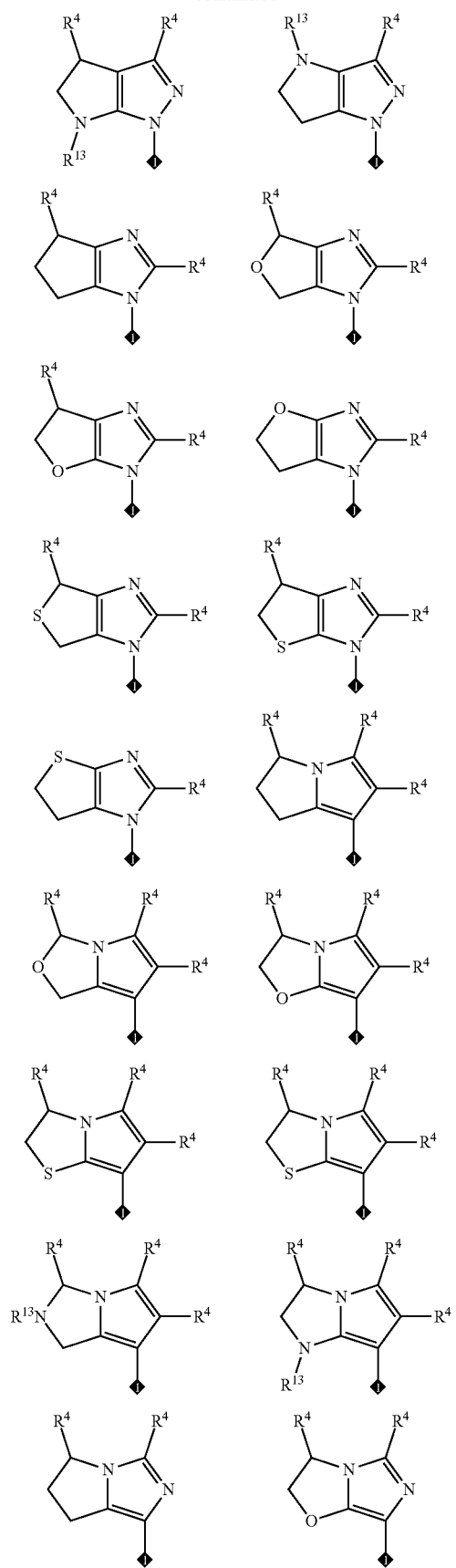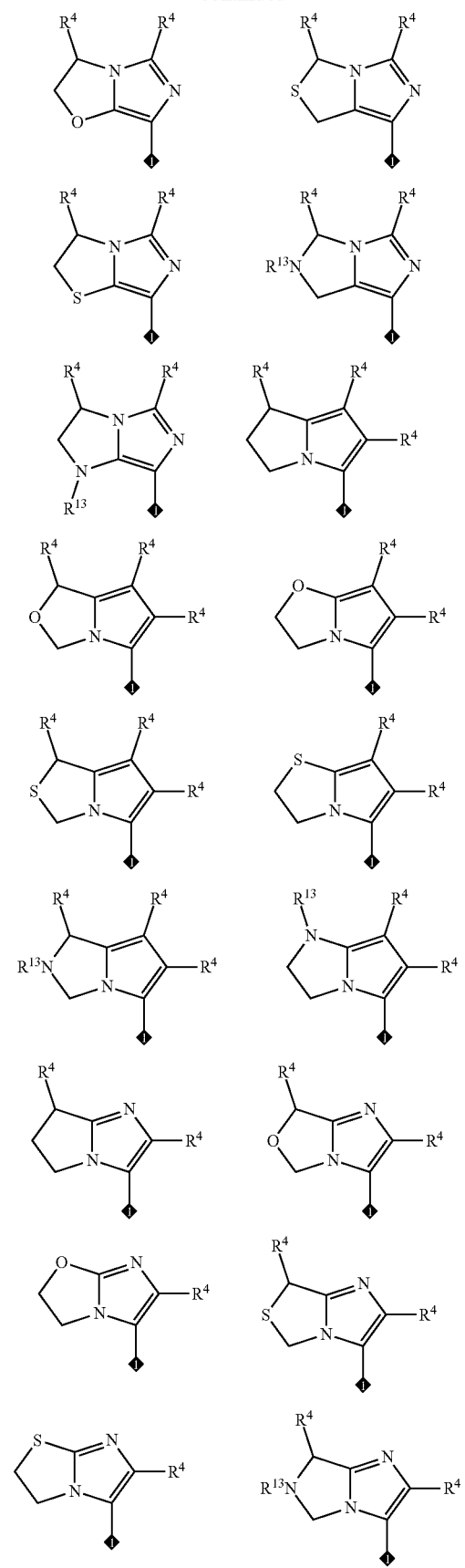

197

-continued

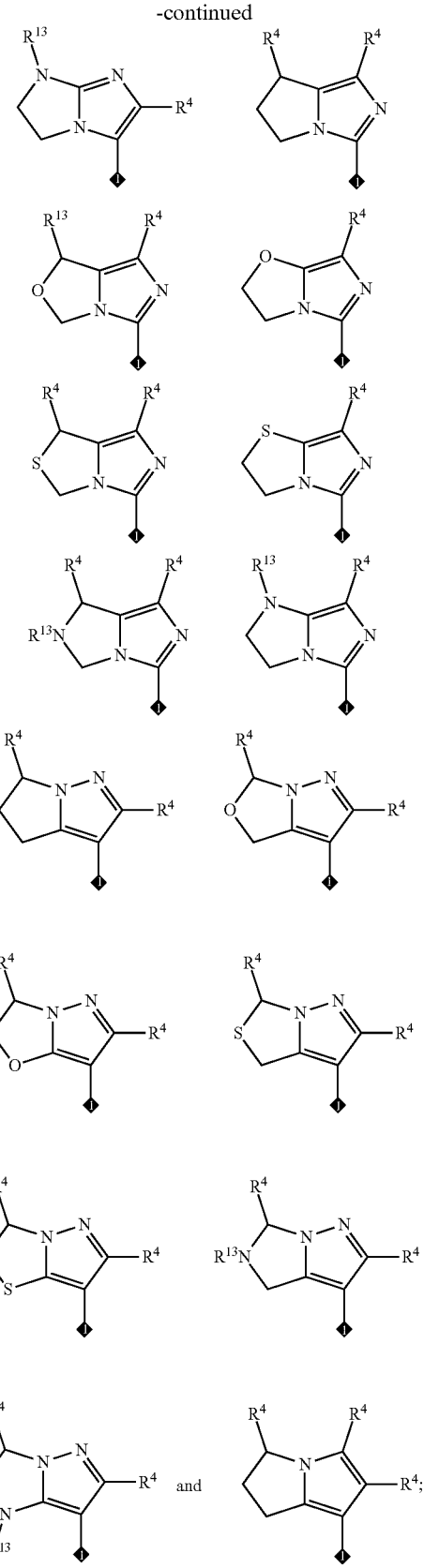

wherein R^x, R^4, and R^13 have the same definitions as described for formula (I) or formula (IA).

198

In one embodiment of formula (IIA$^3$), A$^3$ is

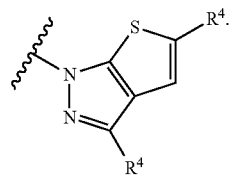

In one embodiment, the present invention relates to a compound of the formula (IIA$^{4a}$)

(IIA$^{4a}$)

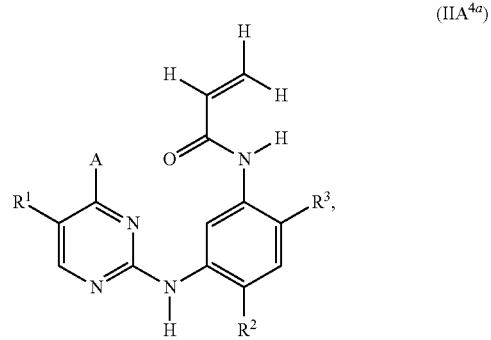

or a stereoisomer or a pharmaceutically acceptable salt, solvate, ester, or prodrug thereof;
wherein:
A is A$^{4a}$

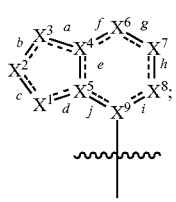

each of a, b, c, d, and e are independently either (formal) double bonds or (formal) single bonds, and none of X$^1$, X$^2$, X$^3$, X$^4$, and X$^5$ has two (formal) double bonds attached thereto:

each of X$^1$, X$^2$, X$^3$, X$^6$, X$^7$, X$^8$, and X$^9$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$;

X$^1$ is N, NR$^{13}$, C(R$^4$)$_2$, C(O), S(O)$_x$, or CR$^4$;
X$^2$ is N, NR$^{13}$, C(R$^4$)$_2$, S(O)$_x$, C(O), or CR$^4$;
X$^3$ is N, NR$^{13}$, C(R$^4$)$_2$, C(O), S(O)$_x$, or CR$^4$;
at least two of X$^1$, X$^2$ and X$^3$ are CR$^4$ or N, and X$^4$ and X$^5$ are C or N; and when X$^4$ and X$^5$ are both C, then one of X$^1$, X$^2$ and X$^3$ can be NR$^{10}$, O or S.

X$^6$, X$^7$, X$^8$, and X$^9$ are independently N or CR$^4$, with the provisos that (1) at most two of X$^6$, X$^7$, X$^8$, and X$^9$ are N; and (2) if X$^8$ or X$^9$ is directly bonded to the central ring, then the point of attachment atom is C; and R$^1$, R$^2$, R$^3$, R$^4$, R$^{10}$, and R$^{13}$ are as defined in formula (I) or (IA).

In one embodiment of formula (IIA$^{4a}$), A$^{4a}$ is selected from the group consisting of:

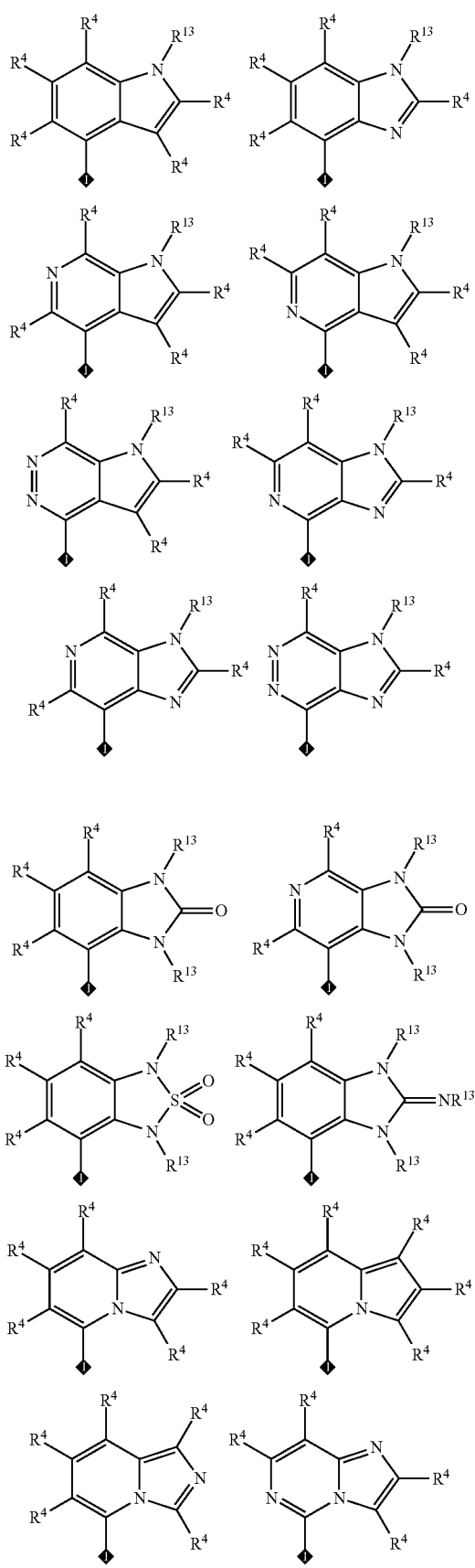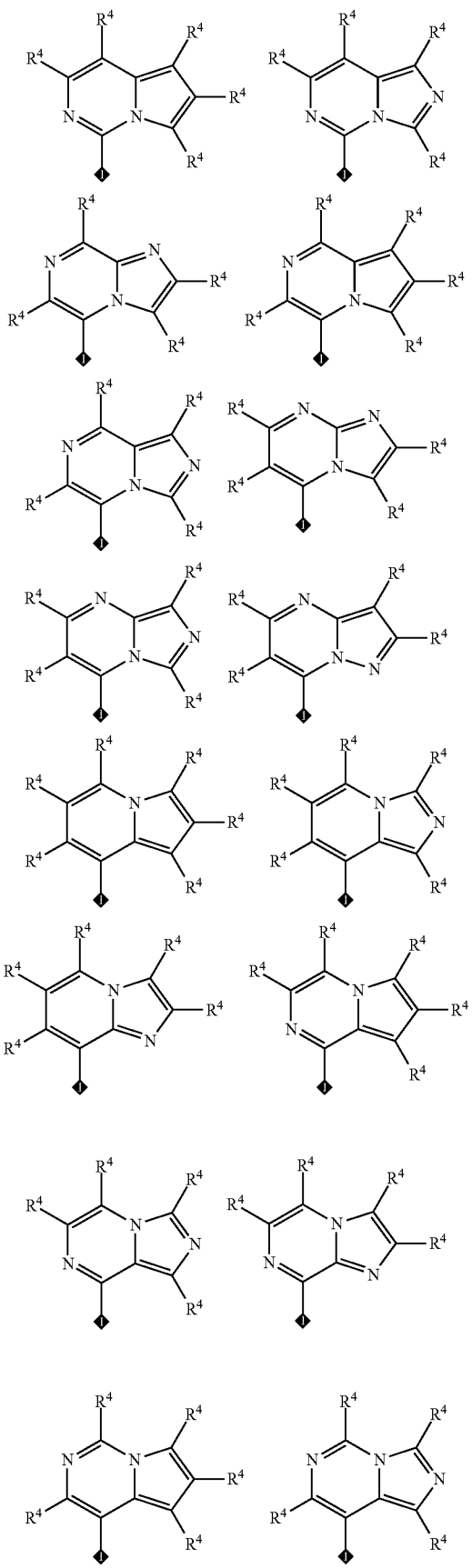

201
-continued
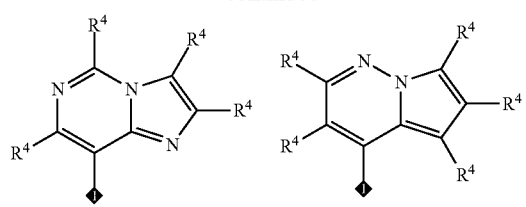
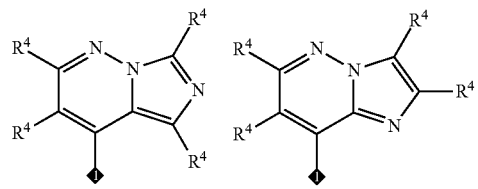
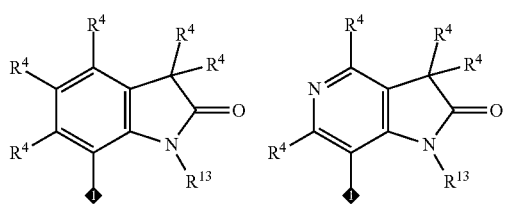
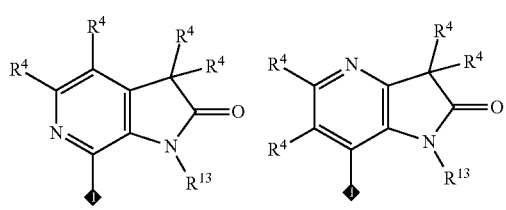
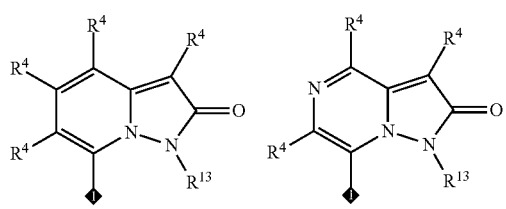
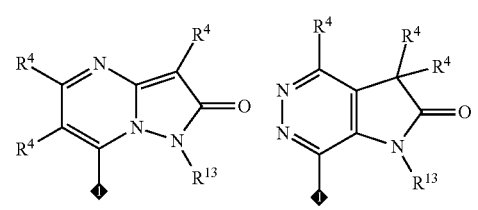
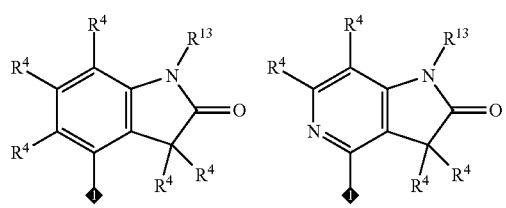
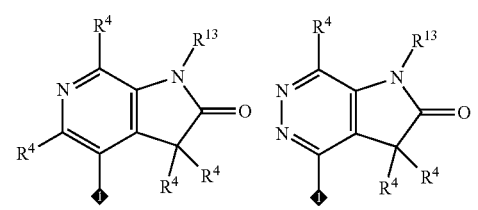
202
-continued
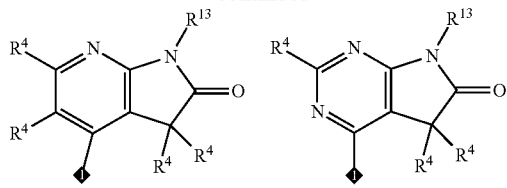
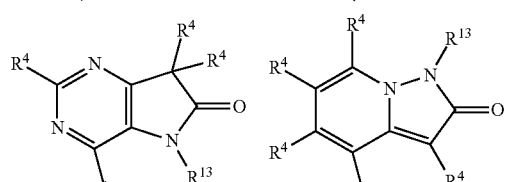
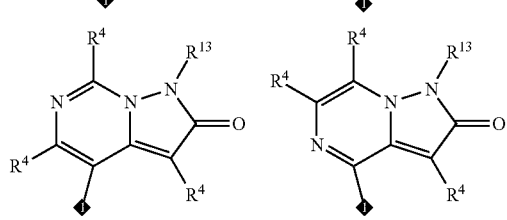
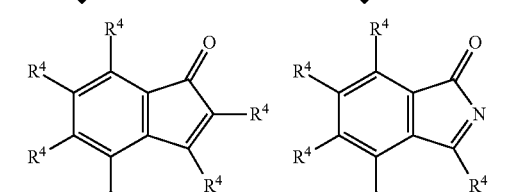
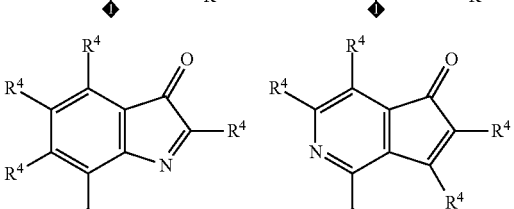
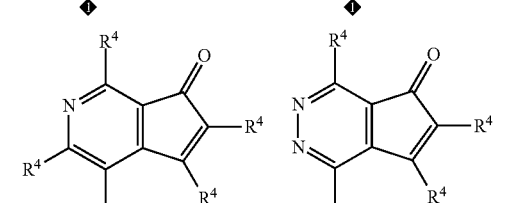
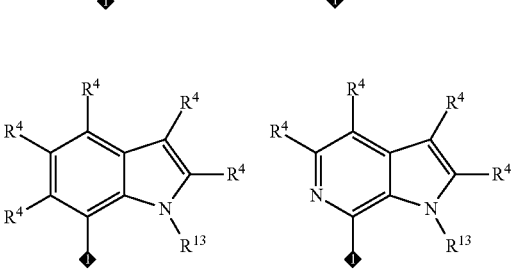
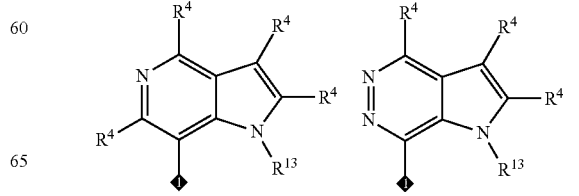

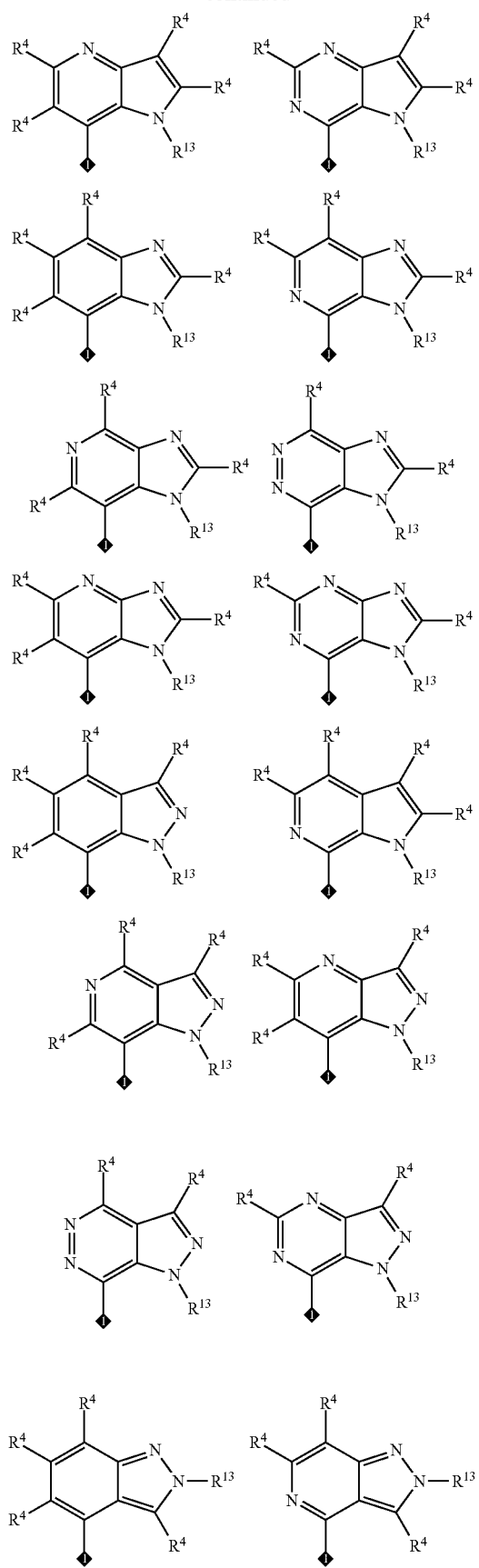
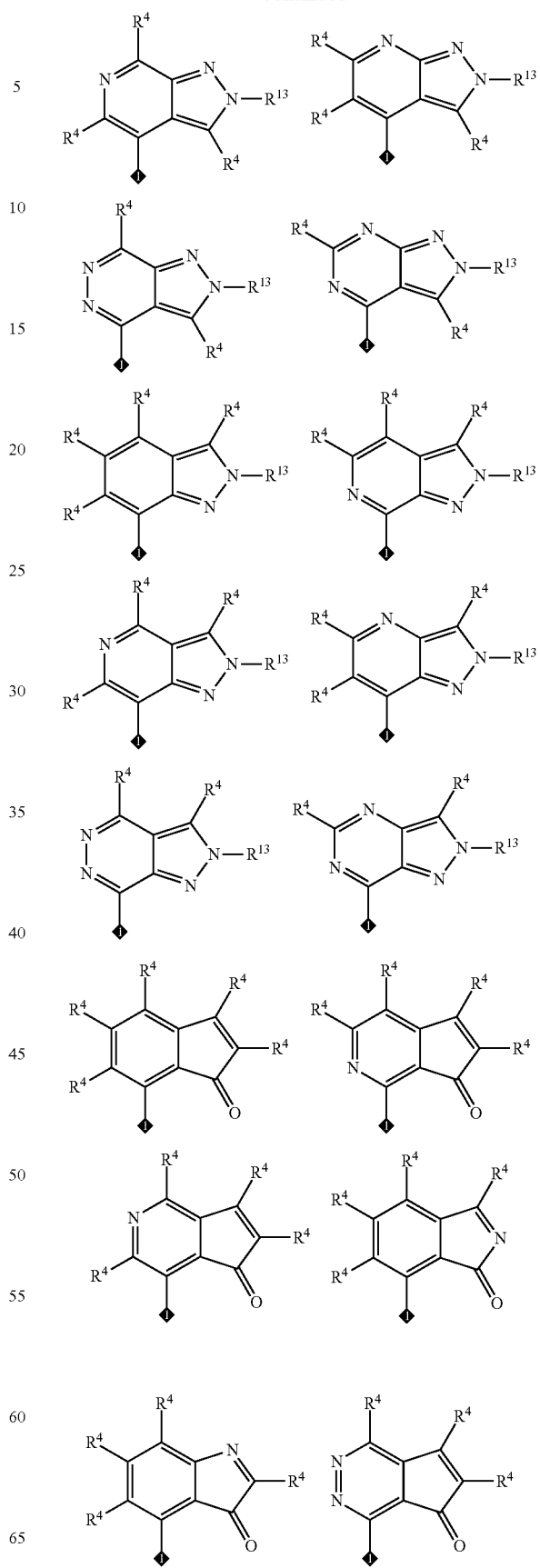

-continued
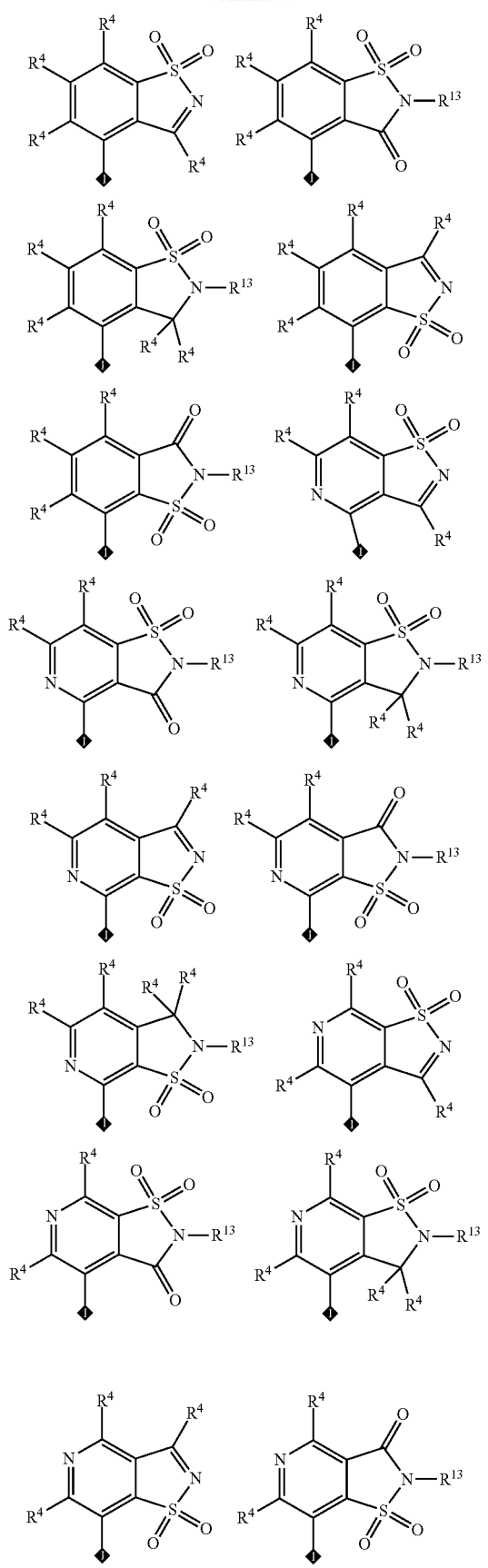
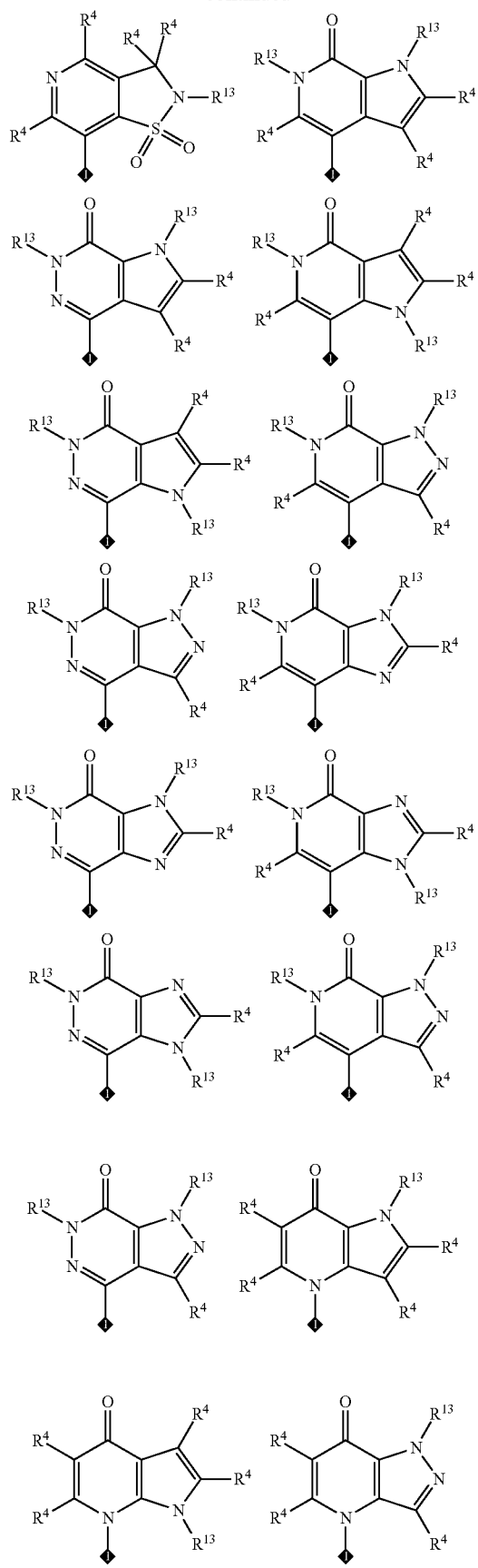

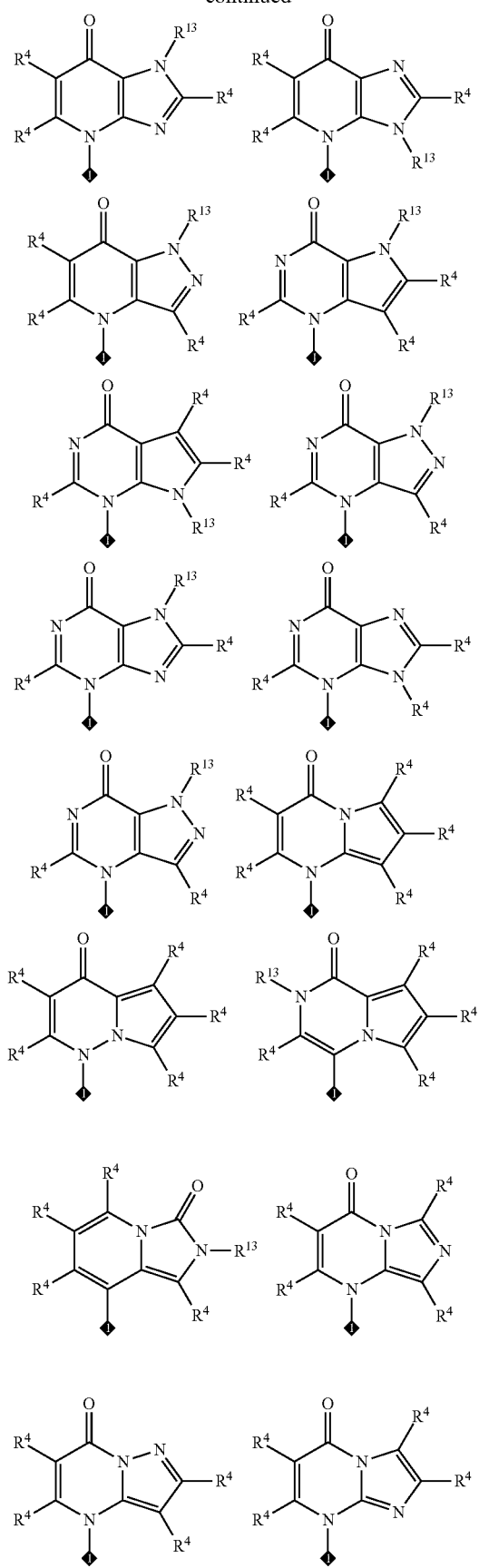
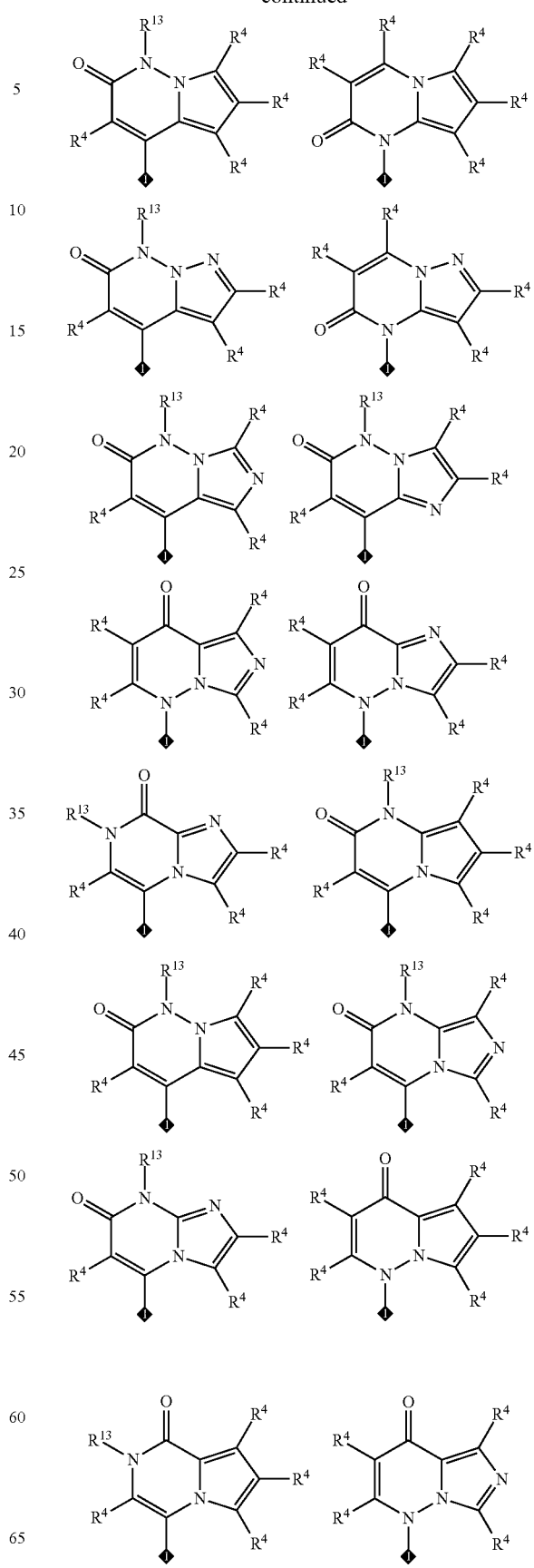

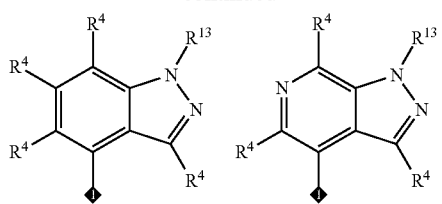
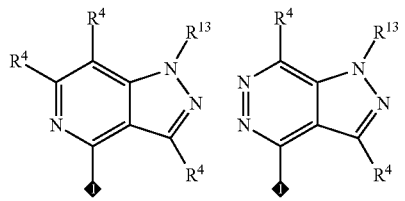
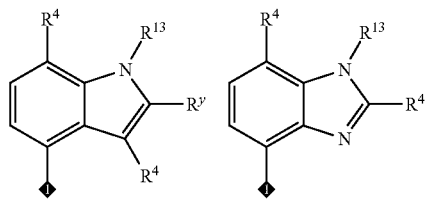
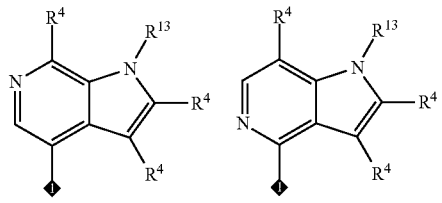
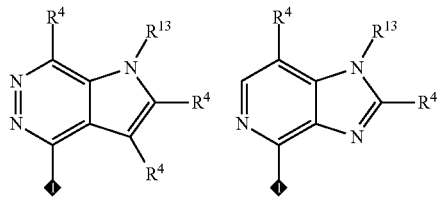
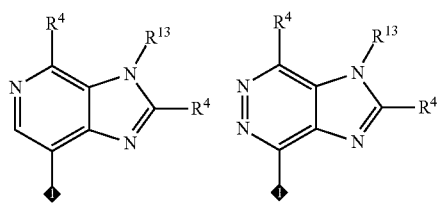
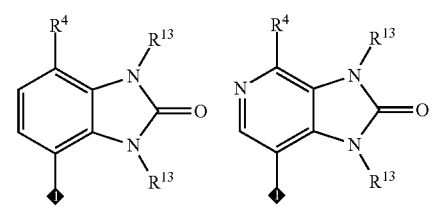
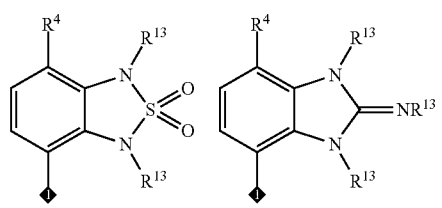
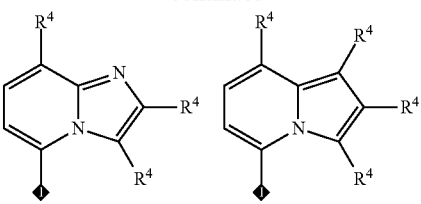
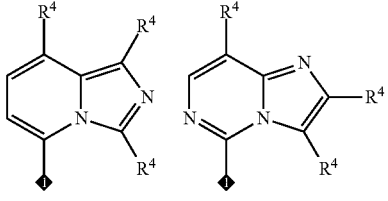
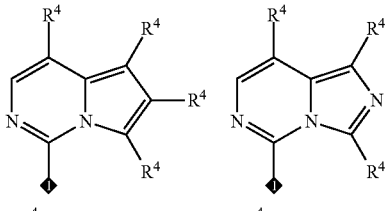
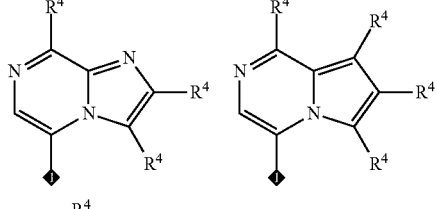
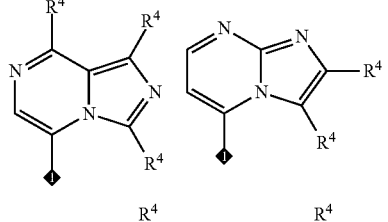
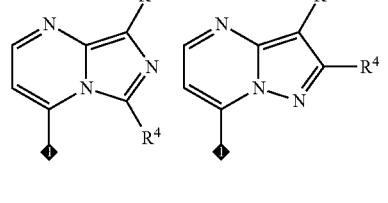
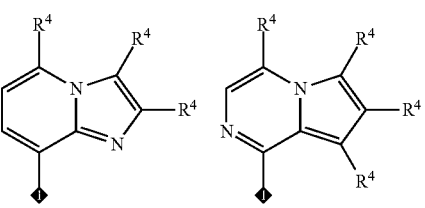

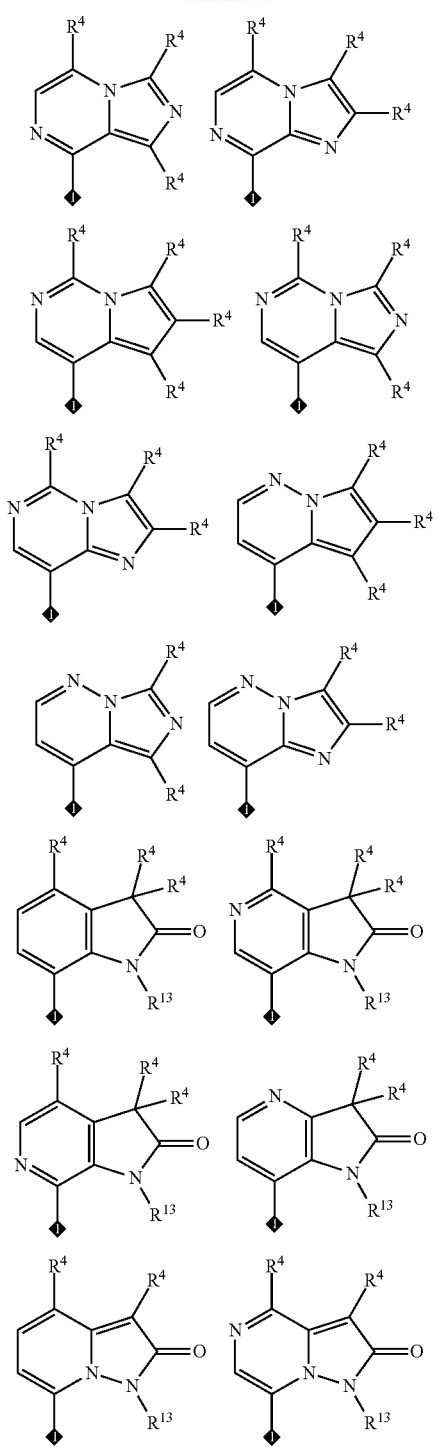
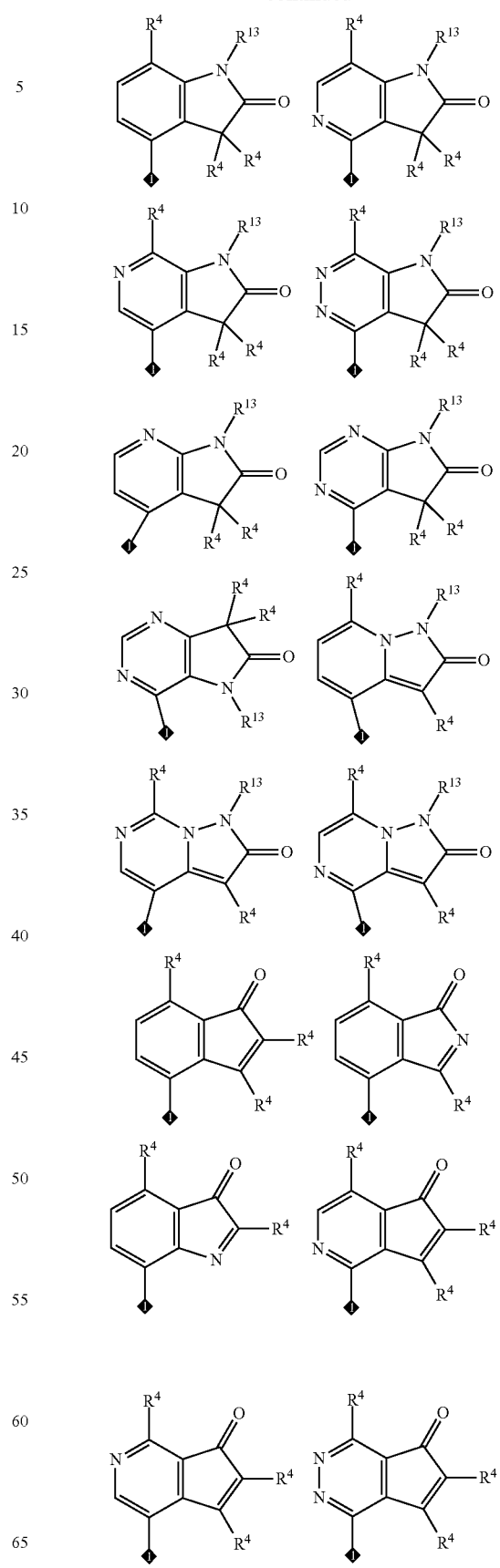

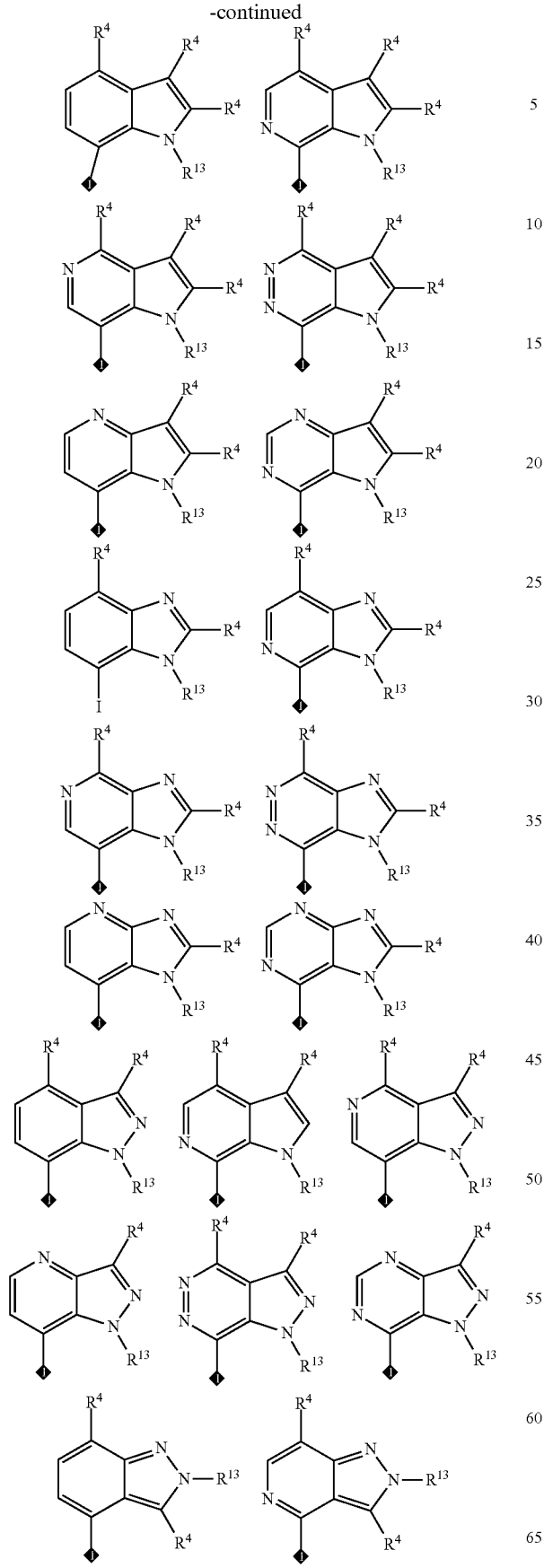
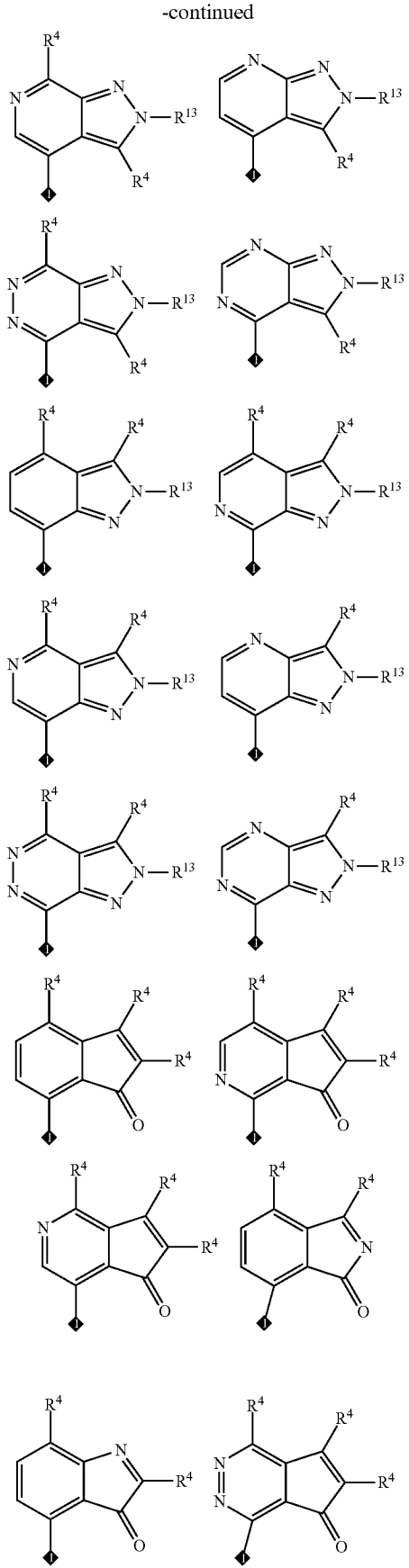

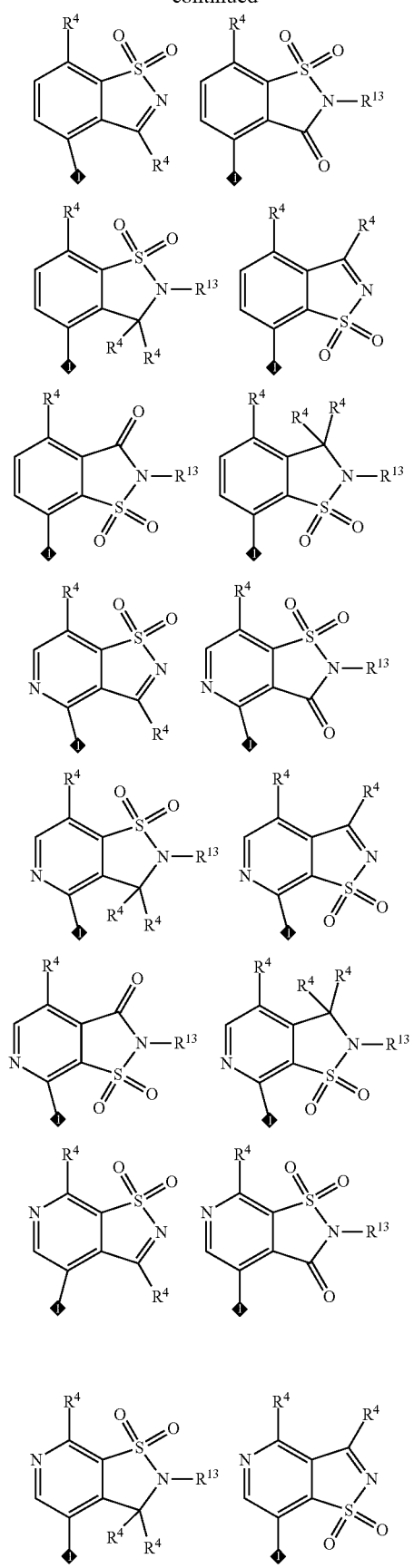
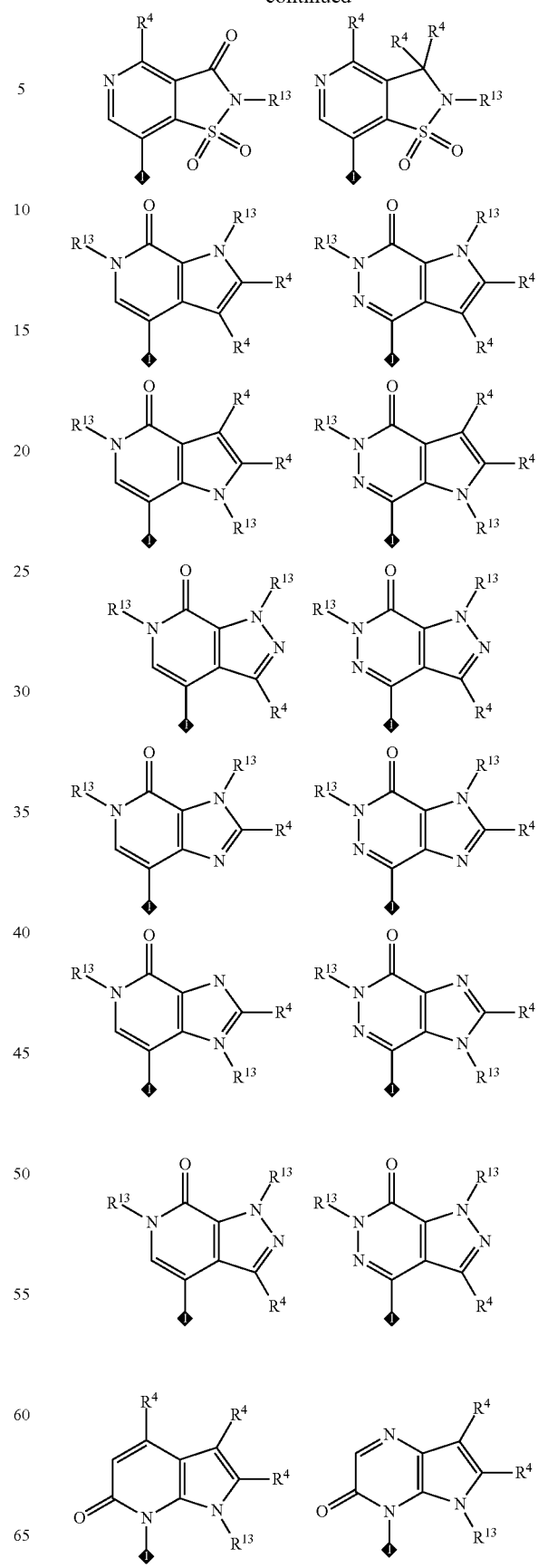

-continued
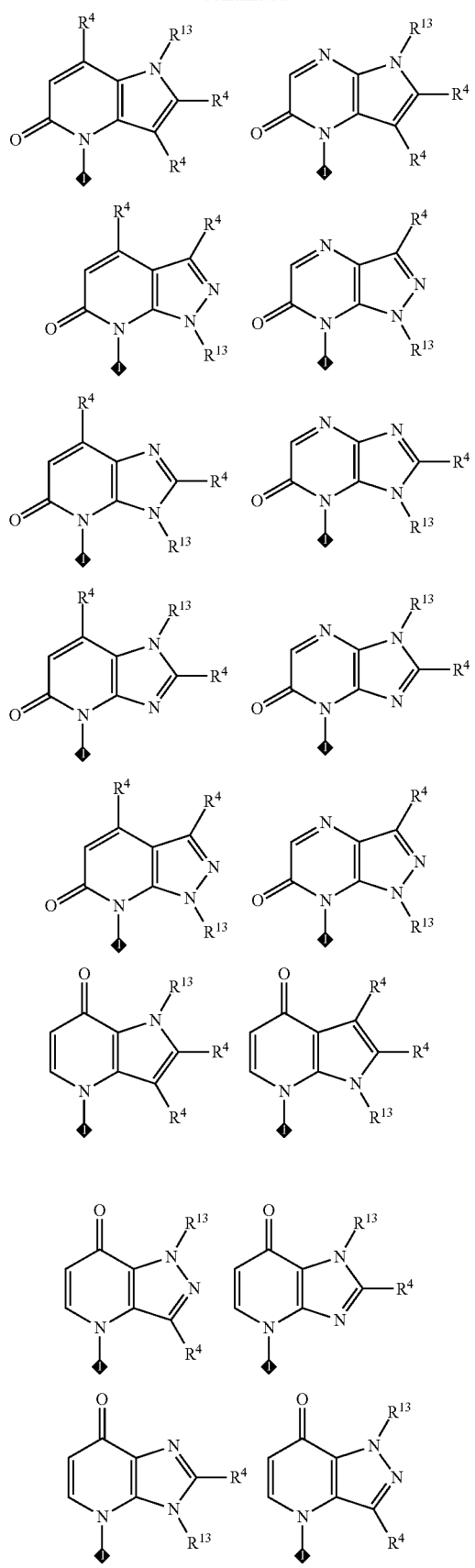
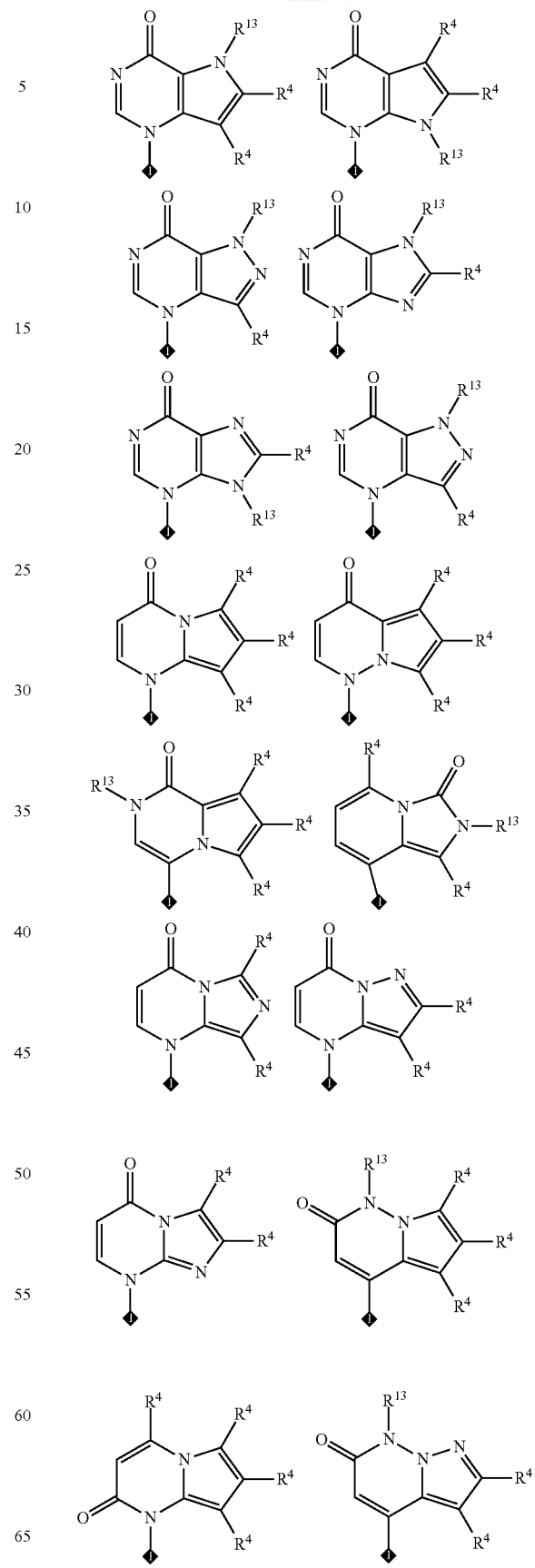

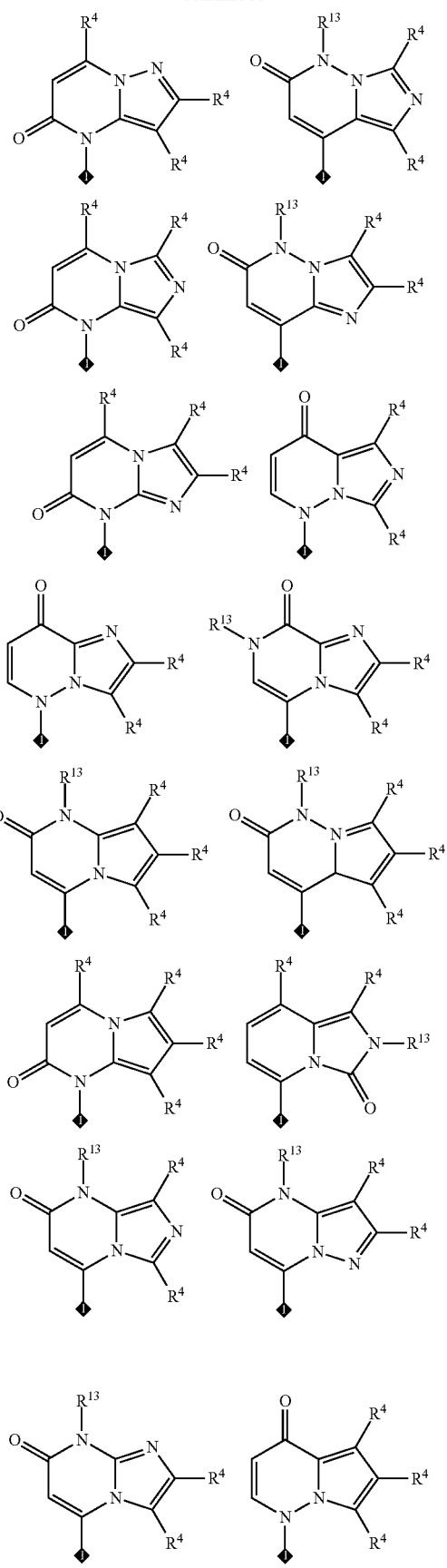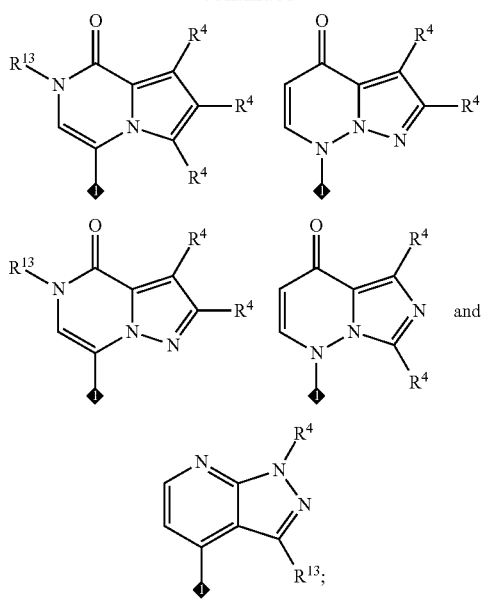
wherein $R^4$ and $R^{13}$ are as previously defined in formula (I) or (IA).
In one embodiment of formula $(IIA^{4a})$, $A^{4a}$ is selected from the group consisting of:
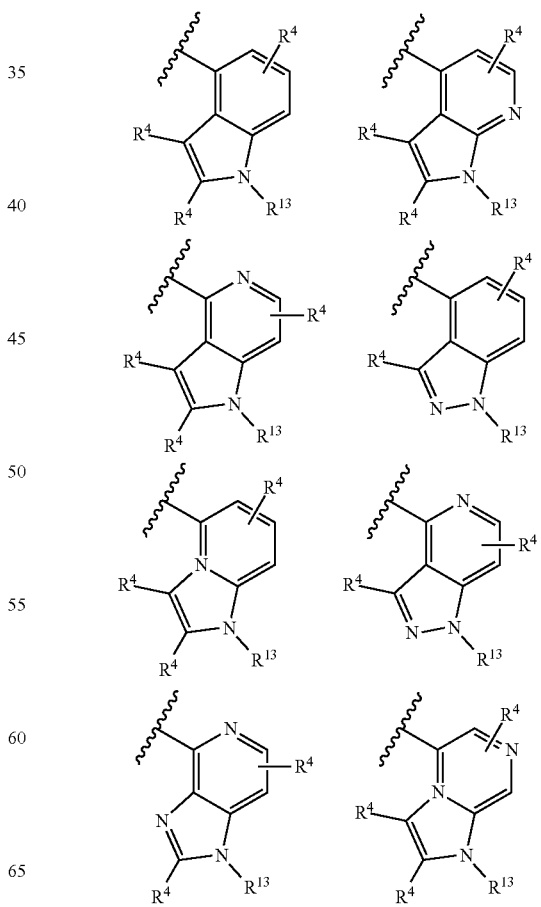

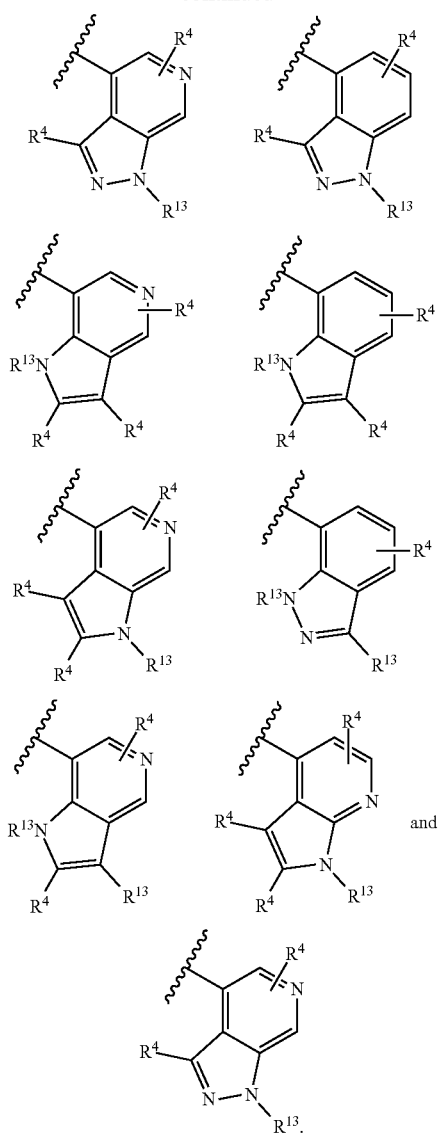
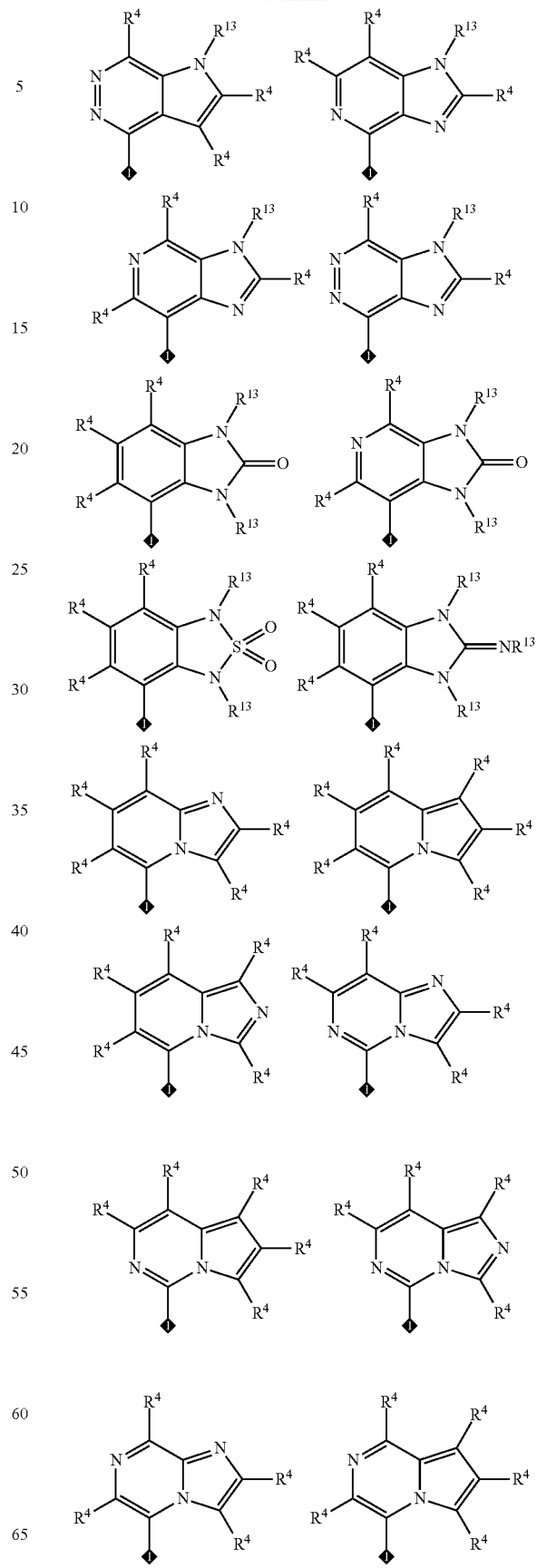
In one embodiment, the present disclosure relates to the compound of formula (IIA$^{4a}$), wherein A$^{4a}$ is selected from the group consisting of:
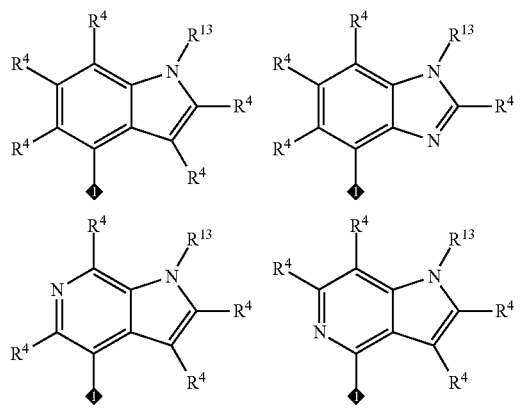

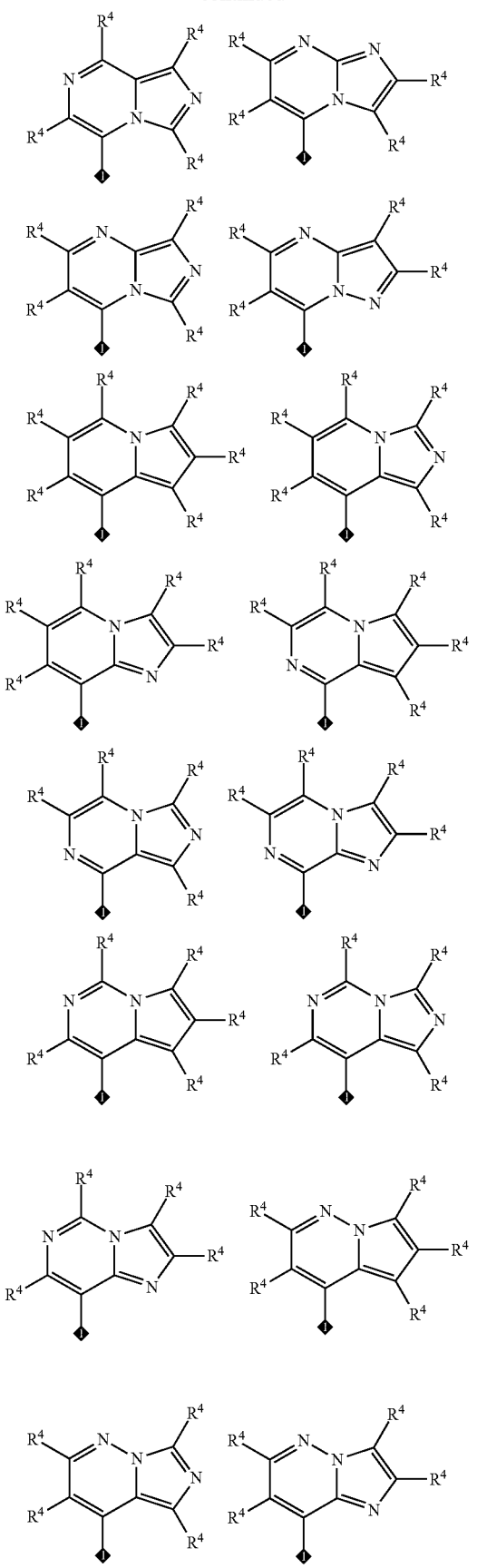
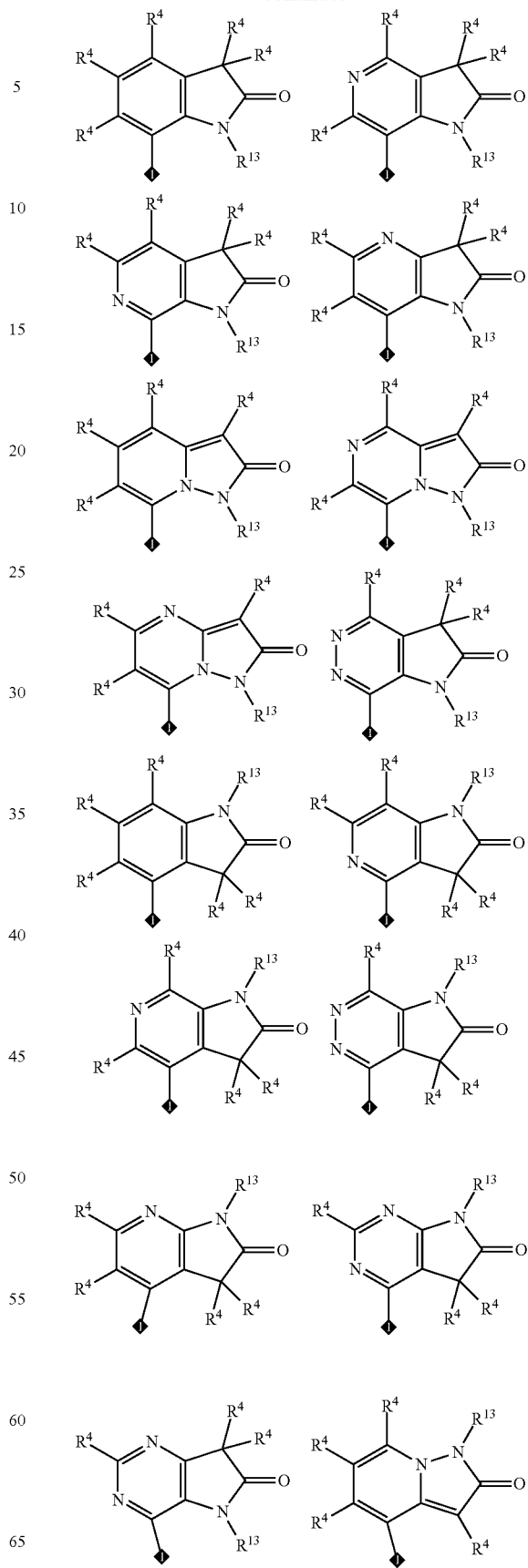

225
-continued
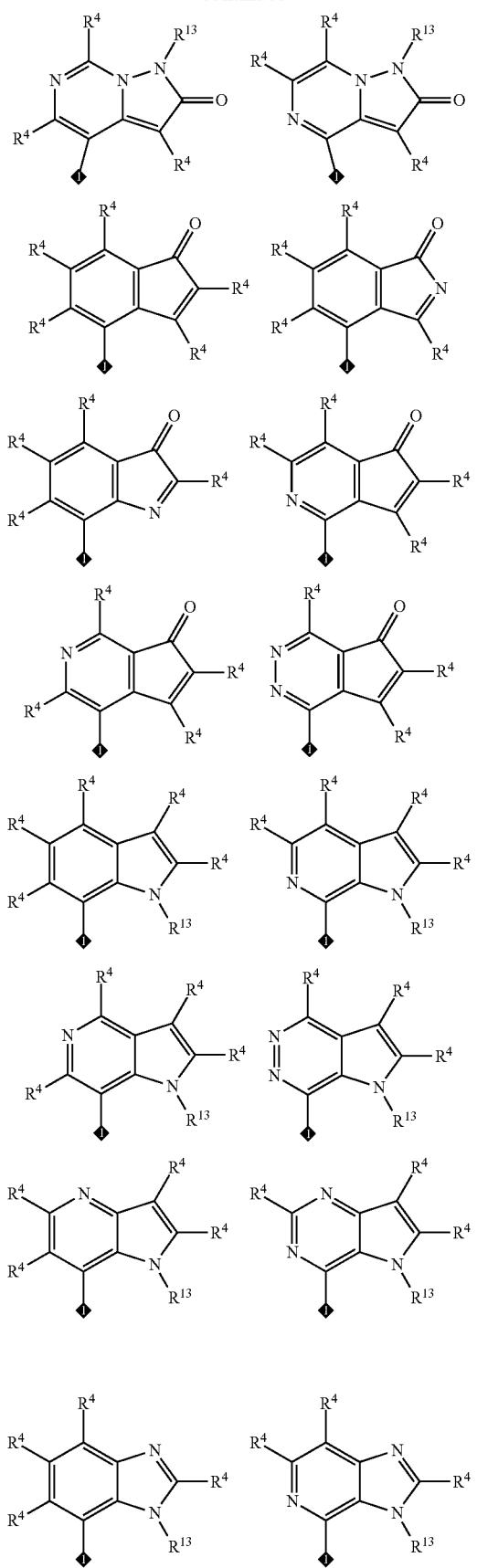
226
-continued
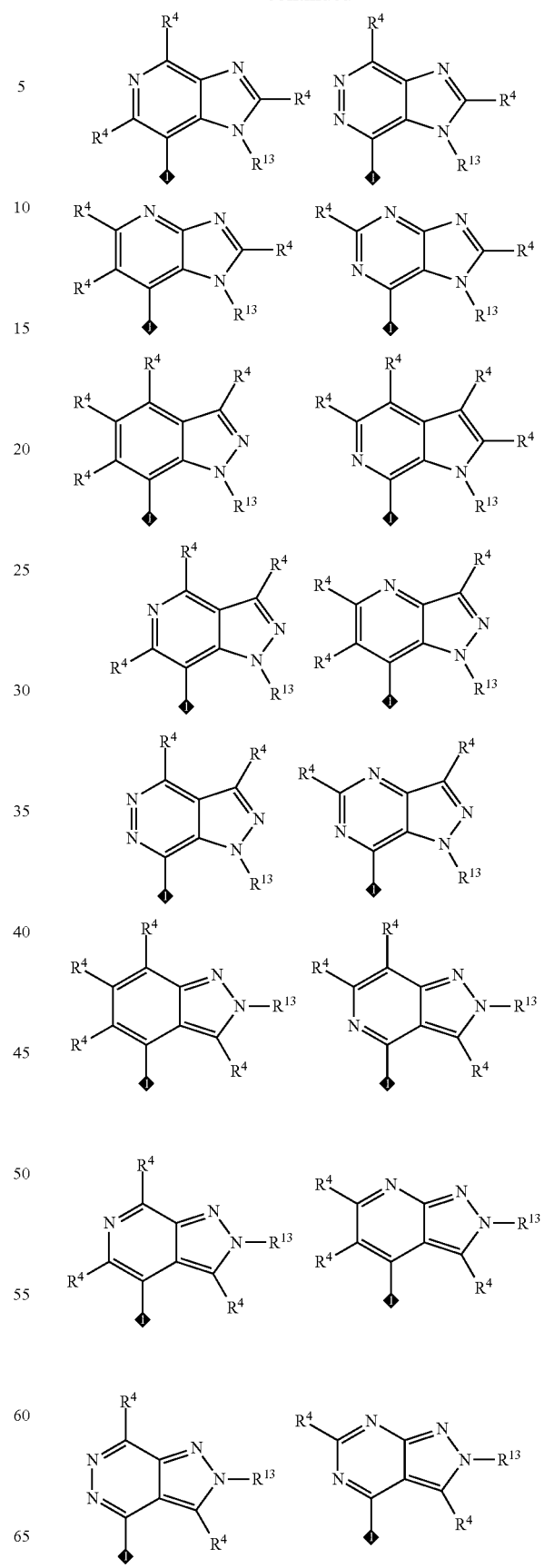

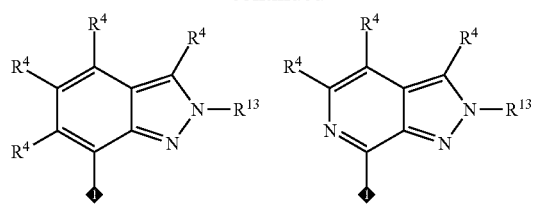
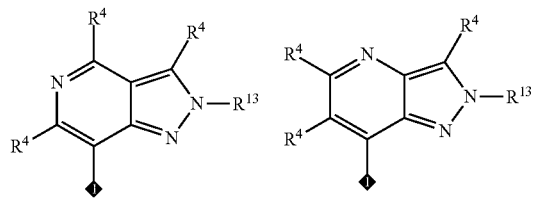
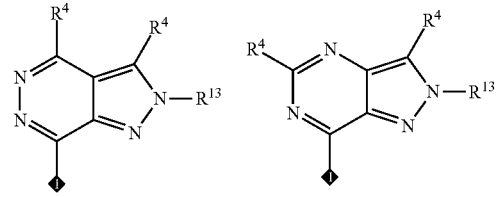
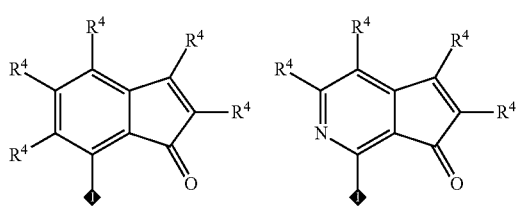
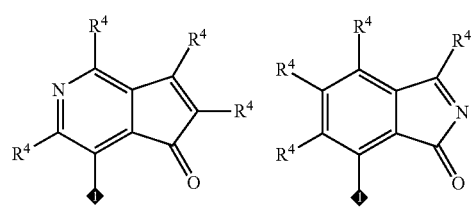
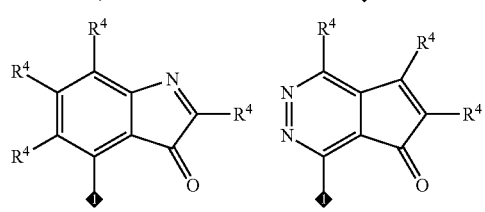
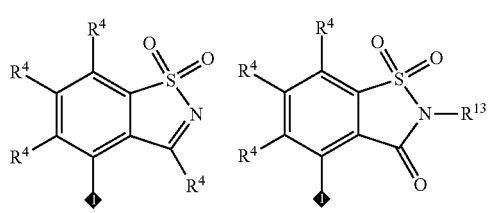
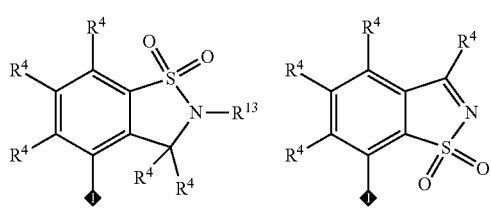
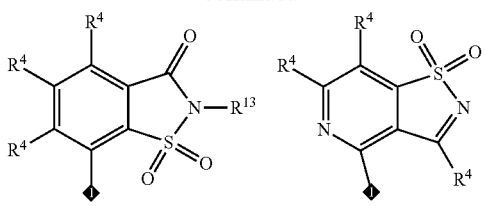
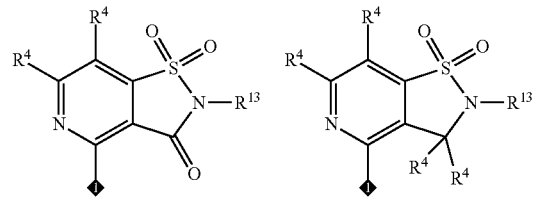
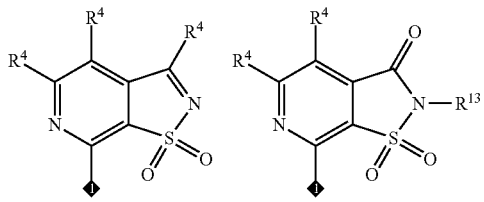
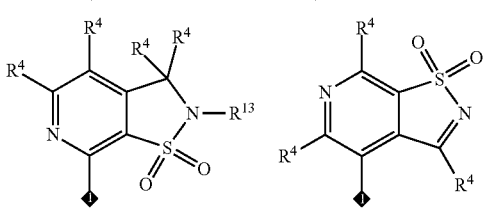
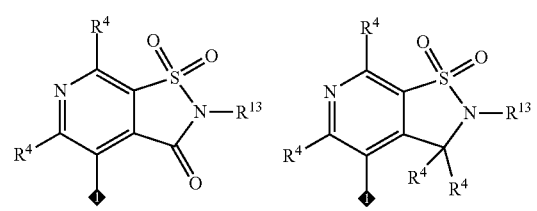
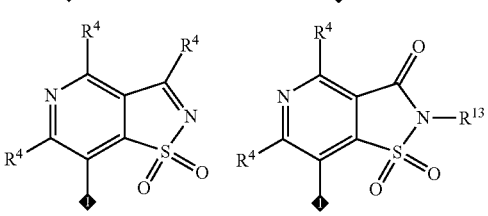
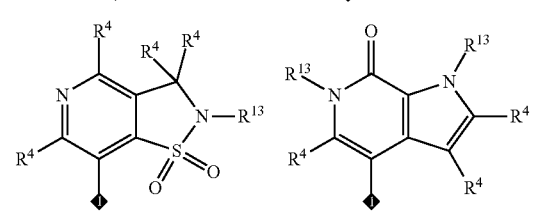
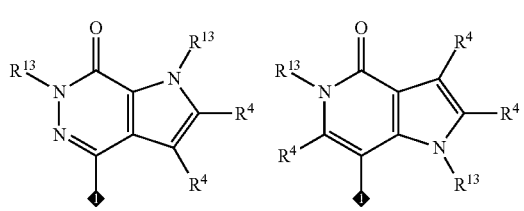

-continued
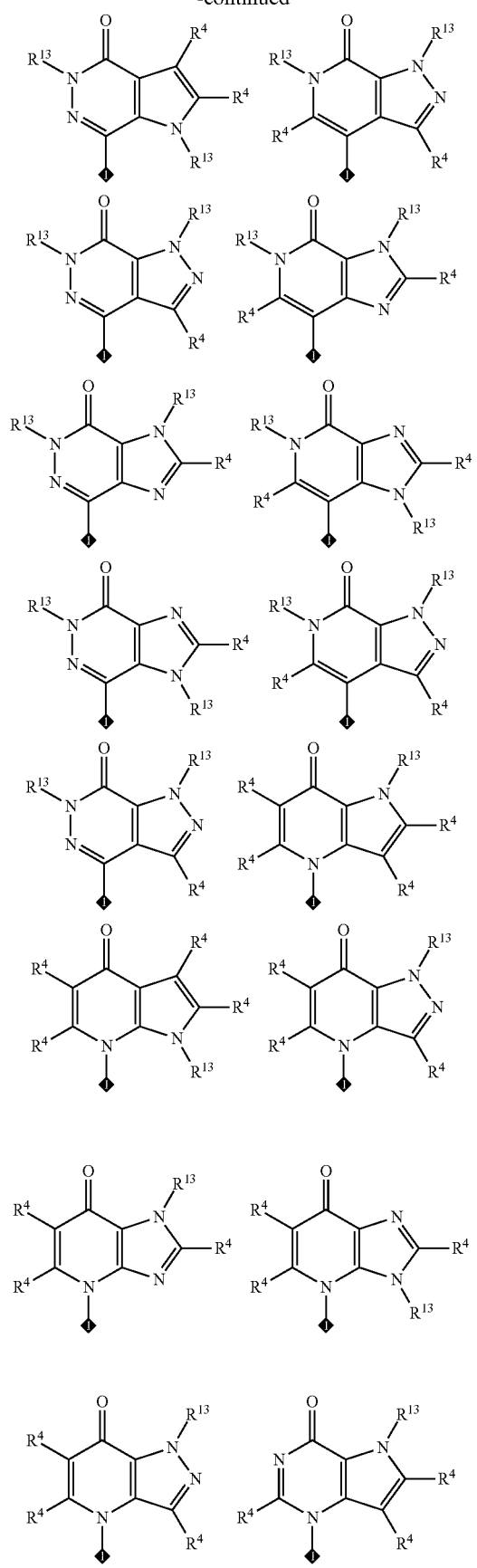
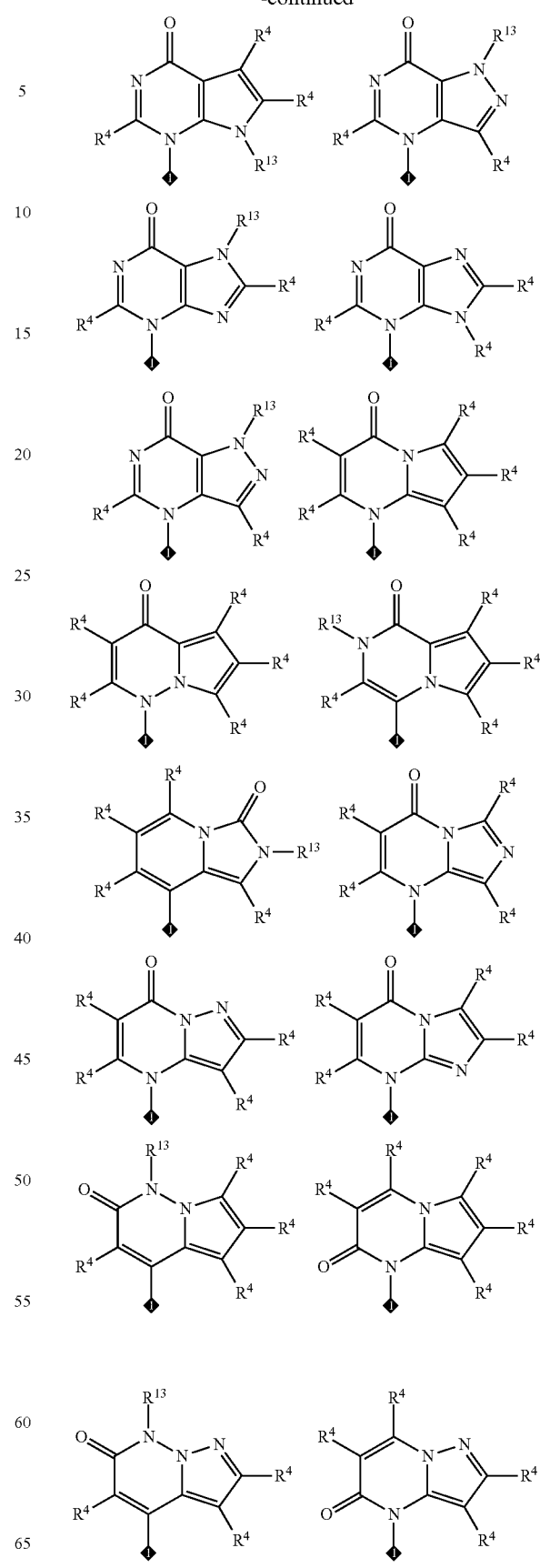

-continued

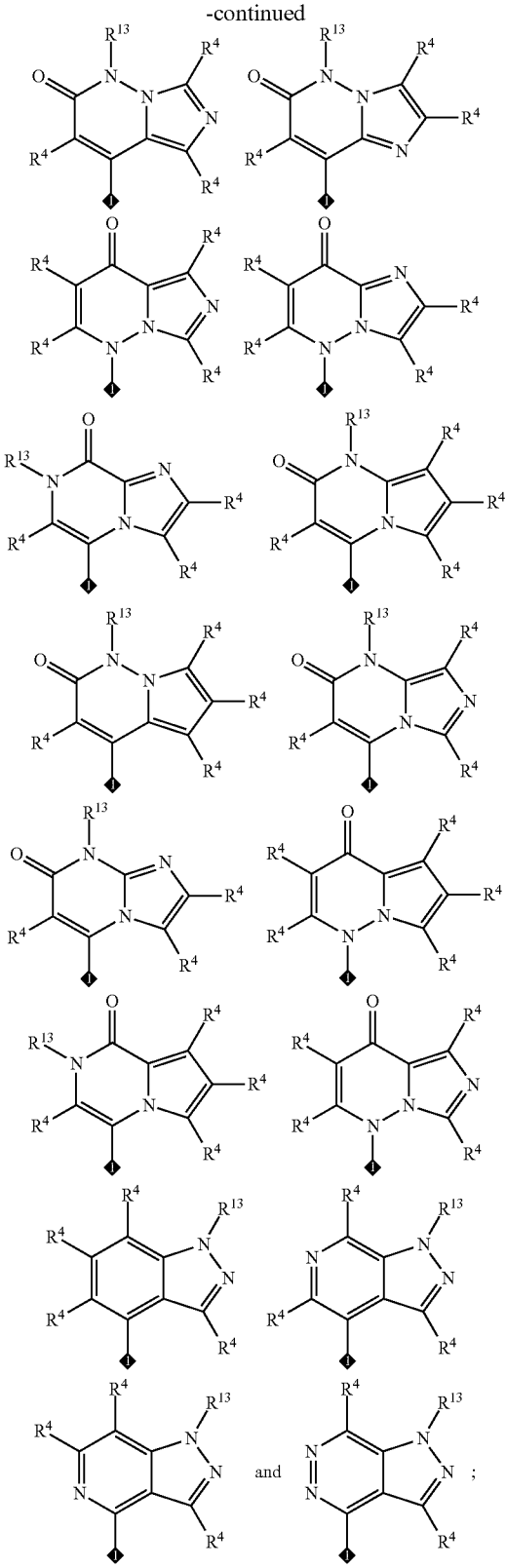

wherein R⁴ and R¹³ are the same as defined above for formula (I) or (IA).

In one embodiment, the present invention relates to a compound of the formula (IIA⁴ᵇ)

(IIA⁴ᵇ)

or a stereoisomer or a pharmaceutically acceptable salt, solvate, ester, or prodrug thereof;

wherein:

A is

A⁴ᵇ each of a, b, c, d, and e are independently either (formal) double bonds or (formal) single bonds, and none of $X^1$, $X^2$, $X^3$, $X^4$, and $X^5$ has two (formal) double bonds attached thereto;

each of $X^1$, $X^2$, $X^3$, $X^6$, $X^7$, $X^8$, and $X^9$ is optionally substituted and is independently C or a heteroatom selected from the group consisting of N, S, and O; and the optional substituent is selected from the group consisting of =O (oxo), =S, =NR¹³, (=O)₂, (O)(NR¹³), R⁴, and R¹³;

$X^1$ is N, NR¹³, C(R⁴)₂, C(O), S(O)ₓ, or CR⁴;

$X^2$ is N, NR¹³, C(R¹⁰)₂, S(O)ₓ, C(O), or CR⁴;

$X^1$ is N, NR¹³, C(R⁴)₂, C(O), S(O)ₓ, or CR⁴;

at least two of $X^1$, $X^2$ and $X^3$ are CR⁴ or N, and $X^4$ and $X^5$ are C or N; and when $X^4$ and $X^5$ are both C, then one of $X^1$, $X^2$ and $X^3$ can be NR¹⁰, O or S.

$X^6$, $X^7$, $X^8$, and $X^9$ are independently N or CR⁴, with the provisos that (1) at most two of $X^6$, $X^7$, $X^8$, and $X^9$ are N; and (2) if $X^8$ or $X^9$ is directly bonded to the central ring, then the point of attachment atom is C; and R¹, R², R³, R⁴, R¹⁰, and R¹³ are as defined in formula (I) or (IA).

In one embodiment of formula (IIA⁴ᵇ), A⁴ᵇ is selected from the group consisting of:

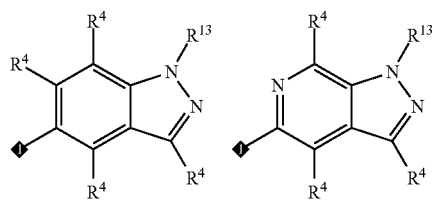

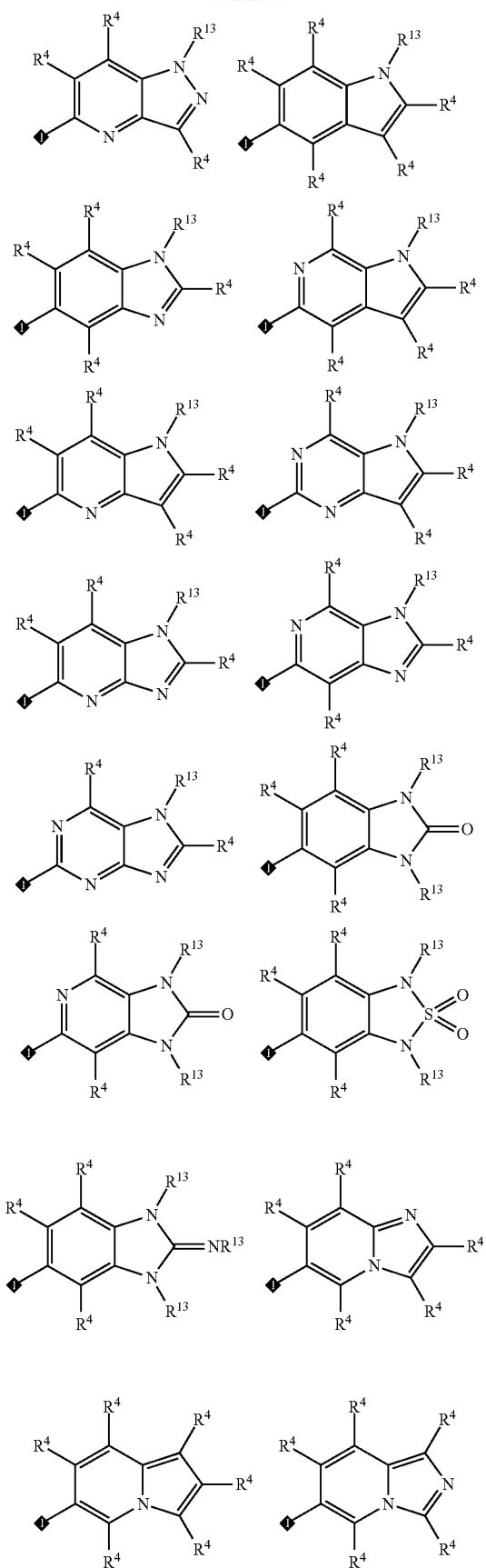
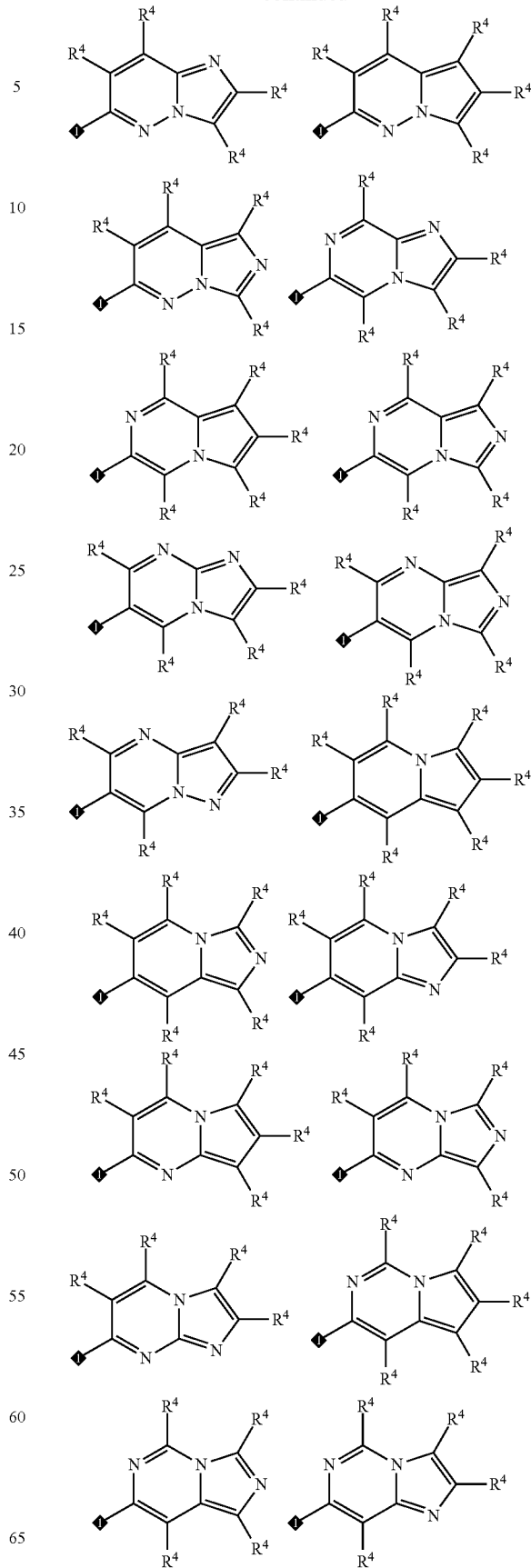

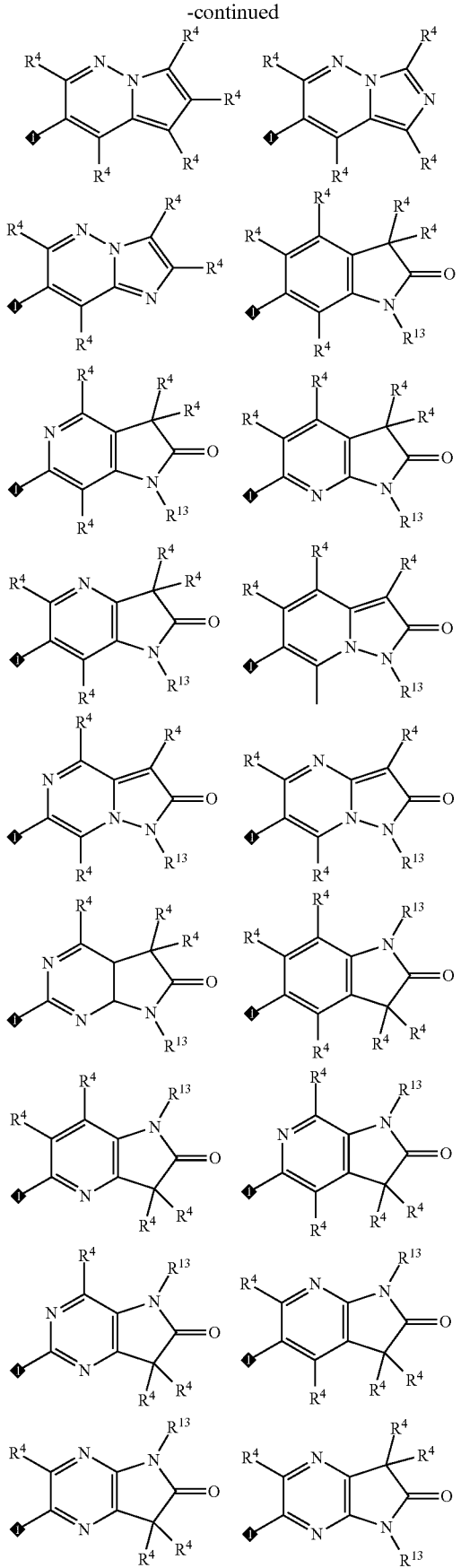
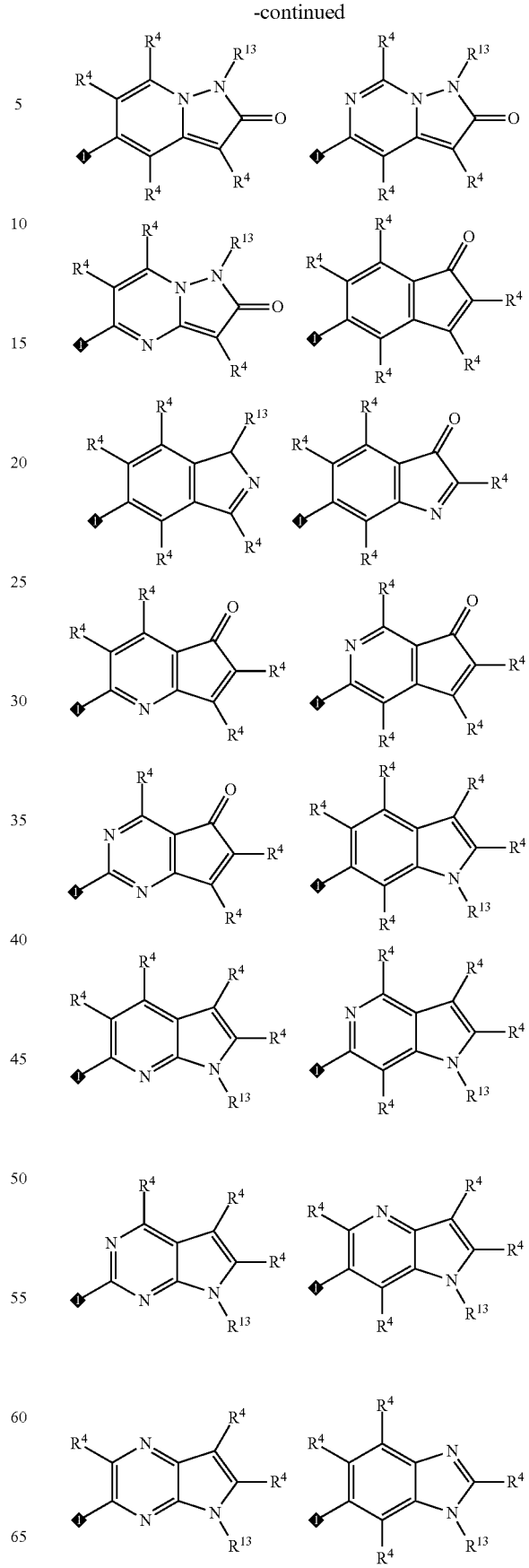

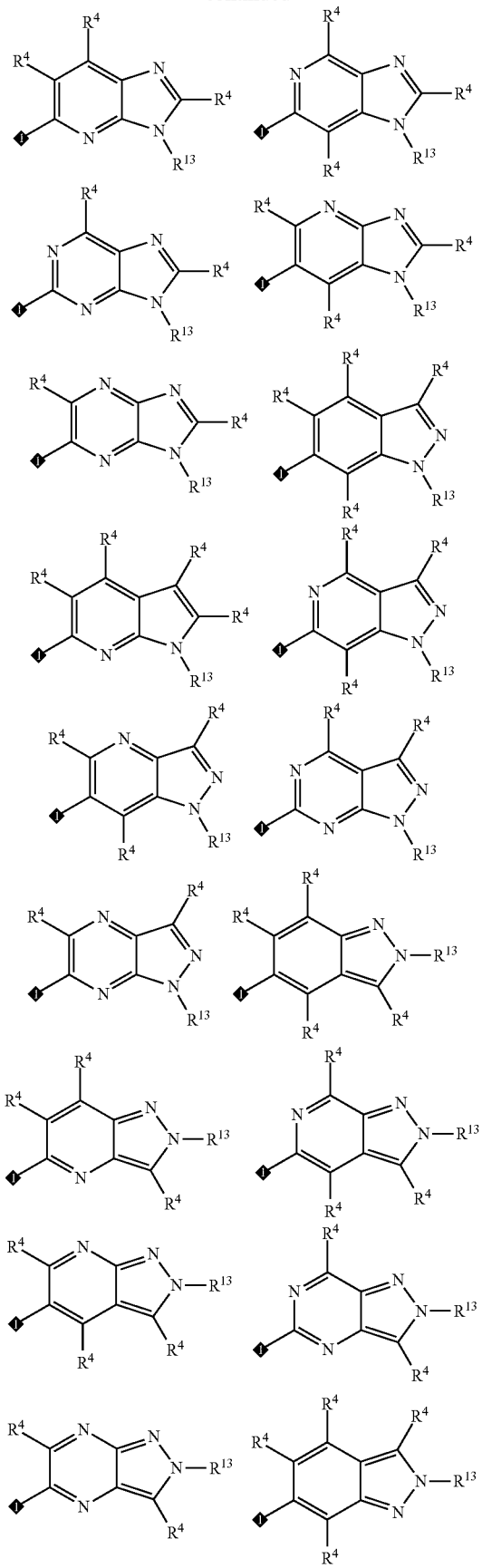
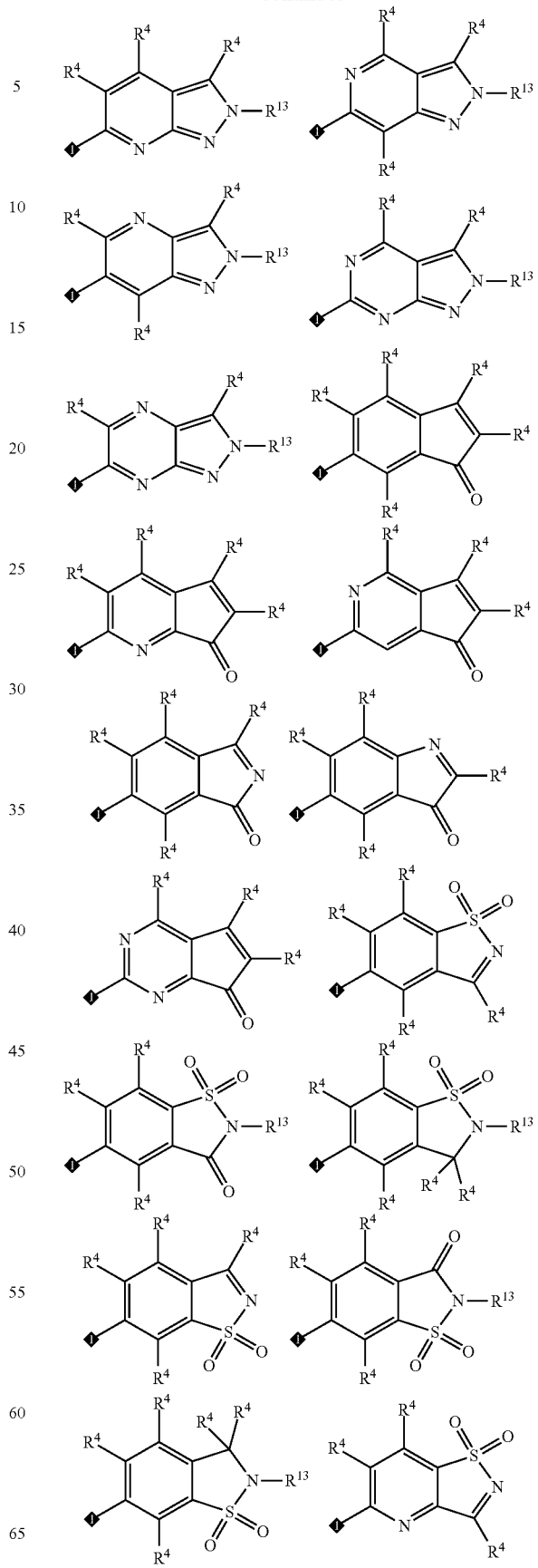

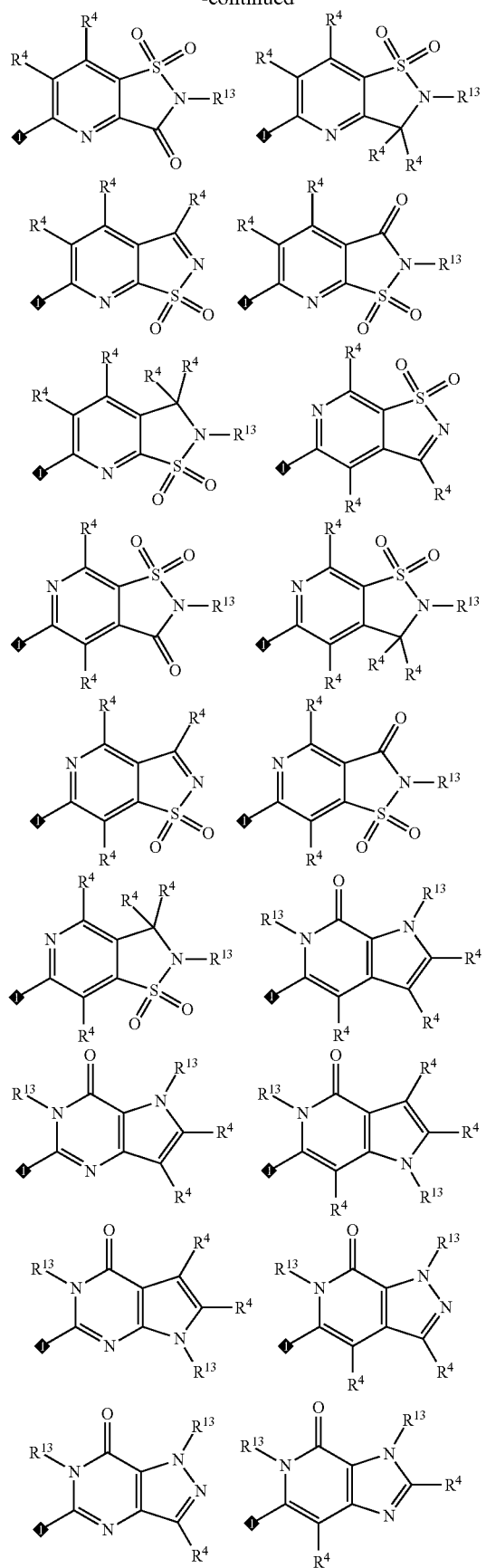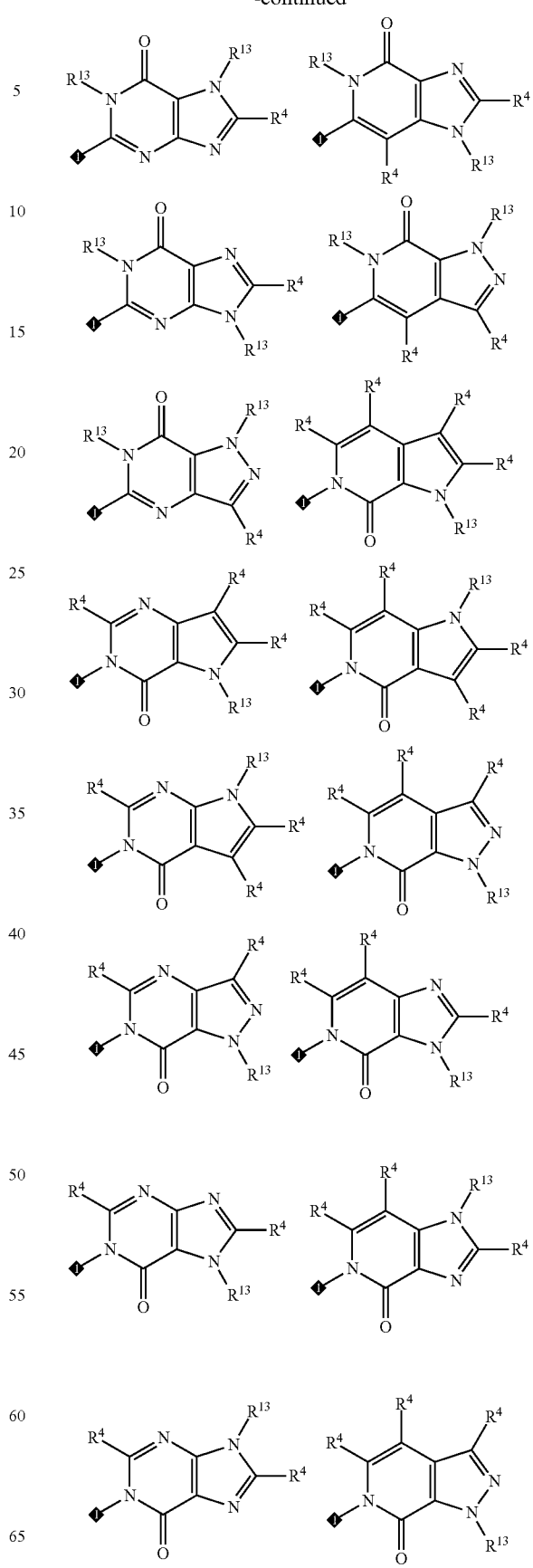

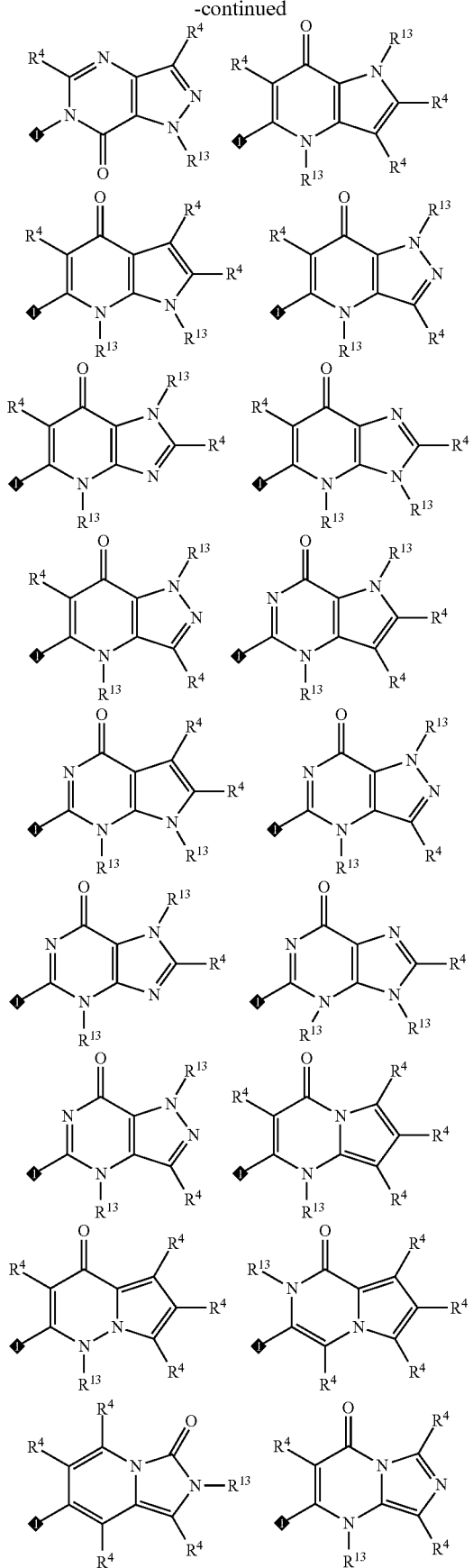
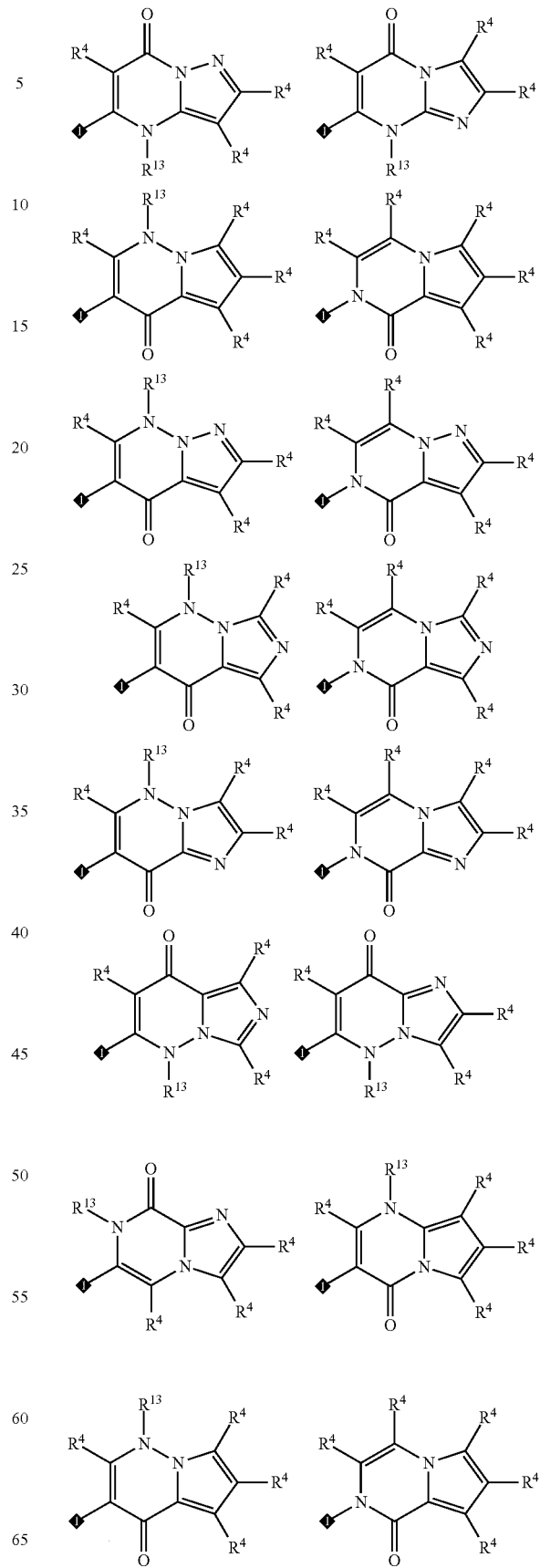

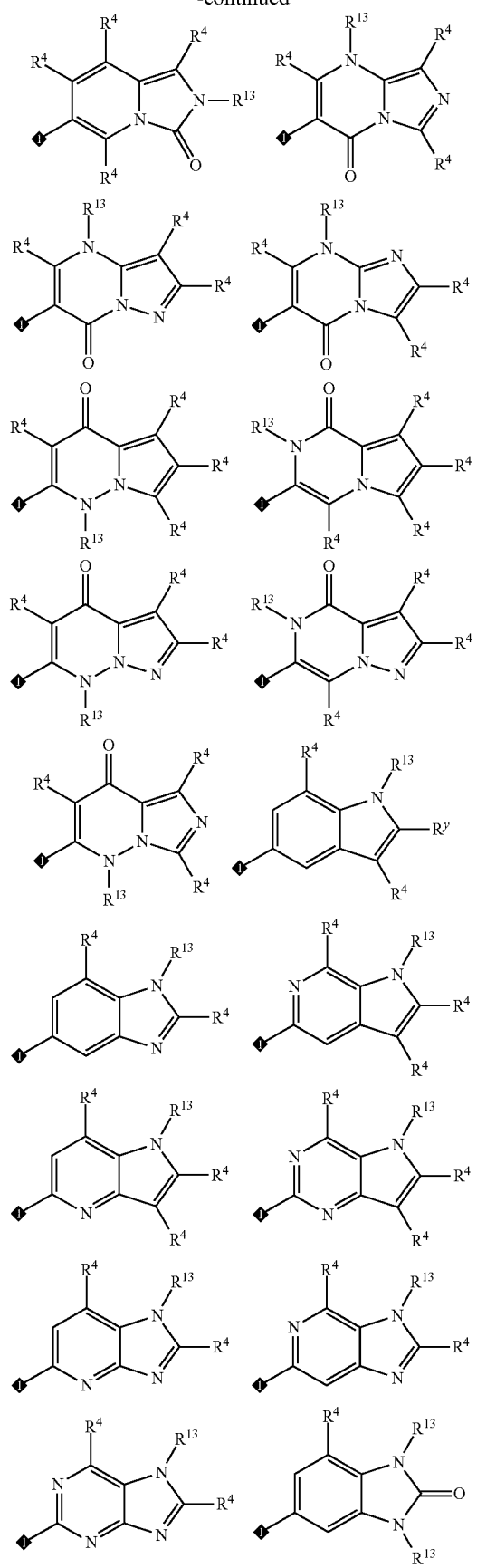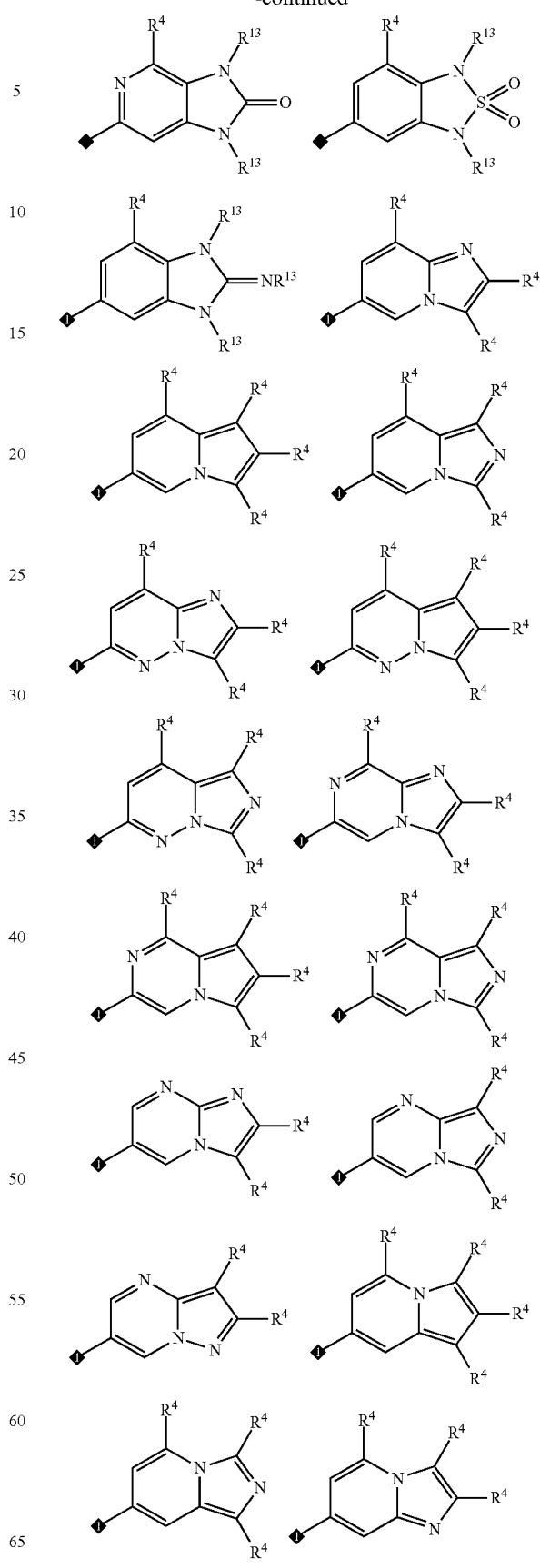

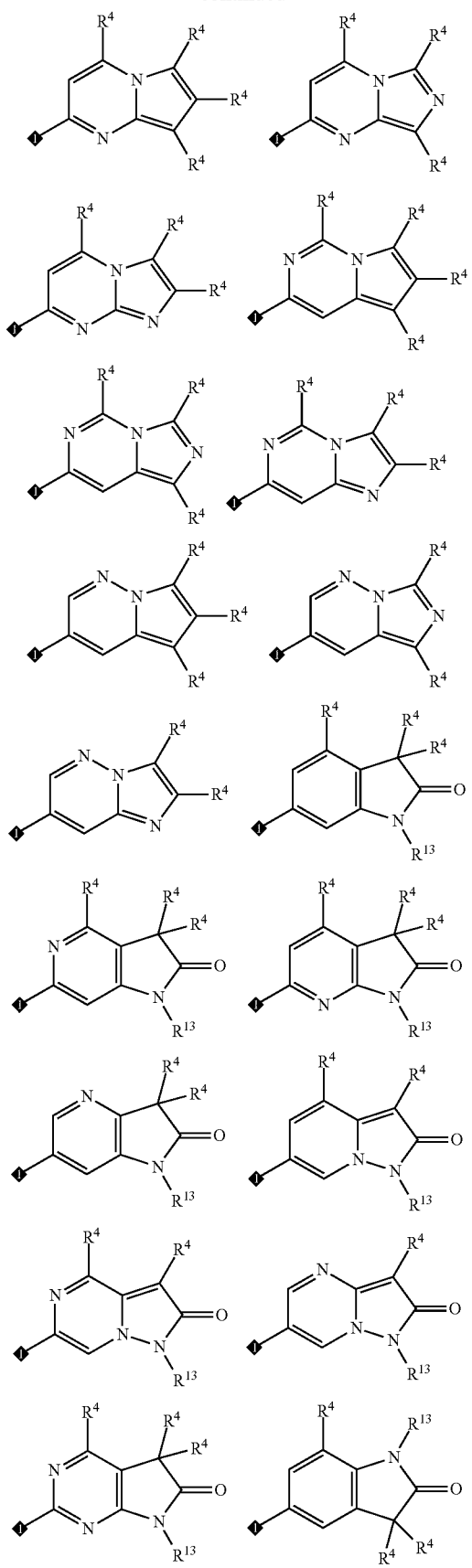
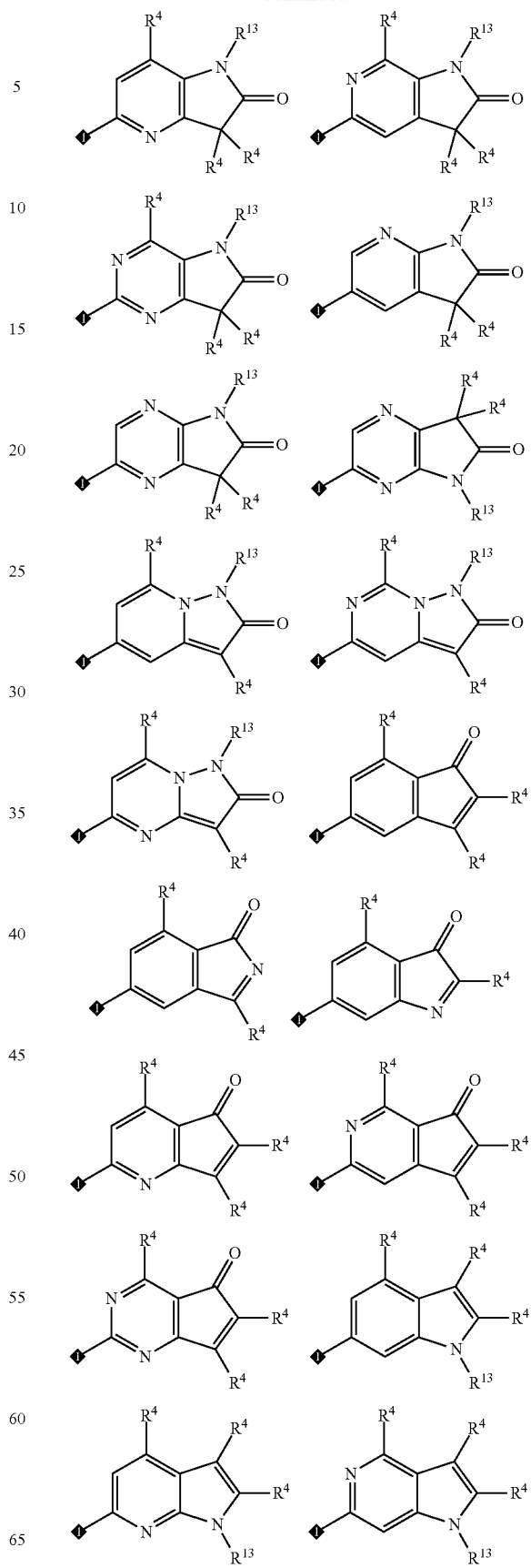

247
-continued
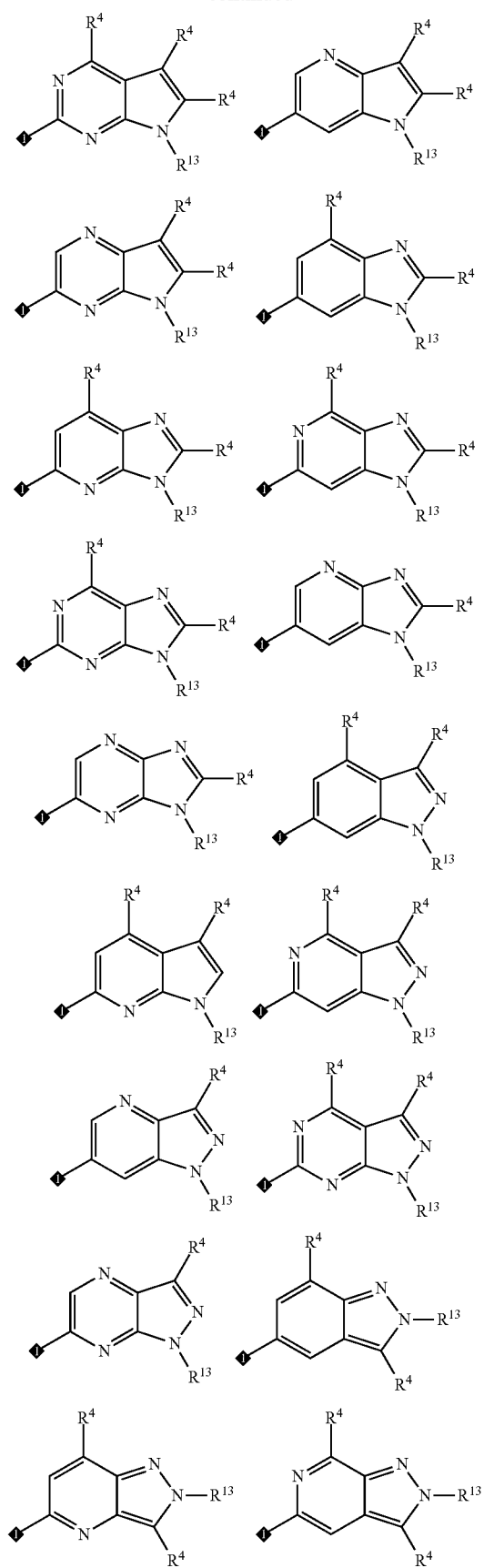
248
-continued
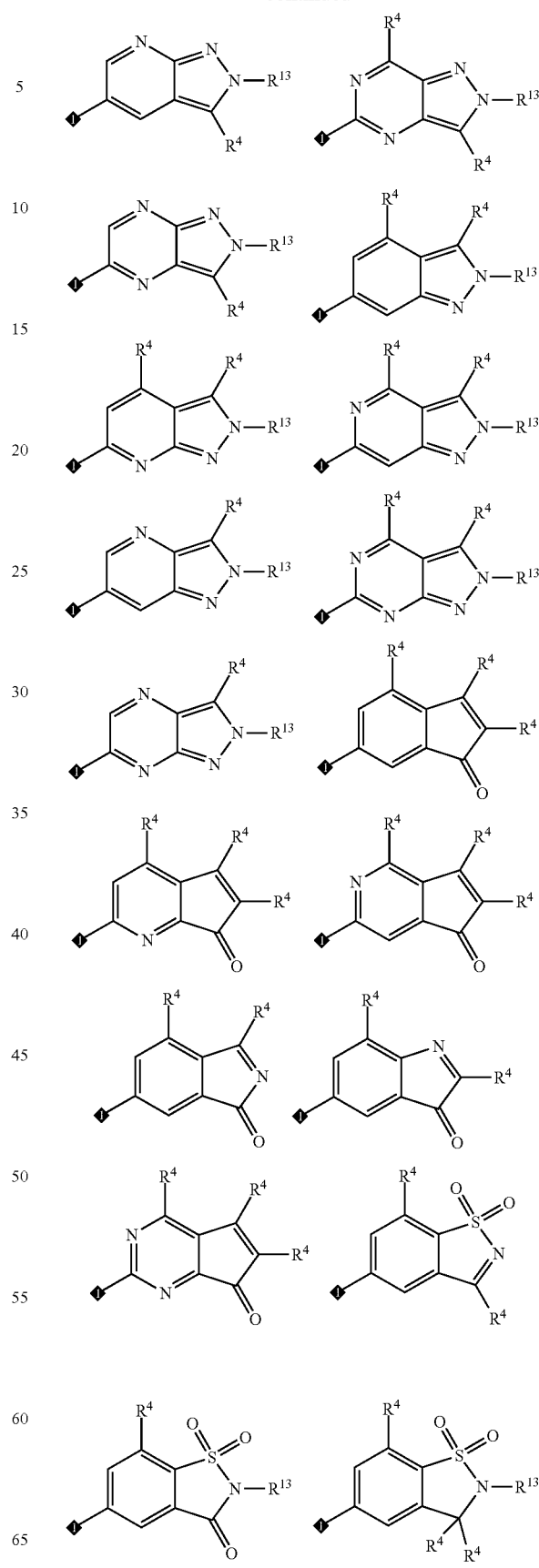

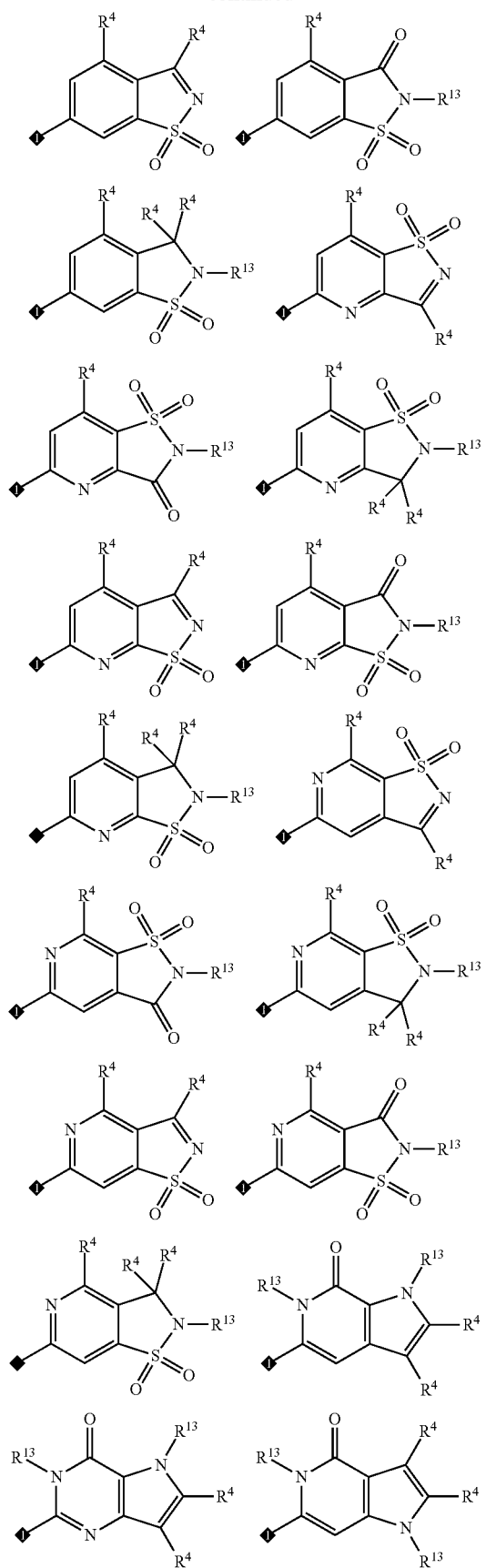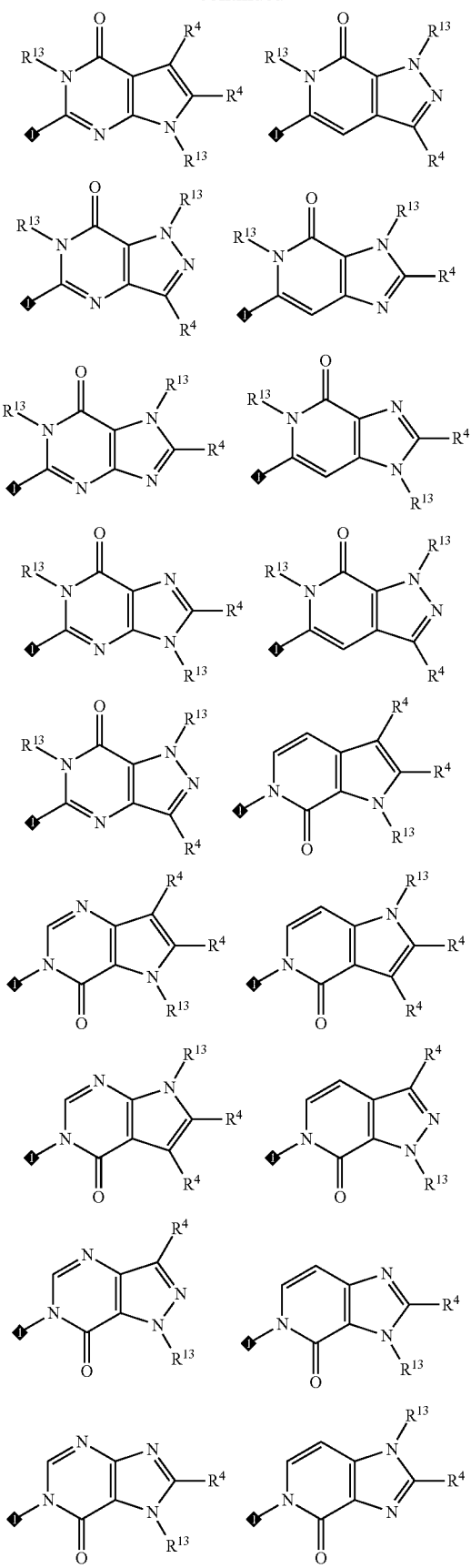

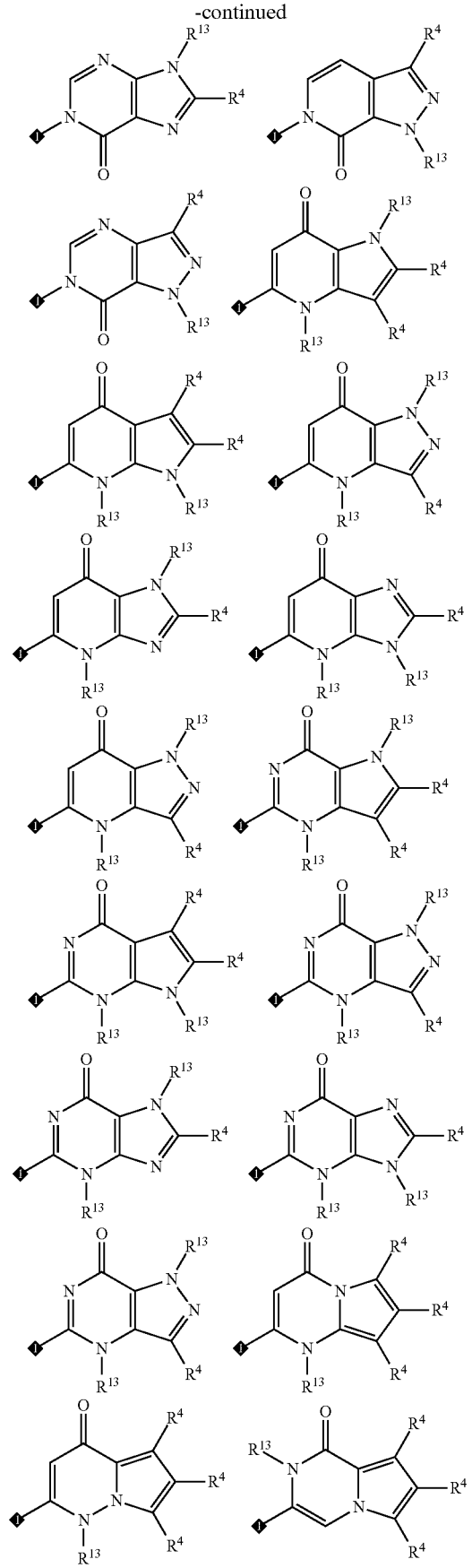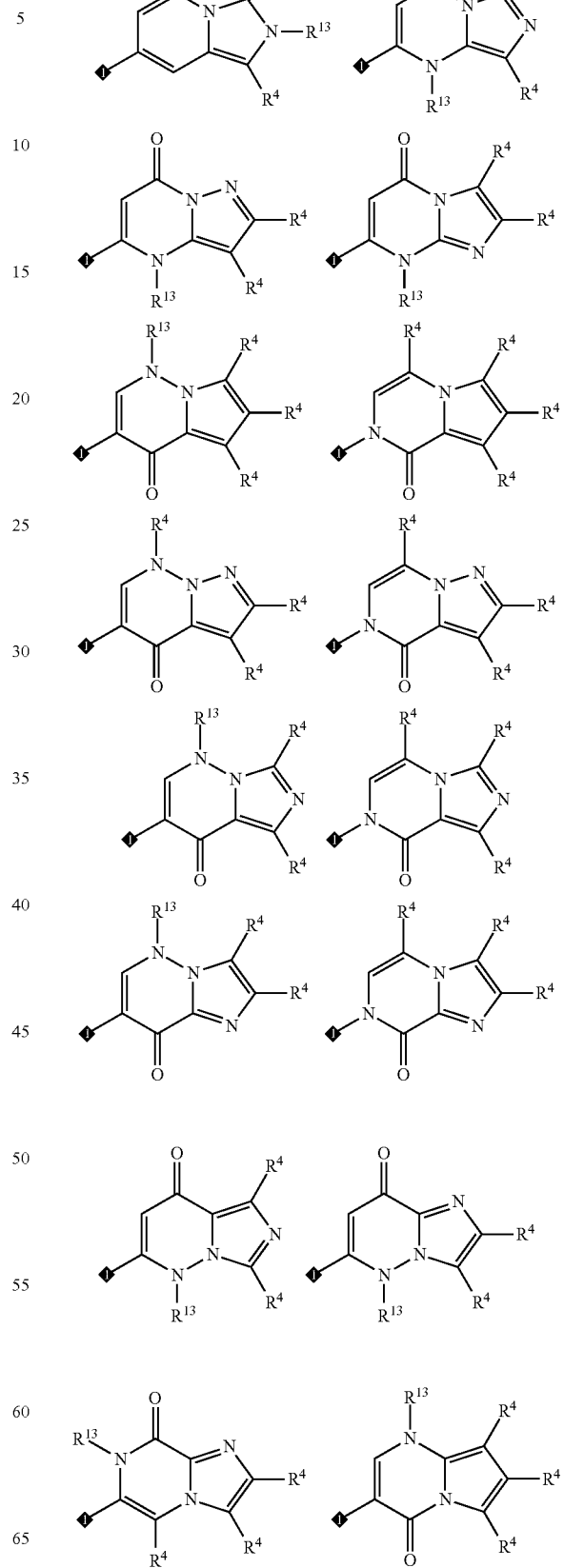

-continued
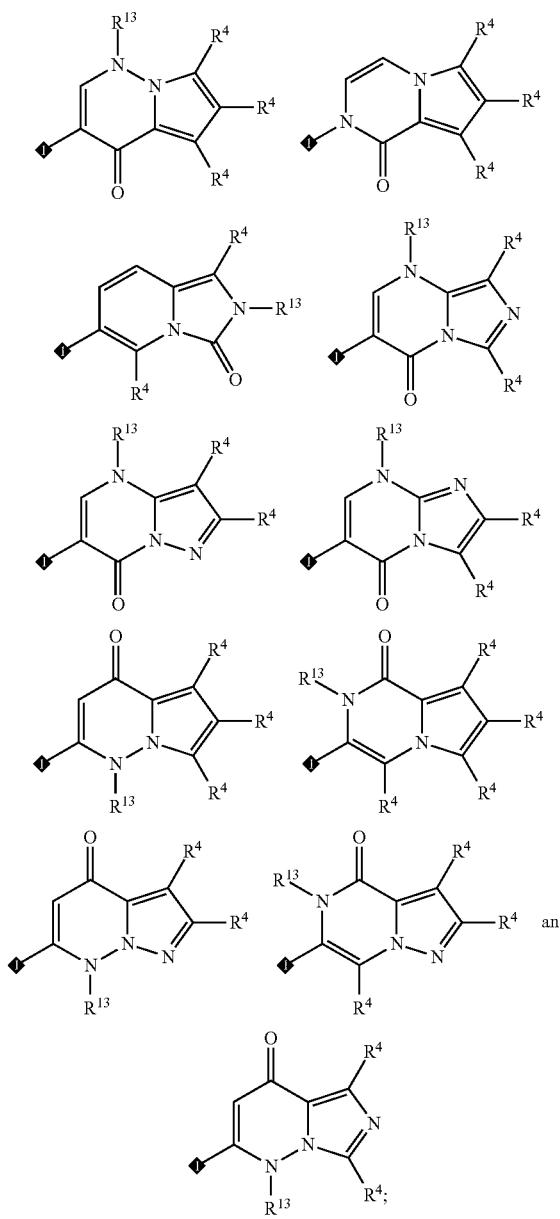
wherein R⁴ and R¹³ are as defined above for formulae (I) or (IA).
In one embodiment of formula (IIA^{4b}), A^{4b} is selected from the group consisting of:
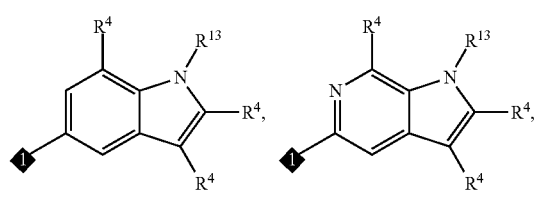
-continued
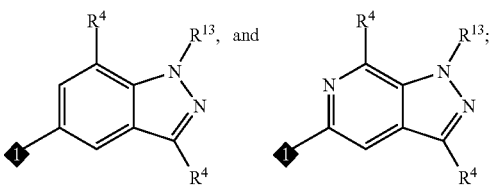
wherein R⁴ and R¹³ are as defined above for formulae (I) or (IA).
In one embodiment, the present disclosure relates to the compound of formula (IIA^{4b}), wherein A^{4b} is selected from the group consisting of:
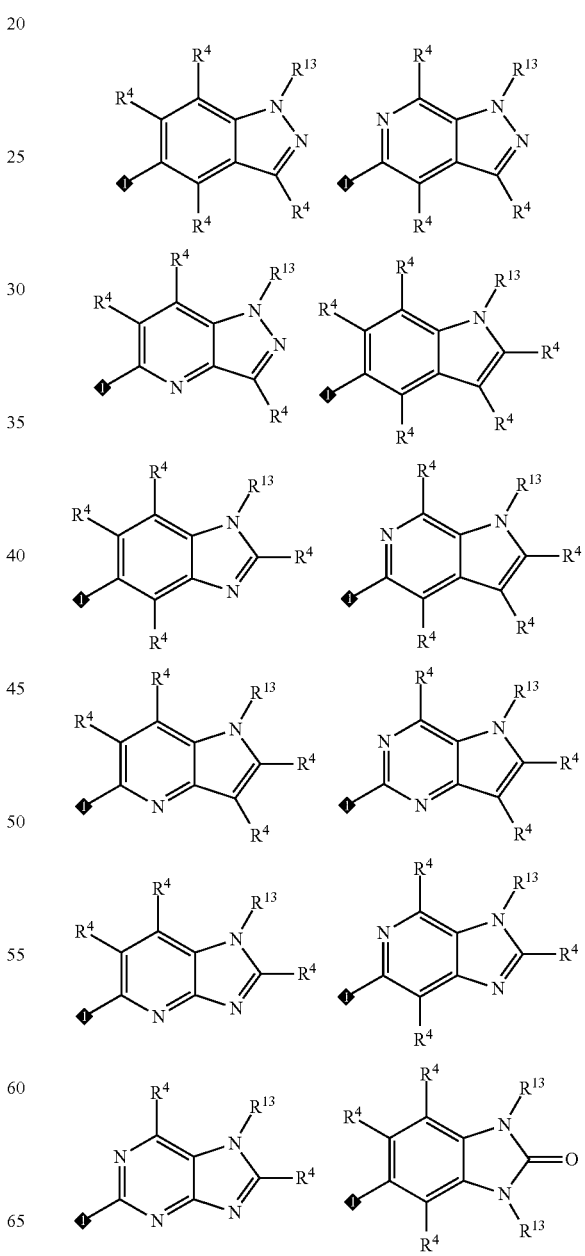

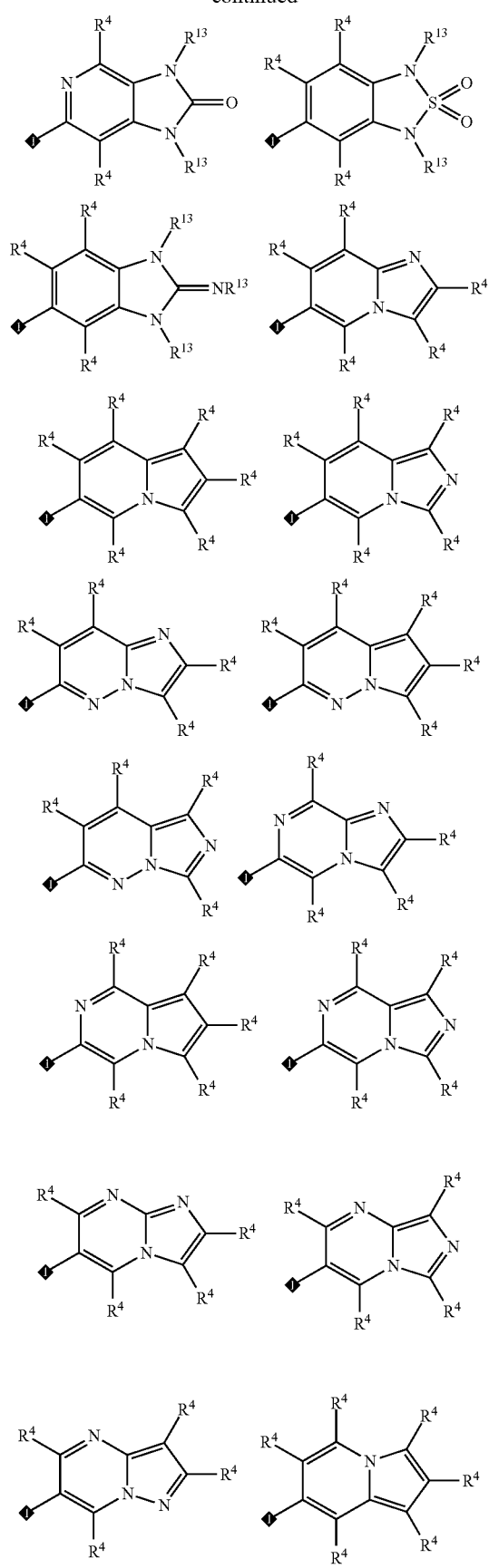
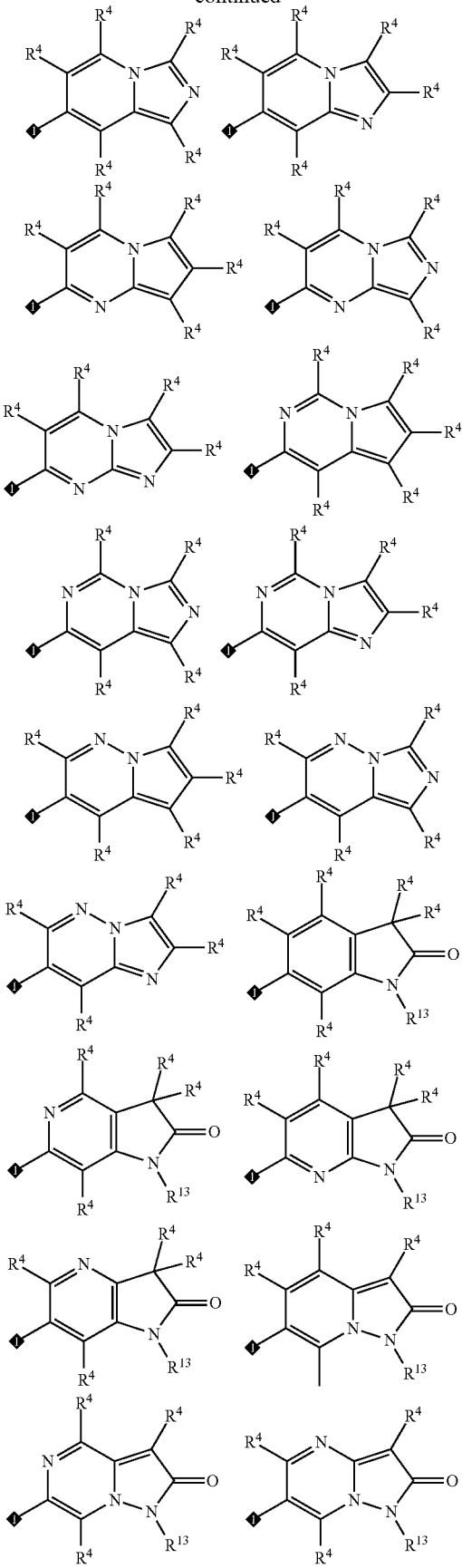

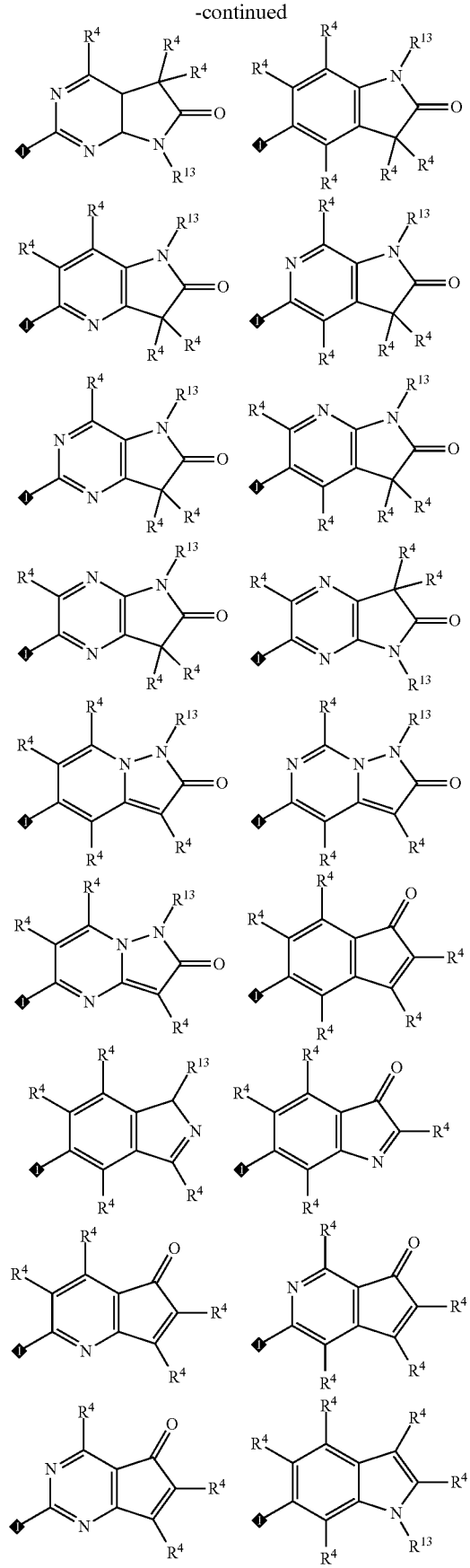
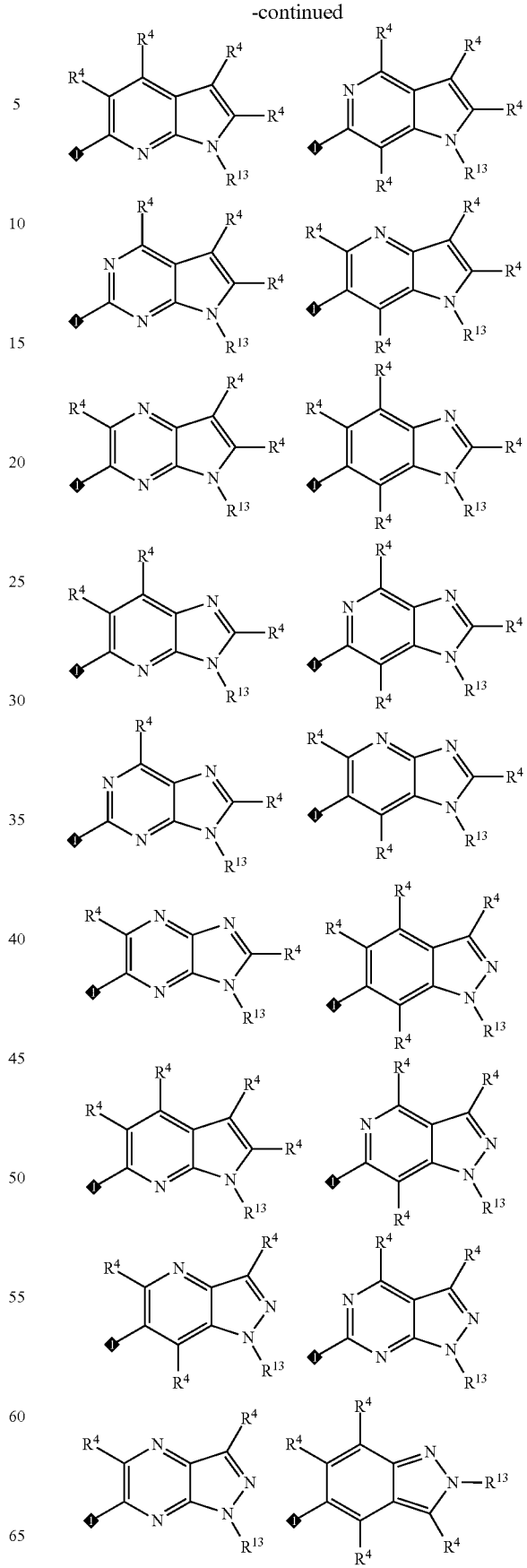

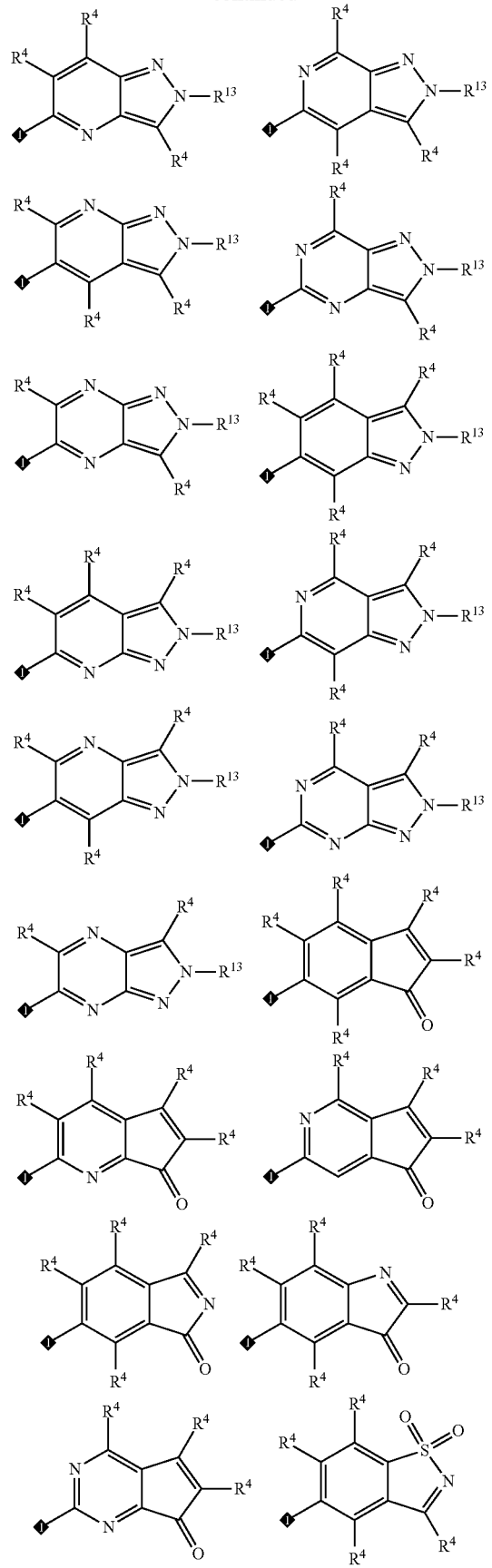
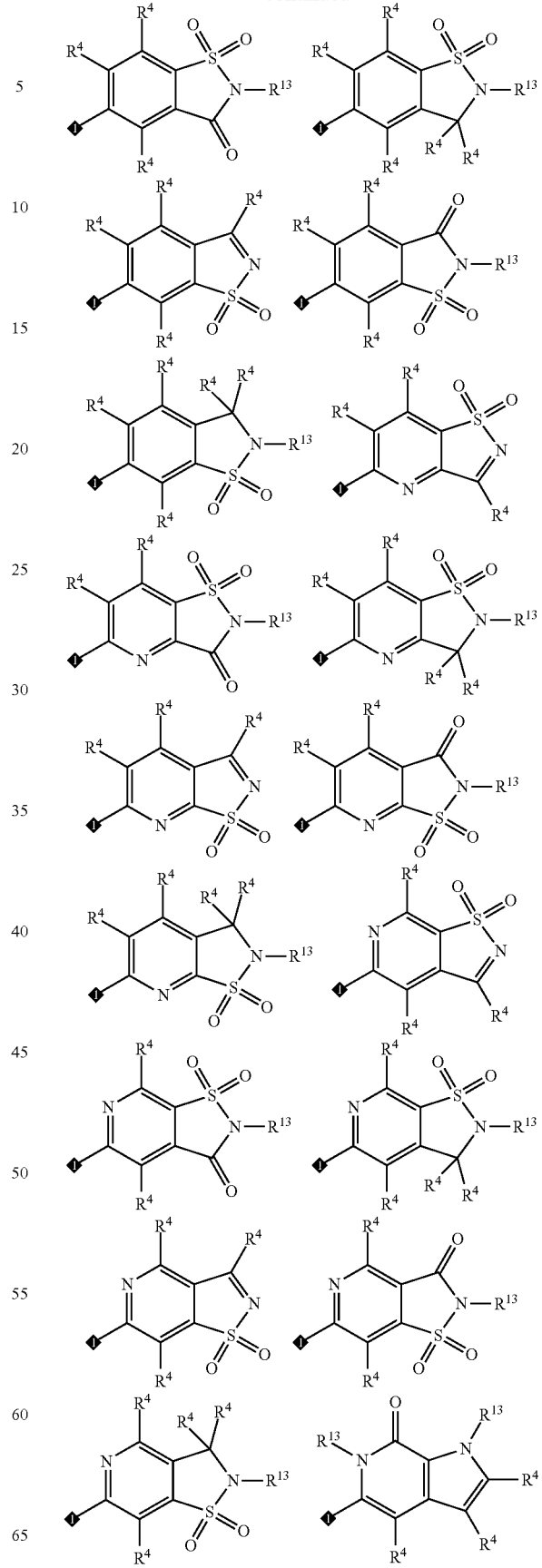

261
-continued
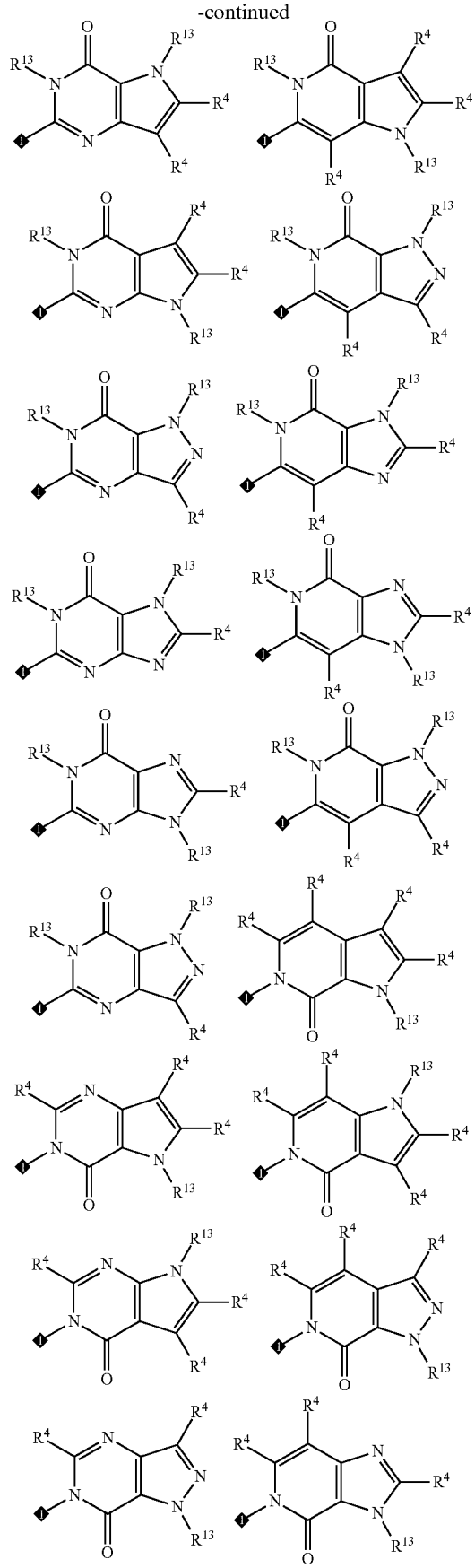
262
-continued
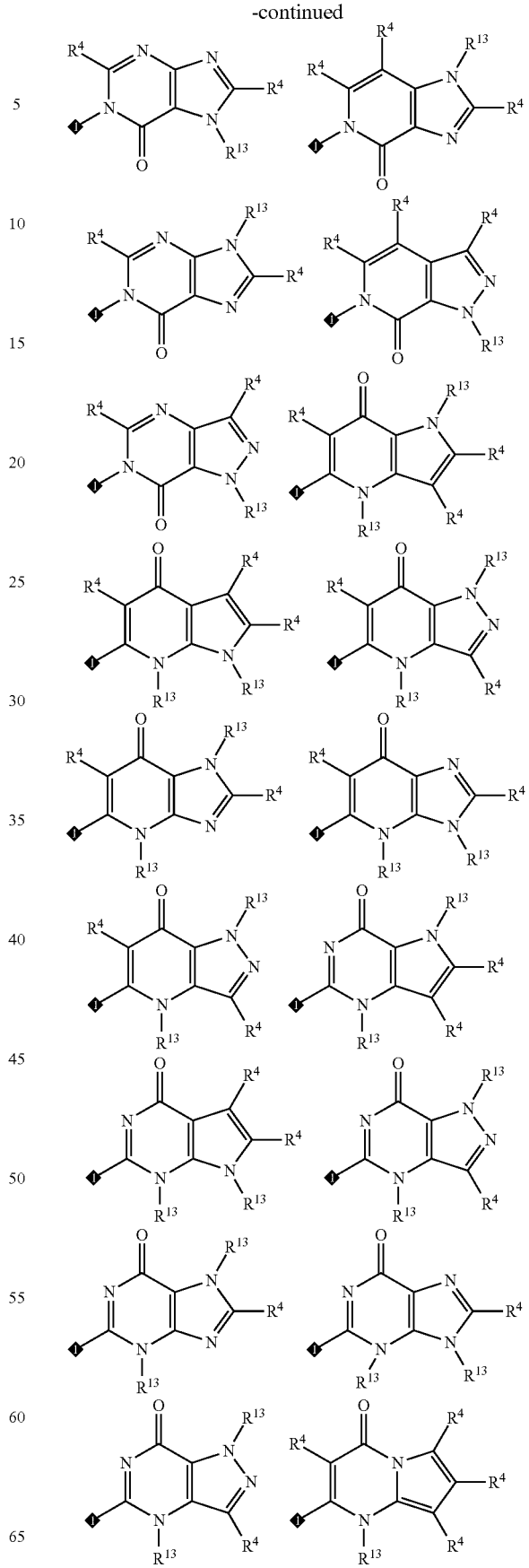

-continued
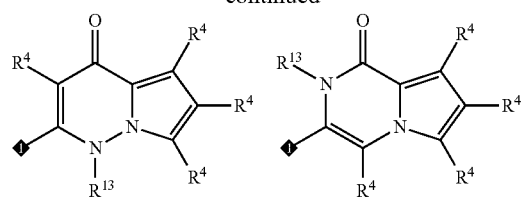
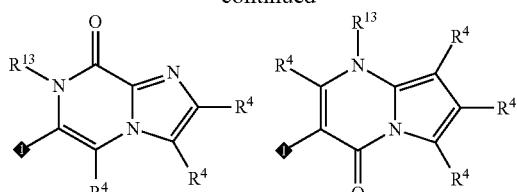
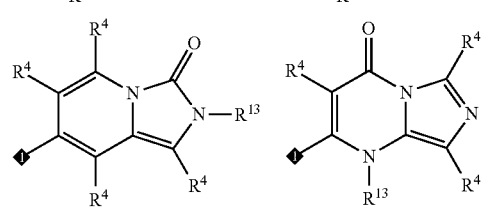
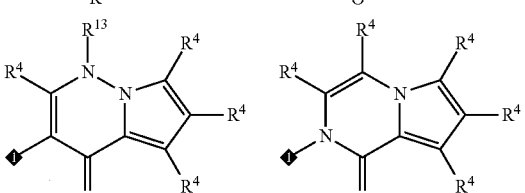
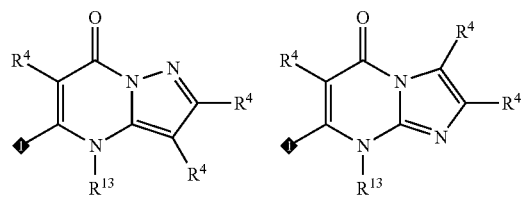
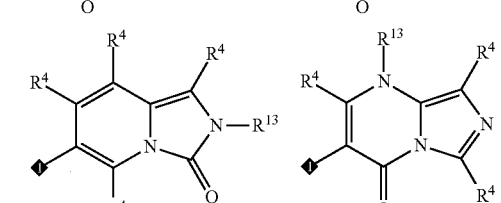
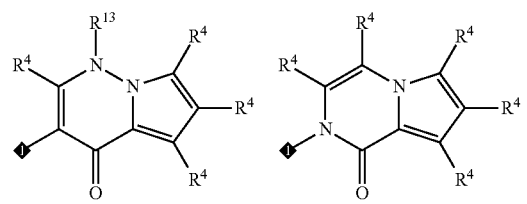
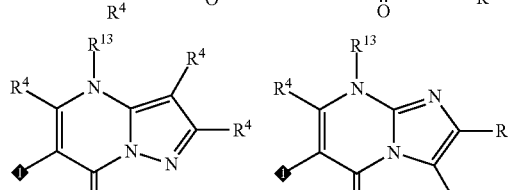
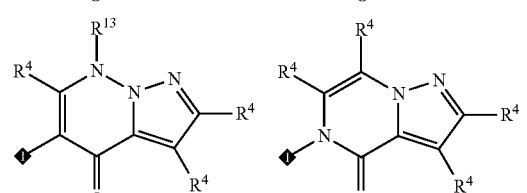
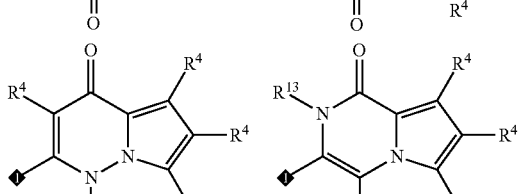
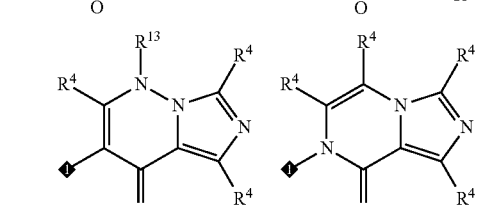
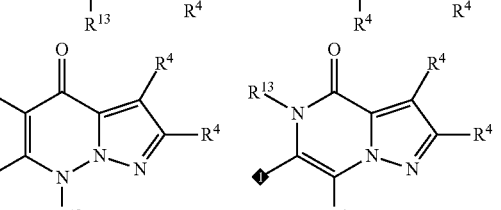
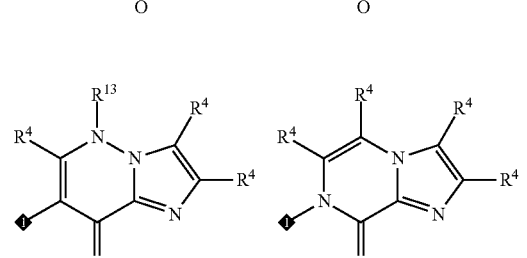
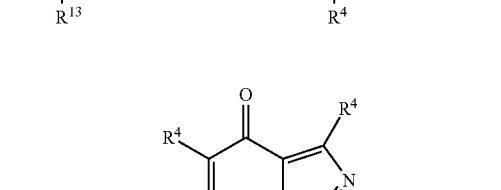
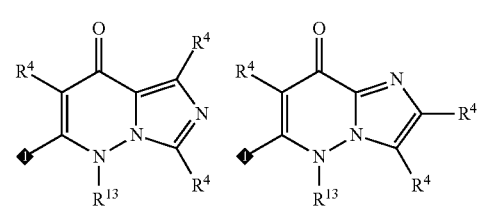
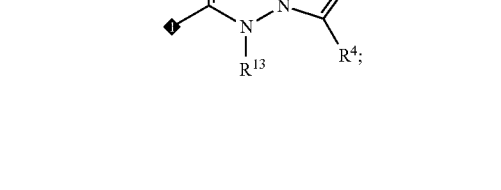
wherein $R^4$ and $R^{13}$ have the same definitions as described in for formula (I) or formula (IA).
In one embodiment, the present invention relates to a compound of the formula (IIA$^5$)

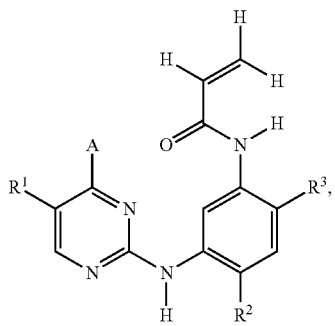

(IIA⁵)

or a stereoisomer or a pharmaceutically acceptable salt, solvate, ester, or prodrug thereof;

wherein:

A is

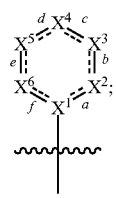

A⁵ each of a, b, c, d, and e are independently either (formal) double bonds or (formal) single bonds, and none of $X^1$, $X^2$, $X^3$, $X^4$, $X^5$ and $X^6$ has two (formal) double bonds attached thereto;

each of $X^2$, $X^3$, $X^4$, $X^5$, $X^6$ is optionally substituted and is independently C or N; and the optional substituent is selected from the group consisting of =O (oxo), =S, =NR¹³, R⁴, and R¹³; or alternatively $X^2$, $X^3$, $X^4$, $X^5$, and $X^6$ are independently C, CH, CR⁴, C(R⁴)₂, CR¹³, CH₂, C=O, C=S, C=NR¹³, N, NR⁴, NR¹³, or N(O);

$X^1$ is C, CH, or N; and

R¹, R², R³, R⁴, R⁸, R⁹ and R¹³ are as previously defined in formula (I) or (IA).

In one embodiment of formula (IIA⁵), A⁵ is selected from:

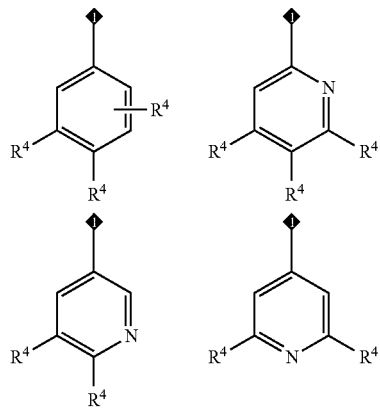

-continued

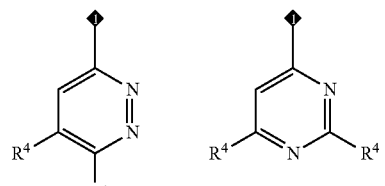

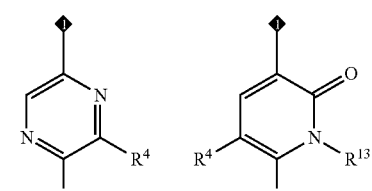

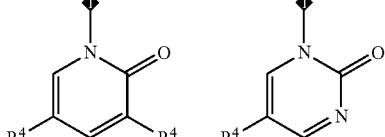

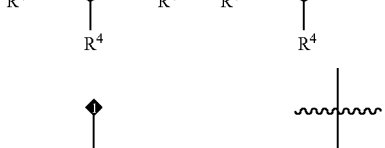

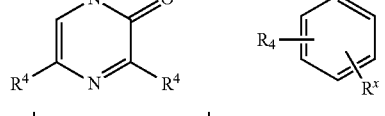

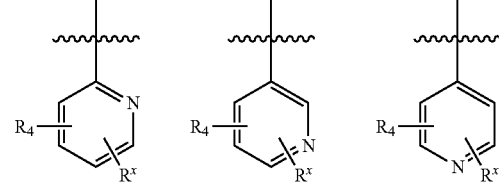

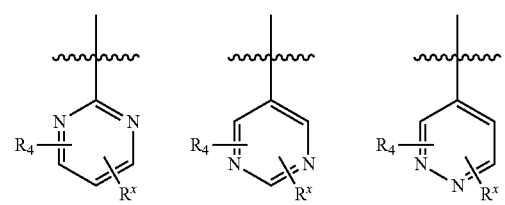

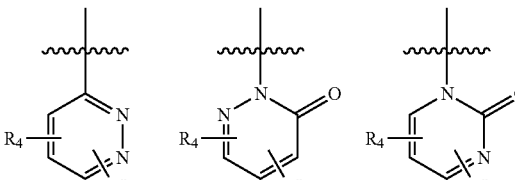

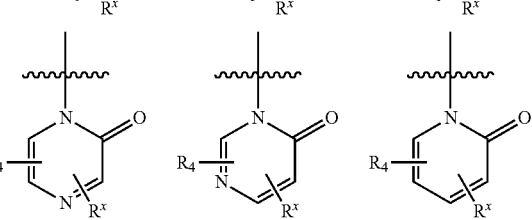

-continued

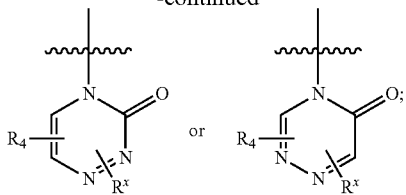

wherein $R^x$ is $R^{13}$; and $R^4$ and $R^{13}$ are as previously defined.

In one embodiment of formula (IIA$^5$), A$^5$ is selected from the group consisting of:

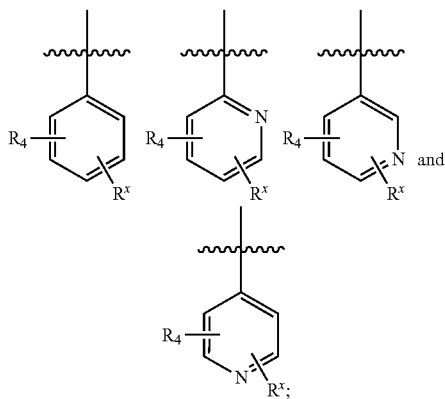

wherein $R^x$ is $R^{13}$; and $R^4$ and $R^{13}$ are as previously defined.

In one embodiment of formulae (IIA$^1$), (IIA$^2$), (IIA$^3$), (IIA$^{4a}$), (IIA$^{4b}$), and/or (IIA$^5$), $R^3$ is —N(R$^{10}$)C$_{2-6}$ alkyl-NR$^{10}$R$^{10}$. In another embodiment, $R^3$ is —N(CH$_3$)—CH$_2$—CH$_2$—N(CH$_3$)$_2$.

In one embodiment of formulae (IIA$^1$), (IIA$^2$), (IIA$^3$), (IIA$^{4a}$), (IIA$^{4b}$), and/or (IIA$^5$), $R^2$ is —OCF$_3$, —OCHF$_2$, —OCF$_2$CF$_3$, —OCH$_2$CHF$_2$, —OCH$_2$CF$_3$, methoxy, ethoxy, or isopropoxy.

In one embodiment of formulae (IIA$^1$), (IIA$^2$), (IIA$^3$), (IIA$^{4a}$), (IIA$^{4b}$), and/or (IIA$^5$), $R^1$ is hydrogen;

In one embodiment, the present invention relates to a compound of the formula (VII)

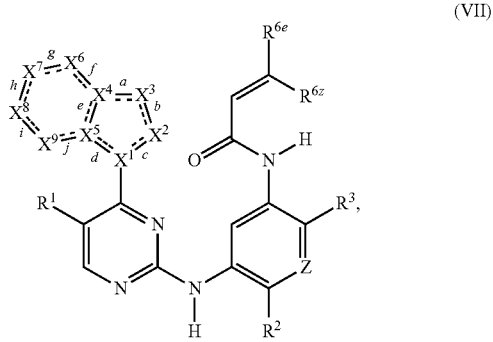

(VII)

or stereoisomers and pharmaceutically acceptable salts or solvates thereof;

each of a, b, c, d, e, f, g, h, i and j are independently either (formal) double bonds or (formal) single bonds, and none of X$^1$, X$^2$, X$^3$, X$^4$, X$^5$, X$^6$, X$^7$, X$^8$, and X$^9$ has two (formal) double bonds attached thereto;

each of X$^1$, X$^2$, X$^3$, X$^6$, X$^7$, X$^8$, and X$^9$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$;

X$^1$ is C, CH or N;

X$^2$ is N, NR$^{13}$, C(R$^4$)$_2$, S(O)$_x$, C(O), or CR$^4$;

X$^3$ is N, NR$^{13}$, C(R$^4$)$_2$, C(O), S(O)$_x$, or C(R$^4$);

X$^4$ and X$^5$ are independently C or N, with the proviso that X$^4$ and X$^5$ are not both N; and if X$^1$, X$^4$ and X$^5$ are all C, then one of X$^2$ and X$^3$ is O, S or NR$^{10}$;

X$^6$, X$^7$, X$^8$, and X$^9$ are independently CR$^4$ or N, with the proviso that at most two of X$^6$, X$^7$, X$^8$, and X$^9$ are N; and $R^1$, $R^2$, $R^3$, $R^{6e}$, and $R^{6z}$ have the same definitions as described above for formula (I).

In one embodiment, the present invention relates to a compound of the formula (VIII)

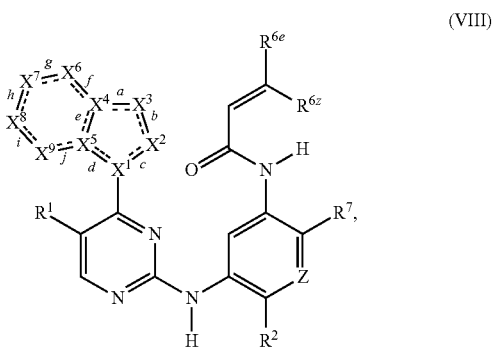

(VIII)

or stereoisomers and pharmaceutically acceptable salts or solvates thereof;

$R^7$ is selected from the group consisting of (3R)-3-(dimethylamino)pyrrolidin-1-yl, (3S)-3-(dimethyl-amino)pyrrolidin-1-yl, 3-(dimethylamino)azetidin-1-yl, [2-(dimethylamino)ethyl]-(methyl)amino, [2-(methylamino)ethyl](methyl)amino, 5-methyl-2,5-diazaspiro[3.4]oct-2-yl, (3aR,6aR)-5-methylhexa-hydro-pyrrolo[3,4-b]pyrrol-1(2H)-yl, 1-methyl-1,2,3,6-tetrahydropyridin-4-yl, 4-methylpiperizin-1-yl, 4-[2-(dimethylamino)-2-oxoethyl]piperazin-1-yl, methyl[2-(4-methylpiperazin-1-yl)ethyl]amino, methyl[2-(morpholin-4-yl)ethyl]amino, 1-amino-1,2,3,6-tetrahydropyridin-4-yl and 4-[(2S)-2-aminopropanoyl]piperazin-1-yl;

$R^{13}$ is a fused, bridged or spirocyclic bicyclic diamine of 7-12 ring atoms, which may be partially or fully saturated, and in which up to two further carbon atoms may be replaced with N, NR$^{10}$, O, S(O)$_x$, S(O)(NR$^{10}$), P=O, P(=O)(OR$^8$), OP(=O)(OR$^8$)O; all of which are optionally substituted with OH, OR$^{11}$, oxo, halogen, R$^{10}$, CH$_2$OR$^{10}$ NR$^8$R$^9$ or CH$_2$NR$^8$R$^9$; and $R^1$, $R^2$, $R^7$, $R^{6e}$, and $R^{6z}$ have the same definitions as described above for formula (I). In one embodiment of formulae (VII), or (VIII), A$^1$ is selected from the group consisting of

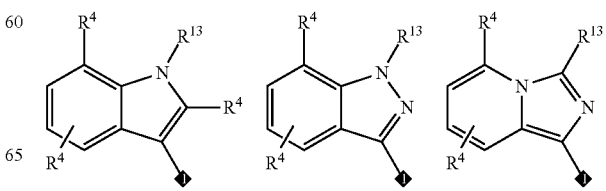

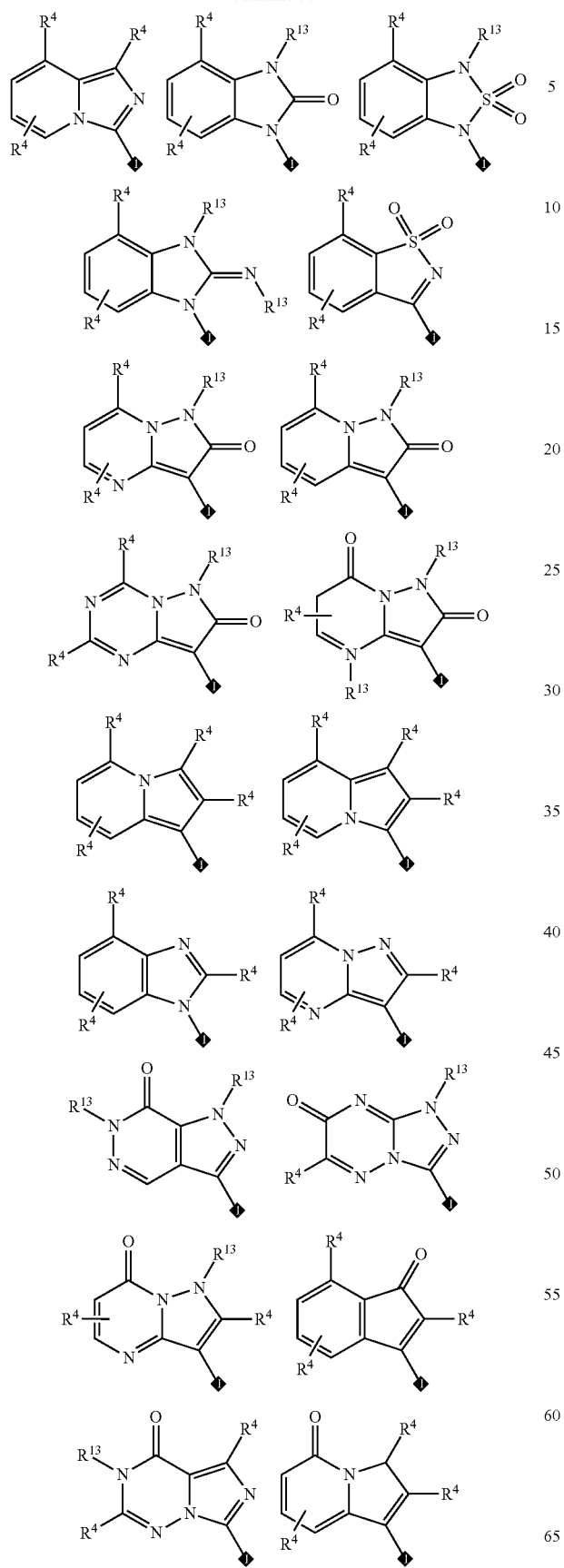
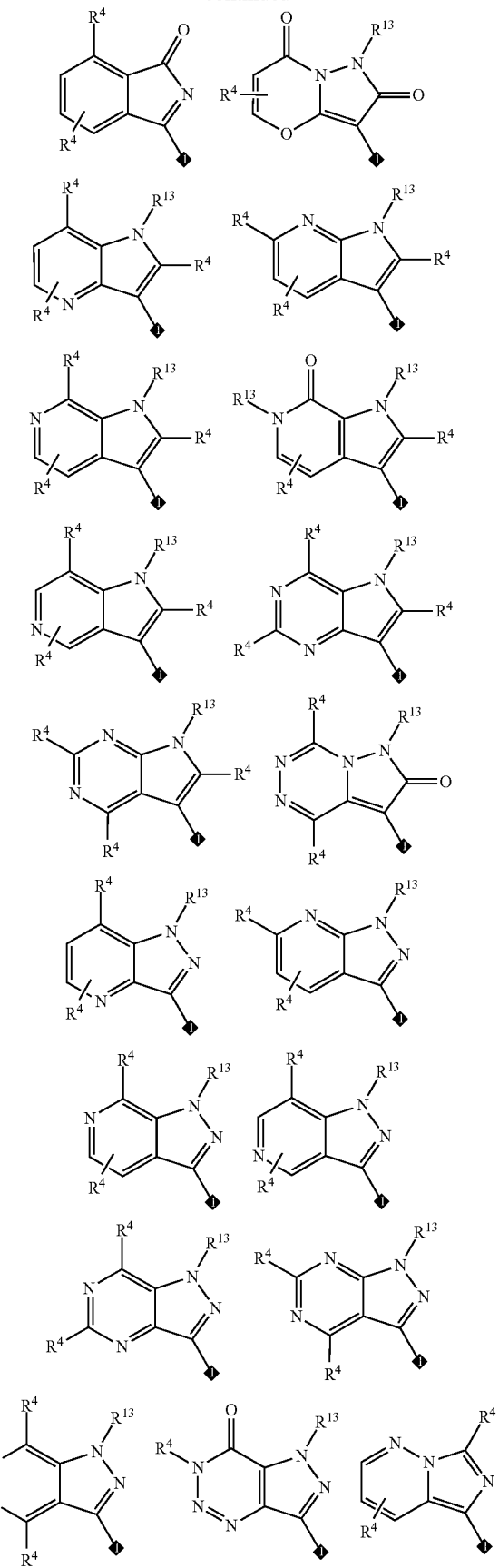

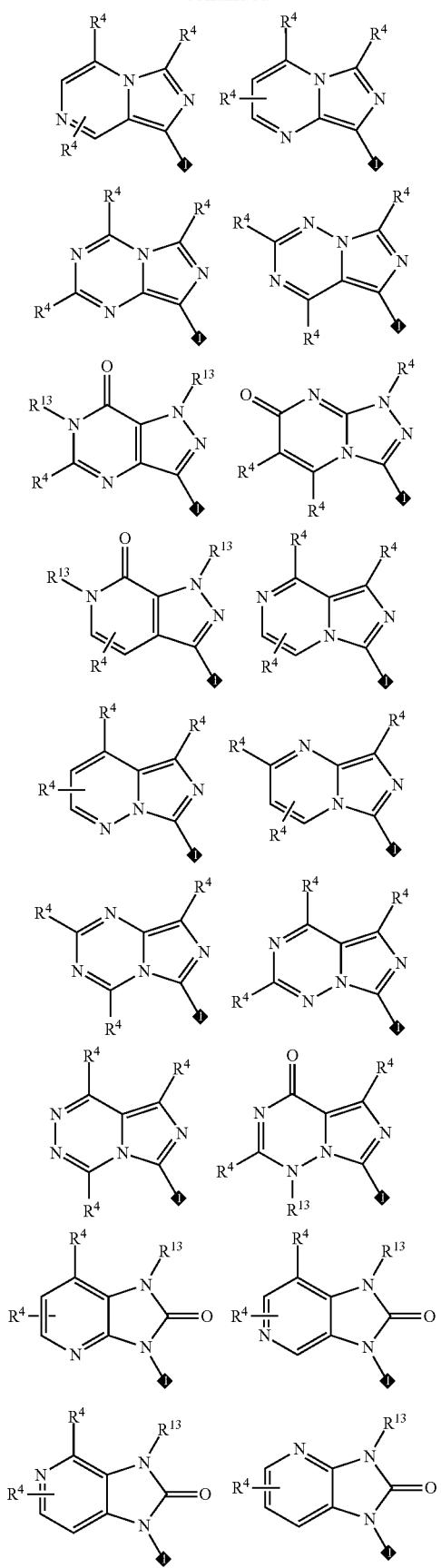
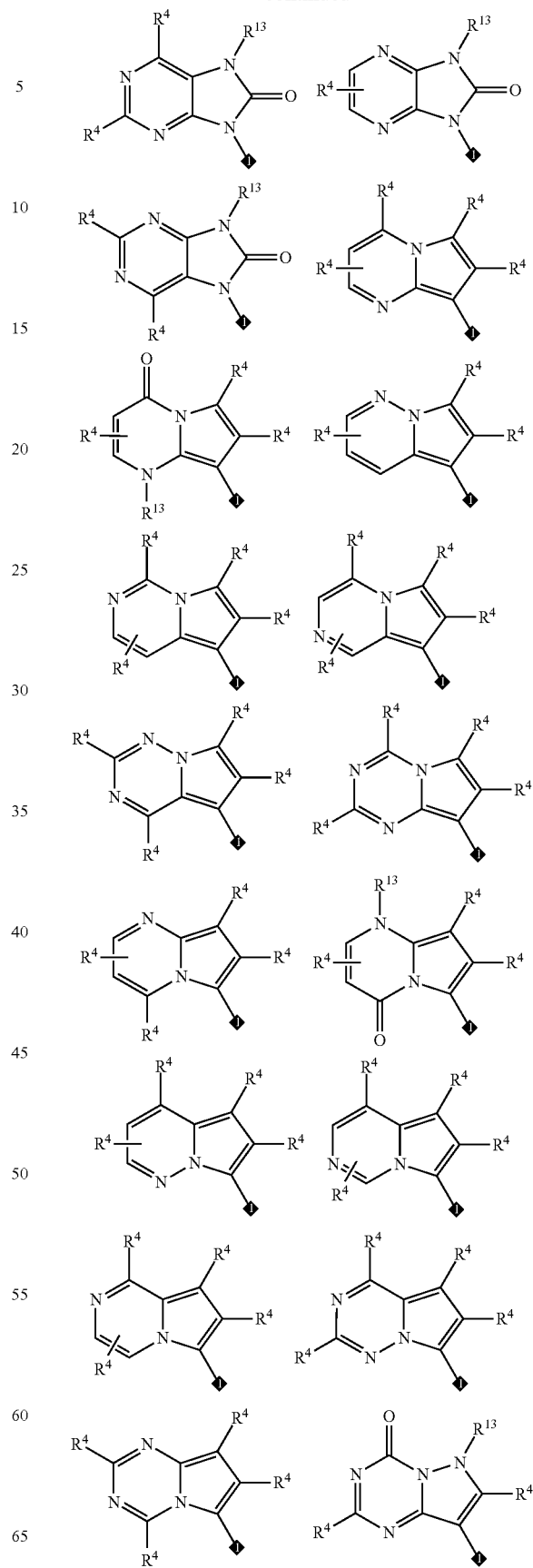

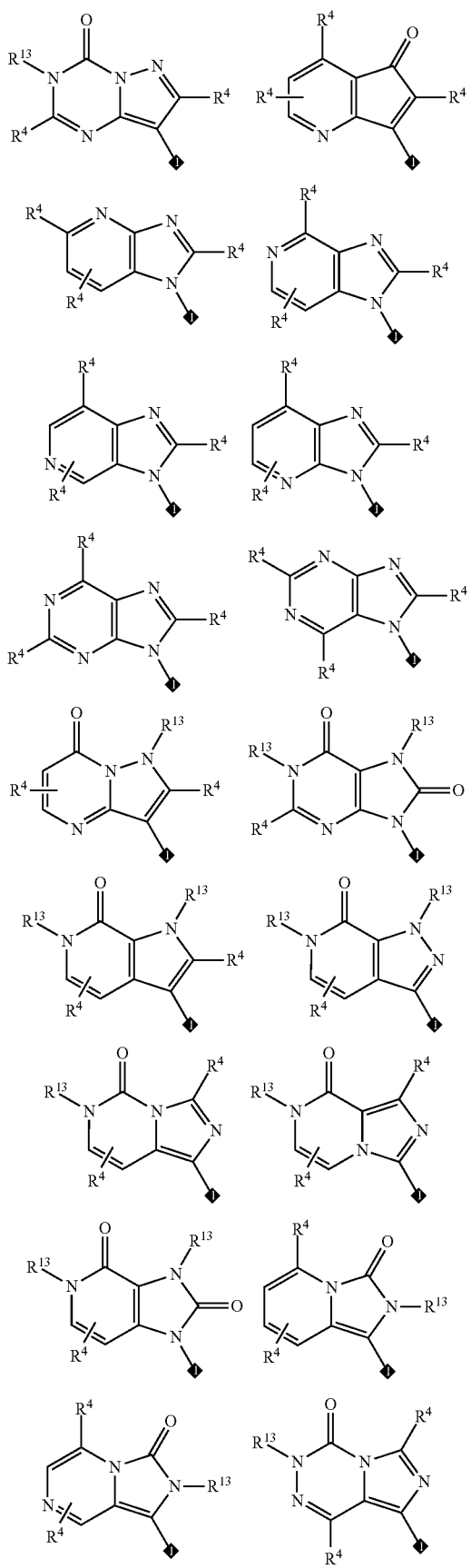
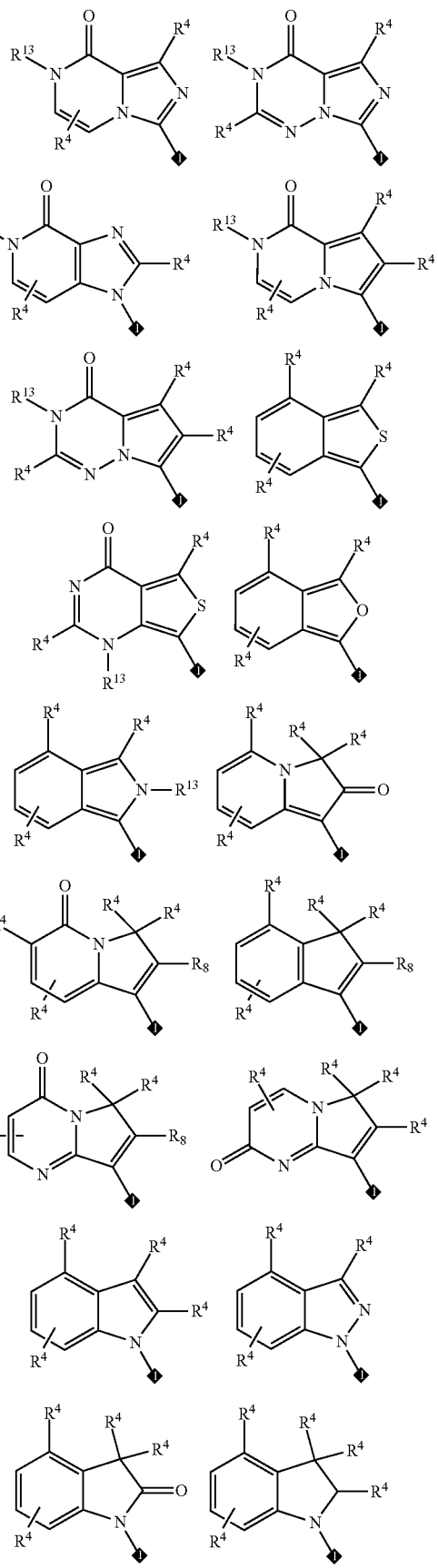

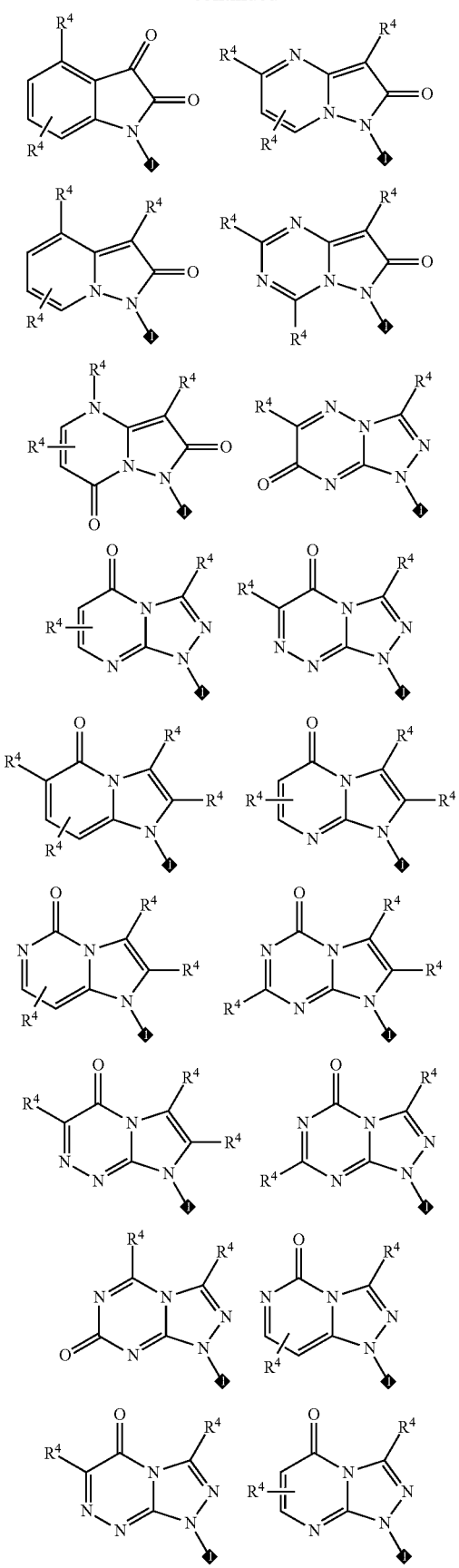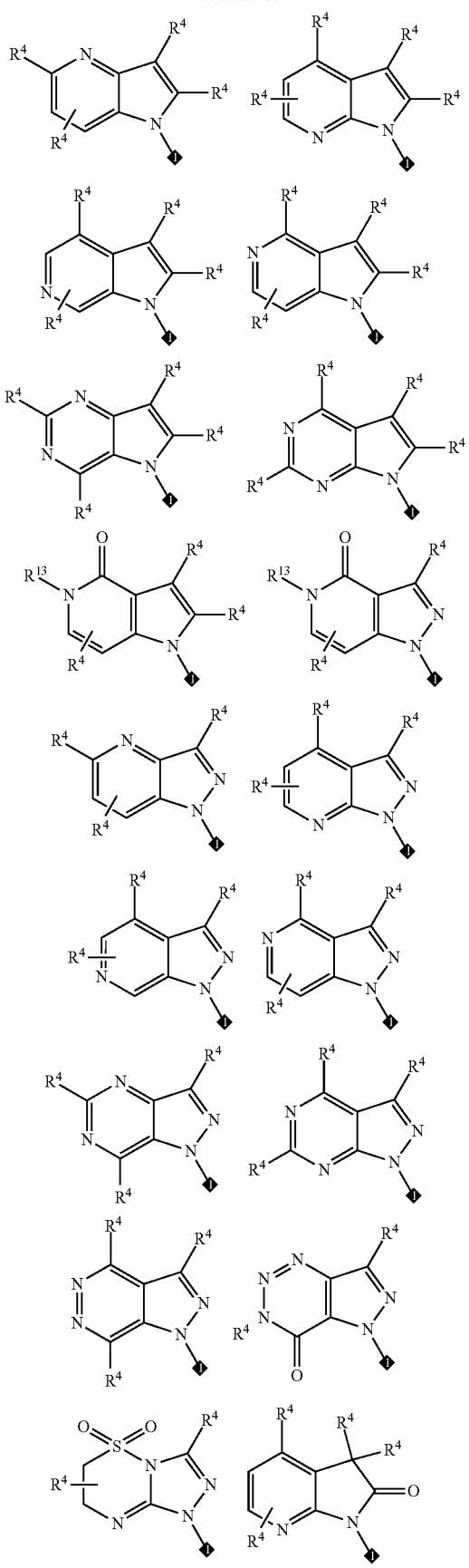

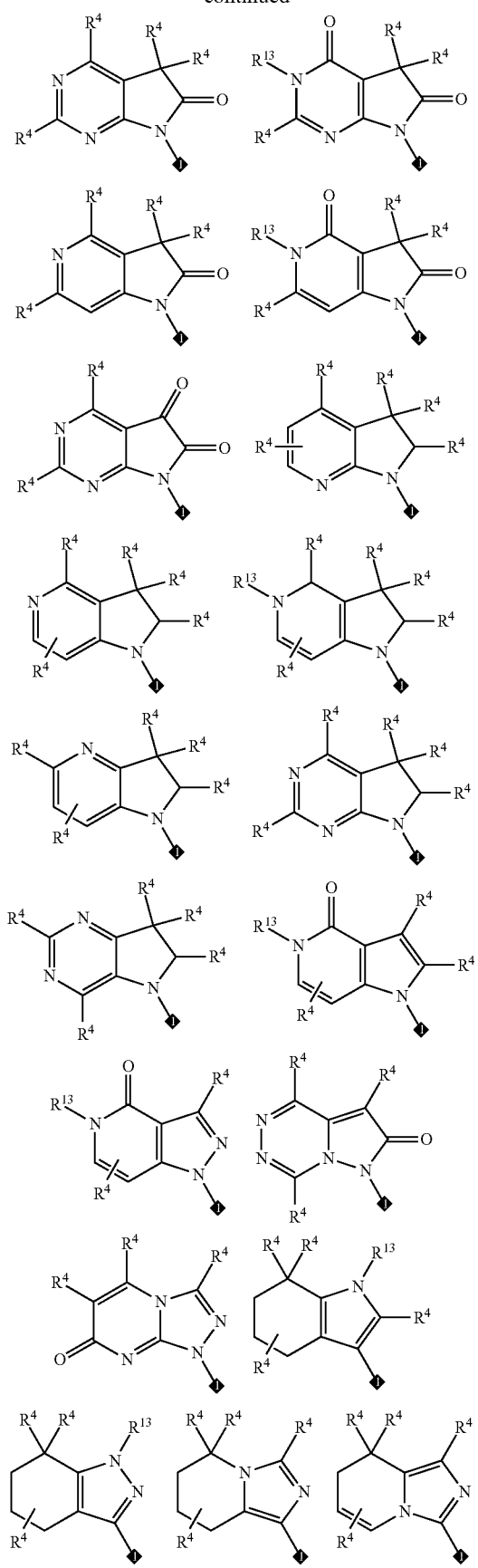
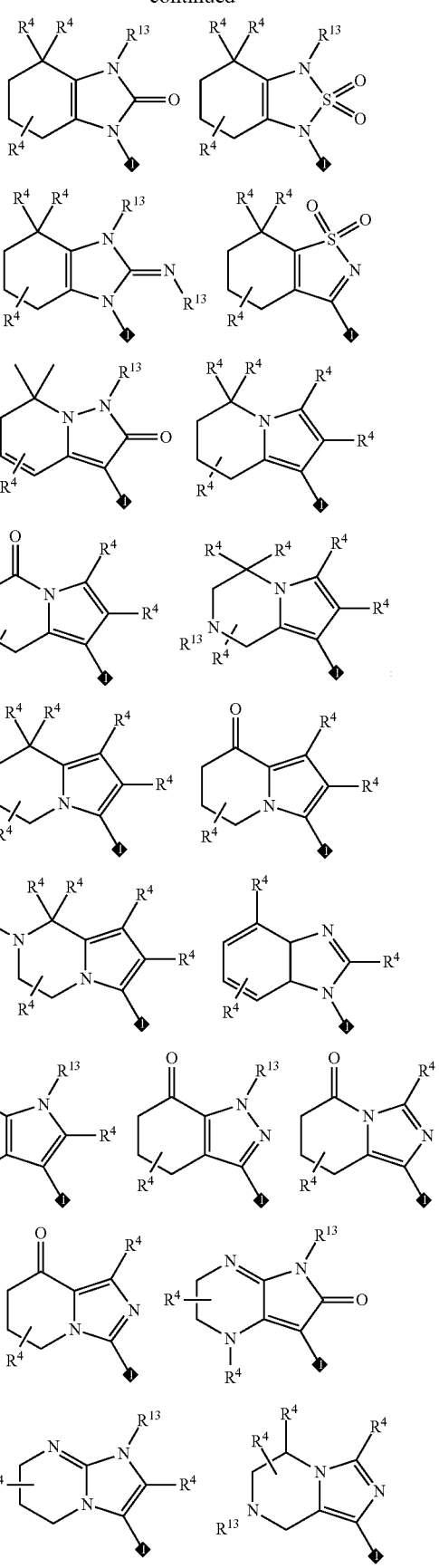

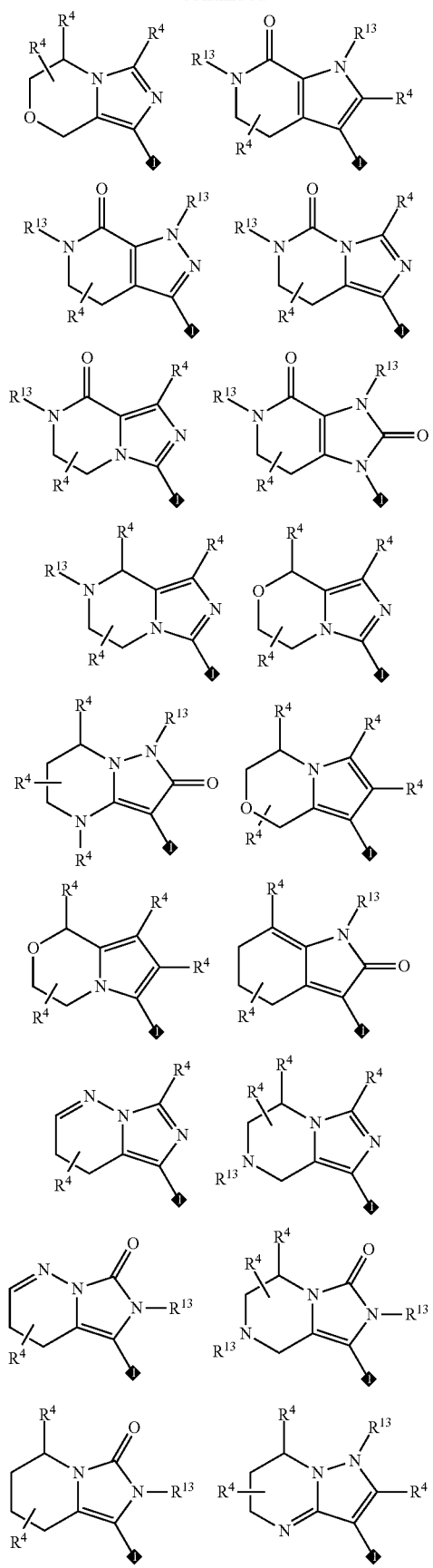
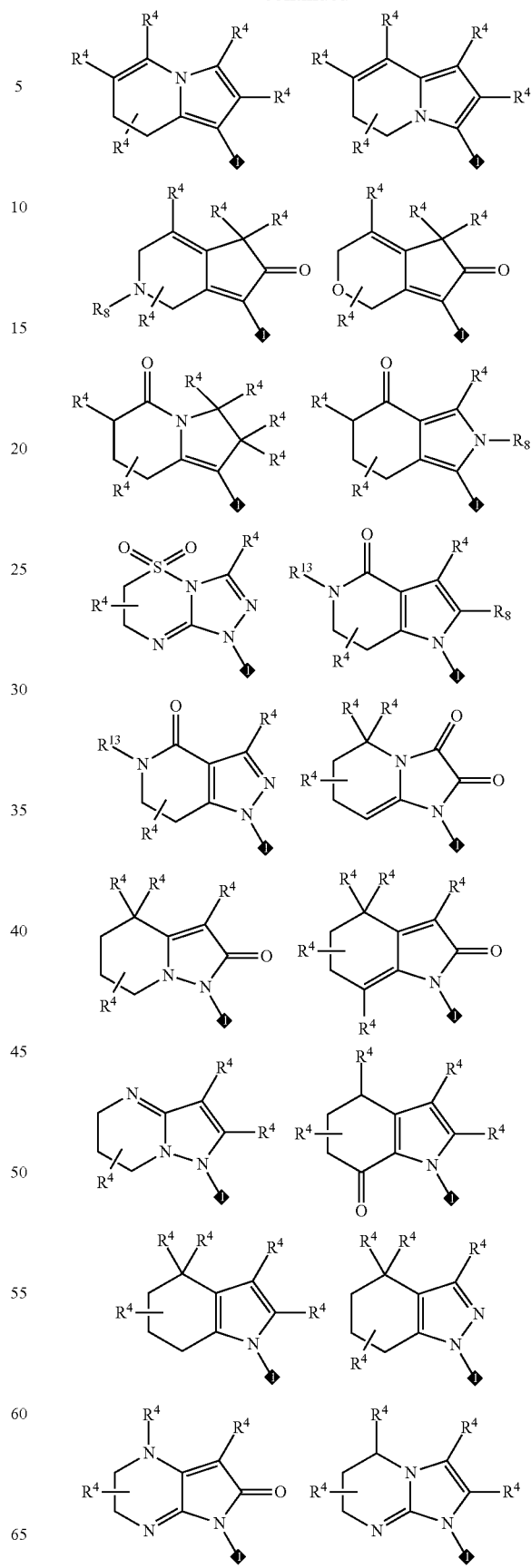

-continued wherein $R^x$, $R^4$, and $R^{13}$ have the same definitions as described above for formula (I).

In one embodiment of formulae (VII) or (VIII), $R^{6e}$ and $R^{6z}$ are each H.

In one embodiment of formulae (VII) or (VIII), $R^3$ is —N($R^{10}$)$C_{2-6}$ alkyl-NR$^{10}$R$^{10}$. In another embodiment $R^3$ is —N(CH$_3$)—CH$_2$—CH$_2$—N(CH$_3$)$_2$.

In one embodiment of formulae (VII) or (VIII), $R^2$ is methoxy, ethoxy, or isopropoxy.

In one embodiment of formulae (VII) or (VIII), $R^1$ is hydrogen.

In one embodiment, the present invention relates to a compound of tire formula (IX), (IX)

or a stereoisomer or a pharmaceutically acceptable salt, solvate, ester, or prodrug thereof,
wherein
each of a, b, c, d, e, f, g, h, i and j are independently either (formal) double bonds or (formal) single bonds, and none of $X^1$, $X^2$, $X^3$, $X^4$, $X^5$, $X^6$, $X^7$, $X^8$, and $X^9$ has two (formal) double bonds attached thereto;
each of $X^1$, $X^2$, $X^3$, $X^6$, $X^7$, $X^8$, and $X^9$ is optionally substituted and is independently C or a heteroatom selected from the group consisting of N, S, and O; and the optional substituent is selected from the group consisting of =O (oxo), =S, =NR$^{13}$, (=O)$_2$, (O)(NR$^{13}$), R$^4$, and R$^{13}$; $X^1$ is C, CH or N;
$X^1$ is C, CH or N;
$X^2$ is N, NR$^{13}$, C(R$^4$)$_2$, S(O)$_x$, C(O), or CR$^4$;
$X^3$ is N, NR$^{13}$, C(R$^4$)$_2$, C(O), S(O)$_x$, or C(R$^4$);
$X^4$ and $X^5$ are independently C or N, with the proviso that $X^4$ and $X^5$ are not both N; and if $X^1$, $X^4$ and $X^3$ are all C, then one of $X^2$ and $X^3$ is O, S or NR$^{10}$;

$X^6$, $X^7$, $X^8$, and $X^9$ are independently CR$^4$ or N, with the proviso that at most two of
X$^6$, X7, X8, and $X^9$ are N;
Z is CH or N;
$R^2$ is methoxy, ethoxy, or isopropoxy; and
each R$^{10}$ is independently H or C$_{1-6}$ alkyl.

In one embodiment of formula (IX), wherein $X^1$ is not C, or $X^2$ is not CH, or $X^3$ is not N—CH$_3$. In another embodiment, $X^1$ is N.

In one embodiment of formula (IX), wherein at least one of $X^6$, $X^7$, $X^8$, and $X^9$ is not CH.

In one embodiment, the compound of the present disclosure relates to compound of formula (IB)

(IB)

or a stereoisomer or a pharmaceutically acceptable salt, solvate, ester, tautomer, or prodrug thereof;
wherein,
A is $A^{1a}$ $A^{2a}$ $A^{4a'}$ $A^{4b'}$ -continued $A^{1b}$
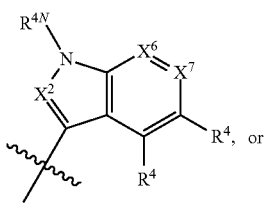

each of $X^2$, $X^3$, $X^4$, $X^5$, $X^6$, $X^7$, and $X^8$ is independently $CR^4$ or N; wherein not more than two of $X^2$, $X^3$, $X^4$, $X^5$, $X^6$, $X^7$, and $X^8$ are N;

each of $X^{10}$ and $X^{12}$ is independently S, N, or $CR^4$; wherein at least one of $X^{10}$ and $X^{12}$ is S;

Z is CH or N;

Y is $A^{5a}$
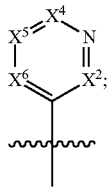

$Y^1$
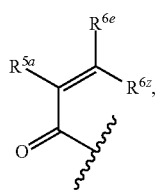

$Y^2$
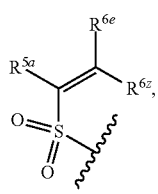

$Y^3$
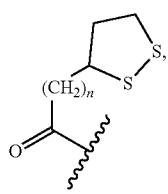

$Y^4$
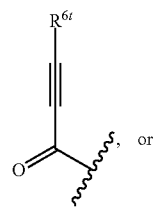

$Y^5$
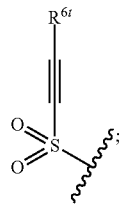

$R^1$ is independently selected from hydrogen, fluoro, chloro, bromo, methyl, ethyl, hydroxyl, methoxy, ethoxy, isopropoxy, cyclopropoxy, —$OCF_3$, —$OCH_2CF_3$, —$OCH_2CHF_2$, ethenyl, ethynyl, —$CF_3$, —$CHF_2$, —CHO, —$CH_2OH$, —$CONH_2$, —$CO_2Me$, —CONHMe, —$CONMe_2$, and cyano;

$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropoxy;

$R^3$ is —$N(R^{10})C_{2-6}$ alkyl-$NR^{10}R^{10}$, —$N(R^{10})C_{2-6}$ alkyl-$R^7$, —$O(CH_2)_pR^1$, —$N(R^{10})C(\!=\!O)(CH_2)_pR^7$, or $R^7$;

each $R^4$ is independently H, cyano, nitro, halo, —$C_{1-6}$ alkyl, —$C_{1-6}$ haloalkyl, -carboxy-$C_{1-6}$ alkyl, —$C_{1-6}$ hydroxyalkyl, $R^8R^9N$—$C_{1-6}$ alkyl-, —$C_{2-6}$ alkenyl, —$C_{2-6}$ alkynyl. $C_{1-6}$ acyl-, $R^7$—$(CH_2)_pC(\!=\!O)$—, $C_{1-6}$ hydroxyalkyl-C(=O)—, carboxy, —$C_{1-6}$ alkoxycarbonyl, —$C(\!=\!O)NR^8R^9$, hydroxyl, —$C_{1-6}$ alkoxy, —$C_{1-6}$ acyloxy, —$NR^8R^9$, $C_{1-6}$ acyl-$N(R^{10})$—, pyrazole, 123-triazole, tetrazole, ($C_{1-6}$ alkyl)$SO_2$—, or $R^7SO_2$—;

$R^{4N}$ is H, —$CD_3$, —$C_{1-6}$ alkyl, —$C_{1-6}$ haloalkyl, or —$CH_2C(\!=\!O)NR^8R^9$;

in $Y^1$ and $Y^2$, $R^{5a}$ is H, F, Cl, $CF_3$, $CHF_2$, $CF_2C_{1-6}$ alkyl, $CF_2CH_2NR^8R^9$, $CH_2NR^8R^9$. CN, or $C_{1-6}$ alkyl;

in $Y^1$ and $Y^2$, $R^{6e}$ is $R^{10}$, H, F, aryl, heteroaryl, cycloalkyl, heterocycloalkyl, $(CH_2)_mCHR^{10}R^{10}$, $CF_2(CH_2)_mCHR^{10}R^{10}$, or $C(R^{10})_2R^7$;

in $Y^4$ and $Y^5$, $R^{6z}$ is $C_{1-6}$ alkyl, $C_{3-6}$ cycloalkyl, aryl, heteroaryl, heterocycloalkyl, $(CH_2)_mCHR^{10}R^7$, $C(R^{10})_2R^7$;

in $Y^1$ and $Y^2$, $R^{6z}$ is H, F, Cl, $CF_3$, $CHF_2$, $CF_2C_{1-6}$ alkyl or $C_{1-6}$ alkyl; or alternatively in $Y^1$ and $Y^2$, $R^{6e}$ and $R^{6z}$, taken together, form =$CR^{6e'}R^{6z'}$ (allene), wherein $R^{6e'}$ is $R^{10}$, H, F, aryl, heteroaryl, cycloalkyl, heterocycloalkyl, $(CH_2)_mCHR^{10}R^7$, $CF_2(CH_2)_mCHR^{10}R^7$, or $C(R^{10})_2R^7$ and wherein, $R^{6z'}$ is H, F, Cl, $CF_3$, $CHF_2$, $CF_2C_{1-6}$ alkyl or $C_{1-6}$ alkyl; or alternatively in $Y^1$ and $Y^2$, $R^{6e}$ and $R^{6z}$, taken together with the $sp^2$ carbon atom to which both are attached, form an alicyclic ring of 4 to 7 members wherein one of the ring atoms are optionally replaced by $NR^8$, O, $S(O)_x$, S(=O)(=$NR^8$), P=O, P(=O)($OR^8$), OP(=O)($OR^8$)O, and the alicyclic ring is optionally substituted with one or more substituents selected from the group consisting of halogen, oxo, OH, $OR^8$, and $NR^8R^9$;

$R^7$ is OH, $NR^8R^9$, $O(CH)_qNR^8R^9$, $C_{1-6}$ alkoxy, $C_{1-6}$ alkoxy-$C_{1-6}$ alkoxy, $C_{2-6}$ hydroxyalkoxy, oxetanyl, oxetanyloxy, oxetanylamino, oxolanyl, oxolanyloxy, oxolanylamino, oxanyl oxanyloxy, oxanylamino, oxepanyl, oxepanyloxy, oxepanylamino, azetidinyl, azetidinyloxy, azetidylamino, pyrrolidinyl, pyrolidinyloxy, pyrrolidinylamino, piperidinyl, piperidinyloxy, piperidinylamino, azepanyl, azepanyloxy, azepanylamino, dioxolanyl, dioxanyl, morpholino, thiomorpholino, thiomorpholino-S,S-dioxide, piperazino, dioxepanyl, dioxepanyloxy, dioxepanylamino, oxazepanyl, oxazepanyloxy, oxazepanylamino, diazepanyl, diazepanyloxy, diazepanylamino, (3R)-3-(dimethylamino)pyrrolidin-1-yl, (3S)-3-(dimethylamino)pyrrolidin-1-yl, 3-(dimethylamino)azetidin-1-yl, [2-(dimethylamino)ethyl](methyl)amino, [2-(methylamino)ethyl](methyl)amino, 5-methyl-2,5diazaspiro[3.4]oct-2-yl, (3aR,6aR)-5-methylhexa-hydro-pyrrolo[3,4-b]pyrrol-1(2H)-yl, l-methyl-1,2,3,6-tetrahydropyridin-4-yl, 4-methylpiperizin-1-yl, 4-[2(dimethylamino)-2-oxoethyl]piperazin-1-yl, methyl[2-(4-methylpiperazin-1yl)ethyl]amino, methyl[2-(morpholin-4-yl)ethyl]amino, 1-amino-1,2,3,6tetrahydropyridin-4-yl, 4-[(2S)-2-aminopropanoyl]piperazin-1-yl, all of which may be optionally substituted with OH, $OR^{10}$, oxo, halogen, $R^{10}$, $CH_2OR^{10}$, or $CH_2NR^8R^9$;

$R^8$ and $R^9$ are each independently H, $—CD_3$, $C_{1-6}$ alkyl, $C_{2-6}$ alkenyl, $C_{3-6}$ alkynyl, $C_{3-8}$ cycloalkyl, $—(C_{1-3}$ alkyl)-$(C_{3-8}$ cycloalkyl), $C_{3-8}$ cycloalkenyl, $C_1$-$C_6$ acyl, 4-12 membered monocyclic or bicyclic heterocyclyl, 4-12 membered monocyclic or bicyclic heterocyclyl-$C_1$-$C_6$ alkyl-, $C_6$-$C_{12}$ aryl, 5-12 membered heteroaryl; wherein $R^8$ and $R^9$ may be further independently substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom selected from O, S, or $NR^{11}$, or a heterobicyclic ring of 7-12 members which may be fused, bridged or spiro, and contain up to two other heteroatoms chosen from O, $S(O)_x$, or $NR^{11}$, and these heterocyclic rings are optionally substituted with up to three substituents chosen from hydroxyl, $C_{1-6}$ alkoxy, $C_{1-6}$ hydroxyalkyl, C t alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, $—CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$;

alternatively, two $R^{10}$ on the same N atom to which they are both attached, form a heterocyclic ring of 5-6 members, containing up to one other heteroatom selected from O, S, or $NR^{11}$;

each $R^{11}$ is independently hydrogen or $C_1$-$C_6$ alkyl, which is optionally substituted with up to three substituents selected from hydroxyl, oxo, thiono, cyano or halo;

m is 0, 1, 2, or 3;
p=0, 1, 2, 3, or 4;
q=2, 3, or 4; and
x=0, 1, or 2.

In one embodiment, the compound of the present disclosure relates to compounds of formula (IIIB):

(IIIB)

or a stereoisomer or a pharmaceutically acceptable salt, solvate, ester, tautomer, or prodrug thereof;

wherein:
$X^2$ is CH, C($C_{1-6}$ alkyl) or N;
$X^6$ is $CR^4$ or N;
Z is CH or N;
$R^1$ is independently selected from hydrogen, fluoro, chloro, bromo, methyl, ethyl, ethynyl, $CF_3$, $CHF_2$ or cyano;
$R^2$ is $—OCF_3$, $—OCHF_2$, $—OCF_2CF_3$, $—OCH_2CHF_2$, $—OCH_2CF_3$, cyclopropoxy, methoxy, $—OCD_3$, ethoxy, or isopropoxy;
$R^3$ is $N(R^{10})C_{2-6}$ alkyl-$NR^{10}R^{10}$ or $N(R^{10})C_{2-6}$ alkyl-$R^7$;
$R^4$ is H, cyano, halo, $—C_{1-6}$ alkyl, or $—C_{1-6}$ haloalkyl;
$R^{4a}$ is, cyano, $—C_{1-6}$ haloalkyl, $—C_{1-6}$ hydroxyalkyl, $—C(=O)OH$, $—C(=O)CH_2OH$, $C_{1-6}$ acyl-, pyrazole, 123-triazole, tetrazole, $—C(=O)NR^8R^9$, $—CH_2NR^8R^9$, $—NR^8R^9$, $C_{1-6}$ acyl-$N(R^{10})$—, $(C_{1-3}$ alkyl)$SO_2NH$—, $(C_{1-6}$ alkyl)$SO_2$— or $R^7SO_2$—;
$R^7$ is OH, $NR^8R^9$ or $—O(CH_2)_qNR^8R^9$;
$R^8$ and $R^9$ are independently H, $—CD_3$, $C_{1-6}$ alkyl, cyclopropyl, monocyclic or bicyclic $C_{4-8}$ cycloalkyl, $(C_{3-6}$ cycloalkyl)-$(C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, each $R^{10}$ is independently H, $—CD_3$, $C_{1-6}$ alkyl, $C_{3-8}$ cycloalkyl, $C_{2-6}$ hydroxyalkyl, $C_{2-6}$ alkyl-$NR^8R^9$;

alternatively, two $R^{10}$ on the same N atom to which they are both attached, form a heterocyclic ring of 5-6 members, containing up to one other heteroatom selected from O, S, or $NR^{11}$;

each $R^{11}$ is independently hydrogen or $C_1$-$C_6$alkyl, which is optionally substituted with up to three substituents selected from hydroxyl, oxo, thiono, cyano and halo;

p=0, 1, 2, 3, or 4; and
q=2, 3, or 4.

In one embodiment of the compounds of formula (IIIB), Z is N; and
$R^2$ is $—OCF_3$, $—OCHF_2$, $—OCF_2CF_3$, $—OCH_2CHF_2$, $—OCH_2CF_3$, or cyclopropoxy, methoxy, $—OCD_3$, ethoxy, or isopropoxy.

In one embodiment, the compound of the present disclosure relates to compounds of formula (IVB):

(IVB)

or a stereoisomer or a pharmaceutically acceptable salt, solvate, ester, tautomer, or prodrug thereof;
wherein
$X^2$ is CH, $CCH_3$, or N;
$X^6$ is $CR^4$ or N;
Z is CH or N;

R[1] is selected from hydrogen, methyl, fluoro, chloro, bromo, —CF$_3$, or cyano;

R[2] is —OCF$_3$, —OCHF$_2$, —OCF$_2$CF$_3$, —OCH$_2$CHF$_2$, —OCH$_2$CF$_3$, cyclopropoxy, methoxy, —OCD$_3$, ethoxy, or isopropoxy;

R[3] is N(R[10])C$_{2-6}$ alkyl-NR[10]R[10];

R[4] is H, cyano, halo, —C$_{1-6}$ alkyl, —C$_{1-6}$ haloalkyl;

R[4a] is independently cyano, —C$_{1-6}$ hydroxyalkyl, C$_{1-6}$ acyl-, pyrazole, 123-triazole, tetrazole, —C(=O)NR[8]R[9], —NR[8]R[9], C$_{1-6}$ acyl-N(R[10])—, (C$_{1-3}$ alkyl)SO$_2$NH—, (C$_{1-6}$ alkyl)SO$_2$—, or R[7]SO$_2$—;

R[7] is —OH or —NR[8]R[9];

R[8] and R[9] are independently H, —CD$_3$, C$_{1-6}$ alkyl, C$_{3-8}$ cycloalkyl, C$_{3-8}$ cycloalkyl-(C$_{1-3}$ alkyl)-, C$_1$-C$_6$acyl, phenyl, monocyclic heteroaryl, or monocyclic heterocyclyl; and R[8] and R[9] may be further independently substituted with up to three substituents chosen from hydroxyl, C$_{1-6}$ alkoxy, oxo, thiono, cyano or halo; or alternatively, R[8] and R[9], taken together with the N atom to which they are both attached, form a heterocyclic ring of 4-7 members, containing up to one other heteroatom chosen from O, S, or NR[11], each R[10] is independently H, —CD$_3$, C$_{1-6}$ alkyl, C$_{3-6}$ cycloalkyl, C$_{2-6}$ hydroxyalkyl, C$_{2-6}$ alkyl-NR[8]R[9];

alternatively, two R[10] on the same N atom to which they are both attached, form a heterocyclic ring of 5-6 members, containing up to one other heteroatom selected from O, S, or NR[11];

each R[11] is independently hydrogen or C$_1$-C$_6$ alkyl, which is optionally substituted with up to three substituents selected from hydroxyl, oxo, thiono, cyano and halo; and q=2, 3, or 4.

In one embodiment of compounds of formula (IVB),
X[2] is CH, CCH$_3$, or N;
X[6] is CH, CCH$_3$, or N;
Z is CH or N;
R[1] is hydrogen, methyl, or chloro;
R[2] is —OCF$_3$, —OCHF$_2$, —OCH$_2$CHF$_2$, —OCH$_2$CF$_3$, cyclopropoxy, methoxy, ethoxy, or isopropoxy;
R[3] is —N(CH$_3$)CH$_2$CH$_2$NR[10]R[10];
R[4a] is —NR[8]R[9];
R[8] and R[9] are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

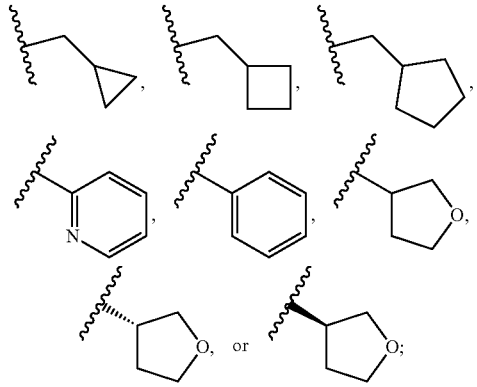

or alternatively, R[8] and R[9], taken together with the N atom to which they are both attached, form a heterocyclic ring of 5-6 members, containing up to one other heteroatom chosen from O, S, or NR[11];

each R[10] is independently H, —CD$_3$, methyl, ethyl, or isopropyl; or alternatively, two R[10] on the same N atom to which they are both attached, form a heterocyclic ring of 5-6 members, containing up to one other heteroatom selected from O, S, or NR[11].

In one embodiment of compounds of formula (IVB),
X[2] is CH or N;
X[6] is CH or N;
Z is CH or N;
R[1] is hydrogen;
R[2] is —OCH$_2$CHF$_2$, methoxy, ethoxy, or isopropoxy;
R[3] is —N(CH$_3$)CH$_2$CH$_2$NR[10]R[10];
R[4a] is —NR[8]R[9];
R[8] and R[9] are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

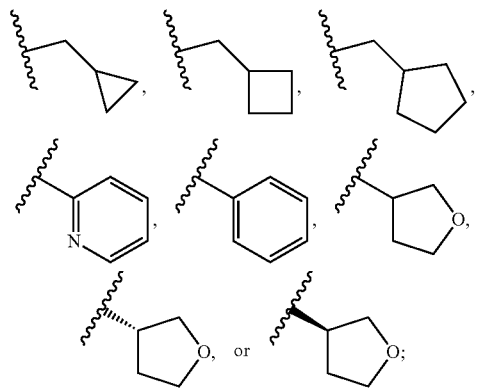

or alternatively, R[8] and R[9], taken together with the N atom to which they are both attached, form a heterocyclic ring of 5-6 members, containing up to one other heteroatom chosen from O, S, or NR[11]; and each R[10] is independently H, —CD$_3$, methyl, ethyl, or isopropyl.

In one embodiment of compounds of formula (IVB),
X[2] is N;
X[6] is CH, CCH$_3$, or N;
Z is CH or N;
R[1] is hydrogen, methyl, or chloro;
R[2] is —OCF$_3$, —OCHF$_2$, —OCH$_2$CHF$_2$, —OCH$_2$CF$_3$, cyclopropoxy, methoxy, ethoxy, or isopropoxy;
R[3] is —N(CH$_3$)CH$_2$CH$_2$NR[10]R[10];
R[4a] is —NR[8]R[9];
R[8] and R[9] are independently H, —CD$_3$, methyl, ethyl, isopropyl, cyclopropyl, —C(=O)CH$_3$, —C(=O)CH$_2$CH$_3$, —C(=O)CH(CH$_3$)$_2$,

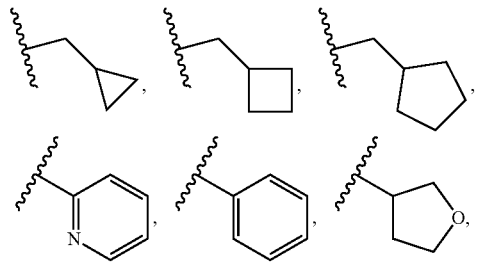

289

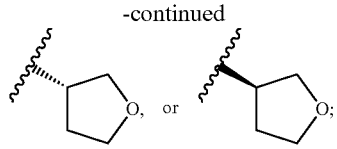

alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, $-CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (IVB),
$X^2$ is N;
$X^6$ is CH or N;
Z is CH or N;
$R^1$ is hydrogen;
$R^2$ is $-OCH_2CHF_2$, methoxy, ethoxy, or isopropoxy;
$R^3$ is $-N(CH_3)CH_2CH_2NR^{10}R^{10}$;
$R^{4a}$ is $-NR^8R^9$;
$R^8$ and $R^9$ are independently H, $-CD_3$, methyl, ethyl, isopropyl, cyclopropyl, $-C(=O)CH_3$, $-C(=O)CH_2CH_3$, $-C(=O)CH(CH_3)_2$,

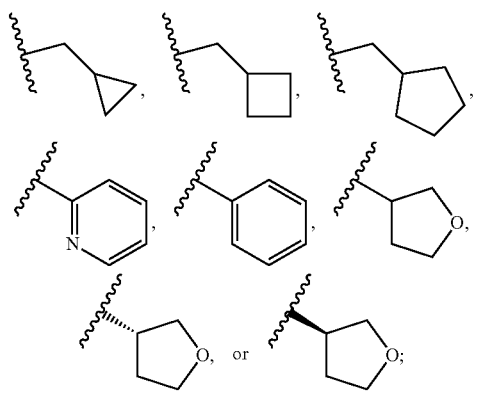

or
alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, $-CD_3$, methyl, ethyl, or isopropyl.

In one embodiment of compounds of formula (IVB),
$X^2$ is N or CH;
$X^6$ is CH;
Z is CH;
$R^1$ is hydrogen;
$R^2$ is $-OCF_3$, $-OCHF_2$, $-OCH_2CHF_2$, $-OCH_2CF_3$, cyclopropoxy, methoxy, ethoxy, or isopropoxy;
$R^3$ is $N(CH_3)CH_2CH_2NR^{10}R^{10}$;
$R^{4a}$ is $-CH_2OH$, $-CH(OH)(CH_3)$, $-C(OH)(CH_3)_2$, $-CH(OH)(CH_2CH_3)$, $-C(OH)(CH_2CH_3)_2$, or $-C(OH)(CH_3)(CH_2CH_3)$; and
each $R^{10}$ is independently H, $-CD_3$, methyl, ethyl, or isopropyl.

290

In one embodiment of compounds of formula (IVB),
$X^2$ is N or CH;
$X^6$ is CH;
Z is CH;
$R^1$ is hydrogen;
$R^2$ is methoxy, ethoxy, or isopropoxy;
$R^3$ is $-N(CH_3)CH_2CH_2NR^{10}R^{10}$;
$R^{4a}$ is $-CH_2OH$, $-CH(OH)(CH_3)$, or $-C(OH)(CH_3)_2$; and
each $R^{10}$ is independently H, $-CD_3$, methyl, ethyl, or isopropyl.

In one embodiment of compounds of formula (IVB),
$X^2$ is N or CH;
$X^6$ is CH, $CCH_3$, or N;
Z is CH;
$R^1$ is hydrogen;
$R^2$ is $-OCF_3$, $-OCHF_2$, $-OCH_2CHF_2$, $-OCH_2CF_3$, cyclopropoxy, methoxy, ethoxy, or isopropoxy;
$R^3$ is $-N(CH_3)CH_2CH_2NR^{10}R^{10}$;
$R^{4a}$ is $-C(=O)NR^8R^9$;
$R^8$ and $R^9$ are independently H, $-CD_3$, methyl, ethyl, or isopropyl; and
each $R^{10}$ is independently H, $-CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (IVB),
$X^2$ is N or CH;
$X^6$ is N or CH;
Z is CH;
$R^1$ is hydrogen;
$R^2$ is methoxy, ethoxy, or isopropoxy;
$R^3$ is $-N(CH_3)CH_2CH_2NR^{10}R^{10}$;
$R^{4a}$ is $-C(=O)NR^8R^9$;
$R^8$ and $R^9$ are independently H, $-CD_3$, methyl, ethyl, or isopropyl; and
each $R^{10}$ is independently H, $-CD_3$, methyl, ethyl, or isopropyl.

In one embodiment of compounds of formula (IVB), $R^2$ is $-OCH_2CHF_2$, $-OCH_2CF_3$, cyclopropoxy, methoxy, $-OCD_3$, ethoxy, or isopropoxy.

In one embodiment, the compound of the present disclosure relates to compounds of formula (VB):

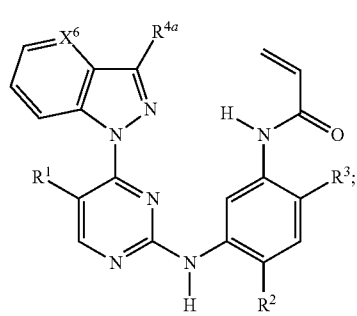

(VB)

or a stereoisomer or a pharmaceutically acceptable salt, solvate, ester, tautomer, or prodrug thereof;
wherein
$X^6$ is $CR^4$ or N;
$R^1$ is selected from hydrogen, methyl, fluoro, chloro, bromo, $CF_3$, or cyano;

$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;

$R^3$ is $N(R^{10})C_{2-6}$ alkyl-$NR^{10}R^{10}$;

$R^4$ is H, cyano, halo, —$C_{1-6}$ alkyl, or —$C_{1-6}$ haloalkyl;

$R^{4a}$ is cyano, —$C_{1-6}$ haloalkyl, —$C_{1-6}$ hydroxyalkyl, —C(=O)$NR^8R^9$, —$CH_2NR^8R^9$, —$NR^8R^9$, $C_{1-6}$ acyl-N($R^{10}$)—, ($C_{1-3}$ alkyl)$SO_2NH$—, ($C_{1-6}$ alkyl)$SO_2$— or $R^7SO_2$—;

$R^7$ is —$NR^8R^9$;

$R^8$ and $R^9$ are independently H, —$CD_3$, $C_{1-6}$ alkyl, cyclopropyl, monocyclic or bicyclic $C_{4-8}$ cycloalkyl, —($C_{1-3}$ alkyl)-($C_{3-8}$ cycloalkyl), $C_1$-$C_6$ acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$; and each $R^{10}$ is independently H, —$CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$alkyl, which is optionally substituted with up to three substituents selected from hydroxyl, oxo, thiono, cyano and halo.

In one embodiment of compounds of formula (VB), $X^6$ is CH, $CCH_3$, or N;

$R^1$ is hydrogen, methyl, or chloro;

$R^2$ is —$OCF_3$, —$OCHF_2$, —$OCH_2CHF_2$, —$OCH_2CF_3$, cyclopropoxy, methoxy, ethoxy, or isopropoxy;

$R^3$ is —$N(CH_3)CH_2CH_2NR^{10}R^{10}$;

$R^{4a}$ is —$NR^8R^9$;

$R^8$ and $R^9$ are independently H, —$CD_3$, methyl, ethyl, isopropyl, cyclopropyl, —C(=O)$CH_3$, —C(=O)$CH_2CH_3$, —C(=O)$CH(CH_3)_2$,

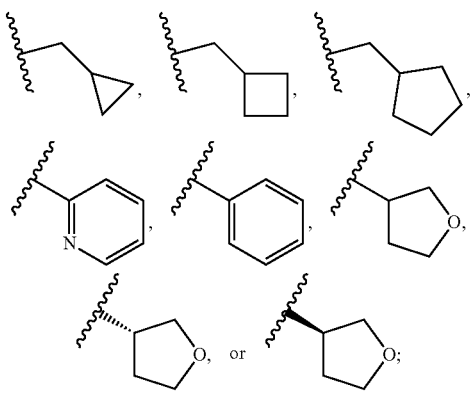

or alternatively, $R^8$ and $R^9$, taken together with the N atom to which they are both attached, form a heterocyclic ring of 5-6 members, containing up to one other heteroatom chosen from O, S, or $NR^{11}$, each $R^{10}$ is independently H, —$CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VB), $X^6$ is CH or N;

$R^1$ is hydrogen;

$R^2$ is methoxy, ethoxy, or isopropoxy;

$R^3$ is —$N(CH_3)CH_2CH_2NR^{10}R^{10}$;

$R^{4a}$ is —$NR^8R^9$;

$R^8$ and $R^9$ are independently H, —$CD_3$, methyl, ethyl, isopropyl, cyclopropyl, —C(=O)$CH_3$, —C(=O)$CH_2CH_3$, —C(=O)$CH(CH_3)_2$,

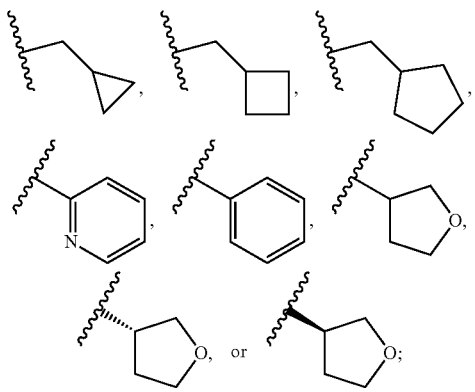

or alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, —$CD_3$, methyl, ethyl, or isopropyl.

In one embodiment of compounds of formula (VB), $X^6$ is CH;

$R^1$ is hydrogen, methyl, or chloro;

$R^2$ is —$OCF_3$, —$OCHF_2$, —$OCH_2CHF_2$, —$OCH_2CF_3$, cyclopropoxy, methoxy, ethoxy, or isopropoxy;

$R^3$ is —$N(CH_3)CH_2CH_2NR^{10}R^{10}$;

$R^{4a}$ is —$NR^8R^9$;

$R^8$ and $R^9$ are independently H, —$CD_3$, methyl, ethyl, isopropyl, cyclopropyl, —C(=O)$CH_3$, —C(=O)$CH_2CH_3$, —C(=O)$CH(CH_3)_2$,

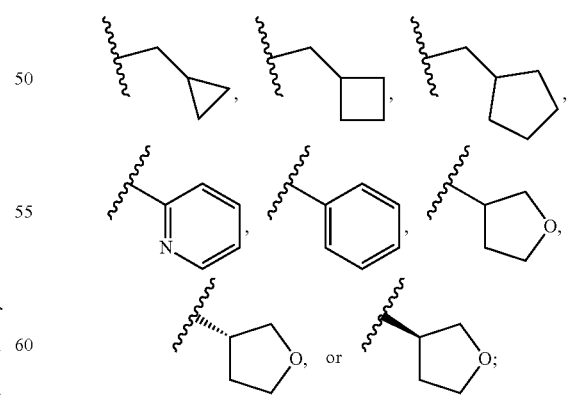

alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, —$CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VB),
$X^6$ is CH;
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, cyclopropyl, —$C(=O)CH_3$, —$C(=O)CH_2CH_3$, —$C(=O)CH(CH_3)_2$,

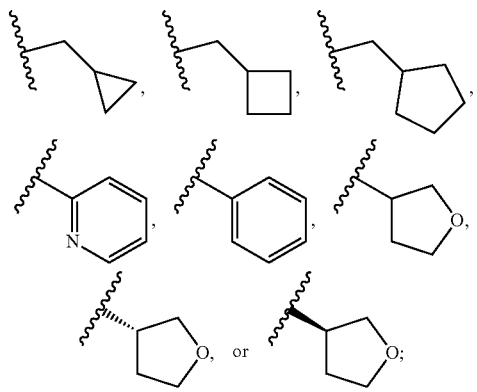

or alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, —$CD_3$, methyl, ethyl, or isopropyl.

In one embodiment of compounds of formula (VB),
$X^6$ is N;
$R^1$ is hydrogen;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl; or alternatively, $R^8$ and $R^9$, taken together with the N atom to which they are both attached, form a heterocyclic ring of 5-6 members, containing up to one other heteroatom chosen from O, S, or $NR^{11}$; and each $R^{10}$ is independently H, —$CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VB),
$X^6$ is N;
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, or isopropyl; and each $R^{10}$ is independently H, —$CD_3$, methyl, ethyl, or isopropyl.

In one embodiment of compounds of formula (VB).
$X^6$ is CH;
$R^1$ is hydrogen;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$CH_2OH$, —$CH(OH)CH_3$, —$C(OH)(CH_3)_2$, —$CH(OH)(CH_2CH_3)$, —$C(OH)(CH_2CH_3)_2$, or —$C(OH)(CH_3)(CH_2CH_3)$; and each $R^{10}$ is independently H, —$CD_3$, methyl, ethyl, or isopropyl.

In one embodiment of compounds of formula (VB),
$X^6$ is CH;
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is —$CH_2OH$, —$CH(OH)(CH_3)$, or —$C(OH)(CH_3)_2$; and each $R^{10}$ is independently H, —$CD_3$, methyl, ethyl, or isopropyl.

In one embodiment of compounds of formula (IVB) or formula (VB), $R^2$ is —$OCH_2CHF_2$, —$OCH_2CF_3$, methoxy, —$OCD_3$, or ethoxy.

In one embodiment of compounds of formula (IVB) or formula (VB), $R^3$ is —$N(CH_3)CH_2CH_2N(R^{10})_2$. In another embodiment, $R^3$ is —$N(CH_3)CH_2CH_2N(CH_3)_2$.

In one embodiment of compounds of formula (NB) or formula (VB), $R^{10}$ is H, —$CH_3$, —$CD_3$, —$CH_2CH_3$, or isopropyl.

In one embodiment of compounds of formula (NB) or formula (VB), $R^{4a}$ is —$NR^8R^9$ or —$C(=O)NR^8R^9$. In another embodiment, $R^{4a}$ is —$C_{1-6}$ hydroxyalkyl.

In one embodiment of compounds of formula (IVB) or formula (VB), $R^8$ and $R^9$ are independently H, —$CH_3$, —$CD_3$, —$CH_2CH_3$, isopropyl, cyclopropyl, —$C(=O)CH_3$, —$C(=O)CH_2CH_3$, —$C(=O)CH(CH_3)_2$,

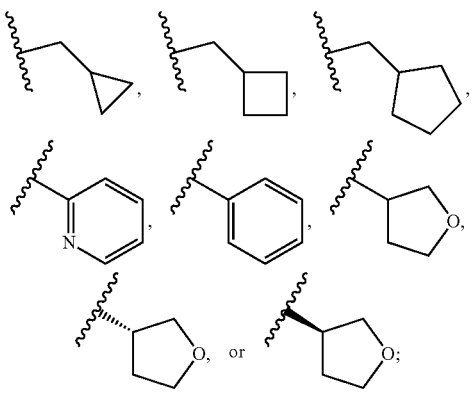

In another embodiment, $R^8$ and $R^9$ are independently H, —$CH_3$, —$CD_3$, —$CH_2CH_3$, or isopropyl.

In one embodiment of compounds of formula (IVB) or formula (VB), $X^6$ is N, CH, or $C(CH_3)$.

One embodiment of the present disclosure relates to compounds of formula (VIB):

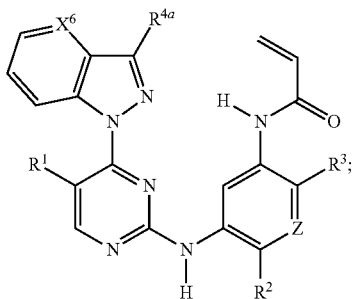

(VIB)

or a stereoisomer or a pharmaceutically acceptable salt, solvate, ester, tautomer, or prodrug thereof;
wherein
$X^6$ is $CR^4$ or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^4$ is H, $CH_3$, $CH_2CH_3$, or isopropyl;
$R^{4a}$ is cyano, —$C_{1-6}$ haloalkyl, $C_{1-6}$ hydroxyalkyl-C(=O)—, —C(=O)$NR^8R^9$, —$NR^8R^9$, $C_{1-6}$ acyl-$N(R^{10})$—, $(C_{1-3}$alkyl)$SO_2NH$— or $R^7SO_2$—;
$R^7$ is —$NR^8R^9$;
$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or
alternatively, $R^8$ and $R^9$, taken together with the N atom to which they are both attached, form a heterocyclic ring of 4-7 members, containing up to one other heteroatom chosen from O, S, or $NR^{11}$; and
each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (VIB).
$X^6$ is CH, $CCH_3$, or N;
$R^1$ is hydrogen, methyl, or chloro;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, cyclopropyl, —C(=O)$CH_3$, —C(=O)$CH_2CH_3$, C(=O)CH($CH_3$)$_2$,

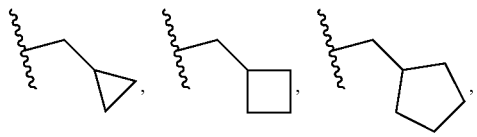

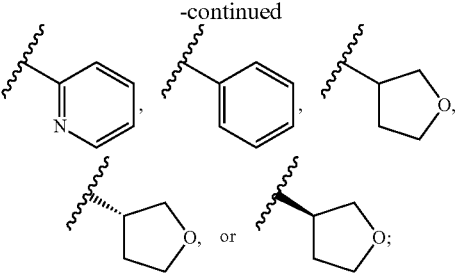

or
alternatively, $R^8$ and $R^9$, taken together with the N atom to which they are both attached, form a heterocyclic ring of 5-6 members, containing up to one other heteroatom chosen from O, S, or $NR^{11}$; and
each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VIB),
$X^4$ is CH or N;
$R^1$ is hydrogen;
$R^2$ is —$OCH_2CHF_2$, methoxy, ethoxy, or isopropoxy;
$R^3$ is —$N(CH_3)CH_2CH_2R^{10}R^{10}$;
$R^{4a}$ is —$NR^8R^9$;
$R^8$ and $R^9$ are independently H, —$CD_3$, methyl, ethyl, or isopropyl; and
each $R^{10}$ is independently H, —$CD_3$, methyl, ethyl, or isopropyl.

In one embodiment of compounds of formula (VIB),
$X^6$ is CH;
$R^1$ is hydrogen;
$R^2$ is —$OCF_3$, —$OCHF_2$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, isopropyl, —C(=O)$CH_3$, —C(=O)$CH_2CH_3$, or —C(=O)CH($CH_3$)$_2$; or
alternatively, $R^8$ and $R^9$, taken together with the N atom to which they are both attached, form a heterocyclic ring of 5-6 members, containing up to one other heteroatom chosen from O, S, or $NR^{11}$; and
each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (VIB),
$X^6$ is CH;
$R^1$ is hydrogen;
$R^2$ is —$OCH_2CHF_2$, methoxy, ethoxy, or isopropoxy;
$R^3$ is —$N(CH_3)CH_2CH_2NR^{10}R^{10}$;
$R^{4a}$ is —$NR^8R^9$;
$R^8$ and $R^9$ are independently H, —$CD_3$, methyl, ethyl, or isopropyl; and
each $R^{11}$ is independently H, —$CD_3$, methyl, ethyl, or isopropyl.

In one embodiment of compounds of formula (VIB), $R^2$ is —$OCH_2CHF_2$, —$OCH_2CF_3$, cyclopropoxy, methoxy, —$OCD_3$, or ethoxy.

In one embodiment of compounds of formula (VIB), $R^3$ is —N(CH$_3$)CH$_2$CH$_2$N(CH$_3$)$_2$.

In one embodiment of compounds of formula (VIB), $R^{10}$ is H, —CH$_3$, —CD$_3$, —CH$_2$CH$_3$, or isopropyl.

In one embodiment of compounds of formula (VIB), $R^{4a}$ is —NR$^8$R$^9$.

In one embodiment of compounds of formula (VIB), $R^8$ and $R^9$ are independently H, —CH$_3$, —CD$_3$, —CH$_2$CH$_3$, isopropyl, or cyclopropyl.

One embodiment of the present disclosure relates to compounds of formula (VIIB):

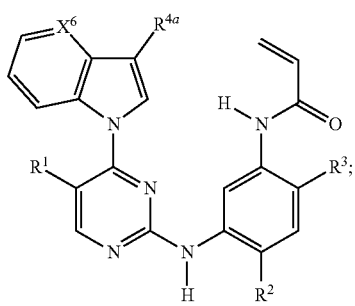

(VIIB)

or a stereoisomer or a pharmaceutically acceptable salt, solvate, ester, tautomer, or prodrug thereof;
wherein
$X^6$ is CR$^4$ or N;
$R^1$ is selected from hydrogen, methyl, fluoro, chloro, bromo, CF$_3$, or cyano;
$R^2$ is —OCF$_3$, —OCHF$_2$, —OCF$_2$CF$_3$, —OCH$_2$CHF$_2$, —OCH$_2$CF$_3$, cyclopropoxy, methoxy, —OCD$_3$, ethoxy, or isopropoxy;
$R^3$ is N(R$^{10}$)C$_{2-6}$ alkyl-NR$^{10}$R$^{10}$;
$R^4$ is H, cyano, halo, —C$_{1-6}$ alkyl, or —C$_{1-6}$ haloalkyl;
$R^{4a}$ is cyano, halo, C$_{1-s}$ acyl-, —C$_{1-6}$ hydroxyalkyl, pyrazole, 123-triazole, tetrazole, —C(=O)OH, —C(=O)CH$_2$OH, —C(=O)NR$^8$R$^9$, —CH$_2$NR$^8$R$^9$, —NR$^8$R$^9$, C$_{1-6}$ acyl-N(R$^{10}$)—, (C$_{1-3}$alkyl)SO$_2$NH—, R$^{10}$SO$_2$— or R$^7$SO$_2$—:
$R^7$ is —NR$^8$R$^9$;
$R^8$ and $R^9$ are independently H, —CD$_3$, C$_{1-6}$ alkyl, C$_{3-8}$ cycloalkyl, C$_{3-8}$ cycloalkyl-(C$_{1-3}$ alkyl)-, C$_1$-C$_6$acyl, phenyl, monocyclic heteroaryl, or monocyclic heterocyclyl; and $R^8$ and $R^9$ may be further independently substituted with up to three substituents chosen from hydroxyl, C$_{1-6}$ alkoxy, oxo, thiono, cyano or halo; and
each $R^{10}$ is independently H, —CD$_3$, or C$_{1-6}$ alkyl; or
alternatively, two $R^{10}$ on the same N atom to which they are both attached, form a heterocyclic ring of 5-6 members, containing up to one other heteroatom selected from O, S, or NR$^{11}$; and
each $R^{11}$ is independently hydrogen or C$_1$-C$_6$alkyl, which is optionally substituted with up to three substituents selected from hydroxyl, oxo, thiono, cyano and halo.

In one embodiment of compounds of formula (VIIB),
$X^6$ is CH;
$R^1$ is hydrogen, methyl, or chloro;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is —C(=O)CH$_3$, —C(=O) CH$_2$CH$_3$, or —C(=O)CH(CH$_3$)$_2$; and each $R^{10}$ is independently H, —CD$_3$, methyl, ethyl, or isopropyl.

In one embodiment of compounds of formula (VIIB),
$X^6$ is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ is —C(=O)CH$_3$, —C(=O) CH$_2$CH$_3$, or —C(=O) CH(CH$_3$)$_2$; and
each $R^{10}$ is independently H, —CD$_3$, methyl, ethyl, or isopropyl.

In one embodiment of compounds of formula (VIIB),
$X^6$ is CH;
$R^1$ is hydrogen;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{1i}$R$^{1i}$;
$R^{4a}$ is R$^7$SO$_2$—;
$R^7$ is —NR$^8$R$^9$;
$R^8$ and $R^9$ are independently H, —CD$_3$, methyl, ethyl, or isopropyl; and
each $R^{10}$ is independently H, —CD$_3$, methyl, ethyl, or isopropyl; or
alternatively, two $R^{10}$ on the same N atom to which they are both attached, form a heterocyclic ring of 5-6 members, containing up to one other heteroatom selected from O, S, or NR$^{11}$.

In one embodiment of compounds of formula (VIIB),
$X^6$ is CH;
$R^1$ is hydrogen;
$R^2$ is methoxy, ethoxy, or isopropoxy;
$R^3$ is —N(CH$_3$)CH$_2$CH$_2$R$^{10}$R$^{10}$;
$R^{4a}$ is R$^7$SO$_2$—;
$R^7$ is —NR$^8$R$^9$;
$R^8$ and $R^9$ are independently H, —CD$_3$, methyl, ethyl, or isopropyl; and
each $R^{10}$ is independently H, —CD$_3$, methyl, ethyl, or isopropyl.

In one embodiment of compounds of formula (VIIB),
$X^6$ is N, CH, or CCH$_3$;
$R^1$ is hydrogen;
$R^2$ is —OCF$_3$, —OCHF$_2$, —OCH$_2$CHF$_2$, —OCH$_2$CF$_3$, cyclopropoxy, methoxy, ethoxy, or isopropoxy;
$R^3$ is —N(CH$_3$)CH$_2$CH$_2$NR$^{10}$R$^{10}$;
$R^{4a}$ is

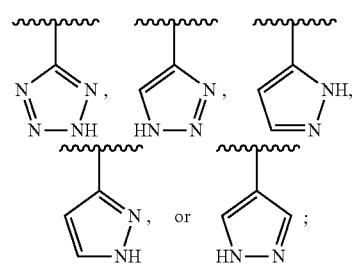

each $R^{10}$ is independently H, —CD$_3$, methyl, ethyl, or isopropy.

In one embodiment of compounds of formula (VIIB),
$X^6$ is N or CH;
$R^1$ is hydrogen;
$R^2$ is methoxy, ethoxy, or isopropoxy;
$R^3$ is N(CH$_3$)CH$_2$ CH$_2$NR$^{10}$R$^{10}$;
$R^3$ is N(CH$_3$)CH$_2$CH$_2$NR$^{10}$R$^{10}$;

$R^{4a}$ is

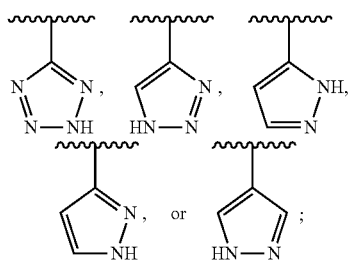

and each $R^{10}$ is independently H, —CD$_3$, methyl, ethyl, or isopropyl.

In one embodiment of compounds of formula (VIIB), $R^2$ is methoxy, —OCD$_3$, ethoxy, or isopropoxy.

In one embodiment of compounds of formula (VIIB), $R^3$ is —N(CH$_3$)CH$_2$CH$_2$N(CH$_3$)$_2$.

In one embodiment of compounds of formula (VIIB), $R^{10}$ is H, —CH$_3$, —CD$_3$, —CH$_2$CH$_3$, or isopropyl.

In one embodiment of compounds of formula (VIIB), $R^{4a}$ is —C(=O)NR$^8$R$^9$, —NR$^8$R$^9$ or R$^7$SO$_2$—. In another embodiment, $R^{4a}$ is cyano, halo, C$_{1-6}$ acyl-, —C$_{1-6}$ hydroxyalkyl, C$_{1-6}$ alkyl or —C$_{1-6}$ haloalkyl. In some embodiments, $R^{4a}$ is —C(=O)CH$_3$, —C(=O)CH$_2$CH$_3$, or —C(=O)CH(CH$_3$)$_2$.

In one embodiment of compounds of formula (VIIB), $R^8$ and $R^9$ are independently H, —CH$_3$, —CD$_3$, —CH$_2$CH$_3$, isopropyl, or cyclopropyl.

One embodiment of the present disclosure relates to compounds of formula (VIIIB):

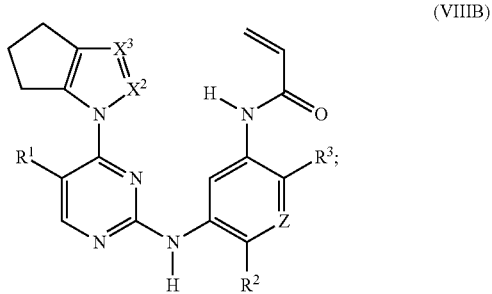

(VIIIB)

or a stereoisomer or a pharmaceutically acceptable salt, solvate, ester, tautomer, or prodrug thereof,
wherein:

each of $X^2$ and $X^3$ is independently CR$^4$ or N; wherein one of $X^2$ and $X^3$ is N and the other is CR$^4$;

Z is CH or N;

$R^1$ is independently selected from hydrogen, fluoro, chloro, bromo, methyl, ethyl, hydroxyl, methoxy, ethoxy, isopropxy, cyclopropoxy, —OCF$_3$, —OCH$_2$CF$_3$, —OCH$_2$CHF$_2$, ethenyl, ethynyl, CF$_3$, CHF$_2$, CHO, CH$_2$OH, CONH$_2$, CO$_2$Me, CONHMe, CONMe$_2$, and cyano;

$R^2$ is —OCF$_3$, —OCHF$_2$, —OCF$_2$CF$_3$, —OCH$_2$CHF$_2$, —OCH$_2$CF$_3$, cyclopropyl, cyclopropoxy, methoxy, —OCD$_3$, ethoxy, or isopropoxy;

$R^3$ is N(R$^{10}$)C$_{1-6}$ alkyl-NR$^{10}$R$^{10}$, N(R$^{10}$)C$_{2-6}$ alkyl-R$^7$, O(CH$_2$)$_p$R$^7$, N(R$^{10}$)C(=O)(CH$_2$)$_p$R$^7$ or R$^7$;

each $R^4$ is independently H, cyano, nitro, halo, —C$_{1-6}$ alkyl, —C$_{1-6}$ haloalkyl, carboxy-C$_{1-6}$ alkyl, —C$_{1-6}$ hydroxyalkyl, R$^8$R$^9$N—C$_{1-6}$ alkyl-, —C$_{2-6}$ alkenyl, —C$_{2-6}$ alkynyl, C$_{1-6}$ acyl-, R$^7$—(CH$_2$)$_p$C(=O)—, C$_{1-6}$ hydroxyalkyl-C(=O)—, carboxy, —C$_{1-6}$ alkoxycarbonyl, —C(=O)NR$^8$R$^9$, hydroxyl, alkoxy, C$_{1-6}$ acyloxy, —NR$^8$R$^9$, C$_{1-6}$acyl-N(R$^{10}$)—, R$^7$SO$_2$—, $R^7$ is OH, NR$^8$R$^9$, O(CH$_2$)$_q$NR$^8$R$^9$, C$_{1-6}$ alkoxy, or C$_{2-6}$ hydroxyalkoxy;

$R^8$ and $R^9$ are independently H, —CD$_3$, C$_{1-6}$ alkyl, C$_{1-6}$ alkenyl, C$_{3-6}$ alkynyl, C$_{3-8}$ cycloalkyl, C$_{3-8}$ cycloalkenyl, C$_1$-C$_6$ acyl, 4-12 membered monocyclic or bicyclic heterocyclyl, 4-12 membered monocyclic or bicyclic heterocyclyl-C$_1$-C$_6$ alkyl-, C$_6$-C$_{12}$ aryl, 5-12 membered heteroaryl; and $R^8$ and $R^9$ may be further independently substituted with up to three substituents chosen from hydroxyl, C$_{1-6}$ alkoxy, C$_{1-6}$ hydroxyalkylC$_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or NR$^{11}$, or a heterobicyclic ring of 7-12 members which may be fused, bridged or spiro, and contain up to two other heteroatoms chosen from O, S(O)$_x$, or NR$^{11}$, and these heterocyclic rings are optionally substituted with up to three substituents chosen from hydroxyl, C$_{1-6}$ alkoxy, C$_{1-6}$ hydroxyalkyl, C$_{1-6}$ alkoxy-C$_{1-6}$ alkyl, C$_{1-6}$ alkoxy-C$_{1-6}$ alkoxy, C$_{2-6}$ hydroxyalkoxy, oxo, thiono, cyano or halo;

each $R^{10}$ is independently H, —CD$_3$, C$_{1-6}$ alkyl, C$_{3-6}$ cycloalkyl, C$_{2-6}$ hydroxyalkyl, C$_{1-6}$ alkoxy-C$_{1-6}$ alkyl or C$_{1-6}$ alkyl-NR$^8$R$^9$; or alternatively, two R$^{10}$ on the same N atom to which they are both attached, form a heterocyclic ring of 5-6 members, containing up to one other heteroatom selected from O, S, or NR$^{11}$:

each $R^{11}$ is independently hydrogen or C$_1$-C$_6$ alkyl, which is optionally substituted with up to three substituents selected from hydroxyl, oxo, thiono, cyano and halo;

p=0, 1, 2, 3, or 4;

q=2, 3, or 4; and x=0, 1, or 2.

One embodiment of the present disclosure relates to compounds of formula (IXB):

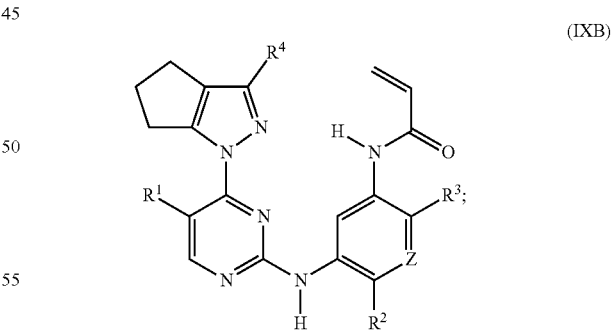

(IXB)

or a stereoisomer or a pharmaceutically acceptable salt, solvate, ester, tautomer, or prodrug thereof;
wherein Z is CH or N;

$R^1$ is selected from hydrogen, methyl, fluoro, chloro, bromo, CF$_3$, or cyano;

$R^2$ is —OCF$_3$, —OCHF$_2$, —OCF$_2$CF$_3$, —OCH$_2$CHF$_2$, —OCH$_2$CF$_3$, cyclopropoxy, methoxy, —OCD$_3$, ethoxy, or isopropoxy;

$R^3$ is $N(R^{10})C_{2-6}$ alkyl-$NR^{10}R^{10}$;

$R^4$ is H, cyano, halo, —$C_{1-6}$ alkyl, —$C_1$—haloalkyl, $C_{1-6}$ hydroxyalkyl-C(=O)—, —C(=O)$NR^8R^9$, —$NR^8R^9$, $C_{1-6}$ acyl-N($R^{10}$)—, ($C_{1-3}$alkyl)SO$_2$NH— or $R^7SO_2$—;

$R^7$ is —$NR^8R^9$;

$R^8$ and $R^9$ are independently H, —CD$_3$, $C_{1-6}$ alkyl, $C_{3-6}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$; and each $R^{10}$ is independently H, —CD$_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (IXB), Z is CH.

In one embodiment of compounds of formula (IXB), $R^2$ is —OCH$_2$CHF$_2$, —OCH$_2$CF$_3$, methoxy, —OCD$_3$, or ethoxy.

In one embodiment of compounds of formula (IXB), $R^3$ is —N(CH$_3$)CH$_2$CH$_2$N(CH$_3$)$_2$.

In one embodiment of compounds of formula (IXB), $R^{10}$ is H, —CH$_3$, —CD$_3$, —CH$_2$CH$_3$, or isopropyl.

In one embodiment of compounds of formula (IXB), $R^4$ is —C(=O)$NR^8R^9$, —$NR^8R^9$ or $R^7SO_2$—.

In one embodiment of compounds of formula (IXB), $R^8$ and $R^9$ are independently H, —CH$_3$, —CD$_3$, —CH$_2$CH$_3$, isopropyl, or cyclopropyl.

One embodiment of the present disclosure relates to compounds of formula (XIIIB):

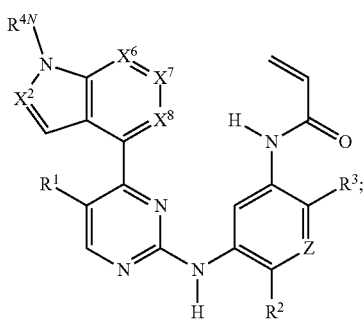

(XIIIB)

or a stereoisomer or a pharmaceutically acceptable salt, solvate, ester, tautomer, or prodrug thereof;
wherein:
each of $X^2$, $X^6$, $X^7$, and $X^8$ is independently $CR^4$ or N; wherein not more than two of $X^2$, $X^6$, $X^7$, and $X^8$ are N;
Z is CH or N;
$R^1$ is independently selected from hydrogen, fluoro, chloro, bromo, methyl, ethyl, hydroxyl, methoxy, ethoxy, isopropxy, cyclopropoxy, —OCF$_3$, —OCH$_2$CF$_3$, —OCH$_2$CHF$_2$, ethenyl, ethynyl, CF$_3$, CHF$_2$, CHO, CH$_2$OH, CONH$_2$, CO$_2$Me, CONHMe, CONMe$_2$, and cyano;

$R^2$ is —OCF$_3$, —OCHF$_2$, —OCF$_2$CF$_3$, —OCH$_2$CHF$_2$, —OCH$_2$CF$_3$, cyclopropyl, cyclopropoxy, methoxy, —OCD$_3$, ethoxy, or isopropoxy;

$R^3$ is $N(R^{10})C_{2-6}$ alkyl-$NR^{10}R^{10}$, $N(R^{10})C_{2-6}$ alkyl-$R^7$, $O(CH_2)_pR^7$, $N(R^{10})C(=O)(CH_2)_pR^7$ or $R^7$;

each $R^4$ is independently H, cyano, nitro, halo, —$C_{1-6}$ alkyl, —$C_{1-6}$ haloalkyl, carboxy-$C_{1-6}$ alkyl, —$C_{1-6}$ hydroxyalkyl, $R^8R^9N$—$C_{1-6}$ alkyl-, —$C_{2-6}$ alkenyl, —$C_{2-6}$ alkynyl, $C_{1-6}$ acyl-, $R^7$—(CH$_2$)$_p$C(=O)—, $C_{1-6}$ hydroxyalkyl-C(=O)—, carboxy, —$C_{1-6}$ alkoxycarbonyl, —C(=O)$NR^8R^9$, hydroxyl, alkoxy, —OCD$_3$, $C_{1-6}$ acyloxy, —$NR^8R^9$, $C_{1-6}$ acyl-N($R^{10}$)—, $R^7SO_2$—;

$R^{4N}$ is H, —CD$_3$, —$C_1$—alkyl, or —$C_{1-6}$ haloalkyl;

wherein when $X^6$ is C—OH, $X^7$ is N, and $X^8$ is $CR^4$, then the bicyclic ring containing $X^2$ can be tautomerized between

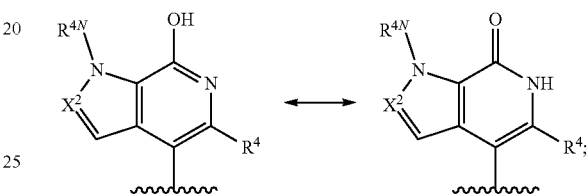

$R^7$ is OH, $NR^8R^9$, $O(CH_2)_qNR^8R^9$, $C_{1-6}$ alkoxy, or $C_{2-6}$ hydroxyalkoxy;

$R^8$ and $R^9$ are independently H, —CD$_3$, $C_{1-6}$ alkyl, $C_{3-6}$ alkenyl, $C_{3-6}$ alkynyl, $C_{3-8}$ cycloalkyl, $C_{3-8}$ cycloalkenyl, $C_1$-$C_6$acyl, 4-12 membered monocyclic or bicyclic heterocyclyl, 4-12 membered monocyclic or bicyclic heterocyclyl-$C_1$-$C_6$ alkyl-, $C_6$-$C_{12}$ aryl, 5-12 membered heteroaryl; and $R^8$ and $R^9$ may be further independently substituted with up to three substituents chosen from hydroxyl, $C_{1-6}$ alkoxy, $C_{1-6}$ hydroxyalkyl$C_{2-6}$ hydroxyalkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$, or a heterobicyclic ring of 7-12 members which may be fused, bridged or spiro, and contain up to two other heteroatoms chosen from O, S(O)$_x$, or $NR^{11}$, and these heterocyclic rings are optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;

each $R^{10}$ is independently H, —CD$_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$; or alternatively, two $R^{10}$ on the same N atom to which they are both attached, form a heterocyclic ring of 5-6 members, containing up to one other heteroatom selected from O, S, or $NR^{11}$;

each $R^{11}$ is independently hydrogen or $C_1$-$C_6$ alkyl, which is optionally substituted with up to three substituents selected from hydroxyl, oxo, thiono, cyano and halo;

p=0, 1, 2, 3, or 4:

q=2, 3, or 4; and x=0, 1, or 2.

One embodiment of the present disclosure relates to compounds of formula (XIVB):

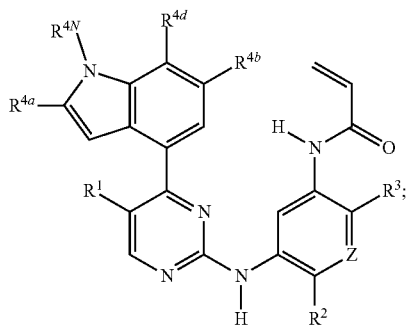

(XIVB)

or a stereoisomer or a pharmaceutically acceptable salt, solvate, ester, tautomer, or prodrug thereof;
wherein;
Z is CH or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^{4a}$ is H, cyano, halo, —$C_{1-6}$ alkyl, or —$C_{1-6}$ haloalkyl;
one of $R^{4b}$ and $R^{4d}$ is —C(=O)$NR^8R^9$ or —$NR^8R^9$ and the other is H;
$R^{4N}$ is H, —$C_{1-6}$ alkyl, or —$CD_3$;
$R^8$ and $R^9$ are independently H, —$CD_3$, $C_{1-6}$ alkyl, $C_{3-6}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and
each $R^{11}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (XIVB),
Z is CH;
$R^1$ is hydrogen, methyl, or chloro;
$R^2$ is —$OCH_2CHF_2$, cyclopropoxy, methoxy, ethoxy, or isopropoxy;
$R^3$ is $N(CH_3)CH_2CH_2NR^{10}R^{10}$
$R^{4a}$ is H, chloro, methyl, or —$CF_3$;
$R^{4b}$ is —C(=O)$NR^8R^9$;
$R^{4d}$ is H;
$R^{4N}$ is H, —$CD_3$, methyl, ethyl, or isopropyl;
$R^8$ and $R^9$ are independently H, methyl, ethyl, or isopropyl; and
each $R^{10}$ is independently H, —$CD_3$, methyl, ethyl, or isopropyl; or
alternatively, two $R^{10}$ on the same N atom to which they are both attached, form a heterocyclic ring of 5-6 members, containing up to one other heteroatom selected from O, S, or $NR^{11}$.

In one embodiment of compounds of formula (XIVB),
Z is CH;
$R^1$ is hydrogen or chloro;
$R^2$ is methoxy, ethoxy, or isopropoxy;
$R^3$ is $N(CH_3)CH_2CH_2NR^{10}R^{10}$ $R^{4a}$ is H, chloro, methyl, or —$CF_3$;
$R^{4b}$ is —C(=O)$NR^8R^9$;
$R^{4d}$ is H;
$R^{4N}$ is H, —$CD_3$, methyl, ethyl, or isopropyl;
$R^8$ and $R^9$ are independently H, methyl, ethyl, or isopropyl; and
each $R^{10}$ is independently H, —$CD_3$, methyl, ethyl, or isopropyl.

In one embodiment of compounds of formula (XIVB),
Z is CH;
$R^1$ is hydrogen;
$R^2$ is —$OCF_3$, —$OCHF_2$, —$OCF_2CF_3$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4a}$ is H, chloro, methyl, or —$CF_3$;
$R^{4d}$ is —C(=O)$NR^8R^9$;
$R^{4b}$ is H;
$R^{4N}$ is H, —$CD_3$, methyl, ethyl, or isopropyl;
$R^8$ and $R^9$ are independently H or methyl; and
each $R^{10}$ is independently H, —$CD_3$, methyl, ethyl, or isopropyl.

In one embodiment of compounds of formula (XIVB),
Z is CH;
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is H, chloro, methyl, or —$CF_3$;
$R^{4d}$ is —C(=O)$NR^8R^9$;
$R^{4b}$ is H;
$R^{4N}$ is H, —$CD_3$, methyl, ethyl, or isopropyl;
$R^8$ and $R^9$ are independently H or methyl; and
each $R^{10}$ is independently H, —$CD_3$, methyl, ethyl, or isopropyl.

In one embodiment of compounds of formula (XIVB), $R^2$ is methoxy, —$OCD_3$, or ethoxy.

In one embodiment of compounds of formula (XIVB), R is —$N(CH_3)CH_2CH_2N(CH_3)_2$.

In one embodiment of compounds of formula (XIVB), $R^{10}$ is H, —$CH_3$, —$CD_3$, —$CH_2CH_3$, or isopropyl.

In one embodiment of compounds of formula (XIVB), $R^{4N}$ is H, or —$CH_3$, —$CD_3$, —$CH_2CH_3$.

In one embodiment of compounds of formula (XIVB), $R^{4a}$ is H, —$CH_3$, or halo.

In one embodiment of compounds of formula (XIVB), $R^{4b}$ is —C(=O)$NR^8R^9$ or —$NR^8R^9$, and $R^{4d}$ is H.

In one embodiment of compounds of formula (XIVB), $R^{4d}$ is —C(=O)$NR^8R^9$ or —$NR^8R^9$, and $R^{4b}$ is H.

In one embodiment of compounds of formula (XIVB), $R^8$ and $R^9$ are independently H, —$CH_3$, —$CD_3$, —$CH_2CH_3$, isopropyl, or cyclopropyl.

One embodiment of the present disclosure relates to compounds of formula (XVB):

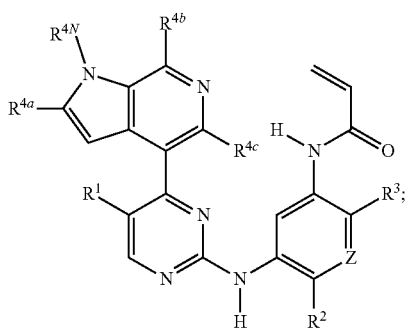

(XVB)

or a stereoisomer or a pharmaceutically acceptable salt, solvate, ester, tautomer, or prodrug thereof;
wherein;
Z is CH or N;
$R^1$ is selected from hydrogen, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^{4a}$ is H, cyano, halo, —$C_1$— alkyl, or —$C_{1-6}$ haloalkyl;
$R^{4b}$ is hydrogen, hydroxyl, —$OCD_3$, methoxy, ethoxy, isopropoxy, cyclopropoxy, —C(=O)$NR^8R^9$ or —$NR^8R^9$;
$R^{4c}$ is H;
$R^{4N}$ is H, —$C_{1-6}$ alkyl, or —$CD_3$;
wherein when $R^{4b}$ is —OH, then the bicyclic ring containing can be tautomerized between

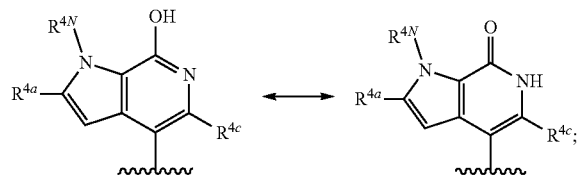

$R^7$ is —$NR^8R^9$;
$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and
each $R^{10}$ is independently H, —$CD_3$, or $C_{1-6}$ alkyl; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo.
In one embodiment of compounds of formula (XVB),
Z is CH;
$R^1$ is hydrogen;
$R^2$ is —$OCH_2CHF_2$, cyclopropoxy, methoxy, ethoxy, or isopropoxy;
$R^3$ is —$N(CH_3)CH_2CH_2NR^{10}R^{10}$;
$R^{4a}$ is H, chloro, methyl, or —$CF_3$;
$R^{4b}$ is —$OCD_3$, methoxy, ethoxy, isopropoxy, or —$NR^8R^9$;
$R^{4c}$ is H;
$R^{4N}$ is H, —$CD_3$, methyl, ethyl, or isopropyl;
$R^8$ and $R^9$ are independently H, methyl, or ethyl; and
each $R^{11}$ is independently H, —$CD_3$, methyl, ethyl, or isopropyl.
In one embodiment of compounds of formula (XVB),
Z is CH;
$R^1$ is hydrogen;
$R^2$ is —$OCD_3$, methoxy, ethoxy, or isopropoxy;
$R^3$ is —$N(CH_3)CH_2CH_2NR^{10}R^{10}$;
$R^{4a}$ is H, chloro, methyl, or —$CF_3$;
$R^{4b}$ is —$OCD_3$, methoxy, ethoxy, isopropoxy;
$R^{4c}$ is H; and
$R^{4N}$ is H, —$CD_3$, methyl, ethyl, or isopropyl:
each $R^{10}$ is independently H, —$CD_3$, methyl, ethyl, or isopropyl.
In one embodiment of compounds of formula (XVB), $R^2$ is —$OCH_2CHF_2$, methoxy, —$OCD_3$, or ethoxy.
In one embodiment of compounds of formula (XVB), $R^3$ is —$N(CH_3)CH_2CH_2N(CH_3)_2$.
In one embodiment of compounds of formula (XVB), $R^{10}$ is H, —$CH_3$, —$CD_3$, —$CH_2CH_3$, or isopropyl.
In one embodiment of compounds of formula (XVB), $R^{4N}$ is H, or —$CH_3$, —$CD_3$, —$CH_2CH_3$.
In one embodiment of compounds of formula (XVB), $R^{4a}$ is H, —$CH_3$, or halo.
In one embodiment of compounds of formula (XVB), $R^{4b}$ is H, methoxy, —$OCD_3$, ethoxy, —C(=O)$NR^8R^9$ or —$NR^8R^9$, and $R^{4c}$ is H.
In one embodiment of compounds of formula (XVB), $R^8$ and $R^9$ are independently H, —$CH_3$, —$CD_3$, —$CH_2CH_3$, isopropyl, or cyclopropyl.
One embodiment of the present disclosure relates to compounds of formula (XVIB):

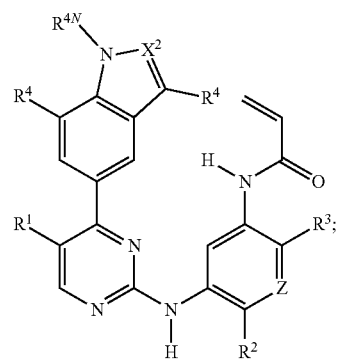

(XVIB)

or a stereoisomer or a pharmaceutically acceptable salt, solvate, ester, tautomer, or prodrug thereof,
wherein:
$X^2$ is $CR^4$ or N;
Z is CH or N;
$R^1$ is independently selected from hydrogen, fluoro, chloro, bromo, methyl, ethyl, hydroxyl, methoxy, ethoxy, isopropxy, cyclopropoxy, —$OCF_3$, —$OCH_2CF_3$, —$OCH_2CHF_2$, ethenyl, ethynyl, $CF_3$, $CHF_2$, CHO, $CH_2OH$, $CONH_2$, $CO_2Me$, CONHMe, $CONMe_2$, and cyano;
$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropoxy;

R³ is N(R¹⁰)C₂₋₆ alkyl-NR¹⁰R¹⁰, N(R¹⁰)C₂₋₆ alkyl-R⁷, O(CH₂)ₚR⁷, N(R¹⁰)C(=O)(CH₂)ₚR⁷ or R⁷;

each R⁴ is independently H, cyano, halo, —C₁₋₆ alkyl, —C₁₋₆ haloalkyl, carboxy-C₁₋₆ alkyl, —C₁₋₆ hydroxyalkyl, R⁸R⁹N—C₁₋₆ alkyl-, —C₂₋₆ alkenyl, —C₁₋₆ alkynyl, C₁₋₆ acyl-, R⁷—(CH₂)ₚC(=O)—, C₁₋₆ hydroxyalkyl-C(=O)—, carboxy, —C₁₋₆ alkoxycarbonyl, —C(=O)NR⁸R⁹, hydroxyl, alkoxy, C₁₋₆ acyloxy, —NR⁸R⁹, C₁₋₆ acyl-N(R¹⁰)—, R⁷SO₂—, R⁴ᴺ is H, —CD₃, —C₁₋₆ alkyl, or —C₁₋₆ haloalkyl;

R⁷ is OH, NR⁸R⁹, O(CH₂)qNR⁸R⁹, C₁₋₆ alkoxy, or C₂₋₆ hydroxyalkoxy;

R⁸ and R⁹ are independently H, —CD₃, C₁₋₆ alkyl, C₃₋₆ alkenyl, C₃₋₆ alkynyl, C₃₋₈ cycloalkyl, C₃₋₈ cycloalkenyl, C₁-C₆ acyl, 4-12 membered monocyclic or bicyclic heterocyclyl, 4-12 membered monocyclic or bicyclic heterocyclyl-C₁-C₆ alkyl-, C₆-C₁₂ aryl, 5-12 membered heteroaryl; and R⁸ and R⁹ may be further independently substituted with up to three substituents chosen from hydroxyl, C₁₋₆ alkoxy, C₁₋₆ hydroxyalkylC₂₋₆ hydroxyalkoxy, oxo, thiono, cyano or halo; or alternatively, R⁸ and R⁹, taken together with the N atom to which they are both attached, form a heterocyclic ring of 4-7 members, containing up to one other heteroatom chosen from O, S, or NR¹¹, or a heterobicyclic ring of 7-12 members which may be fused, bridged or spiro, and contain up to two other heteroatoms chosen from O, S(O)ₓ, or NR¹¹, and these heterocyclic rings are optionally substituted with up to three substituents chosen from hydroxyl, C₁₋₆ alkoxy, C₁₋₆ hydroxyalkyl, C₁₋₆ alkoxy-C₁₋₆ alkyl, C₁₋₆ alkoxy-C₁₋₆ alkoxy, C₂₋₆ hydroxyalkoxy, oxo, thiono, cyano or halo;

each R¹⁰ is independently H, —CD₃, C₁₋₆ alkyl, C₃₋₈ cycloalkyl, C₁₋₆ hydroxyalkyl, C₁₋₆ alkoxy-C₁₋₆ alkyl or C₁₋₆ alkyl-NR⁸R⁹; or alternatively, two R¹⁰ on the same N atom to which they are both attached, form a heterocyclic ring of 5-6 members, containing up to one other heteroatom selected from O, S, or NR¹¹;

each R¹¹ is independently hydrogen or C₁-C₆ alkyl, which is optionally substituted with up to three substituents selected from hydroxyl, oxo, thiono, cyano and halo;

p=0, 1, 2, 3, or 4;
q=2, 3, or 4; and
x=0, 1, or 2.

One embodiment of the present disclosure relates to compounds of formula (XVIIB):

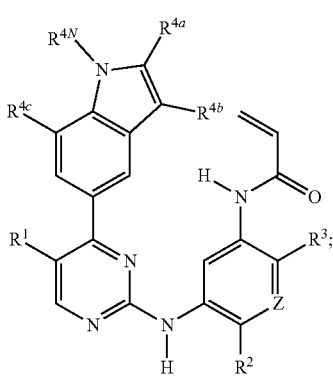

(XVIIB)

or a stereoisomer or a pharmaceutically acceptable salt, solvate, ester, tautomer, or prodrug thereof;

wherein;
Z is CH or N;
R¹ is selected from hydrogen, methyl, fluoro, chloro, bromo, CF₃, or cyano;
R² is —OCF₃, —OCHF₂, —OCF₂CF₃, —OCH₂CHF₂, —OCH₂CF₃, cyclopropoxy, methoxy, —OCD₃, ethoxy, or isopropoxy;
R³ is N(R¹⁰)C₂₋₆ alkyl-NR¹⁰R¹⁰;
R⁴ᵃ and R⁴ᵇ are each independently H, halo, —C₁₋₆ alkyl, or —C₁₋₆ haloalkyl;
R⁴ᶜ is cyano, —C(=O)NR⁸R⁹ or —NR⁸R⁹;
R⁴ᴺ is H, —C₁₋₆ alkyl, or —CD₃;
R⁸ and R⁹ are independently H, —CD₃, C₁₋₆ alkyl, C₃₋₆ cycloalkyl, C₃₋₆ cycloalkyl-(C₁₋₃ alkyl)-, C₁-C₆acyl, phenyl, monocyclic heteroaryl, or monocyclic heterocyclyl; and R⁸ and R⁹ may be further independently substituted with up to three substituents chosen from hydroxyl, C₁₋₆ alkoxy, oxo, thiono, cyano or halo; and each R¹⁰ is independently H, —CD₃, or C₁₋₆ alkyl; or
alternatively, two R¹⁰ on the same N atom to which they are both attached, form a heterocyclic ring of 5-6 members, containing up to one other heteroatom selected from O, S, or NR¹¹; and each R¹¹ is independently hydrogen or C₁-C₆ alkyl, which is optionally substituted with up to three substituents selected from hydroxyl, oxo, thiono, cyano and halo.

In one embodiment of compounds of formula (XVIIB),
Z is CH;
R¹ is hydrogen;
R² is —OCH₂CHF₂, cyclopropoxy, methoxy, ethoxy, or isopropoxy;
R³ is —N(CH₃)CH₂CH₂NR¹⁰R¹⁰;
R⁴ᵃ and R⁴ᵇ are each independently H, chloro, methyl, or —CF₃;
R⁴ᶜ is cyano or —C(=O)NR⁸R⁹;
R⁴ᴺ is H, —CD₃, methyl, or ethyl;
R⁸ and R⁹ are independently H or methyl; and
each R¹⁰ is independently H, —CD₃, methyl, ethyl, or isopropyl; or
alternatively, two R¹⁰ on the same N atom to which they are both attached, form a heterocyclic ring of 5-6 members, containing up to one other heteroatom selected from O, S, or NR¹¹.

In one embodiment of compounds of formula (XVIIB),
Z is CH;
R¹ is hydrogen;
R² is methoxy, ethoxy, or isopropoxy;
R³ is —N(CH₃)CH₂CH₂NR¹⁰R¹⁰;
R⁴ᵃ and R⁴ᵇ are each independently H, chloro, methyl, or —CF₃;
R⁴ᶜ is cyano or —C(=O)NR⁸R⁹;
R⁴ᴺ is H, —CD₃, methyl, or ethyl;
R⁸ and R⁹ are independently H or methyl; and
each R¹⁰ is independently H, —CD₃, methyl, ethyl, or isopropyl.

In one embodiment of compounds of formula (XVIIB), R² is methoxy, —OCD₃, or ethoxy.

In one embodiment of compounds of formula (XVIIB), R³ is —N(CH₃)CH₂CH₂N(CH₃)₂.

In one embodiment of compounds of formula (XVIIB), R¹⁰ is H, —CH, —CD₃, —CH₂CH₃, or isopropyl.

In one embodiment of compounds of formula (XVIIB), R⁴ᴺ is H, or —CH₃, —CD₃, —CH₂CH₃.

In one embodiment of compounds of formula (XVIIB), R⁴ᵃ and R⁴ᵇ is each H, —CH₃, or halo.

In one embodiment of compounds of formula (XVIIB), R⁴ᶜ is cyano, —C(=O)NR⁸R⁹ or —NR⁸R⁹.

In one embodiment of compounds of formula (XVIIB), $R^8$ and $R^9$ are independently H, —$CH_3$, —$CD_3$, —$CH_2CH_3$, isopropyl, or cyclopropyl.

One embodiment of the present disclosure relates to compounds of formula (XVIIIB):

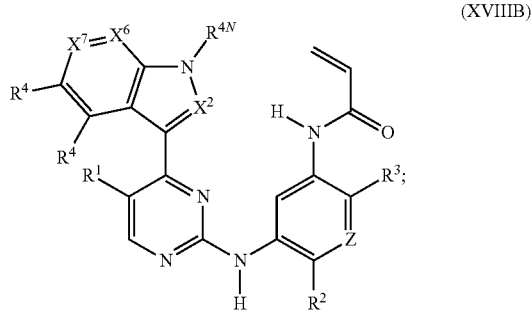

(XVIIIB)

or a stereoisomer or a pharmaceutically acceptable salt, solvate, ester, tautomer, or prodrug thereof;
wherein:
$X^2$, $X^6$, and $X^7$ is each independently $CR^4$ or N; wherein not more than two of $X^5$, $X^6$, and $X^7$ are N;
Z is CH or N;
$R^1$ is independently selected from hydrogen, fluoro, chloro, bromo, methyl, ethyl, hydroxyl, methoxy, ethoxy, isopropxy, cyclopropoxy, —$OCF_3$, —$OCH_2CF_3$, —$OCH_2CHF_2$, ethenyl, ethynyl, $CF_3$, $CHF_2$, CHO, $CH_2OH$, $CONH_2$, $CO_2Me$, CONHMe, $CONMe_2$, and cyano;
$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropoxy;
$R^3$ is $N(R^{10})C_{2-6}$ alkyl-$NR^{10}R^{10}$, —$N(R^{10})C_{2-6}$ alkyl-$R^7$, $O(CH_2)_pR^{10}$, $N(R^{10})C(=O)(CH_2)_pR^7$ or $R^7$;
each $R^4$ is independently H, cyano, nitro, halo, —$C_{1-6}$ alkyl, —$C_{1-6}$ haloalkyl, carboxy-$C_{1-6}$ alkyl, —$C_{1-6}$ hydroxyalkyl, $R^8R^9N$—$C_{1-6}$ alkyl-, —$C_{2-6}$ alkenyl, —$C_{2-6}$ alkynyl, $C_{1-6}$ acyl-, $R^7$—$(CH_2)_pC(=O)$—, $C_{1-6}$ hydroxyalkyl-C(=O)—, carboxy, —$C_{1-6}$ alkoxycarbonyl, —C(=O)$NR^8R^9$, hydroxyl, alkoxy, $C_{1-6}$ acyloxy, —$NR^8R^9$, $C_{1-6}$ acyl-$N(R^{10})$—, $R^7SO_2$—;
$R^{4N}$ is H, —$CD_3$, —$C_{1-6}$ alkyl, —$C_{1-6}$ haloalkyl, or —$CH_2C(=O)NR^8R^9$;
wherein when $X^6$ is C—OH and $X^7$ is N, then the bicyclic ring containing $X^2$ can be tautomerized between

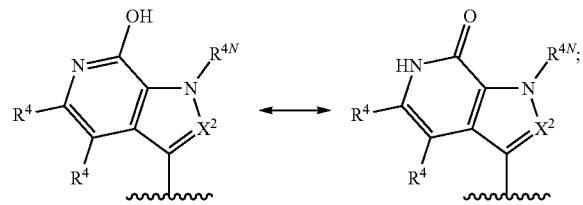

$R^7$ is OH, $NR^8R^9$, $O(CH_2)_qNR^8R^9$, $C_{1-6}$ alkoxy, or $C_{2-6}$ hydroxyalkoxy;
$R^8$ and $R^9$ are independently H, —$CD_3$, $C_{1-6}$ alkyl, $C_{3-6}$ alkenyl, $C_{3-6}$ alkynyl, $C_{3-8}$ cycloalkyl, $C_{3-8}$ cycloalkenyl, $C_1$-$C_6$ acyl, 4-12 membered monocyclic or bicyclic heterocyclyl, 4-12 membered monocyclic or bicyclic heterocyclyl-$C_1$-$C_6$ alkyl-, $C_6$-$C_{12}$ aryl, 5-12 membered heteroaryl; and $R^8$ and $R^9$ may be further independently substituted with up to three substituents chosen from hydroxyl, $C_{1-6}$ alkoxy, $C_{1-6}$ hydroxyalkyl$C_{2-6}$ hydroxyalkoxy, oxo, thiono, cyano or halo; or
alternatively, $R^8$ and $R^9$, taken together with the N atom to which they are both attached, form a heterocyclic ring of 4-7 members, containing up to one other heteroatom chosen from O, S, or $NR^{11}$, or a heterobicyclic ring of 7-12 members which may be fused, bridged or spiro, and contain up to two other heteroatoms chosen from O, $S(O)_x$, or $NR^{11}$, and these heterocyclic rings are optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;
each $R^{10}$ is independently H, —$CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$; or
alternatively, two $R^{10}$ on the same N atom to which they are both attached, form a heterocyclic ring of 5-6 members, containing up to one other heteroatom selected from O, S, or $NR^{11}$; and
each $R^{11}$ is independently hydrogen or $C_1$-$C_6$ alkyl, which is optionally substituted with up to three substituents selected from hydroxyl, oxo, thiono, cyano and halo;
p=0, 1, 2, 3, or 4;
q=2, 3, or 4; and
x=0, 1, or 2.

One embodiment of the present disclosure relates to compounds of formula (XIXB):

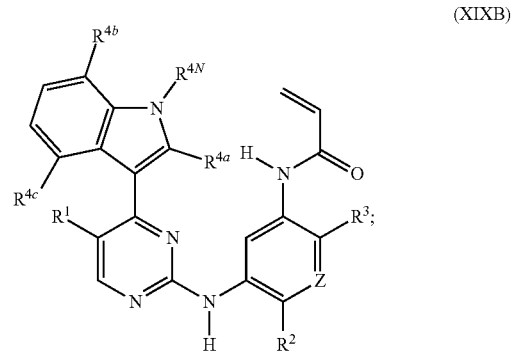

(XIXB)

or a stereoisomer or a pharmaceutically acceptable salt, solvate, ester, tautomer, or prodrug thereof;
wherein;
Z is CH or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^{4a}$ is H, halo, or —$C_{1-6}$ alkyl;
$R^{4b}$ is H, halo, cyano, —C(=O)$NR^8R^9$, —$NR^8R^9$, or $R^7SO_2$—;
$R^{4c}$ is H, halo, methyl, ethyl, or cyano;
$R^{4N}$ is H, —$C_{1-6}$ alkyl, —$CH_2C(=O)NR^8R^9$, or —$CD_3$;
wherein, at least one of $R^{4a}$, $R^{4b}$, or $R^{4c}$ is not H;
$R^7$ is —$NR^8R^9$;
$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, —$CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (XIXB), $R^2$ is —$OCH_2CHF_2$, methoxy, —$OCD_3$, or ethoxy.

In one embodiment of compounds of formula (XIXB), $R^3$ is —$N(CH_3)CH_2CH_2N(CH_3)_2$.

In one embodiment of compounds of formula (XIXB), $R^{10}$ is H, —$CH_3$, —$CD_3$, —$CH_2CH_3$, or isopropyl.

In one embodiment of compounds of formula (XIXB), $R^{4N}$ is H, or —$CH_3$, —$CD_3$, —$CH_2CH_3$.

In one embodiment of compounds of formula (XIXB), $R^{4a}$ is H, —$CH_3$, or halo.

In one embodiment of compounds of formula (XIXB), $R^{4b}$ is —$C(=O)NR^8R^9$, —$NR^8R^9$.

$R^7SO_2$—, —$C_{1-6}$ alkyl or cyano, and R is H. In another embodiment. $R^{4c}$ is methyl, ethyl, or halo, and $R^{4b}$ is H.

In one embodiment of compounds of formula (XIXB), $R^8$ and $R^9$ are independently H, —$CH_3$, —$CD_3$, —$CH_2CH_3$, isopropyl, or cyclopropyl.

One embodiment of the present disclosure relates to compounds of formula (XXB):

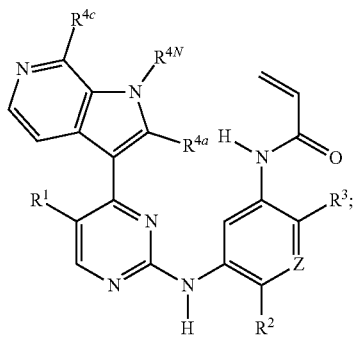

(XXB)

or a stereoisomer or a pharmaceutically acceptable salt, solvate, ester, tautomer, or prodrug thereof,
wherein;

Z is CH or N;

$R^1$ is selected from hydrogen, methyl, fluoro, chloro, bromo, $CF_3$, or cyano;

$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;

$R^3$ is $N(R^{10})C_{2-6}$ alkyl-$NR^{10}R^{10}$;

$R^{4a}$ is H, halo, or —$C_{1-6}$ alkyl;

$R^{4c}$ is H, halo, hydroxyl, —$C_{1-6}$ alkyl, —$C_{1-6}$ alkoxy, cyano, —$C(=O)NR^8R^9$, or —$NR^8R^9$;

$R^{4N}$ is H, —$C_{1-6}$ alkyl, or —$CD_3$;

wherein when R is —OH, then the bicyclic ring can be tautomerized between

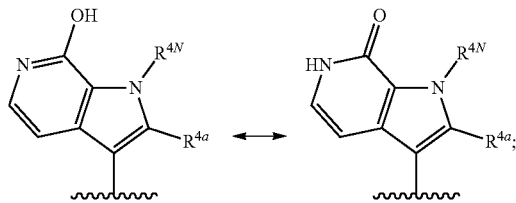

$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, —$CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$alkyl, which is optionally substituted with up to three substituents selected from hydroxyl, oxo, thiono, cyano and halo.

In one embodiment of compounds of formula (XXB),
Z is CH;
$R^1$ is hydrogen;
$R^2$ is cyclopropoxy, methoxy, ethoxy, or isopropoxy;
$R^3$ is —$N(CH_3)CH_2CH_2NR^{10}R^{10}$;
R is H;
$R^4$ is —$OCD_3$, methoxy, ethoxy, or —$NR^8R^9$;
$R^{4N}$ is H, —$CD_3$, methyl, ethyl, or isopropyl;
$R^8$ and $R^9$ are independently H or methyl; and
each $R^{10}$ is independently H, —$CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

In one embodiment of compounds of formula (XXB).
Z is CH;
$R^1$ is hydrogen;
$R^2$ is methoxy, ethoxy, or isopropoxy;
$R^3$ is —$N(CH_3)CH_2CH_2NR^{10}R^{10}$;
$R^{4a}$ is H;
$R^{4c}$ is —$OCD_3$, methoxy, ethoxy, or —$NR^8R^9$;
$R^{4N}$ is H, —$CD_3$, methyl, ethyl, or isopropyl;
$R^8$ and $R^9$ are independently H or methyl; and
each $R^{10}$ is independently H, —$CD_3$, methyl, ethyl, or isopropyl.

In one embodiment of compounds of formula (XXB), $R^2$ is methoxy, —$OCD_3$, or ethoxy.

In one embodiment of compounds of formula (XXB), $R^3$ is —$N(CH_3)CH_2CH_2N(CH_3)_2$.

In one embodiment of compounds of formula (XXB), $R^{10}$ is H, —$CH_3$, —$CD$_, —$CH_2CH_3$, or isopropyl.

In one embodiment of compounds of formula (XXB), $R^{4N}$ is H, or —$CH_3$, —$CD_3$, —$CH_2CH_3$.

In one embodiment of compounds of formula (XXB), $R^{4a}$ is H, —$CH_3$, or halo.

In one embodiment of compounds of formula (XXB), $R^{4c}$ is methoxy, —$OCD_3$, ethoxy, isopropoxy, cyclopropoxy, or —$NR^8R^9$.

In one embodiment of compounds of formula (XXB), $R^8$ and $R^9$ are independently H, —$CH_3$, —$CD_3$, —$CH_2CH_3$, isopropyl, or cyclopropyl.

One embodiment of the present disclosure relates to compounds of formula (XXIB):

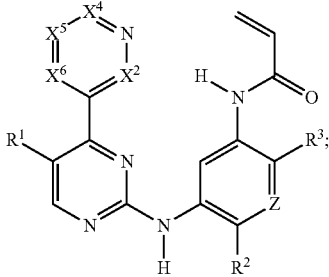

(XXIB)

or a stereoisomer or a pharmaceutically acceptable salt, solvate, ester, tautomer, or prodrug thereof;
wherein:
each of $X^2$, $X^4$, $X^5$, and $X^6$ is independently $CR^4$ or N; wherein not more than two of $X^2$, $X^4$, $X^5$, and $X^6$ are N;
Z is CH or N;
$R^1$ is independently selected from hydrogen, fluoro, chloro, bromo, methyl, ethyl, hydroxyl, methoxy, ethoxy, isopropxy, cyclopropoxy, —$OCF_3$, —$OCH_2CF_3$, —$OCH_2CHF_2$, ethenyl, ethynyl, $CF_3$, $CHF_2$, CHO, $CH_2OH$, $CONH_2$, $CO_2Me$, CONHMe, $CONMe_2$, and cyano;
$R^2$ is —$OCF_3$, —$OCHF_2$, —$OCF_2CF_3$, —$OCH_2CHF_2$, —$OCH_2CF_3$, cyclopropyl, cyclopropoxy, methoxy, —$OCD_3$, ethoxy, or isopropoxy;
$R^3$ is $N(R^{10})C_{2-6}$ alkyl-$NR^{10}R^{10}$, $N(R^{10})C_{2-6}$ alkyl-$R^7$, $O(CH_2)_pR^7$, $N(R^{10})C(=O)(CH_2)_pR^7$ or $R^7$;
each $R^4$ is independently H, cyano, nitro, halo, —$C_{1-6}$ alkyl, —$C_{1-6}$ haloalkyl, carboxy-$C_{1-6}$ alkyl, —$C_{1-6}$ hydroxyalkyl, $R^8R^9N$—$C_{1-6}$ alkyl-, —$C_{2-6}$ alkenyl, —$C_{2-6}$ alkynyl, $C_{1-6}$ acyl-, $R^7$—$(CH_2)_pC(=O)$—, $C_{1f}$ hydroxyalkyl-C(=O)—, carboxy, —$C_{1-6}$ alkoxycarbonyl, —C(=O)$NR^8R^9$, hydroxyl, alkoxy, $C_{1-6}$acyloxy, —$NR^8R^9$, $C_{1-6}$ acyl-$N(R^{10})$—, $R^7SO_2$—,
wherein when $X^5$ is $CR^4$ and $X^4$ is C—OH, then the ring containing $X^2$ can be tautomerized between

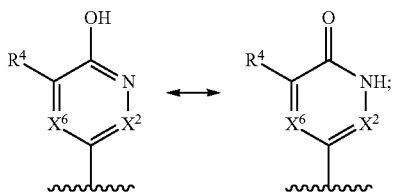

wherein when $X^4$ is $CR^4$ and $X^2$ is C—OH, then the ring containing $X^2$ can be tautomerized between

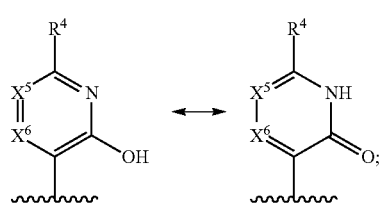

$R^7$ is OH, $NR^8R^9$, $O(CH_2)_qNR^8R^9$, $C_{1-6}$ alkoxy, or $C_{2-6}$ hydroxyalkoxy;
$R^8$ and $R^9$ are independently H, —$CD_3$, $C_{1-6}$ alkyl, $C_{3-6}$ alkenyl, $C_{1-6}$ alkynyl, $C_{3-8}$ cycloalkyl, $C_{3-8}$ cycloalkenyl, $C_1$-$C_6$ acyl, 4-12 membered monocyclic or bicyclic heterocyclyl, 4-12 membered monocyclic or bicyclic heterocyclyl-$C_1$-$C_6$ alkyl-, $C_6$-$C_{12}$ aryl, 5-12 membered heteroaryl; and $R^8$ and $R^9$ may be further independently substituted with up to three substituents chosen from hydroxyl, $C_{1-6}$ alkoxy, $C_{1-6}$ hydroxyalkyl$C_{2-6}$ hydroxyalkoxy, oxo, thiono, cyano or halo; or
alternatively, $R^8$ and $R^9$, taken together with the N atom to which they are both attached, form a heterocyclic ring of 4-7 members, containing up to one other heteroatom chosen from O, S, or $NR^{11}$, or a heterobicyclic ring of 7-12 members which may be fused, bridged or spiro, and contain up to two other heteroatoms chosen from O, $S(O)_x$, or $NR^{11}$, and these heterocyclic rings are optionally substituted with up to three substituents chosen from hydroxyl, $C_{1-6}$ alkoxy, $C_{1-6}$ hydroxyalkyl, $C_{1-6}$ alkoxy-$C_{1-6}$ alkyl, $C_{1-6}$ alkoxy-$C_{1-6}$ alkoxy, $C_{2-6}$ hydroxyalkoxy, oxo, thiono, cyano or halo;
each $R^{10}$ is independently H, —$CD_3$, $C_{1-6}$ alkyl, $C_{3-6}$ cycloalkyl, $C_{2-6}$ hydroxyalkyl, $C_{1-6}$ alkoxy-$C_{1-6}$ alkyl or $C_{2-6}$ alkyl-$NR^8R^9$; or
alternatively, two $R^{10}$ on the same N atom to which they are both attached, form a heterocyclic ring of 5-6 members, containing up to one other heteroatom selected from O, S, or $NR^{11}$;
each $R^{11}$ is independently hydrogen or $C_1$-$C_6$alkyl, which is optionally substituted with up to three substituents selected from hydroxyl, oxo, thiono, cyano and halo;
p=0, 1, 2, 3, or 4:
q=2, 3, or 4; and
x=0, 1, or 2.
One embodiment of the present disclosure relates to compounds of formula (XXIIB):

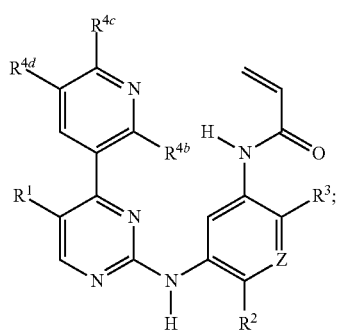

(XXIIB)

or a stereoisomer or a pharmaceutically acceptable salt, solvate, ester, tautomer, or prodrug thereof;
wherein;
Z is CH or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^{4b}$, $R^{4c}$ and $R^{4d}$ is each H, halo, hydroxyl, —$C_{1-6}$ alkyl, cyano, $C_{1-6}$ acyl-, —C(=O)$NR^8R^9$, or —$NR^8R^9$;
wherein when $R^{4b}$ is hydroxyl, then the pyridine ring with $R^{4b}$ substituent can be tautomerized between

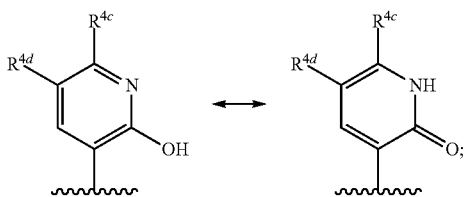

wherein when $R^{4c}$ is hydroxyl, then the pyridine ring with $R^{4c}$ substituent be tautomerized between

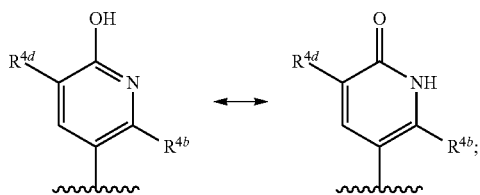

$R^8$ and $R^9$ are independently H, —$CD_3$, $C_{1-6}$ alkyl, $C_{3-8}$ cycloalkyl, $C_{3-8}$ cycloalkyl-($C_{1-3}$ alkyl)-, $C_1$-$C_6$acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, —$CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

In one embodiment of compounds of formula (XXIIB), Z is CH;
$R^1$ is hydrogen, methyl, or chloro;
$R^2$ is —$OCF_3$, —$OCHF_2$, —$OCF_2CF_3$, —$OCH_2CHF_2$, —$OCH_2CF_3$, cyclopropoxy, methoxy, ethoxy, or isopropoxy;
$R^3$ is —$N(CH_3)CH_2CH_2NR^{10}R^{10}$;
$R^{4b}$ is H:
$R^{4c}$ is —$NHR^8$; wherein $R^8$ is H, —$CD_3$, methyl, ethyl, or isopropyl;
$R^{4d}$ is —$C(=O)CH_3$, —$C(=O)CH_2CH_3$, —$C(=O)CH(CH_3)_2$, —$C(=O)NH_2$, —$C(=O)NHCH_3$, or —$C(=O)N(CH_3)_2$; and
each $R^{10}$ is independently H, —$CD_3$, methyl, ethyl, or isopropyl.

In one embodiment of compounds of formula (XXIIB), Z is CH;
$R^1$ is hydrogen or chloro;
$R^2$ is methoxy, ethoxy, or isopropoxy;
$R^3$ is —$N(CH_3)CH_2CH_2R^{10}R^{10}$;
$R^{4b}$ is H;
$R^{4c}$ is —$NHR^8$; wherein $R^8$ is H, —$CD_3$, methyl, ethyl, or isopropyl;
$R^{4d}$ is —$C(=O)CH_3$, —$C(=O)CH_2CH_3$, —$C(=O)CH(CH_3)_2$, —$C(=O)NH_2$, —$C(=O)NHCH_3$, or —$C(=O)N(CH_3)_2$; and
each $R^{10}$ is independently H, —$CD_3$, methyl, ethyl, or isopropyl.

In one embodiment of compounds of formula (XXIIB), $R^2$ is —$OCH_2CHF_2$, methoxy, —$OCD_3$, or ethoxy.

In one embodiment of compounds of formula (XXIIB), $R^3$ is —$N(CH_3)CH_2CH_2N(CH_3)_2$.

In one embodiment of compounds of formula (XXIIB), $R^{10}$ is H, —$CH_3$, —$CD_3$, —$CH_2CH_3$, or isopropyl.

In one embodiment of compounds of formula (XXIIB), $R^{4b}$ is H, or —$CH_3$, —$CD_3$, —$CH_2CH_3$. In another embodiment $R^{4b}$ is H.

In one embodiment of compounds of formula (XXIIB), $R^4$ is H, $C_{1-6}$ acyl-, —$C(=O)NR^8R^9$, or —$NR^8R^9$. In another embodiment, R is H or —$NR^8R^9$.

In one embodiment of compounds of formula (XXIIB), $R^{4d}$ is H, $C_{1-6}$ acyl-, —$C(=O)NR^8R^9$, or —$NR^8R^9$. In another embodiment, $R^{4d}$ is H, $C_{1-6}$ acyl-, or —$C(=O)NR^8R^9$.

In one embodiment of compounds of formula (XXIIB), $R^8$ and $R^9$ are independently H, —$CH_3$, —$CD_3$, —$CH_2CH_3$, isopropyl, or cyclopropyl.

In one embodiment, the present disclosure relates to one or more of the following compounds selected from:

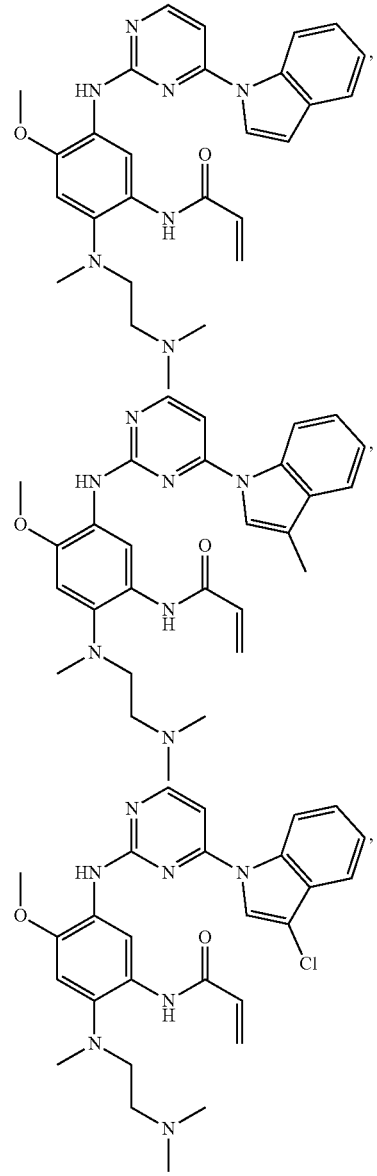

317
-continued
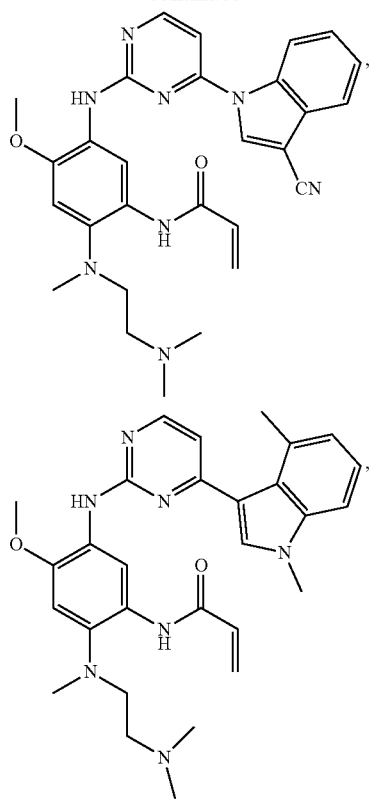
318
-continued
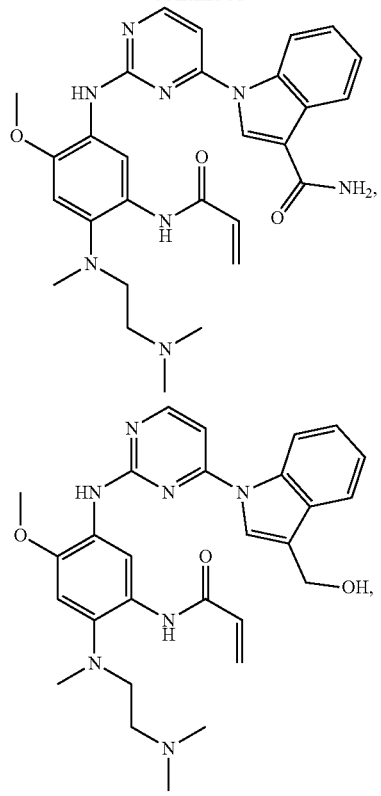
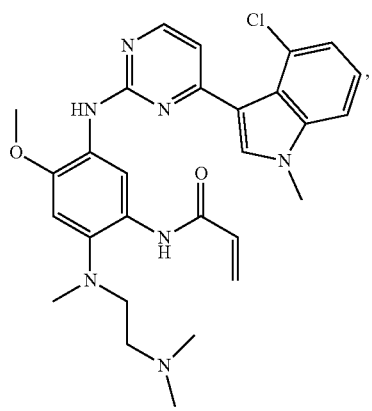
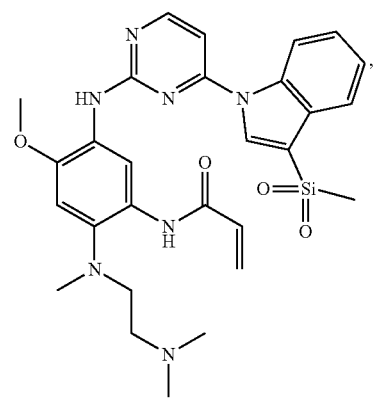
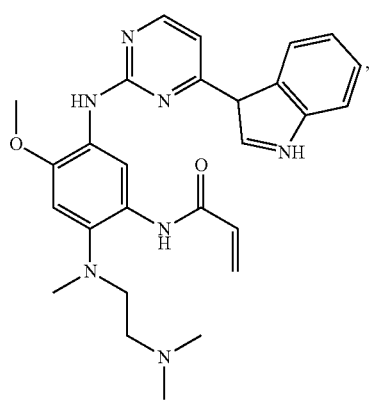
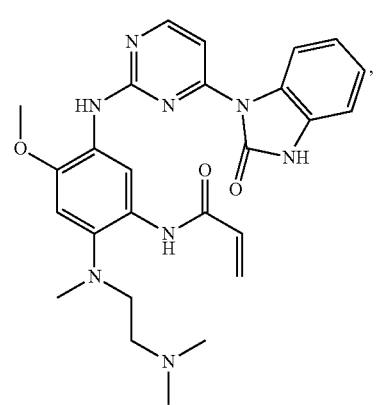

319
-continued
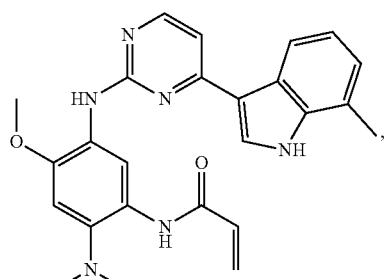
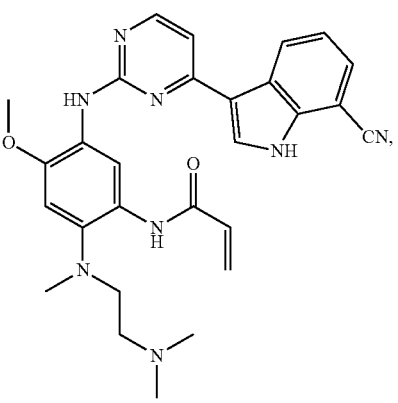
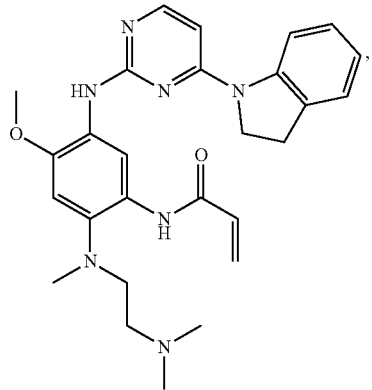
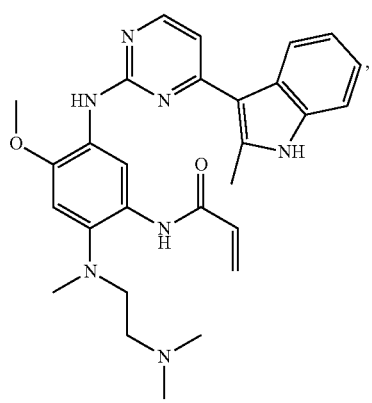
320
-continued
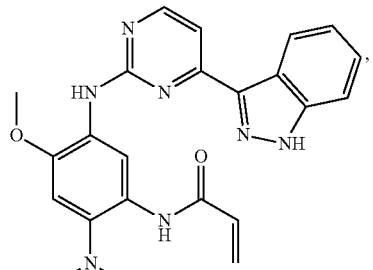
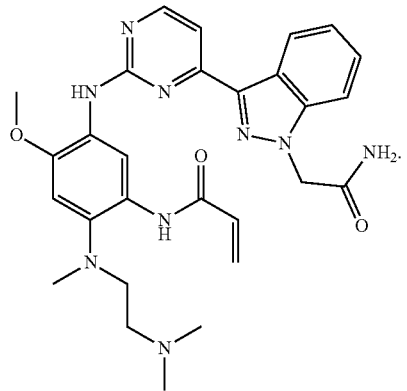
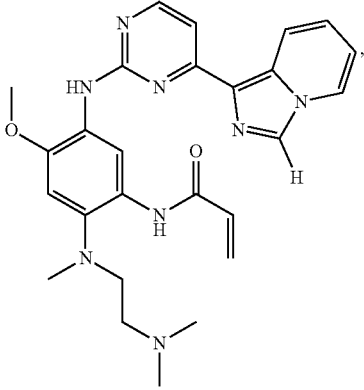
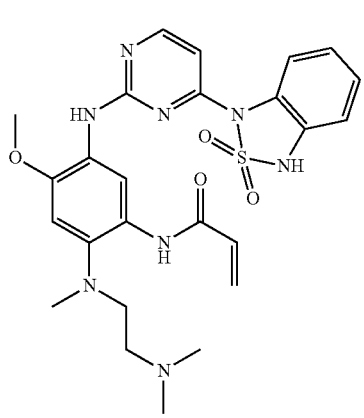

321
-continued
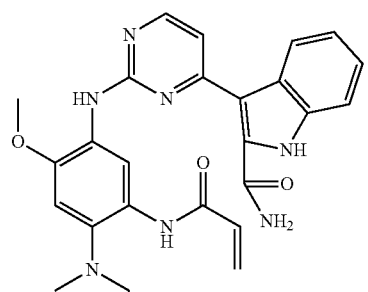
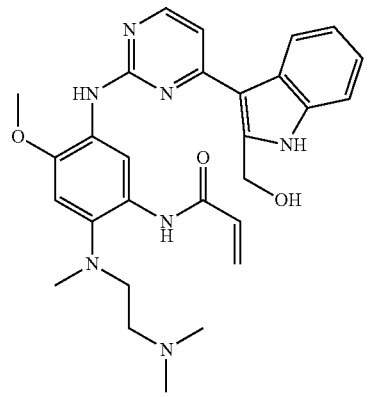
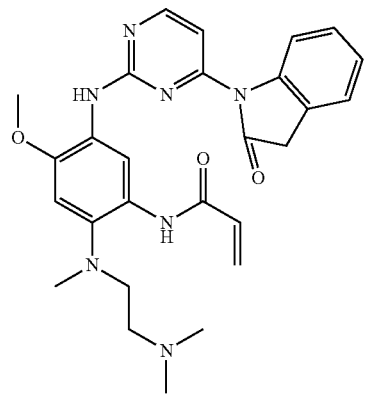
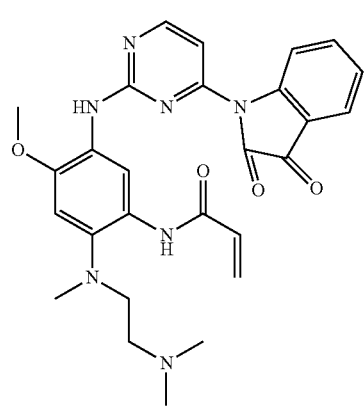
322
-continued
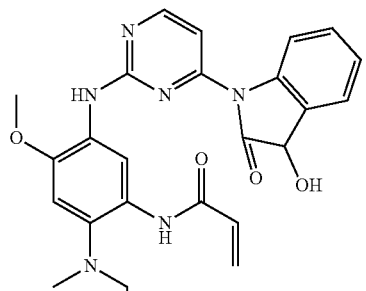
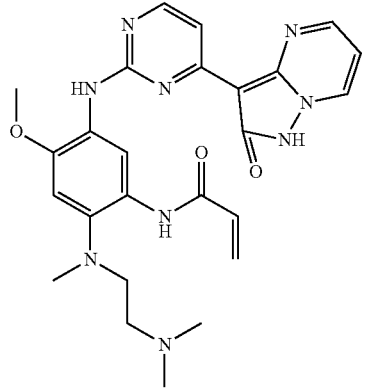
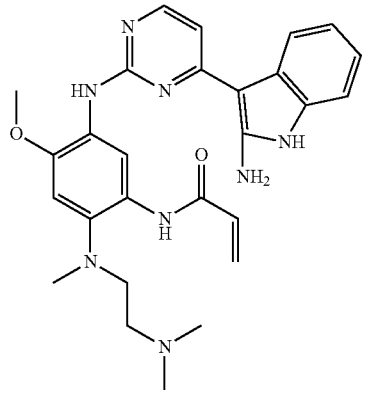
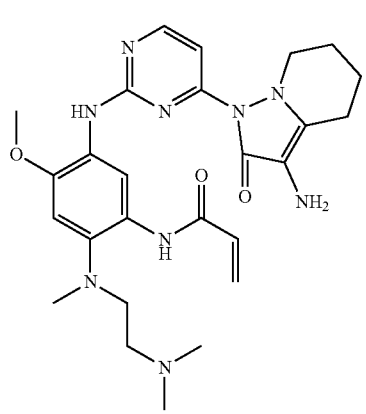

323
-continued
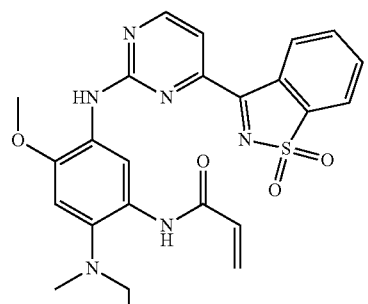
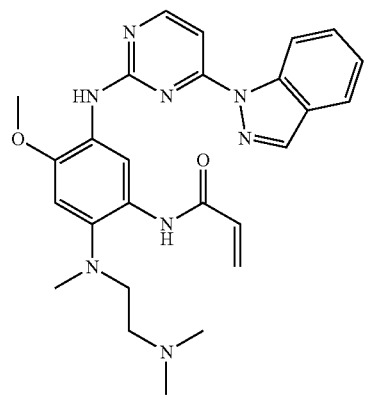
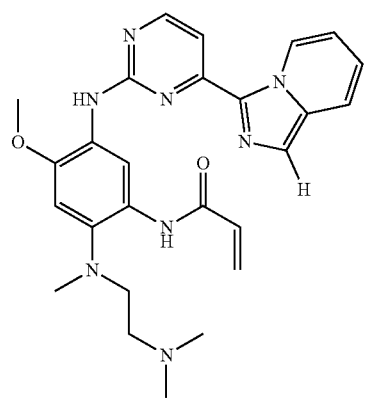
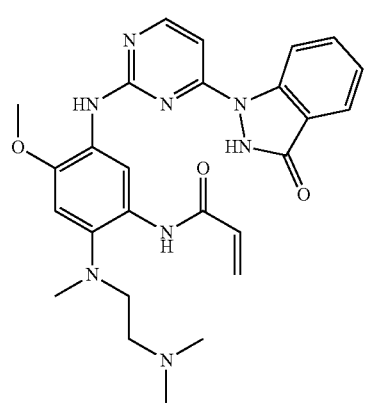
324
-continued
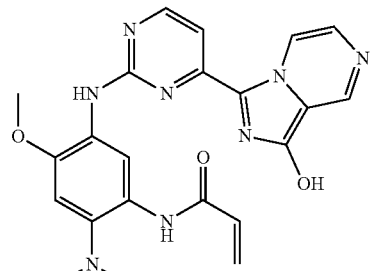
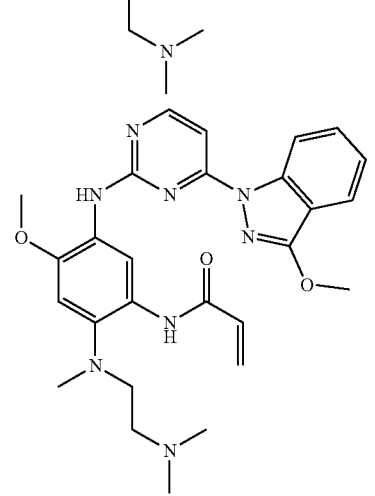
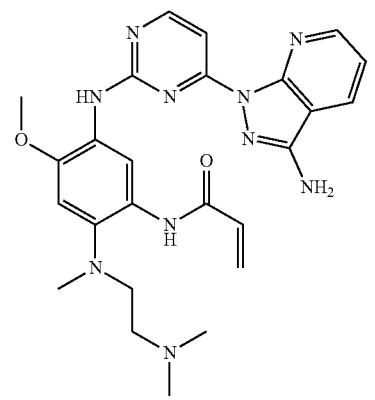
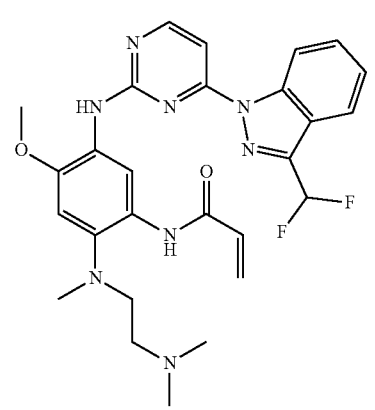

325
-continued
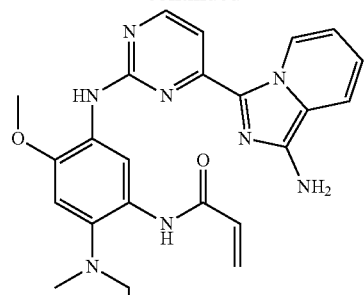
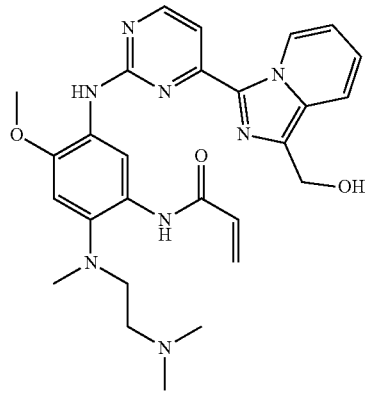
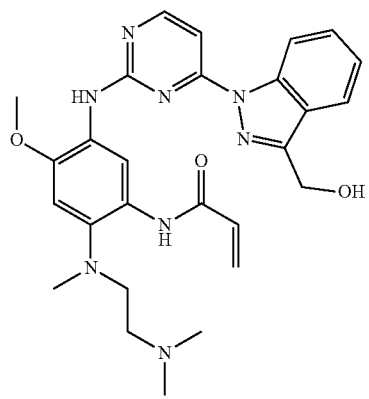
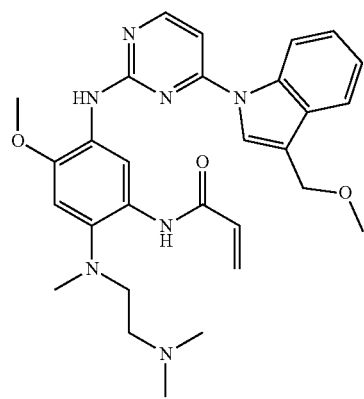
326
-continued
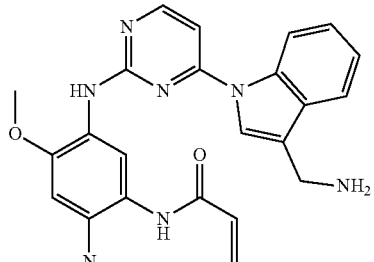
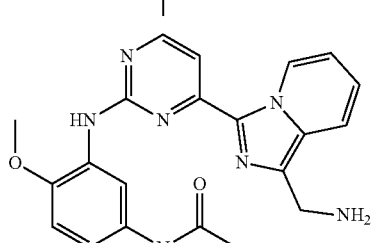
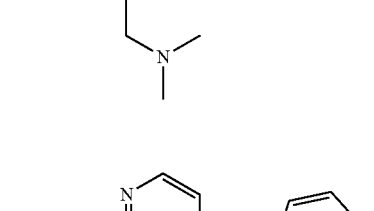
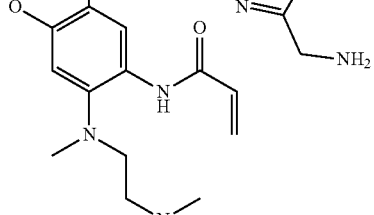
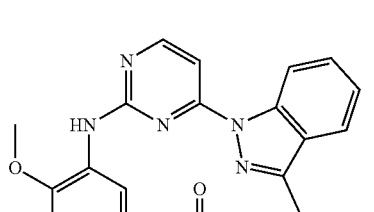

| 327 | 328 |
|---|---|
| 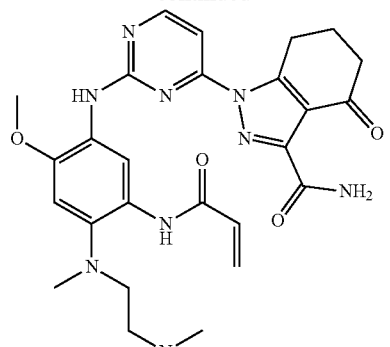 | 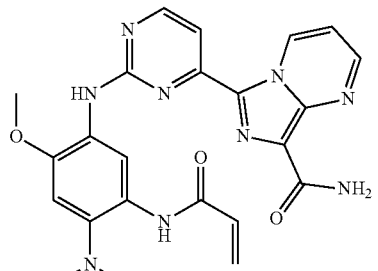 |
| 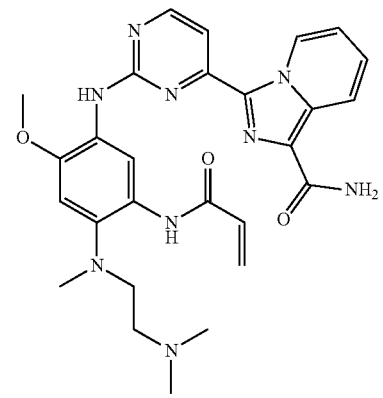 | 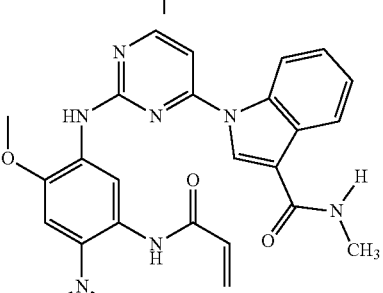 |
| 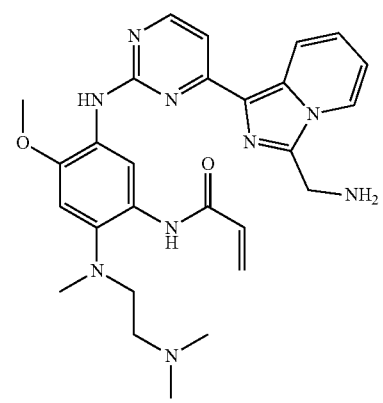 | 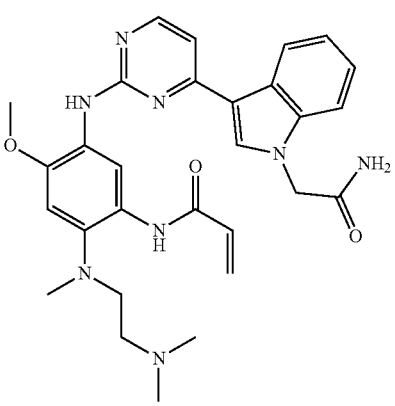 |
| 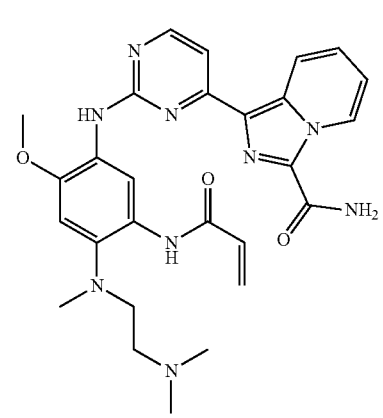 | 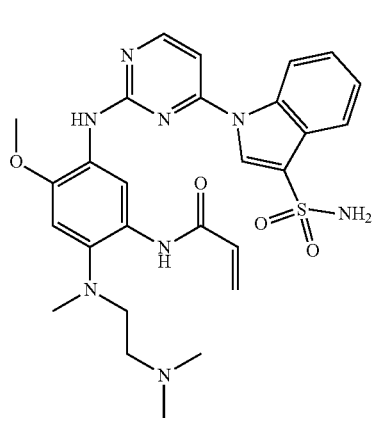 |

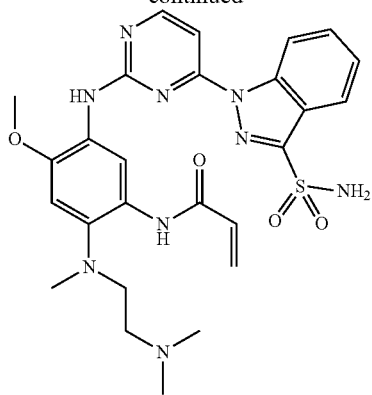
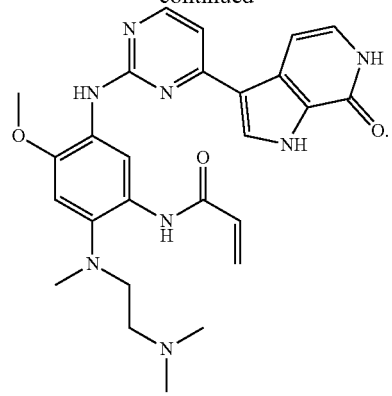
In one embodiment, the compounds of the invention include, but are not limited to:
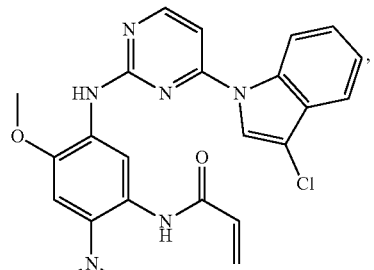

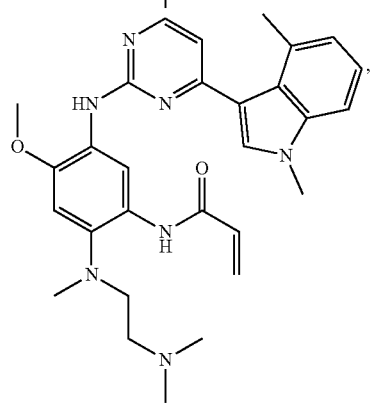

331
-continued
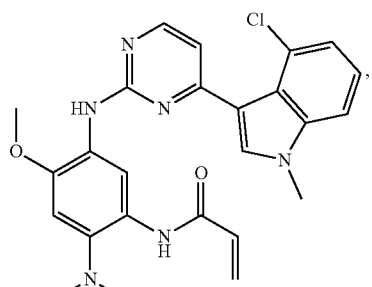
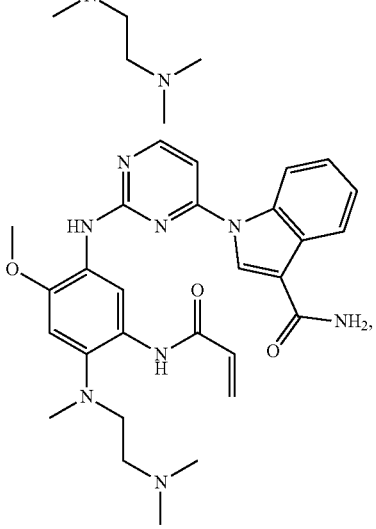
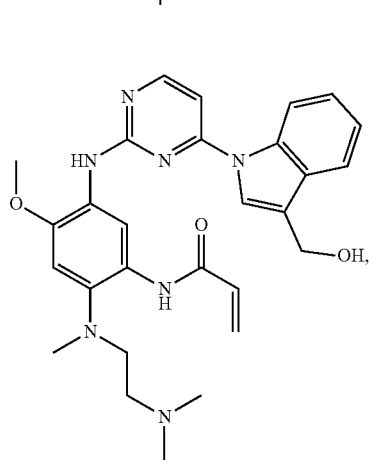
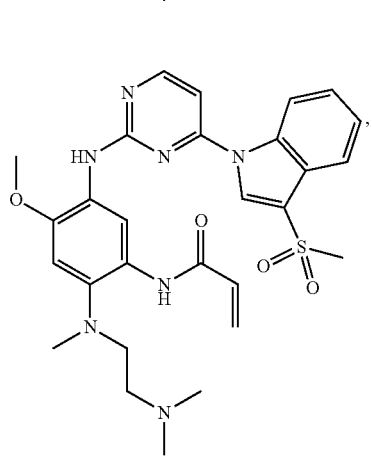
332
-continued
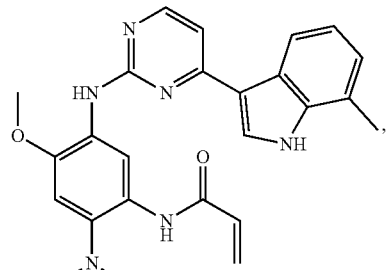
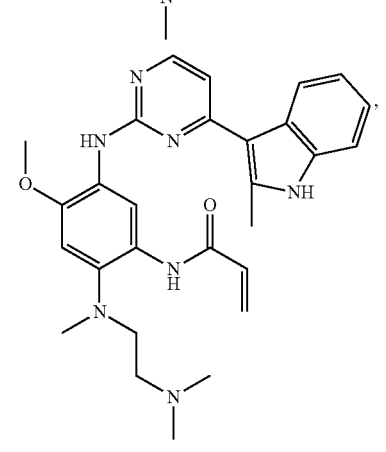
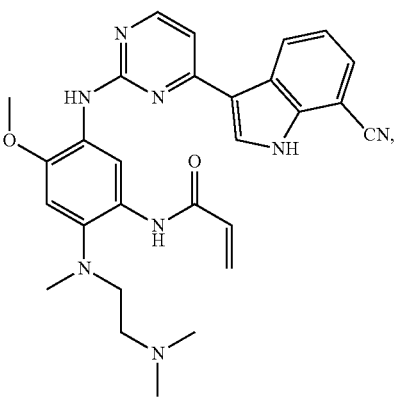
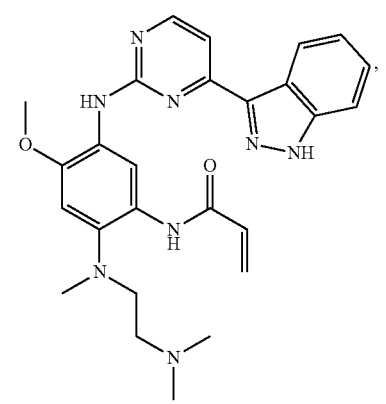

333
-continued
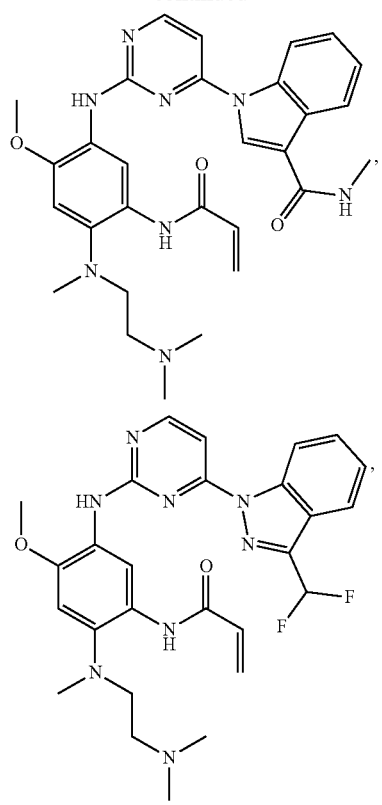
334
-continued
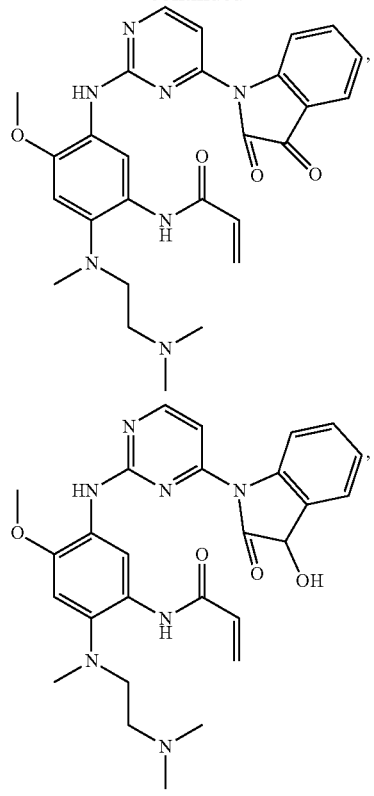
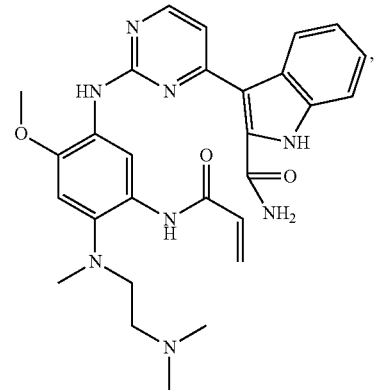
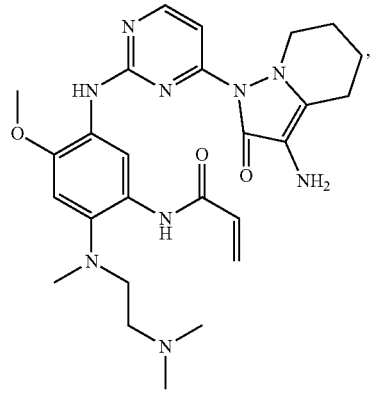
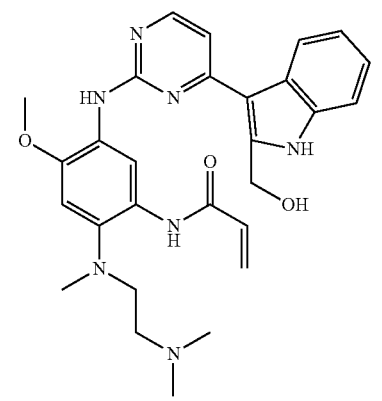
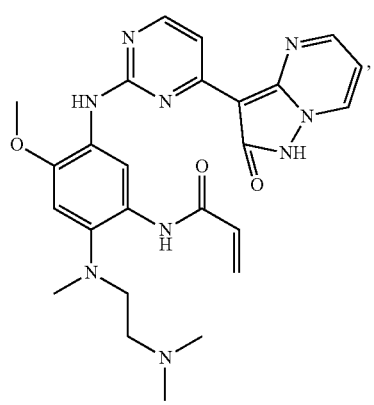

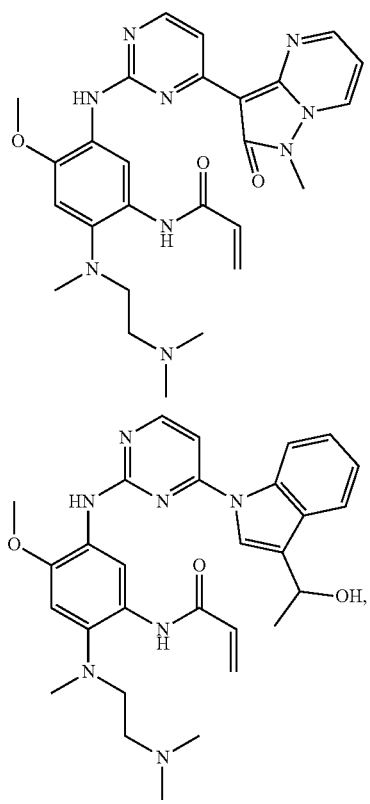
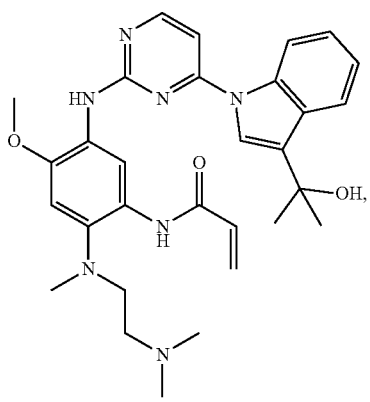
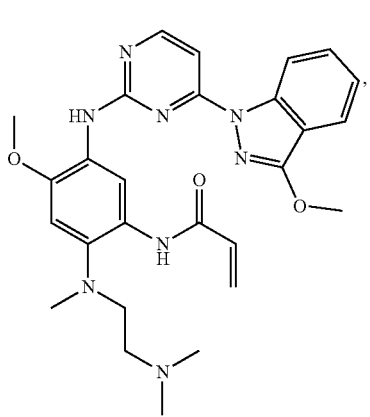
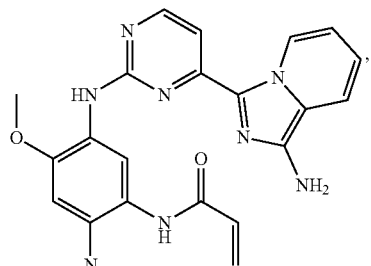
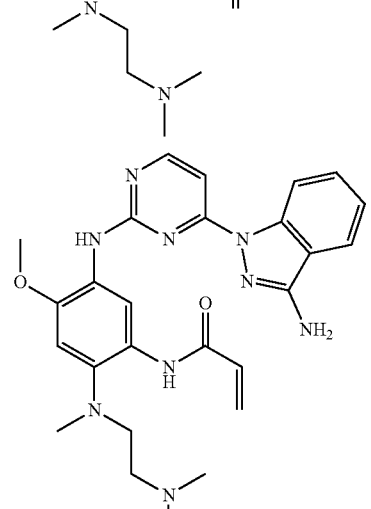
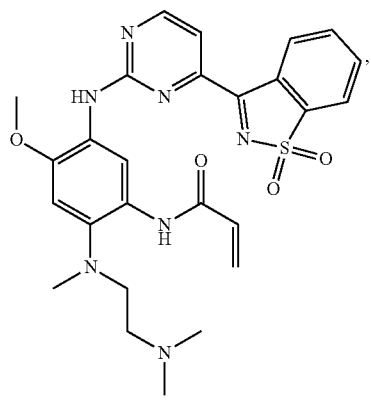
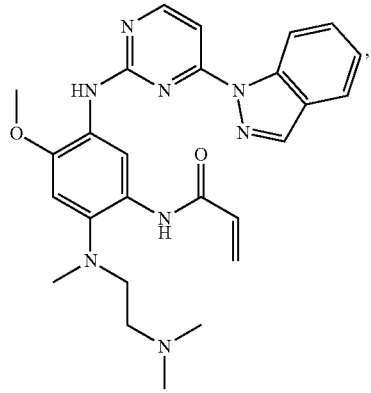

337
-continued
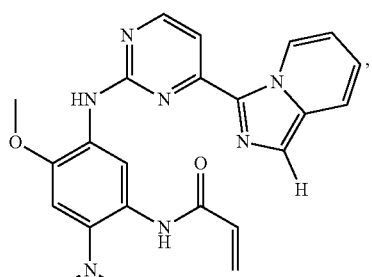
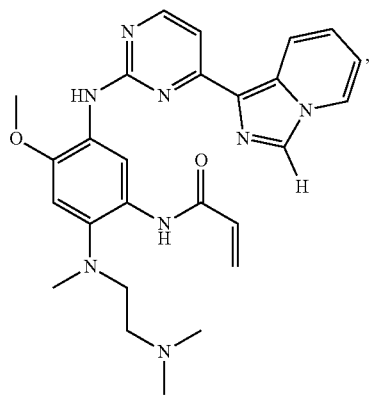
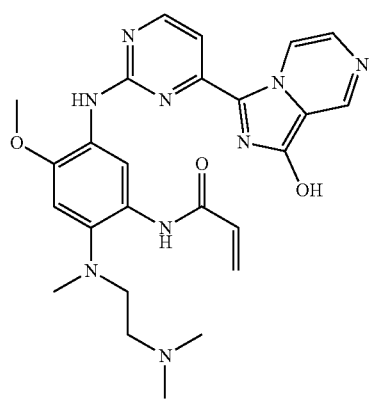
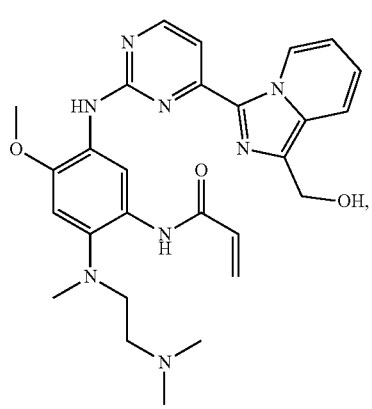
338
-continued
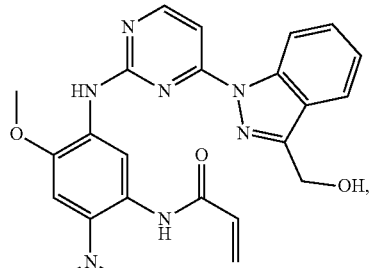
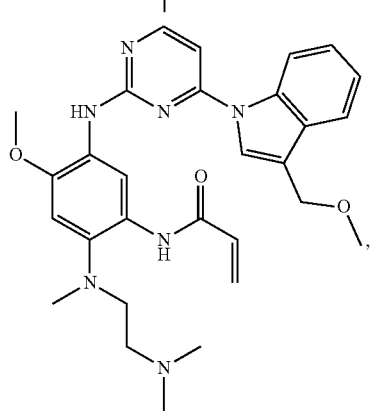
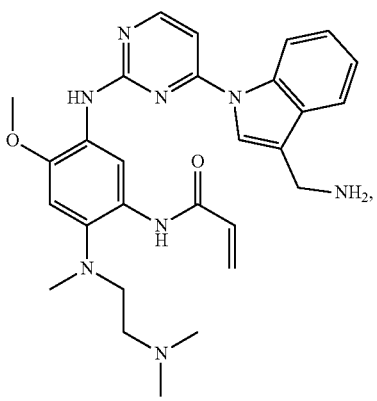
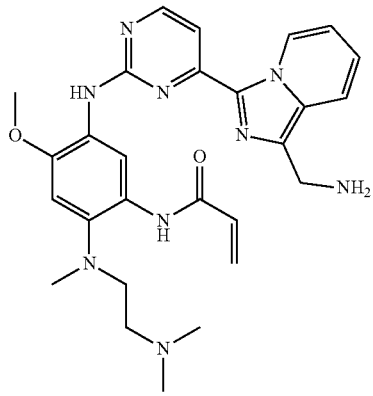

339
-continued
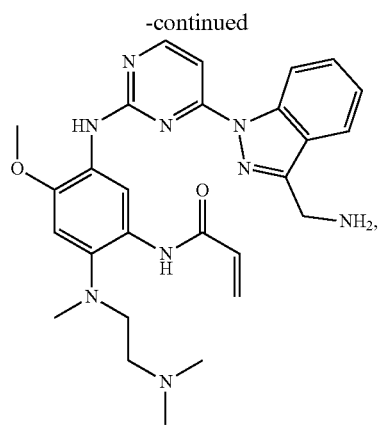
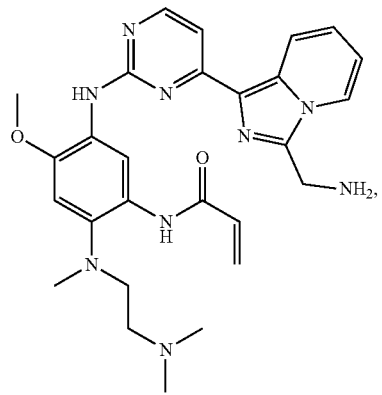
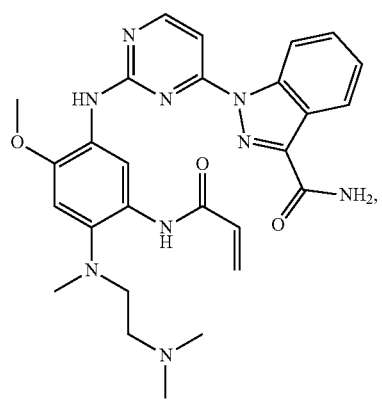
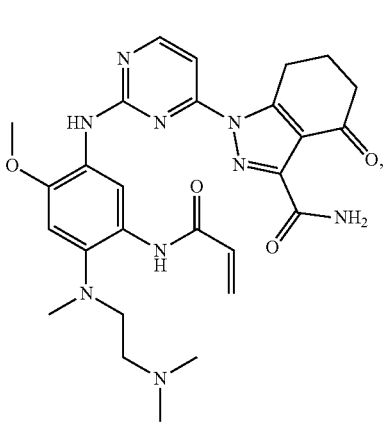
340
-continued
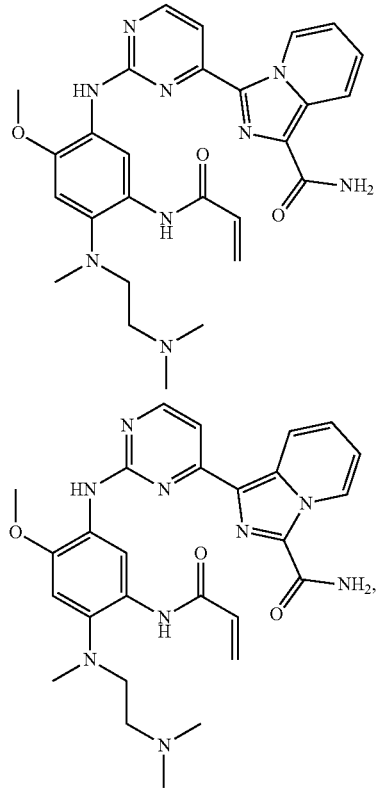
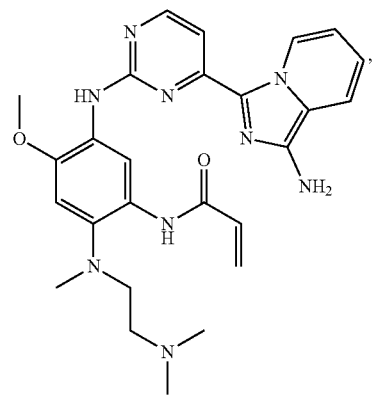
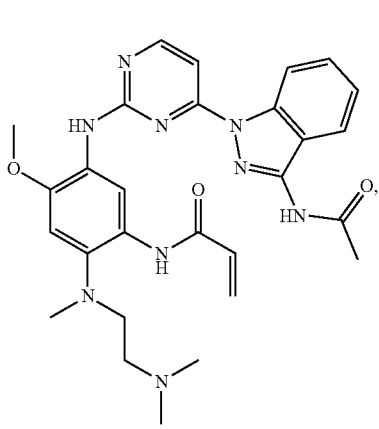

341
-continued
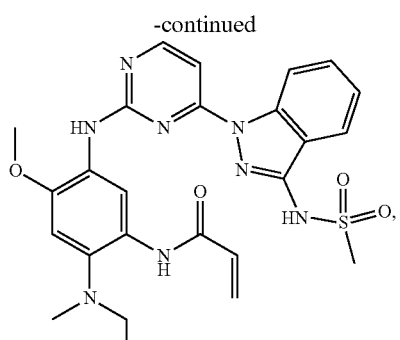
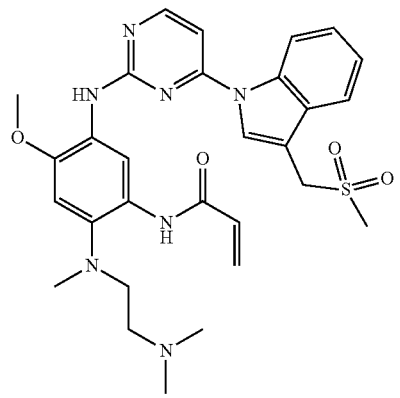
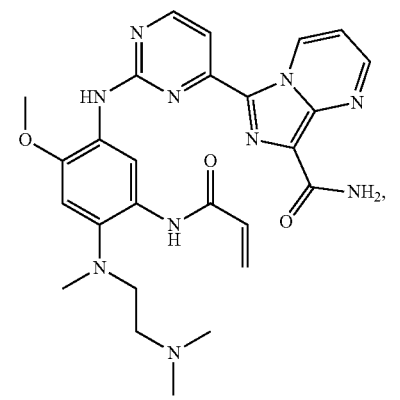
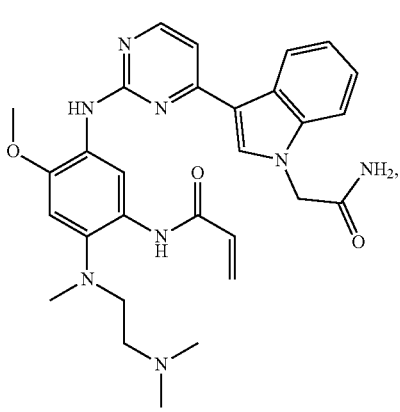
342
-continued
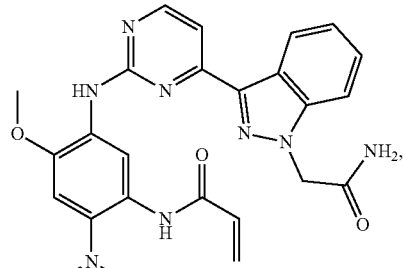
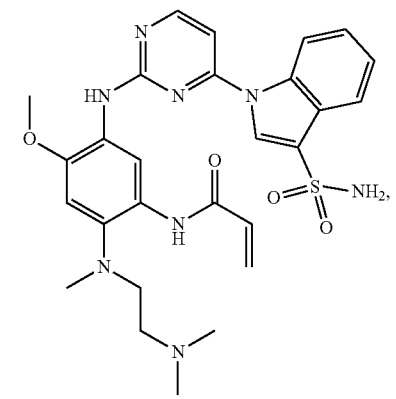
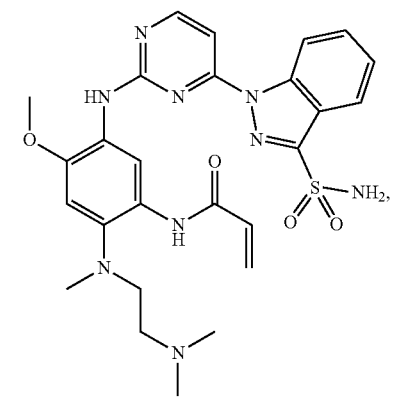
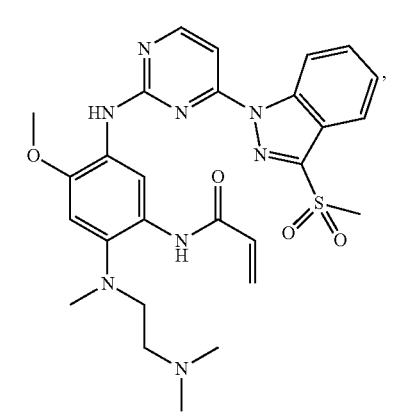

343                                    344
-continued                          -continued
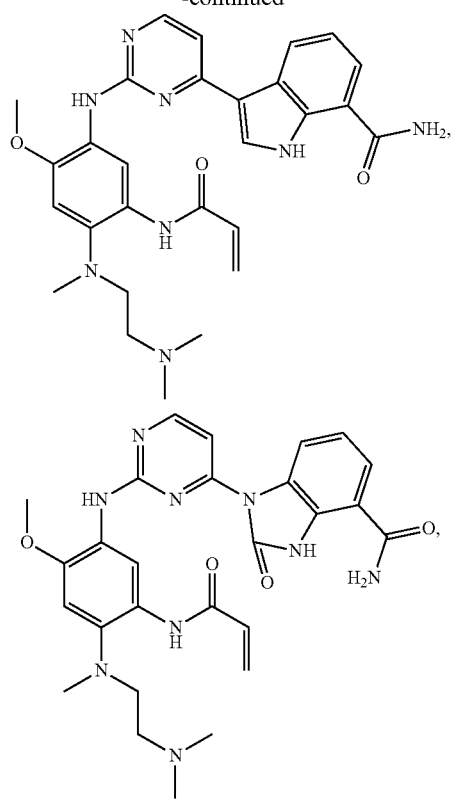
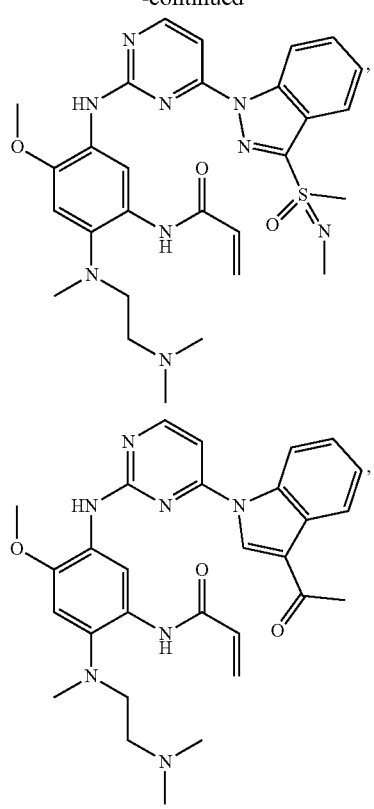
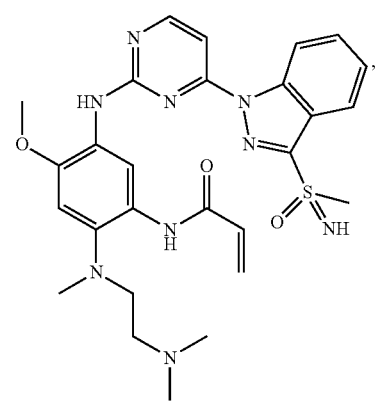
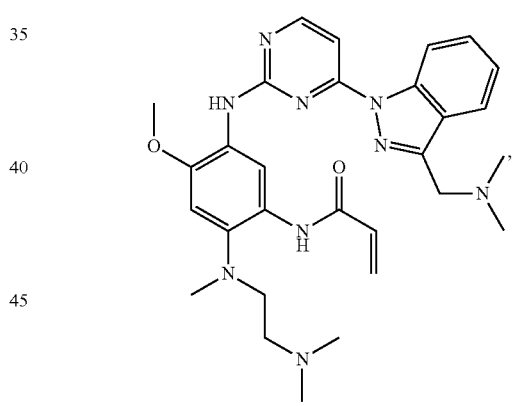
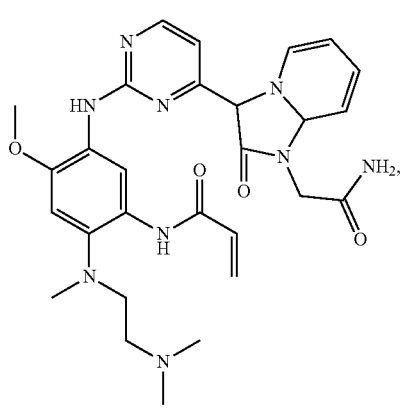
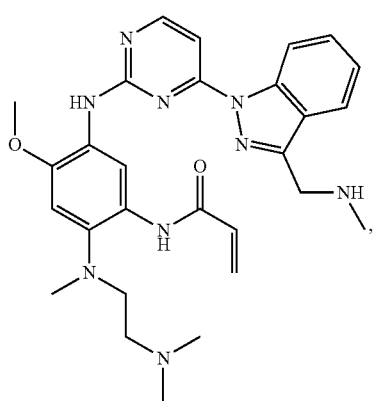

345
-continued
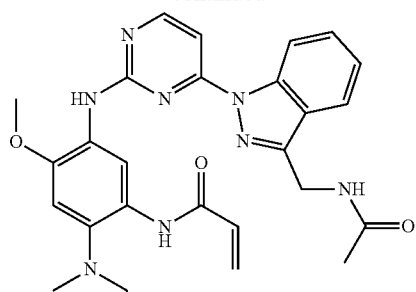
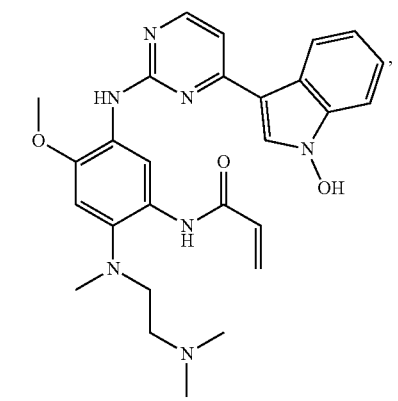
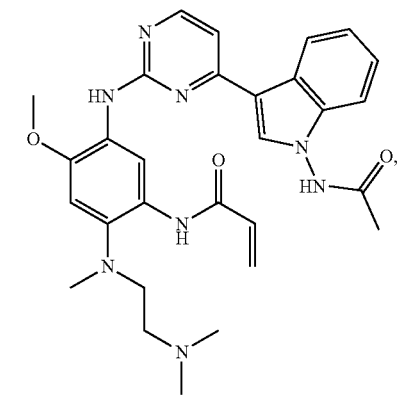
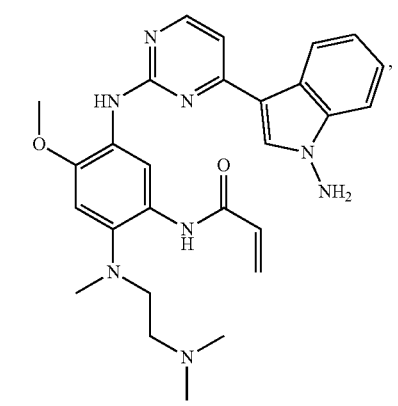
346
-continued
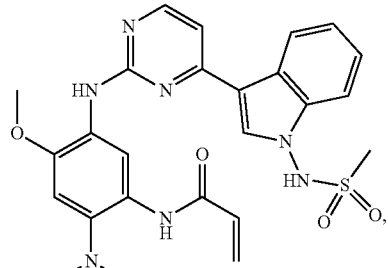
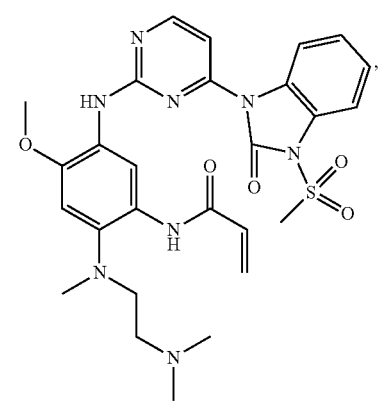
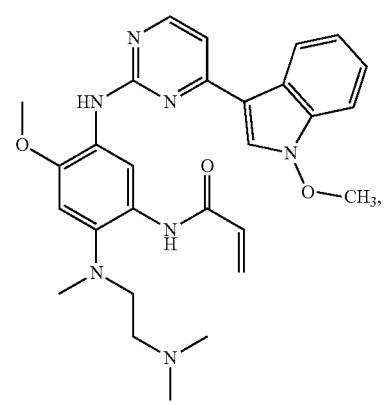
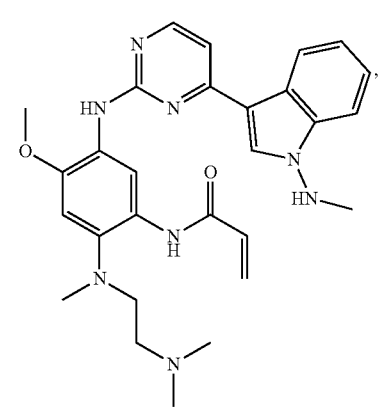

347
-continued
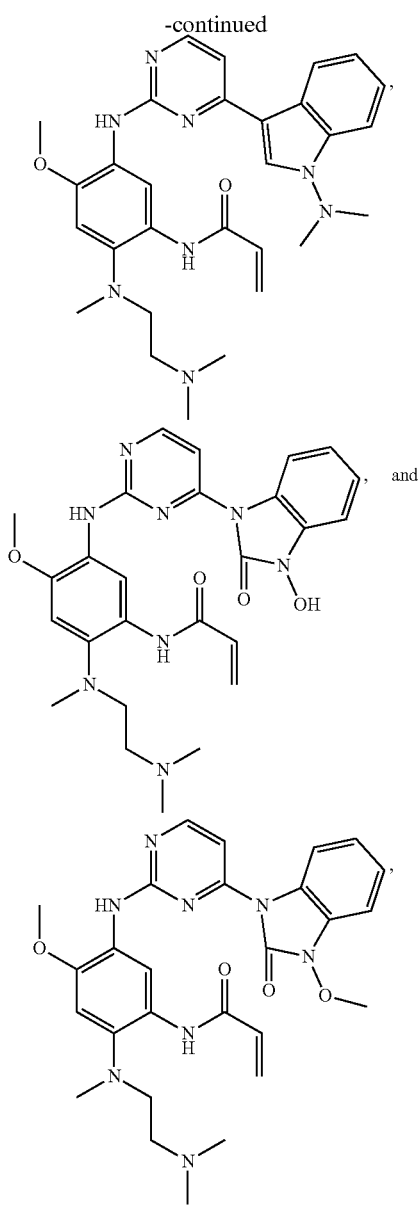
and
In one embodiment, the compounds of the invention include, but are not limited to:
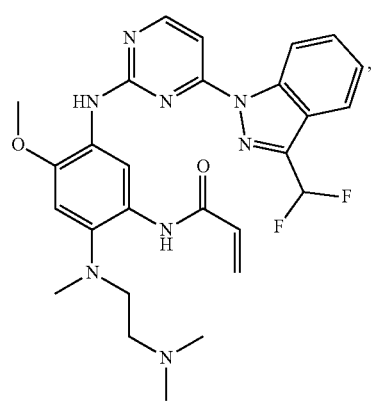
348
-continued
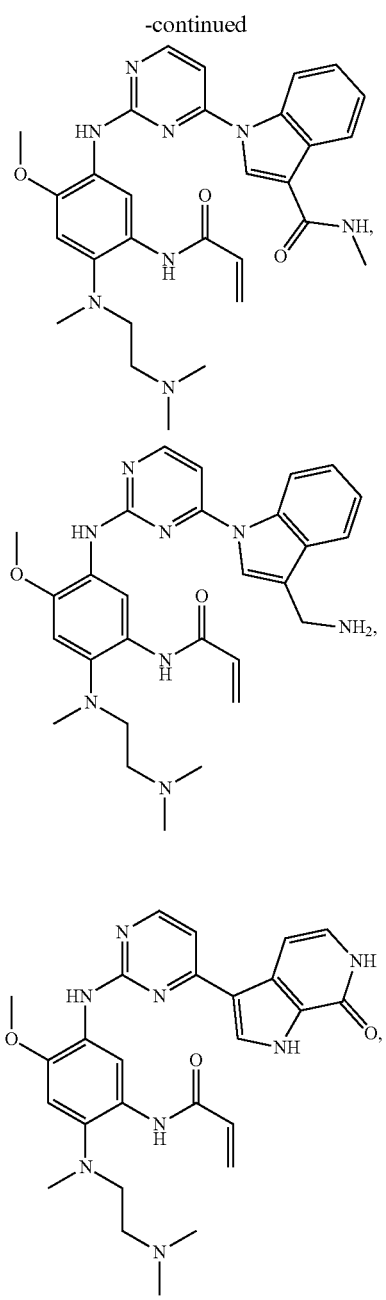
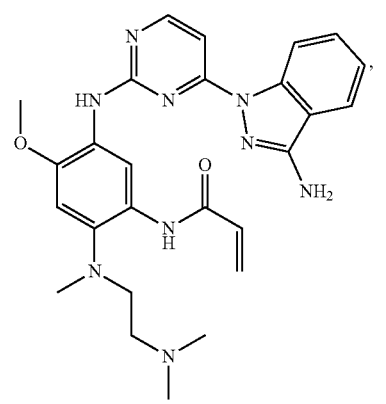

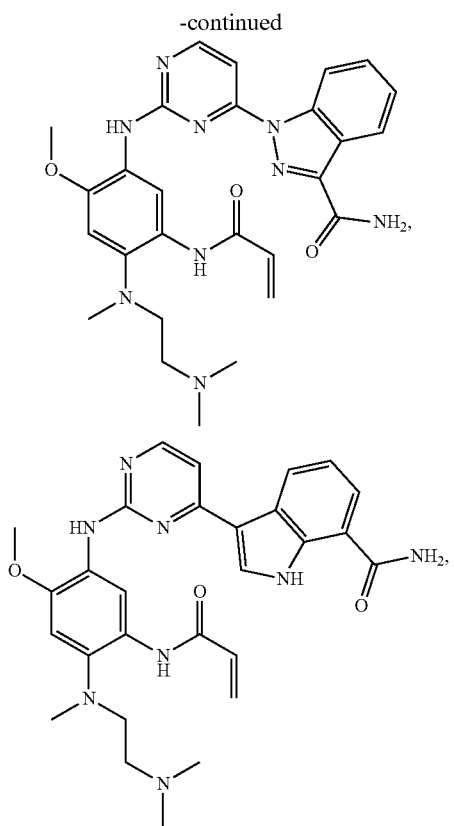
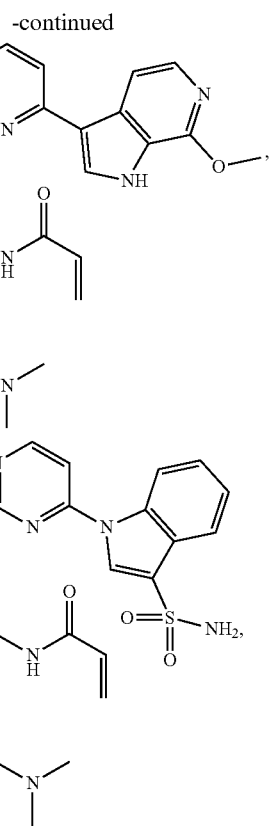
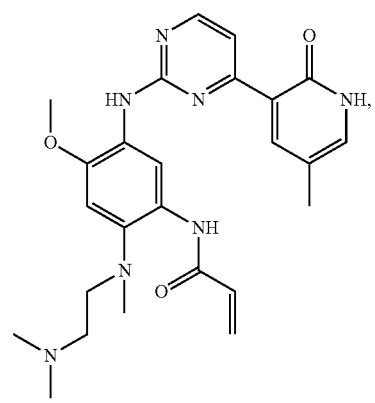
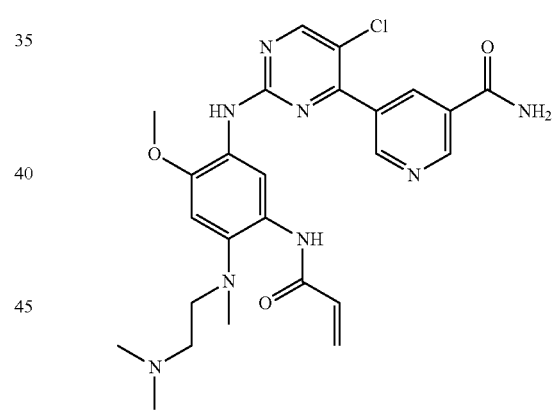
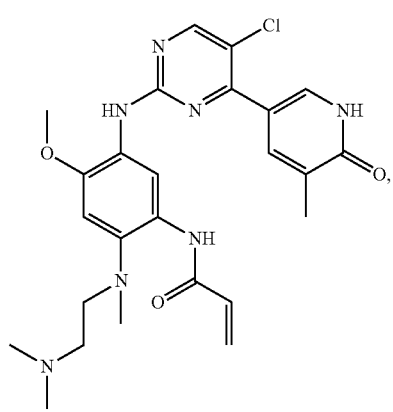
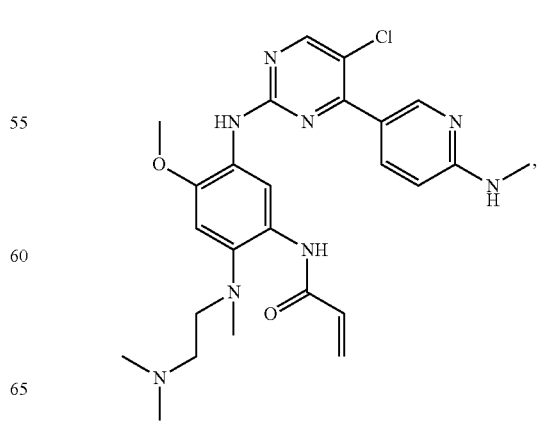

351
-continued
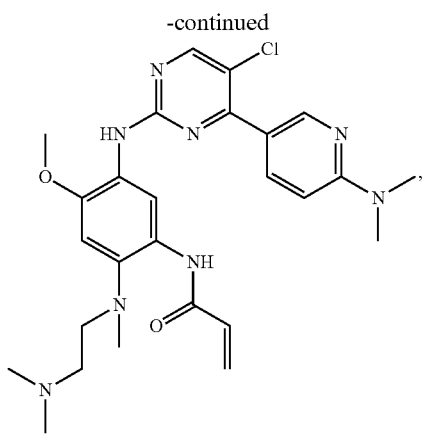
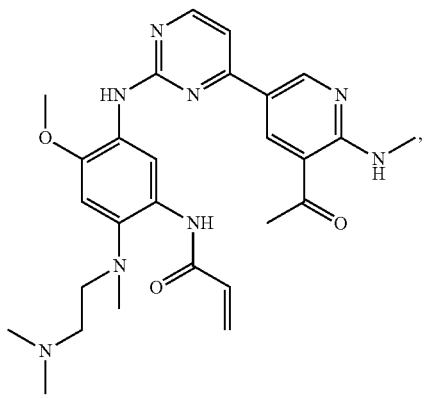
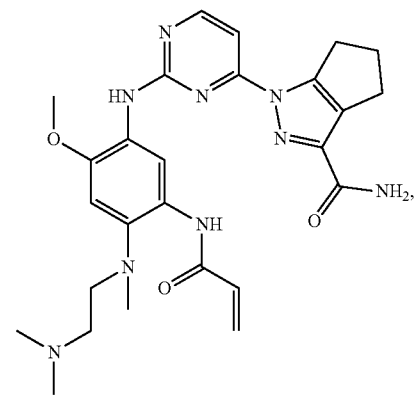
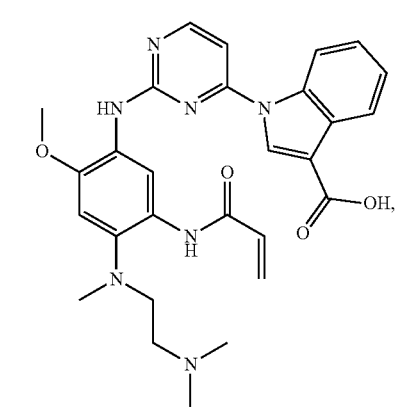
352
-continued
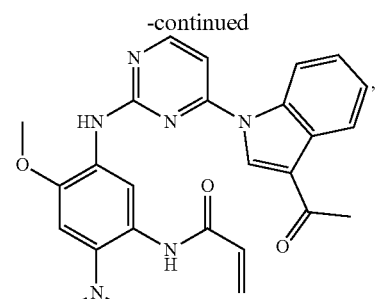
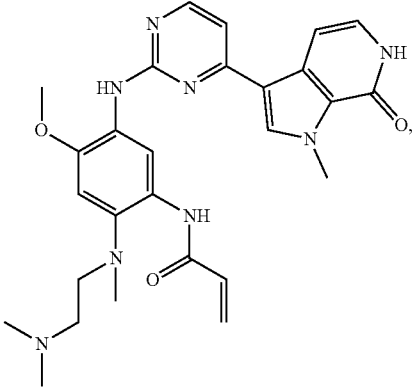
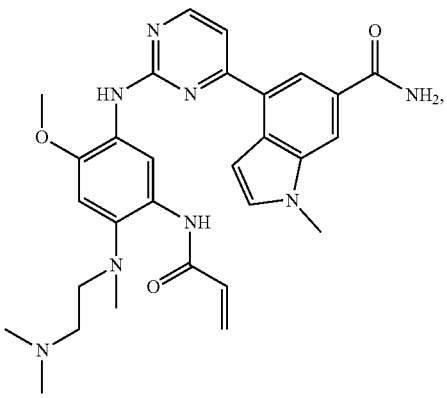
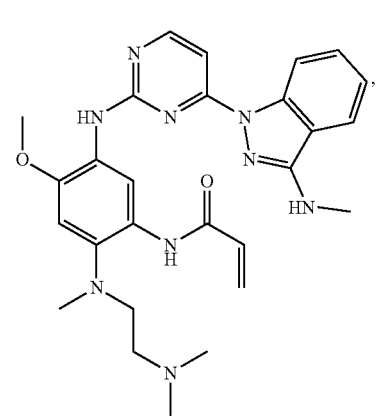

353
-continued
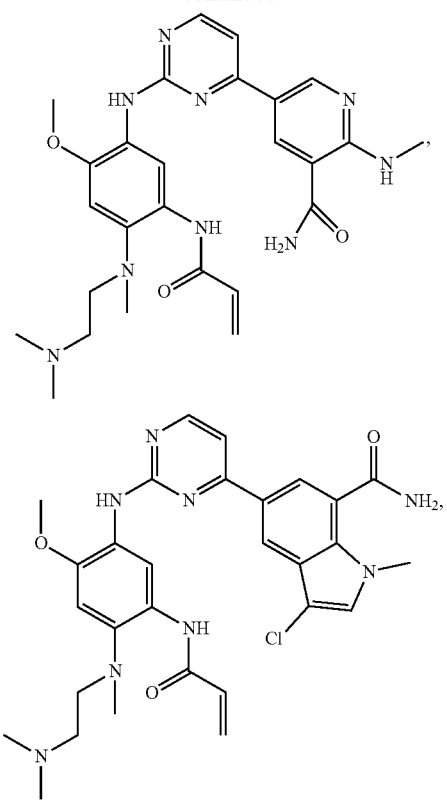
354
-continued
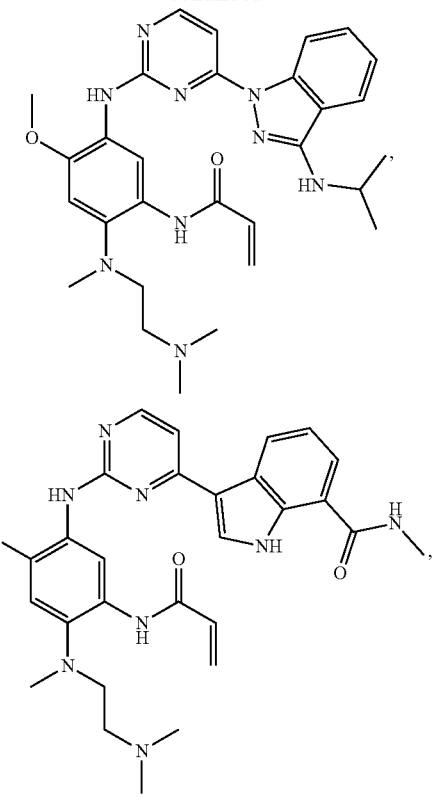
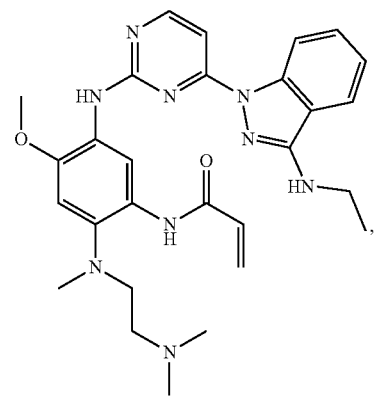
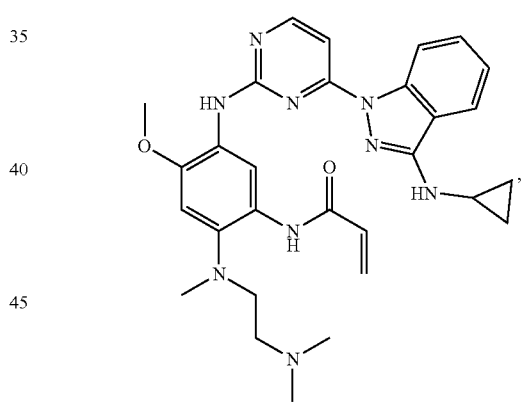
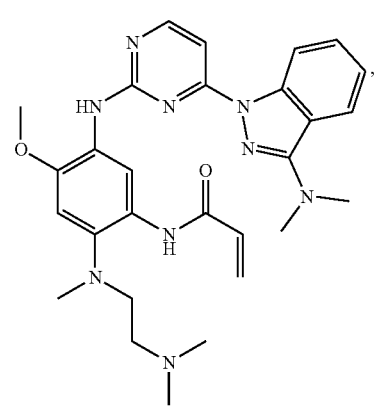
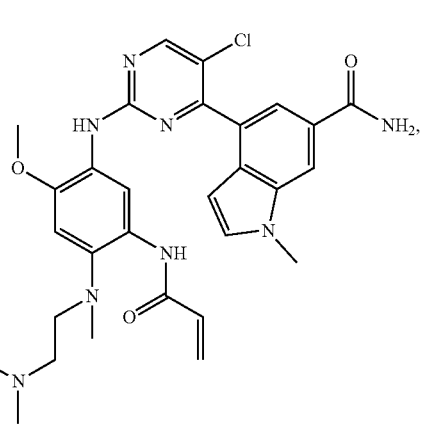

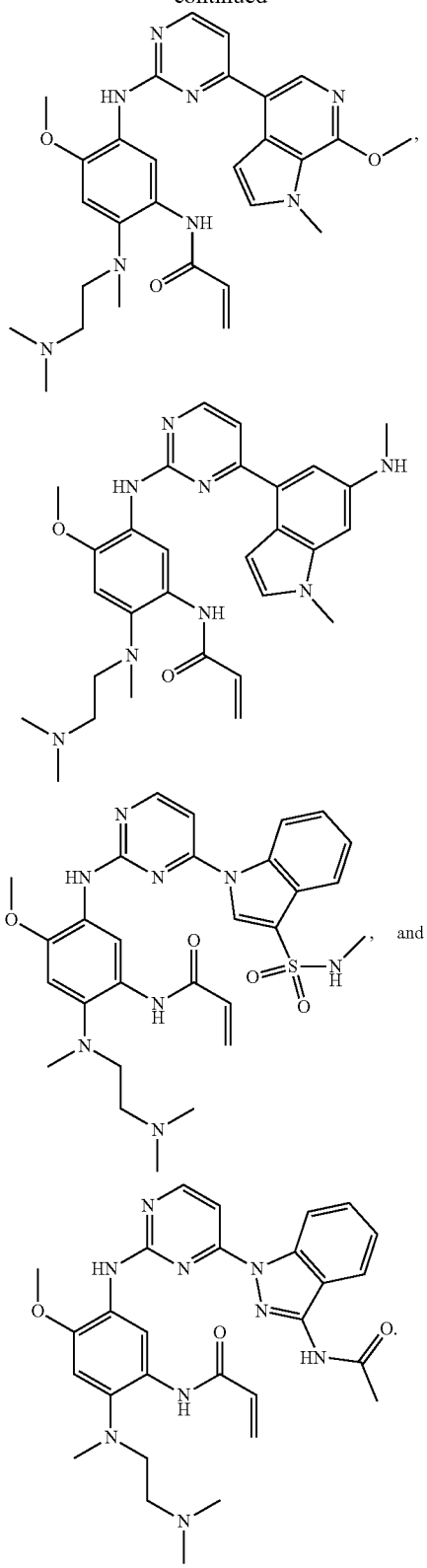
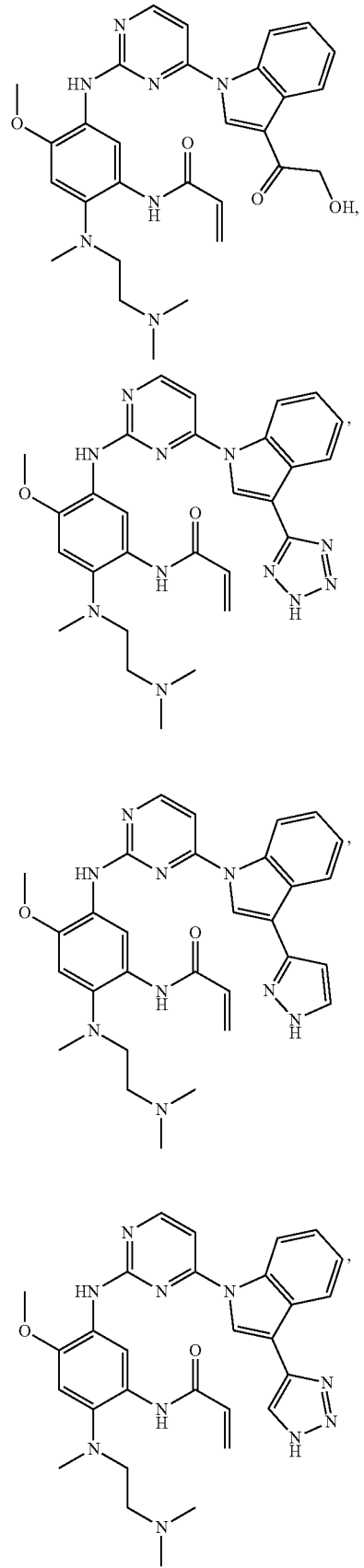
In one embodiment, the compounds of the invention include, but are not limited to:

357
-continued
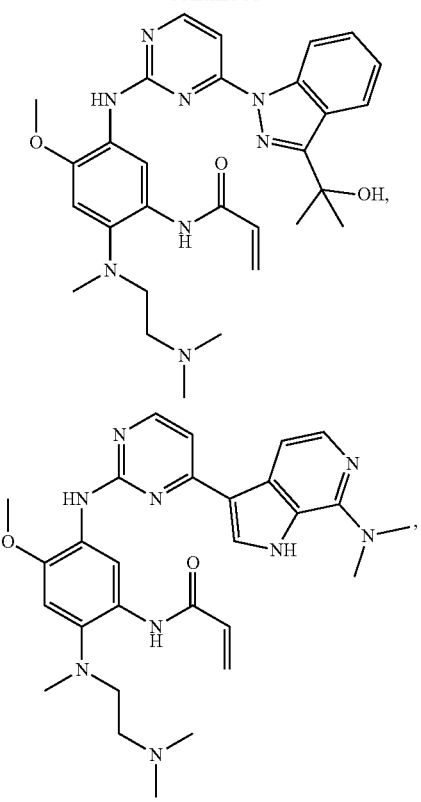
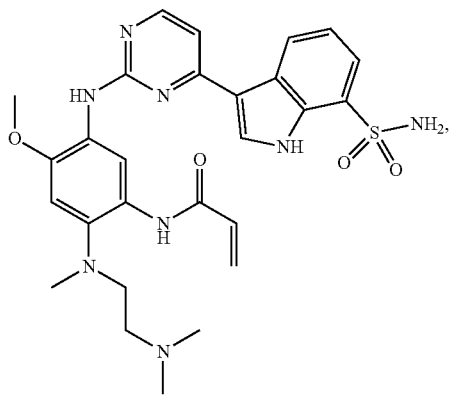
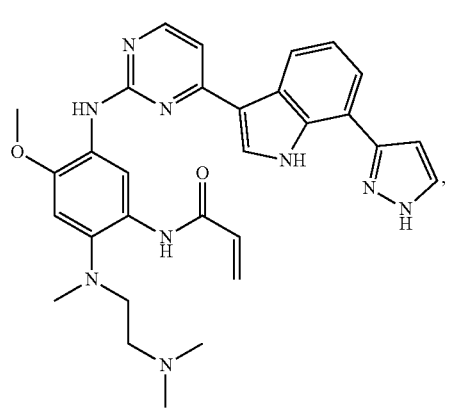
358
-continued
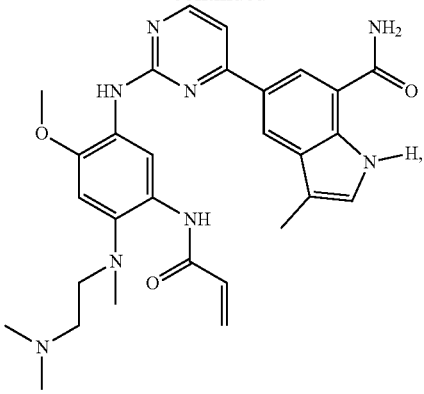
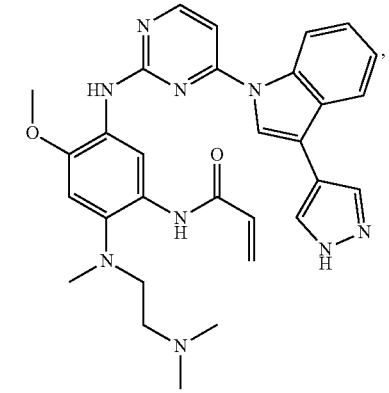
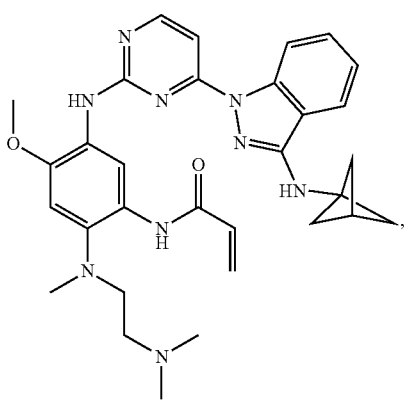
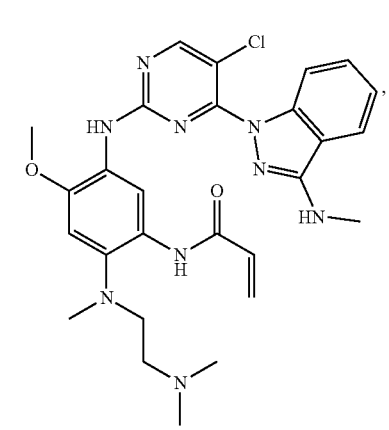

359
-continued
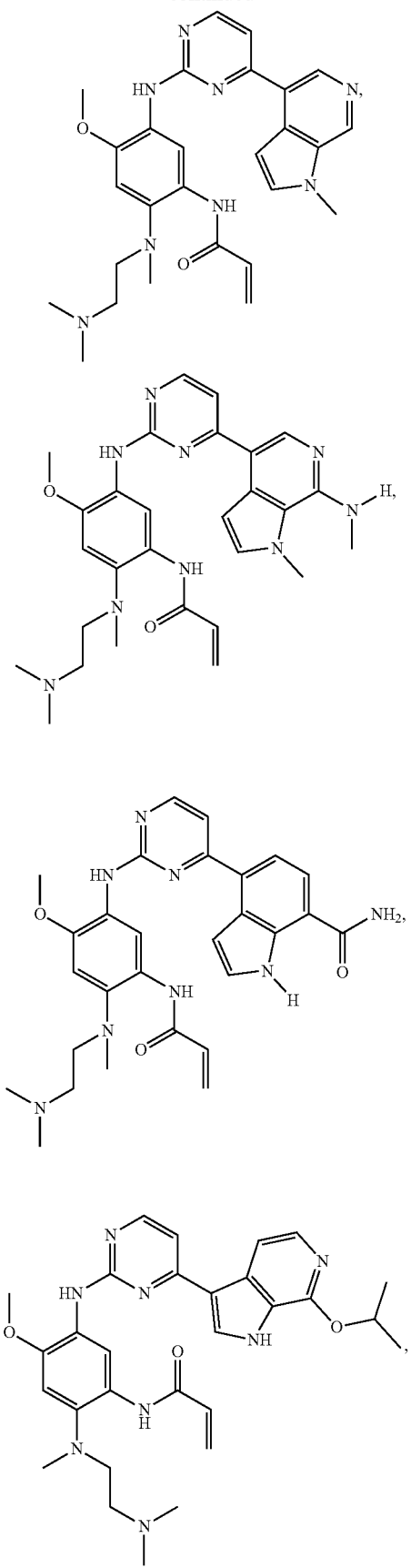
360
-continued
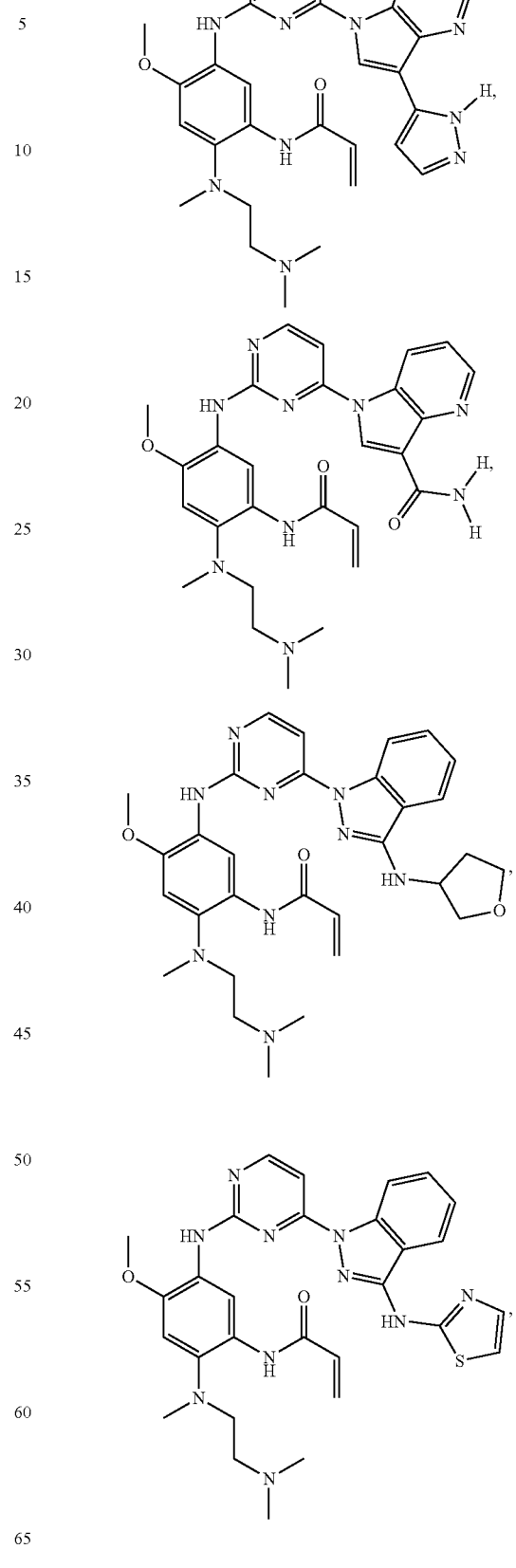

361
-continued
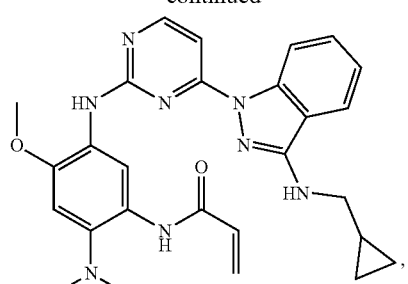
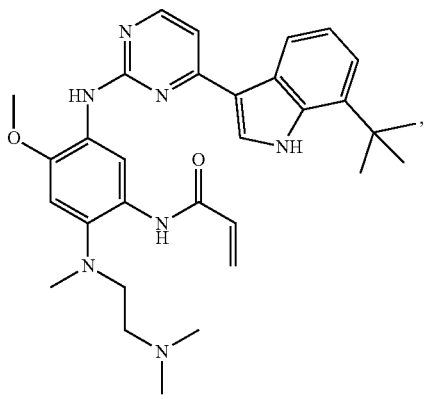
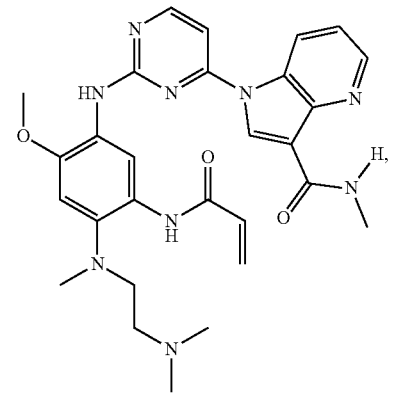
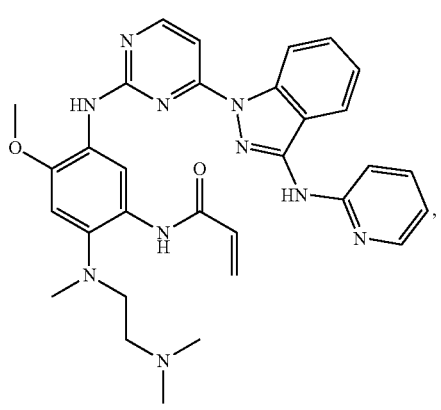
362
-continued
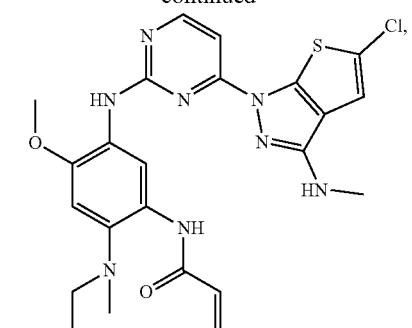
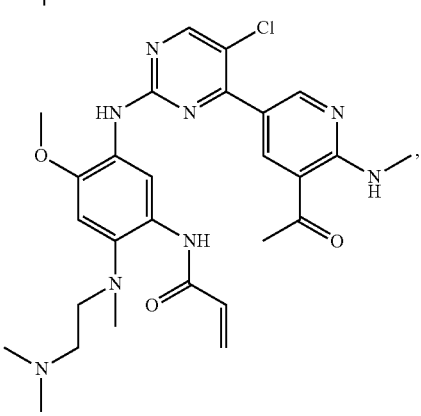
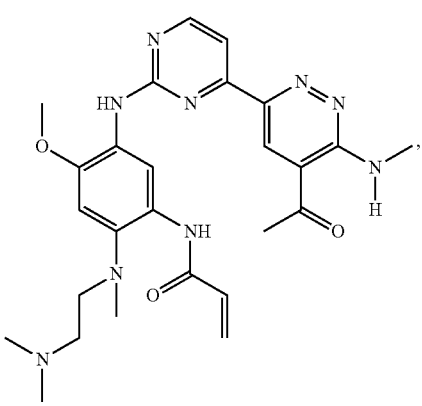
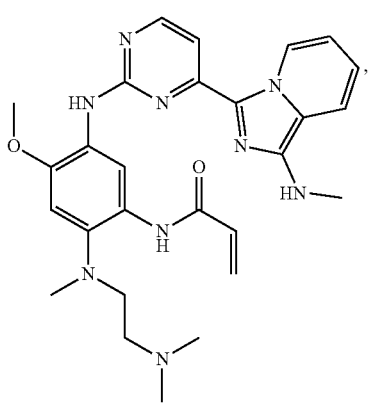

363
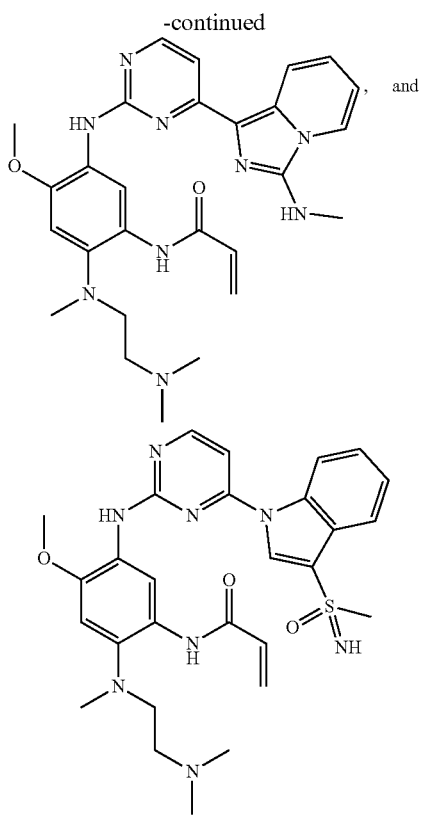
364
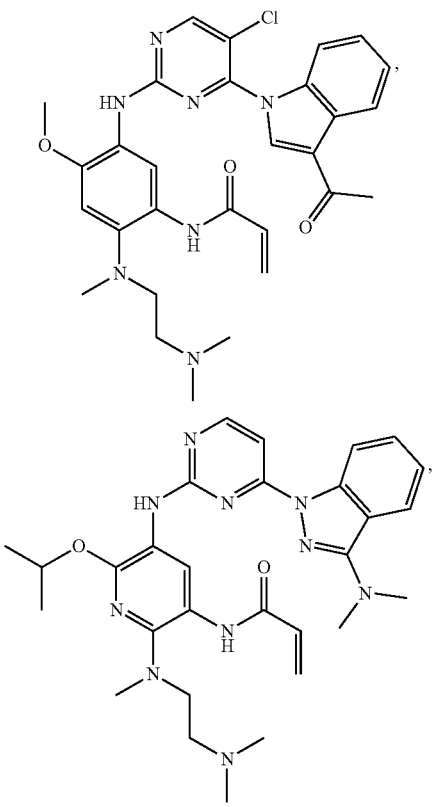
In one embodiment, the compounds of the invention include, but are not limited to:
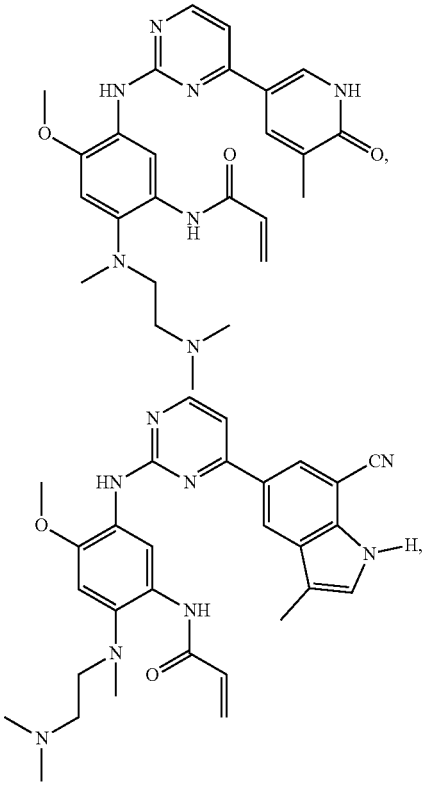

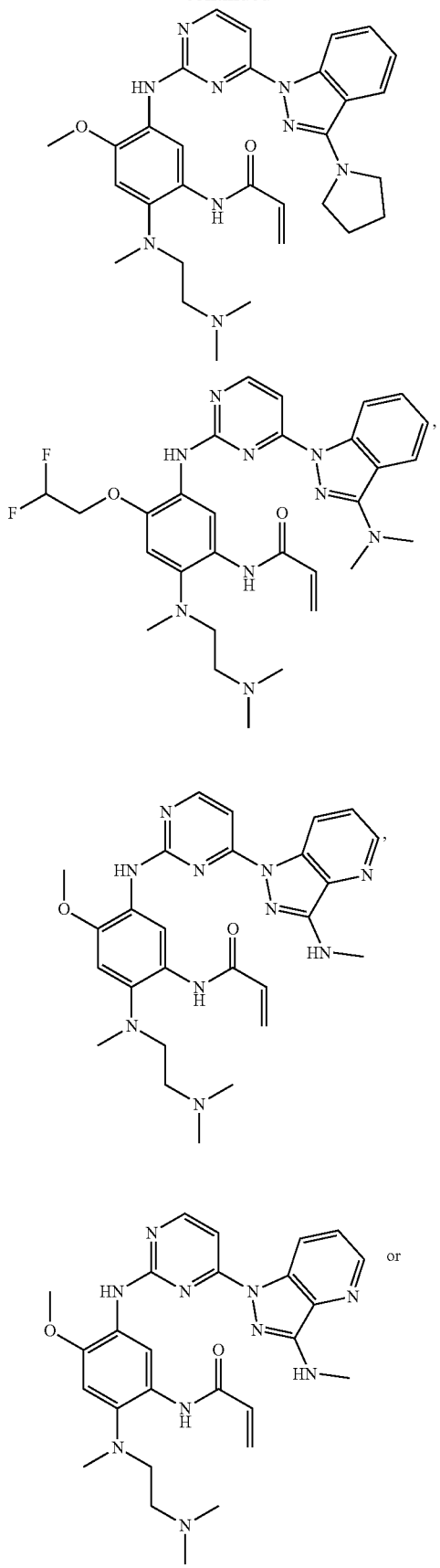

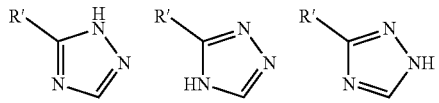

In one embodiment, the compounds of the invention exclude the compounds exemplified in CN 105085489 A, WO 2015/127872, WO2013/014448, CN 105001208 A, CN 104844580 A, WO 2015/175632, WO 2015/188777, WO 2016/105525, WO2016060443, WO 2016/029839, WO 2016/054987, WO 2016/015453, WO 2016/070816, and/or WO 2015/195228.

In one embodiment, the compounds of the invention exclude the compounds exemplified in CN 104761585 A and/or CN 104761544 A.

In one embodiment of formula (IB) or any subgenera thereof, $R^{4a}$, $R^{4b}$, $R^{4c}$, and $R^{4d}$ etc are embodiments of $R^4$. Similarly A1a of formula (IB) is an embodiment of A1 of formula (I). Furthermore, $A^{4a'}$ and $A^{4b'}$ of formula (IB) are embodiments of $A^{4a}$ and $A^{4b}$ of formula (I), respectively. Similar numbering system is used throughout this disclosure.

Compounds of the present disclosure may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium. For example, ketone and enol are two tautomeric forms of one compound. In another example, a substituted 1,2,4-triazole derivative may exist in at least three tautomeric forms as shown below:

R' is an optionally substituted alkyl.

One skilled in the art will recognize that substituents, variables, and other moieties of the compounds of Formula (I), Formula (IB), or subgeneric structures or species thereof, should be selected in order to provide a compound which is sufficiently stable to provide a pharmaceutically useful compound which can be formulated into an acceptably stable pharmaceutical composition. Furthermore, one skilled in the art will recognize that substituents, variables, and other moieties of the compounds of Formula (I), Formula (IB), or subgeneric structures or species thereof, should be selected as such that it would not yield any compound which has structural feature in violation of the basic principles of the chemistry art. For example, in one embodiment of Formula (I), or subgeneric structures or species thereof, two bonds of a, b, c, d, and e are (formal) double bonds and the remaining ones are (formal) single bonds, such that none of the atoms $X^1$, $X^2$, $X^3$, $X^4$, and $X^5$ has two double bonds attached thereto. In another embodiment of Formula (I), wherein $A^1$, $A^2$ and $A^3$, when $X^1$ is N, $X^2$ is C=O, C=NR$^{10}$ or C=S, $X^3$ is O, S or NR$^{10}$ and $X^4$ and $X^5$ are C, then only e is a formal double bond. In another embodiment of Formula (I), wherein $A^1$ and $A^3$, when $X^1$ and one of $X^4$ and $X^5$ are N, then only b will be a (formal) double bond. In another embodiment of Formula (I), wherein $A^3$, when $X^1$ is C, and $X^3$ is O, S or NR$^{10}$, and one of $X^4$ and $X^5$ is N, then only c will be a (formal) double bond.

Pharmaceutical Compositions

In one embodiment, the present disclosure relates to a pharmaceutical composition comprising a compound of the invention, or a pharmaceutically acceptable salt, solvate, ester, or prodrug thereof, and a pharmaceutically acceptable carrier.

As used in the preparations and examples the following terms have the indicated meanings; "ng" refers to nanograms; "μg" refers to micrograms; "mg" refers to milligrams; "g" refers to grams; "kg" refers to kilograms; "nmole" or "nmol" refers to nanomoles; "mmol" refers to millimoles; "mol" refers to moles; "M" refers to molar, "mM" refers to millimolar, "μM" refers to micromolar, "nM" refers to nanomolar, "L" refers to liters, "mL" refers to milliliters, "μL" refers to microliters.

Pharmaceutically acceptable salts of the compounds of the invention include the acid addition and base salts (including disalts) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of the invention may be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds of the present invention are all stereoisomers, geometric isomers and tautomeric forms of the compounds of the invention, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Compounds of the current invention may also exhibit atropisomerism, where restricted rotation, especially around the bond joining two aryl rings in a biaryl, causes different rotational isomers to be not interconvertible at normal ambient temperatures, and quite possibly not at temperatures where the molecule as a whole remains thermally stable. In such cases distinct stereoisomers due to atropisomerism are also claimed.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC), especially in a simulated moving bed (SMB) configuration.

Alternatively, the racemate (or a racemic precursor) may be reacted with a suitable optically active compound, for example, an alcohol, or, in the case where the compound of the invention contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically labeled compounds of the invention wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may be administered as prodrugs. Thus certain derivatives of compounds of the invention which may have little or no pharmacological activity themselves can, when administered into or onto the body, be converted into compounds of formula 1 (or other formulae disclosed herein) having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in the compounds of the invention with certain moieties known to those skilled in the art as 'pro-moieties' as described, for example, in "Design of Prodrugs" by H Bundgaard (Elsevier, 1985).

Some examples of such prodrugs include:
where the compound contains a carboxylic acid functionality (—COOH), an ester thereof, for example, replacement of the hydrogen with C1-C6 alkyl;
where the compound contains an alcohol functionality (—OH), an ether thereof, for example, replacement of the hydrogen with $C_1$-$C_6$ alkanoyloxymethyl (—$C_1$-$C_6$ acyloxymethyl); and
where the compound contains a primary or secondary amino functionality (—NH$_2$ or —NHR where R is not H), an amide thereof, for example, replacement of one or both hydrogens with ($C_1$-$C_{10}$)alkanoyl (—$C_1$-$C_{10}$ acyl).

Further examples of replacement groups in accordance with the foregoing examples and examples of other prodrug types may be found in the aforementioned references.

Finally, certain compounds of the invention may themselves act as prodrugs of other compounds of the invention.

Methods of Treatment

In one embodiment, the present invention relates to a method useful for treating cancer selected from lung cancer, colorectal cancer, pancreatic cancer, head and neck cancers, breast cancer, ovarian cancer, uterine cancer, liver cancer, and stomach cancer. In another embodiment, the cancer is non-small cell lung cancer (NSCLC).

In one embodiment, the method disclosed herein relates to treatment of cancer, wherein the cancer results from a mutation in the exon 20 domain of EGFR. In some embodiments, the mutation in the exon 20 domain of EGFR is selected from NPG, ASV, or T790M. In one embodiment, the mutation in the exon 20 domain of EGFR is T790M concurrent with an exon 19 insertion mutation or an exon 21 point mutation.

In one embodiment, the method of treatment of cancer is particularly useful for patient who is resistant to a kinase inhibitor other that a compound of the invention, or a pharmaceutically acceptable salt, solvate, ester, or prodrug thereof. In another embodiment, the kinase inhibitor is an EGFR inhibitor.

The invention also relates to a method for inhibiting EGFR, or a mutation thereof, in a patient in need thereof, comprising administering to the patient a therapeutically effective amount of a compound of the invention, or a pharmaceutically acceptable salt, solvate, ester, or prodrug thereof. In one embodiment, the mutation is in the exon 20 domain of EGFR.

The invention further relates to therapeutic methods and uses comprising administering the compounds of the invention, or pharmaceutically acceptable salts thereof, alone or in combination with other therapeutic or palliative agents.

In one embodiment, the invention relates to a method for treating or inhibiting cell proliferation, cell invasiveness, metastases, apoptosis, or angiogenesis in a mammal comprising administering to the mammal a therapeutically effective amount of a compound of the invention, or pharmaceutically acceptable salt thereof.

In another embodiment, the invention relates to a method for treating or inhibiting cell proliferation, cell invasiveness, metastases, apoptosis, or angiogenesis in a mammal comprising administering to the mammal a therapeutically effective amount of a compound of the invention, or pharmaceutically acceptable salt thereof, in combination with a with a second therapeutic agent wherein the amounts of the compound of the invention and the second therapeutic agent together are effective in treating or inhibiting said cell proliferation, cell invasiveness, metastases, apoptosis, or angiogenesis.

In one embodiment, the second therapeutic agent is an anti-tumor agent which is selected from the group consisting of mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, antihormones, and anti-androgens.

In other embodiments, the cell proliferation, cell invasiveness, metastases, apoptosis, or angiogenesis is mediated by members of the erbB family of RTKs, mainly EGFR, and most probably T790M mutant forms of EGFR.

In a further embodiment, the cell proliferation, cell invasiveness, metastases, apoptosis, or angiogenesis is associated with a cancer selected from the group consisting of glioblastoma, lung cancer (e.g., squamous cell carcinoma, non-small cell lung cancer, adenocarcinoma, bronchioloalveolar carcinoma (BAC), BAC with focal invasion, adenocarcinoma with BAC features, and large cell carcinoma), pancreatic cancer, head and neck cancers (e.g., squamous cell carcinoma), breast cancer, colorectal cancer, epithelial cancer (e.g., squamous cell carcinoma), ovarian cancer, and prostate cancer, and any other cancer which overexpresses members of the erbB family, or which contains oncogenicall activating mutants of the erbB family, regardless of whether those proteins are overexpressed in the tumor.

A further embodiment of the invention relates to a compound of the invention for use as a medicament, and in particular for use in the treatment of diseases where the inhibition of EGFR and/or a mutant EGFR protein, e.g., L858R/T790M EGFR, activity may induce benefit, such as cancer. A still further embodiment of the present invention relates to the use of the compounds of the invention, or pharmaceutically acceptable salts thereof, for the manufacture of a drug having an EGFR inhibitory activity for the treatment of EGFR mediated diseases and/or conditions, in particular the diseases and/or conditions listed above.

The term "therapeutically effective amount" refers to that amount of a compound being administered which will relieve to some extent one or more of the symptoms of the disorder being treated. Regarding the treatment of cancer, a therapeutically effective amount refers to that amount which has the effect of reducing the size of the tumor, inhibiting (i.e., slowing or stopping) tumor metastases, inhibiting (i.e. slowing or stopping) tumor growth or tumor invasiveness, and/or relieving to some extent one or more signs or symptoms related to the cancer.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered, the mode of administration; the bioavailability characteristic of the preparation administered; the dose regimen selected; the use of concomitant medication; and other relevant circumstances.

The term "treating", as used herein, unless otherwise indicated, means reversing, alleviating, inhibiting the progress of, or preventing the disorder or condition to which such term applies, or one or more symptoms of such disorder or condition. The term "treatment" also refers to the act of treating as "treating" is defined immediately above. The term "treating" also includes adjuvant treatment of a mammal.

As used herein "cancer" refers to any malignant and/or invasive growth or tumor caused by abnormal cell growth, including solid tumors named for the type of cells that form them, cancer of blood, bone marrow, or the lymphatic system. Examples of solid tumors include but not limited to sarcomas and carcinomas. Examples of cancers of the blood include but not limited to leukemias, lymphomas and myeloma. The term "cancer" includes but is not limited to a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type.

In another embodiment, the invention provides a method for inhibiting cell proliferation, comprising contacting cells with a compound of the invention or a pharmaceutically acceptable salt thereof in an amount effective to inhibit proliferation of the cells. In another embodiment, the invention provides methods for inducing cell apoptosis, comprising contacting cells with a compound described herein in an amount effective to induce apoptosis of the cells.

"Contacting" refers to bringing a compound or pharmaceutically acceptable salt of the invention and a cell expressing mutant EGFR or one of the other target kinases which is playing a transforming role in the particular cell type, together in such a manner that the compound can affect the activity of EGFR, or the other kinase, either directly or indirectly. Contacting can be accomplished in vitro (i.e., in an artificial environment such as, e.g., without limitation, in a test tube or culture medium) or in vivo (i.e., within a living organism such as, without limitation, a mouse, rat or rabbit.)

In some embodiments, the cells are in a cell line, such as a cancer cell line. In other embodiments, the cells are in a tissue or tumor, and the tissue or tumor may be in a mammal, including a human.

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Dosage unit form, as used herein, refers to physically discrete units suited as unitary dosages for the mammalian mammals to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Appropriate dosages may vary with the type and severity of the condition to be treated and may include single or multiple doses. An attending diagnostician understands that for any particular mammal, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

Useful dosages of the compounds of the invention can be determined by comparing their in vitro activity, and in vivo activity in animal models. The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compounds of the present invention can be administered to a patient at dosage levels in the range of about 0.1 to about 2,000 mg per day. For a normal human adult having a body weight of about 70 kilograms, a dosage in the range of about 0.01 to about 10 mg per kilogram of body weight per day is preferable. However, the specific dosage used can vary.

For example, the dosage can depended on a numbers of factors including the requirements of the patient, the severity of the condition being treated, and the pharmacological activity of the compound being used. The determination of optimum dosages for a particular patient is well-known to those skilled in the art. In some instances, dosage levels below the lower limit of the aforesaid range may be more than adequate, while in other cases still larger doses may be employed without causing harmful side effect, provided that such larger doses are first divided into several smaller doses for administration throughout the day.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid.

The compounds of the invention may also be used in fast-dissolving, fast-disintegrating dosage forms such as those described in Expert Opinion in Therapeutic Patents, 11 (6), 981986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colorants, flavoring agents, preservatives and taste-masking agents.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated, it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration discussed above may be formulated to be immediate and/or modified release. Modified release formulations include delayed-, sustained-, pulsed-, controlled-, targeted and programmed release. Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Thus, compounds of the invention may be formulated as a solid, semi-solid, or thixotropic liquid for administration as an implanted depot providing modified release of the active compound. Examples of such formulations include drug-coated stents and poly(glycolide-co-dl-lactide) or PGLA microspheres.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

The term "combination therapy" refers to the administration of a compound of the invention together with at least one additional pharmaceutical or medicinal agent, either sequentially or simultaneously. Combination therapy encompasses the use of the compounds of the present invention and other therapeutic agents either in discreet dosage forms or in the same pharmaceutical formulation. The compounds of the invention may be used in combination (administered simultaneously, sequentially, or separately) with one or more therapeutic agents.

In one embodiment of the present invention the anti-cancer agent used in conjunction with a compound of the invention and pharmaceutical compositions described herein is an antiangiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCI3 inhibitors, CQX-2 (cyclooxygenase II) inhibitors, integrins (alpha-v/beta-3), MMP-2 (matrix-metalloprotienase 2) inhibitors, and MMP-9 (matrixmetalloprotienase 9) inhibitors. Preferred anti-angiogenesis agents include sunitinib (SutenFM), bevacizumab (Avastin™), and axitinib (AG 13736).

Additional anti-angiogenesis agents include vatalanib (CGP 79787), Sorafenib (Nexavar™), pegaptanib octasodium (Macugen™), vandetanib (Zactimam™), PF-0337210 (Pfizer), SU 14843 (Pfizer), AZD 2171 (AstraZeneca), ranibizumab (Lucentis™), Neovastat™ (AE 941), tetrathio-molybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other examples of anti-angiogenesis agents which can be used in conjunction with a compound of the invention and pharmaceutical compositions described herein include celecoxib (Celebrex™), parecoxib (Dynastat™), deracoxib (SC 59046), lumiracoxib (Preige™), valdecoxib (Bextram), rofecoxib (Vioxx™), iguratimod (Careram), IP 751 (Invedus), SC-58125 (Pharmacia) and etoricoxib (Arcoxia™). Other anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Other anti-angiogenesis agents include ABT 510 (Abbott), apratastat (TMI 005), AZD 8955 (AstraZeneca), incyclinide (Metastat™), and PCK 3145 (Procyon). Other antiangiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR), ErbB-2, pan erb, IGF1 R inhibitors, MEK, c-Kit inhibitors, FLT-3 inhibitors, K-Ras inhibitors, Pl3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors. Preferred signal transduction inhibitors include gefitinib (Iressa™), cetuximab (Erbitux™), erlotinib (Tarcevam™), trastuzumab (Herceptin™), sunitinib (Sutent™), and imatinib (Gleevec™).

Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMO 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples of signal transduction inhibitor include PF-2341 066 (Pfizer), PF-299804 (Pfizer), canertinib, pertuzumab (Omnitarg™), Lapatinib (Tycerb™), pelitinib (EKB 569), miltefosine (Miltefosin™), BMS 599626 (Bristol-Myers Squibb), Lapuleucel-T (Neuvenge™). NeuVax™ (E75 cancer vaccine), Osidem™, mubritinib (TAK-165), panitumumab (Vectibix™), lapatinib (Tycerb™), pelitinib (EKB 569), and pertuzumab (Omnitarg™). Other examples of signal transduction inhibitors include ARRY 142886 (Array Biopharm), everolimus (Certican™), zotarolimus (Endeavor™), temsirolimus (Torisel™), and AP 23573

(ARIAO). Additionally, other signal transduction inhibitors include XL 647 (Exelixis), sorafenib (Nexavar™), LE-AON (Georgetown University), and GI-4000 (Globelmmune). Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PO 0332991 (Pfizer), and AG 024322 (Pfizer).

Among the signal transduction inhibitors that agents of the invention will be useful in in combination, other erbB family inhibitors, exemplified by erlotinib, gefitinib, lapatinib, icotinib, afatinib, neratinib, peletinib and dacomitinib, are recognized to be of especial interest. All of these compounds have enough wild-type erbB kinase inhibitory activity to have mechanism-based dose limiting toxicities, but all can be dosed at tolerable levels, and demonstrate good clinical activity. One of their main weaknesses is that tumors which respond well to these medications tend to have erbB mutations which make the tumor unusually susceptible to the inhibitor, but which when combined with a second mutation, tend to make the tumor very resistant to these agents. The selection pressures which accelerate this process have been discussed above. Compounds of the current invention target the main resistance mutants, and because they have very little activity against the wild type enzymes will not add appreciably to mechanism based toxicity. However, they will put the evolving double mutants under the same selection disadvantage as the original susceptible mutants, and will therefore greatly slow or perhaps prevent altogether the emergence of the resistant strains. Therefore, this combination will prove to be clinically very useful.

This invention contemplates the use of compounds of the invention together with classical antineoplastic agents. Classical antineoplastic agents include hormonal modulators such as hormonal, anti-hormonal, androgen agonist, androgen antagonist and anti-estrogen therapeutic agents, histone deacetylase (HOAC) inhibitors, gene silencing agents or gene activating agents, ribonucleases, proteosomics, Topoisomerase I inhibitors, Camptothecin derivatives. Topoisomerase II inhibitors, alkylating agents, anti-metabolites, poly(AOP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of antineoplastic agents used in combination with compounds of the invention include Velcade (bortezomib), 9-aminocamptothecin, belotecan, camptothecin, diflomotecan, edotecarin, exatecan (Daiichi), gimatecan, 10-hydroxycamptothecin, irinotecan HCI (Camptosar), lurtotecan, Orathecin (rubitecan, Supergen), topotecan, camptothecin, 10-hydroxycamptothecin, 9-aminocamptothecin, irinotecan, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, altretamine, AP-5280, apaziquone, brostallicin, bendamustine, busulfan, carboquone, carmustine, chlorambucil, dacarbazine, estramustine, fotemustine, glufosfamide, ifosfamide, lomustine, mafosamide, mechlorethamine, melphalan, mitobronitol, mitolactol, mitomycin C, mitoxatrone, nimustine, ranimustine, temozolomide, thiotepa, and platinumcoordinated alkylating compounds such as cisplatin, Paraplatin (carboplatin), eptaplatin, lobaplatin, nedaplatin, Eloxatin (oxaliplatin, Sanofi), streptozocin, satraplatin, and combinations thereof.

The invention also contemplates the use of the compounds of the invention together with dihydrofolate reductase inhibitors (such as methotrexate and trimetrexate glucuronate), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil). Alimta (premetrexed disodium), capecitabine (Xeloda™), cytosine arabinoside, Gemzar™ (gemcitabine), Tegafur, doxifluridine, carmofur, cytarabine (including ocfosfate, phosphate stearate, sustained release and Iiposomal forms), enocitabine, 5-azacitidine (Vidaza), decitabine, and ethynylcytidine) and other antimetabolites such as eflomithine, hydroxyurea, leucovorin, nolatrexed (Thymitaq), triapine, trimetrexate, and N-(5-[N-(3,4-dihydro-2-methyl-4-oxoquinazolin-6-ylmethyl)-N-methylamino]-2thenoyl)-L-glutamic acid, and combinations thereof.

Other examples of classical antineoplastic cytotoxic agents used in combination therapy with a compound of the invention, optionally with one or more other agents include Abraxane (Abraxis BioScience, Inc.), Batabulin (Amgen), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcytar™), DMXAA (Antisoma), ibandronic acid, L-asparaginase, pegaspargase (Oncaspar™), Efaproxiral (Efaproxyn™—radiation therapy)), bexarotene (Targretin™), Tesmilifene, Theratope™ (Biomira), Tretinoin (Vesanoid™), tirapazamine (Trizaone™), motexafin gadolinium (Xcytrin™) Cotara™ (mAb), and NBI-3001 (ProtoxbTherapeutics), polyglutamate-paclitaxel (Xyotax™) and combinations thereof.

EXAMPLES

Experimentals

Synthesis of Compounds of the Invention

The compounds of the current invention can be made by a variety of processes, which are known to one of skill in the art, and some synthetic schemes to make these compounds are illustrated below.

The compounds of the current invention can be regarded as consisting of four concatenate components, the A-ring (A') which may be monocyclic or bicyclic, the central azine ring, (B') which is usually a 2,4,(5)-substituted pyrimidine, (or a bicyclic homologue), the aniline (C') or 3-aminopyridine moiety, and the electrophilic side chain (D') on that C' ring to form the concatenated A'-B'-C'-D' structure. This allows for each of the four components to be used combinatorially with the other three components, allowing for a large number of analogues to be synthesized from relatively few building blocks in a parsimonious and efficient fashion.

Most syntheses illustrated in this document start by preparing the A' subunit, and then attaching it to the B' subunit, to form an A'-B' moiety, via a variety of chemistries known to one of skill in the art, many of which are exemplified below. The C-unit is now attached, by displacement of a halogen atom on the B' ring by the C-unit free primary amine, to form an A'-B'-C' entity. The C-entity has an incipient primary amine unmasked, either by reduction of a precursor group such as nitro or azido, or by deprotection of a protected primary amine, and then the D-subunit is attached to this free amine via an acylation or sulfonation reaction.

In many cases, the D-subunit, although acting as an electrophile in vivo is in fact a rather weak electrophile and can survive a reasonable variety of chemical reaction conditions, which appears to be especially true of acrylamido and crotonamido D' species. Furthermore, the A'-subunits once incorporated into larger entities can be of quite different chemical reactivities to one another, sometimes allowing them to be modified late in the synthesis, and other times leaving them generally inert during subsequent reactions. The azine ring in an A'-B'-C' concatenated entity tends to be chemically of low activity. This allows for other reaction orders to be used. For example, if the A' moiety is somewhat chemically reactive sometimes a final chemical modification can be made to the A'-moiety, after the A'-B' coupling, or after the A'-B'-C' entity is assembled, or sometimes even after complete assembly of an A'-B'-C'-D' entity. Or an A'-B'-C' entity can be assembled, and then the C-ring can be modified, for example by displacement of an electrophilic fluorine ortho to a nitro group by an $R^3$ amine, thiol, or alcoholate nucleophile. One of skill in the art can find many opportunities for such deviations from the "canonical" linear A to D assembly, and several such reaction sequences are illustrated in the reactions below.

A'-B' Couplings

The central azine rings of the invention can all be commercially obtained with two halogen atoms ($Q^1$ and $Q^2$) in a 1,3-relationship to one another, and one of these halogens can always be displaced preferentially to the other (even if the original azine was symmetric). Normally the more reactive Q group, which in the case of 2,4-dichloropyrimidines, is the 4-chloro, can be displaced by a nitrogen or carbon nucleophile in good yields, leaving the other group to be displaced later by an amine nucleophile under potentially drastic conditions. In the case of pyrimidines the A'-B' biaryl moiety is normally a 4-substituted-2-chloropyrimidine, and as most syntheses disclosed in this patent use such intermediates. They are listed as the A intermediates in the experimental section.

The biaryls described here may be linked to via either a C or N atom to a C atom of the central azine. If the A' ring is 6-membered ring then the biaryl has to be prepared by a carbon-carbon bond formation. Such syntheses are very well known to one of skill in the art, and can involve, Stille, Negishi Ullmann or Suzuki type catalyzed reactions, or many variants thereof, along with numerous other reaction sequences, all known of one of skill in the art. If the linking portion of the A'-moiety is a five membered aromatic ring containing an N atom, the ring can often be attached through either a C atom or an N atom. Proton extraction can drive one towards C or N alkylation depending on the exact system and the nature of the counterions and catalysts present, and especially with indole-like aromatics, N versus C alkylation is usually well controllable to one of skill in the art.

Furthermore, once one has formed the A'-B' biaryl, it is often possible to do reactions selectively on the A' portion of the molecule, as the second halogen is often of quite low reactivity. Several such examples are illustrated in the experimental disclosures below.

The C'-subunit contains a primary amine which will be used to displace the second Q species. This can be done under conditions of acid catalysis (most common method) or basic catalysis, or with transition metal catalysis, and all of these are well exemplified in the prior art, eg. Buchwald reactions, and in some of the examples below. Although it is not specifically discussed above, or exemplified below, one can also have a halogen replace the primary amine of the aniline, and displace the second Q group with ammonia or suitable precursor (azide, trifluoroacetamide, sulfonamide, etc., modify it as required, and then displace the halogen on the C-unit under conditions of transition metal catalysis, followed by removal of the activating group from nitrogen, if such were used. The C'-moiety also contains a precursor for the amine used to attach the electrophilic D'-moiety, especially nitro, or as a protected amine, especially t-Bocamino. The advantage of a 3-nitro is that it can activate a leaving group ortho to it at the 4-position to nucleophilic substitution, allowing the easy introduction of many $R^3$ side chains especially amines at that position. Having the 4-substituent on the C' moiety fluorine is especially advantageous for facilitation of this reaction, but other side chains, including carbon linked ones can be made by having other halogens at the 4-position, and then doing transition metal coupled reactions, such as Stille, Suzuki, Sonagishira and Buchwald reactions.

A'-B'-C' entities can be readily constructed to facilitate modification on either the A' or this C' moieties. As the amine on the C' aromatic ring to be linked to the D'-electrophile is a primary amine, it needs to be protected during the B'-C' coupling, so there is almost invariably a need for a reaction on this position, and most syntheses revealed herein have such a reaction. However, if the 3-amine precursor is highly activating, to displacement of a 4-halogen (eg nitro) one can do the (A'-)B'-C' coupling prior to introducing $R^3$, and some examples of the introduction of $R^3$ onto an A'-B'-C' entity are disclosed below.

Usually the electrophilic D' moiety is added at the end of the synthesis to give the completed compound of the invention. However, as mentioned above, several of the D'-groups are of low enough chemical reactivity, especially when present as relatively weakly electron-withdrawing amides, to allows for a variety of transformations to be done on completed A'-B-'C'-D' entities, especially when introducing certain groups onto the A'-moiety, which might have interfered with some of the earlier chemistry, and some such examples are also disclosed below.

In principle, the B'-C' coupling should work with the complete C'-D' fragment preformed, as the aniline/3-aminopyridine fragment with the D' unit attached is going to have at least as nucleophilic a primary amine for the B'-C' coupling most of the "monomeric" C' moieties one would use. Here, the same C' moiety starting materials can be employed as previously, but one needs to protect the 1-amine, unmask the 3-amine, acylate or sulfonate it, and then deprotect the 1-amine. Then one can use this C'-D' fragment to couple to a suitable A'-B' fragment to form the final A'-B'-C'-D' entity, and several such syntheses are disclosed below.

Thus, the reactions described within this patent application enable one to prepare not only the exemplified compounds of the invention, but using the reactions described herein, and variants of them in the chemical literature ready available to one of skill in the art, also allows one to produce many other compounds including those claimed within this patent application, which are not specifically exemplified. Furthermore, as mentioned earlier, because of the modular nature of the compounds of the invention, and the ability to make several examples of each module, one has the ability to produce a very large number of compounds using the chemistry enabled by disclosures in this application. For example, one can use 3-aminopyridyl C' moieties in place of the 3-anilino C' moieties in combination with most of the A'-B' moieties disclosed in this patent using reaction conditions discussed in this application. As another example, the displacement of the 4-fluoro group on the nitroanilines of the precursor to the C'-moiety can be displaced by a very wide array of amines, using the conditions disclosed in this document.

Scheme 1 shows a generic scheme to make compounds of the current invention, illustrated with A being $A^1$, a 6,5-bicyclic system connected to the central azine ring through the 1-(3-)position of the five membered ring, and Y being an α,β-unsaturated enamide. The synthesis involves preparing five components, a suitably substituted azine 1A, which contains leaving groups $Q^1$ and $Q^2$, usually but not necessarily halogens, ortho and para to the obligate nitrogen, a suitable A group 2A ($A^1$ in this case), where $T^1$ represents a group which is a suitable coupling partner for $Q^1$, an appropriate meta-nitroaniline, or 3-amino-5-nitropyridine 4A with a leaving group $Q^3$, probably halogen, an appropriate side chain $R^3T^2$, 5A, where $T^2$, usually hydrogen, is an appropriate leaving group for coupling via displacement of $Q^3$, and lastly an appropriate electrophile 9A, here illustrated by an enoyl chloride, where $Q^4$ is an appropriate leaving group for coupling with an aromatic amine. Some of the components 1A, 2A, 4A, 5A and 9A, may be commercially available, and if they are not they can be made by methods known to one of ordinary skill in the art.

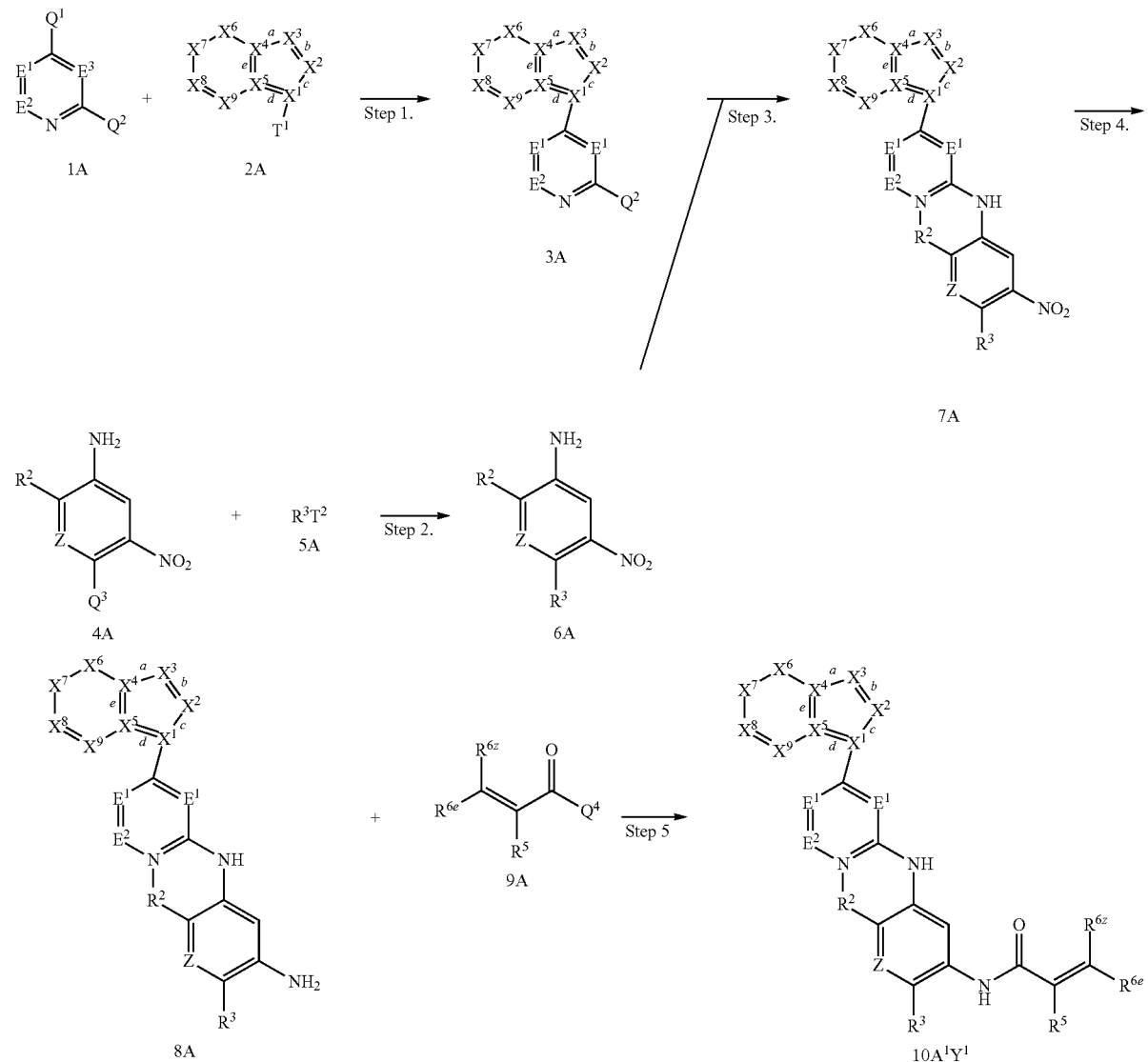

Scheme 1. Generic Synthesis with [6.5]-bicyclic A groups and Enoyl Y-groups.

This synthetic scheme describes a commonly used strategy, which has essentially A' linked sequentially to B', which is then attached to a C' moiety, which already has the R3 side chain attached, and then after reduction of the nitro group, D' is attached to complete the synthesis. In the first step of Scheme 1, the azine 1A, being the B' moiety is coupled at its 4-position with the A' moiety a, [6.5]-bicycle, 2A either at its 1- or 3-position, with an overall loss of $Q^1T^1$ to form intermediate 3A. Such couplings will frequently be a displacement of halide ion by nitrogen, or a nitrogen based anion, but equally can involve formation of a carbon-carbon bond, by methods familiar to one of skill in the art, such as Stille, Negishi or Suziuki couplings, or Freidel-Crafts aryl substitutions. In Step 2 $Q^3$ on 4A is displaced by 5A, with a loss of $Q^3T^2$, to form intermediate 6A, the complete C' moiety. Such couplings will frequently be a displacement of halide ion by nitrogen, or a nitrogen based anion, but equally can involve formation of a carbon-carbon bond, by methods familiar to one of skill in the art, such as Stille, Negishi or Suziuki couplings.

In step 3, the amino nitrogen of 6A is used to displace $Q^2$ from the A'B' moiety, intermediate 3A, to form an A'-B'-C' concatenated intermediate 7A, using methods known to one of skill in the art. The nitro group of 7A is then reduced to the amino group of intermediate 8A, using methods such as iron/acetic acid or catalytic hydrogenation, well known to those of ordinary skill in the art. The synthesis of the complete A'-B'-C'-D' final product, $10A^1Y^1$ in this illustrative general case, is completed by an amide coupling of amine 8A with a suitable enoic acid derivative 9A, where the leaving group $Q^4$ can be a halide, activated ester, acid plus coupling agent, or other activated acid derivative suitable for peptide coupling, known to one of skill in the art. Other compounds of the invention are made by analogous processes, with different A and Y groups, using appropriate starting materials and coupling reactions, all of which are well known to one of skill in the art.

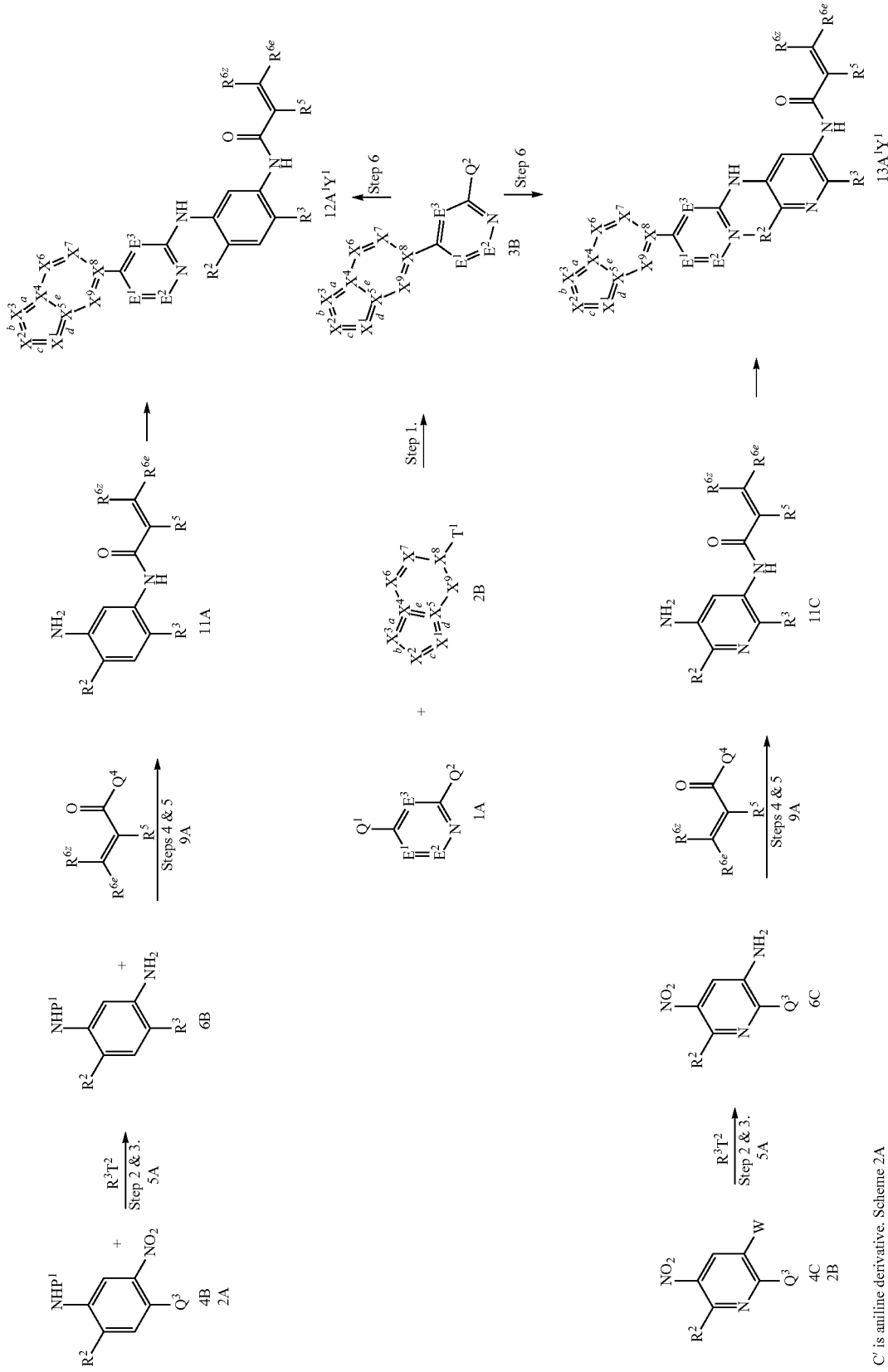

In Scheme 2, one of the alternative strategies is illustrated, using similar components as in Scheme 1. In this case the illustrative $A^1$ (A') component is a 5-linked 6,5-azaaromatic system. The first step is the same as before with the A' moiety 2B being coupled to the B' azine 1A by the same types of reactions described previously to form 3B the A'-B' entity, as in Scheme 1. Two alternative routes 2A and 2B are illustrated here to form the C'-D' fragment, which will be coupled late, or at the end of the sequence with the A'-B', as optimal chemistries have to differ rather more than needed in Scheme 1 for anilines and pyridines.

In scheme 2A, the starting nitroaniline 4B is similar to 4A, except that the amine is suitably protected. The R3 moiety is introduced as before by displacement of $Q^3$, and then the nitro group is reduced to an unprotected amine to give the appropriate C' fragment 6B. This is then acylated with the D' moiety 9A on the free amine, and the coupling ready C'D' entity 11B is completed by removal of the protecting group from the original amine. In scheme 2B the high, and selective reactivity of halonitropyridines allows for an easy preparation of 4C moieties, where W is a group that can be readily turned into an amine later. This can even be a proton, as after $R^3$ has been introduced by 5A displacement of $Q^3$, the 5-position of the pyridine is quite highly activated to electrophilic aromatic substitution. Replacement of W with a free amine under non-reducing conditions will give the C' entity as a nitroaniline 6C, with the free amine at the correct position for acylation by the D' entity 9A. A mild reduction of the 3-nitro group to the amine completes the preparation of this C'-D' moiety 11C, in a form ready for the final coupling.

In what in many cases will be the last step of the synthesis, the Q2 fragment on 3A is displaced by the free amine on 11B or 11C using the same sorts of couplings that were used to couple the A'B' fragment to the C' moiety as described for Scheme 1, to produce entities $12A^1Y^1$ and $13A^1Y^1$. Many of the same conditions can be employed here, as acrylamide D' moieties especially are often robust enough to survive the amine displacement reactions used here. Alternatively, one can use precursors to the final D' electrophile in this reaction and activate the final electrophilic species, after this coupling is complete.

INTERMEDIATES

A1. 2-Chloro-4-indol-1-ylpyrimidine

To a solution of indole (3.93 g, 33.56 mmol) in DMF (50 mL) was added NaH (60% in mineral oil, 1.61 g, 40.27 mmol) portionwise at 0° C. After stirring at 0° C. for 30 min, 2,4-dichloropyrimidine (5.00 g, 33.56 mmol) was added, then the mixture was allowed stirred at 15° C. for 12 hrs. The resulting mixture was quenched with water (300 mL) and the mixture was extracted with EtOAc (200 mL×3), the combined organic layers were washed with water (300 mL×4), dried with $Na_2SO_4$ and concentrated in vacuo. The residue was purified by silica gel chromatography (petroleum ether:EtOAc=10:1), to give 2-Chloro-4-indol-1-ylpyrimidine (2.00 g, 26%) as white solid.

$^1$H NMR: (MeOD 400 MHz): δ 8.62 (d, J=8.8 Hz, 1H), 8.56 (d, J=6.0 Hz, 1H), 7.93 (d, J=4.0 Hz, 1H), 7.68-7.61 (m, 2H), 7.35 (t, J=7.2 Hz, 1H), 7.26 (t J=7.2 Hz, 1H), 6.83 (d, J=3.6 Hz, 2H).

A2. 2-Chloro-4-(3-methylindol-1-yl)pyrimidine

To a solution of 3-methylindole (4.40 g, 33.56 mmol) in DMF (60 mL) was added NaH (60% in mineral oil, 1.61 g, 40.27 mmol) portionwise at 0° C. After stirring at 0° C. for 30 min, 2,4-dichloropyrimidine (5.00 g, 33.56 mmol) was added, and the mixture was allowed to stir at 15° C. for 12 hrs. The resulting mixture was quenched with water (200 mL) and extracted with EtOAc (200 mL×3), the combined organic layers were washed with water (200 mL×4), dried ($Na_2SO_4$) and concentrated in vacuo. The residue was purified by silica gel chromatography (petroleum ether:EtOAc=10:1) to give 2-chloro-4-(3-methylindol-1-yl)pyrimidine (2.90 g, 35%) as yellow solid.

$^1$H NMR: (400 MHz, DMSO-$d^6$): δ 8.64 (d, J=6.0 Hz, 1H), 8.56 (d, J=8.4 Hz, 1H), 7.96 (s, 1H), 7.79 (d, J=5.6 Hz, 1H), 7.59 (d, J=7.6 Hz, 1H), 7.37 (t, J=7.2 Hz, 1H), 7.28 (t, J=7.2 Hz, 1H), 2.28 (s, 3H).

A3. 2-Chloro-4-(3-chloroindol-1-yl)pyrimidine

To a solution of indole (4.00 g, 34.14 mmol) in DMF (40 mL) was added NCS (4.56 g, 34.14 mmol) at 0° C. under $N_2$. The mixture was stirred at 15° C. for 4 hours, and was poured into $H_2O$ (200 mL), filtered and washed with $H_2O$ (20 mL). The solid was dried to give 3-chloroindole (5.00 g, 96%).

$^1$H NMR: (400 MHz, DMSO-$d^6$): δ 11.34 (s, 1H), 7.51-7.49 (m, 2H), 7.47-7.41 (m, 1H), 7.18-7.16 (m, 1H), 7.12-7.10 (m, 1H).

To a solution of 3-chloroindole (3.00 g, 19.79 mmol) in DMF (40 mL) was added NaH (60% in mineral oil, 950 mg, 23.75 mmol) at 0° C. under $N_2$ and the mixture was stirred for 30 mins. Then 2,4-dichloropyrimidine (2.95 g, 19.79 mmol) was added and stirred at 15° C. for 4 hours. The mixture was poured into $H_2O$ (200 mL), filtered and washed with $H_2O$ (100 mL). The solid was washed with EtOAc (200 mL). The solid was dried to give 2-chloro-4-(3-chloroindol-1-yl)pyrimidine (1.20 g, 23%).

$^1$H NMR: (400 MHz $CDCl_3$): δ 8.58 (d, J=5.6 Hz, 1H), 8.53 (d, J=8.4 Hz, 1H), 7.73 (s, 1H), 7.69-7.67 (m, 1H), 7.50-7.46 (m, 1H), 7.41-7.28 (m, 1H), 7.27-7.26 (m, 1H).

A4. 2-Chloro-4-(3-cyanoindol-1-yl)pyrimidine

To a solution of 3-cyanoindole (3.05 g, 21.48 mmol) in DMF (60 mL) was added NaH (60% in mineral oil, 1.03 g, 25.78 mmol) portionwise at 0° C. After stirring at 0° C. for 30 min. 2,4-dichloropyrimidine (3.20 g, 21.48 mmol) was added, and the mixture was allowed to stir at 15° C. for 12 hrs. The resulting mixture was quenched with water (200 mL) and the mixture was extracted with EtOAc (100 mL×3), combined the organic layer and washed with water (100 mL×4), dried with $Na_2SO_4$ and concentrated in vacuo. The residue was purified by silica gel chromatography (petroleum ether:EtOAc=10:1), to give 2-chloro-4-(3-cyanoindol-1-yl)pyrimidine (3.20 g, 58.5%) as a white solid.

$^1$H NMR: (400 MHz DMSO-$d^6$): δ 9.15 (s, 1H), 8.89 (d, J=5.6 Hz, 1H), 8.62 (d, J=8.4 Hz, 1H), 8.02 (d, J=6.4 Hz, 1H), 7.76 (d, J=7.6 Hz, 1H), 7.57-7.52 (m, 2H).

A5. 2-Chloro-4-(4-methylindol-3-yl)pyrimidine

Methylmagnesium bromide (27.21 g, 2.7.21 g, 228 mmol) in ether was added dropwise to a solution of 4-methylindole (29.94 g, 228.22 mmol) in THF (300 mL) stirred under $N_2$ at 0° C. (The reaction was exothermic, while keeping internal temperature between 0-1° C.) The solution was stirred for 1 hr at 0° C., and allowed to warm to room temperature. Then 2,4-dichloropyrimidine (17.00 g, 114.11 mmol) was added to the reaction mixture (no exotherm) and heated to 80° C., with stirring for 15 hrs, when LCMS showed 70% of 4-methylindole remained. The reaction solution was quenched with MeOH (500 mL), and the solution was pre-adsorbed onto silica gel (100 g). The crude product was purified by column chromatography on silica gel eluted with (PE/EtOAc 10:1→3:1) to give 2-chloro-4-(4-methylindol-3-yl)pyrimidine (4.00 g, 14.4%) as a yellow solid.

$^1$H NMR (400 MHz, METHANOL-d$_4$) δ: 8.48-8.45 (m, 1H), 7.84-7.82 (m, 1H), 7.64-7.61 (m, 1H), 7.31-7.28 (m, 1H), 7.15-7.10 (m, 1H), 6.97 (s, 1H), 2.64 (s, 3H).

A6.
2-Chloro-4-(1N,4-dimethylindol-3-yl)pyrimidine

To a solution of 2-chloro-4-(4-methylindol-3-yl)pyrimidine (3.00 g, 12.3 mmol) in DMF (30 mL) at 0° C. was added NaH (60% in mineral oil, 354.53 mg, 14.8 mmol). After 1 hr MeI (3.53 g, 24.9 mmol) was added drop wise to the solution (while keeping internal temperature between 0° C.-5° C.) and stirred for another 3 hrs. The reaction mixture was poured into water (60 mL) and extracted with MTBE (30 mL×3). The organic phase was washed with saturated brine (100 mL), dried over Na$_2$SO$_4$ and concentrated in vacuum to give 2-chloro-4-(1N,4-dimethylindol-3-yl)pyrimidine (3.00 g, 94.6%) as a white solid.

$^1$H NMR (400 MHz, METHANOL-d4) δ: 8.48-8.45 (m, 1H), 7.83-7.81 (m, 1H), 7.63-7.59 (m, 1H), 7.33-7.29 (m, 1H), 7.23-7.17 (m, 1H), 7.03-6.99 (m, 1H), 3.88 (s, 3H), 2.65 (s, 3H).

A7. 2-Chloro-4-(4-chloro-1,N-methylindol-3-yl)pyrimidine

To a mixture of 4-chloroindole (4.00 g, 26.4 mmol) in THF (40 mL) at 0° C. was added NaH (60% in mineral oil, 760 mg, 31.7 mmol). After the solution was stirred at 0° C. for 30 mins, MeI (11.80 g, 83.1 mmol) was added at 0° C., and then the mixture was stirred for 4 hrs at 25° C. The reaction mixture was poured into water (100 mL) and extracted with MTBE (30 mL×3). The organic phase washed with saturated brine (50 mL), dried over Na$_2$SO$_4$ and concentrated in vacuum to give 4-chloro-1,N-methylindole (4.00 g, 91.5% crude) as a colourless solid.

$^1$H NMR (400 MHz, CHLOROFORM-d) δ: 7.26-7.21 (m, 1H), 7.15 (s, 2H), 7.11-7.09 (m, 1H), 6.64-6.57 (m, 1H), 3.80 (s, 3H).

NBS (8.60 g, 48.3 mmol) was added in portions to a solution of 4-chloro-1,N-methylindole (8.00 g, 48.3 mmol) in DMF 60 mL), stirred under N$_2$ at 0° C. After a further 20 min, the reaction solution was poured into water (60 mL), the solid collected by vacuum filtration, rinsed with water (20 mL×4) and dried in vacuo to give 3-bromo-4-chloro-1,N-methylindole (8.00 g, 67.7%, crude) as a white solid.

$^1$H NMR (400 MHz, CHLOROFORM-d) δ: 7.24-7.21 (m, 1H), 7.16-7.10 (m, 3H), 3.76 (s, 3H).

n-BuLi (1.83 g, 28.63 mmol) was added dropwise to a solution of 3-bromo-4-chloro-1,N-methylindole (7.00 g, 28.6 mmol) in THF (70 mL) stirred under N$_2$ at −78° C. After 2 hrs at this temperature 2-isopropoxy-4,4,5,5-tetramethyl-1,3,2-dioxaborolane (5.33 g, 28.6 mmol) was added into the solution and stirred for another 2 hrs. TLC indicated compound 6 was consumed completely and two new spots formed. The reaction mixture was quenched with saturated aqueous NH$_4$Cl (30 mL) and extracted with EtOAc (30 mL×3). The combine organic phases were washed with saturated brine (100 mL), dried over Na$_2$SO$_4$ and concentrated in vacuum. The crude product was purified by column chromatography on silica gel eluted with (PE/EtOAc 20:1→10:1→5:1) to give 2-(4-chloro-1,N-methylindol-3-yl) 4,4,5,5-tetramethyl-1,3,2-dioxaborolane (2.00 g, 6.86 mmol, 23.96% yield) as a white solid.

$^1$H NMR (400 MHz, CHLOROFORM-d) δ: 7.53 (s, 1H), 7.21-7.10 (m, 3H), 3.79 (s, 3H), 1.40 (s, 1H).

A mixture of 2-(4-chloro-1,N-methylindol-3-yl) 4,4,5,5-tetramethyl-1,3,2-dioxaborolane (1.50 g, 5.14 mmol), 2,4-dichloropyrimidine (1.53 g, 10.29 mmol) K$_2$CO$_3$ (2.13 g, 15.43 mmol), and Pd(dppf)Cl$_2$.CH$_2$Cl$_2$ (420.11 mg, 0.514 mmol) in dioxane (10 mL) and H$_2$O (1.0 mL) was stirred at 80° C. for 4 hrs under N$_2$. The reaction mixture was poured into water (30 mL) and extracted with EtOAc (30 mL×3). The organic phase washed with saturated brine (50 mL), dried over Na$_2$SO$_4$ and concentrated in vacuum. The crude product was purified by column chromatography on silica gel eluted with (PE/EtOAc 20:1-10:1) to give 2-chloro-4-(4-chloro-1,N-methylindol-3-yl)pyrimidine (1.40 g, 98%) as a white solid.

$^1$H NMR (400 MHz, CHLOROFORM-d) δ: 8.56-8.49 (m, 1H), 7.78-7.76 (m, 1H), 7.72-7.69 (m, 1H), 7.34-7.31 (m, 1H), 7.26 (m, 2H), 3.89 (m, 3H)

A8.
2-Chloro-4-(3-(carboxymethyl)indol-1-yl)pyrimidine

A solution of methyl indole-3-carboxylate (11.76 g, 67 mmol) in DMF (70 mL), was added dropwise to a slurry of NaH oil suspension (2.68 g, 60%, 67.1 mmol) in DMF (40 mL) stirred at 0° C. under N$_2$. After 0.5 h, 2,4-dichloropyrimidine (10.00 g, 67.12 mmol) in DMF (90 ml) was added dropwise, still at 0° C. Then the mixture warmed to 25° C., and stirred for 1.5 hr. HPLC (5-95) indicated that the reaction was complete. The reaction mixture was quenched by addition of water (300 mL), and was then extracted with EtOAc (2×200 mL). The combined organic extracts were dried (Na$_2$SO$_4$) filtered and concentrated under reduced pressure. The residue was purified by column chromatography (SiO$_2$, Petroleum ether/Ethyl acetate=50/1 to 3/1) and then purified by prep-HPLC (HCl) to afford 2-chloro-4-(3-(carboxymethyl)indol-1-yl)pyrimidine (5.00 g, 17.38 mmol, 25.89% yield) as yellow solid.

A9. 2-Chloro-4-(3-formylindol-1-yl)pyrimidine

A solution of indole-3-carbaldehyde (24.36 g, 167.8 mmol) in DMF (100 mL), was added dropwise to a stirred slurry of NaH (60% oil suspension, 6.71 g, 167.81 mmol) in DMF (100 mL) at 0° C. under N$_2$ and stirred for 0.5 h. Then 2,4-dichloropyridine (25.00 g, 167.81 mmol) in DMF (100 ml) was added dropwise. The mixture was warmed to 25° C. stirred for 1.5 hr. TLC (petroleum ether/ethyl acetate=1/1, R$_f$=0.35) indicated that the reaction was complete. The reaction mixture was quenched by addition of water (500 mL), and then extracted with EtOAc (2×300 mL). The combined organic extracts were washed with saturated brine (100 mL) dried (Na$_2$SO$_4$), filtered and concentrated under reduced pressure. The residue was purified by column chromatography (SiO2, Petroleum ether/Ethyl acetate=50/1 to 3/1) and then purified further by prep-HPLC (HCl) to afford 2-chloro-4-(3-formylindol-1-yl)pyrimidine (14.00 g, 54.33 mmol, 32.38% yield) as a yellow solid.

A10.
2-Chloro-4-(3-methylsulfonylindol-1-yl)pyrimidine

3-Methylthioindole

A slurry of N-chlorosuccinimide (5.7 g, 42.7 mmol) in DCM (125 mL) was degassed and purged with N$_2$ 3 times at 25° C., and then the mixture was cooled to 0° C. Dimethylsulfide (530 mg, 8.54 mmol, 624 µL) was added to the mixture. After stirring at 0° C. for 15 min, the mixture was cooled to −20° C., and a solution of indole (5.0 g, 42.7 mmol) in DCM (125 mL) was added slowly. After addition, the reaction mixture was warmed to 25° C., and stirred for 1 hour. Then the mixture was concentrated to give a residue, and the residue was dissolved in xylene (250 mL) and stirred at 150° C. under $N_2$ for 0.5 hour. LC-MS (5-95) showed indole was consumed completely and one main peak with desired MS was detected. The reaction mixture was cooled to 25° C., and filtered. The filtrate as red liquid was used in next step directly.

3-Methylsulfonylindole

Crude 3-methylthioindole prepared above in xylenes was stirred at 0° C., and mCPBA (85%, 17.3 g, 85.4 mmol) was added. Then the reaction mixture was warmed to 25° C., and stirred for 2 hours. The reaction mixture was cooled to 0° C., and quenched by addition of satd. $Na_2SO_3$ solution (25 mL) until there was no detectable peroxide in the solution, tested by potassium iodide-starch paper. Then water (100 mL) was added to the mixture, and the mixture was extracted with dichloromethane (3×100 mL), the organic layers were combined, washed with satd brine (100 mL), dried ($Na_2SO_4$), filtered and concentrated to give a residue. The residue was purified by column chromatography on silica gel eluted with petroleum ether/ethyl acetate (10/1 to 5/1) to give 3-methylsulfonylindole (5.1 g, 61% on 2 steps) as earthy yellow solid.
$^1$H NMR ($d_6$-DMSO) δ 12.6 (s, 1H), 8.02-8.01 (m, 1H), 7.80 (d, J=8 Hz, 1H), 7.54 (d, J=8 Hz, 1H), 7.27-7.22 (m, 2H), 3.18 (s, 3H).

2-Chloro-4-(3-methylsulfonylindol-1-yl)pyrimidine

A solution of 3-methylsulfonylindole (6.8 g, 34.8 mmol) in DMF (70 mL) was cooled to 0° C., and NaH (60% oil suspension, 1.4 g, 34.8 mmol) was added in several portions. The reaction mixture was stirred at 0° C. for 0.5 hour, and then 2,4-dichloropyrimidine (5.2 g, 34.8 mmol) was added to the reaction mixture in one portion. The reaction mixture was warmed to 25° C., and stirred for 3.5 hours. The reaction mixture was cooled to 0° C., quenched with sat. $NH_4Cl$ solution (15 mL) and water (30 mL), extracted with EtOAc (3×80 mL), the organic layers were combined and washed with water (2×30 mL), satd brine (30 mL), dried ($Na_2SO_4$), filtered and concentrated to give a residue. The residue was purified by column chromatography on silica gel eluted with petroleum ether/ethyl acetate (10/1 to 1/1) to give 2-chloro-4-(3-methylsulfonylindol-1-yl)pyrimidine (2.80 g, 26.1%) as a white solid.
$^1$H NMR ($d_6$-DMSO) δ 8.86-8.85 (m, 2H), 8.62 (d, J=8.4 Hz, 1H), 8.21-8.20 (m, 1H), 7.93 (d, J=8.0 Hz, 1H), 7.54 (t, J=7.2 Hz, 1H), 7.46 (t, J=7.4 Hz, 1H), 3.33 (s, 3H).

A11. 2-Chloro-4-(3-hydroxyindol-1-yl-)pyrimidine

Intermediate A11 can be synthesized according to procedures disclosed herein or by common synthesis procedures known in the art.

A12.
2-Chloro-4-(2-hydroxybenzimidazol-1-yl)pyrimidine 4-(2-Aminoanilino)-4-chloropyrimidine 2,4-Dichloropyrimidine (5.5 g, 37 mmol) and DIPEA (9.6 g, 74 mmol, 13 mL) were added to a solution of 1,2-diaminobenzene (4.0 g, 37 mmol) in n-butanol (160 mL) at 25° C. The reaction mixture was degassed and purged with $N_2$ 3 times, and then the mixture was stirred at 100° C. for 4 hours under $N_2$. TLC (petroleum ether/ethyl acetate=1/1, $R_f$=0.5) showed the reaction was complete. The reaction mixture was cooled to 25° C., and concentrated to give a residue. The residue was stirred with aqueous HCl (0.1 M, 60 mL) for 20 min, then EtOAc (100 mL) was added, the phases separated and the aqueous phase was extracted with EtOAc (2×30 mL). The organic layers were combined and washed with satd brine (50 mL), dried ($Na_2SO_4$), filtered and concentrated to give a crude product. The crude product was washed with DCM (50 mL) to give 4-(2-aminoanilino)-4-chloropyrimidine (5.30 g, 65% yield) as a light yellow solid.
$^1$H NMR ($d_6$-DMSO) δ 9.16 (s, 1H), 8.04-8.02 (m, 1H), 7.06-6.98 (m, 2H), 6.78-6.76 (m, 1H), 6.59-6.56 (m, 1H), 6.32 (brs, 1H), 4.99 (brs, 2H).

2-Chloro-4-(2-hydroxybenzimidazol-1-yl)pyrimidine

CDI (5.5 g, 34 mmol) was added to a solution of 4-(2-aminoanilino)-4-chloropyrimidine (5.3 g, 24 mmol) in DMF (60 mL) at 25° C. The reaction mixture was degassed and purged with $N_2$ 3 times, and then the mixture was stirred at 80° C. for 17 hours under $N_2$. TLC (petroleum ether/ethyl acetate=1/1, $R_f$=0.58) showed the reaction was complete. The reaction mixture was cooled to 25° C., and concentrated to give a residue. The residue was dissolved in water (20 mL), extracted with EtOAc (3×20 mL), and the combined organic layers were washed with said brine (20 mL), dried over $Na_2SO_4$, filtered and concentrated to give 2-chloro-4-(2-hydroxybenzimidazol-1-yl)pyrimidine (1.0 g, 16%) as an off-white solid.

A13. 2-Chloro-4-(7-methylindol-3-yl)pyrimidine

A solution of 4-methylindole (5.0 g, 38 mmol) in DCE (250 mL) was degassed and purged with $N_2$ 3 times, and was cooled to 0° C. MeMgBr in ether (3 M, 12.7 mL) was added dropwise at 0° C. After the addition, the mixture was stirred at 0° C. for 0.5 hour, and then 2,4-dichloropyrimidine (8.4 g, 56 mmol) was added in one portion. The reaction mixture was warmed to 25° C., and stirred for 16 hours when TLC (petroleum ether/ethyl acetate=1/1, $R_f$=0.5) showed the reaction was complete. The mixture was cooled to 0° C., MeOH (30 mL) was added to the mixture with stirring, then the mixture was concentrated to give a residue. The residue was purified by column chromatography on silica gel eluted with petroleum ether/ethyl acetate (10/1 to 1/1) to give 2-Chloro-4-(7-methylindol-3-yl)pyrimidine (4 g, 43% yield) as yellow solid.
$^1$H NMR (MeOD) δ 8.38-8.37 (m, 1H), 8.23-8.21 (m, 2H), 7.72-7.71 (m, 1H), 7.12 (t, J=14.8 Hz, 1H), 7.04-7.02 (m, 1H), 2.52 (s, 3H).

A14. 2-Chloro-4-(1,N-(t-butoxycarbonyl-7-cyanoindol-3-yl)pyrimidine

1,N-(t-Butoxycarbonyl)-7-cyanoindole $(Boc)_2O$ (3.38 g, 15.48 mmol, 1.10 eq) was added to a solution of 7-cyanoindole (2.00 g, 14.07 mmol), $Et_3N$ (4.27 g, 42.21 mmol) and DMAP (344 mg, 2.81 mmol) in DCM (40 mL) stirred at 0° C. Then the reaction mixture was stirred at 25° C. for 2 hrs. TLC (petroleum ether/ethyl acetate=10/1, $R_f$=0.4) showed the reaction was complete.

The reaction mixture was quenched by adding water (50 mL) at 0° C., and then diluting with DCM (50 mL). The phases were separated, and the aqueous phase extracted with further DCM (3×30 mL). The combined organic layers were washed with satd brine (50 mL), dried (Na$_2$SO$_4$), filtered and concentrated under reduced pressure to give a residue. The residue was purified by column chromatography (SiO$_2$, Petroleum ether/Ethyl acetate=100/1 to 40/1) to afford 1,N-(t-butoxycarbonyl)-7-cyanoindole (3.00 g, 12.38 mmol, 88% yield) as a white solid.

3-Bromo-1,N-(t-butoxycarbonyl)-7-cyanoindole

NBS (2.42 g, 13.62 mmol) was added to a solution of 1,N-(t-butoxycarbonyl)-7-cyanoindole (3.0 g, 12.38 mmol) in DCM (150 mL) stirred at 25° C., and then the mixture was refluxed for 32 hr. TLC (petroleum ether/ethyl acetate=6/1, R$_f$=0.35) indicated that the reaction was complete. The mixture was concentrated in vacuum to remove the solvent, and the residue was purified by column chromatography (SiO$_2$, petroleum ether/ethyl acetate=100/1 to 30/1) to afford 3-Bromo-1,N-(t-butoxycarbonyl)-7-cyanoindole (3.40 g, 85.5% yield) as a green solid.

1,N-(t-Butoxycarbonyl)-7-cyano-3-(4,4,5,5-tetramethyl-1,3,2-dioxabor-2-yl)indole A solution of 3-bromo-1,N-(t-butoxycarbonyl)-7-cyanoindole (1.00 g, 3.11 mmol) tricyclohexylphosphane (192 mg, 0.68 mmol), potassium acetate (763 mg, 7.78 mmol), bis(pinacolato)diboron (947.7 mg, 3.73 mmol) and Pd$_2$(dba)$_3$ (142.4 mg, 0.156 mol) in dioxane (12 mL) at 25° C. was sparged with N$_2$ for 10 minutes and warmed to 50° C. with stirring for 16 hr. LC-MS (5-95) indicated that the reaction was complete. The reaction mixture was filtered and concentrated under vacuum. The residue was purified by column chromatography (SiO$_2$, petroleum ether/ethyl acetate=10/1) to afford 1,N-(t-butoxycarbonyl)-7-cyano-3-(4,4,5,5-tetramethyl-1,3,2-dioxabor-2-yl)indole (600 mg, 52.4) as a yellow solid.

2-Chloro-4-(1,N-(t-butoxycarbonyl)-7-cyanoindol-3-yl)pyrimidine

A mixture of 1,N-(t-butoxycarbonyl)-7-cyano-3-(4,4,5,5-tetramethyl-1,3,2-dioxabor-2-yl)indole (550 mg, 1.49 mmol) 2,4-dichloropyrimidine (222 mg, 1.49 mmol), KOAc (292.5 mg, 2.98 mmol) and Pd(dppf) (48.67 mg, 0.06 mmol) in dioxane (30 mL) and water (6 mL) under N$_2$ was stirred at 60° C. stirred for 18 hr. Then the mixture was filtered and concentrated in vacuum to remove the solvent. The residue was purified by prep-HPLC to afford 2-chloro-4-(1,N-(t-butoxycarbonyl)-7-cyanoindol-3-yl)pyrimidine (120 mg, 22.7% yield) as a white solid.

$^1$H NMR (d$_6$-DMSO) δ: 12.94 (br. s., 1H), 8.79 (d, J=8.0 Hz, 1H), 8.71 (s, 1H), 8.62 (d, J=5.5 Hz, 1H), 8.04 (d, J=5.0 Hz, 1H), 7.77 (d, J=7.5 Hz, 1H), 7.41 (t, J=7.8 Hz, 1H).

A15. 2-Chloro-4-indazol-1-ylpyrimidine

A stirred solution of 1H-indazole 15 (590.5 mg, 5.0 mmol) in dry DMF (15 mL) at 0° C. was treated with NaH (200 mg, 5.0 mmol, 60% in mineral oil). After stirring at 25° C. for 2 hr the mixture was recooled to 0° C., and 2,4-dichloropyrimidine (740 mg, 5.0 mmol) was added. After stirring for 4 hr at 25° C. the mixture was quenched with water (and extracted with EtOAc (3×25 mL), The combined organic extracts were washed with satd brine (25 mL), dried (MgSO$_4$) and the solvent was removed under reduced pressure. The residue was purified by column chromatography (SiO$_2$, Pet/EtOAc 20/1) to afford 2-chloro-4-indazol-1-ylpyrimidine (250 mg, 26%) as a white solid.

$^1$H NMR (CDCl$_3$) δ: 7.39 (1H, t, J=8.0 Hz), 7.62 (1H, t, J=8.0 Hz), 7.79 (1H, dd, J=8.0, 0.8 Hz), 7.92 (1H, d, J=5.6 Hz), 8.27 (1H, s), 8.57 (1H, d, J=5.6 Hz), 8.81 (1H, dd, J=8.4, 0.8 Hz).

HR-MS (m/z): 231.0358.

A16. 2-Chloro-4-(2,3-dihydroindol-1-yl)pyrimidine

A solution of 2,4-dichloropyrimidine (6.25 g, 42 mmol) 2,3-dihydroindole (5.00 g, 42 mmol, 4.72 mL) and DIPEA (5.42 g, 42 mmol, 7.33 mL) in n-BuOH (100.00 mL) was stirred at 100° C. for 12 hr. TLC (petroleum ether/ethyl acetate=2/1, R$_f$=0.45) showed the reaction was completed. The mixture was filtered and concentrated in vacuo to remove the solvent. The residue was purified by column chromatography (SiO$_2$, Petroleum ether/Ethyl acetate=20/1 to 3/1) to afford 2-chloro-4-(2,3-dihydroindol-1-yl)pyrimidine (2.00 g, 20.6%) as a white solid.

$^1$H NMR (MeOD) δ 8.33 (d, J=7.5 Hz, 1H), 8.16 (d, J=6.2 Hz, 1H), 7.27-7.15 (m, 2H), 7.05-6.95 (m, 1H), 6.70 (d, J=6.2 Hz, 1H), 4.02 (t, J=8.6 Hz, 2H), 3.23 (t, J=8.4 Hz, 2H).

A17. 2-Chloro-4-(3-(difluoromethyl)indol-1-yl)pyrimidine 3-(Difluoromethyl)indazole S-(Bis(2-methoxyethyl)amino)sulfur trifluoride (2.6 g, 16.6 mmol) in DCM (4 mL) was added dropwise to a solution of indazole-3-carbaldehyde (5.66 g, 25.6 mmol, 5.6 mL) in DCM (10 mL) stirred under N$_2$ at 0° C., and the solution was then stirred for 1 hour at 25° C. The reaction was quenched with sat.NaHCO$_3$ solution (10 mL) and extracted with DCM (10 mL×2). The combined organic phase was concentrated in vacuo to give a crude product. The crude product was purified by prep-HPLC to afford 3-(difluoromethyl)indazole (430 mg, 14.4%) as a yellow solid.

1H NMR (d$_6$-DMSO) δ: 13.68-13.54 (brs, 1H), 7.86-7.82 (m, 1H), 7.64 (d, J=8.4 Hz, 1H), 7.47 (d, J=7.9 Hz, 1H), 7.27-7.21 (m, 2H).

2-Chloro-4-(3-(difluoromethyl)indazol-1-yl)pyrimidine

To a suspension of NaH (142.8 mg, 3.57 mmol, 60% purity) in DMF (4 mL) was added dropwise 3-(difluoromethyl)indazole (600 mg, 3.57 mmol) in DMF (3 mL) at 0° C. under N$_2$. Then the mixture was stirred at 0° C. for 5 minutes before 2,4-dichloropyrimidine (532 mg, 3.57 mmol) in DMF (3 mL) was added dropwise. The mixture was stirred at 25° C. for 2 hours. The reaction was quenched with water (10 mL) and extracted with EtOAc (10 mL×2). The combined organic layers were washed with saturated brine (10 mL×2), dried with anhydrous Na$_2$SO$_4$, filtered and concentrated in vacuum to give a crude product. The crude product was purified by prep-HPLC (TFA) to afford 2-chloro-4-(3-(difluoromethyl)indazol-1-yl)pyrimidine (450 mg, 1.6 mmol, 34% yield) as a white solid.

1H NMR (d$_6$-DMSO) δ: 8.83 (d, J=5.6 Hz, 1H), 8.75-8.68 (m, 1H), 8.05-7.98 (m, 2H), 7.86-7.77 (m, 1H), 7.58-7.54 (m, 2H).

A18. 2-Chloro-4-(3-ethynylindol-1-yl)pyrimidine

Intermediate A18 can be synthesized according to procedures disclosed herein or by common synthesis procedures known in the art.

A19. 2-Chloro-4-(2-methylindol-3-yl)pyrimidine

MeMgBr (3 M in ether, 2.54 mL, 7.6 mmol) was added dropwise at 0° C. to a solution of 2-methylindole (1.00 g, 7.62 mmol) in DCE (32. mL) and stirred for 30 minutes, 2,4-Dichloropyrimidine (1.70 g, 11.43 mmol) was then added in one portion. The reaction mixture was stirred at 25° C. for 16 hr, and then cooled to 0° C. Methanol (3 mL) was added dropwise, and the reaction mixture was quenched with dilute hydrochloric acid (0.5 M, 20 mL). The phases were separated and the aqueous phase was extracted with DCE (2×10 mL). The combined organic phases were washed with satd brine (20 mL), dried ($Na_2SO_4$), filtered, and the filtrate was concentrated under vacuum. The residue was purified by column chromatography ($SiO_2$, Petroleum ether/Ethyl acetate=50/1 to 1:5) to afford 2-chloro-4-(2-methylindol-3-yl)pyrimidine (700 mg, 37.7% yield) as a yellow solid.

$^1$H NMR ($d_6$-DMSO) δ 11.90 (s, 1H), 8.56 (s, 1H), 8.18-8.15 (m, 1H), 7.69-7.42 (m, 1H), 7.41-7.30 (s, 1H), 7.18-7.16 (s, 2H), 2.74 (s, 3H).

A20. 2-Chloro-4-(7-oxopyrrolo[2,3-c]pyrid-3-yl)pyrimidine

Intermediate A20 can be synthesized according to procedures disclosed herein or by common synthesis procedures known in the art by hydrolysis of 2-chloro-4-(7-methoxypyrrolo[2,3-c]pyrid-3-yl)pyrimidine described in A28 below.

A21. 2-Chloro-4-(1,N-(t-butoxycarbonyl)indazol-3-ylpyrimidine

1,N-(t-Butoxycarbonyl)indazole

DMAP (62 mg, 0.51 mmol) and $(Boc)_2O$ (6.7 g, 30 mmol, 7.0 mL) were added to a solution of indazole (3.0 g, 25 mmol) in MeCN (100 mL) stirred at 25° C. under $N_2$ for 4 hr. TLC (petroleum ether/ethyl acetate=5/1, $R_f$=0.5) showed the reaction was complete. The reaction mixture was concentrated to give a residue which was partitioned between EtOAc (50 mL) and water (30 mL), the aqueous layer was separated and extracted with EtOAc (2×30 mL). The organic layers were combined and washed with sat. $NaHCO_3$ solution (50 mL), brine (50 mL), dried ($Na_2SO_4$), filtered and concentrated to give a crude product. The crude product was purified by column chromatography ($SiO_2$, petroleum ether/ethyl acetate=30/1 to 10/1) to give 1,N-(t-butoxycarbonyl)indazole (4.5 g, 81% yield) as light yellow oil.

$^1$H NMR ($d_6$-DMSO) δ 8.42 (s, 1H), 8.09 (d, J=8.4 Hz, 1H), 7.89 (d, J=8 Hz, 1H), 7.61 (t, J=8.0 Hz, 1H), 7.38 (t, J=7.4 Hz, 1H), 1.65 (s, 9H).

1,N-(t-Butoxycarbonyl)-3-(4,4,5,5-tetramethyl-1,3,2-dioxabor-2-yl)indazole

[Ir(COD)OMe]$_2$ (152 mg, 0.23 mmol), 4,4'-di-t-butyl-2,2'-pyryidyl (184 mg, 0.69 mmol) and bispinacolatodiboron (4.1 g, 16 mmol) were added to a solution of 1,N-(t-butoxycarbonyl)indazole (5.0 g, 22 mmol) in MTBE (50 mL) was added [Ir(COD)OMe]$_2$ (152 mg, 229 umol), dtbpy (184 mg, 687 umol) and $B_2pin_2$ (4.1 g, 16 mmol) at 25° C., the reaction mixture was degassed and purged with $N_2$ 3 times, and then the mixture was stirred at 80° C. for 2 hours under $N_2$. TLC (dichloromethane/methanol=10/1. $R_f$=0.5) showed the reaction was complete. The reaction mixture was cooled to 25° C. and concentrated under reduced pressure. The residue was purified by silica gel chromatography eluting with DCM to give crude 1,N-(t-butoxycarbonyl)-3-(4,4,5,5-tetramethyl-1,3,2-dioxabor-2-yl)indazole (7.5 g) as a yellow oil.

2-Chloro-4-(1,N-(t-butoxycarbonyl)indazol-3-ylpyrimidine

A solution of crude 1,N-(t-butoxycarbonyl)-3-(4,4,5,5-tetramethyl-1,3,2-dioxabor-2-yl)indazole (7.0 g) 2,4-dichloropyrimidine (3.0 g, 20 mmol), $K_3PO_4$ (13 g, 61 mmol) and $PdCl_2$(dppf) (1.5 g, 2.0 mmol) in 1,4-dioxane (140 mL) at 25° C. was degassed and purged with $N_2$ 3 times, and then the mixture was stirred at 100° C. for 14 hr under $N_2$. The reaction mixture was cooled to 25° C. filtered and the filtrate was concentrated to give a residue. The residue was purified by column chromatography on silica gel eluted with petroleum ether/ethyl acetate (50/1 to 30/1) to give 2-chloro-4-(1,N-(t-butoxycarbonyl)indazol-3-ylpyrimidine (2.5 g, 37% yield) as white solid.

$^1$H NMR ($d_6$-DMSO) δ 8.92 (s, 1H), 8.54-8.52 (m, 1H), 8.18-8.15 (m, 2H), 7.71 (s, 1H), 7.54 (s, 1H), 1.70 (s, 9H).

A22. 7-(Carboxymethyl)-1-(2-chloropyrimidin-4-yl)-1H-indole

To a 500 mL four-neck flask were added 2,4-dichloropyrimidine (15.3 g, 100 mmol), $AlCl_3$ (14 g, 100 mmol) and DME (300 mL). The mixture was stirred for 5 minutes before methyl indole-7-carboxylate (20 g, 110 mmol) was added. The reaction was then stirred at 80° C. for 24 h. After completion, the mixture was cooled to RT, poured into water (300 mL) and extracted with EtOAc (200 mL×3). The combined organic layer was washed with brine (200 mL×3), dried over anhydrous $Na_2SO_4$ and concentrated. The residue was triturated with MTBE. The mixture was filtered to give 7-(carboxymethyl)-1-(2-chloropyrimidin-4-yl)-1H-indole. (11 g, 34%) as a red solid.

$^1$H NMR (300 MHz, $CDCl_3$) δ=10.43 (br, 1H), 8.76-8.74 (m, 1H), 8.53 (s, 1H), 8.13-8.11 (m, 1H), 8.01-7.99 (m, 1H), 7.56-7.55 (m, 1H), 7.39-7.29 (m, 1H), 4.05 (s, 3H).

A23
2-Chloro-4-(3-sulfonylamidoindol-1-yl)pyrimidine

To a solution of 2-chloro-4-indol-1-ylpyrimidine (5 g, 22 mmol, 1 eq Prep A1) in DCM (100 mL) was added dropwise a solution of chlorosulfonic acid (6.1 g, 52 mmol, 2.4 eq) in DCM (20 mL) at 0° C. under nitrogen. After addition, the mixture was stirred at this temperature till completion. The precipitate formed was collected by filtration, washed with DCM and dried to give the desired sulfonic acid (8 g, crude) which was used in the next step without further purification.

$^1$H NMR (300 MHz, $CD_3OD$) δ 8.68-8.63 (m, 2H), 8.29 (s, 1H), 8.04-8.02 (m, 1H), 7.81 (d, J=5.4 Hz, 1H), 7.44-7.37 (m, 2H).

To a 500 mL three-neck flask were added 1-(2-chloropyrimid-4-yl)indole-3-sulfonic acid (8 g, 25. 8 mmol, 1 eq), $CHCl_3$ (160 mL) and $PCl_5$ (8.4 g, 77.5 mmol, 3 eq). The mixture was refluxed overnight. The reaction was monitored by TLC and LCMS. After completion the reaction mixture was cooled to RT and sparged with ammonia gas for 2 h. The resulting mixture was stirred at RT overnight before water (160 mL) was added. The organic layer was separated and the aqueous layer was extracted with DCM (80 mL×3). The combined organic layer was washed with brine (80 mL×3), dried and concentrated to give 2-chloro-4-(3-sulfonylamidoindol-1-yl)pyrimidine (4 g, 37% for 2 steps) as an off-white solid.

$^1$H NMR (300 MHz, DMSO-$d_6$) δ=8.82 (d, J=5.4 Hz, 1H), 8.66-8.60 (m, 2H), 8.18 (d, J=5.7 Hz, 1H), 8.00 (d, J=6.6 Hz, 1H), 7.61 (s, 1H), 7.53-7.44 (m, 3H).

A24. Ethyl 1-(2-chloropyrimidin-4-yl)-1H-indazole-3-carboylate

To a solution of ethyl indazole-3-carboxylate (19 g, 100 mmol) in DMF (200 ml) was added NaH (4 g, 100 mmol) portion-wise at 0° C. The mixture was stirred at this temperature for 10 minutes till no bubbles appeared. 2,4-Dichloropyrimidine (14.9 g, 100 mmol) was added portion-wise and the mixture was stirred at RT overnight. After completion, the reaction was quenched with saturated NH$_4$Cl (34 mL) and diluted with water (600 mL). The solid formed was collected by filtration, washed with water (300 mL×2) and purified by silica gel chromatography to give ethyl 1-(2-chloropyrimidin-4-yl)-1H-indazole-3-carboylate as a brown solid (12 g, 40%).

$^1$HNMR (300 MHz, CDCl$_3$) δ=8.84 (d, J=8.7 Hz, 1H), 8.66 (d, J=5.7 Hz, 1H), 8.29-8.26 (m, 1H), 8.11-8.09 (m, 1H), 7.69-7.64 (m, 1H), 7.52-7.47 (m, 1H), 4.62-4.55 (q, J=7.2 Hz, 2H), 1.54 (t, J=7.2 Hz, 3H).

A25. 3-(N-t-Butoxycarbonylaminomethyl)-1-(2-chloropyrimidin-4-yl)-1H-indole

To a 1 L four-neck flask were added dioxane (200 mL), THF (100 mL) and 3-cyanoindole (30 g, 211 mmol). The solution was cooled to 0° C., and LiAlH$_4$ (30 g, 780 mmol) was added portion-wise. After stirring at 0° C. for 10 minutes, the mixture was heated to reflux for 0.5 h until TLC showed completion. The mixture was carefully quenched with water (300 mL) at 0° C., filtered, and the filtrate was separated. The aqueous layer was extracted with EA (500 mL×2). The combined organic layers were dried over sodium sulfate, concentrated and washed with PE/EA to give 3-aminomethylindole (21 g, 70%) as a brick red solid.

$^1$H NMR (300 MHz, DMSO-$d_6$) δ 10.80 (br, 1H), 7.59 (d, J=7.5 Hz, 1H), 7.34 (d, J=8.1 Hz, 1H), 7.20 (s, 1H), 7.09-7.04 (m, 1H), 6.99-6.94 (m, 1H), 3.87 (s, 2H).

To a 500 mL four-neck flask were added 3-aminomethylindole (21 g, 144 mmol), DCM (200 mL), TEA (29 g, 288 mmol) and DMAP (3.5 g, 29 mmol). Boc$_2$O (35.5 g, 158 mmol) in THF was added dropwise and the mixture was stirred at RT for 2 h. After completion, the mixture was washed with water (100 mL×2), dried over sodium sulfate, concentrated and purified by column chromatography to give 3-(N-r-Butoxycarbonylaminomethyl)indole (15.9 g, 46%).

$^1$H NMR (300 MHz, DMSO-$d_6$) δ=10.87 (br, 1H), 7.59 (s, 1H), 7.34 (s, 1H), 7.18-6.99 (m, 4H), 4.26 (s, 2H), 1.39 (s, 9H).

To a mixture of 3-(N-t-Butoxycarbonylaminomethyl)indole (15 g, 60 mmol) in THF (150 mL) was added dropwise a solution of t-BuOK (8.2 g, 72 mmol) in THF (20 mL). After stirring at RT for 30 minutes, a solution of 2,4-dichloropyrimidine (9 g, 60 mmol) in THF (20 mL) was added dropwise. The mixture was stirred at RT till completion. The reaction was quenched with water (50 mL) and extracted with DCM (200 mL×2). The combined organic layer was dried over sodium sulfate, concentrated and purified by column chromatography to give 3-(N-t-butoxycarbonylaminomethyl)-1-(2-chloropyrimidin-4-yl)-1H-indole (7.2 g, 33%).

$^1$H NMR (300 MHz, DMSO-$d_6$)=8.69 (d, J=5.7 Hz, 1H), 8.57 (d, J=8.1 Hz, 1H), 8.05 (s, 1H), 7.87 (d, J=6 Hz, 1H), 7.74-7.72 (m, 1H), 7.41-7.29 (m, 3H), 4.31 (d, J=5.7 Hz, 2H), 1.39 (s, 9H).

A26. 3-Amino-1-(2-chloropyrimid-4-yl)indazole

To a solution of 3-aminoindazole (40 g, 300 mmol) in DMF (600 ml) was added NaH (14.44 g, 360 mmol) portion-wise at 0° C. The mixture was stirred at this temperature for 10 minutes till no bubbles appeared. 2,4-Dichloropyrimidine (49 g, 330 mmol) was added portion-wise and the reaction was stirred at RT overnight. After completion, the reaction was quenched with saturated NH$_4$Cl (34 mL) and diluted with water (1800 mL). The solid formed was collected by filtration, washed with water (300 mL×2) and purified by silica gel chromatography to give 3-amino-1-(2-chloropyrimid-4-yl)indazole as a brown solid (12 g, 16%).

$^1$HNMR (300 MHz, DMSO-$d_6$) δ=8.52-8.50 (m, 2H), 7.96-7.94 (m, 1H), 7.66-7.61 (m, 1H), 7.52 (d, J=5.7 Hz, 1H), 7.38-7.33 (m, 1H), 6.68 (s, 2H).

A27. 1-(2-Chloropyrimidin-4-yl)-3-(N-methylamino)-3-(N-t-butoxycarbonyl)$_1$H-indazole A3 L three-neck flask was charged with indazole-3-carboxylic acid (40 g, 247 mmol) and t-BuOH (800 mL) under nitrogen. After stirring for 10 mins, TEA (30 g, 296 mmol) and DPPA (81 g, 296 mmol) were added. The mixture was heated to 80° C., and stirred for 5 hours. After completion, the mixture was concentrated and purified by silica gel column chromatography to give 3-(t-butoxycarbonylamino)indazole (10 g, 17%).

A500 mL four-neck flask was charged with DMF (150 mL) and 3-(N-t-butoxycarbonylamino)indazole (10 g, 43 mmol). After cooling down to 0° C., NaH (2.1 g, 52.5 mmol) was added carefully. The mixture was stirred at 0° C. for 10 minutes till no bubbles generated. 2,4-dichloropyrimidine (7 g, 47.3 mmol) was added and the mixture was stirred at RT overnight. After completion, the mixture was quenched with sat. NH$_4$Cl (34 mL) and diluted with water (600 mL). The precipitate was collected by filtration and washed with water (300 mL×2). The filter cake was purified by silica gel column chromatography to give 1-(2-chloropyrimidin-4-yl)-3-(N-t-butoxycarbonylamino)-1H-indazole (2.4 g, 16%).

$^1$HNMR (300 MHz, CDCl$_3$) δ=8.72 (d, J=8.4 Hz, 1H), 8.64 (d, J=5.1 Hz, 1H), 8.22 (d, J=8.1 Hz, 1H), 7.62-7.57 (m, 1H), 7.40-7.34 (m, 2H), 7.15-7.14 (m, 1H), 1.56 (s, 9H).

A 100 mL round-bottom flask was charged with 1-(2-chloropyrimidin-4-yl)-3-(N-t-butoxycarbonylamino)-1H-indazole (2.4 g, 7 mmol) and DMF (14 mL). After cooling down to 0° C., NaH (0.28 g, 7 mmol) was added carefully and the mixture was stirred at this temperature for 30 minutes before MeI (0.98 g, 7 mmol) was added dropwise. After addition, the mixture was warmed to RT and stirred for 2 hours till completion. The mixture was poured into water (50 mL) and extracted with EA (50 mL×3). The combined organic layer was washed with brine twice, dried over sodium sulfate, concentrated and purified by silica column chromatography to give 1-(2-chloropyrimidin-4-yl)-3-(N-methylamino)-3-(N-t-butoxycarbonyl) 1H-indazole (1.2 g, 48%).

¹HNMR (300 MHz, DMSO-d₆) δ=8.72 (d, J=5.7 Hz, 1H), 8.66-8.63 (m, 1H), 7.86-7.79 (m, 2H), 7.74-7.69 (m, 1H), 7.49-7.44 (m, 1H), 3.42 (s, 3H), 1.43 (s, 9H).

A28. 2-Chloro-4-(7-methoxypyrrolo[2,3-c]pyrid-3-yl)pyrimidine

To a solution of 2-chloro-3-nitropyridine (50 g, 315 mmol, 1.0 eq) in THF (1.5 L) was added dropwise vinylmagnesium bromide (1 M in THF, 946.14 mL, 3.00 eq) at −78° C. After the addition was complete, the mixture was allowed to warm to 25° C., and stirred for 14 h. TLC (petroleum ether:ethyl acetate=3:1, R_f=0.25) showed that the reaction was complete. The reaction was quenched with saturated NH₄Cl (400 mL) and extracted with EtOAc (500 mL×3). The combined organic layer was concentrated and the residue was purified by silica gel column chromatography (petroleum ether:ethyl acetate=2:1 to 1:1) to give 7-chloropyrrolo[2,3-c]pyridine (18 g, 118 mmol, 37% yield) as a yellow solid.

¹H NMR (400 MHz CDCl₃) δ=8.72 (br s, 1H), 8.07 (d, J=5.6 Hz, 1H), 7.52 (d, J=5.6 Hz, 1H), 7.46-7.44 (m, 1H), 6.66 (t, J=2.8 Hz, 1H).

ESI-MS (m/z): 153.1 (M+H)⁺

Step 2

A mixture of 7-chloropyrrolo[2,3-c]pyridine (1 g, 6.5 mmol, 1.0 eq) and NaOMe (4.2 M, 10 mL, 6.4 eq) was stirred under microwave at 110° C. for 4 h. LCMS showed that the reaction was complete. 18 Small batches were done and combined for workup. The combined mixture was diluted with sat. NH₄Cl (aq.) (30 mL) and extracted with EtOAc (100 mL×3). The combined organic layer was concentrated and purified by prep-HPLC (column: Phenomenex luna C18 250*80 mm*10 um; mobile phase: [water(0.1% TFA)-ACN]; B %: 0%-15%, 20 min) to give 7-methoxypyrrolo[2,3-c]pyridine (8 g, 54 mmol, 46% yield) as a yellow solid. About 5 g of starting material was recovered.

¹H NMR 400 MHz CDCl₃ S=8.82 (br s, 1H), 7.68 (d, J=5.6 Hz, 1H), 7.30-7.15 (m, 1H), 7.10 (d, J=5.6 Hz, 1H), 6.46 (t, J=2.4 Hz, 1H), 4.07 (s, 3H).

ESI-MS (m/z): 149.0 (M+H)⁺

Step 3

To a solution of 7-methoxypyrrolo[2,3-c]pyridine (8.0 g, 54 mmol, 1.0 eq) in THF (160 mL) was added NaH (4.32 g, 108 mmol, 60% purity, 2.0 eq) at 0° C. The mixture was stirred at 0° C. for 0.5 h. TIPSCl (15.6 g, 81 mmol, 17.4 mL, 1.5 eq) was added and the mixture was stirred at 25° C. for 14 h. TLC (petroleum ether:ethyl acetate=3:1, R=0.2) showed that the reaction was complete. The mixture was poured into sat. NH₄Cl (500 ml) and extracted with EtOAc (400 mL×3). The combined organic layer was concentrated and purified by silica gel column chromatography (petroleum ether:ethyl acetate=10:1 to 1:1) to give 7-methoxy-1,N-(triisopropylsilyl)pyrrolo[2,3-c]pyridine (16 g, 52.6 mmol, 97% yield) as a yellow oil.

¹H NMR 400 MHz CDCl₃ δ 7.69 (d, J=5.5 Hz, 1H), 7.31 (d, J=3.2 Hz, 1H), 7.09 (d. J=5.6 Hz, 1H), 6.49 (d, J=3.2 Hz, 1H), 3.99 (s, 3H), 1.72-1.56 (m, 3H), 1.10-0.94 (d, 18H).

ESI-MS (m/z): 305.2 (M+H)⁺

Step 4

To a solution of 7-methoxy-1,N-(triisopropylsilyl)pyrrolo[2,3-c]pyridine (22 g, 72.3 mmol, 1.0 eq) in MTBE (440 mL) was added (1Z,5Z)-cycloocta-1,5-diene; 2,4-dimethyl-BLAHbicyclo[1.1.0]butane (CAS:12148-71-9) (4789 mg, 723 umol, 0.01 eq), Pin₂B₂(18.4 g, 72.3 mmol, 1.0 eq) and 4-tert-butyl-2-(4-tert-butyl-2-pyridyl)pyridine (CAS:69641-93-6) (582 mg, 2.17 mmol, 0.03 eq) at 25° C. The reaction mixture was degassed and purged with N₂ 3 times and stirred at 80° C. for 2 hours. TLC (petroleum ether:ethyl acetate=10:1, R_f=0.5) showed that the reaction was complete. The solvent was evaporated and the residue was purified by silica gel column chromatography (petroleum ether:ethyl acetate=100:1 to 10:1) to give 2-(7-methoxy-1, N-(triisopropylsilyl)pyrrolo[2,3-c]pyrid-3-yl)-4,4,5,5-tetramethyl-1,3,2-dioxaborolane (20 g, 46.5 mmol, 64% yield) as a white solid.

¹H NMR 400 MHz CDCl₃ δ 7.79 (d, J=5.2 Hz, 1H), 7.73 (s, 1H), 7.56 (d, J=5.2 Hz, 1H), 4.04 (s, 3H), 1.80-1.58 (m, 3H), 1.34 (s, 12H), 1.14 (d, 18H).

ESI-MS (m/z): 431.3 (M+H)⁺

Step 5

To a solution of 2-(7-methoxy-1,N-(triisopropylsilyl)pyrrolo[2,3-c]pyrid-3-yl)-4,4,5,5-tetramethyl-1,3,2-dioxaborolane (10 g, 23 mmol, 1.0 eq) in MeCN (150 mL) and H₂O (7.5 mL) was added 2 (3.46 g, 23 mmol, 1.0 eq), Na₂CO₃ (4.92 g, 46.5 mmol, 2.0 eq) and 4-ditert-butylphosphanyl-N,N-dimethyl-aniline; dichloropalladium (CAS:887919-35-9) (822 mg, 1.16 mmol, 0.05 eq) at 25° C. The reaction mixture was degassed and purged with N₂ 3 times and stirred at 70° C. for 14 hours. LC-MS showed that the reaction was complete. The reaction was quenched with water (100 mL) and extracted with EtOAc (300 mL×3). The combined organic layer was concentrated to give a residue which was purified by silica gel column chromatography (petroleum ether:ethyl acetate=3:1 to 1:1) to give 2-chloro-4-(7-methoxypyrrolo[2,3-c]pyrid-3-yl)pyrimidine (2.5 g, 9.6 mmol, 41% yield) as a white solid.

¹H NMR 400 MHz MeOD δ 8.46 (d, J=5.6 Hz, 1H), 8.27 (s, 1H), 7.90 (d, J=6.0 Hz, 1H), 7.79 (s, 1H), 7.74 (d, J=5.2 Hz, 1H), 4.08 (s, 3H).

ESI-MS (m/z): 260.1 (M+H)⁺

A29. 2,5-Dichloro-4-(5-(carboxymethyl)pyrid-3-yl)pyrimidine

To a solution of methyl 5-bromonicotinate (10 g, 46.3 mmol) in DMF (100 mL) was added B₂Pin₂ (17.6 g, 69.4 mmol), KOAc (9.1 g, 92.6 mmol) and Pd(dppf)Cl₂ (1.69 g, 2.3 mmol) at 20° C. The reaction mixture was stirred at 80° C. for 4 hours. LC-MS showed compound 57 was consumed completely and one major peak with desired MS was detected. The mixture was cooled to 20° C. and concentrated to give a residue. The residue was purified by silica gel column chromatography (petroleum ether/ethyl acetate=10/1 to 4/1) to give 2-(5-(carboxymethyl)pyridine-3-yl)-4,4,5,5-tetramethyl-1,3,2-dioxaborolane (8.0 g, 66% yield) as a yellow solid.

¹H NMR 400 MHz CDCl₃ δ 9.26 (m, 1H), 9.08-9.07 (m, 1H), 8.66 (m, 1H), 3.94 (s, 3H), 1.36 (s, 12H)

ESI-MS (m/z): 264.2 (M+H)⁺

To a solution of 2-(5-(carboxymethyl)pyridine-3-yl)-4,4,5,5-tetramethyl-1,3,2-dioxaborolane (8.0 g, 30.4 mmol) in dioxane (80 mL) was added 2,4,5-trichloropyrimidine (5.58 g, 30.4 mmol), K$_3$PO$_4$ (19.4 g, 91.2 mmol) and Pd(dppf)Cl$_2$ (1.11 g, 1.52 mmol) at 20° C. The reaction mixture was stirred at 100° C. for 2 hours under N$_2$. TLC (petroleum ether/ethyl acetate=3/1, R=0.3) showed that the reaction was complete. The mixture was cooled to 20° C. and concentrated to give a residue. The residue was purified by silica gel column chromatography (petroleum ether/ethyl acetate=30/1 to 10/1) to give 2,5-dichloro-4-(5-(carboxymethyl)pyrid-3-yl)pyrimidine (2.7 g, 31% yield) as a yellow solid.

$^1$H NMR 400 MHz DMSO δ 9.26-9.25 (m, 1H), 9.23 (m, 1H), 9.09 (s, 1H), 8.69-8.68 (m, 1H), 3.94 (s, 3H)

ESI-MS (m/z): 284.1 (M+H)$^+$

A30. 2,5-Dichloro-4-(6-(N-methyl-N-(t-butoxycarbonyl)amino)pyrid-3-yl)pyrimidine NaHMDS (1 M, 12 mL) was added slowly to a mixture of 5-bromo-2-(N-methylamino)pyridine (2.0 g, 10.7 mmol) and (Boc)$_2$O (2.8 g, 12.8 mmol, 3.0 mL) in THF (20 mL) at 0° C. under N$_2$. The resulting mixture was allowed to warm to 20° C., and stirred for 13 hours. TLC (petroleum ether/ethyl acetate=3/1) showed trace amount of compound 64 and a major new spot with lower polarity. The mixture was quenched with sat. NaHCO$_3$ (30 mL) and extracted with EtOAc (50 mL×2). The organic layers were combined, washed with brine (30 mL), dried over Na$_2$SO$_4$, filtered and concentrated to give a residue. The residue was purified by silica gel column chromatography (petroleum ether/ethyl acetate=10/1 to 3/1) to give 5-bromo-2-(N-methyl-N-(t-butoxycarbonyl)amino)pyridine (2.8 g, 91% yield) as a light yellow liquid.

$^1$H NMR 400 MHz CDCl$_3$ δ 8.40-8.39 (m, 1H), 7.71-7.65 (m, 2H), 3.37 (s, 3H), 1.49 (s, 9H).

ESI-MS (m/z): 287.0 (M+H)$^+$.

To a solution of 5-bromo-2-(N-methyl-N-(t-butoxycarbonyl)amino)pyridine (2.8 g, 9.8 mmol) in DMSO (20 mL) was added B$_2$Pin$_2$ (3.71 g, 14.6 mmol), KOAc (2.87 g, 29.3 mmol) and Pd(dppf)Cl$_2$.DCM (398 mg, 488 umol) at 20° C. The reaction mixture was degassed and purged with N$_2$ 3 times and stirred at 80° C. for 14 hours. Reaction was complete by TLC (petroleum ether/ethyl acetate=3/1, R$_f$=0.6). Desired MS was detected by LCMS. The mixture was cooled to 20° C., diluted with water (30 mL) and extracted with EtOAc (50 mL×3). The organic layers were combined, dried over Na$_2$SO$_4$, filtered and concentrated to give a residue. The residue was purified by silica gel column chromatography (petroleum ether/ethyl acetate=10/1 to 3/1) to give 2-(2-(N-methyl-N-(t-butoxycarbonyl)amino)pyrid-5-yl-4,4,5,5-tetramethyl-1,3,2-dioxaborolane (3.3 g, crude) as a white solid.

ESI-MS (m/z): 335.2 (M+H)$^+$.

To a solution of 2-(2-(N-methyl-N-(t-butoxycarbonyl)amino)pyrid-5-yl-4,4,5,5-tetramethyl-1,3,2-dioxaborolane (1.8 g, 5.4 mmol) in dioxane (20 mL) and H$_2$O (2 mL) was added 2,4,5-trichloropyrimidine (1.48 g, 8.1 mmol), K$_3$PO$_4$ (3.43 g, 16.2 mmol) and Pd(dppf)Cl$_2$ (197 mg, 270 umol) at 20° C. The reaction mixture was stirred at 100° C. in a sealed tube for 12 hours. TLC (petroleum ether/ethyl acetate=5/1, R$_f$=0.6) showed that the reaction was complete. The mixture was cooled to 20° C. and concentrated to give a residue. The residue was purified by silica gel column chromatography (petroleum ether/ethyl acetate=10/1 to 5/1) to give 2,5-dichloro-4-(6-(N-methyl-N-(i-butoxycarbonyl)amino)pyrid-3-yl)pyrimidine. (920 mg, 48% yield) as a light yellow solid.

$^1$H NMR 400 MHz DMSO δ=9.01 (s, 1H), 8.86 (m, 1H), 8.24-8.21 (m, 1H), 7.93-7.91 (m, 1H), 3.38 (s, 3H), 1.5 (s, 9H)

ESI-MS (m/z): 355.1 (M+H)$^+$.

A31. 2,5-Dichloro-4-(6-(N,N-dimethylamino)pyrid-3-yl)pyrimidine

To a solution of 5-bromo-2-(NN-dimethylamino)pyridine (8.5 g, 42.3 mmol) and 4,4,4,4',5,5,5',5'-octamethyl-2,2'-bi(1,3,2-dioxaborolane) (12.9 g, 50.7 mmol) in dioxane (10 mL) was added KOAc (8.3 g, 84.6 mmol) and Pd(dppf)Cl$_2$ (1.55 g, 2.1 mmol) at 25° C. under N$_2$. The mixture was heated to 100° C., and stirred at this temperature for 12 hours. LCMS showed that the reaction was complete. The mixture was filtered and concentrated under reduced pressure to give a residue which was purified by silica gel column chromatography (petroleum ether/ethyl acetate=50/1 to 3/1) to give 2-(2-(N,N-dimethylamino)pyrid-5-yl-4,4,5,5-tetramethyl-1,3,2-dioxaborolane (8 g, 32.2 mmol, 76% yield) as a yellow solid $^1$H NMR 400 MHz CDCl3 δ=8.53 (s, 1H), 7.75-7.78 (d, 1H), 6.43-6.45 (d, 1H), 3.09 (s, 6H), 1.22-1.30 (m, 12H).

ESI-MS (m/z): 249.2 (M+H)$^+$

To a solution of 2-(2-(N,N-dimethylamino)pyrid-5-yl-4,4,5,5-tetramethyl-1,3,2-dioxaborolane (8 g, 32.2 mmol) and 2,4,5-trichloropyrimidine (7.1 g, 38.7 mmol) in dioxane (80 mL) and H$_2$O (20 mL) was added Na$_2$CO$_3$ (10.3 g, 96.7 mmol) and Pd(dppf)Cl$_2$ (1.2 g, 1.6 mmol) at 25° C. under N$_2$. The mixture was heated to 100° C., and stirred at this temperature for 12 hours. LCMS showed that the reaction was complete. The mixture was filtered and concentrated under reduced pressure to give a residue, which was purified by prep-HPLC (column: Phenomenex luna C18 250*80 mm*10 um; mobile phase: [water (0.1% TFA)-ACN]; B %: 10%-40%, 20 min). 2,5-Dichloro-4-(6-(N,N-dimethylamino)pyrid-3-yl)pyrimidine (3.5 g, 13 mmol, 40% yield) was obtained as a light yellow solid.

ESI-MS (m/z): 269.1 (M+H)$^+$.

A32. 2-Chloro-4-(5-acetyl-6-(N-methylamino)pyrid-3-yl)pyrimidine

To a solution of 5-bromo-2-chloronicotinic acid (50 g, 211 mmol) in MeOH (200 mL) was added H$_2$SO$_4$ (20.7 g, 211.46 mmol) at 25° C. The mixture heated to 90° C., and stirred for 12 hours. LCMS showed that the reaction was complete. The reaction was neutralized with Na$_2$CO$_3$ to pH=7-8 and concentrated under reduced pressure to remove MeOH. The residue was extracted with EtOAc (300 mL×3). The combined organic layer was concentrated under reduced pressure to give methyl 5-bromo-2-chloronicotinate (45 g, 180 mmol, 85% yield) as a brown solid.

ESI-MS (m/z): 249.9 (M+H)$^+$

A solution of methyl 5-bromo-2-chloronicotinate (8 g, 31.9 mmol) in methylamine (2 M, 79.85 mL) was stirred at 25° C. in autoclave for 16 hours. TLC (dichloromethane:methanol=10:1) showed that the reaction was complete. Three reactions were done and combined. The combined mixture was filtered and concentrated under reduced pressure to give a crude product which was purified by silica gel column chromatography (dichloromethane:methanol=100:1 to 10:1). Methyl 5-bromo-2-(N-methylamino)nicotinate (12 g, 49 mmol, 51% yield) was obtained as a white solid.

To a solution of methyl 5-bromo-2-(N-methylamino)nicotinate (10 g, 40.8 mmol) and tert-butoxycarbonyl tert-butyl carbonate (10.7 g, 48.9 mmol) in THF (50 mL) was added NaHMDS (I M, 44.89 mL) slowly at 0° C. The mixture was stirred at 25° C. for 6 hours. TLC (petroleum ether:ethyl acetate=5:1) showed that the reaction was complete. The mixture was diluted with H$_2$O (500 mL) and extracted with EtOAc (500 mL×3). The organic layers were combined and concentrated under reduced pressure to give a crude product which was purified by silica gel column chromatography (petroleum ether/ethyl acetate=50:1 to 10:1). Methyl 5-bromo-2-(N-methyl-N-(t-butoxycarbonyl)amino)nicotinate (13 g, 37.7 mmol, 92% yield) was obtained as a brown oil.

$^1$H NMR 400 MHz CDCl3 δ=8.55 (s, 1H), 8.21 (s, 1H), 3.88 (s, 3H), 3.38 (s, 3H), 1.25-1.61 (m, 9H).

ESI-MS (m/z): 345.0 (M+H)$^+$

To a solution of methyl 5-bromo-2-(N-methyl-N-(t-butoxycarbonyl)amino)nicotinate (15 g, 43.5 mmol) in H$_2$O (80 mL) and THF (80 mL) was added LiOH.H$_2$O (5.5 g, 130 mmol) at 25° C. The mixture was stirred at 25° C. for 6 hours. LCMS showed that the reaction was complete. The reaction mixture was concentrated under reduced pressure to remove THF. The residue was diluted with H$_2$O (200 mL) and extracted with EtOAc (200 mL×10). The organic layers were combined and concentrated under reduced pressure to give 5-bromo-2-(N-methyl-N-(t-butoxycarbonyl)amino)nicotinic acid (10 g, 30.2 mmol, 70% yield) as a yellow solid.

ESI-MS (m/z): 231.1 (M+H)$^+$.

To a solution of N-methoxyanethylamine (3.98 g, 40.8 mmol, HCl) in DMF (90 mL) was added DIEA (10.5 g, 81.54 mmol). The mixture was stirred at 25° C. for 30 minutes. 5-Bromo-2-(N-methyl-N-(t-butoxycarbonyl)amino)nicotinic acid (9 g, 27.2 mmol) and HATU (15.5 g, 40.8 mmol) were added and the mixture was stirred at 25° C. for 11.5 hours. LCMS showed that the reaction was complete. The reaction mixture was diluted with water (400 mL) and extracted with EtOAc (300 mL×3). The organic layers were combined and concentrated under reduced pressure to give a crude product which was purified by silica gel column chromatography (petroleum ether/ethyl acetate=50:1 to 5:1). O-Methyl-N-methyl 5-bromo-2-(N-methyl-N-(t-butoxycarbonyl)amino)nicotinic hydroxamate (8 g, 21.4 mmol, 79% yield) was obtained as a yellow oil.

ESI-MS (m/z): 274.1 (M+H)$^+$.

To a solution of O-Methyl-N-methyl 5-bromo-2-(N-methyl-N-(t-butoxycarbonyl)amino)nicotinic hydroxamate (8 g, 21.4 mmol) in THF (80 mL) was added MeMgBr (3 M, 21. mL) slowly at 0° C. under N$_2$. The mixture was stirred at 20° C. for 6 hours. LCMS showed that the reaction was complete. Citric acid was added to the mixture to adjust pH to 5-6. The resulting mixture was diluted with H$_2$O (150 mL) and extracted with EtOAc (150 mL×3). The organic layers were combined and concentrated under reduced pressure to give 3-acetyl-5-bromo-2-(N-methylamino)pyridine (4 g, 17.5 mmol, 82% yield) as a yellow solid.

ESI-MS (m/z): 229.1 (M+H)$^+$.

To a solution of 3-acetyl-5-bromo-2-(N-methylamino)pyridine (4 g, 17.5 mmol) and 4,4,4',4',5,5,5',5'-octamethyl-2,2'-bi(1,3,2-dioxaborolane) (5.32 g, 20.9 mmol) in dioxane (15 mL) was added KOAc (3.43 g, 34.9 mmol) and Pd(dppf)Cl$_2$ (639 mg, 873 umol) at 25° C. under N$_2$. The mixture was stirred at 100° C. for 12 hours. LCMS showed that the reaction was complete. The mixture was filtered and concentrated under reduced pressure to give a crude product which was purified by silica gel column chromatography (petroleum ether/ethyl acetate=50/1 to 3:1). 2-(3-Acetyl-5-bromo-2-(N-methylamino)pyrid-5-yl)-4,4,5,5-tetramethyl-1,3,2-dioxaborolane (4 g, 14.5 mmol, 83% yield) was obtained as a yellow solid.

ESI-MS (m/z): 277.2 (M+H)$^+$.

To a solution of 2-(3-acetyl-5-bromo-2-(N-methylamino)pyrid-5-yl)-4,4,5,5-tetramethyl-1,3,2-dioxaborolane (4 g, 14.5 mmol) and 2,4-dichloropyrimidine (2.37 g, 15.9 mmol) in dioxane (40 mL) and H$_2$O (8 mL) was added Na$_2$CO$_3$ (3.07 g, 28.9 mmol) and Pd(dppf)Cl$_2$ (530 mg, 724 umol) at 25° C. under N$_2$. The mixture was stirred at 100° C. for 12 hours.

TLC (petroleum ether/ethyl acetate=3:1) showed that the reaction was complete. The mixture was filtered and concentrated under reduced pressure to give a crude product which was purified by silica gel column chromatography (petroleum ether/ethyl acetate=100:1 to 1:1). 2-Chloro-4-(5-acetyl-6-(N-methylamino)pyrid-3-yl)pyrimidine (3 g, 11.4 mmol, 79% yield) was obtained as a yellow solid.

$^1$H NMR 400 MHz CDCl3 δ=8.96 (s, 1H), 8.83 (s, 1H), 8.55-8.57 (d, 1H), 7.53-7.55 (d, 1H), 3.17 (d, 3H), 2.70 (d, 3H).

ESI-MS (m/z): 263.2 (M+H)$^+$

A33. 2-Chloro-4-(5-(carboxymethyl)-6-(N-methylamino)pyrid-3-yl)pyrimidine

To a solution of methyl 5-bromo-2-(N-methylamino)nicotinate (10 g, 40.8 mmol) and 4,4,4',4',5,5,5',5'-octamethyl-2,2'-bi(1,3,2-dioxaborolane) (12.4 g, 48.9 mmol) in dioxane (100 mL) was added KOAc (8 g, 81.6 mmol) and Pd(dppf)Cl$_2$ (1.49 g, 2.04 mmol) at 25° C. under N$_2$. The mixture was stirred at 100° C. for 12 hours. LCMS showed that the reaction was complete. The mixture was filtered and concentrated under reduced pressure to give a crude product which was purified by silica gel column chromatography (petroleum ether/ethyl acetate=50/1 to 3:1). 2-(5-(Carboxymethyl)-6-(N-methylamino)pyrid-3-yl)-4,4,5,5-tetramethyl-1,3,2-dioxaborolane (8 g, 27.4 mmol, 67% yield) was obtained as a yellow solid.

ESI-MS (m/z): 293.4 (M+H)$^+$.

To a solution of 2-(5-(carboxymethyl)-6-(N-methylamino)pyrid-3-yl)-4,4,5,5-tetramethyl-1,3,2-dioxaborolane (7 g, 23.9 mmol) and 2,4-dichloropyrimidine (4.28 g, 28.8 mmol) in dioxane (50 mL) and H$_2$O (10 mL) was added Na$_2$CO$_3$ (7.62 g, 71.9 mmol) and Pd(dppf)Cl$_2$ (877 mg, 1.20 mmol) at 25° C. under N$_2$. The mixture was stirred at 100° C. for 6 hours. LCMS showed that the reaction was complete. The reaction mixture was filtered and concentrated under reduced pressure to give a crude product which was purified by silica gel column chromatography (petroleum ether/ethyl acetate=50:1 to 5:1). 2-Chloro-4-(5-(carboxymethyl)-6-(N-methylamino)pyrid-3-yl)pyrimidine (2 g, 7.18 mmol, 30% yield) was obtained as a yellow solid.

ESI-MS (m/z): 279.1 (M+H)$^+$.

A34. 2-Chloro-4-(3-(carboxymethyl)cyclopenta[c]pyrazol-1-yl)pyrimidine

To a solution of cyclopenta[c]pyrazole-3-carboxylic acid (8.00 g, 52.6 mmol) in MeOH (80 mL) was added H$_2$SO$_4$ (5.16 g, 52.6 mmol, 2.80 mL) at 25° C. The mixture was heated to 85° C., and stirred for 18 hrs. TLC indicated that the reaction was complete. The reaction was quenched by NaHCO$_3$ (60 mL) at 0° C. and concentrated under reduced pressure to remove MeOH. The aqueous phase was extracted with EtOAc (50 mL×3). The combined organic phase was washed with saturated brine (50 mL×2), dried with anhydrous Na$_2$SO$_4$, filtered and concentrated under reduced pressure to give methyl cyclopenta[c]pyrazole-3-carboxylate (6.00 g, 36.1 mmol, 69% yield) as a white solid.

$^1$H NMR: CDCl$_3$ 400 MHz CDCl$_3$ δ=3.86 (d, J=14.8 Hz, 3H), 2.86-2.71 (m, 4H), 2.50-2.43 (m, 2H).

ESI-MS (m/z): 167.0 (M+H)$^+$

To a solution of methyl cyclopenta[c]pyrazole-3-carboxylate (5.00 g, 30.1 mmol) in DMF (50 mL) was added NaH (1.81 g, 45.1 mmol, 60% purity) at 0° C. The mixture was stirred at 0° C. for 0.5 h before 2,4-dichloropyrimidine (5.38 g, 36.1 mmol) was added. The mixture was warmed to 25° C., and stirred for 18 hrs. LC-MS indicated that the reaction was complete. The reaction was quenched with H$_2$O (100 mL) at 0° C., and extracted with EtOAc (50 mL×3). The combined organic layers were washed with brine (100 mL×2), dried with anhydrous Na$_2$SO$_4$, filtered and concentrated under reduced pressure. The residue was purified by silica gel column chromatography (petroleum ether/ethyl acetate 10/1=2/1) to give 2-chloro-4-(3-(carboxymethyl)cyclopenta[c]pyrazol-1-yl)pyrimidine (7.00 g, 25.1 mmol, 83% yield) as a white solid.

ESI-MS (m/z): 279.1 (M+H)$^+$.

A35. 2-Chloro-4-(3-carboxymethyl)indol-1-yl)pyrimidine

To a suspension of NaH (1.14 g, 28.5 mmol, 60% purity) in DMF (100 mL) was added methyl indole-3-carboxylate (5 g, 28.5 mmol) at 0° C. under N$_2$. The mixture was stirred at 0° C. for 30 minutes before 2,4-dichloropyrimidine (4.25 g, 28.5 mmol) in DMF (50 mL) was added. The mixture was stirred at 20° C. for 1.5 hours. TLC (petroleum ether:ethyl acetate=5:1, R$_f$=0.16) showed that starting material was consumed completely and two new spot were formed. The reaction was quenched with water (100 mL) at 0° C., and extracted with EtOAc (50 mL×3). The combined organic layers were washed with brine (100 mL), dried over Na$_2$SO$_4$, filtered and concentrated under reduced pressure to give a residue. The residue was purified by silica gel column chromatography (petroleum ether/ethyl acetate=100/1 to 10:1) to afford 2-chloro-4-(3-carboxymethyl)indol-1-yl)pyrimidine (3 g, 10.4 mmol, 37% yield) as a white solid.

$^1$H NMR (400 MHz DMSO) δ=8.87 (s, 1H), 8.80-8.82 (d, J=5.7 Hz, 1H), 8.57-8.59 (d, J=8.2 Hz, 1H), 8.18 (d, J=5.8 Hz, 1H), 8.11 (d, J=7.9 Hz, 1H), 7.38-7.46 (m, 2H), 3.90 (s, 3H).

ESI-MS (m/z): 288.0 (M+H)$^+$

A36. 2-Chloro-4-(3-acetylindol-1-yl)pyrimidine

To a suspension of NaH (1.26 g, 31.4 mmol, 60% purity) in DMF (50 mL) was added 3-acetylindole (5 g, 31.4 mmol) at 0° C. under N$_2$. The mixture was stirred at 0° C. for 30 minutes before 2,4-dichloropyrimidine (4.68 g, 31.4 mmol) in DMF (20 mL) was added. The mixture was stirred at 20° C. for 1.5 hours. LC-MS showed that compound 105 was consumed completely and two new peaks with desired MS were detected. The reaction was quenched with water (50 mL) and extracted with EtOAc (30 mL×3). The combined organic layers were washed with brine (30 mL), dried over Na$_2$SO$_4$, filtered and concentrated under reduced pressure to give a residue. The residue was purified by silica gel column chromatography (petroleum ether/ethyl acetate=80/1 to 10:1) to afford 2-chloro-4-(3-acetylindol-1-yl)pyrimidine (2 g, 7.36 mmol, 23% yield) as a yellow solid.

$^1$H NMR (400 MHz CDCl$_3$) δ=8.68 (d, J=5.6 Hz, 1H), 8.44 (d, J=8.8 Hz, 1H), 8.40 (s, 1H), 8.24 (d, J=8.4 Hz, 1H), 7.52 (d, J=5.6 Hz, 1H), 7.39-7.44 (m, 2H), 2.62 (s, 3H).

ESI-MS (m/z): 272.1 (M+H)$^+$.

A37. Methyl 3-chloro-5-(2-chloropyrimidin-4-yl)-1-(N-methyl)-(1H-indole-7-carboxylate To a solution of indoline (40 g, 336 mmol, 37.7 mL) and TEA (3.4 g, 33.6 mmol, 4.65 mL) in DCM (400 mL) was added (Boc)$_2$O (91.6 g, 420 mmol, 96.4 mL) dropwise at 0° C. The reaction mixture was stirred at 0° C. for 5 hours then at 20° C. for 13 hours. TLC (petroleum ether:ethyl acetate=3:1, R$_f$=0.8) showed that compound 109 was consumed completely and a new spot with lower polarity was detected. The reaction mixture was washed with 1N citric acid (120 mL), sat. NaHCO$_3$ (120 mL) and brine (120 mL). The organic phase was dried over Na$_2$SO$_4$, filtered and concentrated under reduced pressure to give a residue. The residue was purified by silica gel column chromatography (petroleum ether/ethyl acetate=80/1 to 10:1) to give 1,N-(t-butoxycarbonyl)indoline (50 g, 68% yield).

$^1$H NMR 400 MHz MeOD δ=7.70 (s, 1H), 7.09-7.16 (m, 2H), 6.89-6.93 (m, 1H), 3.91-3.95 (t, 2H), 3.05-3.09 (t, 2H), 1.47 (s, 9H).

ESI-MS (m/z): 220.1 (M+H)$^+$

To a solution of 1,N-(t-butoxycarbonyl)indoline (50 g, 228 mmol) and sec-BuLi (1.3 M, 351 mL) in THF (600 mL) was added TMEDA (58.3 g, 502 mmol, 75.7 mL) dropwise at −78° C. The mixture was stirred at −78° C. for 1.5 hours before methyl carbonochloridate (52.8 g, 559 mmol, 43.3 mL) was added. The mixture was warmed up to 20° C., and stirred for 12 hours. LCMS showed ~10% of starting material and one new peak with desired MS. The reaction was quenched with water (500 mL) and extracted with EtOAc (300 mL×3). The combined organic phase was concentrated under reduced pressure to give a residue. The residue was purified by silica gel column chromatography (petroleum ether/ethyl acetate=100/1 to 5:1) to give methyl 1,N-(t-butoxycarbonyl)indoline-7-carboxylate (23.5 g, 37% yield) as a yellow solid.

$^1$H NMR 400 MHz DMSO δ=7.34-7.40 (m, 2H), 7.04-7.08 (m, 1H), 4.00-4.04 (t, 2H), 3.69 (s, 3H), 3.04-3.08 (t, 2H), 1.44 (s, 9H).

ESI-MS (m/z): 278.1 (M+H)$^+$

To a solution of methyl 1,N-(t-butoxycarbonyl)indoline-7-carboxylate (23.5 g, 84.7 mmol) in DCM (300 mL) was added NBS (15.1 g, 84.7 mmol). The mixture was stirred at 20° C. for 16 hours. TLC (petroleum ether:ethyl acetate=5:1, R$_f$=0.5) indicated that starting material was consumed completely and a major new spot with lower polarity was detected.

The reaction mixture was adjusted to pH=8 with sat. NaHCO$_3$. The organic phase was separated and concentrated under reduced pressure to give a residue. The residue was purified by silica gel column chromatography (petroleum ether/ethyl acetate=1/0 to 5:1) to give methyl 5-bromo-1,N-(t-butoxycarbonyl)indoline-7-carboxylate (28.5 g, 94% yield) as a yellow solid.

$^1$H NMR 400 MHz DMSO δ=7.59 (s, 1H), 7.45 (s, 1H), 4.02 (m, 2H), 3.70 (s, 3H), 3.08 (m, 2H), 1.43 (s, 9H).

ESI-MS (m/z): 356.0 (M+H)$^+$

A mixture of methyl 5-bromo-1,N-(t-butoxycarbonyl)indoline-7-carboxylate (19.5 g, 54.7 mmol) in TFA (15 mL) was stirred at 25° C. for 16 hours. TLC (petroleum ether:ethyl acetate=10:1, R$_f$=0.35) indicated that starting material was consumed completely and a major new spot with lower polarity was detected. The reaction was diluted with DCM (100 mL) and adjusted to pH=9 with sat. NaHCO₃. The organic phase was separated and concentrated under reduced pressure to give compound methyl 5-bromoindoline-7-carboxylate (13.5 g, 96% yield) as a brown solid.

$^1$H NMR (400 MHz DMSO) δ=7.45 (s, 1H), 7.27 (s, 1H), 6.72 (s, 1H), 3.77 (s, 3H), 3.61 (m, 2H), 2.99 (m, 2H).

ESI-MS (m/z): 260.0 (M+H)$^+$

To a solution of methyl 5-bromoindoline-7-carboxylate (13.5 g, 52.7 mmol) in DCM (160 mL) was added MnO₂ (45.8 g, 527 mmol). The mixture was stirred at 25° C. for 48 hours. TLC (petroleum ether:ethyl acetate=10:1, R$_f$=0.3) indicated that starting material was consumed completely and a major new spot with higher polarity was detected. The reaction mixture was filtered and the filtrate was concentrated under reduced pressure to afford of methyl 5-bromoindole-7-carboxylate (11 g, 82% yield) as a brown solid.

$^1$H NMR (400 MHz DMSO) δ=11.38 (s, 1H), 8.06 (s, 1H), 8.79 (s, 1H), 7.47 (d, J=6 Hz, 1H), 6.56 (d, J=3.6 Hz, 1H), 3.93 (s, 3H).

ESI-MS (m/z): 253.9 (M+H)$^+$

To a solution of methyl 5-bromoindole-7-carboxylate (4.5 g, 17.7 mmol) in DMF (100 mL) at 0° C. was added NaH (1.06 g, 26.6 mmol, 60% purity). The mixture was stirred at 0° C. for 15 minutes. Iodomethane (4 g, 28.2 mmol, 1.75 mL) was added and the mixture was stirred at 25° C. for 30 minutes. TLC (petroleum ether:ethyl acetate=10:1, R$_f$=0.35) indicated that starting material was consumed completely and a major new spot with lower polarity was detected. The reaction mixture was diluted with water (100 mL) and extracted with EtOAc (100 mL×2). The combined organic phase was concentrated in vacuum to afford methyl 5-bromo-1,N-methylindole-7-carboxylate (1.5 g, 32% yield) as a brown liquid.

$^1$H NMR 400 MHz DMSO δ=7.99 (s, 1H), 7.58 (s, 1H), 7.46 (d, J=3.2 Hz, 1H), 6.56 (d, J=3.2 Hz, 1H), 3.91 (s, 3H), 3.79 (s, 3H).

ESI-MS (m/z): 268.0 (M+H)$^+$

To a solution of methyl 5-bromo-1,N-methylindole-7-carboxylate (1.5 g, 5.59 mmol) in DCM (15 mL) was added NCS (970 mg, 7.27 mmol). The mixture was stirred at 25° C. for 12 hours. TLC (etroleum ether:ethyl acctate=10:1, R$_f$=0.3) indicated that starting material was consumed completely and a major new spot with higher polarity was detected. The reaction was quenched with water (20 mL) and extracted with DCM (10 mL×2). The combined organic phase was concentrated under reduced pressure to afford methyl 5-bromo-3-chloro-1,N-methylindole-7-carboxylate (1.6 g, 95% yield) as a brown solid.

$^1$H NMR (400 MHz DMSO) S=7.86 (s, 1H), 7.72 (s, 1H), 7.68 (s, 1H), 3.92 (s, 3H), 3.78 (s, 3H).

ESI-MS (m/z): 301.9 (M+H)$^+$

To a solution of methyl 5-bromo-3-chloro-1,N-methylindole-7-carboxylate (1.55 g, 5.12 mmol) in dioxane (30 mL) was added Pin₂B₂ (2.6 g, 10.2 mmol), KOAc (1 g, 10.2 mmol) and Pd(dppf)Cl₂ (375 mg, 512 umol). The mixture was stirred at 100° C. under N₂ for 12 hours. LC-MS showed that starting material was consumed completely and a new peak with desired MS was detected. The reaction was quenched with water (30 mL) and extracted with EtOAc (20 mL×2). The organic phases were combined and concentrated under reduced pressure to afford 2-(7-(carboxymethyl)-3-chloro-1,N-methylindol-5-yl)-4,4,5,5-tetramethyl-1,3,2-dioxaborolane (1.5 g, 84% yield) as a brown solid which was used in the next step without further purification.

ESI-MS (m/z): 350.1 (M+H)$^+$

To a mixture of 2-(7-(carboxymethyl)-3-chloro-1,N-methylindol-5-yl)-4,4,5,5-tetramethyl-1,3,2-dioxaborolane (1.5 g, 4.29 mmol) and 2,4-dichloropyrimidine (639 mg, 4.29 mmol) in dioxane (30 mL) and H₂O (6 mL) was added Na₂CO₃ (909 mg, 8.58 mmol) and Pd(PPh₃)₂Cl₂ (301 mg, 429 umol) under N₂ at 25° C. The mixture was stirred at 80° C. for 12 hours. TLC (petroleum ether:ethyl acetate=5:1, R$_f$=0.3) indicated that starting material was consumed completely and one new spot with higher polarity was detected. The reaction was diluted with water (50 mL) and extracted with EtOAc (30 mL×3). The organic layers were combined and concentrated under reduced pressure to give a residue. The residue was purified by silica gel column chromatography (petroleum ether/ethyl acetate=100/1 to 10:1) to give methyl 3-chloro-5-(2-chloropyrimidin-4-yl)-1-(N-methyl)-(1H-indole-7-carboxylate (1.14 g, 79% yield) as an orange solid.

$^1$H NMR 400 MHz DMSO δ=8.79 (d, J=5.6 Hz, 1H), 8.57 (s, 1H), 8.44 (s, 1H), 8.31-8.33 (d, J=5.6 Hz, 1H), 7.80 (s, 1H), 3.98 (s, 3H), 3.84 (s, 3H).

ESI-MS (m/z): 336.0 (M+H)$^+$

A38. 2-Chloro-4-(1,N-methyl-7-methoxypyrrolo[2,3-c]pyrid-4-yl)pyrimidin

To a mixture of 5-bromo-2-chloro-3-nitropyridine (50 g, 210 mmol) in THF (1.40 L) at −78° C. was added bromo(vinyl)magnesium (1 M, 842 mL) under N₂. The mixture was stirred at −78° C. for 4 h then at −20° C. for 2 h. LCMS showed that the starting material was consumed completely. The mixture was poured into aqueous NH₄Cl (500 mL) and extracted with ethyl acetate (300 mL×3). The combined organic phase was washed with brine (500 mL), dried with anhydrous Na₂SO₄, filtered and concentrated under reduced pressure. The residue was purified by silica gel column chromatography (petroleum ether/ethyl acetate, from 50/1 to 1/1) to give 4-bromo-7-chloro[pyrrolo[2,3-c]pyridine as a yellow solid.

ESI-MS (m/z): 233 (M+H)$^+$.

A20 mL microwave vial was charged with 4-bromo-7-chloro[pyrrolo[2,3-c]pyridine (1.5 g, 6.48 mmol) and NaOMe (15 mL). The mixture was heated at 120° C. for 3 h. LCMS showed that the starting material was consumed completely. The reaction was quenched with water (40 mL) and extracted with ethyl acetate (20 mL×3). The combined organic layer was washed with saturated brine (20 mL), dried over Na₂SO₄ and concentrated to give 4-bromo-7-methoxy[pyrrolo[2,3-c]pyridine (6.0 g, crude).

$^1$H NMR 400 MHz CDCl₃: δ=8.82-8.56 (m, 1H), 7.87 (s, 1H), 7.34 (s, 1H), 6.62-6.57 (m, 1H), 4.10 (s, 3H).

ESI-MS (m/z): 229 (M+H)$^+$.

To a mixture of 4-bromo-7-methoxy[pyrrolo[2,3-c]pyridine (5.0 g, 22 mmol) in EtOH (50 mL) and H₂O (5 mL) were added CH₃I (3.13 g, 22 mmol, 1.37 mL) and NaOH (1.76 g, 44 mmol) at 25° C. under N₂. The mixture was stirred at 25° C. for 14 h. TLC (petroleum ether/ethyl acetate=3/1, R$_f$=0.4) showed that the starting material was consumed completely. The solution was acidified with 6 M HCl to pH=7 and concentrated under reduced pressure. The residue was diluted with water (30 mL) and extracted with ethyl acetate (15 mL×3). The combined organic layer was washed with brine (10 mL), dried over Na₂SO₄ and concentrated. The residue was purified by silica gel column chromatography (petroleum ether/ethyl acetate, from 50/1 to 20/1) to give 4-bromo-7-methoxy-1,N-methyl[pyrrolo[2,3-c]pyridine (4 g, 16.59 mmol, 75% yield) as a white solid.

¹H NMR 400 MHz CDCl₃: δ=7.69 (s, 1H), 7.00 (d, J=2.9 Hz, 1H), 6.37 (d, J=2.9 Hz, 1H), 4.15 (s, 3H), 3.98 (s, 3H).

ESI-MS (m/z): 241.0 (M+H)⁺.

To a mixture of 4-bromo-7-methoxy-1,N-methyl[pyrrolo [2,3-c]pyridine (1.2 g, 4.98 mmol), Pin₂B₂ (1.90 g, 7.47 mmol) and KOAc (1.47 g, 14.93 mmol) in dioxane (12 mL) was added PdCl₂ (dppf) (203 mg, 249 umol) at 25° C. under N₂. The mixture was stirred at 25° C. for 30 min then heated to 100° C., and stirred for 14 h. LCMS showed that the starting material was consumed completely. The reaction was quenched with water (15 mL) and extracted with ethyl acetate (7 mL×3). The combined organic layers were washed with brine (3 mL), dried over Na₂SO₄ and concentrated to give (2-(7-methoxy-1,N-methyl[pyrrolo[2,3-c] pyridine-4-yl)-4,4,5,5-tetramethyl-1,3,2-dioxaborolane (1.0 g, crude) as a white solid.

¹H NMR 400 MHz CDCl₃: δ=8.44 (s, 1H), 7.56-7.48 (m, 1H), 7.12-7.03 (m, 1H), 4.23 (s, 3H), 4.05 (s, 3H), 1.65 (s, 12H).

ESI-MS (m/z): 289 (M+H)⁺.

To a mixture of (2-(7-methoxy-1,N-methyl[pyrrolo[2,3-c]pyridine-4-yl)-4,4,5,5-tetramethyl-1,3,2-dioxaborolane (1.2 g, 4.16 mmol) and 2,4-dichloropyrimidine (931 mg, 6.25 mmol) in MeCN (2 mL) and H₂O (200 uL) were added Na₂CO₃ (883 mg, 8.33 mmol) and 4-ditert-butylphosphanyl-N,N-dimethyl-aniline; dichloropalladium (147 mg, 208 umol, 147 uL) at 25° C. under N₂. The mixture was stirred at 25° C. for 30 min then heated to 100° C. and stirred for 10 h. LC-MS showed that starting material was consumed completely. The reaction was quenched with water (10 mL), filtered and concentrated to give 2-chloro-4-(1,N-methyl-7-methoxypyrrolo[2,3-c]pyrid-4-yl)pyrimidine (1.0 g, 3.64 mmol, 88% yield) as a brown solid.

¹H NMR (400 MHz MeOD) δ=8.81-8.76 (m, 1H), 8.07-8.02 (m, 1H), 7.31-7.28 (m, 1H), 7.17 (s, 1H), 6.98-6.89 (m, 1H), 4.10 (s, 3H), 3.99 (s, 3H).

ESI-MS (m/z): 275 (M+H)⁺.

A39. 2-Chloro-4-(6-(carboxymethyl)-1,N-methylindol-4-yl)pyrimidine

To a mixture of methyl 4-bromoindole-6-carboxylate (3 g, 11.8 mmol) and NaH (945 mg, 23.6 mmol, 60% purity) in DMF (30 mL) was added MeI (3.35 g, 23.6 mmol, 1.47 mL) at 0° C. The mixture was warmed to 20° C., and stirred for 3 hours. TLC (petroleum ether:ethyl acetate=5:1, R$_f$=0.4) indicated that starting material was consumed completely and one new spot was formed. The reaction was quenched with water (100 mL) and extracted with MTBE (100 mL×3). The combined organic layer was washed with water (80 mL×2) and brine (80 mL), dried over anhydrous Na₂SO₄ and concentrated under reduced pressure to give methyl 4-bromo-1,N-methylindole-6-carboxylate (3.34 g, crude) as a yellow solid.

¹H NMR 400 MHz CDCl₃ δ=8.06 (s, 1H), 7.99 (s, 1H), 7.27 (d, J=1.6 Hz, 1H), 6.58 (d, J=2.8 Hz, 1H), 3.96 (s, 3H), 3.87 (s, 3H).

ESI-MS (m/z): 268.0 (M+H)⁺

Pd(dppf)Cl₂ (278 mg, 340 umol), KOAc (3.34 g, 34.02 mmol) and Pin₂B₂ (2.88 g, 11.3 mmol) were pre-mixed and flushed with nitrogen. A solution of 4-bromo-1,N-methyl-indole-6-carboxylate (3.04 g, 11.34 mmol, 1.00 eq) in dioxane (150 mL) was added. The mixture was heated to 80° C., and stirred for 18 hours. TLC (petroleum ether:ethyl acetate=3:1, R$_f$=0.5) indicated that starting material was consumed completely and one new spot was formed. The mixture was poured into H₂O (150 mL) and extracted with EtOAc (200 mL×3). The combined organic phase was washed with brine (100 mL), dried with anhydrous Na₂SO₄, filtered and concentrated under reduced pressure. The residue was purified by silica gel column chromatography (petroleum ether/ethyl acetate=50/1 to 10/1) to afford 2-(6-carboxymethyl)1,N-methylindol-4-yl)-4,4,5,5-tetramethyl-1,3,2-dioxaborolane (2.71 g, 76% yield) as a gray solid.

¹H NMR (400 MHz CDCl₃) δ=8.30 (s, 1H), 8.20 (s, 1H), 7.27 (d, J=4.4 Hz, 1H), 7.01 (d, J=2.8 Hz, 1H), 3.96 (s, 3H), 3.87 (s, 3H), 1.40 (s, 12H).

ESI-MS (m/z): 305.2 (M+H)⁺

To a mixture of 2-(6-carboxymethyl)1,N-methylindol-4-yl)-4,4,5,5-tetramethyl-1,3,2-dioxaborolane (2.71 g, 76% yield) (1.9 g, 6.03 mmol) and 2,4-dichloropyrimidine (898 mg, 6.03 mmol) in H₂O (1 mL) and dioxane (5 mL) were added Na₂CO₃ (1.28 g, 12.1 mmol) and Pd(dppf)Cl₂ (148 mg, 181 umol) at 25° C. under N₂. The mixture was heated to 100° C., and stirred for 16 hours. TLC (petroleum ether:ethyl acetate=3:1, R$_f$=0.3) indicated that starting material was consumed completely and one new spot was formed. The reaction was quenched with H₂O (80 mL) and extracted with EtOAc (160 mL×3). The combined organic layer was washed with brine (80 mL×2), dried with anhydrous Na₂SO₄, filtered and concentrated under reduced pressure to give a residue, which was purified by silica gel column chromatography (petroleum ether/ethyl acetate=15/1 to 8/1) to give 2-chloro-4-(6-(carboxymethyl)-1,N-methylindol-4-yl)pyrimidine (1.4 g, 77% yield) as a yellow solid.

¹H NMR (400 MHz CDCl₃) δ=8.69 (d, J=5.2 Hz, 1H), 8.40 (s, 1H), 8.27 (s, 1H), 7.84 (d, J=5.2 Hz, 1H), 7.41 (d, J=3.2 Hz, 1H), 7.27 (s, 1H), 4.00 (s, 3H), 3.95 (s, 3H).

ESI-MS (m/z): 302.0 (M+H)⁺

A40. 2-Chloro-(4-3-(difluoromethyl)indazol-1-yl)pyrimidine

To a solution of indazole-3-carbaldehyde (5.66 g, 25.6 mmol, 5.6 mL) in DCM (10 mL) was added compound IA (2.6 g, 17.8 mmol) in DCM (4 mL) at 0° C. The mixture was stirred at 25° C. for 1 hour. LCMS showed that the desired product was formed. The reaction was quenched with sat. NaHCO₃ (10 mL) and extracted with DCM (10 mL×2). The combined organic phase was concentrated under reduced pressure to give a crude product which was purified by prep-HPLC (acid) to afford 3-(difluoromethyl)indazole (430 mg, 2.56 mmol, 14.4% yield) as a yellow solid.

¹H NMR (400 MHz DMSO) δ=13.68-13.54 (m, 1H), 7.86-7.82 (m, 1H), 7.64 (d, J=8.4 Hz, 1H), 7.47 (d, J=7.9 Hz, 1H), 7.34 (s, 2H).

ESI-MS (m/z): 169.0 (M+H)⁺

A solution of 3-(difluoromethyl)indazole (600 mg, 3.57 mmol) in DMF (3 mL) was added dropwise to a suspension of NaH (142.8 mg, 3.57 mmol, 60% purity) in DMF (4 mL) at 0° C. under N₂. The mixture was stirred at 0° C. for 5 minutes before compound 2 (532 mg, 3.57 mmol) in DMF (3 mL) was added dropwise. The resulting mixture was stirred at 25° C. for 2 hours. LC-MS indicated that the desired product was formed. The reaction was quenched with water (10 mL) and extracted with EtOAc (10 mL×2). The combined organic layer was washed with brine (10 mL×2), dried with anhydrous Na₂SO₄, filtered and concentrated under reduced pressure to give a crude product. The crude product was purified by prep-HPLC (TFA) to afford 2-chloro-(4-3-(difluoromethyl)indazol-1-yl)pyrimidine (450 mg, 1.6 mmol, 34% yield) as a white solid.

¹H NMR (400 MHz DMSO) δ=8.88-8.80 (m, 1H), 8.75-8.68 (m, 1H), 8.06-7.96 (m, 2H), 7.86-7.77 (m, 1H), 7.72-7.40 (m, 2H).
ESI-MS (m/z): 281.0 (M+H)⁺

A41. 7-(N-Methylcarboxamido)-1-(2-chloropyrimidin-4-yl)-1H-indole

To a suspension of NaH (2.68 g, 67.1 mmol, 60% purity) in DMF (40 mL) was added dropwise a solution of methyl indole-3-carboxylate (11.8 g, 67.1 mmol) in DMF (70 mL) at 0° C. under $N_2$. After stirring for 0.5 hours, 2,4-dichloropyrimidine (10 g, 67.1 mmol) in DMF (90 ml) was added. The mixture was warmed to 25° C., and stirred for 1.5 hours. HPLC indicated that the reaction was complete. The reaction was quenched with $H_2O$ (300 mL) and extracted with EA (200 mL×2). The combined organic layer was filtered and concentrated under vacuum. The residue was purified by silica gel column chromatography (petroleum ether/ethyl acetate=50/1 to 3/1) followed by prep-HPLC (TFA) to afford 7-(N-methylcarboxamido)-1-(2-chloropyrimidin-4-yl)-1H-indole (5 g, 17.4 mmol, 26% yield) as a yellow solid.
ESI-MS (m/z): 288.0 (M+H)⁺

A42. 2-Chloro-4-(1,N-(methoxymethyl)5-methyl-2-oxopyrid-3-yl)pyrimidine

To a solution of 3-bromo-5-methylpyrid-2-one (16.8 g, 89.2 mmol, 1.00 eq) in DCM (170 mL) at 0° C. was added DIEA (17.3 g, 134 mmol, 1.50 eq) followed by addition of MOMCl (13.5 g, 168 mmol, 1.88 eq) dropwise. The mixture was stirred at 20° C. for 12 hours. LCMS showed ~10% of starting material with several new peaks and ~90% of desired compound. The reaction was quenched with $H_2O$ (200 mL) and extracted with DCM (170 mL). The combined organic layers were washed with $H_2O$ (200 mL×3), dried over $Na_2SO_4$, filtered and concentrated under reduced pressure to give a residue which was purified by silica gel column chromatography (petroleum ether/ethyl acetate=20/1 to 0:1) to give 3-bromo-1,N-(methoxyl)5-methyl-2-oxopyridine (10.4 g, 45% yield) as a yellow oil.
ESI-MS (m/z): 232.0 (M+H)⁺
A mixture of 3-bromo-1,N-(methoxymethyl)5-methyl-2-oxopyridine (2.0 g, 8.62 mmol, 1.00 eq), 4,4,5,5-tetramethyl-2-(4,4,5,5 tetramethyl-1,3,2-dioxaborolan-2-yl)-1,3,2-dioxaborolane (2.6 g, 10.3 mmol, 1.20 eq), Pd(dppf)Cl₂ (315.30 mg, 430.90 umol, 0.05 eq) and KOAc (1.69 g, 17.2 mmol, 2.00 eq) in 1,4-dioxane (10 mL) was degassed, purged with $N_2$ 3 times and stirred at 100° C. for 1.5 hours under N, atmosphere. LCMS showed 10% of compound 152 with several new peaks and 80% of desired compound. The reaction mixture was filtered and concentrated under reduced pressure to give 2-(1,N-(methoxymethyl)5-methyl-2-oxopyrid-3-yl)-4,4,5,5-tetramethyl-1,3,2-dioxaborolane (5.00 g, crude) which was used in the next step without further purification.
ESI-MS (m/z): 280.2 (M+H)⁺
A mixture of 2,4-dichloropyrimidine (1.50 g, 5.37 mmol), 2-(1,N-(methoxymethyl)5-methyl-2-oxopyrid-3-yl)-4,4,5,5-tetramethyl-1,3,2-dioxaborolane (801 mg, 5.37 mmol), Pd(dppf)Cl₂CH₂Cl₂ (219 mg, 269 umol) and Na₂CO₃ (1.14 g, 10.7 mmol) in 1,4-dioxane (15 mL) and H₂O (1.50 mL) was degassed and purged with $N_2$ 3 times. The mixture was heated to 100° C., and stirred for 3 hours under $N_2$ atmosphere. LC-MS showed that 2,4-dichloropyrimidine was consumed completely. Several new peaks were observed and 80% of the desired compound was detected. The reaction mixture was filtered and concentrated under reduced pressure to give a residue, which was purified by silica gel column chromatography (petroleum ether/ethyl acetate=10/1 to 0:1) to give 2-chloro-4-(1,N-(methoxymethyl)5-methyl-2-oxopyrid-3-yl)pyrimidine (1.40 g, 5.27 mmol, 98% yield) as a yellow solid.
¹H NMR (400 MHz CDCl₃) δ=8.69 (d, J=5.3 Hz, 1H), 8.62-8.56 (m, 2H), 7.42-7.41 (m, 1H), 5.38 (s 21-), 3.43 (s, 3H), 2.22 (s, 3H).
ESI-MS: m/z 266.1 (M+H)⁺.

A43. 2,5-Dichloro-4-(2-(methoxymethoxy)₃-methylpyrid-5-yl)pyrimidine

To a solution of 5-bromo-3-methylpyrid-2-one (24.0 g, 128 mmol, 1.00 eq) in DCM (240 mL) at 0° C. was added DIEA (24.8 g, 191 mmol, 33.5 mL, 1.50 eq). MOMCl (12.3 g, 1538 mmol, 1.20 eq) was added dropwise and the reaction mixture was stirred at 20° C. for 12 hours under $N_2$. TLC (petroleum ether:ethyl acetate=5:1) indicated that starting material ($R_f$=0.1) was consumed completely and two new spots formed. The reaction solution was washed with water (200 mL×3). The organic phase was dried over Na₂SO₄ and concentrated under vacuum. The residue was purified by silica gel column chromatography (petroleum ether/ethyl acetate=1/1 to 5:1) to give 5-bromo-(2-methoxymethoxy)-3-methylpyridine (12.0 g, 41% yield) as a white solid.
¹H NMR (400 MHz CDCl₃) δ=8.07-8.02 (m, 1H), 7.55-7.52 (m, 1H), 5.52 (s, 2H), 3.52 (s, 3H), 2.21 (s, 3H)
ESI-MS (m/z): 232.0 (M+H)⁺
To a solution of 5-bromo-(2-methoxymethoxy)-3-methylpyridine (16 g, 69 mmol) in dioxane (200 mL) were added B₂Pin₂ (26.3 g, 103 mmol), KOAc (20.3 g, 207 mmol) and Pd(dppf)Cl₂ (2.52 g, 3.45 mmol) at 20° C. The reaction mixture was degassed, purged with $N_2$ 3 times and stirred at 100° C. for 12 hours under $N_2$ atmosphere. TLC (petroleum ether/ethyl acetate=3/1, $R_f$=0.6) showed that the reaction was complete. The mixture was cooled to 20° C., filtered and the filtrate was concentrated to give a residue, which was purified by silica gel column chromatography (petroleum ether/ethyl acetate=10/1 to 3/1) to give 2-(2-methoxymethoxy)-3-methylpyrid-5-yl)-4,4,5,5-tetramethyl-1,3,2-dioxaborolane (15 g, 78% yield) as a white solid.
¹H NMR (400 MHz CDCl₃) δ 8.37-8.36 (m, 1H), 7.77-7.76 (m, 1H), 5.58 (s, 2H), 3.51 (s, 3H), 2.20 (s, 3H), 1.3 (s, 12H)
ESI-MS (m/z): 280.1 (M+H)⁺
To a solution of 2-(2-methoxymethoxy)-3-methylpyrid-5-yl)-4,4,5,5-tetramethyl-1,3,2-dioxaborolane (7.20 g, 25.8 mmol, 1.00 eq) in dioxane (70 mL) and H₂O (7.0 mL) were added 2,4,5-trichloropyrimidine (7.10 g, 38.7 mmol, 1.50 eq) and Na₂CO₃ (5.47 g, 51.6 mmol, 2.00 eq). The suspension was degassed under vacuum and purged with $N_2$ several times. Pd(dppf)Cl₂.CH₂Cl₂ (2.11 g, 2.58 mmol, 0.10 eq) was added and the mixture was purged with $N_2$ several times. The reaction mixture was heated to 100° C., and stirred for 4 hours under $N_2$. LCMS showed that starting material was consumed completely and one major peak with desired MS was detected. The mixture was filtered through a celite pad and the filtrate was concentrated to give the crude product which was purified by silica gel column chromatography (petroleum ether/ethyl acetate=1/0 to 5:1). 2-Chloro-4-(1,N-(methoxymethyl)5-methyl-2-oxopyrid-3-yl)pyrimidine. (4.0 g, 52% yield) was obtained as a white solid.

¹H NMR (400 MHz CDCl₃) δ=8.72 (d, J=2.0 Hz, 1H), 8.63 (s, 1H), 8.04 (dd, J=0.8, 2.3 Hz, 1H), 5.65 (s, 2H), 3.57 (s, 3H), 2.32 (s, 3H).

ESI-MS (m/z): 300.0 (M+H)⁺

A44.
2-Chloro-4-(7-(carboxamido)indol-3-yl)pyrimidine

To a four-neck flask were added 2-chloro-4(7-(carboxymethyl)indol-3-yl)pyrimidine (9 g, 31 mmol, 1 eq), water (90 mL) and THF (90 mL), followed by LiOHH₂O (3.69 g, 155 mmol, 5 eq). The mixture was stirred at rt till completion. The mixture was washed with MTBE (100 mL×3) and the aqueous layer was adjusted to pH=1-2 with 1 M HCl. The solid formed was filtered, washed with water (20 mL×3) and dried to afford 2-chloro-4-(7-(carboxy)indol-3-yl)pyrimidine (7 g, 82%) as a yellow solid.

¹HNMR (300 MHz, DMSO-d₆): δ 11.94 (br, 1H), 8.74 (d, J=8.1 Hz, 1H), 8.56 (d, J=5.4 Hz, 1H), 8.48 (s, 1H), 8.03 (d, J=5.4 Hz, 1H), 7.88 (d, J=7.5 Hz, 1H), 7.38-7.32 (m, 1H).

LCMS: (M+H)⁺: 273.8.

To a solution of 2-chloro-4-(7-(carboxy)indol-3-yl)pyrimidine (2 g, 7.3 mmol, 1 eq) in DMF (20 mL) were added 2M MeNH₂/THF (4 mL, 8 mmol, 1.1 eq), HATU (4.16 g, 10.9 mmol, 1.5 eq) and DIPEA (2.36 g, 18.3 mmol, 2.5 eq). The mixture was stirred at rt overnight. After completion, the mixture was poured into water (40 mL) and extracted with EA (100 mL×3). The combined organic layer was washed with brine (100 mL×3), dried over sodium sulfate and concentrated. The residue was washed with MTBE/MeOH (20:1) to give 2-chloro-4(7-(carboxamido)indol-3-yl)pyrimidine (800 mg, 40%) as a yellow solid.

¹HNMR (300 MHz, DMSO-d₆): δ 12.01 (br, 1H), 8.62-8.59 (m, 2H), 8.52 (s, 1H), 8.43 (s, 1H), 7.98 (d, J=5.7 Hz, 1H), 7.73 (d, J=7.5 Hz, 1H), 7.33-7.28 (m, 1H), 2.87 (s, 3H).

LCMS: (M+H)⁺: 286.8.

A.45 2-Chloro-4-(6-(N-methylamino)-1,N-methylindol-4-yl)pyrimidine

A mixture of 2,4-dinitrotoluene (9.1 g, 50 mmol, 1.0 eq) in conc. H₂SO₄ (30 mL) was heated to 60° C. till completely dissolution, then NBS (10.7 g, 60 mmol, 1.2 eq) was added portionwise. The mixture was stirred at this temperature for 2.5 h. After cooling down to it, the mixture was poured into ice-water (150 g), stirred for 15 minutes, and extracted with ether (250 mL). The organic layer was washed with sodium thiosulfate (200 mL) and aq. NaHCO₃ (100 mL×3), dried over sodium sulfate and concentrated to afford 6-bromo-2,4-dinitrotoluene (13 g, crude) which was used in next step directly.

To a solution of 6-bromo-2,4-dinitrotoluene (13 g, 50 mmol, 1.0 eq) in DMF (40 mL) was added DMF-DMA (7.1 g, 60 mmol, 1.2 eq). The mixture was stirred at rt overnight. After completion, the mixture was poured into water (120 mL) and extracted with EA (100 mL×2). The combined organic layers were washed with water (100 mL×2) and brine (100 mL×2), dried over sodium sulfate and concentrated to afford 2-(dimethylamino)-1-(6-bromo-2,4-dinitrophenyl)ethene (11 g, crude) which was used in next step directly.

¹HNMR (300 MHz, DMSO-d₆): δ 8.49 (s, 1H), 8.41 (s, 1H), 7.16 (d, J=13.2 Hz, 1H), 7.17 (d, J=13.2 Hz, 1H), 2.98 (s, 6H).

LCMS: (M+Na)⁺: 338.0.

To a solution of 2-(dimethylamino)-1-(6-bromo-2,4-dinitrophenyl)ethene (10.5 g, 30 mmol, 1.0 eq) in MeOH (100 mL) was added conc. HCl (9 mL, 108 mmol, 3.6 eq) dropwise. After addition, the mixture was heated to 50° C., and stirred for 5 h. After cooling down to rt the mixture was diluted with water (100 mL) and EA (100 mL). The organic layer was separated, washed with sat. NH₄Cl (50 mL), dried over sodium sulfate and concentrated. The residue was purified by silica gel column chromatography to afford 2,2-(dimethoxy)-1-(6-bromo-2,4-dinitrophenyl)ethane (7.1 g, 42.7% for 3 steps).

¹HNMR (300 MHz, CDCl₃): δ 8.65 (s, 1H), 8.55 (s, 1H), 4.50 (t, J=5.4 Hz, 1H), 3.67 (d, J=5.4 Hz, 2H), 3.31 (s, 6H).

To a solution of 2,2-(dimethoxy)-1-(6-bromo-2,4-dinitrophenyl)ethane (6 g, 18 mmol, 1.0 eq) in HOAc (150 mL) was added Fe (10 g, 180 mmol, 10 eq) powder. The mixture was heated to 85° C., and stirred for 16 h. After completion, the mixture was filtered. The filtrate was concentrated under vacuum to remove part of the solvent, adjusted to pH=8 with 1N HCl and extracted with EA (100 mL). The organic layer was dried over sodium sulfate, concentrated and purified by silica gel column chromatography to afford 4-bromo-6-(acetamido)indole (3.2 g, 70.2%).

¹HNMR (300 MHz, DMSO-d₆): δ 9.93 (br, 1H), 7.89 (s, 1H), 7.37 (s, 2H), 6.30 (s, 1H), 2.05 (s, 3H).

LCMS: (M+H)⁺: 252.7.

To a solution of 4-bromo-6-(acetamido)indole (1 g, 4 mmol, 1.0 eq) in THF (15 mL) was added NaH (0.48 g, 12 mmol, 3.0 eq) portion-wise at 0° C. The mixture was stirred at this temperature for 30 minutes before MeI (1.25 g, 8.8 mmol, 2.2 eq) was added dropwise and stirred at rt for 1 h. After completion, the reaction was quenched with water (15 mL) and extracted with EA (30 mL). The organic layer was washed with brine (30 mL), dried over sodium sulfate and concentrated to afford 4-bromo-6-(N-methylacetamido)-1,N-methylindole (0.6 g, 54%) which was used in next step directly.

¹HNMR (300 MHz, CDCl₃): δ 7.19-7.12 (m, 3H), 6.57 (s, 1H), 3.81 (s, 3H), 3.31 (s, 3H), 1.91 (s, 3H).

LCMS: (M+H)⁺: 281.8.

A solution of 4-bromo-6-(N-methylacetamido)-1,N-methylindole (7 g, 25 mmol, 1.0 eq) in conc. HCl (50 mL) was heated to reflux overnight. After completion, the mixture was cooled to rt, adjusted to pH=9 with 1 N NaOH, and extracted with EA (100 mL). The organic layer was dried over sodium sulfate, concentrated and purified by silica gel column chromatography to afford 4-bromo-6-(N-methylamino)-1,N-methylindole (3.2 g, 54%).

¹HNMR (300 MHz, DMSO-d₆): δ 7.06 (d, J=3 Hz, 1H), 6.66 (s, 1H), 6.39 (s, 1H), 6.14 (d, J=3 Hz, 1H), 5.60 (br, 1H), 3.65 (s, 3H), 2.71 (d, 3H).

LCMS: (M+H)⁺: 239.9.

To a solution of 4-bromo-6-(N-methylamino)-1,N-methylindole (1.2 g, 5 mmol, 1.0 eq) in dioxane (15 mL) were added KOAc (1.5 g, 15 mmol, 3 eq), bis(pinacolato)diborane (1.6 g, 6.5 mmol, 1.3 eq) and Pd(dppf)Cl₂.CH₂Cl₂ (0.45 g, 0.5 mmol, 0.1 eq). The mixture was purged with nitrogen 3 times and stirred at 90° C. overnight. After cooling down to rt, the mixture was filtered and washed with EA. The filtrate was washed with brine (25 mL×2), dried over sodium sulfate, concentrated and purified by silica gel column chromatography to afford 2-(4-bromo-6-(N-methylamino)-1,N-methylindol-4-yl) 4,4,5,5-tetramethyl-1,3,2-dioxaborolane (0.7 g, 50%).

¹HNMR (300 MHz, CDCl₃): δ 7.15 (s, 1H), 6.95 (s, 1H), 6.86-6.81 (m, 2H), 3.73 (s, 3H), 2.96 (s, 3H), 1.38 (s, 12H).

LCMS: (M+H)⁺: 287.0.

To a solution of 2-(4-bromo-6-(N-methylamino)-1,N-methylindol-4-yl) 4,4,5,5-tetramethyl-1,3,2-dioxaborolane (286 mg, 1 mmol, 1.0 eq) in dioxane (10 mL) and water (2 mL) were added 2,4-dichloropyrimidine (160 mg, 1.1 mmol, 1.1 eq), $K_2CO_3$ (414 mg, 3 mmol, 3.0 eq) and $Pd(PPh_3)_4$ (116 mg, 0.1 mmol, 0.1 eq). The mixture was bubbled with nitrogen for 10 minutes, then purged with nitrogen 3 times and stirred at 100° C. for 3 hours. After cooling down to rt, the mixture was filtered and washed with EA. The filtrate was washed with brine (25 mL×2), dried over sodium sulfate, concentrated and purified by silica gel column chromatography to afford 2-chloro-4-(6-(N-methylamino)-1,N-methylindol-4-yl)pyrimidine (125 mg, 46%).

$^1$HNMR (300 MHz, DMSO-$d_6$): δ 8.76 (d, J=5.4 Hz, 1H), 7.99 (d, J=5.1 Hz, 1H), 7.22-7.18 (m, 2H), 6.82 (s, 1H), 6.70 (s, 1H), 5.69 (br, 1H), 3.73 (s, 3H), 2.80 (d, J=4.8 Hz, 3H).

LCMS: (M+H)$^+$: 272.9.

A46. 3-(N-Ethylamino)-1,N-(2-chloropyrimidin-4-yl)indazole

A mixture of 3-aminoindazole (26.6 g, 200 mmol, 1.0 eq) in pyridine (260 mL) was cooled to −10° C., then AcCl (17.2 g, 220 mmol, 1.1 eq) was added dropwise. The mixture was stirred at this temperature for 30 min. After TLC and LCMS indicated completion, the reaction was quenched with water (20 mL), concentrated in vacuo, then diluted with EA (500 mL), washed with brine (100 mL×3), dried over sodium sulfate, concentrated and purified by silica column affording 3-acetamidoindazole (20 g, 57%).

LCMS: (M+H)$^+$: 176.0.

A solution of 3-acetamidoindazole (20 g, 114.28 mmol, 1 eq) in THF (400 mL) was cooled to 0° C., then LiAlH. (13.05 g, 342.85 mmol, 3 eq) was added in portions. The mixture was stirred at room temperature for 1 hour. After TLC and LCMS indicated completion, the reaction was quenched by addition of water (13.05 mL) at 0° C., followed by addition of 15% NaOH (13.05 mL) and water (39.15 mL). Then sodium sulfate was added, the mixture was stirred for 10 minutes, filtered and the filtrate was concentrated and purified by silica column affording 3-ethylaminoindazole (20 g, 57%).

$^1$HNMR (300 MHz, DMSO-$d_6$): δ 11.34 (s, 1H), 7.69-7.66 (d, J=7.8 Hz, 1H), 7.21 (d, J=3.9 Hz, 2H), 6.90-6.85 (m, 1H), 5.84-5.81 (m, 1H), 3.26 (q, J=7.2 Hz, 2H), 1.22 (t, J=7.2 Hz, 3H).

LCMS: (M+H)$^+$: 162.0

To 100 mL four-neck flask were added DMF (24 mL) and 3-ethylaminoindazole (2.41 g, 14.97 mmol, 1.0 eq). After cooling down to 0° C., 60% NaH (0.718 g, 17.96 mmol, 1.2 eq) was added carefully. The mixture was stirred at this temperature for 30 minutes till no gas bubbled. Then a solution of 2,4-dichloropyrimidine (2.45 g, 16.46 mmol, 1.1 eq) in DMF (6 mL) was added. The mixture was stirred at rt for 3 hours. After completion, the mixture was quenched with sat. $NH_4Cl$ aqueous (10 mL) and water (100 mL), then filtered, the filter cake was washed with water, then purified by silica column to give 3-(N-ethylamino)-1,N-(2-chloropyrimidin-4-yl)indazole (1 g, 25%).

$^1$HNMR (300 MHz, DMSO-$d_6$): δ 8.53-8.49 (m, 2H), 7.95 (d, J=7.5 Hz, 1H), 7.65-7.59 (m, 2H), 7.37-7.33 (m, 1H), 7.20-7.19 (m, 1H), 3.45-3.41 (m, 2H), 1.31-1.27 (m, 3H).

LCMS: (M+H)$^+$: 273.9.

A47. 1-(2-Chloropyrimidin-4-yl)-3-(N,N-dimethylamino)-1H-indazole

To a solution of 3-amino-1,N-(2-chloropyrimid-4-yl)indazole (1.5 g, 6.1 mmol, 1 eq, in DMF (30 mL) was added NaH (0.54 g, 13.5 mmol, 2.2 eq) at 0° C. After stirring at this temperature for 30 minutes, iodomethane (1.92 g, 13.5 mmol, 2.2 eq) was added dropwise. The mixture was stirred at rt for 2 h. After completion, the mixture was poured into water (90 mL) and extracted with EA (50 mL×3). The combined organic layer was washed with brine, dried over sodium sulfate, concentrated and purified by silica gel column chromatography to afford 1-(2-chloropyrimidin-4-yl)-3-(N,N-dimethylamino)-1H-indazole (1.3 g, 77%).

$^1$HNMR (300 MHz, CDCl$_3$): δ 8.83 (d, J=8.4 Hz, 1H), 8.41 (d, J=8.4 Hz, 1H), 7.87 (d, J=8.1 Hz, 1H), 7.68 (d, J=5.7 Hz, 1H), 7.59-7.54 (m, 1H), 7.32-7.28 (m, 1H), 3.27 (s, 6H).

A48. 1-(2-Chloropyrimidin-4-yl)-3-(N-prop-2-ylamino)-1H-indazole

To a solution of 3-amino-1,N-(2-chloropyrimid-4-yl)indazole (1.22 g, 5 mmol, 1 eq) in DMF (18 mL) was added NaH (0.3 g, 7.5 mmol, 1.5 eq) at 0° C. After stirring at this temperature for 30 minutes, 2-iodopropane (1.01 g, 6 mmol, 1.2 eq) was added dropwise. The mixture was stirred at rt for 2 h. After completion, the mixture was poured into water (30 mL) and extracted with EA (30 mL×3). The combined organic layer was washed with brine, dried over sodium sulfate, concentrated and purified by silica gel column chromatography to afford 1-(2-chloropyrimidin-4-yl)-3-(N-prop-2-ylamino)-1H-indazole (0.3 g, 21%).

$^1$HNMR (300 MHz, DMSO-$d_6$): δ 8.52-8.49 (m, 2H), 8.00 (d, J=7.8 Hz, 1H), 7.65-7.59 (m, 2H), 7.37-7.32 (m, 1H), 7.01 (d, J=6.9 Hz, 1H), 4.02-4.00 (m, 1H), 1.31 (d, J=6.3 Hz, 6H).

A49. 1-(2-Chloropyrimidin-4-yl)-3-(methylsulonylamino)-1H-indazole

To a solution of 3-amino-1,N-(2-chloropyrimid-4-yl)indazole (500 mg, 2 mmol, 1 eq) in DCM (10 mL) was added DIPEA (310 mg, 2.4 mmol, 1.2 eq) and MsCl (275 mg, 2.4 mmol, 1.2 eq) at 0° C. The mixture was stirred at rt for 2 h, TLC indicated completion. The reaction was diluted with DCM (30 mL), washed with brine (30 mL×3), dried over sodium sulfate, concentrated and purified on silica column affording 1-(2-chloropyrimidin-4-yl)-3-(methylsulonylamino)-1H-indazole (290 mg, 44%). $^1$HNMR (300 MHz, DMSO-$d_6$): δ 11.52 (br, 1H), 8.70-8.68 (m, 1H), 8.61-8.55 (m, 1H), 8.08-8.02 (m, 1H), 7.82-7.66 (m, 2H), 7.46-7.38 (m, 1H), 3.48 (d, J=6.3 Hz, 3H).

LCMS: (M−H)$^-$: 321.7.

A50. 1,N-(2-Chloropyrimidin-4-yl)-3-(1-hydroxy-1-methylethyl)-1H-indazole

To a solution of ethyl indazole-3-carboxylate (3.8 g, 20 mmol, 1.0 eq) in DMF (50 mL) was added NaH (0.88 g, 22 mmol, 1.1 eq) portion wise at 0° C., the mixture was kept at 0° C. for 30 minutes. Then a solution of 2,4-dichloropyrimidine (3.13 g, 21 mmol, 1.05 eq) in DMF (10 mL) was added dropwise. After addition, the mixture was stirred at room temperature for 3 h. The reaction mixture was quenched with water (600 mL), the precipitate formed was filtered, washed with water (20 mL×2), then dissolved in EA (100 mL), dried over sodium sulfate, concentrated and purified by silica column chromatography affording ethyl 1,N-(2-chloropyrimid-4-yl)indazole-3-carboxylate (2.7 g, 45%).

$^1$HNMR (300 MHz, CDCl$_3$): δ 8.85 (d, J=8.7 Hz, 1H), 8.67 (d, J=5.7 Hz, 1H), 8.29 (d, J=8.1 Hz, 1H), 8.12 (d, J=5.7

Hz, 1H), 7.70-7.65 (m, 1H), 7.53-7.47 (m, 1H), 4.59 (q, J=7.2 Hz, 2H), 1.55 (t, J=7.2 Hz, 3H).

LCMS: (M+H)$^+$: 302.8.

To a solution of ethyl 1,N-(2-chloropyrimid-4-yl)indazole-3-carboxylate (2 g, 6.6 mmol, 1.0 eq) in THF (20 mL) was added 1M MeMgBr (19.6 ml, 19.6 mmol, 3 eq) dropwise. The mixture was stirred at this temperature for 2 h. After completion, the mixture was quenched with water (20 mL), extracted with EA (50 mL×3), washed with water (20 mL×3) and brine (25 mL×2), dried over sodium sulfate, concentrated and purified by silica column chromatography affording 1,N-(2-chloropyrimidin-4-yl)-3-(1-hydroxy-1-methylethyl)-1H-indazole (1.1 g, 58%).

$^1$HNMR (300 MHz, CDCl$_3$): δ 8.83 (d, J=8.4 Hz, 1H), 8.56 (d, J=5.7 Hz, 1H), 8.03 (d, J=8.1 Hz, 1H), 7.89 (d, J=5.7 Hz, 1H), 7.65-7.60 (m, 1H), 7.42-7.37 (m, 1H), 1.82 (s, 6H).

LCMS: (M+H)$^+$: 288.9.

A51. 2-Chloro-4-(7-(1,N-(tetrahydropyran-2-yl) pyrazol-3-yl)indol-3-yl)pyrimidine To a four-neck flask were added 2,4-dichloropyrimidine (3.42 g, 23 mmol, 0.9 eq). AlCl$_3$ (5.54 g 42 mmol, 1.6 eq) and DME (50 mL), stir for 5 minutes, then 7-bromoindole (5 g, 25.5 mmol, 1 eq) was added. The mixture was stirred at 80° C. for 24 h. After cooling down to rt, the reaction was diluted with water (100 mL), extracted with EA (100 mL×2). The combined organic layers were washed with brine (100 mL×2), dried over sodium sulfate, concentrated. The residue was triturated with MTBE (150 mL), filtered and washed with MTBE affording 7-bromo-3-(2-chloropyrimid-4-yl)indole (1.2 g, 15%) as red solid.

$^1$HNMR (300 MHz, CDCl$_3$): δ 8.89-8.88 (m, 1H), 8.54-8.53 (m, 1H), 8.37-8.35 (m, 1H), 8.13 (s, 1H), 7.58-7.56 (m, 1H), 7.51-7.49 (m, 1H).

LCMS: (M+H)$^+$: 307.7.

To a solution of 7-bromo-3-(2-chloropyrimid-4-yl)indole (500 mg, 1.6 mmol, 1 eq) and 2-(1,N-(tetrahydropyran-2-yl)pyrazol-3-yl)-4,4,5,5-tetramethyl-1,3,2-dioxaborolane (676 mg, 2.4 mmol, 1.5 eq) in dioxane/water (5:1, v/v, 6 mL) were added K$_2$CO$_3$ (672 mg, 4.8 mmol, 3 eq) and Pd(dppf)Cl$_2$ (118 mg, 0.16 mmol, 0.1 eq) under nitrogen. The mixture was then purged with nitrogen for 3 times and stirred at 100° C. overnight. After TLC indicated completion, the mixture was filtered, concentrated and the residue was purified by silica column affording 2-chloro-4-(7-(1,N-(tetrahydropyran-2-yl)pyrazol-3-yl)indol-3-yl)pyrimidine (400 mg, 65%).

$^1$HNMR (300 MHz, DMSO-d$_6$): δ 11.82 (s, 1H), 8.56-8.50 (m, 3H), 8.03-8.01 (m, 1H), 7.73 (s, 1H), 7.40-7.31 (m, 2H), 6.60 (s, 1H), 5.17-5.14 (m, 1H), 4.03-3.91 (m, 2H), 2.00-1.80 (m, 4H), 1.30-1.28 (m, 2H).

LCMS: (M+H)$^+$: 379.8.

A52. 2,5-Dichloro-4-(6-(carboxymethyl)-1,N-methylindol-4-yl)pyrimidine

To a solution of methyl 4-bromoindole-6-carboxylate (1 g, 4 mmol, 1 eq) in THF (15 mL) was added NaH (0.24 g, 6 mmol, 1.5 eq) portionwise. The mixture was stirred at this temperature for 30 minutes, then MeI (0.63 g, 4.4 mmol, 1.1 eq) was added dropwise. After addition, the mixture was stirred at rt for 1 h, TLC and LCMS indicated completion. The reaction was quenched with water (5 mL), extracted with EA (10 mL×2). The combined organic layers were washed with brine (10 mL×2), dried over sodium sulfate, concentrated affording methyl 4-bromo-1,N-methylindole-6-carboxylate (886 mg, 84%) which was used in next step directly.

$^1$HNMR (300 MHz, CDCl$_3$): δ 8.04 (s, 1H), 7.97 (s, 1H), 7.25 (s, 1H), 6.57 (s, 1H), 3.95 (s, 3H), 3.86 (s, 3H).

To a solution of methyl 4-bromo-1,N-methylindole-6-carboxylate (1.3 g, 5 mmol, 1.0 eq) in dioxane (15 mL) were added KOAc (1.5 g, 15 mmol, 3 eq) and bis(pinacolato)diborane (1.6 g, 6.5 mmol, 1.3 eq). The mixture was purged with nitrogen 3 times and then Pd(dppf)Cl$_2$CH$_2$Cl$_2$ (0.45 g, 0.5 mmol, 0.1 eq) was added. The mixture was re-purged with nitrogen 3 times, then stirred at 90° C. overnight. After cooling down to rt, the mixture was filtered, washed with EA. The filtrate was washed with brine (25 mL×2), dried over sodium sulfate, concentrated and purified by silica column affording 2-(6-(carboxymethyl)-1,N-methylindol-4-yl)-4,4,5,5-tetramethyl-1,3,2-dioxaborolane (0.7 g, 50%).

$^1$HNMR (300 MHz, CDCl$_3$): δ 8.31 (s, 1H), 8.17 (s, 1H), 7.25 (s, 1H), 7.01 (s, 1H), 3.96 (s, 3H), 3.88 (s, 3H), 1.41 (s, 12H).

LCMS: (M+H)$^+$: 315.9.

To a solution of 2-(6-(carboxymethyl)-1,N-methylindol-4-yl)-4,4,5,5-tetramethyl-1,3,2-dioxaborolane (315 mg, 1 mmol, 1.0 eq) in dioxane (10 mL) and water (2 mL) were added 2,4,5-trichloropyrimidine (201 mg, 1.1 mmol, 1.1 eq), K$_2$CO$_3$ (414 mg, 3 mmol, 3.0 eq) and Pd(PPh$_3$)$_4$ (116 mg, 0.1 mmol, 0.1 eq). The mixture was bubbled with nitrogen for 10 minutes, then purged with nitrogen 3 times and stirred at 100° C. for 3 hours. After cooling down to rt, the mixture was filtered, washed with EA. The filtrate was washed with brine (50 mL×2), dried over sodium sulfate, concentrated and purified by silica column affording 2,5-dichloro-4-(6-(carboxymethyl)-1,N-methylindol-4-yl)pyrimidine (63 mg, 23%).

$^1$HNMR (300 MHz, DMSO-d$_6$): δ 9.04 (s, 1H), 8.29 (s, 1H), 7.97 (s, 1H), 7.72 (s, 1H), 7.63 (s, 1H), 3.94 (s, 3H), 3.90 (s, 3H).

LCMS: (M−H)$^-$: 334.6.

A53. 7-(1,1-Dimethylethyl)-3-(2-chloropyrimidin-4-yl)-H-indole

To a solution of 2-t-butylaniline (45 g, 0.3 mol, 1 eq) in DMF (250 mL) was added NBS (53.6 g, 0.3 mmol, 1 eq) portionwise at 0° C. The mixture was stirred at it overnight, TLC indicated completion. The reaction was poured into ice-water (500 mL), extracted with EA (200 mL×3). The combined organic layers were washed with brine (200 mL×3), dried over sodium sulfate, concentrated affording 4-bromo-2-t-butylaniline (75 g, crude, containing DMF) which was used in next step directly.

$^1$HNMR (300 MHz, CDCl$_3$): δ 7.32 (s, 1H), 7.14-7.11 (d, J=10.5 Hz, 1H), 6.53 (d, J=8.4 Hz, 1H), 3.74 (br, 2H), 1.41 (s, 9H).

A mixture of 4-bromo-2-t-butylaniline (70 g, 0.3 mol, 1 eq) and I$_2$ (78 g, 0.3 mol, 1 eq) in cyclohexane (350 mL) was heated to 50° C. for 30 minutes, after the mixture was clear, 30% H$_2$O$_2$ (25 g, 0.3 mol, 1 eq) was added dropwise. And then the mixture was stirred at this temperature for 4 hours. After cooling down to rt, the mixture was diluted with EA (500 mL), washed with aqueous Na$_2$SO$_3$ (300 mL×3) and brine (300 mL×3), dried over sodium sulfate, concentrated and purified by silica column affording 4-bromo-2-t-butyl-6-iodoaniline (90 g, 83%).

$^1$HNMR (300 MHz, CDCl$_3$): δ 7.70 (s, 1H), 7.31 (s, 1H), 1.41 (s, 9H).

A mixture of 4-bromo-2-t-butyl-6-iodoaniline (90 g, 0.25 mol, 1 eq). TEA (108 mL), ethynyltrimethylsilane (37.2 g, 0.38 mmol, 1.5 eq). Pd(PPh$_3$)$_2$Cl$_2$ (8.91 g, 12.5 mmol, 0.05 eq) and CuI (2.4 g, 12.5 mmol, 0.05 eq) in THF (900 mL) was stirred at it overnight. After completion, the mixture was diluted with water (200 mL), extracted with EA (300 mL×3), the combined organic layers were washed with brine (300 mL×3), dried over sodium sulfate, concentrated to give 4-bromo-2-t-butyl-6-(2-trimethylsilylethynyl)aniline as a brown oil (74.2 g, 89%).

$^1$HNMR (300 MHz, CDCl$_3$): δ 7.51-7.31 (m, 2H), 4.60 (br, 2H), 1.20 (s, 9H), 0.27-0.20 (m, 9H).

To a solution of 4-bromo-2-t-butyl-6-(2-trimethylsilylethynyl)aniline (74.2 g, 0.23 mol, 1 eq) in THF (750 mL) was added a solution of TBAF (59.6 g, 0.23 mol, 1 eq) in THF (160 mL) dropwise. After addition, the mixture was stirred at rt till completion. The mixture was diluted with water (1 L), extracted with EA (300 mL×3), the combined organic layers were washed with brine (300 mL×3), dried over sodium sulfate, concentrated and purified by silica column affording 4-bromo-2-t-butyl-6-ethynylaniline (30.6 g, 53.6%).

LCMS: (M+H)$^+$: 251.9.

To a suspension of KOtBu (27.2 g, 0.24 mol, 2 eq) in NMP (300 mL) was added 4-bromo-2-t-butyl-6-ethynylaniline (30.6 g, 0.12 mol, 1 eq). The mixture was stirred at rt overnight. The mixture was poured into water (500 mL), extracted with EA (300 mL×3), the combined organic layers were washed with brine (300 mL×3), dried over sodium sulfate, concentrated affording crude 5-bromo-7-t-butylindole (20 g, crude).

$^1$HNMR (300 MHz, CDCl$_3$): δ 8.34 (br, 1H), 7.74-7.67 (m, 1H), 7.28-7.22 (m, 2H), 6.57-6.52 (m, 1H), 1.51 (s, 9H).

LCMS: (M+H)$^+$: 251.9.

To a solution of 5-bromo-7-t-butylindole (3 g, 11.9 mmol, 1 eq) in MeOH (30 mL) was added NaOAc (1.14 g, 13.9 mmol, 1.2 eq) and 10% Pd/C (1.8 g). The mixture was purged with hydrogen 3 times and stirred under hydrogen atmosphere at rt overnight. Filtered through celite, and washed with DCM, the filtrate was concentrated affording 7-t-butylindole as yellow solid (1.8 g, 90%).

$^1$HNMR (300 MHz, CDCl$_3$): δ 8.31 (br, 1H), 7.58-7.56 (m, 1H), 7.37-7.27 (m, 1H), 7.25-7.01 (m, 2H), 6.61-6.60 (m, 1H), 1.53 (s, 9H).

LCMS: (M+H)$^+$: 173.9.

To a four-neck flask were added 2,4-dichloropyrimidine (387 mg, 2.6 mmol, 0.9 eq), AlCl$_3$ (346.8 mg, 2.6 mmol, 0.9 eq) and DME (10 mL), stir for 5 minutes, then 7-t-butylindole (500 mg, 2.9 mmol, 1 eq) was added. The mixture was stirred at 80° C. for 24 h. After cooling down to rt, the reaction was diluted with water (20 mL), extracted with EA (50 mL×3). The combined organic layers were washed with brine (50 mL×3), dried over sodium sulfate, concentrated and purified by silica column affording 7-(1,1-dimethylethyl)-3-(2-chloropyrimidin-4-yl)-1H-indole (275 mg, 33%).

$^1$HNMR (300 MHz, CDCl$_3$) δ: 8.85 (br, 1H), 8.50-8.49 (m, 1H), 8.29-8.27 (m, 1H), 8.07 (s, 1H), 7.57-7.56 (m, 1H), 7.32-7.27 (m, 2H), 1.55 (s, 9H).

LCMS: (M−H)$^-$: 283.8.

A54. 3-(Carboxymethyl)-1N-(2-chloropyrimidin-4-yl)-pyrrolo[3,2-b]pyridine

To a stirred suspension of NaH (60%) (1.84 g, 46 mmol, 2.3 eq) in dry DMF (50 mL), diethyl malonate (7.36 g, 46 mmol, 2.3 eq) was added dropwise over a period of 20 min and was stirred at it for 30 min. Then to this mixture 2-chloro-3-nitropyridine (3.17 g, 20 mmol, 1.0 eq) was added. The mixture was heated to 100° C. for 1 hour. The mixture was poured into water (50 mL), extracted with EA (50 mL×2). The organic layer was washed with water (50 mL×2) and brine (30 mL×2), dried over sodium sulfate, and concentrated under reduced pressure. The crude product was purified by silica gel column chromatography eluting with ethyl acetate in hexane affording diethyl 2-(3-nitropyrid-2-yl)malonate (4.1 g, 73%).

$^1$HNMR (300 MHz, CDCl$_3$): δ 8.84-8.82 (m, 1H), 8.51-8.48 (m, 1H), 7.56-7.52 (m, 1H), 5.54 (s, 1H), 4.32 (q. J=7.2 Hz, 4H), 1.30 (t, J=7.2 Hz, 6H).

To a stirred solution of diethyl 2-(3-nitropyrid-2-yl)malonate (2.8 g, 10 mmol, 1.0 eq) in DMSO/H$_2$O=30/1 (31 mL) was added LiCl (1.1 g, 25 mmol, 2.5 eq) and the reaction mixture was stirred at 100° C. overnight. Then the reaction mixture was poured in to water (50 mL) and extracted with ethyl acetate (50 mL). The combined organic extracts were washed with water (50 mL×2), brine (50 mL×2), dried over sodium sulfate, and concentrated under reduced pressure. The crude product was purified by silica gel column chromatography eluting with ethyl acetate in hexane affording ethyl 2-(3-nitropyrid-2-yl)acetate (1.8 g, 90%).

$^1$HNMR (300 MHz, CDCl$_3$): δ 8.80-8.78 (m, 1H), 8.43-8.40 (m, 1H), 7.50-7.45 (m, 1H), 4.32 (s, 2H), 4.17-4.10 (m, 2H), 1.28 (t, J=7.2 Hz, 3H).

LCMS: (M+H)$^+$: 210.9.

To a solution of ethyl 2-(3-nitropyrid-2-yl)acetate (1.05 g, 5 mmol, 1.0 eq) in DMF (10 mL) was added DMF-DMA (0.9 g, 7.5 mmol, 1.5 eq). The mixture was stirred at rt overnight. The mixture was poured into water (50 mL), extracted with EA (50 mL×2). The organic layer was washed with water (50 mL×2) and brine (50 mL×2), dried over sodium sulfate, concentrated to afford ethyl 3-(dimethylamino)-2-(3-nitropyrid-2-yl)propenoate (650 mg, 50%) which was used in next step directly.

LCMS: (M+H)$^+$: 265.9.

To a solution of ethyl 3-(dimethylamino)-2-(3-nitropyrid-2-yl)propenoate (2.65 g, 10 mmol, 1.0 eq) in HOAc (30 mL) was added Fe (5.6 g, 100 mmol, 10 eq) powder. The mixture was heated to 60° C. for 2 h. After completion, the mixture was filtered, the filtrate was concentrated in vacuo to remove part of the solvent, then adjusted to pH=8 with 1N HCl, extracted with EA (50 mL), dried over sodium sulfate, concentrated and purified by silica column chromatography affording 3-(carboxyethyl)pyrrolo[3,2-b]pyridine (630 mg, 33%).

$^1$HNMR (300 MHz, DMSO-d$_6$): δ 8.48-8.47 (m, 1H), 8.29 (s, 1H), 7.87-7.84 (m, 1H), 7.22-7.18 (m, 1H), 4.27 (q, J=7.2 Hz, 2H), 1.31 (t, J=7.2 Hz, 3H).

LCMS: (M+H)$^+$: 191.0.

A mixture of 3-(carboxyethyl)pyrrolo[3,2-b]pyridine (1.9 g, 10 mmol, 1.0 eq), 2,4-dichloropyrimidine (1.79 g, 12 mmol, 1.2 eq, HOBT (270 mg, 2 mmol, 0.2 eq) and K$_2$CO$_3$ (1.93 g, 14 mmol, 1.4 eq) in DMA (20 mL) was heated to 80° C. for 12 h. The mixture was poured into water (50 mL), extracted with EA (50 mL×2). The organic layer was washed with water (50 mL×2) and brine (30 mL×2), dried over sodium sulfate, concentrated and purified by silica column chromatography affording 3-(carboxyethyl)-1,N-(2-chloropyrimidin-4-yl)-pyrrolo[3,2-b]pyridine (630 mg, 21%).

$^1$HNMR (300 MHz, CDCl$_3$): δ 8.92-8.89 (m, 1H), 8.80-8.79 (m, 1H), 8.72-8.70 (m, 1H), 8.59 (s, 1H), 7.47-7.45 (m, 1H), 7.41-7.37 (m, 1H), 4.51 (q, J=7.2 Hz, 2H), 1.46 (t, J=7.2 Hz, 3H).

LCMS: (M+H)$^+$: 302.8.

A55. 2-Chloro-4-(7-(NN-dimethylamino)pyrrolo[2,3-c]pyrid-3-yl)pyrimidine

To a solution of 2-chloro-4-methyl-3-nitropyridine (15 g, 87.2 mmol, 1.0 eq) in MeCN (150 mL) was added triethylamine (26.4 g, 261 mmol, 3.0 eq). The reaction mixture was cooled to 0° C., and dimethylamine hydrochloride (14.1 g, 174.4 mmol, 2.0 eq) was added. After addition the reaction mixture was allowed to warm to room temperature. The mixture was then poured into water (100 mL) and extracted with EA (300 mL). The organic layer was washed with aq. NaCl (100 mL), dried over sodium sulfate, concentrated to afford 2-dimethylamino-4-methyl-3-nitropyridine (21 g, crude) which was used in next step directly.

$^1$HNMR (300 MHz, CDCl$_3$): δ 8.09 (d, J=4.8 Hz, 1H), 6.52 (d, J=4.8 Hz, 1H), 3.02 (s, 6H), 2.31 (s, 3H).

LCMS: (M+H)$^+$: 181.9.

To a solution of 2-dimethylamino-4-methyl-3-nitropyridine (21 g, 116 mmol, 1.0 eq) in DMF (63 mL) was added DMF-DMA (41.4 g, 348 mmol, 3.0 eq. The mixture was stirred at 130° C. overnight. TLC and LCMS indicated completion, the mixture was diluted with water (250 mL), extracted with EA (100 mL×3), the combined organic layers were washed with brine (3×150 mL), dried over sodium sulfate, concentrated and purified by silica column chromatography affording 2-dimethylamino-4-(2-(dimethylamino)ethen-1-yl)-3-nitropyridine (15.3 g, 74% for 2 steps).

$^1$HNMR (300 MHz, CDCl$_3$): δ 7.88 (d, J=5.7 Hz, 1H), 7.08 (d, J=13.2 Hz, 1H), 6.62 (d, J=5.7 Hz, 1H), 5.19 (d, J=13.2 Hz, 1H), 2.99 (s, 6H), 2.92 (s, 6H).

LCMS: (M+H)$^+$: 237.0.

To a solution of 2-dimethylamino-4-(2-(dimethylamino)ethen-1-yl)-3-nitropyridine (15.3 g, 64.8 mmol, 1.0 eq) in EtOH (300 mL) was added Pd/C (4 g). After addition, the mixture was purged with H, three times and stirred at rt overnight. The mixture was filtered, washed with EtOH (100 mL). The filtrate was concentrated to afford 7-(dimethylamino)pyrrolo[2,3-c]pyridine (6.5 g, 65%).

$^1$HNMR (300 MHz, CDCl$_3$): δ 8.60 (br, 1H), 7.87 (d, J=5.7 Hz, 1H), 7.09 (d, J=5.7 Hz, 1H), 6.53 (d, J=3 Hz, 1H), 3.18 (s, 6H).

To a solution of 7-(dimethylamino)pyrrolo[2,3-c]pyridine (2 g, 12.4 mmol, 1.0 eq) in MeCN (150 mL) was added DMAP (0.9 g, 7.4 mmol, 0.6 eq) and Boc$_2$O (4.9 g, 22.4 mmol, 1.8 eq. The mixture was heated to 40° C. for 12 h. After completion, the mixture was concentrated in vacuo to remove the solvent and purified by silica column chromatography affording the desired 7-(dimethylamino)-1,N-(t-butoxycarbonyl)pyrrolo[2,3-c]pyridine (2.7 g, 83%).

$^1$HNMR (300 MHz, CDCl$_3$): δ 8.02 (d, J=5.7 Hz, 1H), 7.60 (d, J=3.6 Hz, 1H), 6.95 (d, J=5.7 Hz, 1H), 6.51 (d, J=3.6 Hz, 1H), 2.99 (s, 6H), 1.44 (s, 9H).

LCMS: (M+H)$^+$: 262.0.

In a glove box, 7-(dimethylamino)-1,N-(t-butoxycarbonyl)pyrrolo[2,3-c]pyridine (2.7 g, 10.3 mmol, 1.0 eq), bis(pinacolato)diboron (3.1 g, 12.4 mmol, 1.2 eq), Di-mu-methoxobis(1,5-cyclooctadiene)diiridium(I) (0.34 g, 0.5 mmol, 0.05 eq), 4,4'-Di-tert-butyl-[2,2']bipyridinyl (0.28 g, 1 mmol, 0.1 eq) and THF (20 mL) were added to a four-neck flask. The mixture was heated to 80° C. overnight under nitrogen. After completion, the mixture was cooled to rt and diluted with water (40 mL), extracted with EA (30 mL×3). The combined organic layers were washed with brine, dried over sodium sulfate, concentrated and purified by silica column chromatography affording 2-(7-(dimethylamino)-1,N-(t-butoxycarbonyl)pyrrolo[2,3-c]pyrid-3-yl)-4,4,5,5-tetramethyl-1,3,2-dioxaborolane (1.4 g, 35%).

$^1$HNMR (300 MHz, CDCl$_3$): δ 8.06 (d, J=5.4 Hz, 1H), 7.99 (s, 1H), 7.40 (d, J=5.4 Hz, 1H), 2.98 (s, 6H), 1.64 (s, 9H), 1.37 (s, 12H).

LCMS: (M+H)$^+$: 387.9.

To a solution of 2-(7-(dimethylamino)-1,N-(t-butoxycarbonyl)pyrrolo[2,3-c]pyrid-3-yl)-4,4,5,5-tetramethyl-1,3,2-dioxaborolane (500 mg, 1.3 mmol, 1.0 eq) in dioxane (12.5 mL) and water (2.5 mL) were added Pd(dppf)Cl (95 mg, 0.1 mmol, 0.1 eq), K$_2$CO$_3$ (138 mg, 3.9 mmol, 3.0 eq) and 2,4-dichloropyrimidine (194 mg, 1.3 mmol, 1 eq). The mixture was purged with nitrogen 3 times, then stirred at 90° C. overnight. After cooling down to it, the mixture was filtered, washed with EA (50 mL). The filtrate was washed with brine (50 mL), dried over sodium sulfate, concentrated and purified by silica column affording 2-chloro-4-(7-(N,N-dimethylamino)pyrrolo[2,3-c]pyrid-3-yl)pyrimidine (150 mg, 42%).

$^1$HNMR (300 MHz, DMSO-d$_6$): δ 12.08 (br, 1H), 8.57 (d, J=5.4 Hz, 1H), 8.46 (s, 1H), 7.98 (d, J=5.4 Hz, 1H), 7.86-7.76 (m, 2H), 3.08 (s, 6H).

LCMS: (M+H)$^+$: 273.9.

A56. 3-(N-methylcarboxamido)-1,N-(2-chloropyrimidin-4-yl)-pyrrolo[3,2-b]pyridine Into a sealed tube, ethyl pyrrolo[3,2-b]pyridine-3-carboxylate (1.9 g, 10 mmol, 1 eq) was dissolved in a 2N methylamine in tetrahydrofuran solution (20 mL, 40 mmol, 4 eq). The mixture was heated to reflux overnight. The reaction was concentrated under reduced pressure to afford N-methyl pyrrolo[3,2-b]pyridine-3-carboxamide (1.8 g, crude) which was used in next step directly.

LCMS: (M+H)$^+$: 175.9.

A mixture of afford N-methyl pyrrolo[3,2-b]pyridine-3-carboxamide (1.75 g, 10 mmol, 1.0 eq), 2,4-dichloropyrimidine (1.79 g, 12 mmol, 1.2 eq), HOBT (270 mg, 2 mmol, 0.2 eq) and K$_2$CO$_3$ (1.93 g, 14 mmol, 1.4 eq) in DMA (20 mL) was heated to 80° C. for 12 h. After TLC and LCMS indicated completion, the mixture was poured into water (50 mL), extracted with EA (50 mL×2). The organic layer was washed with water (50 mL×2) and brine (30 mL×2), dried over sodium sulfate, concentrated and purified by silica column chromatography affording 3-(N-methylcarboxamido)-1,N-(2-chloropyrimidin-4-yl)-pyrrolo[3,2-b]pyridine (820 mg, 28.6%).

$^1$HNMR (300 MHz, DMSO-d$_6$): δ 9.18 (s, 1H), 9.06-8.76 (m, 3H), 8.65-8.64 (m, 1H), 8.28-8.26 (m, 1H), 7.60-7.52 (m, 1H), 2.95 (s, 3H).

LCMS: (M+H)$^+$: 287.8.

A57. 1,N-(2,5-Dichloropyrimidin-4-yl)-3-N-t-butoxycarbonyl-N-methylamino)-1H-indazole A 500 mL four-neck flask was charged with DMF (80 mL) and 3-(N-t-butoxycarbonyl)indazole (4.66 g, 20 mmol, 1 eq). After cooling down to 0° C., NaH (0.96 g, 24 mmol, 1.2 eq) was added carefully. The mixture was stirred at this temperature for 10 minutes till no gas bubbled. Then a solution of compound 2,4-dichloropyrimidine (4 g, 22 mmol, 1.1 eq) was added. The mixture was stirred at rt overnight. After completion, the mixture was quenched with aq sat.NH$_4$Cl (20 mL) and then diluted with water (300 mL), extracted with EA (200 mL×3). The combined organic layers were washed with water (300 mL×2), concentrated and purified by column chromatography on silica to give 1,N-(2,5-dichloropyrimidin-4-yl)-3-(N-t-butoxycarbonylamino)-1H-indazole (2 g, 26%).

$^1$HNMR (300 MHz, CDCl$_3$): δ 8.62 (s, 1H), 8.49 (d, J=8.4 Hz, 1H), 8.16 (d, J=8.4 Hz, 1H), 7.63-7.58 (m, 1H), 7.42-7.37 (m, 1H), 7.22 (s, 1H), 1.55 (s, 9H).

LCMS: (M−H)$^-$: 377.7.

To 100 mL round-bottom flask were added DMF (10 mL) and 1,N-(2,5-dichloropyrimidin-4-yl)-3-(N-t-butoxycarbonylamino)-1H-indazole (1 g, 2.6 mmol, 1 eq). After cooling down to 0° C. NaH (124 mg, 3.1 mmol, 1.2 eq) was added carefully. The mixture was stirred at this temperature for 10 minutes till no gas bubbled. Then MeI (440 mg, 3.1 mmol, 1.2 eq) was added. The mixture was stirred at rt overnight. After completion, the mixture was diluted with water (30 mL), extracted with EA (30 mL×3). The combined organic layers were washed with water (50 mL×2), concentrated and purified by column chromatography on silica to give the 1,N-(2,5-dichloropyrimidin-4-yl)-3-(N-t-butoxycarbonyl-N-methylamino)-1H-indazole (0.5 g, 48%).

$^1$HNMR (300 MHz, CDCl$_3$): δ 8.64 (s, 1H), 8.52 (d, J=8.4 Hz, 1H), 7.81 (d, J=8.4 Hz, 1H), 7.62-7.56 (m, 1H), 7.41-7.36 (m, 1H), 3.52 (s, 3H), 1.50 (s, 9H).

A58. 1,N-(2-Chloropyrimidin-4-yl)-3-(acetamido)-1H-indazole

To a solution of 3-amino-1,N-(2-chloropyrimid-4-yl)indazole (270 mg, 1.1 mmol, 1 eq) in pyridine (5 mL) was added AcCl (214 mg, 2.75 mmol, 2.5 eq) dropwise at 0° C. The mixture was then stirred at rt for 2 hours. After TLC and LCMS indicated completion, the reaction was diluted with water (30 mL), extracted with EA (30 mL×2). The combined organic layers were washed with brine (30 mL×2), dried over sodium sulfate, concentrated and purified to give the crude 1,N-(2-Chloropyrimidin-4-yl)-3-(acetamido)-1H-indazole (260 mg) which was used in next step directly without purification.

$^1$HNMR (300 MHz, DMSO-d$_6$): δ 10.93 (s, 1H), 8.71-8.61 (m, 2H), 8.06-8.03 (m, 1H), 7.77-7.67 (m, 2H), 7.43-7.38 (m, 1H), 2.22 (s, 3H).

LCMS: (M−H)$^-$: 285.8.

To a solution of 235 (5 g, 37.3 mmol, 1.0 eq) in pyridine (50 mL) was added AcCl (3.22 g, 41 mmol, 1.1 eq) dropwise at −10° C. The mixture was stirred at this temperature for 30 mins. TLC and LCMS indicated completion. The mixture was diluted with EA (100 mL), washed with brine (50 mL×3), dried over sodium sulfate, concentrated and purified by silica column affording desired product 236 (5.4 g, 82%).

$^1$HNMR (300 MHz, DMSO-d$_6$): δ 10.89 (s, 1H), 8.70 (d, J=3.3 Hz, 1H), 8.47-8.44 (m, 1H), 7.70-6.99 (m, 1H), 2.16 (s, 3H).

LCMS: (M+H)$^+$: 177.0.

A59. 2-Chloro-4-(3-N-ethylamino)pyrazolo[4,3-b]pyrid-1-yl)pyrimidine

To a solution of 3-acetamidopyrazolo[4,3-b]pyridine (5.4 g, 30.7 mmol, 1.0 eq) in THF (100 mL) was added LiAlH$_4$ (3.4 g, 92 mmol, 3 eq) carefully at 0° C. under nitrogen. The mixture was stirred at room temperature for 1 h. TLC and LCMS indicated completion. The mixture was re-cooled to 0° C., quenched by addition of water (3.4 mL), 15% NaOH aqueous (3.4 mL) and water (10.2 mL), then sodium sulfate was added to the reaction mixture, stirred for 10 mins, filtered and the filtrate was concentrated and purified by silica column affording desired product 3-(ethylamino)pyrazolo[4,3-b]pyridine (2 g, 40%).

$^1$HNMR (300 MHz, DMSO-d$_6$): δ 8.26-8.25 (m, 1H), 7.70-7.67 (m, 1H), 7.26-7.22 (m, 1H), 5.81-5.79 (m, 1H), 3.34-3.28 (m, 2H), 1.20 (t, J=7.2 Hz, 3H).

LCMS: (M+H)$^+$: 163.0.

To 100 mL four-neck flask were added DMF (10 mL) and 3-(ethylamino)pyrazolo[4,3-b]pyridine (1 g, 6.17 mmol, 1.0 eq). After cooling down to 0° C., tBuOK (0.83 g, 7.4 mmol, 1.2 eq q) was added carefully. The mixture was stirred at this temperature for 30 minutes. Then a solution of compound 2,4-dichloropyrimidine (1.01 g, 6.79 mmol, 1.1 eq) in DMF (5 mL) was added. The mixture was stirred at rt for 3 h, TLC and LCMS indicated completion, the mixture was poured into water (50 mL), filtered and the filter cake was washed with water (10 mL×3), dried in vacuo to give 2-chloro-4-(3-(N-ethylamino)pyrazolo[4,3-b]pyrid-1-yl)pyrimidine (0.4 g, 23%).

LCMS: (M+H)$^+$: 274.9.

A60. 2-Chloro-4-(3-(N,N-dimethylamino)pyrazolo[4,3-b]pyrid-1-yl)pyrimidine

To a round-bottom flask were added 3-amino-1,N-(2-chloropyrimid-4-yl)pyrrolo[4,3-b]pyridine (1 g, 4.06 mmol, 1 eq) and DMF (20 mL). After cooling down to 0° C., NaH (0.358 g, 8.94 mmol, 2.2 eq) was added carefully and the mixture was stirred at this temperature for 30 minutes. Then MeI (1.27 g, 8.94 mmol, 2.2 eq) was added dropwise. After addition, the mixture was warmed to rt and stirred for 2 hours till completion. The mixture was poured into water (100 mL), extracted with EA (50 mL×3). The combined organic layers were washed with brine twice, dried over sodium sulfate, concentrated and purified by silica column chromatography to give 2-chloro-4-(3-(N,N-dimethylamino)pyrazolo[4,3-b]pyrid-1-yl)pyrimidine (0.6 g, 54%).

LCMS: (M+H)$^+$: 274.9.

A61. 2-Chloro-4-(3-(N-methylamino)pyrazolo[4,3-b]pyrid-1-yl)pyrimidine

A mixture of 3-fluoropicolinonitrile (40 g, 327.8 mmol, 1.0 eq) and hydrazine hydrate (49 g, 980 mmol, 1.2 eq) in n-butanol (400 mL) was heated at reflux under nitrogen for 12 h. The reaction mixture was allowed to cool to it and the solid was collected by filtration and washed with ethyl acetate (100 mL), dried to give 3-aminopyrazolo[4,3-b]pyridine (32 g, 73%).

$^1$HNMR (300 MHz, DMSO-d$_6$): δ 11.57 (br, 1H), 8.28-8.27 (m, 1H), 7.71-7.68 (m, 1H), 7.26-7.22 (m, 1H), 5.37 (s, 2H).

To a solution of 3-aminopyrazolo[4,3-b]pyridine (20 g, 149 mmol, 1.0 eq) in DMF (300 mL) was added tBuOK (20 g, 179 mmol, 1.2 eq) portionwise at 0° C., the mixture was kept at 0° C. for 30 minutes. Then a solution of 2,4-dichloropyrimidine (24.4 g, 164 mmol, 1.1 eq) in DMF (100 mL) was added dropwise. After addition, the mixture was stirred at room temperature for 4 h. The reaction mixture was poured into water (1800 mL), the precipitate formed was filtered, washed with water (300 mL×2), then dissolved in EA (500 mL), dried over sodium sulfate, concentrated and purified by silica column chromatography affording 2-chloro-4-(3-aminopyrazolo[4,3-b]pyrid-1-yl)pyrimidine (9 g, 24%).

¹HNMR (300 MHz, DMSO-d₄): δ 8.75 (d, J=7.8 Hz, 1H), 8.62-8.56 (m, 2H), 7.67-7.63 (m, 1H), 7.56 (d, J=7.8 Hz, 1H), 6.73 (s, 2H).

LCMS: (M+H)⁺: 246.9.

To a solution of 2-chloro-4-(3-aminopyrazolo[4,3-b]pyrid-1-yl)pyrimidine (2 g, 8.1 mmol, 1.0 eq) in DCM (20 mL) was added DIPEA (1.6 g, 12.2 mmol, 1.5 eq). Then trifluoroacetic anhydride (2.6 g, 12.2 mmol, 1.5 eq) was added dropwise at 0° C. After addition, the mixture was stirred at 25° C. for 1 h. TLC and LCMS indicated completion. The reaction mixture was concentrated and purified by silica column chromatography affording 2-chloro-4-(3-(triflouroacetamido)pyrazolo[4,3-b]pyrid-1-yl)pyrimidine (2.2 g, 79%).

LCMS: (M+H)⁺: 342.8

To a solution of 2-chloro-4-(3-(triflouroacetamido)pyrazolo[4,3-b]pyrid-1-yl)pyrimidine (1.2 g, 3.5 mmol, 1.0 eq) in DMF (24 mL) was added tBuOK (0.47 g, 4.2 mmol, 1.2 eq) portionwise at 0° C. the mixture was kept at 0° C. for 30 minutes. Then MeI (0.592 g, 4.2 mmol, 1.2 eq) was added dropwise. After addition, the mixture was stirred at room temperature for 2 h. The reaction mixture was poured into water (50 mL), extracted with EA (50 mL×2), the combined organic layers were washed with brine, dried over sodium sulfate, concentrated to give 2-chloro-4-(3-(N-methyltriflouroacetamido)pyrazolo[4,3-b]pyrid-1-yl)pyrimidine (1.1 g, crude) which was used in next step directly without purification.

LCMS: (M+H)⁺: 356.7.

To a solution of 2-chloro-4-(3-(N-methyltriflouroacetamido)pyrazolo[4,3-b]pyrid-1-yl)pyrimidine (1.1 g, 3.08 mmol, 1.0 eq) in MeOH (10 mL) was added 8N NaOH solution (3.8 mL, 30.8 mmol, 10 eq). After stirring for 30 mins, TLC indicated completion. The mixture was concentrated and extracted with EA (30 mL), the organic layer was washed with brine (30 mL), dried over sodium sulfate, purified on silica column affording 2-chloro-4-(3-(N-methylamino)pyrazolo[4,3-b]pyrid-1-yl)pyrimidine (0.4 g, 50%).

LCMS: (M+H)⁺: 260.8.

A62. 2-Chloro-4-(7-methoxypyrrolo[2,3-c]pyrid-4-yl)pyrimidine

5-Bromo-2-methoxy-3-nitropyridine (25 g, 108.2 mmol, 1.0 eq) was dissolved in dry THF (1000 mL) under nitrogen. After the solution was cooled to −78° C., vinylmagnesium bromide (1.0M in THF, 500 mL, 500 mmol, 4.6 eq) was added dropwise. The reaction temperature was maintained at −78° C. for 1 h, and then at −20° C. for another 2 h before it was quenched by addition of 20% NH₄Cl aqueous solution (750 mL). The aqueous phase was extracted with EtOAc (3×350 mL). The combined organic layer was dried over MgSO₄, filtered and the filtrate was concentrated in vacuo to give a residue which was purified by silica gel column chromatography (EtOAc/Hexane, 1/10) to afford 4-bromo-7-methoxypyrrolo[2,3-c]pyridine (4.8 g, 19%).

¹HNMR (300 MHz, CDCl₃): δ 8.79 (br, 1H), 7.86 (s, 1H), 7.34 (s, 1H), 6.59 (s, 1H), 4.10 (s, 3H).

LCMS: (M+H)⁺: 226.8.

A mixture of 4-bromo-7-methoxypyrrolo[2,3-c]pyridine (4.5 g, 19.8 mmol, 1.0 eq), iodomethane (13.9 g, 99 mmol, 5 eq) and anhydrous K₂CO₃ (19.3 g, 59.4 mmol, 3 eq) in dry acetone (225 mL) was refluxed 3 h. The mixture was evaporated and the residue was dissolved in ethyl acetate (100 mL) and water (100 mL). The organic layer was separated, washed with water (100 mL) and brine (100 mL), dried over MgSO₄ and evaporated. Purification by chromatography on silica gel affording 4-bromo-7-methoxy 1,N-methylpyrrolo[2,3-c]pyridine (4 g, 83%).

¹HNMR (300 MHz, CDCl₃): δ 7.76 (s, 1H), 7.27 (s, 1H), 6.42 (s, 1H), 4.05 (s, 3H), 4.02 (s, 3H).

LCMS: (M+H)⁺: 240.8.

To a solution of 4-bromo-7-methoxy 1,N-methylpyrrolo[2,3-c]pyridine (2.6 g, 10.78 mmol, 1.0 eq) in 1,4-dioxane (50 mL) were added bis(pinacolato)diboron (4.11 g, 16.2 mmol, 1.5 eq), KOAc (3.17 g, 32.34 mmol, 3 eq) and Pd(dppf)Cl₂DCM (0.88 g, 1.08 mmol, 0.1 eq) under nitrogen. The mixture was purged with nitrogen 3 times and stirred at 90° C. for 4 hours. After cooling down to rt, the mixture was concentrated and the residue was purified by chromatography on silica gel to give 2-(7-methoxy 1,N-methylpyrrolo[2,3-c]pyrid-4-yl)-4,4,5,5-tetramethyl-1,3,2-dioxaborolane (1 g, 32%).

¹HNMR (300 MHz, CDCl₃): δ 7.70 (d, J=5.7 Hz, 1H), 7.12 (d, J=5.7 Hz, 1H), 6.41 (d, J=3 Hz, 1H), 4.10 (s, 3H), 4.07 (s, 3H), 1.22 (s, 12H).

LCMS: (M+H)⁺: 288.9.

To a solution of 2-(7-methoxy 1,N-methylpyrrolo[2,3-c]pyrid-4-yl)-4,4,5,5-tetramethyl-1,3,2-dioxaborolane (1 g, 3.47 mmol, 1.0 eq) in 1,4-dioxane (25 mL) and water (5 mL) were added 2,4-dichloropyrimidine (0.57 g, 3.82 mmol, 1.1 eq), K₂CO₃ (1.43 g, 10.41 mmol, 3 eq) and Pd(PPh₃)₄ (0.4 g, 0.347 mmol, 0.1 eq) under nitrogen. The mixture was bubbled with nitrogen for 10 minutes, then purged with nitrogen 3 times and stirred at 100° C. for 3 hours. After cooling down to rt, the mixture was concentrated and the residue was purified by chromatography on silica gel to give 2-chloro-4-(7-methoxypyrrolo[2,3-c]pyrid-4-yl)pyrimidine (0.4 g, 42%).

¹HNMR (300 MHz, CDCl₃): δ 8.59 (s, 1H), 8.37 (s, 1H), 7.68 (s, 1H), 7.21-7.20 (m, 2H), 4.17 (s, 3H), 4.12 (s, 3H).

LCMS: (M+H)⁺: 274.8.

A63. 1,N-(2-Chloropyrimidin-4-yl)-3-(N-(pyrid-2-yl)amino)-1H-indazole

To a solution of 3-amino-1,N-(2-chloropyrimid-4-yl)indazole 32 (0.5 g, 2.04 mmol, 1 eq) and 2-bromopyridine (0.322 g, 2.04 mmol, 1 eq) in dioxane (10 mL) were added Cs₂CO₃ (1.326 g, 4.08 mmol, 2 eq). Xantphos (0.235 g, 0.408 mmol, 0.2 eq) and Pd₂(dba)₃ (0.186 g, 0.204 mmol, 0.1 eq). The mixture was purged with nitrogen three times and then stirred at 100° C. for 3 h. TLC and LCMS indicated completion, the mixture was concentrated and purified by silica column affording 1,N-(2-chloropyrimidin-4-yl)-3-(N-(pyrid-2-yl)amino)-1H-indazole (0.2 g, 30%).

LCMS: (M+H)⁺: 322.8.

A64. 1-(2-Chloropyrimidin-4-yl)-3-(1,N-pyrrolidinyl)-1H-indazole

To a solution of 3-iodo-1,N-tritylindazole (5 g, 10.3 mmol, 1 eq) in DMSO (50 mL) were added CuI (0.39 g, 2 mmol, 0.2 eq), K₃PO₄ (4.36 g, 20.6 mmol, 2 eq), L-proline (0.47 g, 4 mmol, 0.4 eq) and pyrrolidine (3.65 g, 30.8 mmol, 3 eq). The mixture was bubbled with nitrogen for 2 minutes, then stirred at 80° C. for 12 h. The mixture was monitored by TLC and LCMS, after completion, the mixture was poured into water (200 mL) and extracted with EA (100 mL×3). The combined organic layers were washed with brine (100 mL×2), concentrated and purified by column chromatography on silica to give 3-(pyrrolidin-1-yl)-1,N-tritylindazole (3.1 g, 70%).

¹HNMR (300 MHz, DMSO-d₆): δ 7.78-7.76 (m, 1H), 7.27 (br, 15H), 6.95-6.86 (m, 2H), 6.27 (d, J=7.8 Hz, 1H), 3.43-3.40 (m, 4H), 1.89-1.86 (m, 4H).

LCMS: (M−H)⁻: 527.9

To a solution of 3-(pyrrolidin-1-yl)-1,N-tritylindazole (3.1 g, 7.2 mmol, 1.0 eq) in DCM (15 mL) was added TFA (15 mL). The reaction mixture was stirred at 25° C. for 30 min. TLC and LCMS indicated completion, the mixture was concentrated and adjusted to pH=7 with sat. NaHCO₃, extracted with DCM (100 mL×2), the combined organic layers were washed with brine, dried over sodium sulfate, concentrated and purified by silica column affording 3-(pyrrolidin-1-yl)indazole (0.9 g, 66%).

¹HNMR (300 MHz, DMSO-d₆): δ 11.66 (br, 1H), 7.79 (d, J=8.1 Hz, 1H), 7.28-7.19 (m, 2H), 6.91-6.86 (m, 1H), 3.51-3.50 (m, 4H), 1.93-1.91 (m, 4H).

LCMS: (M+H)⁺: 188.0.

To 100 mL four-neck flask were added DMF (14 mL) and 3-(pyrrolidin-1-yl)indazole (0.9 g, 4.81 mmol, 1.0 eq). After cooling down to 0° C., tBuOK (0.647 g, 5.77 mmol, 1.2 eq) was added. The mixture was stirred at this temperature for 30 minutes. Then a solution of compound 2,4-dichloropyrimidine (0.789 g, 5.3 mmol, 1.1 eq) in DMF (4 mL) was added. The mixture was stirred at rt for 4 h, TLC and LCMS indicated completion, the mixture was poured into water (60 mL), filtered and the filter cake was washed with water (10 mL×3), dried in vacuo to give 1-(2-chloropyrimidin-4-yl)-3-(1,N-pyrrolidinyl)-1H-indazole (0.7 g, 49%).

LCMS: (M+H)⁺: 299.9.

A65. 1,N-(2-Chloropyrimidin-4-yl)-3-(N-ethyl-N-methylamino)-1H-indazole

To a round-bottom flask were added 1,N-(2-chloropyrimid-4-yl)-3-(N-ethylamino)indazole (0.65 g, 2.38 mmol, 1 eq) and DMF (10 mL). After cooling down to 0° C., NaH (0.19 g, 4.76 mmol, 2 eq) was added carefully and the mixture was stirred at this temperature for 30 minutes. Then MeI (1.01 g, 7.14 mmol, 3 eq) was added dropwise. After addition, the mixture was warmed to rt and stirred for 2 hours till completion. The mixture was poured into water (30 mL), extracted with EA (50 mL×3). The combined organic layers were washed with brine twice, dried over sodium sulfate, concentrated and purified by silica column chromatography to give 1,N-(2-chloropyrimidin-4-yl)-3-(N-ethyl-N-methylamino)-1H-indazole 59 (0.5 g, 73%).

¹HNMR (300 MHz, DMSO-d₆): δ 8.65 (d, J=8.7 Hz, 1H), 8.55 (d, J=6 Hz, 1H), 8.02 (d, J=7.8 Hz, 1H), 7.68-7.63 (m, 2H), 7.39-7.34 (m, 1H), 3.68 (q, J=7.2 Hz, 2H), 3.19 (s, 3H), 1.21 (t, J=7.2 Hz, 3H).

LCMS: (M+H)⁺: 287.9.

A66. 2-Chloro-4-(3-1,2,3-triazol-4-yl)indol-1-yl)pyrimidine

Into a round bottom flask fitted with a magnetic stir bar and rubber septum were added indole-3-carbaldehyde (14.5 g, 100 mmol, 1.0 eq) and DMF (100 mL) under nitrogen. The resulting solution was cooled to 0° C., with an ice-water bath. 60% NaH (4.4 g, 110 mmol, 1.1 eq) was then added. Once gas evolution ceased, 2,4-dichloropyrimidine (14.9 g, 100 mmol, 1 eq) was added. The reaction was then left to stir overnight with gradual warming to room temperature. TLC and HPLC analysis of the crude reaction mixture shows complete reaction. The reaction was quenched with 100 mL of saturated NH₄Cl (aq). This mixture was then diluted with 100 mL of water and extracted with EtOAc (100 mL). The EtOAc extracts are then washed with water and brine, combined, dried over anhydrous Na₂SO₄, filtered, and concentrated under reduced pressure. The residue was purified with flash chromatography (PE:EA=5:1) to give 1,N-(2-chloropyrimid-4-yl)indole-3-carbaldehyde as white solid (10.2 g, 40%).

LCMS: (M+H)⁺: 257.8.

To a solution of 1,N-(2-chloropyrimid-4-yl)indole-3-carbaldehyde (5.14 g, 20 mmol, 1 eq) in MeNO₂ (40 mL) was added NH₄OAc (4.6 g, 60 mmol, 3 eq). The mixture was stirred at reflux for 4 hours. After cooling, the MeNO₂ solvent was removed in vacuo and the residue was diluted with water (120 mL) and extracted with EA (100 mL×2). The organic layer was washed with brine (100 mL×2), dried over sodium sulfate, concentrated and purified with flash chromatography (PE:EA=10:1) to afford 1,N-(2-chloropyrimid-4-yl)-3-(2-nitroethen-1-yl)indole (3.1 g, 52%).

¹HNMR (300 MHz, DMSO-d₆): δ 9.16 (s, 1H), 8.91 (d, J=5.4 Hz, 1H), 8.75 (d, J=8.7 Hz, 1H), 8.52 (d, J=13.5 Hz, 1H), 8.27 (d, J=13.5 Hz, 1H), 8.12 (d, J=7.5 Hz, 1H), 7.66-7.65 (m, 1H), 7.53-7.39 (m, 2H).

To a solution of 1,N-(2-chloropyrimid-4-yl)-3-(2-nitroethen-1-yl)indole (1.5 g, 5 mmol, 1 eq) in DMF (25 mL) was added NaN₃ (490 mg, 7.5 mmol, 1.5 eq) in portions. After addition, TsOH (430 mg, 2.5 mmol, 0.5 eq) was added to the mixture carefully with stirring and then the mixture was heated to 60° C. for 1 h. After cooling down to rt, the mixture was diluted with water (50 mL) and extracted with EA (3×50 mL), the combined organic layers were washed with brine (50 mL), dried over sodium sulfate, concentrated and purified by silica column chromatography (PE:EA=5:1) affording 2-chloro-4-(3-(1,2,3-triazol-4-yl)indol-1-yl)pyrimidine (450 mg, 30%) as yellow solid.

A67. 2-Chloro-4-(3-(N-methylsulfonylamido)indol-1-yl)pyrimidine

To a 2 L four-neck flask were added DMA (750 mL), indole (50 g, 0.43 mol, 1.0 eq), 2,4-dichloropyrimidine (127.2 g, 0.52 mol, 1.2 eq), HOBt (11.5 g, 0.085 mol, 0.2 eq) and K₂CO₃ (83 g, 0.6 mol, 1.4 eq). The mixture was stirred at 80° C. overnight. After TLC and LCMS indicated completion, the mixture was cooled down to rt, poured into water (2250 mL), the precipitate formed was collected by filtration, the filter cake was dissolved in EA (1 L), washed with brine (300 mL×3), dried over sodium sulfate, concentrated and purified by silica column affording 1,N-(2-chloropyrimid-4-yl)indole as white solid (31 g, 32%).

¹HNMR (300 MHz, CDCl₃): δ 8.57-8.53 (m, 2H), 7.72-7.71 (m, 1H), 7.66-7.64 (m, 1H), 7.41-7.39 (m, 1H), 7.34-7.31 (m, 2H), 6.82 (d, J=3 Hz, 1H).

To a solution of 1,N-(2-chloropyrimid-4-yl)indole (5 g, 21.8 mmol, 1 eq) in DCM (100 mL) was added a solution of chlorosulfonic acid (12.2 g, 105 mmol, 4.8 eq) in DCM (20 mL) dropwise at 0° C. The reaction was monitored by TLC and LCMS, after completion, the mixture was filtered and the filter cake was dried affording 1,N-(2-chloropyrimid-4-yl)indole-3-sulfonic acid (8 g, crude).

¹HNMR (300 MHz, DMSO-d₆): δ 8.72-8.67 (m, 1H), 8.55 (d, J=8.4 Hz, 1H), 8.16 (s, 1H), 8.03-8.01 (m, 1H), 7.90-7.88 (m, 1H), 7.44-7.28 (m, 2H).

LCMS: (M−H)⁻: 307.6.

A67. 2-Chloro-4-(3-(N-methylsulfonylamido)indol-1-yl)pyrimidine

To a solution of 1,N-(2-chloropyrimid-4-yl)indole-3-sulfonic acid (2 g, 6.4 mmol, 1 eq) in CHCl₃ (20 mL) was added PCl$_5$ (4.2 g, 19.2 mmol, 3 eq). The mixture was then refluxed overnight. After TLC and LCMS indicated completion, the mixture was cooled to rt, a 2M methylamine/THF solution (12 mL) was added dropwise and the mixture was stirred at rt overnight. The mixture was diluted with water (50 mL), separated and the aqueous layer was extracted with DCM (30 mL×3). The combined organic layers were washed with brine (30 mL×3), dried over sodium sulfate, concentrated and purified by silica column affording desired product N-methyl 1,N-(2-chloropyrimid-4-yl)indole-3-sulfonamide (200 mg, 10%) as white solid.

$^1$HNMR (300 MHz, CDCl$_3$): δ 8.72 (d, J=6 Hz, 1H), 8.53 (d, J=8.4 Hz, 1H), 8.33 (s, 1H), 7.97-7.95 (m, 1H), 7.56-7.43 (m, 3H), 2.75 (s, 3H).

LCMS: (M+H)$^+$: 322.8.

A68. 2,5-Dichloro-4-(5-acetyl-6-(N-methylamino) pyrid-3-yl)pyrimidine

To a solution of methyl 5-bromo-2-chloronicotinate (5 g, 33.2 mmol, 1 eq) in THF (50 mL) was added methylamine solution (2.0 M in THF, 33 mL, 66.4 mmol, 2 eq) at room temperature. The reaction mixture was then stirred at room temperature overnight. The solvent was evaporated under reduced pressure and the residue was dissolved in ethyl acetate (100 mL) and water (50 mL). The organic layer was separated and the aqueous layer was extracted with ethyl acetate (50 mL×2). The combined organic layers were washed with brine solution (100 mL), dried over anhydrous MgSO$_4$ and evaporated under reduced pressure to provide methyl 5-bromo-2-(methylamino)nicotinate (4 g, 82%) which was used in the next step without purification.

$^1$HNMR (300 MHz, CDCl$_3$): δ 8.33 (s, 1H), 8.20 (s, 1H), 7.89 (br, 1H), 3.88 (s, 3H), 3.04 (s, 3H).

LCMS: (M+H)$^+$: 244.8.

To a solution of methyl 5-bromo-2-(methylamino)nicotinate (4 g, 16.3 mmol, 1.0 eq) in MeOH (40 mL) was added NaOH (1.3 g, 32.6 mmol, 2 eq) in water (20 mL). The mixture was stirred at t overnight. Most of MeOH was removed and the aqueous phase was adjusted to PH=1-2 with 1 N HCl. The precipitate formed was collected by filtration and dried to give 5-bromo-2-(methylamino)nicotinic acid (3.5 g, 94%) as a white solid.

$^1$HNMR (300 MHz, DMSO-d$_6$): δ 8.34 (s, 1H), 8.10 (s, 1H), 2.92 (s, 3H).

LCMS: (M+H)$^+$: 230.8.

To a solution of N,O-dimethylhydroxylamine hydrochloride (2.2 g, 22.6 mmol, 1.5 eq) in DMF (35 mL) was added DIPEA (5.1 g, 45.2 mmol, 3 eq) at rt. After 30 minutes, 5-bromo-2-(methylamino)nicotinic acid (3.5 g, 15.1 mmol, 1 eq) and HATU (8.6 g, 22.6 mmol, 1.5 eq) were added and the mixture was stirred overnight. After completion, the mixture was diluted with water (100 mL) and EA (100 mL), the organic layer was separated, washed with sat. NaCl (50 mL), dried over sodium sulfate, concentrated and purified by silica column chromatography affording N,O-dimethyl 5-bromo-2-(methylamino)nicotinic hydroxamate (2.7 g, 65%).

$^1$HNMR (300 MHz, CDCl$_3$): δ 8.25 (s, 1H), 7.88 (s, 1H), 6.70 (br, 1H), 3.57 (s, 3H), 3.35 (s, 3H), 2.81 (s, 3H).

LCMS: (M+H)$^+$: 273.8

To a solution of N,O-dimethyl 5-bromo-2-(methylamino) nicotinic hydroxamate (2.7 g, 9.85 mmol, 1.0 eq) in THF (27 mL) was added methylmagnesium bromide (1.0 M in THF, 39.5 mL, 39.5 mmol, 4 eq) dropwise at 0° C. under N$_2$. The mixture was stirred at 25° C. for 5-6 h. After completion, the mixture was adjusted to pH=5-6 with 1N HCl at 0° C., extracted with EA (25 mL×2), the organic layer was dried over sodium sulfate, concentrated to give 3-acetyl-5-bromo-2-(methylamino)pyridine (2.1 g, yield, 93%) which was used in the next step without purification.

$^1$HNMR (300 MHz, CDCl$_3$): δ 8.45 (s, 1H), 8.05 (s, 1H), 3.06 (s, 3H), 2.56 (s, 3H).

LCMS: (M+H)$^+$: 228.8.

To a solution of 3-acetyl-5-bromo-2-(methylamino)pyridine (2.1 g, 9.2 mmol, 1.0 eq) in dioxane (21 mL) were added KOAc (2.7 g, 27.6 mmol, 3 eq), bis(pinacolato)diborane (2.8 g, 11.1 mmol, 1.2 eq) and Pd(dppf)Cl$_2$CH$_2$Cl$_2$ (0.34 g, 0.46 mmol, 0.05 eq). The mixture was purged with nitrogen 3 times and then stirred at 90° C. overnight. After cooling down to it, the mixture was filtered, washed with EA (10×3 mL). The filtrate was washed with brine (25 mL×2), dried over sodium sulfate, concentrated and purified by silica column affording 2-(3-acetyl-2-(methylamino)pyrid-5-yl)-4,4,5,5-tetramethyl-1,3,2-dioxaborolane (0.65 g, 25%).

$^1$HNMR (300 MHz, CDCl$_3$): δ 9.16 (br, 1H), 8.66 (s, 1H), 8.33 (s, 1H), 3.10 (s, 3H), 2.61 (s, 3H), 1.34 (s, 12H).

To a solution of 2-(3-acetyl-2-(methylamino)pyrid-5-yl)-4,4,5,5-tetramethyl-1,3,2-dioxaborolane (650 mg, 2.4 mmol, 1.0 eq) in dioxane (6.5 mL) and water (1.3 mL) were added 2,4,5-trichloropyrimidine (524 mg, 2.9 mmol, 1.2 eq), Na$_2$CO$_3$ (509 mg, 4.8 mmol, 3.0 eq) and Pd(dppf)Cl$_2$CHCl$_2$ (88 mg, 0.12 mmol, 0.05 eq). The mixture was bubbled with nitrogen for 10 minutes, then purged with nitrogen 3 times and stirred at 100° C. overnight. After cooling down to rt, the mixture was filtered, washed with EA (5×3 mL). The filtrate was washed with brine (5 mL×2), dried over sodium sulfate, concentrated and purified by silica column affording 2,5-dichloro-4-(5-acetyl-6-(N-methylamino)pyrid-3-yl)pyrimidine (260 mg, 37%).

$^1$HNMR (300 MHz, CDCl$_3$): δ 9.32 (br, 1H), 9.13 (s, 1H), 8.74 (s, 1H), 8.59 (s, 1H), 3.18 (s, 3H), 2.66 (s, 3H). LCMS: (M+H)$^+$: 296.7

A69. Methyl 4-(2-chloropyrimid-4-yl)indole-7-carboxylate

To a mixture of 4-bromo-2-nitrobenzoic acid (10 g, 41 mmol, 1 eq) and K$_2$CO$_3$ (11.3 g, 82 mmol, 2 eq) in 100 mL of DMF was added CH$_3$I (7.1 g, 50 mmol, 1.2 eq) dropwise and the mixture was stirred at 80° C. for 3 hrs. After cooling to rt, the mixture was filtered, the filtrated was poured into water and extracted with EtOAc (150 mL×3), washed with water (150 mL×3) and brine (150 mL×2), dried over anhydrous Na$_2$SO$_4$ and concentrated in vacuo. The crude product was purified by column chromatography to give methyl 4-bromo-2-nitrobenzoate (10 g, 94%).

$^1$HNMR (300 MHz, DMSO-d$_6$): δ 8.34 (s, 1H), 8.08-8.05 (m, 1H), 7.85-7.82 (m, 1H), 3.85 (s, 3H).

To a solution of methyl 4-bromo-2-nitrobenzoate (10 g, 38.4 mmol, 1 eq) in 60 mL of dry THF was added vinylmagnesium bromide (1.0 M in THF, 136 mL, 136 mmol, 3.5 eq) dropwise at −60° C. under nitrogen. The reaction mixture was stirred at −30° C.~−40° C. for 2 h. Then the mixture was treated with saturated aq. NH$_4$Cl (50 mL), the resulting mixture was extracted with EtOAc (50 mL×3), the combined organic phase was washed with water (50 mL), brine (50 mL), dried over anhydrous Na$_2$SO$_4$, and concentrated. The residue was purified by column chromatography to afford methyl 4-bromoindole-7-carboxylate (3.2 g, 33%).

$^1$HNMR (300 MHz, CDCl$_3$): δ 9.98 (br, 1H), 7.76-7.73 (m, 1H), 7.39-7.33 (m, 2H), 6.67 (s, 1H), 4.00 (s, 3H).

LCMS: (M−H)$^−$: 251.8

To a solution of methyl 4-bromoindole-7-carboxylate (3.2 g, 12.6 mmol, 1 eq) in dioxane (32 mL) were added KOAc (3.7 g, 37.8 mmol, 3 eq), bis(pinacolato)diborane (3.8 g, 15.1 mmol, 1.2 eq) and Pd(dppf)Cl$_2$CH$_2$Cl$_2$ (0.46 g 0.63 mmol, 0.05 eq). The mixture was purged with nitrogen 3 times, then stirred at 90° C. overnight. After cooling down to rt, the mixture was filtered, washed with EA (10×3 mL). The filtrate was washed with brine (25 mL×2), dried over sodium sulfate, concentrated and purified by silica column affording methyl 4-(pinacolatoboryl)indole-7-carboxylate as yellow solid (1.6 g, 42%).

$^1$HNMR (300 MHz, CDCl$_3$): δ 9.86 (br, 1H), 7.88 (d, J=7.2 Hz, 1H), 7.65 (d, J=7.5 Hz, 1H), 7.38 (s, 1H), 7.10 (s, 1H), 4.00 (s, 3H), 1.42 (s, 12H).

LCMS: (M-14+H)$^+$: 287.8

To a solution of methyl 4-(pinacolatoboryl)indole-7-carboxylate (1.6 g 5.3 mmol, 1.0 eq) in DME (16 mL) and water (3.2 mL) were added 2,4-dichloropyrimidine (1.16 g, 6.4 mmol, 1.2 eq), Na$_2$CO$_3$ (1.12 g, 10.6 mmol, 2.0 eq) and Pd(PPh$_3$)$_4$ (0.36 g, 0.27 mmol, 0.05 eq). The mixture was bubbled with nitrogen for 10 minutes, then purged with nitrogen 3 times and stirred at 80° C. overnight. After cooling down to rt, the mixture was filtered, washed with EA (10 mL×3). The filtrate was concentrated and purified by silica column affording methyl 4-(2-chloropyrimid-4-yl)indole-7-carboxylate (1.1 g, 71%).

$^1$HNMR (300 MHz, CDCl$_3$): δ 10.15 (br, 1H), 8.73 (d, J=5.4 Hz, 1H), 8.01 (d, J=8.1 Hz, 1H), 7.83 (d, J=5.4 Hz, 1H), 7.76-7.74 (m, 1H), 7.51 (s, 1H), 7.22-7.21 (m, 1H), 4.05 (s, 3H).

LCMS: (M-14+H)$^+$: 287.7

A70. 1-(2-Chloropyrimidin-4-yl)-3-(N-oxolan-3-ylamino)-1H-indazole

To a four-neck flask were added THF (122 mL) and 3-iodoindazole (12.2 g, 50 mmol, 1.0 eq). After cooling down to 0° C. NaH (2.4 g, 60 mmol, 1.2 eq) was added carefully. The mixture was stirred at this temperature for 10 minutes till no gas bubbled. Then TrtCl (15 g, 55 mmol, 1.1 eq) was added. The mixture was stirred at rt for 2 h. After completion, the mixture was quenched by addition of water (10 mL) at 0° C., and then extracted with EA (100 mL×3). The combined organic layers were washed with brine (100 mL×2), concentrated and purified by column chromatography on silica to give 3-iodo-1,N-tritylindazole (17 g, 70%).

To a solution of 3-iodo-1,N-tritylindazole (8 g, 16.46 mmol, 1 eq) in DMSO (80 mL) were added CuI (0.626 g, 3.3 mmol, 0.2 eq), K$_3$PO$_4$ (13.96 g, 65.8 mmol, 4 eq), L-proline (0.756 g, 6.6 mmol, 0.2 eq) and tetrahydrofuran-3-amine hydrochloride (4 g, 32.92 mmol, 2 eq). The mixture was bubbled with nitrogen for 2 mins, then stirred at 60° C. for 4 h. The mixture was monitored by TLC and LCMS, after completion, the mixture was poured into water (200 mL) and extracted with EA (100 mL×3). The combined organic layers were washed with brine (100 mL×2), concentrated and purified by column chromatography on silica to give 3-(N-oxolan-3-ylamino)-1,N-tritylindazole (4.6 g, 63%).

$^1$HNMR (300 MHz, DMSO-d$_6$): δ 7.68-7.66 (m, 1H), 7.36-7.18 (m, 15H), 6.99-6.85 (m, 2H), 6.34-6.26 (m, 2H), 3.99-3.97 (m, 1H), 3.76-3.65 (m, 3H), 3.54-3.49 (m, 1H), 2.09-2.03 (m, 1H), 1.87-1.83 (m, 1H).

LCMS: (M+H)$^+$: 445.9.

To a solution of 3-(N-oxolan-3-ylamino)-1,N-tritylindazole (4.6 g, 10.33 mmol, 1.0 eq) in DCM (20 mL) was added TFA (10 mL). The reaction mixture was stirred at 25° C. for 1 h. Concentrated and adjusted to pH=8 with sat. NaHCO$_3$, extracted with DCM (100 mL×2), the combined organic layers were washed with brine, dried over sodium sulfate, concentrated and purified by silica column affording 3-(N-oxolan-3-ylamino)indazole (1.2 g, 57%).

$^1$HNMR (300 MHz, DMSO-d$_6$): δ 11.45 (s, 1H), 7.72-7.70 (m, 1H), 7.22 (s, 2H), 6.90-6.88 (m, 1H), 6.14-6.12 (m, 1H), 4.23-4.21 (m, 1H), 3.93-3.84 (m, 2H), 3.73-3.61 (m, 2H), 2.09-2.03 (m, 1H), 1.87-1.83 (m, 1H).

LCMS: (M+H)$^+$: 204.0.

To a 100 mL four-neck flask were added DMF (15 mL) and 3-(N-oxolan-3-ylamino)indazole (1.2 g, 5.91 mmol, 1.0 eq). After cooling down to 0° C., tBuOK (0.794 g, 7.09 mmol, 1.2 eq) was added. The mixture was stirred at this temperature for 30 minutes. Then a solution of compound 2,4-dichloropyrimidine (0.968 g, 6.5 mmol, 1.1 eq) in DMF (4 mL) was added. The mixture was stirred at it for 4 h, TLC and LCMS indicated completion, the mixture was poured into water (60 mL), filtered and the filter cake was washed with water (10 mL×3), dried in vacuo to give 1-(2-chloropyrimidin-4-yl)-3-(N-oxolan-3-ylamino)-1H-indazole (0.9 g 48%).

LCMS: (M-72+H)$^+$: 244.7.

A71. 1-(2-Chloropyrimidin-4-yl)-3-(N-cyclopropylmethylamino)-1H-indazole

To a solution of 1,N-(2-chloropyrimid-4-yl)-3-iodoindazole (4 g, 11.2 mmol, 1 eq) in DMSO (40 mL) were added CuI (0.426 g, 2.25 mmol, 0.2 eq), K$_3$PO$_4$ (5.95 g, 28.09 mmol, 2.5 eq), L-proline (0.516 g, 4.5 mmol, 0.2 eq) and cyclopropylmethanamine (1.148 g, 16.8 mmol, 1.5 eq). The mixture was bubbled with nitrogen for 2 mins, then stirred at 60° C. for 4 h. The mixture was monitored by TLC and LCMS. After completion, the mixture was poured into water (200 mL) and extracted with EA (60 Ml×3). The combined organic layers were washed with brine (60 mL×2), concentrated and purified by column chromatography on silica to give 1-(2-chloropyrimidin-4-yl)-3-(N-cyclopropylmethylamino)-1H-indazole (0.3 g, 9/%).

LCMS: (M+H)$^+$: 299.8.

A72. 7-Cyano-5-(2-chloropyrimidin-4-yl)-3-methyl-1H-indole

To a solution of anthranilonitrile (5 g, 42.3 mmol, 1.0 eq) in MeCN (100 mL) was added NBS (18.8 g, 105 mmol, 2.5 eq) portionwise at 0° C. The mixture was stirred at rt overnight, TLC indicated completion. The reaction was poured into ice-water (200 mL), extracted with EA (200 mL×3). The combined organic layers were washed with brine (200 mL×3), dried over sodium sulfate, concentrated affording 2-amino-3,5-dibromobenzonitrile (7 g, crude) which was used in next step directly.

$^1$HNMR (300 MHz, CDCl$_3$): δ 7.74 (s, 1H), 7.50 (s, 1H), 4.91 (br, 2H).

To a solution of 2-amino-3,5-dibromobenzonitrile (2.75 g, 10 mmol, 1.0 eq) in THF (20 mL) was added a solution of t-BuOK (1.68 g, 15 mmol, 1.5 eq) in THF dropwise at 0° C. The mixture was kept at this temperature for 10 min. Then 3-bromoprop-1-ene (1.2 g, 10 mmol, 1 eq) was added dropwise and the mixture was stirred at rt for 2 h. After TLC and LCMS indicated completion, the mixture was quenched with water (100 mL), extracted with EA (100 mL×3). The combined organic layers were washed with brine (100 mL×2), dried over sodium sulfate, concentrated affording 2-(N-allylamino)-3,5-dibromobenzonitrile (2 g, crude) which was used in next step directly.

¹HNMR (300 MHz, CDCl₃): δ 7.73 (s, 1H), 7.51 (s, 1H), 6.01-5.92 (m, 1H), 5.34-5.25 (m, 2H), 4.31 (d, J=5.4 Hz, 2H).

To a solution of 2-(N-allylamino)-3,5-dibromobenzonitrile (1.2 g, 3.8 mmol, 1.0 eq) in MeCN (10 mL) were added TEA (6.8 g, 67 mmol, 18 eq), Pd(OAc)₂ (85 mg, 0.38 mmol, 0.1 eq) and trio-tolylphosphine (231 mg, 0.76 mmol, 0.2 eq). The mixture was purged with nitrogen three times, then refluxed for 2 hours. After TLC and LCMS indicated completion, the mixture was diluted with water (30 mL), extracted with EA (50 mL×3). The combined organic layers were washed with sat. NH₄Cl (50 mL), dried over sodium sulfate, concentrated and purified on silica column affording 5-bromo-7-cyano-3-methylindole (500 mg, 51%).

¹HNMR (300 MHz, CDCl₃): δ 8.67 (br, 1H), 7.92 (s, 1H), 7.60 (s, 1H), 7.12 (s, 1H), 2.32 (s, 3H).

To a solution of 5-bromo-7-cyano-3-methylindole (500 mg, 2.1 mmol, 1.0 eq) in dioxane (50 mL) were added bis(pinacolato)diboron (592 mg, 2.3 mmol, 1.1 eq), KOAc (125 mg, 6.3 mol, 3 eq) and Pd(dppf)Cl₂ (124 mg, 0.168 mmol, 0.08 eq). The mixture was purged with nitrogen three times, then heated at 85° C. under nitrogen for 6 hours. After TLC and LCMS indicated completion, the mixture was filtered, the filtrate was concentrated and purified on silica column affording 2-(7-cyano-3-methylindol-5yl)-4,4,5,5-tetramethyl-1,3,2-dioxaborolane (310 mg, 51%).

¹HNMR (300 MHz, CDCl₃): δ 8.56 (br, 1H), 8.29 (s, 1H), 7.98 (s, 1H), 7.09 (s, 1H), 2.37 (s, 3H), 1.39 (s, 12H).

LCMS: (M−H)⁻: 280.9.

To a solution of 2-(7-cyano-3-methylindol-5yl)-4,4,5,5-tetramethyl-1,3,2-dioxaborolane (282 g, 1 mmol, 1.0 eq) in dioxane (5 mL) and water (1 mL) were added 2,4-dichloropyrimidine (162 mg, 1.1 mmol, 1.1 eq), Pd(PPh₃)₄ (115 mg, 0.1 mmol, 0.1 eq) and K₂CO₃ (411 mg, 3 mmol, 3 eq). The mixture was purged with nitrogen three times, then heated at 100° C. under nitrogen for 3 hours. After TLC and LCMS indicated completion, the mixture was filtered, the filtrate was concentrated and purified on silica column affording 7-cyano-5-(2-chloropyrimidin-4-yl)-3-methyl-1H-indole (150 mg, 55%).

¹HNMR (300 MHz, DMSO-d₆): δ 8.75 (d, J=5.4 Hz, 1H), 8.68 (s, 1H), 8.36 (s, 1H), 8.25 (d, J=5.4 Hz, 1H), 7.37 (s, 1H), 2.35 (s, 3H).

LCMS: (M−H)⁻: 266.8.

A73. 1,N-(2-Chloropyrimidin-4-yl)-3-(cyclopropylamino)indazole

A 500 mL four-neck flask was charged with DMF (80 mL) and 3-iodoindazole (5 g, 20 mmol, 1 eq). After cooling down to 0° C., NaH (0.96 g, 24 mmol, 1.2 eq) was added carefully. The mixture was stirred at this temperature for 10 minutes till no gas bubbled. Then a solution of compound 2,4-dichloropyrimidine (3.28 g, 22 mmol, 1.1 eq) was added. The mixture was stirred at RT overnight. After completion, the mixture was quenched with aq sat.NH₄Cl (20 mL) and then diluted with water (300 mL), extracted with EA (200 mL×3). The combined organic layers were washed with water (300 mL×2), concentrated and purified by column chromatography on silica to give the desired product 1,N-(2-chloropyrimidin-4-yl)-3-iodoindazole (5 g, 70%).

¹HNMR (300 MHz, CDCl₃) δ 8.78 (d, J=8.4 Hz, 1H), 8.60 (d, J=5.7 Hz, 1H), 7.94 (d, J=5.7 Hz, 1H), 7.72-7.67 (m, 1H), 7.57 (d, J=7.8 Hz, 1H), 7.48-7.43 (m, 1H).

LCMS: (M+H)⁺: 356.6.

To a sealed tube were added DMSO (40 mL), followed by 1,N-(2-chloropyrimidin-4-yl)-3-iodoindazole (5 g, 14.04 mmol, 1 eq), CuI (0.533 g, 2.8 mmol, 0.2 eq), K₃PO₄ (7.44 g, 35.1 mmol, 2.5 eq), L-proline (0.646 g, 2.8 mmol, 0.2 eq) and cyclopropanamine (1.2 g, 21.06 mmol, 1.5 eq). The mixture was bubbled with nitrogen for 2 mins and then stirred at 60° C. for 4 h. The reaction was monitored by TLC and LCMS. After completion, the mixture was poured into water and extracted with EA (3×60 mL). The combined organic layers were washed with brine (3×60 mL), dried over sodium sulfate, concentrated and purified on silica column affording desired product 1,N-(2-chloropyrimidin-4-yl)-3-(cyclopropylamino)indazole (0.5 g, 12%).

LCMS: (M+H)⁺: 285.9.

A74. 2,5-Dichloro-4-(3-acetylindol-1-yl)pyrimidine

To a solution of 3-acetylindole (2.0 g, 12.6 mmol) in DMF (30 mL) at 0° C. was added NaH (603 mg, 15.0 mmol, 60% purity). Then the reaction solution was stirred at 0° C. for 30 minutes. Then 2,4,5-trichloropyrimidine (2.3 g, 12.6 mmol) was added and stirred at 20° C. for another 2 hours. TLC (Petroleum ether:Ethyl acetate=3:1) indicated compound 1 (R_f=0.24) was consumed completely and one new spot (R=0.43) formed. The reaction solution was adjusted to pH=7 with saturated aqueous NH₄Cl, then extracted with EtOAc (20 mL*4). The combined organic phase were washed with saturated brine (50 mL*2), dried over Na₂SO₄ and concentrated in vacuum. The residue was purified by column chromatography (SiO₂, Petroleum ether/Ethyl acetate=1/0 to 10:1) to give 2,5-Dichloro-4-(3-acetylindol-1-yl)pyrimidine (600 mg, 16% yield) as a yellow solid.

¹H NMR 400 MHz CDCl₃: δ=8.81 (s, 1H), 8.45 (dd, J=3.2, 5.6 Hz, 1H), 8.37 (s, 1H), 7.85 (dd, J=3.2, 6.4 Hz, 1H), 7.43 (dd, J=3.2, 6.4 Hz, 2H), 2.62 (s, 3H)

ESI-MS (m/z): 306.1 (M+H)⁺

A75. 1,N-(2-Chloropyrimid-4-yl)-3-(2,N-(tetrahydropyran-2-yl)pyrazol-3-yl)pyrrolo[3,2-b]pyridine To a solution of 3-bromopyrrolo[3,2-b]pyridine (2.28 g, 11.5 mmol, 1.0 eq) in THF (20 mL) was added 2.5 N n-BuLi (4.6 mL, 11.5 mmol, 1 eq) dropwise at −78° C. After addition, the mixture was stirred at this temperature for 30 mins, then chlorotriisopropylsilane (2.6 g, 13.8 mmol, 1.2 eq) was added dropwise. After addition, the mixture was stirred at RT for 2 h. After TLC and LCMS indicated completion, the mixture was quenched by addition of water (40 mL), extracted with EA (40 mL×2). The combined organic layers were dried, concentrated and purified by silica column affording the desired 1,N-TIPS pyrrolopyridine (3.1 g, 77%).

¹HNMR (300 MHz, CDCl₃): δ 8.57 (d, J=4.5 Hz, 1H), 7.79 (d, J=8.7 Hz, 1H), 7.51 (s, 1H), 7.18-7.13 (m, 1H), 1.70-1.65 (m, 3H), 1.14-1.06 (m, 18H).

LCMS: (M+H)⁺: 352.8.

To a solution of the above 1,N-TIPS pyrrolopyridine (100 mg, 0.28 mmol, 1.0 eq) in dioxane and water (5/1, v/v, 2/0.5 mL) were added 2-(2,N-(tetrahydropyran-2-yl)pyrazol-3-yl)-4,4,5,5-tetramethyl-1,3,2-dioxaborolane (82 mg, 0.28 mmol, 1 eq), K₂CO₃ (117 mg, 0.84 mmol, 3 eq) and Pd(PPh₃)₄ (32 mg, 0.028 mmol, 0.1 eq). The mixture was purged with nitrogen three times and then stirred at 80° C. overnight. TLC and LCMS indicated completion, the mixture was quenched with water (30 mL), extracted with EA (50 mL*2). The combined organic layers were washed with brine (100 mL×2), concentrated and purified by silica column affording the desired N-tetrahydropanylated pyrazolylpyrrolopyridine (10 mg, 13%).

LCMS: (M+H)$^+$: 269.0.

A solution of the above N-tetrahydropanylated pyrazolylpyrrolopyridine (110 mg 0.0.41 mmol, 1.0 eq) in DMF (3 mL) in a 50 mL 50 mL three-neck flask was cooled to 0° C. 60% NaH (25 mg, 0.61 mmol, 1.5 eq) was added. The mixture was stirred at this temperature for 30 minutes. Then a solution of 2,4-dichloropyrimidine (60 mg, 0.41 mmol, 1 eq) in DMF (1 mL) was added. The mixture was stirred at RT for 2 h, TLC and LCMS indicated completion, and the mixture was poured into water (40 mL), filtered and the filter cake was washed with water (3×10 mL), dried and purified by silica column to give 1,N-(2-chloropyrimid-4-yl)-3-(2,N-(tetrahydropyran-2-yl)pyrazol-3-yl)pyrrolo[3,2-b]pyridine (10 mg 6.4%).

LCMS: (M+H)$^+$: 380.8.

A76. 1-(2-Chloropyrimidin-4-yl)-3-(1H-pyrazol-4-yl)-1H-indole

To a solution of pyrazole (60 g, 882 mmol, 1 eq) in toluene (250 mL) was added TFA (3.4 mL). The mixture was heated to 80° C. then 3,4-dihydro-2H-pyran (78 g, 926 mmol, 1.05 eq) was added dropwise over a period of 60 min. After addition, the reaction was stirred at this temperature for 2 h till TLC indicated completion. The mixture was concentrated in vacuo affording 1,N-tetrahydropyran-2-ylpyrazole (140 g, crude) which was used in next step directly.

To a solution of 1,N-tetrahydropyran-2-ylpyrazole (43 g, 0.28 mol, 1 eq) in THF (400 mL) was added n-BuLi (2.5 M, 120 mL, 0.31 mol, 1.1 eq) dropwise at −50° C. The mixture was stirred at this temperature for 1 h, then Triisopropyl borate (58 g, 0.31 mol, 1.1 eq) was added dropwise over 10 minutes, followed by pinacol (36 g, 0.31 mol, 1.1 eq) and HOAc (2 eq). The mixture was then stirred at RT for 4 h. After completion, the mixture was quenched with sat. NaHCO$_3$, extracted with PE, the organic layer was washed with brine, dried over sodium sulfate, concentrated and purified by silica column, then recrystallized (PE:MTBE=4:1) affording the desired pinacolborated pyrazole (20 g, 25%).

$^1$HNMR (300 MHz, CDCl$_3$): δ 7.59 (s, 1H), 6.76 (s, 1H), 5.89-5.85 (m, 1H), 4.09-4.05 (m, 1H), 3.72-3.64 (m, 1H), 2.50-2.42 (m, 1H), 2.10-1.97 (m, 2H), 1.78-1.70 (m, 2H), 1.68-1.56 (m, 1H), 1.35 (s, 12H).

LCMS: (M+H)$^+$:279.0.

To a solution of 3-iodo-1,N-(phenylsulfonyl)indole (2 g, 5.2 mmol, 1 eq) in DMF/H$_2$O (15 mL/3 mL) was added the above pinacolborated pyrazole (1.8 g, 6.7 mmol, 1.3 eq), Cs$_2$CO$_3$ (5 g, 15.6 mmol, 3 eq) and Pd(dppf)Cl$_2$ (570 mg, 0.78 mmol, 0.15 eq) The mixture was purged with nitrogen 3 times, then heated to reflux till completion. After cooling down to RT, the mixture was diluted with water (50 mL), extracted with EA (50 mL×3). The combined organic layers were washed with brine, dried over sodium sulfate, concentrated and purified by silica column affording the desired N,N'-diprotected pyrazolylindole (1.42 g, 49%).

$^1$HNMR (300 MHz, CDCl$_3$): δ 8.19-8.17 (m, 1H), 8.10-8.08 (m, 2H), 7.96 (s, 1H), 7.70-7.27 (m, 7H), 6.54-6.51 (m, 1H), 5.24-5.20 (m, 1H), 4.22-4.10 (m, 1H), 3.71-3.65 (m, 1H), 2.64-2.60 (m, 1H), 2.27-2.06 (m, 2H), 1.94-1.90 (m, 1H), 1.81-1.77 (m, 1H), 1.63-1.56 (m, 1H).

LCMS: (M-DHP+H)$^+$: 323.8.

The phenylsulfonyl group was selectively cleaved from the above N,N'-diprotected pyrazolylindole (1.4 g, 3.4 mmol, 1.0 eq) by treatment with KOH (952 mg, 17 mmol, 5 eq) in EtOH (7 mL). The mixture was stirred at 40° C. overnight. TLC and LCMS indicated completion, the mixture was diluted with EA (70 mL), dried over sodium sulfate, concentrated and purified by silica column chromatography affording 3-(indol-2-yl)-2,N-(tetrahydropyranyl)pyrazole (200 mg, 22%).

$^1$HNMR (300 MHz, CDCl$_3$): δ 8.58 (br, 1H), 7.80-7.67 (m, 2H), 7.52-7.49 (m, 2H), 7.33-7.22 (m, 2H), 6.55 (s, 1H), 5.39 (d, J=8.1 Hz, 1H), 4.19-4.16 (m, 1H), 3.67-3.59 (m, 1H), 2.75-2.67 (m, 1H), 2.25-1.85 (m, 3H), 1.71-1.58 (m, 2H).

LCMS: (M+H)$^+$: 267.9.

To a solution of 3-(indol-2-yl)-2,N-(tetrahydropyranyl) pyrazole (150 mg, 0.56 mmol, 1.0 eq) in THF (10 mL) was added NaH (34 mg, 0.84 mmol, 1.5 eq) portion wise at 0° C., the mixture was kept at 0° C. for 30 minutes. Then a solution of 2,4-dichloropyrimidine (99 mg, 0.67 mmol, 1.2 eq) in THF (3 mL) was added dropwise. After addition, the mixture was stirred at room temperature for 3 h. The reaction mixture was quenched with water (50 mL). Extracted with EA, dried over sodium sulfate, concentrated and purified by silica column chromatography affording the desired 4-indolylpyrimidine (150 mg, 75%).

LCMS: (M+H)$^+$:379.9.

The above 4-indolylpyrimidine (100 mg, 0.26 mmol, 1 eq) was dissolved in MeOH (3 mL), then 4N HCl/dioxane (2.6 mmol, 10 eq) was added. The mixture was stirred at RT till completion. The mixture was adjusted to pH=8 with sat. NaHCO$_3$, extracted with EA, washed with brine, dried and concentrated to give the desired deprotected pyrazole (60 mg, 78%).

LCMS: (M+H)$^+$: 295.9.

To a solution of the above deprotected pyrazole (200 mg, 0.67 mmol, 1 eq) and DMAP (8 mg, 0.067 mmol, 0.1 eq) in MeCN (10 mL) was added Boc$_2$O (175 mg, 0.8 mmol, 1.2 eq). The mixture was then stirred at RT overnight. After TLC indicated completion, the mixture was diluted with EA (20 mL), washed with water (20 mL×2) and brine (20 mL×2). The organic layer was dried over sodium sulfate, concentrated and purified by silica column affording tert-butyl 5-(1-(2-chloropyrimidin-4-yl)-1H-indol-3-yl)-1H-pyrazole-1-carboxylate (100 mg, 37%). LCMS: (M-Boc+H)$^+$: 295.9.

A77. 1-(2-chloropyrimidin-4-yl)-3-(1H-pyrazol-5-yl)-1H-indole

A solution of indole (5 g, 42.7 mmol, 1 eq) in 50 mL of DMF was treated with KOH (6 g, 107 mmol, 2.5 eq) and allowed to stir at room temperature for 20 min. I$_2$ (11.9 g, 47 mmol, 1.1 eq) was dissolved in 5 mL of DMF and added to the reaction. The resulting solution was stirred for an additional 1 h. The reaction mixture was poured into 400 mL of ice water and the precipitate was collected by filtration, washed with water and dried by azeotropic distillation with toluene to yield 3-iodoindole as a beige powder (8 g, 77%).

LCMS: (M+H)$^+$: 243.8.

To a solution of NaOH (6.6 g, 166 mmol, 1.3 eq) dissolved in water (40 mL) and Bu$_4$NHSO$_4$ (440 mg, 1.3 mmol, 0.01 eq) was added 3-iodoindole (31 g, 128 mmol, 1 eq) at 0° C., then benzenesulfonyl chloride (45 g, 256 mmol, 2 eq) in THF (30 mL) was added dropwise. The mixture was allowed to react for 3 h at room temperature. The mixture was extracted with ethyl acetate. The extract was dried with magnesium sulfate, and then concentrated. Purification by flash column chromatography from EtOAc-n-hexane affords 1,N-benzenesulfonyl-3-iodoindole (31 g, 61%).

¹HNMR (300 MHz, CDCl₃): δ 8.00-7.93 (m, 3H), 7.72 (s, 1H), 7.64-7.55 (m, 1H), 7.49-7.38 (m, 2H), 7.37-7.27 (m, 3H).

LCMS: (M+H)⁺: 383.8.

To a solution of 1,N-benzenesulfonyl-3-iodoindole (5 g, 13 mmol, 1 eq) in DMF/H₂O (65 mL/15 mL) was added tert-butyl 4-(4,4,5,5-tetramethyl-1,3,2-dioxaborolan-2-yl)-1H-pyrazole-1-carboxylate (4.6 g, 15.6 mmol, 1.2 eq), Cs₂CO₃ (12.6 g, 39 mmol, 3 eq) and Pd(dppf)Cl₂ (1.4 g, 1.95 mmol, 0.15 eq). The mixture was purged with nitrogen 3 times, then heated to reflux till completion. After cooling down to RT, the mixture was diluted with water (50 mL), extracted with EA (50 mL*3). The combined organic layers were washed with brine, dried over sodium sulfate, concentrated and purified by silica column affording the desired N-sulfonated pyrazolylindole (2 g, 48%).

LCMS: (M+H)⁺: 323.8.

To a solution of the above N-sulfonated pyrazolylindole (500 mg, 1.5 mmol, 1 eq) in toluene (10 mL) was added TFA (0.3 mL). The mixture was heated to 80° C. then 3,4-dihydro-2H-pyran (133 mg, 1.58 mmol, 1.05 eq) was added dropwise. After addition, the reaction was stirred at this temperature for 2 h till TLC indicated completion. The mixture was concentrated in vacuo affording the desired N-sulfonated-N-tetrahydropyranated pyrazolylindole (610 mg, crude) which was used in next step directly.

LCMS: (M+H)⁺: 407.8.

The phenylsulfonyl group was selectively cleaved from the above N,N'-diprotected pyrazolylindole (610 mg, 1.5 mmol, 1.0 eq) by treatment with KOH (419 mg, 7.5 mmol, 5 eq), in EtOH (10 mL). The mixture was stirred at 40° C. overnight. TLC and LCMS indicated completion, the mixture was diluted with EA (70 mL), washed with brine, dried over sodium sulfate, concentrated and purified by silica column chromatography affording the desired N-tetrapyranated pyrazoloindole (300 mg, 75%).

LCMS: (M+H)⁺: 267.9.

To a solution of the above N-tetrapyranated pyrazoloindole (1 g, 3.7 mmol, 1.0 eq) in DMF (10 mL) was added NaH (225 mg, 5.6 mmol, 1.5 eq) portion wise at 0° C., the mixture was kept at 0° C. for 30 minutes. Then a solution of 2,4-dichloropyrimidine (652 mg, 4.44 mmol, 1.2 eq) in THF (25 mL) was added dropwise. After addition, the mixture was stirred at room temperature for 3 h. The reaction mixture was quenched with water (50 mL), extracted with EA, dried over sodium sulfate, concentrated and purified by silica column chromatography affording 1-(2-chloropyrimidinm-4-yl)-3-(1,N-tetrahydropyran-2-yl-1H-pyrazol-4-yl)-1H-indole (400 mg, 28%).

LCMS: (M+H)⁺: 379.8.

1-(2-chloropyrimidin-4-yl)-3-(1,N-tetrahydropyran-2-yl-1H-pyrazol-4-yl)-1H-indole (100 mg, 0.26 mmol, 1 eq) was dissolved in MeOH (3 mL), then 4N HCl/dioxane (2.6 mmol, 10 eq) was added. The mixture was stirred at RT till completion. The mixture was adjusted to pH=8 with sat. NaHCO₃, extracted with EA, washed with brine, dried and concentrated to give 1-(2-chloropyrimidin-4-yl)-3-(H-pyrazol-4-yl)-1H-indole (50 mg, 65%).

LCMS: (M+H)⁺: 295.8.

A78. 2-Chloro-4-(1,N-methylindazol-3-yl)pyrimidine

To a solution of 2-chloro-4-(indazol-3-yl)pyrimidine (2.84 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na₂SO₄ and concentrated in vacuum to give 2-chloro-4-(1,N-methylindazol-3-yl)pyrimidine as a white solid.

A79. 2-Chloro-4-(N-(trideuteriomethyl)indazol-3-yl) pyrimidine

To a solution of 2-chloro-4-(indazol-3-yl)pyrimidine (2.84 g, 12.3 mmol) in DMF (30 mL) at 0° C. is added NaH (60% in mineral oil, 354.53 mg, 14.8 mmol). After 1 hr CD₃I (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na₂SO₄ and concentrated in vacuum to give 2-chloro-4-(1,N-(trideuteriomethyl)indazol-3-yl)pyrimidine as a white solid.

A80. 2-Chloro-4-benzimidaz-1-ylpyrimidine

To a solution of benzimidazole 2.54 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture was allowed to stir at 15° C. for 12 hrs. The resulting mixture is quenched with water (200 mL) and the mixture is extracted with EtOAc (100 mL×3), and washed with water (100 mL×4), dried with Na₂SO₄ and concentrated in vacuo. The residue is purified by silica gel chromatography (petroleum ether:EtOAc=10:1), to give 2-chloro-4-benzimidaz-1-ylpyrimidine. See BMCL 2004, 14, 2245.

A81. 2-Chloro-4-(pyrrolo[3,2-b]pyrid-1-yl)pyrimidine

To a solution of pyrrolo[3,2-b]pyridine (2.54 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with Na₂SO₄ and concentrated in vacuo. The residue is purified by silica gel chromatography (petroleum ether:EtOAc=10:1), to give 2-chloro-4-(pyrrolo[3,2-b]pyrid-1-ylpyrimidine.

A82. 2-Chloro-4-(pyrrolo[3,2-c]pyrid-1-yl)pyrimidine

To a solution of pyrrolo[3,2-c]pyridine (2.54 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with Na₂SO₄ and concentrated in vacuo. The residue is purified by silica gel chromatography (petroleum ether:EtOAc=10:1), to give 2-chloro-4-(pyrrolo[3,2-c]pyrid-1-ylpyrimidine.

A83. 2-Chloro-4-(pyrrolo[2,3-c]pyrid-1-yl)pyrimidine

To a solution of pyrrolo[2,3-c]pyridine (2.54 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(pyrrolo[3,2-c]pyrid-1-ylpyrimidine.

A84. 2-Chloro-4-(pyrrolo[2,3-b]pyrid-1-yl)pyrimidine

To a solution of pyrrolo[2,3-b]pyridine (2.54 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(pyrrolo[3,2-b]pyrid-1-ylpyrimidine.

A85. 2-Chloro-4-(3-methylpyrrolo[3,2-b]pyrid-1-yl)pyrimidine

To a solution of 3-methylpyrrolo[3,2-b]pyridine (2.84 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(3-methylpyrrolo[3,2-b]pyrid-1-ylpyrimidine.

A86. 2-Chloro-4-(3-chloropyrrolo[3,2-b]pyrid-1-yl)pyrimidine

To a solution of 3-chloropyrrolo[3,2-b]pyridine (3.28 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(3-chloropyrrolo[3,2-b]pyrid-1-ylpyrimidine.

A87. 2-Chloro-4-(5-methylpyrrolo[3,2-b]pyrid-1-yl)pyrimidine

To a solution of 5-methylpyrrolo[3,2-b]pyridine (2.84 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(5-methylpyrrolo[3,2-b]pyrid-1-ylpyrimidine.

A88. 2-Chloro-4-(5-methylpyrrolo[2,3-c]pyrid-1-yl)pyrimidine

To a solution of 5-methylpyrrolo[2,3-c]pyridine (2.84 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(5-methylpyrrolo[2,3-c]pyrid-1-ylpyrimidine.

A89. 2-Chloro-4-(4-methylpyrrolo[3,2-c]pyrid-1-yl)pyrimidine

To a solution of 4-methylpyrrolo[3,2-c]pyridine (2.84 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(4-methylpyrrolo[3,2-c]pyrid-1-ylpyrimidine.

A90. 2-Chloro-4-(6-methylpyrrolo[3,2-c]pyrid-1-yl)pyrimidine

To a solution of 6-methylpyrrolo[3,2-c]pyridine (2.84 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(6-methylpyrrolo[3,2-c]pyrid-1-ylpyrimidine.

A91. 2-Chloro-4-(pyrazolo[4,3-b]pyrid-1-yl)pyrimidine

To a solution of pyrazolo[4,3-b]pyridine (2.56 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12

A92. 2-Chloro-4-(pyrazolo[4,3-c]pyrid-1-yl)pyrimidine

To a solution of pyrazolo[4,3-c]pyridine (2.56 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(pyrazolo[4,3-c]pyrid-1-ylpyrimidine.

A93. 2-Chloro-4-(pyrazolo[3,4-c]pyrid-1-yl)pyrimidine

To a solution of pyrazolo[3,4-c]pyridine (2.56 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(pyrazolo[3,4-c]pyrid-1-ylpyrimidine.

A94. 2-Chloro-4-(pyrazolo[3,4-b]pyrid-1-yl)pyrimidine

To a solution of pyrazolo[3,4-b]pyridine (2.56 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with $Na_2SO_4$ and concentrated in vacuo. The residue is purified by silica gel chromatography (petroleum ether:EtOAc=10:1), to give 2-chloro-4-(pyrazolo[3,4-b]pyrid-1-ylpyrimidine.

95. 2,5-Dichloro-4-indol-1-ylpyrimidine

To a solution of indole (3.93 g, 33.56 mmol) in DMF (50 mL) was added NaH (60% in mineral oil, 1.61 g, 40.27 mmol) portionwise at 0° C. After stirring at 0° C. for 30 min, 2,4,5-triichloropyrimidine (5.00 g, 33.56 mmol) was added, then the mixture was allowed stirred at 15° C. for 12 hrs. The resulting mixture was quenched with water (300 mL) and the mixture was extracted with EtOAc (200 mL×3), the combined organic layers were washed with water (300 mL×4), dried with $Na_2SO_4$ and concentrated in vacuo. The residue was purified by silica gel chromatography (petroleum ether:EtOAc=10:1), to give 2,5-dichloro-4-indol-1-ylpyrimidine (2.00 g, 26%) as white solid.

A96. 2,5-Dichloro-4-indazol-3-ylpyrimidine

2,5-Dichloropyrimid-4-ylboronic acid 2,5-dichloropyrimidine (745 mg, 5.0 mmol) in THF (10 mL) is added dropwise to a solution of 2,2,6,6-tetramethylpiperidine zinc magnesium chloride lithium chloride complex (0.79M, 2.75 mmol) in THF (6.95 mL) (*Chem. Eur. J.* 15. 1468 (2009)), stirred under $N_2$ at 25° C. After 45 min, triisopropylborate (1.41 g, 7.5 mmol) is added, and the reaction mixture is stirred for a further 4 h at 25° C. (Tetra 61, 1417 (2005)). The reaction mixture is quenched with dilute hydrochloric acid (0.5 M, 50 mL) and extracted with EtOAc (3×25 mL). The combined extracts are washed with water (50 mL), saturated brine (50 mL) and dried ($Na_2SO_4$). The solvent is removed under reduced pressure, and the residue is dissolved up in THF (25 mL) and aqueous sodium hydroxide (1N, 25 mL) is added dropwise at 25° C. After a further 1 hr, the reaction mixture is cooled on an ice/salt bath, and the pH is lowered to 4 by dropwise addition of hydrochloric acid (6 M) keeping the internal temperature below 5° C. The aqueous solution is extracted with ethyl acetate (3×25 mL), and the organic phase is washed with water, 2×25 mL, saturated brine (25 mL) and dried ($Na_2SO_4$). The solvent is evaporated under reduced pressure, and the residue is recrystallized from diethyl ether to give 2,5-dichloropyrimid-4-ylboronic acid.

2,5-Dichloro-4-indazol-3-ylpyrimidine

1,N-(t-butoxycarbonyl)-3-iodoindazole and 2,5-dichloropyrimid-4-ylboronic acid are heated together in DMF at 80° C. in the presence of excess $K_3PO_4$, 10% tri-o-tolylphosphine and 5% $Pd(dba)_2$ for 12 hr. The reaction mixture is poured onto water, and extracted with EtOAc, washed with water, dried ($Na_2SO_4$), and the solvent removed under reduced pressure. The residual solid is dissolved in methanolic hydrogen chloride at 20° C. for 3 h, the volatiles are stripped, and the material is purified by silica gel chromatography eluting with EtOAc/hexanes to give 2,5-dichloro-4-indazol-3-ylpyrimidine. See BMCL, 2014, 24, 1327 for relevant procedures.

A97. 2,5-Dichloro-4-(1,N-methylindazol-3-yl)pyrimidine

To a solution of 2,5-dichloro-4-(indazol-3-yl)pyrimidine (3.26 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2,5-dichloro-4-(1,N-methylindazol-3-yl)pyrimidine as a white solid.

A98. 2,5-Dichloro-4-(1,N-(trideuteriomethyl)indazol-3-yl)pyrimidine

To a solution of 2,5-dichloro-4-(indazol-3-yl)pyrimidine (3.26 g, 12.3 mmol) in DMF (30 mL) at 0° C. is added NaH (60% in mineral oil, 354.53 mg, 14.8 mmol). After 1 hr $CD_3I$ (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum to give 2,5-dichloro-4-(1,N-(trideuteriomethyl)indazol-3-yl)pyrimidine as a white solid.

A99. 2-Chloro-4-indazol-3-yl-5-trifluoromethylpyrimidine

2-Chloro-5-trifluoromethylprimid-4-ylboronic acid 2-chloro-5-trifluoromethylpyrimidine (993 mg, 5.0 mmol) in THF (10 mL) is added dropwise to a solution of 2,2,6,6-tetramethylpiperidine zinc magnesium chloride lithium chloride complex (0.79M, 2.75 mmol) in THF (6.95 mL) (*Chem. Eur. J*=15. 1468 (2009)), stirred under N$_2$ at 25° C. After 45 min, triisopropylborate (1.41 g, 7.5 mmol) is added, and the reaction mixture is stirred for a further 4 h at 25° C. (Tetra 61, 1417 (2005)). The reaction mixture is quenched with dilute hydrochloric acid (0.5 M, 50 mL) and extracted with EtOAc (3×25 mL). The combined extracts are washed with water (50 mL), saturated brine (50 mL) and dried (Na$_2$SO$_4$). The solvent is removed under reduced pressure, and the residue is dissolved up in THF (25 mL) and aqueous sodium hydroxide (1N, 25 mL) is added dropwise at 25° C. After a further 1 h, the reaction mixture is cooled on an ice/salt bath, and the pH is lowered to 4 by dropwise addition of hydrochloric acid (6 M) keeping the internal temperature below 5° C. The aqueous solution is extracted with ethyl acetate (3×25 mL), and the organic phase is washed with water, 2×25 mL, saturated brine (25 mL) and dried (Na$_2$SO$_4$). The solvent is evaporated under reduced pressure, and the residue is recrystallized from diethyl ether to give 2-chloro-5-trifluoromethylpyrimid-4-ylboronic acid.

2-Chloro-4-indazol-3-yl-5-trifluoromethylpyrimidine

1,N-(t-butoxycarbonyl)-3-iodoindazole and 2-chloro-5-trifluoromethylpyrimid-4-ylboronic acid are heated together in DMF at 80° C. in the presence of excess K$_3$PO$_4$, 10% tri-o-tolylphosphine and 5% Pd(dba)$_2$ for 12 hr. The reaction mixture is poured onto water, and extracted with EtOAc, washed with water, dried (Na$_2$SO$_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-4-indazol-3-yl-5-trifluoromethylpyrimidine.

A100. 2-chloro-4-(1,N-methylindazol-3-yl)-5-trfluoromethylpyrimidine

To a solution of 2-chloro-4-indazol-3-yl-5-trifluoromethylpyrimidine (3.26 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum to give 2,5-dichloro-4-(1,N-methylindazol-3-yl)pyrimidine as a white solid.

A101. 2-Chloro-4-(1,N-(trideuteriomethyl)indazol-3-yl)-5-trifluoromethylpyrimidine To a solution of 2,5-dichloro-4-(indazol-3-yl)pyrimidine (3.67 g, 12.3 mmol) in DMF (30 mL) at 0° C. is added NaH (60% in mineral oil, 354.53 mg, 14.8 mmol). After 1 hr CD$_3$I (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum to give 2-chloro-4-(1,N-(trideuteriomethyl)indazol-3-yl)-5-trifluoromethylpyrimidine as a white solid.

A102. 2-Chloro-5-cyano-4-indazol-3-ylpyrimidine

2-Chloro-5-cyanopyrimid-4-ylboronic acid. 2-chloro-5-cyanopyrimidine (777 mg, 5.0 mmol) in THF (10 mL) is added dropwise to a solution of 2,2,6,6-tetramethylpiperidine zinc magnesium chloride lithium chloride complex (0.79M, 2.75 mmol) in THF (6.95 mL) (*Chem. Eur. J.* 15. 1468 (2009)), stirred under N$_2$ at 25° C. After 45 min, triisopropylborate (1.41 g, 7.5 mmol) is added, and the reaction mixture is stirred for a further 4 h at 25° C. (Tetra 61, 1417 (2005)). The reaction mixture is quenched with dilute hydrochloric acid (0.5 M, 50 mL) and extracted with EtOAc (3×25 mL). The combined extracts are washed with water (50 mL), saturated brine (50 mL) and dried (Na$_2$SO$_4$). The solvent is removed under reduced pressure, and the residue is dissolved up in THF (25 mL) and aqueous sodium hydroxide (1N, 25 mL) is added dropwise at 25° C. After a further 1 h, the reaction mixture is cooled on an ice/salt bath, and the pH is lowered to 4 by dropwise addition of hydrochloric acid (6 M) keeping the internal temperature below 5° C. The aqueous solution is extracted with ethyl acetate (3×25 mL), and the organic phase is washed with water, 2×25 mL, saturated brine (25 mL) and dried (Na$_2$SO$_4$). The solvent is evaporated under reduced pressure, and the residue is recrystallized from diethyl ether to give 2-chloro-5-cyanopyrimid-4-ylboronic acid.

2-Chloro-5-cyano-4-indazol-3-ylpyrimidine

1,N-(t-butoxycarbonyl)-3-iodoindazole and 2-chloro-5-cyanopyrimid-4-ylboronic acid are heated together in DMF at 80° C. in the presence of excess K$_3$PO$_4$, 10% tri-o-tolylphosphine and 5% Pd(dba)$_2$ for 12 hr. The reaction mixture is poured onto water, and extracted with EtOAc, washed with water, dried (Na$_2$SO$_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-5-cyano-4-indazol-3-ylpyrimidine.

A103. 2-chloro-5-cyano-4-(1,N-methylindazol-3-ylpyrimidine

To a solution of 2-chloro-5-cyano-4-indazol-3-ylpyrimidine (3.26 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum to give 2,5-dichloro-4-(1,N-methylindazol-3-yl)pyrimidine as a white solid.

A104. 2-Chloro-5-cyano-4-(1,N-(trideuteriomethyl)indazol-3-yl)pyrimidine

To a solution of 2-chloro-5-cyano-4-(indazol-3-yl)pyrimidine (3.14 g, 12.3 mmol) in DMF (30 mL) at 0° C. is added NaH (60% in mineral oil, 354.53 mg, 14.8 mmol). After 1 hr CD$_3$I (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum to give 2-chloro-5-cyano-4-(1,N-(trideuteriomethyl)indazol-3-yl)pyrimidine as a white solid.

A105. 1-(2,5-Dichloropyrimidin-4-yl)-1H-indazole

A solution of 1H-indazole (590.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4,5-trichloropyrimidine (917 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford the 1-(2,5-dichloropyrimidin-4-yl)-1H-indazole as a white solid.

A106. 1-(2-Chloro-5-cyanopyrimidin-4-yl)-1H-indazole

A solution of 1H-indazole (590.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-cyanopyrimidine (870 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford the 1-(2-chloro-5-cyanopyrimidin-4-yl)-1H-indazole as a white solid.

A107. 1-(2-Chloro-5-trifluoromethylpyrimidin-4-yl)-1H-indazole

A solution of 1H-indazole (590.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-trifluoromethylpyrimidine (1.085 g, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford the 1-(2-chloro-5-trifluoromethylpyrimidin-4-yl)-1H-indazole as a white solid.

A108. 1-(2-Chloropyrimidin-4-yl)-3-fluoro-1H-indazole

A solution of 3-flouroindazole (680.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4,5-trichloropyrimidine (917 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford 1-(2-chloropyrimidin-4-yl)-3-fluoro-1H-indazole as a white solid.

A109. 1-(2,5-Dichloropyrimidin-4-yl)-3-fluoro-1H-indazole

A solution of 3-fluoroindazole (680.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4,5-trichloropyrimidine (917 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford 1-(2,5-dichloropyrimidin-4-yl)-3-fluoro-1H-indazole as a white solid.

A110. 1-(2-Chloro-5-cyanopyrimidin-4-yl)-3-fluoro-1H-indazole

A solution of 3-fluoroindazole (680.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-cyanopyrimidine (870 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford the 1-(2-chloro-5-cyanopyrimidin-4-yl)-3-fluoro-1H-indazole as a white solid.

A111. 1-(2-Chloro-5-trifluoromethylpyrimidin-4-yl)-3-fluoro-1H-indazole

A solution of 3-fluoroindazole (680.5 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-trifluoromethylpyrimidine (1.085 g, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford the 1-(2-chloro-5-trifluoromethylpyrimidin-4-yl)-3-fluoro-1H-indazole as a white solid.

A112. 1-(2-Chloropyrimidin-4-yl)-3-trifluoromethyl-1H-indazole

A solution of 3-triflouromethylindazole (931 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4,5-dichloropyrimidine (745 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford 1-(2-chloropyrimidin-4-yl)-3-trifluoromethyl-1H-indazole as a white solid.

A113. 1-(2,5-Dichloropyrimidin-4-yl)-3-trifluoromethyl-1H-indazole

A solution of 3-triflouromethylindazole (931 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4,5-trichloropyrimidine (917 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford 1-(2,5-dichloropyrimidin-4-yl)-3-trifluoromethyl-1H-indazole as a white solid.

A114. 1-(2-Chloro-5-cyanopyrimidin-4-yl)-3-trifluoromethyl-1H-indazole

A solution of 3-triflouromethylindazole (931 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-cyanopyrimidine (870 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford the 1-(2-chloro-5-cyanopyrimidin-4-yl)-3-trifluoromethyl-1H-indazole as a white solid.

A115. 1-(2-Chloro-5-trifluoromethylpyrimidin-4-yl)-3-trifluoromethyl-1H-indazole A solution of 3-triflouromethylindazole (931 mg, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-trifluoromethylpyrimidine (1.085 g, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford 1-(2-chloro-5-trifluoromethylpyrimidin-4-yl)-3-trifluoromethyl-1H-indazole as a white solid.

A116. 3-Amino-1-(2-chloropyrimidin-4-yl)-1H-indazole

A solution of 3-aminoindazole (670.5 mg, 5.0 mmol) and 2-chloro-3-iodopyrimidine (1.202 g, 5 mmol) ((Chem Eur J=15, 1468 (2009)), in dry dioxan (25 mL), containing CuI (47.5 mg, 0.25 mmol) trans-1,2-diaminocyclohexane (114 mg, 1.0 mmol) and K$_3$PO$_4$ (1.06 g, 5 mmol) is refluxed under N, for 24 hrs. (Bioorg Med Chem Letters 22, 4358 (2012)) The mixture is cooled to 25° C., and quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 10/1) to afford 3-amino-1-(2-chloropyrimidin-4-yl)-1H-indazole as a white solid.

A117. 3-Amino-1-(2,5-dichloropyrimidin-4-yl)-1H-indazole

A solution of 3-aminoindazole (670.5 mg, 5.0 mmol) and 2,5-dichloro-4-iodopyrimidine (1.375 g, 5 mmol) ((Chem Eur J=15, 1468 (2009)), in dry dioxan (25 mL), containing CuI (47.5 mg, 0.25 mmol) trans-1,2-diaminocyclohexane (114 mg, 1.0 mmol) and K$_3$PO$_4$ (1.06 g, 5 mmol) is refluxed under N$_2$ for 24 hrs. (Bioorg Med Chem Letters 22, 4358 (2012)) The mixture is cooled to 25° C., and quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 10/1) to afford 3-amino-1-(2, 5-dichloropyrimidin-4-yl)-1H-indazole as a white solid.

A118. 3-Amino-1-(2-chloro-5-cyanopyrimidin-4-yl)-1H-indazole

2-Chloro-5-cyano-4-iodopyrimidine 2-chloro-5-cyanopyrimidine (698 mg, 5.0 mmol) in THF (10 mL) is added dropwise to a solution of 2,2,6,6-tetramethylpiperidine zinc magnesium chloride lithium chloride complex (0.79M, 2.75 mmol) in THF (6.95 mL) (Chem. Eur. J. 15. 1468 (2009)), stirred under N, at 25° C. After 45 min, iodine (1.27 g, 5 mmol) in THF (5 mL) is added dropwise over 5 min, and the reaction is stirred for a further 30 minutes. The reaction mixture is quenched with saturated NH$_4$Cl (100 mL) and extracted with diethyl ether (3×50 mL). The extracts are washed with water (50 mL), saturated brine (50 mL) and dried (MgSO$_4$). The solvent is removed under reduced pressure, and the residue is purified by silica gel chromatography eluting with 1:5 DCM/hexanes to give 2-chloro-5-cyano-4-iodopyrimidine as a white solid.

3-Amino-1-(2-chloro-5-cyanopyrimidin-4-yl)-1H-indazole

A solution of 3-aminoindazole (670.5 mg, 5.0 mmol) and 2-chloro-5-cyano-4-iodopyrimidine (1.326 g, 5 mmol) in dry dioxan (25 mL), containing CuI (47.5 mg, 0.25 mmol) trans-1,2-diaminocyclohexane (114 mg, 1.0 mmol) and K$_3$PO$_4$ (1.06 g, 5 mmol) is refluxed under N$_2$ for 24 hrs. (Bioorg Med Chem Letters 22, 4358 (2012)) The mixture is cooled to 25° C., and quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 10/1) to afford 3-amino-1-(2-chloro-5-cyanopyrimidin-4-yl)-1H-indazole as a white solid.

A119. 3-Amino-1-(2-chloro-5-trifluoromethylpyrimidin-4-yl-1H-indazole

2-Chloro-5-trifluoromethyl-4-iodopyrimidine 2-chloro-5-trifluoromethylpyrimidine (912 mg, 5.0 mmol) in THF (10 mL) is added dropwise to a solution of 2,2,6,6-tetramethylpiperidine zinc magnesium chloride lithium chloride complex (0.79M, 2.75 mmol) in THF (6.95 mL) (Chem. Eur. J. 15. 1468 (2009)), stirred under $N_2$ at 25° C. After 45 min, iodine (1.27 g, 5 mmol) in THF (5 mL) is added dropwise over 5 min, and the reaction is stirred for a further 30 minutes. The reaction mixture is quenched with saturated $NH_4Cl$ (100 mL) and extracted with diethyl ether (3×50 mL). The extracts are washed with water (50 mL), saturated brine (50 mL) and dried ($MgSO_4$). The solvent is removed under reduced pressure, and the residue is purified by silica gel chromatography eluting with 1:5 DCM/hexanes to give 2-chloro-5-trifluoromethyl-4-iodopyrimidine as a white solid.

3-Amino-1-(2-chloro-5-trifluoromethylpyrimidin-4-yl)-1H-indazole

A solution of 3-aminoindazole (670.5 mg, 5.0 mmol) and 2-chloro-5-trifluoromethyl-4-iodopyrimidine (1.504 g, 5 mmol) in dry dioxan (25 mL), containing CuI (47.5 mg, 0.25 mmol) trans-1,2-diaminocyclohexane (114 mg, 1.0 mmol) and $K_3PO_4$ (1.06 g, 5 mmol) is refluxed under $N_2$ for 24 hrs. (Bioorg Med Chem Letters 22, 4358 (2012)) The mixture is cooled to 25° C., and quenched with water (50 mL) and extracted with ethyl acetate (3×25 mL), washed with water (2×25 mL) and saturated brine (25 mL), and dried over $MgSO_4$. The solvent is removed under reduced pressure, and the residue is purified by column chromatography (Pet/EtOAc 10/1) to afford 3-amino-1-(2-chloro-5-trifluoromethylpyrimidin-4-yl)-1H-indazole as a white solid.

A120. 3-t-Butyldiphenylsiloxy)-1-(2-chloropyrimidin-4-yl)-1H-indazole 3-(t-Butyldiphenylsiloxy-1H-indazole A solution of 1,2-dihydroindazol-3-one (1.341 g, 10 mmol), t-butyldiphenylsilyl chloride (2.749 g, 10 mmol) and imidazole (1.02 g, 15 mmol) in DMF (20 mL) is stirred for 24 hr at 25° C. under $N_2$. The solution is added slowly to stirred ice-water, (200 mL) containing acetic acid (2 L), and the white solid is collected by vacuum filtration, rinsed copiously with water, and dried to give 3-(t-butyldiphenylsiloxy-1H-indazole, as a white solid.

3-(t-Butyldiphenylsiloxy)-1-(2-chloropyrimidin-4-yl)-1H-indazole

A solution of 3-(t-butyldiphenylsiloxy-1H-indazole (1.863 g, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloropyrimidine (750 mg, 5.0 mmol) is added. After stirring for 4 h the mixture is quenched with water (50 mL) and extracted with ethyl acetate (3×25 mL), washed with water (2×25 mL) and saturated brine (25 mL), and dried over $MgSO_4$. The solvent is removed under reduced pressure, and the residue is purified by column chromatography (Pet/EtOAc 20/1) to afford 3-(t-butyldiphenylsiloxy)-1-(2-chloropyrimidin-4-yl)-1H-indazole as a white solid.

A121. 3-(t-Butyldiphenylsiloxy)-1-(2,5-chloropyrimidin-4-yl)-1H-indazole

A solution of 3-(t-butyldiphenylsiloxy-1H-indazole (1.863 g, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4,5-trichloropyrimidine (917 mg, 5.0 mmol) is added. After stirring for 4 h the mixture is quenched with water (50 mL) and extracted with ethyl acetate (3×25 mL), washed with water (2×25 mL) and saturated brine (25 mL), and dried over $MgSO_4$. The solvent is removed under reduced pressure, and the residue is purified by column chromatography (Pet/EtOAc 20/1) to afford 3-(t-butyldiphenylsiloxy)-1-(2,5-dichloropyrimidin-4-yl)-1H-indazole as a white solid.

A122. 3-(t-Butyldiphenylsiloxy)-1-(2-chloro-5-cyanopyrimidin-4-yl)-1H-indazole

A solution of 3-(t-butyldiphenylsiloxy-1H-indazole (1.863 g, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-cyanopyrimidine (870 mg, 5.0 mmol) is added. After stirring for 4 h the mixture is quenched with water (50 mL) and extracted with ethyl acetate (3×25 mL), washed with water (2×25 mL) and saturated brine (25 mL), and dried over $MgSO_4$. The solvent is removed under reduced pressure, and the residue is purified by column chromatography (Pet/EtOAc 20/1) to afford 3-(t-butyldiphenylsiloxy)-1-(2-chloro-5-cyanopyrimidin-4-yl)-1H-indazole as a white solid.

A123. 3-(t-Butyldiphenylsiloxy)-1-(2-chloro-5-trifluoromethylpyrimidin-4-yl)-1H-indazole A solution of 3-(t-butyldiphenylsiloxy-1H-indazole (1.863 g, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloro-5-trifluoromethylpyrimidine (1.085 g, 5.0 mmol) is added. After stirring for 4 h the mixture is quenched with water (50 mL) and extracted with ethyl acetate (3×25 mL), washed with water (2×25 mL) and saturated brine (25 mL), and dried over $MgSO_4$. The solvent is removed under reduced pressure, and the residue is purified by column chromatography (Pet/EtOAc 20/1) to afford 3-(t-butyldiphenylsiloxy)-1-(2-chloro-5-trifluoromethylpyrimidin-4-yl)-1H-indazole as a white solid.

A124. 2-Chloro-4-(pyrazol-1-yl)pyrimidine

Commercially available.

A125. 2-Chloro-4-(3-methylpyrazol-1-yl)pyrimidine

Commercially available.

A126. 2-Chloro-4-(4-methylpyrazol-1-yl)pyrimidine

Commercially available.

A127.
2-Chloro-4-(3,5-dimethylpyrazol-1-yl)pyrimidine

Commercially available.

A128.
2-Chloro-4-(3,4-dimethylpyrazol-1-yl)pyrimidine

A solution of N-(2-chloropyrimid-4-yl)hydrazine (1.45 g, 10 mmol and 2-methyl-3-oxobutanal (1.00 g, 10 mmol) is stirred in MeOH (25 mL) at 25° C. for 30 min, and then refluxed for 8 hrs. The reaction mixture is cooled on an ice bath, and the solid is collected by vacuum filtration, rinsed with cold methanol (5 mL) and dried to give 2-chloro-4-(3,4-dimethylpyrazol-1-yl)pyrimidine.

A129. 2-chloro-4-(3,4,5-trimethylpyrazol-1-yl)pyrimidine

A solution of N-(2-chloropyrimid-4-yl)hydrazine (1.45 g, 10 mmol and 3-methylacetylacetone (1.14 g, 10 mmol) is stirred in MeOH (25 mL) at 25° C. for 30 min, and then refluxed for 8 hrs. The reaction mixture is cooled on an ice bath, and the solid is collected by vacuum filtration, rinsed with cold methanol (5 mL) and dried to give 2-chloro-4-(3,4,5-trimethylpyrazol-1-yl)pyrimidine.

A130. 2-Chloro-4-(3-iodo-4,5-trimethylpyrazol-1-yl)pyrimidine

3-Iodo-4,5-dimethylpyrazole is prepared as described in WO 2014/008197, and a solution of it (1.11 g, 5.0 mmol) in dry DMF (15 mL) cooled to 0° C. is treated with NaH (200 mg, 5.0 mmol, 60% in mineral oil). After stirring at 25° C. for 2 h the mixture is cooled to 0° C., and 2,4-dichloropyrimidine (745 mg, 5.0 mmol) is added. After stirring for 4 h the mixture is quenched with water (50 mL) and extracted with ethyl acetate (3×25 mL), washed with water (2×25 mL) and saturated brine (25 mL), and dried over MgSO$_4$. The solvent is removed under reduced pressure, and the residue is purified by column chromatography (Pet/EtOAc 20/1) to afford 2-chloro-4-(3-iodo-4,5-trimethylpyrazol-1-yl)pyrimidine as a white solid.

A131. 2-Chloro-4-(4-trifluoromethylmethylpyrazol-1-yl)pyrimidine

Commercially available.

A132. 2-Chloro-4-(3-trifluoromethylmethylzpyrazol-1-yl)pyrimidine

Prepared from 2,4-dichloropyrimidine and 3-trifluoromethylpyrazole as described in WO 1998/040379 p 11.

A133. 2-Chloro-4-(4,5-dimethylpyrazol-3-yl)pyrimidine

1,N-(t-Butoxycarbonyl)-3-iodo-4,5-dimethylpyrazole

3-Iodo-4,5-dimethylpyrazole is prepared as described in WO 2014/008197, and a solution of it (4.44 g, 20 mmol) is placed in a foil-covered round-bottom flask in THF (100 ml). 4-Dimethylaminopyridine (0.24 g, 1.9 mmol, 0.1 equiv) is added, followed by di-tert-butyl dicarbonate (5.4 ml, 24 mmol, 1.2 equiv). Triethylamine (5.4 ml, 39 mmol, 2.0 equiv) is slowly added to the solution by syringe, and stirred at 25° C. for a further 2 hours. The reaction mixture is diluted with water (75 ml) and extracted with EtOAc (50×3 ml). The combined organic layers are washed with water (2×50 mL), saturated brine (100 ml), dried (MgSO4), and concentrated under reduced pressure to give a red oil which is purified by chromatography over silica gel (hexanes/ethyl acetate: 100/0 to 90/10) to give 1,N-(t-butoxycarbonyl)-3-iodo-4,5-dimethylpyrazole.

2-Chloro-4-(4,5-dimethylpyrazol-3-yl)pyrimidine

1,N-(t-Butoxycarbonyl)-3-iodo-4,5-dimethylpyrazole and 2-chloropyrimid-4-ylboronic acid are heated together in DMF at 80° C. in the presence of excess K$_3$PO$_4$. 10% tri-o-tolylphosphine and 5% Pd(dba)$_2$ for 12 hr. The reaction mixture is poured onto water, and extracted with EtOAc, washed with water, dried (Na$_2$SO$_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-(4,5-dimethylpyrazol-3-yl)pyrimidine.

A134. 2-Chloro-4-(1N,4,5-trimethylpyrazol-3-yl)pyrimidine

To a solution of 2-chloro-(4,5-dimethylpyrazol-3-yl)pyrimidine (2.57 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum. The residue is purified by silica gel chromatography eluting with 0-10% EtOAc in hexanes to give 2-chloro-4-(1N,4,5-trimethylpyrazol-3-yl)pyrimidine as a white solid.

A135. 2-Chloro-4-(4,5-dimethyl-1,N-(trideuteriomethyl)pyrazol-3-yl)pyrimidine

To a solution of 2-chloro-(4,5-dimethylpyrazol-3-yl)pyrimidine (2.57 g, 12.3 mmol) in DMF (30 mL) at 0° C. is added NaH (60% in mineral oil, 354.53 mg, 14.8 mmol). After 1 hr CD$_3$I (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over Na$_2$SO$_4$ and concentrated in vacuum. The residue is purified by silica gel chromatography eluting with 0-10% EtOAc in hexanes to give 2-chloro-4-(4,5-dimethyl-1,N-(trideuteriomethyl)pyrazol-3-yl)pyrimidine as a white solid.

A136. 2-Chloro-4-(4,5,6,7-tetrahydroindazol-3-yl)pyrimidine

1,N-(t-butoxycarbonyl)-3-iodo-4,5,6,7-tetrahydroindazole

3-Iodo-4,5,6,7-tetrahydroindazole (4.96 g, 20 mmol) in THF (100 ml) is placed in a foil-covered round-bottom flask. 4-Dimethylaminopyridine (0.24 g, 1.9 mmol, 0.1 equiv) is added, followed by di-tert-butyl dicarbonate (5.4 ml, 24 mmol, 1.2 equiv). Triethylamine (5.4 ml, 39 mmol, 2.0 equiv) is slowly added to the solution by syringe, and stirred at 25° C. for a further 2 hours. The reaction mixture is diluted with water (75 ml) and extracted with EtOAc (50×3 ml). The combined organic layers are washed with water (2×50 mL), saturated brine (100 ml), dried (MgSO4), and concentrated under reduced pressure to give a red oil which is purified by chromatography over silica gel (hexanes/ethyl acetate: 100/0 to 90/10) to give 1,N-(t-butoxycarbonyl)-3-iodo-4,5,6,7-tetrahydroindazole.

2-Chloro-4-(4,5,6,7-tetrahydroindazol-3-yl)pyrimidine

1,N-(t-butoxycarbonyl)-3-iodo-4,5,6,7-tetrahydroindazole and 2-chloropyrimid-4-ylboronic acid are heated together in DMF at 80° C. in the presence of excess $K_3PO_4$. 10% tri-o-tolylphosphine and 5% $Pd(dba)_2$ for 12 hr. The reaction mixture is poured onto water, and extracted with EtOAc, washed with water, dried ($Na_2SO_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-4-(4,5,6,7-tetrahydroindazol-3-yl)pyrimidine.

A137. 2-Chloro-4-(1,N-methyl-4,5,6,7-tetrahydroindazol-3-yl)pyrimidine

To a solution of 2-chloro-4-(4,5,6,7-tetrahydroindazol-3-yl)pyrimidine (2.89 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2-chloro-4-(1,N-methyl-4,5,6,7-tetrahydroindazol-3-yl)pyrimidine as a white solid.

A138. 2-Chloro-4-(1,N-(trideuteriomethyl)-4,5,6,7-tetrahydroindazol-3-yl)pyrimidine To a solution of 2-chloro-4-(4,5,6,7-tetrahydroindazol-3-yl)pyrimidine (2.89 g, 12.3 mmol) in DMF (30 mL) at 0° C. is added NaH (60% in mineral oil, 354.53 mg, 14.8 mmol). After 1 hr $CD_3I$ (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2-chloro-4-(1,N-(trideuteriomethyl)-(4,5,6,7-tetrahydroindazol-3-yl)pyrimidine as a white solid.

A139. 2-Chloro-4-(1,4,5,6-tetrahydrocyclontapyrazol-3-yl)pyrimidine 3-iodo-1,4,5,6-tetrahydrocyclopentapyrazole N-Iodosuccinimide (5.64 g, 25 mmol is added in portions to a solution of 4,5,6,7-tetrahydrocyclopentapyrazole (2.10 g 20 mmol) in acetonitrile (50 mL) and the solution was heated to reflux for 16 hrs. The slurry is cooled to °) C, and the solids are collected by vacuum filtration, rinsed with cold acetonitrile (2×20 mL) and dried to give 3-iodo-1,4,5,6-tetrahydrocyclopentapyrazole.

1,N-(t-butoxycarbonyl)-3-iodo-1,4,5,6-tetrahydrocyclonentanpyrazole

3-Iodo-1,4,5,6-tetrahydrocyclopentapyrazole (4.68 g, 20 mmol) in THF (100 ml) is placed in a foil-covered round-bottom flask. 4-Dimethylaminopyridine (0.24 g, 1.9 mmol, 0.1 equiv) is added, followed by di-tert-butyl dicarbonate (5.4 ml, 24 mmol, 1.2 equiv). Triethylamine (5.4 ml, 39 mmol, 2.0 equiv) is slowly added to the solution by syringe, and stirred at 25° C. for a further 2 hours. The reaction mixture is diluted with water (75 ml) and extracted with EtOAc (3×50 ml). The combined organic layers are washed with water (2×50 mL), saturated brine (100 ml), dried ($MgSO_4$), and concentrated under reduced pressure to give a red oil which is purified by chromatography over silica gel (hexanes/ethyl acetate: 100/0 to 90/10) to give 1,N-(t-butoxycarbonyl)-3-iodo-1,4,5,6-tetrahydrocyclopentapyrazole.

2-Chloro-4-(1,4,5,6-tetrahydrocyclopentapyrazol-3-yl)pyrimidine

1,N-(t-butoxycarbonyl)-3-iodo-1,4,5,6-tetrahydrocyclopentapyrazole and 2-chloropyrimid-4-ylboronic acid are heated together in DMF at 80° C. in the presence of excess $K_3PO_4$, 10% tri-o-tolylphosphine and 5% $Pd(dba)_2$ for 12 hr. The reaction mixture is poured onto water, and extracted with EtOAc, washed with water, dried ($Na_2SO_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-4-(1,4,5,6-tetrahydrocyclopentapyrazol-3-yl)pyrimidine.

A140. 2-Chloro-4-(1,N-methyl-1,4,5,6-tetrahydrocyclopentapyrazol-3-yl)pyrimidine To a solution of 2-chloro-4-(1,4,5,6-tetrahydrocyclopentapyrazol-3-yl)pyrimidine (2.71 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2-chloro-4-(1,N-methyl-0,4,5,6-tetrahydrocyclopentapyrazol-3-yl)pyrimidine as a white solid.

A141. 2-Chloro-4-(1,N-(trideuteriomethyl(-1,4,5,6-tetrahydrocyclopentapyrazol-3-yl)pyrimidine To a solution of 2-chloro-4-(1,4,5,6-tetrahydrocyclopentapyrazol-3-yl)pyrimidine (2.71 g, 12.3 mmol) in DMF (30 mL) at 0° C. is added NaH (60% in mineral oil, 354.53 mg, 14.8 mmol). After 1 hr $CD_3I$ (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2-chloro-4-(1,N-(trideuteriomethyl(-1,4,5,6-tetrahydrocyclopentapyrazol-3-yl)pyrimidine as a white solid.

A142. 2-Chloro-4-(5,6-dihydrothieno[3,2-c]pyrazol-1-yl)pyrimidine

A solution of (2-((N,N-dimethylamino)methylidene)-4,5-dihydrothiophen-3-one (1.57 g, 10 mmol), prepared as described in Tetrahedron Letters 54 4171 (2013) and 2-chloropyrimid-4-ylhydrazine (2.07 g, 15 mmol) in isopropanol (30 mL) are refluxed for 4 hr. The reaction mixture is cooled to 25° C., and the solid is collected by vacuum filtration and rinsed with ethanol (2×15 mL), and dried to give 2-chloro-4-(5,6-dihydrothieno[3,2-c]pyrazol-1-yl)pyrimidine.

A143. 2-Chloro-4-(4,6-dihydrothieno[3,4-c]pyrazol-1-yl)pyrimidine

A solution of 4-((N,N-dimethylamino)methylidene)-4,5-dihydrothiophen-3-one (1.57 g, 10 mmol), prepared as described in Tetrahedron Letters 54 4171 (2013) and 2-chloropyrimid-4-ylhydrazine (2.07 g, 15 mmol) in isopropanol (30 mL) are refluxed for 4 hr. The reaction mixture is cooled to 25° C., and the solid is collected by vacuum filtration and rinsed with ethanol (2×15 mL), and dried to give 2-chloro-4-(4,6-dihydrothieno[3,4-c]pyrazol-1-yl)pyrimidine.

A144. 2-Chloro-4-(4,5-dihydro-3-iodothieno[2,3-c]pyrazol-1-yl)pyrimidine 4,5-Dihydrothieno-4-oxo[2,3-c]pyrazole Ethyl 2-thioacetate (1.20 g, 10 mmol) is added dropwise to sodium hydride (60% oil suspension 440 mg, 11 mmol) stirred in DMF (25 mL) at 25° C. When gas evolution ceases, ethyl 3-bromopyrazole-4-carboxylate (2.19 g, 10 mmol) is added in one portion, and the reaction mixture is heated to 60° C. for 4 hr. Potassium hydroxide (3M, 5 mL) is added, and after a further 2 hrs, the reaction mixture is poured onto ice-water (100 mL), acidified with hydrochloric acid (1N, 25 mL). The crude solid is collected by vacuum filtration, rinsed with MTBE (2×25 mL) and dried. The solid is heated to 200° C. until gas evolution ceases, and the material is purified by chromatography (EtOAc/hexanes) to give 4,5-dihydrothieno-4-oxo[2,3-c]pyrazole.

4,5-Dihydrothieno[2,3-c]pyrazole 4,5-Dihydrothieno-4-oxo[2,3-c]pyrazole (1.54 g, 10 mmol) and hydrazine hydrate (~50%, 2 mL) in ethylene glycol (25 mL) is heated to 100° C. for 1 hr. The reaction mixture is allowed to cool to 25° C., and potassium hydroxide (2.8 g, 50 mmol) is added and the mixture is heated rapidly to 180° C. After 20 min, the reaction mixture is allowed to cool considerably, poured onto ice water (100 mL), and extracted with EtOAc (3×25 mL). The combined extracts are washed with dilute hydrochloric acid (0.5 M, 25 mL) water (2×25 mL), saturated brine and dried ($MgSO_4$). The solvent is removed under reduced pressure and the residue purified by silica gel chromatography eluting with EtOAc/hexanes to give 4,5-dihydrothieno[2,3-c]pyrazole.

4,5-Dihydro-3-iodothieno[2,3-c]pyrazole

Dihydrothieno[2,3-c]pyrazole (0.70 g, 5 mmol), iodine (1.27 g, 5 mmol) and sodium hydroxide (0.40 g, 10 mmol) are stirred in DMF (20 mL) at 25° C. for 2 hrs. The reaction mixture is poured onto dilute hydrochloric acid (0.2 M, 50 mL) and extracted with EtOAc (3×25 mL). The combined organic extracts are washed with dilute sodium thiosulfate solution, (25 mL), water (25 mL) saturated brine (25 mL) and dried ($MgSO_4$). The solvent is removed under reduced pressure, and the residue purified by silica gel chromatography to give 4,5-dihydro-3-iodothieno[2,3-c]pyrazole.

2-Chloro-4-(4,5-dihydro-3-iodothieno[2,3-c]pyrazol-1-yl)pyrimidine 4,5-Dihydro-3-iodothieno[2,3-c]pyrazole (1.33 g, 5 mmol) and 2,4-dichloropyrimidine (745 mg, 5.0 mmol) are stirred in DMF (20 mL) containing $K_2CO_3$ (828 mg, 6 mmol) at 25° C. for 4 hrs. The reaction mixture is poured onto water (100 mL) and extracted with EtOAc (3×25 mL), and the combined extracts are rinsed with water (2×25 mL) saturated brine (25 mL) and dried ($MgSO_4$). The solvent is removed under reduced pressure and the residual solid is purified by silica gel chromatography to give 2-chloro-4-(4,5-dihydro-3-iodothieno[2,3-c]pyrazol-1-yl)pyrimidine as a white solid.

A145. 2-Chloro-4-(4,5-dihydrothieno[2,3-c]pyrazol-3-yl)pyrimidine

1,N-t-Butoxycarbonyl-4,5-dihydro-3-iodothieno[2,3-c]pyrazole

A solution of 4,5-dihydro-3-iodothieno[2,3-c]pyrazole (5.04 g, 20 mmol) in THF (100 ml) is placed in a foil-covered round-bottom flask. 4-Dimethylaminopyridine (0.24 g, 1.9 mmol, 0.1 equiv) is added, followed by di-tert-butyl dicarbonate (5.4 ml, 24 mmol, 1.2 equiv). Triethylamine (5.4 ml, 39 mmol, 2.0 equiv) is slowly added to the solution by syringe, and stirred at 25° C. for a further 2 hours. The reaction mixture is diluted with water (75 ml) and extracted with EtOAc (50×3 ml). The combined organic layers are washed with water (2×50 mL), saturated brine (100 ml), dried ($MgSO_4$), and concentrated under reduced pressure to give a red oil which is purified by chromatography over silica gel (hexanes/ethyl acetate: 100/0 to 90/10) to give 1,N-t-butoxycarbonyl-4,5-dihydro-3-iodothieno[2,3-c]pyrazole.

2-Chloro-4-(4,5-dihydrothieno[2,3-c]pyrazol-3-yl)pyrimidine

1,N-t-butoxycarbonyl-4,5-dihydro-3-iodothieno[2,3-c]pyrazole and 2-chloropyrimid-4-ylboronic acid are heated together in DMF at 80° C. in the presence of excess $K_3PO_4$, 10% tri-o-tolylphosphine and 5% $Pd(dba)_2$ for 12 hr. The reaction mixture is poured onto water, and extracted with EtOAc, washed with water, dried ($Na_2SO_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-4-(4,5-dihydrothieno[2,3-c]pyrazol-3-yl)pyrimidine.

A146. 2-Chloro-4-1,N-methyl-4,5,6,7-tetrahydroindazol-3-yl)pyrimidine

To a solution of 2-chloro-4-(4,5-dihydrothieno[2,3-c]pyrazol-3-yl)pyrimidine (2.94 g, 12.3 mmol) in DMF (30 mL) at 0° C. is added NaH (60% in mineral oil, 354.53 mg, 14.8 mmol). After 1 hr MeI (3.53 g, 24.9 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2-chloro-4-(1,N-methyl-4,5,6,7-tetrahydroindazol-3-yl)pyrimidine as a white solid.

A147. 2-Chloro-4-(1,N-(trideuteriomethyl-4,5-dihydrothieno[2,3-c]pyrazol-3-yl)pyrimidine To a solution of 2-chloro-4-(4,5-dihydrothieno[2,3-c]pyrazol-3-yl)pyrimidine (2.94 g, 12.3 mmol) in DMF (30 mL) at 0° C. is added NaH (60% in mineral oil, 354.53 mg, 14.8 mmol). After 1 hr $CD_3I$ (3.60 g, 25 mmol) is added drop wise to the solution (while keeping internal temperature between 0° C.-5° C.) and stirred for another 3 hrs. The reaction mixture is poured into water (60 mL) and extracted with MTBE (30 mL×3). The organic phase is washed with saturated brine (100 mL), dried over $Na_2SO_4$ and concentrated in vacuum to give 2-chloro-4-(1,N-(trideuteriomethyl-4,5-dihydrothieno[2,3-c]pyrazol-3-yl)pyrimidine as a white solid.

A148. 2-Chloro-4(indolin-1-yl)pyrimidine

Prepared from 2,4-dichloropyrimidine and indoline as described in WO 2000/053595 at p56.

A149. 2-Chloro-4-(furano[2,3-c]pyrazol-1-yl)pyrimidine

A solution of 2-bromofuran-3-carbaldehyde (875 mg, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO 5 mL, and $K_3PO_4$ (2.12 g 10 mmol) and CuI (1 mg, 0.005 mmol), and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried (MgSO4). The solvent is removed under reduced pressure, and the residue purified by silica gel chromatography to give 2-chloro-4-(furano[2,3-c]pyrazol-1-yl)pyrimidine.

A150. 2-Chloro-4-(thieno[2,3-c]pyrazol-1-yl)pyrimidine

A solution of 2-bromothiophene-3-carbaldehyde (955 mg, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO 5 mL, and $K_3PO_4$ (2.12 g 10 mmol) and CuI (1 mg, 0.005 mmol), and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(thieno[2,3-c]pyrazol-1-yl)pyrimidine.

A151. 2-Chloro-4-(3-methylthieno[2,3-c]pyrazol-1-yl)pyrimidine

A solution of 3-acetyl-2-bromothiophene (1.025 g, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO 5 mL, and $K_3PO_4$ (2.12 g 10 mmol) and CuI (1 mg, 0.005 mmol), and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(3-methylthieno[2,3-c]pyrazol-1-yl)pyrimidine.

A152. 2-Chloro-4-(furano[3,2-c]pyrazol-1-yl)pyrimidine

A solution of 3-bromofuran-2-carbaldehyde (875 mg, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled 10 to 25° C., poured onto water (100 mL) and extracted with EtOAc (3×25 mL). The combined organic extracts are rinsed with water (2×25 mL) saturated brine (25 mL) and dried (MgSO4). The solvent is removed under reduced pressure, and the residue purified by silica gel chromatography to give 2-chloro-4-(furano[3,2-c]pyrazol-1-yl)pyrimidine.

A153. 2-Chloro-4-(thieno[3,2-c]pyrazol-1-yl)pyrimidine

A solution of 3-bromothiophene-2-carbaldehyde (955 mg, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(thieno[3,2-c]pyrazol-1-yl)pyrimidine.

A154. 2-Chloro-4-(3-methylthieno[3,2-c]pyrazol-1-yl)pyrimidine

A solution of 2-acetyl-3-bromothiophene (1.025 g, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(3-methylthieno[3,2-c]pyrazol-1-yl)pyrimidine.

A155. 2-Chloro-4-(furano[2,3-c]pyrazol-3-yl)pyrimidine

N-(2-(t-Butyldimethylsilyl)ethyl)hydrazine 2-(t-Butyldimethylsilyl)acetaldehyde (Synthesis 1993, 1003) (3.17 g, 20 mmol) is added dropwise to a solution of hydrazine hydrate (~50%, 3 mL, ~50 mmol) in methanol (25 mL) containing acetic acid (0.2 mL), stirred under $N_2$ at 0° C. After 1 hr, further acetic acid (5 mL) is added, followed by sodium cyanoborohydride (0.57 g, 25 mmol), and the reaction mixture is allowed to warm slowly to 25° C. After 8 hrs, the reaction mixture is poured onto cold aqueous sodium carbonate solution, and after gas evolution has ceased, the mixture is extracted with MTBE (3×50 mL). The organic extracts are washed with water (2×25 mL) saturated brine, and dried ($MgSO_4$). The solvent is removed under reduced pressure, and the product is purified by vacuum distillation to give 2-N-(2-)t-butyldimethylsilyl)ethyl)hydrazine.

1,N-(2-(t-Butyldimethylsilyl)ethyl)furano[2,3-c]pyrazole

A solution of 2-N-(2-)t-butyldimethylsilyl)ethyl)hydrazine (1.744 g, 10 mmol) and 3-bromofuran-2-carbaldehyde (1.75 g, 10 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (10 mL), and $K_3PO_4$ (2.12 g 10 mmol) and CuI (2 mg, 0.01 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 1,N-(2-(t-butyldimethylsilyl)ethyl)furano[2,3-c]pyrazole.

3-Iodofurano[2,3-c]pyrazole

1,N-(2-(t-Butyldimethylsilyl)ethyl)furano[2,3-c]pyrazole (1.25 g, 5 mmol) and anhydrous tetramethylammonium fluoride (0.47 g, 5 mmol) are stirred in anhydrous t-butanol/THF (1:1, 5 mL) at 0° C. for 10 minutes, and then cooled to −25° C. N-iodosuucinimide (1.12 g, 5 mmol) in THF (5 mL) is added dropwise, and after 1 hr the reaction mixture is quenched with acetic acid, (1 mL). The reaction mixture is poured onto water (50 mL), and extracted with MTBE (3×25 mL). The combined organic phases are washed with water (2×25 mL), saturated brine (25 mL) and dried $MgSO_4$). The solvent is removed under reduced pressure and the residue is chromatographed on silica gel eluting with EtOAc/hexanes to give 3-iodofurano[2,3-c]pyrazole.

1,N-(t-Butoxycarbonyl)-3-iodofurano[2,3-c]pyrazole

A solution of 3-iodofurano[2,3-c]pyrazole (2.34 g, 10 mmol) in THF (50 ml) is placed in a foil-covered round-bottom flask. 4-Dimethylaminopyridine (0.12 g, 1 mmol, 0.1 equiv) is added, followed by di-tert-butyl dicarbonate (2.7 ml, 12 mmol, 1.2 equiv). Triethylamine (2.7 ml, 20 mmol, 2.0 equiv) is slowly added to the solution by syringe, and stirred at 25° C. for a further 2 hours. The reaction mixture is diluted with water (75 ml) and extracted with EtOAc (50×3 ml). The combined organic layers are washed with water (2×50 mL), saturated brine (100 ml), dried ($MgSO_4$), and concentrated under reduced pressure to give a red oil which is purified by chromatography over silica gel (hexanes/ethyl acetate: 100/0 to 90/10) to give 1,N-t-butoxycarbonyl-3-iodofurano[2,3-c]pyrazole.

2-Chloro-4-(4,5-dihydrothieno[2,3-c]pyrazol-3-yl)pyrimidine

1,N-t-butoxycarbonyl-3-iodofurano[2,3-c]pyrazole and 2-chloropyrimid-4-ylboronic acid are heated together in DMF at 80° C. in the presence of excess $K_3PO_4$, 10% tri-o-tolylphosphine and 5% $Pd(dba)_2$ for 12 hr. The reaction mixture is poured onto water, and extracted with EtOAc, washed with water, dried ($Na_2SO_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-4-(furano[2,3-c]pyrazol-3-yl)pyrimidine.

A156. 2-Chloro-4-(thieno[2,3-c]pyrazol-3-yl)pyrimidine

1,N-(2-(t-Butyldimethylsilyl)ethyl)thieno[2,3-c]pyrazole. A solution of 2-N-(2-)t-butyldimethylsilyl)ethyl)hydrazine (1.744 g, 10 mmol, see A97p) and 3-bromofthiophene-2-carbaldehyde (1.91 g, 10 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (10 mL), and $K_3PO_4$ (2.12 g 10 mmol) and CuI (2 mg, 0.01 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 1,N-(2-(t-butyldimethylsilyl)ethyl)thieno[2,3-c]pyrazole.

3-Iodothieno[2,3-c]pyrazole

1,N-(2-(t-Butyldimethylsilyl)ethyl)thieno[2,3-c]pyrazole (1.33 g, 5 mmol) and anhydrous tetramethylammonium fluoride (0.47 g, 5 mmol) are stirred in anhydrous t-butanol/THF (1:1, 5 mL) at 0° C. for 10 minutes, and then cooled to −25° C. N-iodosuucinimide (1.12 g, 5 mmol) in THF (5 mL) is added dropwise, and after 1 hr the reaction mixture is quenched with acetic acid, (1 mL). The reaction mixture is poured onto water (50 mL), and extracted with MTBE (3×25 mL). The combined organic phases are washed with water (2×25 mL), saturated brine (25 mL) and dried $MgSO_4$). The solvent is removed under reduced pressure and the residue is chromatographed on silica gel eluting with EtOAc/hexanes to give 3-iodothieno[2,3-c]pyrazole.

1,N-(t-Butoxycarbonyl)-3-iodothieno[2,3-c]pyrazole

A solution of 3-iodothieno[2,3-c]pyrazole (2.50 g, 10 mmol) in THF (50 ml) is placed in a foil-covered round-bottom flask. 4-Dimethylaminopyridine (0.12 g, 1 mmol, 0.1 equiv) is added, followed by di-tert-butyl dicarbonate (2.7 ml, 12 mmol, 1.2 equiv). Triethylamine (2.7 ml, 20 mmol, 2.0 equiv) is slowly added to the solution by syringe, and stirred at 25° C. for a further 2 hours. The reaction mixture is diluted with water (75 ml) and extracted with EtOAc (50×3 ml). The combined organic layers are washed with water (2×50 mL), saturated brine (100 ml), dried ($MgSO_4$), and concentrated under reduced pressure to give a red oil which is purified by chromatography over silica gel (hexanes/ethyl acetate: 100/0 to 90/10) to give 1,N-t-butoxycarbonyl-3-iodothieno[2,3-c]pyrazole.

2-Chloro-4-(thieno[2,3-c]pyrazol-3-yl)pyrimidine

1,N-t-butoxycarbonyl-3-iodofurano[2,3-c]pyrazole and 2-chloropyrimd-4-ylboronic acid are heated together in DMF at 80° C. in the presence of excess $K_3PO_4$, 10% tri-o-tolylphosphine and 5% $Pd(dba)_2$ for 12 hr. The reaction mixture is poured onto water, and extracted with EtOAc, washed with water, dried ($Na_2SO_4$), and the solvent removed under reduced pressure. The residual solid is dissolved in methanolic hydrogen chloride at 20° C. for 3 hr, the volatiles are stripped, and the material is purified by silica gel chromatography eluting with EtOAc/hexanes to give 2-chloro-4-(thieno[2,3-c]pyrazol-3-yl)pyrimidine.

A157. 2-Chloro-4-(pyrazolo[4,3-d]thiazol-1-yl)pyrimidine

5-Bromothiazole-4-carboxaldehyde (0.96 g, 5 mmol), prepared from the corresponding carboxylic acid as described in J Med Chem 55, 1593 (2012), and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29. 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(pyrazolo[4,3-d]thiazol-1-yl)pyrimidine.

A158. 2-Chloro-4-(pyrazolo[3,4-d]thiazol-1-yl)pyrimidine

4-Bromothiazole-5-carboxaldehyde (0.96 g, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled 10 to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(pyrazolo[3,4-d]thiazol-1-yl)pyrimidine.

A159. 2-Chloro-4-(pyrazolo[3,4-d]oxazol-1-yl)pyrimidine

5-Bromooxazole-4-carboxaldehyde (0.92 g, 5 mmol), prepared as described in WO 2010/142934 p. 15, and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(pyrazolo[3,4-d]oxazol-1-yl)pyrimidine.

A160. 2-Chloro-4-(6,N-methylpyrazolo[3,4-e]imidazol-1-yl)pyrimidine

5-Bromo-1,N-methylimidazole-4-carbaldehyde (0.90 g, 5 mmol), prepared as described in WO 2009/077728, and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(6,N-methylpyrazolo[3,4-e]imidazol-1-yl)pyrimidine.

A161. 2-Chloro-4-(pyrazolo[4,3-c]isothiazol-1-yl)pyrimidine

4-Bromo-3-methylisothiazole is oxidized with two equivalents of NBS, and hydrolyzed with $AgNO_3$ to 4-bromoisothiazole-3-carbaldehyde as described in J. Chem Soc 1964, 3114. 4-Bromoisothiazole-3-carbaldehyde (0.96 g, 5 mmol) and 2-chloropyrimd-4-ylhydrazine (720 mg, 5 mmol) in ethanol (20 mL) containing acetic acid (10 mg, 0.17 mmol) is refluxed for 2 h to form the hydrazone, and then the volatiles are removed rigorously under reduced pressure as described in Chinese J Chem 29, 1199 (2011). The residue is dissolved in DMSO (5 mL), and $K_3PO_4$ (2.12 g 10 mmol) and CuI (1 mg, 0.005 mmol) are added, and the reaction mixture is heated to 100° C. under Ar for 12 hrs. The reaction mixture is cooled to 25° C., poured onto water (100 mL) and extracted with EtOAc (3×25 mL). The combined organic extracts are rinsed with water (2×25 mL) saturated brine (25 mL) and dried ($MgSO_4$). The solvent is removed under reduced pressure, and the residue purified by silica gel chromatography to give 2-chloro-4-(pyrazolo[4,3-c]isothiazol-1-yl)pyrimidine.

A162. 2-Chloro-4-(1,3-dihydro-2-oxobenzimimidazol-1-yl)pyrimidine

To a solution of 1,3-dihydro-1,N-methyl-2-oxobenzimimidazole (3.185 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with Na$_2$SO$_4$ and concentrated in vacuo. The residue is purified by silica gel chromatography (petroleum ether:EtOAc=10:1), to give 2-chloro-4-(1,3-dihydro-3,N-methyl-2-oxobenzimimidazol-1-yl)pyrimidine.

A163. 2-Chloro-4-(1,3-dihydro-3,N-methyl-2-oxobenzimimidazol-1-yl)pyrimidine To a solution of 1,3-dihydro-1,N-methyl-2-oxobenzimimidazole (3.185 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with Na$_2$SO$_4$ and concentrated in vacuo. The residue is purified by silica gel chromatography (petroleum ether:EtOAc=10:1), to give 2-chloro-4-(1,3-dihydro-3,N-methyl-2-oxobenzimimidazol-1-yl)pyrimidine.

A164. 2-Chloro-4-(1,3-dihydro-3,N-cyclopropyl-2-oxobenzimimidazol-1-yl)pyrimidine To a solution of 1,3-dihydro-1,N-cyclopropyl-2-oxobenzimimidazole (3.24 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with Na$_2$SO$_4$ and concentrated in vacuo. The residue is purified by silica gel chromatography (petroleum ether:EtOAc=10:1), to give 2-chloro-4-(1,3-dihydro-3,N-cyclopropyl-2-oxobenzimimidazol-1-yl)pyrimidine.

A165. 2-Chloro-4-(1,3-dihydro-3,N-cyclopropyl-2-oxobenzimimidazol-1-yl)pyrimidine To a solution of 1,3-dihydro-1,N-cyclopropyl-2-oxobenzimimidazole (3.24 g, 21.5 mmol) in DMF (60 mL) is added NaH (60% in mineral oil, 1.03 g, 25.78 mmol) portionwise at 0° C. After stirring at 0° C. for 30 min. 2,4-dichloropyrimidine (3.20 g, 21.5 mmol) is added, and the mixture is allowed to stir at 15° C. for 12 hrs. The resulting mixture is quenched with water (200 mL) and the mixture is extracted with EtOAc (100 mL×3), and washed with water (100 mL×4), dried with Na$_2$SO$_4$ and concentrated in vacuo. The residue is purified by silica gel chromatography (petroleum ether:EtOAc=10:1), to give 2-chloro-4-(1,3-dihydro-3,N-cyclopropyl-2-oxobenzimimidazol-1-yl)pyrimidine.

A166. 2-Chloro-4-(3-methylimidazo[1,5-a]pyrid-1-yl)pyrimidine

1-Bromo-3-methylimidazo[1,5-a]pyridine

N-Bromosuccinimide (3.76 g, 20 mmol) is added portionwise to a solution of 3-methylimidazo[1,5-a]pyridine (2.642 g, 20 mmol) in CH$_2$Cl$_2$ (50 mL) stirred under N, at 0° C., and the solution is then allowed to stir at RT for 2 hr. (See Journal of Organic Chemistry, 77, 5381(2012). The reaction mixture is poured onto dilute sodium sulfite solution (0.2 M, 50 mL) and the layers are separated. The aqueous layer is extracted with CH$_2$I2 (2×25 mL) and the combined organic phases are washed with water (2×25 mL) saturated brine (25 mL) and dried (MgSO4). The solvent is removed under reduced pressure and the residue is chromatographed on silica gel, eluting with EtOAc/hexanes to give 1-bromo-3-methylimidazo[1,5-a]pyridine.

2-Chloro-4-(3-methylimidazo[1,5-a]pyrid-1-yl)pyrimidine

1-Bromo-3-methylimidazo[1,5-a]pyridine (4.223 g, 20 mmol) and 2-chloropyrimid-4-ylboronic acid (3.167 g, 20 mmol) are heated together in DMF (100 mL) at 80° C. in the presence of K$_3$PO$_4$, (8.48 g, 40 mmol) tri-o-tolylphosphine (6.09 g 2 mmol) and Pd$_2$(dba)$_3$ (0.916 g, 1.0 mmol) for 12 hr. The reaction mixture is poured onto water (250 mL), and extracted with EtOAc (3×50 mL), washed with water (2×50 mL), and saturated brine (50 mL), dried (Na$_2$SO$_4$), and the solvent removed under reduced pressure. The residual solid is purified by silica gel chromatography eluting with EtOAc/hexanes to give 2-chloro-4-(3-methylimidazo[1,5-a]pyrid-1-yl)pyrimidine.

A167. 2-Chloro-4-(1-methylimidazo[1,5-a]pyrid-3-yl)pyrimidine

3-Bromo-1-methylimidazo[1,5-a]pyridine

N-Bromosuccinimide (3.76 g, 20 mmol) is added portionwise to a solution of 1-methylimidazo[1,5-a]pyridine (2.642 g, 20 mmol) in CH$_2$Cl$_2$ (50 mL) stirred under N$_2$ at 0° C., and the solution is then allowed to stir at RT for 2 hr. (See Journal of Organic Chemistry, 77, 5381(2012). The reaction mixture is poured onto dilute sodium sulfite solution (0.2 M, 50 mL) and the layers are separated. The aqueous layer is extracted with CH$_2$I2 (2×25 mL) and the combined organic phases are washed with water (2×25 mL) saturated brine (25 mL) and dried (MgSO4). The solvent is removed under reduced pressure and the residue is chromatographed on silica gel, eluting with EtOAc/hexanes to give 3-bromo-1-methylimidazo[1,5-a]pyridine.

2-Chloro-4-(1-methylimidazo[1,5-a]pyrid-3-yl)pyrimidine 3-bromo-1-methylimidazo[1,5-ca]pyridine (4.223 g, 20 mmol) and 2-chloropyrimid-4-ylboronic acid (3.167 g, 20 mmol) are heated together in DMF (100 mL) at 80° C. in the presence of K$_3$PO$_4$, (8.48 g, 40 mmol) tri-o-tolylphosphine (6.09 g 2 mmol) and Pd$_2$(dba)$_3$ (0.916 g, 1.0 mmol) for 12 hr. The reaction mixture is poured onto water (250 mL), and extracted with EtOAc (3 20×50 mL), washed with water (2×50 mL), and saturated brine (50 mL), dried (Na$_2$SO$_4$), and the solvent removed under reduced pressure. The residual solid is purified by silica gel chromatography eluting with EtOAc/hexanes to give 2-chloro-4-(1-methylimidazo[1,5-a]pyrid-3-yl)pyrimidine.

B1. 4-(N-(2-N,N-dimethylamino)ethyl)-N-methylamino)-2-methoxy-5-nitroaniline

4-Fluoro-2-methoxy-5-nitroaniline

4-Fluoro-2-methoxyaniline (50.0 g, 354 mmol) was added to stirred sulfuric acid (300 mL) at 0° C. in portions, ensuring that the temperature did not rise above 10° C. When all of the solid had dissolved up, potassium nitrate (36 g 354 mmol) was added in portions keeping the temperature below 10° C. The reaction mixture allowed to warm to 25°

C., and stirred for 16 hr. It was then poured onto was poured onto ice-water (1 L) with vigorous stirring, and the solid was collected by vacuum filtration, rinsed with water (2×250 mL), and dried to give 4-fluoro-2-methoxy-5-nitroaniline (54 g, 82%) as a light yellow solid. $^1$H NMR: (CDCl$_3$) δ 7.35, (1H, d, J=8 Hz), 7.03 (1H, d, J=11 Hz), 5.21, (2H, brs), 3.91 (3H, s).

4-(N-(2(-N,N-Dimethylamino)ethyl)-N-methyl-amino)-2-methoxy-5-nitroaniline

To a stirred solution of 4-fluoro-2-methoxy-5-nitroaniline (10.00 g, 53.72 mmol) and N,N-diisopropylethylamine (6.5 g, 50 mmol) in DMA (120 mL) under N$_2$ at 15° C. N,N',N'-trimethylethylenediamine (8.23 g, 80.58 mmol) was added in one portion. The resulting mixture was heated to 85° C., and stirred for 12 hrs. The resulting mixture was cooled to 15° C., water (600 mL) was added and the mixture was extracted with EtOAc (300 mL×3), combined the organic layer and washed with water (200 mL×4) and brine (200 mL), dried with Na$_2$SO$_4$ and concentrated in vacuo to give 4-(N-(2-(N,N-dimethylamino)ethyl)-N-methylamino)-2-methoxy-5-nitroaniline (16.0 g, crude).
$^1$H NMR: (CDCl$_3$): δ 7.23 (s, 1H), 6.58 (s, 1H), 3.88 (s, 3H), 3.76 (br.s., 2H), 3.12 (t, J=7.2 Hz, 2H), 2.78 (s, 3H), 2.46 (t, J=7.2 Hz, 2H), 2.21 (s, 6H).

B2. 4-Bromo-2-methoxy-5-nitroaniline

Guanidinium nitrate (6.10 g, 50 mmol) was added in portions to a solution of 4-bromo-2-methoxyaniline (10.10 g, 50 mmol) in sulfuric acid (85%, 80 mL) at 0° C., over 10 minutes. After stirring 1 hr at 0° C. the reaction mixture was poured slowly onto ice (600 g) and 50% NaOH solution (200 mL), and the solid was collected by vacuum filtration, rinsed with water (3×100 mL), and dried to give 4-bromo-2-methoxy-5-nitroaniline (7.10 g, 57.5%) as a light yellow solid.
$^1$H NMR (CDCl$_3$) δ: 7.17 (s, 1H), 6.90 (s, 1H), 3.98 (br, 2H), 3.84 (s, 3H).

B3. 4-(E,4-(N,N-dimethylamino)but-2-en-2-yl)-2-methoxy-5-nitroaniline

N-(t-Butoxycarbonyl)-4-bromo-2-methoxy-5-nitroaniline

To a solution of 4-bromo-2-methoxy-5-nitroaniline (24.70 g, 100 mmol) and di-t-butyl dicarbonate (24 g, 110 mmol) in MeCN (500 mL), was added DMAP (244 mg, 2 mmol) in one portion at 20° C. under N$_2$. The reaction was heated to 50° C., and stirred for 12 hours. The mixture was cooled to 20° C. and concentrated under reduced pressure at 40° C. The residue was purified by silica gel chromatography (PE/EA=10/1, 5/1) to afford N-(t-butoxycarbonyl)-4-bromo-2-methoxy-5-nitroaniline (18.0 g, 51.8% yield) as a yellow solid.
$^1$H NMR (CDCl$_3$) δ 8.82 (s, 1H), 7.10 (s, 1H), 7.08 (s, 1H), 3.98 (s, 3H), 1.54 (s, 9H).

Z,3-(4,4,5,5-Tetramethyl-1,3,2-dioxabor-2-yl)but-2-en-1-ol

To a solution of but-2-yn-1-ol (20 g, 285 mmol) in Et$_2$O (500 mL), was added P(C$_6$H$_4$OMe-p)$_3$ (6.0 g, 17 mmol), bis-(pinacolato)diboron (86.9 g, 340 mmol), CuCl (1.4 g, 14.1 mmol) and K$_2$CO$_3$ (7.9 g, 57 mmol) in one portion at 20° C. under N$_2$ and stirred for 5 hours. The mixture was filtered and the filtrate was concentrated under reduced pressure. The residue was purified by silica gel chromatography (100-200 mesh silica gel. PE/EA=3/1) to afford Z,3-(4,4,5,5-tetramethyl-1,3,2-dioxabor-2-yl)but-2-en-1-ol (29.0 g, 51.4%) as a colourless oil.

N-(t-Butoxycarbonyl)-4-(E,4-hydroxybut-2-en-2-yl)-2-methoxy-5-nitroaniline

To a stirred solution of 4-bromo-2-methoxy-5-nitroaniline (15.00 g, 43.21 mmol) and Z,3-(4,4,5,5-tetramethyl-1,3,2-dioxabor-2-yl)but-2-en-1-ol (9.41 g, 47.53 mmol) in dioxane (160 mL), was added Pd(dppf)Cl$_2$ (1.90 g, 2.59 mmol) and K$_2$CO$_3$ (11.94 g, 86.42 mmol) in one portion at 25° C. under N$_2$. The reaction mixture was heated to 80° C., and stirred for 2 hours. The mixture was cooled to 25° C. and concentrated under reduced pressure. The residue was purified by silica gel chromatography (PE/EA=10/1. 5/1) to afford N-(t-butoxycarbonyl)-4-(E,4-hydroxybut-2-en-2-yl)-2-methoxy-5-nitroaniline (13.70 g, 93.7%) as a yellow oil.
$^1$H NMR (CDCl$_3$) δ: 8.79 (s, 1H), 7.08 (s, 1H), 6.67 (s, 1H), 5.57 (t, 1H), 4.32 (d, 2H, J=6.8), 3.96 (s, 3H), 1.98 (s, 3H), 1.54 (s, 9H).

N-(t-Butoxycarbonyl)-4-(E,4-(N,N-dimethylamino)but-2-en-2-yl)-2-methoxy-5-nitroaniline To a solution of N-(t-butoxycarbonyl)-4-(E,4-hydroxy-but-2-en-2-yl)-2-methoxy-5-nitroaniline (13.40 g, 39.6 mmol) and triethylamine (4.04 g, 40 mmol) in THF (15 mL) was added MsCl (4.54 g, 39.6 mmol) at 0° C. under N$_2$. The mixture was stirred at 0° C. for 5 min. Then dimethylamine (18 g, 0.4 mol) in THF (15 mL) was added and stirred for 3 hours at 25° C. The mixture was poured into ice-water (w/w=1/1) (50 mL) and concentrated under reduced pressure. The aqueous phase was extracted with EtOAc (3×30 mL). The combined organic phase was washed with saturated brine (2×20 mL), dried (Na$_2$SO$_4$), filtered and concentrated in under to afford N-(t-butoxycarbonyl)-4-(E,4-(N,N-dimethylamino)but-2-en-2-yl)-2-methoxy-5-nitroaniline (12.60 g, 87%) as a yellow oil.
$^1$H NMR (CDCl$_3$) δ: 8.76 (s, 1H), 7.06 (s, 1H), 6.65 (s, 1H), 5.48 (m, 1H), 3.94 (s, 3H), 3.05 (d, 2H, J=6.8), 2.30 (s, 6H), 1.96 (s, 3H), 1.54 (s, 9H).

4-(E,4-(N,N-dimethylamino)but-2-en-2-yl)-2-methoxy-5-nitroaniline

A solution of N-(t-butoxycarbonyl)-4-(E,4-(N,N-dimethylamino)but-2-en-2-yl)-2-methoxy-5-nitroaniline (12.60 g, 37.56 mmol, 1.00 Eq) in DCM (120 mL) and TFA (40 mL) was stirred at 25° C. for 12 hours. The mixture was concentrated rigorously under vacuum to afford compound 4-(E,4-(N,N-dimethylamino)but-2-en-2-yl)-2-methoxy-5-nitroaniline (10.30 g, crude) as a crude black oil.
$^1$H NMR (CDCl$_3$) δ: 7.44 (s, 1H), 6.52 (s, 1H), 5.45 (m, 1H), 3.93 (s, 3H), 3. (d, 2H, J=8.0), 2.85 (s, 6H), 2.01 (s, 3H).

B4. 5-(N-Acrylamido)-4-(N,1-(2-(N,N-dimethylamino)ethyl)-N,1-methyl)amino)-2-methoxyaniline A solution of 4-fluoro-2-methoxy-5-nitroaniline (50 g, 268 mmol, 1 eq) and TEA (40 g, 402 mmol, 1.5 eq) in DCM (500 mL) was cooled to 0-5° C. in an ice/water bath. Boc$_2$O (58 g, 268 mmol, 1 eq) in DCM (150 mL) was added slowly to the mixture. The progress of the reaction was monitored by TLC. After completion of the reaction, the mixture was concentrated to dryness under reduced pressure. The residue was purified by silica gel column chromatography eluting with 10-40% EtOAc in hexane to yield N-(t-butoxycarbonyl)-4-fluoro-2-methoxy-5-nitroanilide (37 g, 49%) as a yellow solid.

$^1$HNMR (300 MHz, CDCl$_3$): δ 8.90 (br, 1H), 6.98 (s, 1H), 6.72 (d, J=12 Hz, 1H), 3.98 (s, 3H), 1.55 (s, 9H).

N1,N1,N2-Trimethylethane-1,2-diamine (15.8 g, 155 mmol) was added to a solution of N-(t-butoxycarbonyl)-4-fluoro-2-methoxy-5-nitroanilide (37 g, 129 mmol) and DIPEA (16.6 g, 129 mmol) in DMA (400 mL). The mixture was heated to 60° C., and stirred at this temperature for 2 h. After cooling to rt, the reaction was diluted with water (1 L) and extracted with DCM (300 mL×3). The combined extracts were dried over anhydrous magnesium sulfate. The solvent was removed under vacuum to give N-(t-butoxycarbonyl))-4-(N,1-(2-(N,N-dimethylamino)ethyl)-N,1-methyl)amino)-2-methoxy-5-nitroanilide as an orange solid (44 g, 92%).

$^1$HNMR (300 MHz, DMSO-d$_6$): δ 8.14-8.10 (m, 1H), 6.72 (s, 1H), 3.88 (s, 3H), 3.21-3.18 (m, 2H), 2.79 (s, 3H), 2.45-2.43 (m, 2H), 2.13 (s, 6H), 1.44 (s, 9H).

To a solution of N-(t-butoxycarbonyl))-4-(N,1-(2-(N,N-dimethylamino)ethyl)-N, 1-methyl)amino)-2-methoxy-5-nitroanilide (44 g, 119 mmol) in MeOH (450 mL) was added 10% Pd/C (5 g). The reaction was purged with hydrogen 3 times, then stirred at rt under H$_2$ atmosphere for 2 h. The mixture was filtered through celite and concentrated under vacuum to afford N-(t-butoxycarbonyl)) 5-amino-4-(N,1-(2-(N,N-dimethylamino)ethyl)-N, 1-methyl)amino)-2-methoxy-5-anilide (38 g, 95%).

$^1$HNMR (300 MHz, DMSO-d$_6$): δ 7.53 (s, 1H), 7.07 (s, 1H), 6.66 (s, 1H), 4.55 (br, 2H), 3.68 (s, 3H), 2.82-2.78 (m, 2H), 2.56 (s, 3H), 2.32-2.27 (m, 2H), 2.14 (s, 6H), 1.44 (s, 9H).

LCMS: (M+H)$^+$: 338.9.

Acryloyl chloride (112 mL, 1M in THF, 112 mmol) was added dropwise to a solution of N-(t-butoxycarbonyl)) 5-amino-4-(N, 1-(2-(N,N-dimethylamino)ethyl)-N,1-methyl)amino)-2-methoxy-5-anilide (38 g, 112 mmol) and DIPEA (14.4 g, 112 mmol) in THF (400 mL) at 0° C. The resulting mixture was stirred at 0° C. for 2 h. The reaction mixture was quenched with water (400 mL) and extracted with DCM (200 mL×2). The combined organic extract was washed sequentially with saturated NaHCO$_3$ (150 mL), water (150 mL) and brine (150 mL). The organic layer was concentrated to afford the crude product which was purified by silica gel column chromatography eluting with 0-10% MeOH in DCM to yield N-(t-butoxycarbonyl)) 5-(N-acrylamino)-4-(N,1-(2-(NN-dimethylamino)ethyl)-N,1-methyl)amino)-2-methoxy-5-anilide as a brown oil (22 g, 50%).

$^1$HNMR (300 MHz, CDCl$_3$): δ 10.04 (br, 1H), 9.11 (s, 1H), 6.90 (s, 1H), 6.71 (s, 1H), 6.46-6.40 (m, 1H), 6.32-6.29 (m, 1H), 5.67-5.63 (m, 1H), 3.82 (s, 3H), 2.85 (t, J=5.4 Hz, 2H), 2.67 (s, 3H), 2.26-2.65 (m, 8H), 1.52 (s, 9H).

LCMS: 392.9.

N-(t-Butoxycarbonyl)) 5-(N-acrylamino)-4-(N,1-(2-(N,N-dimethylamino)ethyl)-N,1-methyl)amino)-2-methoxy-5-anilide (22 g, 56 mmol) was dissolved in 3N HCl/MeOH (200 mL) and the mixture was stirred at room temperature overnight. The solvent was removed under reduced pressure. The residue was neutralized with saturated aqueous NaHCO$_3$ and extracted with DCM (100 mL×3). The combined organic layers were concentrated to give the crude product, which was purified by silica gel column chromatography eluting with 0-10% MeOH in DCM to yield 5-(N-acrylamido)-4-(N, 1-(2-(N,N-dimethylamino)ethyl)-N,1-methyl)amino)-2-methoxyaniline (14 g, 87%).

$^1$HNMR (300 MHz, CDCl$_3$): δ 10.03 (br, 1H), 7.63 (s, 1H), 6.79 (s, 1H), 6.35-6.15 (m, 2H), 5.72-5.68 (m, 1H), 4.61 (br, 2H), 3.73 (s, 3H), 2.81-2.77 (m, 2H), 2.59 (s, 3H), 2.20-2.18 (m, 8H).

B5. N-(5-Amino-2-((2-(dimethylamino)ethyl)(methyl)amino)-6-isopropoxypyridin-3-yl) acrylamide A 500 mL four-neck flask was treated with THF (120 mL) and 2,6-dichloro-3-nitropyridine (23 g, 120 mmol, 1 eq). After cooling down to 0° C., 60% NaH (8 g, 200 mmol, 1.6 eq) was added carefully. The mixture was stirred at this temperature for 30 minutes. Then propan-2-ol (6.9 g, 115 mmol, 0.95 eq) was added dropwise at 0° C. The mixture was stirred at RT for 2 hours. After completion, the mixture was quenched with water (100 mL), extracted with EA (3×150 mL), the combined organic layers were dried, concentrated and purified by silica column to give 2-chloro-6-isopropoxy-3-nitropyridine (16.5 g, 67%).

$^1$HNMR (300 MHz, CDCl$_3$): δ 8.23 (d, J=8.4 Hz, 1H), 6.99 (d, J=8.4 Hz, 1H), 5.55-5.47 (m, 1H), 1.44 (d, J=6 Hz, 6H).

N$^1$,N$^1$,N$^2$-Trimethylethane-1,2-diamine (8.7 g, 83.5 mmol, 1.1 eq) was added to a solution of 2-chloro-6-isopropoxy-3-nitropyridine (16.5 g, 76.1 mmol, 1 eq) and DIPEA (11.8 g, 91.4 mmol, 1.2 eq) in EtOH (80 mL). The mixture was heated at reflux for 2 h, TLC and LCMS indicated completion. The mixture was concentrated and purified by silica column affording N$^1$-(6-isopropoxy-5-nitropyridin-2-yl)-N$^1$,N$^2$,N$^2$-trimethylethane-1,2-diamine (13 g, 60%).

LCMS: (M+H)$^+$: 283.0

To a solution of N-(6-isopropoxy-5-nitropyridin-2-yl)-N$^1$,N$^2$-trimethylethane-1,2-diamine (13 g 46.1 mmol, 1 eq) in MeCN (200 mL) was added NBS (12.3 g, 69.1 mmol, 1.5 eq) portion wise at 0° C. The mixture was stirred at RT for 1 h, TLC indicated completion and the precipitate formed was filtered, washed with 0.5N NaOH, and dried affording N$^1$-(3-bromo-6-isopropoxy-5-nitropyridin-2-yl)-N$^1$,N$^2$,N$^2$-trimethylethane-1,2-diamine (7 g, 42%).

$^1$HNMR (300 MHz, DMSO-d$_6$): δ 8.38 (s, 1H), 5.38-5.30 (m, 1H), 3.79-3.75 (m, 2H), 3.24 (s, 3H), 2.76-2.72 (m, 2H), 2.23 (s, 6H), 1.34 (d, J=6.3 Hz, 6H).

LCMS: (M+H)$^+$: 360.8.

To a mixture of N$^1$-(3-bromo-6-isopropoxy-N$^2$-methyl-5-nitropyridin-2-yl)-N$^2$,N$^2$-dimethylethane-1,2-diamine (6 g, 16.7 mmol, 1 eq) and diphenylmethanimine (3.9 g, 21.7 mmol, 1.3) in toluene (100 mL) were added Pd$_2$(dba)$_3$ (1.5 g, 1.6 mmol, 0.1 eq), BINAP (1.2 g, 2 mmol, 0.12 eq) and t-BuONa (2.1 g, 21.7 mmol, 1.3 eq) under nitrogen. The reaction was purged with nitrogen three times, then stirred at 110° C. for 12 hours. TLC and LCMS indicated completion; the mixture was concentrated and purified by silica column to give N$^2$-(2-(dimethylamino)ethyl)-N$^3$-(diphenylmethylene)-6-isopropoxy-N$^2$-methyl-5-nitropyridine-2,3-diamine (4 g, 52%).

LCMS: (M+H)$^+$: 461.8.

To a solution of N$^2$-(2-(dimethylamino)ethyl)-N$^3$-(diphenylmethylene)-6-isopropoxy-N$^2$-methyl-5-nitropyridine-2,3-diamine (4 g, 8.6 mmol, 1 eq) in MeOH (50 mL) was added conc. HCl (2.5 mL). The mixture was stirred at RT for 1 h. TLC and LCMS indicated completion. The mixture was neutralized with sat. NaHCO$_3$, extracted with EA (50 mL×3). The combined organic layers were washed with brine, concentrated and purified by silica column affording $N^2$-(2-(dimethylamino)ethyl)-6-isopropoxy-N-methyl-5-nitropyridine-2,3-diamine (1.5 g, 58%).

LCMS: (M+H)$^+$: 298.0.

Acryloyl chloride (690 mg, 7.6 mmol, 1.5 eq) was added dropwise to $N^2$-(2-(dimethylamino)ethyl)-6-isopropoxy-$N^2$-methyl-5-nitropyridine-2,3-diamine (1.5 g, 5 mmol, 1 eq) and DIPEA (780 mg, 6 mmol, 1.2 eq) in THF (30 mL) at 0° C. The resulting mixture was stirred at RT for 1 h. The reaction mixture was quenched with sat. NaHCO$_3$ (20 mL), extracted with EA (30 mL×3) and the organic extract was washed with brine (30 mL), dried over sodium sulfate, concentrated affording N-(2-((2-(dimethylamino)ethyl)(methyl)amino)-6-isopropoxy-5-nitropyridin-3-yl)acrylamide (500 mg, crude) which was used in next step directly without further purification.

LCMS: (M+H)$^+$: 351.9.

To a solution of N-(2-((2-(dimethylamino)ethyl)(methyl)amino)-6-isopropoxy-5-nitropyridin-3-yl)acrylamide (100 mg, 0.28 mmol, 1 eq) in EtOH (3 mL) and water (0.5 mL) were added Fe powder (160 mg, 2.8 mmol, 10 eq). NH$_4$Cl (90 mg, 1.68 mmol, 6 eq). The mixture was then refluxed for 2 h. TLC and LCMS indicated completion. The mixture was filtered, the filter cake was washed with DCM/MeOH (10:1, 20 mL×2), dried and purified by silica column affording N-(5-amino-2-((2-(dimethylamino)ethyl)(methyl)amino)-6-isopropoxypyridin-3-yl) acrylamide (60 mg, 66%). LCMS: (M+H)$^+$: 322.0.

B6. N-(5-amino-6-(2,2-difluoroethoxy)-2-((2-(dimethylamino)ethyl(methyl)amino)pyridin-3-yl) acrylamide A 1 L four-neck flask was charged with THF (155 mL) and 2,6-dichloro-3-nitropyridine (30 g, 155.4 mmol, 1 eq). After cooling down to 0° C., 60% NaH (6.2 g, 155.4 mmol, 1 eq) was added carefully. The mixture was stirred at this temperature for 30 minutes till no gas bubbled. Then a solution of 2,2-difluoroethanol (12.1 g, 147.6 mmol, 0.95 eq) was added dropwise. The mixture was stirred at RT for 2 hours. After completion, the mixture was quenched with water (100 mL), extracted with EA (3×250 mL), the combined organic layers were dried, concentrated and purified by silica column to give 2-chloro-6-(2,2-difluoroethoxy)-3-nitropyridine (14 g, 38%).

$^1$HNMR (300 MHz, CDCl$_3$): δ 8.34 (d, J=8.1 Hz, 1H), 8.16 (d, J=8.1 Hz, 1H), 6.19 (tt, J=54.9 Hz, 4.2 Hz, 1H), 4.77-4.67 (m, 2H).

N1,N1,N2-Trimethylethane-1,2-diamine (7.21 g, 70.6 mmol, 1.2 eq) was added to a solution of give 2-chloro-6-(2,2-difluoroethoxy)-3-nitropyridine (14 g 58.8 mmol, 1 eq) and DIPEA (22.8 g, 176.5 mmol, 3 eq) in EtOH (140 mL). The mixture was heated at reflux for 3 h, TLC and LCMS indicated completion. The mixture was concentrated and the crude residue was washed with EA (30 mL), dried affording $N^1$-(6-(2,2-difluoroethoxy)-5-nitropyridin-2-yl)-$N^1$,$N^2$,$N^2$-trimethylethane-1,2-diamine (15 g, 84%).

$^1$HNMR (300 MHz, DMSO-d$_6$): δ 10.77 (s, 1H), 8.52 (s, 1H), 6.46 (t, J=54.9 Hz, 1H), 4.77 (m, J=15.0 Hz, 3.0 Hz, 2H), 4.00 (t, J=7.8 Hz, 2H), 3.32 (s, 3H), 2.80 (s, 6H), 2.56-2.50 (m, 2H). LCMS: (M+H)$^+$: 304.9

To a solution of $N^1$-(6-(2,2-difluoroethoxy)-5-nitropyridin-2-yl)-$N^1$,$N^2$,$N^2$-trimethylethane-1,2-diamine (10 g, 32.98 mmol, 1 eq) in MeCN (100 mL) was added NBS (8.77 g, 49.3 mmol, 1.5 eq) portion wise at 0° C. The mixture was stirred at RT for 1 h, TLC indicated completion. The reaction mixture was concentrated and purified by silica column affording $N^1$-(3-bromo-6-(2,2-difluoroethoxy)-5-nitropyridin-2-yl)-$N^1$,$N^2$,$N^2$-trimethylethane-1,2-diamine (9 g, 71%).

$^1$HNMR (300 MHz, CDCl$_3$): δ 8.50 (s, 1H), 6.17 (t, J=25.2 Hz, 1H), 4.62 (m, J=13.2 Hz, 3.9 Hz, 2H), 3.81 (t, J=6.9 Hz, 2H), 3.31 (s, 3H), 2.64 (t, J=6.9 Hz, 2H), 2.30 (s, 6H).

LCMS: (M+H)$^+$: 382.7

To a mixture of $N^1$-(3-bromo-6-(2,2-difluoroethoxy)-5-nitropyridin-2-yl)-$N^1$,$N^2$,$N^2$-trimethylethane-1,2-diamine (10 g, 26.1 mmol, 1 eq) and benzophenone imine (6.14 g, 33.9 mmol, 1.3 eq) in toluene were added Pd$_2$(dba)$_3$ (3.58 g, 3.9 mmol, 0.15 eq), BINAP (2.92 g, 4.7 mmol, 0.18 eq) and t-BuONa (3.26 g, 33.9 mmol, 1.3 eq) under nitrogen. The reaction was purged with nitrogen three times, then stirred at 110° C. for 12 hours. TLC and LCMS indicated completion; the mixture was concentrated and purified by silica column to give 6-(2,2-difluoroethoxy)-$N^2$-(2-(dimethylamino)ethyl)-N-(diphenylmethylene)-$N^2$-methyl-5-nitropyridine-2,3-diamine as brown oil (2.5 g, 20%). LCMS: (M+H)$^+$: 483.8.

To a solution of 6-(2,2-difluoroethoxy)-$N^2$-(2-(dimethylamino)ethyl)-$N^3$-(diphenylmethylene)-$N^2$-methyl-5-nitropyridine-2,3-diamine (2.5 g, 5.17 mmol, 1 eq) in MeOH (50 mL) was added conc. HCl (2.5 mL). The mixture was stirred at RT for 1 h. TLC and LCMS indicated completion. The mixture was neutralized with sat. NaHCO$_3$, extracted with EA (50 mL×3). The combined organic layers were washed with brine, concentrated and purified by silica column affording 6-(2,2-difluoroethoxy)-$N^2$-(2-(dimethylamino)ethyl)-$N^2$-methyl-5-nitropyridine-2,3-diamine (0.56 g, 34%).

LCMS: (M+H)$^+$: 319.9

Acryloyl chloride (237 mg, 2.63 mmol, 1.5 eq) was added dropwise to 6-(2,2-difluoroethoxy)-$N^2$-(2-(dimethylamino)ethyl)-N-methyl-5-nitropyridine-2,3-diamine (560 mg, 1.75 mmol, 1 eq) and DIPEA (226 mg, 1.75 mmol, 1.5 eq) in THF (10 mL) at 0° C. The resulting mixture was stirred at RT for 1 h. The reaction mixture was quenched with sat. NaHCO$_3$ (15 mL), extracted with EA (30 mL×3) and the organic extract was washed with brine (30 mL), dried over sodium sulfate, concentrated affording N-(6-(2,2-difluoroethoxy)-2-((2-(dimethylamino)ethyl)(methyl)amino)-5-nitropyridin-3-yl) acrylamide (290 mg, crude) which was used in next step directly without further purification.

LCMS: (M+H)$^+$: 373.9.

To a solution of N-(6-(2,2-difluoroethoxy)-2-((2-(dimethylamino)ethyl)(methyl)amino)-5-nitropyridin-3-yl) acrylamide (290 mg, 0.78 mmol, 1 eq) in EtOH/water (5:1; 8 mL) were added Fe powder (870 mg, 15.5 mmol, 20 eq), NH$_4$Cl (249 mg, 4.66 mmol, 6 eq). The mixture was then refluxed for 2 h. TLC and LCMS indicated completion. The mixture was filtered, the filter cake was washed with DCM/MeOH (10:1, 20 mL×2), dried and purified by silica column affording N-(5-amino-6-(2,2-difluoroethoxy)-2-((2-(dimethylamino)ethyl)(methyl)amino)pyridin-3-yl)acrylamide (35 mg, 13%).

LCMS: (M+H)$^+$: 343.9.

B7 N-(5-Amino-2-((2-(dimethylamino)ethyl)(methyl)amino)-6-methoxypyridin-3-yl)acrylamide To a 500 mL four-neck flask were treated with THF (120 mL), MeOH (3.66 g, 115 mmol, 0.95 eq) and 2,6-dichloro-3-nitropyridine (23 g, 120 mmol, 1 eq). After cooling down to 0° C., 60% NaH (6.8 g, 170 mmol, 1.7 eq) was added carefully. The mixture was stirred at this temperature for 30 minutes, then at RT for 2 hours. After completion, the mixture was quenched with water (100 mL), extracted with EA (3×150 mL), the combined organic layers were dried, concentrated and purified by silica column to give 2-chloro-6-methoxy-3-nitropyridine (12 g, 56%).

$^1$HNMR (300 MHz, CDCl$_3$): δ 8.37-8.24 (m, 1H), 7.07-7.05 (m, 1H), 4.15 (s, 3H).

N1,N1,N2-Trimethylethane-1,2-diamine (7.8 g, 76.5 mmol, 1.2 eq) was added to a solution of 2-chloro-6-methoxy-3-nitropyridine (12 g, 63.8 mmol, 1 eq) and DIPEA (9.8 g, 76.5 mmol, 1.2 eq) in EtOH (80 mL). The mixture was heated at reflux for 2 h, TLC and LCMS indicated completion. The mixture was concentrated and purified by silica column eluting with PE/EA=10:1 affording N$^1$-(6-methoxy-5-nitropyridin-2-yl)-N$^1$,N$^2$,N$^2$-trimethylethane-1,2-diamine (13 g, 80%).

$^1$HNMR (300 MHz, DMSO-d$_6$): δ 8.24 (d, J=9.3 Hz, 1H), 6.42-6.40 (m, 1H), 4.04-3.95 (m, 5H), 3.15 (s, 3H), 2.74 (s, 6H), 2.53-2.45 (m, 2H).

To a solution of N$^1$-(6-methoxy-5-nitropyridin-2-yl)-N$^1$,N$^2$,N$^2$-trimethylethane-1,2-diamine (13 g, 51.1 mmol, 1 eq) in MeCN (200 mL) was added NBS (13.6 g, 76.6 mmol, 1.5 eq) portion wise at 0° C. The mixture was stirred at RT for 1 h, TLC indicated completion and the precipitate formed was filtered, washed with 0.5N NaOH, dried affording N$^1$-(3-bromo-6-methoxy-5-nitropyridin-2-yl)-N$^1$,N$^2$,N-trimethylethane-1,2-diamine (7 g, 41%).

$^1$HNMR (300 MHz, DMSO-d$_6$): δ 8.47 (s, 1H), 4.02-4.00 (m, 5H), 3.34 (s, 3H), 2.80 (s, 6H), 2.51-2.50 (m, 2H).

LCMS: (M+H)$^+$: 332.8.

To a mixture of N$^1$-(3-bromo-6-methoxy-5-nitropyridin-2-yl)-N$^1$,N$^2$,N$^2$-trimethylethane-1,2-diamine (7 g, 21 mmol, 1 eq) and diphenylmethanimine (4.9 g, 27.3 mmol, 1.3 eq) in toluene (70 mL) were added Pd$_2$(dba)$_3$ (1.9 g, 2.1 mmol, 0.1 eq), BINAP (1.5 g, 2.5 mmol, 0.12 eq) and tBuONa (2.6 g, 27.3 mmol, 1.3 eq) under nitrogen. The reaction was purged with nitrogen three times, then stirred at 110° C. for 12 hours. TLC and LCMS indicated completion, the mixture was concentrated and purified by silica column to give the N$^2$-(2-(dimethylamino)ethyl)-N$^3$-(diphenylmethylene)-6-methoxy-N-methyl-5-nitropyridine-2,3-diamine (2 g, 22%).

LCMS: (M+H)$^+$: 433.8.

To a solution of N$^2$-(2-(dimethylamino)ethyl)-N$^3$-(diphenylmethylene)-6-methoxy-N$^2$-methyl-5-nitropyridine-2,3-diamine (2 g, 4.6 mmol, 1 eq) in MeOH (20 mL) was added conc. HCl (2 mL). The mixture was stirred at RT for 1 h. TLC and LCMS indicated completion. The mixture was neutralized with sat. NaHCO$_3$, extracted with EA (50 mL×3). The combined organic layers were washed with brine, concentrated and purified by silica column affording N$^2$-(2-(dimethylamino)ethyl)-6-methoxy-N$^2$-methyl-5-nitropyridine-2,3-diamine (600 mg, 48%).

LCMS: (M+H)$^+$: 269.9.

Acryloyl chloride (300 mg, 3.3 mmol, 1.5 eq) was added dropwise to N$^2$-(2-(dimethylamino)ethyl)-6-methoxy-N$^2$-methyl-5-nitropyridine-2,3-diamine (600 mg, 2.2 mmol, 1 eq) and DIPEA (340 mg, 2.6 mmol, 1.2 eq) in THF (10 mL) at 0° C. The resulting mixture was stirred at RT for 1 h. The reaction mixture was quenched with sat. NaHCO$_3$ (20 mL), extracted with EA (20 mL×3) and the organic extract was washed with brine (30 mL), dried over sodium sulfate, concentrated affording N-(2-((2-(dimethylamino)ethyl)(methyl)amino)-6-methoxy-5-nitropyridin-3-yl)acrylamide (200 mg, crude) which was used in next step directly without further purification.

LCMS: (M+H)$^+$: 323.9.

To a solution of N-(2-((2-(dimethylamino)ethyl)(methyl)amino)-6-methoxy-5-nitropyridin-3-yl)acrylamide (100 mg, 0.28 mmol, 1 eq) in EtOH (3 mL) and water (0.5 mL) were added Fe powder (174 mg, 3.1 mmol, 10 eq), NH$_4$Cl (100 mg, 1.86 mmol, 6 eq). The mixture was then refluxed for 2 h. TLC and LCMS indicated completion. The mixture was filtered, the filter cake was washed with DCM/MeOH (10:1, 20 mL×2), dried and purified by prep-TLC affording N-(5-amino-2-((2-(dimethylamino)ethyl)(methyl)amino)-6-methoxypyridin-3-yl)acrylamide (20 mg, 22%).

LCMS: (M+H)$^+$: 294.0

The following examples further illustrate the present invention but should not be construed as in any way limiting its scope.

Example 1. N-(2-(N-(2-(N,N-Dimethylamino) ethyl)-N-methylamino)-4-methoxy-5-(4-(indol-1-yl) pyrimidin-2-yl)amino)phenyl) propenamide

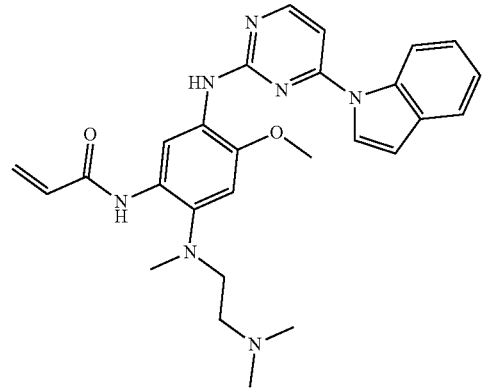 [SMILES: C=CC(=O)Nc1cc(Nc2nccc(-n3ccc4ccccc43)n2)c(OC)cc1N(C)CCN(C)C]

2-(4-(N—(N,N-Dimethylamino)ethyl)-N-methylamino)-2-methoxy-5-nitroanilino)-4-indol-1-ylpyrimidine TsOH.H$_2$O (1.56 g, 8.20 mmol) was added in one portion to a mixture of 4-(N-(2-N,N-dimethylamino)ethyl)-N-methylamino)-2-methoxy-5-nitroanisole (2.00 g, 7.45 mmol) and 2-chloro-4-(indol-1-yl)pyrimidine (1.71 g, 7.45 mmol) in butan-2-ol (120 mL). The resulting mixture was heated to 100° C., and stirred for 12 hrs. The reaction mixture was filtered and the solid was washed with butan-2-ol (10 mL), then dried in vacuo to give crude 2-(4-(N-(2-(N,N-dimethylamino)ethyl)-N-methylamino)-2-methoxy-5-nitroanilino)-4-indol-1-yl)pyrimidine (2.50 g, 73%) as a brown solid.

2-(5-Amino-4-(N-(2-(N,N-dimethylamino)ethyl)-N-methylamino)-2-methoxyanilino)-4-indol-1-ylpyrimidine A stirred mixture of 2-(4-(N-(2-(N,N-dimethylamino) ethyl)-N-methylamino)-2-methoxy-5-nitroanilino)-4-indol-1-yl)pyrimidine (2.50 g, 5.42 mmol). Fe (1.82 g, 32.50 mmol), NH$_4$Cl (203 mg, 3.8 mmol) in aqueous EtOH (1:6, 70 mL was refluxed for 2 h. The reaction mixture was filtered through celite, rinsed with EtOH and concentrated in vacuo. The residue was purified by prep-HPLC to give 2-(5-amino-4-(N-(2-(N,N-dimethylamino)ethyl)-N-methylamino)-2-methoxyanilino)-4-indol-1-ylpyrimidine (400 mg, 17%) as a brown solid. ESI-MS m/z: 432.2 (M+H)+. 1H NMR (400 MHz CDCl3) δ: 8.52 (d, J=8.4 Hz, 1H), 8.42 (d, J=5.6 Hz, 1H), 8.01 (s, 1H), 7.74 (d, J=3.6 Hz, 1H), 7.66-7.64 (m, 2H), 7.36-7.33 (m, 1H), 6.83 (d, J=5.2 Hz, 1H), 6.75-6.73 (m, 2H), 3.86 (s, 3H), 3.02-2.99 (m, 2H), 2.70 (s, 3H), 2.49-2.47 (m, 2H), 2.32 (s, 6H).

N-(2-(N-(2-(N,N-Dimethylamino)ethyl)-N-methylamino)-4-methoxy-5-(4-(indol-1-yl)pyrimidin-2-ylamino)phenyl)propenamide Propenoyl chloride (42 mg, 463 umol) in THF (0.5 mL) was added dropwise over a period of 20 minutes to a solution of 2-(5-amino-4-(N-(2-(N,N-dimethylamino)ethyl)-N-methylamino)-2-methoxyanilino)-4-indol-1-ylpyrimidine (200 mg, 463 umol) and DIPEA (66 mg, 510 umol) in THF (20 mL), stirred under N2 at 0° C. The reaction mixture was warmed to 20° C. for 2 hour quenched by slowly pouring onto ice-water (50 mL) and then extracted with DCM (4×30 mL). The combined extracts were washed with water (2×30 mL) saturated brine (30 mL) and dried (Na2SO4). The solution was concentrated in vacuo, and the residue was purified by prep-HPLC to give N-[2-[2-(dimethylamino)ethyl-methyl-amino]-5-[4-(indol-1-ylpyrimidin-2-ylamino]-4-methoxyphenyl] prop-2-enamide hydrochloride (103.00 mg, 41.74% yield) as a white solid.

1H NMR (MeOH-d4) δ: 8.27-8.20 (m, 1H), 8.01 (d, J=4.0 Hz, 1H), 7.83-7.74 (m, 1H), 7.68-7.61 (m, 1H), 7.41 (d, J=7.5 Hz, 1H), 7.37-7.22 (m, 3H), 7.13-7.09 (m, 1H), 6.95 (d, J=4.0 Hz, 1H), 6.80-6.67 (m, 1H), 6.46 (d, J=17.1 Hz, 1H), 5.86 (d, J=10.5 Hz, 1H), 3.97 (s, 3H), 3.63-3.58 (m, 2H), 3.43-3.39 (m, 2H), 2.93 (s, 6H), 2.85 (s, 3H).

ESI-MS m/z: 486.2 (M+H)+.

Example 2. N-(2-(N-(2-(N,N-Dimethylamino)ethyl)-N-methylamino)-4-methoxy-5-(4-(3-methylindol-1-yl)pyrimidin-2-ylamino)phenyl) propenamide

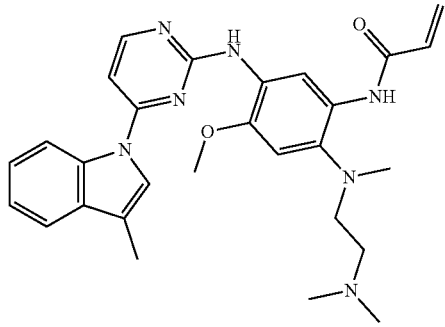 [SMILES: C=CC(=O)Nc1cc(Nc2nccc(-n3cc(C)c4ccccc43)n2)c(OC)cc1N(C)CCN(C)C]

N-(2-(N-(2-(N,N-Dimethylamino)ethyl)-N-methylamino)-4-methoxy-5-(4-(3-methylindol-1-yl)pyrimidin-2-ylamino)phenyl) propenamide was prepared from 4-(N-(2-N,N-dimethylamino)ethyl)-N-methylamino)-2-methoxy-5-nitroanisole and 2-chloro-4-(3-methylindol-1-yl)pyrimidine using the procedure disclosed in Example 1.

1H NMR (MeOH-d4) δ 8.19 (brs, 1H), 7.79 (s, 2H), 7.60 (d, J=6.3 Hz, 1H), 7.32 (d, J=7.0 Hz, 3H), 7.10 (s, 1H), 6.72-6.62 (m, 2H), 6.51-6.44 (m, 1H), 5.88 (d, J=9.8 Hz, 1H), 3.97 (s, 3H), 3.61-3.57 (m, 2H), 3.41-3.37 (m, 2H), 2.93 (s, 6H), 2.85-2.81 (m, 3H), 2.37 (d, J=1.0 Hz, 3H).

ESI-MS m/z: 500.2 (M+H)+.

Example 3. N-(2-(N,N-(2-(N,N-Dimethylamino)ethyl)-N-methylamino)-4-methoxy-5-(4-(3-chloroindol-1-yl)pyrimidin-2-ylamino)phenyl) propenamide

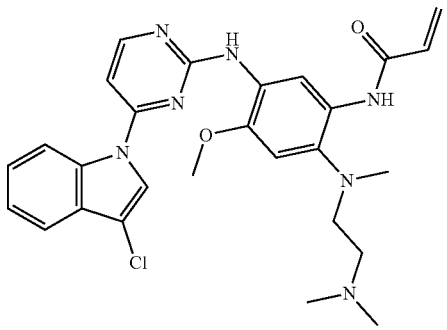 [SMILES: C=CC(=O)Nc1cc(Nc2nccc(-n3cc(Cl)c4ccccc43)n2)c(OC)cc1N(C)CCN(C)C]

N-(2-(N-(2-(N,N-Dimethylamino)ethyl)-N-methylamino)-4-methoxy-5-(4-(3-chloroindol-1-yl)pyrimidin-2-ylamino)phenyl) propenamide was prepared from 4-(N-(2-N,N-dimethylamino)ethyl)-N-methylamino)-2-methoxy-5-nitroanisole and 2-chloro-4-(3-chloroindol-1-yl)pyrimidine using the procedure disclosed in Example 1.

1H NMR: (MeOH-d4) δ: 8.25-8.18 (m, 1H), 8.11 (s, 1H), 7.99-7.85 (m, 1H), 7.60-7.53 (m, 1H), 7.51-7.30 (m, 3H), 7.28 (d, J=7.3 Hz, 1H), 7.18 (s, 1H), 6.95-6.84 (m, 1H), 6.45 (dd. J=1.6, 16.9 Hz, 1H), 5.85 (dd. J=1.6, 10.4 Hz, 1H), 3.98 (s, 3H), 3.69-3.63 (m, 2H), 3.49-3.43 (m, 2H), 2.95 (s, 6H), 2.90 (s, 3H).

ESI-MS m/z: 520.2 (M+H)+.

Example 4. N-(2-(N-(2-(N,N-Dimethylamino)ethyl)-N-methylamino)-4-methoxy-5-(4-(3-cyanoindol-1-yl)pyrimidin-2-ylamino)phenyl) propenamide

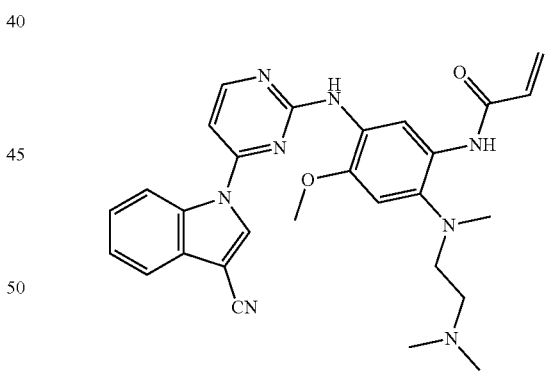

N-(2-(N-(2-(N,N-Dimethylamino)ethyl)-N-methylamino)-N-methoxy-5-(4-(3-cyanoindol-1-yl)pyrimidin-2-ylamino)phenyl) propenamide was prepared from 4-(N-(2-N,N-dimethylamino)ethyl)-N-methylamino)-2-methoxy-5-nitroanisole and 2-chloro-4-(3-cyanoindol-1-yl)pyrimidine using the procedure disclosed in Example 1.

1H NMR: (MeOH-d4) δ 8.87 (s, 1H), 8.40 (d, J=6.0 Hz, 1H), 7.84 (s, 1H), 7.77-7.73 (m, 1H), 7.49-7.47 (m, 4H), 7.08 (s, 1H), 7.68-7.64 (m, 1H), 6.46 (d, J=16.8 Hz, 1H), 5.85 (d, J=10.4 Hz, 1H), 3.96 (s, 3H), 3.58-3.55 (m, 2H), 3.38-3.35 (m, 2H), 2.91 (s, 6H), 2.81 (s, 3H).

ESI-MS m/z: 511.2 (M+H)+.

Example 5. N-(2-(N-(2-(N,N-Dimethylamino)ethyl)-N-methylamino)-4-methoxy-5-(4-(1 N,4-dimethylindol-3-yl)pyrimidin-2-ylamino)phenyl)propenamide

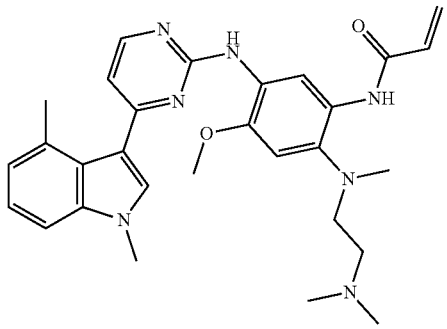 [SMILES: C=CC(=O)Nc1cc(Nc2nccc(-c3cn(C)c4cccc(C)c34)n2)c(OC)cc1N(C)CCN(C)C]

N-(2-(N-(2-(N,N-Dimethylamino)ethyl)-N-methylamino)-4-methoxy-5-(4-(1 N,4-dimethylindol-3-yl)pyrimidin-2-ylamino)phenyl) propenamide was prepared from 4-(N-(2-N,N-dimethylamino)ethyl)-N-methylamino)-2-methoxy-5-nitroanisole and 2-chloro-4-(1N,4-dimethylindol-3-yl)pyrimidine using the procedure disclosed in Example 1.

$^1$H NMR (MeOH-d4) δ=8.27 (s, 1H), 8.08-7.99 (m, 1H), 8.04-8.02 (m, 1H), 7.34-7.30 (m, 2H), 7.26-7.20 (m, 1H), 7.10-7.01 (m, 2H), 6.81-6.72 (m, 1H), 6.46-6.38 (m, 1H), 5.86-5.78 (m, 1H), 4.13-4.06 (m, 1H), 3.96 (s, 3H), 3.91 (s, 3H), 3.63-3.53 (m, 2H), 3.41-3.36 (m, 2H), 2.90 (s, 6H), 2.81 (s, 3H), 2.63 (s, 3H).

ESI-MS m/z: 514.3 (M+H)$^+$.

Example 6. N-(2-(N-(2-(N,N-Dimethylamino)ethyl)-N-methylamino)-4-methoxy-5-(4-(4-chloro-1N-methylindol-3-yl)pyrimidin-2-ylamino)phenyl)propenamide

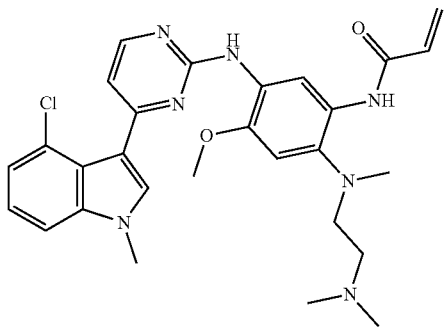 [SMILES: C=CC(=O)Nc1cc(Nc2nccc(-c3cn(C)c4cccc(Cl)c34)n2)c(OC)cc1N(C)CCN(C)C]

N-(2-(N-(2-(N,N-Dimethylamino)ethyl)-N-methylamino)-4-methoxy-5-(4-(4-chloro-1N-methylindol-3-yl)pyrimidin-2-ylamino)phenyl) propenamide was prepared from 4-(N-(2-N,N-dimethylamino)ethyl)-N-methylamino)-2-methoxy-5-nitroanisole and 2-chloro-4-(4-chloro-1N-methylindol-3-yl)pyrimidine using the procedure disclosed in Example 1.

$^1$H NMR (MeOH-d$_4$) δ: 8.45 (brs, 2H), 8.28-8.17 (m, 1H), 7.59-7.46 (m, 2H), 7.30 (s, 2H), 7.17-7.08 (m, 1H), 6.95-6.80 (m, 1H), 6.50-6.40 (m, 1H), 5.91-5.79 (m, 1H), 4.03 (s, 3H), 3.97 (s, 3H), 3.66-3.55 (m, 2H), 3.40 (br. s., 2H), 2.90 (s, 6H), 2.84 (s, 3H).

ESI-MS m/z: 534.2 (M+H)$^+$.

Example 7. N-(2-(N-(2-(N,N-Dimethylamino)ethyl)-N-methylamino)-4-methoxy-5-(4-(3-carboxamidoindol-1-yl)pyrimidin-2-ylamino)phenyl) propenamide

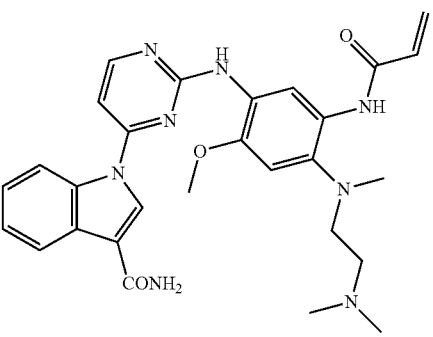 [SMILES: C=CC(=O)Nc1cc(Nc2nccc(-n3cc(C(N)=O)c4ccccc43)n2)c(OC)cc1N(C)CCN(C)C]

2-(4-(N-(2-(N,N-Dimethylamino)ethyl)-N-methylamino)-2-methoxy-5-nitroanilino)-4-(3-(carboxymethyl)indol-1-yl)pyrimidine A solution of 2-chloro-4-(3-(carboxymethyl)indol-1-yl) pyrimidine (3.00 g, 10.43 mmol), 4-(N-(2-N,N-dimethylamino)ethyl)-N-methylamino)-2-methoxy-5-nitroanisole (2.80 g, 10.43 mmol, 1.00 eq) and PTSA (2.16 g, 12.52 mmol, 1.20 eq) in butan-2-ol (50.00 mL) was heated to 100° C. and stirred for 3 hr. The mixture was filtered and concentrated in vacuum to remove the solvent. The residue was purified by prep-HPLC to afford 2-(4-(N-(2-(N,N-dimethylamino)ethyl)-N-methylamino)-2-methoxy-5-nitroanilino)-4-(3-(carboxymethyl)indol-1-yl)pyrimidine (2.20 g, 40.6% yield) as a red solid.

$^1$H NMR (CDCl$_3$) δ: 9.05 (s, 1H), 8.56-8.49 (m, 2H), 8.29-8.22 (m, 2H), 7.60 (s, 1H), 7.42-7.34 (m, 2H), 7.00 (d, J=5.5 Hz, 1H), 6.70 (s, 1H), 4.05-3.93 (m, 6H), 3.30 (t, J=7.0 Hz, 2H), 2.89 (s, 3H), 2.59 (t, J=7.0 Hz, 2H), 2.34-2.25 (m, 6H).

2-(4-(N-(2-(N,N-Dimethylamino ethyl)-N-methylamino)-2-methoxy-5-nitroanilino)-4-(3-(carboxy) indol-1-yl)pyrimidine A solution of 2-(4-(N-(2-(N,N-dimethylamino)ethyl)-N-methylamino)-2-methoxy-5-nitroanilino)-4-(3-(carboxymethyl)indol-1-ylpyrimidine (1.00 g, 1.92 mmol) and sodium hydroxide (153.6 mg, 3.84 mmol) in aqueous THF (1:2, 45 mL) was stirred at 25° C. for 50 hrs. The reaction mixture was quenched with dilute hydrochloric acid (0.1 M, 30 mL at 0° C., and then extracted with DCM (3×40 mL). The combined organic layers were washed with saturated brine (2×25 mL), dried (Na$_2$SO$_4$), filtered and concentrated in vacuum to afford 2-(4-(N-(2-(N,N-dimethylamino)ethyl)-N-methylamino)-2-methoxy-5-nitroanilino)-4-(3-(carboxy)indol-1-yl)pyrimidine (550 mg, crude) as a red solid.

$^1$H NMR (MeOH-d$_4$) δ: 8.61 (d, J=8.0 Hz, 1H), 8.29 (s, 1H), 8.23 (d, J=6.0 Hz, 1H), 7.82 (d, J=8.0 Hz, 1H), 7.46 (t, J=7.8 Hz, 1H), 7.29 (t, J=7.3 Hz, 1H), 7.16 (br. s., 1H), 6.92 (s, 1H), 6.56 (d, J=6.0 Hz, 1H), 3.79 (s, 3H), 3.13 (t, J=7.0 Hz, 2H), 2.74 (s, 3H), 2.58 (t, J=6.8 Hz, 2H), 2.34 (s, 6H).

2-(4-(N-(2-(N,N-Dimethylamino)ethyl)-N-methyl-amino)-2-methoxy-5-nitroanilino)-4-(3-(carboxamido)indol-1-yl)pyrimidine EDAC (125.1 mg, 0.65 mmol) was added to a solution of 2-(4-(N-(2-(N,N-dimethylamino)ethylamino)-2-methoxy-5-nitroanilino)-4-(3-(carboxy)indol-1-yl)pyrimidine (300 mg, 0.59 mmol) 1,N-hydroxybenzptriazole (104 mg, 0.77 mmol) and ammonium chloride (47.6 mg, 0.89 mmol) in DMF, (5 mL) stirred under N₂ at 5° C. The reaction mixture was then stirred at 25° C. for 18 hrs, and quenched at 0° C. by addition of water (10 mL), and was extracted with EtOAc (3×10 mL). The combined extracts were washed with saturated brine, and Dried (Na₂SO₄). The solvent was removed under reduced pressure and the residue was purified by prep HPLC to give 2-(4-(N-(2-(N,N-dimethylamino)ethyl)-N-methyl-amino)-2-methoxy-5-nitroanilino)-4-(3-(carboxamido)indol-1-yl)pyrimidine (53 mg, 17.7%) as a red solid.

2-(5-Amino-4-(N-(2-(N,N-dimethylamino)ethyl)-N-methylamino)-2-methoxy-5-nitroanilino)-4-(3-(carboxamido)indol-1-yl)pyrimidine Powdered zinc (233 mg, 3.57 mmol) and ammonium chloride (74.2 mg, 1.4 mmol) were added to a stirred solution of 2-(4-(N-(2-(N,N-dimethylamino)ethyl)-N-methylamino)-2-methoxy-5-nitroanilino)-4-(3-(carboxamido)indol-1-yl)pyrimidine (100 mg, 0.198 mmol) in acetone (5 mL) containing water (0.5 mL) at 25° C. After 30 min, the reaction mixture was vacuum filtered, and the residue rinsed with acetone (3×10 mL). The combined filtrates were evaporated under reduced pressure, and the residue was purified by preparative HPLC to give 2-(5-amino-4-(N-(2-(N,N-dimethylamino)ethyl)-N-methylamino)-2-methoxy-5-nitroanilino)-4-(3-(carboxamido)indol-1-yl)pyrimidine (65 mg, 69%) as a brown solid.

N-(2-(N-(2-(N,N-Dimethylamino)ethyl)-N-methyl-amino)-4-methoxy-5-(4-3-carboxamidoindol-1-yl)pyrimidin-2-ylamino)phenyl) propenamide DIPEA (21.2 mg, 0.164 mmol) and propenoyl chloride (12.4 mg, 0.237 mmol) were added sequentially and dropwise to a solution of 2-(5-amino-4-(N-(2-(N,N-dimethylamino)ethyl)-N-methylamino)-2-methoxy-5-nitroanilino)-4-(3-(carboxamido)indol-1-yl)pyrimidine (65 mg, 0.137 mmol) in THF (5 mL) stirred under N₂ at 0° C. After a further 20 min, the reaction mixture was quenched by addition of hydrogen chloride in EtOAc (0.4 M, 1 mL). The mixture was filtered, and the volatiles were removed under reduced pressure. The residue was purified by preparative HPLC to give N-(2-(N-(2-(N,N-dimethylamino)ethyl)-N-methylamino)-4-methoxy-5-(4-(3-carboxamidoindol-1-yl)pyrimidin-2-ylamino)phenyl) propenamide (7.0 mg, 8.4%) as a yellow solid.

¹H NMR (MeOH-d₄) δ: 8.69 (s, 1H), 8.44-8.29 (m, 2H), 8.24-8.17 (m, 1H), 7.90 (br. s., 1H), 7.45-7.23 (m, 4H), 7.09 (s, 1H), 6.73 (dd, =10.4, 17.0 Hz, 1H), 6.44 (dd, =1.3, 16.8 Hz, 1H), 5.85 (dd. J=1.3, 10.1 Hz, 1H), 4.00-3.92 (m, 3H), 3.59-3.52 (m, 2H), 3.44-3.35 (m, 2H), 2.96-2.87 (m, 6H), 2.84-2.77 (m, 3H).

ESI-MS (m/z): 529.3 (M+H)⁺.

Example 8. N-(2-(N-(2-(N,N-Dimethylamino)ethyl)-N-methylamino)-4-methoxy-5-(4-(3-(hydroxymethyl)indol-1-yl)pyrimidin-2-ylamino)phenyl) propenamide

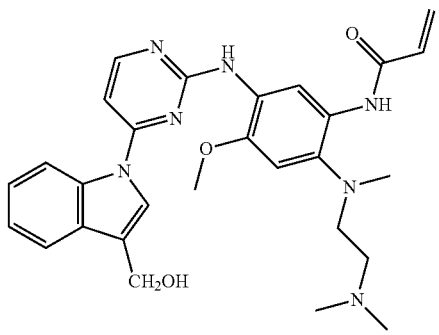 [SMILES: C=CC(=O)Nc1cc(Nc2nccc(-n3cc(CO)c4ccccc43)n2)c(OC)cc1N(C)CCN(C)C]

2-(4-(N-(2-(N,N-Dimethylamino)ethyl)-N-methyl-amino)-2-methoxy-5-nitroanilino)-4-(3-formylindol-1-yl)pyrimidine A solution 2-chloro-4-(3-formylindol-1-yl)pyrimidine (1.00 g, 3.88 mmol), 4-(N-(2-N,N-dimethylamino)ethyl)-N-methylamino)-2-methoxy-5-nitroanisole (1.04 g, 3.88 mmol) and PTSA (802 mg, 4.66 mmol) in butan-2-ol (30.00 mL) was heated to 100° C., with stirring for 3 hr. The mixture was filtered and concentrated in vacuum to remove the solvent. The residue was purified by prep-HPLC (HCl condition) to afford 2-(4-(N-(2-(N,N-dimethylamino)ethyl)-N-methylamino)-2-methoxy-5-nitroanilino)-4-(3-formylindol-1-yl)pyrimidine (900 mg, 47.4%) as an orange solid.

¹H NMR (CDCl₃) δ: 8.64 (s, 1H), 8.55-8.45 (m, 2H), 8.34 (d, J=7.9 Hz, 1H), 7.99 (d, J=8.4 Hz, 1H), 7.43 (t, J=7.7 Hz, 1H), 7.33 (t, J=7.7 Hz, 1H), 7.22 (d, J=6.6 Hz, 2H), 4.03-3.89 (m, 3H), 3.63-3.54 (m, 2H), 3.48 (d, J=5.3 Hz, 2H), 3.09-2.80 (m, 8H).

2-(4-(N-(2-(N,N-Dimethylamino)ethyl)-N-methyl-amino)-2-methoxy-5-nitroanilino)-4-(3-(hydroxymethyl)indol-1-yl)pyrimidine NaBH₄ (162.3 mg, 4.3 mmol) was added in portions to a solution of 2-(4-(N-(2-(N,N-dimethylamino)ethylamino)-2-methoxy-5-nitroanilino)-4-(3-formylindol-1-yl)pyrimidine (700 mg, 1.43 mmol) in MeOH (7 mL) stirred at 0° C. The reaction mixture was allowed to warm to 25° C. for 3 hrs, cooled to 0° C., and quenched by addition of aqueous NH₄Cl solution (10 mL). The mixture was extracted with EtOAc (3×20 mL) and the combined organic phases were washed with saturated brine (2×10 mL) and dried (Na₂SO₄). The solvent was removed under reduced pressure to give 2-(4-(N-(2-(N,N-dimethylamino)ethyl)-N-methylamino)-2-methoxy-5-nitroanilino)-4-(3-(hydroxymethyl)indol-1-yl)pyrimidine (550 mg, 78.5%/6) as a light brown solid.

¹H NMR (MeOH-d₄) δ: 8.88-8.79 (m, 1H), 8.41-8.37 (m, 1H), 8.36-8.28 (m, 1H), 7.92 (s, 1H), 7.73-7.63 (m, 1H), 7.29-7.16 (m, 2H), 7.07 (d, J=6.0 Hz, 1H), 6.99-6.92 (m, 1H), 4.04-4.00 (m, 3H), 3.47-3.41 (m, 2H), 3.25-3.16 (m, 2H), 2.83 (br. s., 3H), 2.79-2.69 (m, 6H).

N-(2-(N-(2-(N,N-Dimethylamino)ethyl)-N-methyl-amino)-4-methoxy-5-(4-(3-(hydroxymethyl)indol-1-yl)pyrimidin-2-ylamino)phenyl) propenamide. 2-(4-(N-(2-(N,N- dimethylamino)ethyl)-N-methylamino)-2-methoxy-5-nitroanilino)-4-(3-(hydroxymethyl)indol-1-yl)pyrimidine was reduced with zinc and acylated with propenoyl chloride as described in Example 7 to give N-(2-(N-(2-(N,N-dimethylamino)ethyl)-N-methylamino)-4-methoxy-5-(4-(3-(hydroxy)methyl)indol-1-yl)pyrimidin-2-ylamino)phenyl) propenamide (9.0 mg, 1.6% on 2 steps) as a brown solid.

$^1$H NMR (MeOH-d$_4$) δ: 8.44 (brs, 1H), 8.23 (d, J=7.1 Hz, 1H), 7.97-7.84 (m, 2H), 7.68 (dd, J=2.6, 6.2 Hz, 1H), 7.32-7.20 (m, 3H), 7.05 (s, 1H), 6.63-6.54 (m, 1H), 6.49-6.39 (m, 1H), 5.84 (dd, J=1.3, 10.1 Hz, 1H), 3.93 (s, 3H), 3.54 (t, J=5.7 Hz, 2H), 3.34 (t, J=5.7 Hz, 2H), 2.90 (s, 6H), 2.83-2.73 (m, 3H).

ESI-MS (m/z): 516.3 (M+H)$^+$.

Example 9. N-(2-(N-(2-(N,N-Dimethylamino)ethyl)-N-methylamino)-4-methoxy-5-(4-(3-(methylsulfonyl)indol-1-yl)pyrimidin-2-ylamino)phenyl) propenamide

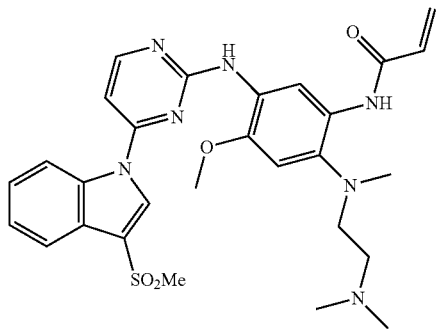

2-(4-(N-(2-(N,N-Dimethylamino)ethyl)-N-methylamino)-2-methoxy-5-nitroanilino)-4-(3-(methylsulfonyl)indol-1-yl)pyrimidine A solution of 4-(N-(2-N,N-dimethylamino)ethyl)-N-methylamino)-2-methoxy-5-nitroanisole (680 mg, 2.5 mmol) 2-chloro-4-(3-(methylsulfonyl)indol-1-yl)pyrimidine (780 mg, 2.5 mmol) and TsOH.H$_2$O (579 mg, 3.0 mmol) in n-butanol (50 mL) was stirred at 100° C. for 2 hours. The reaction was cooled to 25° C. and concentrated to give a residue. The residue was purified by prep-HPLC (HCl condition) to give 2-(4-(N-(2-(N,N-dimethylaminoethyl)-N-methylamino)-2-methoxy-5-nitroanilino)-4-(3-(methylsulfonyl)indol-1-yl)pyrimidine (200 mg, 15% yield) as a red solid.

2-(4-(N-(2-(5-Amino-N,N-dimethylamino)ethyl)-N-methylamino)-2-methoxyanilino)-4-(3-(methylsulfonyl)indol-1-yl)pyrimidine To a solution of 2-(4-(N-(2-(N,N-dimethylaminoethyl)-N-methylamino)-2-methoxy-5-nitroanilino)-4-(3-(methylsulfonyl)indol-1-yl)pyrimidine (260 mg, 0.482 mmol) in acetone (26 mL) and H$_2$O (2.6 mL) was added zinc powder (567 mg, 8.67 mmol) and NH$_4$Cl (180 mg, 3.37 mmol) at 25° C., then reaction mixture was degassed and purged with N$_2$ 3 times, and then the mixture was stirred at 25° C. for 5 min under N$_2$. The mixture was filtered and the filtrate was concentrated to give a residue. The residue was purified by prep-HPLC to give 2-(4-(N-(2-(5-amino-N,N-dimethylamino)ethyl)-N-methylamino)-2-methoxyanilino)-4-(3-(methylsulfonyl)indol-1-yl)pyrimidine (60 mg, 24% yield) as a dark brown solid.

N-(2-(N-(2-(N,N-Dimethylamino)ethyl)-N-methylamino)-4-methoxy-5-(4-(3-(methylsulfonyl)indol-1-yl)pyrimidin-2-ylamino)phenyl) propenamide A solution of 2-(4-(N-(2-(5-amino-N,N-dimethylamino)ethyl)-N-methylamino)-2-methoxyanilino)-4-(3-(methylsulfonyl)indol-1-yl)pyrimidine (60 mg, 0.118 mol) in THF (4 mL) was degassed and purged with N$_2$ 3 times at 25° C., and the mixture was cooled to 0° C. under N$_2$. Then a solution of DIPEA (18 mg, 141 umol, 25 uL) in THF (0.2 mL) was added slowly to the mixture at 0° C., after stirring for 5 min, a solution of prop-2-enoyl chloride (11 mg, 0.118 mmol, 9.6 uL) in THF (0.2 mL) was added slowly to the mixture at 0° C. Then the reaction mixture was stirred at 0° C. for 20 min. The mixture was quenched with HCl/EtOAc (0.4 M, 0.5 mL) at 0° C., and concentrated to give a residue. The residue was purified by prep-HPLC to give N-(2-(N-(2-(N,N-dimethylamino)ethyl)-N-methylamino)-4-methoxy-5-(4-(3-(methylsulfonyl)indol-1-yl)pyrimidin-2-ylamino)phenyl) propenamide (8 mg, 11%) as a yellow solid.

$^1$H NMR (d$_4$-MeOH) δ 8.58 (s, 1H), 8.55-8.53 (m, 1H), 8.45-8.44 (m, 1H), 8.19 (s, 1H), 7.95-7.93 (m, 1H), 7.41-7.38 (m, 2H), 7.26-7.25 (m, 1H), 6.98 (s, 1H), 6.47-6.45 (m, 2H), 5.86-5.83 (m, 1H), 3.98 (s, 3H), 3.52-3.49 (m, 3H), 3.27 (s, 3H), 3.11 (s, 1H), 2.87 (s, 6H), 2.73 (s, 3H).

ESI-MS (m/z): 564.3 (M+H)$^+$

Example 10. N-(2-(N-(2-(N,N-Dimethylamino)ethyl)-N-methylamino)-4-methoxy-5-(4-(2-oxo-2,3-dihydrobenzimidazol-1-yl)pyrimidin-2-ylamino)phenyl) propenamide

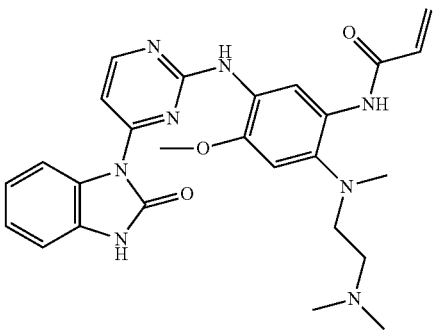 [SMILES: C=CC(=O)Nc1cc(Nc2nccc(-n3c(=O)[nH]c4ccccc43)n2)c(OC)cc1N(C)CCN(C)C]

2-(4-4N-(2-(N,N-dimethylamino)ethyl)-N-methylamino)-2-methoxy-5-nitroanilino)-4-(2,3-dihydro-2-oxobenzimidazol-1-yl)pyrimidine A solution of 4-(N-(2-N,N-dimethylamino)ethyl)-N-methylamino)-2-methoxy-5-nitroanisole (1.30 g, 4.8 mmol) 2-chloro-4-(2,3-dihydro-2-oxobenzimidazol-1-yl)pyrimidine (1.10 g, 4.8 mmol) and TsOH.H$_2$O (1.00 g, 5.3 mmol) in n-butanol (50 mL) was stirred at 100° C. for 2 hours. The mixture was cooled to 25° C. and concentrated to give a residue. The residue was purified by prep-HPLC to give 2-(4-(N-(2-(N,N-dimethylamino)ethyl)-N-methylamino)-2- methoxy-5-nitroanilino)-4-(2,3-dihydro-2-oxobenzimidazol-1-yl)pyrimidine (170 mg, 8%) as an orange solid.

$^1$H NMR (d$_4$-MeOH) δ 8.55 (s, 1H), 8.45 (d, J=5.6 Hz, 1H), 8.10-8.08 (m, 1H), 7.75 (d, J=5.6 Hz, 1H), 7.15-7.15 (m, 1H), 7.07-7.06 (m, 1H), 7.00-6.99 (m, 1H), 6.88 (s, 1H), 3.99 (s, 3H), 2.88 (s, 4H), 2.73-2.70 (m, 3H), 2.36 (s, 6H), 2-(4-(N-(5-Amino-2-(N,N-dimethylamino)ethyl)-N-methylamino)-2-methoxyanilino)-4-(2,3-dihydro-2-oxobenzimidazol-1-yl)pyrimidine.

To a solution of 2-(4-(N-(2-(N,N-dimethylamino)ethyl)-N-methylamino)-2-methoxy-5-nitroanilino)-4-(2,3-dihydro-2-oxobenzimidazol-1-yl)pyrimidine (170 mg, 0.355 mmol) in acetone (17 mL) and H$_2$O (1.7 mL) was added zinc dust (418 mg, 6.40 mmol) and NH$_4$-Cl (133 mg, 2.49 mmol) at 25° C., the reaction mixture was degassed and purged with N$_2$ for 3 times, and then the mixture was stirred at 25° C. for 5 min under N$_2$. The mixture was filtered and the filtrate was concentrated to give a residue. The residue was purified by prep-HPLC to give 2-(4-(N-(5-amino-2-(N,N-dimethylamino)ethyl)-N-methylamino)-2-methoxyanilino)-4-(2,3-dihydro-2-oxobenzimidazol-1-yl)pyrimidine (110 mg, 69% yield) as a dark brown solid.

N-(2-(N-(2-(N,N-Dimethylamino)ethyl)-N-methylamino)-4-methoxy-5-(4-(2-oxo-2,3-dihydrobenzimidaz-1-yl)pyrimidin-2-ylamino)phenyl) propenamide. A mixture of 2-(4-(N-(5-amino-2-(N,N-dimethylamino)ethyl)-N-methylamino)-2-methoxyanilino)-4-(2,3-dihydro-2-oxobenzimidazol-1-yl)pyrimidine (110 mg, 0.245 mmol) in THF (6 mL) was degassed and purged with N$_2$ 3 times at 25° C., and the mixture was cooled to 0° C. under N$_2$. Then a solution of DIPEA (38 mg, 0.294 mmol, 51 μL) in THF (0.3 mL) was added slowly to the mixture at 0° C., and after stirring for 5 min, a solution of prop-2-enoyl chloride (22 mg, 0.245 mmol, 20 μL) in THF (0.3 mL) was added slowly to the mixture at 0° C. Then the reaction mixture was stirred at 0° C. for 20 min under N$_2$. The mixture was quenched with HCl/EtOAc (0.4 M, 2 mL) at 0° C., and concentrated to give a residue. The residue was purified by prep-HPLC to give N-(2-(N-(2-(N,N-dimethylamino)ethyl)-N-methylamino)-4-methoxy-5-(4-(2-oxo-2,3-dihydrobenzimidaz-1-yl)pyrimidin-2-ylamino)phenyl) propenamide (27 mg, 20%) as a yellow solid.

$^1$H NMR (d$_4$-MeOH) δ 8.42 (d, J=6 Hz, 1H), 8.16-8.14 (m, 1H), 8.08 (s, 1H), 7.83 (d, J=6.4 Hz, 1H), 7.14-7.09 (m, 1H), 7.07-6.98 (m, 3H), 6.45-6.43 (m, 3H), 5.85-5.82 (m, 1H), 3.97 (s, 3H), 3.52-3.49 (m, 3H), 3.12 (s, 1H), 2.87 (s, 6H), 2.73 (s, 3H). ESI-MS (m/z): 503.3 (M+H)$^+$

Example 11. N-(2-(N-(2-(N,N-Dimethylamino)ethyl)-N-methylamino)-4-methoxy-5-(4-(7-methylindol-3-yl)pyrimidin-2-ylamino)phenyl) propenamide

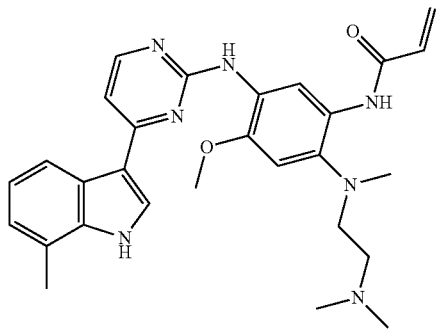 [SMILES: C=CC(=O)Nc1cc(Nc2nccc(-c3c[nH]c4c(C)cccc34)n2)c(OC)cc1N(C)CCN(C)C]

2-(4-(N-(2-(N,N-Dimethylamino)ethyl)-N-methylamino)-2-methoxy-5-nitroanilino)-4-(7-methylindol-3-yl)pyrimidine A solution of 2-chloro-4-(7-methylindol-3-yl)pyrimidine (3.0 g, 11 mmol) in butan-2-ol (150 mL), 4-(N-(2-N,N-dimethylamino)ethyl)-N-methylamino)-2-methoxy-5-nitroanisole (2.7 g, 11 mmol) and TsOH.H$_2$O (2.6 g, 13 mmol) was stirred at 100° C. under N$_2$ for 14 hours. The mixture was concentrated to give a residue. The residue was purified by column chromatography on silica gel eluted with dichloromethane/methanol (100/1 to 5/1) to give 2-(4-(N-(2-(N,N-dimethylamino)ethyl)-N-methylamino)-2-methoxy-5-nitroanilino)-4-(7-methylindol-3-yl)pyrimidine (1.6 g, 30%) as a red solid.

2-(5-Amino-4-(N-(2-(N,N-dimethylamino)ethyl)-N-methylamino)-2-methoxyanilino)-4-(7-methylindol-3-ylpyrimidine To a solution of 2-(4-(N-(2-(N,N-dimethylamino)ethyl)-N-methylamino)-2-methoxy-5-nitroanilino)-4-(7-methylindol-3-yl)pyrimidine (1.60 g, 3.4 mmol) in acetone (160 mL) and H$_2$O (16 mL) was added zinc dust (3.95 g, 61 mmol) and NH$_4$Cl (1.26 g, 24 mmol) at 25° C., the reaction mixture was degassed and purged with N, 3 times, and then the mixture was stirred at 25° C. for 10 min under N$_2$. The reaction mixture was filtered and the filtrate was concentrated to give a residue. Water (10 mL) was added to the residue, the mixture was extracted with EtOAc (3×30 mL), the organic layers were combined and washed with brine (30 mL), dried (Na$_2$SO$_4$), filtered and concentrated to give a crude product. The crude product was purified by prep-HPLC to give 2-(5-amino-4-(N-(2-(N,N-dimethylamino)ethyl)-N-methylamino)-2-methoxyanilino)-4-(7-methylindol-3-yl)pyrimidine (400 mg, 27% yield) as a dark brown solid.

$^1$H NMR (CDCl$_3$) δ 8.95 (s, 1H), 8.35-8.34 (m, 1H), 8.29-8.26 (m, 1H), 8.21 (s, 1H), 7.99-7.98 (m, 1H), 7.61 (s, 1H), 7.22-7.18 (m, 1H), 7.09-7.06 (m, 2H), 6.67 (s, 1H), 3.83 (s, 3H), 3.11-3.08 (m, 2H), 2.70-2.68 (m, 5H), 2.54 (s, 3H), 2.50 (s, 6H), 2.05 (s, 1H).

N-(2-(N-(2-(N,N-Dimethylamino)ethyl)-N-methylamino)-4-methoxy-5-(4-(7-methylindol-3-yl)pyrimidin-2-ylamino)phenyl) propenamide A solution of 2-(5-amino-4-(N-(2-(N,N-dimethylamino)ethyl)-N-methylamino)-2-methoxyanilino)-4-(7-methylindol-3-yl)pyrimidine (400 mg, 0.898 mmol) in THF (16 mL) was degassed and purged with N$_2$ 3 times at 25° C., and the mixture was cooled to 0° C. Then a solution of DIPEA (139 mg, 1.08 mmol, 188 μL) in THF (0.8 mL) was added slowly to the mixture at 0° C., after stirring for 5 min, a solution of prop-2-enoyl chloride (81.3 mg, 0.898 mmol, 73 μL) in THF (0.8 mL) was added slowly to the above mixture, then the reaction mixture was stirred at 0° C. for 25 min. The reaction mixture was quenched with HCl/EtOAc (0.4 M, 3 mL), and concentrated to give a crude product. The crude product was purified by prep-HPLC to give N-(2-(N-(2-(N,N-Dimethylamino)ethyl)-N-methylamino)-4-methoxy-5-(4-(7-methylindol-3-yl)pyrimidin-2-ylamino)phenyl) propenamide (65 mg, 13% yield) as a yellow solid.

$^1$H NMR (d$_4$-MeOH) δ: 8.52 (s, 1H), 8.17 (s, 1H), 7.99-7.98 (m, 1H), 7.88 (s, 1H), 7.48-7.46 (m, 1H), 7.12-7.04 (m, 3H), 6.66-6.63 (m, 1H), 6.48-6.43 (m, 1H), 5.86-

5.83 (m, 1H), 3.96 (s, 3H), 3.56-3.54 (m, 2H), 3.36 (s, 2H), 2.90 (s, 6H), 2.79 (s, 3H), 2.53 (s, 3H). ESI-MS (m/z): 500.3 (M+H)$^+$

Example 12. N-(2-(N-(2-(N,N-Dimethylamino)ethyl)-N-methylamino)-4-methoxy-5-(4-(7-cyanoindol-3-yl)pyrimidin-2-ylamino)phenyl) propenamide

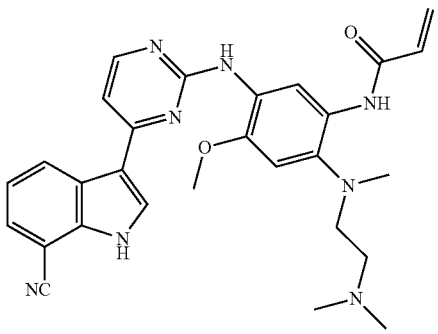 [SMILES: C=CC(=O)Nc1cc(Nc2nccc(-c3c[nH]c4c(C#N)cccc34)n2)c(OC)cc1N(C)CCN(C)C]

2-(4-(N-(2-(N,N-Dimethylamino)ethyl)-N-methylamino)-2-methoxy-5-nitroanilino)-4-(7-cyanoindol-3-yl)pyrimidine A solution of 2-chloro-4-(N,1-(t-butoxycarbonyl) 7-cyanoindol-3-yl)pyrimidine (100 mg, 0.39 mmol), 4-(N-(2-N,N-dimethylamino)ethyl)-N-methylamino)-2-methoxy-5-nitroanisole (105.4 mg, 0.39 mmol) and PTSA (81 mg, 0.47 mmol) in butan-2-ol (3.00 mL), was stirred at 100° C. for 12 hr. The mixture was filtered and concentrated in vacuum to remove the solvent. The residue was purified by prep-HPLC to afford 2-(4-(N-(2-(N,N-dimethylamino)ethyl)-N-methylamino)-2-methoxy-5-nitroanilino)-4-(7-cyanoindol-3-yl)pyrimidine (35.0 mg, 18.3%) as a brown solid.

2-(5-Amino-4-(N-(2-(N,N-dimethylamino)ethyl)-N-methylamino)-2-methoxyanilino)-4-(7-cyanoindol-3-ylpyrimidine Zinc dust (97 mg, 1.48 mmol) and NH$_4$Cl (30.8 mg, 0.58 mmol) were added to a solution of 2-(4-(N-(2-(N,N-dimethylamino)ethyl)-N-methylamino)-2-methoxy-5-nitroanilino)-4-(7-cyanoindol-3-yl)pyrimidine (40 mg, 0.08 mmol) in acetone (5 mL) and H$_2$O (0.5 mL), and stirred at 25° C. for 0.5 hr. The mixture was vacuum filtered, and the residue rinsed with acetone (3×10 mL), and the combined filtrates were concentrated under vacuum. The residue was purified by prep-HPLC to afford 2-(5-amino-4-(N-(2-(N,N-dimethylamino)ethyl)-N-methylamino)-2-methoxyanilino)-4-(7-cyanoindol-3-yl)pyrimidine (15 mg, 0.033 mmol, 40%) as a yellow solid.

N-(2-(N-(2-(N,N-Dimethylamino)ethyl)-N-methylamino)-4-methoxy-5-(4-(7-cyanoindol-3-yl)pyrimidin-2-ylamino)phenyl) propenamide A solution of 2-(5-amino-4-(N-(2-(N,N-dimethylamino)ethyl)-N-methylamino)-2-methoxyanilino)-4-(7-cyanoindol-3-yl)pyrimidine (15.0 mg, 0.031 mmol) in THF (3.00 mL) was degassed and purged with N$_2$ 3 times at 25° C., cooled to 0° C., and then DIPEA (4.8 mg, 0.037 mmol, 6.5 µL) was added. After stirring for 5 min a solution of prop-2-enoyl chloride (2.8 mg, 0.031 mmol, 2.5 µL) in THF (1 mL) was added slowly, then the mixture was stirred at 0° C. for 20 min. The reaction mixture was quenched by addition HCl(g)/EA (0.4M, 1 mL), then the mixture was filtered and the filtrate concentrated in vacuum to remove the solvent. The residue was purified by prep-HPLC to afford N-(2-(N-(2-(N,N-dimethylamino)ethyl)-N-methylamino)-4-methoxy-5-(4-(7-cyanoindol-3-yl)pyrimidin-2-ylamino)phenyl) propenamide (5.0 mg, 29.6%/o) as a yellow solid.

$^1$H NMR (d$_4$-MeOH) δ=8.67 (s, 2H), 8.09 (d, J=6.2 Hz, 1H), 7.83 (br. s., 1H), 7.67 (d, J=7.5 Hz, 1H), 7.54 (d, J=7.1 Hz, 1H), 7.35 (t, J=7.7 Hz, 1H), 7.08 (s, 1H), 6.70 (dd, J=10.1, 17.2 Hz, 1H), 6.44 (dd, J=1.3, 16.8 Hz, 1H), 5.84 (dd, J=1.5, 10.4 Hz, 1H), 4.00-3.90 (m, 3H), 3.56 (t, J=5.5 Hz, 2H), 3.41-3.33 (m, 2H), 3.01-2.85 (m, 5H), 2.80 (s, 3H) ESI-MS (m/z): 511.3 (M+H)$^+$.

Example 13. N-(2-(N-(2-(N,N-Dimethylamino)ethyl)-N-methylamino)-4-methoxy-5-(4-(2,3-dihydroindol-1-yl)pyrimidin-2-ylamino)phenyl) propenamide

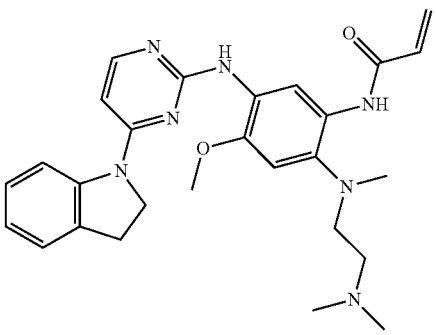 [SMILES: C=CC(=O)Nc1cc(Nc2nccc(N3CCc4ccccc43)n2)c(OC)cc1N(C)CCN(C)C]

A solution of 2-chloro-4-(2,3-dihydroindol-1-yl)pyrimidine (2.10 g, 9.06 mmol), 4-(N-(2-N,N-dimethylamino)ethyl)-N-methylamino)-2-methoxy-5-nitroanisole (2.43 g, 9.06 mmol) and PTSA (1.87 g, 10.87 mmol) in butan-2-ol (50 mL) was heated at 100° C. with stirring for 12 hr. The mixture was filtered and the filtrates concentrated in vacuum to remove the solvent. The residue was purified by column chromatography (SiO$_2$, DCM/MeOH, 80/1 to 5/1) to afford 2-(4-(N-(2-(N,N-dimethylamino)ethyl)-N-methylamino)-2-methoxy-5-nitroanilino)-4-(2,3-dihydroindol-1-yl)pyrimidine (3.20 g, 78.6%) as a red solid.

$^1$H NMR (d$_4$-MeOH) δ: 8.27 (br. s., 1H), 8.10 (br. s., 1H), 7.94 (d, J=7.5 Hz, 1H), 7.69 (d, J=8.0 Hz, 3H), 7.31 (d, J=7.0 Hz, 1H), 7.21 (d, J=8.0 Hz, 3H), 7.14-7.02 (m, 3H), 6.58 (br. s., 1H), 4.24 (t, J=7.5 Hz, 2H), 4.00 (s, 3H), 3.68-3.60 (m, 2H), 3.53-3.46 (m, 2H), 2.98 (s, 6H), 2.94 (s, 3H), 2.34 (s, 4H).

2-(4-(N-(5-Amino-2-(N,N-dimethylamino)ethyl)-N-methylamino)-2-methoxyanilino)-4-(2,3-dihydroindol-1-yl)pyrimidine Zinc dust (2.54 g, 38.9 mmol) and NH$_4$Cl (809 mg, 15.12 mmol) were added to a solution of 2-(4-(N-(2-(N,N-dimethylamino)ethyl)-N-methylamino)-2-methoxy-5-nitroanilino)-4-(2,3-dihydroindol-1-yl)pyrimidine (1.00 g, 2.16 mmol) in acetone (100 mL) and H$_2$O (10 mL) at 25° C., and stirred for 15 min. The mixture was vacuum filtered, and the residue rinsed with acetone (3×10 mL), and the combined filtrates were concentrated under vacuum. The residue was purified by prep-HPLC to afford 2-(4-(N-(5-amino-2-(N,N-dimethylamino)ethyl)-N-methylamino)-2-methoxyanilino)-4-(2,3-dihydroindol-1-yl)pyrimidine (0.60 g, 64%) as black solid.

$^1$H NMR (d$_4$-MeOH) δ=8.18 (d, J=8.0 Hz, 1H), 8.00 (d, J=6.0 Hz, 1H), 7.66 (s, 1H), 7.19 (d, J=7.0 Hz, 1H), 7.13 (t, J=7.5 Hz, 1H), 6.95-6.88 (m, 1H), 6.84 (s, 1H), 6.24 (d, J=6.0 Hz, 1H), 4.04 (t, J=8.5 Hz, 2H), 3.82 (s, 3H), 3.18 (t, J=8.5 Hz, 2H), 3.07 (t, J 6.8 Hz, 2H), 2.68 (s, 3H), 2.56 (t, J=6.8 Hz, 2H), 2.41-2.27 (m, 6H).

N-(2-(N-(2-(N,N-Dimethylamino)ethyl)-N-methylamino)-4-methoxy-5-(4-(2,3-dihydroindol-1-yl)pyrimidin-2-ylamino)phenyl) propenamide. A solution of prop-2-enoyl chloride (75.2 mg, 0.83 mmol, 67.7 L) in THF (2 mL) was added slowly to a solution of 2-(4-(N-(5-amino-2-(N,N-dimethylamino)ethyl)-N-methylamino)-2-methoxyanilino)-4-(2,3-dihydroindol-1-yl)pyrimidine (360 mg, 0.83 mmol) and DIPEA (129 mg, 1.0 mmol, 174 μL) in THF (25 mL) which had been degassed and purged with N$_2$ 3 times, at 0° C. under N$_2$. The above mixture was stirred at 0° C. for 25 min, and was quenched by addition of HCl(g)/EA (0.4M, 3 mL). The mixture was filtered and concentrated in vacuum. The residue was purified by prep-HPLC to afford N-(2-(N-(2-(N,N-dimethylamino)ethyl)-N-methylamino)-4-methoxy-5-(4-(2,3-dihydroindol-1-yl)pyrimidin-2-ylamino)phenyl) propenamide (50 mg, 12.3%) as a yellow solid.

$^1$H NMR (d$_4$-MeOH) δ=8.30 (br. s., 1H), 7.93 (d, J=7.5 Hz, 1H), 7.80 (br. s., 1H), 7.32 (d, J=6.0 Hz, 1H), 7.19-7.04 (m, 3H), 6.68 (dd, J=10.3, 16.8 Hz, 1H), 6.55 (d, J=7.5 Hz, 1H), 6.45 (dd, J=1.0, 17.1 Hz, 1H), 5.86 (d, J=11.5 Hz, 1H), 4.26 (t, J=7.8 Hz, 2H), 4.01-3.91 (m, 3H), 3.57 (t, J=5.3 Hz, 2H), 3.42-3.34 (m, 4H), 2.92 (s, 6H), 2.85-2.75 (m, 3H).

ESI-MS (m/z): 488.3 (M+H)$^+$.

Example 14. N-(2-(N-(2-(N,N-Dimethylamino)ethyl)-N-methylamino)-4-methoxy-5-(4-(2-methylindol-3-yl)pyrimidin-2-ylamino)phenyl) propenamide

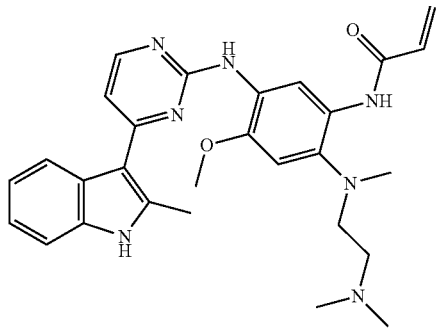 [SMILES: C=CC(=O)Nc1cc(Nc2nccc(-c3c(C)[nH]c4ccccc34)n2)c(OC)cc1N(C)CCN(C)C]

2-(4-(N-(2-(N,N-Dimethylamino)ethyl)-N-methylamino)-2-methoxy-5-nitroanilino)-4-(2-methylindol-3-yl)pyrimidine A stirred mixture of 4-(2-methylindol-3-yl)pyrimidine (500 mg, 2.05 mmol), 4-(N-(2-N,N-dimethylamino)ethyl)-N-methylamino)-2-methoxy-5-nitroanisole (550.5 mg, 2.05 mmol) and TsOH·H$_2$O (468 mg, 2.46 mmol) in 2-butanol (10 mL) was heated to 100° C. for 16 hrs The mixture was concentrated by under vacuum. The residue was purified by column chromatography (SiO$_2$. DCM:MeOH=8:1) to afford 2-(4-(N-(2-(N,N-dimethylamino)ethyl)-N-methylamino)-2-methoxy-5-nitroanilino)-4-(2-methylindol-3-yl)pyrimidine (0.60 g, 61.6%) was obtained as a brown oil.

$^1$H NMR (d$_6$-DMSO) δ: 11.82 (s, 1H), 9.88 (s, 1H), 8.56 (s, 1H), 8.34 (d, J=5.6, 1H), 7.99-7.43 (m, 1H), 7.43-7.33 (m, 5H), 7.15 (s, 1H), 7.13 (s, 1H), 7.09 (s, 1H), 7.01 (s, 1H), 6.92 (s, 1H), 3.90-3.68 (m, 3H), 3.48-3.41 (m, 4H), 3.30 (s, 4H), 6.13 (s, 3H), 2.88 (s, 9H), 2.79 (s, 3H), 2.67 (s, 7H).

2-(5-Amino-4-(N-(2-(N,N-dimethylamino)ethyl)-N-methylamino)-2-methoxyanilino)-4-(2-methylindol-3-yl)pyrimidine Zinc dust (1.48 g, 22.7 mmol) and NH$_4$Cl (472 mg, 8.8 mmol) were added to a solution of 2-(4-(N-(2-(N,N-dimethylamino)ethyl)-N-methylamino)-2-methoxy-5-nitroanilino)-4-(2-methylindol-3-yl)pyrimidine (0.60 g, 1.26 mmol) in acetone/H$_2$O=10:1 (66 mL) and stirred at 25° C. for 20 mins. The reaction mixture was filtered through a pad of celite, which was rinsed with acetone (3×10 mL) and the combined filtrates were concentrated under reduced pressure. The residue was purified by prep-HPLC to afford 2-(5-amino-4-(N-(2-(N,N-dimethylamino)ethyl)-N-methylamino)-2-methoxyanilino)-4-(2-methylindol-3-yl)pyrimidine (0.20 g, 35%) as a brown solid.

$^1$H NMR (CDCl$_3$) δ: 8.41 (s, 1H), 8.31 (s, 1H), 8.19-8.14 (m, 1H), 7.35 (s, 1H), 7.34 (s, 1H), 7.21 (s, 1H), 7.20-7.19 (m, 1H), 7.00 (s, 1H), 4.07 (s, 1H), 3.84 (s, 3H), 3.07-3.04 (m, 2H), 2.74 (d, J=10.8 Hz, 3H), 2.71 (s, 3H), 2.67 (s, 3H), 2.60-2.57 (m, 6H), 2.05 (s, 1H), 1.59-1.57 (m, 1H), 1.38-1.36 (s, 1H), 1.27 (s, 1H), 0.98-0.83 (m, 1H).

N-(2-N-(2-(N,N-Dimethylamino)ethyl)-N-methylamino)-4-methoxy-5-(4-(2-methylindol-3-yl)pyrimidin-2-ylamino)phenyl) propenamide Prop-2-enoyl chloride (30.5 mg, 0.337 mmol, 27.45 μL) in THF (0.5 mL) was added dropwise to a stirred solution of 2-(5-amino-4-(N-(2-(N,N-dimethylamino)ethyl)-N-methylamino)-2-methoxyanilino)-4-(2-methylindol-3-yl)pyrimidine (150 mg, 0.337 mmol) DIPEA (52.2 mg, 0.404 mmol, 70.1 μL) in THF (11.5 mL) under N$_2$ at −5° C. Then the reaction mixture was stirred at −5-0° C. for 1 h. The reaction mixture was quenched with HCl(g)/EA (0.4M, 2 mL). The residue was purified by prep-HPLC to afford N-(2-(N-(2-(N,N-dimethylamino)ethyl)-N-methylamino)-4-methoxy-5-(4-(2-methylindol-3-yl)pyrimidin-2-ylamino)phenyl) propenamide (50 mg, 27.71%) was obtained as an orange solid.

$^1$H NMR (d$_4$-MeOH) δ: 8.18 (s, 1H), 8.08 (s, 1H), 7.85 (s, 1H), 7.42-7.40 (m, 2H), 7.23-7.21 (d, J=5.6 Hz, 2H), 7.20 (s, 1H), 6.72-6.67 (m, 1H), 6.47-6.43 (m, 1H), 5.87-5.84 (m, 1H), 3.80 (s, 3H), 36.2-3.57 (m, 2H), 3.40-3.37 (m, 2H), 3.31 (s, 6H), 2.92 (s, 3H), 2.78 (s, 3H).

ESI-MS (m/z): 500.3 (M+H)$^+$.

Example 15. N-(2-(N-(2-(N,N-Dimethylamino)ethyl)-N-methylamino)-4-methoxy-5-(4-(indazol-3-yl)pyrimidin-2-ylamino)phenyl) propenamide

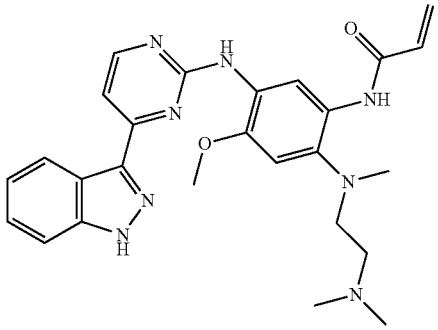 [SMILES: C=CC(=O)Nc1cc(Nc2nccc(-c3n[nH]c4ccccc34)n2)c(OC)cc1N(C)CCN(C)C]

2-(4-(N-(2-(N,N-Dimethylamino)ethyl)-N-methylamino)-2-methoxy-5-nitroanilino)-4-(indazol-3-yl)pyrimidine A mixture of 4-(1,N-(t-butoxycarbonyl)indazol-3-yl)pyrimidine, (500 mg, 1.5 mmol) 4-(N-(2-N,N-dimethylamino)ethyl)-N-methylamino)-2-methoxy-5-nitroanisole (405 mg, 1.5 mmol) and TsOH.H₂O (345 mg, 1.8 mmol) butan-2-ol (25 mL) at 25° C., was degassed and purged with N₂ 3 times, and then the mixture was stirred at 100° C. for 16 hours under N₂ atmosphere. The reaction mixture was cooled to 25° C., and concentrated under reduced pressure to give a residue. The residue was purified by prep-HPLC to give 2-(4-(N-(2-(N,N-dimethylamino)ethyl)-N-methylamino)-2-methoxy-5-nitroanilino)-4-(indazol-3-yl)pyrimidine (150 mg, 21%) as a red solid.

2-(5-Amino-4-(N-(2-(N,N-dimethylamino)ethyl)-N-methylamino)-2-methoxyanilino)-4-(indazol-3-yl)pyrimidine Zinc dust (382 mg, 5.8 mmol) and NH₄Cl (121 mg, 2.3 mmol) were added to a solution of 2-(4-(N-(2-(N,N-dimethylamino)ethyl)-N-methylamino)-2-methoxy-5-nitroanilino)-4-(indazol-3-yl)pyrimidine (150 mg, 0.32 mmol) in acetone (15 mL) and H₂O (1.5 mL)) at 25° C., the reaction mixture was degassed and purged with N₂ 3 times, and then the mixture was stirred at 25° C. for 5 min under N₂. The reaction mixture was filtered through a pad of celite, which was rinsed with acetone (3×10 mL) and the combined filtrates were concentrated under reduced pressure. The residue was purified by prep-HPLC to give 2-(5-amino-4-(N-(2-(N,N-dimethylamino)ethyl)-N-methylamino)-2-methoxyanilino)-4-(indazol-3-yl)pyrimidine (40 mg, 29% yield) as light yellow solid.

N-(2-(N-2-(N,N-Dimethylamino)ethyl)-N-methylamino)-4-methoxy-5-(4-(indazol-3-yl)pyrimidin-2-ylamino)phenyl) propenamide A solution of 2-(5-amino-4-(N-(2-(N,N-dimethylamino)ethyl)-N-methylamino)-2-methoxyanilino)-4-(indazol-3-yl)pyrimidine (40 mg, 0.092 mmol) and DIPEA (14 mg, 0.11 mmol, 19 μL) in THF (2.1 mL) was degassed and purged with N₂ 3 times at 25° C., and was cooled to 0° C. under N₂ atmosphere. A solution of prop-2-enoyl chloride (8 mg, 0.092 mmol, 8 μL) in THF (0.1 mL) was added slowly to the mixture and the reaction mixture was stirred at 0° C. under N₂ atmosphere for 20 min. The reaction mixture was quenched with HCl/EtOAc (0.4 M, 0.5 mL) at 0° C., and the mixture was concentrated to give a residue. The residue was purified by prep-HPLC to give N-(2-(N-(2-(N,N-dimethylamino)ethyl)-N-methylamino)-4-methoxy-5-(4-(indazol-3-yl)pyrimidin-2-ylamino)phenyl) propenamide (20 mg, 40%) as a yellow solid.

$^1$H NMR (d₄-MeOH) δ: 8.44-8.39 (m, 2H), 8.21 (s, 1H), 7.71 (d, J=5.6 Hz, 1H), 7.60 (d, J=8.8 Hz, 1H), 7.41 (t, J=7.8 Hz, 1H), 7.23 (t, J=7.6 Hz, 1H), 7.02 (s, 1H), 6.51-6.49 (m, 2H), 5.88-5.85 (m, 1H), 4.00 (s, 3H), 3.54-3.51 (m, 3H), 3.13 (s, 1H), 2.92 (s, 6H), 2.75 (s, 3H).

ESI-MS (m/z): 487.3 (M+H)⁺.

Example 16. 3-(2-(5-Acrylamido-4-((2-(dimethylamino)ethyl)(methyl)amino)-2-methoxyphenylamino)pyrimidin-4-yl)-1H-indole-7-carboxamide

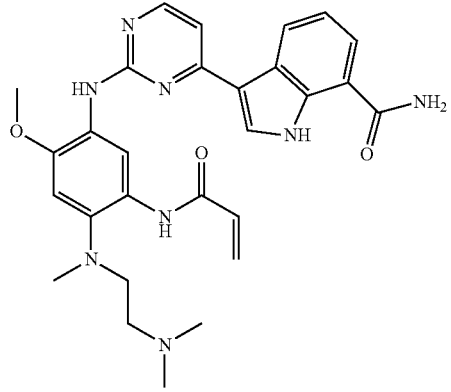 [SMILES: C=CC(=O)Nc1cc(Nc2nccc(-c3c[nH]c4c(C(N)=O)cccc34)n2)c(OC)cc1N(C)CCN(C)C]

To a solution of 4-fluoro-2-methoxy-5-nitroaniline (6.5 g, 33 mmol) and 7-(Carboxymethyl)-1-(2-chloropyrimidin-4-yl)-1H-indole (10 g, 30 mmol) in 2-pentanol (100 mL) was added PTSA (7.3 g, 33 mmol). The reaction was stirred at 120° C. for 2-3 hours. After completion, the reaction was cooled down to rt, filtered and washed with 2-pentanol (20 mL×2) and CH₃CN (40 mL×2). The filtrate was poured into water (100 mL) and adjusted to pH=8-9 with ammonia water. The mixture was filtered and the residue was rinsed with water and dried to give the desired diarylamine as a yellow solid (8 g, 53%).

1H NMR (300 MHz, DMSO-d6) δ=11.86 (s, 1H), 8.99 (d, J=8.7 Hz, 1H), 8.78 (d, J=8.1 Hz, 1H), 8.49-8.38 (m, 3H), 7.88-7.86 (m, 1H), 7.50-7.48 (m, 1H), 7.41-7.36 (m, 1H), 7.25-7.22 (m, 1H), 4.02 (s, 3H), 3.96 (s, 3H).

LCMS: (M+H)⁺: 437.8

Step 3

To a scalable tube were added the above diarylamine (4 g, 10 mmol), DIPEA (3.55 g, 30 mmol), DMAc (40 mL) and N,N,N'-trimethylethylenediamine (1.4 g, 15 mmol). The reaction was sealed and stirred at 140-150° C. for 1-2 h till completion. After cooling down, the reaction mixture was poured into water (120 mL) and extracted with EtOAc (40 mL×3). The combined organic layer was washed with brine (40 mL×3), dried and concentrated. The residue was triturated with MTBE to give the desired 1,4-diaminobenzene (3 g, 65%) as a red solid.

¹H NMR (300 MHz, CDCl₃) δ=10.56 (s, 1H), 9.62 (s, 1H), 8.83-8.80 (m, 1H), 8.67 (d, J=5.1 Hz, 1H), 8.47-8.46 (m, 1H), 8.23-8.21 (m, 1H), 7.82 (s, 1H), 7.62-7.56 (m, 1H), 7.42-7.40 (m, 1H), 6.99 (s, 1H), 4.26 (s, 6H), 3.63-3.60 (m, 2H), 3.15 (s, 3H), 3.00-2.93 (m, 2H), 2.64 (s, 6H).
LCMS (M-14-H)⁺: 503.8.

Step 4

To a solution of the above 1,4-diaminobenzene (1.5 g, 3 mmol) in MeOH (15 mL) was added Pd/C (1 g). The mixture was stirred under hydrogen for 3 hours. After completion, the reaction mixture was filtered and washed with MeOH (20 mL×2). The filtrate was concentrated in vacuo to give the desired 1,2,4-triaminobenzene (I g, 75%) as a yellow solid which was used in the next step without further purification.
¹H NMR (300 MHz, DMSO-d₆) δ 11.75 (br, 1H), 8.81-8.79 (m, 1H), 8.31-8.27 (m, 2H), 7.93-7.83 (m, 2H), 7.33-7.20 (m, 3H), 6.76 (s, 1H), 4.57 (s, 2H), 3.96 (s, 3H), 3.72 (s, 3H), 2.92-2.87 (m, 2H), 2.64 (s, 3H), 2.38-2.17 (m, 2H), 1.96 (s, 6H).
LCMS (M+H)⁺: 490.0

Step 5

To a solution of the above (1 g, 2 mmol) and DIPEA (0.3 g, 2.2 mmol) in THF (20 mL) was added dropwise a solution of acryloyl chloride (0.22 g, 2.4 mmol) in THF (10 mL) at −5 to 0° C. After addition, the reaction was stirred at this temperature for 2-3 h till completion. The reaction was diluted with DCM (100 mL), washed with saturated NaHCO₃ (30 mL), water (25 mL) and brine (25 mL). The organic layer was dried and concentrated to give the desired acrylamide (1.1 g, crude) which was used in the next step without purification.
¹H NMR (300 MHz, CDCl₃) δ=10.25 (s, 1H), 10.02 (s, 1H), 9.68 (s, 1H), 8.70 (s, 1H), 8.41-8.35 (m, 2H), 7.86 (d, J=7.5 Hz, 1H), 7.61 (s, 1H), 7.08-7.06 (m, 1H), 6.73 (s, 1H), 6.37-6.32 (m, 2H), 5.66-5.62 (m, 1H), 5.23 (s, 1H), 3.94 (s, 3H), 3.82 (s, 3H), 2.85-2.82 (m, 2H), 2.63 (s, 3H), 2.27-2.22 (m, 2H), 1.18 (s, 6H).
LCMS (M+H)⁺: 543.9

Step 6

To a solution of the above acrylamide (1.5 g, 2.76 mmol) and NH₄Cl (0.45 g, 9.41 mmol) in THF (50 mL) was added 1M LiHMDS (28 mL, 28 mmol) dropwise at 0° C. After addition, the mixture was warmed to 50° C., and stirred at this temperature for 2 h. The mixture was concentrated, diluted with water (100 mL) and extracted with DCM (40 mL×5). The combined organic layer was washed with brine (30 mL×3), dried and concentrated. The residue was purified by silica gel chromatography to give 3-(2-(5-acrylamido-4-((2-(dimethyl)(methyl)amino)-2-methoxyphenylamino)pyrimidin-4-yl)-1H-indole-7-carboxamide (150 mg, 10%) as an off-white solid.
¹H NMR (300 MHz, CDCl₃) δ=11.71 (s, 1H), 10.14 (s, 1H), 8.74 (s, 1H), 8.59-8.56 (m, 1H), 8.27-8.25 (m, 2H), 8.11 (s, 2H), 7.72 (d, =8.1 Hz, 1H), 7.48-7.47 (m, 1H), 7.27 (d, J=5.4 Hz, 1H), 7.09-7.03 (m, 2H), 6.40-6.37 (m, 1H), 6.22-6.20 (m, 1H), 5.74-5.71 (m, 1H), 3.82 (s, 3H), 2.91-2.90 (m, 2H), 2.74 (s, 3H), 2.34-2.32 (m, 2H), 2.23 (s, 6H).
LCMS (M+H)⁺528.9.

Example 17. N-(2-((2-(Dimethylamino)ethyl)(methyl)amino)-4-methoxy-5-(4-(3-sulfamoyl-1H-indol-1-yl)pyrimidin-2-ylamino)phenyl) acrylamide

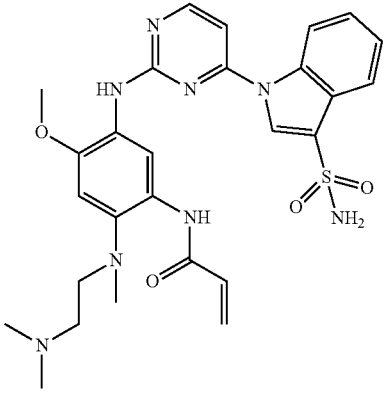 [SMILES: C=CC(=O)Nc1cc(Nc2nccc(-n3cc(S(N)(=O)=O)c4ccccc43)n2)c(OC)cc1N(C)CCN(C)C]

2-Chloro-4-((3-sulfamoyl)indol-1-yl)pyrimidine and 4-fluoro-2-methoxy-5-nitroaniline were reacted together to form the desired diarylamine as described elsewhere in this document.

The desired 1,4-diaminobenzene was prepared by fluoride displacement from the above diarylamine with N,N,N'-trimethylethylene-1,2-diamine in DMA containing DIPEA at 100° C., as described elsewhere in this document.
¹H NMR (300 MHz, CDCl₃) δ=9.20 (s, 1H), 8.58 (d, J=4.5 Hz, 2H), 8.14 (d, J=9 Hz, 1H), 8.04 (d, J=6.3 Hz, 1H), 7.69 (s, 1H), 7.46-7.42 (m, 2H), 7.06 (d, J=5.1 Hz, 1H), 6.77 (s, 1H), 5.30 (br, 2H), 4.04 (s, 3H), 3.41-3.40 (m, 2H), 2.92 (s, 3H), 2.74-2.70 (m, 2H), 2.41 (s, 6H).
LCMS: (M+H)⁺540.8

The desired 1,2,4-triaminobenzene was prepared from the above nitrodiaminobenzene, by Pd/C reduction in MeOH as described elsewhere in this document, and was used in next step without further purification.
¹H NMR (300 MHz, CDCl₃) δ=8.46 (d, J=5.1 Hz, 1H), 8.34-8.29 (m, 2H), 7.95-7.92 (m, 1H), 7.87 (s, 1H), 7.69 (s, 1H), 7.41-7.35 (m, 2H), 6.83 (d, J=5.1 Hz, 1H), 6.70 (s, 1H), 3.85 (s, 3H), 3.00-2.95 (m, 2H), 2.69 (s, 3H), 2.48-2.30 (m, 2H), 2.09 (s, 6H).
LCMS: (M+H)⁺: 510.9

To a solution of the above 1,2,4-triaminobenzene (1 g, 1.96 mmol, 1 eq) and DIPEA (280 mg, 2.15 mmol, 1.1 eq) in THF (20 mL) was added dropwise a solution of acryloyl chloride (220 mg, 2.43 mmol, 1.2 eq) in THF (20 mL) at −5° C. to 0° C. After addition, the mixture was allowed to warm to rt and stirred for 1 h. The mixture was diluted with DCM (100 mL) and two layers were separated. The organic layer washed with saturated NaHCO₃ (40 mL) and brine (40 mL), dried over Na₂SO₄, concentrated and purified by silica gel chromatography to give N-(2-((2-(dimethylamino)ethyl)(methyl)amino)-4-methoxy-5-(4-(3-sulfamoyl-1H-indol-1-yl)pyrimidin-2-ylamino)phenyl) acrylamide as a white solid (50 mg, 5%).
¹H NMR (300 MHz, CD₃OD) δ=8.61-8.59 (m, 2H), 8.37-8.35 (m, 1H), 8.01-8.00 (m, 1H), 7.82 (s, 1H), 7.52-7.45 (m, 3H), 7.09 (s, 1H), 6.75-6.66 (m, 1H), 6.48-6.43 (m, 1H), 5.86 (d, J=10.5 Hz, 1H), 3.97 (s, 3H), 3.58-3.56 (m, 2H), 3.39-3.32 (m, 2H), 2.92 (s, 6H), 2.82 (s, 3H).
LCMS: (M+H)⁺:564.9

Example 18. 1-(2-(5-Acrylamido-4-((2-(dimethylamino)ethyl)(methyl)amino)-2-methoxyphenylamino)pyrimidin-4-yl)-1H-indazole-3-carboxamide

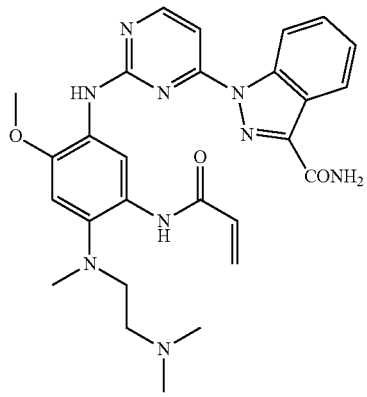 [SMILES: C=CC(=O)Nc1cc(Nc2nccc(-n3nc(C(N)=O)c4ccccc43)n2)c(OC)cc1N(C)CCN(C)C]

Ethyl 1,N-(2-chloropyrimid-4-yl)indazole-3-carboxylate and 4-fluoro-2-methoxy-5-nitroaniline were reacted together in pentanol at 100° C. in the presence of PTSA, as described elsewhere in this document, to give the desired diarylamine (4.4 g, 66%).

LCMS: (M+H)$^+$: 452.8

The desired 1,4-diaminobenzene (3 g, 85%) was prepared by fluoride displacement from the above diarylamine with N,N,N'-trimethylethylene-1,2-diamine in DMA containing DIPEA at 100° C., as described elsewhere in this document.

$^1$HNMR (300 MHz, DMSO-d) δ=9.08 (s, 1H), 8.52 (d, J=5.7 Hz, 1H), 8.19-8.15 (m, 2H), 7.49-7.47 (m, 2H), 7.33 (d, J=5.4 Hz, 1H), 6.86 (s, 1H), 4.48-4.46 (q, J=6.9 Hz, 2H), 3.89 (s, 3H), 3.34-3.30 (m, 5H), 2.94-2.89 (m, 2H), 2.17 (s, 6H), 1.41 (t, J=6.9 Hz, 3H).

LCMS: (M+H)$^+$: 534.8

The desired 1,2,4-triaminobenzene (2.3 g, 81%) was prepared from the above nitrodiaminobenzene, by Pd/C reduction in MeOH as described elsewhere in this document, and was used in next step without purification.

LCMS: (M+H)$^+$:505.0

To a solution of the above 1,2,4-triaminobenzene (2.3 g, 4.56 mmol) in DCM (12 mL) was added acryloyl chloride (0.5 g, 5.47 mmol) dropwise at −5 to 0° C. After addition, the reaction was warmed to rt and stirred for 1 hour. The reaction was diluted with DCM (30 mL), washed with saturated NaHCO$_3$ (20 mL), water (20 mL) and brine (20 mL). The organic layer was dried and concentrated to give the crude acrylamide product (2.1 g, 82%).

LCMS: (M+H)$^+$:558.9

To a solution of the above acrylamide (2.1 g, 3.76 mmol) and NH$_4$Cl (604 mg, 11.3 mmol) in THF (50 mL) was added LiHMDS (37 mL, 37 mmol) dropwise at 0° C. After addition, the mixture was stirred at this temperature for 2 h. The mixture was concentrated, diluted with water (20 mL) and extracted with EtOAc (30 mL×2). The combined organic layer was washed with brine (30 mL), dried and concentrated. The residue was purified by silica gel chromatography to give 1-(2-(5-acrylamido-4-((2-(dimethylamino)methyl)amino)-2-methoxyphenylamino)pyrimidin-4-yl)-1H-indazole-3-carboxamide (210 mg, 10%).

$^1$HNMR (300 MHz, DMSO-d$_6$) δ=8.96 (s, 1H), 8.51-8.47 (m, 3H), 8.23-8.20 (m, 2H), 7.72 (s, 1H), 7.49 (d, J=5.7 Hz, 1H), 7.39 (s, 2H), 7.08 (s, 1H), 6.45-6.36 (m, 1H), 6.21-6.14 (m, 1H), 5.74-5.70 (m, 1H), 3.76 (s, 3H), 2.95-2.93 (m, 2H), 2.77 (s, 3H), 2.46-2.24 (m, 2H), 2.22 (s, 6H).

LCMS: (M+H)$^+$:529.9.

Example 19. N-(5-(4-(3-(Aminomethyl)-1H-indol-1-yl)pyrimidin-2-ylamino)-2-((2-(dimethylamino)ethyl)(methyl)amino)-4-methoxyphenyl) acrylamide

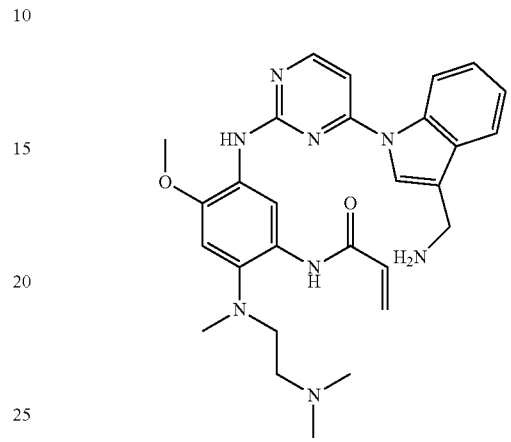

A 250 mL four-neck flask was charged with 3-(N-(t-butoxycarbonyl)aminomethyl)-1-(2-chloropyrimidin-4-yl)-1H-indole (5.4 g, 15 mmol), 4-fluoro-2-methoxy-5-nitroaniline (2.3 g, 16.5 mmol), 2-pentanol (60 mL) and PTSA (3.14 g, 16.5 mmol). The mixture was heated to reflux for 2 h. After completion, the mixture was filtered and the filter cake was washed with CH$_3$CN (10 mL), ammonium hydroxide (5 mL) and water (50 mL×2). The filter cake was then triturated with CH$_3$CN (15 mL), filtered and washed again with CH$_3$CN (10 mL). The solid was collected and dried to give the desired diarylamine (3.6 g, 59%).

$^1$H NMR (300 MHz, DMSO-d$_6$) δ=8.74 (d, J=8.7 Hz, 1H), 8.52-8.50 (m, 1H), 8.12 (s, 1H), 7.75-7.31 (m, 1H), 7.48-7.39 (m, 2H), 7.26-7.18 (m, 2H), 7.12-7.09 (m, 1H), 4.06 (s, 2H), 3.99 (s, 3H).

LCMS: (M+H)$^+$:408.9

A 100 mL sealable tube was charged with the above diarylamine (4.1 g, 10 mmol), DIPEA (3.9 g, 30 mmol), DMAc (30 mL) and N,N,N'-trimethylethane-1,2-diamine (1.5 g, 15 mmol). The mixture was stirred at 120° C. till completion. After cooling down to rt, the mixture was poured into water (150 mL). The precipitate was collected by filtration. The filter cake was washed with water and dried to give the crude 1,4-diaminobenzene (2.8 g. crude).

LCMS: (M+H)$^+$:490.9.

To a 250 mL four-neck flask were added the above 1,4-diaminobenzene (2.8 g, 5.7 mmol), DCM (30 mL). TEA (1.32 g, 13 mmol), Boc$_2$O (1.42 g, 6.5 mmol) and DMAP (0.16 g, 1.3 mmol). The mixture was stirred at rt for 2 hours. After completion, the mixture was diluted with DCM (100 mL), washed with saturated NH$_4$Cl (100 mL×2) and brine, dried over sodium sulfate and concentrated to give the desired N-Bocced primary amine (3.2 g, 54% for 2 steps).

$^1$H NMR (300 MHz, CDCl$_3$) δ=9.21 (s, 1H), 8.48-8.46 (m, 1H), 8.19-8.10 (m, 2H), 7.72-7.60 (m, 3H), 6.97 (d, J=5.4 Hz, 1H), 6.77 (s, 1H), 6.59 (d, J=6.9 Hz, 1H), 4.59-4.56 (m, 2H), 4.04 (s, 3H), 3.11-3.08 (m, 2H), 2.92 (s, 3H), 2.77-2.70 (m, 2H), 2.41 (s, 6H), 1.49 (s, 9H).

LCMS: (M+H)$^+$:590.9.

The desired 1,2,4-triaminobenzene (1.17 g) was prepared from the above nitrodiaminobenzene, by Pd/C reduction in MeOH as described elsewhere in this document, and was used in next step without purification.

$^1$H NMR (300 MHz, CDCl$_3$) δ 8.48 (d, J=8.1 Hz, 1H), 8.38 (d, J=5.7 Hz, 1H), 8.20 (d, J=6 Hz, 1H), 7.97 (s, 1H), 7.69-7.65 (m, 3H), 7.38-7.24 (nm, 2H), 6.79-6.73 (m, 2H), 6.49 (d, J=6 Hz, 1H), 4.52 (d, J=4.8 Hz, 2H), 3.86 (s, 3H), 3.00-2.97 (m, 2H), 2.69 (s, 3H), 2.47-2.43 (m, 2H), 2.29 (s, 6H), 1.48 (s, 9H).

To a solution of the above 1,2,4-triaminobenzene (1.17 g, 2 mmol) in DCM (12 mL) was added acryloyl chloride (0.22 g, 2.4 mmol) at −5 to 0° C. After stirring at rt for 1 h, the mixture was diluted with DCM (30 mL) and washed with saturated NaHCO$_3$ (10 mL) and brine (10 mL). The organic layer was separated, dried over sodium sulfate and concentrated to give the desired acrylamide (0.72 g, crude).

To a solution of the above acrylamide (720 mg, 1.2 mmol) in dioxane (10 mL) was added 4M HCl in dioxane (10 mL). The mixture was stirred at rt for 2 hours and then concentrated in vacuo. The residue was purified by prep-HPLC (TFA condition). The correct fractions were collected and concentrated in vacuo. The residue was treated with 30 ml of 0.2% (V/V) aqueous HCl and lyophilized to give N-(5-(4-(3-(aminomethyl)-1H-indol-1-yl)pyrimidin-2-ylamino)-2-((2-(dimethylamino)ethyl)(methyl)amino)-4-methoxyphenyl) acrylamide (5 mg, 0.4% for 3 steps).

$^1$HNMR (300 MHz, CD$_3$OD) δ=9.02 (s, 1H), 8.34 (d, J=5.7 Hz, 1H), 8.24-8.19 (m, 2H), 7.61 (d, J=6.9 Hz, 1H), 7.25-7.16 (m, 2H), 7.06 (d, J=5.7 Hz, 1H), 6.98 (s, 1H), 6.59-6.50 (m, 1H), 6.34-6.28 (m, 1H), 5.77 (d, J=10.5 Hz, 1H), 4.01 (s, 2H), 3.90 (s, 3H), 3.06-3.02 (m, 2H), 2.69 (s, 3H), 2.46-2.42 (m, 2H), 2.28 (s, 6H).

LCMS: 515.0 (M+H)$^+$.

Example 20. N-(5-(4-(3-Amino-1H-indazol-1-yl)pyridin-2-ylamino)-2-(N-(2-(dimethylamino)ethyl)-N-methylamino)-4-methoxyphenyl) acrylamide

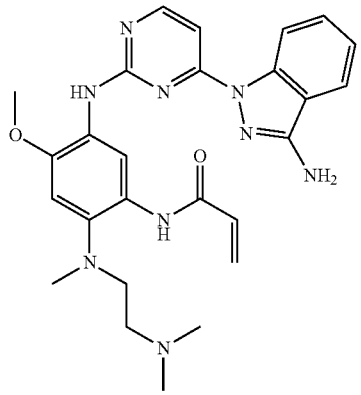 [SMILES: C=CC(=O)Nc1cc(Nc2nccc(-n3nc(N)c4ccccc43)n2)c(OC)cc1N(C)CCN(C)C]

To a solution of 3-amino-1-(2-chloropyrimid-4-yl)indazole (2.3 g, 9.38 mmol) and 4-fluoro-2-methoxy-5-nitroaniline (1.89 g, 10. 2 mmol) in 2-pentanol (40 mL) was added PTSA (1.93 g, 10.2 mmol). The reaction was refluxed for 2 hours. After cooling down to rt, the reaction was filtered and washed with CH$_3$CN (10 mL). The residue was pulped with 1 N NaOH (5 mL), filtered and washed with water (50 mL×2) and pulped once more with CH$_3$CN (15 mL). The residue was filtered, washed with CH$_3$CN (10 mL) and dried to give the desired diarylamine (2.88 g, 77%)

LCMS: (M+H)$^+$: 395.8

The desired 1,4-diaminobenzene was prepared by fluoride displacement from the above diarylamine with N,N,N'-trimethylethylene-1,2-diamine as described above (2 g, 56%).

$^1$HNMR (300 MHz, DMSO-d$_6$) δ=8.62 (s, 1H), 8.52-8.49 (br, 1H), 8.37-8.32 (m, 2H), 7.96-7.93 (m, 1H), 7.41-7.39 (m, 1H), 7.34-7.29 (m, 1H), 7.06 (d, J=5.7 Hz, 1H), 6.92 (s, 1H), 6.48 (s, 2H), 3.99 (s, 3H), 3.45-3.43 (m, 2H), 3.40-3.36 (m, 2H), 2.97 (s, 3H), 2.25 (s, 6H).

LCMS: 478.1 (M+H)$^+$. LCMS: (M+H)$^+$: 477.9

To a solution of the above 1,4-diaminobenzene (2 g, 4.2 mmol) in DCM (60 mL) was added TEA (0.85 g, 8.4 mmol), DMAP (0.1 g, 0.83 mmol) and Boc$_2$O (4.56 g, 20.9 mmol). The reaction was stirred at rt overnight. After completion, the reaction was washed with saturated NaHCO$_3$ and brine, dried and concentrated in vacuo to give the desired 3-(N,N-diBocamino)indazole (1.4 g, 43%) which was used in the next step without purification.

LCMS: (M+H)$^+$: 677.9

The above 3-(N,N-DiBocamino)indazole was hydrogenated over Pd/C in ethanol as described previously to give the desired 1,2,4-triaminobenzene (2.3 g, 81%) which was used in the next step without purification.

LCMS: (M+H)$^+$: 647.9

The above 1,2,4-triaminobenzene was acylated with acroyl chloride and TEA, as described previously to give the desired acrylamide (1.05 g, 83%).

LCMS: (M+H)$^+$: 701.9

To a solution of the above acrylamide (1.05 g, 1.5 mmol) in DCM (10 mL) was added TFA (4 mL). The mixture was stirred at it for 1 h. After completion, the mixture was concentrated and the residue was adjusted to pH=8-9 with 0.5 N NaOH and extracted with DCM (10 mL×2). The combined organic layer was washed with water (20 mL) and brine (20 mL), dried and concentrated. The residue was purified by silica gel chromatography to give N-(5-(4-(3-amino-1H-indazol-1-yl)pyrimidin-2-ylamino)-2-(N-(2-(dimethylamino)ethyl)-N-methylamino)-4-methoxyphenyl) acrylamide (150 mg, 20%).

$^1$HNMR (300 MHz, MeOD) δ=8.79 (s, 1H), 8.49-8.51 (m, 1H), 8.22 (d, J=5.7 Hz, 1H), 7.73-7.71 (m, 1H), 7.38-7.34 (m, 1H), 7.14-7.12 (m, 2H), 7.00 (s, 1H), 6.52-6.55 (m, 1H), 6.29-6.26 (m, 1H), 5.76-5.74 (m, 1H), 3.89 (s, 3H), 3.10-3.08 (m, 2H), 2.74 (s, 3H), 2.54-2.50 (m, 2H), 2.32 (s, 6H).

LCMS: (M+H)$^+$: 501.9.

Example 21. N-(2-((2-(Dimethylamino)ethyl)(methyl)amino)-4-methoxy-5-(4-(3-(methylamino)-1H-indazol-1-yl)pyrimidin-2-ylamino)phenyl) acrylamide

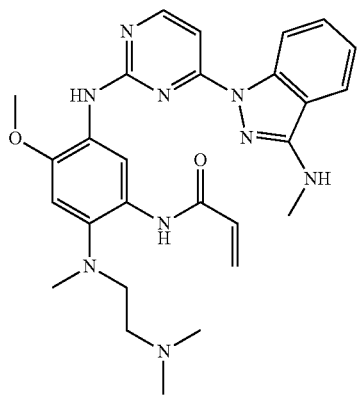 [SMILES: C=CC(=O)Nc1cc(Nc2nccc(-n3nc(NC)c4ccccc43)n2)c(OC)cc1N(C)CCN(C)C]

1-(2-Chloropyrimidin-4-yl)-3-(N-(t-butoxycarbonyl-N-methylamino)-1H-indazole and 4-fluoro-2-methoxy-5-nitroaniline were reacted together in n-pentanol containing PTSA, as described previously to give the desire diarylamine (400 mg, 29%).

$^1$HNMR (300 MHz, DMSO-$d_6$) δ=8.81 (d, J=8.1 Hz, 1H), 8.68 (br, 1H), 8.59 (d. J=7.8 Hz, 1H), 8.35 (d, J=5.4 Hz, 1H), 7.84 (d, J=7.8 Hz, 1H), 7.44-7.39 (m, 2H), 7.28-7.23 (m, 1H), 7.18 (d, J=5.7 Hz, 1H), 6.97 (br, 1H), 3.99 (s, 3H), 2.98 (s, 3H).

LCMS: (M+H)$^+$: 409.8.

The desired 1,4-diaminobenzene was prepared by fluoride displacement from the above diarylamine with N,N,N'-trimethylethylene-1,2-diamine as described above (467 mg, 56%).

1HNMR (300 MHz, DMSO-d6) δ=8.48-8.43 (m, 2H), 8.29-8.26 (m, 2H), 7.82 (d. J=8.1 Hz, 1H), 7.36-7.31 (m, 1H), 7.36-7.31 (m, 1H), 7.08 (d, J=5.7 Hz, 1H), 6.94-6.92 (m, 1H), 6.84 (s, 1H), 3.91 (s, 3H), 2.97-2.94 (m, 4H), 2.88 (s, 3H), 2.79 (s, 3H), 2.17 (s, 6H).

LCMS: (M+H)$^+$: 491.9

A 100 mL round-bottom flask was charged with the above 1,4-diaminobenzene (467 mg, 0.95 mmol), DCM (10 mL), TEA (124 mg, 1.22 mmol). DMAP (15 mg, 0.12 mmol) and Boc$_2$O (333 mg, 1.52 mmol). The mixture was stirred at it overnight. The reaction was monitored by TLC. After completion, the mixture was diluted with DCM (30 mL), washed with aq. NH$_4$Cl (30 mL). NaHCO$_3$ (30 mL) and brine. The organic layer was dried over sodium sulfate and concentrated to give the desired 3-(N-Bocamino)indazole (650 mg, crude).

LCMS: (M+H)$^+$: 691.9

The above 3-(N-Bocamino)indazole was hydrogenated over Pd/C in ethanol as described previously to give the desired 1,2,4-triaminobenzene (450 mg) which was used in the next step without purification.

LCMS: (M+H)$^+$: 661.9

The above 1,2,4-triaminobenzene was acylated with acroyl chloride and TEA, as described previously to give the desired acrylamide (420 mg, crude).

LCMS: (M+H)$^+$: 715.9

To a solution of the above acrylamide (420 mg, 0.59 mmol) in DCM (5 mL) was added TFA (5 mL) at 0° C. The mixture was stirred at rt for 2 h. The reaction was monitored by TLC and LCMS. After completion, the mixture was concentrated and adjusted to pH=8-9 with 0.5 N NaOH and extracted with DCM (10 mL×2). The combined organic layer was washed with water (20 mL) and brine (20 mL), dried over sodium sulfate and concentrated. The residue was purified by prep-HPLC to give the desired product N-(2-((2-(dimethylamino)ethylmethyl)amino)-4-methoxy-5-(4-(3-(methylamino)-1H-indazol-1-yl)pyrimidin-2-ylamino) phenyl) acrylamide (55 mg, 11% for 4 steps).

$^1$HNMR (300 MHz, DMSO-$d_6$) δ=10.09 (br, 1H), 8.52 (s, 1H), 8.43-8.37 (m, 2H), 8.25 (d, J=5.7 Hz, 1H), 7.79 (d, J=7.5 Hz, H), 7.31-7.28 (m, 1H), 7.20-7.15 (m, 1H), 7.04-7.00 (m, 2H), 6.89 (br, 1H), 6.46-6.37 (m, 1H), 6.19-6.13 (m, 1H), 5.71 (d, J=10.5 Hz, 1H), 3.77 (s, 3H), 2.97-2.95 (m, 5H), 2.75 (s, 3H), 2.48-2.44 (m, 2H), 2.24 (s, 6H).

LCMS: (M+H)$^+$: 515.9.

Example 22. N-(2-((2-(Dimethylamino)ethyl)(methyl)amino)-4-methoxy-5-((4-(7-oxo-6,7-dihydro-1H-pyrrolo[2,3-c]pyridin-3-yl)pyrimidin-2-yl)amino)phenyl) acrylamide

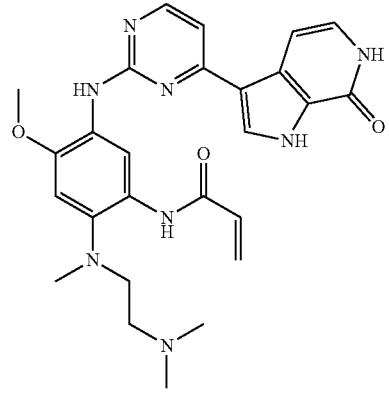 [SMILES: C=CC(=O)Nc1cc(Nc2nccc(-c3c[nH]c4c(=O)[nH]ccc34)n2)c(OC)cc1N(C)CCN(C)C]

To a solution of 4-(N-(2-(N,N-dimethylamino)ethyl)-N-methylamino)-2-methoxy-5-nitroaniline (515 mg, 1.92 mmol, 1.0 eq) in butan-2-ol (25 mL) was added 2-chloro-4-(7-methoxypyrrolo[2,3-c]pyrid-3-yl)pyrimidine (500.00 mg, 1.92 mmol, 1.00 eq) and TsOH.H2O (438 mg, 2.30 mmol, 1.2 eq) at 25° C. The reaction mixture was degassed and purged with N2 3 times and stirred at 100° C. for 14 hours. LC-MS showed that the reaction was complete. The reaction was concentrated to give a residue which was purified by prep-HPLC (column: Waters Xbridge 150*25 5 u; mobile phase: [water (10 mM NH$_4$HCO$_3$)-ACN]; B %: 15%-45%, 12 min) to give the desired diarylamine (110 mg, 230 umol, 12% yield) as a yellow solid.

1H NMR 400 MHz DMSO-d6 δ 11.1 (br s, 1H), 8.44 (s, 1H), 8.29 (d, J=5.2 Hz, 1H), 8.14 (d, J=6.8 Hz, 2H), 7.75 (d, J=9.2 Hz, 1H), 7.21 (d, J=5.2 Hz, 1H), 7.15 (d, J=7.2 Hz, 1H), 6.89-6.81 (m, 1H), 6.80 (s, 1H), 6.58 (d, J=2.4 Hz, 0.5H), 6.43 (d, J=2.4, 0.5H), 3.91 (s, 3H), 3.26-3.14 (m, 2H), 2.81 (s, 3H), 2.45-2.36 (m, 2H), 2.12 (s, 6H), 2.08 (s, 3H).

ESI-MS (m/z): 479.3 (M+H)$^+$

To a solution of the above diarylamine (100 mg, 209 umol, 1.0 eq) in acetone (10 mL) and H2O (1.0 mL) was added Zn (246 mg, 3.76 mmol, 18 eq) and NH$_4$Cl (78.3 mg, 1.46 mmol, 7.0 eq) at 25° C. The reaction mixture was degassed and purged with N2 3 times and stirred at 25° C. for 10 minutes. LCMS showed that the reaction was complete. The mixture was filtered and the filtrate was concentrated to give a residue which was purified by prep-HPLC (column: Luna C18 100*30 5 u; mobile phase: [water(0.1% TFA)-ACN]; B %: 1%-30%, 12 min) to give the desired 1,2,4-triaminobenzene (50 mg, 111 umol, 53% yield) as a brown solid.

ESI-MS (m/z): 449.4 (M+H)$^+$

A solution of the above 1,2,4-triaminobenzene (25 mg, 55.7 umol, 1.0 eq) in THF (1.0 mL) was cooled to 0° C. DIEA (8.64 mg, 66.9 umol, 11.7 uL, 1.2 eq) in THF (0.1 mL) was added followed by prop-2-enoyl chloride (5.04 mg, 55.7 umol, 4.54 uL, 1.0 eq) in THF (0.1 mL) dropwise. The mixture was stirred at 0° C. for 0.5 h. LCMS showed that the reaction was complete. The reaction mixture was concentrated to give a residue which was purified by prep-HPLC (column: Luna C18 100*30 5 u, mobile phase: [water(0.1% TFA)-ACN]; B %: 5%-25%, 12 min) to give N-(2-((2-

(dimethylamino)ethyl)(methyl)amino)-4-methoxy-5-((4-(7-oxo-6,7-dihydro-1H-pyrrolo[2,3-c]pyridin-3-yl)pyrimidin-2-yl)amino)phenyl) acrylamide (28 mg, 55.7 umol, 96% purity, 48% yield) as a yellow solid.

$^1$H NMR 400 MHz DMSO-d$_6$ δ 12.62 (br s, 1H), 11.11 (br s, 1H), 9.57 (s, 1H), 9.20 (s, 1H), 8.40 (s, 1H), 8.27 (d, J=5.6 Hz, 2H), 7.25 (d, J=5.6 Hz, 1H), 7.14 (d, J=7.2 Hz, 1H), 6.97 (s, 1H), 6.92-6.84 (m, J=6.0, 1H), 6.57 (d, J=10.0, 1H), 6.32 (dd, J=2.0, 17.0 Hz, 1H), 5.81-5.72 (m, 1H), 3.85 (s, 3H), 3.36-3.15 (m, 4H), 2.85-2.65 (m, 6H), 2.60 (s, 3H).

ESI-MS (m/z): 503.3 (M+H)$^+$. LCMS (220 nm): 96.58%

Example 23. N-(2-((2-(Dimethylamino)ethyl)(methyl)amino)-4-methoxy-5-((4-(7-methoxy-1H-pyrrolo[2,3-c]pyridin-3-yl)pyrimidin-2-yl)amino)phenyl) acrylamide

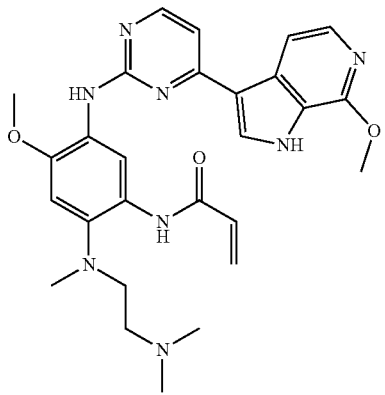 [SMILES: C=CC(=O)Nc1cc(Nc2nccc(-c3c[nH]c4c(OC)nccc34)n2)c(OC)cc1N(C)CCN(C)C]

To a solution of 4-(N-(2-(N,N-dimethylamino)ethyl)-N-methylamino)-2-methoxy-5-nitroaniline (618 mg, 2.3 mmol, 1.2 eq) in DMF (10.00 mL) was added 2-chloro-4-(7-methoxypyrrolo[2,3-c]pyrid-3-yl)pyrimidine (500 mg, 1.92 mmol, 1.0 eq), Pd(OAc)$_2$ (43.1 mg, 192 umol, 0.1 eq), Cs$_2$CO$_3$ (750 mg, 2.3 mmol, 1.2 eq) and Xantphos (111 mg, 192 umol, 0.1 eq) at 25° C. The reaction mixture was degassed and purged with N$_2$ 3 times and stirred at 100° C. for 14 hours. LC-MS showed that the reaction was complete. The reaction was quenched with water (30 mL) and extracted with EtOAc (30 mL×3). The combined organic layer was concentrated to give a residue which was purified by prep-HPLC (column: Phenomenex luna C18 250*50 mm*10 um; mobile phase: [water(0.1% TFA)-ACN]; B %: 5%-35%, 0, 20 min) to give the desired diarylamine (230 mg, 467 umol, 24% yield) as a brown solid.

$^1$H NMR 400 MHz DMSO-d$_6$ δ 12.53 (br s, 1H), 9.49 (br s, 1H), 8.67 (s, 1H), 8.6 (br s, 1H), 8.43 (d, J=3.2 Hz, 1H), 8.33 (d, J=5.6 Hz, 1H), 7.82 (d, J=4.0 Hz, 1H), 7.67 (d, J=5.6 Hz, 1H), 7.37 (d, J=5.6 Hz, 1H), 6.93 (s, 1H), 4.00 (s, 3H), 3.96 (s, 3H), 3.46 (t, J=6.6 Hz, 2H), 3.37 (t, 2H), 2.82 (s, 6H), 2.81 (s, 3H).

ESI-MS (m/z): 493.3 (M+H)$^+$

The desired 1,2,4-triaminobenzene was prepared (100 mg, 216 umol, 53% yield) as a brown solid by reducing the above diarylamine with Zn and NH$_4$Cl as described elsewhere in this application.

$^1$H NMR 400 MHz DMSO-d$_6$ δ 12.60 (br s, 1H), 8.85 (br s, 1H), 8.52 (br s, 1H), 8.33 (d, J=5.6 Hz, 1H), 7.84 (br s, 1H), 7.73 (d, J=5.6 Hz, 1H), 7.39 (d, J=6.0 Hz, 1H), 7.05 (s, 1H), 4.01 (s, 3H), 3.86 (s, 3H), 3.33 (m, 4H), 2.84 (s, 6H), 2.60-2.48 (s, 3H).

ESI-MS (m/z): 463.2 (M+H)

To a solution of the above 1,2,4-triaminobenzene (50 mg, 108 umol, 1.0 eq) in THF (1.0 mL) was added DIEA (27.9 mg, 216 umol, 37.8 uL, 2.0 eq) in THF (100.00 uL). Prop-2-enoyl chloride (9.78 mg, 108 umol, 8.81 uL, 1.0 eq) in THF (100 uL) was added dropwise and the mixture was stirred at 0° C. for 0.5 h. LCMS showed that the reaction was complete. The solvent was concentrated to give a residue which was purified by prep-HPLC (column: Waters Xbridge 150*25 5 u; mobile phase: [water (10 mM NH$_4$HCO$_3$)-ACN]; B %: 25%-55%, 12 min) to give N-(2-((2-(dimethylamino)ethyl)(methyl)amino)-4-methoxy-5-((4-(7-methoxy-1H-pyrrolo[2,3-c]pyridin-3-yl)pyrimidin-2-yl)amino)phenyl) acrylamide (8.0 mg, 15.5 umol, 7% yield) as a white solid.

$^1$H NMR 400 MHz MeOD δ 9.18 (br s, 1H), 8.43 (s, 1H), 8.30 (d, J=5.6 Hz, 1H), 7.79 (d, J=6.0 Hz, 1H), 7.68 (d, J=5.6 Hz, 1H), 7.22 (d, J=5.5 Hz, 1H), 6.96 (s, 1H), 6.54 (dd, J=10.0, 17.2 Hz, 1H), 6.37 (dd, J=1.6, 17.2 Hz, 1H), 5.79-5.74 (m, 1H), 4.07 (s, 3H), 3.92 (s, 3H), 3.05 (t, J=5.6 Hz, 2H), 2.69 (s, 3H), 2.45 (t, J=5.6 Hz, 2H), 2.29 (s, 6H).

ESI-MS (m/z): 517.3 (M+H)$^+$, LCMS (220 nm): 95.14%

Example 24. 5-(2-((5-Acrylamido-4-((2-(dimethylamino)ethyl)(methyl)amino)-2-methoxyphenyl)amino)-5-chloropyrimidin-4-yl)nicotinamide hydrochloride

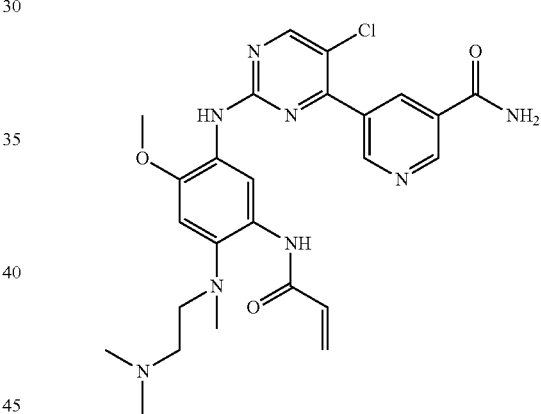

To a solution of 4-(N-(2-(N,N-dimethylamino)ethyl)-N-methylamino)-2-methoxy-5-nitroaniline (2.83 g, 10.6 mmol) in dioxane (30 mL) was added 2,5-dichloro-4-(6-(carboxymethyl)pyrid-3-yl)pyrimidine (3.0 g, 10.6 mmol), Cs$_2$CO$_3$ (6.88 g, 21 mmol). Xantphos (1.22 g, 2.1 mmol) and Pd$_2$(dba)$_3$ (967 mg, 1.1 mmol) at 20° C. The reaction mixture was degassed and purged with N$_2$ 3 times and stirred at 120° C. for 14 hours. TLC (dichloromethane/methanol=10/1, R$_f$=0.38) showed that the reaction was complete. The mixture was cooled to 20° C., filtered and the filtrate was concentrated to give a residue. The residue was purified by silica gel column chromatography (dichloromethane/methanol=100/1 to 5/1) to give the desired diarylamine (2.0 g, crude) as a red solid.

ESI-MS (m/z): 516.2 (M+H)

To a solution of the above diarylamine (1.8 g, crude) in acetone (100 mL) and H$_2$O (10 mL) was added Zn (4.1 g, 63 mmol) and NH$_4$Cl (1.3 g, 24 mmol) at 20° C. The reaction mixture was degassed and purged with N$_2$ 3 times and stirred at 20° C. for 10 minutes. LC-MS and HPLC showed starting material was consumed completely and one major peak with desired MS was detected. The mixture was filtered and the filtrate was concentrated to give a residue. The residue was extracted with DCM (30 mL×3). The organic layers were combined, dried over Na$_2$SO$_4$, filtered and concentrated to give a residue. The residue was purified by prep-HPLC (TFA condition) to give the desired 1,2,4-triaminobenzene (680 mg, 36% yield) as a dark red solid.

$^1$H NMR 400 MHz MeOD δ 9.27-9.26 (m, 2H), 8.89-8.88 (m, 1H), 8.64 (s, 1H), 8.53 (s, 1H), 7.15 (s, 1H), 4.01 (s, 6H), 3.43 (m, 2H), 3.41-3.38 (m, 2H), 2.91 (s, 6H), 2.69 (s, 3H)

ESI-MS (m/z): 486.2 (M+H)$^+$

To a solution of give the above 1,2,4-triaminobenzene (630 mg, 1.3 mmol) in THF (2.5 mL). MeOH (1 mL) and H$_2$O (2.5 mL) was added NaOH (208 mg, 5.2 mmol) at 20° C. The reaction mixture was stirred at 20° C. for 1 hour. TLC (dichloromethane/methanol=5/1, R$_f$=0.1) showed that the reaction was complete. The mixture was adjusted to pH=5 with 1N HCl and concentrated to give the desired nicotinic acid (1.0 g, crude) as a red solid which was used in the next step without further purification.

ESI-MS (m/z): 472.2 (M+H)$^+$

To a solution of the above nicotinic acid (1.0 g, crude) in THF (10 mL) was added NH$_4$Cl (170 mg, 3.2 mmol), HOBt (344 mg, 2.5 mmol) and EDCI (487 mg, 2.5 mmol) at 20° C. The reaction mixture was degassed and purged with N$_2$ 3 times and stirred at 20° C. for 2 hour. LC-MS and HPLC showed starting material was consumed completely and one major peak with desired MS was detected. The mixture was concentrated to give a residue which was purified by prep-HPLC (neutral condition) to give the desired nicotinamide (37 mg, 3.7% yield) as a brown solid.

ESI-MS (m/z): 471.2 (M+H)$^+$.

To a solution of the above nicotinamide (32 mg, 68 umol) in THF (2 mL) was added a solution of DIEA (17.6 mg, 136 umol, 24 uL) in THF (0.5 mL) at 0° C. under N$_2$. A solution of prop-2-enoyl chloride (6.2 mg, 68 umol, 5.5 uL) in THF (0.5 mL) was added slowly. The resulting mixture was stirred at 0° C. for 20 minutes. LC-MS and HPLC showed starting material was consumed completely and one major peak with desired MS was detected. The mixture was concentrated to give a residue which was purified by prep-HPLC (TFA condition). The correct fractions were collected and concentrated under vacuum to give a residue which was treated with 30 ml of 0.2% (V/V) aqueous HCl and lyophilized to give. 5-(2-((5-acrylamido-4-((2-(dimethyl-amino)ethyl)(methyl)amino)-2-methoxyphenyl)amino)-5-chloropyrimidin-4-yl)nicotinamide hydrochloride (30 mg, 79% yield, 100% purity, HCl) as a red solid.

$^1$H NMR 400 MHz MeOD δ 9.23 (d, J=2.4 Hz, 1H), 9.15 (d, J=2.4 Hz, 1H), 8.83-8.82 (m, 1H), 8.59 (s, 1H), 8.34 (s, 1H), 6.94 (s, 1H), 6.55-6.48 (m, 1H), 6.44-6.40 (m, 1H), 5.85-5.82 (m, 1H), 3.99 (s, 3H), 3.47-3.23 (m, 2H), 3.30-3.26 (m, 2H), 2.84 (s, 6H), 2.70 (s, 3H)

LCMS (m/z): 525.3 (M+H)$^+$, HPLC (220 nm): 100%

Example 25. N-(5-((5-Chloro-4-(6-(methylamino) pyridin-3-yl)pyrimidin-2-yl)amino)-2-((2-(dimethyl-amino)ethyl)(methyl)amino)-4-methoxyphenyl) acrylamide

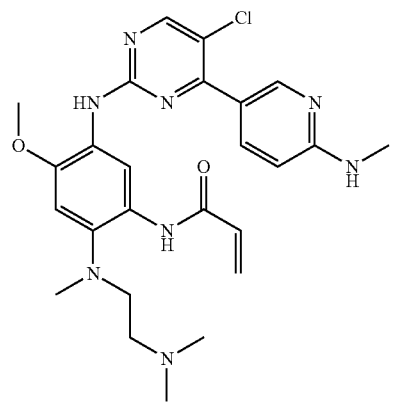 [SMILES: C=CC(=O)Nc1cc(Nc2ncc(Cl)c(-c3ccc(NC)nc3)n2)c(OC)cc1N(C)CCN(C)C]

To a solution of 4-(N-(2-(N,N-dimethylamino)ethyl)-N-methylamino)-2-methoxy-5-nitroaniline (1.03 g, 3.86 mmol) in dioxane (15 mL) was added 2,5-dichloro-4-(6-(N-(t-butoxycarbonyl)-N-methylamino)pyrid-3-yl)pyrimidine (1.37 g, 3.86 mmol), Cs$_2$CO$_3$ (2.51 g, 7.7 mmol), Xantphos (446 mg, 771 umol) and Pd$_2$(dba)$_3$ (353 mg, 386 umol) at 20° C. The reaction mixture was degassed and purged with N$_2$ 3 times and stirred at 120° C. for 12 hours. TLC (dichloromethane/methanol=10/1, R$_f$=0.43) showed that the reaction was complete. The mixture was cooled to 20° C. and concentrated to give a residue. The residue was purified by silica gel column chromatography (dichloromethane/methanol=100/1 to 20/1) to give the desired diarylamine (290 mg, 13% yield) as a red solid.

ESI-MS (m/z): 587.2 (M+H)$^+$

To a solution of the above diarylamine (240 mg, 409 umol) in acetone (24 mL) and H$_2$O (4 mL) was added Zn (481 mg, 7.4 mmol) and NH$_4$Cl (153 mg, 2.9 mmol) at 20° C. The reaction mixture was degassed and purged with N$_2$ 3 times and stirred at 20° C. for 5 minutes. LC-MS showed starting material was consumed completely and one major peak with desired MS was detected. The mixture was filtered and concentrated to remove most of acetone and extracted with DCM (5 mL×3). The organic layers were combined, dried over Na$_2$SO$_4$, filtered and concentrated to give a residue. The residue was purified by prep-HPLC (TFA condition) to give the desired 1,2,4-triaminobenzene (110 mg, 48% yield) as a dark red solid.

ESI-MS (m/z): 557.3 (M+H)$^+$.

To a solution of the above 1,2,4-triaminobenzene (90 mg, 162 umol) in EtOAc (2 mL) was added HCl in EtOAc (5 mL, 4M) at 20° C. The reaction mixture was stirred at 20° C. for 1 hour. TLC (dichloromethane/methanol=5/1, R$_f$=0.0) showed that the reaction was complete. The mixture was concentrated under reduced pressure to give the desired deblocked pyridylamine (90 mg, 93% yield, HCl) as a yellow solid.

ESI-MS (m/z): 457.2 (M+H)$^+$.

A solution of DIEA (42 mg, 324 umol, 57 uL) in THF (200 uL) was added to a mixture of the above aniline (80 mg, 162 umol, HCl) in THF (500 uL) at 0° C. under N$_2$. After stirring at 0° C. for 5 min, a solution of prop-2-enoyl chloride (29 mg, 324 umol, 26 uL) in THF (200 uL) was added. The resulting mixture was stirred at 0° C. for 20 min. LC-MS showed ~43% of starting material and a major new peak with desired MS. The mixture was stirred at 0° C. for another 20 min then concentrated to give a residue. The residue was purified by prep-HPLC (TFA condition). The correct fractions were collected and concentrated under vacuum. The residue was treated with 30 ml of 0.2% (V/V) aqueous HCl and lyophilized to give N-(5-((5-chloro-4-(6-(methylamino)pyridin-3-yl)pyrimidin-2-yl)amino)-2-((2-(dimethylamino)ethyl)(methyl)amino)-4-methoxyphenyl) acrylamide (40 mg, 39% yield, 99% purity, HCl) as a brown oil.

$^1$H NMR (400 MHz MeOD) δ 8.59-8.49 (m, 4H), 7.15 (d, J=9.2 Hz, 1H), 6.97 (s, 1H), 6.58-6.55 (m, 1H), 6.47-6.43 (m, 1H), 5.86 (d, J=10 Hz, 1H), 3.99 (s, 3H), 3.46-3.33 (m, 2H), 3.31-3.28 (m, 2H), 3.12 (s, 3H), 2.88 (s, 6H), 2.7 (s, 3H).

LCMS (m/z): 511.3 (M+H)$^+$, HPLC (220 nm): 98.5%0

Example 26. N-(5-((5-Chloro-4-(6-(dimethylamino) pyridin-3-yl)pyrimidin-2-yl)amino)-2-((2-(dimethylamino)ethyl)(methyl)amino)-4-methoxyphenyl) acrylamide

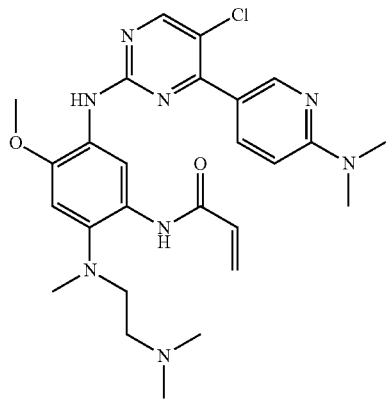 [SMILES: C=CC(=O)Nc1cc(Nc2ncc(Cl)c(-c3ccc(N(C)C)nc3)n2)c(OC)cc1N(C)CCN(C)C]

To a solution of compound 2,5-dichloro-4-(6-(N,N-dimethylamino)pyrid-3-yl)pyrimidine (2 g, 7.43 mmol) and 4-(N-(2-(N,N-dimethylamino)ethyl)-N-methylamino)-2-methoxy-5-nitroaniline (2 g, 7.43 mmol) in 2-pentanol (20 mL) was added TsOH (1.7 g, 8.92 mmol) at 25° C. The mixture was heated to 100° C., and stirred at this temperature for 12 hours. LCMS showed that the reaction was complete. The reaction mixture was concentrated under reduced pressure to remove 2-pentanol. The residue was diluted with H$_2$O (200 mL) and extracted with DCM (200 mL×3). The organic layers were combined and concentrated under reduced pressure to give a crude product which was purified by prep-HPLC (column: Luna C18 100*30 5 u; mobile phase: [water(0.1% TFA)-ACN]; B %: 20%-50%, 12 min). The desired diarylamine (350 mg, 699 umol, 9.4% yield) was obtained as a brown solid.

ESI-MS (m/z): 501.3 (M+H)$^+$.

To a solution of the above diarylamine (300 mg, 599 umol) in acetone (50 mL) and H$_2$O (5 mL) was added NH$_4$Cl (224 mg, 4.19 mmol) and Zn (705 mg, 10.78 mmol) at 25° C. under N$_2$. The mixture was stirred at 25° C. for 10 minutes. LCMS showed that the reaction was complete. The mixture was filtered and concentrated under reduced pressure to give a crude product which was purified by prep-HPLC (column: Luna C18 100*30 5 u; mobile phase: [water(0.1% TFA)-ACN]; B %: 1/%-40%, 12 min). The desired 1,2,4-triaminobenzene (120 mg, 207 umol, 35% yield, 3HCl) was obtained as a brown solid.

ESI-MS (m/z): 471.3 (M+H)$^+$.

To a solution of the above 1,2,4-triaminobenzene (100 mg, 172 umol, 3HCl) in THF (5 mL) was added acryloyl chloride (15.6 mg, 172 umol) and DIEA (24.5 mg, 189.53 umol) at 0° C. under N$_2$. The mixture was stirred at 0° C. for 30 minutes. LCMS showed that the reaction was complete. The reaction mixture was concentrated under reduced pressure to give a residue. The residue was purified by prep-HPLC (column: Luna C18 100*30 5 u; mobile phase: [water(0.1% TFA)-MeOH]; B %: 22%-52%, 12 min) to give N-(5-((5-chloro-4-(6-(dimethylamino)pyridin-3-yl)pyrimidin-2-yl)amino)-2-((2-(dimethylamino)ethyl)(methyl) amino)-4-methoxyphenyl) acrylamide (40 mg, 63 umol, 37% yield) as a brown solid.

$^1$H NMR 400 MHz MeOD δ=8.65-8.68 (m, 2H), 8.55 (s, 1H), 8.47-8.48 (d, 1H), 7.35-7.37 (d, 1H), 6.98 (s, 1H), 6.66-6.72 (m, 1H), 6.42-6.46 (m, 1H), 5.83-5.86 (d, 1H), 3.99 (s, 3H), 3.47-3.50 (m, 2H), 3.39 (d, 6H), 2.86 (s, 6H), 2.73 (s, 3H).

LCMS (m/z): 525.3 (M+H)$^+$, HPLC (220 nm): 98.98%

Example 27. N-(5-((4-(5-Acetyl-6-(methylamino) pyridin-3-yl)pyrimidin-2-yl)amino)-2-((2-(dimethylamino)ethyl)(methyl)amino)-4-methoxyphenyl) acrylamide

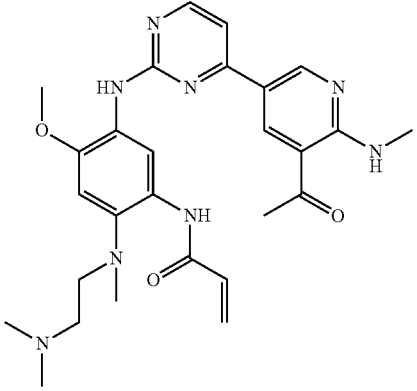

To a solution of 2-chloro-4-(5-acetyl-6-(N-methylamino) pyrid-3-yl)pyrimidine (2.8 g, 10.7 mmol) and int 2 (2.86 g, 10.7 mmol) in dioxane (30 mL) was added (5-diphenylphosphanyl-9,9-dimethyl-xanthen-4-yl)-diphenyl-phosphane (1.23 g, 2.13 mmol), Cs$_2$CO$_3$ (6.95 g, 21.3 mmol) and Pd$_2$(dba)$_3$ (976 mg, 1.07 mmol) at 25° C. under N$_2$. The mixture was stirred at 100° C. for 3 hours. LCMS showed that the reaction was complete. The reaction was filtered and concentrated under reduced pressure to give the desired diarylamine (6 g, crude) as a brown oil.

ESI-MS (m/z): 495.3 (M+H)$^+$

To a solution of the above diarylamine (6 g, 3.64 mmol) in H$_2$O (1 mL) and acetone (10 mL) was added Zn (4.28 g, 65.5 mmol) and NH$_4$Cl (1.36 g, 25.5 mmol) at 25° C. under N$_2$. The mixture was stirred at 25° C. for 10 minutes. LCMS showed that the reaction was complete. The mixture was filtered and concentrated under reduced pressure to give the crude product which was purified by prep-HPLC (column: Phenomenex luna C18 250×50 mm 10 um; mobile phase:

[water(0.1% TFA)-ACN]; B %: 5%-35%, 20 min). The desired 1,2,4-triaminobenzene (1 g, 1.73 mmol, 47% yield, TFA) was obtained as a brown solid.

ESI-MS (m/z): 495.4 (M+H)+.

To a solution of the above 1,2,4-triaminobenzene (300 mg, 518 umol, TFA) and prop-2-enoyl chloride (42.2 mg, 467 umol) in THF (3 mL) was added DIEA (73.7 mg, 570 umol) at 0° C. under N?. The mixture was stirred at 0° C. for 30 minutes. LCMS showed that the reaction was complete. The reaction was concentrated under reduced pressure to give a crude product which was purified by prep-HPLC (column: Luna C18 100*30 5 u; mobile phase: [water(0.1% TFA)-MeOH]; B %: 35%-58%, 12 min) to give N-(5-((4-(5-acetyl-6-(methylamino)pyridin-3-yl)pyrimidin-2-yl)amino)-2-((2-(dimethylamino)ethyl)(methyl)amino)-4-methoxyphenyl) acrylamide (120 mg, 216 umol, 42% yield, HCl) as a brown solid.

1H NMR (400 MHz MeOD) δ=9.07 (s, 1H), 8.99 (s, 1H), 8.37-8.38 (m, 1H), 8.26 (s, 1H), 7.48-7.49 (m, 1H), 7.00 (s, 1H), 6.54-6.61 (m, 1H), 6.43-6.47 (m, 1H), 5.85-5.88 (m, 1H), 3.99 (s, 3H), 3.48-3.51 (m, 2H), 3.30-3.32 (m, 2H), 3.15 (s, 3H), 2.87 (s, 6H), 2.73 (s, 3H), 2.66 (s, 3H).

LCMS (m/z): 519.4 (M+H)+. HPLC (220 nm): 99.03%

Example 28. 5-(2-((5-Acrylamido-4-((2-(dimethylamino)ethyl)(methyl)amino)-2-methoxyphenyl)amino)pyrimidin-4-yl)-2-(methylamino)nicotinamide

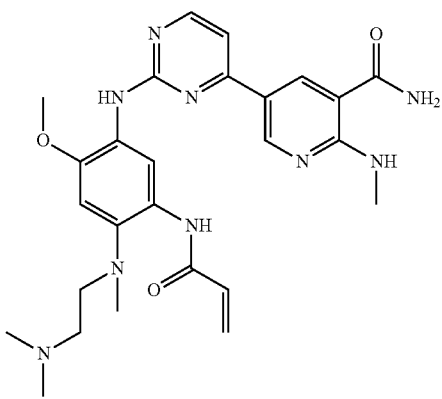 [SMILES: C=CC(=O)Nc1cc(Nc2nccc(-c3cnc(NC)c(C(N)=O)c3)n2)c(OC)cc1N(C)CCN(C)C]

To a solution of 2-chloro-4-(5-(carboxymethyl)-6-(N-methylamino)pyrid-3-yl)pyrimidine (3 g, 10.8 mmol) and int 2 (2.89 g, 10.8 mmol) in dioxane (30 mL) were added Cs2CO3 (7 g, 21.52 mmol), (5-diphenylphosphanyl-9,9-dimethyl-xanthen-4-yl)-diphenyl-phosphane (1.25 g, 2.15 mmol) and Pd2(dba)3 (986 mg, 1.08 mmol) at 25° C. under N2. The mixture was stirred at 100° C. for 3 hours. LCMS showed that the reaction was complete. The reaction mixture was filtered and concentrated under reduced pressure to give the desired diarylamine (7 g, crude) as a brown solid.

ESI-MS (m/z): 511.4 (M+H)+.

To a solution of the above diarylamine (6.8 g, 3.46 mmol) in THF (35 mL) and H2O (35 mL) was added LiOH.H2O (436 mg, 10.4 mmol) at 25° C. The mixture was stirred at 25° C. for 12 hours. LCMS showed that the reaction was complete. The reaction mixture was concentrated under reduced pressure to give the desired nicotinic acid (5 g, crude) as a brown oil.

ESI-MS (m/z): 497.3 (M+H)+.

To a solution of the above nicotinic acid (4.8 g, 9.67 mmol) in DMF (3 mL) were added NH4Cl (1.55 g, 29 mmol), DIEA (3.75 g, 29 mmol) and HATU (5.51 g, 14.5 mmol) at 25° C. The mixture was stirred at 25° C. for 4 hours. LCMS showed that the reaction was complete. The reaction mixture was concentrated under reduced pressure to give the desired nicotinamide (2 g, crude) as a black solid.

ESI-MS (m/z): 496.3 (M+H)+.

To a solution of the above nicotinamide (2 g, 4.04 mmol) in acetone (20 mL) and H2O (4 mL) was added Zn (4.76 g, 72.7 mmol) and NH4Cl (1.51 g, 28.3 mmol) at 25° C. under N2. The mixture was stirred at 25° C. for 10 minutes. LCMS showed that the reaction was complete. The mixture was filtered and concentrated under reduced pressure to give a crude product which was purified by prep-HPLC (column: Luna C18 100*30 5 u; mobile phase: [water(0. 1% TFA)-ACN]; B %: 1%-30%, 12 min). The desired 1,2,4-triaminobenzene (1 g, 2.15 mmol, 53% yield) was obtained as a brown solid.

ESI-MS (m/z): 466.3 (M+H)+.

To a solution of the above 1,2,4-triaminobenzene (80 mg, 172 umol) in THF (2 mL) were added DIEA (24.4 mg, 189 umol) and prop-2-enoyl chloride (15.6 mg, 172 umol) at 0° C. The mixture was stirred at 0° C. for 20 minutes. LCMS showed that the reaction was complete. The reaction was concentrated under reduced pressure to give a residue which was purified by prep-HPLC (column: Luna C18 100*30 5 u; mobile phase: [water(0.1% TFA)-MeOH]; B %: 20%-45%, 12 min) to give 5-(2-((5-acrylamido-4-((2-(dimethylamino)ethyl)(methyl)amino)-2-methoxyphenyl)amino)pyrimidin-4-yl)-2-(methylamino)nicotinamide (13 mg, 23.4 umol, 14% yield) as a yellow solid.

1H NMR (400 MHz MeOD) δ=8.95 (s, 1H), 8.82 (s, 1H), 8.41-8.44 (m, 2H), 7.37-7.38 (m, 1H), 6.97 (s, 1H), 6.54-6.60 (m, 1H), 6.43-6.47 (m, 1H), 5.85-5.88 (m, 1H), 3.99 (s, 3H), 3.48-3.49 (m, 2H), 3.33-3.35 (m, 2H), 3.13 (s, 3H), 2.86 (s, 6H), 2.73 (s, 3H).

ESI-MS (m/z): 520.4 (M+H)+, HPLC (220 nm): 98.98%

Example 29. 1-(2-((5-Acrylamido-4-((2-(dimethylamino)ethyl)(methyl)amino)-2-methoxyphenyl)amino)pyrimidin-4-yl) cyclopenta[c]pyrazole-3-carboxamide

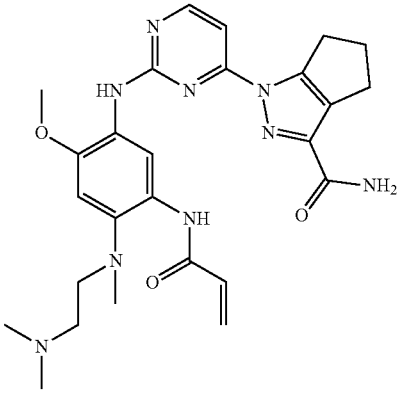 [SMILES: C=CC(=O)Nc1cc(Nc2nccc(-n3nc(C(N)=O)c4c3CCC4)n2)c(OC)cc1N(C)CCN(C)C]

To a solution of 2-chloro-4-(3-(carboxymethyl)cyclopenta[c]pyrazol-1-yl)pyrimidine (3.00 g, 10.7 mmol) in 2-pentanol (60 mL) were added 4-(N-(2-(N,N-dimethylamino)ethyl)-N-methylamino)-2-methoxy-5-nitroaniline (2.89 g, 10.7 mmol) and PTSA (2.22 g, 12.91 mmol) at 25°

C. The mixture was heated to 100° C., and stirred for 36 hrs. LC-MS indicated that the reaction was complete. The reaction mixture was concentrated under reduced pressure to give the desired diarylamine (5.00 g, 9.79 mmol, 91% yield) as a brown solid.

ESI-MS (m/z): 511.3 (M+H)+.

To a solution of the above diarylamine (1.20 g, 2.35 mmol) in THF (10 mL), H$_2$O (5.00 mL) and MeOH (5.00 mL) was added NaOH (376 mg, 9.40 mmol). The mixture was stirred at 25° C. for 12 h. LC-MS showed that starting material was consumed completely. Several new peaks were observed with ~60% of desired compound. The reaction mixture was concentrated under reduced pressure to give a residue which was purified by silica gel column chromatography (DCM:MeOH=20/1 to 1:1) to give the desired pyrazolo carboxylic acid (700 mg, 1.41 mmol, 60% yield) as a red solid.

ESI-MS (m/z): 497.3 (M+H)+.

A mixture of the above pyrazolo carboxylic acid (300 mg, 604 umol), NH$_4$Cl (64.6 mg, 1.21 mmol, 42.3 uL), DIEA (234 mg, 1.81 mmol, 316 uL) and HATU (344 mg, 906 umol) in DMF (10 mL) was degassed and purged with N, 3 times and stirred at 25° C. for 2 hours under N$_2$ atmosphere. LC-MS showed that starting material was consumed completely. Several new peaks were observed with 50% of desired compound. The reaction mixture was filtered and concentrated under reduced pressure to give the desired pyrazolo carboxamide (1.00 g, crude) which was used in the next step without further purification.

ESI-MS (m/z): 496.3 (M+H)+.

A mixture of the above pyrazolo carboxamide (1.00 g, 2.02 mmol), Zn (2.38 g, 36.3 mmol) and NH$_4$Cl (756 mg, 14.1 mmol, 494 uL) in acetone (4.00 mL) and H$_2$O (400 uL) was degassed and purged with N$_2$ 3 times and stirred at 25° C. for 30 minutes. LC-MS showed that starting material was consumed completely. Several new peaks were observed with 60% of desired compound. The reaction mixture was filtered and concentrated under reduced pressure to give a residue. The residue was purified by prep-HPLC (column: Phenomenex luna C18 250*80 mm*10 um; mobile phase: [water(0.1% TFA)-ACN]; B %: 0%-28%, 20 min) to give the desired 1,2,4-triaminobenzene (130.00 mg, 279.24 umol, 11.92% yield) as a yellow solid.

$^1$H NMR (400 MHz DMSO-d$_6$) δ=8.60-8.58 (m, 1H), 8.50-8.48 (m, 1H), 7.68-7.66 (m, 1H), 7.53-7.51 (m, 1H), 7.43-7.40 (m, 1H), 7.28 (d, J=5.2 HZ, 1H), 6.98 (s, 1H), 3.79 (s, 3H), 3.30-3.27 (m, 4H), 2.86-2.84 (m, 2H), 2.78 (s, 6H), 2.67-2.63 (m, 2H), 2.58 (s, 3H), 2.45-2.42 (m, 2H).

ESI-MS (m/z): 466.3 (M+H)+.

A solution of the above 1,2,4-triaminobenzene (43.0 mg, 92.4 umol) in THF (5.00 mL) was degassed and purged with N, 3 times at 25° C. The mixture was cooled to 0° C. under N$_2$ atmosphere before DIEA (14 mg, 111 umol, 19.3 uL) was added dropwise. The mixture was stirred at this temperature for 5 min then prop-2-enoylchloride (8.36 mg, 92.3 umol, 7.53 uL) was added dropwise. The resulting mixture was warmed to 25° C., and stirred for 15 min under N, atmosphere. LC-MS showed that starting material was consumed completely. Several new peaks were observed with 80% of the desired compound. The reaction mixture was filtered and concentrated under reduced pressure to give a residue. The residue was purified by prep-HPLC (column: Luna C18 100*30 5 u; mobile phase: [water (0.1% TFA)-MeOH]; B %: 20%-50%, 12 min) to give 1-(2-((5-acrylamido-4-((2-(dimethylamino)ethyl)(methyl)amino)-2-methoxyphenyl)amino) pyrimidin-4-yl) cyclopenta[c]pyrazole-3-carboxamide (13 mg, 24 umol, 21% yield, 97.8% purity) as a yellow solid.

$^1$H NMR 400 MHz MeOD δ=8.47 (d, J=5.6 Hz, 1H), 8.07 (s, 1H), 7.45 (d, J=5.6 Hz, 1H), 6.96 (s, 1H), 6.54-6.50 (m, 2H), 5.91-5.88 (m, 1H), 3.98 (s, 3H), 3.50-3.49 (m, 2H), 3.30-3.25 (m, 2H), 3.12-3.08 (m, 2H), 2.86 (s, 6H), 2.78-2.75 (m, 2H), 2.74 (s, 3H), 2.54-2.50 (m, 2H)

ESI-MS (m/z): 520.4 (M+H)+, HPLC (220 nm): 97.8%

Example 30. 1-(2-((5-Acrylamido-4-((2-(dimethylamino)ethyl)(methyl)amino)-2-methoxyphenyl) amino)pyrimidin-4-yl)-1H-indole-3-carboxylic acid

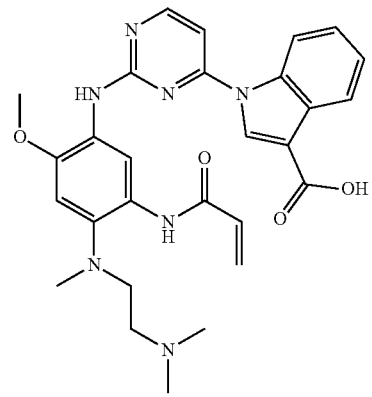 [SMILES: C=CC(=O)Nc1cc(Nc2nccc(-n3cc(C(=O)O)c4ccccc43)n2)c(OC)cc1N(C)CCN(C)C]

To a solution of 4-(N-(2-(N,N-dimethylamino)ethyl)-N-methylamino)-2-methoxy-5-nitroaniline (933 mg, 3.48 mmol) in butan-2-ol (50 mL) was added compound 2-chloro-4-(3-carboxylmethyl)indol-1-yl)pyrimidine (1 g, 3.48 mmol) and TsOH.H$_2$O (728 mg, 3.83 mmol) at 20° C. The mixture was stirred at 100° C. for 3 hours. TLC (dichloromethane:methanol=10:1, R$_f$=0.4) showed ~20% of starting material and one major new spot with higher polarity. The reaction mixture was concentrated under reduced pressure to give a residue. The residue was purified by silica gel column chromatography (DCM:MeOH=200:1 to 5:1) to afford the desired diarylamine (800 mg, 1.54 mmol, 44% yield) as an orange solid.

ESI-MS (m/z): 520.3 (M+H)+.

To a solution of the above diarylamine (800 mg, 1.54 mmol) in H$_2$O (10 mL) and acetone (100 mL) was added Zn (1.81 g, 27.7 mmol) and NH$_4$Cl (577 mg, 10.8 mmol) at 20° C. The reaction mixture was degassed, purged with N$_2$ 3 times and stirred at 20° C. for 5 minutes. LC-MS and HPLC showed that starting material was consumed completely and one new peak with desired MS was detected. The reaction mixture was filtered and the filtrate was concentrated under reduced pressure to give the desired 1,2,4-triaminobenzene (750 mg, crude) as a brown solid which was used in the next step without further purification.

ESI-MS (m/z): 490.4 (M+H)+.

To a solution of the desired 1,2,4-triaminobenzene (750 mg, 1.53 mmol) in THF (8 mL) and H$_2$O (4 mL) was added NaOH (184 mg, 4.59 mmol). The mixture was stirred at 20° C. for 48 hours. LCMS showed no reaction. MeOH (5 mL) was added and stirred at 20° C. for another 24 hours. LC-MS and HPLC showed that starting material was consumed completely and one new peak with desired MS was detected. The reaction mixture was concentrated under reduced pressure. The residue was purified by prep-HPLC (TFA condition) to give the desired indole carboxylic acid (150 mg, 315 umol, 21% yield) as a brown solid.

ESI-MS (m/z): 476.3 (M+H)+.

A solution of the above indole carboxylic acid (150 mg, 315 umol) in THF (3 mL) was degassed and purged with N₂ 3 times at 20° C. The mixture was cooled to 0° C. before a solution of DIEA (48.9 mg, 379 umol, 66.1 uL) in THF (100 uL) was added slowly. After stirring for 5 minutes, a solution of prop-2-enoyl chloride (28.6 mg, 315 umol, 25.7 uL) in THF (100 uL) was added slowly and stirred at 0° C. for 15 minutes. LCMS showed that the desired product was formed. The reaction was quenched with HCl (g)/EA (4M, 0.5 mL) and concentrated under reduced pressure to give a residue. The residue was purified by prep-HPLC (TFA condition). The correct fractions were collected and concentrated under vacuum. The residue was treated with 30 ml of 0.2% (V/V) aqueous HCl and lyophilized to afford 1-(2-((5-acrylamido-4-((2-(dimethylamino)ethyl)(methyl)amino)-2-methoxyphenyl)amino)pyrimidin-4-yl)-1H-indole-3-carboxylic acid (10.1 mg, 17.3 umol, 5% yield, 97.01% purity) as a white solid.

¹H NMR (400 MHz MeOD) δ=8.59 (s, 1H), 8.51 (d, J=5.5 Hz, 1H), 8.43 (d, J=9.2 Hz, 1H), 8.22 (s, 1H), 8.19-8.16 (m, 1H), 7.28-7.31 (m, 2H), 7.22-7.24 (d, J=5.2 Hz, 1H), 6.99 (s, 1H), 6.45-6.47 (m, 2H), 5.84-5.87 (dd, J=5.0, 6.9 Hz, 1H), 4.00 (s, 3H), 3.51-3.53 (m, 2H), 3.27-3.30 (m, 2H), 2.89 (s, 6H), 2.74 (s, 3H).

ESI-MS (m/z): 530.3 (M+H)⁺, HPLC (220 nm): 97.01%

Example 31. N-(5-((4-(3-Acetyl-1H-indol-1-yl)pyrimidin-2-yl)amino)-2-((2-(dimethylamino)ethyl)(methyl)amino)-4-methoxyphenyl) acrylamide

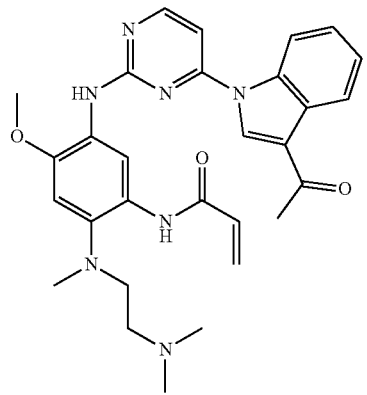 [SMILES: C=CC(=O)Nc1cc(Nc2nccc(-n3cc(C(C)=O)c4ccccc43)n2)c(OC)cc1N(C)CCN(C)C]

To a solution of 4-(N-(2-(N,N-dimethylamino)ethyl)-N-methylamino)-2-methoxy-5-nitroaniline (494 mg, 1.84 mmol) in butan-2-ol (25 mL) was added 2-chloro-4-(3-acetylindol-1-yl)pyrimidine (500 mg, 1.84 mmol) and PTSA (385 mg, 2.02 mmol) at 20° C. The mixture was stirred at 100° C. for 3 hours. LC-MS showed that starting material was consumed completely and one major peak with desired MS was detected. The reaction mixture was concentrated under reduced pressure to give a residue which was purified by silica gel column chromatography (DCM:MeOH=50:1 to 5:1) to afford the desired diarylamine (600 mg, 1.19 mmol, 65% yield) as a red solid.

ESI-MS (m/z): 504.3 (M+H)⁺.

To a solution of the above diarylamine (400 mg, 794 umol) in H₂O (4 mL) and acetone (40 mL) was added Zn (935 mg, 14.3 mmol) and NH₄Cl (297 mg, 5.56 mmol) at 20° C. The reaction mixture was degassed, purged with N₂ 3 times and stirred at 20° C. for 5 minutes. LC-MS showed that starting material was consumed completely and one new peak with desired MS was detected. The reaction mixture was filtered and the filtrate was concentrated under reduced pressure to give the desired 1,2,4-triaminobenzene (400 mg, crude) as a brown solid which was used in the next step without further purification.

ESI-MS (m/z): 474.3 (M+H)⁺.

A solution of the above 1,2,4-triaminobenzene (400 mg, 845 umol) in THF (4 mL) was degassed and purged with N₂ 3 times at 20° C. The mixture was cooled to 0° C. under N₂ atmosphere before a solution of DIPEA (131 mg, 1.01 mmol, 177 uL) in THF (1 mL) was added slowly. After stirring for 5 minutes, a solution of prop-2-enoyl chloride (76.5 mg, 845 umol, 68.9 uL) in THF (1 mL) was added slowly and the mixture was stirred at 0° C. for 15 minutes. LC-MS and HPLC showed 20% of starting material remaining and one main peak with desired MS was detected. The reaction was quenched with HCl (g)/EA (4M, 0.5 mL) and concentrated under reduced pressure to give a residue. The residue was purified by prep-HPLC (TFA condition). The correct fraction was collected and concentrated under vacuum. The residue was treated with 30 ml of 0.2% (V/V) aqueous HCl and lyophilized to afford N-(5-((4-(3-acetyl-1H-indol-1-yl)pyrimidin-2-yl)amino)-2-((2-(dimethylamino)ethyl)(methyl)amino)-4-methoxyphenyl) acrylamide (25 mg, 41.9 umol, 5% yield, 94.58% purity, HCl) as a yellow solid.

¹H NMR 400 MHz MeOD δ=8.81 (s, 1H), 8.55 (d, J=6.0 Hz, 1H), 8.38-8.41 (d. J=9.2 Hz, 1H), 8.32-8.34 (m, 1H), 8.26 (s, 1H), 7.30-7.32 (m, 3H), 6.99 (s, 1H), 6.47 (s, 1H), 6.46 (s, 11-), 5.86 (dd, J=5.1, 6.6 Hz, 1H), 3.99 (s, 3H), 3.51 (t, J=5.7 Hz, 2H), 3.28 (br d, 0.5.3 Hz, 2H), 2.88 (s, 6H), 2.73 (s, 3H), 2.62 (s, 3H).

ESI-MS (m/z): 528.4 (M+H)⁺, HPLC (220 nm): 94.58%

Example 32. 5-(2-((5-Acrylamido-4-((2-(dimethylamino)ethyl)(methyl)amino)-2-methoxyphenyl)amino)pyrimidin-4-yl)-3-chloro-1N-methyl-1H-indole-7-carboxamide hydrochloride

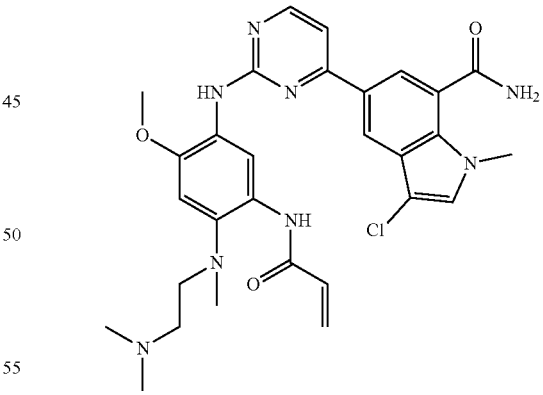

To a solution of 4-(N-(2-(N,N-dimethylamino)ethyl)-N-methylamino)-2-methoxy-5-nitroaniline (798 mg, 2.97 mmol) and methyl 3-chloro-5-(2-chloropyrimidin-4-yl)-1-(N-methyl)-1H-indole-7-carboxylate (1 g, 2.97 mmol) in dioxane (140 mL) was added Cs₂CO₃ (1.94 g, 5.95 mmol), Xantphos (344 mg, 595 umol) and Pd₂(dba)₃ (272 mg, 297 umol). The mixture was stirred at 100° C. under N₂ for 12 hours. TLC (dichloromethane:methanol=10:1, R_f=0.4) showed that starting material was consumed completely and one new spot with lower polarity was detected. The mixture was concentrated under reduced pressure to give a residue, which was purified by silica gel column chromatography (DCM:MeOH=50/1 to 10:1) to give the desired diarylamine (700 mg, 38% yield) as a red oil.

ESI-MS (m/z): 568.2 (M+H)+

To a mixture of the desired diarylamine (650 mg, 1.14 mmol) in MeOH (5 mL), H$_2$O (5 mL) and THF (10 mL) was added NaOH (182 mg, 4.56 mmol). The mixture was stirred at 25° C. for 2 hours. LC-MS showed that starting material was consumed completely and one major peak with desired MS was detected. The reaction mixture was concentrated under reduced pressure to afford the desired indole carboxylic acid (450 mg, crude) as a red oil which was used in the next step without further purification.

ESI-MS (m/z): 554.2 (M+H)+

To a solution of the above indole carboxylic acid (400 mg, 722 umol) in DMF (10 mL) were added NH$_4$Cl (386 mg, 7.22 mmol, 252 uL), HATU (1.1 g, 2.89 mmol) and DIEA (373 mg, 2.89 mmol, 504 uL). The mixture was stirred at 25° C. for 12 hours. LC-MS showed that starting material was consumed completely and one major peak with desired MS was detected. The reaction mixture was concentrated under reduced pressure to give a residue, which was purified by prep-HPLC (TFA condition) to afford the desired indole carboxamide (110 mg, 28% yield) as a brown solid.

ESI-MS (m/z): 553.2 (M+H)+

To a solution of the above indole carboxamide (20 mg, 36.2 umol) in acetone (2 mL) and H$_2$O (200 uL) were added Zn (42.6 mg, 651 umol) and NH$_4$Cl (13.5 mg, 253 umol, 8.85 uL) at 25° C. The reaction mixture was degassed, purged with N$_2$ 3 times then stirred at 25° C. for 5 minutes. LC-MS showed that starting material was consumed completely and one major peak with desired MS was detected. The reaction mixture was filtered and the filtrate was concentrated under reduced pressure to afford the desired 1,2,4-triaminobenzene (18 mg, crude) as a yellow solid which was used in the next step without further purification.

ESI-MS (m/z): 523.2 (M+H)+

A solution of the above 1,2,4-triaminobenzene (18 mg, 34.4 umol) in THF (1 mL) was degassed and purged with N$_2$ 3 times at 25° C. then cooled to 0° C. under N$_2$ atmosphere. A solution of DIEA (6.67 mg, 51.6 umol, 9.01 uL) in THF (100 uL) was added slowly to the mixture at 0° C. After stirring for 5 minutes, a solution of prop-2-enoyl chloride (3.11 mg, 34.4 umol, 2.81 uL) in THF (100 uL) was added slowly and the mixture was stirred at 0° C. for 15 minutes. LC-MS and HPLC showed that starting material was consumed completely and one major peak with desired MS was detected. The reaction was quenched with HCl (g)/EA (4M, 0.1 mL) and concentrated under reduced pressure to give a residue, which was purified by prep-HPLC (TFA condition). The correct fraction was collected and concentrated under vacuum. The residue was treated with 30 ml of 0.2% (V/V) aqueous HCl and lyophilized to afford 5-(2-((5-acrylamido-4-((2-(dimethylamino)ethyl)(methyl)amino)-2-methoxyphenyl)amino)pyrimidin-4-yl)-3-chloro-1N-methyl-1H-indole-7-carboxamide hydrochloride (2.7 mg, 14% yield, 99.47% purity) as a yellow solid.

$^1$H NMR (400 MHz MeOD) δ=8.52 (d, J=2 Hz, 1H), 8.50 (m, 2H), 8.45 (d, J=5.6 Hz, 1H), 8.18 (s, 1H), 7.52 (d, J=4.4 Hz, 1H), 7.39 (s, 1H), 6.99 (m, 1H), 6.52-6.55 (m, 1H), 6.44-6.48 (m, 1H), 5.88-5.89 (d, J=4.0 Hz, 1H), 4.01 (s, 3H), 3.90 (s, 3H), 3.27 (m, 2H), 3.13 (m, 2H), 2.88 (s, 6H), 2.73 (s, 3H).

ESI-MS (m/z): 577.3 (M+H), HPLC (220 nm) 99.47%.

Example 33. N-(2-((2-(Dimethylamino)ethyl)(methyl)amino)-4-methoxy-5-((4-(1N-methyl-7-oxo-6,7-dihydro-1H-pyrrolo[2,3-c]pyridin-4-yl)pyrimidin-2-yl)amino)phenyl) acrylamide

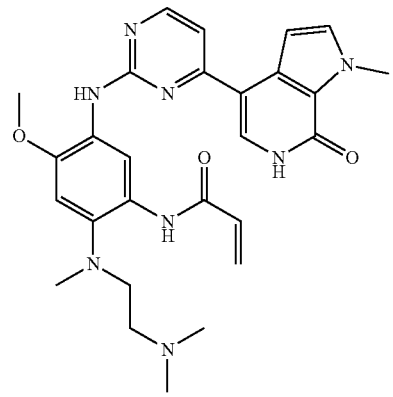 [SMILES: C=CC(=O)Nc1cc(Nc2nccc(-c3c[nH]c(=O)c4c3ccn4C)n2)c(OC)cc1N(C)CCN(C)C]

To a mixture of 2-chloro-4-(1,N-methyl-7-methoxypyrrolo[2,3-c]pyrid-4-yl)pyrimidine (400 mg, 1.46 mmol), 4-(N-(2-(N,N-dimethylamino)ethyl)-N-methylamino)-2-methoxy-5-nitroaniline (392 mg, 1.46 mmol), Cs$_2$CO$_3$ (951 mg, 2.92 mmol) and Xantphos (169 mg, 292 umol) in dioxane (8 mL) was added Pd$_2$(dba)$_3$ (133.70 mg, 146 umol) at 25° C. under N$_2$. The mixture was stirred at 25° C. for 30 min then heated to 100° C., and stirred for 5 h. The mixture was filtered and concentrated under reduced pressure. The residue was purified by prep-HPLC (column: Phenomenex luna C18 250×50 mm, 10 um; mobile phase: [water(0.1% TFA)-ACN]; B %: 12%-42%, 20 min) to give the desired diarylamine (180 mg, 355 umol, 24% yield) as a red oil.

$^1$H NMR (400 MHz CDCl$_3$) δ=9.21 (s, 1H), 8.51-8.45 (m, 1H), 8.31-8.27 (m, 1H), 7.65-7.58 (m, 1H), 7.22-7.16 (m, 2H), 7.06 (d, J=2.4 Hz, 1H), 6.69 (s, 1H), 4.13 (d, J=16.4 Hz, 5H), 4.20-4.07 (m, 1H), 3.98 (s, 3H), 3.26 (s, 2H), 2.88 (s, 3H), 2.57 (s, 2H), 2.28 (s, 6H).

ESI-MS (m/z): 507 (M+H)+.

To a mixture of the above diarylamine (200 mg, 395 umol) in acetone (2 mL) and H$_2$O (200 uL) were added Zn (465 mg, 7.11 mmol) and NH$_4$Cl (148 mg, 2.76 mmol, 96.6 uL) at 25° C. under N$_2$. The mixture was stirred at 25° C. for 10 min. LC-MS showed that starting material was consumed completely. The mixture was filtered and concentrated under reduced pressure to give the desired 1,2,4-triaminobenzene (200 mg, crude) as a red oil.

ESI-MS (m/z): 477 (M+H)+.

To a mixture of the above 1,2,4-triaminobenzene (75 mg, 158 umol) in DMF (2 mL) were added LiCl (20 mg, 472.11 umol, 9.67 uL) and TsOH.H$_2$O (89.8 mg, 472 umol) at 25° C. under N$_2$. The mixture was heated to 120° C., and stirred for 0.5 h. LC-MS showed that starting material was consumed completely. The mixture was concentrated under reduced pressure to give the desired pyrrolopyridone (90 mg, crude) as a black solid.

ESI-MS (m/z): 463 (M+H)+.

To a mixture the above pyrrolopyridone (70 mg, 151 umol) and prop-2-enoyl chloride (13.7 mg, 151 umol, 12.34 uL) in DMF (2 mL) was added DIEA (78.2 mg, 605 umol, 106 uL) at 25° C. under N$_2$. The mixture was stirred at 25° C. for 14 h. LC-MS showed starting material was consumed completely. The mixture was concentrated under reduced pressure. The residue was purified by prep-HPLC (column: Luna C18 150×25 5 u; mobile phase: [water (0.225% FA)-ACN]; B %: 15%-30° %, 12 min) to give N-(2-((2-(dimethylamino)ethyl)(methyl)amino)-4-methoxy-5-((4-(1N-methyl-7-oxo-6,7-dihydro-1H-pyrrolo[2,3-c]pyridin-4-yl)pyrimidin-2-yl)amino)phenyl) acrylamide (10 mg, 19.2 umol, 13% yield, 99% purity).

$^1$H NMR (400 MHz CDCl$_3$) δ=9.76-9.57 (m, 1H), 9.32-9.16 (m, 1H), 9.11-9.01 (m, 1H), 8.98-8.88 (m, 1H), 8.33-8.12 (m, 1H), 6.70-6.66 (m, 2H), 6.70-6.66 (m, 1H), 6.61-6.60 (m, 1H), 6.51-6.48 (m, 1H), 5.80-5.76 (m, 1H), 4.20 (s, 3H), 3.93 (s, 3H), 3.41-3.33 (m, 2H), 3.26-3.16 (m, 2H), 2.88 (s, 6H), 2.76 (s, 3H).

ESI-MS (m/z): 517.3 (M+H)$^+$, HPLC (220 nm): 99.01%

Example 34. 4-(2-((5-Acrylamido-4-((2-(dimethylamino)ethyl)(methyl)amino)-2-methoxyphenyl)amino)pyrimidin-4-yl)-1N-methyl-1H-indole-6-carboxamide hydrochloride

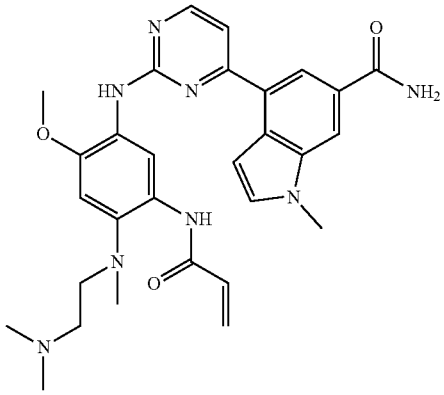 [SMILES: C=CC(=O)Nc1cc(Nc2nccc(-c3cc(C(N)=O)cc4c3ccn4C)n2)c(OC)cc1N(C)CCN(C)C]

To a mixture of 4-(N-(2-(N,N-dimethylamino)ethyl)-N-methylamino)-2-methoxy-5-nitroaniline (1.07 g, 3.98 mmol), 2-chloro-4-(6-(carboxymethyl)-1,N-methylindol-4-yl)pyrimidine (1.2 g, 3.98 mmol) and Cs$_2$CO$_3$ (2.59 g, 7.96 mmol) in dioxane (30 mL) were added Pd$_2$(dba)$_3$ (364 mg, 398 umol) and Xantphos (460 mg, 796 umol) in one portion at 25° C. under N$_2$. The mixture was heated to 100° C., and stirred for 4 hours. TLC (dichloromethane:methanol=20:1, R$_f$=0.4) indicated that starting material was consumed completely and one new spot was formed. The mixture was filtered and the filtrate was concentrated under reduced pressure to give a residue, which was purified by silica gel column chromatography (dichloromethane:methanol=100/1 to 30/1) to give the desired diarylamine (1.27 g, 60% yield) as a brown solid.

$^1$H NMR (400 MHz CDCl$_3$) δ=9.22 (s, 1H), 8.56 (d, J=5.3 Hz, 1H), 8.34 (d, J=5.3 Hz, 1H), 8.23 (s, 1H), 7.68 (s, 1H), 7.37-7.35 (m, 1H), 7.32 (d, J=5.1 Hz, 1H), 7.14 (d, J=2.4 Hz, 1H), 6.69 (s, 1H), 4.00 (s, 3H), 3.96 (s, 3H), 3.94 (s, 3H), 3.27-3.24 (m, 2H), 2.88 (s, 3H), 2.56-2.53 (m, 2H), 2.27 (s, 6H).

ESI-MS (m/z): 534.2 (M+H)$^+$

To a mixture of the above diarylamine (1.4 g, 2.62 mmol) in H$_2$O (7 mL), THF (7 mL) and MeOH (3 mL) was added NaOH (419 mg, 10.5 mmol). The mixture was stirred at 25° C. for 12 hours. LC-MS showed that starting material was consumed completely and one major peak with desired MS was detected. The reaction mixture was concentrated under reduced pressure to remove the solvent. The residue was dissolved in MeOH (15 mL) and filtered. The filtrate was concentrated under vacuum to afford the desired indole carboxylic acid (1 g, 73% yield) as a red solid.

ESI-MS (m/z): 520.4 (M+H)$^+$.

To a solution of the above indole carboxylic acid (500 mg, 962 umol) in DMF (15 mL) were added EDCI (369 mg, 1.92 mmol), HOBt (260 mg, 1.92 mmol) and NH$_3$.H$_2$O (506 mg, 14.4 mmol, 556 uL). The mixture was stirred at 80° C. for 12 hours. LC-MS showed that starting material was consumed completely and one major peak with desired MS was detected. The reaction mixture was concentrated under reduced pressure to afford the desired indole carboxamide (450 mg, crude) as a red solid which was used in the next step directly.

ESI-MS (m/z): 519.3 (M+H)$^+$.

To a mixture of the desired indole carboxamide (450 mg, 868 umol) in acetone (45 mL) and H$_2$O (4.5 mL) were added Zn (1.02 g, 15.6 mmol) and NH$_4$Cl (325 mg, 6.07 mmol). The mixture was degassed, purged with N$_2$ 3 times and stirred at 25° C. for 10 minutes. LC-MS and HPLC showed that starting material was consumed completely and one major peak with desired MS was detected. The reaction mixture was filtered and the filtrate was concentrated under reduced pressure to give a residue. The residue was purified by prep-HPLC (TFA condition) to afford the desired 1,2,4-triaminobenzene (46 mg, 10% yield) as a yellow solid.

ESI-MS (m/z): 489.4 (M+H)$^+$.

A mixture of the above 1,2,4-triaminobenzene (46 mg, 94.2 umol) in THF (1 mL) was degassed and purged with N, 3 times at 20° C. then cooled to 0° C. under N, atmosphere. A solution of DIEA (14.6 mg, 113 umol, 19.7 uL) in THF (100 uL) was added slowly to the mixture at 0° C. After stirring for 5 minutes, a solution of acryloyl chloride (8.52 mg, 94.2 umol, 7.68 uL) in THF (100 uL) was added slowly and stirred at 0° C. for 15 minutes. LC-MS and HPLC showed that starting material was consumed completely and one major peak with desired MS was detected. The reaction mixture was quenched with HCl (g)/EA (4M, 0.5 mL) and concentrated under reduced pressure to give a residue which was purified by prep-HPLC (TFA condition). The correct fraction was collected and concentrated under vacuum. The residue was treated with 30 ml of 0.2% (V/V) aqueous HCl and lyophilized to afford 4-(2-((5-acrylamido-4-((2-(dimethylamino)ethyl)(methyl)amino)-2-methoxyphenyl)amino)pyrimidin-4-yl)-1N-methyl-1H-indole-6-carboxamide hydrochloride (12.6 mg, 24% yield, 95.53% purity) as a yellow solid.

$^1$H NMR (400 MHz MeOD) δ=8.49 (d, J=5.7 Hz, 1H), 8.41 (s, 1H), 8.36 (s, 1H), 8.22-8.24 (m, 1H), 7.55 (d, J=5.5 Hz, 1H), 7.46 (d, J=3.1 Hz, 1H), 7.09-7.12 (m, 1H), 6.98 (s, 1H), 6.47-6.57 (m, 2H), 5.86-5.88 (m, 1H), 4.00 (s, 3H), 3.94 (s, 3H), 3.47-3.54 (m, 2H), 3.23-3.30 (m, 2H), 2.87 (s, 6H), 2.74 (s, 3H).

ESI-MS (m/z): 543.3 (M+H)$^+$, HPLC (220 nm): 95.53%

Example 35. N-(5-((4-(3-(Difluoromethyl)-1H-indazol-1-yl)pyrimidin-2-yl)amino)-2-((2-(dimethylamino)ethyl)(methyl)amino)-4-methoxyphenyl) acrylamide hydrochloride

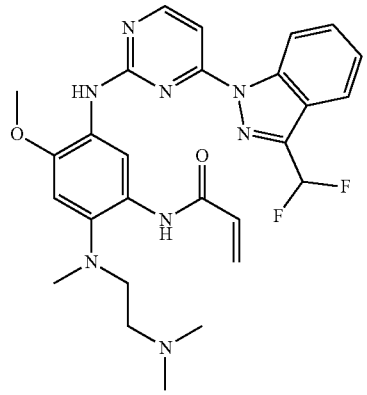 [SMILES: C=CC(=O)Nc1cc(Nc2nccc(-n3nc(C(F)F)c4ccccc43)n2)c(OC)cc1N(C)CCN(C)C]

To a solution of 4-(N-(2-(N,N-dimethylamino)ethyl)-N-methylamino)-2-methoxy-5-nitroaniline (286.8 mg, 1.07 mmol) in 2-pentanol (3 mL) were added 2-chloro-(4-3-(difluoromethyl)indazol-1-yl)pyrimidine (300 mg, 1.07 mmol) and TsOH.H2O (223.7 mg, 1.18 mmol) at 25° C. The mixture was heated to 100° C., and stirred for 3 hours. LC-MS showed that the desired product was formed. The reaction mixture was concentrated under reduced pressure to give a crude product which was purified by prep-HPLC (TFA) to afford the desired diarylamine (290 mg, 565.8 umol, 53% yield) as a brown solid.

$^1$H NMR (400 MHz MeOD) δ=8.73-8.63 (m, 2H), 8.50-8.45 (m, 1H), 7.98-7.90 (m, 1H), 7.62-7.54 (m, 1H), 7.53-7.49 (m, 1H), 7.46-7.40 (m, 1H), 7.31-7.02 (m, 2H), 4.01 (s, 3H), 3.58-3.50 (m, 2H), 3.48-3.41 (m, 2H), 2.99 (s, 6H), 2.91 (s, 3H).

ESI-MS (m/z): 513.2 (M+H)$^+$

To a solution of the above diarylamine (150 mg, 292.7 umol) in acetone (15 mL) and H$_2$O (1.5 mL) were added Zn (344.5 mg, 5.27 mmol) and NH$_4$Cl (109.6 mg, 2.05 mmol, 71.63 uL) at 25° C. The reaction mixture was degassed, purged with N, 3 times and stirred at 25° C. for 5 minutes. LC-MS showed that the desired product was formed. The reaction mixture was filtered and washed with acetone (10 mlx3). The filtrate was concentrated in vacuum. The residue was purified by prep-HPLC (TFA) to afford the desired 1,2,4-triaminobenzene (90 mg, 186.5 umol, 64% yield) as a brown solid.

ESI-MS (m/z): 483.2 (M+H)$^+$

A mixture of the above 1,2,4-triaminobenzene (90 mg, 186.5 umol) in THF (4.5 mL) was degassed and purged with N$_2$ 3 times at 25° C. The mixture was cooled to 0° C. under N$_2$ atmosphere before a solution of DIEA (28.9 mg, 223.8 umol, 39.1 uL) in THF (200 uL) was added slowly. After stirring for 5 minutes, a solution of prop-2-enoyl chloride (16.9 mg, 186.5 umol, 15.2 uL) in THF (200 uL) was added slowly at 0° C., and stirred under N$_2$ atmosphere for 15 minutes. LC-MS showed that the reaction was complete. The reaction was quenched with HCl (g)/EA (0.4M) (1 mL) at 25° C., filtered and concentrated under reduced pressure. The residue was purified by prep-HPLC (TFA, MeOH). The correct fraction was collected and concentrated under vacuum. The residue was treated with 30 ml of 0.2% (V/V) aqueous HCl and lyophilized to afford N-(5-((4-(3-(difluoromethyl)-1H-indazol-1-yl)pyrimidin-2-yl)amino)-2-((2-(dimethylamino)ethyl)(methyl)amino)-4-methoxyphenyl) acrylamide hydrochloride (35 mg, 61.1 umol, 33% yield, HCl) as a yellow solid.

$^1$H NMR (400 MHz MeOD) δ=8.74-8.67 (m, 1H), 8.53-8.42 (m, 1H), 8.03 (s, 1H), 7.99-7.92 (m, 1H), 7.62-7.54 (m, 1H), 7.54-7.48 (m, 1H), 7.45-7.38 (m, 1H), 7.32-7.00 (m, 2H), 6.53-6.45 (m, 2H), 5.91-5.83 (m, 1H), 3.99 (s, 3H), 3.55-3.52 (m, 2H), 3.44-3.34 (m, 2H), 2.90 (s, 6H), 2.77 (s, 3H).

ESI-MS (m/z): 537.3 (M+H)$^+$. HPLC (220 nm): 99.25%

Example 36. N-Methyl 1-(2-((5-acrylamido-4-((2-(dimethylamino)ethyl)(methyl)amino)-2-methoxyphenyl)amino)pyrimidin-4-yl)-1H-indole-3-carboxamide hydrochloride

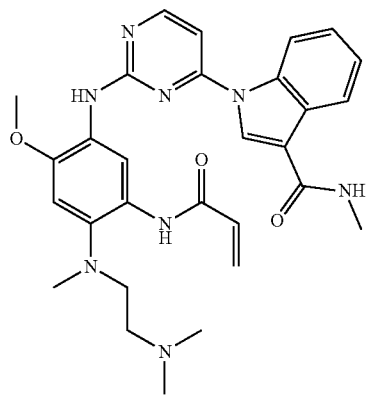

To a solution of methyl 1N-(2-chloropyrimidin-4-yl)-1H-indole-3-carboxylate (3 g, 10.4 mmol) in 2-pentanol (50 mL) were added 4-(N-(2-(N,N-dimethylamino)ethyl)-N-methylamino)-2-methoxy-5-nitroaniline (2.8 g, 10.4 mmol) and PTSA (2.16 g, 12.5 mmol) at 25° C. The mixture was heated to 100° C., and stirred for 3 hours. LC-MS indicated that the reaction was complete. The mixture was filtered and concentrated in vacuum to remove the solvent. The residue was purified by prep-HPLC (HCl condition) to afford the desired diarylamine (2.2 g, 4.23 mmol, 41% yield) as a red solid.

$^1$H NMR (400 MHz CDCl$_3$) δ=9.05 (s, 1H), 8.56-8.49 (m, 2H), 8.29-8.22 (m, 2H), 7.60 (s, 1H), 7.42-7.34 (m, 2H), 7.00 (d, J=5.5 Hz, 1H), 6.70 (s, 1H), 4.05-3.93 (m, 6H), 3.30 (t, J=7.0 Hz, 2H), 2.89 (s, 3H), 2.59 (t, J=7.0 Hz, 2H), 2.34-2.25 (m, 6H).

ESI-MS (m/z): 520.2 (M+H)

To a solution of the above diarylamine (1 g, 1.92 mmol) in THF (10 mL) and H$_2$O (5 mL) was added NaOH (230.4 mg, 5.76 mmol) at 25° C. The reaction mixture was stirred at 25° C. for 12 hours. LC-MS indicated that 80% of the reactant was still remaining. NaOH (153.6 mg, 3.84 mmol) was added and the mixture was stirred at 25° C. for 24 hours. LC-MS indicated that 40% of the reactant was still remaining. More NaOH (153.6 mg, 3.84 mmol) was added and the reaction mixture was stirred for another 24 hours. LC-MS showed that the reaction was complete. The reaction was quenched with HCl (0.1 M/ml) at 0° C. to pH=6 and extracted with EA (10 mLx3). The combined organic layers were washed with brine (25 mLx2), dried with anhydrous Na₂SO₄, filtered and concentrated under vacuum to afford the desired indole carboxylic acid (800 mg, crude) as a red solid.

ESI-MS (m/z): 506.2 (M+H)⁺

To a solution of the above indole carboxylic acid (300 mg, 593.5 umol) in THF (1 mL) were added methanamine (2 M, 890 uL), DIEA (230.1 mg, 1.78 mmol, 310.9 uL), HOBt (120.3 mg, 890.2 umol) and EDCI (170.7 mg, 890.2 umol) at 0° C. The reaction mixture was stirred at 25° C. for 12 hours. LC-MS showed that the reaction was complete. The reaction was quenched with H₂O (5 mL) at 0° C., and extracted with EA (5 mL×3). The combined organic layers were concentrated to afford the desired indole carboxamide (340 mg, crude) as red oil.

¹H NMR (400 MHz MeOD) δ=8.75 (s, 1H), 8.47-8.40 (m, 2H), 8.29-8.12 (m, 2H), 7.28 (br. s., 2H), 7.11-7.04 (m, 1H), 6.78 (s, 1H), 3.97 (s, 3H), 3.30-3.24 (m, 2H), 2.97 (s, 3H), 2.88 (s, 3H), 2.63 (br. s, 2H), 2.29 (s, 6H).

ESI-MS (m/z): 519.2 (M+H)⁺

To a solution of the above indole carboxamide (290 mg, 559.2 umol) in acetone (3 mL) and H₂O (300 uL) were added Zn (658.2 mg, 10.1 mmol) and NH₄Cl (209.4 mg, 3.91 mmol, 136.9 uL) at 25° C. The mixture was degassed, purged with N₂ 3 times and stirred at 25° C. for 5 minutes. LC-MS showed that the reaction was complete. The reaction mixture was filtered, washed with acetone (10 mL×3) and concentrated under vacuum. The residue was purified by prep-HPLC (TFA condition) to afford the desired 1,2,4-triaminobenzene (100 mg, 204.7 umol, 37% yield) as a brown solid.

ESI-MS (m/z): 489.3 (M+H)⁺

A solution of the above 1,2,4-triaminobenzene (100 mg, 204.7 umol) in THF (1 mL) was degassed and purged with N₂ 3 times at 25° C. The mixture was cooled to 0° C. under N₂ atmosphere, then a solution of DIPEA (26.5 mg, 204.7 umol, 35.7 uL) in THF (200 uL) was added slowly. After stirring for 5 minutes, a solution of prop-2-enoyl chloride (18.5 mg, 204.7 umol, 16.7 uL) in THF (200 uL) was added slowly and stirred for 15 minutes. LC-MS showed that the desired product was formed. The reaction was quenched with HCl (g)/EA (0.4M) (1 mL) at 25° C., filtered and concentrated under vacuum to remove solvent. The residue was purified by prep-HPLC (TFA, MeOH). The correct fraction was collected and concentrated under vacuum. The residue was treated with 30 ml of 0.2% (V/V) aqueous HCl and lyophilized to afford N-methyl 1-(2-((5-acrylamido-4-((2-(dimethylamino)ethyl)(methyl)amino)-2-methoxyphenyl)amino)pyrimidin-4-yl)-1H-indole-3-carboxamide hydrochloride (10 mg, 16.9 umol, 8.27% yield, 98% purity) as a yellow solid.

¹H NMR (400 MHz MeOD) δ=8.52-8.48 (m, 2H), 8.45-8.39 (m, 1H), 8.28-8.25 (m, 1H), 8.19-8.14 (m, 1H), 7.32-7.26 (m, 2H), 7.18-7.14 (m, 1H), 7.00 (s, 1H), 6.48-6.42 (m, 2H), 5.88-5.84 (m, 1H), 3.99 (s, 3H), 3.53-3.48 (m, 2H), 3.41-3.35 (m, 2H), 2.96 (s, 3H), 2.88 (s, 6H), 2.74 (s, 3H).

ESI-MS: m/z 543.2 (M+H)⁺. HPLC (220 nm) 98.55%

Example 37. N-(2-((2-(Dimethylamino)ethyl)(methyl)amino)-4-methoxy-5-((4-(5-methyl-2-oxo-1,2-dihydropyridin-3-yl)pyrimidin-2-yl)amino)phenyl)acrylamide

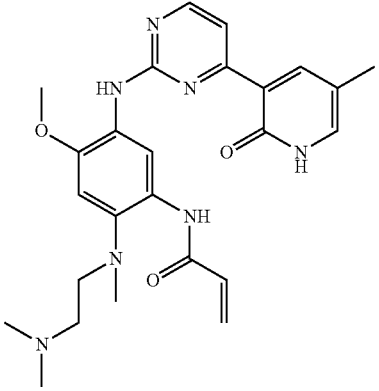

A mixture of 4-(N-(2-(N,N-dimethylamino)ethyl)-N-methylamino)-2-methoxy-5-nitroaniline (605 mg, 2.26 mmol), 2-chloro-4-(1,N-methoxymethyl)5-methylpyrid-3-yl)pyrimidine (600 mg, 2.26 mmol), Cs₂CO₃ (1.47 g, 4.52 mmol), Xantphos (261 mg, 452 umol), (1E,4E)-1,5-diphenylpenta-1,4-dien-3-one and palladium (207 mg, 226 umol) in dioxane (40 mL) was degassed and purged with N₂ 3 time. The reaction mixture was heated to 100° C., and stirred for 3 hours under N₂ atmosphere. LC-MS showed that starting material was consumed completely. Several new peaks were observed and 40% of the desired compound was detected. The reaction mixture was filtered and concentrated under reduced pressure to give the crude desired diarylamine (3.00 g, crude) which was used in the next step without further purification.

ESI-MS: m/z 498.3 (M+H)⁺.

A mixture of the above diarylamine (3.00 g, 6.03 mmol), Zn (3.55 g, 54.3 mmol) and NH₄Cl (1.94 g, 36.2 mmol, 1.26 mL) in MeOH (60 mL) and H₂O (3.00 mL) was degassed, purged with N₂ 3 times and stirred at 25° C. for 15 min. LC-MS showed 2% of starting material with several new peaks and 70% of the desired compound. The reaction mixture was filtered and concentrated under reduced pressure to give a residue, which was purified by silica gel column chromatography (DCM:MeOH=20/1 to 10:1) to give the desired 1,2,4-triaminobenzene (1.30 g, 2.78 mmol, 46.1% yield) as a yellow solid.

¹H NMR (400 MHz MeOD) δ=8.74 (br s, 1H), 8.51-8.49 (m, 2H), 7.93 (d, J=5.3 Hz, 1H), 7.70 (m, 1H), 7.19 (s, 1H), 5.40 (s, 2H), 4.00 (s, 3H), 3.59 (s, 3H), 3.41-3.39 (m, 2H), 3.35 (s, 6H), 3.25-3.23 (m, 2H), 2.85 (s, 3H), 2.26 (s, 3H).

ESI-MS: m/z 468.3 (M+H)⁺.

A mixture of the above 1,2,4-triaminobenzene (10 mg, 21.4 umol) in HCl/MeOH (3.00 mL) was degassed, purged with N₂ 3 times and stirred at 25° C. for 24 hours under N₂ atmosphere. LC-MS showed that starting material was consumed completely and one major peak with desired MS was detected. The reaction mixture was filtered and concentrated under reduced pressure to give a residue, which was purified by prep-HPLC (column: Phenomenex luna C18 250*50 mm*10 um; mobile phase: [water(0.1% TFA)-ACN]; B %: 1%-20%, 20 min) to give the desired pyridone (50 mg, 118 umol, 21% yield) as a yellow solid.

$^1$H NMR (400 MHz MeOD-d$_6$) δ=8.53-8.47 (m, 3H), 7.93 (d, J=5.3 Hz, 1H), 7.48 (d, J=1.5 Hz, 1H), 7.12 (s, 1H), 3.99 (s, 3H), 3.40-3.32 (m, 4H), 2.91 (s, 6H), 2.71 (s, 3H), 2.25 (s, 3H).

ESI-MS: m/z 424.2 (M+H)$^+$.

A solution of the above pyridone (40 mg, 94.5 umol) in THF (4.00 mL) was degassed and purged with N$_2$ 3 times at 25° C. The mixture was cooled to 0° C. under N$_2$ atmosphere and DIEA (14.7 mg, 113 umol, 19.8 uL) was added dropwise. The mixture was stirred at this temperature for 5 minutes before prop-2-enoyl chloride (8.55 mg, 94.5 umol, 7.70 uL) was added dropwise. The resulting mixture was stirred at 25° C. for 15 min under N$_2$ atmosphere. LC-MS showed that starting material was consumed completely. Several new peaks were observed and 80% of the desired compound was detected. The reaction mixture was filtered and concentrated under reduced pressure to give a residue, which was purified by prep-HPLC (column: Luna C18 100*30 5 u; mobile phase; [water (0.1% TFA)-MeOH]; B %: 200-45%, 12 min). The desired fraction was concentrated at 30° C. to remove the low boiling solvent. The residue was treated with 30 mL of 0.2% (V/V) HCl (aq.) and lyophilized to give N-(2-((2-(dimethylamino)ethyl)(methyl)amino)-4-methoxy-5-((4-(5-methyl-2-oxo-1,2-dihydropyridin-3-yl) pyrimidin-2-yl)amino)phenyl) acrylamide (7.00 mg, 12.6 umol, 11% yield, 86.1% purity) as a red solid.

$^1$H NMR (400 MHz DMSO-d$_6$) δ=9.47 (s, 1H), 8.90 (s, 1H), 8.61 (d, J=2.4 Hz, 1H), 8.47 (d, J=5.3 Hz, 1H), 8.17 (d, J=5.1 Hz, 1H), 8.06 (br s, 1H), 7.44 (s, 1H), 7.01 (s, 1H), 6.67 (dd, J=10.1, 17.0 Hz, 1H), 6.30 (dd, J=1.9, 16.9 Hz, 1H), 5.82-5.74 (m, 1H), 3.90 (s, 3H), 3.26 (br s, 4H), 2.80 (d, J=3.7 Hz, 6H), 2.60 (s, 3H), 2.57-2.52 (m, 3H), 2.11 (s, 3H)

ESI-MS: m/z 478.3 (M+H)$^+$, HPLC (220 nm): 86.1%

Example 38. N-(5-((5-Chloro-4-(3-methyl-2-oxo-1, 6-dihydropyridin-5-yl)pyrimidin-2-yl)amino)-2-((2-(dimethylamino)ethyl)(methyl)amino)-4-methoxyphenyl) acrylamide

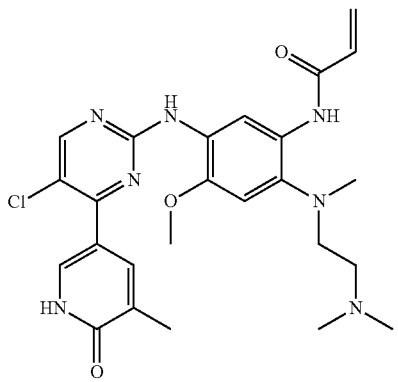 [SMILES: C=CC(=O)Nc1cc(Nc2ncc(Cl)c(-c3c[nH]c(=O)c(C)c3)n2)c(OC)cc1N(C)CCN(C)C]

To a solution of 2,5-dichloro-4-(5-methyl-6-(methoxymethoxy)-pyrid-3-yl)pyrimidine (3.0 g, 10.0 mmol, 1.00 eq) in dioxane (60 mL) were added 4-(N-(2-(N,N-dimethylamino)ethyl)-N-methylamino)-2-methoxy-5-nitroaniline (3.22 g, 12.0 mmol, 1.20 eq) and Cs$_2$CO$_3$ (6.51 g, 20.0 mmol, 2.00 eq). The suspension was degassed under vacuum and purged with N$_2$ several times. Xantphos (1.16 g, 2.00 mmol, 0.20 eq) and Pd$_2$(dba)$_3$ (915 mg, 1.00 mmol, 0.10 eq) were added and the mixture was purged with N, several times. The reaction mixture was heated to 100° C., and stirred for 6 hours under N$_2$. LCMS showed that compound 161 was consumed completely and one major peak with desired MS was detected. The mixture was filtered through a celite pad and the filtrate was concentrated to give the crude product which was purified by silica gel column chromatography (DCM/MeOH=1/0 to 10:1). The desired diarylamine (2.0 g, 38% yield) was obtained as a red solid.

$^1$H NMR (400 MHz CDCl$_3$) δ=9.22 (s, 1H), 8.77 (s, 1H), 8.45 (s, 1H), 8.17 (s, 1H), 7.63 (s, 1H), 6.67 (s, 1H), 5.65 (s, 2H), 3.98 (s, 3H), 3.58 (s, 3H), 3.28 (br d, J=7.3 Hz, 2H), 2.89 (s, 3H), 2.57 (t, J=6.9 Hz, 2H), 2.39 (s, 3H), 2.27 (s, 6H)

ESI-MS (m/z): 532.0 (M+H)$^+$

To a solution of the above diarylamine (1.5 g, 2.82 mmol, 1.00 eq) in MeOH (30 mL) were added Zn (3.32 g, 50.7 mmol, 18.0 eq) and NH$_4$Cl (905 mg, 16.9 mmol, 6.00 eq). The reaction mixture was stirred at 20° C. for 2 hours under N$_2$. LCMS and HPLC showed that compound 162 was consumed completely and one major peak with desired MS was detected. The mixture was filtered through a celite pad and the filtrate was concentrated to give the crude product which was purified by prep-HPLC (TFA condition). The desired 1,2,4-triaminobenzene 3 (400 mg, 28% yield) was obtained as a brown solid.

ESI-MS (m/z): 502.2 (M+H)$^+$

To a solution of the above 1,2,4-triaminobenzene (400 mg, 797 umol, 1.00 eq) in MeOH (5.0 mL) was added HCl/MeOH (4 M, 4.00 mL, 20.08 eq). The reaction mixture was stirred at 20° C. for 30 min under N$_2$. LCMS showed that compound 163 was consumed completely and one major peak with desired MS was detected. The reaction mixture was concentrated under vacuum to give the desired pyridone (300 mg, 82% yield) as a yellow solid.

ESI-MS (m/z): 458.2 (M+H)$^+$

To a solution of the above pyridone (300 mg, 655 umol, 1.00 eq) in THF (10.0 mL) was added DIEA (169 mg, 1.31 mmol, 2.00 eq) at 0° C. Prop-2-enoyl chloride (71.1 mg, 786 umol, 1.20 eq) was added dropwise and the resulting mixture was stirred at 20° C. for 0.5 hours under N$_2$. LCMS and HPLC showed 5% of compound 164 with several new peaks and 60% of desired compound. MeOH (10 mL) was added to the reaction solution and the mixture was concentrated under vacuum. The residue was purified by prep-HPLC (TFA condition) to give N-(5-((5-chloro-4-(3-methyl-2-oxo-1,6-dihydropyridin-5-yl)pyrimidin-2-yl)amino)-2-((2-(dimethylamino)ethyl)(methyl)amino)-4-methoxyphenyl) acrylamide (83 mg, 24% yield, 95.04% purity) as a yellow solid.

$^1$H NMR (400 MHz CDCl$_3$) δ=9.59 (s, 1H), 9.08 (s, 1H), 8.73 (br s, 1H), 8.42 (s, 2H), 7.79 (s, 1H), 6.90 (dd, J=10.1, 16.9 Hz, 1H), 6.73 (s, 1H), 6.53-6.40 (m, 1H), 5.81-5.70 (m, 1H), 3.90 (s, 3H), 3.30-3.23 (m, 2H), 3.16-3.14 (m, 2H), 2.84 (s, 6H), 2.64 (s, 3H), 2.29 (s, 3H).

MS: (M+H$^+$=512.3), HPLC: 98.46%

Example 39. N-Methyl 3-(2-((5-acrylamido-4-((2-(dimethylamino)ethyl)(methyl)amino)-2-methoxyphenyl)amino)pyrimidin-4-yl)-1H-indole-7-carboxamide

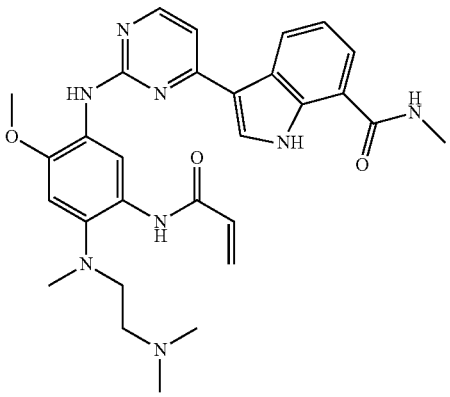 [SMILES: C=CC(=O)Nc1cc(Nc2nccc(-c3c[nH]c4c(C(=O)NC)cccc34)n2)c(OC)cc1N(C)CCN(C)C]

To a solution of compound 2-chloro-4-(7-(carboxamido)indol-3-yl)pyrimidine (800 mg, 2.7 mmol, 1 eq) and 5-(N-acrylamido)-4-(N, 1-(2-(N,N-dimethylamino)ethyl)-N,1-methyl)amino)-2-methoxyaniline (800 mg, 2.7 mmol, 1 eq) in 2-pentanol (8 mL) was added PTSA (584 mg, 3 mmol, 1.1 eq). The reaction was stirred at 120° C. for 2-3 hours. After cooling down to rt, the mixture was concentrated and the residue was purified by silica gel column chromatography to afford N-methyl 3-(2-((5-acrylamido-4-((2-(dimethylamino)ethyl)(methyl)amino)-2-methoxyphenyl)amino)pyrimidin-4-yl)-1H-indole-7-carboxamide 4 (70 mg, 4.7%) as an off-white solid.

$^1$HNMR (300 MHz, DMSO): δ 11.70 (br, 1H), 10.10 (s, 1H), 8.78 (s, 1H), 8.57-8.54 (m, 2H), 8.27 (d, J=5.1 Hz, 2H), 8.06 (s, 1H), 7.64 (d, J=7.2 Hz, 1H), 7.27 (s, 1H), 7.11-7.02 (m, 2H), 6.45-6.36 (m, 1H), 6.22-6.17 (m, 1H), 5.72 (d, J=11.1 Hz, 1H), 3.82 (s, 3H), 2.90-2.85 (m, 5H), 2.73 (s, 3H), 2.33-2.31 (m, 2H), 2.21 (s, 6H).

LCMS: (M+H)$^+$: 542.8, HPLC: 96.5%.

Example 40. N-(5-(4-(1-Methyl-6-(methylamino)-1H-indol-4-yl)pyrimidin-2-ylamino)-2-(N-(2-(dimethylamino)ethyl)-N-methylamino)-4-methoxyphenyl) acrylamide

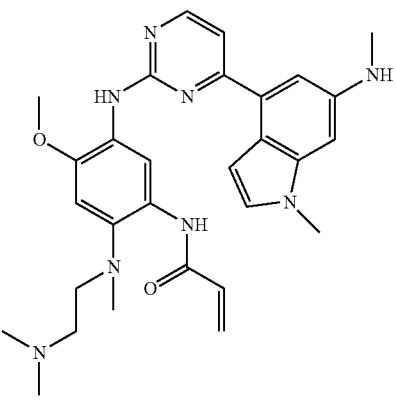

To a solution of 2-chloro-4-(6-(N-methylamino)-1,N-methylindol-4-yl)pyrimidine (544 mg, 2 mmol, 1.0 eq) in dioxane (10 mL) were added N-(5-amino-2-((2-(dimethylamino)ethyl)methyl)amino)-4-methoxyphenyl)acrylamide (526 mg, 1.8 mmol, 0.9 eq), Cs$_2$CO$_3$ (1.3 g, 4 mmol, 2.0 eq), Pd(PPh$_3$)$_4$ (183 mg, 0.2 mmol, 0.1 eq) and Xantphos (231 mg, 0.4 mmol, 0.2 eq). The mixture was bubbled with nitrogen for 10 minutes, then purged with nitrogen 3 times and stirred at 100° C. for 3 hours. After cooling down to rt, the mixture was diluted with DCM (50 mL), filtered through celite, and washed with DCM (20 mL). The filtrate was concentrated and purified by prep-HPLC to afford the desired product N-(5-(4-(1-methyl-6-(methylamino)-1H-indol-4-yl)pyrimidin-2-ylamino)-2-(N-(2-(dimethylamino)ethyl)-N-methylamino)-4-methoxyphenyl) acrylamide (80 mg, 8%).

$^1$HNMR (300 MHz, DMSO-d$_6$): δ 10.24 (s, 1H), 9.08 (s, 1H), 8.48 (d, J=5.1 Hz, 1H), 8.02 (s, 1H), 7.54 (s, 1H), 7.34 (d, J=5.1 Hz, 1H), 7.10 (s, 1H), 7.04 (s, 1H), 6.70 (d, J=13.3 Hz, 1H), 6.60 (s, 1H), 6.48-6.39 (m, 1H), 6.28-6.23 (m, 1H), 5.82 (d, J=10.2 Hz, 1H), 5.67 (d, J=5.4 Hz, 1H), 3.86 (s, 3H), 3.72 (s, 3H), 2.88-2.86 (m, 2H), 2.80 (s, 3H), 2.70 (s, 3H), 2.27-2.25 (m, 2H), 2.00 (s, 6H).

LCMS: (M+H)$^+$: 528.8. HPLC: 96.9%.

Example 41. N-(2-((2-(Dimethylaminoethyl)(methyl)amino)-5-(4-(3-(ethylamino)-1H-indazol-1-yl)pyrimidin-2-ylamino)-4-methoxyphenyl) acrylamide

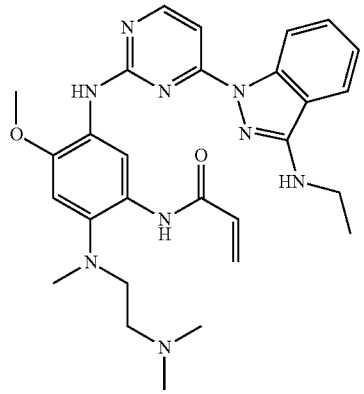 [SMILES: C=CC(=O)Nc1cc(Nc2nccc(-n3nc(NCC)c4ccccc43)n2)c(OC)cc1N(C)CCN(C)C]

To a solution of compound 3-(N-ethylamino)-1-(2-chloropyrimidin-4-yl)indazole (350 mg, 1.28 mmol, 1 eq) and 5-(N-acrylamido)-4-(N,1-(2-(N,N-dimethylamino)ethyl)-N, 1-methyl)amino)-2-methoxyaniline (441 mg, 1.41 mmol, 1.1 eq) in 2-pentanol (6 mL) was added PTSA (268 mg, 1.41 mmol, 1.1 eq). The reaction was stirred at 110° C. for 2 hours. After completion, the mixture was cooled to it and diluted with sat. NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (20 mL×2) and brine (20 mL), dried, concentrated and purified by prep-HPLC affording desired product N-(2-((2-(dimethylamino)ethyl)(methyl)amino)-5-(4-(3-(ethylamino)-1H-indazol-1-yl)pyrimidin-2-ylamino)-4-methoxyphenyl) acrylamide (52 mg, 7.7%).

$^1$HNMR (300 MHz, DMSO-d$_6$): δ 10.08 (br, 1H), 8.53 (s, 1H), 8.41-8.37 (m, 2H), 8.25 (d, J=5.7 Hz, 1H), 7.84 (d, J=8.1 Hz, 1H), 7.30-7.25 (m, 1H), 7.20-7.15 (m, 1H), 7.04-7.01 (m, 2H), 6.84-6.83 (m, 1H), 6.45-6.36 (m, 1H), 6.19-6.14 (m, 1H), 5.73-5.69 (m, 1H), 3.76 (s, 3H), 3.41-3.37 (m, 2H), 2.93-2.91 (m, 2H), 2.75 (s, 3H), 2.38-2.36 (m, 2H), 2.23 (s, 6H), 1.28 (t, J=7.2 Hz, 3H).

LCMS: (M+H)$^+$: 529.8. HPLC: 98.6%.

Example 42. N-(5-((4-(3-(Dimethylamino)-1H-indazol-1-yl)pyrimidin-2-yl)amino)-2-((2-(dimethylamino)ethyl)(methyl)amino)-4-methoxyphenyl) acrylamide

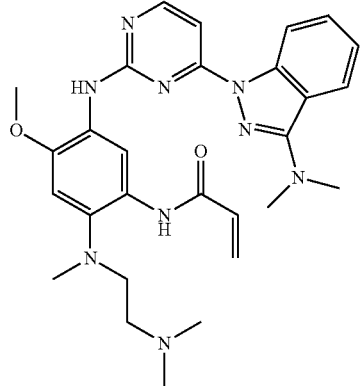 [SMILES: C=CC(=O)Nc1cc(Nc2nccc(-n3nc(N(C)C)c4ccccc43)n2)c(OC)cc1N(C)CCN(C)C]

A 100 mL four-neck flask was charged with compound. 1-(2-chloropyrimidin-4-yl)-3-(N,N-dimethylamino)-1H-indazole (500 mg, 1.83 mmol), N-(5-amino-2-((2-(dimethylamino)ethyl)(methyl)amino)-4-methoxyphenyl) acrylamide (535 mg, 1.83 mmol), 2-pentanol (5 mL) and TsOH.H₂O (380 mg, 2 mmol). The mixture was stirred at 120° C. for 2 h. After completion, the mixture was cooled to rt and diluted with water (10 mL) and DCM/MeOH (10/1. 10 mL). The organic layer was separated and the aqueous layer was extracted with DCM (5 mL×2). The combined organic layers were washed with NaHCO₃ (10 mL×2) and brine (10 mL), dried over sodium sulfate, concentrated and purified by prep-HPLC to afford the desired product N-(5-((4-(3-(dimethylamino)-1H-indazol-1-yl)pyrimidin-2-yl)amino)-2-((2-(dimethylamino)ethyl)(methyl)amino)-4-methoxyphenyl) acrylamide (63 mg, 7%).

¹HNMR (300 MHz, DMSO-d₆): δ 10.10 (s, 1H), 8.54-8.51 (m, 3H), 8.29 (d, J=5.7 Hz, 1H), 7.96 (d, J=8.4 Hz, 1H), 7.32-7.17 (m, 2H), 7.08-7.05 (m, 2H), 6.45-6.36 (m, 1H), 6.19-6.14 (m, 1H), 5.71 (d, J=9.9 Hz, 1H), 3.76 (s, 3H), 3.16 (s, 6H), 2.93-2.91 (m, 2H), 2.75 (s, 3H), 2.37-2.34 (m, 2H), 2.23 (s, 6H).

LCMS: (M+H)⁺: 529.8. HPLC: 99.3%.

Example 43. N-(2-((2-(Dimethylamino)ethyl)methyl)amino)-5-((4-(3-(isopropylamino)-1H-indazol-1-yl)pyrimidin-2-yl)amino)-4-methoxyphenyl) acrylamide

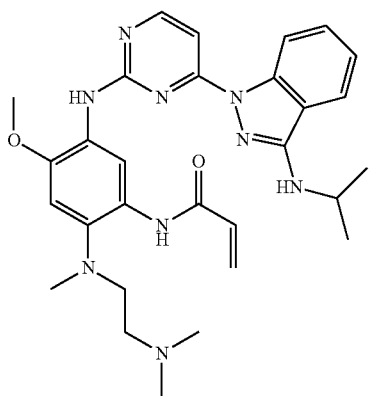 [SMILES: C=CC(=O)Nc1cc(Nc2nccc(-n3nc(NC(C)C)c4ccccc43)n2)c(OC)cc1N(C)CCN(C)C]

A 100 mL four-neck flask was charged with compound 1-(2-chloropyrimidin-4-yl)-3-(N-prop-2-ylamino)-1H-indazole (195 mg, 0.68 mmol), N-(5-amino-2-((2-(dimethylamino)ethyl)(methyl)amino)-4-methoxyphenyl) acrylamide (198 mg, 0.68 mmol), 2-pentanol (5 mL) and TsOH.H₂O (142 mg, 0.75 mmol). The mixture was stirred at 120° C. for 2 h. After completion, the mixture was cooled to rt and diluted with water (10 mL) and DCM/MeOH (10/1, 10 mL). The organic layer was separated and the aqueous layer was extracted with DCM (5 mL×2). The combined organic layers were washed with NaHCO₃ (10 mL×2) and brine (10 mL), dried over sodium sulfate, concentrated and purified by prep-HPLC affording desired product N-(2-((2-(dimethylamino)ethyl)(methyl)amino)-5-((4-(3-(isopropylamino)-1H-indazol-1-yl)pyrimidin-2-yl)amino)-4-methoxyphenyl) acrylamide (15 mg, 4%).

¹HNMR (300 MHz, CDCl₃): δ 9.98 (br, 1H), 9.43 (s, 1H), 8.73 (d, J=7.8 Hz, 1H), 8.38 (d, J=5.1 Hz, 1H), 7.49-7.32 (m, 3H), 7.27-7.25 (m, 1H), 7.19-7.14 (m, 1H), 6.80 (s, 1H), 6.44-6.32 (m, 2H), 5.69-5.65 (d, J=11.1 Hz, 1H), 4.17-4.16 (m, 1H), 3.90 (s, 3H), 2.99-2.93 (m, 2H), 2.74 (s, 3H), 2.45-2.38 (m, 8H), 1.38 (d, J=6.3 Hz, 6H).

LCMS: (M+H)⁺: 543.8, HPLC: 95.8%.

Example 44. N-(5-(4-(3-(N-methanesulfonylamido)-1H-indazol-1-yl)pyrimidin-2-ylamino)-2-(N-(2-(dimethylamino)ethyl)-N-methylamino)-4-methoxyphenyl) acrylamide

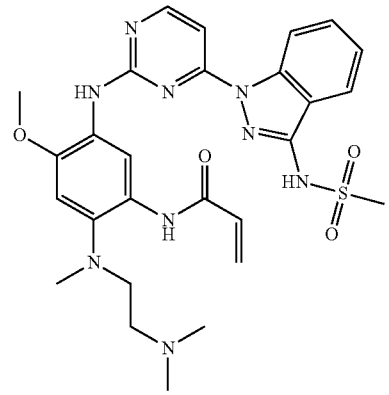 [SMILES: C=CC(=O)Nc1cc(Nc2nccc(-n3nc(NS(C)(=O)=O)c4ccccc43)n2)c(OC)cc1N(C)CCN(C)C]

To a 100 mL four-neck flask were added 1-(2-chloropyrimidin-4-yl)-3-(methylsulfonylamino)-1H-indazole (290 mg, 0.89 mmol, 1 eq), 5-(N-acrylamido)-4-(N,1-(2-(N,N-dimethylamino)ethyl)-N,1-methyl)amino)-2-methoxyaniline (284 mg, 0.98 mmol, 1.1 eq), 2-pentanol (5 mL) and p-TsOH.H₂O (185 mg, 0.97 mmol, 1.1 eq). The mixture was stirred at 120° C. for 2 h. After completion, the mixture was cooled to rt and diluted with water (10 mL) and DCM/MeOH (10/1, 20 mL), the organic layer was separated and the aqueous layer was extracted with DCM (5 mL×2). The combined organic layers were washed with NaHCO₃ (20 mL×2) and brine (20 mL), the combined organic layers were dried, concentrated and purified by prep-HPLC affording desired product N-(5-(4-(3-(N-methanesulfonylamino)-1H-indazol-1-yl)pyrimidin-2-ylamino)-2-(N-(2-(dimethylamino)ethyl)-N-methylamino)-4-methoxyphenyl) acrylamide (20 mg, 4%).

¹HNMR (300 MHz, DMSO-d₆): δ 10.09 (br, 1H), 8.52 (s, 1H), 8.44 (s, 1H), 8.37-8.34 (m, 1H), 8.27 (s, 1H), 7.69-7.66 (m, 1H), 7.28-7.23 (m, 1H), 7.20-7.13 (m, 1H), 7.06-7.04

(m, 2H), 6.46-6.41 (m, 1H), 6.37-6.14 (m, 1H), 5.73-5.69 (m, 1H), 3.76 (s, 3H), 3.10 (s, 3H), 2.94-2.92 (m, 2H), 2.75 (s, 3H), 2.43-2.41 (m, 2H), 2.25 (s, 6H).
LCMS: (M−H)⁻: 577.7. HPLC: 95.0%.

Example 45. N-(2-((2-(Dimethylamino)ethyl) methyl)amino)-5-(4-(3-(2-hydroxypropan-2-yl)-1H-indazol-1-yl)pyrimidin-2-ylamino)-4-methoxyphenyl) acrylamide

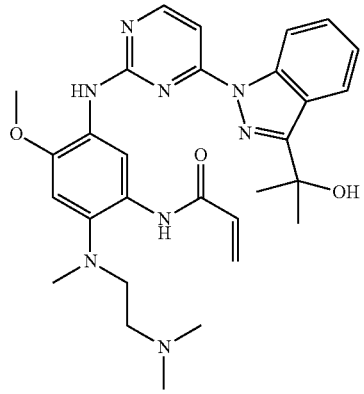 [SMILES: C=CC(=O)Nc1cc(Nc2nccc(-n3nc(C(C)(C)O)c4ccccc43)n2)c(OC)cc1N(C)CCN(C)C]

To a solution of 1-(2-chloropyrimidin-4-yl)-3-(1-hydroxy-1-methylethyl)-1H-indazole (1 g, 3.47 mmol, 1.0 eq) and 5-(N-acrylamido)-4-(N,1-(2-(N,N-dimethylamino)ethyl)-N, 1-methyl)amino)-2-methoxyaniline (N-(5-amino-2-((2-(dimethylamino)ethyl)(methyl)amino)-4-methoxyphenyl)acrylamide) (1.01 g, 3.46 mmol, 1.0 eq) in 2-pentanol (20 mL) was added PTSA (0.73 g, 3.8 mmol, 1.1 eq). The reaction was stirred at 120° C. for 2 hours. After cooling down to rt, the mixture was diluted with DCM/MeOH (10/1, v/v, 110 mL), washed with sat. NaHCO₃ (50 mL×2) and brine (50 mL×2), concentrated and the residue was purified by prep-HPLC affording the desired product N-(2-((2-(dimethylamino)ethyl)(methyl)amino)-5-(4-(3-(2-hydroxypropan-2-yl)-1H-indazol-1-yl)pyrimidin-2-ylamino)-4-methoxyphenyl) acrylamide (10 mg, 0.5%).
¹HNMR (300 MHz, DMSO-d₆): δ 10.14 (br, 1H), 8.91 (s, 1H), 8.75-8.70 (m, 3H), 8.12-8.11 (m, 1H), 7.39-7.23 (m, 3H), 7.06 (s, 1H), 6.50-6.49 (m, 1H), 6.19-6.15 (m, 1H), 5.73-5.70 (m, 1H), 5.51 (s, 1H), 3.77 (s, 3H), 2.98-2.93 (m, 2H), 2.76 (s, 3H), 2.41-2.38 (m, 2H), 2.23 (s, 6H), 1.65 (s, 6H).
LCMS: (M+H)⁺: 544.8. HPLC: 96.0%.

Example 46, N-(5-(4-(7-(1H-Pyrazol-3-yl)-1H-indol-3-yl)pyrimidin-2-ylamino)-2-(N-(2-(dimethylamino)ethyl)-N-methylamino)-4-methoxyphenyl) acrylamide

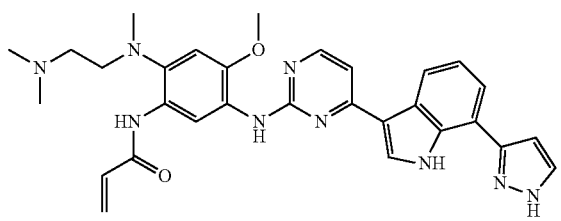 [SMILES: C=CC(=O)Nc1cc(Nc2nccc(-c3c[nH]c4c(-c5cc[nH]n5)cccc34)n2)c(OC)cc1N(C)CCN(C)C]

To a solution of 2-chloro-4-(7-(1,N-tetrahydropyran-2-yl)pyrazol-3-yl)indol-3-yl)pyrimidine (200 mg, 0.53 mmol, 1 eq) and 5-(N-acrylamido)-4-(N,1-(2-(N,N-dimethylamino)ethyl)-N,1-methyl)amino)-2-methoxyaniline (150 mg, 0.51 mmol, 0.98 eq) in 2-pentanol (2 mL) was added PTSA (110 mg, 0.58 mmol, 1.1 eq). The reaction was stirred at 120° C. for 2-3 hours. After cooling down to rt, the mixture was diluted with water (2 mL), extracted with EA, the combined organic layers were dried, concentrated and the residue was purified by silica column affording the desired product N-(5-(4-(7-(1H-pyrazol-3-yl)-1H-indol-3-yl)pyrimidin-2-ylamino)-2-(N-(2-(dimethylamino)ethyl)-N-methylamino)-4-methoxyphenyl) acrylamide (15 mg, 5.1%).
¹HNMR (300 MHz, DMSO-d₆): δ 10.22 (br, 1H), 8.77 (s, 1H), 8.32-8.26 (m, 3H), 8.10 (s, 1H), 7.88 (s, 1H), 7.58 (d, J=6 Hz, 1H), 7.47 (d, J=6.6 Hz, 1H), 7.26 (s, 1H), 7.13-7.03 (m, 2H), 6.91 (s, 1H), 6.45-6.36 (m, 1H), 6.22-6.16 (m, 1H), 5.74-5.71 (m, 1H), 3.81 (s, 3H), 2.89-2.87 (m, 2H), 2.73 (s, 3H), 2.31-2.28 (m, 2H), 2.21 (s, 6H).
LCMS: (M+H)⁺: 551.9. HPLC: 76.7%.

Example 47. 4-(2-(5-Acrylamido-4-((2-(dimethylamino)ethyl)(methyl)amino)-2-methoxyphenylamino)-5-chloropyrimidin-4-yl)-1-methyl-1H-indole-6-carboxamide

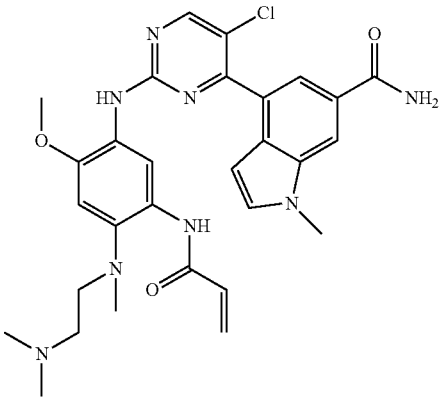 [SMILES: C=CC(=O)Nc1cc(Nc2ncc(Cl)c(-c3cc(C(N)=O)cc4c3ccn4C)n2)c(OC)cc1N(C)CCN(C)C]

To a solution of 2,5-dichloro-4-(6-(carboxymethyl)-1,N-methylindol-4-yl)pyrimidine (335 mg, 2 mmol, 1.0 eq) in dioxane (5 mL) were added 5-(N-acrylamido)-4-(N, 1-(2-(N,N-dimethylamino)ethyl)-N,1-methyl)amino)-2-methoxyaniline (263 mg, 0.9 mmol, 0.9 eq), Cs₂CO₃ (0.65 g, 2 mmol, 2.0 eq), Pd(PPh₃)₄ (91 mg, 0.1 mmol, 0.1 eq) and Xantphos (115 mg, 0.2 mmol, 0.2 eq). The mixture was bubbled with nitrogen for 10 minutes, then purged with nitrogen 3 times and stirred at 100° C. for 3 hours. After cooling down to rt, the mixture was diluted with DCM (25 mL), filtered through celite, washed with DCM (10 mL). The filtrate was concentrated and purified by silica column affording the desired diarylamine (141 mg, 26.7%).
LCMS: (M+H)⁺: 591.9.
To a solution of the above diarylamine (141 mg, 0.23 mmol, 1.0 eq) and NH₄Cl (43 mg, 0.8 mmol, 3.4 eq) in THF (2 mL) was added LiHMDS (2.4 mL, 2.4 mmol, 10.0 eq) dropwise at 0° C. After addition, the mixture was heated to 50° C. for 2 h. LCMS indicated completion, the reaction was quenched by sat. NH₄Cl (5 mL), then extracted with DCM (10 mL), dried over sodium sulfate, concentrated and purified by prep-HPLC affording 4-(2-(5-acrylamido-4-((2-(dimethylamino)ethyl)(methyl)amino)-2-methoxyphenylamino)-5-chloropyrimidin-4-yl)-1-methyl-1H-indole-6-carboxamide (7 mg, 5.1%).

$^1$HNMR (300 MHz, DMSO-d$_6$): δ 10.13 (br, 1H), 8.74-8.56 (m, 3H), 8.18 (s, 1H), 8.09 (s, 1H), 7.84 (s, 1H), 7.60 (s, 1H), 7.45 (s, 1H), 6.97 (s, 1H), 6.39-6.32 (m, 2H), 6.24-6.15 (m, 1H), 5.75 (s, 1H), 3.88 (s, 3H), 3.80 (s, 3H), 2.84-2.82 (m, 2H), 2.69 (s, 3H), 2.29-2.26 (m, 2H), 2.18-1.98 (m, 6H).

LCMS: (M+H)$^+$: 576.7. HPLC: 96.4%.

Example 48. N-(5-(4-(7-t-Butyl-1H-indol-3-yl)pyrimidin-2-ylamino)-2-(N-(2-(dimethylamino)ethyl)-N-methylamino)-4-methoxyphenyl) acrylamide

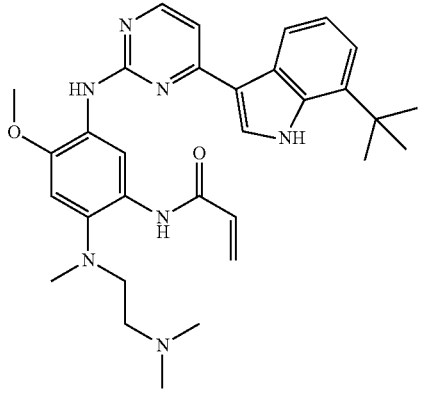 [SMILES: C=CC(=O)Nc1cc(Nc2nccc(-c3c[nH]c4c(C(C)(C)C)cccc34)n2)c(OC)cc1N(C)CCN(C)C]

To a solution of 5-(N-acrylamido)-4-(N,1-(2-(N,N-dimethylamino)ethyl)-N,1-methyl)amino)-2-methoxyaniline (292 mg, 1 mmol, 1 eq) and 7-(1,1-dimethylethyl)-3-(2-chloropyrimidin-4-yl)-1H-indole (280 mg, 1 mmol, 1 eq) in 2-pentanol (8 mL) was added PTSA (197 mg, 1.1 mmol, 1.1 eq). The reaction was stirred at 120° C. for 2-3 hours. After cooling down to rt, the mixture was concentrated and the residue was purified by prep-HPLC affording the desired product N-(5-(4-(7-t-butyl-1H-indol-3-yl)pyrimidin-2-ylamino)-2-(N-(2-(dimethylamino)ethyl)-N-methylamino)-4-methoxyphenyl) acrylamide (30 mg, 6%).

$^1$HNMR (300 MHz, DMSO-d$_6$) δ:11.37 (br, 1H), 10.17 (br, 1H), 8.78 (s, 1H), 8.29-8.24 (m, 3H), 8.03 (s, 1H), 7.29-7.27 (m, 1H), 7.02-6.96 (m, 3H), 6.38-6.35 (m, 1H), 6.23-6.17 (m, 1H), 5.74-5.71 (m, 1H), 3.81 (s, 3H), 2.89-2.87 (m, 2H), 2.72 (s, 3H), 2.31-2.30 (m, 2H), 2.21 (s, 6H), 1.43 (s, 9H).

LCMS: (M–H)$^-$: 539.8. HPLC: 95.4%.

Example 49. 1-(2-(5-Acrylamido-4-((2-(dimethylamino)ethyl)(methyl)amino)-2-methoxyphenylamino)pyrimidin-4-yl)-1H-pyrrolo[3,2-b]pyridine-3-carboxamide

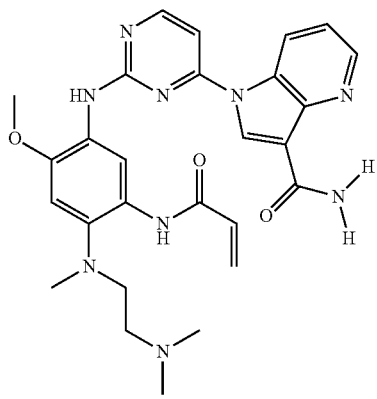 [SMILES: C=CC(=O)Nc1cc(Nc2nccc(-n3cc(C(N)=O)c4ncccc43)n2)c(OC)cc1N(C)CCN(C)C]

To a solution of methyl 1,N-(2-chloropyrimidin-4-yl)-pyrrolo[3,2-b]pyridine-3-carboxylate (604 mg 2 mmol, 1.0 eq) and 5-(N-acrylamido)-4-(N,1-(2-(N,N-dimethylamino)ethyl)-N,1-methyl)amino)-2-methoxyaniline (642 mg, 2.2 mmol, 1.1 eq) in 2-pentanol (10 mL) was added p-toluenesulfonic acid monohydrate over a period of 10 min. The mixture was heated to 100° C. for 2 h. The mixture was poured into water (20 mL), then adjusted to pH=7 with saturated sodium bicarbonate solution. Extracted with EA (20 mL×2), dried over sodium sulfate, concentrated to afford the desired diarylamine (400 mg, crude) which was used in next step directly.

LCMS: (M–H)$^-$: 556.7.

To a solution of the above diarylamine (400 mg 0.7 mmol, 1.0 eq) in THF (50 mL) was added NH$_4$Cl (127 mg, 2.4 mmol, 3.4 eq). The mixture was cooled to 0° C., and 1N LiHMDS (7 mL) was added dropwise. Then the mixture was heated to 50° C. for 2 h. The mixture was poured into water (20 mL), extracted with DCM (20 mL×5). The organic layer was washed with brine (30 mL), dried over sodium sulfate, concentrated and purified by prep-HPLC affording desired product 1-(2-(5-acrylamido-4-((2-(dimethylamino)ethyl)(methyl)amino)-2-methoxyphenylamino)pyrimidin-4-yl)-1H-pyrrolo[3,2-b]pyridine-3-carboxamide (13 mg, 1.3% for 2 steps).

$^1$HNMR (300 MHz, DMSO-d$_6$): δ 10.12 (s, 1H), 8.98-8.93 (m, 2H), 8.80 (br, 1H), 8.55-8.53 (m, 1H), 8.46-8.44 (m, 3H), 7.27 (s, 1H), 7.41-7.38 (m, 1H), 7.19 (br, 1H), 7.06 (s, 1H), 6.44-6.35 (m, 1H), 6.21-6.15 (m, 1H), 5.74-5.71 (m, 1H), 3.75 (s, 3H), 2.91-2.89 (m, 2H), 2.76 (s, 3H), 2.35-2.33 (m, 2H), 2.21 (s, 6H).

LCMS: (M+H)$^+$: 529.8. HPLC: 90.0%.

Example 50. N-(5-(4-(7-(Dimethylamino)-1H-pyrrolo[2,3-c]pyridin-3-yl)pyrimidin-2-ylamino)-2-(N-(2-(dimethylamino)ethyl)-N-methylamino)-4-methoxyphenyl) acrylamide

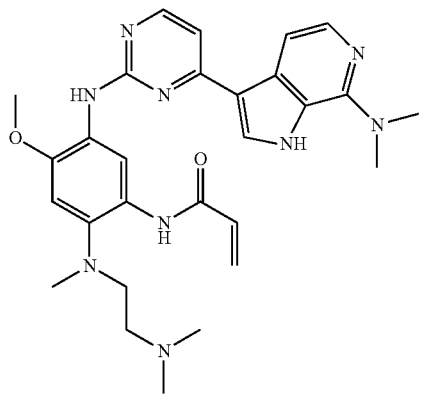 [SMILES: C=CC(=O)Nc1cc(Nc2nccc(-c3c[nH]c4c(N(C)C)nccc34)n2)c(OC)cc1N(C)CCN(C)C]

To a solution of 2-chloro-4-(7-(N,N-dimethylamino)pyrrolo[2,3-c]pyrid-3-yl)pyrimidine (100 mg, 0.36 mmol, 1.0 eq) and 5-(N-acrylamido)-4-(N,1-(2-(N,N-dimethylamino)ethyl)-N,1-methyl)amino)-2-methoxyaniline (139 mg, 0.47 mmol, 1.3 eq) in 2-pentanol (4 mL) was added PTSA (1.5 g, 15 mmol, 3 eq). The mixture was stirred at 120° C. overnight. After cooling down to rt, the mixture was diluted with water (5 mL) and extracted with DCM: isopropanol=(3:1, v/v, 20 mL×3), the combined organic layers were washed with brine (10 mL), dried over sodium sulfate, concentrated and purified by prep-HPLC affording desired product N-(5-(4-(7-(dimethylamino)-1H-pyrrolo[2,3-c]pyridin-3-yl)pyrimidin-2-ylamino)-2-(N-(2-(dimethylamino)ethyl)-N-methylamino)-4-methoxyphenyl) acrylamide (2 mg, 1.6%).

LCMS: (M+H)$^+$: 529.8. HPLC purity 47%.

Example 51. N-Methyl 1-(2-(5-acrylamido-4-((2-(dimethylamino)ethyl)(methyl)amino)-2-methoxyphenylamino)pyrimidin-4-yl)-1H-pyrrolo[3,2-b]pyridine-3-carboxamide

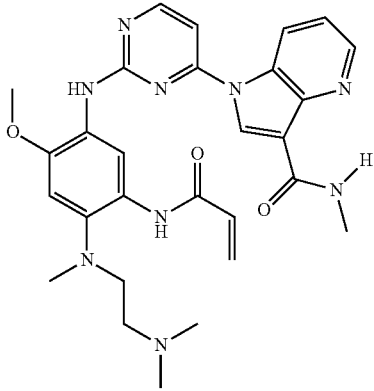 [SMILES: C=CC(=O)Nc1cc(Nc2nccc(-n3cc(C(=O)NC)c4ncccc43)n2)c(OC)cc1N(C)CCN(C)C]

To a solution of 3-(N-methylcarboxamido)-1,N-(2-chloropyrimidin-4-yl)-pyrrolo[3,2-b]pyridine (574 mg, 2 mmol, 1.0 eq) and compound 5-(N-acrylamido)-4-(N,1-(2-(N,N-dimethylamino)ethyl)-N,1-methyl)amino)-2-methoxyaniline (642 mg, 2.2 mmol, 1.1 eq) in 2-pentanol (10 mL) was added p-toluenesulfonic acid monohydrate (418 mg, 2.2 mmol, 1.1 eq) over a period of 10 min. The mixture was heated to 100° C. for 2 h. The mixture was poured into water (10 mL), then adjusted to pH=7 with saturated sodium bicarbonate solution, extracted with EA (10 mL×2). The organic layers were dried over sodium sulfate, concentrated and purified by prep-HPLC affording the desired product N-methyl 1-(2-(5-acrylamido-4-((2-(dimethylamino)ethyl)(methyl)amino)-2-methoxyphenylamino)pyrimidin-4-yl)-1H-pyrrolo[3,2-b]pyridine-3-carboxamide (90 mg, 8%).

$^1$HNMR (300 MHz, DMSO-d$_6$): δ 10.13 (s, 1H), 8.98-8.94 (m, 2H), 8.85-8.84 (m, 2H), 8.55 (s, 1H), 8.44 (d, J=5.7 Hz, 2H), 7.41 (d, J=5.4 Hz, 1H), 7.20 (br, 1H), 7.06 (s, 1H), 6.44-6.35 (m, 1H), 6.20-6.15 (m, 1H), 5.74-5.71 (m, 1H), 3.75 (s, 3H), 2.95-2.91 (m, 5H), 2.76 (s, 3H), 2.35-2.31 (m, 2H), 2.21 (s, 6H).

LCMS: (M+H)$^+$: 543.8. HPLC: 97.5%.

Example 52. N-(5-(5-Chloro-4-(3-(methylamino)-1H-indazol-1-yl)pyrimidin-2-ylamino)-2-(N-(2-(dimethylamino)ethyl)-N-methylamino)-4-methoxyphenyl) acrylamide

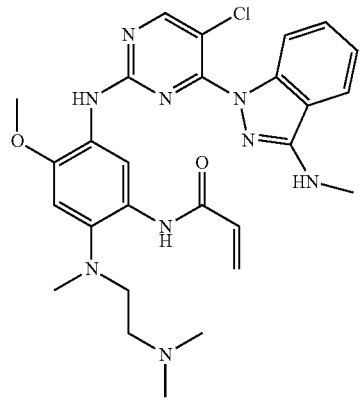 [SMILES: C=CC(=O)Nc1cc(Nc2ncc(Cl)c(-n3nc(NC)c4ccccc43)n2)c(OC)cc1N(C)CCN(C)C]

To a 100 mL four-neck flask were added compound 1-(2,5-Dichloropyrimidin-4-yl)-3-(N-(t-butoxycarbonyl)-N-methylamino)-1H-indazole (500 mg, 1.27 mmol, 1 eq), 5-(N-acrylamido)-4-(N,1-(2-(N,N-dimethylamino)ethyl)-N,1-methyl)amino)-2-methoxyaniline (408 mg, 1.39 mmol, 1.1 eq), 2-pentanol (6 mL) and p-TsOH.H$_2$O (265 mg, 1.39 mmol, 1.1 eq). The mixture was stirred at 120° C. for 2 h. After completion, the mixture was cooled to rt and diluted with water (10 mL) and DCM/MeOH (10/1, 20 mL), the organic layer was separated and the aqueous layer was extracted with DCM (10 mL×2). The combined organic layers were washed with NaHCO$_3$ (20 mL×2) and brine (20 mL), the combined organic layers were dried, concentrated and purified by prep-HPLC affording desired product N-(5-(5-chloro-4-(3-(methylamino)-1H-indazol-1-yl)pyrimidin-2-ylamino)-2-(N-(2-(dimethylamino)ethyl)-N-methylamino)-4-methoxyphenyl) acrylamide (15 mg, 2.1%).

$^1$HNMR (300 MHz, DMSO-d$_6$): δ 10.06 (br, 1H), 8.77 (s, 1H), 8.36-8.33 (m, 2H), 8.08 (d, J=9 Hz, 1H), 7.78 (d, J=7.8 Hz, 1H), 7.25-7.15 (m, 2H), 7.03 (s, 1H), 6.78 (br, 1H), 6.44-6.33 (m, 1H), 6.21-6.15 (m, 1H), 5.74-5.71 (m, 1H), 3.74 (s, 3H), 2.94-2.90 (m, 5H), 2.74 (s, 3H), 2.35-2.33 (m, 2H), 2.21 (s, 6H).

LCMS: (M+H)$^+$: 549.8. HPLC: 97.8%.

Example 53. N-(5-(4-(3-Acetamido-1H-indazol-1-yl)pyrimidin-2-ylamino)-2-((2-(dimethylamino)ethyl)(methyl)amino)-4-methoxyphenyl) acrylamide

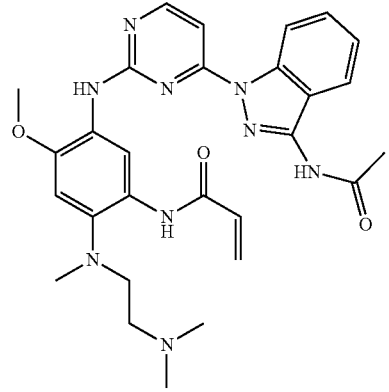 [SMILES: C=CC(=O)Nc1cc(Nc2nccc(-n3nc(NC(C)=O)c4ccccc43)n2)c(OC)cc1N(C)CCN(C)C]

To a 100 mL four-neck flask were added 1-(2-chloropyrimidin-4-yl)-3-(acetamido)-1H-indazole (140 mg, 0.48 mmol, 1.0 eq), 5-(N-acrylamido)-4-(N, 1-(2-(N, N-dimethylamino)ethyl)-N, 1-methyl)amino)-2-methoxyaniline (140 mg, 0.48 mmol, 1.0 eq), 2-pentanol (6.6 mL) and TsOH.H$_2$ (101.6 mg, 0.53 mmol, 1.1 eq). The mixture was stirred at 80° C. for 5 h. After completion, the mixture was cooled to rt, diluted with water (50 mL) and extracted with DCM (50 mL×3). The combined organic layers were washed with brine (50 mL), dried over sodium sulfate, concentrated and purified by prep-HPLC affording desired product N-(5-(4-(3-acetamido-1H-indazol-1-yl)pyrimidin-2-ylamino)-2-((2-(dimethylamino)ethyl)(methyl)amino)-4-methoxyphenyl) acrylamide (85 mg, 32%).

$^1$HNMR (300 MHz, DMSO-d$_6$): δ 10.78 (br, 1H), 10.10 (br, 1H), 8.78 (s, 1H), 8.48-8.38 (m, 3H), 7.94-7.91 (m, 1H), 7.34-7.25 (m, 2H), 7.07-7.05 (m, 2H), 6.39-6.36 (m, 1H), 6.19-6.14 (m, 1H), 5.73-5.70 (m, 1H), 3.80 (s, 3H), 2.93-2.90 (m, 2H), 2.77 (s, 3H), 2.36-2.30 (m, 2H), 2.22 (s, 9H).

LCMS: (M+H)$^+$: 543.8. HPLC: 95.1%.

Example 54. N-(2-((2-(Dimethylamino)ethyl)(methyl)amino)-5-(4-(3-(ethylamino)-1H-pyrazolo[4,3-b]pyridin-1-yl)pyrimidin-2-ylamino)-4-methoxyphenyl) acrylamide

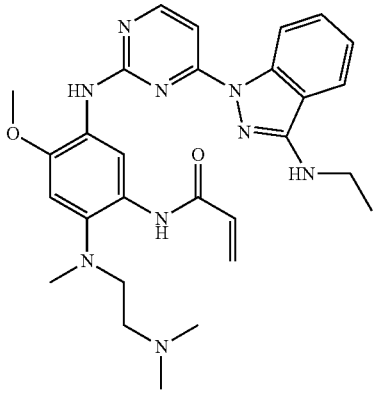 [SMILES: C=CC(=O)Nc1cc(Nc2nccc(-n3nc(NCC)c4ccccc43)n2)c(OC)cc1N(C)CCN(C)C]

To a 100 mL four-neck flask were added 2-chloro-4-(3-(N-ethylamino)pyrazolo[4,3-b]pyrid-1-yl)pyrimidine (200 mg, 0.73 mmol, 1 eq), 5-(N-acrylamido)-4-(N,1-(2-(N,N-dimethylamino)ethyl)-N,1-methyl)amino)-2-methoxyaniline (234 mg, 0.8 mmol, 1.1 eq), 2-pentanol (6 mL) and p-TsOH.H$_2$O (152 mg, 0.8 mmol, 1.1 eq). The mixture was stirred at 120° C. for 2 h. After completion, the mixture was cooled to rt and diluted with sat.NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (20 mL×2) and brine (20 mL), dried, concentrated and purified by prep-HPLC affording desired product N-(2-((2-(dimethylamino)ethyl)(methyl)amino)-5-(4-(3-(ethylamino)-1H-pyrazolo[4,3-b]pyridin-1-yl)pyrimidin-2-ylamino)-4-methoxyphenyl) acrylamide (33 mg, 8.5%).

$^1$HNMR (300 MHz, CDCl$_3$): δ 10.07 (br, 1H), 9.39 (s, 1H), 8.94 (d, J=8.1 Hz, 1H), 8.41-8.39 (m, 2H), 7.37-7.32 (m, 3H), 6.81 (s, 1H), 6.34-6.32 (m, 2H), 5.69-5.66 (m, 1H), 4.85 (s, 1H), 3.90 (s, 3H), 3.62-3.58 (m, 2H), 2.97-2.90 (m, 2H), 2.75 (s, 3H), 2.53-2.51 (m, 8H), 1.37 (t, J=6.6 Hz, 3H).

LCMS: (M+H)$^+$: 530.8. HPLC: 91.3%.

Example 55. N-(5-(4-(3-(Dimethylamino)-1H-pyrazolo[4,3-b]pyridin-1-yl)pyrimidin-2-ylamino)-2-(N-(2-(dimethylamino)ethyl)-N-methylamino)-4-methoxyphenyl) acrylamide

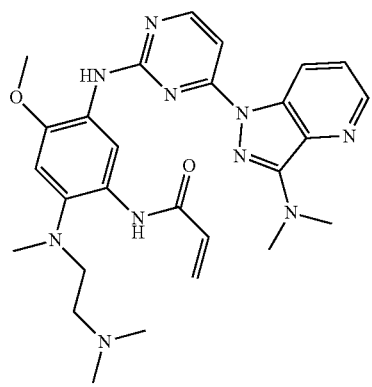 [SMILES: C=CC(=O)Nc1cc(Nc2nccc(-n3nc(N(C)C)c4ncccc43)n2)c(OC)cc1N(C)CCN(C)C]

To a solution of 2-chloro-4-(3-(N,N-dimethylamino)pyrazolo[4,3-b]pyrid-1-yl)pyrimidine (200 mg, 0.73 mmol, 1 eq) and 5-(N-acrylamido)-4-(N,1-(2-(N,N-dimethylamino)ethyl)-N, 1-methyl)amino)-2-methoxyaniline (234 mg, 0.8 mmol, 1.1 eq) in 2-pentanol (8 mL) was added PTSA (152 mg, 0.8 mmol, 1.1 eq). The reaction was stirred at 120° C. for 2 hours. After cooling down to rt, the mixture was diluted with MeOH:DCM=1:10 (30 mL), washed with aq. NaHCO$_3$ (10 mL) and brine (10 mL), concentrated and the residue was purified by prep-HPLC affording the desired product N-(5-(4-(3-(dimethylamino)-1H-pyrazolo[4,3-b]pyridin-1-yl)pyrimidin-2-ylamino)-2-(N-(2-(dimethylamino)ethyl)-N-methylamino)-4-methoxyphenyl) acrylamide (33 mg, 8.5%).

$^1$HNMR (300 MHz, DMSO-d$_6$): δ 10.05 (br, 1H), 8.79 (br, 1H), 8.64 (s, 1H), 8.51-8.47 (m, 2H), 8.33 (d, J=5.4 Hz, 1H), 7.31-7.30 (m, 1H), 7.08-7.03 (m, 2H), 6.48-6.45 (m, 1H), 6.19-6.14 (m, 1H), 5.72 (d, J=10.2 Hz, 1H), 3.77 (s, 3H), 3.31 (s, 6H), 2.99-2.97 (m, 2H), 2.73 (s, 3H), 2.52-2.50 (m, 2H), 2.31 (s, 6H).

LCMS: (M+H)$^+$: 530.8. HPLC: 95.6%.

Example 56. N-(5-(4-(3-(Methylamino)-1H-pyrazolo[4,3-b]pyridin-1-yl)pyrimidin-2-ylamino)-2-(N-(2-(dimethylamino)ethyl)-N-methylamino)-4-methoxyphenyl) acrylamide

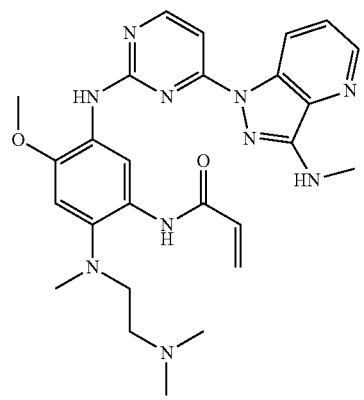 [SMILES: C=CC(=O)Nc1cc(Nc2nccc(-n3nc(NC)c4ncccc43)n2)c(OC)cc1N(C)CCN(C)C]

To a solution of 2-chloro-4-(3-(N-methylamino)pyrazolo[4,3-b]pyrid-1-yl)pyrimidine (200 mg, 0.77 mmol, 1 eq) and 5-(N-acrylamido)-4-(N,1-(2-(N,N-dimethylamino)ethyl)-N, 1-methyl)amino)-2-methoxyaniline (247 mg, 0.84 mmol, 1.1 eq) in 2-pentanol (4 mL) was added PTSA (160 mg, 0.84 mmol, 1.1 eq). The reaction was stirred at 120° C. for 2-3 hours. After cooling down to rt, the mixture was diluted with MeOH:DCM=1:10 (30 mL), washed with aq. NaHCO$_3$ (10 mL) and brine (10 mL), concentrated and the residue was purified by prep-HPLC affording the desired product N-(5-(4-(3-(methylamino)-1H-pyrazolo[4,3-b]pyridin-1-yl)pyrimidin-2-ylamino)-2-(N-(2-(dimethylamino)ethyl)-N-methylamino)-4-methoxyphenyl) acrylamide (78 mg, 19%).

$^1$HNMR (300 MHz, DMSO-d$_6$): δ 10.05 (br, 1H), 8.69 (br, 1H), 8.58 (s, 1H), 8.48-8.46 (m, 2H), 8.30 (d, J=5.7 Hz, 1H), 7.33-7.31 (m, 1H), 7.05-7.03 (m, 2H), 6.93-6.91 (m, 1H), 6.52-6.48 (m, 1H), 6.19-6.14 (m, 1H), 5.73-5.69 (m, 1H), 3.77 (s, 3H), 2.98-2.95 (m, 5H), 2.73 (s, 3H), 2.50-2.48 (m, 2H), 2.31 (br, 6H).

LCMS: (M+H)$^+$: 516.8. HPLC: 95.1%.

Example 57. N-(5-(4-(7-Methoxy-1N-methyl-1H-pyrrolo[2,3-c]pyridin-4-yl)pyrimidin-2-ylamino)-2-(N-(2-(dimethylamino)ethyl)-N-methylamino)-4-methoxyphenyl) acrylamide

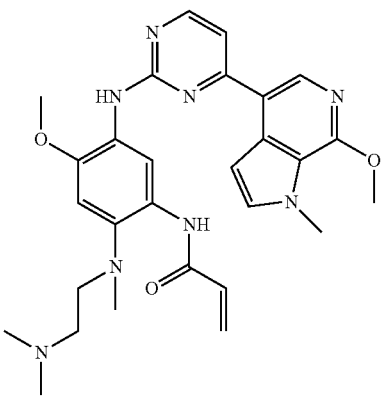

To a solution of 2-chloro-4-(7-methoxypyrrolo[2,3-c]pyrid-4-yl)pyrimidine (306 mg, 1.11 mmol, 1.0 eq) in DMF (6 mL) were added 5-(N-acrylamido)-4-(N,1-(2-(N,N-dimethylamino)ethyl)-N,1-methyl)amino)-2-methoxyaniline (324 mg, 1.11 mmol, 1.0 eq), Cs$_2$CO$_3$ (425 mg, 1.33 mmol, 1.2 eq), Pd(OAc)$_2$ (25 mg, 0.11 mmol, 0.1 eq) and Xantphos (64.5 mg, 0.11 mmol, 0.1 eq). The mixture was purged with nitrogen 3 times and stirred at 100° C. for 3 hours. After cooling down to rt, the mixture was concentrated and purified by prep-HPLC affording desired product N-(5-(4-(7-methoxy-1N-methyl-1H-pyrrolo[2,3-c]pyridin-4-yl)pyrimidin-2-ylamino)-2-(N-(2-(dimethylamino)ethyl)-N-methylamino)-4-methoxyphenyl) acrylamide (24 mg, 4%).

$^1$HNMR (300 MHz, DMSO-d$_6$): δ 10.06 (br, 1H), 8.71 (s, 1H), 8.45-8.39 (m, 1H), 8.25 (s, 1H), 7.41 (d, J=2.4 Hz, 1H), 7.33 (d, J=5.4 Hz, 1H), 7.00-7.19 (m, 2H), 6.52-6.35 (m, 1H), 6.25-6.19 (m, 1H), 5.75-5.72 (m, 1H), 4.05 (s, 3H), 4.04 (s, 3H), 3.80 (s, 3H), 2.89-2.88 (m, 2H), 2.72 (s, 3H), 2.33-2.31 (m, 2H), 2.21 (s, 6H).
LCMS: (M+H)$^+$: 530.8. HPLC: 98.6%.

Example 58. N-(5-(4-(3-(Pyridin-2-ylamino)-1H-indazol-1-yl)pyrimidin-2-ylamino)-2-(N-(2-(dimethylamino)ethyl)-N-methylamino)-4-methoxyphenyl) acrylamide

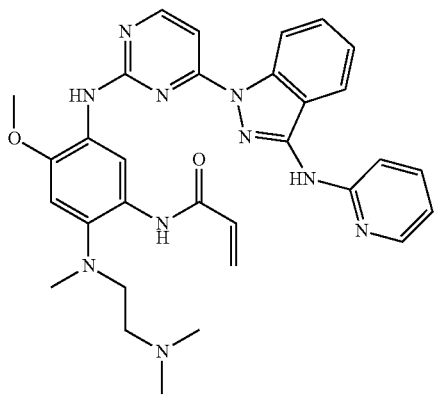 [SMILES: C=CC(=O)Nc1cc(Nc2nccc(-n3nc(Nc4ccccn4)c4ccccc43)n2)c(OC)cc1N(C)CCN(C)C]

To a 100 mL flask were added 1-(2-chloropyrimidin-4-yl)-3-(N-(pyrid-2-yl)amino)-1H-indazole (200 mg, 0.62 mmol, 1 eq), 5-(N-acrylamido)-4-(N,1-(2-(N,N-dimethylamino)ethyl)-N, 1-methyl)amino)-2-methoxyaniline (199 mg, 0.68 mmol, 1.1 eq), 2-pentanol (4 mL) and p-TsOH.H$_2$O (129 mg, 1.92 mmol, 1.1 eq). The mixture was stirred at 120° C. for 2 h. After completion, the mixture was cooled to it and diluted with sat. NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (10 mL×2) and brine (20 mL), dried, concentrated and purified by prep-HPLC affording desired product N-(5-(4-(3-(pyridin-2-ylamino)-1H-indazol-1-yl)pyrimidin-2-ylamino)-2-(N-(2-(dimethylamino)ethyl)-N-methylamino)-4-methoxyphenyl) acrylamide (10 mg, 3%).

$^1$HNMR (300 MHz, DMSO-d$_6$): δ 10.29 (s, 1H), 10.08 (s, 1H), 8.64 (s, 1H), 8.59-8.50 (m, 2H), 8.39-8.29 (m, 4H), 7.89-7.84 (m, 1H), 7.40-7.35 (m, 1H), 7.30-7.19 (m, 2H), 7.06-6.98 (m, 2H), 6.50-6.41 (m, 1H), 6.20-6.15 (m, 1H), 5.74-5.70 (m, 1H), 3.78 (s, 3H), 2.97-2.95 (m, 2H), 2.75 (s, 3H), 2.49-2.47 (m, 2H), 2.28 (s, 6H).
LCMS: (M−H)$^-$: 576.8. HPLC: 95.0%.

Example 59. N-(5-(4-(3-(Pyrrolidin-1-yl)-1H-indazol-1-yl)pyrimidin-2-ylamino)-2-(N-(2-(dimethylamino)ethyl)-N-methylamino)-4-methoxyphenyl) acrylamide

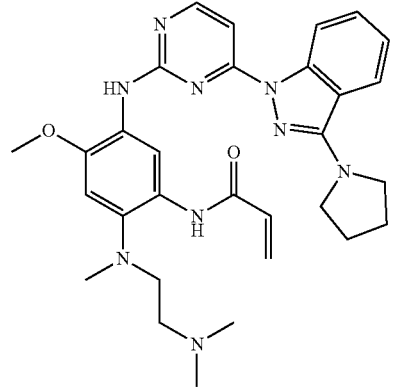 [SMILES: C=CC(=O)Nc1cc(Nc2nccc(-n3nc(N4CCCC4)c4ccccc43)n2)c(OC)cc1N(C)CCN(C)C]

To a 100 mL four-neck flask were added 1-(2-chloropyrimidin-4-yl)-3-(1,N-pyrrolidinyl)-1H-indazole (333 mg, 1.1 mmol, 1.0 eq), 5-(N-acrylamido)-4-(N,1-(2-(N,N-dimethylamino)ethyl)-N,1-methyl)amino)-2-methoxyaniline (314 mg, 1.2 mmol, 1.1 eq), 2-pentanol (6 mL) and p-TsOH.H$_2$O (140 mg, 1.2 mmol, 1.1 eq). The mixture was stirred at 120° C. for 2 h. After completion, the mixture was cooled to it and diluted with sat. NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (20 mL×2) and brine (20 mL), dried, concentrated and purified by prep-HPLC affording desired product N-(5-(4-(3-(pyrrolidin-1-yl)-1H-indazol-1-yl)pyrimidin-2-ylamino)-2-(N-(2-(dimethylamino)ethyl)-N-methylamino)-4-methoxyphenyl) acrylamide (50 mg, 8%).

$^1$HNMR (300 MHz, DMSO-d$_6$): δ 10.12 (br, 1H), 8.52-8.50 (m, 3H), 8.26 (d, J=5.4 Hz, 1H), 7.93 (d, J=7.8 Hz, 1H), 7.31-7.26 (m, 1H), 7.20-7.16 (m, 1H), 7.09-7.04 (m, 2H), 6.46-6.37 (m, 1H), 6.19-6.13 (m, 1H), 5.72 (d, J=9.9 Hz, 1H), 3.76 (s, 3H), 3.35-3.33 (m, 4H), 2.93-2.91 (m, 2H), 2.75 (s, 3H), 2.40-2.38 (m, 2H), 2.24 (s, 6H), 1.98-1.96 (m, 4H).
LCMS: (M+H)$^+$: 555.9. HPLC: 92.8%.

Example 60. N-(5-(4-(3-(N-Ethyl-N-methylamino)-1H-indazol-1-yl)pyrimidin-2-ylamino)-2-(N-(2-(dimethylamino)ethyl)-N-methylamino)-4-methoxyphenyl) acrylamide

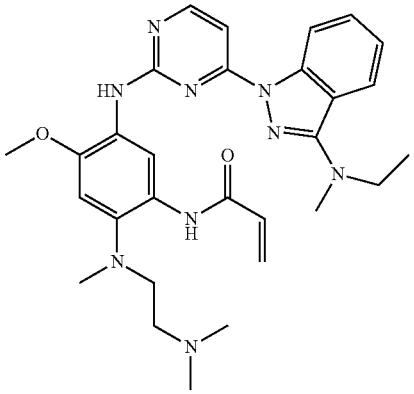 [SMILES: C=CC(=O)Nc1cc(Nc2nccc(-n3nc(N(C)CC)c4ccccc43)n2)c(OC)cc1N(C)CCN(C)C]

To a solution of 1-(2-chloropyrimidin-4-yl)-3-(N-ethyl-N-methylamino)-1H-indazole (500 mg, 1.74 mmol, 1 eq) and 5-(N-acrylamido)-4-(N, 1-(2-(N,N-dimethylamino)ethyl)-N, 1-methyl)amino)-2-methoxyaniline (559 mg, 1.92 mmol, 1.1 eq) in 2-pentanol (10 mL) was added PTSA (364 mg, 1.92 mmol, 1.1 eq). The reaction was stirred at 110° C. for 2 hours. After completion, the mixture was cooled to rt and diluted with sat. NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (20 mL×2) and brine (20 mL), dried, concentrated and purified by prep-HPLC affording desired product N-(5-(4-(3-(N-ethyl-N-methylamino)-1H-indazol-1-yl)pyrimidin-2-ylamino)-2-(N-(2-(dimethylamino)ethyl)-N-methylamino)-4-methoxyphenyl) acrylamide (66 mg, 7%).

$^1$HNMR (300 MHz, DMSO-d$_6$): δ 10.11 (br, 1H), 8.58 (s, 1H), 8.52-8.47 (m, 2H), 8.28 (d, J=5.7 Hz, 1H), 7.89 (d, J=8.7 Hz, 1H), 7.29-7.27 (m, 1H), 7.22-7.19 (m, 1H), 7.06-7.04 (m, 2H), 6.48-6.45 (m, 1H), 6.19-6.14 (m, 1H), 5.73-5.70 (m, 1H), 3.76 (s, 3H), 3.63-3.59 (m, 2H), 3.13 (s, 3H), 2.96-2.94 (m, 2H), 2.74 (s, 3H), 2.50-2.49 (m, 2H), 2.28 (s, 6H), 1.22-1.15 (m, 3H).

LCMS: (M+H)$^+$: 543.9. HPLC: 98.5%.

Example 61. N-(5-(4-(3-(1H-1,2,3-Triazol-4-yl)-1H-indol-1-yl)pyrimidin-2-ylamino)-2-(N-(2-(dimethylamino)ethyl)-N-methylamino)-4-methoxyphenyl) acrylamide

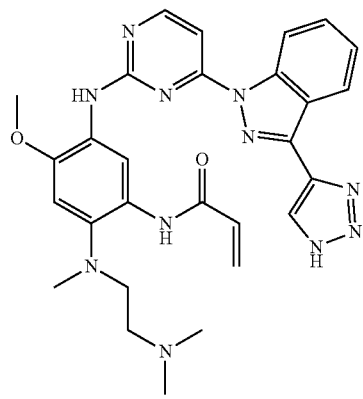 [SMILES: C=CC(=O)Nc1cc(Nc2nccc(-n3nc(-c4c[nH]nn4)c4ccccc43)n2)c(OC)cc1N(C)CCN(C)C]

To a solution of compound 2-chloro-4-(3-(1,2,3-triazol-4-yl)indol-1-yl)pyrimidine (888 mg, 3 mmol, 1.0 eq) in 2-pentanol (10 mL) were added 5-(N-acrylamido)-4-(N,1-(2-(N,N-dimethylamino)ethyl)-N, 1-methyl)amino)-2-methoxyaniline (1.31 g, 4.5 mmol, 1.5 eq) and TsOH—H$_2$O (855 mg, 4.5 mmol, 1.5 eq). The mixture was heated to 100° C. for 1 h. After completion, 50 mL of water was added, then extracted with EA (100 mL), dried over sodium sulfate, concentrated and purified by Prep-HPLC affording the desired product N-(5-(4-(3-(1H-1,2,3-triazol-4-yl)-1H-indol-1-yl)pyrimidin-2-ylamino)-2-(N-(2-(dimethylamino)ethyl)-N-methylamino)-4-methoxyphenyl) acrylamide (4.3 mg, 0.26%).

$^1$HNMR (300 MHz, DMSO-d$_6$): δ 10.17 (br, 1H), 8.88-8.75 (m, 2H), 8.67-8.54 (m, 3H), 8.34-8.32 (m, 1H), 8.19-8.17 (m, 1H), 7.45-7.07 (m, 4H), 6.70 (br, 1H), 6.40-6.37 (m, 1H), 5.73-5.71 (m, 1H), 3.78 (s, 3H), 2.91-2.89 (m, 2H), 2.75 (s, 3H), 2.50-2.48 (m, 2H), 2.21 (s, 6H).

LCMS: (M+H)$^+$: 552.8. HPLC: 84%.

Example 62. N-(5-(3-(N-Methylsulfonamido)$_1$H-indol-4-yl)pyrimidin-2-ylamino)-2-(N-(2-(dimethylamino)ethyl)-N-methylamino)-4-methoxyphenyl) acrylamide

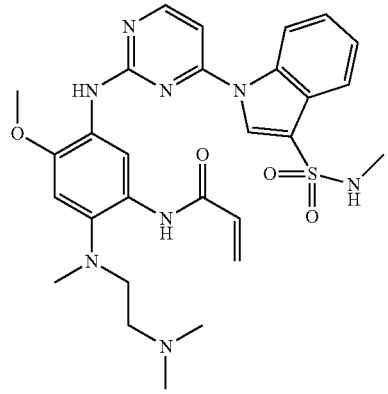 [SMILES: C=CC(=O)Nc1cc(Nc2nccc(-n3cc(S(=O)(=O)NC)c4ccccc43)n2)c(OC)cc1N(C)CCN(C)C]

To a solution of 2-Chloro-4-(3-(N-(methylsulfonyl)amido)indol-1-yl)pyrimidine (200 mg, 0.62 mmol, 1 eq) and 5-(N-acrylamido)-4-(N,1-(2-(N,N-dimethylamino)ethyl)-N, 1-methyl)amino)-2-methoxyaniline (130 mg, 0.68 mmol, 1.1 eq) in 2-pentanol (2 mL) was added PTSA (180 mg, 1.24 mmol, 1 eq). The reaction was stirred at 110° C. for 1-2 hours. After cooling down to rt, the mixture was adjusted to pH=9-10 with ammonia water, extracted with DCM, the organic layer was dried, concentrated and purified by prep-HPLC affording the desired product N-(5-(3-(N-methylsulfonamido)$_1$H-indol-4-yl)pyrimidin-2-ylamino)-2-(N-(2-(dimethylamino)ethyl)-N-methylamino)-4-methoxyphenyl) acrylamide (12 mg, 3%).

$^1$HNMR (300 MHz, DMSO-d$_6$) δ: 10.10 (s, 1H), 8.88 (s, 1H), 8.57 (s, 1H), 8.47-8.45 (m, 3H), 7.87 (d, J=7.5 Hz, 1H), 7.49 (br, 1H), 7.33-7.19 (m, 3H), 7.06 (s, 1H), 6.44-6.35 (m, 1H), 6.21-6.16 (m, 1H), 5.73 (d, J=11.4 Hz, 1H), 3.77 (s, 3H), 2.90-2.88 (m, 2H), 2.75 (s, 3H), 2.45 (s, 3H), 2.33-2.31 (m, 2H), 2.21 (s, 6H).

LCMS: (M+H)$^+$: 578.8. HPLC: 98.6%.

535

Example 63. N-(5-(4-(5-Acetyl-6-(methylamino)pyridin-3-yl)-5-chloropyrimidin-2-ylamino)-2-((2-(dimethylamino)ethyl)amino)-4-methoxyphenyl) acrylamide

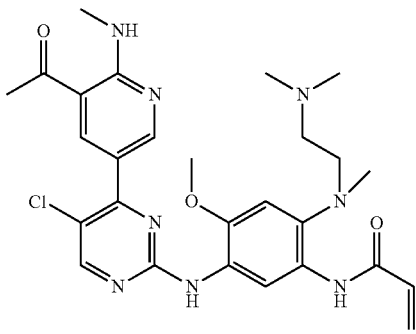 [SMILES: C=CC(=O)Nc1cc(Nc2ncc(Cl)c(-c3cnc(NC)c(C(C)=O)c3)n2)c(OC)cc1N(C)CCN(C)C]

To a solution of compound 274 (260 mg, 0.87 mmol, 1.0 eq) in dioxane (10 mL) were added 5-(N-acrylamido)-4-(N,1-(2-(N,N-dimethylamino)ethyl)-N,1-methyl)amino)-2-methoxyaniline (255 mg, 0.87 mmol, 1 eq), Cs$_2$CO$_3$ (572 mg, 1.74 mmol, 2.0 eq), Pd$_2$(dba)$_3$ (81 mg, 0.087 mmol, 0.1 eq) and Xantphos (102 mg, 0.174 mmol 0.0.2 eq). The mixture was bubbled with nitrogen for 10 minutes, then purged with nitrogen 3 times and stirred at 100° C. for 3 hours. After cooling down to it, the mixture was diluted with EA (10 mL), filtered through celite, washed with EA (3×10 mL). The filtrate was concentrated and purified by prep-HPLC affording desired product N-(5-(4-(5-acetyl-6-(methylamino)pyridin-3-yl)-5-chloropyrimidin-2-ylamino)-2-((2-(dimethylamino)ethyl)(methyl)amino)-4-methoxyphenyl) acrylamide (25 mg, 5%).

$^1$HNMR (300 MHz, DMSO-d$_6$) δ: 10.12 (s, 1H), 9.05 (d, J=4.8 Hz, 1H), 8.92-8.85 (m, 2H), 8.67 (s, 1H), 8.50-8.48 (m, 2H), 7.01 (s, 1H), 6.34-6.30 (m, 1H), 6.17-6.12 (m, 1H), 5.73-5.70 (m, 1H), 3.82 (s, 3H), 3.03 (s, 3H), 2.84-2.82 (m, 2H), 2.69 (s, 3H), 2.55 (s, 3H), 2.30-2.28 (m, 2H), 2.18 (s, 6H).

LCMS: (M+H)$^+$: 552.8. HPLC: 96.6%.

Example 64. 4-(2-(5-Acrylamido-4-((2-(dimethylamino)ethyl)(methyl)amino)-2-methoxyphenylamino)pyrimidin-4-yl)-1H-indole-7-carboxamide

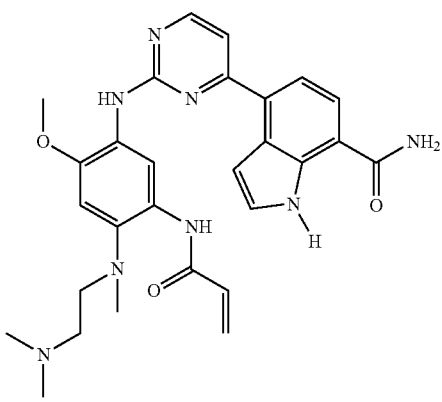 [SMILES: C=CC(=O)Nc1cc(Nc2nccc(-c3ccc(C(N)=O)c4[nH]ccc34)n2)c(OC)cc1N(C)CCN(C)C]

536

To a solution of methyl 4-(2-chloropyrimidin-4-yl)-1H-indole-7-carboxylate (1.1 g, 3.8 mmol, 1.0 eq) and 5-(N-acrylamido)-4-(N,1-(2-(N, N-dimethylamino)ethyl)-N,1-methyl)amino)-2-methoxyaniline (1.1 g, 3.8 mmol, 1.0 eq) in 2-pentanol (15 mL) was added p-toluenesulfonic acid monohydrate (0.81 g, 4.2 mmol, 1.1 eq). The mixture was heated to 100-110° C. for 1-2 h. The mixture was cooled to rt and then adjusted to pH=9-10 with aq. Na$_2$CO$_3$. Then the mixture was extracted with DCM:MeOH (20 mL×5), washed with brine (30 mL×3), dried over sodium sulfate, concentrated and purified by silica column affording the desired diarylamine (210 mg, 10%).

LCMS: (M+H)$^+$: 543.8.

To a solution of the above diarylamine (210 mg, 0.39 mmol, 1.0 eq) in THF (5 mL) was added NH$_4$Cl (63 mg, 1.2 mmol, 3.0 eq), followed by LiHMDS (1.0 M in THF, 4 mL, 4 mmol, 10 eq) dropwise at 0° C., and then the mixture was stirred at rt overnight. After completion, the mixture was diluted with water (10 mL) and stirred for 20 mins, the aqueous layer was then extracted with DCM:MeOH (10 mL×3), the organic layer was dried over sodium sulfate, concentrated and purified by prep-HPLC affording desired product 4-(2-(5-acrylamido-4-((2-(dimethylamino)ethyl)(methyl)amino)-2-methoxyphenylamino)pyrimidin-4-yl)-1H-indole-7-carboxamide (6 mg, 3° %) as white solid.

$^1$HNMR (300 MHz, DMSO-d$_6$): δ 11.30 (br, 1H), 10.11 (br, 1H), 8.80 (s, 1H), 8.50 (d, J=5.1 Hz, 1H), 8.28-8.18 (2H), 7.78 (s, 2H), 7.58-7.39 (m, 2H), 7.03-7.01 (m, 2H), 6.41-6.23 (m, 2H), 5.75-5.73 (m, 1H), 3.82 (s, 3H), 2.87-2.85 (m, 2H), 2.72 (s, 3H), 2.30-2.28 (m, 2H), 2.20 (s, 6H).

LCMS: (M+H)$^+$: 528.8. HPLC: 94.8%.

Example 65. N-(5-(4-(3-(Tetrahydrofuran-3-ylamino)-1H-indazol-1-yl)pyrimidin-2-ylamino)-2-(N-(2-(dimethylamino)ethyl)-N-methylamino)-4-methoxyphenyl) acrylamide

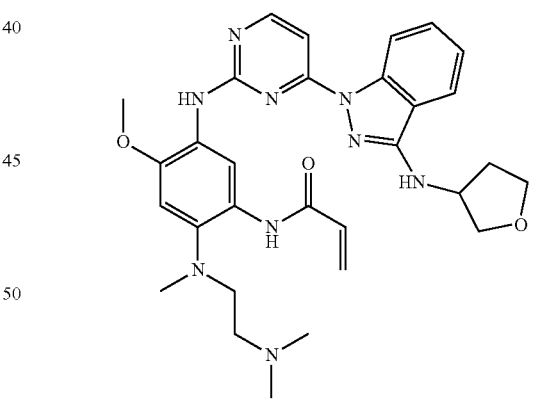

To a 100 mL four-neck flask were added 1-(2-chloropyrimidin-4-yl)-3-(N-oxolan-3-ylamino)-1H-indazole (200 mg, 0.63 mmol, 1.0 eq), 5-(N-acrylamido)-4-(N,1-(2-(N,N-dimethylamino)ethyl)-N,1-methyl)amino)-2-methoxyaniline (204 mg, 0.7 mmol, 1.1 eq), 2-pentanol (4 mL) and p-TsOH.H$_2$O (133 mg, 0.7 mmol, 1.1 eq). The mixture was stirred at 120° C. for 2 h. After completion, the mixture was cooled to rt and diluted with sat. NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (20 mL×2) and brine (20 mL), dried, concentrated and purified by prep-HPLC affording desired product N-(5-(4-(3-(tetrahydrofuran-3-ylamino)-1H-indazol-1-yl)pyrimidin-2-ylamino)-2-(N-(2-(dimethylamino)ethyl)-N-methyl-amino)-4-methoxyphenyl) acrylamide (18 mg, 5%).

$^1$HNMR (300 MHz, DMSO-d$_6$): δ 10.09 (br, 1H), 8.50-8.48 (m, 2H), 8.39-8.36 (m, 1H), 8.27-8.25 (m, 1H), 7.90-7.87 (m, 1H), 7.32-7.26 (m, 1H), 7.21-7.18 (m, 1H), 7.09-7.06 (m, 3H), 6.41-6.37 (m, 1H), 6.19-6.14 (m, 1H), 5.72-5.69 (m, 1H), 4.35-4.33 (m, 1H), 3.97-3.95 (m, 1H), 3.90-3.88 (m, 1H), 3.76-3.74 (m, 5H), 2.94-2.92 (m, 2H), 2.75 (s, 3H), 2.58-2.50 (m, 3H), 2.26-2.15 (m, 6H).

LCMS: (M+H)$^+$: 571.8. HPLC: 90.5%.

Example 66. N-(5-(4-(3-(Cyclopropylmethylamino)-1H-indazol-1-yl)pyrimidin-2-ylamino)-2-((2-(dimethylamino)ethyl)(methyl)amino)-4-methoxyphenyl) acrylamide

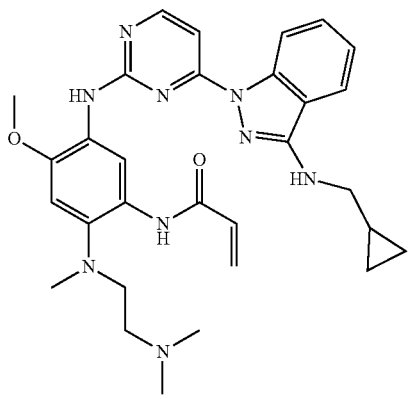 [SMILES: C=CC(=O)Nc1cc(Nc2nccc(-n3nc(NCC4CC4)c4ccccc43)n2)c(OC)cc1N(C)CCN(C)C]

To a 100 mL four-neck flask were added 1-(2-chloropyrimidin-4-yl)-3-(N-cyclopropylmethylamino)-1H-indazole (300 mg, 1 mmol, 1 eq), 5-(N-acrylamido)-4-(N,1-(2-(N,N-dimethylamino)ethyl)-N,1-methyl)amino)-2-methoxyaniline (323 mg, 1.1 mmol, 1.1 eq), 2-pentanol (6 mL) and p-TsOH.H$_2$O (209 mg, 1.1 mmol, 1.1 eq). The mixture was stirred at 120° C. for 2 h. After completion, the mixture was cooled to rt and diluted with sat. NaHCO$_3$ (10 mL) and DCM/MeOH (10/1, 30 mL), the organic layer was separated and the aqueous layer was extracted with DCM (5 mL×2). The combined organic layers were washed with NaHCO$_3$ (20 mL×2) and brine (20 mL), dried, concentrated and purified by prep-HPLC affording desired product N-(5-(4-(3-(cyclopropylmethylamino)-1H-indazol-1-yl)pyrimidin-2-ylamino)-2-((2-(dimethylamino)ethyl)(methyl)amino)-4-methoxyphenyl) acrylamide (27 mg, 4.8%).

$^1$HNMR (300 MHz, DMSO-d$_6$): δ 10.09 (s, 1H), 8.54 (s, 1H), 8.40-8.36 (m, 2H), 8.25-8.23 (m, 1H), 7.90-7.88 (m, 1H), 7.30-7.26 (m, 2H), 7.04-6.98 (m, 3H), 6.44-6.39 (m, 1H), 6.18-6.13 (m, 1H), 5.73-5.69 (m, 1H), 3.77 (s, 3H), 3.26-3.22 (m, 2H), 2.92-2.90 (m, 2H), 2.75 (s, 3H), 2.35-2.33 (m, 2H), 2.22 (s, 6H), 1.23-1.21 (m, 1H), 0.51-0.49 (m, 2H), 0.32-0.30 (m, 2H).

LCMS: (M+H)$^+$: 555.8. HPLC: 97.1%.

Example 67. N-(5-(4-(7-Cyano-3-methyl-1H-indol-5-yl)pyrimidin-2-ylamino)-2-((2-(dimethylamino)ethyl)(methyl)amino)-4-methoxyphenyl) acrylamide

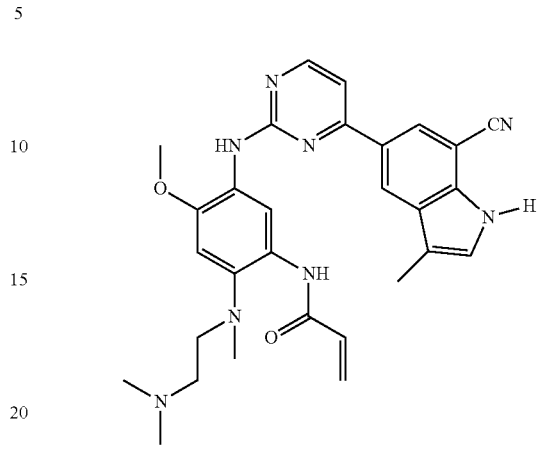

To a solution of compound 7-cyano-5-(2-chloropyrimidin-4-yl)-3-methyl-1H-indole (130 mg, 0.48 mmol, 1.0 eq) and 5-(N-acrylamido)-4-(N,1-(2-(N,N-dimethylamino)ethyl)-N,1-methyl)amino)-2-methoxyaniline (141 mg, 0.48 mmol, 1.0 eq) in 2-pentanol (6.6 mL) was added p-toluenesulfonic acid monohydrate (101.6 mg, 0.528 mmol, 1.1 eq). The mixture was heated to 80° C. for 5 h. After cooling down to it, the mixture was poured into water (50 mL), extracted with DCM (50 mL×3), the combined organic layers were washed with brine (50 mL), dried over sodium sulfate, concentrated and purified by silica column affording desired product N-(5-(4-(7-cyano-3-methyl-1H-indol-5-yl)pyrimidin-2-ylamino)-2-((2-(dimethylamino)ethyl)(methyl)amino)-4-methoxyphenyl) acrylamide (148 mg, 58%).

$^1$HNMR (300 MHz, DMSO-d$_6$): δ 11.90 (br, 1H), 10.19 (br, 1H), 9.14 (s, 1H), 8.73 (s, 1H), 8.52-8.49 (m, 2H), 8.15 (s, 1H), 7.67 (s, 1H), 7.33 (s, 1H), 7.04 (s, 1H), 6.36-6.29 (m, 2H), 5.75-5.72 (m, 1H), 3.86 (s, 3H), 2.86-2.84 (m, 2H), 2.71 (s, 3H), 2.31-2.29 (m, 5H), 2.21 (s, 6H).

LCMS (M+H)$^+$: 524.8. HPLC: 95.1%.

Example 68. 5-(2-(5-Acrylamido-4-((2-(dimethylamino)ethyl)(methyl)amino)-2-methoxyphenylamino)pyrimidin-4-yl)-3-methyl-1H-indole-7-carboxamide

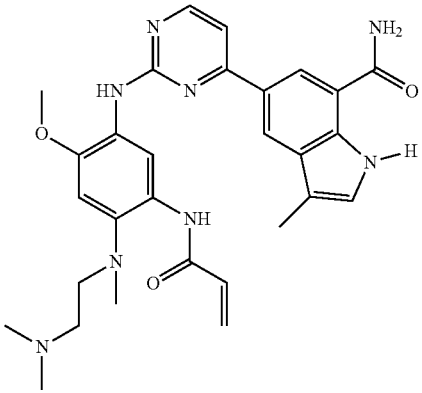 [SMILES: C=CC(=O)Nc1cc(Nc2nccc(-c3cc(C(N)=O)c4[nH]cc(C)c4c3)n2)c(OC)cc1N(C)CCN(C)C]

H₂O₂ (0.51 mL) was added to a solution of N-(5-(4-(7-cyano-3-methyl-1H-indol-5-yl)pyrimidin-2-ylamino)-2-((2-(dimethylamino)ethyl)(methyl)amino)-4-methoxyphenyl) acrylamide (148 mg, 0.28 mmol, 1.0 eq) in EtOH (2 mL) and DMSO (0.5 mL) dropwise, followed by 1N NaOH solution (0.5 mL). The mixture was stirred at rt for 30 minutes. TLC and LCMS indicated completion, the mixture was extracted with DCM/MeOH (10:1, v/v), the combined extracts were dried, concentrated and purified by silica column affording desired product 5-(2-(5-acrylamido-4-((2-(dimethylamino) ethyl)(methyl)amino)-2-methoxyphenylamino)pyrimidin-4-yl)-3-methyl-1H-indole-7-carboxamide (7 mg, 4.6%).

¹HNMR (300 MHz, DMSO-d₆): δ 11.69 (br, 1H), 10.98 (br, 1H), 9.14 (s, 1H), 8.63 (s, 1H), 8.49-8.41 (m, 2H), 8.29 (s, 1H), 8.05 (s, 1H), 7.81-7.70 (m, 1H), 7.57-7.47 (m, 1H), 7.39-7.34 (m, 1H), 7.16 (s, 1H), 7.04 (s, 1H), 6.42-6.33 (m, 1H), 6.21-6.15 (m, 1H), 3.99 (s, 3H), 2.93-2.90 (m, 2H), 2.71 (s, 3H), 2.31-2.29 (m, 5H), 2.21 (s, 6H).

LCMS: (M+H)⁺: 542.8. HPLC: 92.5%.

Example 69. N-(5-(4-(3-(cyclopropylamino)-1H-indazol-1-yl)pyrimidin-2-ylamino)-2-((2-(dimethylamino)ethyl)(methyl)amino)-4-methoxyphenyl) acrylamide

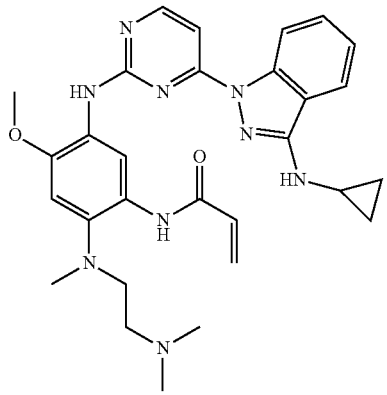 [SMILES: C=CC(=O)Nc1cc(Nc2nccc(-n3nc(NC4CC4)c4ccccc43)n2)c(OC)cc1N(C)CCN(C)C]

To a 100 mL four-neck flask were added 1,N-(2-chloropyrimidin-4-yl)-3-(cyclopropylamino)indazole (500 mg, 1.75 mmol, 1 eq), 5-(N-acrylamido)-4-(N,1-(2-(N,N-dimethylamino)ethyl)-N, 1-methyl)amino)-2-methoxyaniline (511 mg, 1.75 mmol, 1 eq) and 2-pentanol (6 mL) and p-TsOH.H₂O (361 mg, 1.9 mmol, 1.1 eq). The mixture was stirred at 120° C. for 2 h. After completion, the mixture was cooled to RT and diluted with water (10 mL) and DCM/MeOH (10/1, 20 mL), the organic layer was separated and the aqueous layer was extracted with DCM (10 mL×2). The combined organic layers were washed with NaHCO₃ (20 mL×2) and brine (20 mL), dried, concentrated and purified by prep-HPLC affording desired product N-(5-(4-(3-(cyclopropylamino)-1H-indazol-1-yl)pyrimidin-2-ylamino)-2-((2-(dimethylamino)ethyl)(methyl)amino)-4-methoxyphenyl) acrylamide (39 mg, 4.4%).

¹HNMR (300 MHz, DMSO-d₆) δ:10.13 (br, 1H), 8.56 (s, 1H), 8.47 (s, 1H), 8.42-8.39 (m, 1H), 8.29 (d, J=5.4 Hz, 1H), 7.83 (d, J=7.8 Hz, 1H), 7.32-7.27 (m, 1H), 7.19-7.16 (m, 2H), 7.09-7.06 (m, 2H), 6.46-6.37 (m, 1H), 6.20-6.15 (m, 1H), 5.75-5.71 (m, 1H), 3.78 (s, 3H), 2.94-2.92 (m, 2H), 2.77-2.75 (m, 4H), 2.36-2.34 (m, 2H), 2.23 (s, 6H), 0.79-0.77 (m, 2H), 0.59-0.57 (m, 2H).

LCMS: (M−H)⁻: 539.7. HPLC: 97.5%.

Example 70. N-(5-((4-(3-(dimethylamino)-1H-indazol-1-yl)pyrimidin-2-yl)amino)-2-((2-(dimethylamino)ethyl)(methyl)amino)-6-isopropoxypyridin-3-yl) acrylamide

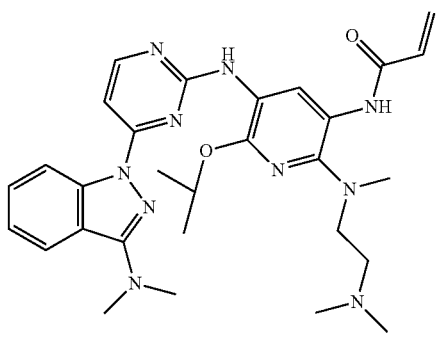 [SMILES: C=CC(=O)Nc1cc(Nc2nccc(-n3nc(N(C)C)c4ccccc43)n2)c(OC(C)C)nc1N(C)CCN(C)C]

A four-neck flask were charged with N-(5-amino-2-((2-(dimethylamino)ethyl)(methyl)amino)-6-isopropoxypyridin-3-yl) acrylamide (60 mg, 0.18 mmol, 1 eq), 1-(2-chloropyrimidin-4-yl)-3-(N,N-dimethylamino)-1H-indazole (51 mg, 0.18 mmol, 1 eq) and 2-pentanol (3 mL) and TsOH.H₂O (34 mg, 0.2 mmol, 1.1 eq). The mixture was refluxed for 2 h. After completion, the mixture was cooled to RT and diluted with MeOH:DCM=1:10 (20 mL) and sat. NaHCO₃ (5 mL). The organic layer was separated, washed with brine, concentrated and purified by prep-HPLC affording. N-(5-((4-(3-(dimethylamino)-1H-indazol-1-yl)pyrimidin-2-yl)amino)-2-((2-(dimethylamino)ethyl)(methyl) amino)-6-isopropoxypyridin-3-yl) acrylamide (12 mg, 11%).

¹HNMR (300 MHz, DMSO-d₆): δ 9.95 (br, 1H), 8.51-8.42 (m, 2H), 8.29 (s, 1H), 8.19 (s, 1H), 7.98-7.94 (m, 1H), 7.36-7.28 (m, 1H), 7.28-7.20 (m, 1H), 7.08-7.04 (m, 1H), 6.64-6.56 (m, 1H), 6.23-6.17 (m, 1H), 5.74-5.70 (m, 1H), 5.20-5.18 (m, 1H), 3.16 (s, 6H), 2.83-2.81 (m, 5H), 2.40-2.36 (m, 8H), 1.21 (d, J=5.4 Hz, 6H).

LCMS: (M+H)⁺: 558.8. HPLC: 95.1%.

Example 71. N-(5-((4-(3-(Dimethylamino)-1H-indazol-1-yl)pyrimidin-2-yl)amino)-2-((2-(dimethylamino)ethyl)(methyl)amino)-6-(2,2-difluoroethoxypyridin-3-yl) acrylamide

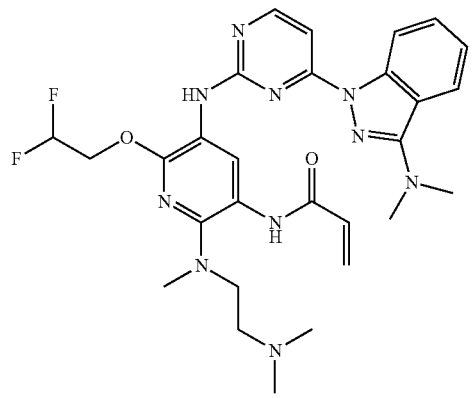 [SMILES: C=CC(=O)Nc1cc(Nc2nccc(-n3nc(N(C)C)c4ccccc43)n2)c(OCC(F)F)nc1N(C)CCN(C)C]

A 100 mL four-neck flask was charged with N-(5-amino-6-(2,2-difluoroethoxy)-2-((2-(dimethylamino)ethyl(methyl)amino)pyridin-3-yl)acrylamide (35 mg, 0.1 mmol, 1 eq), 1-(2-chloropyrimidin-4-yl)-3-(N,N-dimethylamino)-1H-indazole (27.8 mg, 0.1 mmol, 1 eq) and 2-pentanol (3 mL) and TsOH.H$_2$O (21 mg, 0.11 mmol, 1.1 eq). The mixture was refluxed for 2 h. After completion, the mixture was cooled to RT and diluted with MeOH:DCM=1:10 (20 mL) and sat. NaHCO$_3$ (5 mL). The organic layer was separated, washed with brine, concentrated and purified by prep-HPLC affording N-(5-((4-(3-(dimethylamino)-1H-indazol-1-yl)pyrimidin-2-yl)amino)-2-((2-(dimethylamino)ethyl)(methyl)amino)-6-methoxypyridin-3-yl) acrylamide (10 mg, 17%).

$^1$HNMR (300 MHz, DMSO-d$_6$): δ 9.99 (br, 1H), 8.69 (s, 1H), 8.47 (br, 1H), 8.29-8.22 (m, 2H), 7.98 (d, J=7.8 Hz, 1H), 7.38-7.36 (m, 1H), 7.24-7.19 (m, 1H), 7.09 (d, J=5.1 Hz, 1H), 6.58-6.49 (m, 1H), 6.31-6.18 (m, 2H), 5.74 (d, J=9.6 Hz, 1H), 4.58-4.49 (m, 2H), 3.16 (s, 6H), 2.86-2.84 (m, 5H), 2.41-2.38 (m, 8H).

LCMS: (M+H)$^+$: 580.8. HPLC: 91.1%.

Example 72. N-(5-((4-(3-(Dimethylamino)-1H-indazol-1-yl)pyrimidin-2-yl)amino)-2-((2-(dimethylamino)ethyl)(methyl)amino)-6-methoxypyridin-3-yl) acrylamide

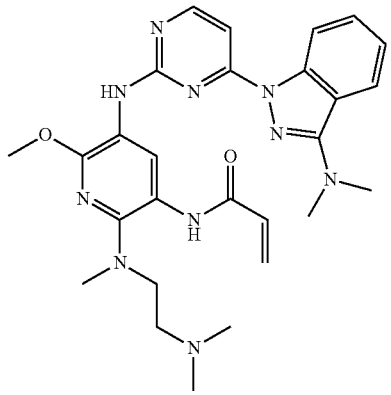 [SMILES: C=CC(=O)Nc1cc(Nc2nccc(-n3nc(N(C)C)c4ccccc43)n2)c(OC)nc1N(C)CCN(C)C]

A four-neck flask was charged with N-(5-amino-2-((2-(dimethylamino)ethyl)(methyl)amino)-6-methoxypyridin-3-yl)acrylamide (20 mg, 0.068 mmol, 1 eq), 1-(2-chloropyrimidin-4-yl)-3-(N,N-dimethylamino)-1H-indazole (19 mg, 0.068 mmol, 1 eq) and 2-pentanol (3 mL) and TsOH.H$_2$O (15 mg, 0.075 mmol, 1.1 eq). The mixture was refluxed for 2 h. After completion, the mixture was cooled to RT and diluted with MeOH:DCM=1:10 (20 mL) and sat. NaHCO$_3$ (5 mL). The organic layer was separated, washed with brine, concentrated and purified by prep-HPLC affording N-(5-((4-(3-(dimethylamino)-1H-indazol-1-yl)pyrimidin-2-yl)amino)-2-((2-(dimethylamino)ethyl)(methyl)amino)-6-methoxypyridin-3-yl) acrylamide (8 mg, 22%).

$^1$HNMR (300 MHz, DMSO-d$_6$): δ 9.99 (br, 1H), 8.66 (s, 1H), 8.56 (br, 1H), 8.29-8.27 (m, 1H), 8.17-8.15 (m, 1H), 7.99-7.97 (m, 1H), 7.42-7.40 (m 1H), 7.24-7.20 (m, 1H), 7.09-6.92 (m, 1H), 6.65-6.63 (m, 1H), 6.26-6.20 (m, 1H), 5.76-5.73 (m, 1H), 3.86 (s, 3H), 3.62-3.59 (m, 2H), 3.16 (s, 6H), 2.83 (s, 3H), 2.53-2.50 (m, 2H), 2.50 (s, 6H).

LCMS: (M+H)$^+$: 530.9. HPLC: 91.4%.

Example 73. N-(5-(4-(3-Acetyl-1H-indol-1-yl)-5-chloropyrimidin-2-ylamino)-2-((2-(dimethylamino)ethyl)(methyl)amino)-4-methoxyphenyl) acrylamide

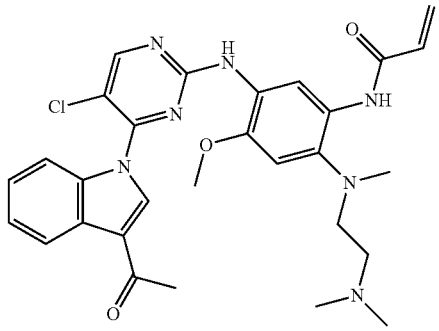 [SMILES: C=CC(=O)Nc1cc(Nc2ncc(Cl)c(-n3cc(C(C)=O)c4ccccc43)n2)c(OC)cc1N(C)CCN(C)C]

To a solution of 2,5-dichloro-4-(3-acetylindol-1-yl)pyrimidine (500 mg, 1.63 mmol), 5-(N-acrylamido)-4-(N,1-(2-(N,N-dimethylamino)ethyl)-N,1-methyl)amino)-2-methoxyaniline (525 mg, 1.96 mmol) in dioxane (20 mL) was added Pd(OAc)$_2$ (73.2 mg, 326 umol). Xantphos (377 mg, 652 umol), Cs$_2$CO$_3$ (797 mg, 2.45 mmol). Then the reaction solution was stirred at 100° C. for 4 hours under N$_2$. LCMS and HPLC showed compound 2 was consumed and ~40% of desired product was detected. The mixture was filtered through a celite pad and the filtrate was concentrated to give the crude product. The residue was purified by prep-HPLC (TFA condition) to give N-(5-(4-(3-acetyl-1H-indol-1-yl)-5-chloropyrimidin-2-ylamino)-2-((2-(dimethylamino)ethyl)(methyl)amino)-4-methoxyphenyl) acrylamide (250 mg, 29% yield) as a black brown solid.

$^1$H NMR 400 MHz CDCl$_3$ δ=9.04 (s, 1H), 8.65 (s, 1H), 8.52-8.42 (m, 1H), 8.33 (s, 1H), 7.86 (s, 1H), 7.76-7.66 (m, 1H), 7.44-7.36 (m, 2H), 6.83 (s, 1H), 4.04 (s, 3H), 3.53-3.50 (m, 2H), 3.35-3.25 (m, 2H), 2.87 (s, 3H), 2.85 (s, 6H), 2.65 (s, 3H).

ESI-MS (m/z): 538.1 (M+H)$^+$

Example 74. N-(5-((4-(3-(1H-Pyrazol-3-yl)-1H-indol-1-yl)pyrimidin-2-yl)amino)-2-((2-(dimethylamino)ethyl)(methyl)amino)-4-methoxyphenyl) acrylamide

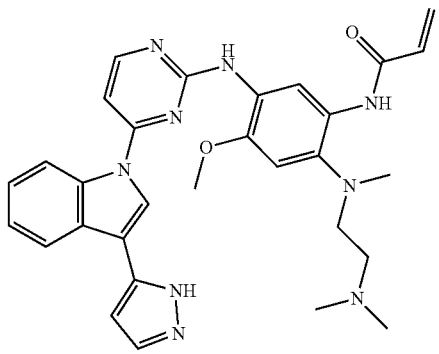 [SMILES: C=CC(=O)Nc1cc(Nc2nccc(-n3cc(-c4ccn[nH]4)c4ccccc43)n2)c(OC)cc1N(C)CCN(C)C]

To a solution of tert-butyl 5-(I-(2-chloropyrimidin-4-yl)-1H-indol-3-yl)-1H-pyrazole-1-carboxylate (79 mg, 0.2 mmol, 1 eq) and 5-(N-acrylamido)-4-(N,1-(2-(N,N-dimethylamino)ethyl)-N,1-methyl)amino)-2-methoxyaniline (70 mg, 0.24 mmol, 1.2 eq) in 2-pentanol (3 mL) was added TsOH—H₂O (41 mg, 0.24 mmol, 1.1 eq). The reaction was stirred at 120° C. for 2 hours. After cooling down to RT, the mixture was diluted with water (2 mL), extracted with EA, the combined organic layers were dried, concentrated and the residue was purified by prep-HPLC affording N-(5-((4-(3-(1H-pyrazol-3-yl)-1H-indol-1-yl)pyrimidin-2-yl)amino)-2-((2-(dimethylamino)ethyl)(methyl)amino)-4-methoxyphenyl) acrylamide (5 mg).

LCMS: (M+H)⁺: 551.8.

Example 75. N-(5-((4-(3-(1H-Pyrazol-4-yl)-1H-indol-1-yl)pyrimidin-2-yl)amino)-2-((2-(dimethylamino)ethyl)(methyl)amino)-4-methoxyphenyl) acrylamide

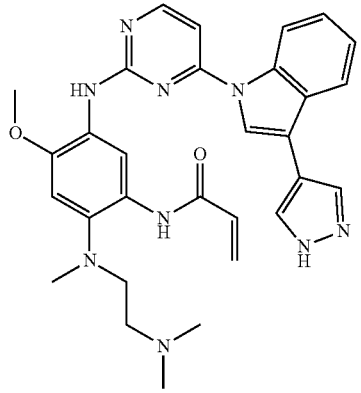 [SMILES: C=CC(=O)Nc1cc(Nc2nccc(-n3cc(-c4cn[nH]c4)c4ccccc43)n2)c(OC)cc1N(C)CCN(C)C]

To a solution of 1-(2-chloropyrimidin-4-yl)-3-(1H-pyrazol-4-yl)-1H-indole (200 mg, 0.68 mmol, 1 eq) and 5-(N-acrylamido)-4-(N,1-(2-(NN-dimethylamino)ethyl)-N,1-methyl)amino)-2-methoxyaniline (237 mg, 0.82 mmol, 1.2 eq) in 2-pentanol (3 mL) was added TsOH—H₂O (148 mg, 0.75 mmol, 1.1 eq). The reaction was stirred at 120° C. for 2 hours. After cooling down to RT, the mixture was diluted with water (2 mL), extracted with EA, the combined organic layers were dried, concentrated and the residue was purified by prep-HPLC affording N-(5-((4-(3-(1H-pyrazol-4-yl)-1H-indol-1-yl)pyrimidin-2-yl)amino)-2-((2-(dimethylamino)ethyl)methyl)amino)-4-methoxyphenyl) acrylamide (30 mg).

LCMS: (M+H)⁺: 551.8. HPLC: 39.2%

Example 76. N-(5-((4-(3-(1H-Pyrazol-5-yl)-1H-pyrrolo[3,2-b]pyridin-1-yl)pyrimidin-2-yl)amino)-2-((2-(dimethylamino)ethyl)(methyl)amino)-4-methoxyphenyl) acrylamide

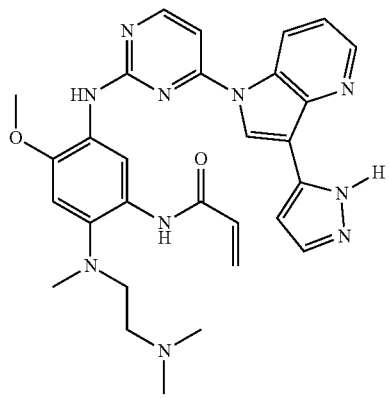 [SMILES: C=CC(=O)Nc1cc(Nc2nccc(-n3cc(-c4ccn[nH]4)c4ncccc43)n2)c(OC)cc1N(C)CCN(C)C]

1,N-(2-chloropyrimid-4-yl)-3-(2,N-(tetrahydropyran-2-yl)pyrazol-3-yl)pyrrolo[3,2-b]pyridine (100 mg, 0.26 mmol, 1.0 eq), and 5-(N-acrylamido)-4-(N,1-(2-(N,N-dimethylamino)ethyl)-N, 1-methyl)amino)-2-methoxyaniline (76 mg, 0.26 mmol, 1.0 eq), and p-TsOH.H₂O (54 mg, 0.28 mmol, 1.1 eq), in 2-pentanol (2 mL) were heated to 100 C with stirring for 3 hr in a 20 mL scaled tube. After completion, the mixture was cooled to RT and diluted with sat-.NaHCO₃ (10 mL) extracted with DCM (50 mL×3). The combined organic layers were washed with NaHCO₃ (20 mL×2) and brine (20 mL), dried, concentrated and purified by prep-HPLC affording N-(5-((4-(3-(1H-pyrazol-5-yl)-1H-pyrrolo[3,2-b]pyridin-1-yl)pyrimidin-2-yl)amino)-2-((2-(dimethylamino)ethyl)(methyl)amino)-4-methoxyphenyl) acrylamide (10 mg).

LCMS: (M−H)⁻: 550.7. HPLC: 24.4%.

Biology

Abbreviations

DMSO dimethylsulfoxide
DTT dithiothreitol
ATP adenosine triphosphate34
EDTA ethylenediaminetetraacetic acid
Ki enzyme inhibition constant
DMEM Dulbecco's Modified Eagle Medium
NCS newborn calf serum
PBS phosphate buffered saline
PMSF phenylmethanesulfonyl fluoride
ELISA enzyme-linked immunosorbent assay
IgG immunoglobulin G
FBS fetal bovine serum
BDNF brain derived neurotrophic factor
Kinase Inhibition Assays Kinase inhibition by the compounds of the invention is measured using commercially available assay kits and services that are well-known to a person having ordinary skill in the art. These kits and services are used to measure the inhibition of a variety of kinases, including without limitation ALK, ABL, AXL, Aur B & C, BLK, erbB-2, erbB-4, EGFR, mutant EGFR, HPK, IRAK1, RON, ROS1, SLK, STK10, TIE2, TRK, c-Met, Lck, Lyn, Src, Fyn, Syk, Zap-70, Itk, Tec, Btk, EGFR, ErbB2, Kdr, Fit-1, Flt-3, Tek, c-Met, InsR, and Atk. Commercial suppliers of these assay kits and services include Promega Corporation and Reaction Biology Corporation, EMD Millipore, and CEREP. In addition to the commercially available assay kits and services, the kinase inhibition activity of the compounds of formulae (I-VIII) is measured by way of the assays described below.

Purification of Epidermal Growth Factor Receptor Tyrosine Kinase Human EGF receptor tyrosine kinase was isolated from A431 human epidermoid carcinoma cells which overexpress EGF receptor by the following methods. Cells were grown in roller bottles in 50% Delbuco's Modified Eagle and 50% HAM F-12 nutrient media (Gibco) containing 10% fetal calf serum. Approximately 10⁹ cells were lysed in two volumes of buffer containing 20 mM 2-(4N-[2-hydroxyethyl]piperazin-1-yl)ethanesulfonic acid (hepes), pH 7.4, 5 mM ethylene glycol bis(2-aminoethyl ether) N,N,N',N'-tetraacetic acid, 1% Triton X-1OO, 10% glycerol. 0.1 mM sodium orthovanadate, 5 mM sodium fluoride, 4 mM pyrophosphate, 4 mM benzamide, 1 mM dithiothreitol, 80 µg/mL aprotinin, 40 µg/mL leupeptin and 1 mM phenylmethylsulfonyl fluoride. After centrifugation at 25,000×g for 10 minutes, the supernatant was equilibrated for 2 h at 400° C., with 10 mL of wheat germ agglutinin sepharose that was previously equilibrated with 50 mM Hepes, 10% glycerol, 0.1% Triton X-100 and 150 mM NaCl, pH 7.5, (equilibration buffer). Contaminating proteins were washed from the resin with 1M NaCl in equilibration buffer, and the enzyme was eluted with 0.5M N-acetyl-1-D-glucosamine in equilibration buffer, followed by 1 mM urea. The enzyme was eluted with 0.1 mg/ml EGF. The receptor appeared to be homogeneous as assessed by Coomassie blue stained polyacrylamide electrophoretic gels.

Using the same technique as described in the previous paragraph, various mutated forms of the epidermal growth factor receptor may be isolated from appropriate cell lines which contain them. For example, the EGFR del746-750 mutant protein may be extracted from PC-9 cells, and the L858R/T790M double mutant EGFR protein may be isolated from H1975 cells.

Determination of $IC_{50}$ Values for Single Mutant EGFR_d746-750

Enzyme assays for $IC_{50}$ determinations were performed in a total volume of 25 µL. Dilute all compounds to 500 µM stock solutions in 100% DMSO and make a serial of 4-fold dilution for 10 doses. "Max" and "Min" control contain 100% DMSO. "Max" stands for DMSO control without enzyme, "Min" stands for low control without compounds. Transfer 10 µl of compounds to 90 µl of 1× kinase base buffer to make intermediate dilution. Transfer 5 µl of intermediate dilution compounds to the 384-well assay plate, then 10 µl 2.5× enzyme buffer containing (12.5 nM EGFR_d746-750, 5 mM DTT, 1× kinase base buffer) were added to assay plate. Incubate at RT for 10 minutes and add 10 µl 2.5× substrate buffer containing (7.5 µM Peptide, 35 µM ATP, 25 mM MgCl$_2$, 1× kinase base buffer) to start reaction. Incubate at RT for 1 hr and 25 µl stop buffer to end up reaction. Collect conversion data from Caliper and conversion data from Caliper program. Fit the data in XLfit to obtain $IC_{50}$ values.

Determination of $IC_{50}$ Values for Double-Mutant EGFR (EGFR_T790M/L858R)

Enzyme assays for $IC_{50}$ determinations were performed in a total volume of 25 µL. Dilute all compounds to 500 µM stock solutions in 100% DMSO and make a serial of 4-fold dilution for 10 does. "Max" and "Min" control contain 100% DMSO. "Max" stands for DMSO control without enzyme, "Min" stands for low control without compounds. Transfer 10 µl of compounds to 90 µl of 1× kinase base buffer to make intermediate dilution. Transfer 5 µl of intermediate dilution compounds to the 384-well assay plate, then 10 µl 2.5× enzyme buffer containing (25 nM EGFR_T790M/L858R, 5 mM DTT, 1× kinase base buffer) were added to assay plate. Incubate at RT for 10 minutes and add 10 µl 2.5× substrate buffer containing (7.5 µM Peptide, 47.5 µM ATP, 25 mM MgCl$_2$, 1× kinase base buffer) to start reaction. Incubate at RT for 1 hr and 25 µl stop buffer to end up reaction. Collect conversion data from Caliper and conversion data from Caliper program. Fit the data in XLfit to obtain $IC_{50}$ values.

Determination of $IC_{50}$ Values for Wt EGFR

Enzyme assays for $IC_{50}$ determinations were performed in a total volume of 25 µL. Dilute all compounds to 500 µM stock solutions in 100% DMSO and make a serial of 4-fold dilution for 10 does. "Max" and "Min" control contain 100% DMSO. "Max" stands for DMSO control without enzyme, "Min" stands for low control without compounds. Transfer 10 µl of compounds to 90 µl of Ix kinase base buffer to make intermediate dilution. Transfer 5 µl of intermediate dilution compounds to the 384-well assay plate, then 10 µl 2.5× enzyme buffer containing (20 nM EGFR, 5 mM DTT, 1× kinase base buffer) were added to assay plate. Incubate at RT for 10 minutes and add 10 µl 2.5× substrate buffer containing (7.5 µM Peptide, 5.75 µM ATP, 25 mM MgCl$_2$, 25 mM MnCl$_2$, 1× kinase base buffer) to start reaction. Incubate at RT for 1 hr and 25 µl stop buffer to end up reaction. Collect conversion data from Caliper and conversion data from Caliper program. Fit the data in XLfit to obtain $IC_{50}$ values.

Other Kinase Inhibition Assays

Assays to determine the inhibition of other kinases by the compounds of formulae (I-VIII) are performed according to procedures known to a person having ordinary skill in the art. These assays include, but are not limited to, assays directed to the inhibition of the following kinases:

Wild-type c-Met Kinase. Inhibition of wild-type c-Met kinase is determined as described in International Publication No. WO 2011/069761, the entire contents of which are incorporated by reference.

LCK and BLK Kinases. Inhibition of LCK and BLK kinases is determined as described in U.S. Pat. No. 7,125,875, the entire contents of which are incorporated by reference.

The compounds described herein are screened in the following manner. Kinases suitable for use in the following protocol to determine kinase activity of the compounds described herein include, but are not limited to: Lck, Lyn, Src, Fyn, Syk, Zap-70, Itk, Tec, Btk, ErbB2, ErbB-4, Kdr, Fit-1, Flt-3, Tek, c-Met, and Atk. Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography essentially as previously described (Lehr et al., 1996; Gish et al., 1995). In some instances, kinases are co-expressed or mixed with purified or partially purified regulatory polypeptides prior to measurement of activity. Kinase activity and inhibition are measured essentially by established protocols (Braunwalder et al., 1996). Briefly, The transfer of $^{32}PO_4$ from ATP to the synthetic substrates poly(Glu-Tyr) 4:1 or poly(Arg-Ser) 3:1 attached to the bioactive surface of microtiter plates serves as the basis to evaluate enzyme activity. After an incubation period, the amount of phosphate transferred is measured by first washing the plate with 0.5% phosphoric acid, adding liquid scintillant, and then counting in a liquid scintillation detector. The $IC_{50}$ is determined by the concentration of compound that causes a 50% reduction in the amount of $^{32}P$ incorporated onto the substrate bound to the plate. Other similar methods whereby phosphate is transferred to peptide or polypeptide substrate containing tyrosine, serine, threonine, or histidine, either alone, in combination, or in combination with other amino acids, in solution or immobilized (i.e., solid phase) are also useful. For example, transfer of phosphate to a peptide or polypeptide can also be detected using scintillation proximity (Wu et al., 2000), ELISA (Cleaveland et al., 1990), Fluorescence Polarization (Seethala and Menzel, 1998), and homogeneous time resolved fluorescence (HTRF, Kolb et al., 1998). Alternatively, kinase activity can be measured using antibody-based methods whereby an antibody or polypeptide is used as a reagent to detect phosphorylated target polypeptide.

REFERENCES

Braunwalder et al. (1996). Anal. Biochem. 234(1):23-26.
Cleaveland et al. (1990). Anal Biochem. 190(2):249-53.
Gish et al. (1995). Protein Eng. 8(6):609-614.
Kolb et al. (1998). Drug Discov. Today. 3:333-342.

Lehr et al. (1996). Gene 169(2):27527-9.
Seethala et al. (1998). Anal Biochem. 255(2):257-62.
Wu et al. (2000). Comb Chem High Throughput Screen. 3(1):27-36.

EGFR Cell Assay Summary Protocols
Cell Proliferation Assays—Method A
H1975 Inhibition Assay (Cell Proliferation)

H1975 cells were cryopreserved in liquid nitrogen. Before thawing the cells, place 15 mL of cell culture medium (RPMI 1640 Medium supplied with 10% fetal bovine serum) into a T75 flask and pre-incubate the flask in humidified 37° C./5% $CO_2$ incubator for 15 minutes to allow medium to equilibrate to the proper pH and temperature. Remove the vial from liquid nitrogen and thaw rapidly by placing at 37° C. in a water bath with gentle agitation for 1-2 minutes and then decontaminated by wiping with 70% ethanol before opening in a Class II biological safety cabinet. Transfer the vial contents drop-wise into 10 mL of cell culture medium in a sterile 15 mL conical tube. Then centrifuged the tube at 200× g for 5 minutes and aspirate the supernatant. Re-suspend the cell pellet with 1 mL of fresh cell culture medium and transfer it in to the T75 flask containing cell culture medium.

To passage H1975 cells, firstly, the adherent cells were rinsed with Trypsin/EDTA. Then add Trypsin/EDTA (3 mL for a T75 flask) into the flask and swirl to ensure the cells coated with trypsin evenly. Then incubate the flasks at 37° C. until the cells detach. Add equal volume of cell culture medium to stop the reaction. Collect the detached cells and centrifuged at 200×g for 5 minutes followed by re-suspended in fresh culture medium. Then, the cells were transferred into a new T75 flask containing cell culture medium. Cells were sub-cultured three times per week at a ratio of 1:2 or 1:4 in culture medium.

Day-1: Harvest cells from flask into cell culture medium as described above and the cell numbers counted using The Nucleo Counter (Chemometec, NC-100). Dilute the cells into 44,000 cells/mL with culture medium and add 90 µL of cell suspension into each well of 96-well cell culture plate as designated. The final concentration was 4,000 cells/well. Add medium only as low control. The plates were covered with lid and placed in 37° C./5% $CO_2$ incubator for 24 hours.

Day-2: Test compounds were dissolved in DMSO at 0.2 mM (200×). 45 µL of compound was transfer into a 96-well compound plate (Corning cat#3797) and serially diluted at 1:3 ratio to create a 9-point dilutions. The same volume of DMSO was adopted as high control. 10 µL of these compounds DMSO dilutes (9 points, from 0.2 mM to 0.030 uM) were dispensed into a new 96-well assay plate (Corning cat#3679) by Pipettor (Apricot Design# PPA-384-M(E)), and add 190 µl complete medium. 10 µL of these diluted compounds Medium dilutes (9 points, from 0.01 mM to 0.0015 µM) were dispensed into cell plate. The plates were covered with a lid and placed in a 37° C./5% $CO_2$ incubator for 72 hours.

Day-5: After 72 hours incubation, remove the plates from incubator and equilibrate at room temperature for 15 minutes. Incubate the CellTiter Glo reagents (Promega, G9243) at 37° C. before the experiment. The buffer was equilibrated to room temperature and used to dissolve the substrate. To determine the cell viability, add 30 µL of CellTiter-Glo reagent into each well to be detected. Then shake the plates at room temperature for 10 min and followed by plate read on Envision (PerkinElmer).

For estimation of $IC_{50}$, the luminescence readout are transformed to % Inhibition by applying the following equation: The $IC_{50}$ was then $$\frac{Lum_{HC} - Lum_{Cpd}}{Lumo_{HC} - Lum_{LC}}.$$

calculated by fitting in XLFit to a four parameters logistic curve.

PC-9 Growth Inhibition Assay (Cell Proliferation)
The inhibition assay for PC-9 cells was processed in the same manner as described for the H1975 cells.
LoVo Growth Inhibition Assay (Cell Proliferation)
The culture medium of LoVo cells was F12K medium supplied with 10% fetal bovine serum. The DMSO dilutions used in LoVo assay was 9 points from 10 nM to 1.52 µM. The rest of the procedure was carried out in the same manner as described for the H1975 cells.
Cell Proliferation Assays—Method B
H1975 Inhibition Assay (Cell Proliferation).

H1975 cells were cryopreserved in liquid nitrogen. Before thawing the cells, place 15 mL of cell culture medium (RPMI 1640 Medium supplied with 10% fetal bovine serum and 1% penicillin/streptomycin) into a T75 flask and pre-incubate the flask in humidified 37° C./5% $CO_2$ incubator for 15 minutes to allow medium to equilibrate to the proper pH and temperature. Remove the vial from liquid nitrogen and thaw rapidly by placing at 37° C. in a water bath with gentle agitation for 1-2 minutes and then decontaminated by wiping with 70% ethanol before opening in a Class II biological safety cabinet. Transfer the vial contents drop-wise into 10 mL of cell culture medium in a sterile 15 mL conical tube. Then centrifuged the tube at 200× g for 5 minutes and aspirate the supernatant. Re-suspend the cell pellet with 1 mL of fresh cell culture medium and transfer it in to the T75 flask containing cell culture medium.

To passage H1975 cells, firstly, the adherent cells were rinsed with Trypsin/EDTA. Then add Trypsin/EDTA (3 mL for a T75 flask) into the flask and swirl to ensure the cells coated with trypsin evenly. Then incubate the flasks at 37° C. until the cells detach. Add equal volume of cell culture medium to stop the reaction. Collect the detached cells and centrifuged at 200×g for 5 minutes followed by re-suspended in fresh culture medium. Then, the cells were transferred into a new T75 flask containing cell culture medium. Cells were sub-cultured three times per week at a ratio of 1:2 or 1:4 in culture medium.

Test compounds were dissolved in DMSO at 30 mM. 45 µL of compound was transferred into a 384-well compound source plate (LABCYTE cat#P-05525) and serially diluted at 1:3 ratio to create a 13-point dilutions. The same volume of DMSO was adopted as high control. 20 nL of these compounds DMSO dilutes (10 points, from 1.11 mM to 0.056 µM) were dispensed into a new 384-well assay plate by Echo 550.

Harvest cells from flask into cell culture medium as described above and the cell numbers were counted using Automated Cell Counter (Thermo Fisher Scientific, Countess™). Dilute the cells into 25,000 cells/mL with culture medium and add 40 µL of cell suspension into each well of 384-well cell culture plate as designated. The final concentration was 1,000 cells/well. Add medium only as low control. The plates were covered with lid and placed in 37° C. 5% $CO_2$ incubator for 72 hours.

After 72 hours incubation, remove the plates from incubator and equilibrate at room temperature for 15 minutes. Incubate the CellTiter Glo reagents (Promega, G9243) at 37° C. before the experiment. The buffer was equilibrated to room temperature and used to dissolve the substrate. To determine the cell viability, add 40 μL of CellTiter-Glo reagent into each well to be detected (at 1:1 to culture medium). Then the place the plates at room temperature for 30 min followed by read on EnSpire (PerkinElmer).

For estimation of $IC_{50}$, the luminescence readout are transformed to % Inhibition by applying the following equation: The $IC_{50}$ was then $$\frac{Lum_{HC} - Lum_{Cpd}}{Lumo_{HC} - Lum_{LC}}.$$

calculated by fitting in XLFit to a four parameters logistic curve.

PC-9 Growth Inhibition Assay (Cell Proliferation).

The inhibition assay of PC-9 cells was conducted in the same manner as described above for H1975 cells.

A431 Inhibition Assay, (Cell Proliferation).

The culture medium of A431 cells was Dulbecco's Modified Eagle Medium supplied with 10% fetal bovine serum and 1% penicillin/streptomycin. The DMSO dilutions used in A431 assay was 10 points from 30 nM to 1.52 uM. The rest procedure was conducted in the same manner as described above for H1975 cells.

TABLE 1

| Ex # | EGFR_d746-750 $IC_{50}$ (nM) | EGFR_L858R/T790 $IC_{50}$ (nM) | EGFR_WT $IC_{50}$ (nM) | PC9 $IC_{50}$ (nM) SM | NCI-H1975 $IC_{50}$ (nM) DM | LoVo $IC_{50}$ (nM) WT |
|---|---|---|---|---|---|---|
| AZD-9291 | 1.2 | 1.5 | 4.4 | 8.4 | 6.5 | 2861 |
| AZD-5104 | 1.1 | 1.5 | 1.6 | 3.4 | 2.2 | 3250 |
| 1 | 2.4 | 0.7 | 4.1 | 6.8 | 3.1 | 3572 |
| 2 | 3.1 | 1.3 | 7.1 | 12.3 | 7.5 | 5026 |
| 3 | 5.3 | 1.5 | 8.4 | 23.3 | 17.9 | 2814 |
| 4 | 2.6 | 0.84 | 3.8 | 25.9 | 18.8 | 2887 |
| 5 | 8.2 | 2.7 | 31 | — | — | — |
| 6 | 9.2 | 7 | 44 | — | — | — |
| 7 | 0.85 | 1.2 | 1.1 | 1.6 | 1.7 | 2626 |
| 8 | 1.2 | 1.8 | 2.1 | 3.5 | 2.9 | 6651 |
| 9 | 1.1 | 1.3 | 1.5 | 3.4 | 2.4 | 5865 |
| 10 | 0.91 | 1.2 | 1.3 | 2.2 | 1.5 | 11973 |
| 11 | 1.0 | 1.3 | 1.5 | 2.9 | 2.3 | 4731 |
| 12 | 1.1 | 1.2 | 1.5 | 5.2 | 3.5 | 2559 |
| 13 | 1.7 | 1.5 | 6.7 | 9.9 | 5.6 | 5808 |
| 14 | 1.0 | 1.8 | 5.0 | 6.1 | 3.7 | 2983 |
| 15 | 1.1 | 1.5 | 1.9 | 3.3 | 2.9 | 13488 |

TABLE 1. Activity of Selected Examples in an enzyme phosphorylation assay, and in cellular proliferation assays. PC9 cells contain EGFR d746-750 single mutant (SM). NCI-1975 cells contain EGFR L858R/T790 double mutant (DM). LoVO cells contain unmutated EGFR wild type (WT).

TABLE 2

Table 2. Cellular Proliferation Assays.

| RUN # | EXAMPLE # | SM (PC9) $IC_{50}$ nM | DM (H1975) $IC_{50}$ nM | WT (A431) $IC_{50}$ nM |
|---|---|---|---|---|
| 1 | AZD-9291 | 13.21 | 22.35 | 861.59 |
| 1 | AZD-5104 | 6.22 | 9.95 | 414.67 |
| 1 | 16 | 0.76 | 0.72 | 121.13 |
| 1 | 17 | 0.93 | 0.94 | 162.23 |
| 1 | 18 | 0.64 | 0.41 | 40.01 |
| 1 | 19 | 16.7* | 12.7* | NT |
| 1 | 20 | 1.92 | 2.35 | 253.38 |
| 1 | 21 | 2.54 | 2.37 | 1024.67 |
| 1 | 22 | 62.61 | 136.84 | 1688.81 |
| 1 | 23 | 3.82 | 2.46 | 865.79 |
| 1 | 24 | 66.99 | 103.36 | 6994.61 |
| 1 | 25 | 63.12 | 19.80 | 2100.70 |
| 1 | 26 | 37.32 | 25.01 | 1034.29 |
| 1 | 30 | 19.18 | 20.45 | 1676.78 |
| 1 | 31 | 8.54 | 13.92 | 1073.86 |
| 1 | 34 | 7.23 | 4.62 | 1774.62 |
| 1 | 35 | 33.30 | 29.36 | 2017.71 |
| 1 | 38 | 82.72 | 82.04 | 1318.64 |
| 2 | AZD-9291 | 17.93 | 34.45 | 654.86 |
| 2 | AZD-5104 | 5.31 | 11.77 | 198.81 |
| 2 | Afatinib | 0.65 | 208.97 | 127.29 |
| 2 | 20 | 1.54 | 2.12 | 117.89 |
| 2 | 21 | 2.33 | 2.01 | 781.87 |
| 2 | 22 | 52.40 | 92.65 | 1191.66 |
| 2 | 23 | 3.38 | 2.63 | 171.67 |
| 2 | 27 | 13.42 | 9.92 | 1623.75 |
| 2 | 28 | 22.04 | 6.84 | 2231.59 |
| 2 | 31 | 8.39 | 11.61 | 942.04 |
| 2 | 32 | 8.52 | 3.92 | 1082.04 |
| 2 | 34 | 10.94 | 3.23 | 928.40 |
| 3 | AZD-9291 | 17.94 | 13.30 | 958.44 |
| 3 | AZD-5104 | 4.80 | 3.66 | 122.72 |
| 3 | Afatinib | 0.70 | 194.05 | 90.31 |
| 3 | 28 | 26.01 | 3.23 | 1710.12 |
| 3 | 29 | 23.69 | 5.24 | 777.33 |
| 3 | 32 | 11.90 | 3.20 | 784.23 |
| 3 | 33 | 9.90 | 6.33 | 88.50 |
| 3 | 37 | 22.00 | 21.91 | 587.89 |
| 4 | AZD-9291 | 5.63 | 7.77 | 325.70 |
| 4 | AZD-5104 | 2.25 | 3.20 | 47.78 |
| 4 | Afatinib | 0.28 | 135.05 | 39.49 |
| 4 | 39 | 0.74 | 0.52 | 42.32 |
| 4 | 40 | 63.05 | 43.54 | 1877.97 |
| 4 | 42 | 2.29 | 2.37 | 395.60 |
| 4 | 43 | 3.30 | 3.96 | 218.33 |
| 4 | 36 | 57.5* | 39.5* | NT |
| 5 | AZD-9291 | 5.09 | 10.26 | 199.31 |
| 5 | AZD-5104 | 2.65 | 5.60 | 33.41 |
| 5 | afatinib | | | 53.05 |
| 5 | 62 | 0.94 | 2.24 | 43.92 |
| 5 | 47 | 12.35 | 8.79 | 403.80 |
| 5 | 57 | 3.63 | 5.10 | 267.43 |
| 5 | 69 | 1.92 | 3.55 | 71.15 |
| 5 | 53 | 3.09 | 6.23 | 82.52 |
| 6 | AZD-9291 | 7.24 | 9.05 | 575.70 |
| 6 | AZD-5104 | 2.61 | 3.31 | 80.64 |
| 6 | afatinib | | | 22.50 |
| 6 | 45 | 4.4 | 2.61 | 461.04 |
| 6 | 63 | 5.79 | 3.03 | 528.49 |
| 6 | 73 | 3.28 | 12.62 | 425.85 |
| 6 | 64 | 5.65 | 7.96 | 425.85 |
| 6 | 66 | 1.96 | 4.99 | 6.04 |
| 6 | 58 | 1.50 | 2.36 | 1.46 |
| 7 | AZD-9291 | 6.78 | 8.97 | 629.98 |
| 7 | AZD-5104 | 1.81 | 3.28 | 79.22 |
| 7 | afatinib | 0.27 | 299.71 | 81.26 |
| 7 | 48 | 4.01 | 3.48 | 265.31 |
| 7 | 49 | 0.61 | 1.84 | 136.96 |
| 7 | 51 | 1.51 | 3.01 | 239.13 |
| 7 | 68 | 2.37 | 0.86 | 264.13 |
| 7 | 67 | 2.07 | 1.05 | 505.52 |
| 8 | AZD-9291 | 14.78 | 17.78 | 417.62 |
| 8 | AZD-5104 | 3.80 | 5.03 | 62.48 |
| 8 | afatinib | 0.82 | 528.09 | 28.73 |
| 8 | PF-06747775 | 7.10 | 27.84 | 656.62 |
| 8 | EGF 816 | 67.26 | 77.92 | 2852.04 |
| 8 | 21 | 4.49 | 2.90 | 312.15 |
| 8 | 41 | 7.52 | 9.23 | 294.67 |
| 8 | 52 | 17.21 | 4.06 | 324.57 |
| 8 | 60 | 11.19 | 8.10 | 544.51 |
| 8 | 59 | 19.72 | 8.45 | 715.79 |
| 9 | AZD-9291 | 8.90 | 8.11 | 441.98 |
| 9 | AZD-5104 | 3.65 | 3.27 | 48.68 |
| 9 | afatinib | 0.75 | 207.11 | 332.71 |
| 9 | 50 | 14.41 | 7.62 | 118.05 |
| 9 | 46 | 21.22 | 115.68 | 253.31 |
| 9 | 65 | 6.46 | 4.21 | 120.75 |
| 9 | 55 | 9.09 | 3.93 | 2800.56 |

TABLE 2-continued

Table 2. Cellular Proliferation Assays.

| RUN # | EXAMPLE # | SM (PC9) IC$_{50}$ nM | DM (H1975) IC$_{50}$ nM | WT (A431) IC$_{50}$ nM |
|---|---|---|---|---|
| 9 | 44 | 474.62 | 173.65 | 9071.58 |
| 10 | AZD-9291 | 3.68 | 7.82 | 602.00 |
| 10 | AZD-5104 | 0.85 | 1.77 | 34.88 |
| 10 | afatinib | 0.33 | 354.82 | 140.50 |
| 10 | 74 | 5.74 | 27.99 | 396.04 |
| 10 | 75 | 27.92 | 89.45 | 438.89 |
| 10 | 61 | 29.54 | 93.98 | 1074.70 |
| 10 | 54 | 0.81 | 1.96 | 439.68 |
| 10 | 56 | 1.66 | 2.77 | 511.04 |
| 10 | 70 | 2.27 | 9.11 | 811.84 |
| 11 | AZD-9291 | 5.16 | 8.64 | 516.32 |
| 11 | AZD-5104 | 2.44 | 3.76 | 42.00 |
| 11 | afatinib | 0.32 | 169.36 | 35.12 |
| 11 | ASP8273 | 15.86 | 12.05 | 674.94 |
| 11 | 71 | 2.45 | 3.29 | 480.38 |
| 11 | 72 | 5.88 | 8.55 | 911.51 |
| 11 | 76 | 3.33 | 2.27 | 152.31 |

Unless otherwise stated proliferation was measured by Method B.
*tested by method A.

Cellular EGFR Autophosphorylation Assays.

L858R/T790M Double Mutant H1975 Autophosphorylation Inhibition Assay (ELISA)

H1975 cells were cryopreserved in liquid nitrogen. Before thawing the cells, place 15 mL of cell culture medium (RPMI 1640 Medium supplied with 10% fetal bovine serum and 1% penicillin/streptomycin) into a T75 flask and pre-incubate the flask in humidified 37° C./5% CO$_2$ incubator for 15 minutes to allow medium to equilibrate to the proper pH and temperature. Remove the vial from liquid nitrogen and thaw rapidly by placing at 37° C. in a water bath with gentle agitation for 1-2 minutes and then decontaminated by wiping with 70% ethanol before opening in a Class II biological safety cabinet. Transfer the vial contents dropwise into 10 mL of cell culture medium in a sterile 15 mL conical tube. Then centrifuged the tube at 200× g for 5 minutes and aspirate the supernatant. Re-suspend the cell pellet with 1 mL of fresh cell culture medium and transfer it in to the T75 flask containing cell culture medium.

To passage H1975 cells, firstly, the adherent cells were rinsed with Trypsin/EDTA. Then add Trypsin/EDTA (3 mL for a T75 flask) into the flask and swirl to ensure the cells coated with trypsin evenly. Then incubate the flasks at 37° C. until the cells detach. Add equal volume of cell culture medium to stop the reaction. Collect the detached cells and centrifuged at 200× g for 5 minutes followed by re-suspended in fresh culture medium. Then, the cells were transferred into a new T75 flask containing cell culture medium. Cells were sub-cultured three times per week at a ratio of 1:4 in culture medium.

Harvest cells from flask into cell culture medium and the cell numbers counted using Automated Cell Counter (Thermo Fisher Scientific, Countess™). Dilute the cells into 250,000 cells/mL with culture medium and add 40 µL of cell suspension into each well of 384-well cell culture plate as designated. The final concentration was 10,000 cells/well. The plates were covered with lid and placed in 37° C. 5% CO$_2$ incubator overnight for cell attachment.

On the second day, test compounds were dissolved in DMSO at 10 mM. 45 uL of compound was transfer into a 384-well compound source plate (LABCYTE cat#P-05525) and serially diluted at 1:3 ratio to create a 13-point dilutions. The same volume of DMSO was adopted as high control. 40 nL of these compounds DMSO dilutes (11 points, from 1.11 mM to 0.019 uM) were dispensed into the H1975 cell plate by Echo 550.

Place the plate back to 37° C. 5% CO$_2$ incubator for 2 hours. Replace the medium of each well with ice-cold HBSS. Then remove the HBSS, add 30 µL cell lysis buffer into each well and shake the plates for 30 mins on a plate shaker. Centrifuge for 5 min at 1,000 rpm to remove bubbles and transfer 25 uL of the lysate supernatant for p-EGFR assay by using a commercial ELISA kit (R&D, DYC1095B-5).

For estimation of IC$_{50}$, the absorption readout are transformed to % relative activity by applying the following equation $$\% \text{ Inhibition} = \frac{\text{Abs}_{HC} - \text{Abs}_{cpd}}{\text{Abs}_{HC}}.$$

The IC$_{50}$ was then calculated by fitting in XLFit (IDBS, Guildford, Surrey) to a four parameters logistic curve.

Wild Type EGFR A431 Autophosphorylation Inhibition Assay (ELISA).

The culture medium of A431 cells was Dulbecco's Modified Eagle Medium supplied with 10% fetal bovine serum and 1% penicillin/streptomycin. The DMSO dilutions used in A431 assay was 11 points from 10 mM to 0.17 uM. After 2 hour treatment with test compounds, add 4.5 µL of EGF (1 µg/mL) into each well and stimulate for 10 min. The rest of the procedure was processed in the same manner as described above for H1975 cells.

Exon19 Deletion EGFR (Activating Single Mutant) PC-9 Cellular Autophosphorylation Assay.

The human lung cell line PC9 (Exon 19 deletion EGFR) is obtained from the American type Culture Collection. PC9 cells are maintained in RPMI 1640, containing 10% fetal calf serum and 2 mM glutamine. Cells are grown in a humidified incubator at 37° C. with 5% CO$_2$. Assays to measure cellular phosphorylation of endogenous p-EGFR in cell lysates are carried out according to the protocol described in the R&D Systems DuoSet IC Human Phospho-EGF R ELISA (R&D Systems catalogue number #DYCI095). 40 µL of cells are seeded (10000 cells/well) in growth medium in Corning black, clear-bottomed 384-well plates and incubated at 37° C., with 5%0/CO$_2$ overnight. Cells are acoustically dosed using an Echo 555, with compounds serially diluted in 100% DMSO. Plates are incubated for a further 2 h, then following aspiration of medium, 40 µL×lysis buffer is added to each well. Greiner black high bind 384 well plates are coated with capture antibody and then blocked with 3% BSA. Following removal of block, 15 µL of lysate are transferred to the Greiner black high bind 384 well plates and incubated for 2 hours. Following aspiration and washing of the plates with PBS, 20 µL of detection antibody are added and incubated for 2 hours. Following aspiration and washing of the plates with PBS, 20 µL of QuantaBlu fluorogenic peroxidase substrate (Thermo Fisher Scientific catalogue number 15169) are added and incubated for 1 hour. 20 µL QuantaBlu stop solution are added to plates and fluorescence read on an Envision plate reader using Excitation 352 nm wavelength and emission 460 nm wavelength. The data obtained with each compound are exported into a suitable software package (such as Origin) to perform curve fitting analysis. From this data an IC$_{50}$ value is determined by calculation of the concentration of compound that is required to give a 50% effect.

TABLE 3

Table 3. Cellular EGFR Autophosphorylation Assays.

| RUN # | EXAMPLE # | H1975 IC$_{50}$ (nM) | PC-9 IC$_{50}$ (nM) | A431 IC$_{50}$ (nM) |
|---|---|---|---|---|
| 1 | AZD-9291 | 11.56 | 7.31 | 1145.47 |
| 1 | AZD-5104 | 3.58 | 2.40 | 77.36 |
| 1 | 23 | 1.15 | 1.37 | 26.07 |
| 1 | 34 | 2.19 | 7.14 | 399.77 |
| 1 | 21 | 0.93 | 1.63 | 208.45 |
| 2 | AZD-9291 | 22.74 | 12.09 | 196.31 |
| 2 | AZD-5104 | 1.84 | 2.91 | 21.50 |
| 2 | PF-06747775 | 8.00 | 7.49 | 78.17 |
| 2 | EGF 816 | 43.70 | 25.39 | 276.32 |
| 2 | ASP8273 | 7.80 | 37.29 | 218.34 |
| 2 | 21 | 2.85 | 7.33 | 66.16 |
| 2 | 27 | 6.78 | 17.80 | 200.27 |
| 2 | 31 | 7.64 | 13.69 | 161.44 |
| 2 | 41 | 11.90 | 6.26 | 136.83 |
| 2 | 42 | 4.19 | 3.69 | 66.30 |
| 2 | 43 | 10.22 | 10.34 | 73.39 |
| 2 | 45 | 3.83 | 10.61 | 76.16 |
| 2 | 54 | 3.05 | 1.69 | 27.23 |
| 2 | 55 | 4.07 | 15.53 | 106.32 |
| 2 | 56 | 6.28 | 4.04 | 79.94 |
| 2 | 57 | 8.50 | 14.00 | 134.20 |
| 2 | 67 | 1.06 | 4.76 | 109.66 |

IGF-1R Inhibition Assay

Test compound was dissolved in DMSO at 30 mM. 45 uL of compound was transfer into a 384-well compound source plate (LABCYTE cat#P-05525) and serially diluted at 1:3 ratio to create a 12-point dilutions. The same volume of DMSO was adopted as high control. 20 nL of these compounds DMSO dilutes were dispensed into a new 384-well assay plate by Echo 550. IGF-1R protein (0.87 nM, CARNA BIOSCIENCE, cat#08-141), florescent labeled substrate FLPeptide13 (2 µM, PerkinElmer, cat#760357) was prepared in kinase assay buffer (100 mM HEPES (pH 7.5), 10 mM MgCl$_2$. 0.05% Brij-35, 0.5 mM DTT and 0.1 mg/ml BSA). 15 uL of kinase assay buffer containing IGF-1R protein and substrate was transferred to assay plate and incubate at RT for 30 minutes. Kinase assay buffer supplemented with substrate peptides was employed as low control to monitor the background. 40 µM ATP was prepared in kinase assay buffer containing and 5 µL of ATP solution was added to each well to start the reaction. The assay plate was incubated at 25° C. for 180 minutes and the reaction was stopped by adding 40 µL of 0.5 M EDTA.

Phosphorylated fluorescent-tagged peptides were differentiated from non-phosphorylated peptides by separating using Caliper EZ Reader II and the detection was directly converted to conversion ratio.

For estimation of IC$_{50}$, the % substrate conversion values are transformed to % relative activity by applying the following equation $$\% \text{ relative activity} = \frac{Ratio_{cpd} - Ratio_{LC}}{Ratio_{HC} - Ratio_{LC}}.$$

The IC$_{50}$ was then calculated by fitting in XLFit (IDBS, Guildford, Surrey) to a four parameters logistic curve.

INSR Inhibition Assay

Test compound was dissolved in DMSO at 30 mM. 45 uL of compound was transfer into a 384-well compound source plate (LABCYTE cat#P-05525) and serially diluted at 1:3 ratio to create a 12-point dilutions. The same volume of DMSO was adopted as high control. 20 nL of these compounds DMSO dilutes were dispensed into a new 384-well assay plate by Echo 550. INSR protein (0.73 nM, CARNA BIOSCIENCE, cat#08-142), florescent labeled substrate FLPeptide13 (2 µM, PerkinElmer, cat#760357) was prepared in kinase assay buffer (100 mM HEPES (pH 7.5), 10 mM MgCl$_2$, 0.05% Brij-35, 0.5 mM DTT and 0.1 mg/ml BSA). 15 uL of kinase assay buffer containing INSR protein and substrate was transferred to assay plate and incubate at RT for 30 minutes. Kinase assay buffer supplemented with substrate peptides was employed as low control to monitor the background. 40 LM ATP was prepared in kinase assay buffer containing and 5 µL of ATP solution was added to each well to start the reaction. The assay plate was incubated at 25° C. for 180 minutes and the reaction was stopped by adding 40 µL of 0.5 M EDTA.

The result is analyzed in the same manner of INSR.

TABLE 4

Table 4. IGF-1R and INSR enzyme assay data.

| Run # | Example # | IC$_{50}$ (nM) IGF-1R | IC$_{50}$ (nM) INSR |
|---|---|---|---|
| 1 | AZD-9291 | 320.68 | 253.20 |
| 1 | AZD-5104 | 75.68 | 72.20 |
| 1 | 16 | 3.94 | 4.76 |
| 1 | 17 | 71.21 | 67.57 |
| 1 | 18 | 2.15 | 2.28 |
| 1 | 20 | 23.51 | 19.26 |
| 1 | 21 | 180.05 | 134.44 |
| 1 | 23 | 270.60 | 325.13 |
| 1 | 27 | 4824 | 13199 |
| 1 | 30 | 210.31 | 206.28 |
| 1 | 31 | 764.54 | 814.24 |
| 1 | 34 | 470.21 | 513.68 |
| 2 | AZD-9291 | 248.90 | 267.12 |
| 2 | AZD-5104 | 35.81 | 49.49 |
| 2 | 41 | 1417.79 | 1271.89 |
| 2 | 42 | 336.62 | 366.25 |
| 2 | 45 | 1272.55 | 1021.11 |
| 2 | 54 | 868.62 | 851.02 |
| 2 | 55 | 1301.33 | 1197.81 |
| 2 | 56 | 636.65 | 432.85 |
| 2 | 57 | 206.88 | 289.74 |
| 2 | 67 | 243.18 | 402.53 |

Various Other Kinases. Inhibition of various other kinases, including but not limited to Lck, Lyn, Src, Fyn, Syk, Zap-70, Itk, Tec, Btk, EGFR, ErbB2, Kdr, Flt-1, Flt-3, Tek, c-Met, InsR, and Atk is determined as described in U.S. Pat. No. 6,881,737, the entire contents of which are incorporated by reference.

Mouse In Vivo PK Study

To determine the drug concentration in plasma of NJB-342, NJB-348 and NJB-463 following intravenous and oral administration in male CDI Mice, to get the pharmacokinetic profile and PK parameters Study Protocol:

Test animals: healthy male CDI mice (body weight 20-30 g, 18 mice, free access to food and water), provided by Sibeifu laboratory.

Dose Level and dose route: dosed the animals via intravenous injection from tail vein for IV group (1 mg/kg, 5 mL/kg, 10% DMSO/40% PEG400/50% water), dosed the animals via oral gavage for PO group (10 mg/kg, 10 mL/kg, (10% DMSO/40% PEG400/50% water), respectively.

Samples collection: the healthy animals were used, weighed the bodyweight and marked at tail and cage card prior to dosing. Blood samples (0.03 mL per time point) were collected from dorsal metatarsal vein at 0.083, 0.25, 0.5, 1, 2, 4, 8, 24 h post dose for IV group and at 0.25, 0.5, 1, 2, 4, 8, 24 h post dose for PO group, the terminal time point was collected from heart (~0.3 mL). The blood samples were put into the tube with heparin-Na coated and then put on the cold box, centrifuged at 4° C. 4000 g, 5 minutes immediately after collecting all samples per time point to get plasma. The plasma samples were stored in a freezer at −75±15° C. prior to analysis.

Determined the drug concentration by LC/MS/MS method, and the parameters were listed in the table below.

TABLE 5

Table 5. Oral PK on Selected Examples.

| PK parameters | Unit | Example 34 | Example 21 | Example 42 |
|---|---|---|---|---|
| Cl | mL/min/kg | 110 | 162.7 | 97 |
| $T_{1/2}$ (IV) | h | 1.11 | 0.73 | 1.32 |
| $C_{max}$ (PO) | ng/mL | 58 | 86 | 176 |
| AUC (PO) | h*ng/mL | 165 | 282 | 677 |
| F | % | 10.3 | 27.2 | 42.1 |

Animal Xenograft Tumor Models
General Protocol.

Appropriately transformed cells, either from ATCC cell lines, known to carry the oncogene of interest, or from deliberate transfections, are suspended in appropriate media, and $5 \times 10^6$ or $1 \times 10^7$ cells are injected into the flank of nu/nu mice. Alternatively trochar placement of fragments of in vivo passaged tumors, usually about 1 mm³ can be used to initiate the tumors. When tumors have reached an appropriate size for the experiment, usually in the 100-300 mg range, animals are randomized into matched groups of 6-10 mice, and tumor size and given vehicle or test article by perioral gavage once or twice daily. Tumor volumes are determined using calipers. The percentage increase in the volume of a xenograft tumor on day n versus day 0 (the day when dosing of the test compound began) is calculated as (tumor volume on day n−tumor volume on day 0/tumor volume on day 0)×100. The mean percentage of tumor growth inhibition in each drug-treated group relative to the vehicle-treated group is calculated as (1−mean percent increase of tumor volume in the drug-treated group/mean percent increase of the tumor volume in the vehicle-treated group)×100. Statistical significance is evaluated using a one-tailed t test.

Wild-Type EGFR Xenograft Assay.

For determination of efficacy against tumors overexpressing wt EGFR, xenografts grown from either A431 epidermoid or LoVo colon carcinoma cells may be used.

EGFR Del746-750 Xenograft Model.

For determination of efficacy against tumors overexpressing EGFR-del746-750, xenografts grown from PC9 NSCLC cells may be used.

EGFR L858R Xenograft Model.

For determination of efficacy against tumors overexpressing EGFR-L858R, xenografts grown from H3255 NSCLC cells may be used.

EGFR L858R/T790M Double-Mutant Xenograft Model.

For determination of efficacy against tumors overexpressing EGFR-L858R/T790M double mutant, xenografts grown from H1975 NSCLC cells may be used.

Pharmacodynamic Assays.

Mice bearing any of the above tumors, preferably of 200-300 mg size, can be euthanized at appropriate intervals after oral administration of drug. The tumors are excised, snap-frozen, and dispersed using a Qiagen Tissue-Lyser in a nondenaturing lysis buffer containing protease and phosphatase inhibitors. The homogenate is lysed at 4° C. for 1 h, clarified by centrifugation, and then analyzed by quantitative Western blotting for phosphor EGFR/erbB-2/3/4 and total receptor. The phospho-RTK signal of each RTK band is normalized with its total RTK signal. Alternatively, the ratio of total ERK to phosphor-ERK can be measured in the tumors by similar techniques, using the appropriate eERK and phosphor-ERK antibodies.

Enzyme assays for $IC_{50}$ determinations for various enzymes were carried out in accordance with the procedures disclosed herein. Table I shows $IC_{50}$ enzyme assay results for compounds of Examples 1-15.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:
1. A compound of formula (VB):

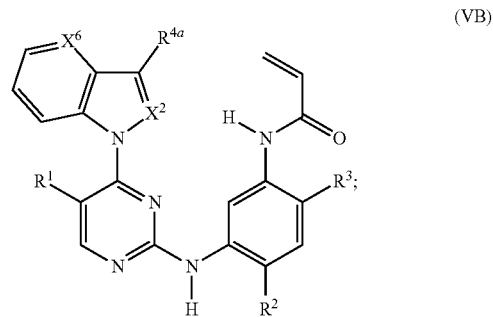

(VB)

or a stereoisomer or a pharmaceutically acceptable salt, solvate, ester, or tautomer thereof;
wherein
$X^6$ is $CR^4$ or N;
$R^1$ is selected from hydrogen, methyl, fluoro, chloro, bromo, $CF_3$, or cyano;
$R^2$ is —$OCF_3$, —$OCHF_2$, —$OCF_2CF_3$, —$OCH_2CHF_2$, —$OCH_2CF_3$, cyclopropoxy, methoxy, —$OCD_3$, ethoxy, or isopropoxy;
$R^3$ is $N(R^{10})C_{2-6}$ alkyl-$NR^{10}R^{10}$;
$R^4$ is H, cyano, halo, —$C_{1-6}$ alkyl, or —$C_{1-6}$ haloalkyl;
$R^{4a}$ is cyano, —$C_{1-6}$ haloalkyl, —$C_{1-6}$ hydroxyalkyl, —C(=O)$NR^8R^9$, —$CH_2NR^8R^9$, —$NR^8R^9$, $C_{1-6}$ acyl-$N(R^{10})$—, $(C_{1-3}$ alkyl)$SO_2NH$—, $(C_{1-6}$ alkyl)$SO_2$— or $R^7SO_2$—;
$R^7$ is —$NR^8R^9$;
$R^8$ and $R^9$ are independently H, —$CD_3$, $C_{1-6}$ alkyl, cyclopropyl, monocyclic or bicyclic $C_{4-8}$ cycloalkyl, —$(C_{1-3}$ alkyl)-$(C_{3-8}$ cycloalkyl), $C_1$-$C_6$ acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; or alternatively, $R^8$ and $R^9$, taken together with the N atom to which they are both attached, form a heterocyclic ring of 4-7 members, containing up to one other heteroatom chosen from O, S, or $NR^{11}$; and each $R^{10}$ is independently H, $-CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

2. A compound of formula (XVIIB):

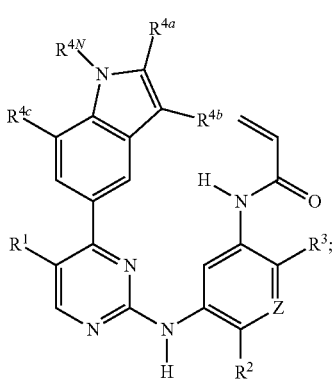

(XVIIB)

or a stereoisomer or a pharmaceutically acceptable salt, solvate, ester, or tautomer thereof;

wherein:

Z is CH or N;

$R^1$ is selected from hydrogen, methyl, fluoro, chloro, bromo, $CF_3$, or cyano;

$R^2$ is $-OCF_3$, $-OCHF_2$, $-OCF_2CF_3$, $-OCH_2CHF_2$, $-OCH_2CF_3$, cyclopropoxy, methoxy, $-OCD_3$, ethoxy, or isopropoxy;

$R^3$ is $N(R^{10})C_{2-6}$ alkyl-$NR^{10}R^{10}$;

$R^{4a}$ and $R^{4b}$ are each independently H, halo, $-C_{1-6}$ alkyl, or $-C_{1-6}$ haloalkyl;

$R^{4c}$ is cyano, $-C(=O)NR^8R^9$ or $-NR^8R^9$;

$R^{4N}$ is H, $-C_{1-6}$ alkyl, or $-CD_3$;

$R^8$ and $R^9$ are independently H, $-CD_3$, $C_{1-6}$ alkyl, $C_{3-8}$ cycloalkyl, $C_{3-8}$ cycloalkyl-($C_{1-3}$ alkyl)-, $C_1$-$C_6$ acyl, phenyl, monocyclic heteroaryl, or monocyclic heterocyclyl; and $R^8$ and $R^9$ may be further independently substituted with up to three substituents chosen from hydroxyl, $C_{1-6}$ alkoxy, oxo, thiono, cyano or halo; and each $R^{10}$ is independently H, $-CD_3$, or $C_{1-6}$ alkyl; or alternatively, two $R^{10}$ on the same N atom to which they are both attached, form a heterocyclic ring of 5-6 members, containing up to one other heteroatom selected from O, S, or $NR^{11}$; and each $R^{11}$ is independently hydrogen or $C_1$-$C_6$ alkyl, which is optionally substituted with up to three substituents selected from hydroxyl, oxo, thiono, cyano and halo.

3. The compound of claim 2, wherein:

Z is CH;

$R^1$ is hydrogen;

$R^2$ is $-OCH_2CHF_2$, cyclopropoxy, methoxy, ethoxy, or isopropoxy;

$R^3$ is $-N(CH_3)CH_2CH_2NR^{10}R^{10}$;

$R^{4a}$ and $R^{4b}$ are each independently H, chloro, methyl, or $-CF_3$;

$R^{4c}$ is cyano or $-C(=O)NR^8R^9$;

$R^{4N}$ is H, $-CD_3$, methyl, or ethyl;

$R^8$ and $R^9$ are independently H or methyl; and each $R^{10}$ is independently H, $-CD_3$, methyl, ethyl, or isopropyl; or alternatively, two $R^{10}$ on the same N atom to which they are both attached, form a heterocyclic ring of 5-6 members, containing up to one other heteroatom selected from O, S, or $NR^{11}$.

4. The compound of claim 2, wherein:

Z is CH;

$R^1$ is hydrogen;

$R^2$ is methoxy, ethoxy, or isopropoxy;

$R^3$ is $-N(CH_3)CH_2CH_2NR^{10}R^{10}$;

$R^{4a}$ and $R^{4b}$ are each independently H, chloro, methyl, or $-CF_3$;

$R^{4c}$ is cyano or $-C(=O)NR^8R^9$;

$R^{4N}$ is H, $-CD_3$, methyl, or ethyl;

$R^8$ and $R^9$ are independently H or methyl; and each $R^{10}$ is independently H, $-CD_3$, methyl, ethyl, or isopropyl.

5. The compound of claim 2, wherein $R^2$ is methoxy, $-OCD_3$, or ethoxy.

6. The compound of claim 2, wherein $R^3$ is $-N(CH_3)CH_2CH_2N(CH_3)_2$.

7. The compound of claim 2, wherein $R^{10}$ is H, $-CH_3$, $-CD_3$, $-CH_2CH_3$, or isopropyl.

8. The compound of claim 2, wherein $R^{4N}$ is H, or $-CH_3$, $-CD_3$, $-CH_2CH_3$.

9. The compound of claim 2, wherein $R^{4a}$ and $R^{4b}$ is each H, $-CH_3$, or halo.

10. The compound of claim 2, wherein $R^{4c}$ is cyano, $-C(=O)NR^8R^9$ or $-NR^8R^9$.

11. The compound of claim 2, wherein $R^8$ and $R^9$ are independently H, $-CH_3$, $-CD_3$, $-CH_2CH_3$, isopropyl, or cyclopropyl.

12. The compound of claim 2 selected from:

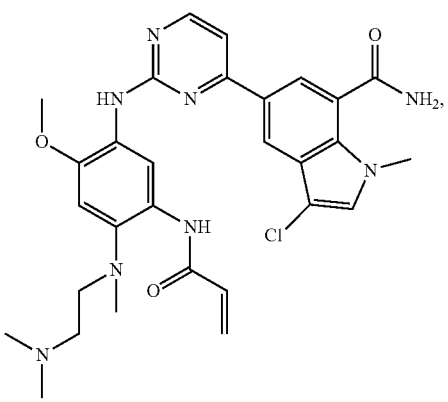

-continued

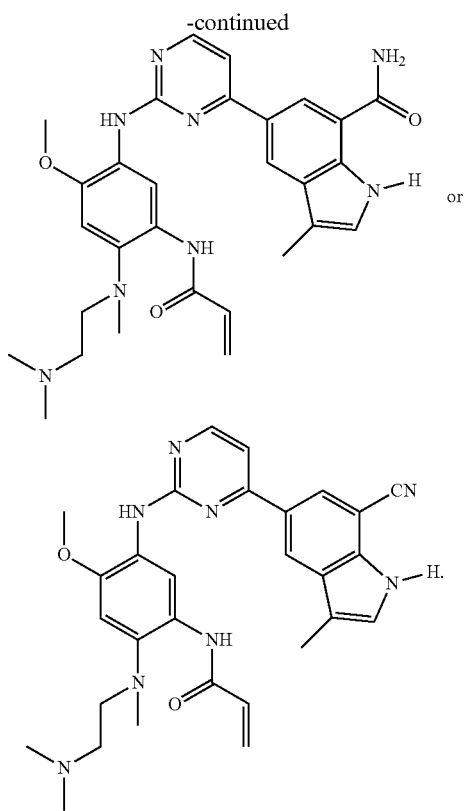

or

13. A pharmaceutical composition comprising a compound of claim 2, or a pharmaceutically acceptable salt, solvate, or ester thereof, and a pharmaceutically acceptable carrier.

14. A method for treating cancer in a patient in need thereof, comprising administering to the patient a therapeutically effective amount of a compound claim 2 or a pharmaceutically acceptable salt, solvate, or ester thereof.

15. The method of claim 14, wherein the cancer is selected from lung cancer, colorectal cancer, pancreatic cancer, head and neck cancers, breast cancer, ovarian cancer, uterine cancer, liver cancer, and stomach cancer.

16. The method of claim 14, wherein the cancer is non-small cell lung cancer (NSCLC).

17. The compound of claim 2, wherein:
Z is CH;
$R^1$ is hydrogen;
$R^2$ is methoxy, ethoxy, or isopropoxy;
$R^3$ is —N(CH$_3$)CH$_2$CH$_2$NR$^{10}$R$^{10}$;
$R^{4a}$ and $R^{4b}$ are each independently H, chloro, methyl, or —CF$_3$;
$R^{4c}$ is cyano;
$R^{4N}$ is H, —CD$_3$, methyl, or ethyl; and
each $R^{10}$ is independently H, —CD$_3$, methyl, ethyl, or isopropyl.

18. The compound of claim 2, wherein:
Z is CH;
$R^1$ is hydrogen;
$R^2$ is methoxy, ethoxy, or isopropoxy;
$R^3$ is —N(CH$_3$)CH$_2$CH$_2$N(CH$_3$)$_2$;
$R^{4a}$ and $R^{4b}$ are each independently H, chloro, methyl, or —CF$_3$;
$R^{4c}$ is cyano; and
$R^{4N}$ is H, —CD$_3$, methyl, or ethyl.

19. A pharmaceutical composition comprising a compound of claim 17, or a pharmaceutically acceptable salt, solvate, or ester thereof, and a pharmaceutically acceptable carrier.

20. The compound of claim 1 selected from:

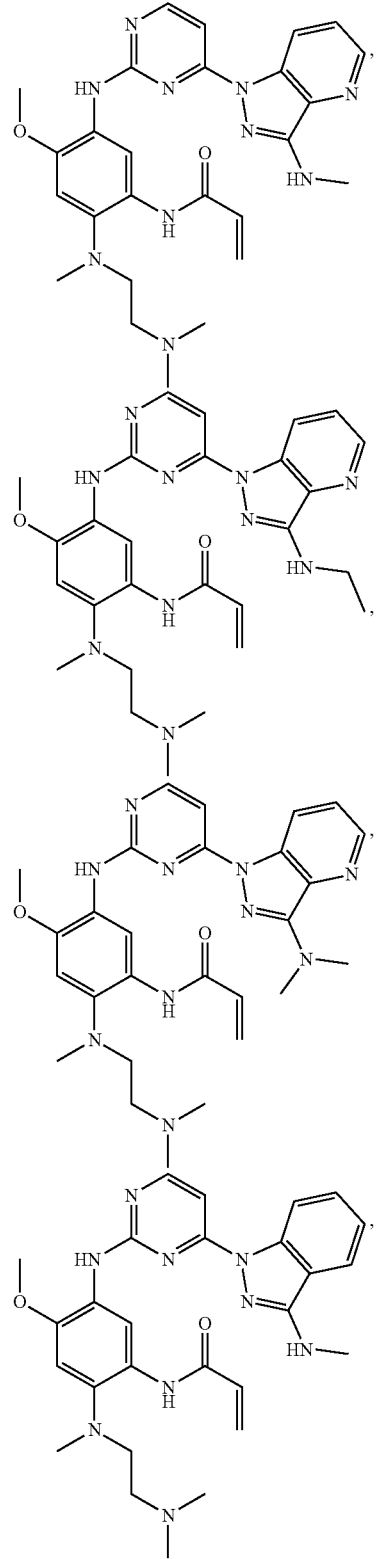

561
-continued
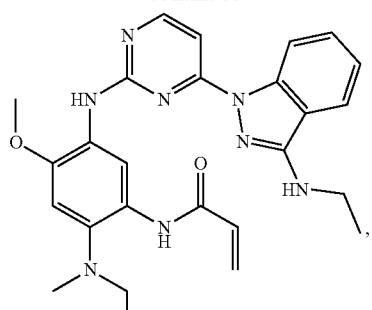
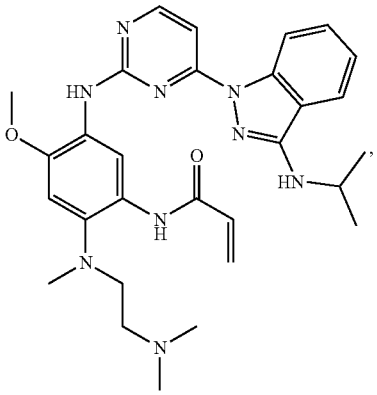
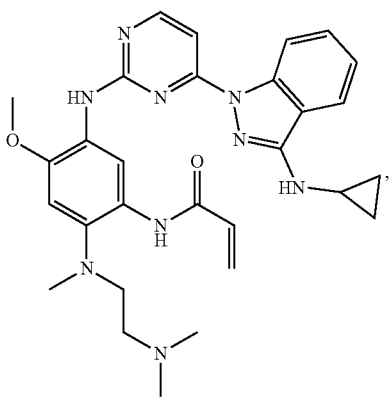
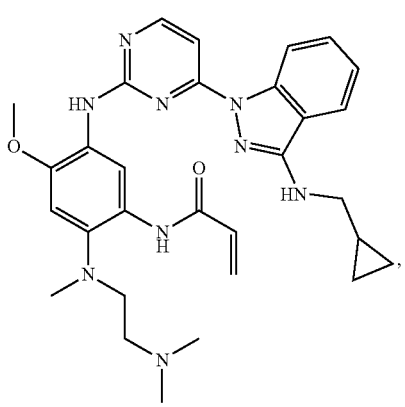
562
-continued
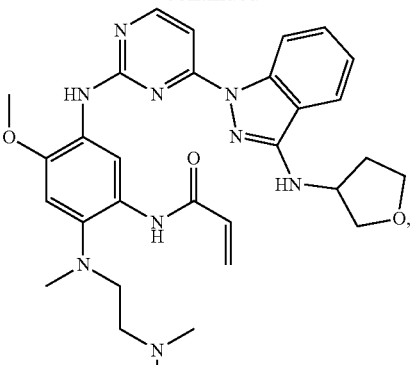
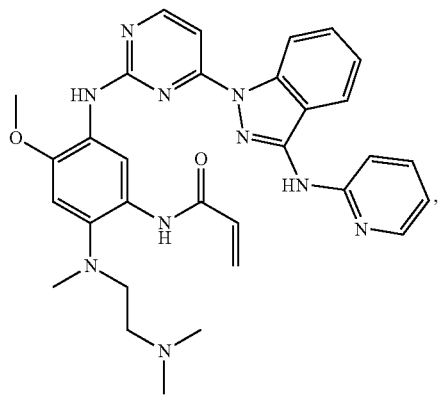
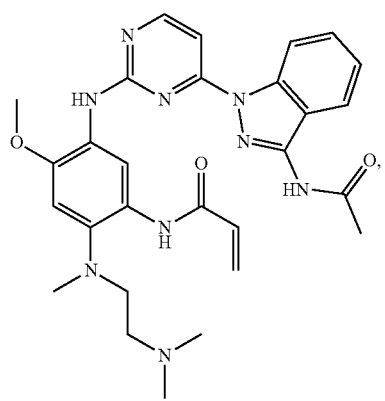
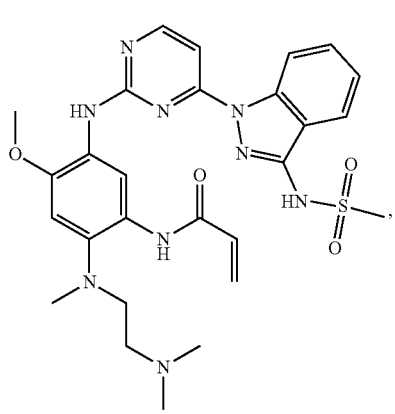

563
-continued
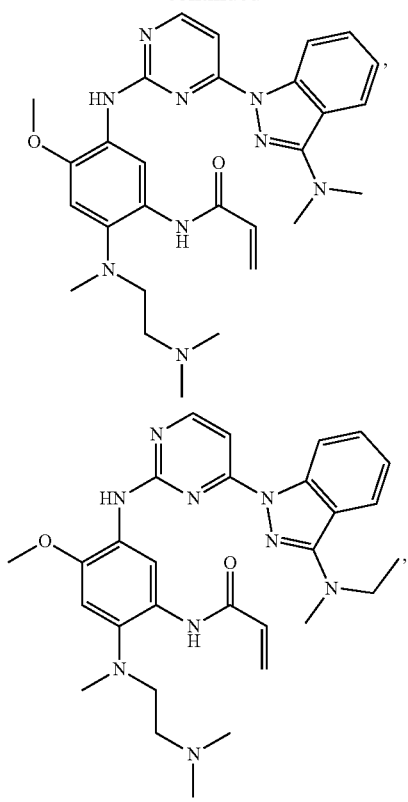
564
-continued
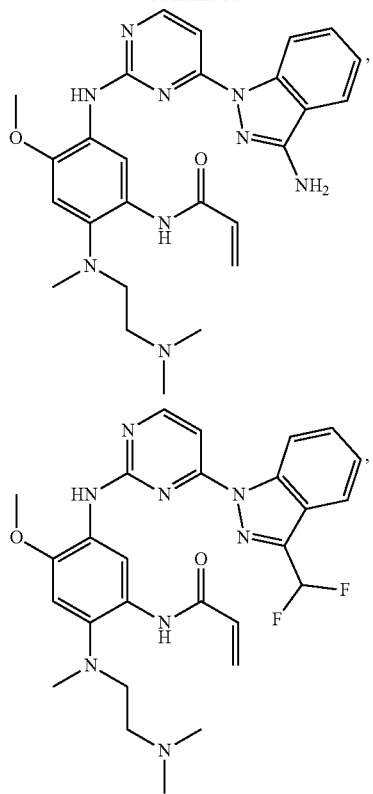
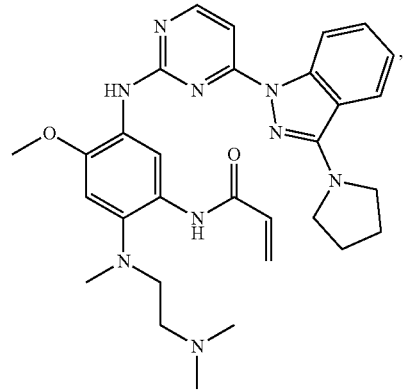
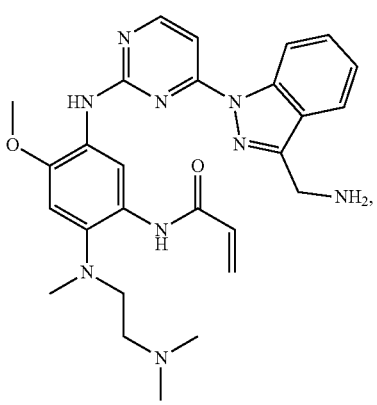
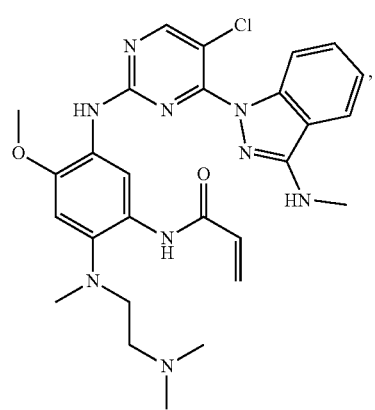
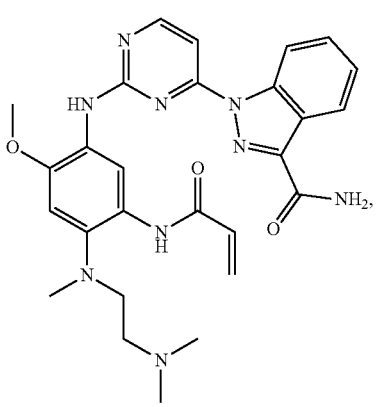

-continued

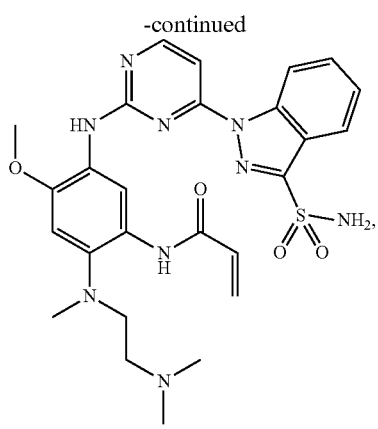

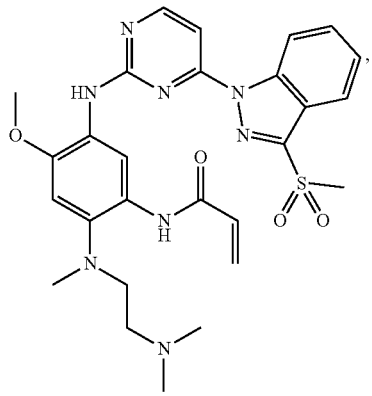

-continued

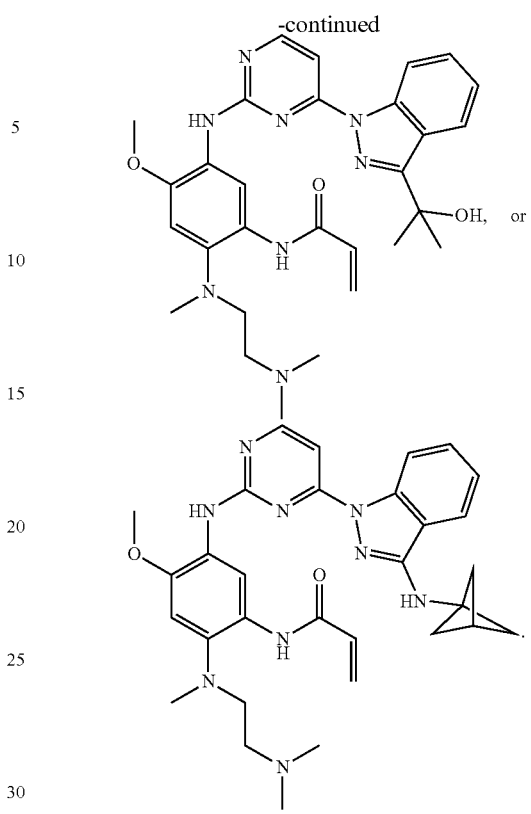

21. A pharmaceutical composition comprising a compound of claim 1, or a pharmaceutically acceptable salt, solvate, or ester thereof, and a pharmaceutically acceptable carrier.

22. A method for treating cancer in a patient in need thereof, comprising administering to the patient a therapeutically effective amount of a compound claim 1 or a pharmaceutically acceptable salt, solvate, or ester thereof.

23. The method of claim 22, wherein the cancer is selected from lung cancer, colorectal cancer, pancreatic cancer, head and neck cancers, breast cancer, ovarian cancer, uterine cancer, liver cancer, and stomach cancer.

24. The method of claim 22, wherein the cancer is non-small cell lung cancer (NSCLC).

* * * * *

UNITED STATES PATENT AND TRADEMARK OFFICE
CERTIFICATE OF CORRECTION

PATENT NO. : 10,435,388 B2
APPLICATION NO. : 16/068559
DATED : October 8, 2019
INVENTOR(S) : Yuntao Song et al.

Page 1 of 1

It is certified that error appears in the above-identified patent and that said Letters Patent is hereby corrected as shown below:

In Claim 1, Column 556, Lines 35-47, please replace:

"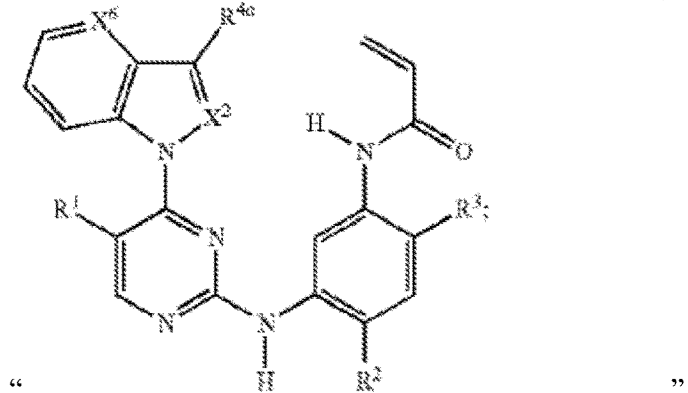"

With:

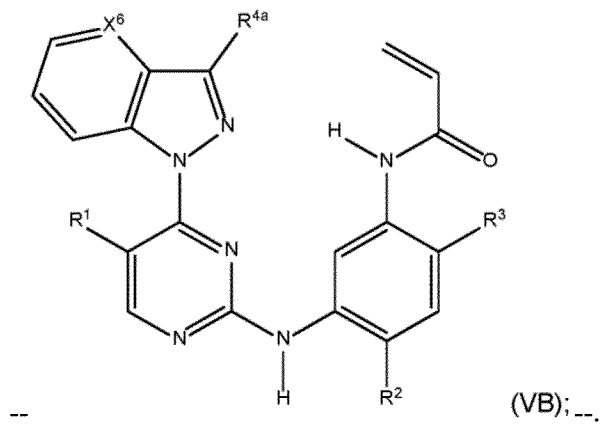 --.

Signed and Sealed this
Twenty-eighth Day of July, 2020

Andrei Iancu
*Director of the United States Patent and Trademark Office*